US012331046B2

(12) United States Patent
Kreutter et al.

(10) Patent No.: US 12,331,046 B2
(45) Date of Patent: Jun. 17, 2025

(54) CTPS1 INHIBITORS AND USES THEREOF

(71) Applicant: Nimbus Clotho, Inc., Cambridge, MA (US)

(72) Inventors: Kevin D. Kreutter, Arlington, MA (US); Lewis Whitehead, Swampscott, MA (US); Angela V. West, Franklin, MA (US); Steven K. Albanese, Brooklyn, NY (US); Andreas Verras, New York, NY (US); Shaughnessy Robinson, Westerly, RI (US); Neelu Kaila, Lexington, MA (US); Sebastien Campos, Hoddesdon (GB); Kevin Demarco, New York, NY (US)

(73) Assignee: Nimbus Clotho, Inc., Boston, MA (US)

( * ) Notice: Subject to any disclaimer, the term of this patent is extended or adjusted under 35 U.S.C. 154(b) by 42 days.

(21) Appl. No.: 17/452,011

(22) Filed: Oct. 22, 2021

(65) Prior Publication Data

US 2023/0077316 A1  Mar. 9, 2023

Related U.S. Application Data

(60) Provisional application No. 63/104,878, filed on Oct. 23, 2020.

(51) Int. Cl.
| | | |
|---|---|---|
| C07D 417/14 | (2006.01) |
| C07D 241/18 | (2006.01) |
| C07D 277/52 | (2006.01) |
| C07D 401/04 | (2006.01) |
| C07D 401/12 | (2006.01) |
| C07D 401/14 | (2006.01) |
| C07D 403/14 | (2006.01) |
| C07D 413/14 | (2006.01) |
| C07D 417/04 | (2006.01) |
| C07D 417/12 | (2006.01) |
| C07D 471/04 | (2006.01) |
| C07D 498/08 | (2006.01) |

(52) U.S. Cl.
CPC ........ *C07D 417/14* (2013.01); *C07D 241/18* (2013.01); *C07D 277/52* (2013.01); *C07D 401/04* (2013.01); *C07D 401/12* (2013.01); *C07D 401/14* (2013.01); *C07D 403/14* (2013.01); *C07D 413/14* (2013.01); *C07D 417/04* (2013.01); *C07D 417/12* (2013.01); *C07D 471/04* (2013.01); *C07D 498/08* (2013.01)

(58) Field of Classification Search
CPC .. C07D 417/14; C07D 401/04; C07D 401/14; C07D 401/12; C07D 277/52; C07D 241/18
USPC ........................................................ 514/365
See application file for complete search history.

(56) References Cited

U.S. PATENT DOCUMENTS

| | | |
|---|---|---|
| 6,552,065 B2 | 4/2003 | Remiszewski et al. |
| 7,390,799 B2 | 6/2008 | Bruncko et al. |
| 8,138,347 B2 | 3/2012 | Knight et al. |
| 2005/0267149 A1 | 12/2005 | Li |
| 2009/0253908 A1 | 10/2009 | Budzik et al. |
| 2016/0116482 A1 | 4/2016 | Manetsch et al. |

FOREIGN PATENT DOCUMENTS

| | | | | |
|---|---|---|---|---|
| WO | 2001042246 A2 | 6/2001 | | |
| WO | 2002088112 A1 | 11/2002 | | |
| WO | 2003063794 A2 | 8/2003 | | |
| WO | 2004019973 A1 | 3/2004 | | |
| WO | 2004089925 A1 | 10/2004 | | |
| WO | 2004106328 A1 | 12/2004 | | |
| WO | 2005007623 A2 | 1/2005 | | |
| WO | 2005113554 A2 | 12/2005 | | |
| WO | 2006078846 A1 | 7/2006 | | |
| WO | WO-2006097817 A1 * | 9/2006 | ........... | C07C 311/08 |
| WO | 2006122806 A2 | 11/2006 | | |
| WO | 2007016176 A2 | 2/2007 | | |
| WO | 2007044729 A2 | 4/2007 | | |
| WO | WO-2007041634 A1 * | 4/2007 | ........... | C07D 239/28 |
| WO | 2007053452 A1 | 5/2007 | | |
| WO | 2007070514 A1 | 6/2007 | | |
| WO | 2007084786 A1 | 7/2007 | | |
| WO | 2007129161 A2 | 11/2007 | | |
| WO | WO-2008036316 A2 * | 3/2008 | ........... | C07D 401/12 |
| WO | 2008039218 A2 | 4/2008 | | |
| WO | 2008109943 A1 | 9/2008 | | |
| WO | 2008118802 A1 | 10/2008 | | |
| WO | 2009114512 A1 | 9/2009 | | |
| WO | 2011090760 A1 | 7/2011 | | |
| WO | 2012014127 A1 | 2/2012 | | |
| WO | 2014074660 A1 | 5/2014 | | |
| WO | 2014074661 A1 | 5/2014 | | |
| WO | 2015089143 A1 | 6/2015 | | |
| WO | 2015131080 A1 | 9/2015 | | |
| WO | 2019106156 A1 | 6/2019 | | |

(Continued)

OTHER PUBLICATIONS

Berge et al., "Pharmaceutical salts," J. Pharmaceutical Sciences 1977; 66(1):1-19.
PCT International Search Report and Written Opinion from PCT/US2021/071999, dated Dec. 11, 2021.
Ramirez et al., "Defining causative factors contributing in the activation of hedgehog signaling in diffuse large B-cell lymphoma," Leuk. Res. 2012;36(10):1267-73.
Rostovtsev et al., "A Stepwise Huisgen Cycloaddition Process: Copper(I)-Catalyzed Regioselective "Ligation" of Azides and Terminal Alkynes," Angew. Chem. Int. Ed. 2002; 41(14):2596-99.

(Continued)

*Primary Examiner* — Kahsay Habte
(74) *Attorney, Agent, or Firm* — Dechert LLP; Andrea L. C. Reid; Joseph W. Arico

(57) ABSTRACT

The present invention provides compounds, compositions thereof, and methods of using the same for the inhibition of CPTS1, and the treatment of CPTS1-mediated disorders.

10 Claims, No Drawings

(56) References Cited

FOREIGN PATENT DOCUMENTS

| WO | WO-2019106146 A1 * | 6/2019 | ........... A61K 31/426 |
|----|---|---|---|
| WO | 2019180244 A1 | 9/2019 | |
| WO | WO-2019179652 A1 * | 9/2019 | ........... A61K 31/506 |
| WO | 2020245664 A1 | 12/2020 | |
| WO | 2020245665 A1 | 12/2020 | |
| WO | 2021053402 A2 | 3/2021 | |
| WO | 2021053403 A1 | 3/2021 | |

OTHER PUBLICATIONS

Sun et al., "Carbohydrate and Protein Immobilization onto Solid Surfaces by Sequential Diels-Alder and Azide-Alkyne Cycloadditions," Bioconjugate Chem. 2006;17(1):52-57.
Third Party Observations from PCT/US2021/071999, dated Feb. 14, 2023.

* cited by examiner

CTPS1 INHIBITORS AND USES THEREOF

CROSS-REFERENCE TO RELATED APPLICATIONS

This application claims the benefit under 35 U.S.C. § 119(e) of U.S. Provisional App. No. 63/104,878, filed on Oct. 23, 2020, the entirety of which is incorporated herein by reference.

TECHNICAL FIELD OF THE INVENTION

The present invention relates to compounds and methods useful for antagonizing CTP synthease 1 (CTPS1). The invention also provides pharmaceutically acceptable compositions comprising compounds of the present invention and methods of using said compositions in the treatment of various disorders.

BACKGROUND OF THE INVENTION

All cells, whether prokaryotic or eukaryotic in origin, utilize nucleotides as key building blocks for cellular metabolic processes, such as deoxyribonucleic acid (DNA) and ribonucleic acid (RNA) synthesis, membrane lipid biosynthesis, and as a cellular store of biochemical energy for many important enzymatic processes. The key cellular metabolic requirements for nucleotides have led to the development of many therapies that target different aspects of nucleotide biosynthesis and which are successfully used for the treatment of diverse diseases, such as cancer or autoimmune diseases.

Cellular pools of the pyrimidine nucleotide CTP (cytidine 5' triphosphate) are derived from two sources; either a salvage pathway or through a de novo biosynthetic pathway that depends on the enzyme CTP synthase (or synthetase). In humans, there are two isoforms of CTP synthase, CTPS1 and CTPS2. These enzymes catalyze the conversion of the pyrimidine UTP (uridine 5' triphosphate) into CTP in a series of coupled reactions that utilize the substrates glutamine and ATP (adenosine 5' triphosphate), converting glutamine to L-glutamate and ATP to ADP (adenosine 5' diphosphate). The specific biological roles of the two different isoforms of CTP synthase in humans have yet to be well delineated.

The immune system in multi-cellular organisms has evolved to provide protection from a diverse range of infectious pathogens. This process generally requires recognition of the pathogen by various immune cells and is often followed by amplification and long-term propagation of the immune response through the rapid expansion, proliferation, and differentiation of responding immune cells. Within this process, the activity of CTP synthase appears to play a key role in providing sufficient CTP via the de novo biosynthesis pathway for rapid expansion of immune lymphocytes following activation.

In humans, clinical data showing that CTPS1 is the critical enzyme for supporting lymphocyte proliferation has been provided through the identification of a loss-of-function homozygous mutation (rs145092287) in this enzyme that causes a severe immunodeficiency, characterized by a strongly reduced capacity of activated T- or B-cells to proliferate in response to antigen receptor-mediated activation. The absence of any other reported clinical phenotypes outside the immune system in homozygous carriers indicates a specific role for CTPS1 in supporting immune cell expansion and proliferation and suggests that CTPS1 activity may be dispensable or compensated by CTPS2 activity outside the immune system in humans.

Given the known therapeutic benefit of therapies targeting nucleotide synthesis and the key role of CTP synthase for de novo CTP generation to fuel metabolic demands of the cell, CTPS1 represents a target for a new class of agents with therapeutic potential, especially as related to immune dysfunction. Pathogenic immune cells, such as autoreactive T or B-cells, are drivers or components of diverse diseases, such as autoimmune diseases, severe allergic reactions, cardiovascular and metabolic disorders, degenerative neurological diseases, and hematological cancers. Inhibition of CTPS1 could provide therapeutic benefit in these or other diseases, and the specific role of CTPS1 in select immune cell subsets could also highlight the potential for an improved therapeutic index over other clinical therapies targeting nucleotide biosynthesis more broadly.

SUMMARY OF THE INVENTION

It has now been found that compounds of this invention, and pharmaceutically acceptable compositions thereof, are effective as inhibitors of CTPS1. In certain embodiments, the invention provides for compounds of the formulae presented herein.

Compounds of the present invention, and pharmaceutically acceptable compositions thereof, are useful for treating a variety of diseases, disorders or conditions, associated with regulation of CTPS1. Such diseases, disorders, or conditions include those described herein.

DETAILED DESCRIPTION OF CERTAIN EMBODIMENTS

1. General Description of Certain Embodiments of the Invention

In certain aspects, the present invention provides a compound of formula I:

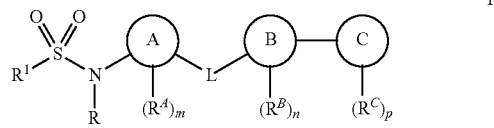

or a pharmaceutically acceptable salt thereof, wherein each of Ring A, Ring B, Ring C, L, $R^1$, $R^A$, $R^B$, $R^C$, m, n, and p, is as defined below and described in embodiments herein, both singly and in combination.

In some embodiments, the present invention provides a pharmaceutical composition comprising a compound of formula I, and a pharmaceutically acceptable carrier, adjuvant, or diluent.

In some embodiments, the present invention provides a method of treating a CTPS1-mediated disease, disorder, or condition comprising administering to a patient in need thereof, a a compound of formula I or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

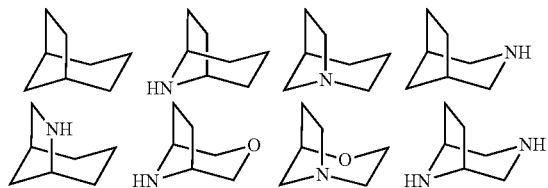
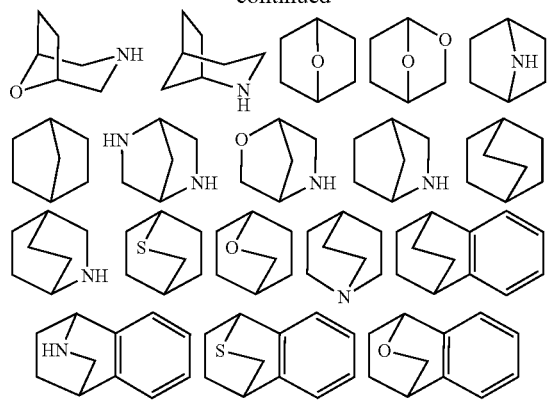

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 n electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, AH quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H pyrrolyl), NH (as in pyrrolidinyl), or $^+$NR (as in N substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$N(R^\circ)C(NR^\circ)N(R^\circ)_2$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$; —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; —$SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —(CH$_2$)$_{0-2}$R$^\bullet$,-(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR', —(CH$_2$)$_{0-2}$NR$^\bullet$$_2$, —NO$_2$, —SiR$^\bullet$$_3$, —OSiR$^\bullet$$_3$, —C(O)SR$^\bullet$—(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR %, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S— wherein each independent occurrence of R*, is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$,-(haloR$^\bullet$), —OH, —OR$^\bullet$, —O(haloR$^\bullet$), —CN, —C(O)OH, —C(O)OR$^\bullet$, —NH$_2$, NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$,-(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphor sulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Unless otherwise indicated, divalent structures or functional groups depicted herein are meant to include either direction at the points of attachment (e.g., the group

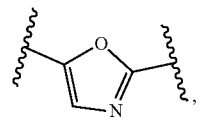 [SMILES: *c1cnc(*)o1]

when part of a Markush group attached to groups "N" and "B", includes both

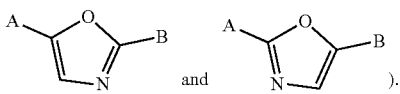

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

As used herein, a "CTPS1 antagonist" or a "CTPS1 inhibitor" is a molecule that reduces, inhibits, or otherwise diminishes one or more of the biological activities of CTPS1. Antagonism using the CTPS1 antagonist does not necessarily indicate a total elimination of the CTPS1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of CTPS1 compared to an appropriate control. The presently disclosed compounds bind directly to CTPS1 and inhibit its activity.

By "specific antagonist" is intended an agent that reduces, inhibits, or otherwise diminishes the activity of a defined target greater than that of an unrelated target. For example, a CTPS1 specific antagonist reduces at least one biological activity of CTPS1 by an amount that is statistically greater than the inhibitory effect of the antagonist on any other protein. In some embodiments, the IC$_{50}$ of the antagonist for the target is about 90%, 80%, 70%, 60%, 50%, 40%, 30%, 20%, 10%, 5%, 1%, 0.1%, 0.01%, 0.001% or less of the IC$_{50}$ of the antagonist for a non-target.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescence resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a CTPS1 activity between a sample comprising a compound of the present invention, or composition thereof, and CTPS1, and an equivalent sample comprising CTPS1, in the absence of said compound, or composition thereof.

3. Description of Exemplary Embodiments

As described above, in certain embodiments, the present invention provides a compound of formula I:

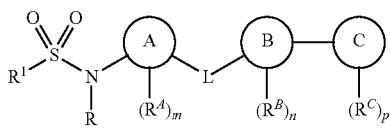

or a pharmaceutically acceptable salt thereof, wherein:

$R^1$ is selected from $C_{1-6}$ aliphatic; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; each of which is substituted with q instances of $R^A$;

Ring A is selected from phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and a 7-11 membered fused bicyclic heteroaryl ring having 1-4 heteroatoms independently selected from nitrogen, oxygen, and sulfur;

L is

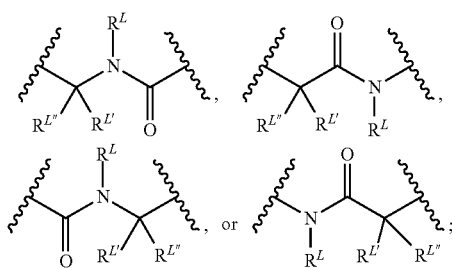

wherein each of $R^L$, $R^{L'}$, and $R^{L''}$ is independently hydrogen, —CN, halogen, or an optionally substituted group selected from $C_{1-6}$ aliphatic; phenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; or two of $R^L$, $R^{L'}$, and $R^{L''}$ groups are taken together with the atoms to which each is attached, to form an optionally substituted 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; or any one of $R^L$, $R^{L'}$, and $R^{L''}$, together with $R^B$ forms a 7-10 membered saturated or partially unsaturated fused bicyclic ring;

Ring B is selected from phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-3 heteroatoms independently selected from nitrogen, oxygen, and sulfur; a 5-11 membered saturated or partially unsaturated fused, bridged, or spiro, bicyclic carbocyclic ring; a 7-11 membered fused bicyclic aryl ring; a 7-11 membered saturated or partially unsaturated fused, bridged, or spiro, bicyclic heterocyclic ring having 1-4 heteroatoms independently selected from nitrogen, oxygen, and sulfur; and a 7-11 membered fused bicyclic heteroaryl ring having 1-4 heteroatoms independently selected from nitrogen, oxygen, and sulfur;

Ring C is selected from a phenyl, 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and a 7-11 membered fused bicyclic heteroaryl ring having 1-4 heteroatoms independently selected from nitrogen, oxygen, and sulfur; or the bond between Ring B and Ring C is absent, and Ring B and Ring C together form a 7-11 membered saturated or partially unsaturated fused, bridged, or spiro, bicyclic carbocyclic ring; a 7-11 membered fused bicyclic aryl ring; a 7-11 membered saturated or partially unsaturated fused, bridged, or spiro, bicyclic heterocyclic ring having 1-4 heteroatoms independently selected from nitrogen, oxygen, and sulfur; or a 7-11 membered fused bicyclic heteroaryl ring having 1-4 heteroatoms independently selected from nitrogen, oxygen, and sulfur;

each instance of $R^A$, $R^B$, and $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^C$ is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of $R^D$;

each instance of $R°$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$;

each R is independently hydrogen, —CN, halogen, or an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or:

two R groups are taken together with the atoms to which each R is attached, to form an optionally substituted 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or m is 0, 1, or 2;

n is 0, 1, or 2;
p is 0, 1, or 2;
each q is independently 0, 1, 2, 3, or 4;
each r is independently 0, 1, 2, 3, or 4; and
each s is independently 0, 1, 2, 3, or 4;
provided that when:
R$^1$ is C$_{1-6}$ aliphatic or a 3-7 membered saturated or partially unsaturated monocyclic carbocyclic ring;
the R group of the sulfonamide moiety

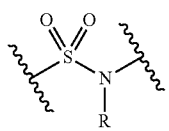

R is hydrogen or para-methoxybenzyl;
L is

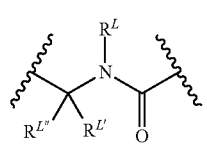

and the R$^L$ and R$^{L'}$ or R$^L$ and R$^{L''}$ groups are not taken together with the atoms to which each is attached to form an optionally substituted 3-7 membered saturated or partially unsaturated monocyclic heterocyclic ring having 1-2 heteroatoms independently selected from nitrogen, oxygen, and sulfur, or L is

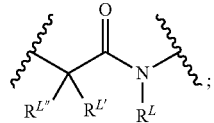

Ring B is phenyl or a 6-membered monocyclic heteroaryl ring having 1-4 heteroatoms independently selected from nitrogen, oxygen, and sulfur; and Ring C is phenyl or a 6-membered monocyclic heteroaryl ring having 1-4 heteroatoms independently selected from nitrogen, oxygen, and sulfur and is attached to Ring B in the para position relative to the L group;

then Ring A and its R$^A$ substituents are other than

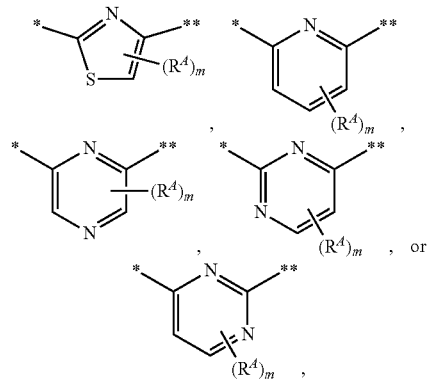

where * denotes attachment to the

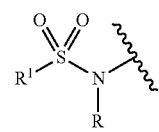

moiety and ** denotes attachment to the

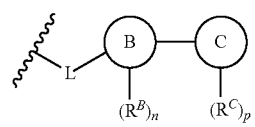

moiety.

In some embodiments, the present invention provides a compound of formula I':

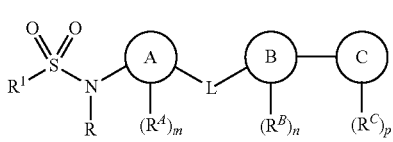

I' or a pharmaceutically acceptable salt thereof, wherein:
$R^1$ is selected from $C_{1-6}$ aliphatic; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; each of which is substituted with q instances of $R^A$;

Ring A is selected from phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and a 7-11 membered fused bicyclic heteroaryl ring having 1-4 heteroatoms independently selected from nitrogen, oxygen, and sulfur;

L is

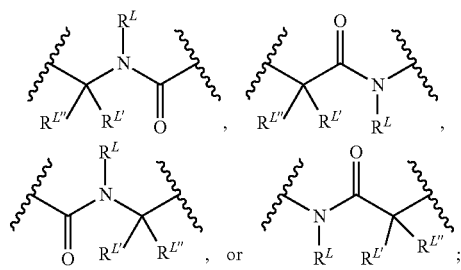

wherein each of $R^L$, $R^{L'}$, and $R^{L''}$ is independently hydrogen, —CN, halogen, or an optionally substituted group selected from $C_{1-6}$ aliphatic; phenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; or two of $R^L$, $R^{L'}$, and $R^{L''}$ groups are taken together with the atoms to which each is attached, to form an optionally substituted 3-7 membered saturated or partially unsaturated monocyclic carbocyclic ring; or a 3-7 membered saturated or partially unsaturated monocyclic heterocyclic ring having 1-2 heteroatoms independently selected from nitrogen, oxygen, and sulfur; or any one of $R^L$, $R^{L'}$, and $R^{L''}$, together with $R^B$ forms a 7-10 membered saturated or partially unsaturated fused bicyclic ring;

Ring B is selected from phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-3 heteroatoms independently selected from nitrogen, oxygen, and sulfur; a 5-11 membered saturated or partially unsaturated fused, bridged, or spiro, bicyclic carbocyclic ring; a 7-11 membered fused bicyclic aryl ring; a 7-11 membered saturated or partially unsaturated fused, bridged, or spiro, bicyclic heterocyclic ring having 1-4 heteroatoms independently selected from nitrogen, oxygen, and sulfur; and a 7-11 membered fused bicyclic heteroaryl ring having 1-4 heteroatoms independently selected from nitrogen, oxygen, and sulfur, Ring C is selected from a phenyl, 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and a 7-11 membered fused bicyclic heteroaryl ring having 1-4 heteroatoms independently selected from nitrogen, oxygen, and sulfur; or the bond between Ring B and Ring C is absent, and Ring B and Ring C together form a 7-11 membered saturated or partially unsaturated fused, bridged, or spiro, bicyclic carbocyclic ring; a 7-11 membered fused bicyclic aryl ring; a 7-11 membered saturated or partially unsaturated fused, bridged, or spiro, bicyclic heterocyclic ring having 1-4 heteroatoms independently selected from nitrogen, oxygen, and sulfur; or a 7-11 membered fused bicyclic heteroaryl ring having 1-4 heteroatoms independently selected from nitrogen, oxygen, and sulfur; each instance of $R^A$, $R^B$, and $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^C$ is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of $R^D$; or two $R^C$ groups are optionally taken together with the atoms to which each $R^C$ is attached, to form an optionally substituted 3-7 membered saturated or partially unsaturated monocyclic carbocyclic ring; a 5-7 membered heteroaryl ring having 1-2 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur; each instance of R° is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR₂, —N(R)C(O)OR, —N(R)C(O)R, —N(R)C(O)NR₂, —N(R)C(NR)NR₂, —N(R)NR₂, —N(R)S(O)₂NR₂, —N(R)S(O)₂R, —N=S(O)R₂, —S(NR)(O)R, —N(R)S(O)R, —N(R)CN, —P(O)(R)NR₂, —P(O)(R)OR or —P(O)R₂;

each R is independently hydrogen, —CN, halogen, or an optionally substituted group selected from C₁₋₆ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or:

two R groups are taken together with the atoms to which each R is attached, to form an optionally substituted 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; or m is 0, 1, or 2;
n is 0, 1, or 2;
p is 0, 1, or 2;
each q is independently 0, 1, 2, 3, or 4;
each r is independently 0, 1, 2, 3, or 4; and
each s is independently 0, 1, 2, 3, or 4;
provided that when:
$R^1$ is C₁₋₆ aliphatic or a 3-7 membered saturated or partially unsaturated monocyclic carbocyclic ring;
the R group of the sulfonamide moiety

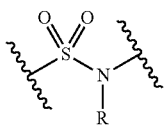

is hydrogen or para-methoxybenzyl;
L is

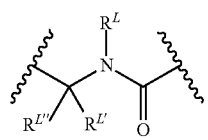

and the $R^L$ and $R^{L'}$ or $R^L$ and $R^{L''}$ groups are not taken together with the atoms to which each is attached to form an optionally substituted 3-7 membered saturated or partially unsaturated monocyclic heterocyclic ring having 1-2 heteroatoms independently selected from nitrogen, oxygen, and sulfur, or L is

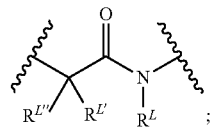

Ring B is phenyl or a 6-membered monocyclic heteroaryl ring having 1-4 heteroatoms independently selected from nitrogen, oxygen, and sulfur; and
Ring C is phenyl or a 6-membered monocyclic heteroaryl ring having 1-4 heteroatoms independently selected from nitrogen, oxygen, and sulfur and is attached to Ring B in the para position relative to the L group;

then Ring A and its $R^A$ substituents are other than

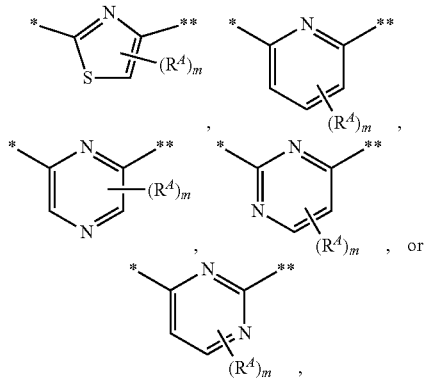

where * denotes attachment to the

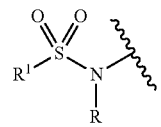

moiety and ** denotes attachment to the

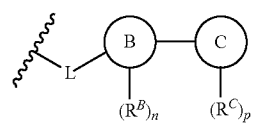

moiety.

In certain embodiments, $R^1$ is selected from C₁₋₆ aliphatic; a 3-7 membered saturated or partially unsaturated monocyclic carbocyclic ring; and a 3-7 membered saturated or partially unsaturated monocyclic heterocyclic ring having 1-2 heteroatoms independently selected from nitrogen, oxygen, and sulfur; each of which is substituted with q instances of $R^A$.

In certain embodiments, $R^1$ is selected from C₁₋₆ haloalkyl, cyclopropyl, cyclobutyl, cyclopentyl, cyclohexyl, cycloheptyl, aziridinyl, azetidinyl, pyrrolidinyl, piperidinyl, oxiranyl, oxetanyl, tetrahydrofuranyl, and tetrahydropyranyl; each of which is substituted with q instances of $R^A$.

In certain embodiments, $R^1$ is selected from $C_{1-6}$ haloalkyl, cyclopropyl, cyclobutyl, aziridinyl, azetidinyl, oxiranyl, and oxetanyl; each of which is substituted with q instances of $R^A$.

In certain embodiments, $R^1$ is —$CF_3$, —$CHF_2$,

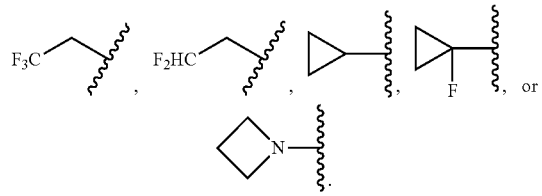

, or

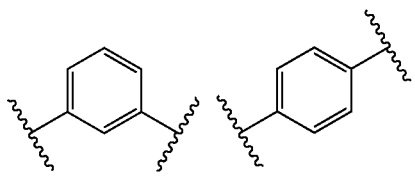

In some embodiments, $R^1$ is selected from those depicted in Table 1, below.

In certain embodiments, Ring A is selected from phenyl; a 5-6 membered monocyclic heteroaryl ring having 1-4 heteroatoms independently selected from nitrogen, oxygen, and sulfur; and a 7-11 membered fused bicyclic heteroaryl ring having 1-4 heteroatoms independently selected from nitrogen, oxygen, and sulfur.

In some embodiments, Ring A is selected from phenyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, furanyl, furazanyl, imidazolyl, 1H-indazolyl, indolenyl, indolinyl, indolizinyl, indolyl, 3H-indolyl, isoindolinyl, isoindolenyl, isobenzofuranyl, isoindazolyl, isoindolinyl, isoindolyl, isoquinolinyl, isothiazolyl, isoxazolyl, oxadiazolyl, 1,2,3-oxadiazolyl, 1,2,4-oxadiazolyl; 1,2,5oxadiazolyl, 1,3,4-oxadiazolyl, oxazolyl, pyrimidinyl, pteridinyl, purinyl, pyranyl, pyrazinyl, pyrazolidinyl, pyrazolinyl, pyrazolyl, pyridazinyl, pyridinyl, pyrimidinyl, pyrrolinyl, 2H-pyrrolyl, pyrrolyl, quinazolinyl, quinolinyl, quinoxalinyl, thiadiazolyl, 1,2,3-thiadiazolyl, 1,2,4-thiadiazolyl, 1,2,5-thiadiazolyl, 1,3,4-thiadiazolyl, thiazolyl, thienyl, thiophenyl, triazinyl, 1,2,3-triazolyl, 1,2,4-triazolyl, 1,2,5-triazolyl, and 1,3,4-triazolyl.

In some embodiments, Ring A is selected from phenyl, benzimidazolyl, imidazolyl, 1H-indazolyl, indolenyl, indolinyl, indolizinyl, indolyl, 3H-indolyl, isoindolinyl, isoindolenyl, isoindazolyl, isoindolinyl, isoindolyl, isoquinolinyl, isothiazolyl, isoxazolyl, oxadiazolyl, 1,2,3-oxadiazolyl, 1,2,4-oxadiazolyl; 1,2,5oxadiazolyl, 1,3,4-oxadiazolyl, oxazolyl, pyrimidinyl, pyranyl, pyrazinyl, pyrazolidinyl, pyrazolinyl, pyrazolyl, pyridazinyl, pyridinyl, pyrimidinyl, pyrrolinyl, 2H-pyrrolyl, pyrrolyl, thiadiazolyl, 1,2,3-thiadiazolyl, 1,2,4-thiadiazolyl, 1,2,5-thiadiazolyl, 1,3,4-thiadiazolyl, and thiazolyl.

In some embodiments, Ring A is selected from phenyl, pyrazolyl, thiazolyl, thiadiazolyl, pyridinyl, pyridazinyl, pyrimidinyl, and indolyl.

In certain embodiments, Ring A is

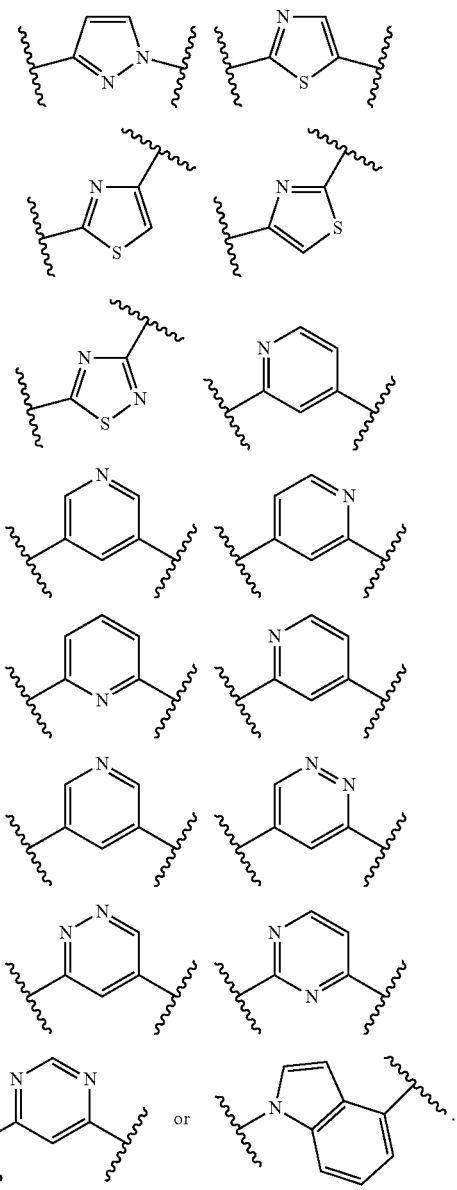

In certain embodiments, Ring A is

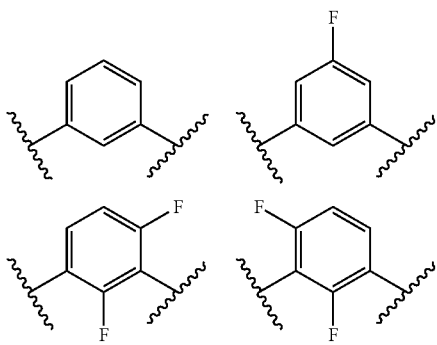

-continued
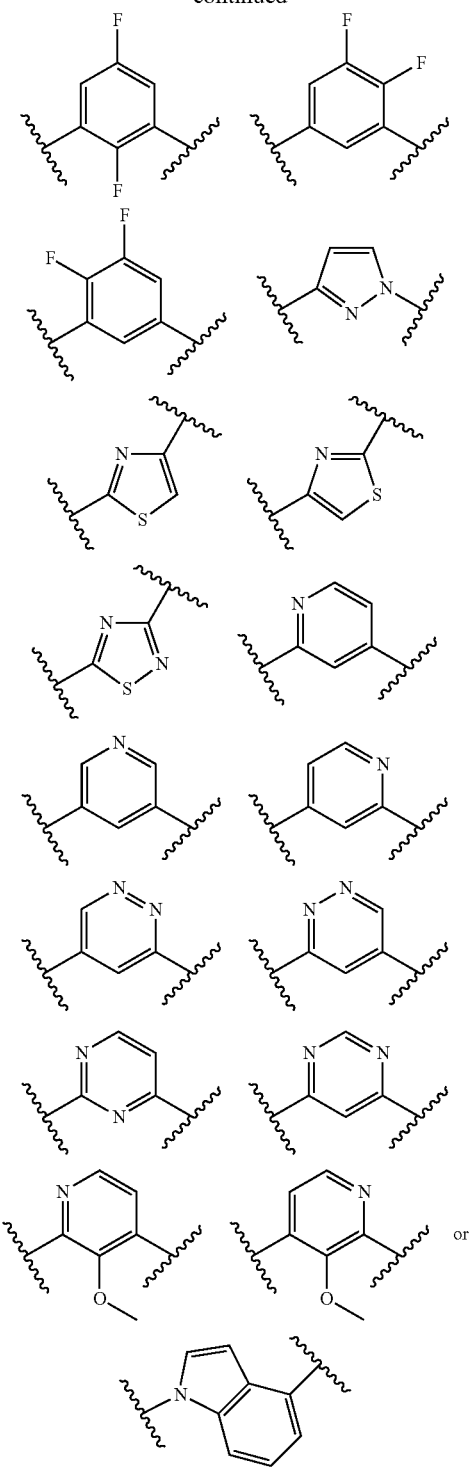
In certain embodiments, Ring A is
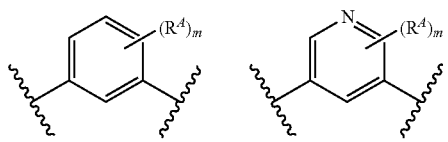
-continued
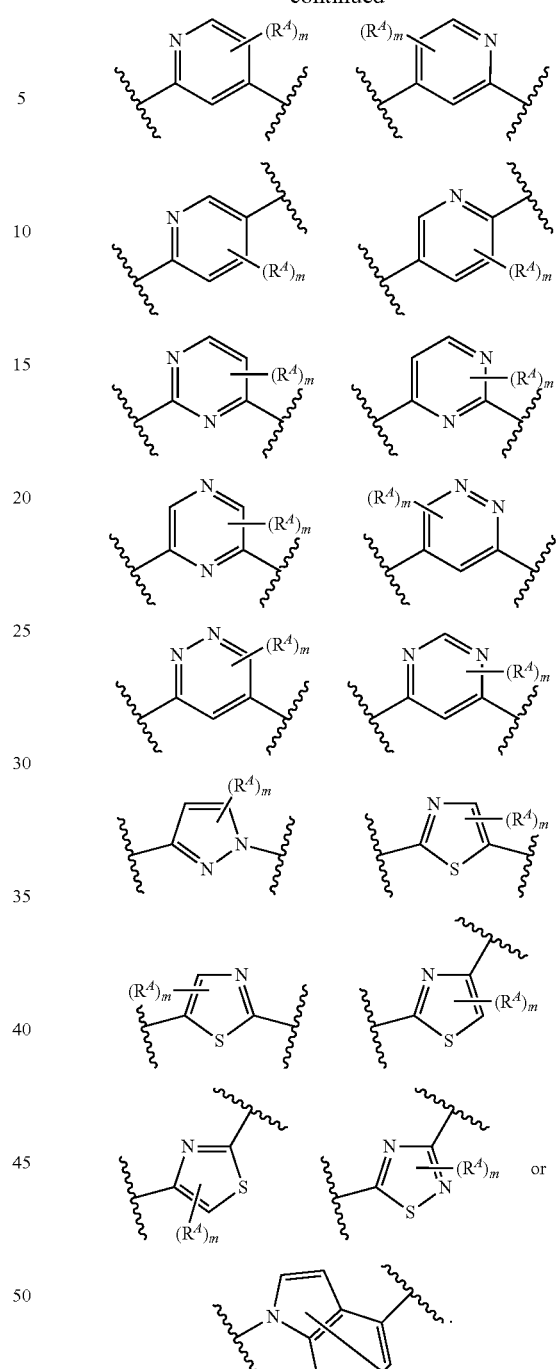
In certain embodiments, Ring A is
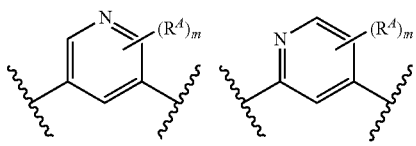

-continued
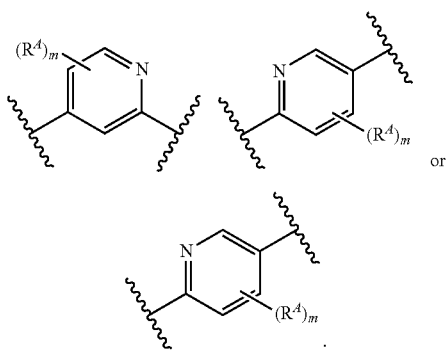
In certain embodiments, Ring A is
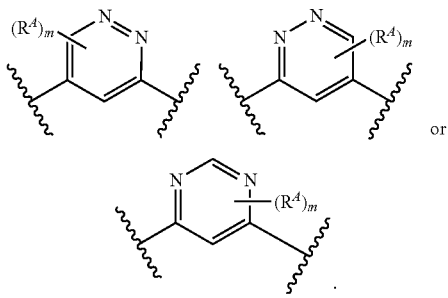
In some embodiments, Ring A is selected from those depicted in Table 1, below.
In some embodiments, L is
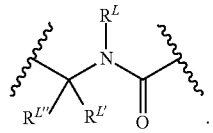
In some embodiments, L is
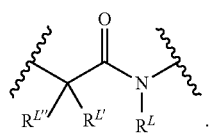
In some embodiments, L is
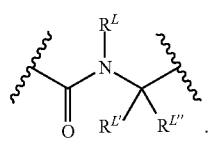
In some embodiments, L is
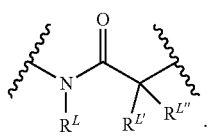
In certain embodiments, L is
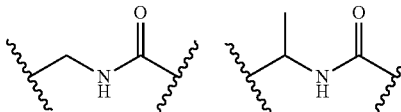
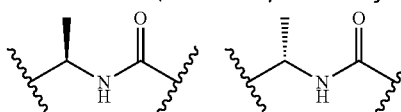
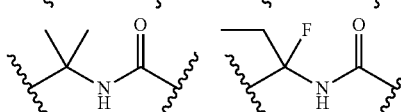
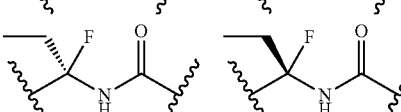
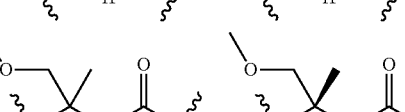
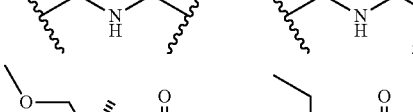
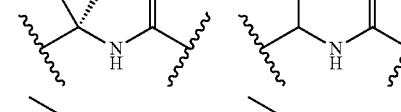
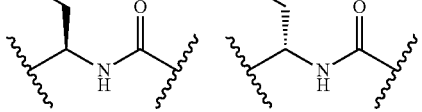
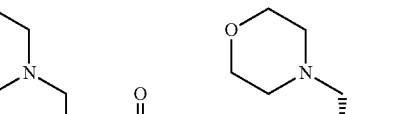
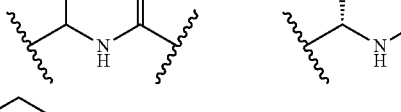
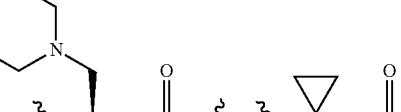
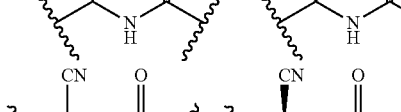

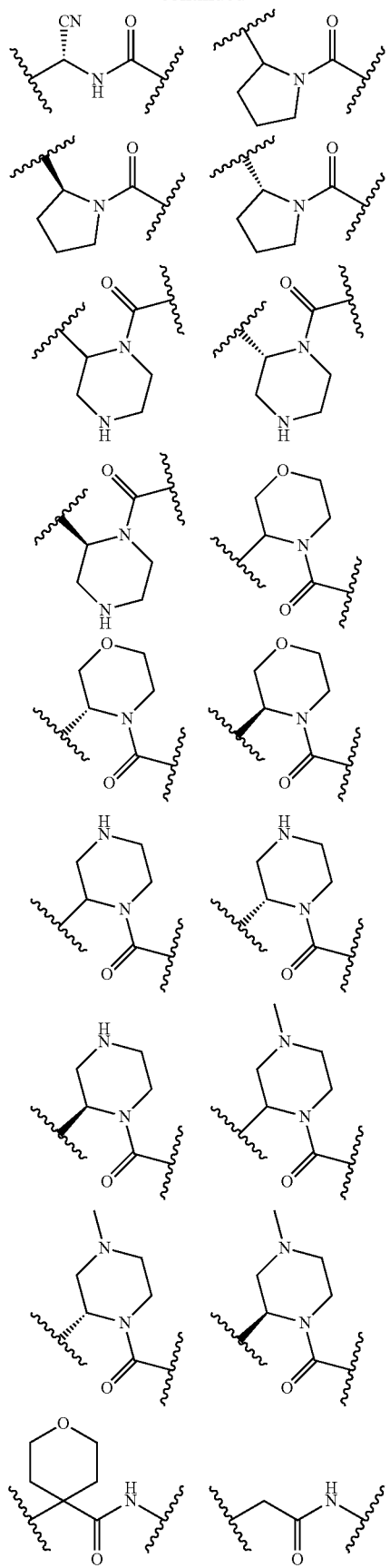
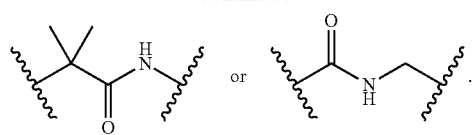
In certain embodiments, L is
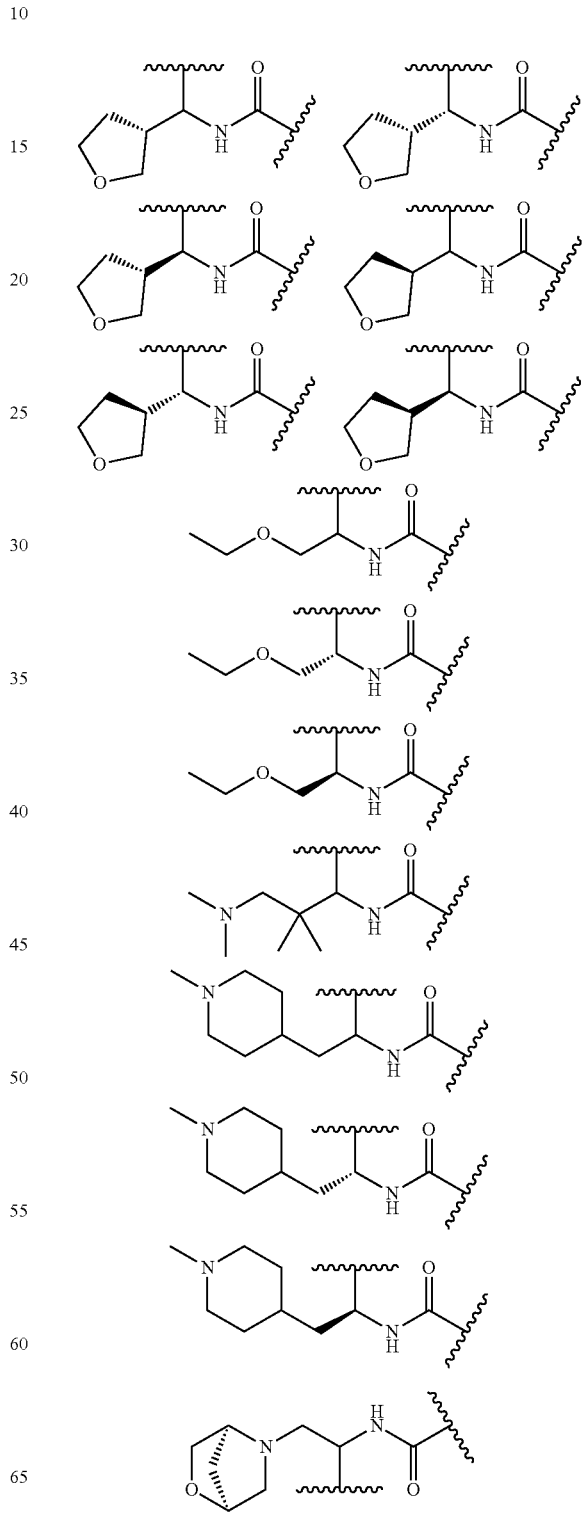

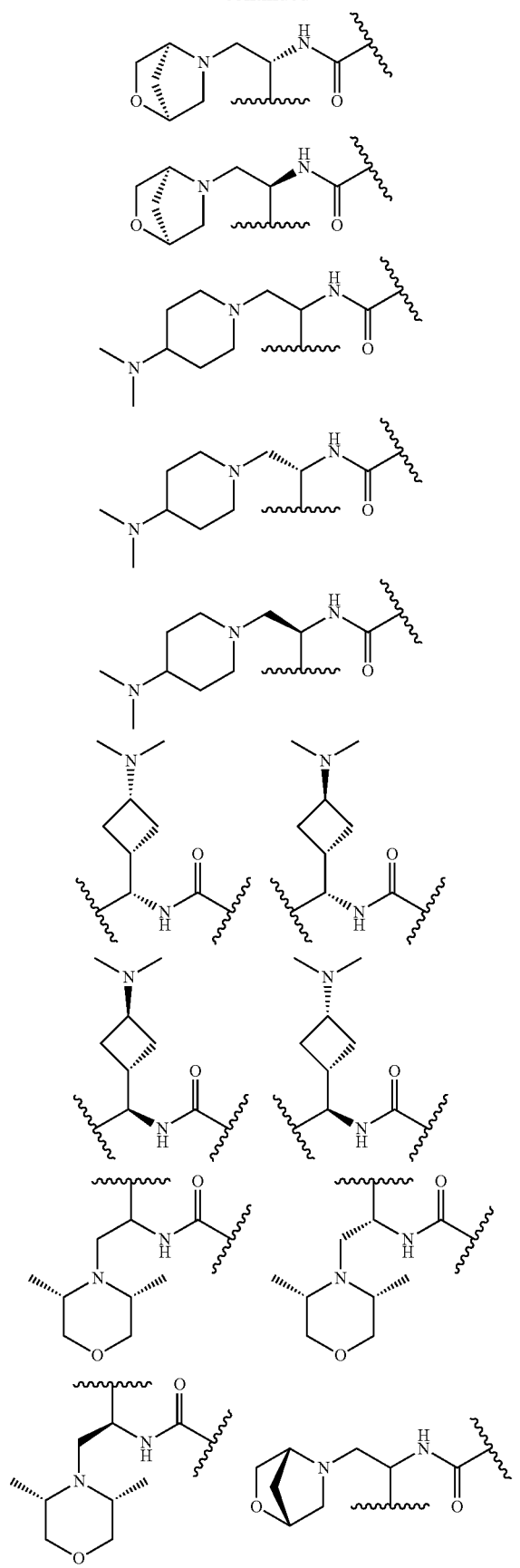
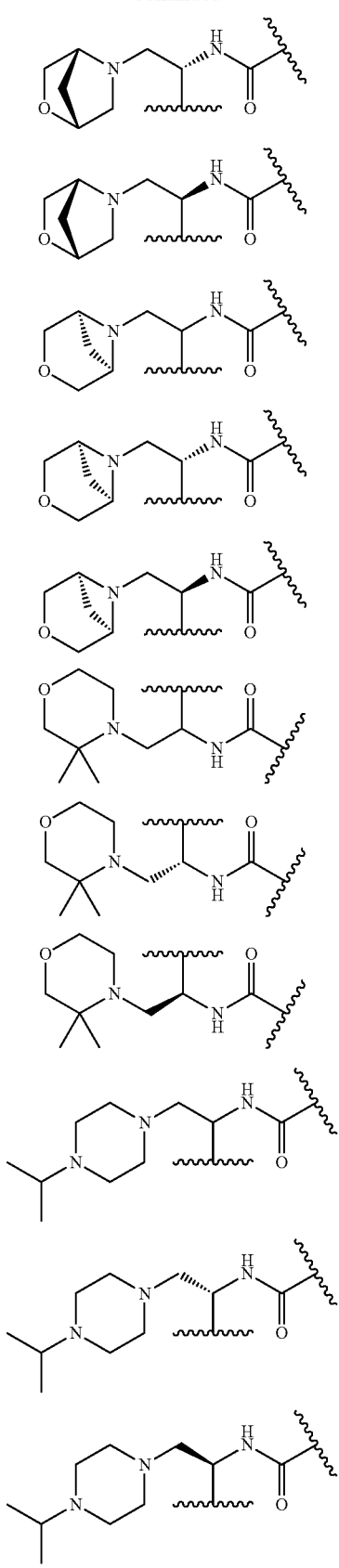

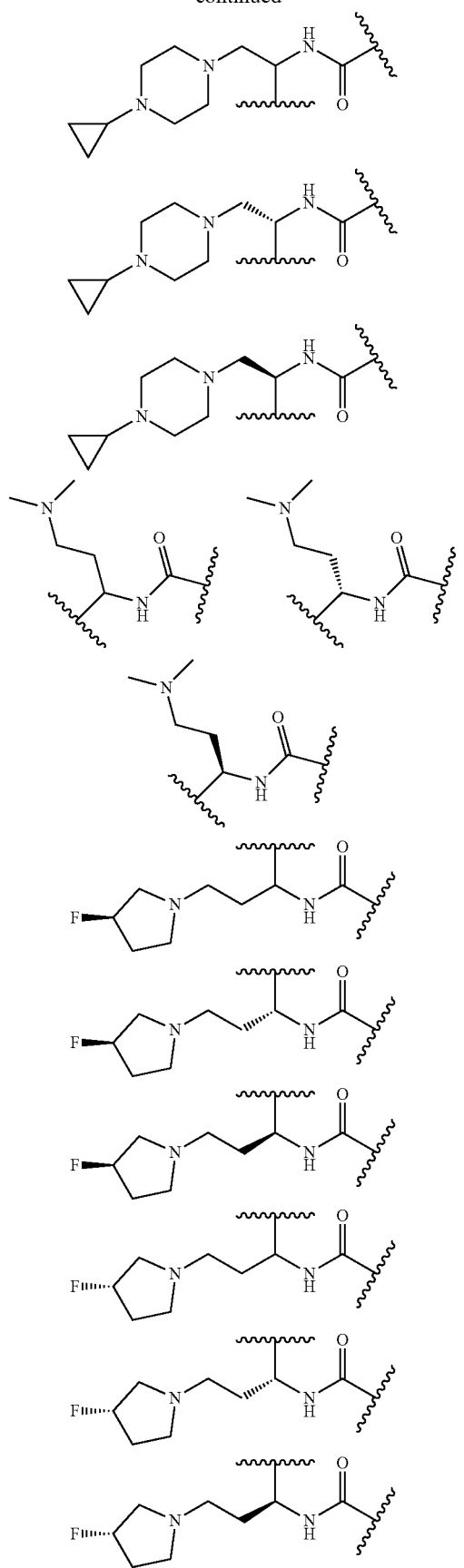
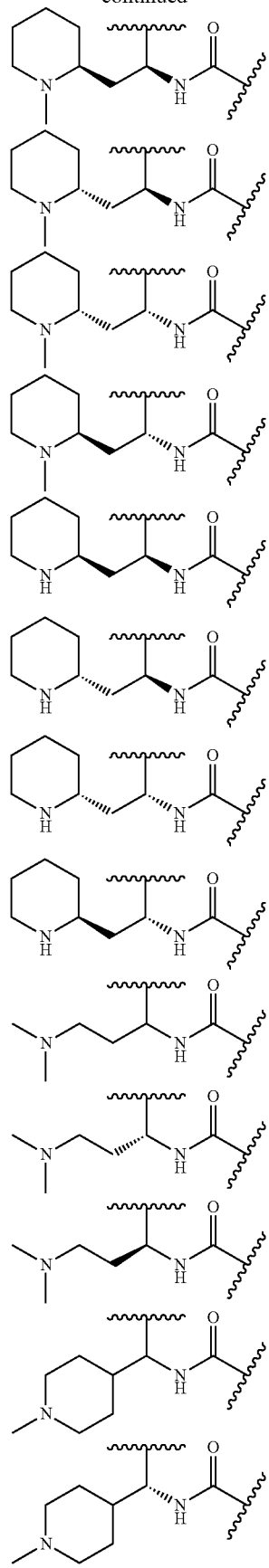

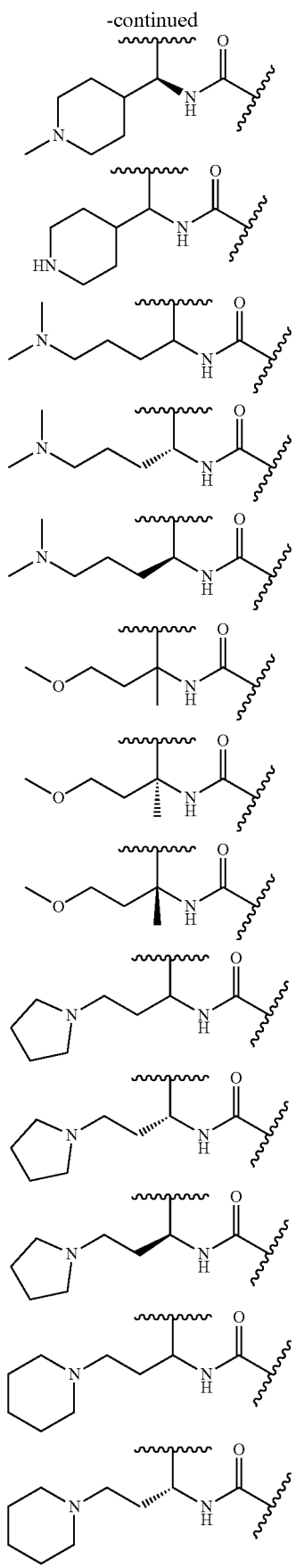
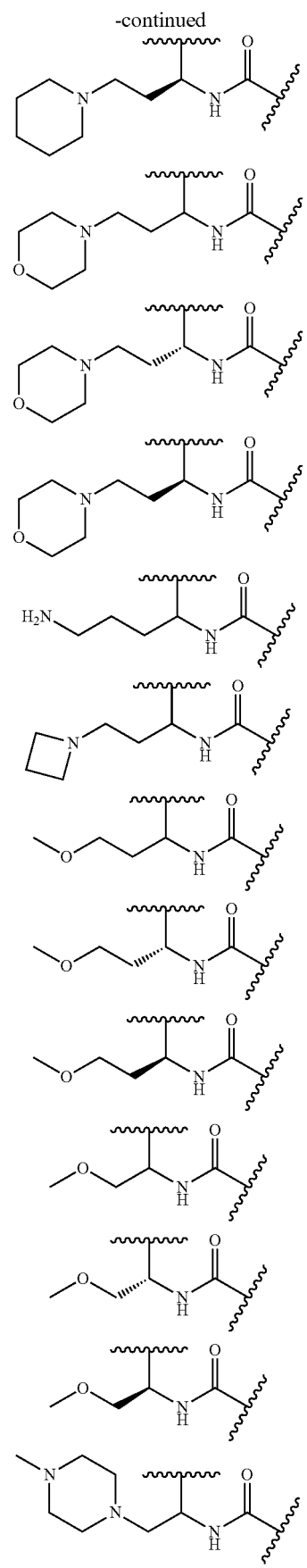

-continued
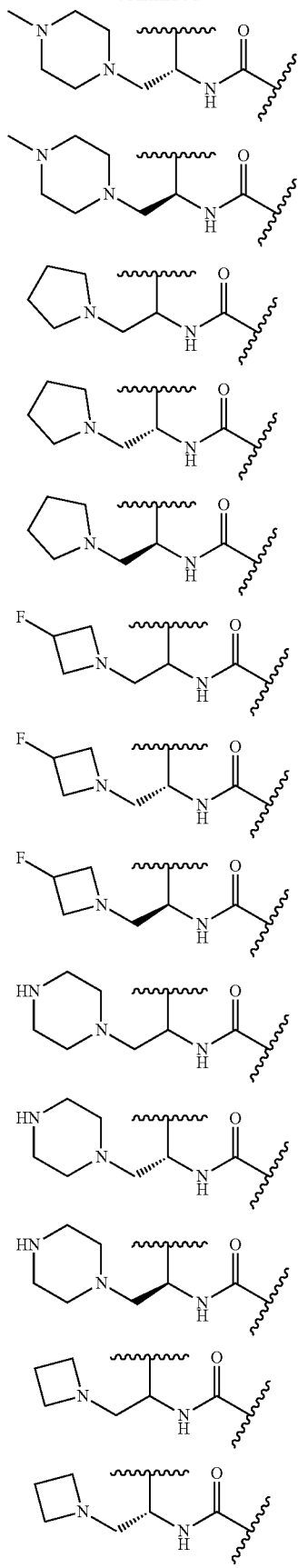
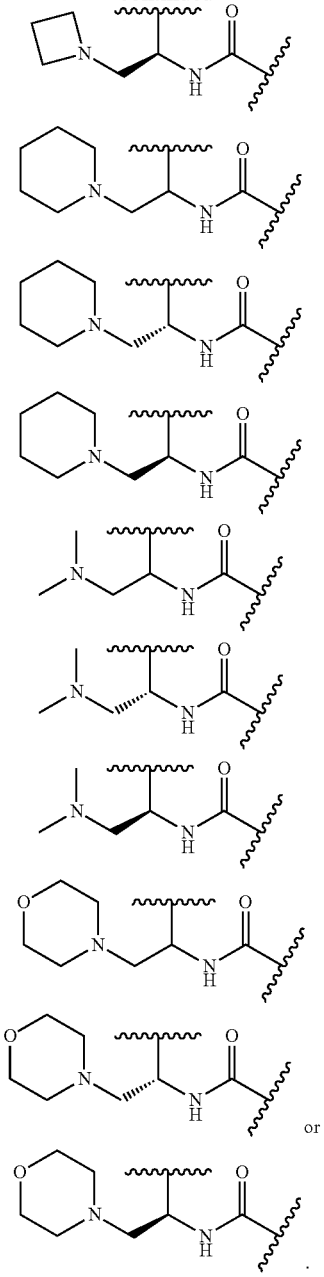
or
In certain embodiments, L is
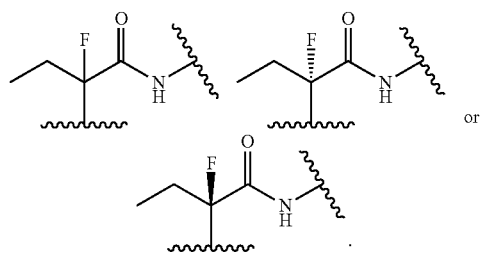
or
.
In some embodiments, each of $R^{L'}$, and $R^{L''}$ is independently

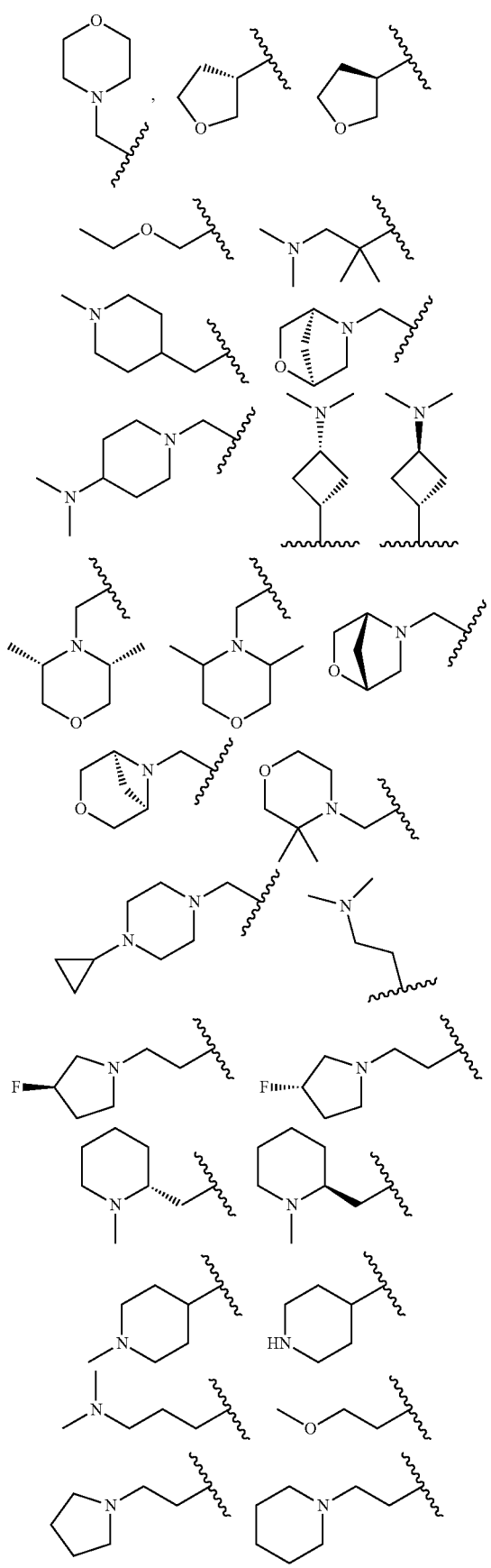

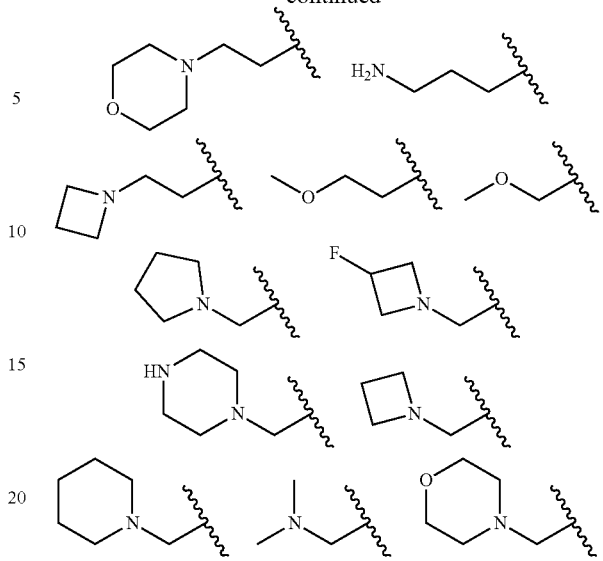

halogen, or an optionally substituted $C_{1-6}$ aliphatic.

In some embodiments, each of $R^{L'}$, and $R^{L''}$ is independently hydrogen, F, —CN, -Me or -Et.

In some embodiments, any one of $R^L$, $R^{L'}$, and $R^{L''}$ together with $R^B$, is

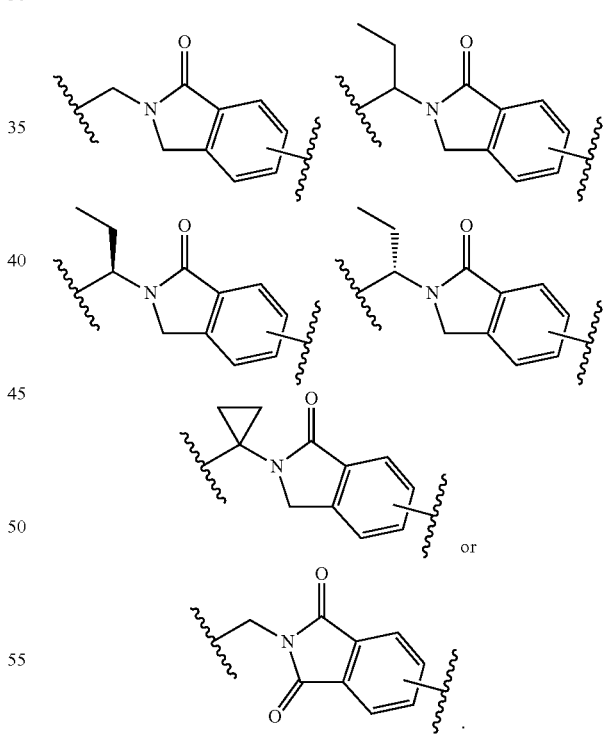

In some embodiments, L is selected from those depicted in Table 1, below.

In some embodiments, Ring B is selected from phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-3 heteroatoms independently selected from nitrogen, oxygen, and sulfur; a 5-11 membered saturated or partially unsaturated fused, bridged, or spiro, bicyclic carbocyclic ring; a 7-11 membered fused bicyclic aryl ring; a 7-11 membered saturated or partially unsaturated fused, bridged, or spiro, bicyclic heterocyclic ring having 1-4 heteroatoms independently selected from nitrogen, oxygen, and sulfur; and a 7-11 membered fused bicyclic heteroaryl ring having 1-4 heteroatoms independently selected from nitrogen, oxygen, and sulfur.

In some embodiments, Ring B is selected from phenyl; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-3 heteroatoms independently selected from nitrogen, oxygen, and sulfur; a 5-11 membered saturated or partially unsaturated fused, bridged, or spiro, bicyclic carbocyclic ring; a 7-11 membered saturated or partially unsaturated fused, bridged, or spiro, bicyclic heterocyclic ring having 1-4 heteroatoms independently selected from nitrogen, oxygen, and sulfur; and a 7-11 membered fused bicyclic heteroaryl ring having 1-4 heteroatoms independently selected from nitrogen, oxygen, and sulfur.

In some embodiments, Ring B is selected from phenyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, decahydroquinolinyl, dihydrofuro [2,3-b] tetrahydrofuran, furanyl, furazanyl, imidazolidinyl, imidazolinyl, isoindolinyl, isoindolenyl, isobenzofuranyl, isoindolinyl, isoindolinonyl, isoquinolinyl, isothiazolyl, isoxazolyl, morpholinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, piperazinyl, piperazinonyl, piperidinyl, pyranyl, pyrazinyl, pyrazolidinyl, pyrazolinyl, pyrazolyl, pyrazolopyridinyl, pyridazinyl, pyridinyl, pyridinonyl, pyrimidinyl, pyrrolidinyl, pyrrolinyl, 2H-pyrrolyl, pyrrolyl, quinazolinyl, quinolinyl, 4H-quinolizinyl, quinoxalinyl, tetrahydrofuranyl, tetrahydropyranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, triazinyl, 1,2,3-triazolyl, 1,2,4-triazolyl, 1,2,5-triazolyl, 1,3,4-triazolyl, oxetanyl, azetidinyl, or bicyclo[1.1.1]pentanyl.

In some embodiments, Ring B is selected from phenyl, isoindolinyl, isoindolinonyl, 1,3,4-oxadiazolyl, oxazolyl, piperazinyl, piperazinonly, pyrazinyl, pyrazolyl, pyrazolopyridinyl, pyridinyl, pyridinonyl, tetrahydroisoquinolinyl, tetrahydroquinolinyl, 1,3,4-thiadiazolyl, thiazolyl, or bicyclo[1.1.1]pentanyl.

In certain embodiments, Ring B is

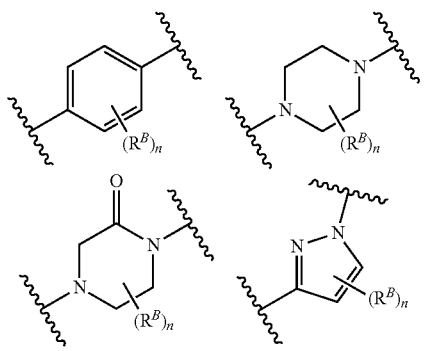

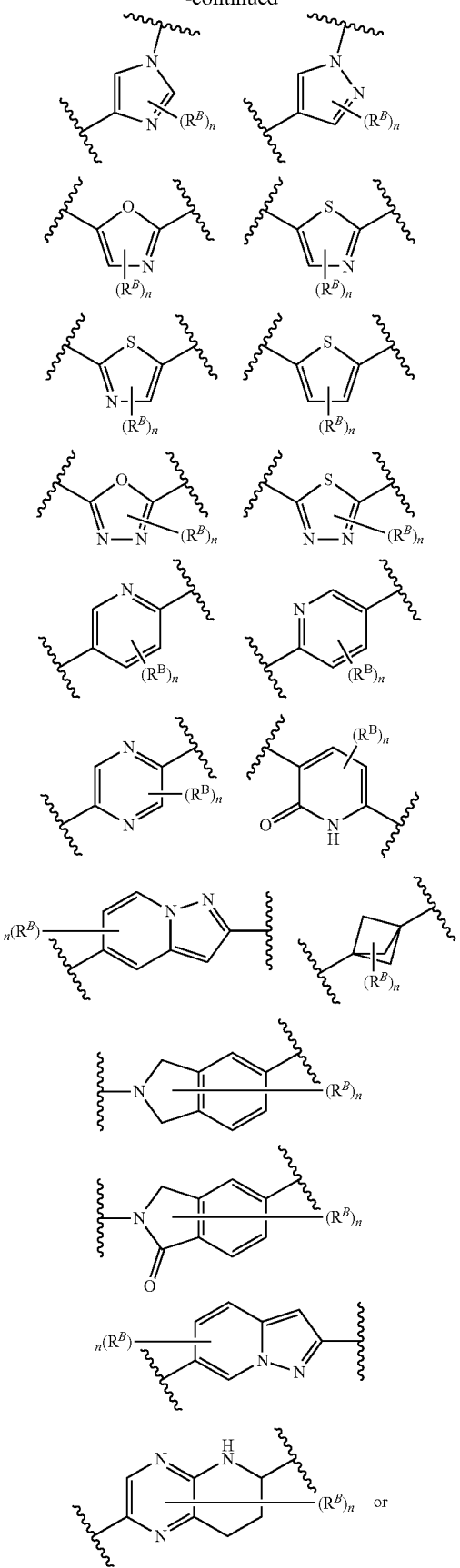

or

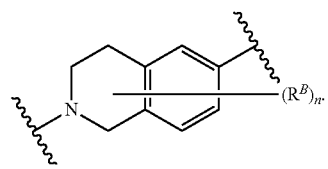

In certain embodiments, Ring B is

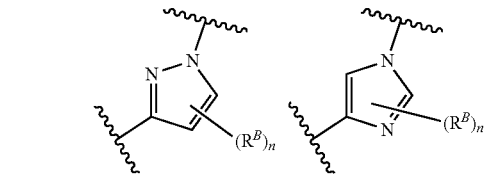

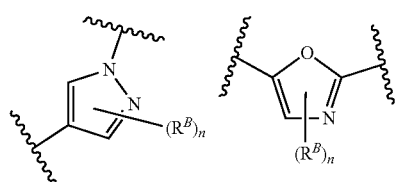

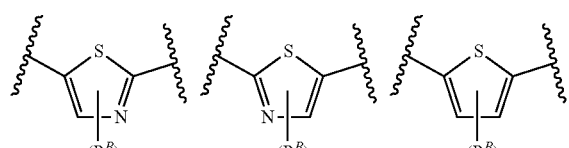

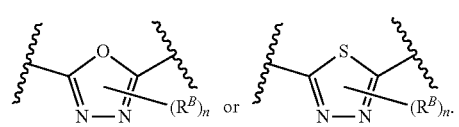

In certain embodiments, Ring B is a 5 membered saturated or partially unsaturated monocyclic carbocyclic ring; a 5 membered monocyclic heteroaryl ring having 1-3 heteroatoms independently selected from nitrogen, oxygen, and sulfur; or a 5 membered saturated or partially unsaturated monocyclic heterocyclic ring having 1-3 heteroatoms independently selected from nitrogen, oxygen, and sulfur.

In certain embodiments, Ring B is

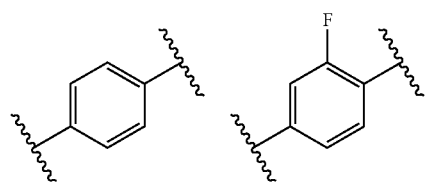

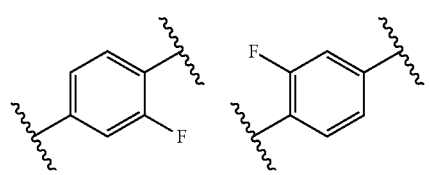

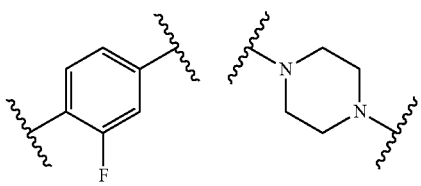

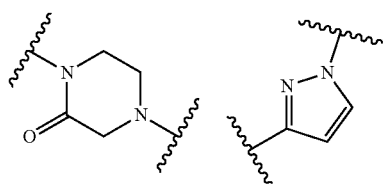

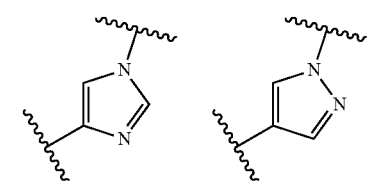

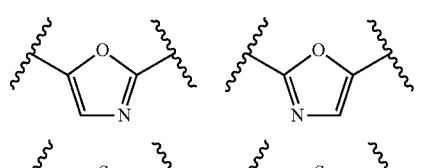

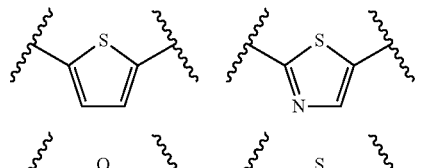

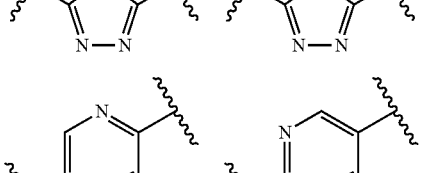

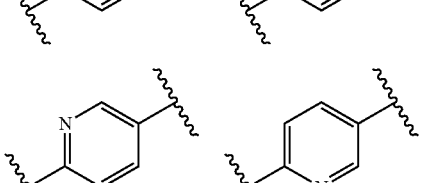

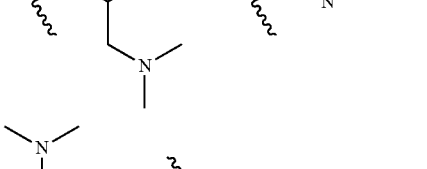

-continued

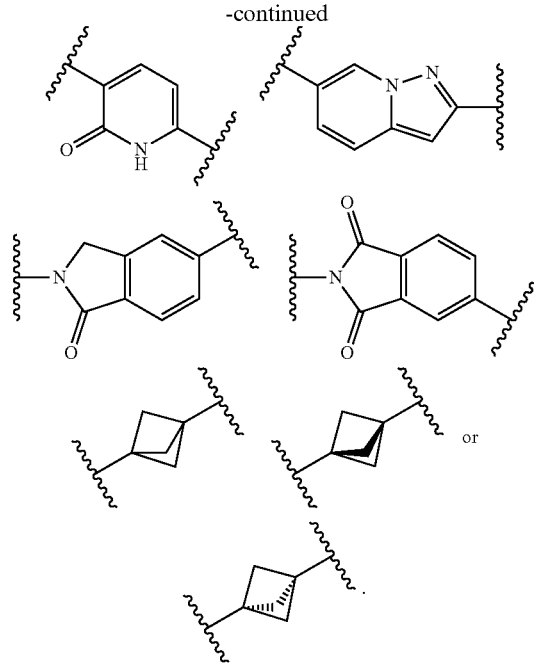

In some embodiments, Ring B is selected from those depicted in Table 1, below.

In certain embodiments, Ring C is selected from a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and a 7-11 membered fused bicyclic heteroaryl ring having 1-4 heteroatoms independently selected from nitrogen, oxygen, and sulfur.

In certain embodiments, Ring C is phenyl, cyclopropyl, cyclobutyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, furanyl, furazanyl, imidazolidinyl, imidazolinyl, imidazolyl, imidazopyrimidine, 1H-indazolyl, indolenyl, indolinyl, indolizinyl, indolyl, 3?7-indolyl, isoindolinyl, isoindolenyl, isobenzofuranyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, oxetanyl, pyrimidinyl, piperazinyl, piperidinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, pyrrolopyridine, quinazolinyl, quinolinyl, 4H-quinolizinyl, tetrahydrofuranyl, tetrahydropyranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, triazinyl, 1,2,3-triazolyl, 1,2,4-triazolyl, 1,2,5-triazolyl, 1,3,4-triazolyl, oxetanyl, or azetidinyl.

In certain embodiments, Ring C is imidazolyl, imidazopyrimidine, oxadiazolyl, 1,2,3-oxadiazolyl, 1,2,4-oxadiazolyl; 1,2,5oxadiazolyl, 1,3,4-oxadiazolyl, piperidinyl, pyrazinyl, pyrrolidinyl, pyrrolopyridine, or azetidinyl.

In certain embodiments, Ring C

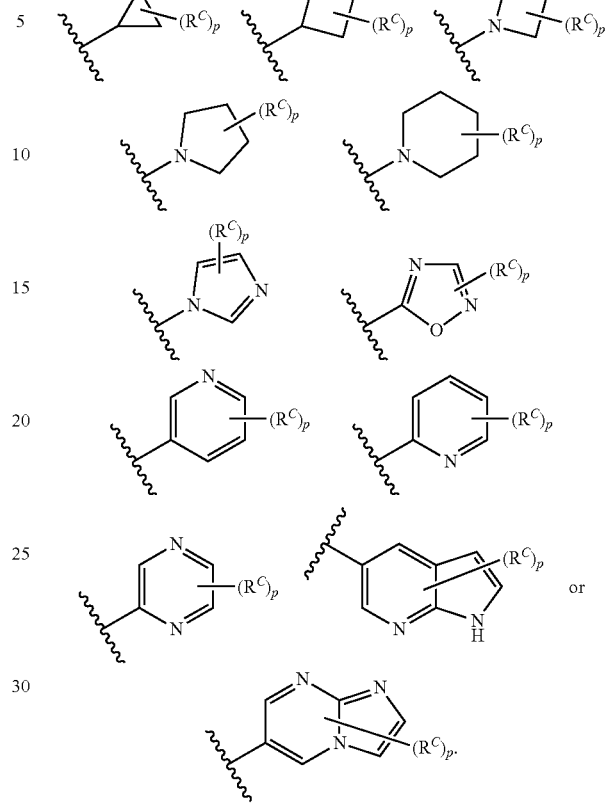

In certain embodiments, Ring C is

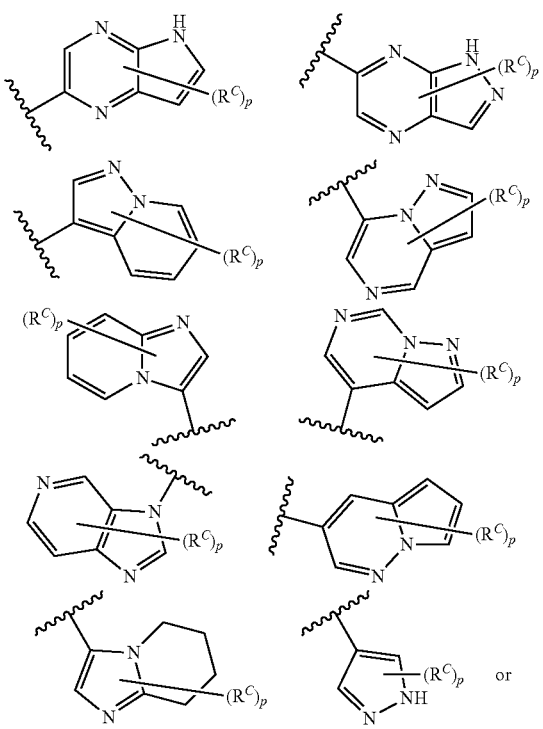

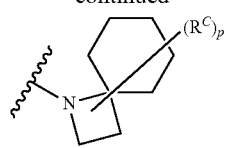
In certain embodiments, Ring C is
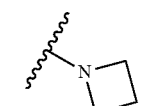 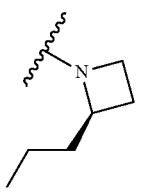 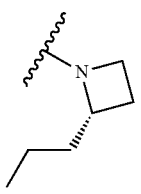
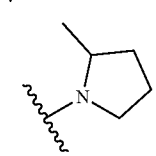 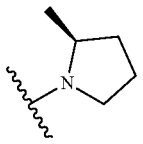 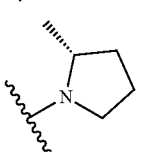
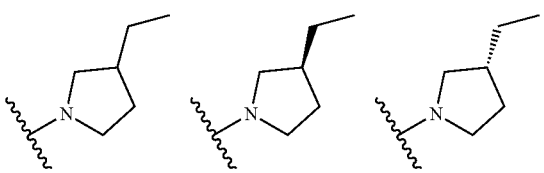
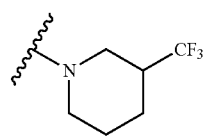 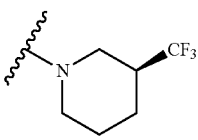
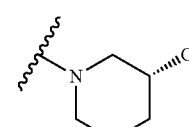 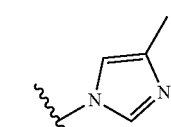
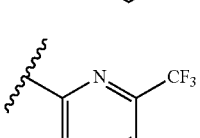 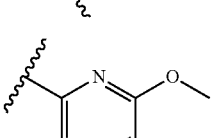
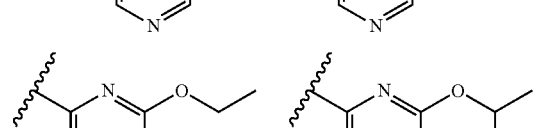
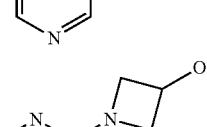 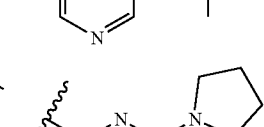
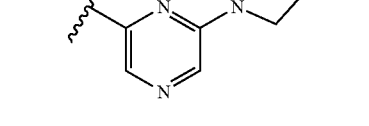
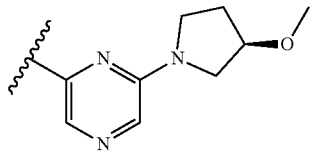
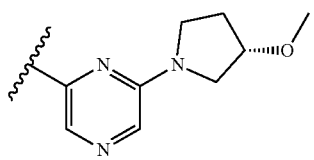
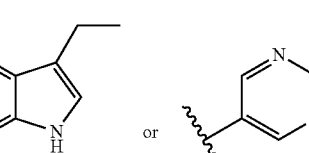 or 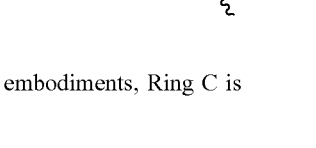.
In certain embodiments, Ring C is
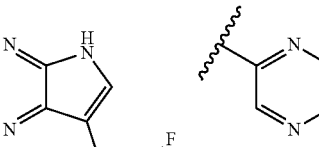
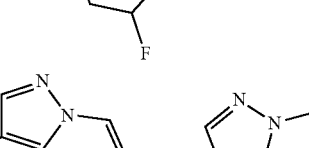
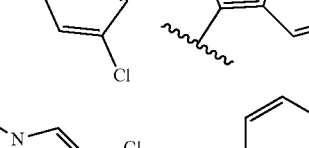
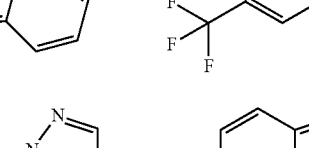
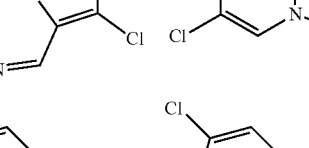
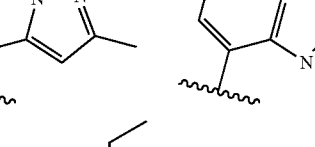
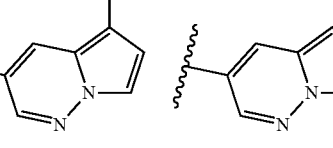

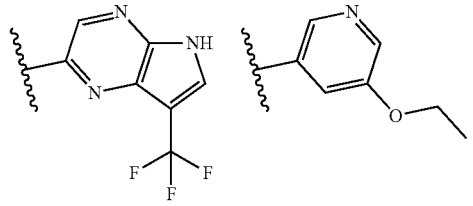

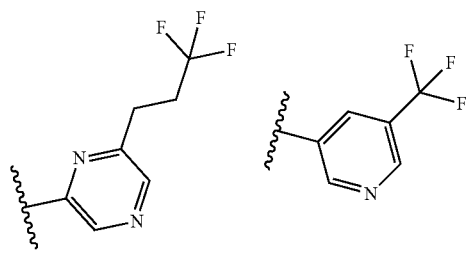

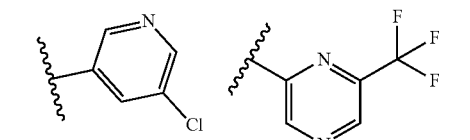

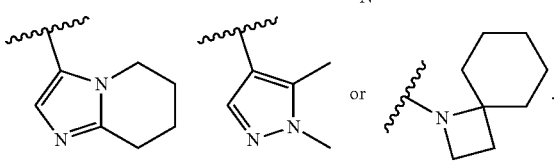

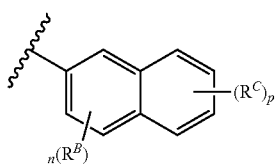

In some embodiments, Ring C is selected from those depicted in Table 1, below.

In some embodiments, the bond between Ring B and Ring C is absent, and Ring B and Ring C together form a 7-11 membered saturated or partially unsaturated fused, bridged, or spiro, bicyclic carbocyclic ring; a 7-11 membered fused bicyclic aryl ring; a 7-11 membered saturated or partially unsaturated fused, bridged, or spiro, bicyclic heterocyclic ring having 1-4 heteroatoms independently selected from nitrogen, oxygen, and sulfur; or a 7-11 membered fused bicyclic heteroaryl ring having 1-4 heteroatoms independently selected from nitrogen, oxygen, and sulfur.

In some embodiments, Ring B and Ring C together form indanyl, tetrahydronaphthyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, decahydroquinolinyl, 1H-indazolyl, indolenyl, indolinyl, indolizinyl, indolyl, 3H-indolyl, isoindolinyl, isoindolenyl, isobenzofuranyl, isoindazolyl, isoindolinyl, isoindolyl, isoquinolinyl, napthalenyl, octahydroisoquinolinyl, pteridinyl, purinyl, quinazolinyl, quinolinyl, 4H-quinolizinyl, quinoxalinyl, tetrahydroisoquinolinyl, or tetrahydroquinolinyl.

In some embodiments, the bond between Ring B and Ring C is absent, and Ring B and Ring C together form Ring B and Ring C together form isoquinolinyl, napthalenyl, or quinolinyl.

In some embodiments, the bond between Ring B and Ring C is absent, and Ring B and Ring C together form In some embodiments, the bond between Ring B and Ring C is absent, and Ring B and Ring C together form

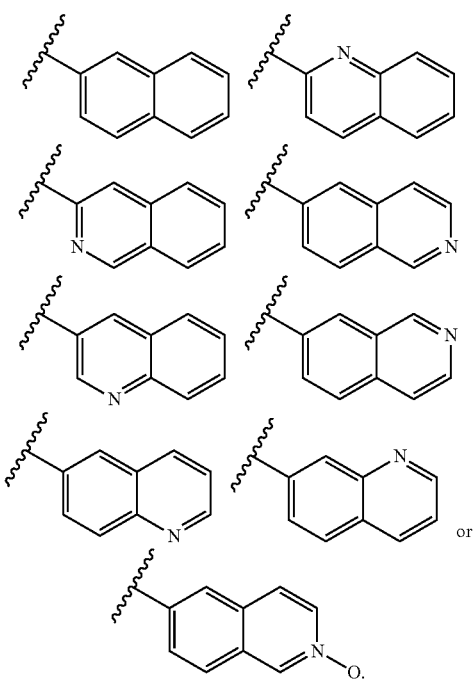

In some embodiments, the bond between Ring B and Ring C is absent, and Ring B and Ring C together form

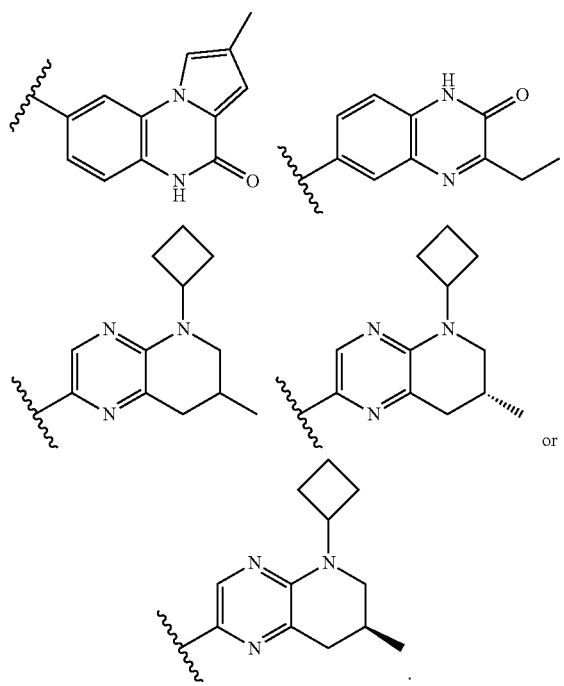

or

In some embodiments, Ring B and Ring C together is selected from those depicted in Table 1, below.

As defined generally above, each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^A$ is independently an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of $R^D$.

In some embodiments, each instance of $R^A$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^A$ is independently an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, each instance of $R^A$ is independently —F or —OCH$_3$.

In some embodiments, each instance of $R^A$ is selected from those depicted in Table 1, below.

As defined generally above, each instance of $R^B$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^B$ is independently an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of $R^D$.

In some embodiments, each instance of $R^B$ is independently oxo, halogen, —CN, —NO$_2$, —OR, —OCH$_3$, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^B$ is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, each instance of $R^B$ is halogen or $C_{1-6}$ aliphatic.

In some embodiments, each instance of $R^B$ is —F or -Me.

In some embodiments $R^B$ is —CH$_2$N(CH$_3$)$_2$.

In some embodiments, each instance of $R^B$ is selected from those depicted in Table 1, below.

As defined generally above, each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^C$ is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of $R^D$.

In some embodiments, each instance of $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^C$ is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, each instance of $R^C$ is —OR, an optionally substituted $C_{1-6}$ aliphatic, or an optionally substituted 3-7 membered saturated or partially unsaturated monocyclic heterocyclic ring having 1-2 heteroatoms independently selected from nitrogen, oxygen, phosphorous, silicon and sulfur.

In some embodiments, each instance of $R^C$ is -Me, -Et, —Pr, —CF$_3$, —OMe, —OEt, —OiPr, azetidine, or pyrrolidine.

In some embodiments, each instance of $R^C$ is —CH$_2$CHF$_2$.

In some embodiments, each instance of $R^C$ is selected from those depicted in Table 1, below.

As defined generally above, each instance of R° is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$.

In some embodiments, R° is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$.

In some embodiments, R$^D$ is selected from those depicted in Table 1, below.

As defined generally above, each R is independently hydrogen, or an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or: two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur.

In some embodiments, R is selected from those depicted in Table 1, below.

As defined generally above, each hydrogen bound to carbon can be optionally and independently replaced by deuterium.

In some embodiments, a hydrogen bound to carbon is replaced by deuterium.

As defined generally above, m is 0, 1, or 2.

In some embodiments, m is 0. In some embodiments, m is 1. In some embodiments, m is 2.

In some embodiments, m is selected from those depicted in Table 1, below.

In some embodiments, n is 0. In some embodiments, n is 1. In some embodiments, n is 2.

In some embodiments, n is selected from those depicted in Table 1, below.

In some embodiments, p is 0. In some embodiments, p is 1. In some embodiments, p is 2.

In some embodiments, p is selected from those depicted in Table 1, below.

As defined generally above, q is 0, 1, 2, 3, or 4. In some embodiments, q is 0. In some embodiments, q is 1, 2, 3, or 4. In some embodiments, q is 1. In some embodiments, q is 2. In some embodiments, q is 3. In some embodiments, q is 4.

In some embodiments, q is selected from those depicted in Table 1, below.

As defined generally above, r is 0, 1, 2, 3, or 4. In some embodiments, r is 0. In some embodiments, r is 1, 2, 3, or 4. In some embodiments, r is 1. In some embodiments, r is 2. In some embodiments, r is 3. In some embodiments, r is 4.

In some embodiments, r is selected from those depicted in Table 1, below.

As defined generally above, s is 0, 1, 2, 3, or 4. In some embodiments, s is 0. In some embodiments, s is 1, 2, 3, or 4. In some embodiments, s is 1. In some embodiments, s is 2. In some embodiments, s is 3. In some embodiments, s is 4.

In some embodiments, s is selected from those depicted in Table 1, below.

In some embodiments, the present invention provides a compound of formula II:

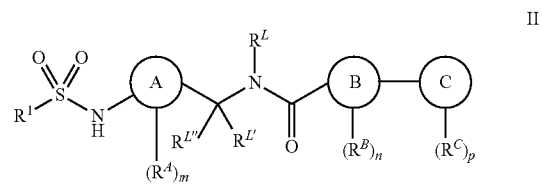

II or a pharmaceutically acceptable salt thereof, wherein each of R$^1$, Ring A, Ring B, Ring C, R$^A$, R$^B$, R$^C$, R$^L$, R$^{L'}$, R$^{L''}$, m, n, and, p, is as defined above and described in embodiments herein, both singly and in combination.

In some embodiments, the present invention provides a compound of formula III:

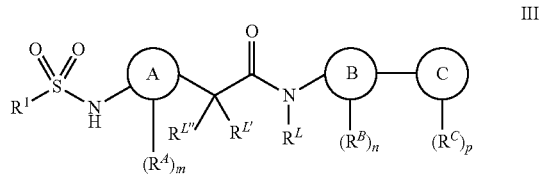

III or a pharmaceutically acceptable salt thereof, wherein each of R$^1$, Ring A, Ring B, Ring C, R$^A$, R$^B$, R$^C$, R$^L$, R$^{L'}$, R$^{L''}$, m, n, and, p, is as defined above and described in embodiments herein, both singly and in combination.

In some embodiments, the present invention provides a compound of formula IV:

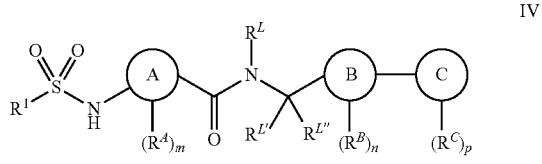

IV or a pharmaceutically acceptable salt thereof, wherein each of R$^1$, Ring A, Ring B, Ring C, R$^A$, R$^B$, R$^C$, R$^L$, R$^{L'}$, R$^{L''}$, m, n, and, p, is as defined above and described in embodiments herein, both singly and in combination.

In some embodiments, the present invention provides a compound of formula V:

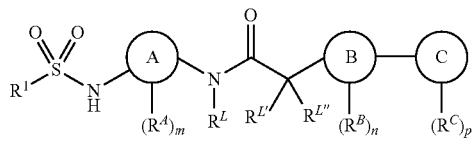

V or a pharmaceutically acceptable salt thereof, wherein each of $R^1$, Ring A, Ring B, Ring C, Ring$^A$, $R^B$, $R^C$, $R^L$, $R^{L'}$, $R^{L''}$, m, n, and, p, is as defined above and described in embodiments herein, both singly and in combination.

In some embodiments, the present invention provides a compound of formula VI:

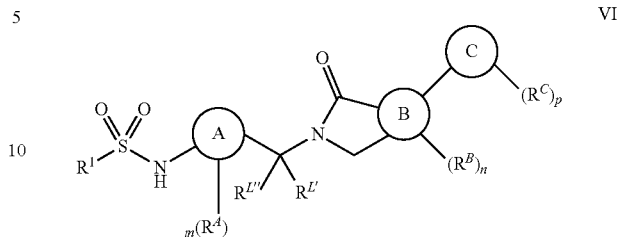

VI or a pharmaceutically acceptable salt thereof, wherein each of $R^1$, Ring A, Ring B, Ring C, $R^A$, $R^B$, $R^C$, $R^L$, $R^{L'}$, $R^{L''}$, m, n, and, p, is as defined above and described in embodiments herein, both singly and in combination.

Exemplary compounds of the invention are set forth in Table 1, below.

TABLE 1

Selected Compounds

| Compound | Structure |
|---|---|
| I-1 | 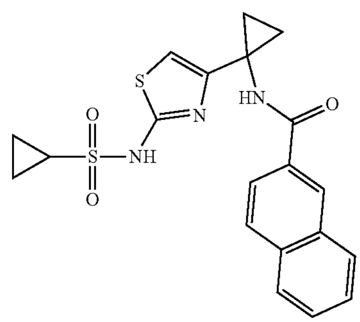 [SMILES: O=C(NC1(c2csc(NS(=O)(=O)C3CC3)n2)CC1)c1ccc2ccccc2c1] |
| I-2 | 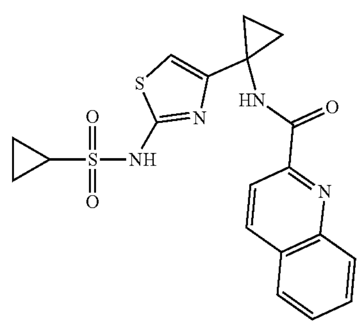 [SMILES: O=C(NC1(c2csc(NS(=O)(=O)C3CC3)n2)CC1)c1ccc2ccccc2n1] |
| I-3 | 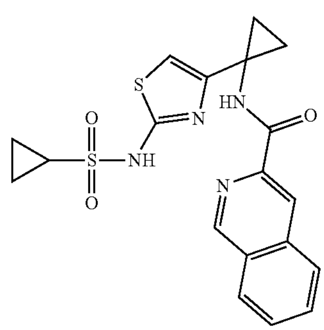 [SMILES: O=C(NC1(c2csc(NS(=O)(=O)C3CC3)n2)CC1)c1cc2ccccc2cn1] |

TABLE 1-continued
Selected Compounds
| Compound | Structure |
|---|---|
| I-4 | 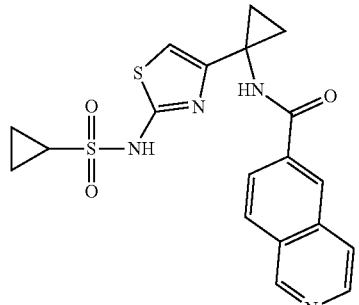 |
| I-5 | 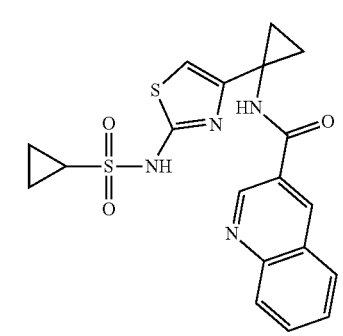 [SMILES: O=C(NC1(c2csc(NS(=O)(=O)C3CC3)n2)CC1)c1cnc2ccccc2c1] |
| I-6 | 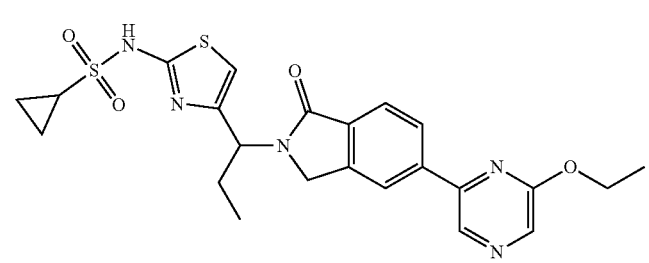 [SMILES: CCOc1cncc(-c2ccc3c(c2)CN(C(CC)c2csc(NS(=O)(=O)C4CC4)n2)C3=O)n1] |
| I-7 | 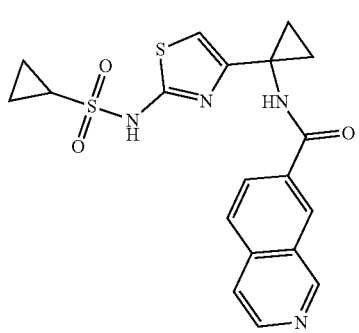 [SMILES: O=C(NC1(c2csc(NS(=O)(=O)C3CC3)n2)CC1)c1ccc2ccncc2c1] |

TABLE 1-continued

Selected Compounds

| Compound | Structure |
|---|---|
| I-8 | 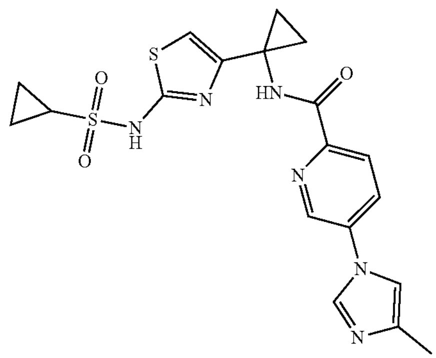 [SMILES: Cc1cn(-c2ccc(C(=O)NC3(c4csc(NS(=O)(=O)C5CC5)n4)CC3)nc2)cn1] |
| I-9 | 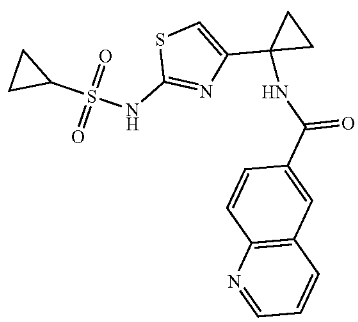 [SMILES: O=C(NC1(c2csc(NS(=O)(=O)C3CC3)n2)CC1)c1ccc2ncccc2c1] |
| I-10 | 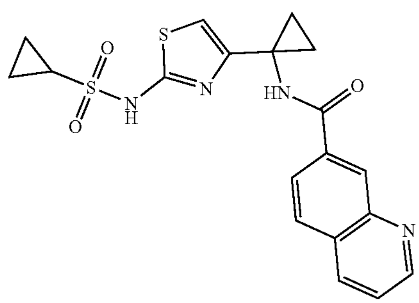 [SMILES: O=C(NC1(c2csc(NS(=O)(=O)C3CC3)n2)CC1)c1ccc2cccnc2c1] |
| I-11 | 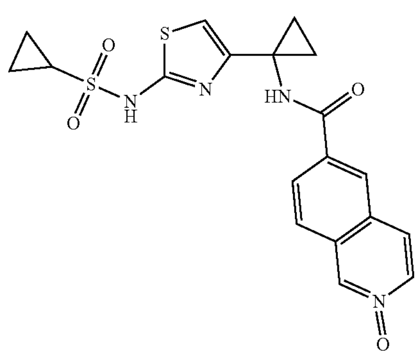 [SMILES: O=C(NC1(c2csc(NS(=O)(=O)C3CC3)n2)CC1)c1ccc2c[n+]([O-])ccc2c1] |

TABLE 1-continued

Selected Compounds

| Compound | Structure |
|---|---|
| I-12 | 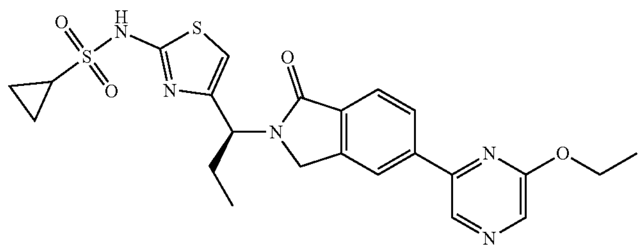 [SMILES: CCOc1cncc(-c2ccc3c(c2)CN([C@@H](CC)c2csc(NS(=O)(=O)C4CC4)n2)C3=O)n1] |
| I-13 | 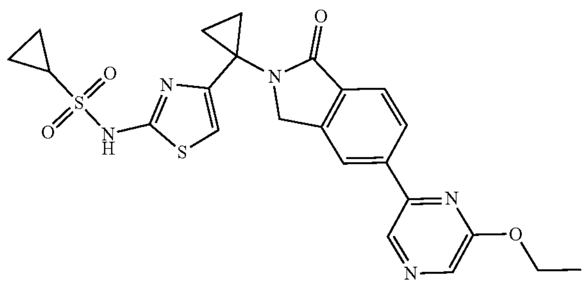 [SMILES: CCOc1cncc(-c2ccc3c(c2)CN(C2(c4csc(NS(=O)(=O)C5CC5)n4)CC2)C3=O)n1] |
| I-12a | 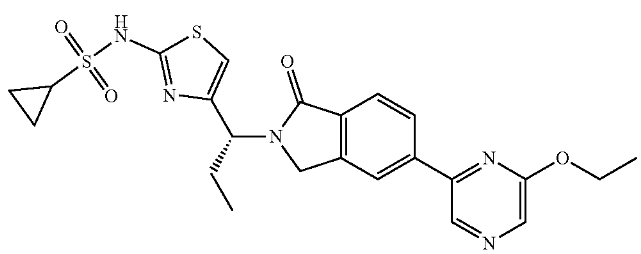 [SMILES: CCOc1cncc(-c2ccc3c(c2)CN([C@H](CC)c2csc(NS(=O)(=O)C4CC4)n2)C3=O)n1] |
| I-14 | 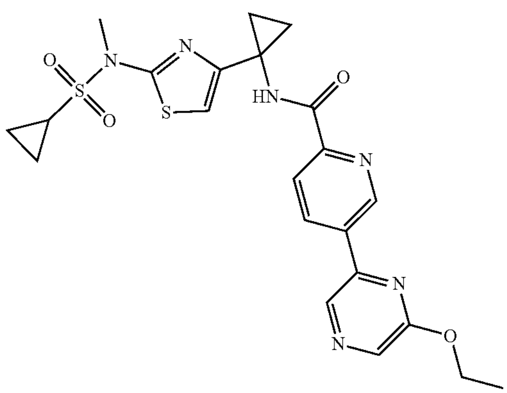 [SMILES: CCOc1cncc(-c2ccc(C(=O)NC3(c4csc(N(C)S(=O)(=O)C5CC5)n4)CC3)nc2)n1] |
| I-15 | 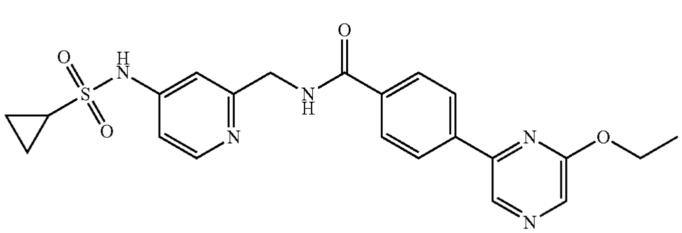 [SMILES: CCOc1cncc(-c2ccc(C(=O)NCc3cc(NS(=O)(=O)C4CC4)ccn3)cc2)n1] |

TABLE 1-continued
Selected Compounds
| Compound | Structure |
|---|---|
| I-16 | 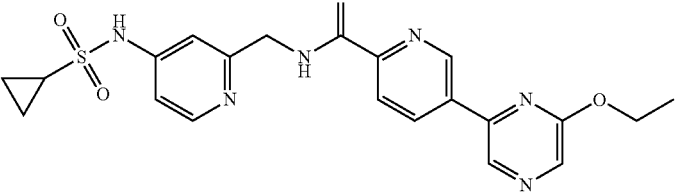 |
| I-17 | 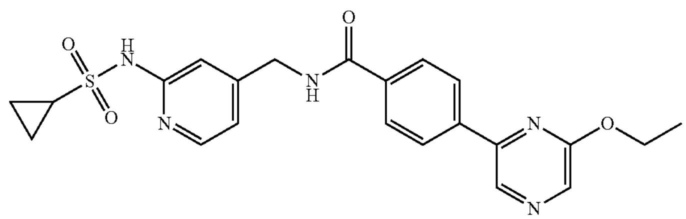 [SMILES: CCOc1cncc(-c2ccc(C(=O)NCc3ccnc(NS(=O)(=O)C4CC4)c3)cc2)n1] |
| I-18 | 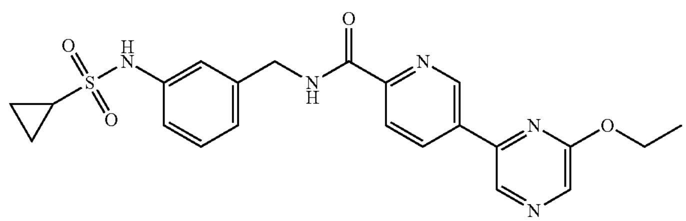 [SMILES: CCOc1cncc(-c2ccc(C(=O)NCc3cccc(NS(=O)(=O)C4CC4)c3)nc2)n1] |
| I-19 | 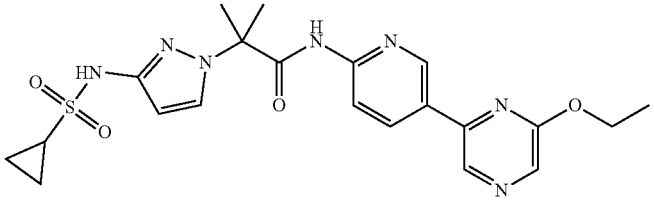 [SMILES: CCOc1cncc(-c2ccc(NC(=O)C(C)(C)n3ccc(NS(=O)(=O)C4CC4)n3)nc2)n1] |
| I-20 | 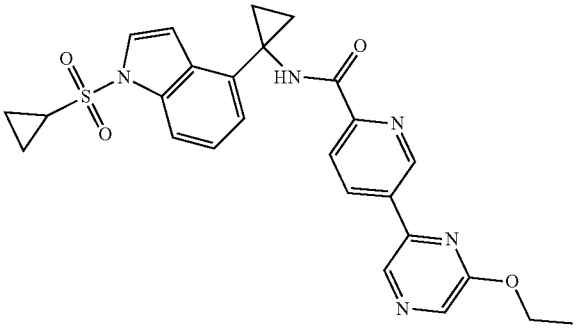 [SMILES: CCOc1cncc(-c2ccc(C(=O)NC3(c4cccc5c4ccn5S(=O)(=O)C4CC4)CC3)nc2)n1] |
| I-22 | 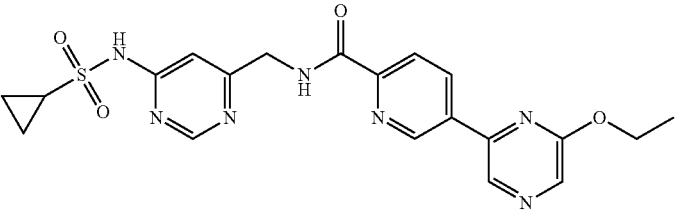 [SMILES: CCOc1cncc(-c2ccc(C(=O)NCc3cc(NS(=O)(=O)C4CC4)ncn3)nc2)n1] |

TABLE 1-continued

Selected Compounds

| Compound | Structure |
|---|---|
| I-23 | 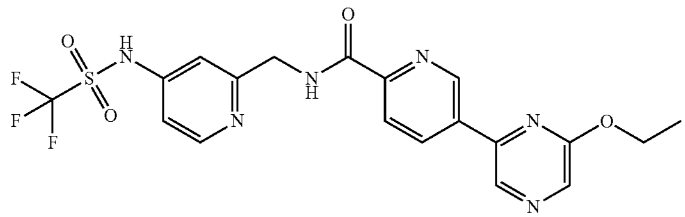 [SMILES: CCOc1cncc(-c2ccc(C(=O)NCc3cc(NS(=O)(=O)C(F)(F)F)ccn3)nc2)n1] |
| I-24 | 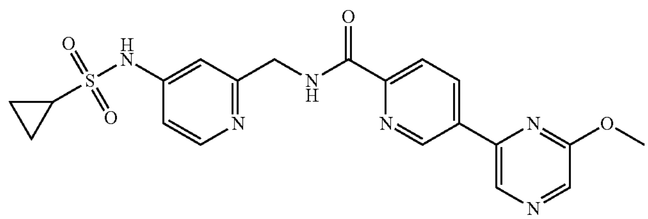 [SMILES: COc1cncc(-c2ccc(C(=O)NCc3cc(NS(=O)(=O)C4CC4)ccn3)nc2)n1] |
| I-25 | 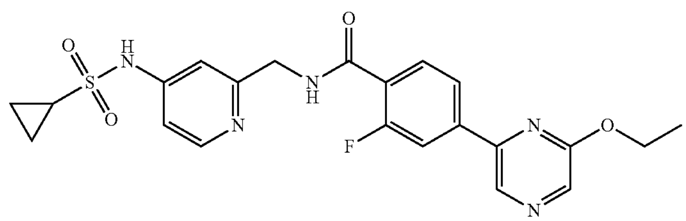 [SMILES: CCOc1cncc(-c2ccc(C(=O)NCc3cc(NS(=O)(=O)C4CC4)ccn3)c(F)c2)n1] |
| I-26 | 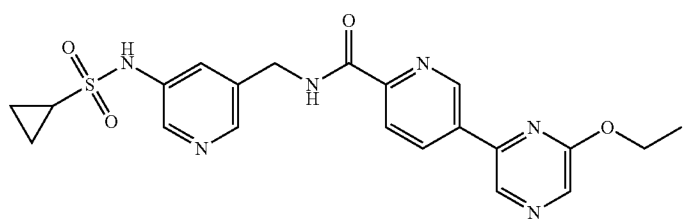 [SMILES: CCOc1cncc(-c2ccc(C(=O)NCc3cncc(NS(=O)(=O)C4CC4)c3)nc2)n1] |
| I-27 | 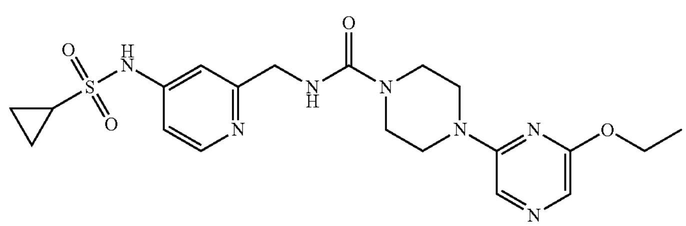 [SMILES: CCOc1cncc(N2CCN(C(=O)NCc3cc(NS(=O)(=O)C4CC4)ccn3)CC2)n1] |
| I-28 | 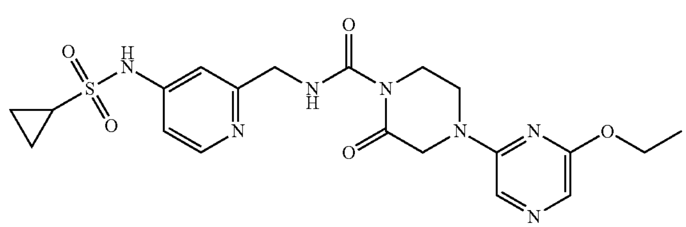 [SMILES: CCOc1cncc(N2CCN(C(=O)NCc3cc(NS(=O)(=O)C4CC4)ccn3)C(=O)C2)n1] |
| I-29 | 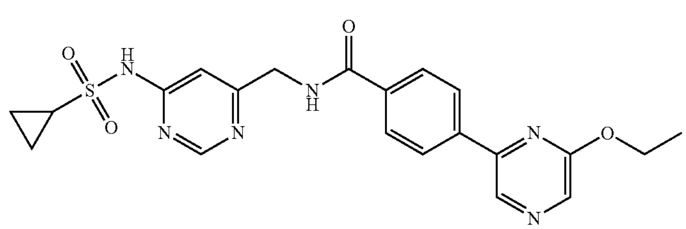 [SMILES: CCOc1cncc(-c2ccc(C(=O)NCc3cc(NS(=O)(=O)C4CC4)ncn3)cc2)n1] |

TABLE 1-continued

Selected Compounds

| Compound | Structure |
|---|---|
| I-30 | 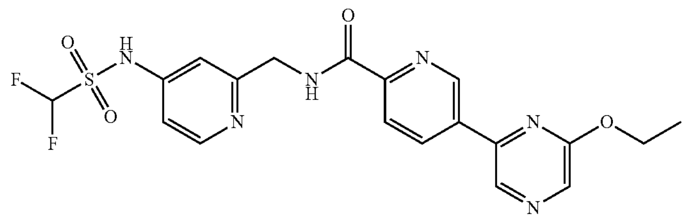 [SMILES: CCOc1cncc(-c2ccc(C(=O)NCc3cc(NS(=O)(=O)C(F)F)ccn3)nc2)n1] |
| I-31 | 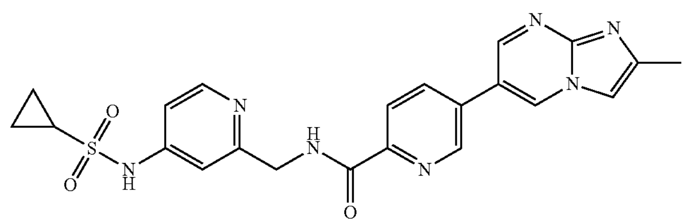 [SMILES: Cc1cn2cc(-c3ccc(C(=O)NCc4cc(NS(=O)(=O)C5CC5)ccn4)nc3)cnc2n1] |
| I-32 | 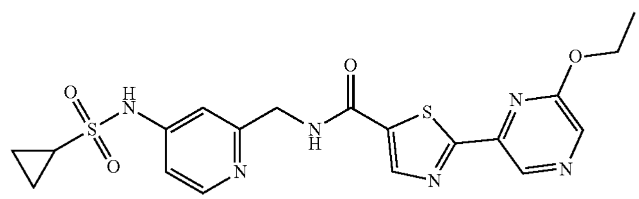 |
| I-33 | 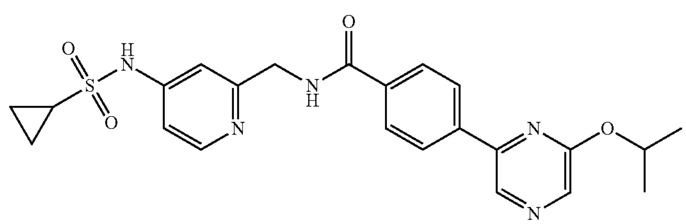 [SMILES: CC(C)Oc1cncc(-c2ccc(C(=O)NCc3cc(NS(=O)(=O)C4CC4)ccn3)cc2)n1] |
| I-34 | 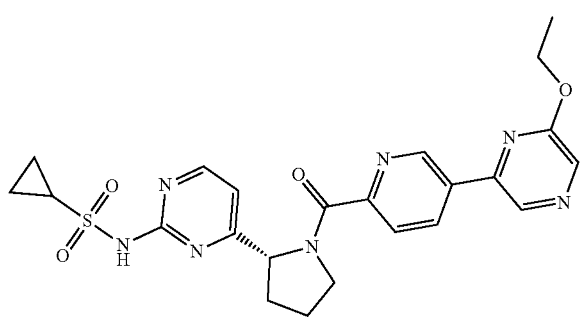 [SMILES: CCOc1cncc(-c2ccc(C(=O)N3CCC[C@@H]3c3ccnc(NS(=O)(=O)C4CC4)n3)nc2)n1] |
| I-35 | 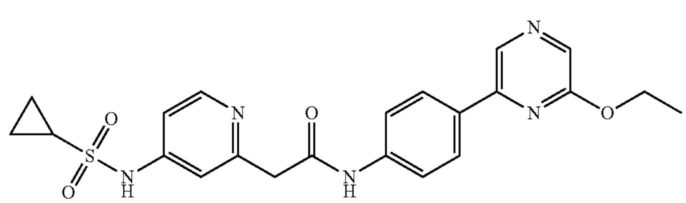 [SMILES: CCOc1cncc(-c2ccc(NC(=O)Cc3cc(NS(=O)(=O)C4CC4)ccn3)cc2)n1] |

TABLE 1-continued

Selected Compounds

| Compound | Structure |
|---|---|
| I-36 | 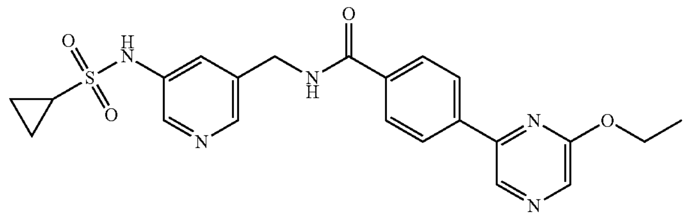 [SMILES: CCOc1cncc(-c2ccc(C(=O)NCc3cncc(NS(=O)(=O)C4CC4)c3)cc2)n1] |
| I-37 | 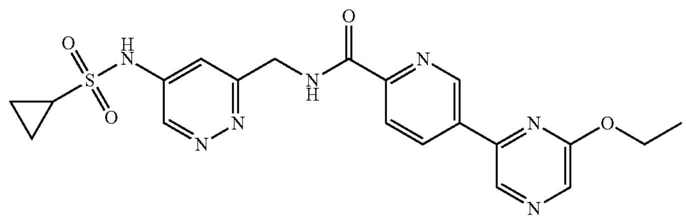 [SMILES: CCOc1cncc(-c2ccc(C(=O)NCc3cc(NS(=O)(=O)C4CC4)cnn3)nc2)n1] |
| I-38 | 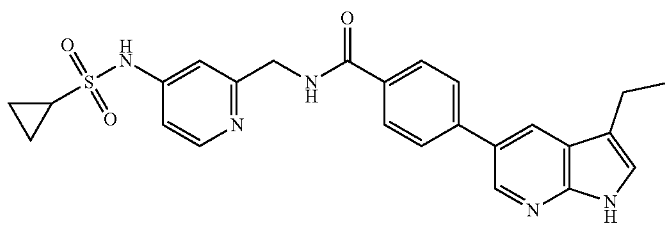 [SMILES: CCc1c[nH]c2ncc(-c3ccc(C(=O)NCc4cc(NS(=O)(=O)C5CC5)ccn4)cc3)cc12] |
| I-39 | 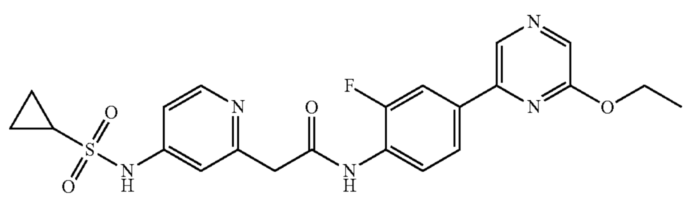 [SMILES: CCOc1cncc(-c2ccc(NC(=O)Cc3cc(NS(=O)(=O)C4CC4)ccn3)c(F)c2)n1] |
| I-40 | 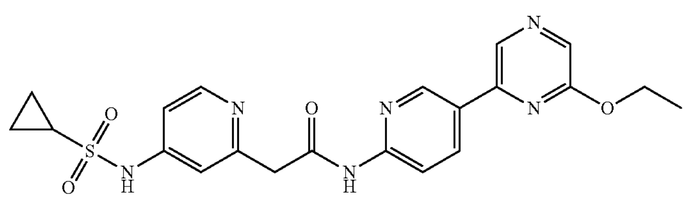 [SMILES: CCOc1cncc(-c2ccc(NC(=O)Cc3cc(NS(=O)(=O)C4CC4)ccn3)nc2)n1] |
| I-41 | 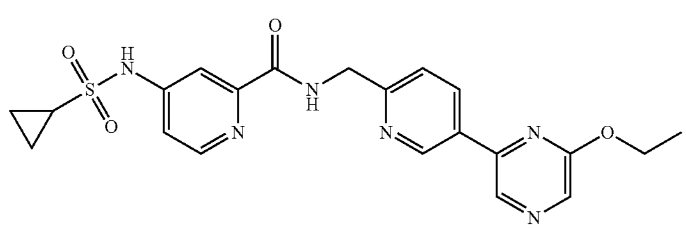 [SMILES: CCOc1cncc(-c2ccc(CNC(=O)c3cc(NS(=O)(=O)C4CC4)ccn3)nc2)n1] |
| I-42 | 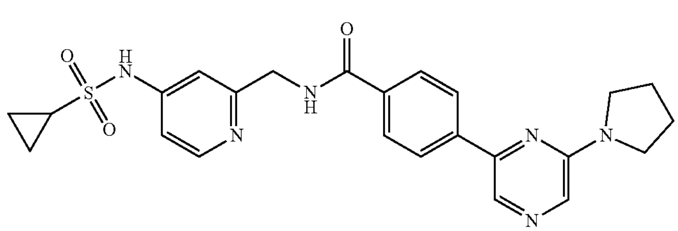 [SMILES: O=C(NCc1cc(NS(=O)(=O)C2CC2)ccn1)c1ccc(-c2cncc(N3CCCC3)n2)cc1] |

TABLE 1-continued

Selected Compounds

| Compound | Structure |
| --- | --- |
| I-43 | 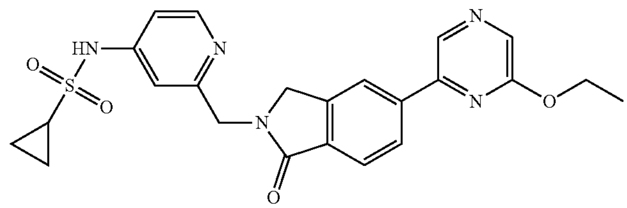 [SMILES: CCOc1cncc(-c2ccc3c(c2)CN(Cc2cc(NS(=O)(=O)C4CC4)ccn2)C3=O)n1] |
| I-44 | 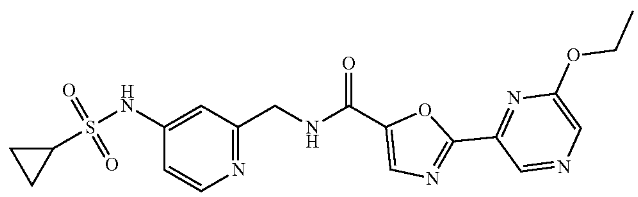 |
| I-45 | 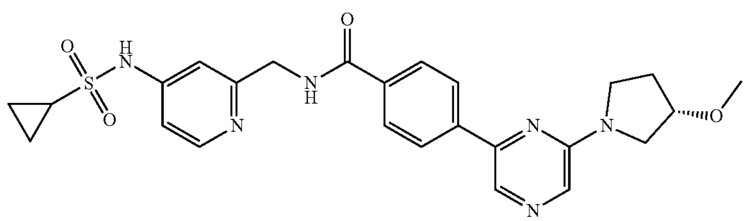 [SMILES: CO[C@H]1CCN(c2cncc(-c3ccc(C(=O)NCc4cc(NS(=O)(=O)C5CC5)ccn4)cc3)n2)C1] |
| I-46 | 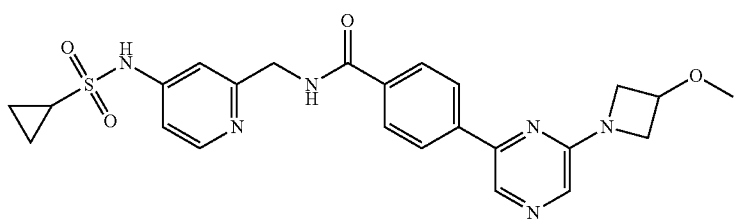 [SMILES: COC1CN(c2cncc(-c3ccc(C(=O)NCc4cc(NS(=O)(=O)C5CC5)ccn4)cc3)n2)C1] |
| I-47 | 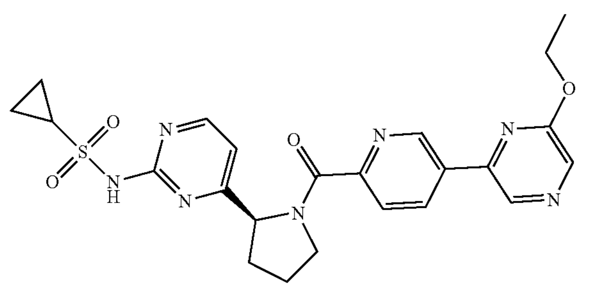 [SMILES: CCOc1cncc(-c2ccc(C(=O)N3CCC[C@H]3c3ccnc(NS(=O)(=O)C4CC4)n3)nc2)n1] |
| I-48 | 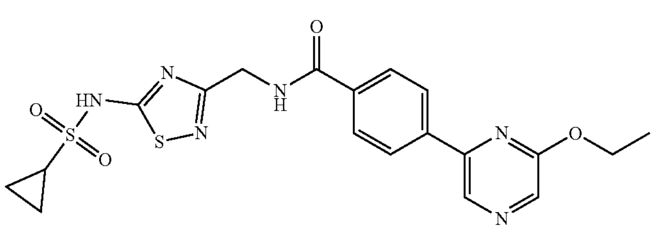 [SMILES: CCOc1cncc(-c2ccc(C(=O)NCc3nsc(NS(=O)(=O)C4CC4)n3)cc2)n1] |

TABLE 1-continued
Selected Compounds
| Compound | Structure |
|---|---|
| I-49 | 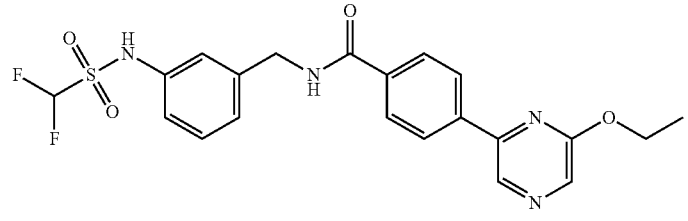 [SMILES: CCOc1cncc(-c2ccc(C(=O)NCc3cccc(NS(=O)(=O)C(F)F)c3)cc2)n1] |
| I-50 | 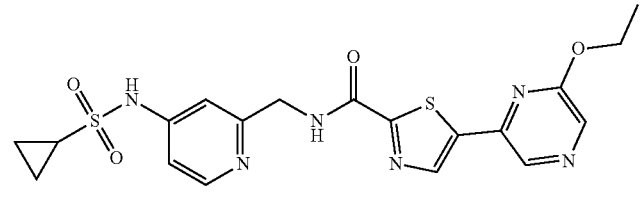 [SMILES: CCOc1cncc(-c2cnc(C(=O)NCc3cc(NS(=O)(=O)C4CC4)ccn3)s2)n1] |
| I-51 | 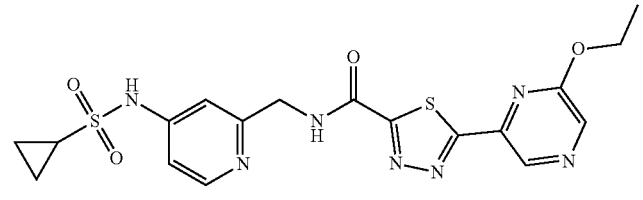 |
| I-52 | 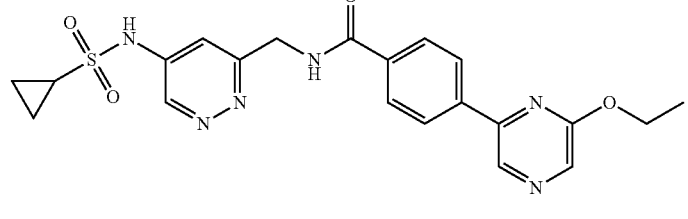 |
| I-53 | 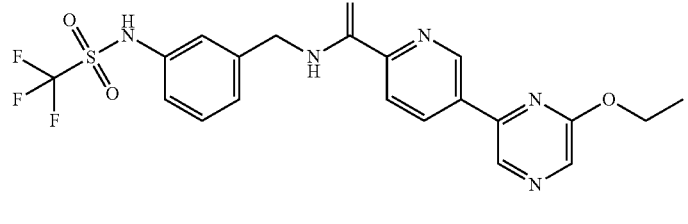 |
| I-54 | 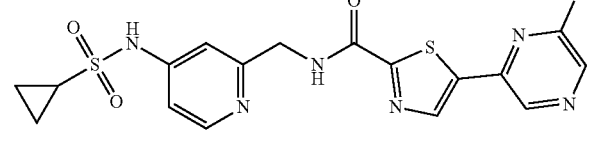 |
| I-55 | 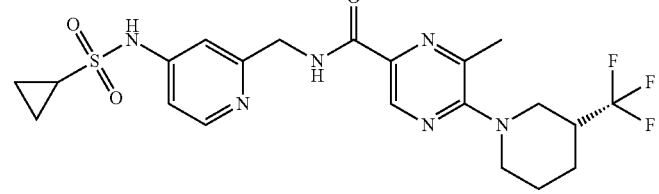 |

TABLE 1-continued
Selected Compounds
| Compound | Structure |
|---|---|
| I-56 | 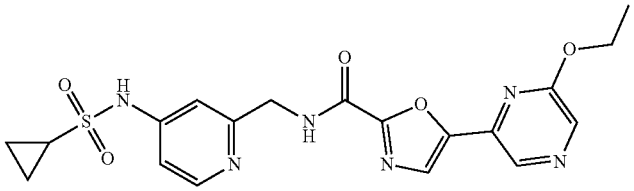 |
| I-57 | 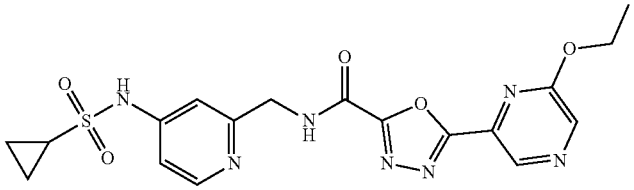 |
| I-58 | 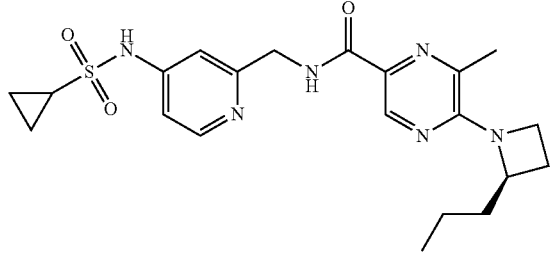 [SMILES: CCC[C@@H]1CCN1c1ncc(C(=O)NCc2cc(NS(=O)(=O)C3CC3)ccn2)nc1C] |
| I-59 | 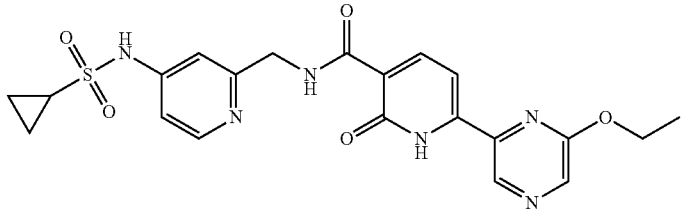 [SMILES: CCOc1cncc(-c2ccc(C(=O)NCc3cc(NS(=O)(=O)C4CC4)ccn3)c(=O)[nH]2)n1] |
| I-60 | 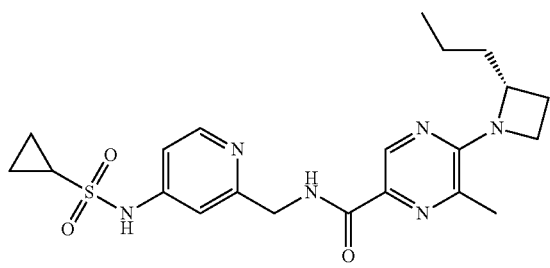 [SMILES: CCC[C@@H]1CCN1c1ncc(C(=O)NCc2cc(NS(=O)(=O)C3CC3)ccn2)nc1C] |
| I-61 | 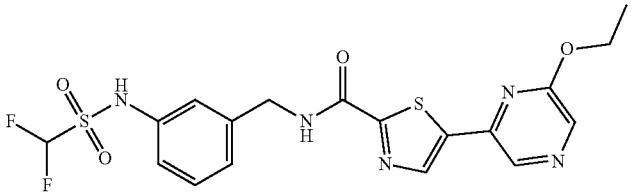 [SMILES: CCOc1cncc(-c2cnc(C(=O)NCc3cccc(NS(=O)(=O)C(F)F)c3)s2)n1] |
| I-62 | 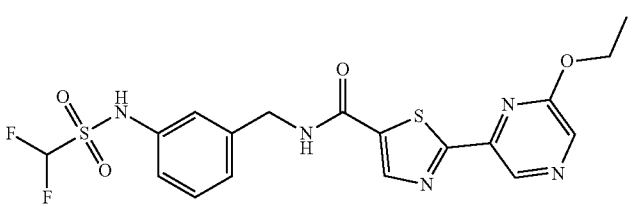 [SMILES: CCOc1cncc(-c2ncc(C(=O)NCc3cccc(NS(=O)(=O)C(F)F)c3)s2)n1] |

TABLE 1-continued

Selected Compounds

| Compound | Structure |
|---|---|
| I-63 | 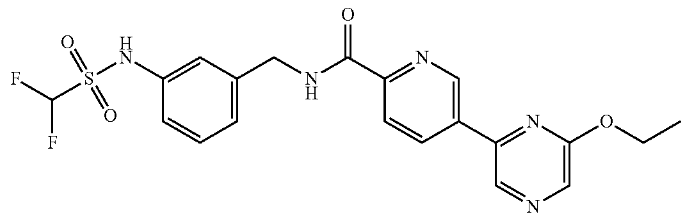 |
| I-64 | 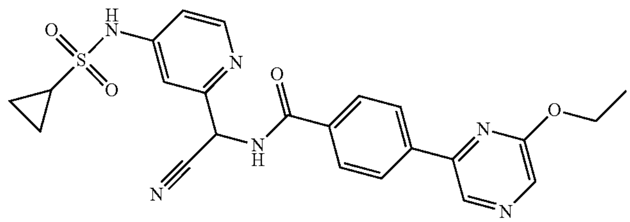 [SMILES: CCOc1cncc(-c2ccc(C(=O)NC(C#N)c3cc(NS(=O)(=O)C4CC4)ccn3)cc2)n1] |
| I-65 | 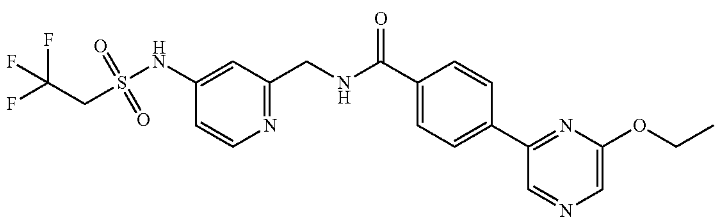 [SMILES: CCOc1cncc(-c2ccc(C(=O)NCc3cc(NS(=O)(=O)CC(F)(F)F)ccn3)cc2)n1] |
| I-66 | 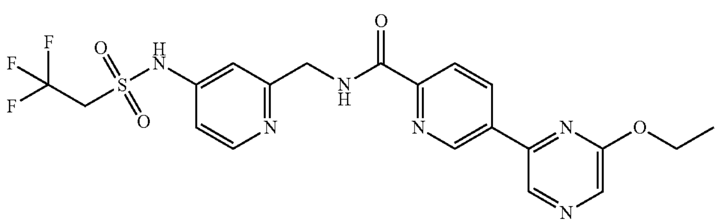 [SMILES: CCOc1cncc(-c2ccc(C(=O)NCc3cc(NS(=O)(=O)CC(F)(F)F)ccn3)nc2)n1] |
| I-67 | 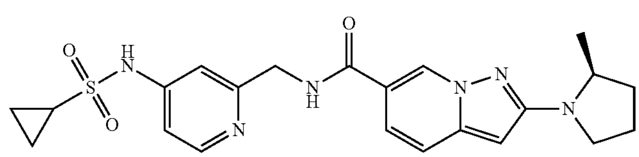 [SMILES: C[C@H]1CCCN1c1cc2ccc(C(=O)NCc3cc(NS(=O)(=O)C4CC4)ccn3)cn2n1] |
| I-68 | 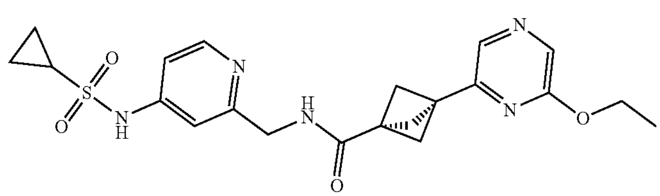 [SMILES: CCOc1cncc([C@]23C[C@](C(=O)NCc4cc(NS(=O)(=O)C5CC5)ccn4)(C2)C3)n1] |
| I-69 | 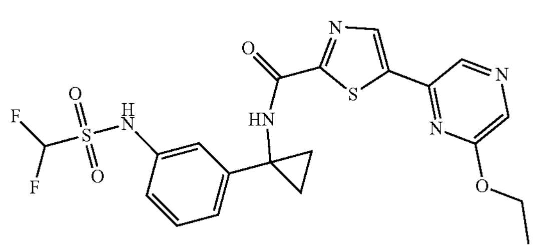 [SMILES: CCOc1cncc(-c2cnc(C(=O)NC3(c4cccc(NS(=O)(=O)C(F)F)c4)CC3)s2)n1] |

TABLE 1-continued

Selected Compounds

| Compound | Structure |
|---|---|
| I-70 | 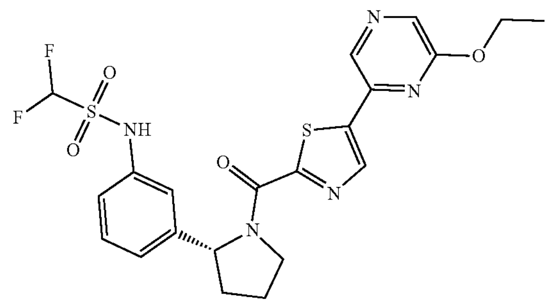 [SMILES: CCOc1cncc(-c2cnc(C(=O)N3CCC[C@@H]3c3cccc(NS(=O)(=O)C(F)F)c3)s2)n1] |
| I-71 | 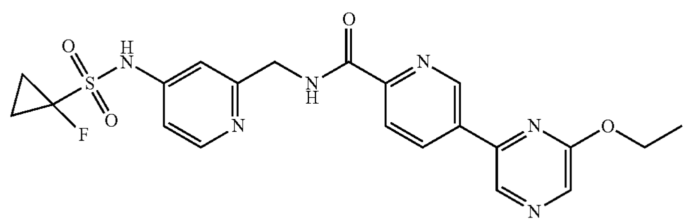 [SMILES: CCOc1cncc(-c2ccc(C(=O)NCc3cc(NS(=O)(=O)C4(F)CC4)ccn3)nc2)n1] |
| I-72 | 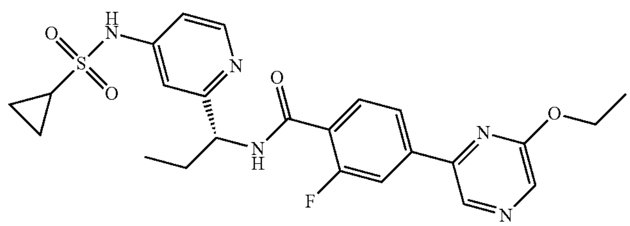 [SMILES: CCOc1cncc(-c2ccc(C(=O)N[C@H](CC)c3cc(NS(=O)(=O)C4CC4)ccn3)c(F)c2)n1] |
| I-73 | 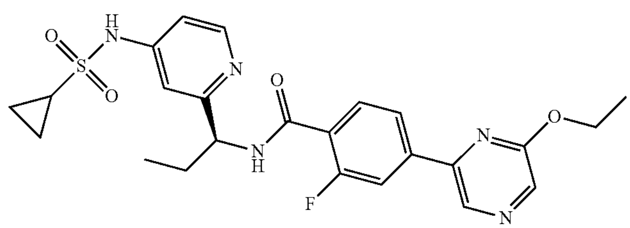 [SMILES: CCOc1cncc(-c2ccc(C(=O)N[C@@H](CC)c3cc(NS(=O)(=O)C4CC4)ccn3)c(F)c2)n1] |
| I-74 | 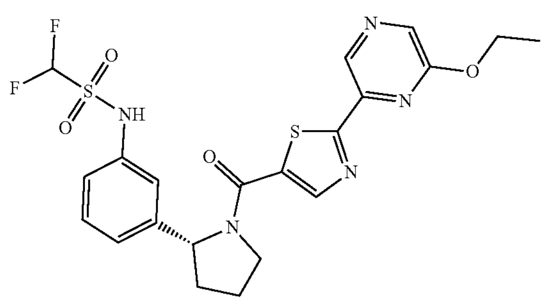 [SMILES: CCOc1cncc(-c2ncc(C(=O)N3CCC[C@@H]3c3cccc(NS(=O)(=O)C(F)F)c3)s2)n1] |
| I-75 | 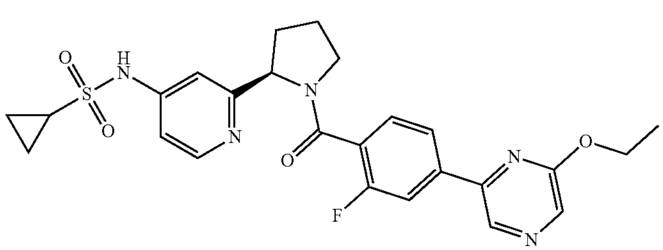 [SMILES: CCOc1cncc(-c2ccc(C(=O)N3CCC[C@@H]3c3cc(NS(=O)(=O)C4CC4)ccn3)c(F)c2)n1] |

TABLE 1-continued
Selected Compounds
| Compound | Structure |
|---|---|
| I-76 | 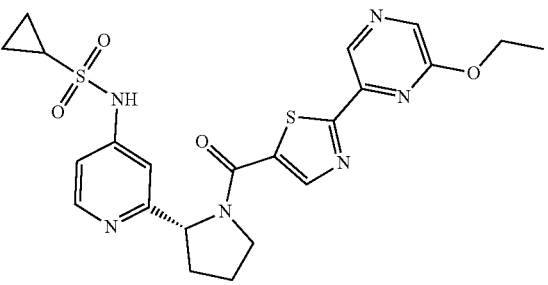 [SMILES: CCOc1cncc(-c2ncc(C(=O)N3CCC[C@@H]3c3cc(NS(=O)(=O)C4CC4)ccn3)s2)n1] |
| I-77 | 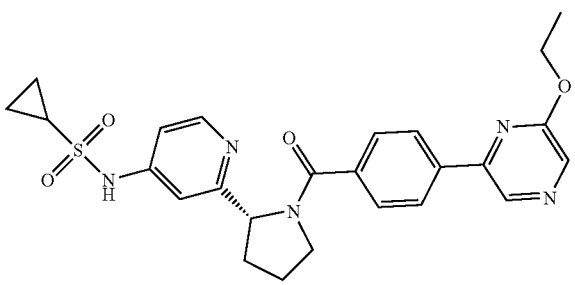 [SMILES: CCOc1cncc(-c2ccc(C(=O)N3CCC[C@@H]3c3cc(NS(=O)(=O)C4CC4)ccn3)cc2)n1] |
| I-78 | 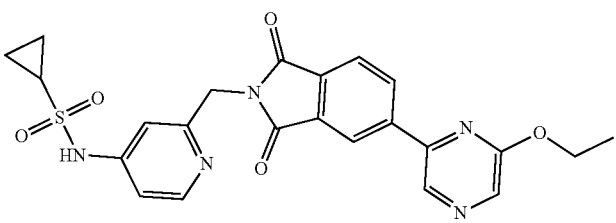 [SMILES: CCOc1cncc(-c2ccc3c(c2)C(=O)N(Cc2cc(NS(=O)(=O)C4CC4)ccn2)C3=O)n1] |
| I-79 | 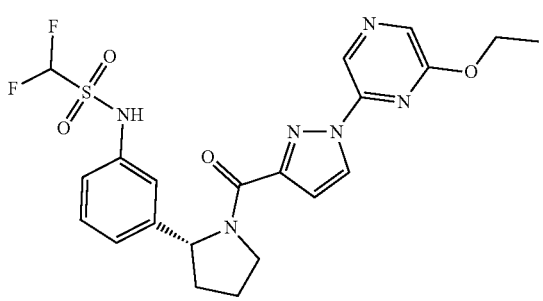 [SMILES: CCOc1cncc(-n2ccc(C(=O)N3CCC[C@@H]3c3cccc(NS(=O)(=O)C(F)F)c3)n2)n1] |
| I-80 | 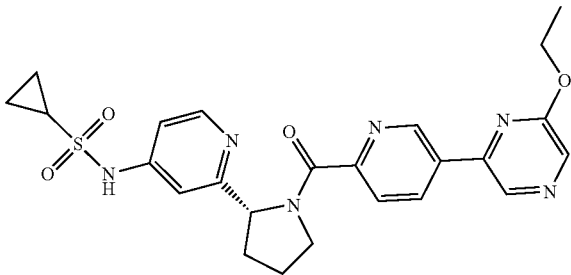 [SMILES: CCOc1cncc(-c2ccc(C(=O)N3CCC[C@@H]3c3cc(NS(=O)(=O)C4CC4)ccn3)nc2)n1] |

TABLE 1-continued
Selected Compounds
| Compound | Structure |
|---|---|
| I-81 | 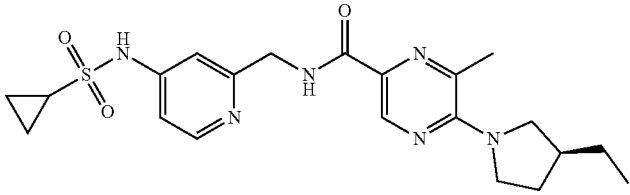 [SMILES: CC[C@H]1CCN(c2ncc(C(=O)NCc3cc(NS(=O)(=O)C4CC4)ccn3)nc2C)C1] |
| I-82 | 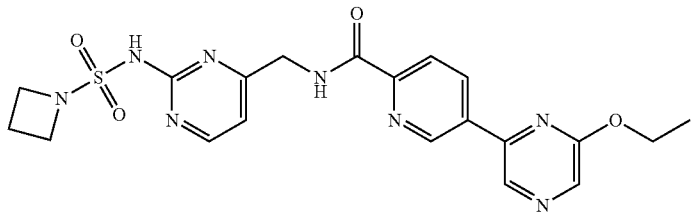 [SMILES: CCOc1cncc(-c2ccc(C(=O)NCc3ccnc(NS(=O)(=O)N4CCC4)n3)nc2)n1] |
| I-83 | 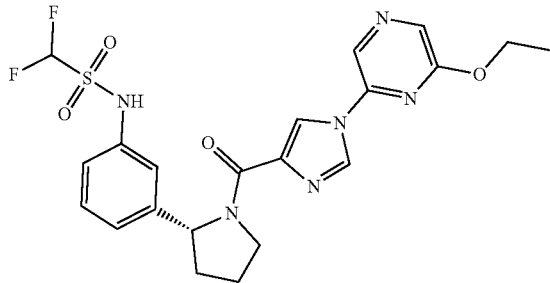 [SMILES: CCOc1cncc(-n2cnc(C(=O)N3CCC[C@@H]3c3cccc(NS(=O)(=O)C(F)F)c3)c2)n1] |
| I-84 | 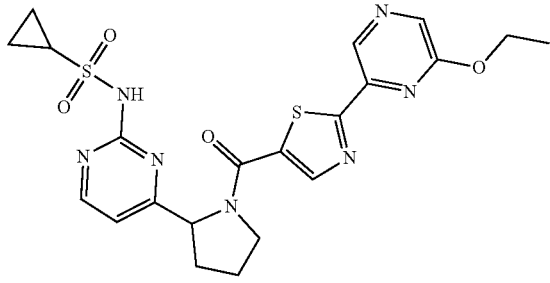 [SMILES: CCOc1cncc(-c2ncc(C(=O)N3CCCC3c3ccnc(NS(=O)(=O)C4CC4)n3)s2)n1] |
| I-85 | 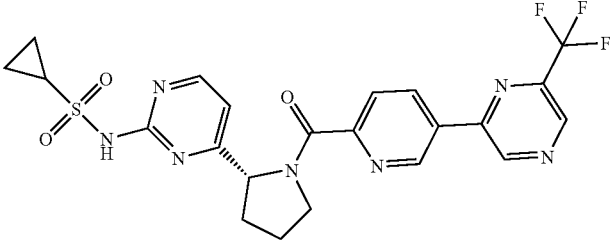 [SMILES: O=C(c1ccc(-c2cncc(C(F)(F)F)n2)cn1)N1CCC[C@@H]1c1ccnc(NS(=O)(=O)C2CC2)n1] |
| I-86 | 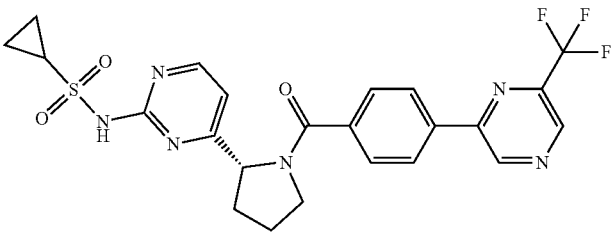 [SMILES: O=C(c1ccc(-c2cncc(C(F)(F)F)n2)cc1)N1CCC[C@@H]1c1ccnc(NS(=O)(=O)C2CC2)n1] |

TABLE 1-continued

Selected Compounds

| Compound | Structure |
|---|---|
| I-87 | 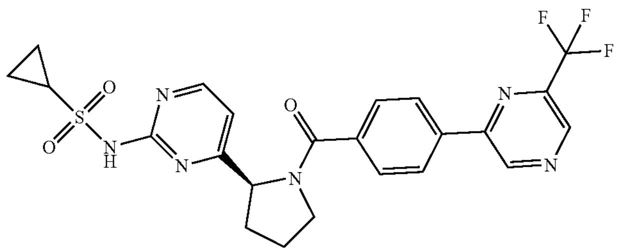 [SMILES: O=C(c1ccc(-c2cncc(C(F)(F)F)n2)cc1)N1CCC[C@H]1c1ccnc(NS(=O)(=O)C2CC2)n1] |
| I-88 | 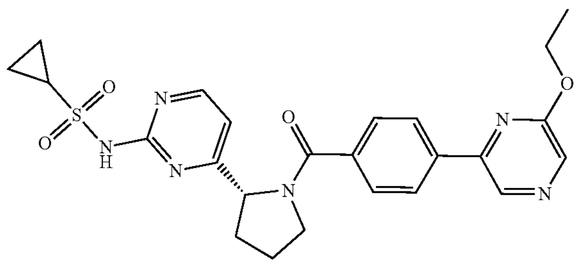 [SMILES: CCOc1cncc(-c2ccc(C(=O)N3CCC[C@@H]3c3ccnc(NS(=O)(=O)C4CC4)n3)cc2)n1] |
| I-89 | 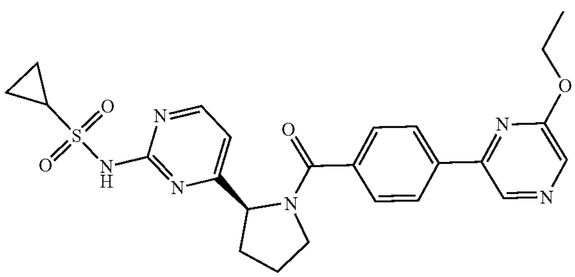 [SMILES: CCOc1cncc(-c2ccc(C(=O)N3CCC[C@H]3c3ccnc(NS(=O)(=O)C4CC4)n3)cc2)n1] |
| I-90 | 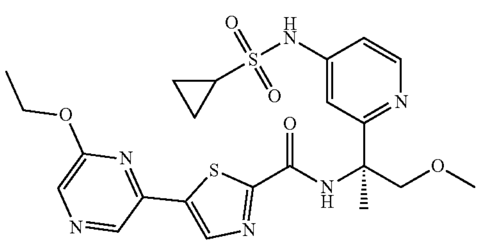 [SMILES: CCOc1cncc(-c2cnc(C(=O)N[C@](C)(COC)c3cc(NS(=O)(=O)C4CC4)ccn3)s2)n1] |
| I-91 | 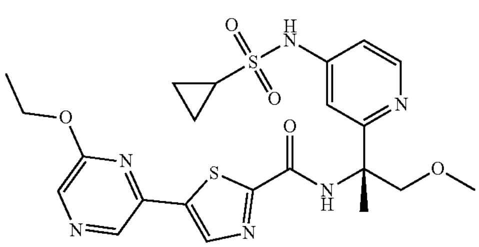 [SMILES: CCOc1cncc(-c2cnc(C(=O)N[C@@](C)(COC)c3cc(NS(=O)(=O)C4CC4)ccn3)s2)n1] |
| I-92 | 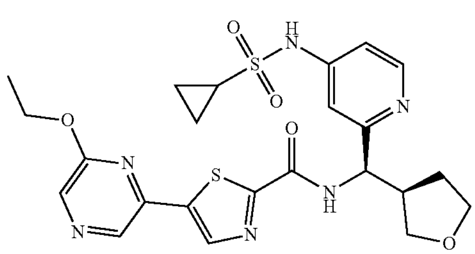 [SMILES: CCOc1cncc(-c2cnc(C(=O)N[C@@H](c3cc(NS(=O)(=O)C4CC4)ccn3)[C@H]3CCOC3)s2)n1] |

TABLE 1-continued

Selected Compounds

| Compound | Structure |
|---|---|
| I-93 | 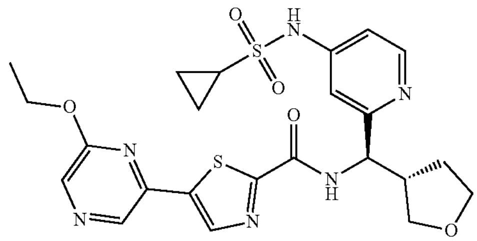 [SMILES: CCOc1cncc(-c2cnc(C(=O)N[C@@H](c3cc(NS(=O)(=O)C4CC4)ccn3)[C@@H]3CCOC3)s2)n1] |
| I-94 | 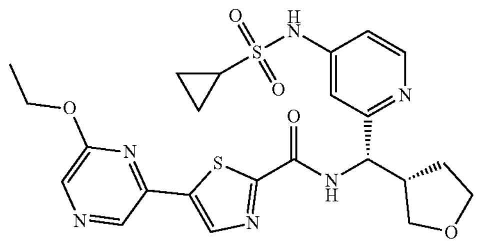 [SMILES: CCOc1cncc(-c2cnc(C(=O)N[C@H](c3cc(NS(=O)(=O)C4CC4)ccn3)[C@@H]3CCOC3)s2)n1] |
| I-95 | 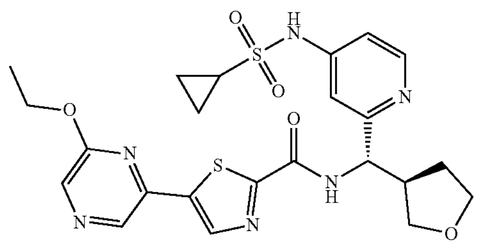 [SMILES: CCOc1cncc(-c2cnc(C(=O)N[C@H](c3cc(NS(=O)(=O)C4CC4)ccn3)[C@H]3CCOC3)s2)n1] |
| I-96 | 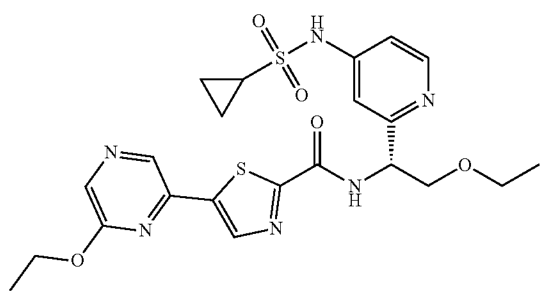 [SMILES: CCOC[C@H](NC(=O)c1ncc(-c2cncc(OCC)n2)s1)c1cc(NS(=O)(=O)C2CC2)ccn1] |
| I-97 | 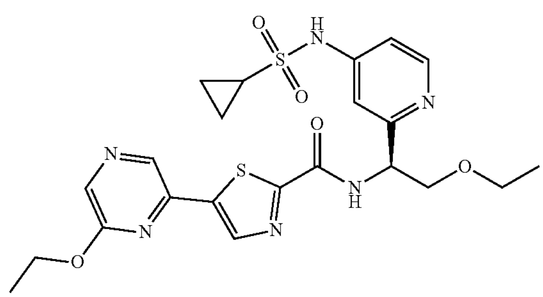 [SMILES: CCOC[C@@H](NC(=O)c1ncc(-c2cncc(OCC)n2)s1)c1cc(NS(=O)(=O)C2CC2)ccn1] |
| I-99 | 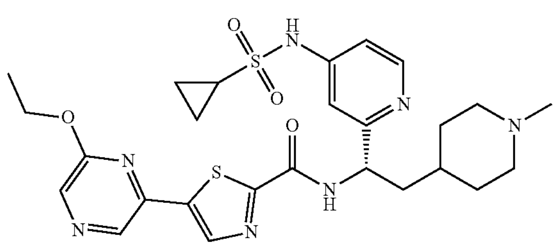 [SMILES: CCOc1cncc(-c2cnc(C(=O)N[C@@H](CC3CCN(C)CC3)c3cc(NS(=O)(=O)C4CC4)ccn3)s2)n1] |

TABLE 1-continued
Selected Compounds
| Compound | Structure |
|---|---|
| I-100 | 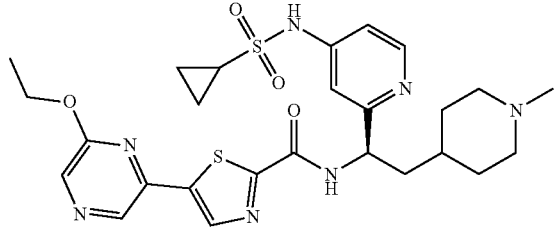 |
| I-101 | 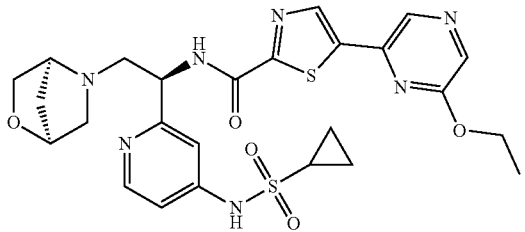 [SMILES: CCOc1cncc(-c2cnc(C(=O)N[C@H](CN3C[C@@H]4C[C@H]3CO4)c3cc(NS(=O)(=O)C4CC4)ccn3)s2)n1] |
| I-102 | 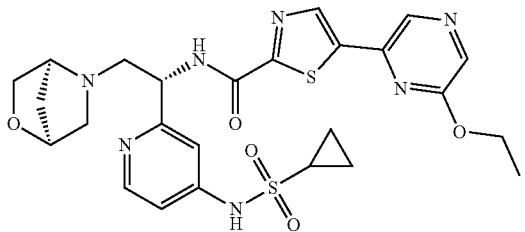 [SMILES: CCOc1cncc(-c2cnc(C(=O)N[C@@H](CN3C[C@@H]4C[C@H]3CO4)c3cc(NS(=O)(=O)C4CC4)ccn3)s2)n1] |
| I-103 | 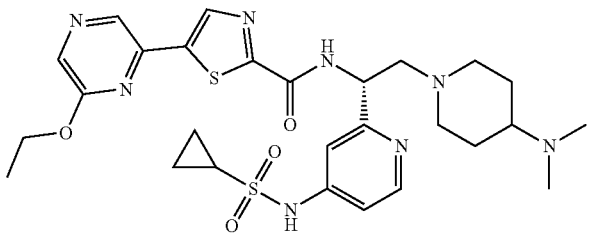 [SMILES: CCOc1cncc(-c2cnc(C(=O)N[C@H](CN3CCC(N(C)C)CC3)c3cc(NS(=O)(=O)C4CC4)ccn3)s2)n1] |
| I-104 | 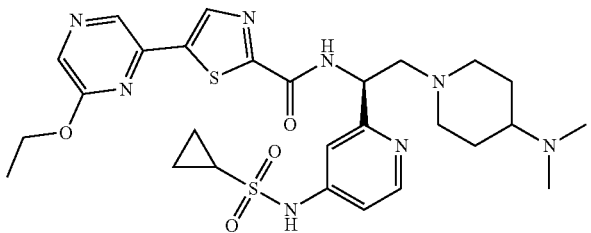 [SMILES: CCOc1cncc(-c2cnc(C(=O)N[C@@H](CN3CCC(N(C)C)CC3)c3cc(NS(=O)(=O)C4CC4)ccn3)s2)n1] |
| I-105 | 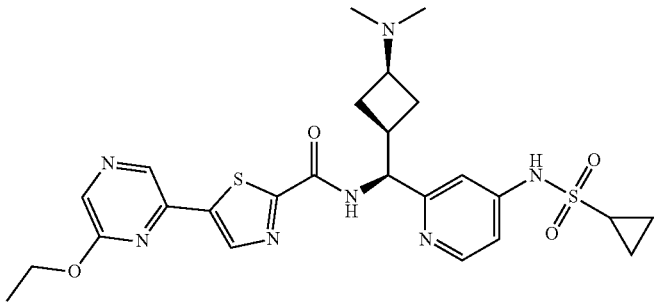 [SMILES: CCOc1cncc(-c2cnc(C(=O)N[C@H](c3cc(NS(=O)(=O)C4CC4)ccn3)[C@H]3C[C@@H](N(C)C)C3)s2)n1] |

TABLE 1-continued

Selected Compounds

| Compound | Structure |
|---|---|
| I-106 | 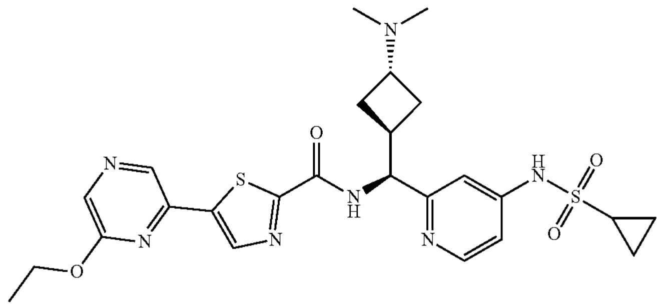 [SMILES: CCOc1cncc(-c2cnc(C(=O)N[C@H](c3cc(NS(=O)(=O)C4CC4)ccn3)[C@H]3C[C@H](N(C)C)C3)s2)n1] |
| I-107 | 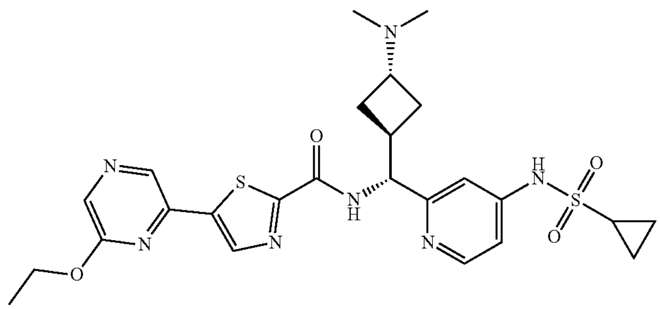 [SMILES: CCOc1cncc(-c2cnc(C(=O)N[C@@H](c3cc(NS(=O)(=O)C4CC4)ccn3)[C@H]3C[C@H](N(C)C)C3)s2)n1] |
| I-108 | 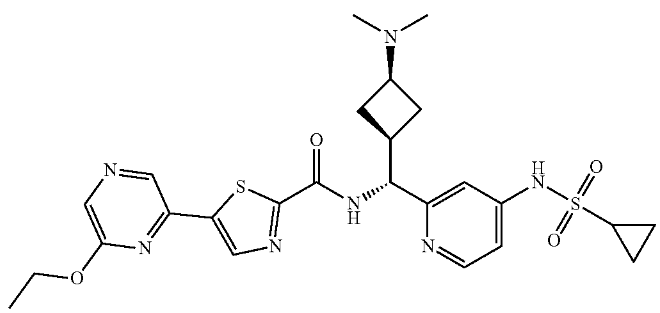 [SMILES: CCOc1cncc(-c2cnc(C(=O)N[C@@H](c3cc(NS(=O)(=O)C4CC4)ccn3)[C@H]3C[C@@H](N(C)C)C3)s2)n1] |
| I-109 | 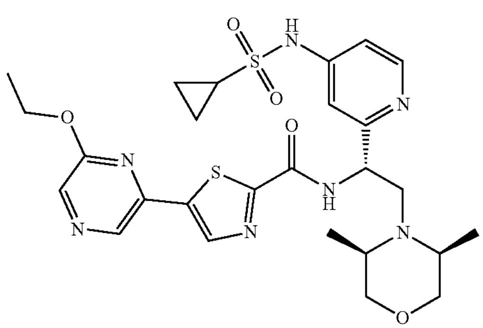 [SMILES: CCOc1cncc(-c2cnc(C(=O)N[C@@H](CN3[C@H](C)COC[C@@H]3C)c3cc(NS(=O)(=O)C4CC4)ccn3)s2)n1] |
| I-110 | 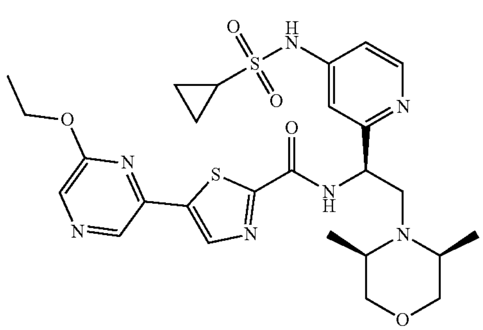 [SMILES: CCOc1cncc(-c2cnc(C(=O)N[C@H](CN3[C@H](C)COC[C@@H]3C)c3cc(NS(=O)(=O)C4CC4)ccn3)s2)n1] |

TABLE 1-continued

Selected Compounds

| Compound | Structure |
|---|---|
| I-111 | 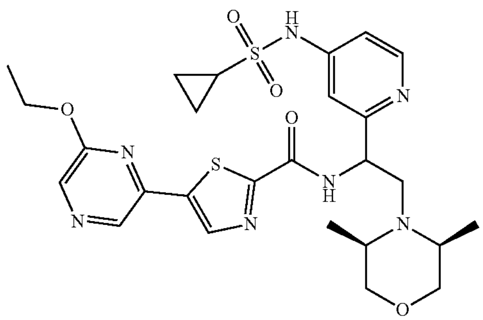 [SMILES: CCOc1cncc(-c2cnc(C(=O)NC(CN3[C@H](C)COC[C@@H]3C)c3cc(NS(=O)(=O)C4CC4)ccn3)s2)n1] |
| I-112 | 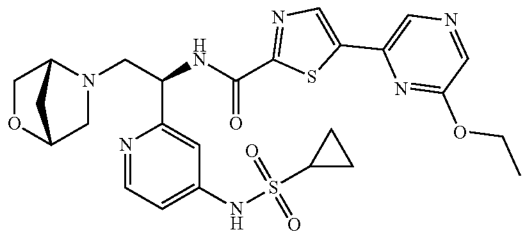 [SMILES: CCOc1cncc(-c2cnc(C(=O)N[C@H](CN3C[C@H]4C[C@@H]3CO4)c3cc(NS(=O)(=O)C4CC4)ccn3)s2)n1] |
| I-113 | 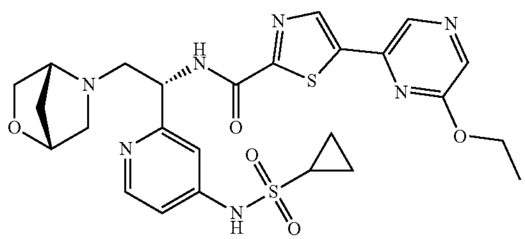 [SMILES: CCOc1cncc(-c2cnc(C(=O)N[C@@H](CN3C[C@H]4C[C@@H]3CO4)c3cc(NS(=O)(=O)C4CC4)ccn3)s2)n1] |
| I-114 | 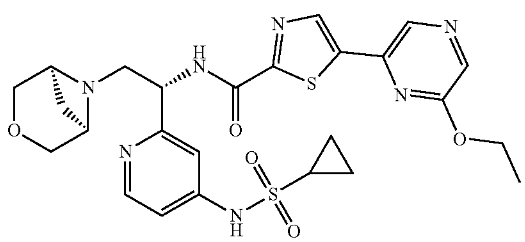 [SMILES: CCOc1cncc(-c2cnc(C(=O)N[C@@H](CN3[C@@H]4COC[C@H]3C4)c3cc(NS(=O)(=O)C4CC4)ccn3)s2)n1] |
| I-115 | 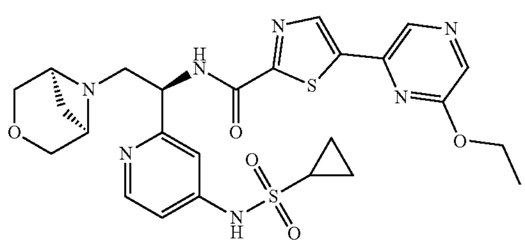 [SMILES: CCOc1cncc(-c2cnc(C(=O)N[C@H](CN3[C@@H]4COC[C@H]3C4)c3cc(NS(=O)(=O)C4CC4)ccn3)s2)n1] |
| I-116 | 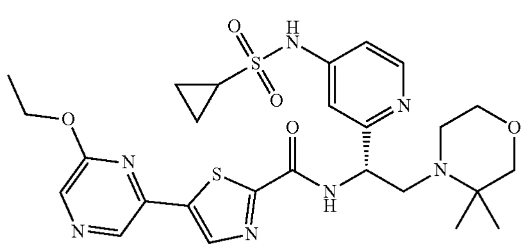 [SMILES: CCOc1cncc(-c2cnc(C(=O)N[C@@H](CN3CCOCC3(C)C)c3cc(NS(=O)(=O)C4CC4)ccn3)s2)n1] |

TABLE 1-continued
Selected Compounds
| Compound | Structure |
|---|---|
| I-117 | 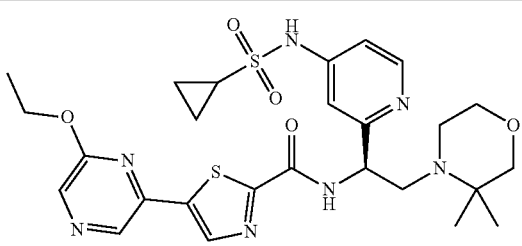 [SMILES: CCOc1cncc(-c2cnc(C(=O)N[C@H](CN3CCOCC3(C)C)c3cc(NS(=O)(=O)C4CC4)ccn3)s2)n1] |
| I-118 | 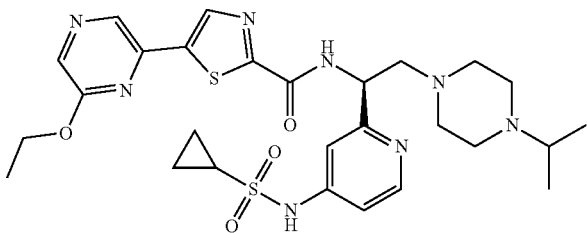 [SMILES: CCOc1cncc(-c2cnc(C(=O)N[C@@H](CN3CCN(C(C)C)CC3)c3cc(NS(=O)(=O)C4CC4)ccn3)s2)n1] |
| I-119 | 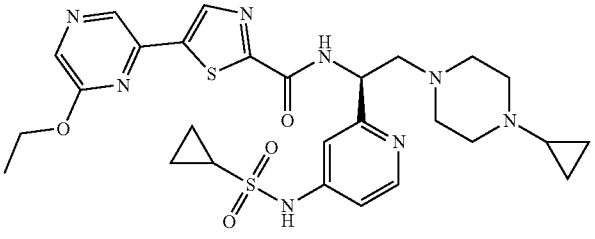 [SMILES: CCOc1cncc(-c2cnc(C(=O)N[C@@H](CN3CCN(C4CC4)CC3)c3cc(NS(=O)(=O)C4CC4)ccn3)s2)n1] |
| I-120 | 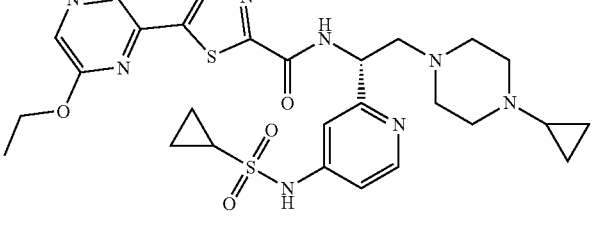 |
| I-121 | 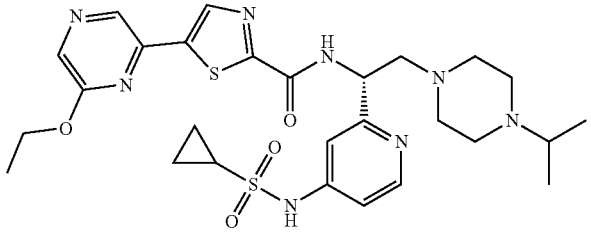 [SMILES: CCOc1cncc(-c2cnc(C(=O)N[C@H](CN3CCN(C(C)C)CC3)c3cc(NS(=O)(=O)C4CC4)ccn3)s2)n1] |
| I-122 | 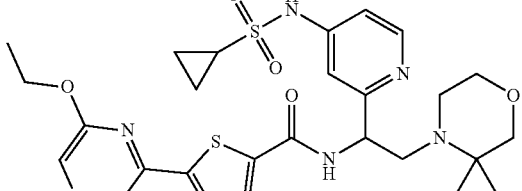 |

TABLE 1-continued

Selected Compounds

| Compound | Structure |
|---|---|
| I-123 | 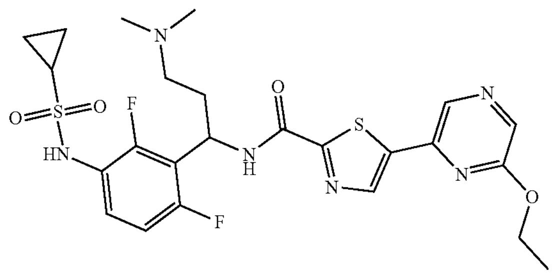 [SMILES: CCOc1cncc(-c2cnc(C(=O)NC(CCN(C)C)c3c(F)ccc(NS(=O)(=O)C4CC4)c3F)s2)n1] |
| I-124 | 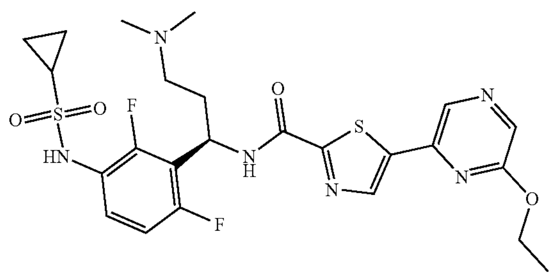 [SMILES: CCOc1cncc(-c2cnc(C(=O)N[C@H](CCN(C)C)c3c(F)ccc(NS(=O)(=O)C4CC4)c3F)s2)n1] |
| I-125 | 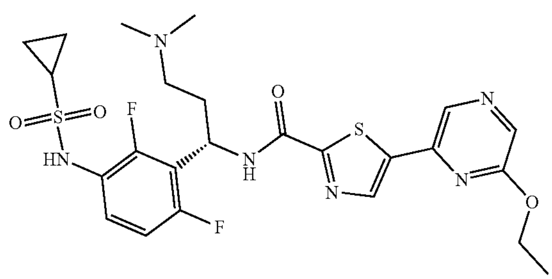 [SMILES: CCOc1cncc(-c2cnc(C(=O)N[C@@H](CCN(C)C)c3c(F)ccc(NS(=O)(=O)C4CC4)c3F)s2)n1] |
| I-126 | 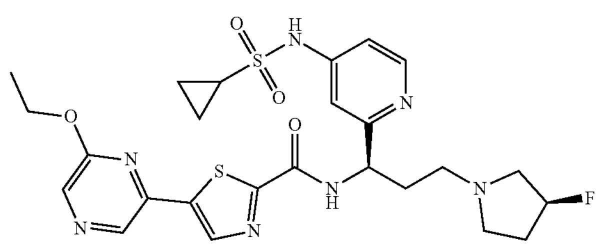 [SMILES: CCOc1cncc(-c2cnc(C(=O)N[C@H](CCN3CC[C@H](F)C3)c3cc(NS(=O)(=O)C4CC4)ccn3)s2)n1] |
| I-127 | 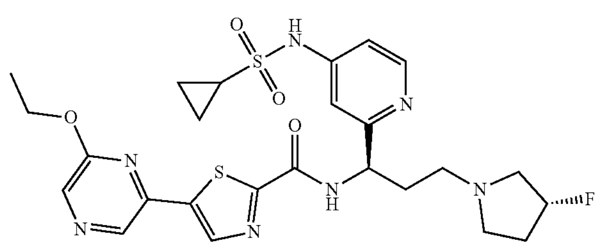 [SMILES: CCOc1cncc(-c2cnc(C(=O)N[C@H](CCN3CC[C@@H](F)C3)c3cc(NS(=O)(=O)C4CC4)ccn3)s2)n1] |
| I-128 | 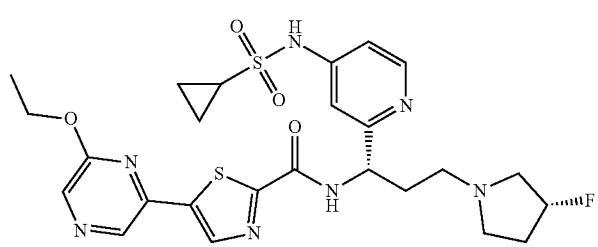 [SMILES: CCOc1cncc(-c2cnc(C(=O)N[C@@H](CCN3CC[C@@H](F)C3)c3cc(NS(=O)(=O)C4CC4)ccn3)s2)n1] |

TABLE 1-continued

Selected Compounds

| Compound | Structure |
| --- | --- |
| I-129 | 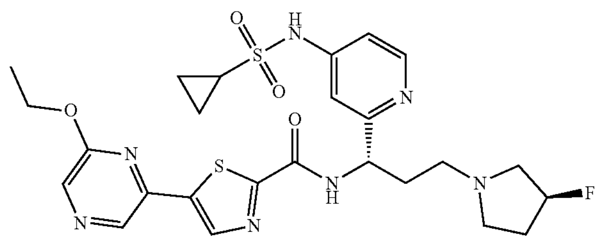 |
| I-130 | 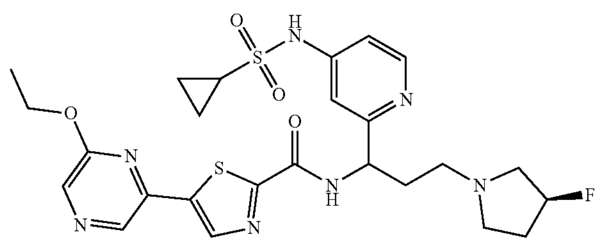 [SMILES: CCOc1cncc(-c2cnc(C(=O)N[C@@H](CCN3CC[C@H](F)C3)c3cc(NS(=O)(=O)C4CC4)ccn3)s2)n1] |
| I-131 | 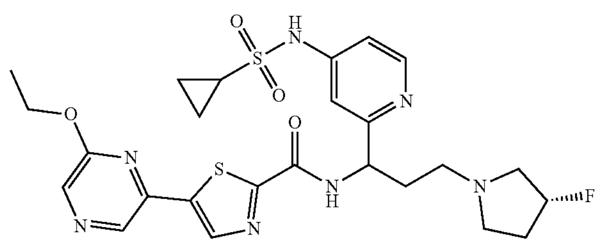 |
| I-132 | 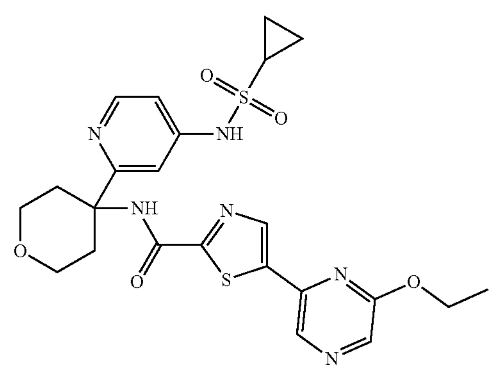 [SMILES: CCOc1cncc(-c2cnc(C(=O)NC3(c4cc(NS(=O)(=O)C5CC5)ccn4)CCOCC3)s2)n1] |
| I-133 | 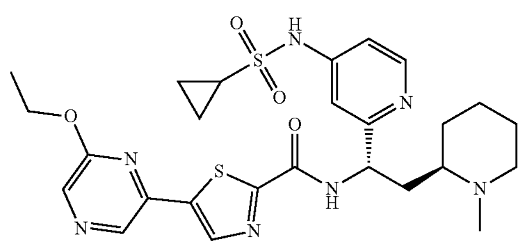 [SMILES: CCOc1cncc(-c2cnc(C(=O)N[C@@H](C[C@H]3CCCCN3C)c3cc(NS(=O)(=O)C4CC4)ccn3)s2)n1] |

TABLE 1-continued

Selected Compounds

| Compound | Structure |
|---|---|
| I-134 | 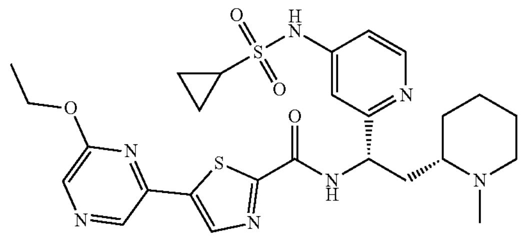 [SMILES: CCOc1cncc(-c2cnc(C(=O)N[C@@H](C[C@@H]3CCCCN3C)c3cc(NS(=O)(=O)C4CC4)ccn3)s2)n1] |
| I-135 | 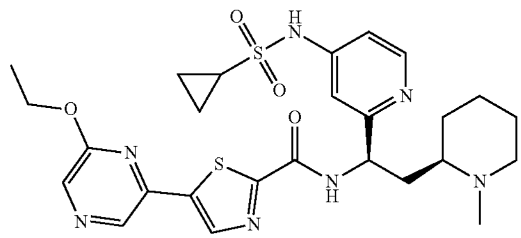 |
| I-136 | 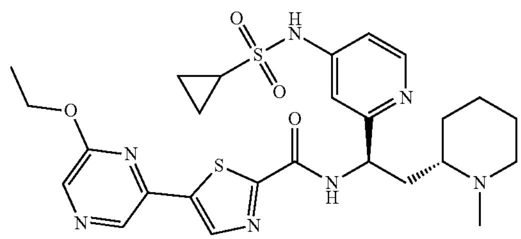 [SMILES: CCOc1cncc(-c2cnc(C(=O)N[C@H](C[C@@H]3CCCCN3C)c3cc(NS(=O)(=O)C4CC4)ccn3)s2)n1] |
| I-137 | 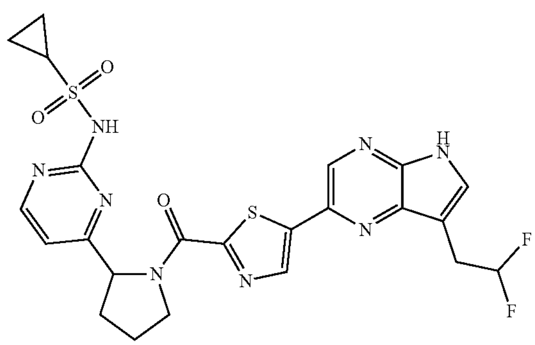 [SMILES: O=C(c1ncc(-c2cnc3[nH]cc(CC(F)F)c3n2)s1)N1CCCC1c1ccnc(NS(=O)(=O)C2CC2)n1] |
| I-138 | 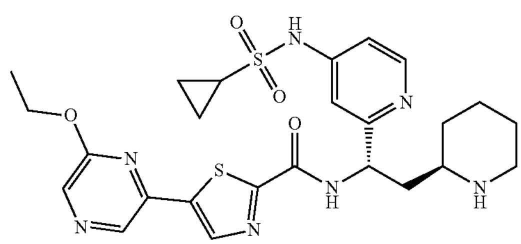 [SMILES: CCOc1cncc(-c2cnc(C(=O)N[C@@H](C[C@H]3CCCCN3)c3cc(NS(=O)(=O)C4CC4)ccn3)s2)n1] |
| I-139 | 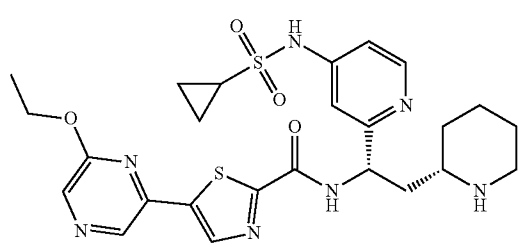 |

TABLE 1-continued
Selected Compounds
| Compound | Structure |
|---|---|
| I-140 | 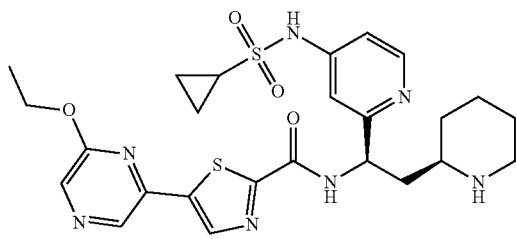 [SMILES: CCOc1cncc(-c2cnc(C(=O)N[C@H](C[C@H]3CCCCN3)c3cc(NS(=O)(=O)C4CC4)ccn3)s2)n1] |
| I-141 | 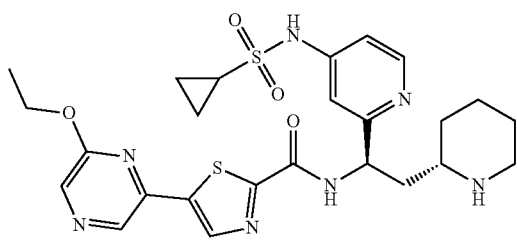 [SMILES: CCOc1cncc(-c2cnc(C(=O)N[C@H](C[C@@H]3CCCCN3)c3cc(NS(=O)(=O)C4CC4)ccn3)s2)n1] |
| I-142 | 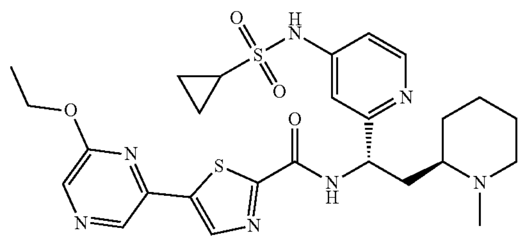 [SMILES: CCOc1cncc(-c2cnc(C(=O)N[C@@H](C[C@H]3CCCCN3C)c3cc(NS(=O)(=O)C4CC4)ccn3)s2)n1] |
| I-143 | 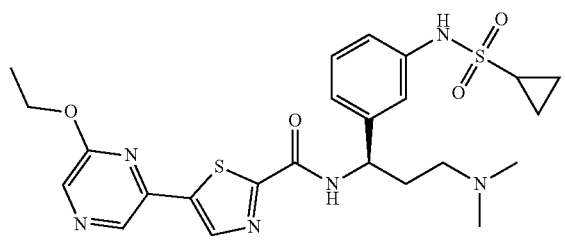 [SMILES: CCOc1cncc(-c2cnc(C(=O)N[C@H](CCN(C)C)c3cccc(NS(=O)(=O)C4CC4)c3)s2)n1] |
| I-144 | 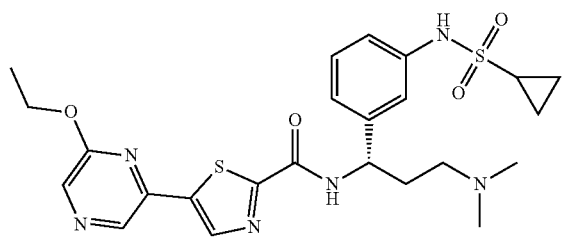 [SMILES: CCOc1cncc(-c2cnc(C(=O)N[C@@H](CCN(C)C)c3cccc(NS(=O)(=O)C4CC4)c3)s2)n1] |
| I-145 | 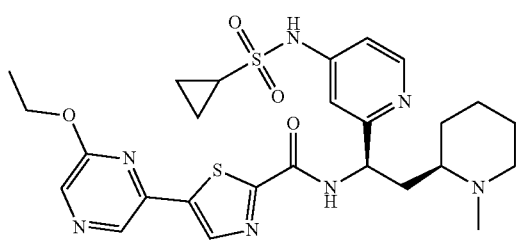 |

TABLE 1-continued
Selected Compounds
| Compound | Structure |
|---|---|
| I-146 | 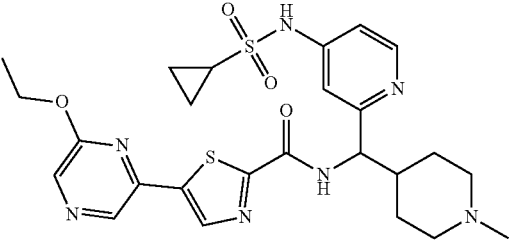 [SMILES: CCOc1cncc(-c2cnc(C(=O)NC(c3cc(NS(=O)(=O)C4CC4)ccn3)C3CCN(C)CC3)s2)n1] |
| I-147 | 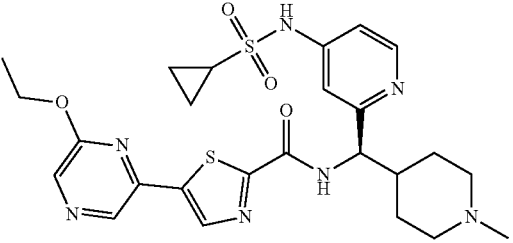 [SMILES: CCOc1cncc(-c2cnc(C(=O)N[C@@H](c3cc(NS(=O)(=O)C4CC4)ccn3)C3CCN(C)CC3)s2)n1] |
| I-148 | 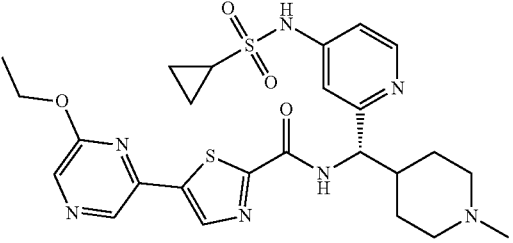 [SMILES: CCOc1cncc(-c2cnc(C(=O)N[C@H](c3cc(NS(=O)(=O)C4CC4)ccn3)C3CCN(C)CC3)s2)n1] |
| I-149 | 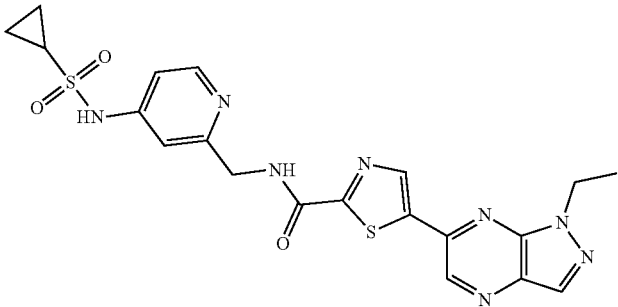 [SMILES: CCn1ncc2ncc(-c3cnc(C(=O)NCc4cc(NS(=O)(=O)C5CC5)ccn4)s3)nc21] |
| I-150 | 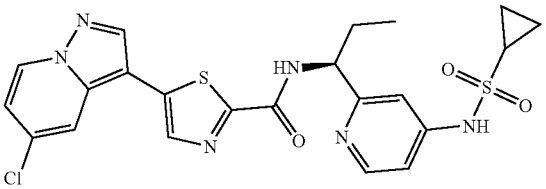 [SMILES: CC[C@H](NC(=O)c1ncc(-c2cnn3ccc(Cl)cc23)s1)c1cc(NS(=O)(=O)C2CC2)ccn1] |
| I-151 | 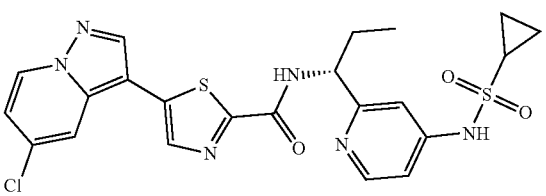 [SMILES: CC[C@@H](NC(=O)c1ncc(-c2cnn3ccc(Cl)cc23)s1)c1cc(NS(=O)(=O)C2CC2)ccn1] |

TABLE 1-continued
Selected Compounds
| Compound | Structure |
|---|---|
| I-152 | 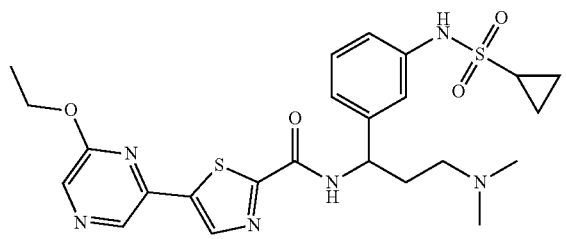 [SMILES: CCOc1cncc(-c2cnc(C(=O)NC(CCN(C)C)c3cccc(NS(=O)(=O)C4CC4)c3)s2)n1] |
| I-153 | 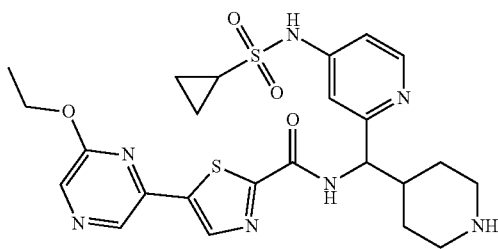 [SMILES: CCOc1cncc(-c2cnc(C(=O)NC(c3cc(NS(=O)(=O)C4CC4)ccn3)C3CCNCC3)s2)n1] |
| I-154 | 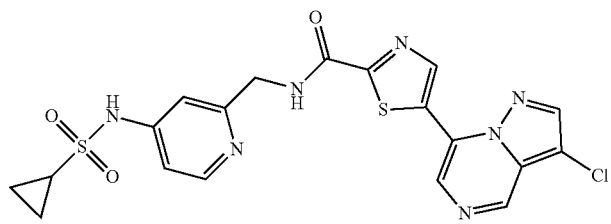 [SMILES: O=C(NCc1cc(NS(=O)(=O)C2CC2)ccn1)c1ncc(-c2cncc3c(Cl)cnn23)s1] |
| I-155 | 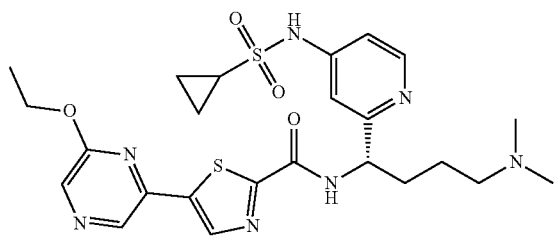 [SMILES: CCOc1cncc(-c2cnc(C(=O)N[C@@H](CCCN(C)C)c3cc(NS(=O)(=O)C4CC4)ccn3)s2)n1] |
| I-156 | 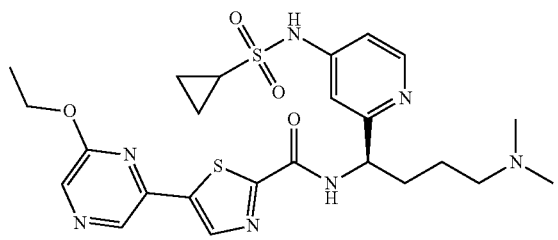 [SMILES: CCOc1cncc(-c2cnc(C(=O)N[C@H](CCCN(C)C)c3cc(NS(=O)(=O)C4CC4)ccn3)s2)n1] |
| I-157 | 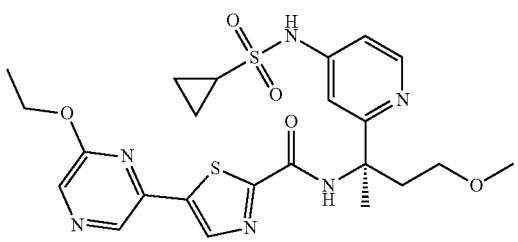 |

TABLE 1-continued

Selected Compounds

| Compound | Structure |
|---|---|
| I-158 | 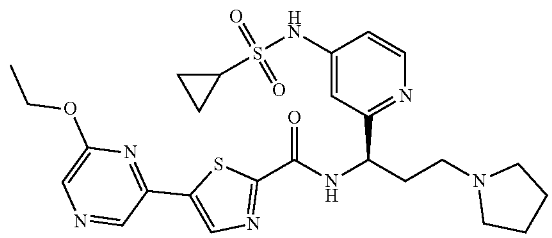 [SMILES: CCOc1cncc(-c2cnc(C(=O)N[C@H](CCN3CCCC3)c3cc(NS(=O)(=O)C4CC4)ccn3)s2)n1] |
| I-159 | 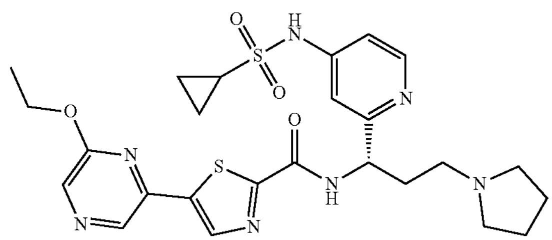 [SMILES: CCOc1cncc(-c2cnc(C(=O)N[C@@H](CCN3CCCC3)c3cc(NS(=O)(=O)C4CC4)ccn3)s2)n1] |
| I-160 | 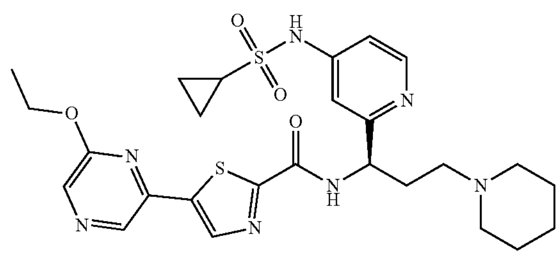 [SMILES: CCOc1cncc(-c2cnc(C(=O)N[C@H](CCN3CCCCC3)c3cc(NS(=O)(=O)C4CC4)ccn3)s2)n1] |
| I-161 | 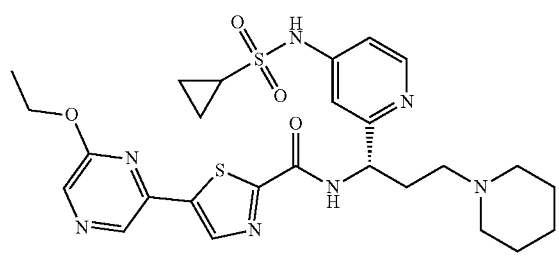 [SMILES: CCOc1cncc(-c2cnc(C(=O)N[C@@H](CCN3CCCCC3)c3cc(NS(=O)(=O)C4CC4)ccn3)s2)n1] |
| I-162 | 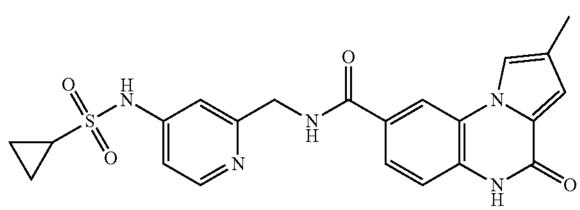 [SMILES: Cc1cc2c(=O)[nH]c3ccc(C(=O)NCc4cc(NS(=O)(=O)C5CC5)ccn4)cc3n2c1] |
| I-163 | 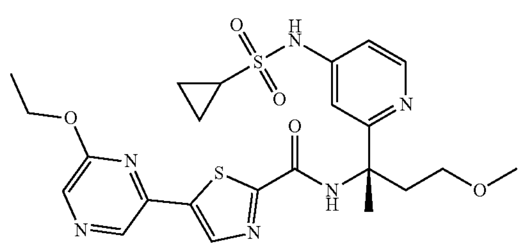 [SMILES: CCOc1cncc(-c2cnc(C(=O)N[C@@](C)(CCOC)c3cc(NS(=O)(=O)C4CC4)ccn3)s2)n1] |

TABLE 1-continued
Selected Compounds
| Compound | Structure |
|---|---|
| I-164 | 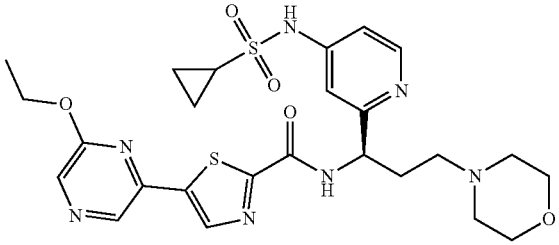 [SMILES: CCOc1cncc(-c2cnc(C(=O)N[C@H](CCN3CCOCC3)c3cc(NS(=O)(=O)C4CC4)ccn3)s2)n1] |
| I-165 | 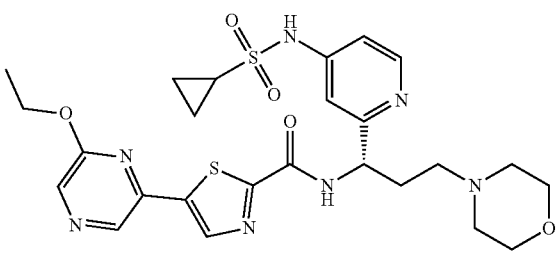 |
| I-166 | 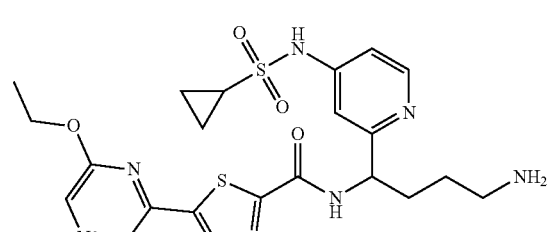 |
| I-167 | 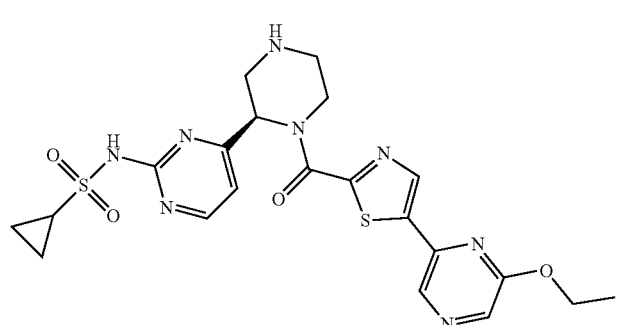 |
| I-168 | 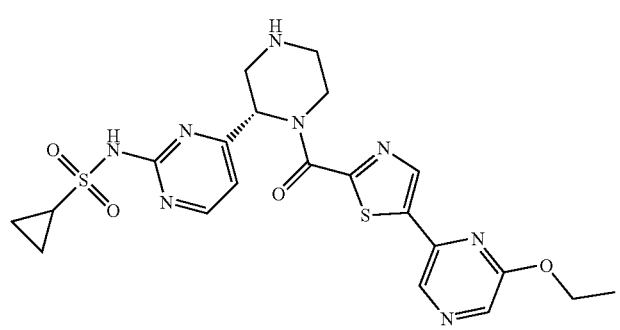 [SMILES: CCOc1cncc(-c2cnc(C(=O)N3CCNC[C@H]3c3ccnc(NS(=O)(=O)C4CC4)n3)s2)n1] |

TABLE 1-continued
Selected Compounds
| Compound | Structure |
|---|---|
| I-169 | 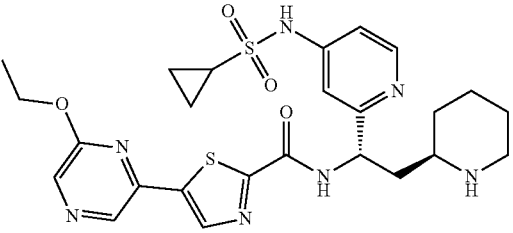 [SMILES: CCOc1cncc(-c2cnc(C(=O)N[C@@H](C[C@H]3CCCCN3)c3cc(NS(=O)(=O)C4CC4)ccn3)s2)n1] |
| I-170 | 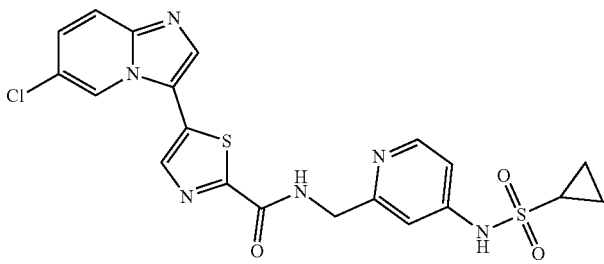 [SMILES: O=C(NCc1cc(NS(=O)(=O)C2CC2)ccn1)c1ncc(-c2cnc3ccc(Cl)cn23)s1] |
| I-171 | 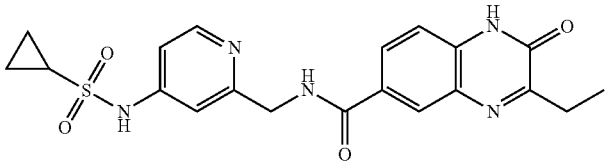 [SMILES: CCc1nc2cc(C(=O)NCc3cc(NS(=O)(=O)C4CC4)ccn3)ccc2[nH]c1=O] |
| I-172 | 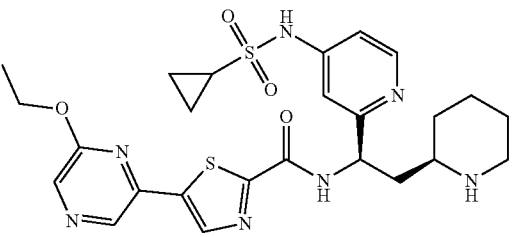 [SMILES: CCOc1cncc(-c2cnc(C(=O)N[C@H](C[C@H]3CCCCN3)c3cc(NS(=O)(=O)C4CC4)ccn3)s2)n1] |
| I-173 | 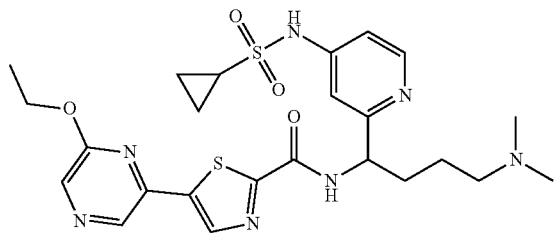 [SMILES: CCOc1cncc(-c2cnc(C(=O)NC(CCCN(C)C)c3cc(NS(=O)(=O)C4CC4)ccn3)s2)n1] |
| I-174 | 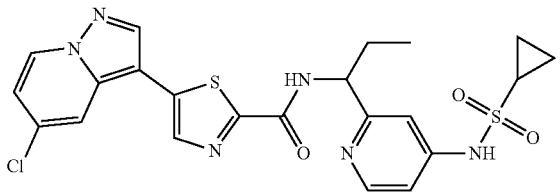 [SMILES: CCC(NC(=O)c1ncc(-c2cnn3ccc(Cl)cc23)s1)c1cc(NS(=O)(=O)C2CC2)ccn1] |

TABLE 1-continued

Selected Compounds

| Compound | Structure |
|---|---|
| I-175 | 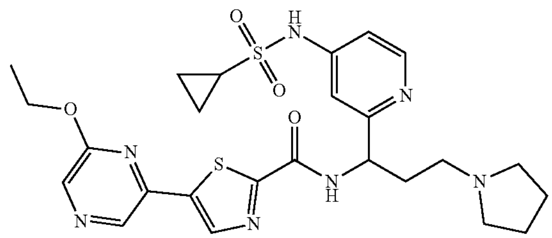 [SMILES: CCOc1cncc(-c2cnc(C(=O)NC(CCN3CCCC3)c3cc(NS(=O)(=O)C4CC4)ccn3)s2)n1] |
| I-176 | 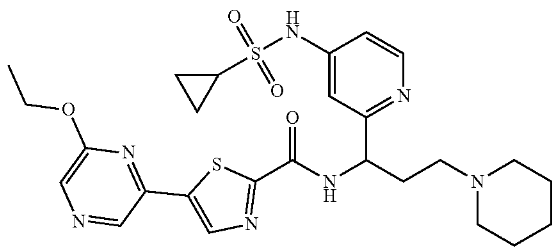 [SMILES: CCOc1cncc(-c2cnc(C(=O)NC(CCN3CCCCC3)c3cc(NS(=O)(=O)C4CC4)ccn3)s2)n1] |
| I-177 | 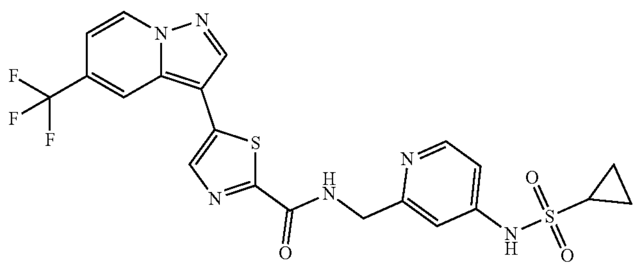 [SMILES: O=C(NCc1cc(NS(=O)(=O)C2CC2)ccn1)c1ncc(-c2cnn3ccc(C(F)(F)F)cc23)s1] |
| I-178 | 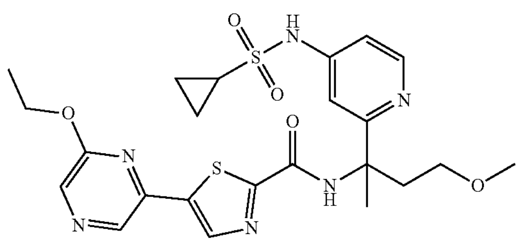 |
| I-179 | 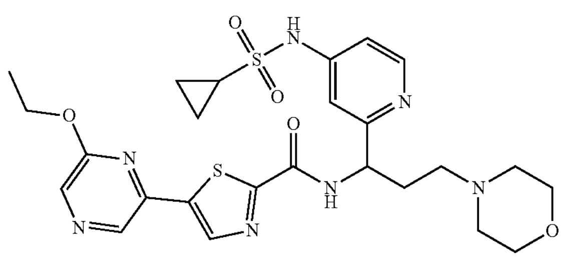 [SMILES: CCOc1cncc(-c2cnc(C(=O)NC(CCN3CCOCC3)c3cc(NS(=O)(=O)C4CC4)ccn3)s2)n1] |
| I-180 | 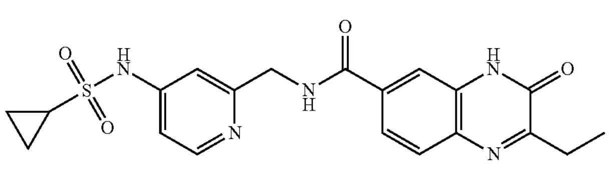 [SMILES: CCc1nc2ccc(C(=O)NCc3cc(NS(=O)(=O)C4CC4)ccn3)cc2[nH]c1=O] |

TABLE 1-continued
Selected Compounds
| Compound | Structure |
|---|---|
| I-181 | 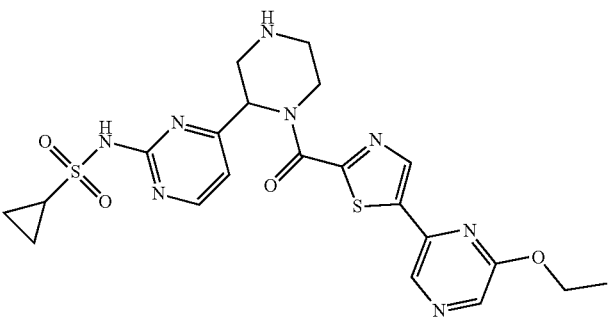 [SMILES: CCOc1cncc(-c2cnc(C(=O)N3CCNCC3c3ccnc(NS(=O)(=O)C4CC4)n3)s2)n1] |
| I-182 | 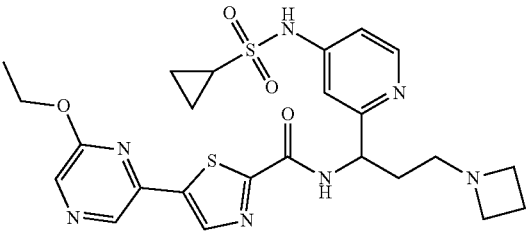 [SMILES: CCOc1cncc(-c2cnc(C(=O)NC(CCN3CCC3)c3cc(NS(=O)(=O)C4CC4)ccn3)s2)n1] |
| I-183 | 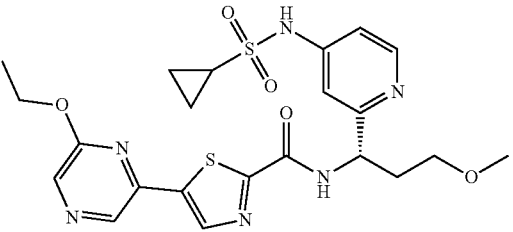 |
| I-184 | 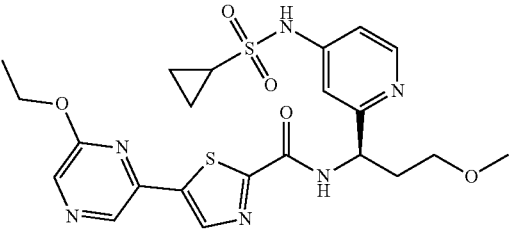 [SMILES: CCOc1cncc(-c2cnc(C(=O)N[C@H](CCOC)c3cc(NS(=O)(=O)C4CC4)ccn3)s2)n1] |
| I-185 | 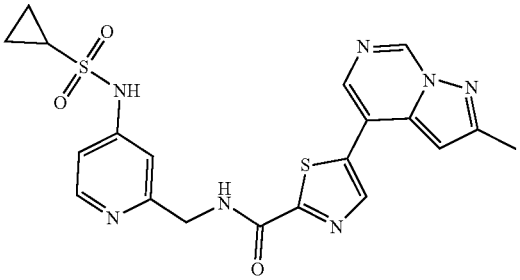 [SMILES: Cc1cc2c(-c3cnc(C(=O)NCc4cc(NS(=O)(=O)C5CC5)ccn4)s3)cncn2n1] |

TABLE 1-continued
Selected Compounds
| Compound | Structure |
|---|---|
| I-186 | 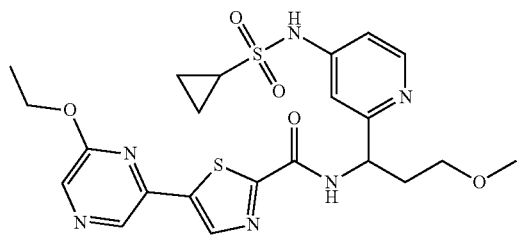 [SMILES: CCOc1cncc(-c2cnc(C(=O)NC(CCOC)c3cc(NS(=O)(=O)C4CC4)ccn3)s2)n1] |
| I-187 | 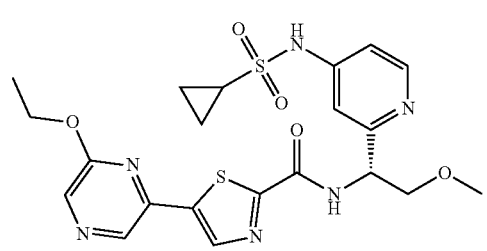 [SMILES: CCOc1cncc(-c2cnc(C(=O)N[C@@H](COC)c3cc(NS(=O)(=O)C4CC4)ccn3)s2)n1] |
| I-188 | 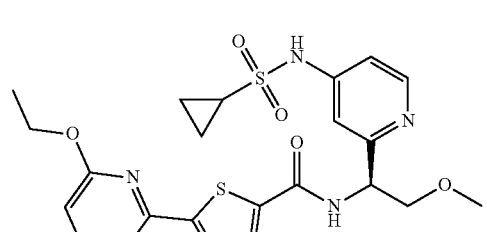 |
| I-189 | 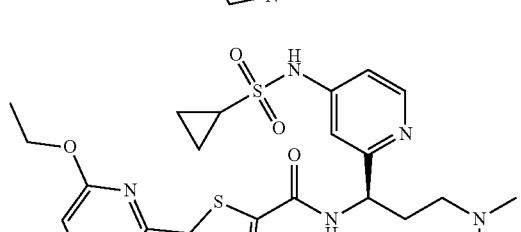 |
| I-190 | 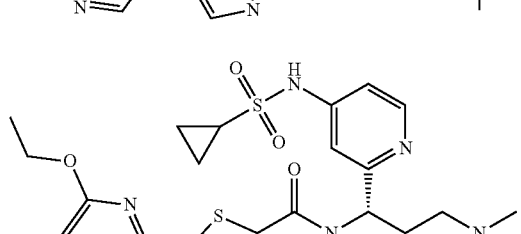 |
| I-191 | 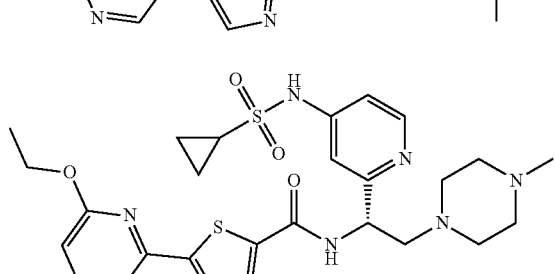 |

TABLE 1-continued

Selected Compounds

| Compound | Structure |
|---|---|
| I-192 | (structure) |
| I-193 | (structure) |
| I-194 | (structure) |
| I-195 | (structure) |
| I-196 | (structure) |
| I-197 | (structure) |

TABLE 1-continued
Selected Compounds
| Compound | Structure |
|---|---|
| I-198 | 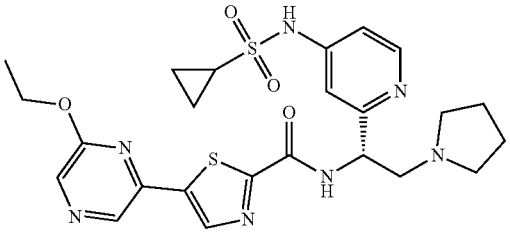 [SMILES: CCOc1cncc(-c2cnc(C(=O)N[C@@H](CN3CCCC3)c3cc(NS(=O)(=O)C4CC4)ccn3)s2)n1] |
| I-199 | 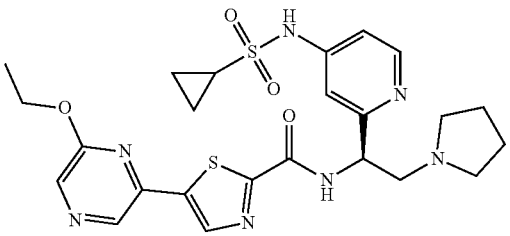 [SMILES: CCOc1cncc(-c2cnc(C(=O)N[C@H](CN3CCCC3)c3cc(NS(=O)(=O)C4CC4)ccn3)s2)n1] |
| I-200 | 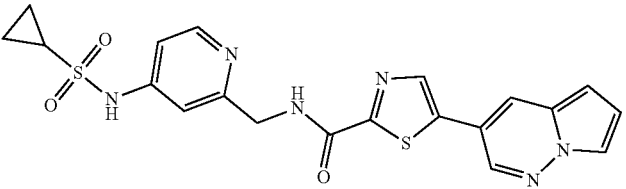 [SMILES: O=C(NCc1cc(NS(=O)(=O)C2CC2)ccn1)c1ncc(-c2cnn3cccc3c2)s1] |
| I-201 | 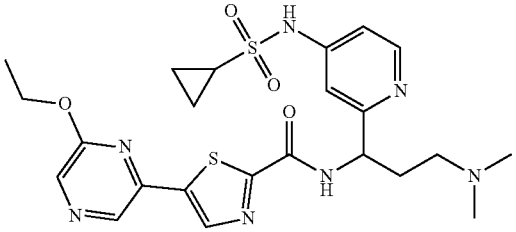 [SMILES: CCOc1cncc(-c2cnc(C(=O)NC(CCN(C)C)c3cc(NS(=O)(=O)C4CC4)ccn3)s2)n1] |
| I-202 | 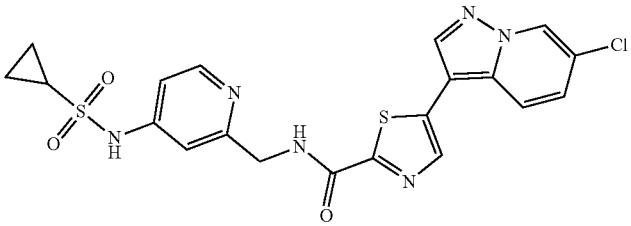 [SMILES: O=C(NCc1cc(NS(=O)(=O)C2CC2)ccn1)c1ncc(-c2cnn3cc(Cl)ccc23)s1] |
| I-203 | 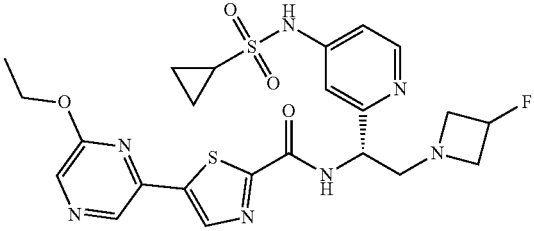 [SMILES: CCOc1cncc(-c2cnc(C(=O)N[C@@H](CN3CC(F)C3)c3cc(NS(=O)(=O)C4CC4)ccn3)s2)n1] |

TABLE 1-continued
Selected Compounds
| Compound | Structure |
|---|---|
| I-204 | 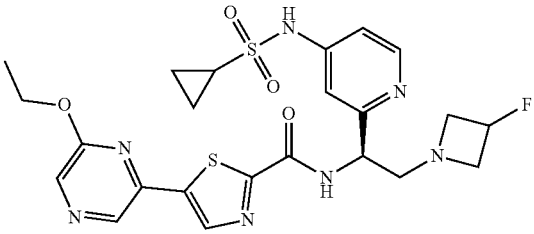 [SMILES: CCOc1cncc(-c2cnc(C(=O)N[C@H](CN3CC(F)C3)c3cc(NS(=O)(=O)C4CC4)ccn3)s2)n1] |
| I-205 | 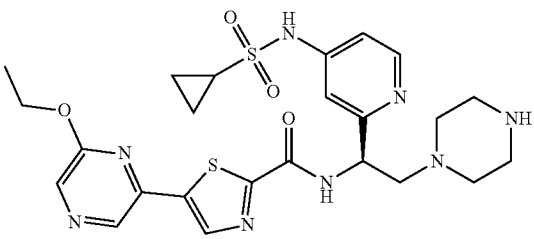 [SMILES: CCOc1cncc(-c2cnc(C(=O)N[C@H](CN3CCNCC3)c3cc(NS(=O)(=O)C4CC4)ccn3)s2)n1] |
| I-206 | 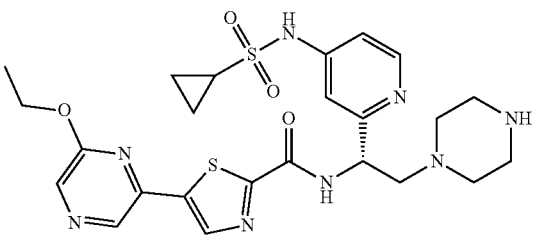 |
| I-207 | 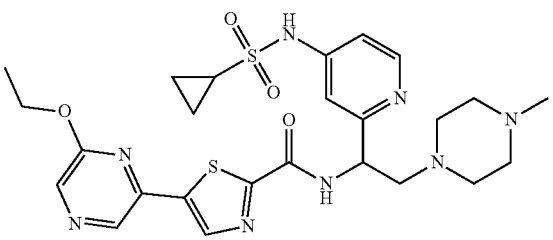 [SMILES: CCOc1cncc(-c2cnc(C(=O)NC(CN3CCN(C)CC3)c3cc(NS(=O)(=O)C4CC4)ccn3)s2)n1] |
| I-208 | 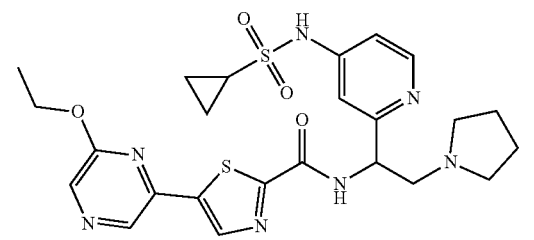 [SMILES: CCOc1cncc(-c2cnc(C(=O)NC(CN3CCCC3)c3cc(NS(=O)(=O)C4CC4)ccn3)s2)n1] |
| I-209 | 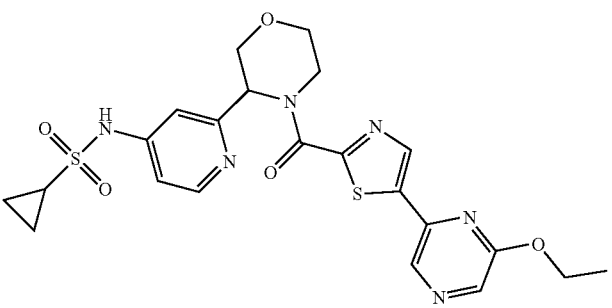 [SMILES: CCOc1cncc(-c2cnc(C(=O)N3CCOCC3c3cc(NS(=O)(=O)C4CC4)ccn3)s2)n1] |

TABLE 1-continued

Selected Compounds

| Compound | Structure |
|---|---|
| I-210 | 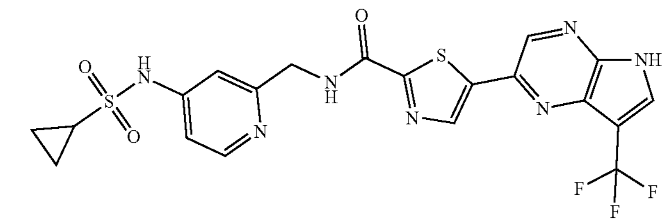 [SMILES: O=C(NCc1cc(NS(=O)(=O)C2CC2)ccn1)c1ncc(-c2cnc3[nH]cc(C(F)(F)F)c3n2)s1] |
| I-211 | 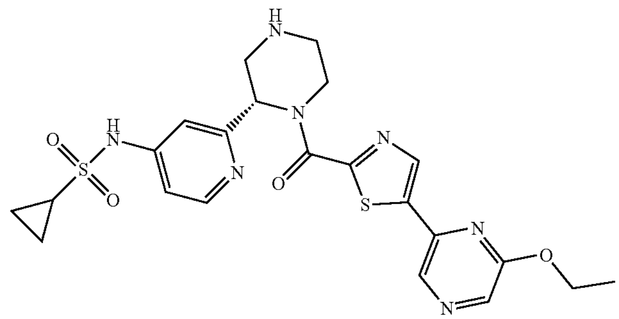 [SMILES: CCOc1cncc(-c2cnc(C(=O)N3CCNC[C@H]3c3cc(NS(=O)(=O)C4CC4)ccn3)s2)n1] |
| I-212 | 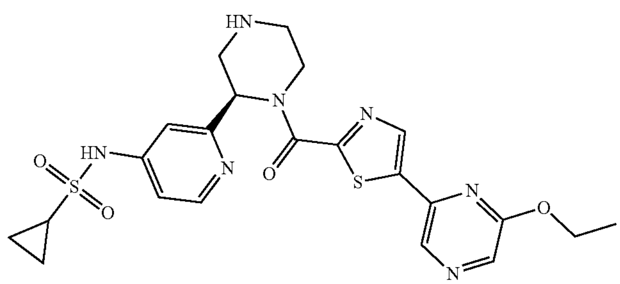 [SMILES: CCOc1cncc(-c2cnc(C(=O)N3CCNC[C@@H]3c3cc(NS(=O)(=O)C4CC4)ccn3)s2)n1] |
| I-213 | 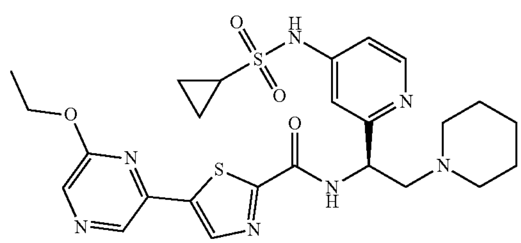 [SMILES: CCOc1cncc(-c2cnc(C(=O)N[C@H](CN3CCCCC3)c3cc(NS(=O)(=O)C4CC4)ccn3)s2)n1] |
| I-214 | 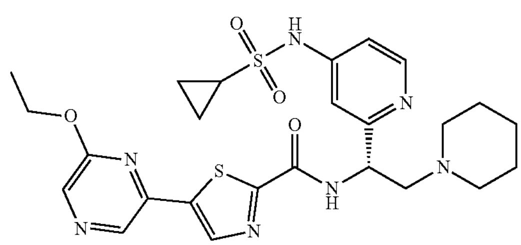 [SMILES: CCOc1cncc(-c2cnc(C(=O)N[C@@H](CN3CCCCC3)c3cc(NS(=O)(=O)C4CC4)ccn3)s2)n1] |
| I-215 | 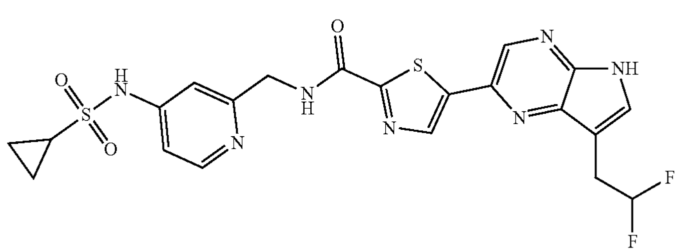 [SMILES: O=C(NCc1cc(NS(=O)(=O)C2CC2)ccn1)c1ncc(-c2cnc3[nH]cc(CC(F)F)c3n2)s1] |

TABLE 1-continued
Selected Compounds
| Compound | Structure |
|---|---|
| I-216 | 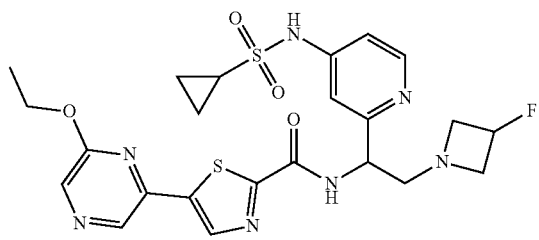 [SMILES: CCOc1cncc(-c2cnc(C(=O)NC(CN3CC(F)C3)c3cc(NS(=O)(=O)C4CC4)ccn3)s2)n1] |
| I-217 | 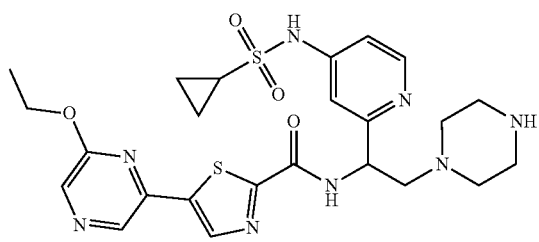 [SMILES: CCOc1cncc(-c2cnc(C(=O)NC(CN3CCNCC3)c3cc(NS(=O)(=O)C4CC4)ccn3)s2)n1] |
| I-218 | 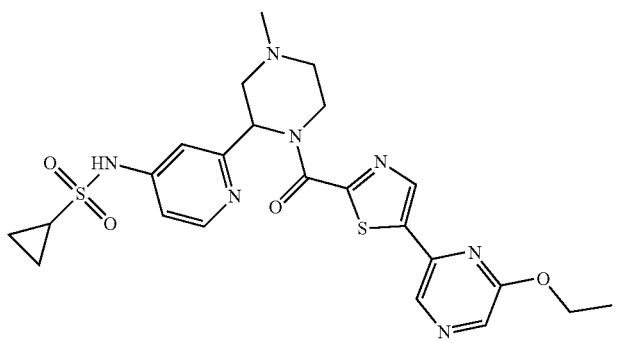 [SMILES: CCOc1cncc(-c2cnc(C(=O)N3CCN(C)CC3c3cc(NS(=O)(=O)C4CC4)ccn3)s2)n1] |
| I-219 | 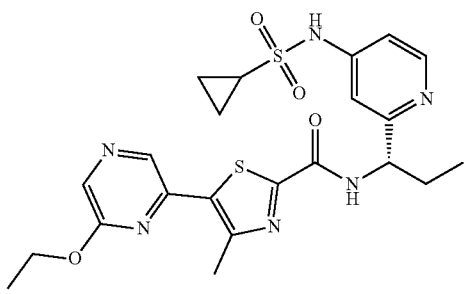 |
| I-220 | 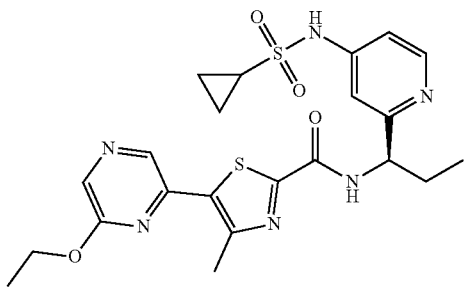 [SMILES: CCOc1cncc(-c2sc(C(=O)N[C@H](CC)c3cc(NS(=O)(=O)C4CC4)ccn3)nc2C)n1] |

TABLE 1-continued
Selected Compounds
| Compound | Structure |
|---|---|
| I-221 | 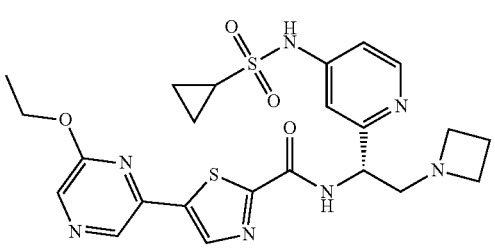 [SMILES: CCOc1cncc(-c2cnc(C(=O)N[C@@H](CN3CCC3)c3cc(NS(=O)(=O)C4CC4)ccn3)s2)n1] |
| I-222 | 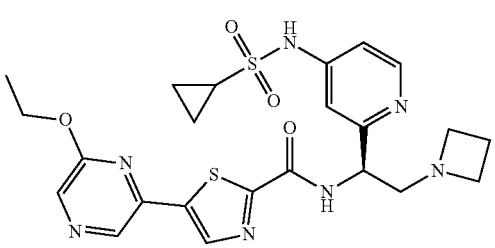 |
| I-223 | 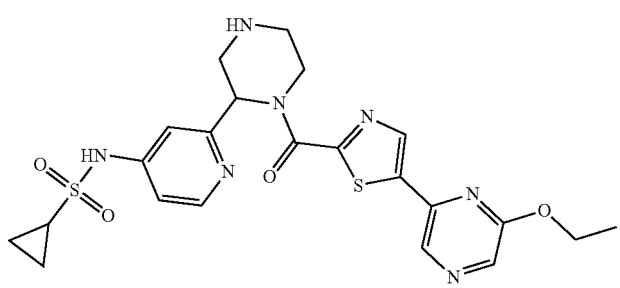 [SMILES: CCOc1cncc(-c2cnc(C(=O)N3CCNCC3c3cc(NS(=O)(=O)C4CC4)ccn3)s2)n1] |
| I-224 | 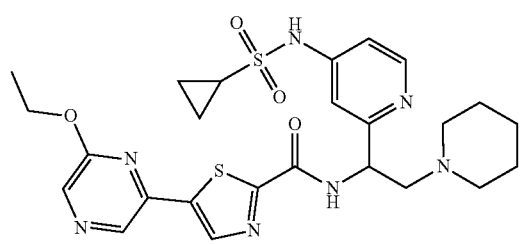 [SMILES: CCOc1cncc(-c2cnc(C(=O)NC(CN3CCCCC3)c3cc(NS(=O)(=O)C4CC4)ccn3)s2)n1] |
| I-225 | 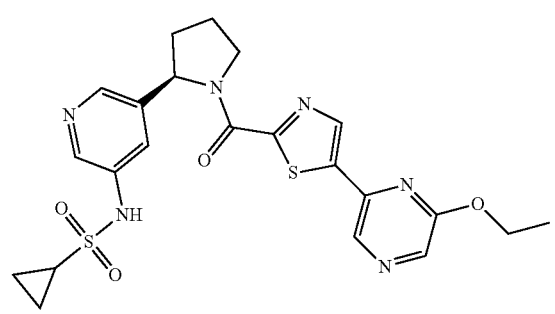 [SMILES: CCOc1cncc(-c2cnc(C(=O)N3CCC[C@@H]3c3cncc(NS(=O)(=O)C4CC4)c3)s2)n1] |

TABLE 1-continued

Selected Compounds

| Compound | Structure |
|---|---|
| I-226 | 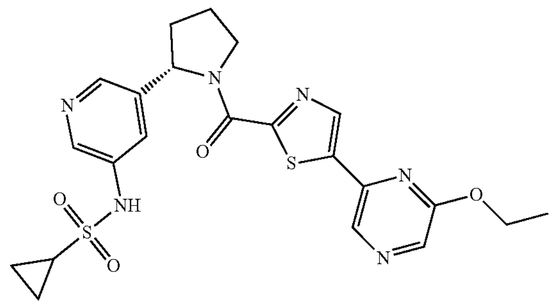 [SMILES: CCOc1cncc(-c2cnc(C(=O)N3CCC[C@H]3c3cncc(NS(=O)(=O)C4CC4)c3)s2)n1] |
| I-227 | 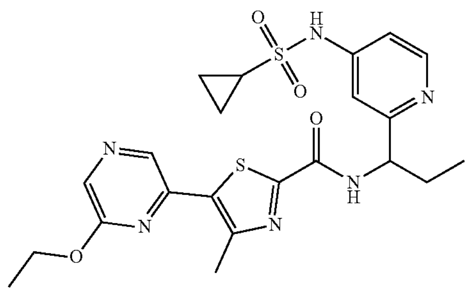 [SMILES: CCOc1cncc(-c2sc(C(=O)NC(CC)c3cc(NS(=O)(=O)C4CC4)ccn3)nc2C)n1] |
| I-228 | 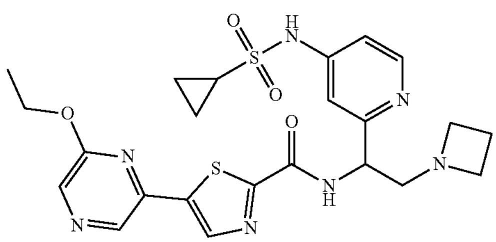 [SMILES: CCOc1cncc(-c2cnc(C(=O)NC(CN3CCC3)c3cc(NS(=O)(=O)C4CC4)ccn3)s2)n1] |
| I-229 | 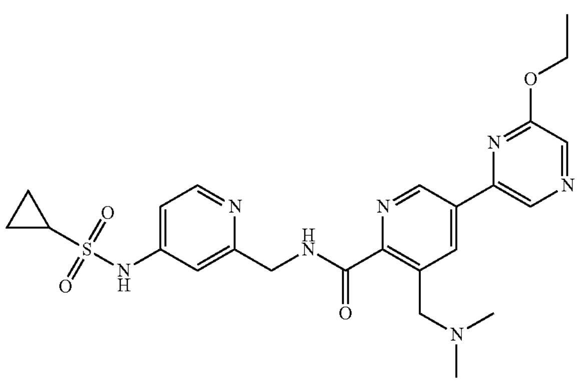 [SMILES: CCOc1cncc(-c2cnc(C(=O)NCc3cc(NS(=O)(=O)C4CC4)ccn3)c(CN(C)C)c2)n1] |
| I-230 | 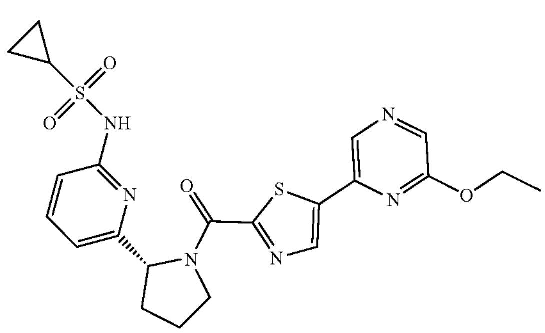 [SMILES: CCOc1cncc(-c2cnc(C(=O)N3CCC[C@@H]3c3cccc(NS(=O)(=O)C4CC4)n3)s2)n1] |

TABLE 1-continued
Selected Compounds
| Compound | Structure |
|---|---|
| I-231 | 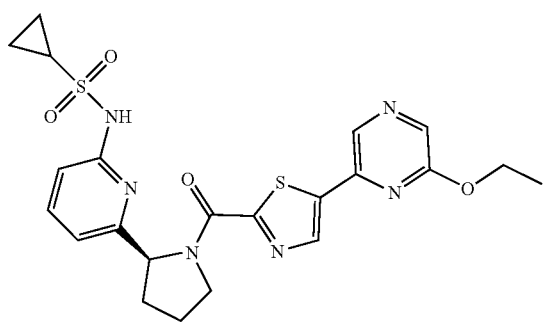 [SMILES: CCOc1cncc(-c2cnc(C(=O)N3CCC[C@H]3c3cccc(NS(=O)(=O)C4CC4)n3)s2)n1] |
| I-232 | 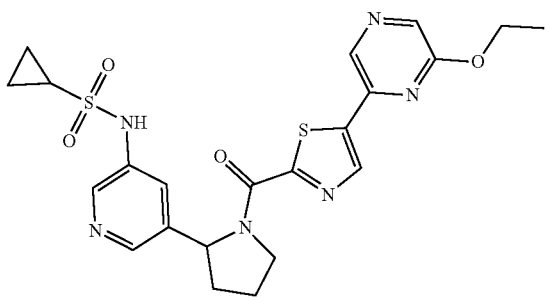 [SMILES: CCOc1cncc(-c2cnc(C(=O)N3CCCC3c3cncc(NS(=O)(=O)C4CC4)c3)s2)n1] |
| I-233 | 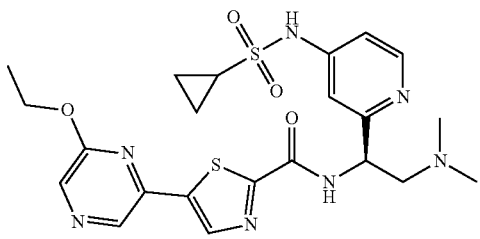 [SMILES: CCOc1cncc(-c2cnc(C(=O)N[C@H](CN(C)C)c3cc(NS(=O)(=O)C4CC4)ccn3)s2)n1] |
| I-234 | 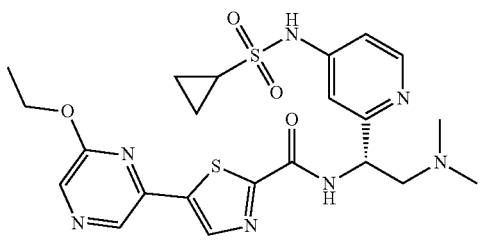 [SMILES: CCOc1cncc(-c2cnc(C(=O)N[C@@H](CN(C)C)c3cc(NS(=O)(=O)C4CC4)ccn3)s2)n1] |
| I-235 | 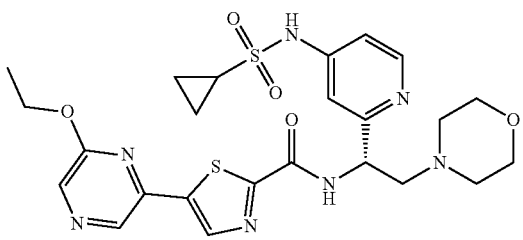 [SMILES: CCOc1cncc(-c2cnc(C(=O)N[C@@H](CN3CCOCC3)c3cc(NS(=O)(=O)C4CC4)ccn3)s2)n1] |

TABLE 1-continued

Selected Compounds

| Compound | Structure |
|---|---|
| I-236 | 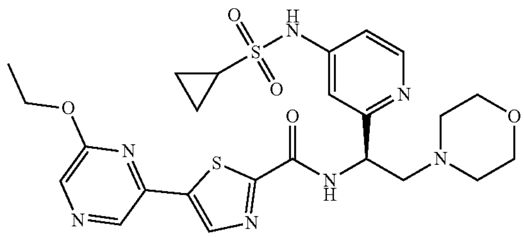 [SMILES: CCOc1cncc(-c2cnc(C(=O)N[C@H](CN3CCOCC3)c3cc(NS(=O)(=O)C4CC4)ccn3)s2)n1] |
| I-237 | 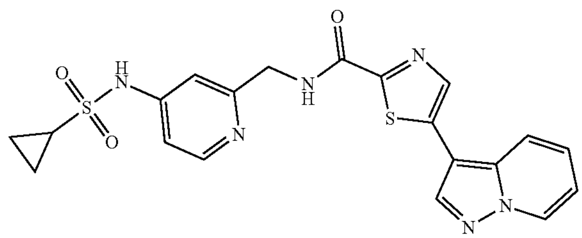 [SMILES: O=C(NCc1cc(NS(=O)(=O)C2CC2)ccn1)c1ncc(-c2cnn3ccccc23)s1] |
| I-238 | 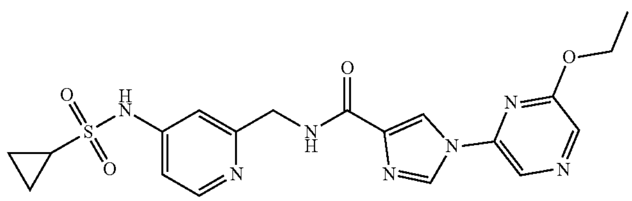 [SMILES: CCOc1cncc(-n2cnc(C(=O)NCc3cc(NS(=O)(=O)C4CC4)ccn3)c2)n1] |
| I-239 | 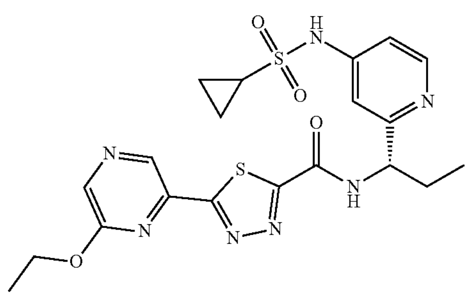 [SMILES: CCOc1cncc(-c2nnc(C(=O)N[C@@H](CC)c3cc(NS(=O)(=O)C4CC4)ccn3)s2)n1] |
| I-240 | 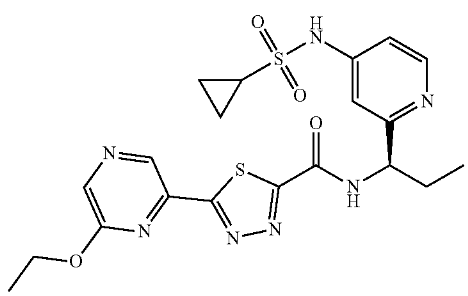 [SMILES: CCOc1cncc(-c2nnc(C(=O)N[C@H](CC)c3cc(NS(=O)(=O)C4CC4)ccn3)s2)n1] |
| I-241 | 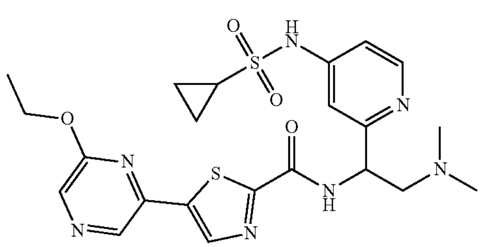 |

137
TABLE 1-continued
Selected Compounds
| Compound | Structure |
|----------|-----------|
| I-242 | 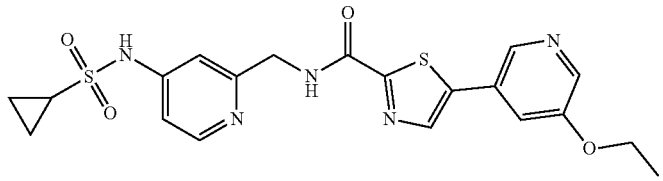 [SMILES: CCOc1cncc(-c2cnc(C(=O)NCc3cc(NS(=O)(=O)C4CC4)ccn3)s2)c1] |
| I-243 | 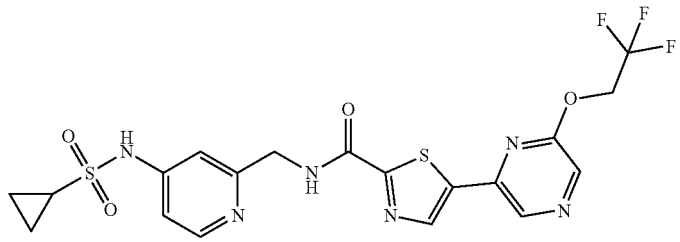 [SMILES: O=C(NCc1cc(NS(=O)(=O)C2CC2)ccn1)c1ncc(-c2cncc(OCC(F)(F)F)n2)s1] |
| I-244 | 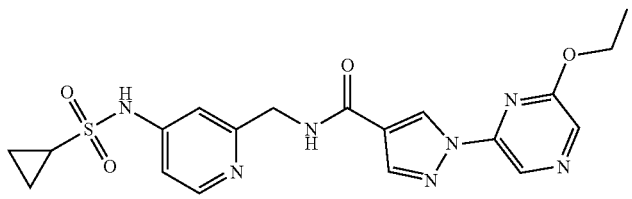 |
| I-245 | 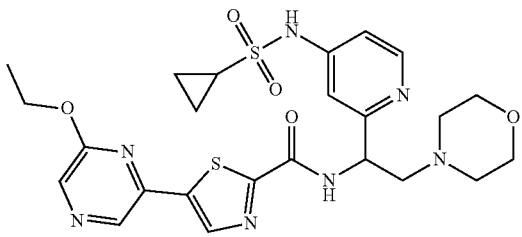 |
| I-246 | 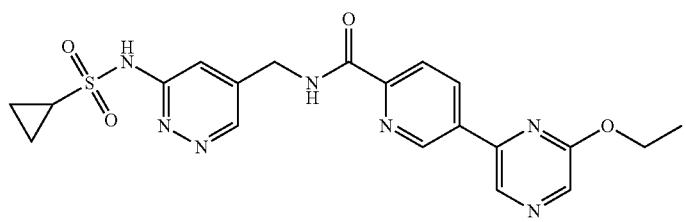 [SMILES: CCOc1cncc(-c2ccc(C(=O)NCc3cnnc(NS(=O)(=O)C4CC4)c3)nc2)n1] |
| I-247 | 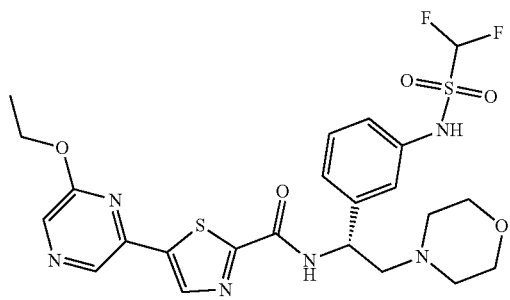 [SMILES: CCOc1cncc(-c2cnc(C(=O)N[C@@H](CN3CCOCC3)c3cccc(NS(=O)(=O)C(F)F)c3)s2)n1] |

TABLE 1-continued

Selected Compounds

| Compound | Structure |
|---|---|
| I-248 | 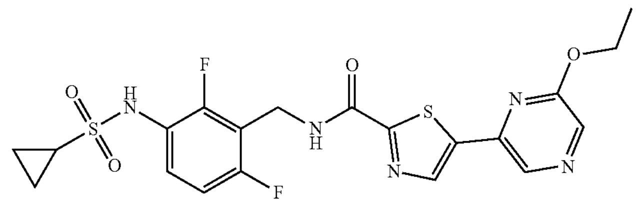 [SMILES: CCOc1cncc(-c2cnc(C(=O)NCc3c(F)ccc(NS(=O)(=O)C4CC4)c3F)s2)n1] |
| I-249 | 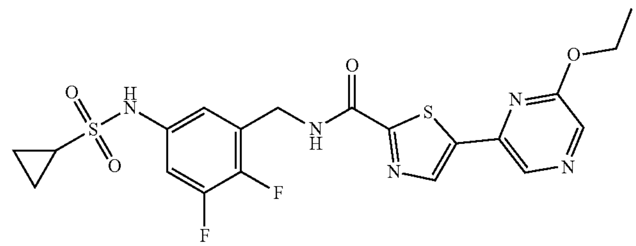 [SMILES: CCOc1cncc(-c2cnc(C(=O)NCc3cc(NS(=O)(=O)C4CC4)cc(F)c3F)s2)n1] |
| I-250 | 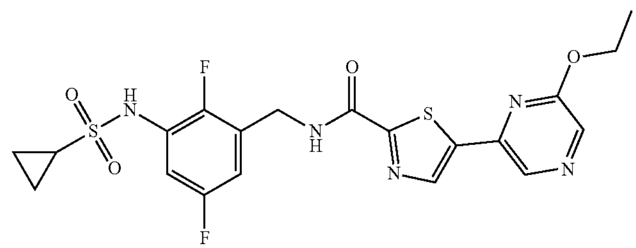 [SMILES: CCOc1cncc(-c2cnc(C(=O)NCc3cc(F)cc(NS(=O)(=O)C4CC4)c3F)s2)n1] |
| I-251 | 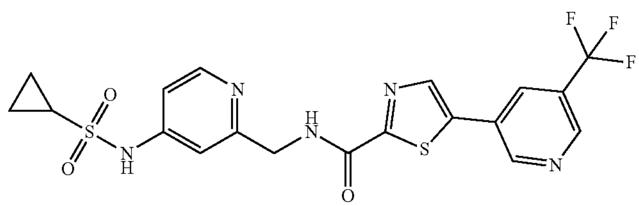 [SMILES: O=C(NCc1cc(NS(=O)(=O)C2CC2)ccn1)c1ncc(-c2cncc(C(F)(F)F)c2)s1] |
| I-252 | 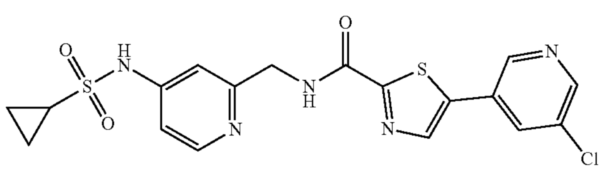 [SMILES: O=C(NCc1cc(NS(=O)(=O)C2CC2)ccn1)c1ncc(-c2cncc(Cl)c2)s1] |
| I-253 | 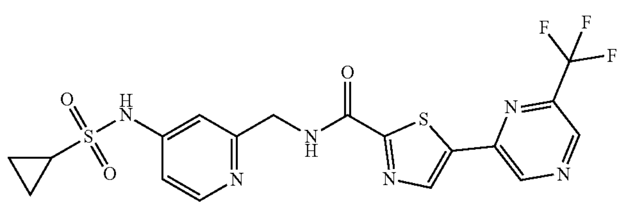 [SMILES: O=C(NCc1cc(NS(=O)(=O)C2CC2)ccn1)c1ncc(-c2cncc(C(F)(F)F)n2)s1] |
| I-254 | 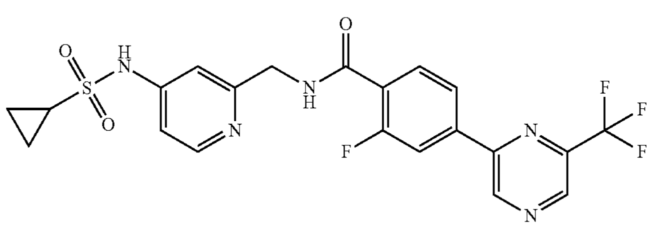 [SMILES: O=C(NCc1cc(NS(=O)(=O)C2CC2)ccn1)c1ccc(-c2cncc(C(F)(F)F)n2)cc1F] |

TABLE 1-continued

Selected Compounds

| Compound | Structure |
|---|---|
| I-255 | 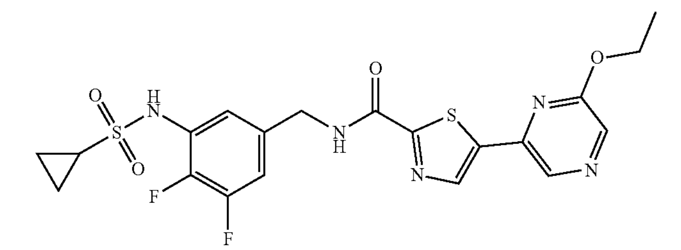 [SMILES: CCOc1cncc(-c2cnc(C(=O)NCc3cc(F)c(F)c(NS(=O)(=O)C4CC4)c3)s2)n1] |
| I-256 | 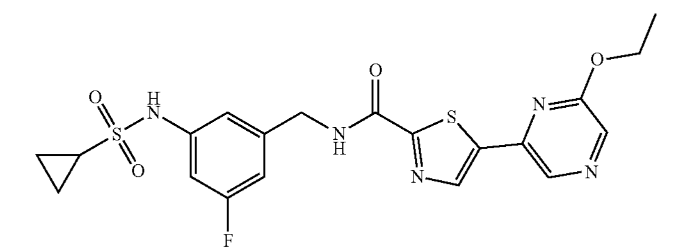 [SMILES: CCOc1cncc(-c2cnc(C(=O)NCc3cc(F)cc(NS(=O)(=O)C4CC4)c3)s2)n1] |
| I-257 | 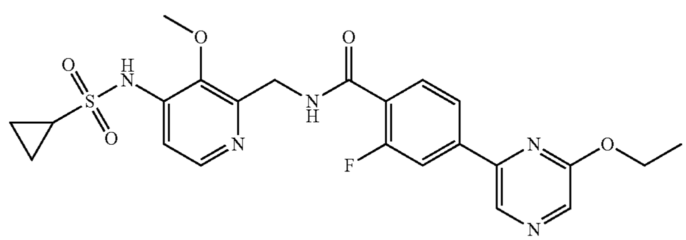 [SMILES: CCOc1cncc(-c2ccc(C(=O)NCc3nccc(NS(=O)(=O)C4CC4)c3OC)c(F)c2)n1] |
| I-258 | 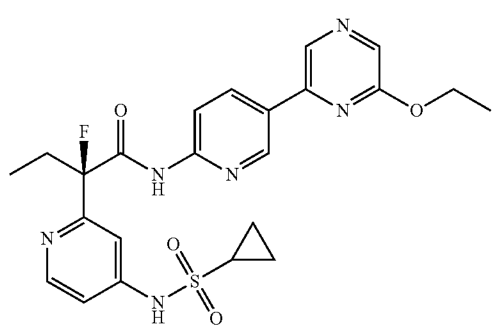 [SMILES: CCOc1cncc(-c2ccc(NC(=O)[C@@](F)(CC)c3cc(NS(=O)(=O)C4CC4)ccn3)nc2)n1] |
| I-259 | 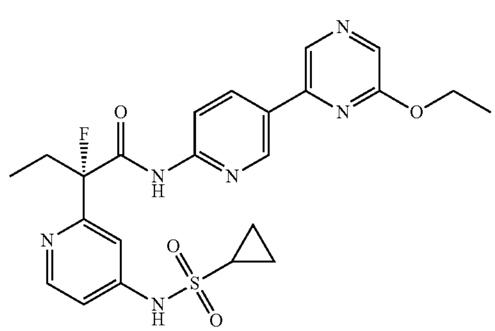 [SMILES: CCOc1cncc(-c2ccc(NC(=O)[C@](F)(CC)c3cc(NS(=O)(=O)C4CC4)ccn3)nc2)n1] |

TABLE 1-continued

Selected Compounds

| Compound | Structure |
|---|---|
| I-260 | 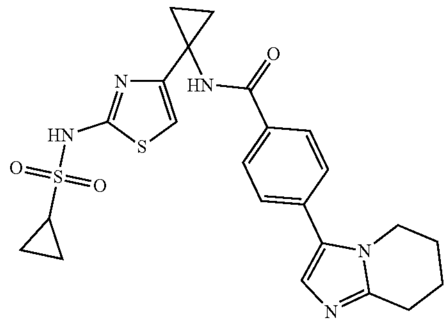 [SMILES: O=C(NC1(c2csc(NS(=O)(=O)C3CC3)n2)CC1)c1ccc(-c2cnc3n2CCCC3)cc1] |
| I-261 | 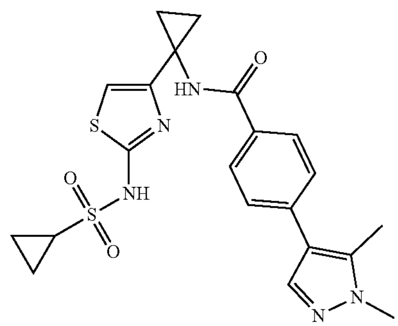 [SMILES: Cc1c(-c2ccc(C(=O)NC3(c4csc(NS(=O)(=O)C5CC5)n4)CC3)cc2)cnn1C] |
| I-262 | 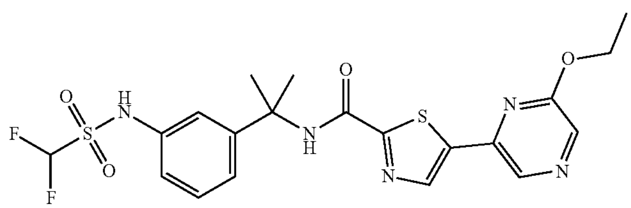 [SMILES: CCOc1cncc(-c2cnc(C(=O)NC(C)(C)c3cccc(NS(=O)(=O)C(F)F)c3)s2)n1] |
| I-263 | 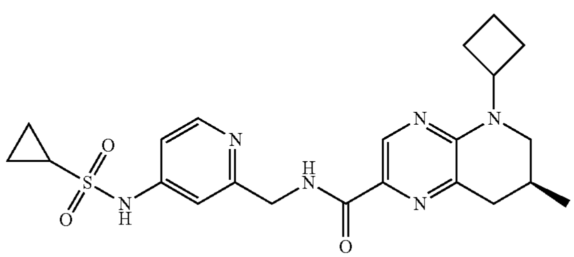 [SMILES: C[C@H]1Cc2nc(C(=O)NCc3cc(NS(=O)(=O)C4CC4)ccn3)cnc2N(C2CCC2)C1] |
| I-264 | 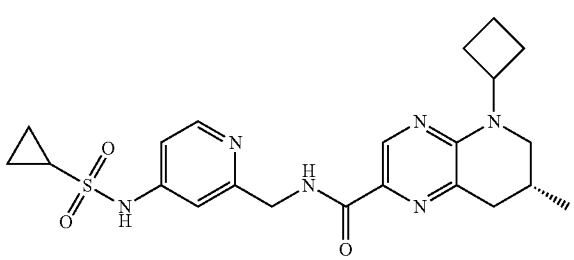 [SMILES: C[C@@H]1Cc2nc(C(=O)NCc3cc(NS(=O)(=O)C4CC4)ccn3)cnc2N(C2CCC2)C1] |
| I-265 | 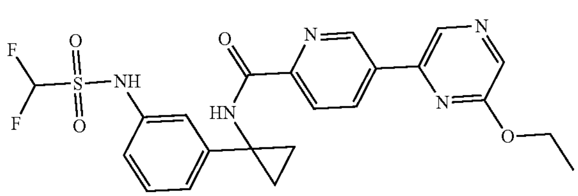 [SMILES: CCOc1cncc(-c2ccc(C(=O)NC3(c4cccc(NS(=O)(=O)C(F)F)c4)CC3)nc2)n1] |

TABLE 1-continued

Selected Compounds

| Compound | Structure |
|----------|-----------|
| I-266 | 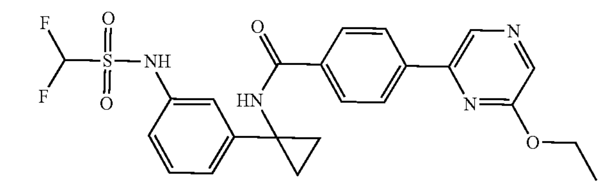 [SMILES: CCOc1cncc(-c2ccc(C(=O)NC3(c4cccc(NS(=O)(=O)C(F)F)c4)CC3)cc2)n1] |
| I-267 | 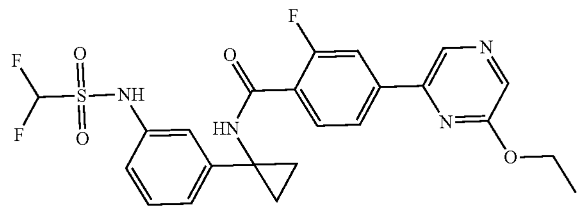 [SMILES: CCOc1cncc(-c2ccc(C(=O)NC3(c4cccc(NS(=O)(=O)C(F)F)c4)CC3)c(F)c2)n1] |
| I-269 | 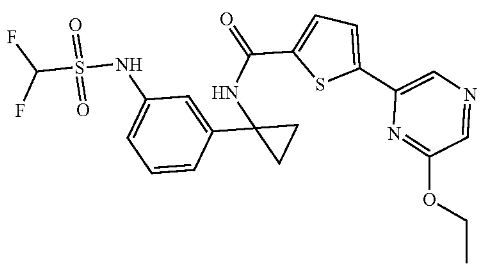 [SMILES: CCOc1cncc(-c2ccc(C(=O)NC3(c4cccc(NS(=O)(=O)C(F)F)c4)CC3)s2)n1] |
| I-270 | 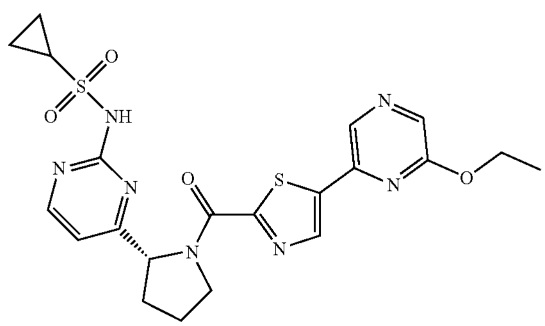 [SMILES: CCOc1cncc(-c2cnc(C(=O)N3CCC[C@@H]3c3ccnc(NS(=O)(=O)C4CC4)n3)s2)n1] |
| I-271 | 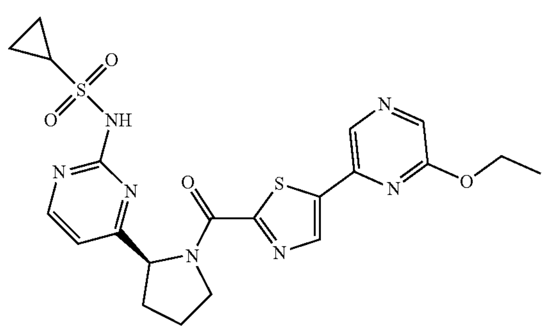 [SMILES: CCOc1cncc(-c2cnc(C(=O)N3CCC[C@H]3c3ccnc(NS(=O)(=O)C4CC4)n3)s2)n1] |
| I-272 | 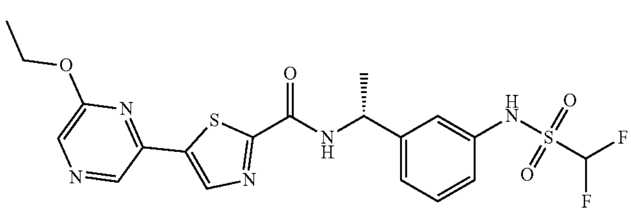 [SMILES: CCOc1cncc(-c2cnc(C(=O)N[C@H](C)c3cccc(NS(=O)(=O)C(F)F)c3)s2)n1] |

TABLE 1-continued

Selected Compounds

| Compound | Structure |
|---|---|
| I-273 | 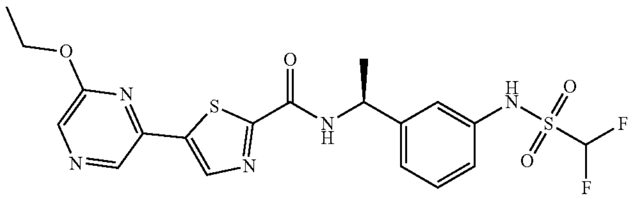 [SMILES: CCOc1cncc(-c2cnc(C(=O)N[C@@H](C)c3cccc(NS(=O)(=O)C(F)F)c3)s2)n1] |
| I-274 | 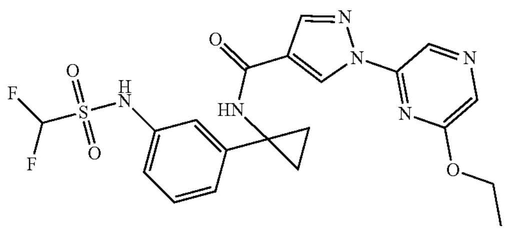 [SMILES: CCOc1cncc(-n2cc(C(=O)NC3(c4cccc(NS(=O)(=O)C(F)F)c4)CC3)cn2)n1] |
| I-275 | 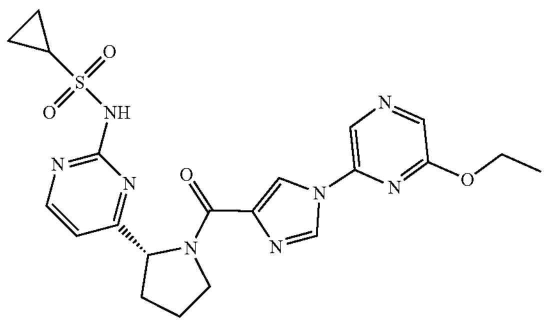 [SMILES: CCOc1cncc(-n2cnc(C(=O)N3CCC[C@@H]3c3ccnc(NS(=O)(=O)C4CC4)n3)c2)n1] |
| I-276 | 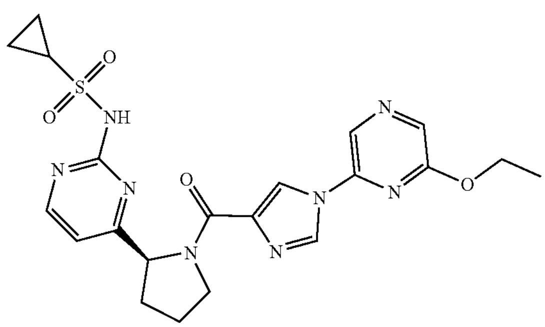 [SMILES: CCOc1cncc(-n2cnc(C(=O)N3CCC[C@H]3c3ccnc(NS(=O)(=O)C4CC4)n3)c2)n1] |
| I-277 | 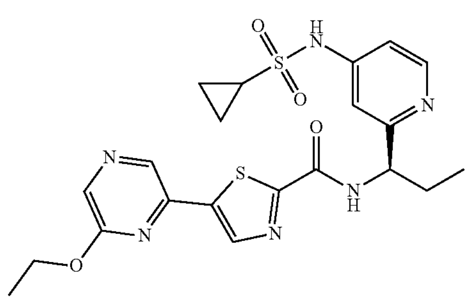 |

TABLE 1-continued
Selected Compounds
| Compound | Structure |
|---|---|
| I-278 | 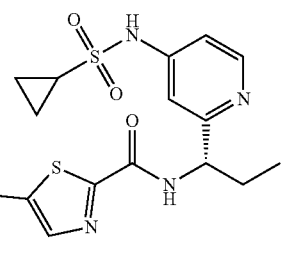 |
| I-279 | 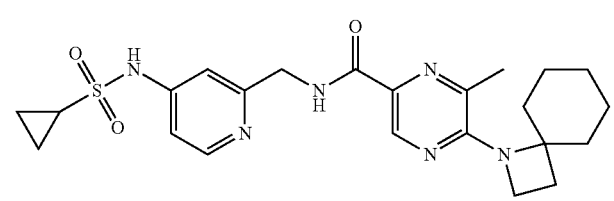 [SMILES: Cc1nc(C(=O)NCc2cc(NS(=O)(=O)C3CC3)ccn2)cnc1N1CCC12CCCCC2] |
| I-280 | 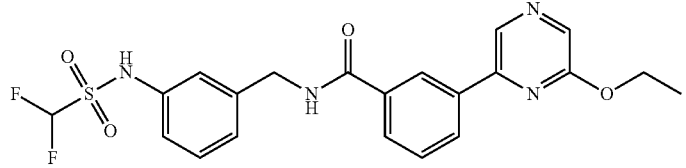 [SMILES: CCOc1cncc(-c2cccc(C(=O)NCc3cccc(NS(=O)(=O)C(F)F)c3)c2)n1] |
| I-282 | 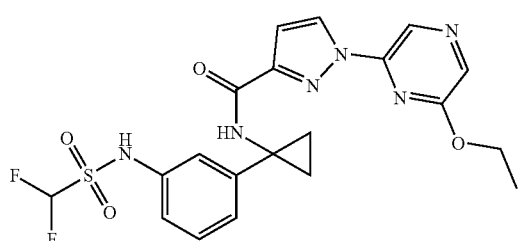 |
| I-283 | 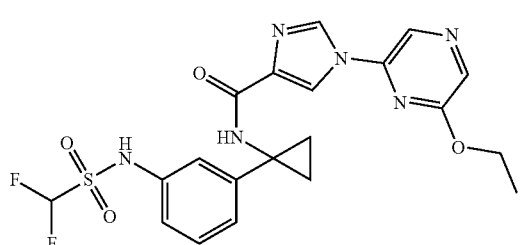 |
| I-284 | 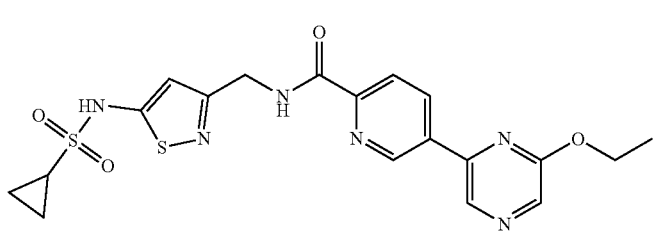 [SMILES: CCOc1cncc(-c2ccc(C(=O)NCc3cc(NS(=O)(=O)C4CC4)sn3)nc2)n1] |

TABLE 1-continued
Selected Compounds
| Compound | Structure |
|---|---|
| I-285 | 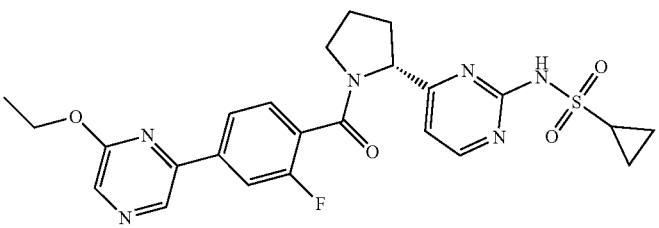 [SMILES: CCOc1cncc(-c2ccc(C(=O)N3CCC[C@@H]3c3ccnc(NS(=O)(=O)C4CC4)n3)c(F)c2)n1] |
| I-286 | 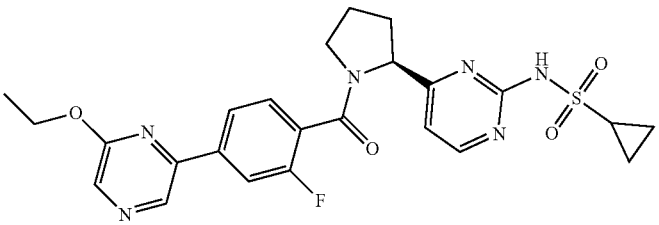 [SMILES: CCOc1cncc(-c2ccc(C(=O)N3CCC[C@H]3c3ccnc(NS(=O)(=O)C4CC4)n3)c(F)c2)n1] |
In some embodiments, the present invention provides a compound set forth in Table 2:
| Compound | Structure |
|---|---|
| Z-1 | 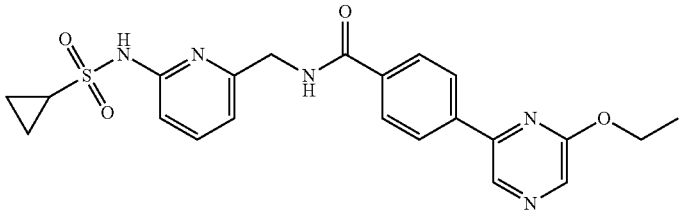 [SMILES: CCOc1cncc(-c2ccc(C(=O)NCc3cccc(NS(=O)(=O)C4CC4)n3)cc2)n1] |
| Z-2 | 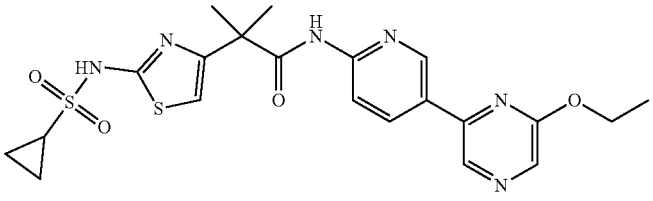 [SMILES: CCOc1cncc(-c2ccc(NC(=O)C(C)(C)c3csc(NS(=O)(=O)C4CC4)n3)nc2)n1] |
| Z-3 | 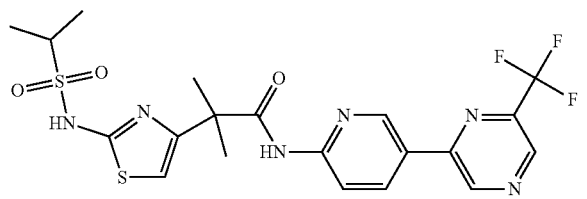 [SMILES: CC(C)S(=O)(=O)Nc1nc(C(C)(C)C(=O)Nc2ccc(-c3cncc(C(F)(F)F)n3)cn2)cs1] |

| Compound | Structure |
|---|---|
| Z-4 | 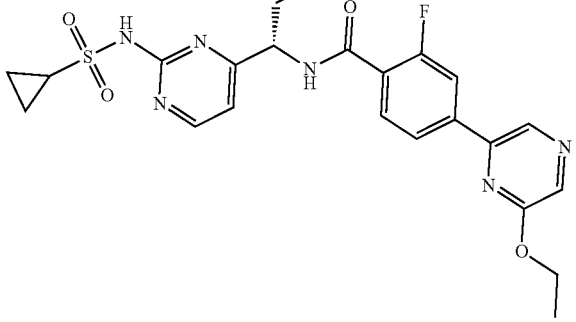 |
| Z-5 | 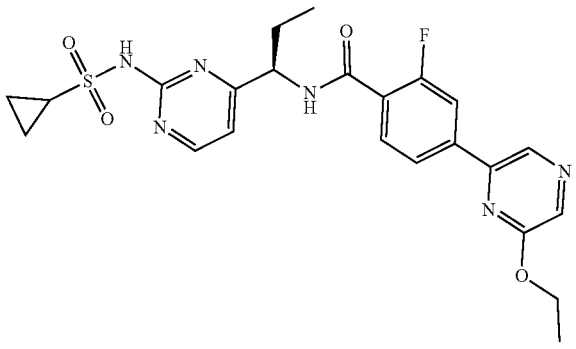 [SMILES: CCOc1cncc(-c2ccc(C(=O)N[C@H](CC)c3ccnc(NS(=O)(=O)C4CC4)n3)c(F)c2)n1] |
| Z-6 | 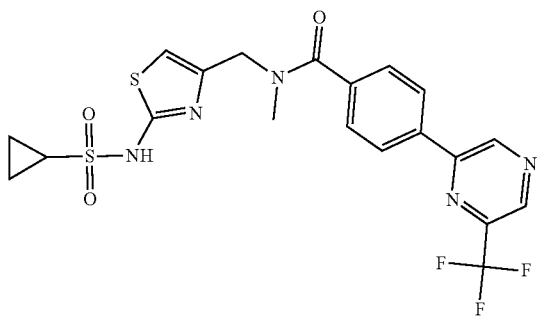 [SMILES: CN(Cc1csc(NS(=O)(=O)C2CC2)n1)C(=O)c1ccc(-c2cncc(C(F)(F)F)n2)cc1] |
| Z-7 | 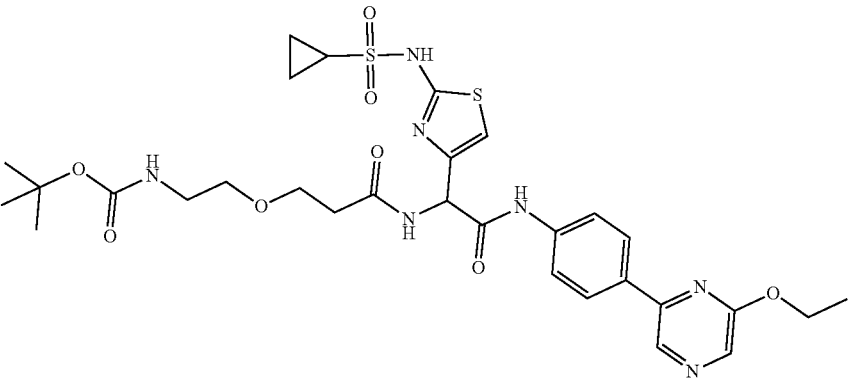 [SMILES: CCOc1cncc(-c2ccc(NC(=O)C(NC(=O)CCOCCNC(=O)OC(C)(C)C)c3csc(NS(=O)(=O)C4CC4)n3)cc2)n1] |

| Compound | Structure |
|---|---|
| Z-8 | (structure) |
| Z-9 | (structure) |
| Z-10 | (structure) |

In some embodiments, the present invention provides a compound set forth in Table 1, above, or a pharmaceutically acceptable salt thereof. In some embodiments, the present invention provides a compound set forth in Table 1, above. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I as defined above, or a pharmaceutically acceptable salt thereof, or a pharmaceutical composition comprising a compound of formula I as defined above, or a pharmaceutically acceptable salt thereof, and a pharmaceutically acceptable carrier, adjuvant, or vehicle for use as a medicament.

In some embodiments, the invention also provides compounds of formula I described herein or pharmaceutical compositions described herein for use in a method for inhibiting CTPS1 as described herein, in a method for enhancing an immune response in a subject in need thereof as described herein and/or in a method for treating a CTPS1-dependent disorder as described herein.

In some embodiments, the invention also provides compounds of formula I described herein or pharmaceutical compositions described herein for use in a method for inhibiting CTPS1 as described herein.

In some embodiments, the invention also provides compounds of formula I described herein or pharmaceutical compositions described herein for use in a method for enhancing an immune response in a subject in need thereof as described herein.

In some embodiments, the invention also provides compounds of formula I described herein or pharmaceutical compositions described herein for use in a method for treating a CTPS1-dependent disorder as described herein.

In some embodiments, the invention also provides the use of a compound of formula I described herein or a pharmaceutical composition described herein for the manufacture of a medicament for inhibiting CTPS1, a medicament for enhancing an immune response in a subject in need thereof and/or a medicament for treating a CTPS1-dependent disorder.

In some embodiments, the invention also provides the use of a compound of formula I described herein or a pharmaceutical composition described herein for the manufacture of a medicament for inhibiting CTPS1.

In some embodiments, the invention also provides the use of a compound of formula I described herein or a pharmaceutical composition described herein for the manufacture of a medicament for enhancing an immune response in a subject in need thereof.

In some embodiments, the invention also provides the use of a compound of formula I described herein or a pharmaceutical composition described herein for the manufacture of a medicament treating a CTPS1-dependent disorder.

In some embodiments, the invention also provides the use of compounds of formula I described herein or pharmaceutical compositions described herein in a method for inhibiting CTPS1 as described herein, in a method for enhancing an immune response in a subject in need thereof as described herein and/or in a method for treating a CTPS1-dependent disorder as described herein.

In some embodiments, the invention also provides the use of compounds of formula I described herein or pharmaceutical compositions described herein in a method for inhibiting CTPS1 as described herein.

In some embodiments, the invention also provides the use of compounds of formula I described herein or pharmaceutical compositions described herein in a method for enhancing an immune response in a subject in need thereof as described herein.

In some embodiments, the invention also provides the use of compounds of formula I described herein or pharmaceutical compositions described herein in a method for treating a CTPS1-dependent disorder as described herein.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CTPS1, or a mutant thereof, in a biological sample or in a patient. In certain embodiments, the amount of compound in compositions of this invention is such that is effective to measurably inhibit CTPS1, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of CTPS1, or a mutant thereof.

The subject matter disclosed herein includes prodrugs, metabolites, derivatives, and pharmaceutically acceptable salts of compounds of the invention. Metabolites include compounds produced by a process comprising contacting a compound of the invention with a mammal for a period of time sufficient to yield a metabolic product thereof. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of the invention can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

All cells utilize nucleotides as key building blocks for cellular metabolic processes, such as deoxyribonucleic acid (DNA) and ribonucleic acid (RNA) synthesis, membrane lipid biosynthesis, and as a cellular store of biochemical energy for many important enzymatic processes. There are two classes of nucleotides which contain either purine (such as guanine or adenine) or pyrimidine (such as cytosine or thymine) bases, and both classes are important for diverse metabolic processes. Nucleotides can be further phosphorylated by kinases to provide mono, di-, or tri-phosphate forms, which are also utilized in biosynthetic processes. Perhaps one of the most well-known uses of nucleotide triphosphates are as the building blocks of DNA within the cell, encoding the information necessary for RNA and protein biosynthesis. Based on the critical role of nucleotides within the cell, many therapies have been developed to target different aspects of nucleotide synthesis, with some inhibiting the generation of purine nucleotides, some pyrimidine nucleotides, or both classes simultaneously. This includes compounds such as leflunomide/teriflunomide, methotrexate, azathioprine, and others.

The pyrimidine nucleotide CTP (cytidine 5' triphosphate) is a precursor required not just for the anabolic generation of both DNA and RNA, but also phospholipids and sialyation of proteins. CTP originates from two sources: a salvage pathway and a de novo synthesis pathway that depends on the enzyme CTP synthase (Evans and Guy 2004; Higgins, et al. 2007; Ostrander, et al. 1998). In humans, there are two highly-homologous isoforms of CTP synthase (CTPS1 and CTPS2), both of which perform the same enzymatic reaction, although evidence suggests that the cellular and metabolic regulation of the two isoforms may be distinct. Although CTP synthase exists as two isozymes in humans and other eukaryotic organisms, detailed functional differences of the two isozymes in cellular or tissue biology are not yet fully delineated (van Kuilenburg, et al. 2000).

CTPS1 and CTPS2 catalyze the conversion of uridine triphosphate (UTP) and glutamine into cytidine triphosphate (CTP) and L-glutamate, with the concurrent hydrolyzation of ATP to ADP:

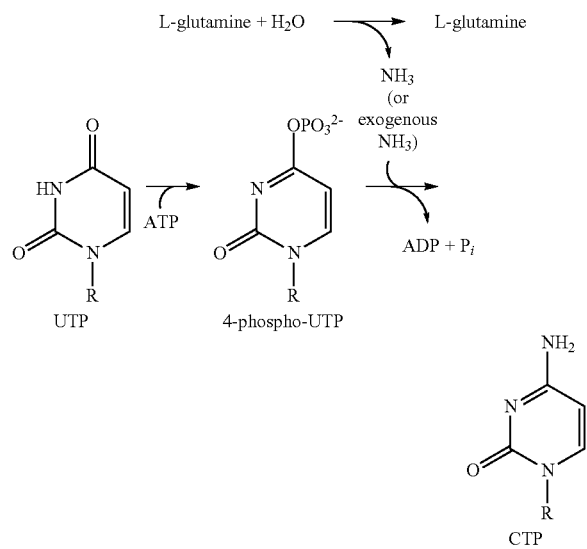

CTP synthase has two functional activities, an N-terminal synthetase domain and a C-terminal glutaminase domain, and the active enzyme is made up of a homotetramer (Kursula, et al. 2006). The synthetase domain of the enzyme transfers a phosphate from adenosine triphosphate (ATP) to the 4-position of UTP to create an activated intermediate, 4-phospho-UTP. The glutaminase domain of the enzyme generates ammonia from glutamine via a covalent thioester intermediate with a conserved active site cysteine, generating glutamate. This ammonium that is generated is transferred from the glutaminase domain to the synthetase domain via a tunnel in the enzyme or can be derived from external ammonium. This ammonium is then used in the synthetase domain to generate CTP from the 4-phospho-UTP (Lieberman, 1956).

Many studies have highlighted a key role of nucleotide synthesis and CTP synthase activity specifically in several aspects of normal and disease cell biology, especially in the cellular context of the high metabolic demands of replication and division where activation of de novo nucleotide synthesis is necessary. For instance, CTPS activity has been shown to be upregulated in a range of tumor types of both hematological and non-hematological origin, suggesting de novo pyrimidine biosynthesis is necessary to support the aggressive growth and division of cancer cells. The mechanistic drivers, cell type, and tissue origin of cancers are obviously diverse, but the underlying result is a breakdown in the control of cell division allowing inappropriate proliferation.

The process of tumorigenesis is highly complex, requiring careful coordination of multiple pathways, many of which remain to be fully characterized. Ultimately any cell division requires the effective replication of the cell's DNA and other constituents and is a metabolically-demanding process. Interfering with a cell's ability to replicate by targeting nucleic acid synthesis has been a core approach in cancer therapy for many years, and examples of therapies acting in this way are 6-thioguanine, 6-mecaptopurine, 5-fluorouracil, cytarabine, gemcitabine, and methotrexate.

Currently, the precise roles that CTPS1 and/or CTPS2 may play in cancer is not well defined. Several non-selective inhibitors of CTP synthase have been previously developed for oncology indications up to phase I/II clinical trials but were likely stopped due to toxicity, poor pharmacokinetic characteristics, or limited efficacy. Most of these early developed inhibitors are nucleoside-analogue prodrugs (3-deazauridine, cyclopentenyl cytosine, carbodine), which are converted by the kinases involved in pyrimidine synthesis into the active tri-phosphorylated metabolite. Other inhibitors (such as acivicin or 6-Diazo-5-oxo-L-norleucine) are reactive analogues of glutamine and irreversibly inhibit the glutaminase domain of CTPS and other glutamine-utilizing enzymes.

Given the high metabolic demands of the proliferating cancer cell and the data suggesting CTP synthase activity in a number of tumor types, selective CTPS inhibitors could offer an attractive alternative approach for the treatment of tumors. Compounds with different activity against CTPS1 and/or CTPS2 may offer important opportunities to target different tumors depending upon their relative dependence on these two enzymes.

In addition to cancer biology, extensive literature highlights the role of nucleotide synthesis and CTP synthase activity in immune biology and disease. The immune system in multi-cellular organisms has evolved to provide protection from a diverse range of infectious pathogens. This process generally requires recognition of the pathogen by various immune cells and is often followed by amplification and long-term propagation of the immune response through the rapid expansion, proliferation, and differentiation of responding immune cells. Within this process, CTP synthase activity appears to play an important role in DNA synthesis and the rapid expansion of lymphocytes following activation (Fairbanks, et al. 1995; van den Berg, et al. 1995).

Direct clinical validation that CTPS1 is the critical enzyme in human lymphocyte proliferation came from the genetic finding that a rare loss-of-function homozygous mutation (rs145092287) in this enzyme causes a severe immunodeficiency, which is characterized by a severely reduced capacity of patient activated T- and B-cells to proliferate in response to antigen receptor-mediated activation. In addition, activated CTPS1-deficient cells from patients were shown to have decreased levels of intracellular CTP compared to normal controls, and normal T-cell proliferation could be restored in CTPS1-deficient cells by expressing wild-type CTPS1 or by the addition of exogenous cytidine. CTPS1 mRNA and protein expression was found to be very low in resting lymphocytes, but rapidly upregulated following activation. The expression of CTPS1 in other tissues was generally low, and it is not known whether expression in other tissues is similarly inducible. CTPS2 seems to be ubiquitously expressed in a range of cells and tissues but at low levels, and the failure of normal levels of CTPS2 to compensate for the mutated CTPS1 in immune cells supports the critical role of CTPS1 in the immune populations affected in the homozygous patients (Martin, et al. 2014). In sum, these findings suggest that CTPS1 activity is critical to meet the metabolic demands of CTP required by several important immune cell populations when they are activated and required to proliferate.

Normally the immune response is tightly regulated to ensure sufficient activity for protection from infection while preventing overactivity or inappropriate recognition of host proteins and cells. In certain diseases or conditions, the control of this process is not effective and can lead to immune-mediated pathology. A wide range of human diseases and pathologies are believed to be due to these types of inappropriate immune responses and are commonly classified as autoimmune diseases or autoinflammatory conditions.

Given the role that pathogenic immune cells, such as autoreactive T and B lymphocytes, are believed to play in a wide range of autoimmune and other diseases, CTPS1 represents a potential therapeutic target for a new class of immunosuppressive agents. Specific CTPS1 inhibitors could therefore provide a novel approach to the functional inhibition of activated lymphocytes and specific other immune cell populations shown to be defective in CTPS1-deficient patients, such as NK (natural killer), MAIT (Mucosal-Associated Invariant T), and iNK (invariant natural killer) cells (Martin, et al. 2014).

In addition to roles in cancer and immune biology, CTPS1 has also been suggested to play a role in vascular smooth muscle cell proliferation (restenosis) following vascular injury or surgery (Tang, et al. 2013).

To date, no specific CTP synthase inhibitors have been described in detail or tested clinically. Available data strongly suggest that inhibitors of CTPS1 could reduce the proliferation of pathogenic immune and cancer cell populations, and potentially other targeted cell populations. Inhibitors of CTPS1 may therefore be expected to have utility for treatment or prophylaxis in a wide range of indications where the pathology is driven by these populations. CTPS1 inhibitors may represent a unique approach for inhibiting selected components of the immune system, such as proliferative pathogenic autoreactive lymphocytes. This could have utility in a number of diseases, such as immune-mediated rejection of transplanted cells, organs or tissues, graft-versus-host disease or reactions, and immune-driven allergies and autoimmune diseases. Additionally, the apparent specificity of the function of CTPS1 in immune cells may suggest that CTPS1 inhibitors could exhibit an improved therapeutic index over other clinically used non-specific nucleotide inhibitors, such as leflunomide or azathioprine. Finally, CTPS1 inhibitors may offer therapeutic potential in a range of cancer indications, especially of hematopoietic origin, and could aid in improving recovery from vascular injury or surgery and reducing morbidity and mortality associated with neointima formation and restenosis.

The present disclosure provides methods of modulating (e.g., inhibiting) CTPS1 activity, said method comprising administering to a patient a compound of the invention, or a pharmaceutically acceptable salt, hydrate, solvate, or prodrug thereof. In certain embodiments, the compounds and compositions described herein are useful for the inhibition of CTPS1.

In one embodiment, the subject matter disclosed herein is directed to a method of inhibiting CTPS1, the method comprising contacting CTPS1 with an effective amount of a compound of the invention, or a pharmaceutically acceptable salt, hydrate, solvate, or prodrug thereof described herein. Such methods comprise contacting CTPS1 with an effective amount of a presently disclosed compound. The compound can be contacted with CTPS1 in vitro or in vivo via administration of the compound to a subject.

In one aspect, the invention provides a method of treating a CTPS1-mediated disease or disorder in a subject, comprising administering a therapeutically effective amount of a compound of the invention, or a pharmaceutically acceptable salt, hydrate, solvate, or prodrug thereof, to the subject.

In another aspect, the invention provides a method of treating a disease or disorder related to CTPS1 regulation in a subject, comprising administering a therapeutically effective amount of a compound of the invention, or a pharmaceutically acceptable salt, hydrate, solvate, or prodrug thereof, to the subject.

In certain embodiments, the disease or disorder is selected from rejection of transplanted cells and tissues, Graft-related diseases or disorders, allergies and autoimmune diseases.

In one embodiment the disease or disorder is the rejection of transplanted cells and tissues. In certain embodiments, the subject may have been transplanted with a graft selected from the group consisting of heart, kidney, lung, liver, pancreas, pancreatic islets, brain tissue, stomach, large intestine, small intestine, cornea, skin, trachea, bone, bone marrow (or any other source of hematopoietic precursor cells and stem cells including hematopoietic cells mobilized from bone marrow into peripheral blood or umbilical cord blood cells), muscle, and bladder. In certain embodiments, the compounds of the invention are used in preventing or suppressing an immune response associated with rejection of a donor tissue, cell, graft or organ transplant in a subject.

In certain embodiments, the disease or disorder is a graft-related disease or disorder. In some embodiments, graft-related diseases or disorders include graft versus host disease (GVHD), such as GVHD associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc, and Host-Versus-Graft-Disease (HVGD). In certain embodiments, the compounds of the invention are used in preventing or suppressing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes). In some embodiments, the compounds of the invention prevent Host-Versus-Graft-Disease (HVGD) and Graft-Versus-Host-Disease (GVHD).

In certain embodiments, the compound of the invention is administered to the subject before, after transplantation and/or during transplantation. In some embodiments, the compound of the invention is administered to the subject on a periodic basis before and/or after transplantation.

In another embodiment, the disease or disorder is an allergy.

In certain embodiments, the autoimmune disease treated by the compound of the invention is Addison's Disease, Adult-onset Still's disease, Alopecia Areata, Alzheimer's disease, Anti-neutrophil Cytoplasmic Antibodies (ANCA)-Associated Vasculitis, Ankylosing Spondylitis, Anti-phospholipid Syndrome (Hughes' Syndrome), Aplastic Anemia, Arthritis, Asthma, Atherosclerosis, Atherosclerotic plaque, Atopic Dermatitis, Autoimmune Hemolytic Anemia, Autoimmune Hepatitis, Autoimmune Hypophysitis (Lymphocytic Hypophysitis), Autoimmune Inner Ear Disease, Autoimmune Lymphoproliferative Syndrome, Autoimmune Myocarditis, Autoimmune Neutropenia, Autoimmune Oophoritis, Autoimmune Orchitis, Auto-Inflammatory Diseases requiring an immunosuppressive treatment, Azoospermia, Bechet's Disease, Berger's Disease, Bullous Pemphigoid, Cardiomyopathy, Cardiovascular disease, Celiac disease including Refractory Celiac Disease (type I and type II), Chronic Fatigue Immune Dysfunction Syndrome (CFIDS), Chronic Idiopathic Polyneuritis, Chronic Inflammatory Demyelinating Polyneuropathy (CIPD), Chronic Relapsing Polyneuropathy (Guillain-Barre syndrome), Churg-Strauss Syndrome (CSS), Cicatricial Pemphigoid, Cold Agglutinin Disease (CAD), chronic obstructive pulmonary disease (COPD), CREST Syndrome, Cryoglobulin Syndromes, Cutaneous Lupus, Dermatitis Herpetiformis, Dermatomyositis, Eczema, Epidermolysis Bullosa Acquisita, Essential Mixed Cryoglobulinemia, Evan's Syndrome, Exophthalmos, Fibromyalgia, Goodpasture's Syndrome, Grave's disease, Hemophagocytic Lymphohistiocytosis (HLH) (including Type 1 Hemophagocytic Lymphohistiocytosis), Histiocytosis/Histiocytic Disorders, Hashimoto's Thyroiditis, Idiopathic Pulmonary Fibrosis, Idiopathic Thrombocytopenia Purpura (FTP), IgA Nephropathy, Immunoproliferative Diseases or Disorders, Inflammatory Bowel Disease (IBD), Interstitial Lung Disease, Juvenile Arthritis, Juvenile Idiopathic Arthritis (JIA), Kawasaki's Disease, Lambert-Eaton Myasthenic Syndrome, Lichen Planus, Localized Scleroderma, Lupus Nephritis, Meniere's Disease, Microangiopathic Hemoytic Anemia, Microscopic Polyangitis, Miller Fischer Syndrome/Acute Disseminated Encephalomyeloradiculopathy, Mixed Connective Tissue Disease, Multiple Sclerosis (MS), Muscular Rheumatism, Myalgic Encephalomyelitis (ME), Myasthenia Gravis, Ocular Inflammation, Pemphigus *Foliaceus*, Pemphigus Vulgaris, Pernicious Anemia, Polyarteritis *Nodosa*, Polychondritis, Polyglandular Syndromes (Whitaker's syndrome), Polymyalgia Rheumatica, Polymyositis, Primary Agammaglobulinemia, Primary Biliary Cirrhosis/Autoimmune Cholangiopathy, Primary Glomerulonephritis, Primary Sclerosing Cholangitis, Psoriasis, Psoriatic Arthritis, Pure Red Cell Anemia, Raynaud's Phenomenon, Reiter's Syndrome/Reactive Arthritis, Relapsing Polychondritis, Restenosis, Rheumatic Fever, Rheumatic Disease, Rheumatoid Arthritis, Sarcoidosis, Schmidt's Syndrome, Scleroderma/Systemic Sclerosis, Sjorgen's Syndrome, Stiff-Man Syndrome, The Sweet Syndrome (Febrile Neutrophilic Dermatosis), Systemic Lupus Erythematosus (SLE), Systemic Scleroderma, Takayasu Arteritis, Temporal Arteritis/Giant Cell Arteritis, Thyroiditis, Type 1 diabetes, Type 2 diabetes, Uveitis, Vasculitis, Vitiligo, Wegener's Granulomatosis, or X-linked lymphoproliferative disease.

In some embodiments, the disease treated by the compound of the invention is driven by T-cell activation and proliferation, selected from alopecia areata, atopic dermatitis, eczema, psoriasis, lichen planus, psoriatic arthritis, vitiligo, uveitis, ankylosing spondylitis, Reiter's syndrome/reactive arthritis, aplastic anemia, autoimmune lymphoproliferative syndrome/disorders, hemophagocytic lymphohistiocytosis, type 1 diabetes, and refractory celiac disease. In some embodiments, the disease is acute rejection of grafted tissues and transplanted organs, acute graft versus host disease (GVHD) after transplantation of bone marrow cells or any other source of allogenic cells including hematopoietic precursors cells and/or stem cells.

In certain embodiments, the disease treated by the compound of the invention is driven by both T- and B-cell activation and proliferation, selected from allergy, cicatricial pemphigoid, bullous pemphigoid, epidermolysis bullosa acquisita, pemphigus *foliaceus*, pemphigus vulgaris, dermatitis herpetiformis, ANCA-associated vasculitis and microscopic polyangitis, vasculitis, Wegener's granulomatosis; Churg-Strauss syndrome (CSS), polyarteritis *nodosa*, cryoglobulin syndromes and essential mixed cryglobulinemia, Systemic lupus erythematosus (SLE), antiphospholipid syndrome (Hughes' syndrome), cutaneous lupus, lupus nephritis, mixed connective tissue disease, Thyroiditis, Hashimoto thyroiditis, Grave's disease, exophthalmos, autoimmune hemolytic anemia, autoimmune neutropenia, ITP, pernicious anaemia, pure red cell anaemia, micro-angiopathic hemolytic anemia, primary glomerulonephritis, Berger's disease, Goodpasture's syndrome, IgA nephropathy, chronic idiopathic polyneuritis, chronic inflammatory demyelinating polyneuropathy (CIPD), chronic relapsing polyneuropathy (Guillain-Barre syndrome), Miller Fischer syndrome, Stiff man syndrome, Lambert-Eaton myasthenic syndrome, and myasthenia gravis.

In certain embodiments, the disease treated by the compound of the invention is Addison's disease, autoimmune oophoritis and azoospermia, polyglandular syndromes (Whitaker's syndrome), Schmidt's syndrome, autoimmune myocarditis, cardiomyopathy, Kawasaki's disease, rheumatoid arthritis, Sjogren's syndrome, mixed connective tissue disease, polymyositis and dermatomyositis, polychondritis, primary glomerulonephritis, Multiple sclerosis, autoimmune hepatitis, primary biliary cirrhosis/autoimmune cholangiopathy, hyper acute rejection of transplanted organs, chronic rejection of graft or transplants, and Chronic Graft versus Host reaction/disease after transplantation of bone marrow cells or hematopoietic precursor cells.

In certain embodiments, the disease treated by the compound of the invention is COPD, idiopathic pulmonary fibrosis, interstitial lung disease, sarcoidosis, adult onset Still's disease, juvenile idiopathic arthritis, Systemic sclerosis, CREST syndrome where B cells and pathogen antibodies may also play a role, the Sweet syndrome; Takayasu arteritis, temporal arteritis/giant cell arteritis, ulcerative cholangitis, inflammatory bowel disease (IBD) including Crohn's disease and ulcerative colitis, primary sclerosing cholangitis, Alzheimer's disease, cardiovascular syndrome, type 2 diabetes, restenosis, chronic fatigue immune dysfunction syndrome (CFIDS), Autoimmune Lymphoproliferative Syndrome and X-linked lymphoproliferative disease.

In certain embodiments, the disease treated by the compound of the invention is inflammatory skin diseases such as psoriasis or lichen planus; acute and/or chronic GVHD such as steroid resistant acute GVHD; acute lymphoproliferative syndrome; systemic lupus erythematosus, lupus nephritis or cutaneous lupus; or transplantation. In addition, the disease or disorder may be selected from myasthenia gravis, multiple sclerosis, and scleroderma/systemic sclerosis.

In certain aspects, the invention provides a method of treating cell proliferation disorders, including cancers, benign papillomatosis, gestational trophoblastic diseases, and benign neoplastic diseases, such as skin papilloma (warts) and genital papilloma.

In one aspect, provided herein is a method for treating of cancer in a subject in need thereof comprising administering to the subject an effective amount of a compound of the invention or a pharmaceutically acceptable salt, prodrug, metabolite, or derivative thereof.

In the methods described herein, a compound of the invention or a pharmaceutical composition thereof is administered to a subject that has cancer.

In certain embodiments, the cancer is selected from the group consisting of colorectal cancer, melanoma, non-small cell lung cancer, ovarian cancer, breast cancer, pancreatic cancer, a hematological malignancy, and a renal cell carcinoma.

In certain embodiments, the cancer is a haematological cancer, selected from Acute myeloid leukemia, Angioimmunoblastic T-cell lymphoma, B-cell acute lymphoblastic leukemia, Sweet Syndrome, T-cell Non-Hodgkins lymphoma (including natural killer/T-cell lymphoma, adult T-cell leukaemia/lymphoma, enteropathy type T-cell lymphoma, hepatosplenic T-cell lymphoma and cutaneous T-cell lymphoma), T-cell acute lymphoblastic leukemia, B-cell Non-Hodgkins lymphoma (including Burkitt lymphoma, diffuse large B-cell lymphoma, Follicular lymphoma, Mantle cell lymphoma, Marginal Zone lymphoma), Hairy Cell Leukemia, Hodgkin lymphoma, Lymphoblastic lymphoma, Lymphoplasmacytic lymphoma, Mucosa-associated lymphoid tissue lymphoma, Multiple myeloma, Myelodysplastic syndrome, Plasma cell myeloma, Primary mediastinal large B-cell lymphoma, chronic myeloproliferative disorders (such as chronic myeloid leukemia, primary myelofibrosis, essential thrombocytemia, polycytemia vera) and chronic lymphocytic leukemia.

In some embodiments, the cancer is a non-haematological cancer, selected from bladder cancer, breast, melanoma, neuroblastoma, malignant pleural mesothelioma, and sarcoma.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In certain embodiments, the cancer is brain cancer, leukemia, skin cancer, prostate cancer, thyroid cancer, colon cancer, lung cancer or sarcoma. In another embodiment the cancer is selected from the group consisting of glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In certain embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In a further embodiment, the cancer is selected from brain and spinal cancers. In particular embodiments, the cancer is selected from the group consisting of anaplastic astrocytomas, glioblastomas, astrocytomas, and estheosioneuroblastomas (olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sPNET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (hepatocellular carcinoma). In particular embodiments, the cancer is bile duct cancer (cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, and chordoma.

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Stemberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, and primary central nervous system lymphomas.

In specific embodiments, the cancer is selected from glandular cancers. In particular embodiments, the cancer is selected from the group consisting of adrenocortical cancer, pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, CTPS 1 inhibitors may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitf s lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

In certain embodiments, the invention provides a method of treating a CTPS1-mediated disease or disorder in a subject, wherein the treatment reduces T-cell and/or B-cell proliferation, comprising administering a therapeutically effective amount of a compound of the invention, or a pharmaceutically acceptable salt, hydrate, solvate, or prodrug thereof, to the subject.

In certain embodiments, the invention provides a method of reducing T-cell and/or B-cell proliferation, comprising administering a therapeutically effective amount of a compound of the invention, or a pharmaceutically acceptable salt, hydrate, solvate, or prodrug thereof, to the subject.

In certain embodiments, the invention provides for the use of a compound of the invention, or a pharmaceutically acceptable salt, solvate, or derivative thereof, in the manufacture of a medicament for the reduction of T-cell and/or B-cell proliferation in a subject.

In certain embodiments, the compounds of the invention are used in enhancing recovery from vascular injury or surgery and reducing morbidity and mortality associated with neointima and restenosis in a subject. For example, the compounds of formula (I) may be used in preventing, reducing, or inhibiting neointima formation. A medical device may be treated prior to insertion or implantation with an effective amount of a composition comprising a compound of formula (I) in order to prevent, reduce, or inhibit neointima formation following insertion or implantation of the device or graft into the subject. The device can be a device that is inserted into the subject transiently, or a device that is implanted permanently. In some embodiments, the device is a surgical device. Examples of medical devices include, but are not limited to, needles, cannulas, catheters, shunts, balloons, and implants such as stents and valves.

In some embodiments, the invention provides a pharmaceutical composition comprising an effective amount of a compound of the invention, or a pharmaceutically acceptable salt, hydrate, solvate, or prodrug thereof, and a pharmaceutically acceptable carrier.

In certain embodiments, the invention provides a compound of the invention, or a pharmaceutically acceptable salt, hydrate, solvate, or prodrug thereof, for use in the treatment or prophylaxis of a disease or disorder provided herein.

In certain embodiments, the invention provides a compound of the invention, or a pharmaceutically acceptable salt, hydrate, solvate, or prodrug thereof, for use as a medicament, for the treatment or prophylaxis of a disease or disorder provided herein.

In certain embodiments, the invention provides a compound of the invention, or a pharmaceutically acceptable salt, hydrate, solvate, or prodrug thereof, in the manufacture of a medicament for the inhibition of CTPS1 in a subject.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The presently disclosed compounds may be administered in any suitable manner known in the art. In some embodiments, the compound of the invention or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the CTPS1 antagonist is administered continuously. In other embodiments, the CTPS1 antagonist is administered intermittently. Moreover, treatment of a subject with an effective amount of a CTPS1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of the invention or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the CTPS1 antagonist is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg.

In the methods described herein, the method can further comprise administering a chemotherapeutic agent to the subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "prophylaxis" or "preventing" is used to mean preventing symptoms of a disease or disorder in a subject or preventing recurrence of symptoms of a disease or disorder in an afflicted subject and is not limited to complete prevention of an affliction.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3 A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfmavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methyl prednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfldine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenic gravis, Steven-Johnson syndrome, idiopathic sprue, autoimmune inflammatory bowel disease) e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting CTPS 1, or a mutant thereof, activity in a biological sample comprising the step of contacting said biological sample with a compound of this invention, or a composition comprising said compound. In certain embodiments, the invention relates to a method of irreversibly inhibiting CTPS1, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of CTPS 1 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of CTPS1, or a mutant thereof, in a patient comprising the step of administering to said patient a compound of the present invention, or a composition comprising said compound. According to certain embodiments, the invention relates to a method of reversibly or irreversibly inhibiting one or more of CTPS1, or a mutant thereof, activity in a patient comprising the step of administering to said patient a compound of the present invention, or a composition comprising said compound. In other embodiments, the present invention provides a method for treating a disorder mediated by CTPS1, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; anti neoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an anti estrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed, under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD 180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAR, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; R°318220 and R°320432; GO 6976; Isis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); l) compounds targeting, decreasing or inhibiting the activity of the epidermal growth factor family of receptor tyrosine kinases (EGFRi ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, $C_{1-10}$33, EKB-569, GW-2016, E1.1, E2.4, E2.5, E6.2, E6.4, E2.11, E6.3 orE7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDCl25, such as okadaic acid or a derivative thereof.

Compounds which induce cell differentiation processes include, but are not limited to, retinoic acid, α-γ- or δ-tocopherol or α-γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zamestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HD AC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Heilman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxy corticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (ParkeDavis), AWD-12-281 (*Asta Medica*), CDC-801 (Celgene), SelCID™ CC-10004 (Celgene), VM554/UM565 (*Vernalis*), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplification

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

Example 1. Synthesis of Intermediates

Synthesis of Int-1.

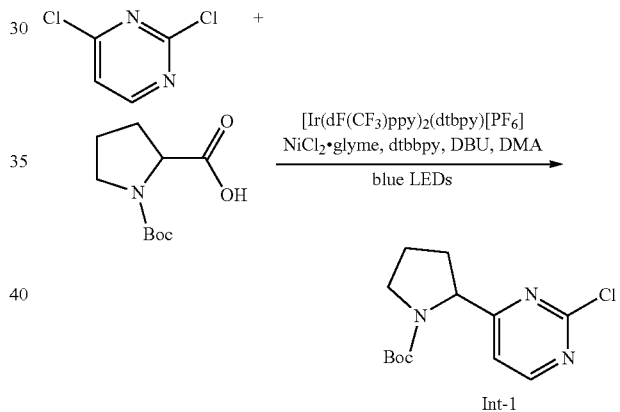

To an 8 mL vial was charged with Ir[dF(Me)ppy]₂(dtbbpy)PF₆ (7.0 mg, 0.006 mmol, 0.01 equiv), NiCl₂·glyme (7.0 mg, 0.034 mmol, 0.05 equiv), dtbbpy (9.0 mg, 0.034 mmol, 0.05 equiv), 2,4-dichloropyrimidine (100 mg, 0.671 mmol, 1.00 equiv), Boc-Pro-OH (216 mg, 1.000 mmol, 1.50 equiv), DBU (153 mg, 1.000 mmol, 1.50 equiv) and DMA (3.0 ml). The reaction mixture was degassed by bubbling nitrogen stream for 20 min, then irradiated in Merck Photoreactor for 24 h. LCMS showed 40% desired product Int-1 was formed.

Synthesis of Int-2.

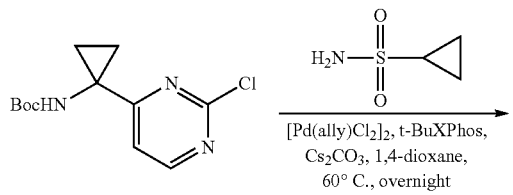

-continued

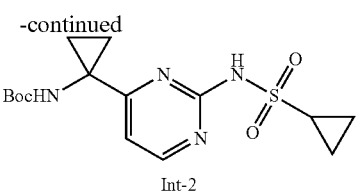

Int-2

To a solution of tert-butyl 1-(2-chloropyrimidin-4-yl) cyclopropylcarbamate (540 mg, 2 mmol, 1.00 equiv) and cyclopropanesulfonamide (564 mg, 4 mmol, 2 equiv) in 1,4-dioxane (15 mL) was added Cs$_2$CO$_3$ (1.956 g, 6 mmol, 3 equiv), t-BuXPhos (85.6 mg, 0.2 mmol, 0.1 equiv) and [Pd(ally)Cl]2 (36.6 mg, 0.1 mmol, 0.05 equiv) at room temperature under nitrogen atmosphere. The reaction mixture was degassed with nitrogen three times and stirred overnight at 60° C. The reaction was monitored by TLC and LCMS. After completion, the mixture was cooled to r.t, diluted with water and extracted with ethyl acetate. The combined organic layer was washed with brine, dried over sodium sulfate and concentrated under reduced pressure. The residue was purified by silica gel column chromatography with ethyl acetate/petroleum ether (1:1). This resulted in 470 mg (66.38%) of tert-butyl 1-(2-(cyclopropanesulfonamido)pyrimidin-4-yl)cyclopropylcarbamate (Int-2) as a yellow solid.

Synthesis of Int-3.

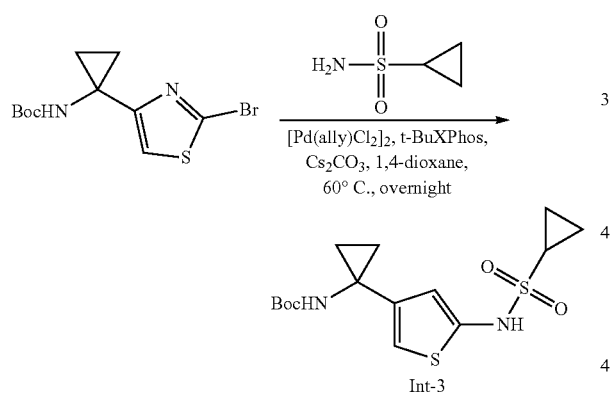

Int-3

To a solution of tert-butyl 1-(2-bromothiazol-4-yl)cyclopropylcarbamate (2.5 g, 7.837 mmol, 1.00 equiv) and cyclopropanesulfonamide (1.897 g, 15.674 mmol, 2 equiv) in 1,4-dioxane (60 mL) was added Cs$_2$CO$_3$ (7.665 g, 23.511 mmol, 3 equiv), t-BuXPhos (335.5 mg, 0.784 mmol, 0.1 equiv) and [Pd(ally)Cl]$_2$ (143.42 mg, 0.392 mmol, 0.05 equiv) at room temperature under nitrogen atmosphere. The reaction mixture was stirred overnight at 60° C. The reaction was monitored by TLC and LCMS. After completion, the mixture was cooled to r.t, diluted with water and extracted with ethyl acetate. The combined organic layer was washed with brine, dried over sodium sulfate and concentrated under reduced pressure. The residue was purified by silica gel column chromatography with ethyl acetate/petroleum ether (1:1), providing 1.5 g (56.41%) of tert-butyl 1-(2-(cyclopropanesulfonamido)thiazol-4-yl)cyclopropylcarbamate (Int-3) as a yellow solid.

Synthesis of 27.3.

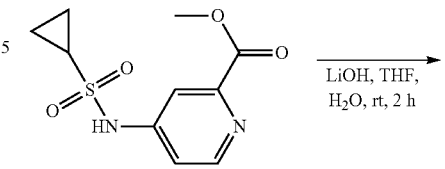

27.3

To a stirred solution of methyl 4-(cyclopropanesulfonamido) picolinate (257 mg, 1 mmol, 1 eq) in tetrahydrofuran (10 mL) and water (2 mL) was added lithium hydroxide (48 mg, 2 mmol, 2 eq). The resulting mixture was stirred for 2 h at room temperature. The mixture was concentrated under vacuum. The residue was diluted with water. The pH value of the solution was adjusted to 3 with 1N hydrochloric acid. The solids were collected by filtration to obtain 4-(cyclopropanesulfonamido) picolinic acid (27.3) as an off-white solid. (140 mg, 57%), MS (ES): m/z 243 [M+H]$^+$.

Synthesis of 28.3.

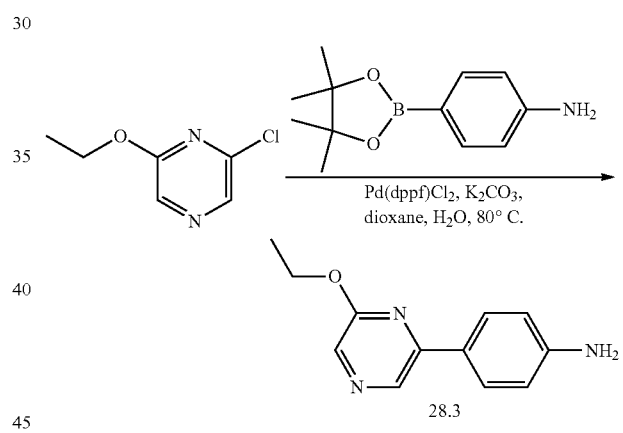

28.3

To a solution of 2-chloro-6-ethoxypyrazine (1.59 g, 10 mmol, 1 eq) and methyl 4-(4,4,5,5-tetramethyl-1,3,2-dioxaborolan-2-yl) aniline (2.63 g, 12 mmol, 1.2 eq) in 1,4-dioxane (40 mL) and water (10 mL) was added potassium carbonate (4.14 g, 30 mmol, 3 eq) and Pd(dppf)Cl$_2$—CH$_2$Cl$_2$ (406 mg, 0.5 mmol, 0.05 eq). The resulting solution was stirred for 2 h at 80° C. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain 4-(6-ethoxypyrazin-2-yl) aniline (28.3) as an off-white solid. (1.76 g, 82%), MS (ES): m/z 216 [M+H]$^+$.

Synthesis of Int A.1.

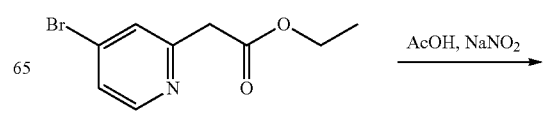

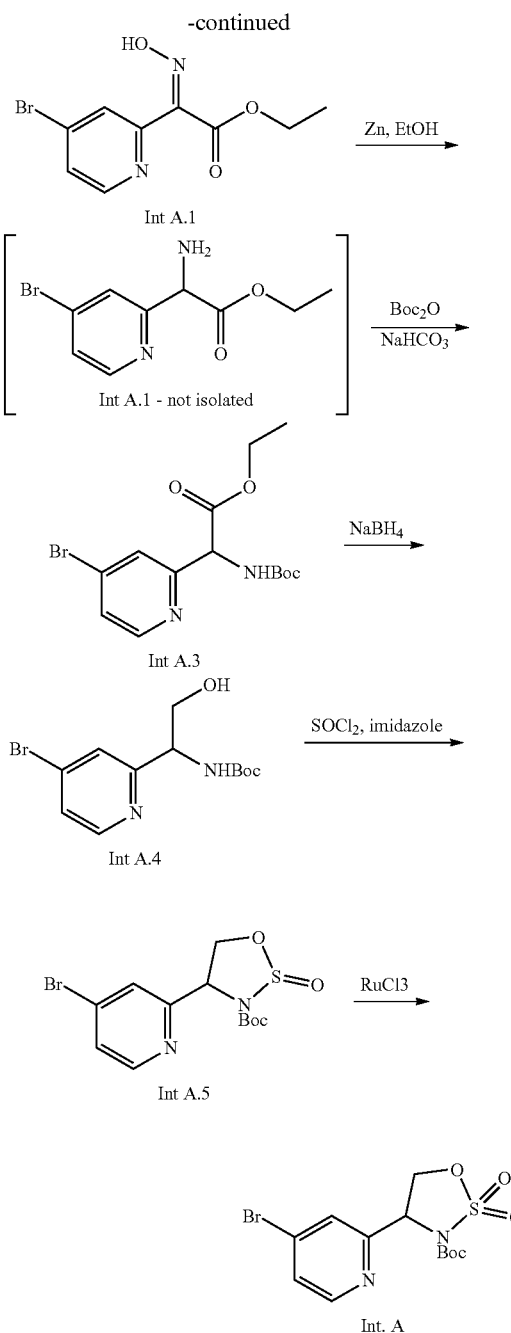

Synthesis of Int A.1. To a stirred mixture of ethyl 2-(4-bromopyridin-2-yl)acetate (5 g, 20.5 mmol, 1 eq) in acetic acid (70 ml) was added sodium nitrite (1.7 g, 24.7 mmol, 1.2 eq) in water (35 mL) dropwise at 0° C. The resulting mixture was stirred for 1 h at room temperature. The mixture was concentrated under reduced pressure. The mixture was basified to pH 7 with saturated aqueous sodium bicarbonate, and was extracted with ethyl acetate. The combined organic layers were washed with brine and dried over anhydrous sodium sulfate, and concentrated under reduced pressure to afford ethyl (E)-2-(4-bromopyridin-2-yl)-2-(hydroxyimino) acetate (Int. A.1, 5.35 g, 95%) as a yellow oil. MS (ES): m/z 273 [M+H]$^+$.

Synthesis of Int A.3. To a stirred mixture of Int A.1 (5.35 g, 19.6 mmol, 1 eq) in ethanol (50 mL) and water (5 mL) were added zinc powder (2.55 g, 39.2 mmol, 2 eq) in portions and acetic acid (5 ml) dropwise at 0° C. The resulting mixture was stirred for 1 h at room temperature. Then triethylamine (5 mL, 36 mmol, 1.8 eq) and di-tert-butyl pyrocarbonate (5 g, 39.2 mmol, 2.0 eq) were added at 0° C. The resulting mixture was basified to pH 8 with saturated aqueous sodium bicarbonate and stirred for 1 h at room temperature. The reaction mixture was filtered and the filtrate was extracted with ethyl acetate. The combined organic layers were washed with brine, dried over sodium sulfate and concentrated under reduced pressure. The residue was purified by flash column chromatography on silica gel (eluted with 20% ethyl acetate in petroleum ether) to afford ethyl 2-(4-bromopyridin-2-yl)-2-((tert-butoxycarbonyl)amino)acetate (Int A.3, 2.35 g, 33%) as a yellow solid. MS (ES): m/z 359 [M+H]$^+$.

Synthesis of IntA.4. To a stirred mixture of IntA.3 (5.1 g, 14.2 mmol, 1 eq) in ethanol (10 mL) and tetrahydrofuran (100 mL) were added sodium borohydride (5.11 g, 142 mmol, 10 eq) and lithium chloride (5.9 g, 142 mmol, 10 eq) at 0° C. The resulting mixture was stirred overnight at 50° C. The reaction mixture was quenched with water and extracted with ethyl acetate. The combined organic layers were washed with brine, dried over sodium sulfate and concentrated under reduced pressure. The residue was purified by flash column chromatography on silica gel (eluted with 50% ethyl acetate in petroleum ether) to afford ethyl tert-butyl (1-(4-bromopyridin-2-yl)-2-hydroxyethyl)carbamate (Int A.4, 3.35 g, 74%) as a yellow solid. MS (ES): m/z 317 [M+H]$^+$.

Synthesis of Int A.5. To a solution of imidazole (3.2 g, 46.8 mmol, 6 eq) in dichloromethane (50 mL) was added thionyl chloride (1N in dichloromethane, 24 mL, 23.4 mmol, 3 eq) dropwise at 0° C. The mixture was stirred at 0° C. for 1 h, followed by the addition of Int A.4 (2.48 g, 7.8 mmol, 1 eq) in dichloromethane (10 mL) dropwise at −10° C. The resulting mixture was stirred at room temperature for 1 h. The reaction was quenched with saturated aqueous citric acid and extracted with dichloromethane. The combined organic layers were washed with brine, dried over anhydrous sodium sulfate and concentrated under reduced pressure. The residue was purified by flash column chromatography on C18 silica (eluted with 80% acetonitrile in water) to afford tert-butyl 4-(4-bromopyridin-2-yl)-1,2,3-oxathiazolidine-3-carboxylate 2-oxide (Int A.5, 2 g, 71%) as light yellow solid. MS (ES): m/z 363 [M+H]$^+$.

Synthesis of Int A. To a solution of Int A.5 (1.7 g, 4.7 mmol, 1 eq) in acetonitrile (50 mL) were added Ruthenium (III) chloride (0.1 g, 0.5 mmol, 0.1 eq) and a solution of sodium tetroxoiodate (1.1 g, 5.2 mmol, 1.1 eq) in water (20 mL) at room temperature. The resulting mixture was stirred at room temperature for 1 h. The reaction was diluted with water and extracted with dichloromethane. The combined organic layers were washed with brine, and dried over anhydrous sodium sulfate and concentrated under reduced pressure. The residue was purified by flash column chromatography on silica gel (eluted with ethyl acetate) to afford tert-butyl 4-(4-bromopyridin-2-yl)-1,2,3-oxathiazolidine-3-carboxylate 2,2-dioxide (Int. A, 1.6 g, 90%) as a light yellow solid. MS (ES): m/z 379 [M+H]$^+$.

Synthesis of Int. B

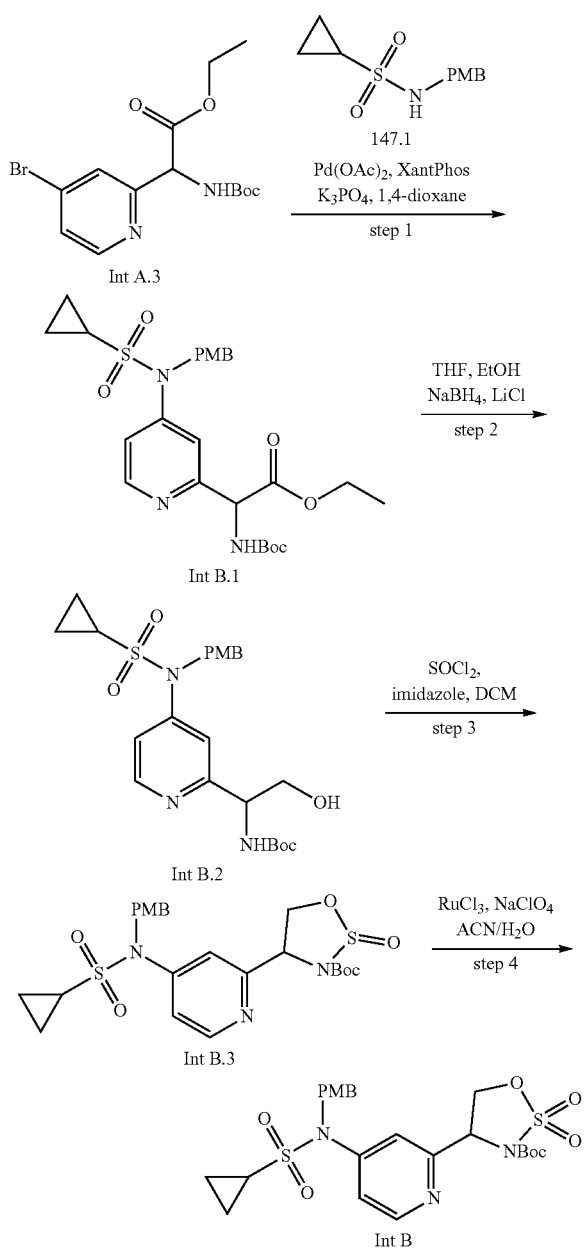

Synthesis of Int B.1. To a stirred mixture of Int A.3 (1.3 g, 3.62 mmol, 1 equiv) and 147.1 (1.3 g, 5.43 mmol, 1.5 equiv) in 1,4-dioxane (20 mL) were added potassium phosphate tribasic (1.54 g, 7.24 mmol, 2 equiv), XantPhos (419 mg, 0.72 mmol, 0.2 equiv) and Pd(OAc)$_2$ (81 mg, 0.36 mmol, 0.1 equiv) in portions at room temperature. The resulting mixture was stirred for 2 h at 100° C. under nitrogen atmosphere. The reaction mixture was filtered through Celite. The filtrate was concentrated under reduced pressure. The residue was purified by flash column chromatography on C18 silica (eluted with acetonitrile/water, 7/1) to afford ethyl 2-((tert-butoxycarbonyl)amino)-2-(4-(N-(4-methoxybenzyl)cyclopropanesulfonamido)pyridin-2-yl)acetate (Int B.1, 1.1 g, 58%) as a white solid. MS (ES): m/z 520 [M+H]$^+$.

Synthesis of Int B.2. To a stirred mixture of Int B.1 (300 mg, 0.58 mmol, 1 equiv) in THF (3 mL) and ethanol (0.3 mL) were added and lithium chloride (49 mg, 1.15 mmol, 2 equiv) and sodium borohydride (87 mg, 2.31 mmol, 4 equiv) in portions at 0° C. The resulting mixture was stirred overnight at room temperature. The reaction was quenched with ice water (10 mL) and extracted with ethyl acetate (3×10 mL). The combined organic layers were concentrated under reduced pressure. The residue was purified by flash column chromatography on silica gel (eluted with petrol ether/ethyl acetate, 1/1) to afford tert-butyl (2-hydroxy-1-(4-(N-(4-methoxybenzyl)cyclopropanesulfonamido)pyridin-2-yl)ethyl)carbamate (Int B.2, 200 mg, 72%) as a white solid. MS (ES): m/z 478 [M+H]$^+$.

Synthesis of Int B.3. To a solution of imidazole (940 mg, 13.8 mmol, 6. equiv) in dichloromethane (12 mL) was added thionyl chloride (1N in dichloromethane, 7 mL, 7.0 mmol, 3 equiv) dropwise at 0° C. The mixture was stirred at 0° C. for 1 h, followed by the addition of Int B.2 (1.1 g, 2.30 mmol, 1 equiv) in dichloromethane (10 mL) dropwise at −10° C. The resulting mixture was stirred at room temperature for 1 h. The reaction was quenched with saturated aqueous citric acid and extracted with dichloromethane. The combined organic layers were washed with brine, dried over anhydrous sodium sulfate and concentrated under reduced pressure. The residue was purified by flash column chromatography on silica gel (eluted with 75% ethyl acetate in petrol ether) to afford tert-butyl 4-(4-(N-(4-methoxybenzyl)cyclopropanesulfonamido)pyridin-2-yl)-1,2,3-oxathiazolidine-3-carboxylate 2-oxide (Int B.3, 900 mg, 75%) as a light yellow solid. MS (ES): m/z 524 [M+H]$^+$.

Synthesis of Int B. To a solution of Int B.3 (1.0 g, 1.91 mmol, 1 equiv) in acetonitrile (10 mL) were added Ruthenium(III) chloride (24 mg, 0.12 mmol, 0.06 equiv) and a solution of sodium tetroxoiodate (449 mg, 2.10 mmol, 1.1 equiv) in water (4 mL) at room temperature. The resulting mixture was stirred at room temperature for 1 h. The reaction was diluted with water and extracted with dichloromethane. The combined organic layers were washed with brine, and dried over anhydrous sodium sulfate and concentrated under reduced pressure. The residue was purified by flash column chromatography on silica gel (eluted with 75% ethyl acetate in petrol ether) to afford tert-butyl 4-(4-(N-(4-methoxybenzyl)cyclopropanesulfonamido)pyridin-2-yl)-1,2,3-oxathiazolidine-3-carboxylate 2,2-dioxide (Int B, 920 mg, 89%) as a light yellow oil. MS (ES): m/z 540 [M+H]$^+$.

Synthesis of Int. F

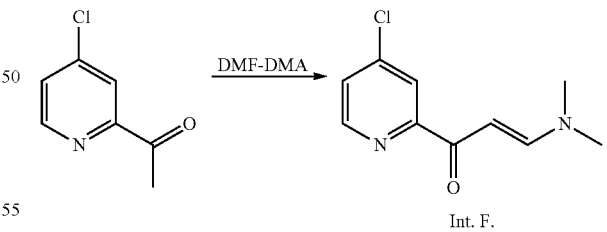

Synthesis of Int. F. A solution of 1-(4-chloropyridin-2-yl)ethanone (1 g, 6.43 mmol, 1 equiv) and DMA-DMF (0.22 g, 9.64 mmol, 1.5 equiv) in N,N-dimethylformamide (10 mL) was stirred for 2 h at 80° C. The reaction was diluted with water (30 mL) and extracted with ethyl acetate (3×25 mL). The combined organic layers were concentrated under reduced pressure to afford (E)-1-(4-chloropyridin-2-yl)-3-(dimethylamino)prop-2-en-1-one (Int. F, 1.2 g, 90%) as a colorless oil, which was used in the next step directly without further purification. MS (ES): m/z 211 [M+H]$^+$.

Example 2: Synthesis of N-(4-(1-(5-(6-ethoxy-pyrazin-2-yl)-1-oxoisoindolin-2-yl)propyl)thiazol-2-yl)cyclopropanesulfonamide (I-6)

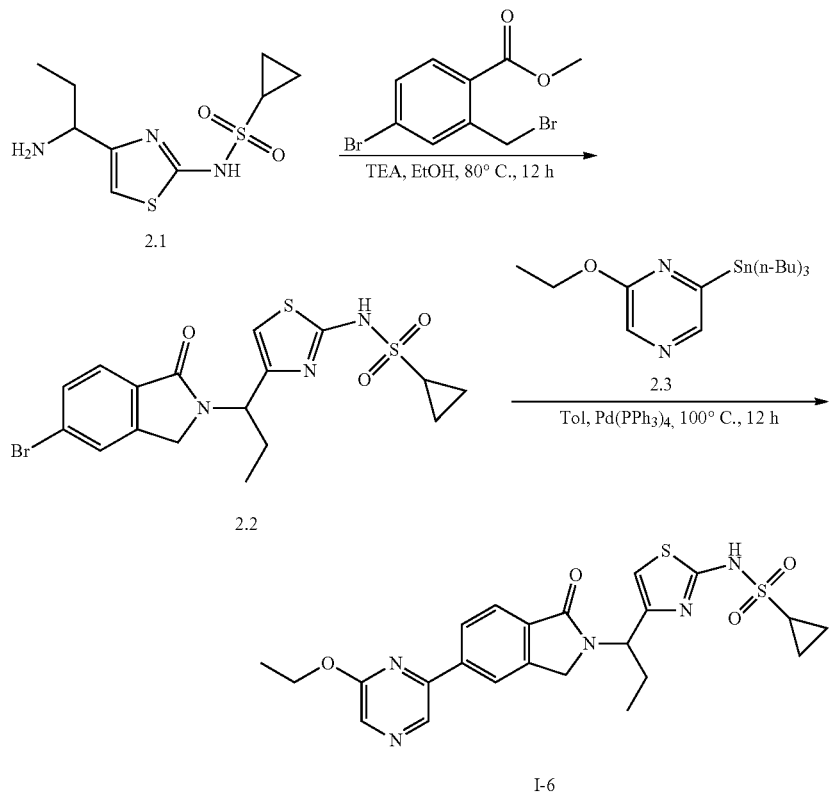

Synthesis of 2.2. To a solution of N-(4-(1-aminopropyl)thiazol-2-yl)cyclopropanesulfonamide (150.0 mg, 0.58 mmol, 1.0 eq) and methyl 4-bromo-2-(bromomethyl)benzoate (177.5 mg, 0.58 mmol, 1 eq) in ethanol (5 mL) was added triethylamine (175.8 mg, 1.74 mmol, 3.0 eq) at r.t. The resulting mixture was stirred for 12 h at 80° C. under nitrogen atmosphere. The mixture was cooled to r.t, diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (10% NH$_4$HCO$_3$) and ACN (28% ACN up to 41% in 10 min); UV detection at 254/220 nm. The product-containing fractions were combined and concentrated under reduced pressure to afford N-(4-(1-(5-bromo-1-oxoisoindolin-2-yl)propyl)thiazol-2-yl)cyclopropanesulfonamide as a yellow solid. (100 mg, 38%), MS (ES): m/z 456/458 [M+H]$^+$.

Synthesis of I-6. To a solution of 2.2 (100.0 mg, 0.22 mmol, 1.0 eq) and 2-ethoxy-6-(tributylstannyl)pyrazine (182.2 mg, 0.44 mmol, 2.0 eq) in toluene (5 mL) were added Pd(PPh$_3$)$_4$ (25.4 mg, 0.02 mmol, 0.1 eq) at r.t. The reaction mixture was stirred for 12 h at 100° C. The reaction was concentrated under reduced pressure. The crude product was purified by Prep-HPLC with the following conditions: Column, XBridge Shield RP18 OBD Column, 30*150 mm, 5 um; mobile phase, Water (0.1% FA) and ACN (21% ACN up to 33% in 7 min); UV detection at 254/220 nm. The product-containing fractions were combined and evaporated partially in vacuo and lyophilized overnight to afford the title compound as a white solid. (22 mg, 20%), MS (ES): m/z 500 [M+H]$^+$; $^1$H NMR (400 MHz, CD$_3$OD) δ 8.74 (s, 1H), 8.31 (s, 1H), 8.28 (d, J=8 Hz, 1H), 8.19 (s, 1H), 7.94 (d, J=8 Hz, 1H), 6.76 (s, 1H), 5.33-5.28 (m, 1H), 4.64-4.60 (m, 1H), 4.57 (q, J=7.2 Hz, 2H), 4.41-4.36 (m, 1H), 2.64-2.57 (m, 1H), 2.24-2.10 (m, 2H), 1.50 (t, J=7.2 Hz, 1H), 1.10-1.06 (m, 2H), 1.01 (t, J=7.2 Hz, 3H), 0.98-0.92 (m, 2H).

Example 3: Synthesis of N-(1-(2-(cyclopropane-sulfonamido)thiazol-4-yl)cyclopropyl)-2-naphth-amide (I-1)

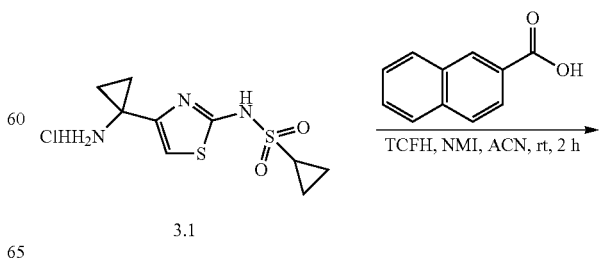

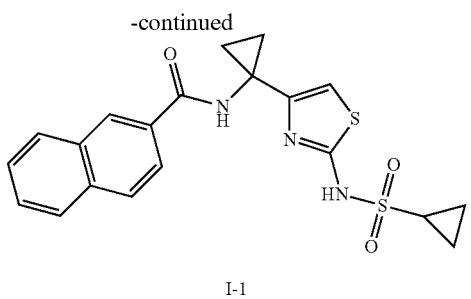

I-1

Synthesis of I-1. To a solution of N-(4-(1-aminocyclopropyl)thiazol-2-yl)cyclopropanesulfonamide hydrochloride (3.1, 50.0 mg, 0.17 mmol, 1.0 eq) and 2-naphthoic acid (29.3 mg, 0.17 mmol, 1.0 eq) in acetonitrile (5 mL) was added TCFH (95.2 mg, 0.34 mmol, 2.0 equiv) and NMI (140.2 mg, 1.71 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (35% ACN up to 48% in 7 min); UV detection at 254/220 nm. The product-containing fractions were combined and evaporated partially in vacuo and lyophilized overnight to afford the title compound as a white solid. (8.9 mg, 13%), MS (ES): m/z 414 [M+H]$^+$; $^1$H NMR (400 MHz, CD$_3$OD) δ 8.43 (s, 1H), 8.02-7.91 (m, 4H), 7.64-7.57 (m, 2H), 6.48 (s, 1H), 2.65-2.58 (m, 1H), 1.47-1.30 (m, 4H), 1.11-1.07 (m, 2H), 0.97-0.92 (m, 2H).

Example 4: Synthesis of N-(1-(2-(cyclopropanesulfonamido)thiazol-4-yl)cyclopropyl)quinoline-2-carboxamide (I-2)

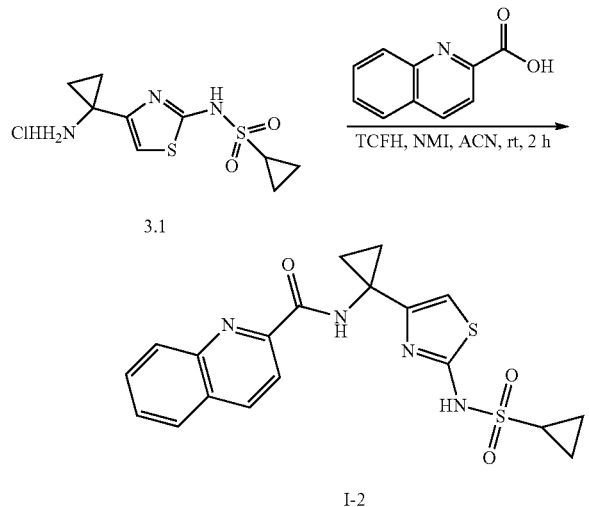

I-2

Synthesis of I-2. To a solution of 3.1 (100.0 mg, 0.34 mmol, 1.0 eq) and quinoline-2-carboxylic acid (58.6 mg, 0.34 mmol, 1.0 eq) in acetonitrile (5 mL) was added TCFH (190.4 mg, 0.68 mmol, 2.0 equiv) and NMI (280.4 mg, 3.42 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (31% ACN up to 42% in 7 min); UV detection at 254/220 nm. The product-containing fractions were combined and evaporated partially in vacuo and lyophilized overnight to afford the title compound as a white solid. (32.2 mg, 23%), MS (ES): m/z 415 [M+H]$^+$; $^1$H NMR (400 MHz, CD$_3$OD) δ 8.49 (d, J=8.4 Hz, 1H), 8.20 (d, J=8.8 Hz, 2H), 8.02 (d, J=8 Hz, 1H), 7.88-7.84 (m, 1H), 7.74-7.70 (m, 1H), 6.54 (s, 1H), 2.63-2.56 (m, 1H), 1.48-1.39 (m, 4H), 1.10-1.06 (m, 2H), 0.97-0.92 (m, 2H).

Example 5: Synthesis of N-(1-(2-(cyclopropanesulfonamido)thiazol-4-yl)cyclopropyl)isoquinoline-3-carboxamide (I-3)

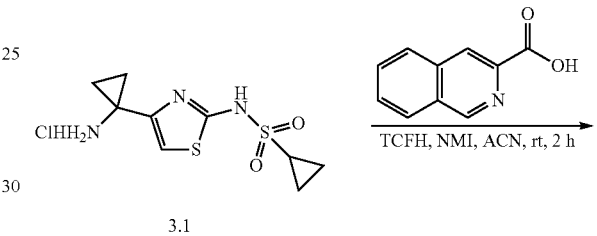

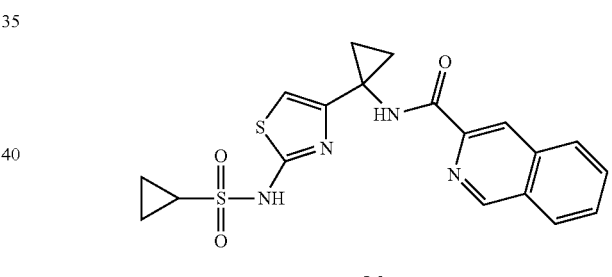

I-3

Synthesis of I-3. To a solution of 3.1 (50.0 mg, 0.17 mmol, 1.0 eq) and isoquinoline-3-carboxylic acid (29.3 mg, 0.17 mmol, 1.0 eq) in acetonitrile (5 mL) was added TCFH (95.2 mg, 0.34 mmol, 2.0 equiv) and NMI (140.2 mg, 1.71 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (33% ACN up to 45% in 7 min); UV detection at 254/220 nm. The product-containing fractions were combined and evaporated partially in vacuo and lyophilized overnight to afford the title compound as a white solid. (13.3 mg, 19%), MS (ES): m/z 415 [M+H]$^+$; $^1$H NMR (400 MHz, CD3OD) δ 9.31 (s, 1H), 8.57 (s, 1H), 8.19 (d, J=8.4 Hz, 1H), 8.10 (d, J=8 Hz, 1H), 7.89-7.80 (m, 4H), 6.53 (s, 1H), 2.62-2.56 (m, 1H), 1.47-1.36 (m, 4H), 1.13-1.06 (m, 2H), 1.00-0.90 (m, 2H).

Example 6: Synthesis of N-(1-(2-(cyclopropane-sulfonamido)thiazol-4-yl)cyclopropyl)quinoline-3-carboxamide (I-5)

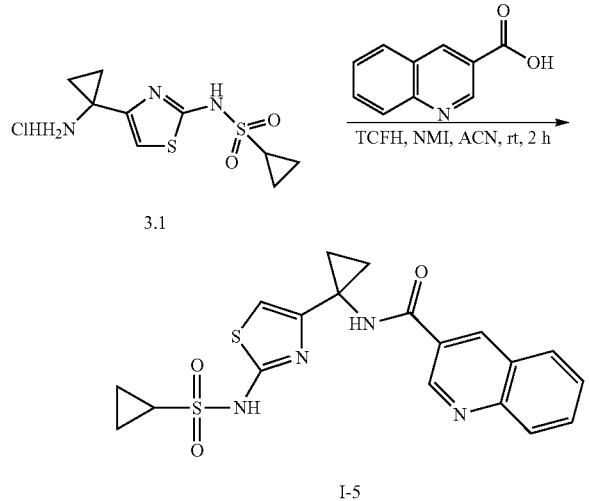

Synthesis of I-5. To a solution of 3.1 (50.0 mg, 0.17 mmol, 1.0 eq) and quinoline-3-carboxylic acid (29.3 mg, 0.17 mmol, 1.0 eq) in acetonitrile (5 mL) was added TCFH (95.2 mg, 0.34 mmol, 2.0 equiv) and NMI (140.2 mg, 1.71 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (32% ACN up to 44% in 7 min); UV detection at 254/220 nm. The product-containing fractions were combined and evaporated partially in vacuo and lyophilized overnight to afford the title compound as a white solid. (11.7 mg, 17%), MS (ES): m/z 415 [M+H]$^+$; $^1$H NMR (400 MHz, d$_6$-DMSO) δ 9.41 (s, 1H), 9.31 (s, 1H), 8.88 (s, 1H), 8.10 (d, J=8.4 Hz, 2H), 7.88 (t, J=8.4 Hz, 1H), 7.71 (t, J=8.4 Hz, 1H), 6.45 (s, 1H), 2.61-2.51 (m, 1H), 1.43-1.37 (m, 2H), 1.32-1.26 (m, 2H), 0.93-0.85 (m, 4H).

Example 7: Synthesis of N-(1-(2-(cyclopropane-sulfonamido)thiazol-4-yl)cyclopropyl)quinoline-6-carboxamide (I-9)

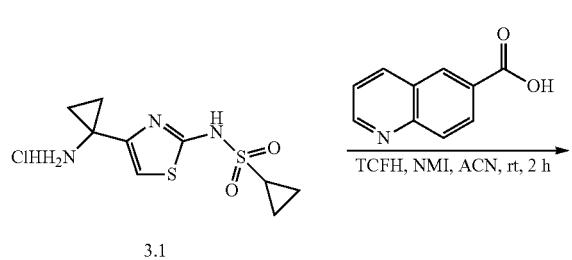

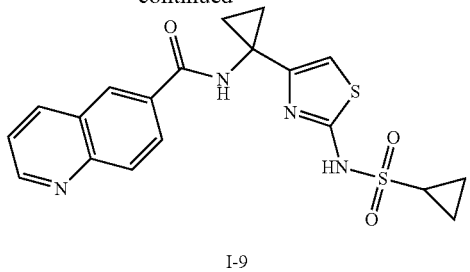

Synthesis of I-9. To a solution of 3.1 (80.0 mg, 0.27 mmol, 1.0 eq) and quinoline-6-carboxylic acid (46.7 mg, 0.27 mmol, 1.0 eq) in acetonitrile (5 mL) was added TCFH (151.2 mg, 0.54 mmol, 2.0 equiv) and NMI (221.4 mg, 2.70 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (30% ACN up to 41% in 7 min); UV detection at 254/220 nm. The product-containing fractions were combined and evaporated partially in vacuo and lyophilized overnight to afford the title compound as a white solid. (25.0 mg, 22%), MS (ES): m/z 415 [M+H]$^+$; $^1$H NMR (400 MHz, CD$_3$OD) δ 8.97 (dd, J=4.4, 1.6 Hz, 1H), 8.56-8.50 (m, 2H), 8.22 (dd, J=8.8, 2.0 Hz, 1H), 8.13 (d, J=8.8 Hz, 1H), 7.65 (dd, J=4.4, 1.6 Hz, 1H), 6.52 (s, 1H), 2.68-2.58 (m, 1H), 1.48-1.28 (m, 4H), 1.12-1.08 (m, 2H), 1.05-0.94 (m, 2H).

Example 8: Synthesis of N-(1-(2-(cyclopropane-sulfonamido)thiazol-4-yl)cyclopropyl)isoquinoline-6-carboxamide (I-4)

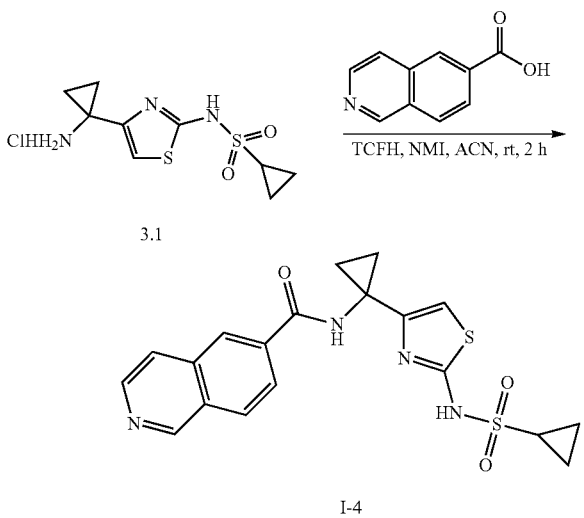

Synthesis of I-4. To a solution of 3.1 (50.0 mg, 0.17 mmol, 1.0 eq) and isoquinoline-6-carboxylic acid (29.4 mg, 0.17 mmol, 1.0 eq) in acetonitrile (5 mL) was added TCFH (95.2 mg, 0.34 mmol, 2.0 equiv) and NMI (139.4 mg, 1.70 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (31% ACN up to 46% in 7 min); UV detection at 254/220 nm. The product-containing fractions were combined and evaporated partially in vacuo and lyophilized overnight to afford the title compound as a white solid. (11.7 mg, 17%), MS (ES): m/z 415 [M+H]$^+$; $^1$H NMR (300 MHz, d$_6$-DMSO) δ 12.28 (br s, 1H), 9.40 (s, 1H), 9.34 (s, 1H), 8.58 (d, J=5.7 Hz, 1H), 8.50 (s, 1H), 8.21 (d, J=8.4 Hz, 1H), 8.08 (d, J=8.4 Hz, 1H), 7.92 (d, J=5.7 Hz, 1H), 6.43 (s, 1H), 2.62-2.54 (m, 1H), 1.41-1.23 (m, 4H), 1.01-0.84 (m, 4H).

Example 9: Synthesis of N-(1-(2-(cyclopropane-sulfonamido)thiazol-4-yl)cyclopropyl)isoquinoline-7-carboxamide (I-7)

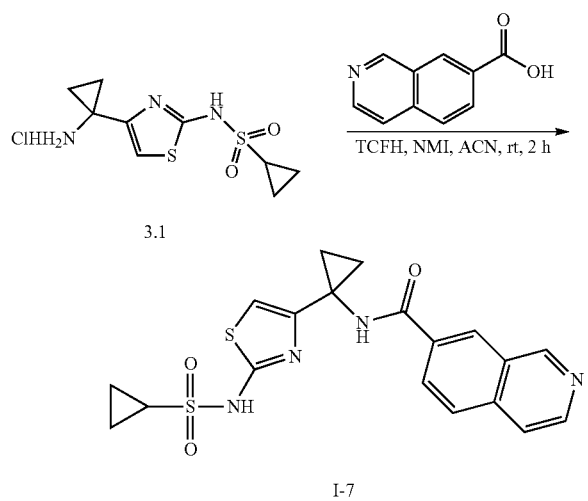

Synthesis of I-7. To a solution of 3.1 (80.0 mg, 0.27 mmol, 1.0 eq) and isoquinoline-7-carboxylic acid (46.7 mg, 0.27 mmol, 1.0 eq) in acetonitrile (5 mL) was added TCFH (151.2 mg, 0.54 mmol, 2.0 equiv) and NMI (221.4 mg, 2.70 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (33% ACN up to 48% in 7 min); UV detection at 254/220 nm. The product-containing fractions were combined and evaporated partially in vacuo and lyophilized overnight to afford the title compound as a white solid. (25.9 mg, 23%), MS (ES): m/z 415 [M+H]$^+$; $^1$H NMR (400 MHz, CD$_3$OD) δ 9.37 (s, 1H), 8.64 (s, 1H), 8.55 (d, J=6.0 Hz, 1H), 8.23 (d, J=8.4 Hz, 1H), 8.06 (d, J=8.8 Hz, 1H), 7.91 (d, J=6.0 Hz, 1H), 6.53 (s, 1H), 2.65-2.58 (m, 1H), 1.52-1.37 (m, 4H), 1.04-1.08 (m, 2H), 1.03-0.94 (m, 2H).

Example 10: Synthesis of N-(1-(2-(cyclopropane-sulfonamido)thiazol-4-yl)cyclopropyl)quinoline-7-carboxamide (I-10)

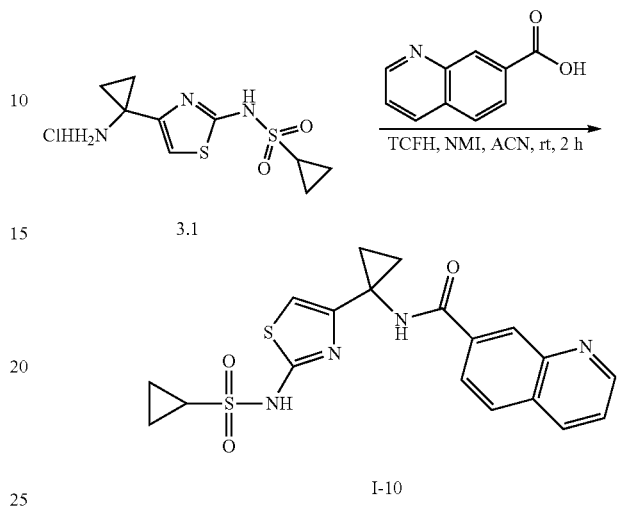

Synthesis of I-10. To a solution of 3.1 (50.0 mg, 0.17 mmol, 1.0 eq) and quinoline-7-carboxylic acid (29.4 mg, 0.17 mmol, 1.0 eq) in acetonitrile (5 mL) was added TCFH (95.2 mg, 0.34 mmol, 2.0 equiv) and NMI (139.4 mg, 1.70 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (31% ACN up to 43% in 7 min); UV detection at 254/220 nm. The product-containing fractions were combined and evaporated partially in vacuo and lyophilized overnight to afford the title compound as a white solid. (11.2 mg, 16%), MS (ES): m/z 415 [M+H]$^+$; $^1$H NMR (400 MHz, CD$_3$OD) δ 8.98 (d, J=4.4 Hz, 1H), 8.45 (d, J=8 Hz, 2H), 8.13-8.03 (m, 2H), 7.65 (dd, J=8.4, 4.0 Hz, 1H), 6.53 (s, 1H), 2.65-2.58 (m, 1H), 1.48-1.37 (m, 4H), 1.18-1.04 (m, 2H), 1.02-0.94 (m, 2H).

Example 11: Synthesis of 6-(1-(2-(cyclopropane-sulfonamido)thiazol-4-yl)cyclopropylcarbamoyl)isoquinoline 2-oxide (I-11)

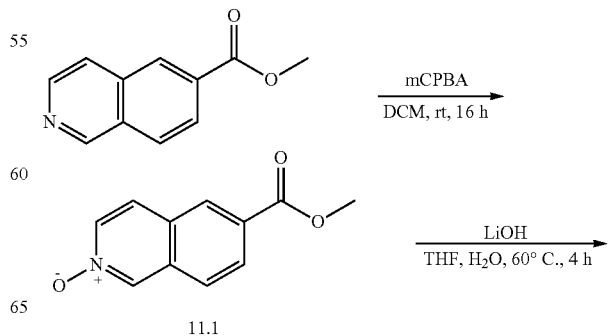

211

-continued

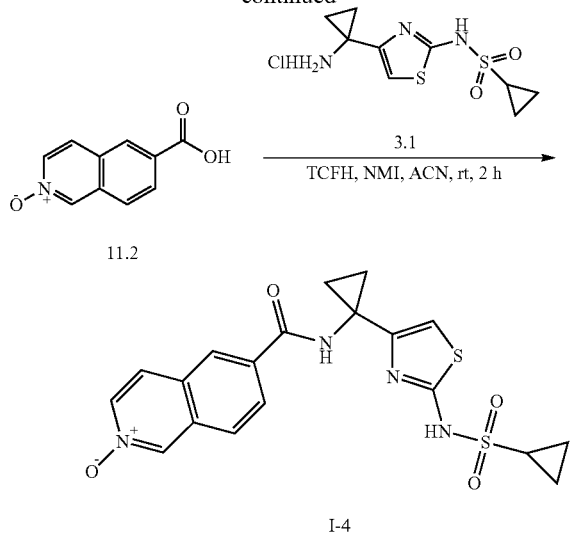

I-4

Synthesis of 11.1. To a solution of methyl isoquinoline-6-carboxylate (1.67 g, 8.93 mmol, 1.0 eq) in dichloromethane (40 mL) was added 3-chloroperoxybenzoic acid (2.30 g, 13.40 mmol, 1.5 eq) at r.t. The resulting solution was stirred for 16 h at r.t. The mixture was quenched with saturated aqueous sodium thiosulfatepentahydrate, then adjusted to pH 8 with saturated aqueous sodium bicarbonate and extracted with dichloromethane. The combined organic layer was washed with brine, dried over sodium sulfate and concentrated under reduced pressure. The residue was purified by silica gel column chromatography and compound was eluted in 50% ethyl acetate in petroleum ether to obtain 6-(methoxycarbonyl)isoquinoline 2-oxide as a yellow solid. (0.54 g, 30%), MS (ES): m/z 204 [M+H]$^+$.

Synthesis of 11.2. To a solution of 11.1 (240.0 mg, 1.18 mmol, 1.0 eq) in tetrahydrofuran (12 mL) and water (3 mL) was added lithium hydroxide (85.0 mg, 3.54 mmol, 3.0 equiv). The resulting solution was stirred for 4 h at 60° C. The mixture was concentrated under vacuum. The residue was diluted with water. The pH value of the solution was adjusted to 3 with 1N hydrochloric acid. The solids were collected by filtration and dried in an oven at 45° C. to obtain 6-carboxyisoquinoline 2-oxide as an off-white solid. (0.12 g, 54%), MS (ES): m/z 190 [M+H]$^+$.

Synthesis of I-11. To a solution of 3.1 (80.0 mg, 0.27 mmol, 1.0 eq) and 11.2 (51.3 mg, 0.27 mmol, 1.0 eq) in acetonitrile (5 mL) was added TCFH (151.2 mg, 0.54 mmol, 2.0 equiv) and NMI (221.4 mg, 2.70 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$+ 0.1% NH$_3$·H$_2$O) and ACN (22% ACN up to 33% in 7 min); UV detection at 254/220 nm. The product-containing fractions were combined and evaporated partially in vacuo and lyophilized overnight to afford the title compound as a white solid. (37.1 mg, 32%), MS (ES): m/z 431 [M+H]$^+$; $^1$H NMR (300 MHz, d$_6$-DMSO) δ 9.28 (s, 1H), 9.02 (s, 1H), 8.49 (s, 1H), 8.21 (d, J=1.5 Hz, 1H), 8.16-8.03 (m, 2H), 7.95 (d, J=8.7 Hz, 1H), 6.26 (s, 1H), 2.47-2.42 (m, 1H), 1.42-1.34 (m, 2H), 1.24-1.18 (m, 2H), 0.92-0.78 (m, 4H).

212

Example 12: Synthesis of N-(1-(2-(cyclopropanesulfonamido)thiazol-4-yl)cyclopropyl)-5-(4-methyl-1H-imidazol-1-yl)picolinamide (I-8)

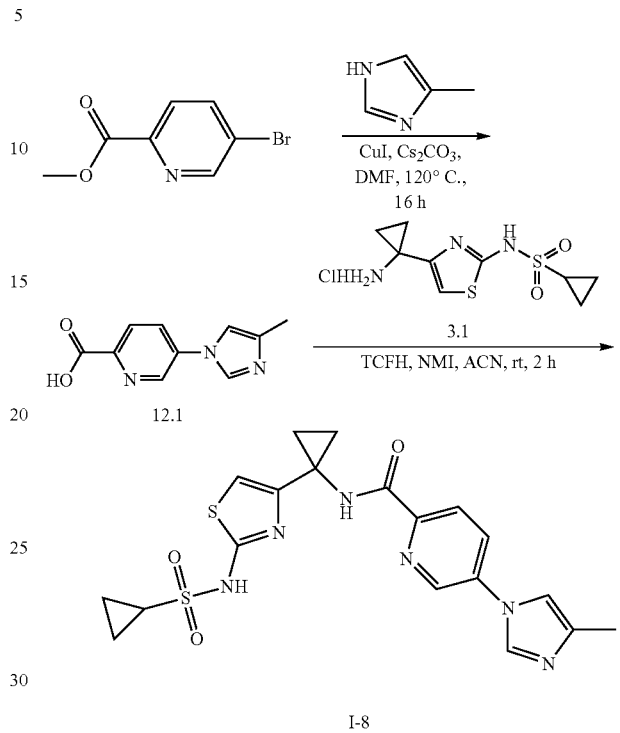

I-8

Synthesis of 12.1. To a solution of methyl 5-bromopyridine-2-carboxylate (500.0 mg, 2.31 mmol, 1.0 eq) and 4-methyl-1H-imidazole (380.0 mg, 4.63 mmol, 2.0 eq) in N,N-dimethylformamide (10 mL) was added cesium carbonate (1.51 g, 4.63 mmol, 2.0 eq) and copper iodide (881.5 mg, 4.63 mmol, 2.0 eq) at r.t. The resulting mixture was stirred for 16 h at 120° C. under nitrogren atmosphere. The mixture was cooled to r.t. The solid was filtered out. The filtrate was concentrated under reduced pressure. The residue was purified by reverse flash with the following conditions: Column, C18 Column; Mobile Phase, water (0.1% FA) and ACN (15% ACN up to 28% in 10 min); UV detection at 254/220 nm. The product-containing fractions were combined and concentrated under reduced pressure to afford 5-(4-methyl-1H-imidazol-1-yl)picolinic acid as a green solid. (70.0 mg, 15%), MS (ES): m/z 204 [M+H]$^+$.

Synthesis of I-8. To a solution of 12.1 (70.0 mg, 0.34 mmol, 1.0 eq) and 3.1 (100.3 mg, 0.34 mmol, 1.0 eq) in acetonitrile (10 mL) were added TCFH (190.4 mg, 0.68 mmol, 2.0 eq) and NMI (278.8 mg, 3.40 mmol, 10.0 eq) at r.t. The resulting mixture was stirred for 2 h at r.t. The mixture was diluted with water and extracted with ethyl acetate. The combined organic layer was washed with brine, dried over sodium sulfate and concentrated under reduced pressure. The crude product was purified by Prep-HPLC with the following conditions: Column, SunFire Prep C18 OBD Column, 19*150 mm, 5 um; Mobile Phase, water (0.1% FA) and ACN (7% ACN up to 17% in 7 min); UV detection at 254/220 nm. The product-containing fractions were combined and evaporated partially in vacuo and lyophilized overnight to afford the title compound as a white solid. (25.6 mg, 17%), MS (ES): m/z 445 [M+H]$^+$; $^1$H NMR (300 MHz, d$_6$-DMSO) δ 12.27 (br s, 1H), 9.30 (s, 1H), 8.98 (s, 1H), 8.39 (s, 1H), 8.26 (d, J=8.4 Hz, 1H), 8.21-8.09 (m, 1H), 7.67 (s, 1H), 6.41 (s, 1H), 2.61-2.55 (m, 1H), 2.19 (s, 3H), 1.37-1.24 (m, 4H), 0.89-0.88 (m, 4H).

Example 13: Synthesis of N-(4-(1-(5-(6-ethoxypyrazin-2-yl)-1-oxoisoindolin-2-yl)cyclopropyl)thiazol-2-yl)cyclopropanesulfonamide (I-13)

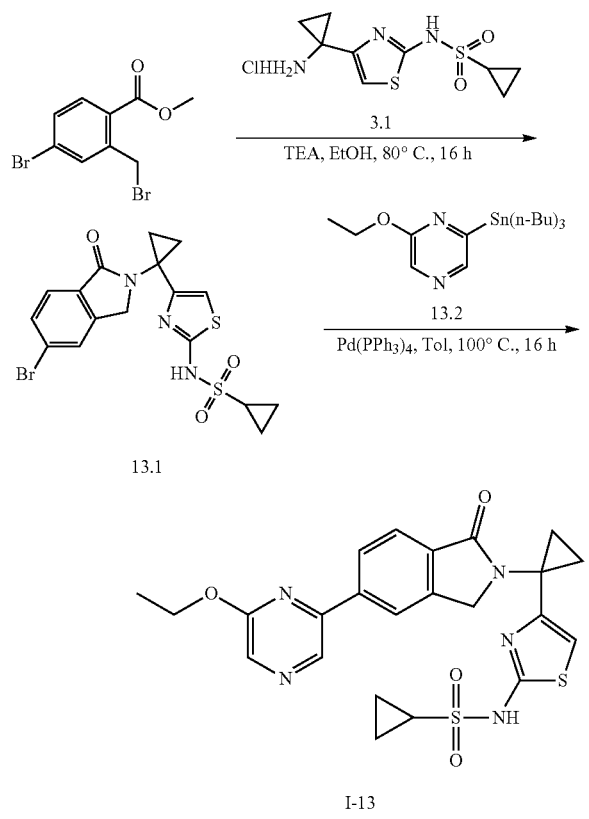

Synthesis of 13.1. To a solution of 3.1 (222.0 mg, 0.75 mmol, 1.0 eq) and methyl 4-bromo-2-(bromomethyl)benzoate (230.0 mg, 0.75 mmol, 1.0 eq) in ethanol (10 mL) was added triethylamine (303.0 mg, 3.00 mmol, 4.0 eq) at r.t. The resulting mixture was stirred for 16 h at 80° C. under nitrogren atmosphere. The mixture was cooled to r.t and concentrated under reduced pressure. The residue was purified by reverse flash with the following conditions: Column, C18 Column; Mobile Phase, water (10% NH₄HCO₃) and ACN (35% ACN up to 48% in 10 min); UV detection at 254/220 nm. The product-containing fractions were combined and concentrated under reduced pressure to afford N-(4-(1-(5-bromo-1-oxoisoindolin-2-yl)cyclopropyl)thiazol-2-yl)cyclopropanesulfonamide as a yellow solid. (100.0 mg, 29%), MS (ES): m/z 454/456 [M+H]⁺.

Synthesis of I-13. To a solution of 13.1 (100.0 mg, 0.22 mmol, 1.0 eq) and 2-ethoxy-6-(tributylstannyl)pyrazine (13.2, 273.3 mg, 0.66 mmol, 3.0 eq) in toluene (10 mL) were added Pd(PPh₃)₄ (23.1 mg, 0.02 mmol, 0.1 eq) at r.t. The resulting mixture was stirred for 16 h at 100° C. under nitrogren atmosphere. The mixture was cooled to r.t, diluted with water and extracted with ethyl acetate. The combined organic layer was washed with brine, dried over sodium sulfate and concentrated under reduced pressure. The crude product was purified by Prep-HPLC with the following conditions: Column, SunFire Prep C18 OBD Column, 19*150 mm, 5 um; Mobile Phase, water (0.1% FA) and ACN (27% ACN up to 41% in 7 min); UV detection at 254/220 nm. The product-containing fractions were combined and evaporated partially in vacuo and lyophilized overnight to afford the title compound as a white solid. (29 mg, 27%), MS (ES): m/z 498 [M+H]⁺; ¹H NMR (400 MHz, d₆-DMSO) δ 12.27 (br s, 1H), 8.91 (s, 1H), 8.35 (s, 1H), 8.32 (s, 1H), 8.26 (d, J=8.0 Hz, 1H), 7.82 (d, J=8.0 Hz, 1H), 6.35 (s, 1H), 4.67 (s, 2H), 4.51 (q, J=7.2 Hz, 2H), 2.59-2.51 (m, 1H), 1.52-1.45 (m, 4H), 1.42 (t, J=7.2 Hz, 3H), 0.95-0.88 (m, 4H).

Example 14: Synthesis of (R)—N-(4-(1-(5-(6-ethoxypyrazin-2-yl)-1-oxoisoindolin-2-yl)propyl)thiazol-2-yl)cyclopropanesulfonamide (I-12) and (S)—N-(4-(1-(5-(6-ethoxypyrazin-2-yl)-1-oxoisoindolin-2-yl)propyl)thiazol-2-yl)cyclopropanesulfonamide (I-12a)

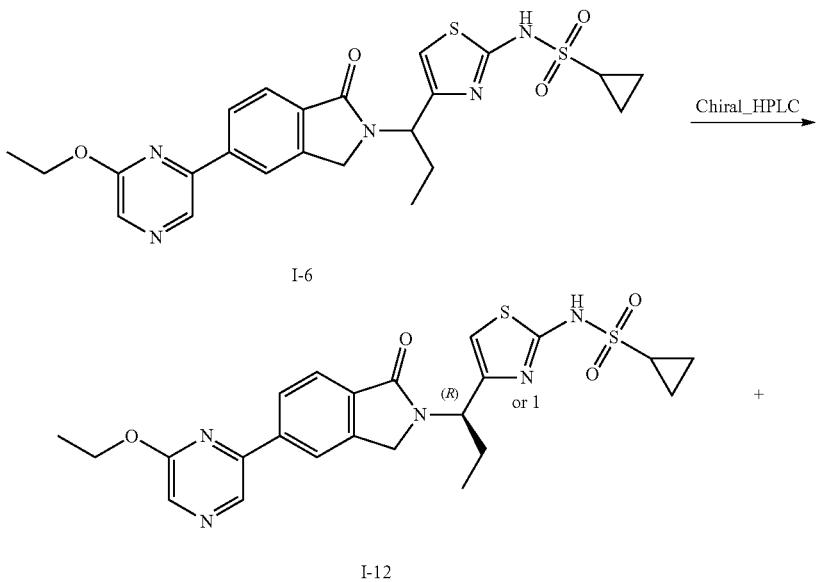

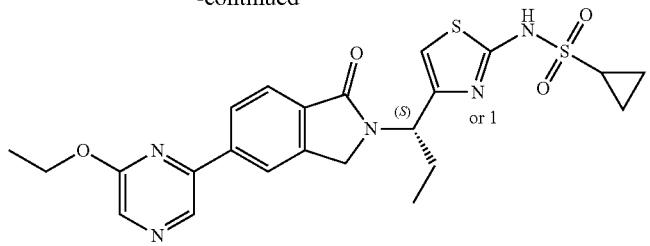

I-12a

Separation of I-12 and I-12a. Compound I-6 (17.0 mg, 0.03 mmol, 1.00 equiv) was separated by Chiral-Prep-HPLC with the following conditions: Column, CHIRALPAK AS-H, 2*25 mm, 5 um; mobile phase, Hex (0.1% FA): ethanol=80:20; Detector, UV 254/220 nm. The product-containing fractions were combined and concentrated under reduced pressure to afford (R)—N-(4-(1-(5-(6-ethoxy-pyrazin-2-yl)-1-oxoisoindolin-2-yl)propyl)thiazol-2-yl)cyclopropanesulfonamide (3.9 mg, 23%, first peak) and (S)—N-(4-(1-(5-(6-ethoxypyrazin-2-yl)-1-oxoisoindolin-2-yl)propyl)thiazol-2-yl)cyclopropanesulfonamide as a white solid. (0.9 mg, 5% second peak).

I-12: MS (ES): m/z 500 [M+H]$^+$; $^1$H NMR (400 MHz, CD$_3$OD) δ 8.74 (s, 1H), 8.31 (s, 1H), 8.28 (d, J=8 Hz, 1H), 8.19 (s, 1H), 7.94 (d, J=8 Hz, 1H), 6.76 (s, 1H), 5.32-5.28 (m, 1H), 4.65-4.60 (m, 1H), 4.57 (q, J=7.2 Hz, 2H), 4.41-4.36 (m, 1H), 2.62-2.58 (m, 1H), 2.21-2.11 (m, 2H), 1.49 (t, J=7.2 Hz, 3H), 1.11-1.08 (m, 2H), 1.03 (t, J=7.2 Hz, 3H), 0.97-0.93 (m, 2H).

I-12a: MS (ES): m/z 500 [M+H]$^+$; $^1$H NMR (400 MHz, CD$_3$OD) δ 8.75 (s, 1H), 8.32 (s, 1H), 8.28 (d, J=8.4 Hz, 1H), 8.19 (s, 1H), 7.94 (d, J=8.4 Hz, 1H), 6.75 (s, 1H), 5.32-5.28 (m, 1H), 4.65-4.60 (m, 1H), 4.57 (q, J=7.2 Hz, 2H), 4.42-4.37 (m, 1H), 2.64-2.57 (m, 1H), 2.24-2.06 (m, 2H), 1.49 (t, J=6.8 Hz, 3H), 1.11-1.08 (m, 2H), 1.03 (t, J=7.2 Hz, 3H), 0.97-0.93 (m, 2H).

Example 15: Synthesis of 5-(6-ethoxypyrazin-2-yl)-N-(1-(2-(N-methylcyclopropanesulfonamido)thiazol-4-yl)cyclopropyl)picolinamide (I-14)

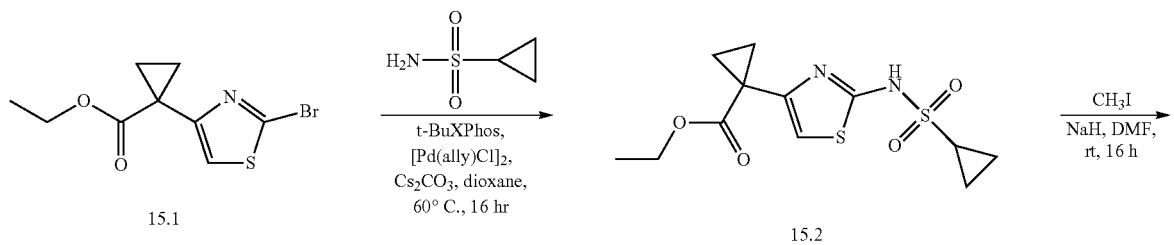

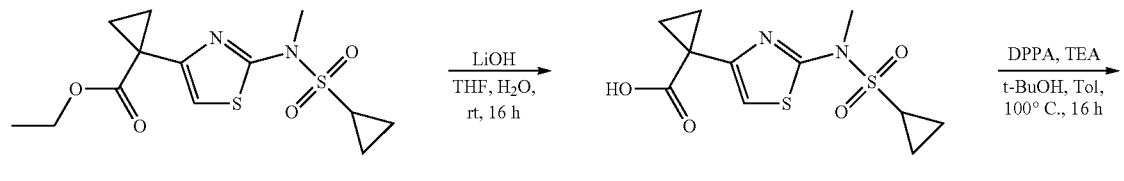

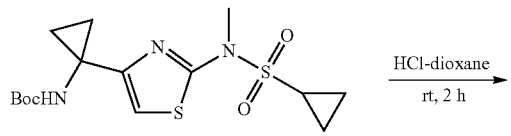

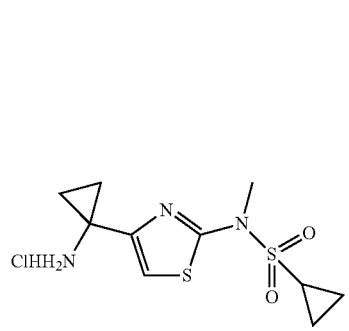
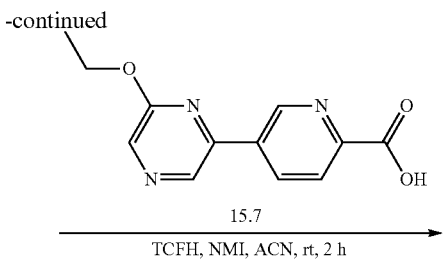
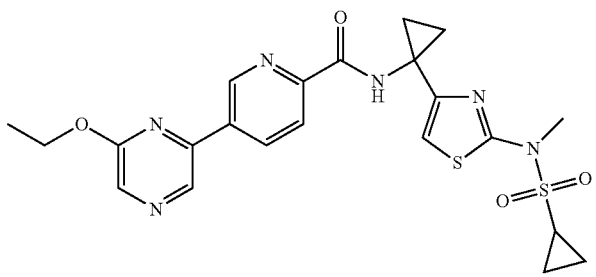

I-14

Synthesis of 15.2. To a solution of ethyl 1-(2-bromothiazol-4-yl)cyclopropane-1-carboxylate (15.1, 1.10 g, 4.00 mmol, 1.00 equiv) and cyclopropanesulfonamide (968.0 mg, 8.00 mmol, 2.0 equiv) in 1,4-dioxane (20 mL) was added cesium carbonate (3.91 g, 12.00 mmol, 3.0 equiv), t-BuXPhos (0.17 g, 0.40 mmol, 0.1 equiv) and [Pd(ally)Cl]$_2$ (73.7 mg, 0.20 mmol, 0.05 equiv) at room temperature under nitrogen atmosphere. The reaction mixture was stirred for 16 h at 60° C. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 50% ethyl acetate in petroleum ether to obtain ethyl 1-(2-(cyclopropanesulfonamido)thiazol-4-yl)cyclopropane-1-carboxylate (15.2) as a yellow solid. (0.85 g, 67%), MS (ES): m/z 317 [M+H]$^+$.

Synthesis of 15.3. To a solution of 15.2 (0.85 g, 2.69 mmol, 1.0 eq) in N,N-dimethylformamide (10 mL) was added sodium hydride (60%, 129.2 mg, 3.23 mmol, 1.2 equiv). After 30 min, iodomethane (573.7 mg, 4.04 mmol, 1.5 eq) was added. The resulting solution was stirred for 16 h at r.t. The mixture was quenched with water and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain ethyl 1-(2-(N-methylcyclopropanesulfonamido)thiazol-4-yl)cyclopropane-1-carboxylate (15.3) as a yellow solid. (0.68 g, 77%), MS (ES): m/z 331 [M+H]$^+$.

Synthesis of 15.4. To a solution of 15.3 (0.68 g, 2.06 mmol, 1.0 eq) in tetrahydrofuran (10 mL) and water (2 mL) was added lithiumol (148.3 mg, 6.18 mmol, 3.0 equiv). The resulting solution was stirred for 16 h at r.t. The mixture was concentrated under vacuum. The residue was diluted with water. The pH value of the solution was adjusted to 3 with 1N hydrochloric acid. The solids were collected by filtration to obtain 1-(2-(N-methylcyclopropanesulfonamido)thiazol-4-yl)cyclopropane-1-carboxylic acid (15.4) as an off-white solid. (0.45 g, 72%), MS (ES): m/z 303 [M+H]$^+$.

Synthesis of 15.5. To a solution of 15.4 (0.45 g, 1.49 mmol, 1.0 eq), trimethylamine (180.8 mg, 1.79 mmol, 1.2 eq), toluene (10 mL) and 2-methylpropan-2-ol (10 mL), was added diphenylphosphoryl azide (0.41 g, 1.49 mmol, 1.0 eq) at r.t. The resulting solution was stirred for 16 h at 100° C. The mixture was cooled to r.t. The pH value of the solution was adjusted to 8 with saturated aqueous sodium bicarbonate and extracted with ethyl acetate. The combined organic layer was washed with brine, dried over sodium sulfate and concentrated under reduced pressure. The residue was purified by silica gel column chromatography and compound was eluted in 40% ethyl acetate in petroleum ether to obtain tert-butyl (1-(2-(N-methylcyclopropanesulfonamido)thiazol-4-yl)cyclopropyl)carbamate (15.5) as a yellow oil. (0.25 g, 45%), MS (ES): m/z 374 [M+H]$^+$.

Synthesis of 15.6. A solution of 15.5 (0.25 g, 0.67 mmol, 1.0 eq) in hydrochloric acid in 1,4-dioxane (4.0 M, 10 mL) was stirred for 2 h at r.t. The mixture was concentrated under reduced pressure to afford N-(4-(1-aminocyclopropyl)thiazol-2-yl)-N-methylcyclopropanesulfonamide hydrochloride as an off-white solid. (207.1 mg, 100%), MS (ES): m/z 274 [M+H]$^+$.

Synthesis of I-14. To a solution of 15.6 (49.1 mg, 0.18 mmol, 1.0 eq) and 5-(6-ethoxypyrazin-2-yl)picolinic acid (15.7, 44.1 mg, 0.18 mmol, 1.0 eq) in acetonitrile (5 mL) was added TCFH (100.8 mg, 0.36 mmol, 2.0 equiv) and NMI (147.6 mg, 1.80 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (38% ACN up to 47% in 8 min); UV detection at 254/220 nm. The product-containing fractions were combined and evaporated partially in vacuo and lyophilized overnight to afford the title compound as a white solid. (12.9 mg, 14%), MS (ES): m/z 501 [M+H]$^+$; $^1$H NMR (400 MHz, d$_6$-DMSO) δ 9.70 (s, 1H), 9.34 (s, 1H), 8.99 (s, 1H), 8.67 (dd, J=8.4 Hz, 1H), 8.37 (s, 1H), 8.12 (dd, J=8.4 Hz, 1H), 6.90 (s, 1H), 4.51 (q, J=7.2 Hz, 2H), 3.65 (s, 3H), 2.63-2.55 (m, 1H), 1.42 (t, J=7.2 Hz, 3H), 1.38-1.32 (m, 4H), 0.97-0.86 (m, 4H).

Example 16: Synthesis of N-((4-(cyclopropane-sulfonamido) pyridin-2-yl) methyl)-4-(6-ethoxy-pyrazin-2-yl) benzamide (I-15)

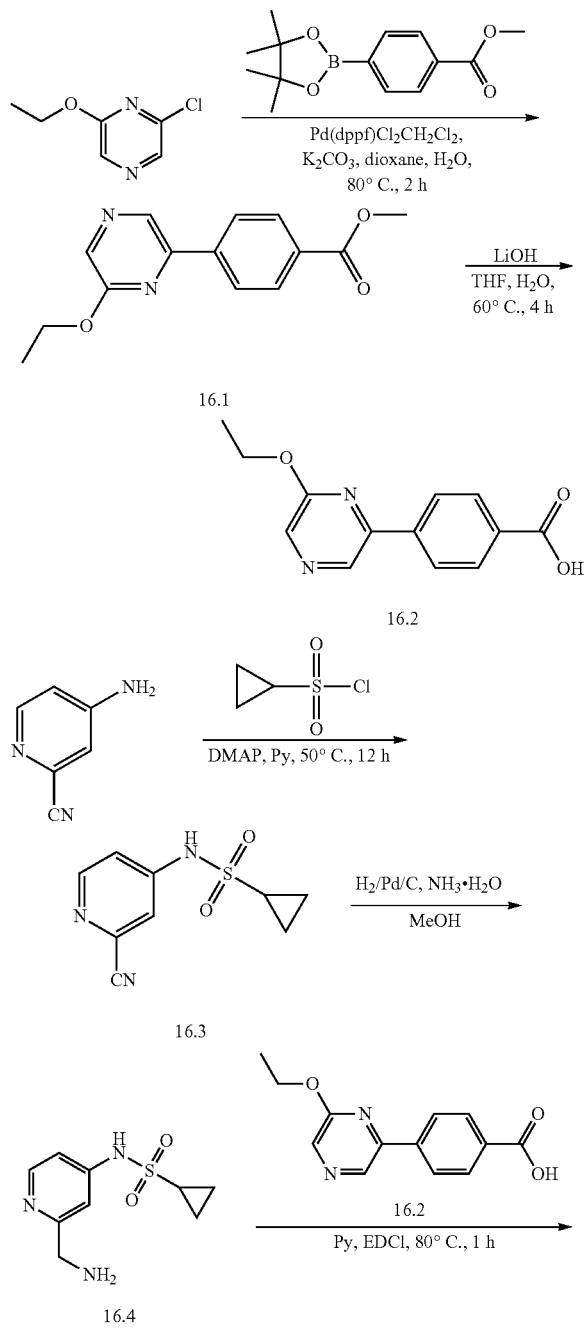

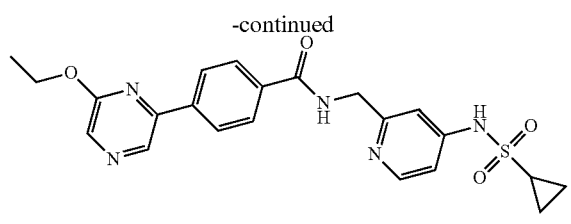

I-15

Synthesis of 16.1. To a solution of 2-chloro-6-ethoxy-pyrazine (3.16 g, 20 mmol, 1 eq) and methyl 4-(4,4,5,5-tetramethyl-1,3,2-dioxaborolan-2-yl) benzoate (6.28 g, 24 mmol, 1.2 eq) in 1,4-dioxane (80 mL) and water (20 mL) was added potassium carbonate (8.28 g, 60 mmol, 3 eq) and Pd(dppf)Cl$_2$CH$_2$C$_{1\text{-}2}$(1.63 g, 2 mmol, 0.1 eq). The resulting solution was stirred for 2 h at 80° C. The mixture was cooled to room temperature, diluted with water and extracted with ethyl acetate. The combined organic layer was washed with brine, dried over sodium sulfate, and concentrated under reduced pressure. The residue was purified by silica gel column chromatography and compound was eluted in 20% ethyl acetate in petroleum ether to obtain methyl 4-(6-ethoxypyrazin-2-yl) benzoate (16.1) as an off-white solid. (4.18 g, 78%), MS (ES): m/z 259 [M+H]$^+$.

Synthesis of 16.2. To a solution of 16.1 (4.18 g, 15.6 mmol, 1 eq) in tetrahydrofuran (80 mL) and water (20 mL) was added lithiumol (1.13 g, 46.86 mmol, 3 equiv). The resulting solution was stirred for 4 h at 60° C. The mixture was cooled to room temperature and concentrated under vacuum. The residue was diluted with water. The pH value of the solution was adjusted to 3 with 1N hydrochloric acid. The solids were collected by filtration to obtain 4-(6-ethoxy-pyrazin-2-yl) benzoic acid (16.2) as a white solid. (2.72 g, 69%), MS (ES): m/z 245 [M+H]$^+$.

Synthesis of 16.3. To a solution of 4-aminopicolinonitrile (1.19 g, 10 mmol, 1 eq) in pyridine (20 mL) was added 4-dimethylaminopyridine (122 mg, 1 mmol, 0.1 eq) and cyclopropanesulfonyl chloride (4.21 g, 30 mmol, 3 eq) at 0° C. The resulting solution was stirred for 12 h at 50° C. The mixture was cooled to room temperature and concentrated under reduced pressure. The residue was purified by reverse flash with the following conditions: Column, C18 Column; Mobile Phase, water (0.1% FA) and ACN (5% ACN up to 30% in 20 min); UV detection at 254/220 nm. The product-containing fractions were combined and concentrated under reduced pressure to obtain N-(2-cyanopyridin-4-yl) cyclo-propanesulfonamide (16.3) as a yellow solid. (1.2 g, 53%), MS (ES): m/z 224 [M+H]$^+$.

Synthesis of 16.4. To a solution of 16.3 (1 g, 4.48 mmol, 1 eq) in methanol (25 mL) and ammonium hydroxide (5 mL) was flushed three times with nitrogen. To the solution was added palladium on carbon (200 mg), followed by flushing with hydrogen. The mixture was stirred 2 h at room temperature under an atmosphere of hydrogen. The solid was filtered out and the solution was concentrated under reduced pressure to obtain crude N-(2-(aminomethyl) pyridin-4-yl) cyclopropanesulfonamide (16.4) as a yellow solid. (900 mg, 88%), MS (ES): m/z 228 [M+H]$^+$.

Synthesis of I-15. To a solution of 16.4 (100 mg, 0.44 mmol, 1 equiv) in pyridine (2 mL) was added 16.2 (118.2 mg, 0.48 mmol, 1.1 eq) and 1-ethyl-3-(3-dimethylamino propyl) carbodiie hydrochlolide (126.5 mg, 0.66 mmol, 1.5 eq) at room temperature. The resulting solution was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column: YMC-Actus Triart C18 30*250.5 um; Mobile Phase, water (0.1% NH$_4$HCO$_3$+0.1% NH$_3$·H$_2$O) and ACN (15% ACN up to 45% in 7 min); UV detection at 254/210 nm. The product-containing fractions were combined and evaporated partially in vacuum and lyophilized overnight to afford the title compound as a white solid. (67.6 mg, 33%), MS (ES): m/z 454 [M+H]$^+$; $^1$H NMR (400 MHz, d$_6$-DMSO) δ 10.83 (brs, 1H), 9.24 (t, J=6.0 Hz, 1H), 8.89 (s, 1H), 8.31-8.19 (m, 4H), 8.05 (d, J=8.4 Hz 2H), 7.08-6.98 (m, 2H), 4.55-4.45 (m, 4H), 2.72-2.65 (m, 1H), 1.41 (t, J=7.0 Hz, 3H), 0.99-0.89 (m, 4H).

Example 17: Synthesis of N-[(4-cyclopropanesulfonamidopyridin-2-yl) methyl]-5-(6-ethoxypyrazin-2-yl) pyridine-2-carboxamide (I-16)

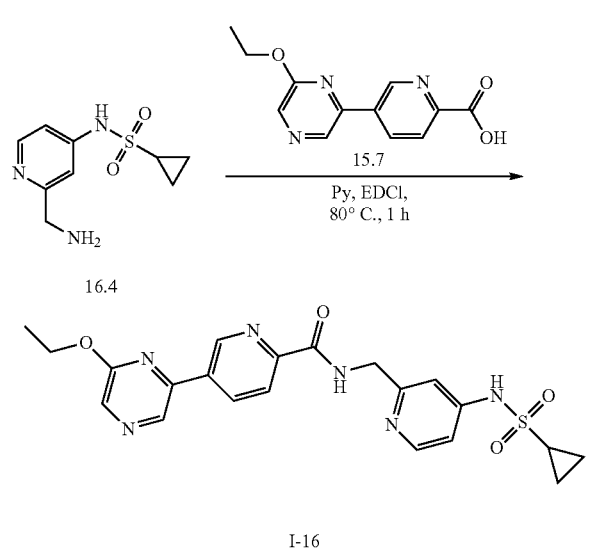

Example 18: Synthesis of N-((5-(cyclopropanesulfonamido) pyridin-3-yl) methyl)-5-(6-ethoxypyrazin-2-yl) picolinamide (I-26)

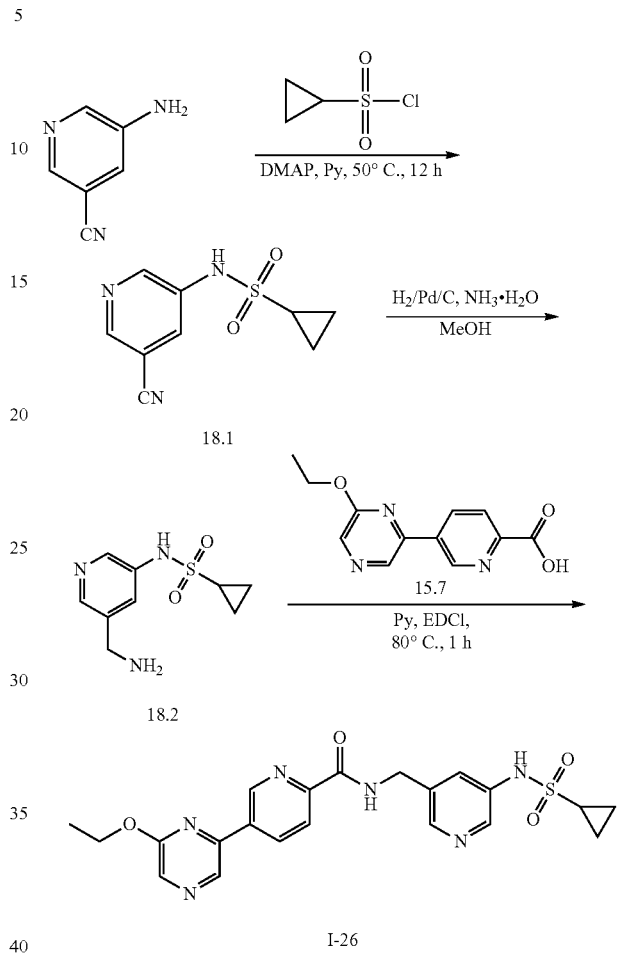

Synthesis of I-16. To a solution of N-(2-(aminomethyl) pyridin-4-yl) cyclopropanesulfonamide (16.4, 44.5 mg, 0.19 mmol, 1 equiv) in pyridine (2 mL) was added 5-(6-ethoxypyrazin-2-yl) pyridine-2-carboxylic acid (15.7, 48 mg, 0.19 mmol, 1 eq) and 1-ethyl-3-(3-dimethylamino propyl) carbodiie hydrochloride (75 mg, 0.38 mmol, 2 eq) at room temperature. The resulting solution was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column: YMC-Actus Triart C18 30*250.5 um; Mobile Phase, water (0.1% NH$_4$HCO$_3$+0.1% NH$_3$·H$_2$O) and ACN (22% ACN up to 33% in 7 min); UV detection at 254/210 nm. The product-containing fractions were combined and evaporated partially in vacuum and lyophilized overnight to afford the title compound as a white solid. (37.7 mg, 42%), MS (ES): m/z 455 [M+H]$^+$; $^1$H NMR (400 MHz, d$_6$-DMSO) δ 10.92 (brs, 1H), 9.47 (t, J=6.0 Hz, 1H), 9.41 (d, J=1.6 Hz, 1H), 9.01 (s, 1H), 8.71 (dd, J=8.4, 2.4 Hz, 1H), 8.37 (s, 1H), 8.25-8.19 (m, 2H), 7.02 (d, J=3.2 Hz, 2H), 4.57-4.49 (m, 4H), 2.74-2.67 (m, 1H), 1.42 (t, J=6.8 Hz, 3H), 0.98-0.95 (m, 4H).

Synthesis of 18.1. To a solution of 5-aminonicotinonitrile (1.19 g, 10 mmol, 1 eq) in pyridine (20 mL) was added 4-dimethylaminopyridine (122 mg, 1 mmol, 0.1 eq) and cyclopropanesulfonyl chloride (4.21 g, 30 mmol, 3 eq) at 0° C. The resulting solution was stirred for 12 h at 50° C. The mixture was cooled to room temperature and concentrated under reduced pressure. The residue was purified by reverse phase flash with the following conditions: Column, C18 Column; Mobile Phase, water (0.1% FA) and ACN (5% ACN up to 30% in 20 min); UV detection at 254/220 nm. The product-containing fractions were combined and concentrated under reduced pressure to obtain N-(5-cyanopyridin-3-yl) cyclopropanesulfonamide (18.1) as a yellow solid. (1.2 g, 53%), MS (ES): m/z 224 [M+H]$^+$.

Synthesis of 18.2. A solution of 18.1 (1 g, 4.48 mmol, 1 eq) in methanol (25 mL) and ammonium hydroxide (5 mL) was flushed three times with nitrogen. To the solution was added palladium on carbon (100 mg, 0.94 mmol, 0.21 eq), followed by flushing with hydrogen. The mixture was stirred 2 hrs at room temperature under an atmosphere of hydrogen. The solid was filtered out and the solution was concentrated under reduced pressure to obtain N-[5-(aminomethyl) pyridin-3-yl] cyclopropaneesulfonamide (18.2) as a yellow solid. (900 mg, 88%), MS (ES): m/z 228 [M+H]$^+$.

Synthesis of I-26. To a solution of 5-(6-ethoxypyrazin-2-yl) pyridine-2-carboxylic acid (15.7, 50 mg, 0.2 mmol, 1 equiv) in pyridine (1 mL) was added 18.2 (50.9 mg, 0.22 mmol, 1.1 eq) and 1-ethyl-3-(3-dimethylamino propyl) carbodiie hydrochlolide (58.6 mg, 0.31 mmol, 1.5 eq) at room temperature. The resulting solution was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column: YMC-Actus Triart C18 30*250.5 um; Mobile Phase, water (0.1% $NH_4HCO_3$+0.1% $NH_3·H_2O$) and ACN (15% ACN up to 45% in 7 min); UV detection at 254/210 nm. The product-containing fractions were combined and evaporated partially in vacuum and lyophilized overnight to afford the title compound as a white solid. (36.5 mg, 39%), MS (ES): m/z 455 [M+H]$^+$; $^1$H NMR (400 MHz, DMSO-d$_6$) δ 9.98 (brs, 1H), 9.57 (t, J=8.4 Hz, 1H), 9.37 (d, J=2.4 Hz, 1H), 9.01 (s, 1H), 8.69 (dd, J=11.2, 2.8 Hz, 1H), 8.35-8.29 (m, 3H), 8.19 (d, J=8.2 Hz, 1H), 7.64 (s, 1H), 4.52 (m, 4H), 2.68-2.58 (m, 1H), 1.42 (t, J=7.0 Hz, 3H), 0.93-0.82 (m, 4H).

Example 19: Synthesis of 5-(6-ethoxypyrazin-2-yl)-N-((4-((trifluoromethyl)sulfonamido) pyridin-2-yl)methyl) picolinamide (I-23)

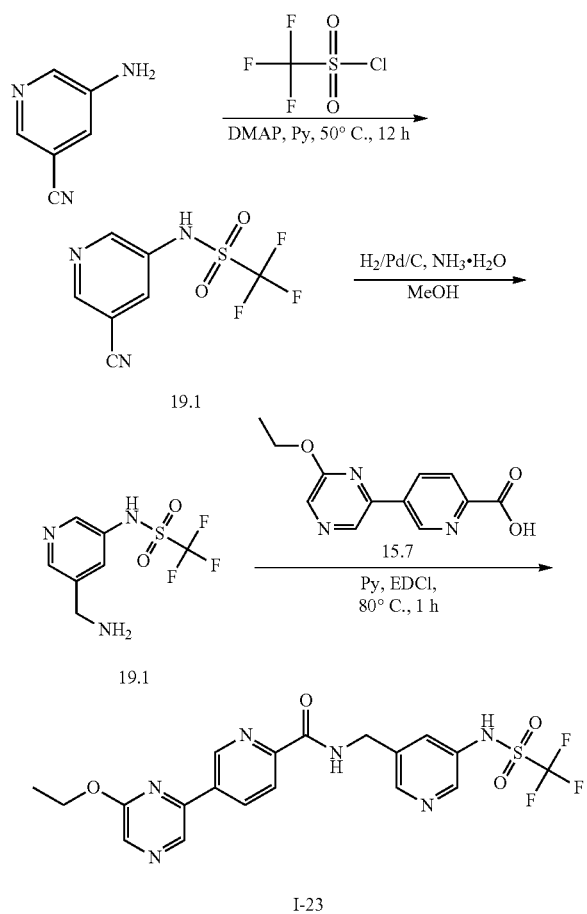

I-23

Synthesis of 19.1. To a solution of 4-aminopicolinonitrile (240 mg, 2 mmol, 1 eq) in pyridine (6 mL) was added 4-dimethylaminopyridine (24.6 mg, 0.2 mmol, 0.1 eq) and cyclopropanesulfonyl chloride (678.9 mg, 4 mmol, 4 eq) at 0° C. The resulting solution was stirred for 12 h at 50° C. The mixture was cooled to room temperature and concentrated under reduced pressure. The residue was purified by reverse phase flash with the following conditions: Column, C18 Column; Mobile Phase, water (0.1% FA) and ACN (5% ACN up to 30% in 20 min); UV detection at 254/220 nm. The product-containing fractions were combined and concentrated under reduced pressure to obtain N-(2-cyanopyridin-4-yl)-1,1,1-trifluoromethanesulfonamide (19.1) as a yellow oil. (200 mg, 39%), MS (ES): m/z 252 [M+H]$^+$.

Synthesis of 19.2. A solution of 19.1 (200 mg, 0.79 mmol, 1 eq) in methanol (6 mL) and ammonium hydroxide (2 mL) was flushed three times with nitrogen. To the solution was added palladium carbon (20 mg), followed by flushing with hydrogen. The mixture was stirred 2 h at room temperature under an atmosphere of hydrogen. The solid was filtered out and the solution was concentrated under reduced pressure to obtain crude N-(2-(aminomethyl) pyridin-4-yl)-1,1,1-trifluoromethanesulfonamide (19.2) as a green solid. (100 mg, 49%), MS (ES): m/z 256 [M+H]$^+$.

Synthesis of compound I-23. To a solution of 5-(6-ethoxypyrazin-2-yl) picolinic acid (15.7, 50 mg, 0.2 mmol, 1 equiv) in pyridine (1 mL) was added 19.2 (57.2 mg, 0.22 mmol, 1.1 eq) and 1-ethyl-3-(3-dimethylamino propyl) carbodiie hydrochlolide (58.6 mg, 0.31 mmol, 1.5 eq) at room temperature. The resulting solution was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column: YMC-Actus Triart C18 30*250.5 um; Mobile Phase, water (0.1% $NH_4HCO_3$+0.1% $NH_3·H_2O$) and ACN (15% ACN up to 33% in 10 min); UV detection at 254/210 nm. The product-containing fractions were combined and evaporated partially in vacuum and lyophilized overnight to afford the title compound as an off-white solid. (28 mg, 28%), MS (ES): m/z 483 [M+H]$^+$; $^1$H NMR (300 MHz, CD$_3$OD) δ 9.38 (d, J=2.0 Hz, 1H), 8.81 (s, 1H), 8.66 (dd, J=8.4, 2.1 Hz, 1H), 8.27 (s, 1H), 8.24 (s, 1H), 8.12 (d, J=6.0 Hz, 1H), 7.24-7.14 (m, 2H), 4.69 (s, 2H), 4.59 (q, J=7.2 Hz, 2H), 1.50 (t, J=7.2 Hz, 3H).

Example 20: Synthesis of N-[(4-cyclopropanesulfonamidopyridin-2-yl)methyl]-4-(6-ethoxypyrazin-2-yl)-2-fluorobenzamide (I-25)

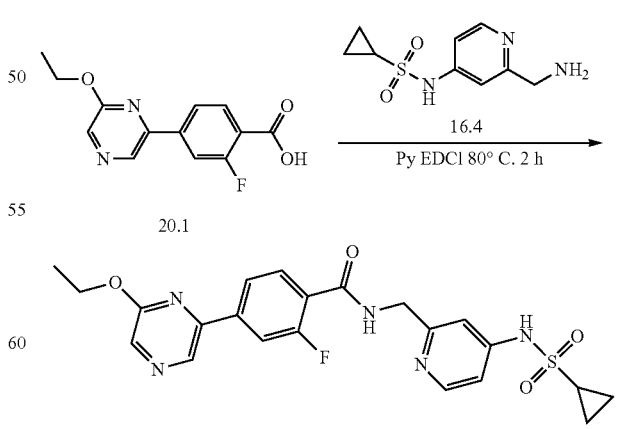

I-25

Synthesis of compound I-25. To a stirred solution of N-[2-(aminomethyl) pyridin-4-yl] cyclopropanesulfonamide (16.4, 43.3 mg, 0.19 mmol, 1 eq) and 1-ethyl-3-(3-dimethylamino propyl) carbodiie hydrochlolide (73.1 mg, 0.38 mmol, 2 eq) in pyridine was added 4-(6-ethoxypyrazin-2-yl)-2-fluorobenzoic acid (20.1, 50 mg, 0.19 mmol, 1 eq). The final reaction mixture was irradiated with microwave radiation for 2 h at 80° C. The mixture was cooled to room temperature, diluted with water and extracted with ethyl acetate. The combined organic layer was washed with brine, dried over sodium sulfate and concentrated under reduced pressure. The crude product (30 mg) was purified by Prep-HPLC with the following conditions Column: YMC-Actus Triart C18 30*250, 5 um; Mobile Phase: Water (0.1% NH$_4$HCO$_3$) and CAN (15% ACN up to 35% in 10 min), UV detection at 254/210 nm. The product-containing fractions were combined and evaporated partially in vacuum and lyophilized overnight to afford the title compound as a white solid. (12.1 mg, 13%), MS (ES): m/z 472 [M+H]$^+$; $^1$H NMR (400 MHz, d$_6$-DMSO) δ 10.77 (br, 1H), 8.99 (m, 1H), 8.94 (s, 1H), 8.33 (s, 1H), 8.19 (d, J=5.6 Hz, 1H), 8.11-8.07 (m, 2H), 7.88-7.84 (m, 1H), 7.06 (s, 1H), 6.97 (dd, J=5.6 Hz, J=1.6 Hz, 1H), 4.54-4.89 (m, 4H), 2.71-2.64 (m, 1H), 1.42 (t, J=7.2 Hz, 3H), 1.24-1.16 (m, 4H).

Example 21: Synthesis of N-[(4-cyclopropanesulfonamidopyridin-2-yl) methyl]-4-(6-ethoxypyrazin-2-yl) piperazine-1-carboxamide (I-27)

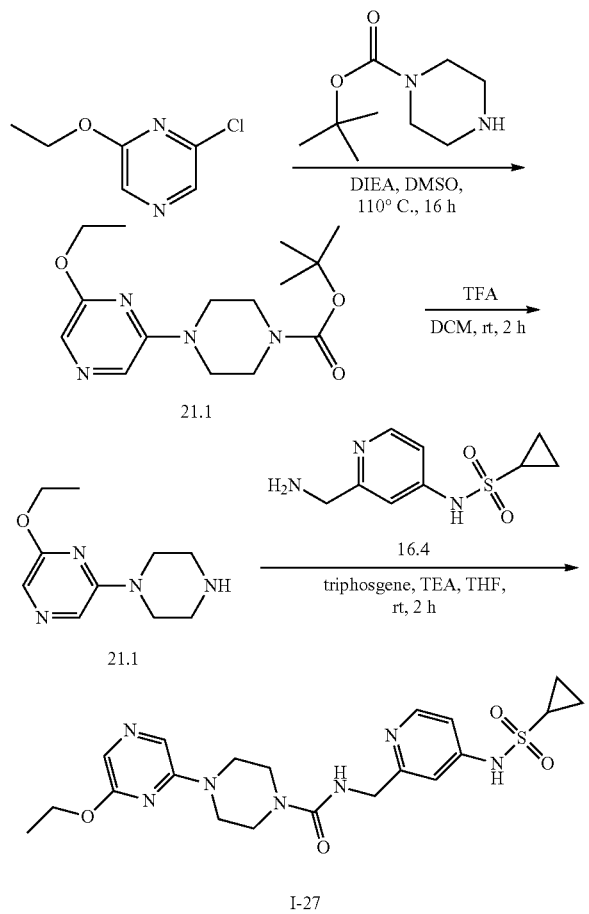

Synthesis of compound 21.1. To a stirred mixture of 2-chloro-6-ethoxy-pyrazine (790 mg, 4.98 mmol, 1 eq) and tert-butyl piperazine-1-carboxylate (1.12 g, 6.01 mmol, 1.2 eq) in dimethyl sulfoxide (15 mL) was added N, N-diisopropylethylamine (1.74 mL, 13.42 mmol, 2 eq) at room temperature. The resulting mixture was stirred for 16 h at 110° C. under nitrogen atmosphere. The mixture was cooled to room temperature. The residue was purified by reverse flash with the following conditions: Column, C18 Column; Mobile Phase, water (10 mmol/L NH$_4$HCO$_3$) and ACN (5% ACN up to 20% in 10 min); UV detection at 254/220 nm. The product-containing fractions were combined and concentrated under reduced pressure to afford tert-butyl 4-(6-ethoxypyrazin-2-yl) piperazine-1-carboxylate (21.1, 880 mg, 57%) as a white solid. MS (ES): m/z 309 [M+H]$^+$.

Synthesis of 21.2. To a stirred mixture of 21.1 (880 mg, 2.85 mmol, 1 equiv) in dichloromethane (10 mL) was added trifluoroacetic acid (3 mL) at room temperature. The resulting mixture was stirred for 2 h at room temperature. The pH value of the solution was adjusted to 8 with saturated aqueous sodium bicarbonate and extracted with ethyl acetate. The combined organic layer was washed with brine, dried over sodium sulfate and concentrated under reduced pressure to afford 2-ethoxy-6-(piperazin-1-yl) pyrazine (21.2, 660 mg, 89%) as a brown oil. MS (ES): m/z 209 [M+H]$^+$.

Synthesis of I-27. To a stirred mixture of 21.2 (45 mg, 0.22 mmol, 1 eq) in tetrahydrofuran (3 mL) were added triphosgene (20.8 mg, 0.07 mmol, 0.3 eq), triethylamine (0.12 mL) and N-[2-(aminomethyl) pyridin-4-yl] cyclopropanesulfonamide (16.4, 74.9 mg, 0.33 mmol, 1.5 eq) at 0° C. The resulting mixture was stirred for 2 h at room temperature. The pH value of the solution was adjusted to 8 with saturated aqueous sodium bicarbonate and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (0.1% NH$_4$HCO$_3$) and ACN (8% ACN up to 35% in 10 min); UV detection at 254/220 nm. The product-containing fractions were combined and evaporated partially in vacuum and lyophilized overnight to afford the title compound (20.2 mg, 20%) as a white solid. MS (ES): m/z 462 [M+H]$^+$; $^1$H NMR (300 MHz, d$_6$-DMSO) δ 8.09 (d, J=6.0 Hz, 1H), 7.82 (s, 1H), 7.47 (d, J=2.4 Hz, 1H), 7.31-7.29 (m, 1H), 6.92-6.88 (m, 2H), 4.31-4.23 (m, 4H), 3.56-3.50 (m, 8H), 2.63-2.56 (m, 1H), 1.33-1.29 (m, 3H), 0.92-0.91 (m, 4H).

Example 22: Synthesis of N-[(4-cyclopropanesulfonamidopyridin-2-yl) methyl]-5-(6-methoxypyrazin-2-yl) pyridine-2-carboxamide (I-24)

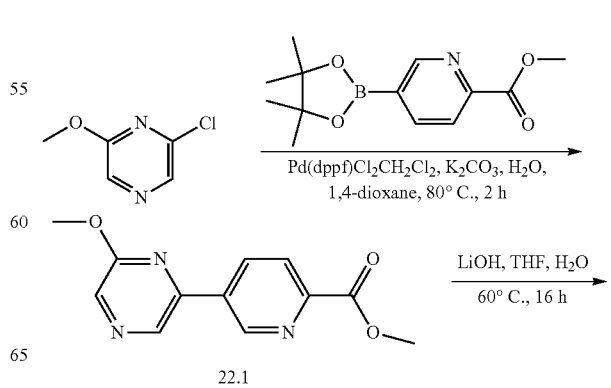

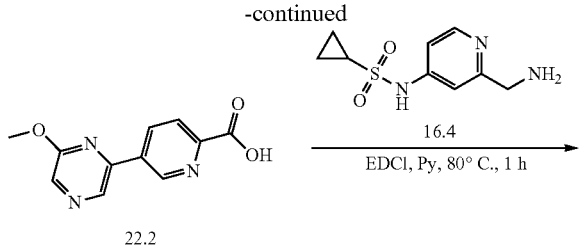

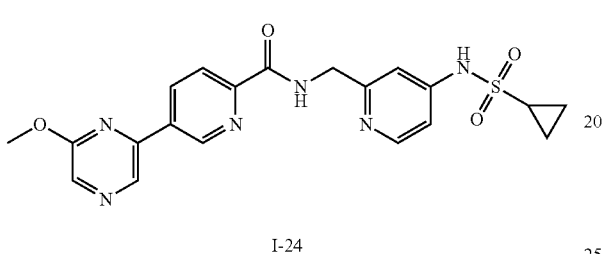

I-24

Synthesis of 22.1. To a stirred mixture of 2-chloro-6-methoxy-pyrazine (432 mg, 2.98 mmol, 1 eq) and methyl 5-(4,4,5,5-tetramethyl-1,3,2-dioxaborolan-2-yl) pyridine-2-carboxylate (786.2 mg, 2.98 mmol, 1 eq) in 1,4-dioxane (12 mL) and water (3 mL) were added potassium carbonate (1.2 g, 8.96 mmol, 3 eq) and Pd(dppf)Cl$_2$CH$_2$C$_{1-2}$(218.6 mg, 0.29 mmol, 0.1 eq) in portions at room temperature under nitrogen atmosphere. The resulting mixture was stirred for 2 h at 80° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 20% ethyl acetate in petroleum ether to obtain methyl 5-(6-methoxypyrazin-2-yl) pyridine-2-carboxylate (22.1) as a white solid. (440 mg, 60%), MS (ES): m/z 246 [M+H]$^+$.

Synthesis of 22.2. To a stirred mixture of 22.1 (440 mg, 1.79 mmol, 1 eq) in tetrahydrofuran (24 mL) and water (6 mL) was added lithiumol (214.8 mg, 8.97 mmol, 5 eq) in portions at room temperature. The resulting mixture was stirred for 16 h at 60° C. The mixture was concentrated under vacuum. The residue was diluted with water. The pH value of the solution was adjusted to 3 with 1N hydrochloric acid. The solids were collected by filtration to obtain 5-(6-methoxypyrazin-2-yl) pyridine-2-carboxylic acid (22.2) as a white solid. (397 mg, 95%), MS (ES): m/z 232 [M+H]$^+$.

Synthesis of I-24. To a stirred mixture of 22.2 (38 mg, 0.16 mmol, 1.1 eq) and N-[2-(aminomethyl) pyridin-4-yl] cyclopropanesulfonamide (16.4, 34 mg, 0.15 mmol, 1 eq) in pyridine (1 mL) was added 1-ethyl-3-(3-dimethylamino propyl) carbodiie hydrochlolide (57.4 mg, 0.3 mmol, 2 eq) at room temperature. The resulting mixture was stirred for 1 h at 80° C. The resulting mixture was concentrated under reduced pressure. The residue was purified by reverse flash with the following conditions: Column, C18 Column; Mobile Phase, water (10 mmol/L NH$_4$HCO$_3$) and ACN (10% ACN up to 50% in 10 min); UV detection at 254/220 nm. The product-containing fractions were combined and concentrated under reduced pressure. The residue was purified by Prep-HPLC with the following conditions: Column, YMC-Actus Triart C18 30*250.5 um; Mobile Phase, water (10 mmol/L NH$_4$HCO$_3$) and ACN (15% ACN up to 35% in 7 min); UV detection at 254/220 nm. The product-containing fractions were combined and evaporated partially in vacuum and lyophilized overnight to afford the title compound (20.3 mg, 30%) as a white solid. MS (ES): m/z 441 [M+H]$^+$; $^1$H NMR (300 MHz, d$_6$-DMSO) δ 10.84 (br, 1H), 9.49 (t, J=6.1 Hz, 1H), 9.42 (d, J=1.8 Hz, 1H), 9.03 (s, 1H), 8.73 (dd, J=8.1, 2.1 Hz, 1H), 8.40 (s, 1H), 8.28-8.16 (m, 2H), 7.03 (s, 2H), 4.57 (d, J=6.0 Hz, 2H), 4.06 (s, 3H), 2.72-2.68 (m, 1H), 1.03-0.86 (m, 4H).

Example 23: Synthesis of N-[(6-cyclopropanesulfo-namidopyrimidin-4-yl) methyl]-5-(6-ethoxypyrazin-2-yl) pyridine-2-carboxamide (I-22)

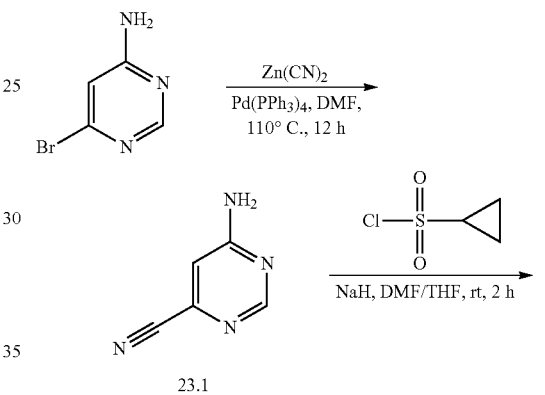

23.1

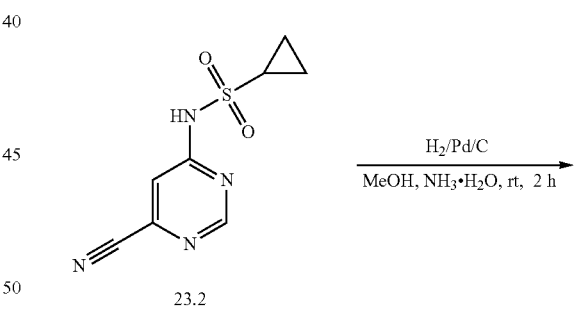

23.2

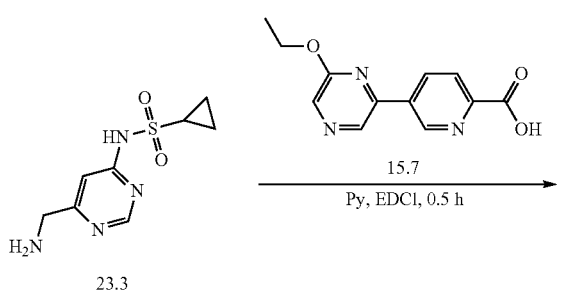

23.3

229
-continued

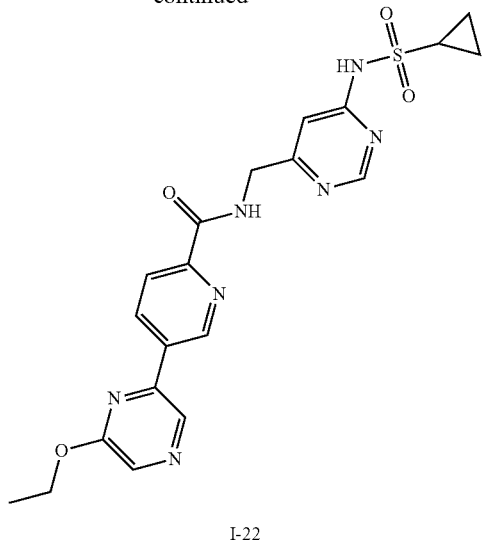

I-22

Synthesis of 23.1. To a stirred solution of 6-bromopyrimidin-4-amine (870 mg, 5 mmol, 1 eq) and zinccyanide (1.17 g, 10 mmol, 2 eq) in dimethyl formamide (20 mL) was added Pd(PPh$_3$)$_4$ (577.8 mg, 0.5 mmol, 0.1 eq) at room temperature. The resulting mixture was stirred for 12 h at 110° C. under nitrogen atmosphere. The mixture was cooled to room temperature and concentrated under reduced pressure. The residue was purified by reverse phase flash with the following conditions: Column, C18 Column; Mobile Phase, water (10 mmol/L NH$_4$HCO$_3$) and ACN (5% ACN up to 30% in 20 min); UV detection at 254/220 nm. The product-containing fractions were combined and concentrated under reduced pressure to obtain 6-aminopyrimidine-4-carbonitrile (23.1) as a white solid. (200 mg, 33%), MS (ES): m/z 121 [M+H]$^+$.

Synthesis of compound 23.2. To a stirred solution of 23.1 (200 mg, 1.66 mmol, 1 eq) in dimethyl formamide (2 mL) and tetrahydrofuran (4 mL) was added sodium hydride (60%, 79.9 mg, 3.33 mmol, 2 eq) at 0° C. The resulting mixture was stirred for 0.5 h at 0° C. under nitrogen atmosphere. Then cyclopropanesulfonyl chloride (702.23 mg, 4.99 mmol, 3 eq) was added dropwised at 0° C. The resulting mixture was stirred for 2 h at room temperature under nitrogen atmosphere. The mixture was quenched with water and extracted with ethyl acetate. The combined organic layer was washed with brine, dried over sodium sulfate and concentrated under reduced pressure. The residue was purified by reverse phase flash with the following conditions: Column, C18 Column; Mobile Phase, water (0.1% FA) and ACN (5% ACN up to 15% in 20 min); UV detection at 254/220 nm. The product-containing fractions were combined and concentrated under reduced pressure to obtain N-(6-cyanopyrimidin-4-yl) cyclopropanesulfonamide (23.2) as a yellow oil. (50 mg, 13%), MS (ES): m/z 225 [M+H]$^+$.

Synthesis of 23.3. A solution of 23.2 (350 mg, 1.56 mmol, 1 eq) in methanol (25 mL) and ammonium hydroxide (5 mL) was flushed three times with nitrogen. To the solution was added palladium carbon (40 mg), followed by flushing with hydrogen. The mixture was stirred 2 h at room temperature under an atmosphere of hydrogen. The solid was filtered out and the solution was concentrated under reduced pressure to obtain crude N-[6-(aminomethyl) pyrimidin-4-yl]cyclopropanesulfonamide (23.3) as a light green solid. (350 mg, 98%), MS (ES): m/z 229 [M+H]$^+$.

Synthesis of compound I-22. A mixture of 23.2 (238 mg, 1.04 mmol, 1 eq), 1-ethyl-3-(3-dimethylamino propyl) carbodiie hydrochlolide (399.7 mg, 2.08 mmol, 2 eq) and 5-(6-ethoxypyrazin-2-yl) pyridine-2-carboxylic acid (15.7, 255.6 mg, 1.04 mmol, 1 eq) in Pyridine (5 mL) was stirred for 0.5 h at 80° C. The residue was purified by reverse flash chromatography with the following conditions: column, C18 silica gel; mobile phase, ACN in water, 10% to 100% gradient in 10 min; detector, LTV 254 nm. The crude product (50 mg) was purified by Prep-HPLC with the following conditions (Column: XBridge Prep OBD C18 Column, 19*250 mm, 5 um; Mobile Phase: Water (0.1% FA) and CAN (50% to 70% in 10 min), LTV detection at 254/210 nm). The product-containing fractions were combined and evaporated partially in vacuum and lyophilized overnight to afford the title compound (27 mg, 5%) as a white solid. MS (ES): m/z 456 [M+H]$^+$; $^1$H NMR (400 MHz, DMSO-d$_6$) δ 11.2 (brs, 1H), 9.55 (t, J=6.1 Hz, 1H), 9.41 (d, J=2.1 Hz, 1H), 9.03 (s, 1H), 8.72 (dd, J=8.2, 2.3 Hz, 2H), 8.38 (s, 1H), 8.21 (d, J=8.2 Hz, 1H), 6.95 (s, 1H), 4.55-4.50 (m, 4H), 3.05-2.98 (m, 1H), 1.43 (t, J=7.0 Hz, 3H), 1.04-1.01 (m, 4H).

Example 24: Synthesis of N-[(4-cyclopropanesulfonamidopyridin-2-yl) methyl]-4-(6-ethoxypyrazin-2-yl)-2-oxopiperazine-1-carboxamide (I-28)

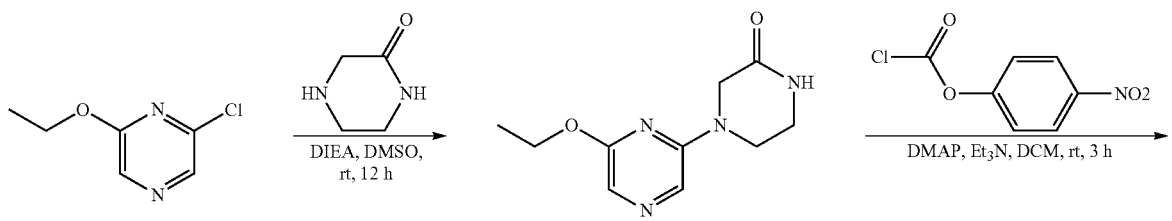

24.1

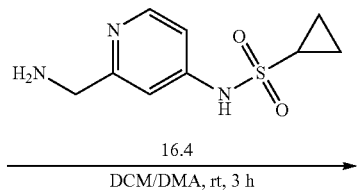

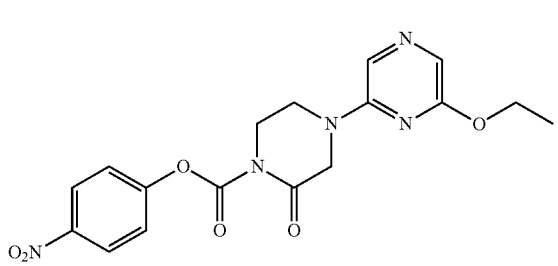

24.2

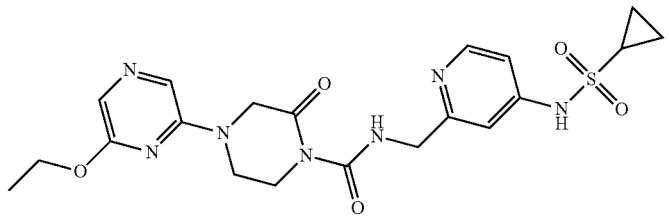

I-28

Synthesis of 24.1. To a stirred solution of 2-chloro-6-ethoxy-pyrazine (790 mg, 5 mmol, 1 eq) and piperazin-2-one (750 mg, 7.5 mmol, 1.5 eq) in dimethyl sulfoxide was added N, N-diisopropylethylamine (1.94 g, 15 mmol, 3 eq). The resulting mixture was stirred for overnight at 100° C. under nitrogen atmosphere. The residue was purified by reverse flash chromatography with the following conditions: column, C18 silica gel; Mobile Phase, water (0.1% NH$_4$HCO$_3$) and ACN (20% ACN up to 35% in 25 min). The product-containing fractions was concentrated under vacuum to obtain 4-(6-ethoxypyrazin-2-yl) piperazin-2-one (24.1) as a yellow green solid, (560 mg, 50%) MS (ES): m/z 223 [M+H]$^+$.

Synthesis of 24.2. To a stirred solution of 24.1 (444 mg, 2 mmol, 1 eq) and 4-nitrophenyl carbonochloridate (1.62 g, 8 mmol, 4 eq) in dichlormethane was added trimethylamine (1.01 g, 10 mmol, 5 eq) and 4-dimethylaminopyridine (24.8 mg, 0.2 mmol, 0.1 eq). The resulting mixture was stirred for 3 h at room temperature. The residue was purified by reverse flash chromatography with the following conditions: column, C18 silica gel; Mobile Phase, water (10 mmol/L NH$_4$HCO$_3$) and ACN (10% ACN up to 50% in 20 min); UV detection at 254/220 nm. The mixture was concentrated under vacuum to obtain 4-nitrophenyl 4-(6-ethoxypyrazin-2-yl)-2-oxopiperazine-1-carboxylate (24.2) as a yellow solid. (200 mg, 26%), MS (ES): m/z 388 [M+H]$^+$.

Synthesis of I-28. To a stirred solution of N-[2-(aminomethyl) pyridin-4-yl] cyclopropanesulfonamide (16.4, 29.9 mg, 0.13 mmol, 1 eq) in dichlormethane (1 mL) and dimethyl acetamide (0.1 mL) were added trimethylamine (40 mg, 0.4 mmol, 3 eq) and 24.2 (51 mg, 0.13 mmol, 1 eq). The resulting mixture was stirred for 3 h at room temperature. The mixture was diluted with water and extracted with ethyl acetate. The combined organic layer was washed with brine, dried over sodium sulfate and concentrated under reduced pressure. The crude product (32 mg) was purified by Prep-HPLC with the following conditions Column: SunFire Prep C18 OBD Column, 19×150 mm 5 um, Mobile Phase Water (0.1% FA) and CAN (31% ACN up to 45% in 10 min); UV detection at 254/210 nm; to afford the title compound as a white solid. (12.8 mg, 20%). MS (ES): m/z 476 [M+H]$^+$, NMR (400 MHz, d$_6$-DMSO) δ 9.59 (t, J=5.6 Hz, 1H), 8.23-8.19 (m, 1H), 7.75 (s, 1H), 7.53 (s, 1H), 7.01 (d, J=5.6 Hz, 2H), 4.46 (d, J=5.2 Hz, 2H), 4.41 (s, 2H), 4.32 (q, J=7.0 Hz, 2H), 3.97 (dd, J=6.8, 4.1 Hz, 2H), 3.78 (dd, J=6.8, 4.1 Hz, 2H), 2.77-2.68 (m, 1H), 1.33 (t, J=7.0 Hz, 3H), 1.03-0.89 (m, 4H).

Example 25: Synthesis of N-[[4-(difluoromethanesulfonamido) pyridin-2-yl]methyl]-5-(6-ethoxy-pyrazin-2-yl) pyridine-2-carboxamide (I-30)

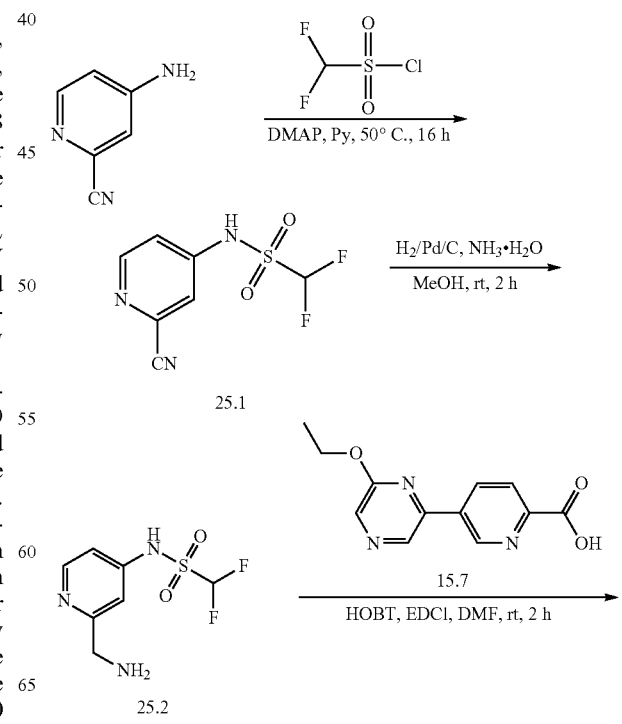

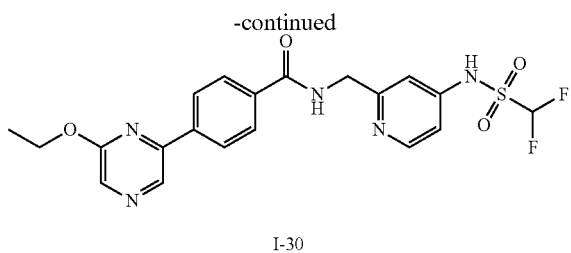

I-30

Synthesis of 25.1. To a stirred solution of 4-aminopyridine-2-carbonitrile (240 mg, 2 mmol, 1 eq) and 4-dimethylaminopyridine (24.6 mg, 0.2 mmol, 0.1 eq) in Pyridine (2 mL) was added difluoromethanesulfonyl chloride (606.4 mg, 4 mmol, 2 eq) at 0° C. The resulting mixture was stirred for 16 h at 50° C. under nitrogen atmosphere. The mixture was cooled to room temperature, purified by reverse flash with the following conditions: Column, C18 Column; Mobile Phase, water (0.1% FA) and ACN (10% ACN up to 50% in 10 min); UV detection at 254/220 nm. The product-containing fractions were combined and concentrated under reduced pressure to obtain N-(2-cyanopyridin-4-yl)-1,1-difluoromethanesulfonamide (25.1) as a brown oil. (50.5 mg, 10%), MS (ES): m/z 232 [M−H]⁻.

Synthesis of 25.2. To a stirred mixture of 25.1 (100 mg, 0.43 mmol, 1 eq) in methanol (10 mL) and ammonium hydroxide (3 mL) was flushed three times with nitrogen. To the solution was added palladium carbon (10 mg), followed by flushing with hydrogen. The mixture was stirred 2 h at room temperature under an atmosphere of hydrogen. The solid was filtered out and the solution was concentrated under reduced pressure to obtain crude N-[2-(aminomethyl)pyridin-4-yl]-1,1-difluoromethanesulfonamide (25.2) as a brown solid. (37 mg, 36%), MS (ES): m/z 238 [M+H]⁺.

Synthesis of I-30. To a stirred mixture of 25.2 (25 mg, 0.1 mmol, 1 eq) and 5-(6-ethoxypyrazin-2-yl) pyridine-2-carboxylic acid (15.7, 12.9 mg, 0.05 mmol, 0.5 eq) in N,N-dimethylformamide (2 mL) was added 1-hydroxybenzotriazole (21.3 mg, 0.15 mmol, 1.5 eq) and 1-ethyl-3-(3-dimethylamino propyl) carbodiie hydrochlolide (30.3 mg, 0.15 mmol, 1.5 eq) at room temperature. The resulting solution was stirred for 2 h at room temperature. The mixture was diluted with water and extracted with ethyl acetate. The combined organic layer was washed with brine, dried over sodium sulfate and concentrated under reduced pressure. The residue was purified by Prep-HPLC with the following conditions Column: Sunfire prep C18 column, 30*150, 5 um; Mobile Phase, Water (0.1% FA) and ACN (23% ACN up to 37% in 7 min); UV detection at 254/220 nm. The product-containing fractions were combined and evaporated partially in vacuum and lyophilized overnight to afford the title compound as a white solid. (5.7 mg, 23%), MS (ES): m/z 465 [M+H]⁺; ¹H NMR (400 MHz, CD₃OD) δ 9.40 (d, J=2.4 Hz, 1H), 8.81 (s, 1H), 8.69-8.66 (m, 1H), 8.27 (s, 1H), 8.25 (s, 1H), 8.09-8.03 (m, 1H), 7.34-7.28 (m, 2H), 6.41 (t, J=14 Hz, 1H), 4.74 (s, 2H), 4.59 (q, J=7.1 Hz, 2H), 1.50 (t, J=7.1 Hz, 3H).

Example 26: Synthesis of N-[(4-cyclopropanesulfonamidopyridin-2-yl) methyl]-5-[2-methylimidazo [1,2-a] pyrimidin-6-yl]pyridine-2-carboxamide (I-31)

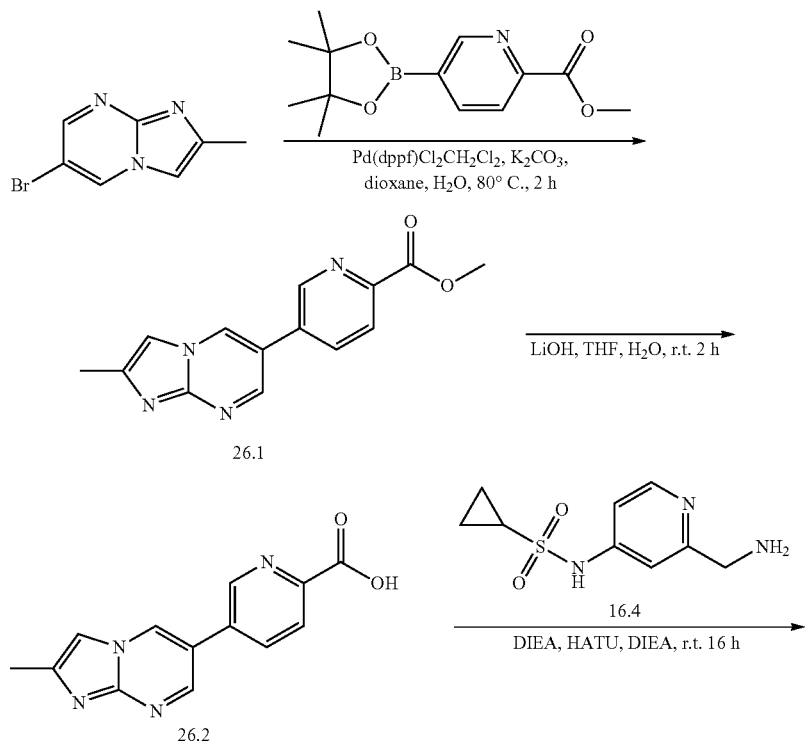

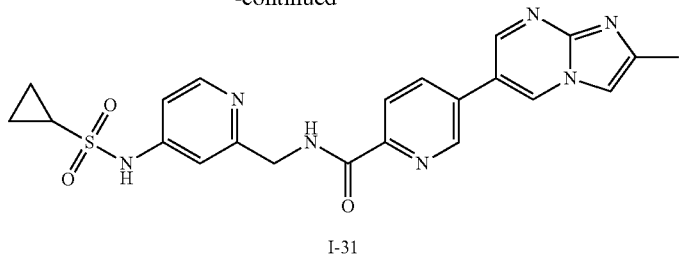

I-31

Synthesis of 26.1. To a stirred solution of 6-bromo-2-methylimidazo[1,2-a] pyrimidine (212 mg, 1 mmol, 1 eq) and methyl 5-(4,4,5,5-tetramethyl-1,3,2-dioxaborolan-2-yl) pyridine-2-carboxylate (315.7 mg, 1.2 mmol, 1.2 eq) in dioxane (8 mL) and water (2 mL) were added potassium carbonate (414 mg, 3 mmol, 3 eq) and Pd(dppf)Cl$_2$CH$_2$C$_{1-2}$ (73.2 mg, 0.1 mmol, 0.1 eq) at room temperature under nitrogen atmosphere. The resulting mixture was stirred for 2 h at 80° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and eluted in 3% methanol in dichloromethane to obtain methyl 5-[2-methylimidazo[1,2-a] pyrimidin-6-yl] pyridine-2-carboxylate (26.1) as a yellow solid. (120 mg, 45%), MS (ES): m/z 269 [M+H]$^+$.

Synthesis of 26.2. To a stirred solution of 26.1 (60 mg, 0.22 mmol, 1 eq) in tetrahydrofuran (10 mL) and water (2 mL) was added lithium hydroxide (26.4 mg, 1.1 mmol, 5 eq). The resulting mixture was stirred for 2 hrs at room temperature. The mixture was concentrated under vacuum. The residue was diluted with water. The pH value of the solution was adjusted to 3 with 1N hydrochloric acid. The solids were collected by filtration to obtain 5-[2-methylimidazo[1,2-a] pyrimidin-6-yl] pyridine-2-carboxylic acid as an off-white solid. (26.2, 40 mg, 70%), MS (ES): m/z 255 [M+H]$^+$.

Synthesis of I-31. To a stirred solution of 26.2 (40 mg, 0.16 mmol, 1 eq) and N-[2-(aminomethyl) pyridin-4-yl] cyclopropanesulfonamide (16.4, 36.3 mg, 0.16 mmol, 1 eq) in dimethyl formamide (3 mL) was added N, N-diisopropylethylamine (103.2 mg, 0.79 mmol, 5 eq) and 2-(-7-Azabenzotriazol-1-yl)-N, N, N', N'-tetramethyluronium hexafluorophosphate (91.2 mg, 0.24 mmol, 1.5 eq). The resulting mixture was stirred for 16 h at room temperature. The residue was purified by reverse flash chromatography with the following conditions: Column, C18 Column; Mobile Phase, water (0.1% FA) and ACN (5% ACN up to 30% in 20 min); UV detection at 254/220 nm. The crude product was re-purified by Prep-HPLC with the following conditions: Column, YMC-Actus Triart C18, 30*250.5 um; Mobile Phase, water (0.1% NH$_4$HCO$_3$) and ACN (2% ACN up to 22% in 8 min); UV detection at 254/220 nm. The product-containing fractions were combined and evaporated partially in vacuum and lyophilized overnight to afford the title compound as a white solid. (11.5 mg, 16%), MS (ES): m/z 464 [M+H]$^+$; $^1$H NMR (400 MHz, J6-DMSO) δ 10.84 (br, 1H), 9.54-9.40 (m, 2H), 9.12 (d, J=2.3 Hz, 1H), 8.95 (d, J=2.5 Hz, 1H), 8.43 (dd, J=8.2, 2.4 Hz, 1H), 8.23-8.18 (m, 2H), 7.74 (s, 1H), 7.02 (s, 2H), 4.56 (d, J=6.0 Hz, 2H), 2.71-2.67 (m, 1H), 2.42 (s, 3H), 0.95-0.92 (m, 4H).

Example 27: Synthesis of N-[(4-cyclopropanesulfonamidopyridin-2-yl) methyl]-5-[2-methylimidazo[1,2-a] pyrimidin-6-yl] pyridine-2-carboxamide (I-41)

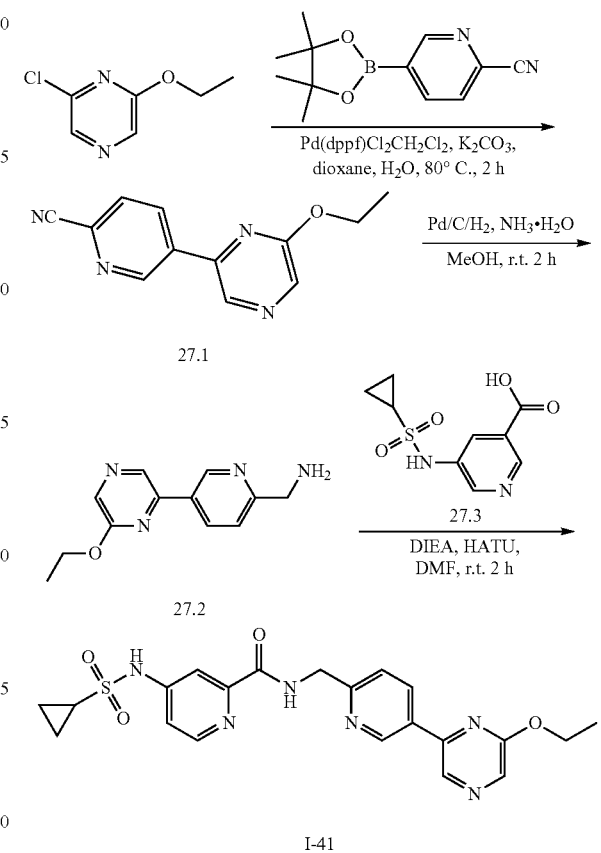

I-41

Synthesis of 27.1. To a stirred solution of 2-chloro-6-ethoxy-pyrazine (159 mg, 1 mmol, 1 eq) and 5-(4,4,5,5-tetramethyl-1,3,2-dioxaborolan-2-yl) pyridine-2-carbonitrile (230 mg, 1 mmol, 1 eq) in 1,4-dioxane (8 mL) and water (2 mL) were added potassium carbonate (415.4 mg, 3 mmol, 3 eq) and Pd(dppf)Cl$_2$—CH$_2$C$_{1-2}$ (58.5 mg, 0.1 mmol, 0.1 eq) at room temperature under nitrogen atmosphere. The resulting mixture was stirred for 2 h at 80° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 8% methanol in dichloromethane to obtain 5-(6-ethoxypyrazin-2-yl) pyridine-2-carbonitrile (27.1) as a yellow solid. (190 mg, 84%), MS (ES): m/z 227 [M+H]$^+$.

Synthesis of 27.2. To a solution of 27.1 (80 mg, 0.35 mmol, 1 eq) in methanol (6 mL) and ammonium hydroxide (2 mL) under nitrogen. To the solution was added palladium on carbon (10%, 5 mg), followed by degassed three times with hydrogen. The mixture was stirred 2 hrs at room temperature under an atmosphere of hydrogen. The solids were filtered out and the filtrate was concentrated under reduced pressure to obtain crude 1-[5-(6-ethoxypyrazin-2-yl) pyridin-2-yl]methanamine (27.2) as a yellow oil. (50 mg, 61%), MS (ES): m/z 231 [M+H]$^+$.

Synthesis of I-41. To a stirred solution of 27.2 (50 mg, 0.21 mmol, 1 eq) and 4-cyclopropanesulfonamidopyridine-2-carboxylic acid (27.3, 70.5 mg, 0.29 mmol, 1.4 eq) in dimethyformamide (5 mL) was added N, N-diisopropylethylamine (154.8 mg, 1.2 mmol, 5.7 eq) and 2-(7-Azabenzotriazol-1-yl)-N, N, N', N'-tetramethyluronium hexafluorophosphate (136.8 mg, 0.36 mmol, 1.7 eq) at r.t. The resulting mixture was stirred for 2 h at room temperature. The residue was purified by reverse flash chromatography with the following conditions, Column, C18 Column; Mobile Phase, water (0.1% FA) and ACN (5% ACN up to 30% in 20 min); UV detection at 254/220 nm. The crude product was purified by Prep-HPLC with the following conditions: Column, YMC-Actus Triart C18, 30*250.5 um; Mobile Phase, water (10 mmol/L NH$_4$HCO$_3$) and ACN (2% ACN up to 22% in 8 min); UV detection at 254/220 nm. The product-containing fractions were combined and evaporated partially in vacuum and lyophilized overnight to afford the title compound as a white solid. (12.2 mg, 16%), MS (ES): m/z 455 [M+H]$^+$; $^1$H NMR (300 MHz, CD$_3$OD) δ 9.22 (d, J=2.3 Hz, 1H), 8.70 (s, 1H), 8.55-8.41 (m, 2H), 8.18 (s, 1H), 7.96 (d, J=2.3 Hz, 1H), 7.56 (d, J=8.3 Hz, 1H), 7.40 (dd, J=5.6, 2.4 Hz, 1H), 4.81 (s, 2H), 4.54 (q, J=7.1 Hz, 2H), 2.85-2.75 (m, 1H), 1.47 (t, J=7.1 Hz, 3H), 1.27-1.14 (m, 2H), 1.11-0.94 (m, 2H).

Example 28: Synthesis of 2-(4-cyclopropanesulfonamidopyridin-2-yl)-N-[4-(6-ethoxypyrazin-2-yl) phenyl] acetamide (I-35)

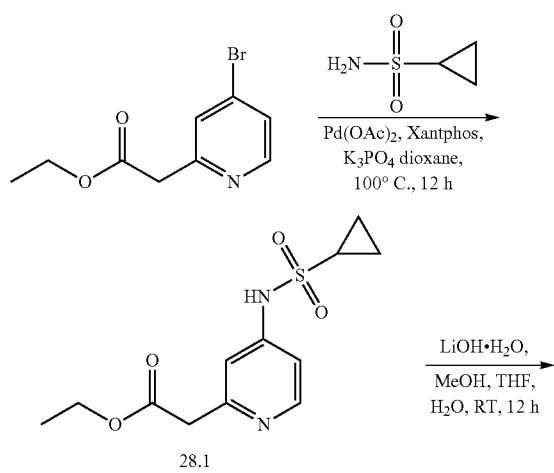

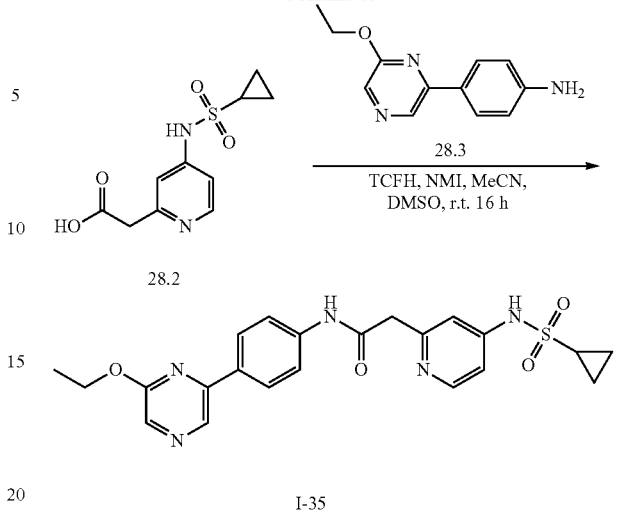

Synthesis of 28.1. To a solution of ethyl 2-(4-bromopyridin-2-yl) acetate (1 g, 4.09 mmol, 1 eq) and cyclopropanesulfonamide (545.9 mg, 4.51 mmol, 1.1 eq) in 1,4-dioxane (20 mL) were added Pd(AcO)$_2$ (91.9 mg, 0.41 mmol, 0.1 eq), Xantphos (474.1 mg, 0.82 mmol, 0.2 eq) and potassium phosphate (2.61 g, 12.29 mmol, 3 eq). The resulting solution was stirred for 12 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (10 mmol/L NH$_4$HCO$_3$) and ACN (45% ACN up to 60% in 10 min); UV detection at 254/220 nm. The product-containing fractions were combined and concentrated under reduced pressure to afford ethyl 2-(4-cyclopropanesulfonamidopyridin-2-yl) acetate (28.1) as a brown solid. (700 mg, 86%), MS (ES): m/z 285 [M+H]$^+$.

Synthesis of 28.2. To a stirred mixture of 28.1 (700 mg, 2.46 mmol, 1 eq) in methanol (12 mL) and tetrahydrofuran (12 mL) was added lithium hydroxide (309.9 mg, 7.39 mmol, 3 eq) in water (6 mL) at room temperature. The resulting mixture was stirred for 12 h at room temperature. The mixture was concentrated under vacuum. The residue was diluted with water. The pH value of the solution was adjusted to 3 with 1N hydrochloric acid. The solids were collected by filtration to obtain (4-cyclopropanesulfonamidopyridin-2-yl) acetic acid (28.2) as a brown solid. (400 mg, 63%), MS (ES): m/z 257 [M+H]$^+$.

Synthesis of I-35. To a solution of 28.2 (60 mg, 0.234 mmol, 1 eq), 4-(6-ethoxypyrazin-2-yl) aniline (28.3, 100.7 mg, 0.47 mmol, 2 eq) and N, N, N', N'-tetramethylchloroformamidinium-hexafluorophosphate (131.4 mg, 0.47 mmol, 2 equiv) in dimethylsulfoxide (4 mL) and acetonitrile (15 mL) was added NMI (153.7 mg, 1.87 mmol, 8 eq) at room temperature. The resulting solution was stirred for 16 h at room temperature. The residue was purified by reverse flash with the following conditions: Column, C18 Column; Mobile Phase, water (0.1% FA) and ACN (15% ACN up to 50% in 20 min); UV detection at 254/220 nm. The residue was purified by Prep-HPLC with the following conditions: Column: Sunfire prep C18 column, 30*150, 5 um; Mobile Phase, Water (0.1% FA), and CAN (13% ACN up to 43% in 7 min); UV detection at 254/220 nm. The product-containing fractions were combined and evaporated partially in vacuum and lyophilized overnight to afford the title compound as a white solid (13 mg, 12%). MS (ES): m/z 454 [M+H]+; 1H NMR (400 MHz, DMSO-d6) δ 10.50 (s, 1H), 8.77 (s, 1H), 8.18 (s, 2H), 8.11 (d, J=8.4 Hz, 2H), 7.77 (d, J=8.4 Hz, 2H), 7.11-6.95 (m, 2H), 4.48 (q, J=7.0 Hz, 2H), 3.82 (s, 2H), 2.74-2.68 (m, 1H), 1.40 (t, J=7.0 Hz, 3H), 1.03-0.92 (m, 4H)

Example 29: Synthesis of 2-(4-(cyclopropanesulfo-namido)pyridin-2-yl)-N-(5-(6-ethoxypyrazin-2-yl)pyridin-2-yl)acetamide (I-40)

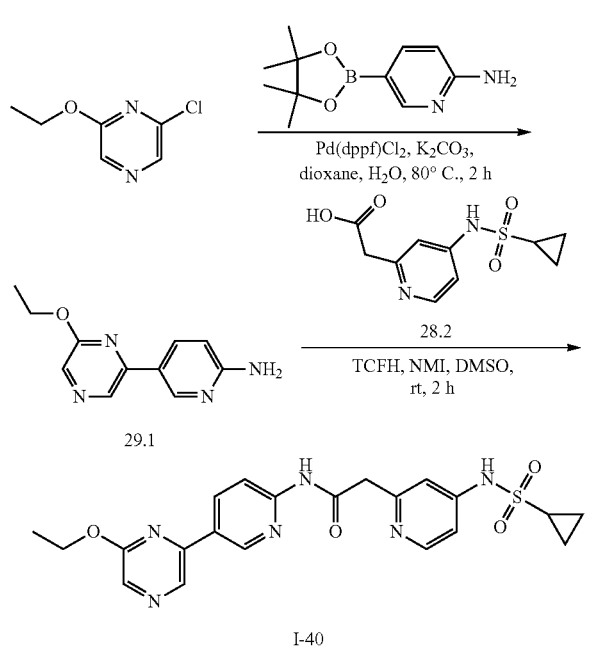

ACN up to 28% in 7 min); UV detection at 254/210 nm. The product-containing fractions were combined and evaporated partially in vacuum and lyophilized overnight to afford the title compound as a white solid. (8.2 mg, 3.8%), MS (ES): m/z 455 [M+H]+; NMR (400 MHz, CD3OD) δ 8.91 (d, J=2.4 Hz, 1H), 8.54 (s, 1H), 8.33 (dd, J=8.8, 2.5 Hz, 1H), 8.12 (dd, J=11.6, 7.4 Hz, 2H), 8.02 (s, 1H), 7.12 (d, J=2.3 Hz, 1H), 7.04 (dd, J=6.2, 2.3 Hz, 1H), 4.43 (q, J=7.1 Hz, 2H), 2.68-2.57 (m, 1H), 1.36 (t, J=7.0 Hz, 3H), 1.10-1.01 (m, 2H), 0.97-0.85 (m, 2H).

Example 30: Synthesis of 2-(4-cyclopropanesulfo-namidopyridin-2-yl)-N-[4-(6-ethoxypyrazin-2-yl)-2-fluorophenyl] acetamide (I-39)

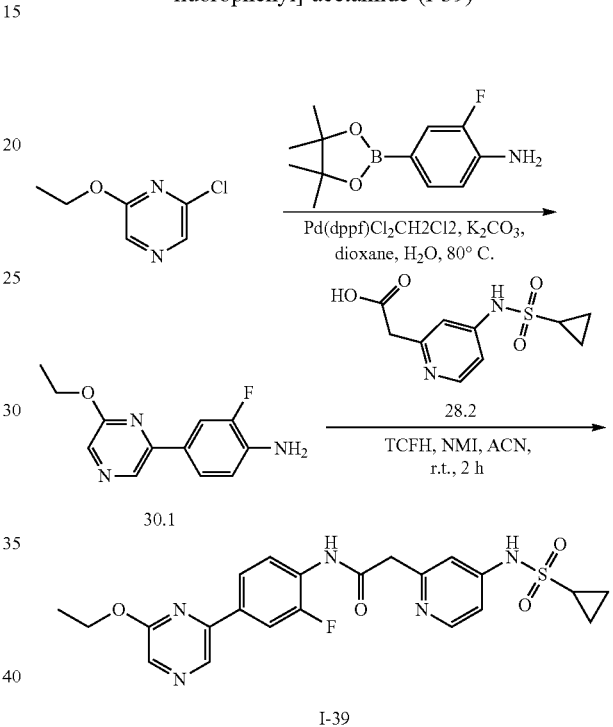

Synthesis of 29.1. To a stirred mixture of 2-chloro-6-ethoxy-pyrazine (2 g, 12.61 mmol, 1 eq) and 5-(4,4,5,5-tetramethyl-1,3,2-dioxaborolan-2-yl)pyridine-2-amine (3.33 g, 15.13 mmol, 1.2 eq) in 1,4-dioxane (60 mL) and water (15 mL) was added potassium carbonate (5.23 g, 37.83 mmol, 3 eq) and Pd(dppf)Cl2 (1.03 g, 1.26 mmol, 0.1 eq). The resulting solution was stirred for 2 h at 80° C. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 25% ethyl acetate in petroleum ether to afford 5-(6-ethoxypyrazin-2-yl)pyridin-2-amine (29.1) as a light brown solid. (2 g, 73%), MS (ES): m/z 217 [M+H]+.

Synthesis of I-40. To a stirred mixture of 29.1 (100 mg, 0.46 mmol, 1 eq) and 28.2 (237 mg, 0.92 mmol, 2 eq) in dimethyl sulfoxide (8 mL) was added TCFH (259.5 mg, 0.92 mmol, 2 eq) and N-methylimidazole (303.7 mg, 3.69 mmol, 8 eq) at 0° C. The resulting mixture was stirred for 2 h at room temperature. The mixture was diluted with water and extracted with ethyl acetate. The combined organic layer was washed with brine, dried over sodium sulfate and concentrated under reduced pressure. The crude product was purified by Prep-HPLC with the following conditions (Column: YMC-Actus Triart C18, 30*250.5 um; mobile phase, water (0.1% NH4HCO3+0.1% NH3·H2O) and ACN (2%

Synthesis of 30.1 To a solution of 2-chloro-6-ethoxypyrazine (158 mg, 1 mmol, 1 eq) and 2-fluoro-4-(4,4,5,5-tetramethyl-1,3,2-dioxaborolan-2-yl) aniline (260.7 mg, 1.1 mmol, 1.1 eq) in 1,4-dioxane (8 mL) and water (2 mL) were added potassium carbonate (414 mg, 3 mmol, 3 eq) and Pd(dppf)Cl2—CH2Cl2 (73.1 mg, 0.1 mmol, 0.1 eq) at room temperature under nitrogen atmosphere. The resulting mixture was stirred for 2 hrs at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain 4-(6-ethoxypyrazin-2-yl)-2-fluoroaniline (30.1) as a yellow solid. (200 mg, 86%), MS (ES): m/z 234 [M+H]+.

Synthesis of I-39. To a solution of 30.1 (30 mg, 0.13 mmol, 1 eq) in acetonitrile (10 mL) were added 28.2 (65.9 mg, 0.26 mmol, 2 eq), NMI (63.3 mg, 0.77 mmol, 6 eq) and N, N, N', N'-tetramethylchloroformamidinium-hexafluoro-phosphate (72.2 mg, 0.258 mmol, 2 eq) at room temperature. The resulting solution was stirred for 2 h at room temperature and concentrated under reduced pressure. The residue was purified by Prep-HPLC with the following conditions:

Column: Sunfire prep C18 column, 30*150, 5 um; Mobile Phase, Water (0.1% FA), and CAN (21% ACN up to 43% in 7 min); UV detection at 254/220 nm. The product-containing fractions were combined and evaporated partially in vacuum and lyophilized overnight to afford the title compound as a white solid (9.4 mg, 15.4%). MS (ES): m/z 472 [M+H]$^+$; $^1$H NMR (400 MHz, J6-DMSO) δ 10.37 (s, 1H), 8.84 (s, 1H), 8.24 (s, 1H), 8.18 (t, J=8.4 Hz, 1H), 8.05 (dd, J=12.4, 2.0 Hz, 1H), 7.98 (dd, J=8.5, 2.0 Hz, 1H), 7.13-6.96 (m, 2H), 4.49 (q, J=7.0 Hz, 2H), 3.93 (s, 2H), 2.74 (s, 1H), 1.40 (t, J=7.0 Hz, 3H), 1.11-0.96 (m, 4H).

Example 31: Synthesis of 5-(6-ethoxypyrazin-2-yl)-N-((4-((2,2,2-trifluoroethyl)sulfonamido)pyridin-2-yl)methyl)picolinamide (I-66)

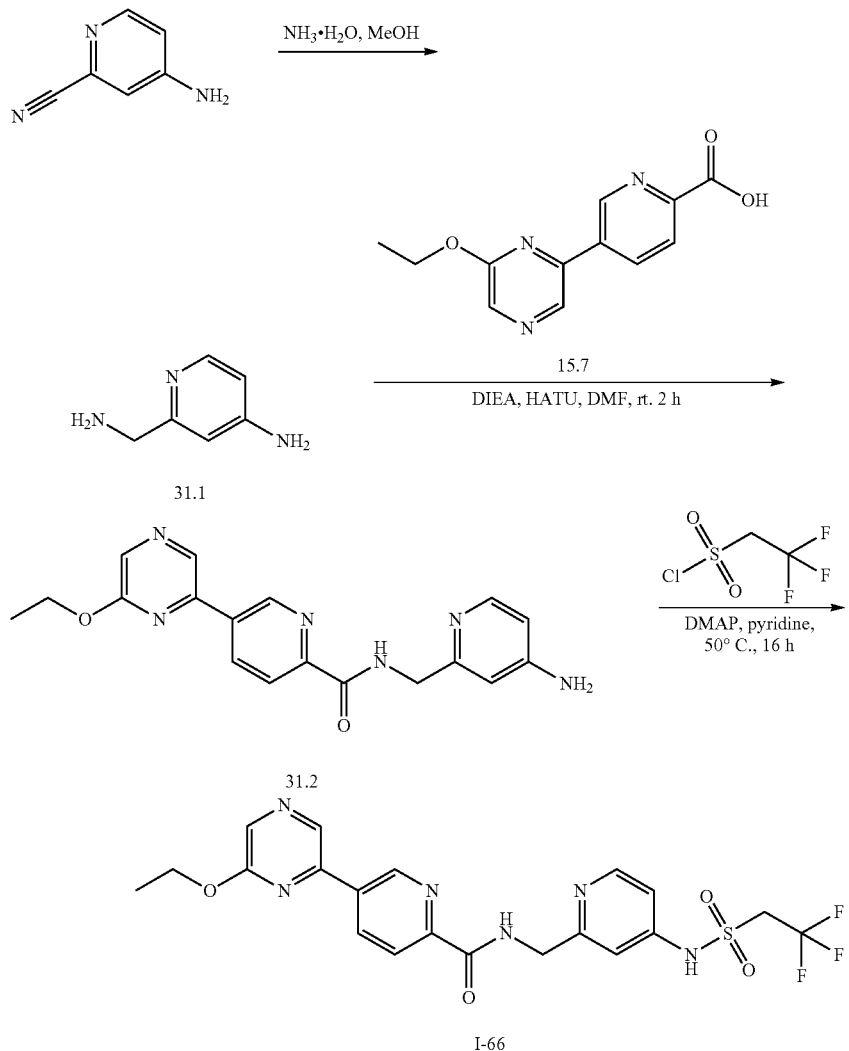

Synthesis of 31.1 A solution of 4-aminopicolinonitrile (1.2 g, 10 mmol, 1 eq) in methanol (25 mL) and NH$_3$·H$_2$O (5 mL) was flushed three times with nitrogen. To the solution was added Pd/C (10%, 100 mg), and degassed with hydrogen three times. The mixture was stirred 2 h at room temperature under an atmosphere of hydrogen. The solids were filtered out and the filtrate was concentrated under reduced pressure to obtain 2-(aminomethyl) pyridin-4-amine (31.1) as a yellow solid. (900 mg, 72%), MS (ES): m/z 124 [M+H]$^+$.

Synthesis of 31.2. To a solution of 31.1 (124 mg, 1 mmol, 1 eq) and 5-(6-ethoxypyrazin-2-yl)picolinic acid (15.7, 245 mg, 1 mmol, 1 eq) in dimethylformamide (5 mL) was added HATU (458 mg, 1.2 mmol, 1.2 eq) and DIEA (389.5 mg, 3 mmol, 3 eq) under nitrogen. The resulting solution was stirred at room temperature for 2 h. The mixture was diluted with water and extracted with ethyl acetate. The combined organic layer was washed with brine, dried over sodium sulfate and concentrated under reduced pressure. The residue was purified by silica gel column chromatography and compound was eluted in 85% ethyl acetate in petroleum ether to obtain N-((4-aminopyridin-2-yl)methyl)-5-(6-ethoxypyrazin-2-yl) picolinamide (31.2) as a yellow solid. (158 mg, 45%), MS (ES): m/z 351 [M+H]$^+$.

Synthesis of I-66. To a solution of 31.2 (50 mg, 0.14 mmol, 1 eq) and 2,2,2-trifluoroethanesulfonyl chloride (78.2 mg, 0.43 mmol, 3 eq) in pyridine (3 mL) was added DMAP (17.4 mg, 0.14 mmol, 1 eq) at room temperature. The resulting solution was stirred for 16 h at 50° C. The mixture was cooled to room temperature and concentrated under reduced pressure. The residue was purified by Prep-HPLC with the following conditions: Column, YMC-Triart Diol Hilic, 20*150 mm 5 um; Mobile Phase, water (0.1% NH$_4$HCO$_3$) and ACN (10% ACN up to 40% in 7 min), UV detection at 254/220 nm. The product-containing fractions were combined and evaporated partially in vacuum and lyophilized overnight to afford to afford the title compound as a white solid. (5 mg, 7%), MS (ES): m/z 497 [M+H]$^+$; $^1$H NMR (400 MHz, d$_6$-DMSO) δ 12.72 (s, 1H), 9.55 (t, J=6.1 Hz, 1H), 9.40 (d, J=2.1 Hz, 1H), 9.02 (s, 1H), 8.73-8.65 (m, 1H), 8.38 (s, 1H), 8.20 (d, J=8.3 Hz, 1H), 8.03 (d, J=6.8 Hz, 1H), 6.92-6.87 (m, 1H), 6.85 (d, J=2.4 Hz, 1H), 4.59-4.47 (m, 4H), 4.09 (d, J=10.0 Hz, 2H), 1.42 (t, J=7.0 Hz, 3H).

Example 32: Synthesis of 4-(6-ethoxypyrazin-2-yl)-N-((4-((2,2,2-trifluoroethyl)sulfonamido)pyridin-2-yl)methyl)benzamide (I-65)

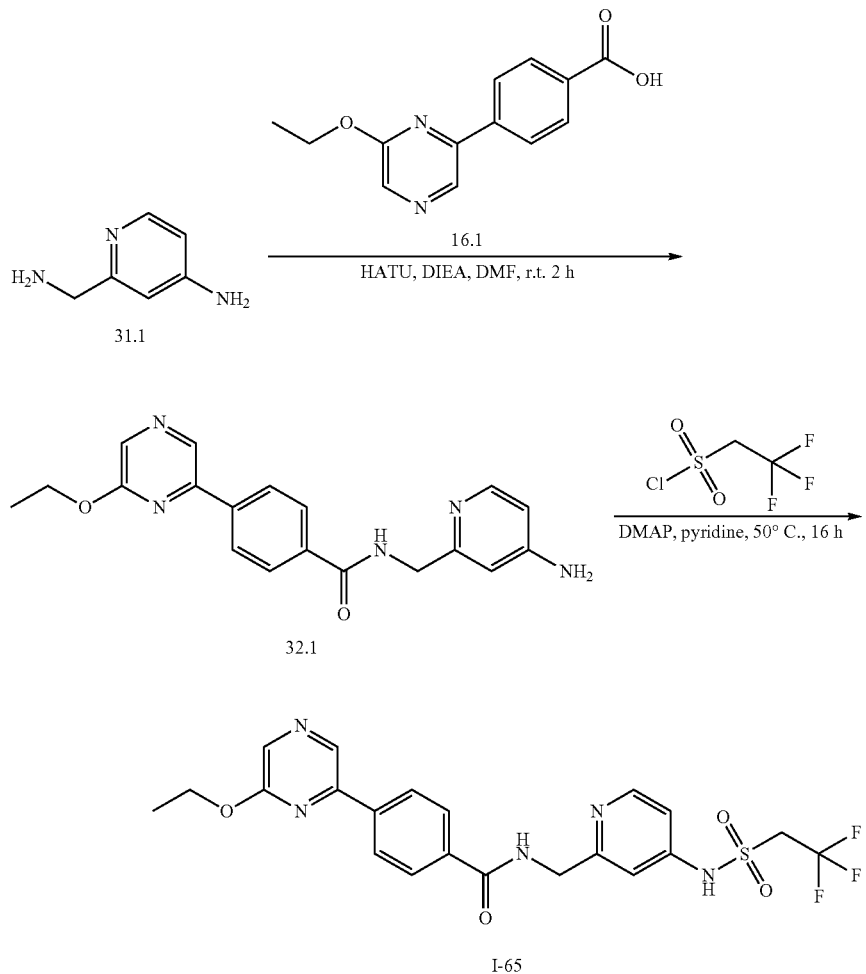

extracted with ethyl acetate. The combined organic layer was washed with brine, dried over sodium sulfate and concentrated under reduced pressure. The residue was purified by silica gel column chromatography and compound was eluted in 85% ethyl acetate in petroleum ether to obtain N-[(4-aminopyridin-2-yl)methyl]-4-(6-ethoxypyrazin-2-yl)benzamide (32.1) as a yellow solid. (164 mg, 47%), MS (ES): m/z 350 [M+H]$^+$.

Synthesis of I-65. To a solution of 32.1 (50 mg, 0.14 mmol, 1 eq) and 2,2,2-trifluoroethanesulfonyl chloride (78.3 mg, 0.43 mmol, 3 eq) in pyridine (2 mL) was added DMAP (17.5 mg, 0.14 mmol, 1 eq) at room temperature. The resulting solution was stirred for 16 h at 50° C. The mixture was cooled to room temperature and concentrated under reduced pressure. The residue was purified by Prep-HPLC with the following conditions: Column, SunFire Prep C18 OBD Column, 19×150 mm, 5 um 10 nm; Mobile Phase, water (0.1% NH$_4$HCO$_3$) and ACN (15% ACN up to 45% in 7 min); UV detection at 254/220 nm; The product-containing fractions were combined and evaporated partially in vacuum and lyophilized overnight to afford the title compound as a white solid. (4.7 mg, 7%), MS (ES): m/z 496 [M+H]$^+$; $^1$H NMR (300 MHz, CD$_3$OD) δ 8.73 (s, 1H), 8.28-8.19 (m, 2H), 8.17 (s, 1H), 8.06 (t, J=6.8 Hz, 3H), 7.14 (d, J=2.2 Hz, 1H), 6.97-6.87 (m, 1H), 8.73 (s, 2H), 4.84 (m, 2H), 4.61-4.49 (m, 4H), 1.49 (t, J=7.1 Hz, 3H).

Synthesis of 32.1. To a solution of 2-(aminomethyl)pyridin-4-amine (31.1, 124 mg, 1 mmol, 1 eq) and 4-(6-ethoxypyrazin-2-yl)benzoic acid (16.2, 244 mg, 1 mmol, 1 eq) in dimethylformamide (5 mL) was added HATU (458 mg, 1.2 mmol, 1.2 eq) and DIEA (389.5 mg, 3 mmol, 3 eq). The resulting solution was stirred at room temperature for 2 h under nitrogen. The mixture was diluted with water and

Example 33: Synthesis of N-[6-([5-[6-(trifluoromethyl)pyrazin-2-yl]-1,3-dihydroisoindol-2-yl]methyl)pyrimidin-4-yl]cyclopropanesulfonamide (I-61)

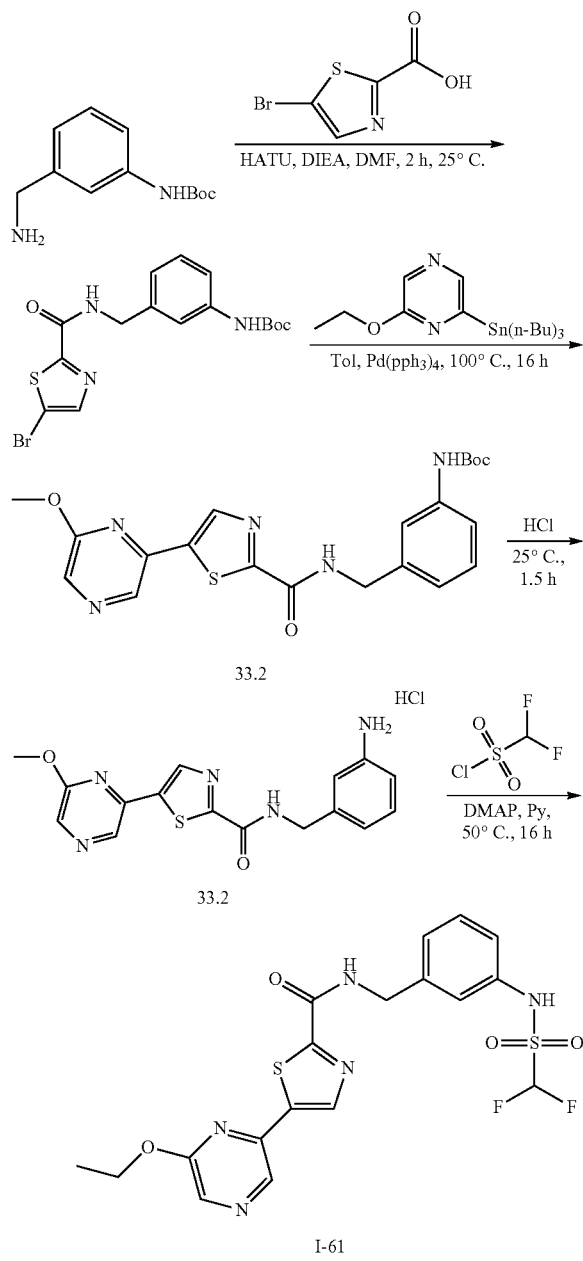

I-61

Synthesis of compound 33.1. Into a solution of tert-butyl N-[3-(aminomethyl)phenyl]carbamate (222 mg, 1 mmol, 1 eq) in N,N-dimethylformamide (5 mL) was added 5-bromo-1,3-thiazole-2-carboxylic acid (208 mg, 1 mmol, 1 eq), HATU (570 mg, 1.5 mmol, 1.5 eq) and DIEA (388 mg, 3 mmol, 3 eq) under nitrogen. The reaction mixture was stirred for 2 h at room temperature. The mixture was diluted with water and extracted with ethyl acetate. The combined organic layer was washed with brine, dried over sodium sulfate and concentrated under reduced pressure. The residue was purified by silica gel column chromatography and compound was eluted in 33% ethyl acetate in petroleum ether to obtain tert-butyl N-(3-[[(5-bromo-1,3-thiazol-2-yl)formamido]methyl]phenyl)carbamate (33.1) as an off-white solid. (305 mg, 74%), MS (ES): m/z 413/415 [M+H]$^+$.

Synthesis of 33.2. Into a solution of 33.1 (100 mg, 0.24 mmol, 1 eq) in toluene (5 mL) was added 2-ethoxy-6-(tributylstannyl)pyrazine (110 mg, 0.27 mmol, 1.1 eq) and Pd(PPh$_3$)$_4$ (28 mg, 0.02 mmol, 0.1 eq). The reaction mixture was degassed three times with nitrogen and stirred for 16 h at 100° C. After completion, the reaction mixture was concentrated under reduced pressure. The residue was purified by reverse flash with the following conditions: Column, C18 Column; Mobile Phase, water (0.1% NH$_4$HCO$_3$) and ACN (10% ACN up to 50% in 20 min); UV detection at 254/220 nm. The product-containing fractions were combined and concentrated under reduced pressure to afford tert-butyl N-[3-([[5-(6-ethoxypyrazin-2-yl)-1,3-thiazol-2-yl]formamido]methyl)phenyl]carbamate (33.2) as an off-white solid. (95 mg, 86%), MS (ES): m/z 456 [M+H]$^+$.

Synthesis of 33.3. A solution of 33.2 (95 mg, 0.21 mmol, 1 eq) in HCl in ethyl acetate (4 M, 4 mL) was stirred for 2 h at room temperature. The mixture was concentrated to afford N-[(3-aminophenyl)methyl]-5-(6-ethoxypyrazin-2-yl)-1,3-thiazole-2-carboxamide hydrochloride (33.3) as a light-yellow solid. (105 mg crude) MS (ES): m/z 356 [M+H]$^+$.

Synthesis of I-61. To a solution of 33.3 (80 mg, 0.23 mmol, 1 eq) in pyridine (4 mL) was added difluoromethanesulfonyl chloride (102 mg, 0.69 mmol, 3 eq) at room temperature. The resulting solution was stirred for 16 h at 50° C. The mixture was cooled to room temperature, diluted with water and extracted with ethyl acetate. The combined organic layer was washed with brine, dried over sodium sulfate and concentrated under reduced pressure. The resulting mixture was concentrated under reduced pressure. The crude product was purified by Prep-HPLC with the following conditions: Column: YMC-Triart Diol Hilic, 20*150 mm 5 um; Mobile Phase: Water (0.1% NH$_4$HCO$_3$+0.1% NH$_3$·H$_2$O) and ACN (10% ACN up to 35% in 8 min); UV detection at 254/220 nm. The product-containing fractions were combined and evaporated partially in vacuum and lyophilized overnight to afford the title compound as a white solid. (9.3 mg, 9%), MS (ES): m/z 470 [M+H]$^+$; $^1$H NMR (400 MHz, DMSO-d$_6$) δ 9.43 (s, 1H), 8.92 (s, 1H), 8.78 (s, 1H), 8.28 (s, 1H), 7.29-6.73 (m, 5H), 4.50-4.35 (m, 4H), 1.40 (t, J=7.0 Hz, 3H).

Example 34: Synthesis of N-(1-(2-(cyclopropane sulfonamido)thiazol-4-yl)cyclopropyl)-5-(6-ethoxypyrazin-2-yl)picolinamide (I-64)

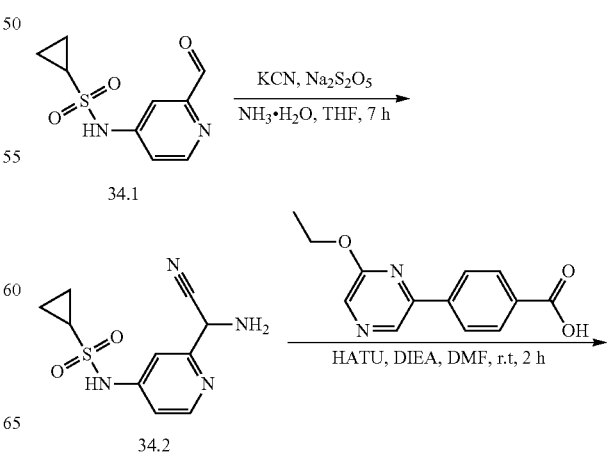

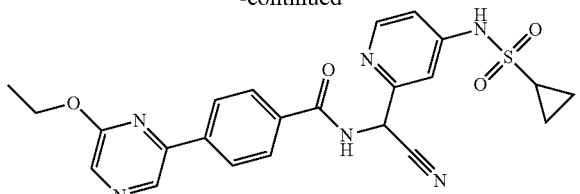

I-64

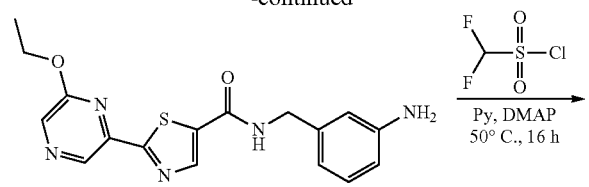 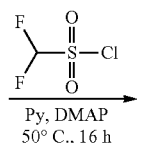

35.1

Synthesis of 34.2. To a solution of N-(2-formylpyridin-4-yl)cyclopropanesulfonamide (260 mg, 1.15 mmol, 1.0 eq) in tetrahydrofuran (3 mL) was added a solution of Sodium metabisulphite (266.5 mg, 1.40 mmol, 1.2 eq) in water (5 mL) at room temperature and stirred for 1 h at room temperature. Then NH$_3$·H$_2$O (1.7 mL) was added to the solution and stirred for 5 h under nitrogen. Then a solution of sodium cyanide (139.9 mg, 2.15 mmol, 1.8 eq) in water (1.5 mL) was added. The resulting solution was stirred for 2 h at r.t under nitrogen atmosphere. The crude product mixture was concentrated under reduced pressure, diluted with DCM, washed with brine. The organic phase was dried over sodium sulphate and concentrated in vacuo to provide crude N-[2-[amino(cyano) methyl] pyridin-4-yl] cyclopropane sulfonamide (34.2) as a brown semi-solid. (300 mg crude), MS (ES): m/z 252 [M+H]$^+$.

Synthesis of I-64. To a solution of 34.2 (289 mg, 1.14 mmol, 1.0 eq) and 4-(6-ethoxypyrazin-2-yl)benzoic acid (16.2, 279.8 mg, 1.14 mmol, 1.0 eq) in dimethylformamide (5 mL) was added HATU (522.6 mg, 1.37 mmol, 1.2 eq) and DIEA (444.1 mg, 3.43 mmol, 3 eq). The resulting solution was stirred at room temperature for 2 h. The reaction mixture was diluted with EtOAc, washed with brine, concentrated in vacuo. The residue was purified by Prep-HPLC with the following conditions: Column, XBridge Prep OBD C18 Column, 30*150 mm, 5 um; Mobile Phase, water (0.1% NH$_4$HCO$_3$) and ACN (31% ACN up to 45% in 8 min); UV detection at 254/220 nm. The product-containing fractions were combined and evaporated partially in vacuum and lyophilized overnight to afford the title compound as a yellow solid. (37.2 mg, 7%), MS (ES): m/z 479 [M+H]$^+$; $^1$H NMR (300 MHz, DMSO-de) δ 10.73 (s, 1H), 9.96 (d, J=7.9 Hz, 1H), 8.91 (s, 1H), 8.44 (d, J=5.6 Hz, 1H), 8.33-8.23 (m, 3H), 8.08 (d, J=8.4 Hz, 2H), 7.32 (d, J=2.1 Hz, 1H), 7.22-7.10 (m, 1H), 6.43 (d, J=7.8 Hz, 1H), 4.50 (q, J=7.0 Hz, 2H), 2.90-2.79 (m, 1H), 1.41 (t, J=7.0 Hz, 3H), 1.10-0.93 (m, 4H).

Example 35: Synthesis of N-[[3-(difluoromethanesulfonamido)phenyl]methyl]-2-(6-ethoxypyrazin-2-yl)-1,3-thiazole-5-carboxamide (I-62)

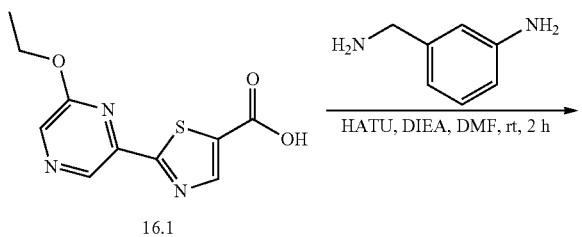

I-62

Synthesis of 35.1. To a mixture of 2-(6-ethoxypyrazin-2-yl)-1,3-thiazole-5-carboxylic acid (16.1, 150 mg, 0.59 mmol, 1.0 eq) and 3-(aminomethyl) aniline (72 mg, 0.59 mmol, 1.0 eq) in N,N-dimethylformamide (3 mL) was added HATU (249.6 mg, 0.65 mmol, 1.1 eq) and DIEA (231.4 mg, 1.79 mmol, 3.0 eq) under nitrogen. The resulting mixture was stirred for 2 h at room temperature. The residue was purified by reverse phase flash with the following conditions: Column, C18 Column; Mobile Phase, water (10 mmol/L NH$_4$HCO$_3$) and ACN (10% ACN up to 50% in 15 min); UV detection at 254/220 nm. The product-containing fractions were combined and concentrated under reduced pressure to afford N-[(3-aminophenyl)methyl]-2-(6-ethoxypyrazin-2-yl)-1,3-thiazole-5-carboxamide as a yellow solid. (99 mg, 46%), MS (ES): m/z 356 [M+H]$^+$.

Synthesis of I-62. To a stirred mixture 35.1 (99 mg, 0.27 mmol, 1 eq) and DMAP (3.4 mg, 0.03 mmol, 0.1 eq) in pyridine (5 mL) was added difluoromethanesulfonyl chloride (125.8 mg, 0.84 mmol, 3 eq) at room temperature. The resulting mixture was stirred for 16 h at 50° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column: SunFire Prep C18 OBD Column, 19×150 mm 5 um 10 nm; Mobile Phase: water (0.1% FA) and ACN (40% to 70% in 7 min, UV detection at 254/210 nm). The product-containing fractions were combined and evaporated partially in vacuum and lyophilized overnight to afford the title compound as a white solid. (30 mg, 23%), MS (ES): m/z 470[M+H]$^+$; $^1$H NMR (400 MHz, CD$_3$OD) δ 8.90 (s, 1H), 8.45 (s, 1H), 8.30 (s, 1H), 7.38-7.30 (m, 2H), 7.26-7.18 (m, 2H), 6.65 (t, J=53.2 Hz, 1H), 4.58-4.50 (m, 4H), 1.49 (t, J=7.0 Hz, 3H).

Example 36: Synthesis of N-[2-[(2R)-1-[5-(6-ethoxypyrazin-2-yl)pyridine-2-carbonyl]pyrrolidin-2-yl]pyridin-4-yl]cyclopropanesulfonamide (I-80)
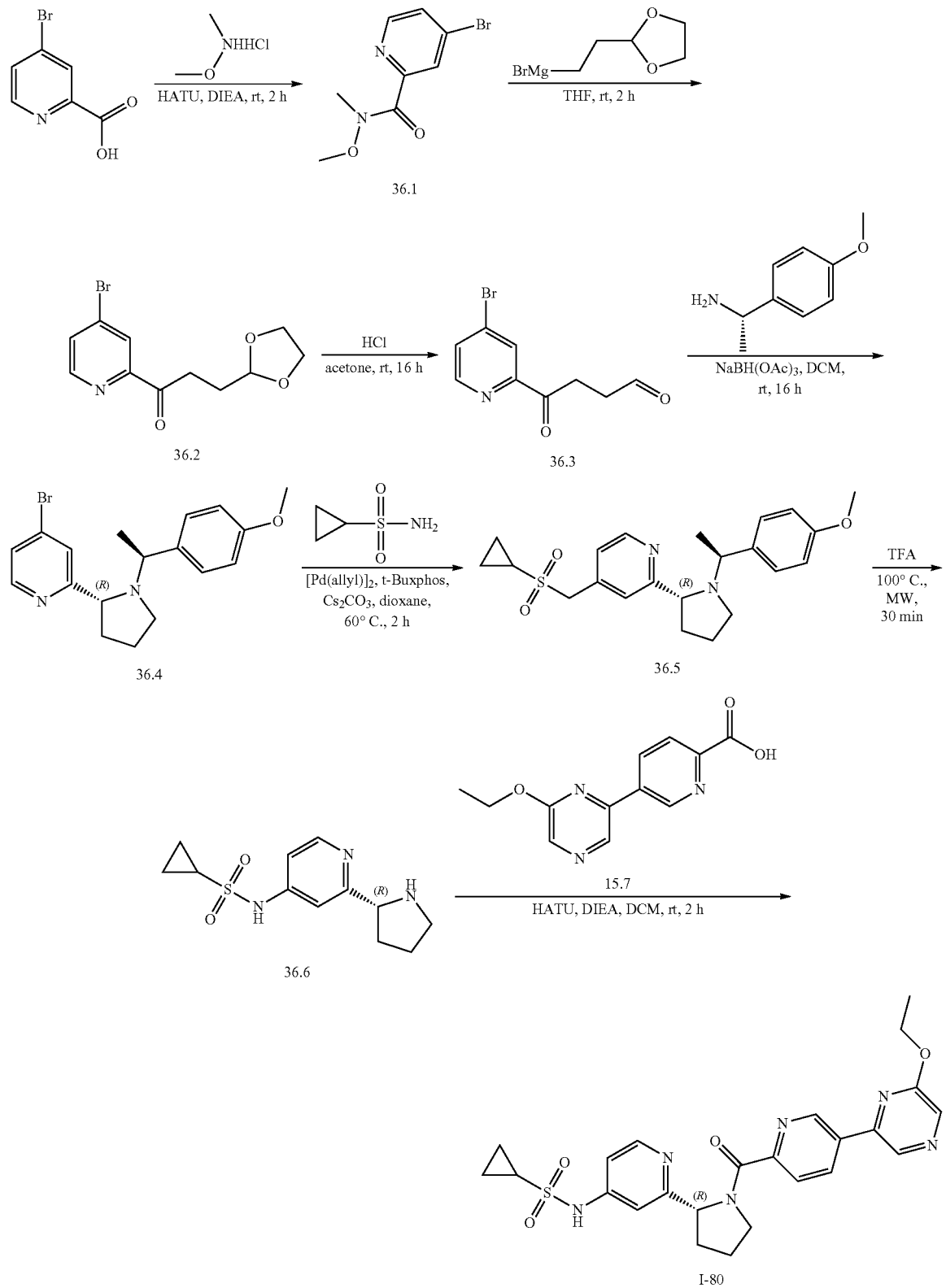

Synthesis of 36.1. To a solution of 4-bromopicolinic acid (10.1 g, 50 mmol, 1.0 equiv) and N, O-dimethylhydroxylamine hydrochloride (7.5 g, 75 mmol, 1.5 eq) in N,N-dimethylformamide (100 mL) was added DIEA (19.3 g, 150 mmol, 3.0 equiv) and HATU (22.1 g, 60 mmol, 1.2 eq) at r.t. The reaction mixture was stirred for 2 h at r.t. The mixture was diluted with water and extracted with ethyl acetate. The combined organic layer was washed with brine, dried over sodium sulfate and concentrated under reduced pressure. The residue was purified by silica gel column chromatography and compound was eluted in 40% ethyl acetate in petroleum ether to obtain 4-bromo-N-methoxy-N-methylpyridine-2-carboxamide (36.1) as a yellow solid. (8.42 g, 69%), MS (ES): m/z 245 [M+H]$^+$.

Synthesis of 36.2. To a stirred solution of 36.1 (6 g, 24.5 mmol, 1.0 eq) in tetrahydrofuran (50 mL) was added 2-[2-(bromomagnesio)ethyl]-1,3-dioxolane (1 M, 73.5 mL, 73.5 mmol, 3.0 eq) at 0° C. under nitrogen atmosphere. The resulting mixture was stirred for 2 h at room temperature under nitrogen atmosphere. The reaction was quenched with ammonium chloride and extracted with ethyl acetate. The combined organic layer was washed with brine, dried over sodium sulfate and concentrated under reduced pressure. The residue was purified by silica gel column chromatography and compound was eluted in 25% ethyl acetate in petroleum ether to obtain 1-(4-bromopyridin-2-yl)-3-(1,3-dioxolan-2-yl)propan-1-one (36.2) as yellow oil. (2.6 g, 34%), MS (ES): m/z 286 [M+H]$^+$.

Synthesis of 36.3. A mixture of 36.2 (2.6 g, 9.12 mmol, 1 eq) and hydrochloric acid (20 mL) in acetone (20 mL) was stirred for 16 h at room temperature. The mixture was neutralized to pH 9 with sodium hydrate. The mixture was diluted with water and extracted with ethyl acetate. The combined organic layer was washed with brine, dried over sodium sulfate and concentrated under reduced pressure to obtain 4-(4-bromopyridin-2-yl)-4-oxobutanal (36.3) a light pink oil. (1.91 g, 87%), MS (ES): m/z 242 [M+H]$^+$.

Synthesis of 36.4. To a stirred mixture of 36.3 (1.91 g, 7.89 mmol, 1 eq) and (1S)-1-(4-methoxyphenyl)ethanamine (1.19 g, 1.64 mmol, 1 eq) in dichlormethane (30 mL) was added sodium triacetoxyborohydride (3.35 g, 15.78 mmol, 2 eq) in portions at 0° C. under nitrogen atmosphere. The resulting mixture was stirred for 16 h at room temperature under nitrogen atmosphere. The mixture was neutralized to pH 9 with saturated sodium bicarbonate. The mixture was diluted with water and extracted with ethyl acetate. The combined organic layer was washed with brine, dried over sodium sulfate and concentrated under reduced pressure. The mixture was purified by reverse flash chromatography with the following conditions: column, C18 silica gel; mobile phase, ACN in water, 30% to 80% gradient in 20 min; detector, UV 254 nm. The mixture was concentrated under vacuum to obtain 4-bromo-2-((R)-1-((S)-1-(4-methoxyphenyl)ethyl)pyrrolidin-2-yl)pyridine (36.4) as yellow oil. (1.08 g, 38%), MS (ES): m/z 361 [M+H]$^+$.

Synthesis of 36.5. To a solution of 36.4 (1.08 g, 3 mmol, 1.0 eq) and cyclopropanesulfonamide (726 mg, 6 mmol, 2.0 equiv) in 1,4-dioxane (20 mL) was added cesium carbonate (2.94 g, 9 mmol, 3.0 equiv), t-BuXPhos (124.1 mg, 0.3 mmol, 0.1 equiv) and [Pd(ally)Cl]$_2$ (54.9 mg, 0.15 mmol, 0.05 equiv) at room temperature under nitrogen atmosphere. The reaction mixture was stirred for 16 h at 60° C. The mixture was cooled to r.t, diluted with water and extracted with ethyl acetate. The combined organic layer was washed with brine, dried over sodium sulfate and concentrated under reduced pressure. The residue was purified by silica gel column chromatography and eluted in 50% ethyl acetate in petroleum ether to obtain N-(2-((R)-1-((S)-1-(4-methoxyphenyl)ethyl)pyrrolidin-2-yl)pyridin-4-yl)cyclopropanesulfonamide (36.5) as a yellow solid. (590 mg, 49%), MS (ES): m/z 402 [M+H]$^+$.

Synthesis of 36.6. A mixture of 36.5 (590 mg, 1.47 mmol, 1.0 eq) in trifluoroacetic acid (10 mL) was irradiated with microwave radiation and was stirred for 0.5 h at 100° C. The resulting mixture was concentrated under vacuum to obtain crude N-[2-[(2R)-pyrrolidin-2-yl]pyridin-4-yl]cyclopropanesulfonamide trifluoroacetate (36.6) as a brown oil. (270 mg), MS (ES): m/z 268 [M+H]$^+$.

Synthesis of I-80. To a stirred mixture of 36.6 (26.7 mg, 0.1 mmol, 1 eq) and 5-(6-ethoxypyrazin-2-yl)pyridine-2-carboxylic acid (15.7, 24.4 mg, 0.1 mmol, 1 equiv) in dichloromethaned (2 mL) were added DIEA (38.7 mg, 0.3 mmol, 3 eq) and HATU (45.5 mg, 0.12 mmol, 1.2 eq) in portions at room temperature. The resulting mixture was stirred for 2 h at room temperature. The resulting mixture was concentrated under reduced pressure. The residue was purified by reverse flash chromatography with the following conditions: Column, C18 silica gel; Mobile phase, water (0.1% FA) and ACN (10% ACN up to 60% in 20 min); UV detection at 254/220 nm. The product-containing fractions were combined and concentrated under reduced pressure. The crude product was purified by Prep-HPLC with the following conditions: Column, XBridge Shield RP18 OBD Column, 30*150 mm, 5 um; mobile phase, Water (0.1% FA) and ACN (8% ACN up to 38% in 7 min); UV detection at 254/220 nm. The product-containing fractions were combined and evaporated partially in vacuum and lyophilized overnight to afford the title compound (19.4 mg) as a white solid. MS (ES): m/z 495 [M+H]$^+$; 1H NMR (400 MHz, Methanol-d$_4$) δ 9.38 (dd, J=2.2, 0.9 Hz, 0.49H), 9.11 (dd, J=2.2, 0.9 Hz, 0.0.49H), 8.80 (s, 0.5H), 8.69 (s, 0.49H), 8.64 (dd, J=8.2, 2.2 Hz, 0.49H), 8.39 (dd, J=8.2, 2.2 Hz, 0.49H), 8.25-8.22 (m, 1H), 8.19 (s, 0.47H), 8.05 (d, J=5.9 Hz, 1H), 7.94 (dd, J=8.3, 0.6 Hz, 1H), 7.61 (dd, J=8.2, 0.4 Hz, 1H), 7.26 (d, J=2.2 Hz, 1H), 7.08 (dd, J=6.0, 2.3 Hz, 1H), 6.87 (dd, J=5.9, 2.2 Hz, 1H), 6.83 (d, J=2.1 Hz, 1H), 5.63-5.61 (m, 0.49H), 5.30-5.27 (m, 0.52H), 4.5 (dq, J=22.2, 7.1 Hz, 2H), 4.17-4.11 (m, 1.50H), 2.75-2.68 (m, 0.5H), 2.56-2.46 (m, 1.46H), 2.14-1.98 (m, 3H), 1.48 (d, J=26.9 Hz, 3H), 1.16-0.85 (m, 4H).

Example 37: Synthesis of (R)—N-(2-(1-(4-(6-ethoxypyrazin-2-yl)benzoyl)pyrrolidin-2-yl)pyridin-4-yl)cyclopropanesulfonamide (I-77)

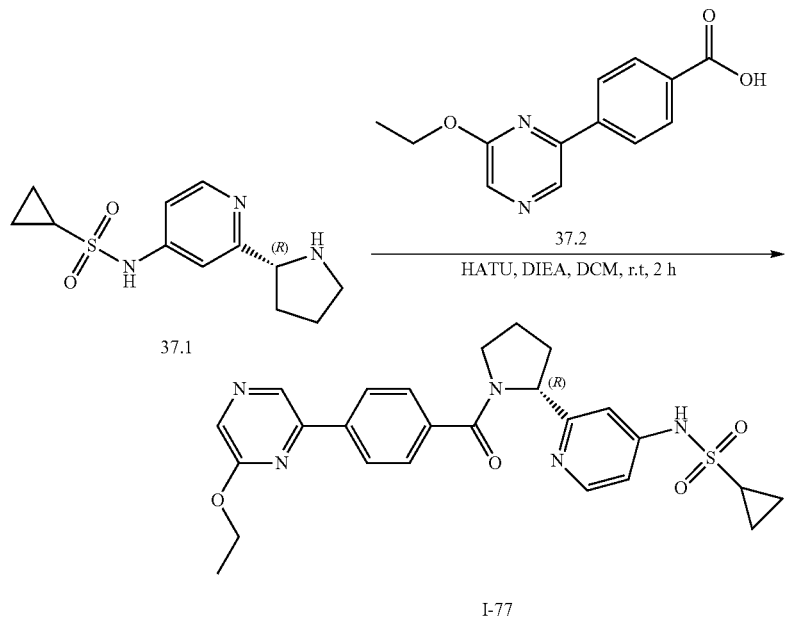

Synthesis of I-77. To a stirred solution of 5-(3-ethoxyphenyl)pyrazine-2-carboxylic acid (37.2 50 mg, 0.2 mmol, 1 eq), DIEA (79.3 mg, 0.61 mmol, 3 equiv) and N-[2-[(2R)-pyrrolidin-2-yl]pyridin-4-yl] cyclopropanesulfonamide (37.1, 54.7 mg, 0.2 mmol, 1 equiv) in Dichloromethane (1 mL) was added HATU (85.6 mg, 0.22 mmol, 1.1 equiv) at room temperature under nitrogen atmosphere for 2 h. The residue was purified by Prep-HPLC with the following conditions: Column: SunFire Prep C18 OBD Column, 19×150 mm 5 um 10 nm; Mobile Phase A: Water (0.1% FA), Mobile Phase B: ACN; Flow rate: 60 mL/min; Gradient: 20% B to 40% B in 10 min, 254/210 nm; The product-containing fractions were combined and evaporated partially in vacuum and lyophilized overnight to afford the title compound as a white solid. (18 mg, 17.7%), MS (ES): m/z 494 [M+H]$^+$; $^1$H NMR (400 MHz, CD$_3$OD) δ 8.72-8.61 (m, 1H), 8.29-7.79 (m, 5H), 7.38-6.84 (m, 3H), 5.27-5.07 (m, 1H), 4.62-4.50 (m, 2H), 3.99-3.65 (m, 2H), 2.79-2.50 (m, 2H), 2.13-1.95 (m, 3H), 1.53-1.42 (m, 3H), 1.10-0.89 (m, 4H).

Example 38: Synthesis of N-[2-[(2R)-1-[2-(6-ethoxypyrazin-2-yl)-1,3-thiazole-5-carbonyl]pyrrolidin-2-yl]pyridin-4-yl]cyclopropanesulfonamide (I-76)

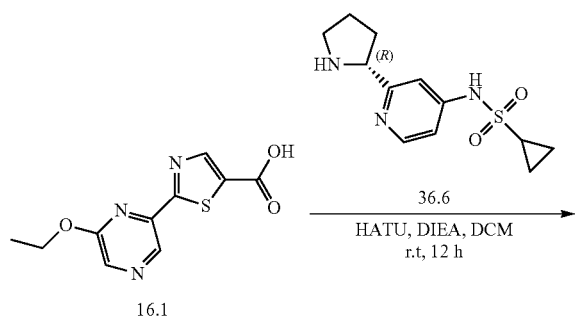

Synthesis of I-76. To a stirred solution of 2-(6-ethoxypyrazin-2-yl)-1,3-thiazole-5-carboxylic acid (16.1, 50 mg, 0.2 mmol, 1 eq) and N-[2-[(2R)-pyrrolidin-2-yl]pyridin-4-yl]cyclopropanesulfonamide (36.6, 53.2 mg, 0.2 mmol, 1 eq) in dichlormethane were added DIEA (77.1 mg, 0.59 mmol, 3 eq) and HATU (75.6 mg, 0.2 mmol, 1 eq). The resulting mixture was stirred for 1 h at room temperature under air atmosphere. The crude product (40 mg) was purified by Prep-HPLC with the following conditions: Column: SunFire Prep C18 OBD Column, 19*150 mm 5 um 10 nm; Mobile Phase: water (0.1% FA) and ACN (30% ACN up to 50% in 10 min), UV detection at 254/210 nm. The product-containing fractions were combined and evaporated partially in vacuum and lyophilized overnight to afford the title compound as a white solid. (22.4 mg, 22%), MS (ES): m/z 501 [M+H]$^+$, $^1$H NMR (300 MHz, CD$_3$OD) δ 8.91-8.76 (m, 1H), 8.47-7.93 (m, 3H), 7.20-7.09 (m, 2H), 5.42-5.22 (m, 1H), 4.54-4.44 (m, 2H), 4.23-3.90 (m, 2H), 2.76-2.45 (m, 2H), 2.19-1.99 (m, 3H), 1.46 (t, J=6.9, 3H), 1.13-0.94 (m, 4H).

Example 39: Synthesis of N-[3-[(2R)-1-[5-(6-ethoxypyrazin-2-yl)-1,3-thiazole-2-carbonyl]pyrrolidin-2-yl]phenyl]-1,1-difluoromethanesulfonamide (I-70)

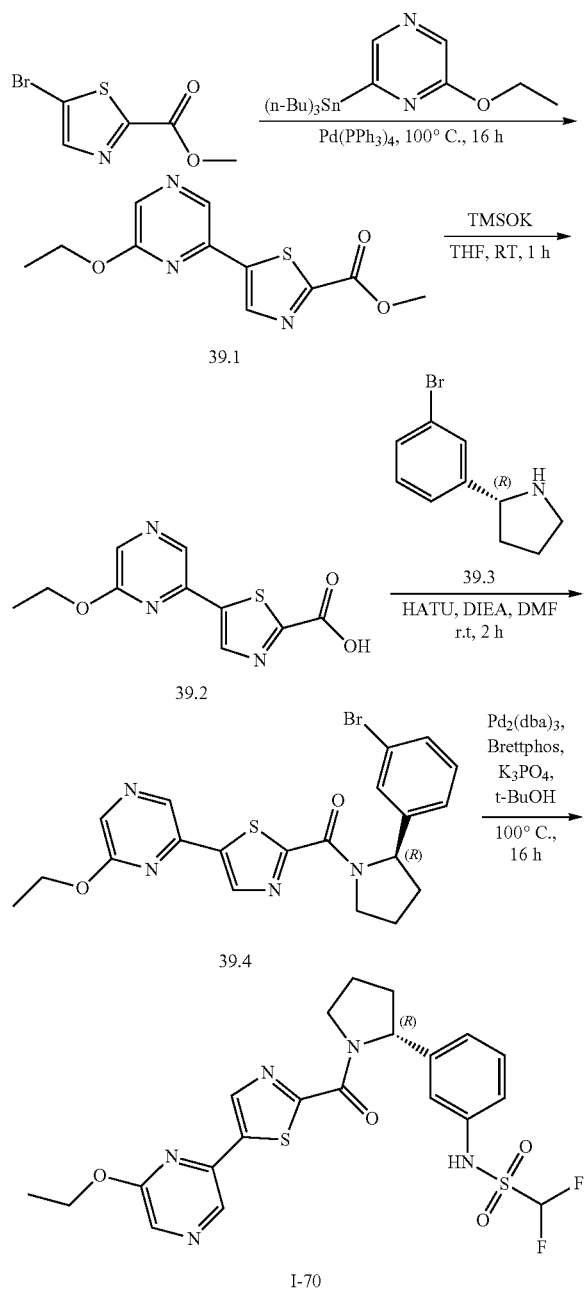

Synthesis of 39.1. To a stirred solution of methyl 5-bromo-1,3-thiazole-2-carboxylate (500 mg, 2.25 mmol, 1 eq) and 2-ethoxy-6-(tributylstannyl)pyrazine (1.12 g, 2.7 mmol, 1.2 eq) in methylbenzene (12 mL) was added Pd(pph$_3$)$_4$ (260.1 mg, 0.22 mmol, 0.1 eq). The resulting mixture was stirred for 16 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 50% ethyl acetate in petroleum ether to obtain methyl 5-(6-ethoxypyrazin-2-yl)-1,3-thiazole-2-carboxylate ((39.1) 192 mg, 30%) as a yellow oil, MS (ES): m/z 266 [M+H]$^+$.

Synthesis of 39.2. A mixture of 39.1 (140 mg, 0.53 mmol, 1 eq) and potassium trimethylsilanolate (81.2 mg, 0.63 mmol, 1.2 eq) in tetrahydrofuran (5 mL) was stirred for 5 h at room temperature. The resulting mixture was concentrated under reduced pressure and used in the next step directly without further purification. MS (ES): m/z 252 [M+H]$^+$.

Synthesis of 39.4. To a stirred mixture of (2R)-2-(3-bromophenyl)pyrrolidine (39.3, 119 mg, 0.53 mmol, 1.0 eq) and 5-(6-ethoxypyrazin-2-yl)-1,3-thiazole-2-carboxylic acid (39.2, 132.2 mg, 0.53 mmol, 1 eq) in N,N-dimethylformamide (5 mL) were added HATU (41.8 mg, 0.11 mmol, 1.1 eq) and DIEA (38.7 mg, 0.3 mmol, 3 eq). The resulting mixture was stirred for 2 h at room temperature under nitrogen atmosphere. The mixture was purified by reverse flash chromatography with the following conditions: column, C18 silica gel; mobile phase, ACN in water, 10% to 40% gradient in 20 min; detector, UV 254 nm. The mixture was concentrated under vacuum to obtain 2-[2-[(2R)-2-(3-bromophenyl)pyrrolidine-1-carbonyl]-1,3-thiazol-5-yl]-6-ethoxypyrazine (39.4, 140 mg, 57%) as a white solid. MS (ES): m/z 460 [M+H]$^+$.

Synthesis of I-70. To a stirred mixture of 39.4 (50 mg, 0.11 mmol, 1 eq), difluoromethanesulfonamide (42.8 mg, 0.33 mmol, 3 eq) and K$_3$PO$_4$ (69.3 mg, 0.33 mmol, 3 eq) in tert-butyl alcohol (3 mL) were added Pd$_2$(dba)$_3$ (9.9 mg, 0.011 mmol, 0.1 eq) and BrettPhos (11.7 mg, 0.02 mmol, 0.2 eq) in portions at room temperature under nitrogen atmosphere. The resulting mixture was stirred for overnight at 100° C. under nitrogen atmosphere. The mixture was cooled to room temperature, purified by reverse flash chromatography and eluted in 35% ACN in water. The crude product (30 mg) was purified by Prep-HPLC with the following conditions: Column: SunFire Prep C18 OBD Column, 19×150 mm 5 um 10 nm; Mobile Phase: Water (0.1% FA) and ACN (45% to 75% in 7 min, UV detection: 254/210 nm). The product-containing fractions were combined and evaporated partially in vacuum and lyophilized overnight to afford the title compound (11 mg, 20%) as a white solid. MS (ES): m/z 510 [M+H]$^+$; $^1$H NMR (300 MHz, Methanol-d$_6$) δ 8.68-8.09 (m, 3H), 7.34-6.99 (m, 4H), 6.59 (td, J=53.1, 16.6 Hz, 1H), 6.28-6.25 (m, 0.5H), 5.36-5.32 (m, 0.5H), 4.51-4.32 (m, 3H), 4.03-3.83 (m, 1H), 2.57-2.37 (m, 1H), 2.14-1.86 (m, 3H), 1.45 (td, J=7.0, 4.4 Hz, 3H).

Example 40: Synthesis of N-[3-[(2R)-1-[2-(6-ethoxypyrazin-2-yl)-1,3-thiazole-5-carbonyl]pyrrolidin-2-yl]phenyl]-1,1-difluoromethanesulfonamide (I-74)

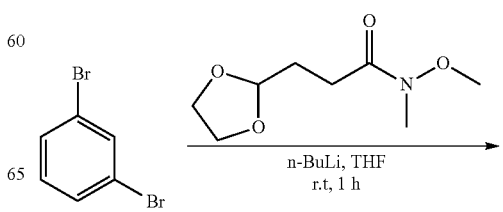

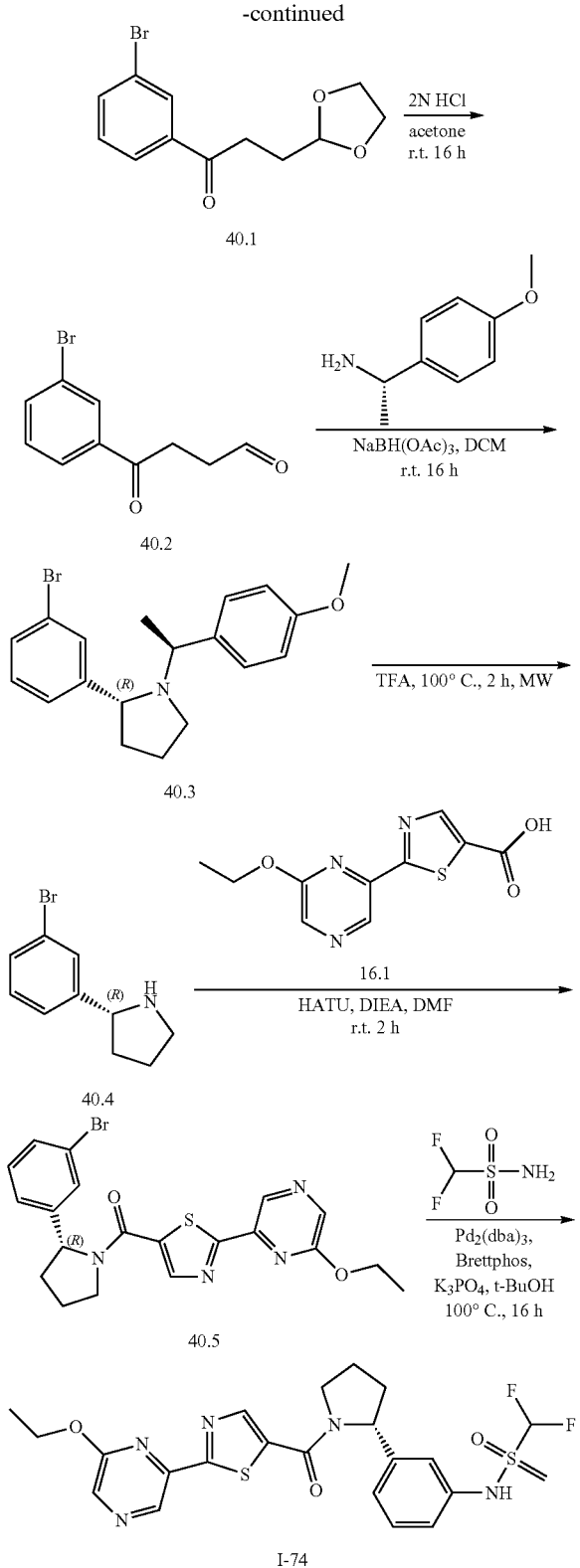

methoxy-N-methylpropanamide (1.92 g, 10.14 mmol, 1.2 eq) in tetrahydrofuran (10 mL) over 10 mins at −78° C. After stirring for 1 h at −78° C., the reaction was quenched with ammonium chloride, diluted with water and extracted with ethyl acetate. The combined organic layers were washed with brine, dried over sodium sulfate and concentrated under reduced pressure. The residue was purified by silica gel column chromatography and eluted in 10% ethyl acetate in petroleum ether to obtain 1-(3-bromophenyl)-3-(1, 3-dioxolan-2-yl) propan-1-one as yellow oil. (40.1, 1 g, 41.4%), MS (ES): m/z 286[M+H]$^+$.

Synthesis of 40.2. A mixture of 40.1 (1 g, 3.51 mmol, 1 eq) and hydrochloric acid (20 mL) in acetone (20 mL) was stirred for 16 h at room temperature under nitrogen atmosphere. The mixture was neutralized to pH 8 with sodium hydroxide (aq.). The mixture was diluted with water and extracted with ethyl acetate. The combined organic layer was washed with brine, dried over sodium sulfate and concentrated under reduced pressure. This resulted in 4-(3-bromophenyl)-4-oxobutanal (40.2, 740 mg, 87%) as a light pink oil. MS (ES): m/z 242 [M+H]$^+$.

Synthesis of 40.3. To a stirred mixture of 40.2 (396 mg, 1.64 mmol, 1.0 eq) and (1S)-1-(4-methoxyphenyl) ethanamine (248.3 mg, 1.64 mmol, 1 eq) in dichlormethane (1 mL) was added sodium triacetoxyborohydride (696.2 mg, 3.28 mmol, 2 eq) in portions at 0° C. under nitrogen atmosphere. The resulting mixture was stirred for 16 h at room temperature under nitrogen atmosphere. The mixture was neutralized to pH 9 with saturated sodium bicarbonate. The mixture was diluted with water and extracted with ethyl acetate. The combined organic layer was washed with brine, dried over sodium sulfate and concentrated under reduced pressure. The mixture was purified by reverse flash chromatography with the following conditions: column, C18 silica gel; mobile phase, ACN in water, 50% to 90% gradient in 20 min; UV detection at 254 nm. The mixture was concentrated under vacuum to obtain (2R)-2-(3-bromophenyl)-1-[(1S)-1-(4-methoxyphenyl)ethyl]pyrrolidine (40.3, 160 mg, 27%) as a dark green oil. MS (ES): m/z 361 [M+H]$^+$.

Synthesis of 40.4. A mixture of 40.3 (230 mg, 0.63 mmol, 1 eq) and TFA (10 mL) in trifluoroacetic acid (1 mL) was stirred for 1.5 h at 100° C. under air atmosphere. The resulting mixture was concentrated under vacuum. The residue was neutralized to pH 9 with saturated sodium bicarbonate. The mixture was diluted with water and extracted with ethyl acetate. The combined organic layer was washed with brine, dried over sodium sulfate and concentrated under reduced pressure. This resulted in (2R)-2-(3-bromophenyl)pyrrolidine (40.3, 200 mg crude) as a brown oil. MS (ES): m/z 227 [M+H]$^+$.

Synthesis of 40.5. To a stirred mixture of 40.4 (158 mg, 0.7 mmol, 1.0 eq) and 2-(6-ethoxypyrazin-2-yl)-1,3-thiazole-5-carboxylic acid (16.1, 210.7 mg, 0.84 mmol, 1.2 eq) in N,N-dimethylformamide (2 mL) were added HATU (292.2 mg, 0.76 mmol, 1.1 eq) and DIEA (270.9 mg, 2.09 mmol, 3 eq) dropwise under nitrogen. The resulting mixture was stirred for 2 h at room temperature. The mixture was purified by reverse flash chromatography with the following conditions: column, C18 silica gel; mobile phase, ACN in water, 10% to 80% gradient in 20 min; UV detection at 254 nm. The fractions were combined and concentrated under vacuum to obtain 2-[5-[(2R)-2-(3-bromophenyl)pyrrolidine-1-carbonyl]-1,3-thiazol-2-yl]-6-ethoxypyrazine (40.5, 97 mg, 30.2%) as a yellow solid. MS (ES): m/z 459[M+H]$^+$.

Synthesis of I-74. To a stirred mixture of 40.5 (50 mg, 0.11 mmol, 1.0 eq), difluoromethanesulfonamide (42.8 mg, Synthesis of 40.1. To a stirred solution of 1,3-dibromobenzene (2 g, 8.48 mmol, 1.0 eq) in anhydrous tetrahydrofuran (15 mL) was added butyl lithium (2.5 M, 3.39 mL, 8.48 mmol, 1.0 eq) at −78° C. under nitrogen atmosphere. The reaction mixture was stirred at −78° C. for 30 mins. To the above mixture was added 3-(1,3-dioxolan-2-yl)-N-

0.33 mol, 3 eq) and potassium phosphate (69.3 mg, 0.33 mmol, 3 eq) in tert-butyl alcohol (3 mL) were added Pd$_2$(dba)$_3$ (9.9 mg, 0.01 mmol, 0.1 eq) and BrettPhos (11.6 mg, 0.02 mmol, 0.2 eq) at room temperature. The resulting mixture was stirred for 16 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The crude product (30 mg) was purified by Prep-HPLC with the following conditions: Column: SunFire Prep C18 OBD Column, 19×150 mm 5 um 10 nm; Mobile Phase: Water (0.1% FA) and CAN (40% to 70% in 7 min, UV detection at 254/210 nm) The product-containing fractions were combined and evaporated partially in vacuum and lyophilized overnight to afford the title compound (10.2 mg, 18%) as a white solid. MS (ES): m/z 511 [M+H]$^+$; $^1$H NMR (400 MHz, CD$_3$OD) δ 8.90 (s, 0.48H), 8.75 (s, 0.42H), 8.44 (s, 0.49H), 8.28 (s, 1H), 7.88 (s, 0.42H), 7.37-7.29 (m, 1H), 7.28-7.05 (m, 3H), 6.62-6.48 (m, 1H), 5.45-5.30 (m, 1H), 4.21-4.06 (m, 2H), 3.94-3.90 (m, 1H), 2.58-2.44 (m, 1H), 2.18-1.90 (m, 1H), 1.47 (q, J=7.0 Hz, 3H).

Example 41: Synthesis of N-[2-[(2R)-1-[4-(6-ethoxypyrazin-2-yl)-2-fluorobenzoyl]pyrrolidin-2-yl]pyridin-4-yl]cyclopropanesulfonamide (I-75)

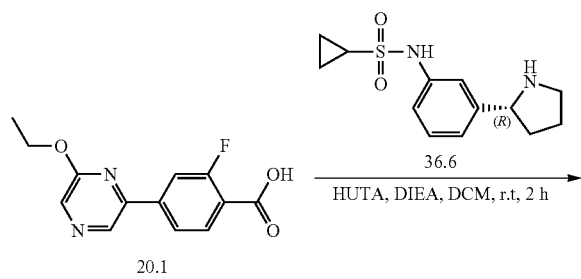

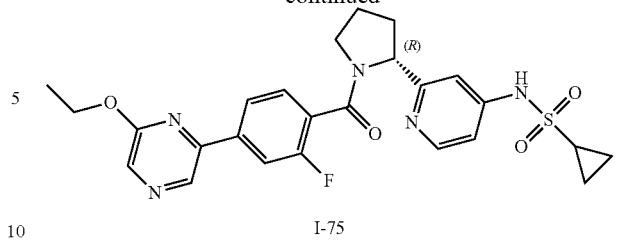

I-75

Synthesis of I-75. To a stirred mixture of 4-(6-ethoxypyrazin-2-yl)-2-fluorobenzoic acid (20.1, 50 mg, 0.19 mmol, 1.0 eq) and N-[2-[(2R)-pyrrolidin-2-yl]pyridin-4-yl]cyclopropanesulfonamide (36.6, 50.9 mg, 0.19 mmol, 1 eq) in dichloromethane (2 mL) were added HATU (87.0 mg, 0.23 mmol, 1.2 eq) and DIEA (73.9 mg, 0.57 mmol, 3 eq). The resulting mixture was stirred for 2 h at room temperature under nitrogen atmosphere. The residue was purified by reverse flash chromatography with the following conditions: column, C18 silica gel; Mobile Phase, water (0.1% FA) and ACN (10% up to 30% in 10 min) and concentrated under reduced pressure. The residue was purified by Prep-HPLC with the following conditions: Column: SunFire Prep C18 OBD Column, 19×150 mm 5 um; Mobile Phase, water (0.1% FA) and CAN (20% ACN up to 50% in 8 min); UV detection at 254/210 nm. The product-containing fractions were combined and evaporated partially in vacuum and lyophilized overnight to afford the title compound as a white solid (16.9 mg, 17%). MS (ES): m/z 512 [M+H]$^+$; $^1$H NMR (400 MHz, CD$_3$OD) δ 8.69 (d, J=46.8 Hz, 1H), 8.30-8.11 (m, 2H), 8.10-7.98 (m, 1H), 7.79-6.76 (m, 4H), 5.37-4.90 (m, 1H), 4.55 (dq, J=20.4, 7.1 Hz, 2H), 4.05-3.53 (m, 2H), 2.78-2.47 (m, 2H), 2.18-1.97 (m, 3H), 1.48 (dt, J=11.2, 7.1 Hz, 3H), 1.27-0.82 (m, 4H).

Example 42: Synthesis of 5-(5-ethoxypyrazin-2-yl)-N-[[4-(1-fluorocyclopropanesulfonamido)pyridin-2-yl]methyl]pyridine-2-carboxamide (I-71)

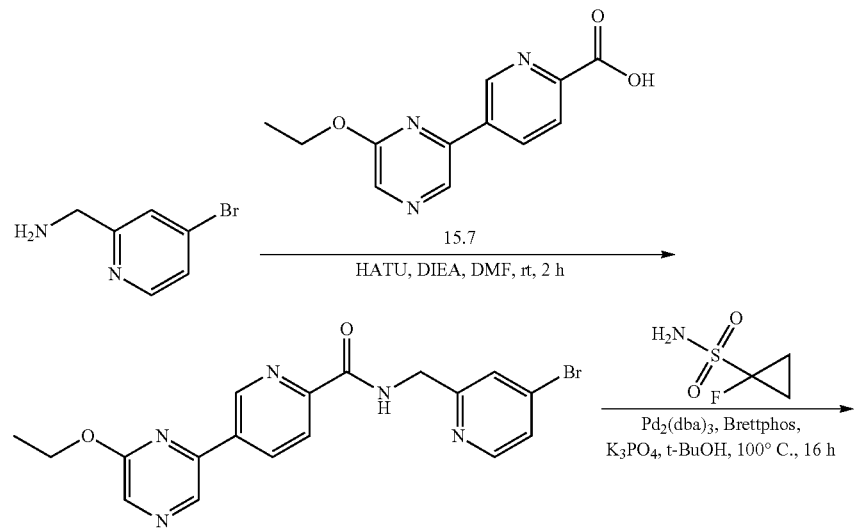

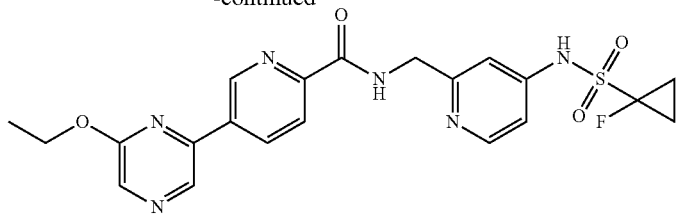

I-71

Synthesis of 42.1. To a solution of (4-bromopyridin-2-yl)methanamine (372 mg, 2 mmol, 1.0 eq) and 5-(6-ethoxy-pyrazin-2-yl)picolinic acid (15.7, 735 mg, 3 mmol, 1.5 eq) in N,N-dimethylformamide (4 mL) was added DIEA (774 mg, 6 mmol, 3 equiv) and HATU (912 mg, 2.4 mmol, 1.2 equiv) at room temperature under nitrogen. The reaction mixture was stirred for 2 h at room temperature. The mixture was diluted with water and extracted with ethyl acetate. The combined organic layer was washed with brine, dried over sodium sulfate and concentrated under reduced pressure. The residue was purified by silica gel column chromatography and compound was eluted in 40% ethyl acetate in petroleum ether to obtain N-[(4-bromopyridin-2-yl)methyl]-5-(5-ethoxypyrazin-2-yl)pyridine-2-carboxamide (42.1) as a yellow solid. (463 mg, 56%), MS (ES): m/z 414/416 [M+H]$^+$.

Synthesis of I-71. To a stirred mixture of 42.1 (41.4 mg, 0.1 mmol, 1 eq), 1-fluorocyclopropane-1-sulfonamide (41.7 mg, 0.3 mmol, 3 eq) and potassium phosphate (63.6 mg, 0.3 mmol, 3 eq) in tert-butyl alcohol (5 mL) was added Pd$_2$(dba)$_3$ (9.1 mg, 0.01 mmol, 0.1 eq) and BrettPhos (10.7 mg, 0.02 mmol, 0.2 eq). The resulting mixture was stirred for overnight at 100° C. under nitrogen atmosphere. The mixture was cooled to room temperature, purified by reverse flash chromatography with the following conditions: column, C18 silica gel; mobile phase, ACN in water, 10% to 50% gradient in 20 min; detector, UV 254 nm. The crude product (30 mg) was purified by Prep-HPLC with the following conditions: Column: SunFire Prep C18 OBD Column, 19×150 mm 5 um 10 nm; Mobile Phase: Water (0.1% FA) and ACN (20% to 50% in 7 min, UV detection at 254/210 nm). The product-containing fractions were combined and evaporated partially in vacuum and lyophilized overnight to afford the title compound (11 mg, 22%) as a white solid, MS (ES): m/z 473[M+H]$^+$; $^1$H NMR (400 MHz, CD$_3$OD) δ 9.26 (s, 1H), 8.69 (s, 1H), 8.54 (dd, J=8.2, 2.4 Hz, 1H), 8.15-8.12 (m, 2H), 7.97 (d, J=6.5 Hz, 1H), 7.17-7.09 (m, 2H), 4.69 (s, 2H), 4.45 (q, J=1.6, 2H), 1.55-1.26 (m, 7H).

Example 43: Synthesis of N-(2-[[5-(6-ethoxy-pyrazin-2-yl)-1,3-dioxoisoindol-2-yl]methyl]pyridin-4-yl) cyclopropane Sulfonamide (I-78)

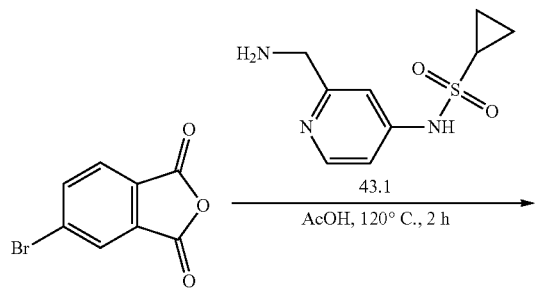

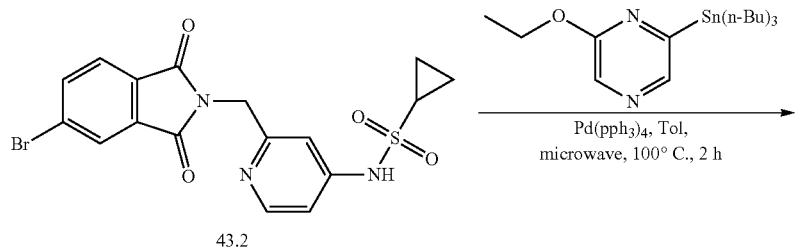

43.2

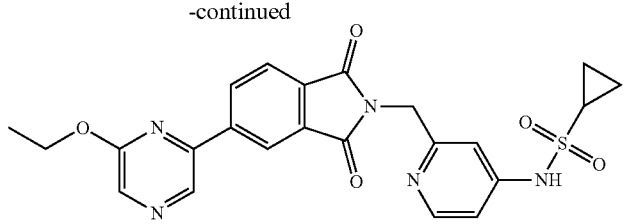

I-78

Synthesis of 43.2. To a stirred mixture of 5-bromo-2-benzofuran-1,3-dione (114 mg, 0.5 mmol, 1 eq) in acetic acid (2.5 mL) was added N-[2-(aminomethyl) pyridin-4-yl] cyclopropane sulfonamide (43.1, 114.1 mg, 0.5 mmol, 1 eq) at room temperature. The resulting mixture was stirred for 2 hrs at 120° C. under nitrogen atmosphere. The resulting mixture was concentrated under reduced pressure. The solids were collected by filtration and washed with water and dried in an oven at 45° C. to afford N-[2-[(5-bromo-1,3-dioxoisoindol-2-yl) methyl] pyridin-4-yl]cyclopropane sulfonamide (43.2) as a white solid. (96 mg, 44%), MS (ES): m/z 436/438 [M+H]+.

Synthesis of I-78. To a stirred mixture of 43.2 (61.1 mg, 0.14 mmol, 1.0 eq) and 2-ethoxy-6-(tributylstannyl) pyrazine (69.5 mg, 0.17 mmol, 1.2 eq) in toluene (1.0 mL) was added Pd(pph$_3$)$_4$ (16.2 mg, 0.01 mmol, 0.1 eq) at room temperature under nitrogen. The reaction mixture was irradiated with microwave radiation for 2 h at 100° C. After completion, the resulting mixture was concentrated under reduced pressure and the residue was diluted with water, extracted with ethyl acetate. The organic phase was concentrated in vacuo. The crude product (40 mg) was purified by Prep-HPLC with the following conditions (Column: Sun Fire Prep C18 OBD Column, 19×150 mm 5 um 10 nm; Mobile Phase: Water and ACN (32% to 52% in 10 min), UV detection at 254/210 nm. The product-containing fractions were combined and evaporated partially in vacuum and lyophilized overnight to afford the title compound as a white solid. (12.7 mg, 19%), MS (ES): m/z 480 [M+H]+; $^1$H NMR (400 MHz, d$_6$-DMSO) δ 10.55 (s, 1H), 9.05 (s, 1H), 8.70-8.59 (m, 2H), 8.38 (s, 1H), 8.25 (d, J=5.7 Hz, 1H), 8.09 (d, J=7.8 Hz, 1H), 7.13 (s, 1H), 7.08 (dd, J=5.8, 2.2 Hz, 1H), 4.90 (s, 2H), 4.53 (q, J=7.0 Hz, 2H), 2.84 (d, J=8.2 Hz, 1H), 1.43 (t, J=7.0 Hz, 3H), 1.02 (t, J=5.9 Hz, 4H).

Example 44: Synthesis of N-[1-[3-(difluoromethanesulfonamido)phenyl]cyclopropyl]-5-(6-ethoxypyrazin-2-yl)-1,3-thiazole-2-carboxamide (I-69)

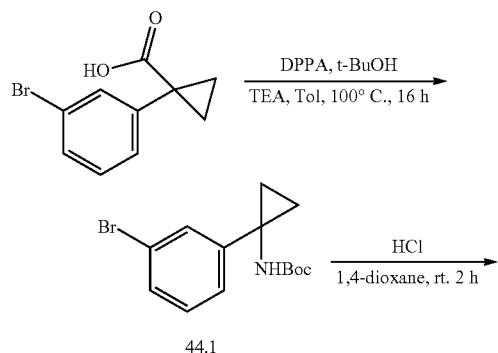

44.1

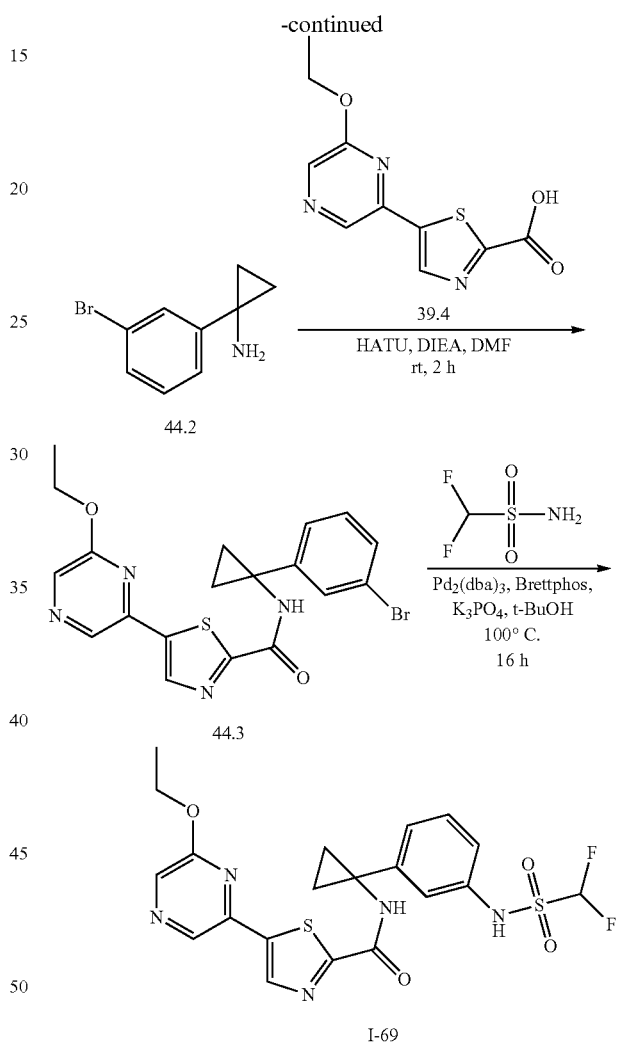

I-69

Synthesis of 44.1. To a solution of 1-(2-bromothiazol-4-yl)cyclopropanecarboxylic acid (6.8 g, 27.42 mmol, 1 eq) and trimethylamine (3.32 g, 32.9 mmol, 1.2 eq) in toluene (60 mL) and tert-butyl alcohol (60 mL) was added diphenylphosphorylazide (7.54 g, 27.42 mmol, 1 eq) at room temperature. The resulting solution was stirred for 16 h at 100° C. The mixture was cooled to room temperature. The pH value of the solution was adjusted to 8 with saturated aqueous sodium bicarbonate and extracted with ethyl acetate. The combined organic layer was washed with brine, dried over sodium sulfate and concentrated under reduced pressure. The residue was purified by silica gel column chromatography and compound was eluted in 25% ethyl acetate in petroleum ether to obtain tert-butyl 1-(2-bromothiazol-4-yl)cyclopropylcarbamate (44.1) as a colorless oil. (7.2 g, 82%), MS (ES): m/z 263/265 [M-56+H]+.

Synthesis of 44.2. A solution of 44.1 (5.78 g, 16.06 mmol, 1 eq) in HCl in 1,4-dioxane (4 M, 60 mL) was stirred for 2 h at room temperature. The mixture was concentrated to afford crude N-(4-(1-aminocyclopropyl)thiazol-2-yl)cyclopropanesulfonamide hydrochloride (44.2) as an off-white solid. (4.74 g), MS (ES): m/z 260 [M+H]+.

Synthesis of 44.3. To a stirred mixture of 44.2 (120 mg, 0.56 mmol, 1.0 eq) and 5-(6-ethoxypyrazin-2-yl)-1,3-thiazole-2-carboxylic acid (39.4, 142.1 mg, 0.56 mmol, 1.0 equiv) in N,N-dimethylformamide (3 mL) was added DIEA (219.3 mg, 1.69 mmol, 3 eq) and HATU (236.6 mg, 0.62 mmol, 1.1 eq). The resulting mixture was stirred for 2 h at room temperature under nitrogen. The mixture was purified by reverse flash chromatography with the following conditions: Column, C18 Column; Mobile Phase, water (0.1% FA) and ACN (5% ACN up to 60% in 20 min); UV detection at 254/220 nm. The desired N-[1-(3-bromophenyl)cyclopropyl]-5-(6-ethoxypyrazin-2-yl)-1,3-thiazole-2-carboxamide (44.3) was obtained as an off-white solid. (108 mg, 42%), MS (ES): m/z 446 [M+H]+.

Synthesis of I-69. To a stirred mixture of 44.3 (50 mg, 0.11 mmol, 1.0 eq) and difluoromethanesulfonamide (44.1 mg, 0.33 mmol, 3.0 eq) in tert-butyl alcohol (1 mL) was added Pd$_2$(dba)$_3$ (10.2 mg, 0.01 mmol, 0.1 eq), potassium phosphate (71.5 mg, 0.33 mmol, 3 eq) and BrettPhos (12 mg, 0.02 mmol, 0.2 eq) at room temperature. The resulting mixture was stirred for 16 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether. The residue was concentrated under vacuum. The crude product (40 mg) was purified by Prep-HPLC with the following conditions: Column: SunFire Prep C18 OBD Column, 19×150 mm 5 um 10 nm; Mobile Phase: water (0.1% FA) and ACN (40% to 70% in 7 min, UV detection at 254/210 nm). The product-containing fractions were combined and evaporated partially in vacuum and lyophilized overnight to afford the title compound as a white solid. (14.7 mg, 25.8%), MS (ES): m/z 496 [M+H]+; $^1$H NMR (300 MHz, CD$_3$OD) δ 8.68 (s, 1H), 8.56 (s, 1H), 8.15 (s, 1H), 7.33-7.19 (m, 2H), 7.14-7.11 (m, 2H), 6.60 (t, J=53.1 Hz, 1H), 4.49 (q, J=7.1 Hz, 2H), 1.56-1.29 (m, 7H).

Example 45: N-[(1R)-1-(4-cyclopropanesulfonamidopyridin-2-yl)propyl]-4-(6-ethoxypyrazin-2-yl)-2-fluorobenzamide (I-72)

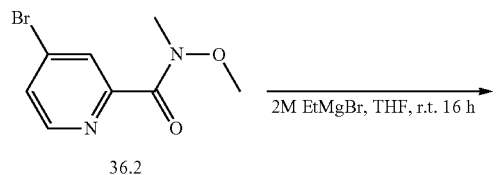

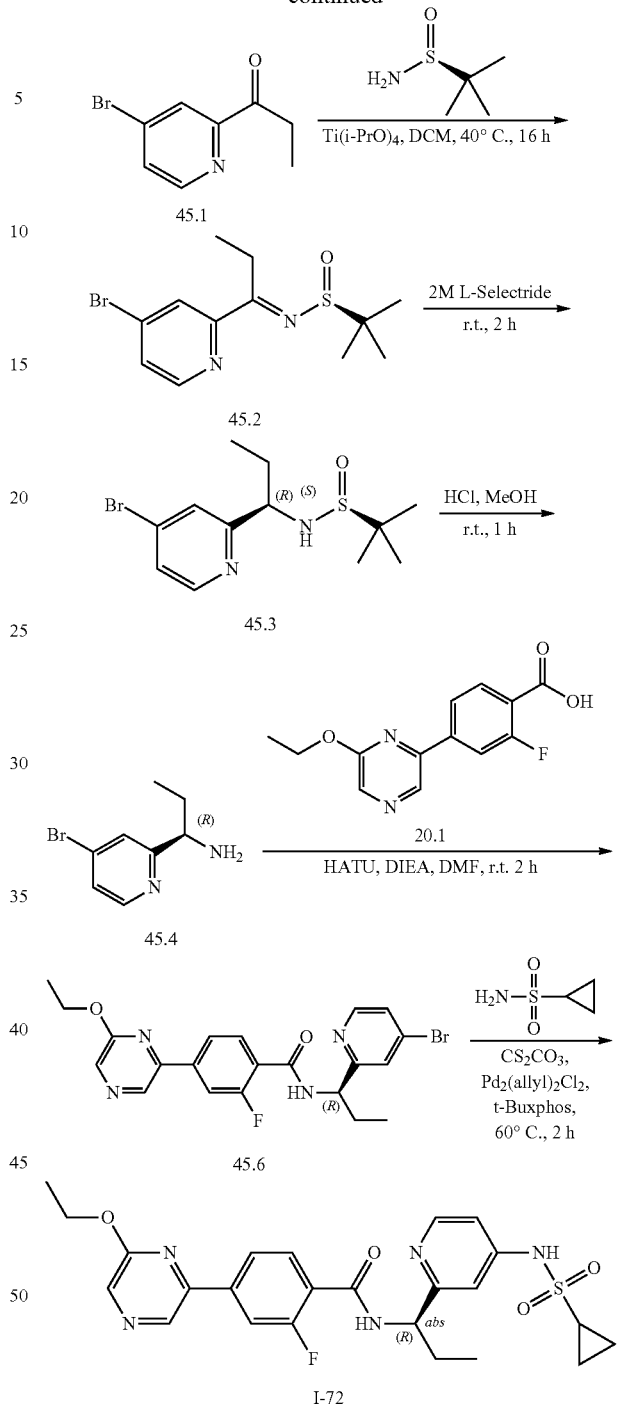

Synthesis of 45.1. To a stirred solution of ethyl 2-4-bromo-N-methoxy-N-methylpicolinamide (36.2, 245 mg, 1 mmol, 1 eq) in tetrahydrofuran (10 mL) was added ethylmagnesium bromide (2 M, 5 mL, 10 mmol, 10 eq) dropwise at 0° C. under nitrogen atmosphere. The resulting mixture was stirred for 16 h at rt under nitrogen atmosphere. The reaction was quenched with saturated aqueous ammonium chloride and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain 1-(4-bromopyridin-2-yl)propan-1-one (45.1, 180 mg, 84%), MS (ES): m/z 214/216 [M+H]+.

Synthesis of 45.2. To a stirred mixture of 45.1 (180 mg, 1 mmol, 1.0 eq) and (S)-2-methylpropane-2-sulfinamide (122.2 mg, 1.2 mmol, 1.20 eq) in dichloromethane (10 mL) was added tetraisopropyl titanate (477.1 mg, 2 mmol, 2.0 eq). The resulting mixture was stirred for 16 h at 40° C. under nitrogen atmosphere. The mixture was quenched with water and extracted with dichloromethane. The combined organic layer was washed with brine, dried over sodium sulfate and concentrated under reduced pressure. The residue was purified by silica gel column chromatography and compound was eluted in 10% ethyl acetate in petroleum to afford (S,E)-N-(1-(4-bromopyridin-2-yl)propylidene)-2-methylpropane-2-sulfmamide (45.2) as a yellow oil. (200 mg, 76%), MS (ES): m/z 317/319 [M+H]+.

Synthesis of 45.3. To a stirred mixture of 45.2 (200 mg, 0.63 mmol, 1 eq) in tetrahydrofuran (5 mL) was added L-Selectride (1 M, 1.2 mL, 1.2 mmol, 2 eq) dropwise at −78° C. under nitrogen atmosphere. The resulting mixture was stirred for 1 h at −78° C. The reaction was quenched by the saturated aqueous ammonium chloride and extracted with dichloromethane. The combined organic layers were washed with brine, dried over anhydrous sodium sulfate and concentrated under reduced pressure to obtain (S)—N—((R)-1-(4-bromopyridin-2-yl)propyl)-2-methylpropane-2-sulfmamide (45.3) as an yellow oil. (160 mg, 80%), MS (ES): m/z 319/321 [M+H]+.

Synthesis of compound 45.4. To a stirred solution of 45.3 (160 mg, 0.40 mmol, 1 eq) in methanol (5 mL) was added HCl in dioxane (4 M, 2 mL) at 0° C. The resulting mixture was stirred for 2 h at room temperature. The resulting mixture was concentrated under reduced pressure to obtain (1R)-1-(4-bromopyridin-2-yl)propan-1-amine hydrochloride (45.4) as a white solid. (100 mg, 93%), MS (ES): m/z 215/217 [M+H]+.

Synthesis of 45.6. To a stirred solution of 45.4 (100 mg, crude) and 4-(6-ethoxypyrazin-2-yl)-2-fluorobenzoic acid (20.1, 123.1 mg, 0.47 mmol, 1 eq) in N,N-dimethylformamide (4 mL) were added DIEA (242.5 mg, 1.88 mmol, 4 eq) and HATU (212.8 mg, 0.56 mmol, 1.2 eq). The resulting mixture was stirred for 2 h at room temperature under nitrogen. The residue was purified by reverse flash chromatography with the following conditions: Column, C18 Column; Mobile Phase, water (0.1% FA) and ACN (5% ACN up to 60% in 20 min); UV detection at 254/220 nm. The product-containing fractions were combined and concentrated under reduced pressure to obtain N-[(1R)-1-(4-bromopyridin-2-yl)propyl]-4-(6-ethoxypyrazin-2-yl)-2-fluorobenzamide as a yellow solid. (45.6, 100 mg, 47%), MS (ES): m/z 459/461 [M+H]+.

Synthesis of I-72. To a stirred solution of 45.6 (100 mg, 0.22 mmol, 1 eq) and cyclopropanesulfonamide (53.2 mg, 0.44 mmol, 2 eq) in dioxane (4 mL) were added cesium carbonate (217.1 mg, 0.66 mmol, 3 eq), Pd2(allyl)2Cl2 (7.3 mg, 0.02 mmol, 0.05 eq) and t-Buxphos (17.1 mg, 0.04 mmol, 0.1 eq) at room temperature under nitrogen atmosphere. The resulting mixture was stirred for 2 h at 60° C. under nitrogen atmosphere. The resulting mixture was concentrated under vacuum. The residue was purified by reverse flash chromatography with the following conditions: Column, C18 Column; Mobile Phase, water (0.1% FA) and ACN (5% ACN up to 60% in 20 min); LTV detection at 254/220 nm. The product-containing fractions were combined and concentrated to obtain the crude product. The crude product was purified by Prep-HPLC with the following conditions, Column: SunFire Prep C18 OBD Column, 19×150 mm 5 um 10 nm; Mobile Phase, water (0.1% FA), ACN (25% ACN up to 45% in 8 min); UV detection at 254/220 nm. The product-containing fractions were combined and evaporated partially in vacuum and lyophilized overnight to afford the title compound as a white solid. (39.6 mg, 36%), MS (ES): m/z 500 [M+H]+; 1H NMR (400 MHz, CD3OD) δ 8.74 (s, 1H), 8.27 (d, J=5.9 Hz, 1H), 8.20 (s, 1H), 8.06-7.97 (m, 2H), 7.87-7.73 (m, 1H), 7.32 (d, J=2.3 Hz, 1H), 7.12 (dd, J=6.0, 2.3 Hz, 1H), 4.92-4.88 (m, 1H), 4.46 (q, J=7.1 Hz, 2H), 2.63-2.59 (m, 1H), 2.10-1.85 (m, 2H), 1.49 (t, J=7.1 Hz, 3H), 1.22-1.11 (m, 2H), 1.11-0.94 (m, 5H).

Example 46: Synthesis of N-[(1S)-1-(4-cyclopropanesulfonamidopyridin-2-yl)propyl]-4-(6-ethoxypyrazin-2-yl)-2-fluorobenzamide (I-73)

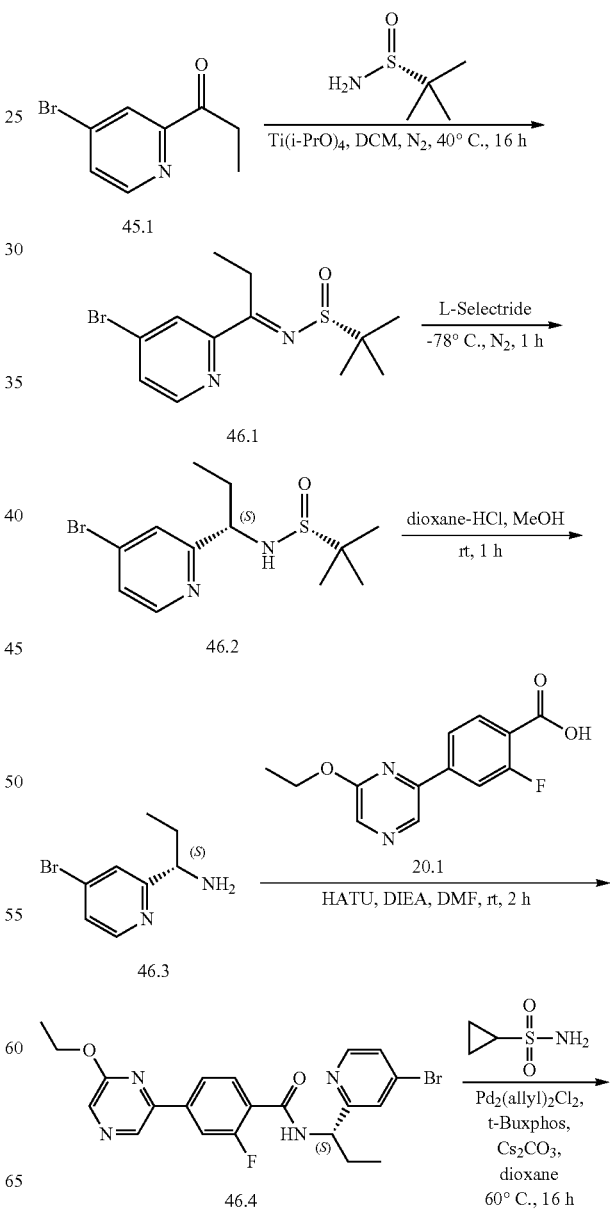

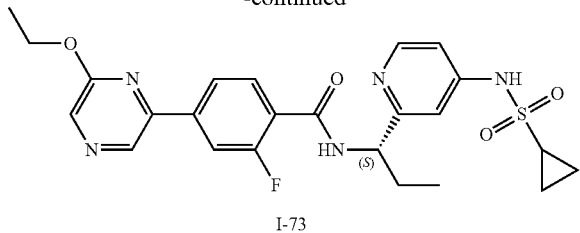

I-73

Synthesis of 46.1. To a stirred mixture of 45.1 (428 mg, 1 mmol, 1.0 eq) and (R)-2-methylpropane-2-sulfmamide (290.8 mg, 1.2 mmol, 1.2 eq) in dichloromethane (10 mL) was added tetraisopropyl titanate (568.2 mg, 2 mmol, 2 eq) in portions at 40° C. under nitrogen atmosphere for overnight. The resulting mixture was concentrated under reduced pressure. The resulting mixture diluted with water, extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain (R)—N-[1-(4-bromopyridin-2-yl)ethylidene]-2-methylpropane-2-sulfinamide (46.1) as a yellow oil (138.6 mg, 21%), MS (ES): m/z 317/319 [M+H]$^+$.

Synthesis of 46.2. To a stirred mixture of 46.1 (138.6 mg, 0.44 mmol, 1 eq) in tetrahydrofuran (8 ml) was added L-Selectride (166.1 mg, 0.87 mmol, 2 eq) at −78° C. The resulting mixture stirred for additional 2 h at −78° C. The mixture quenched with water, extracted with ethyl acetate. The combined organic layer was washed with brine, dried over sodium sulfate and concentrated under reduced pressure to obtain (R)—N—((S)-1-(4-bromopyridin-2-yl)propyl)-2-methylpropane-2-sulfmamide (46.2, 103 mg, 71.%) as a yellow oil MS (ES): m/z 319/321 [M+H]$^+$.

Synthesis of 46.3. A solution of 46.2 (103 mg, 0.32 mmol, 1 eq) in methanol (5 mL) was added HCl in 1,4-dioxane (4 M, 5 mL) was stirred for 2 h at room temperature. The mixture was concentrated to afford 1-(4-bromopyridin-2-yl)propan-1-amine hydrochloride (46.3) as a white solid. (84.6 mg crude), MS (ES): m/z 215/217 [M+H]$^+$.

Synthesis of 46.4. To a stirred mixture of 46.3 (84.6 mg) and 4-(6-ethoxypyrazin-2-yl)-2-fluorobenzoic acid (20.1, 103.1 mg, 0.39 mmol, 1 eq) in dichloromethane (4 ml) were added DIEA (203 mg, 1.57 mmol, 4 eq) and HATU (179.5 mg, 0.47 mmol, 1.2 eq) at room temperature under nitrogen. The resulting solutions stirred for 2 h at ambient temperature. The resulting mixture was concentrated under vacuum. The residue purified by reverse flash with the following conditions: Column, C18 Column; Mobile Phase, water (0.1% NH$_4$HCO$_3$) and ACN (45% ACN up to 60% in 10 min); UV detection at 254/220 nm. The product-containing fractions were combined and concentrated under reduced pressure to afford N-[(1S)-1-(4-bromopyridin-2-yl)propyl]-4-(6-ethoxypyrazin-2-yl)-2-fluorobenzamide (46.4, 100 mg, 53%) as a yellow oil. MS (ES): m/z 459/461 [M+H]$^+$.

Synthesis of I-73. To a stirred mixture of 46.4 (100 mg, 0.22 mmol, 1 eq) and cyclopropanesulfonamide (52.8 mg, 0.44 mmol, 2 eq) in dioxane (10 mL) were added caesium carbonate (212.8 mg, 0.65 mmol, 3 eq) in portions at room temperature under nitrogen atmosphere. To the above mixture was added Pd$_2$(allyl)$_2$Cl$_2$ (4.0 mg, 0.01 mmol, 0.05 eq) and t-Buxphos (9.3 mg, 0.02 mmol, 0.1 eq) at room temperature. The resulting mixture was stirred for additional 16 h at 60° C. The resulting mixture was concentrated under reduced pressure. The residue was purified by Prep-HPLC with the following conditions: Column, XBridge Shield RP18 OBD Column, 30*150 mm, 5 um; mobile phase, Water (0.1% FA) and ACN (22% ACN up to 52% in 7 min); UV detection at 254/220 nm. The product-containing fractions were combined and evaporated partially in vacuum and lyophilized overnight to afford the title compound as a white solid. (38.3 mg, 35%), MS (ES): m/z 500 [M+H]$^+$; $^1$H NMR (400 MHz, CD$_3$OD) δ 8.62 (s, 1H), 8.16 (d, J=6.1 Hz, 1H), 8.08 (s, 1H), 7.92-7.87 (m, 2H), 7.77-7.74 (m, 1H), 7.21 (d, J=2.3 Hz, 1H), 7.01 (dd, J=6.1, 2.3 Hz, 1H), 4.91 (t, J=6.0 Hz, 1H), 4.44 (q, J=7.1 Hz, 2H), 2.64-2.60 (m, 1H), 1.89-1.81 (m, 2H), 1.37 (t, J=7.0 Hz, 3H), 1.06-1.03 (m, 2H), 0.96-0.90 (m, 5H).

Example 47: Synthesis of N-[(4-cyclopropanesulfonamidopyridin-2-yl)methyl]-4-[3-ethyl-1H-pyrrolo[2,3-b]pyridin-6-yl]benzamide (I-38)

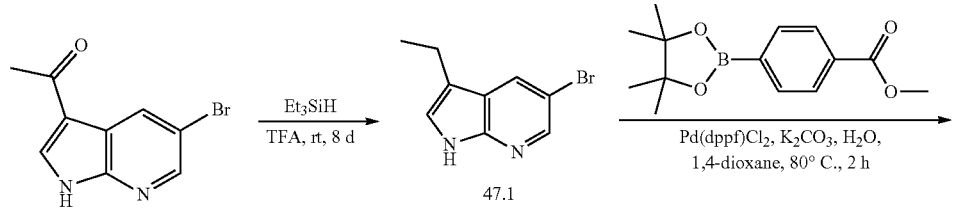

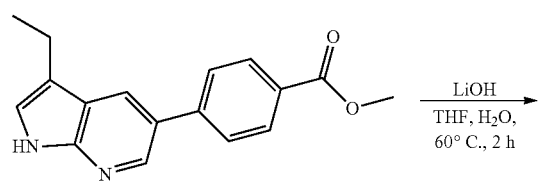

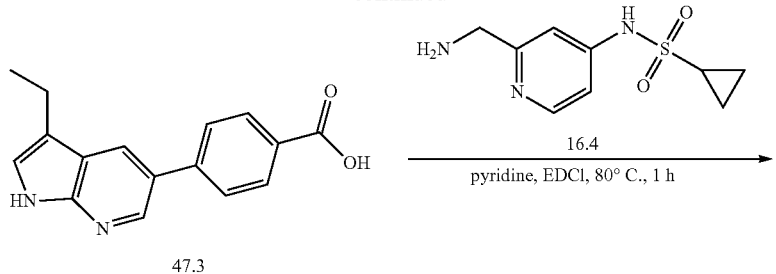

Synthesis of 47.1. To a solution of 1-[5-bromo-1H-pyrrolo[2,3-b]pyridin-3-yl]ethan-1-one (714 mg, 2.99 mmol, 1 eq) in trifluoroacetic acid (3 mL) was added triethylsilane (2.88 mL, 0.22 mmol, 2.2 eq) at room temperature and the reaction mixture was stirred for 8 days at ambient temperature. The resulting mixture was diluted dichloromethane, washed with potassium hydroxide (aq.). The organic layer was washed with brine, dried over sodium sulfate and concentrated under reduced pressure to obtain crude 5-bromo-3-ethyl-1H-pyrrolo[2,3-b]pyridine (47.1) as a white powder. (630 mg, 93%), MS (ES): m/z 225/227 [M+H]$^+$.

Synthesis of 47.2. To a stirred mixture of 47.1 (314.4 mg, 1.2 mmol, 1.2 eq) and 5-bromo-3-ethyl-1H-pyrrolo[2,3-b]pyridine (225 mg, 1 mmol, 1 eq) in dioxane (20 mL) and water (5 mL) were added potassium carbonate (1.58 g, 11.45 mmol, 3 eq) and Pd(dppf)Cl$_2$ (277.8 mg, 0.38 mmol, 0.1 eq) at room temperature under nitrogen atmosphere. The resulting mixture was stirred for 2 h at 80° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted with 10% ethyl acetate in petroleum ether to obtain methyl 4-[3-ethyl-1H-pyrrolo[2,3-b]pyridin-6-yl]benzoate (47.2) as a white solid. (220 mg, 79%), MS (ES): m/z 281 [M+H]$^+$.

Synthesis of 47.3. To a mixture of 47.2 (281 mg, 1 mmol, 1 eq) in tetrahydrofuran (15 mL) and water (3 mL) and was added lithium hydroxide (72 mg, 3 mmol, 3 eq) at room temperature. The resulting mixture was stirred for 2 h at 60° C. The mixture was cooled to room temperature and concentrated under vacuum. The residue was diluted with water. The pH value of the solution was adjusted to 3 with 1N hydrochloric acid. The solids were collected by filtration and dried in an oven at 45° C. to obtain 4-[3-ethyl-1H-pyrrolo[2,3-b]pyridin-6-yl]benzoic acid (47.3) as a red solid. (98 mg, 37%), MS (ES): m/z 267 [M+H]$^+$.

Synthesis of I-38. To a stirred solution of 47.3 (95 mg, 0.36 mmol, 1 eq) and N-[2-(aminomethyl)pyridin-4-yl]cyclopropanesulfonamide (16.4, 81.1 mg, 0.36 mmol, 1 eq) in pyridine (5 mL) was added EDCI (136.8 mg, 0.71 mmol, 2 eq) at room temperature. The resulting mixture was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 5 um, 19*150 mm; Mobile Phase, water (0.1% NH$_4$HCO$_3$) and ACN (10% ACN up to 40% in 10 min); UV detection at 254/220 nm. The product-containing fractions were combined and evaporated partially in vacuum and lyophilized overnight to afford the title compound as a white solid. (27.1 mg, 16%), MS (ES): m/z 476 [M+H]$^+$. $^1$H NMR (300 MHz, d$_6$-DMSO) δ 11.42 (s, 1H), 10.92 (s, 1H), 9.17 (t, J=6.0 Hz, 1H), 8.56 (d, J=2.2 Hz, 1H), 8.30-8.14 (m, 2H), 8.02 (d, J=8.4 Hz, 2H), 7.88 (d, J=8.4 Hz, 2H), 7.28 (s, 1H), 7.12-6.92 (m, 2H), 4.50 (d, J=5.8 Hz, 2H), 2.83-2.58 (m, 3H), 1.28 (t, J=7.5 Hz, 3H), 1.08-0.77 (m, 4H).

Example 48: Synthesis of N-[(5-cyclopropanesulfonamidopyridazin-3-yl)methyl]-5-(6-ethoxypyrazin-2-yl)pyridine-2-carboxamide (I-37)

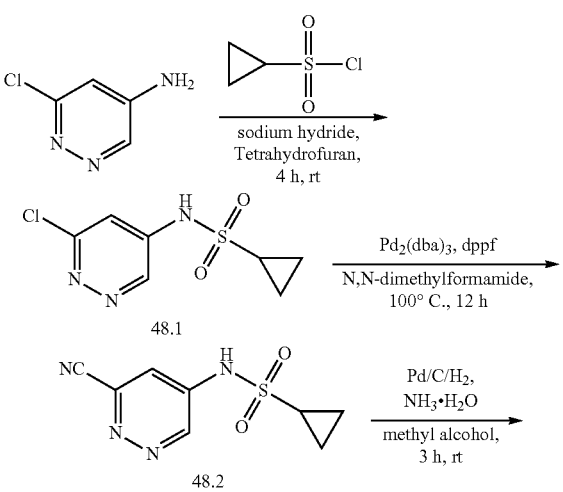

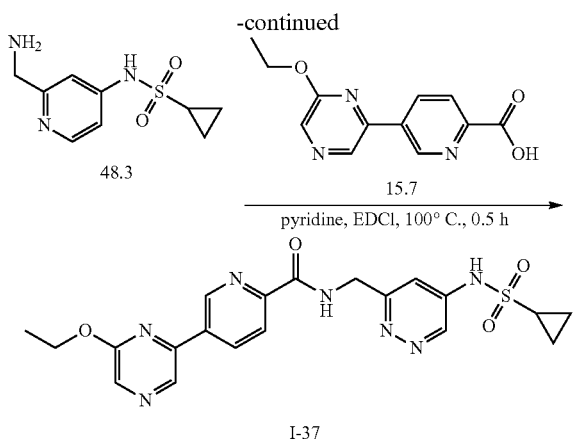

Synthesis of 48.1. To a stirred mixture of 6-chloropyridazin-4-amine (1.3 g, 10 mmol, 1 eq) in tetrahydrofuran was added sodium hydride (1.2 g, 50 mmol, 5 eq) and cyclopropanesulfonyl chloride (4.2 g, 30 mmol, 3 eq) at 0° C. The resulting solution was stirred for 4 h at room temperature. The mixture was diluted with water and extracted with ethyl acetate. The combined organic layer was washed with brine, dried over sodium sulfate and concentrated under reduced pressure. The residue was purified by reverse phase flash with the following conditions: Column, C18 Column; Mobile Phase, water (0.1% NH$_4$HCO$_3$) and ACN (40% ACN up to 60% in 20 min); UV detection at 254/220 nm. The product-containing fractions were combined and concentrated under reduced pressure to obtain N-(6-chloropyridazin-4-yl) cyclopropane sulfonamide (48.1) as a dark yellow solid. (550 mg, 22%), MS (ES):m/z 234[M+H]$^+$.

Synthesis of 48.2. To a stirred mixture of 48.1 (450 mg, 1.91 mmol, 1 eq) and zinc cyanide (452 mg, 3.82 mmol, 2 eq) in N,N-Dimethylformamide (10 mL) were added DPPF (213 mg, 0.38 mmol, 0.2 eq) and Pd$_2$(dba)$_3$ (176 mg, 0.19 mmol, 0.1 eq). The resulting solution was stirred for 12 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by reverse phase flash with the following conditions: Column, C18 Column; Mobile Phase, water (0.1% FA) and ACN (30% ACN up to 60% in 25 min); UV detection at 254/220 nm. This resulted in N-(6-cyanopyridazin-4-yl) cyclopropane sulfonamide (48.2) as a white solid. (120 mg, 28%), MS (ES): m/z 226 [M+H]$^+$.

Synthesis of 48.3. To a stirred mixture of 48.2 (120 mg, 0.5 mmol, 1 eq) in methanol (10 mL) and ammonia (3 mL) was flushed three times with nitrogen. To the solution was added Pd/C (10 mg), then degassed with hydrogen. The mixture was stirred 3 hrs at room temperature under an atmosphere of hydrogen. The solids were filtered out and the filtrate was concentrated under reduced pressure to afford crude N-[6-(amino methyl) pyridazin-4-yl] cyclopropane sulfonamide (48.3) as a yellow oil. (70 mg, 22%), MS (ES): m/z 230 [M+H]$^+$.

Synthesis of I-37. To a stirred mixture of 48.3 (84.0 mg, 0.40 mmol, 1 eq) in pyridine (1 mL) was added 5-(6-ethoxypyrazin-2-yl)pyridine-2-carboxylic acid (15.7, 112 mg, 0.4 mmol, 1 eq) and EDC.HCl (117.2 mg, 0.6 mmol, 1.5 eq) at room temperature. The resulting solution was stirred for 0.5 h at 100° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column: YMC-Actus Triart C18 30*250.5 um; Mobile Phase, water (0.1% NH$_4$HCO$_3$+0.1% NH$_3$·H$_2$O) and ACN (8% ACN up to 35% in 7 min); UV detection at 254/210 nm. The product-containing fractions were combined and evaporated partially in vacuum and lyophilized overnight to afford the title compound as a white solid. (20 mg, 12%) MS (ES): m/z 457 [M+H]$^+$; $^1$H NMR (300 MHz, CD$_3$OD) δ 9.39 (s, 1H), 8.82 (s, 1H), 8.67 (dd, J=8.2, 2.3 Hz, 1H), 8.51 (s, 1H), 8.27 (d, J=7.7 Hz, 1H), 8.25 (s, 1H), 7.36 (s, 1H), 4.77 (s, 2H), 4.59 (q, J=7.0 Hz, 2H), 2.62-2.49 (m, 1H), 1.50 (t, J=7.1 Hz, 3H), 1.06-0.99 (m, 2H), 0.93-0.81 (m, 2H).

Example 49: Synthesis of N-(2-((5-(6-ethoxy-pyrazin-2-yl)-1-oxoisoindolin-2-yl)methyl)pyridin-4-yl)cyclopropanesulfonamide (I-43)

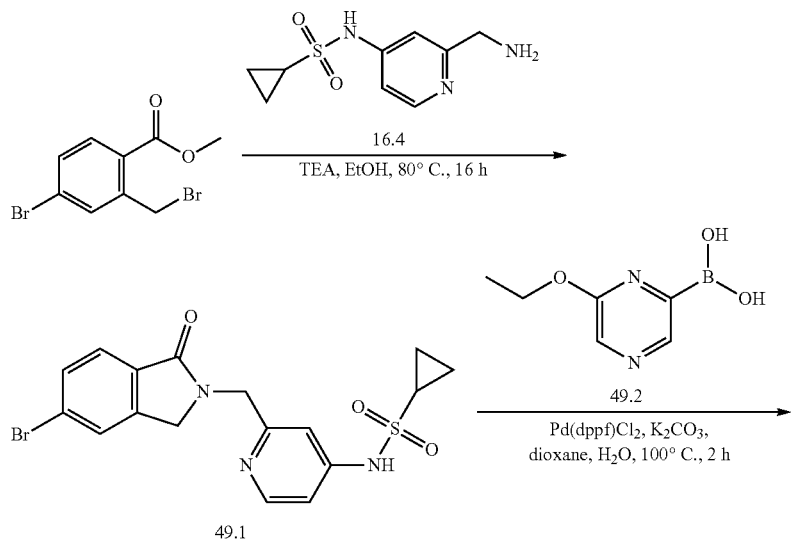

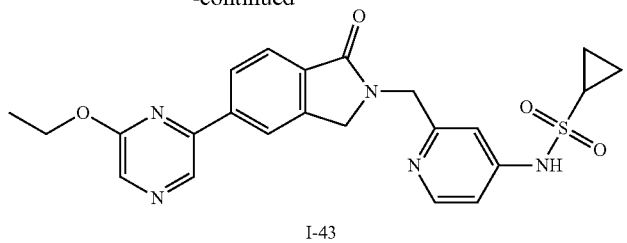

I-43

Synthesis of 49.1. To a stirred solution of methyl 4-bromo-2-(bromomethyl)benzoate (100 mg, 0.32 mmol, 1 eq) and N-[2-(aminomethyl)pyridin-4-yl]cyclopropanesulfonamide (16.4, 73.8 mg, 0.32 mmol, 1 eq) in ethyl alcohol (3 mL), was added trimethylamine (98.6 mg, 0.97 mmol, 3 eq). The resulting solution was stirred for 16 h at 80° C. The mixture was cooled to room temperature. The residue was purified by reverse phase flash with the following conditions: Column, C18 Column; Mobile Phase, water (0.1% $NH_4HCO_3$) and ACN (20% ACN up to 40% in 8 min); UV detection at 254/220 nm. The product-containing fractions were combined and concentrated under reduced pressure to obtain N-[2-[(5-bromo-1-oxo-3H-isoindol-2-yl)methyl]pyridin-4-yl]cyclopropanesulfonamide (49.1) as a yellow solid (95 mg, 69%), MS (ES): m/z 423 [M+H]+.

Synthesis of I-43. To a solution of 49.1 (75 mg, 0.17 mmol, 1 eq) and 6-ethoxypyrazin-2-ylboronic acid (49.2, 149.1 mg, 0.01 mmol, 5 eq) in 1,4-dioxane (4 mL) and water (1 mL), were added potassium carbonate (73.6 mg, 0.53 mmol, 3 eq) and Pd(dppf)Cl$_2$ (12.9 mg, 0.01 mmol, 0.1 eq). The resulting solution was stirred for 2 h at 100° C. under nitrogen. The mixture was diluted with water and extracted with ethyl acetate. The combined organic layer was washed with brine, dried over sodium sulfate and concentrated under reduced pressure. The residue was purified by Prep-HPLC with the following conditions: Column: YMC-Actus Triart C18 30*250.5 um; Mobile Phase, water (0.1% $NH_4HCO_3$+ 0.1% $NH_3 \cdot H_2O$) and ACN (2% ACN up to 30% in 8 min); UV detection at 254/220 nm. The product-containing fractions were combined and evaporated partially in vacuum and lyophilized overnight to afford the title compound as a white solid (15.6 mg, 19%). MS (ES): m/z 466 [M+H]+; $^1$H NMR (400 MHz, d$_6$-DMSO) δ 8.89 (s, 1H), 8.38 (s, 1H), 8.33-8.24 (m, 3H), 7.89 (d, J=8.0 Hz, 1H), 7.06 (d, J=6.0 Hz, 1H), 6.98 (d, J=2.2 Hz, 1H), 4.81 (s, 2H), 4.62 (s, 2H), 4.51 (q, J=7.0 Hz, 2H), 2.80-2.67 (m, 1H), 1.42 (t, J=7.0 Hz, 3H), 1.03-0.90 (m, 4H).

Example 50: Synthesis of N-[(4-cyclopropanesulfonamidopyridin-2-yl)methyl]-4-[6-(pyrrolidin-1-yl)pyrazin-2-yl]benzamide (I-42)

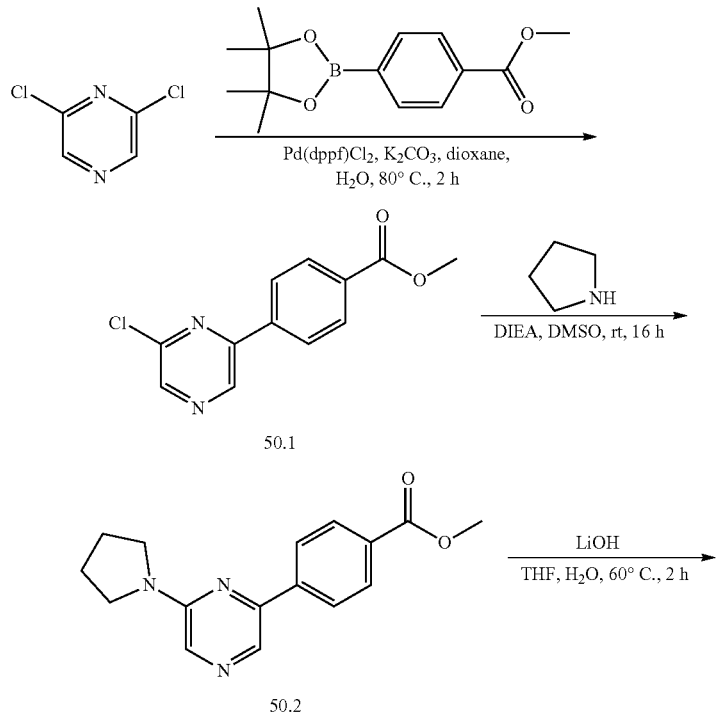

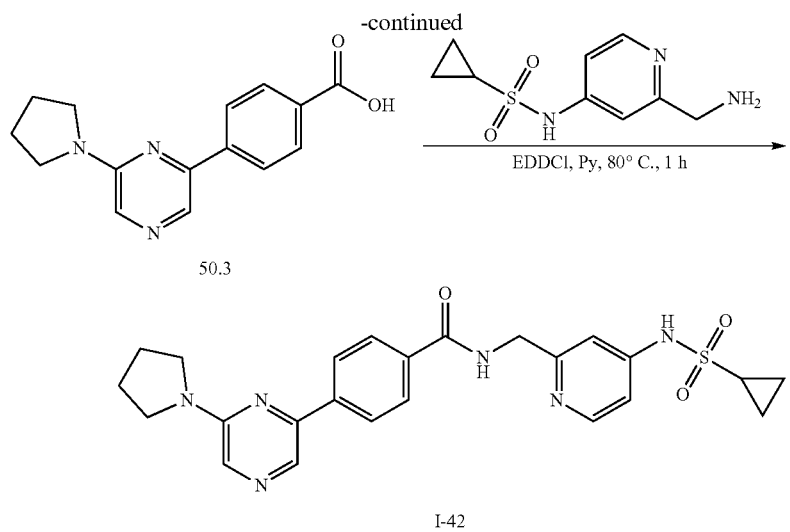

Synthesis of 50.1. To a stirred solution of methyl 4-(4,4,5,5-tetramethyl-1,3,2-dioxaborolan-2-yl)benzoate (1 g, 3.82 mmol, 1 eq) and 2-chloro-6-chloro-pyrazine (1.14 g, 7.63 mmol, 2.0 eq) in dioxane (20 mL) and water (5 mL), were added potassium carbonate (1.58 g, 11.45 mmol, 3.0 eq) and Pd(dppf)Cl$_2$ (277.8 mg, 0.38 mmol, 0.1 eq) at room temperature under nitrogen atmosphere. The resulting mixture was stirred for 2 h at 80° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 20% ethyl acetate in petroleum ether to obtain methyl 4-(6-chloropyrazin-2-yl)benzoate (50.1, 390 mg, 41%) as a brown solid. MS (ES): m/z 249 [M+H]$^+$.

Synthesis of 50.2. To a mixture of 50.1 (124.0 mg, 0.5 mmol, 3 eq) in dimethylsulfoxide (5 mL) were added pyrrolidine (177.2 mg, 2.5 mmol, 5 eq) and DIEA (0.3 mL) at room temperature. The resulting mixture was stirred for 16 h at room temperature. The residue was purified by reverse flash with the following conditions: Column, C18 Column; Mobile Phase, water (0.1% NH$_4$HCO$_3$) and ACN (20% ACN up to 50% in 10 min); UV detection at 254/220 nm. The product-containing fractions were combined and concentrated under reduced pressure to afford methyl 4-[6-(pyrrolidin-1-yl)pyrazin-2-yl]benzoate (50.2, 120 mg, 85%) as a yellow solid. MS (ES): m/z 284 [M+H]$^+$.

Synthesis of 50.3. To a mixture of 50.2 (230 mg, 0.81 mmol, 1 eq) in tetrahydrofuran (5 mL) and water (1 mL), was added lithium hydroxide (38.9 mg, 1.62 mmol, 2 eq) at room temperature. The resulting mixture was stirred for 2 h at 60° C. The mixture was cooled to room temperature and concentrated under vacuum. The residue was diluted with water. The pH value of the solution was adjusted to 3 with 1N hydrochloric acid and extracted with ethyl acetate. The combined organic layer was washed with brine, dried over sodium sulfate and concentrated under reduced pressure to afford 4-[6-(pyrrolidin-1-yl)pyrazin-2-yl]benzoic acid (50.3, 85 mg, 39%) as a yellow solid, MS (ES): m/z 270 [M+H]$^+$.

Synthesis of I-42. To a stirred solution of 50.3 (120 mg, 0.45 mmol, 1 eq) and N-[2-(aminomethyl)pyridin-4-yl]cyclopropanesulfonamide (16.4, 101.3 mg, 0.45 mmol, 1 eq) in pyridine (5 mL) was added EDCI (170.8 mg, 0.89 mmol, 2 eq) at room temperature. The resulting mixture was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 5 um, 19*150 mm; Mobile Phase, water (0.1% FA) and ACN (18% ACN up to 40% in 8 min); E1V detection at 254/220 nm. The product-containing fractions were combined and evaporated partially in vacuum and lyophilized overnight to afford the title compound (33.6 mg, 15%) as a light green solid, MS (ES): m/z 479 [M+H]$^+$; $^1$H NMR (300 MHz, d$_6$-DMSO) δ 11.32 (s, 1H), 9.23 (t, J=5.9 Hz, 1H), 8.46 (s, 1H), 8.27-8.15 (m, 3H), 8.11-7.93 (m, 3H), 7.13-6.99 (m, 2H), 4.51 (d, J=5.8 Hz, 2H), 3.63-3.45 (m, 4H), 2.78-2.61 (m, 1H), 2.05-1.89 (m, 4H), 1.02-0.88 (m, 4H).

Example 51: Synthesis of N-[(4-cyclopropanesulfonamidopyridin-2-yl)methyl]-4-(6-isopropoxypyrazin-2-yl)benzamide (I-33)

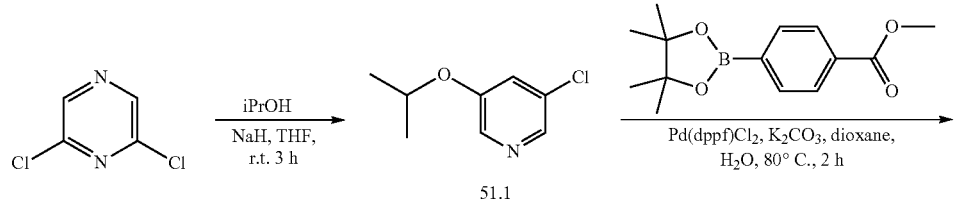

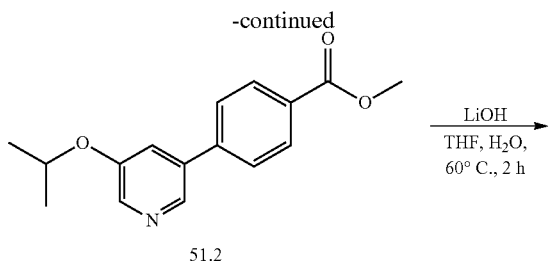

51.2

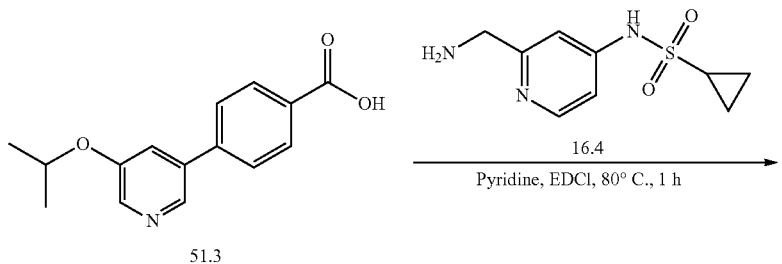

51.3

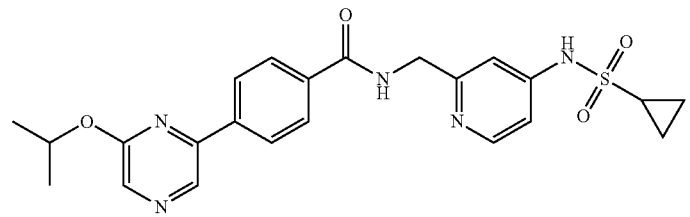

I-33

Synthesis of 51.1. To a stirred mixture of isopropanol (630 mg, 10.48 mmol, 1.05 eq) in tetrahydrofuran (30 ml) was added sodium hydride (0.29 g, 12.08 mmol, 1.21 eq) in portions at 0° C. After 1 h, to the above mixture was added 2-chloro-6-chloro-pyrazine (1.49 g, 10 mmol, 1 eq) at room temperature. The resulting mixture was stirred for additional 3 h at room temperature. The mixture quenched with water and extracted with ethyl acetate. The combined organic layer was washed with brine, dried over sodium sulfate and concentrated under reduced pressure to afford 2-chloro-6-isopropoxypyrazine (51.1) as a yellow solid. (1.4 g, 81%), MS (ES): m/z 173 [M+H]$^+$.

Synthesis of 51.2. To a solution of 51.1 (1.45 g, 8.4 mmol, 1 eq) and methyl 4-(4,4,5,5-tetramethyl-1,3,2-dioxaborolan-2-yl)benzoate (2.64 g, 10.07 mmol, 1.2 eq) in 1,4-dioxane (25 mL) and water (5 mL) were added potassium carbonate (3.48 g, 25.2 mmol, 3 eq) and Pd(dppf)Cl$_2$ (610 mg, 0.83 mmol, 0.1 eq) at room temperature under nitrogen atmosphere. The resulting mixture was stirred for 2 h at 80° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain methyl 4-(6-isopropoxy-pyrazin-2-yl)benzoate (51.2) as a yellow solid. (1.8 g, 79%), MS (ES): m/z 273 [M+H]$^+$.

Synthesis of 51.3. To a stirred mixture of 51.2 (1.96 g, 7.2 mmol, 1 eq) in tetrahydrofuran (20 mL) and water (4 mL) and was added lithium hydroxide (0.69 g, 28.81 mmol, 4 eq) at room temperature. The resulting mixture was stirred for 2 h at 60° C. The mixture was cooled to room temperature and concentrated under vacuum. The residue was diluted with water. The pH value of the solution was adjusted to 3 with 1N hydrochloric acid and extracted with ethyl acetate. The combined organic layer was washed with brine, dried over sodium sulfate and concentrated under reduced pressure to afford 4-(6-isopropoxypyrazin-2-yl)benzoic acid (51.3) as a yellow solid. (1.7 g, 91%), MS (ES): m/z 259 [M+H]$^+$.

Synthesis of I-33. To a stirred mixture of 51.3 (56 mg, 0.22 mmol, 1 eq) in pyridine (3 mL) were added N-[2-(aminomethyl)pyridin-4-yl]cyclopropanesulfonamide (16.4, 49.3 mg, 0.22 mmol, 1 eq) and EDCI (83.1 mg, 0.43 mmol, 2 eq) at room temperature. The resulting mixture was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 5 um, 19*150 mm; Mobile Phase, water (0.1% NH$_4$HCO$_3$) and ACN (20% ACN up to 35% in 8 min); UV detection at 254/220 nm. The product-containing fractions were combined and evaporated partially in vacuum and lyophilized overnight to afford the title compound as a white solid. (20.8 mg, 20%) MS (ES): m/z 468 [M+H]$^+$; 1H NMR (300 MHz, d$_6$-DMSO) δ 10.99 (s, 1H), 9.24 (t, J=5.9 Hz, 1H), 8.89 (s, 1H), 8.31-8.15 (m, 4H), 8.10-8.00 (m, 2H), 7.05-6.98 (m, 2H), 5.50-5.35 (m, 1H), 4.50 (d, J=5.9 Hz, 2H), 2.75-2.60 (m, 1H), 1.39 (d, J=6.2 Hz, 6H), 1.00-0.80 (m, 4H).

Example 52: Synthesis of 2-methyl-2-(2-(1-methyl-ethylsulfonamido)thiazol-4-yl)-N-(5-(6-(trifluoromethyl)pyrazin-2-yl)pyridin-2-yl)propanamide (I-32)

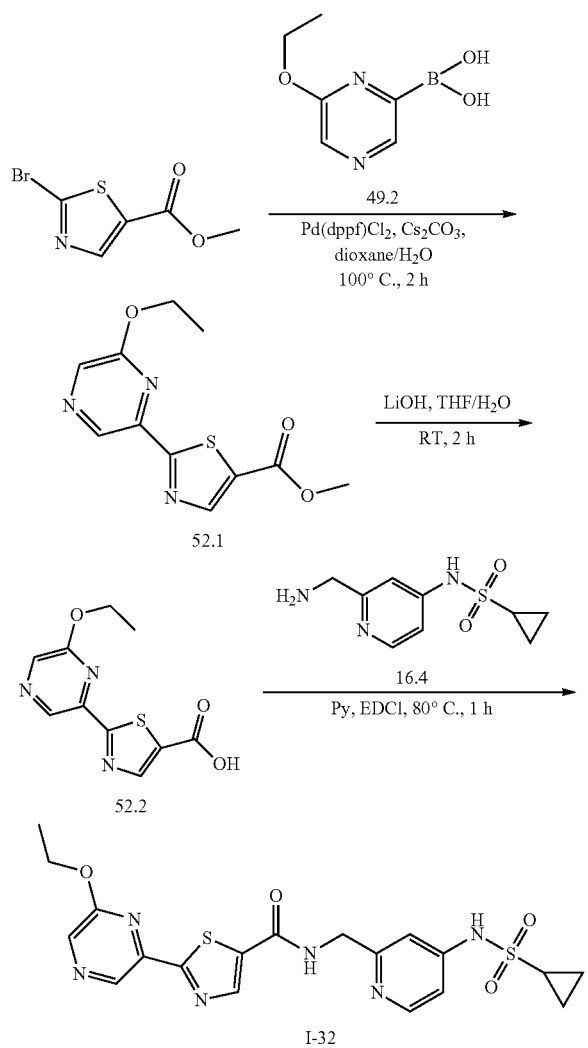

Synthesis of 52.1. To a stirred mixture of methyl 2-bromo-1,3-thiazole-5-carboxylate (111 mg, 0.5 mmol, 1 eq) and 6-ethoxypyrazin-2-ylboronic acid (167.9 mg, 1 mmol, 2 eq) in 1,4-dioxane (5 mL) and water (1 mL) was added cesium carbonate (488.6 mg, 1.5 mmol, 3 eq) and Pd(dppf)Cl₂ (36.5 mg, 0.05 mmol, 0.1 eq). The resulting mixture was stirred for 2 h at 100° C. under nitrogen atmosphere. The mixture was cooled to room temperature, diluted with water and extracted with ethyl acetate. The resulting mixture was concentrated under reduced pressure. The residue was purified by silica gel column chromatography and eluted in 20% ethyl acetate in petroleum ether to afford methyl 2-(6-ethoxypyrazin-2-yl)-1,3-thiazole-5-carboxylate (52.1) as a white solid. (30 mg, 36.9%), MS (ES): m/z 266 [M+H]⁺.

Synthesis of 52.2. A mixture of 52.1 (79 mg, 0.29 mmol, 1 eq) and Lithium hydroxide (62.4 mg, 1.48 mmol, 5 eq) in Tetrahydrofuran (5 mL) and water (1 mL) was stirred for 2 h at room temperature. The mixture was concentrated under vacuum. The residue was diluted with water. The pH value of the solution was adjusted to 3 with 1N hydrochloric acid. The solids were collected by filtration to obtain 2-(6-ethoxy-pyrazin-2-yl)-1,3-thiazole-5-carboxylic acid (52.2) as a white solid. (34 mg, 47.8%), MS (ES): m/z 250 [M−H]⁻.

Synthesis of I-32. A mixture of 52.2 (25 mg, 0.01 mmol, 1 eq), N-[2-(aminomethyl)pyridin-4-yl]cyclopropanesulfonamide (16.4, 22.6 mg, 0.01 mmol, 1 eq) and EDCI (38.1 mg, 0.2 mmol, 2 eq) in Pyridine (2 mL) was stirred for 30 min at 80° C. under nitrogen atmosphere. The mixture was cooled to room temperature, diluted with water and extracted with ethyl acetate. The combined organic layer was washed with brine, dried over sodium sulfate and concentrated under reduced pressure. The crude product was purified by Prep-HPLC with the following conditions: Column, Sunfire prep C18 column, 30*150, 5 um; Mobile Phase Water (0.1% FA) and CAN (30% to 42% in 7 min, UV detection at 254/210 nm). The product-containing fractions were combined and evaporated partially in vacuo and lyophilized overnight to afford the title compound; formic acid as a light yellow solid. (19 mg, 37.7%), MS (ES): m/z 507 [M+H]⁺; ¹H NMR (300 MHz, DMSO-d₆) δ 10.50 (s, 1H), 9.47 (t, J=6.0 Hz, 1H), 8.89 (s, 1H), 8.62 (s, 1H), 8.44 (s, 1H), 8.32 (s, 1H), 8.13 (s, 0.3H), 7.15-0.95 (m, 2H), 4.59-4.39 (m, 4H), 2.77-2.62 (m, 1H), 1.41 (t, J=7.0 Hz, 3H), 1.09-0.80 (m, 4H).

Example 53: Synthesis of 2-methyl-2-(2-(1-methyl-ethylsulfonamido)thiazol-4-yl)-N-(5-(6-(trifluoromethyl)pyrazin-2-yl)pyridin-2-yl)propanamide (I-44)

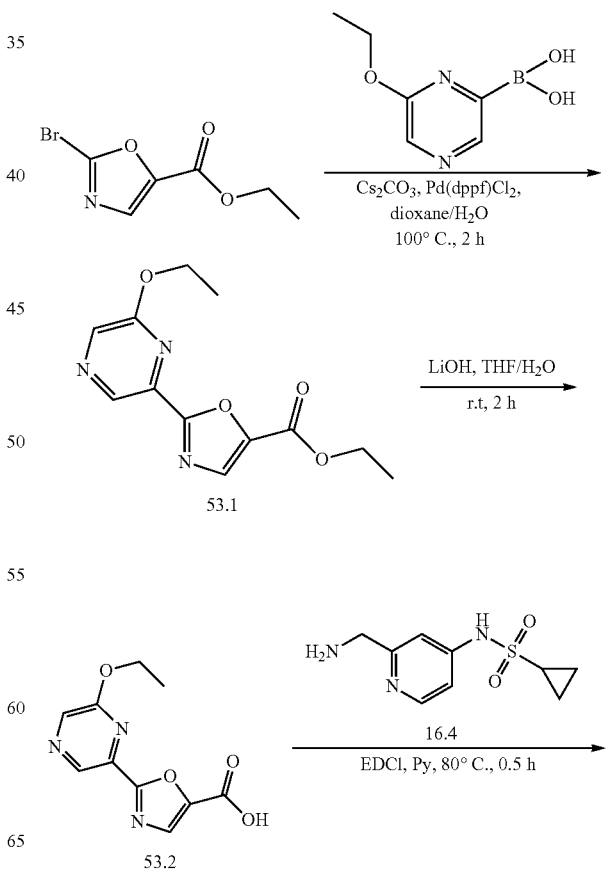

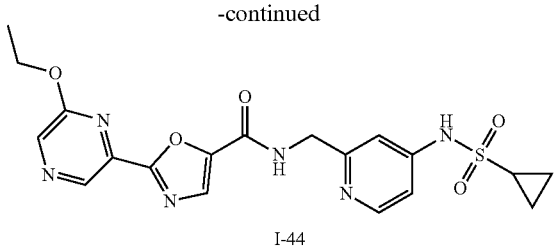

I-44

Synthesis of 53.1. To a stirred mixture of ethyl 2-bromo-1,3-oxazole-5-carboxylate (220 mg, 1 mmol, 1 eq), 6-ethoxypyrazin-2-ylboronic acid (167.9 mg, 1 mmol, 1 eq) and cesium carbonate (977.3 mg, 3 mmol, 3 eq) in 1,4-dioxane (5 mL) and water (1 mL), was added Pd(dppf)Cl$_2$·CH$_2$Cl$_{1-2}$ (81.4 mg, 0.1 mmol, 0.1 eq) in portions for 2 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain ethyl 2-(6-ethoxypyrazin-2-yl)-1,3-oxazole-5-carboxylate (53.1, 220 mg, 83.5%) as a yellow solid. MS (ES): m/z 264 [M+H]$^+$.

Synthesis of 53.2. A mixture of 53.1 (120 mg, 0.45 mmol, 1 eq) and lithium hydroxide (95.6 mg, 2.28 mmol, 5 eq) in tetrahydrofuran (10 mL) and water (2 mL) was stirred for 2 h at room temperature. The mixture was concentrated under vacuum. The residue was diluted with water. The pH value of the solution was adjusted to 3 with 1N hydrochloric acid. The solids were collected by filtration to obtain 2-(6-ethoxypyrazin-2-yl)-1,3-oxazole-5-carboxylic acid (53.2, 40 mg, 37%) as an off-white solid, MS (ES): m/z 236 [M+H]$^+$.

Synthesis of I-44. A mixture of 53.2 (40 mg, 0.17 mmol, 1 eq), N-[2-(aminomethyl)pyridin-4-yl]cyclopropanesulfonamide (16.4, 38.6 mg, 0.17 mmol, 1 eq) and EDCI (65.2 mg, 0.34 mmol, 2 eq) in Pyridine (2 mL) was stirred for 30 min at 80° C. The resulting mixture was concentrated under reduced pressure and purified by Prep-HPLC with the following conditions: Column, YMC-Actus Triart C18 30*250, 5 um; Mobile Phase, Water (0.1% NH$_4$HCO$_3$+0.1% NH$_3$·H$_2$O) and CH$_3$CN (10% to 26% in 10 min; UV detection at 254/210 nm). The product-containing fractions were combined and evaporated partially in vacuum and lyophilized overnight to afford the title compound (13.2 mg, 37%) as a white solid, MS (ES): m/z 445 [M+H]$^+$; $^1$H NMR (400 MHz, DMSO-d$_6$) δ 9.38 (t, J=6.0 Hz, 1H), 8.98 (s, 1H), 8.49 (s, 1H), 8.23 (d, J=5.7 Hz, 1H), 8.08 (s, 1H), 7.03 (d, J=4.9 Hz, 2H), 4.54-4.44 (m, 4H), 2.80-2.67 (m, 1H), 1.43 (t, J=7.0 Hz, 3H), 1.02-0.88 (m, 4H).

Example 54: Synthesis of N-[(4-cyclopropanesulfonamidopyridin-2-yl)methyl]-4-[6-(3-methoxypyrrolidin-1-yl)pyrazin-2-yl]benzamide (I-45)

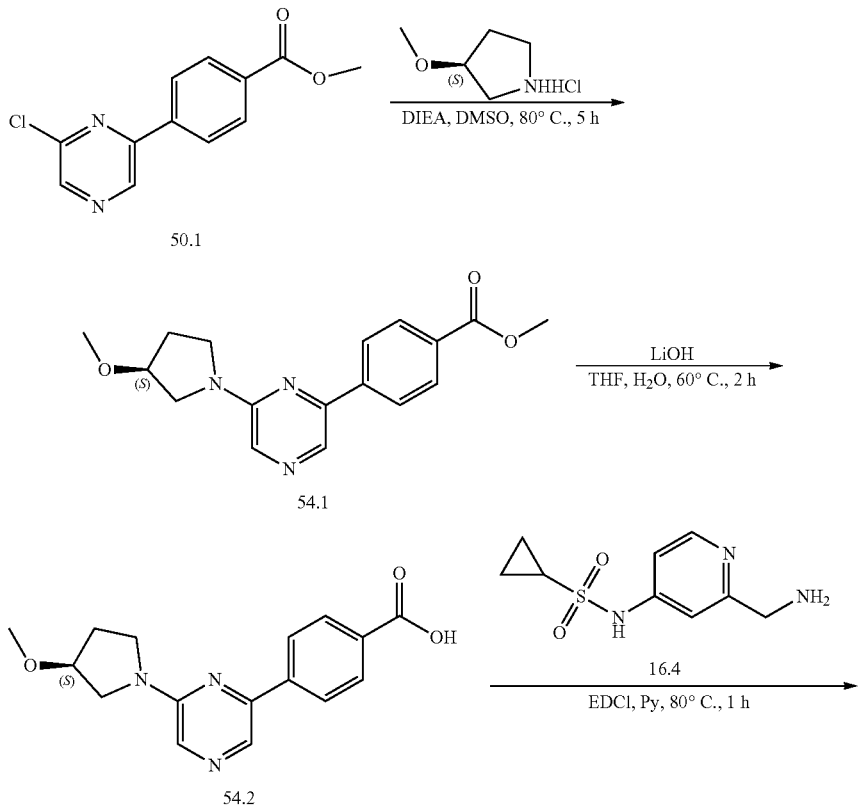

-continued

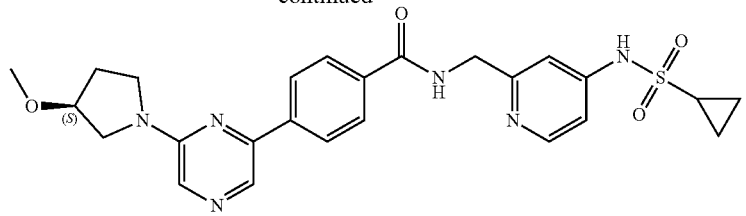

I-45

Synthesis of 54.1. To a mixture of methyl 4-(6-chloropyrazin-2-yl)benzoate (50.1, 150 mg, 0.6 mmol, 1 eq) in dimethyl sulfoxide (5 mL) were added 3-methoxypyrrolidine hydrochloride (249 mg, 1.81 mmol, 3 eq) and DIEA (1 mL, 5.74 mmol, 9.5 eq) at room temperature. The resulting mixture was stirred for 5 h at 80° C. The mixture was cooled to room temperature. The residue was purified by reverse flash with the following conditions: Column, C18 Column; Mobile Phase, water (0.1% NH₄HCO₃) and ACN (31% ACN up to 46% in 10 min); UV detection at 254/220 nm. The product-containing fractions were combined and concentrated under reduced pressure to afford methyl 4-[6-(3-methoxypyrrolidin-1-yl)pyrazin-2-yl]benzoate (54.1, 113 mg, 60%) as a white solid. MS (ES): m/z 314 [M+H]⁺.

Synthesis of 54.2. To a solution of 54.1 (113 mg, 0.36 mmol, 1 eq), tetrahydrofuran (15 mL), and water (3 mL), was added lithium hydroxide (17.2 mg, 0.72 mmol, 2 eq) at room temperature. The resulting mixture was stirred for 2 h at 60° C. The mixture was cooled to room temperature and concentrated under vacuum. The residue was diluted with water. The pH value of the solution was adjusted to 3 with 1N hydrochloric acid and extracted with ethyl acetate. The combined organic layer was washed with brine, dried over sodium sulfate and concentrated under reduced pressure to obtain 4-[6-(3-methoxypyrrolidin-1-yl)pyrazin-2-yl]benzoic acid (54.2.99 mg, 92%) as a yellow solid. MS (ES): m/z 300 [M+H]⁺.

Synthesis of I-45. To a stirred mixture of 54.2 (117 mg, 0.39 mmol, 1 eq) and N-[2-(aminomethyl)pyridin-4-yl]cyclopropanesulfonamide (16.4, 88.8 mg, 0.39 mmol, 1 eq) in pyridine (5 mL) was added EDCI (149.9 mg, 0.78 mmol, 2 eq) at room temperature. The resulting mixture was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 5 um, 19*150 mm; Mobile Phase, water (0.1% NH₄HCO₃) and ACN (5% ACN up to 33% in 8 min); UV detection at 254/220 nm. The product-containing fractions were combined and evaporated partially in vacuum and lyophilized overnight to afford the title compound (34.6 mg, 17%) as a light green solid. MS (ES): m/z 509 [M+H]⁺; ¹H NMR (300 MHz, CD₃OD) δ 8.50 (d, J=6.9 Hz, 1H), 8.34 (s, 1H), 8.27-8.17 (m, 2H), 8.09-7.98 (m, 2H), 7.92 (s, 1H), 7.64 (d, J=2.4 Hz, 1H), 7.60-7.50 (m, 1H), 4.86 (s, 2H), 4.25-4.15 (m, 1H), 3.84-3.49 (m, 4H), 3.41 (s, 3H), 2.97-2.86 (m, 1H), 2.29-2.11 (m, 2H), 1.32-1.19 (m, 2H), 1.18-1.07 (m, 2H).

Example 55: Synthesis of N-[(4-cyclopropanesulfonamidopyridin-2-yl)methyl]-4-[6-(3-methoxyazetidin-1-yl)pyrazin-2-yl]benzamide (I-46)

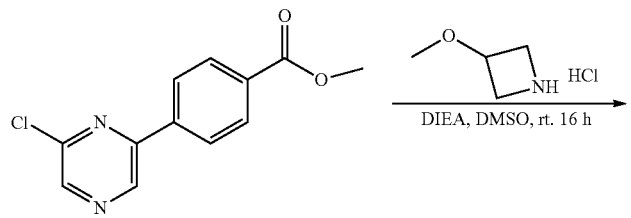

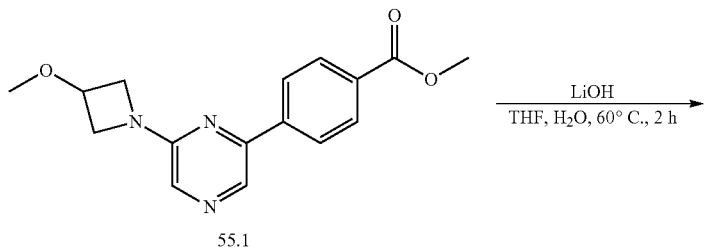

55.1

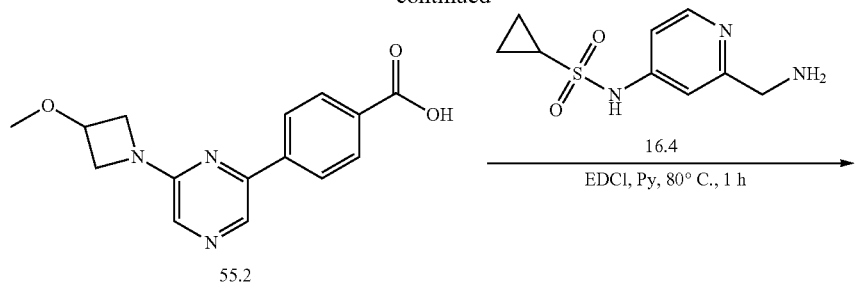

55.2

I-46

Synthesis of 55.1. To a solution of methyl 4-(6-chloro-pyrazin-2-yl)benzoate (50.1, 130 mg, 0.52 mmol, 1 eq) in dimethylsulfoxide (5 mL) were added 3-methoxyazetidine hydrochloride (193.8 mg, 1.57 mmol, 3 eq) and DIEA (1 mL, 5.74 mmol, 10.9 eq) at room temperature. The resulting mixture was stirred for 16 h at room temperature. The residue was purified by reverse flash with the following conditions: Column, C18 Column; Mobile Phase, water (10 mmol/mL NH4HCO3) and ACN (10% ACN up to 40% in 10 min); UV detection at 254/220 nm. methyl 4-[6-(3-methoxyazetidin-1-yl)pyrazin-2-yl]benzoate (55.1, 122 mg, 78%) as a brown oil, MS (ES): m/z 300 [M+H]+.

Synthesis of 55.2. To a solution/mixture of 55.1 (122 mg, 0.41 mmol, 1 eq) in tetrahydrofuran (5 mL) and water (1 mL) and was added lithium hydroxide (19.5 mg, 0.82 mmol, 2 eq) at room temperature. The resulting mixture was stirred for 2 h at 60° C. The mixture was cooled to room temperature and concentrated under vacuum. The residue was diluted with water. The pH value of the solution was adjusted to 3 with 1N hydrochloric acid and extracted with ethyl acetate. The combined organic layer was washed with brine, dried over sodium sulfate and concentrated under reduced pressure to afford 4-[6-(3-methoxyazetidin-1-yl)pyrazin-2-yl]benzoic acid (55.2, 98 mg, 84%) as a white solid, MS (ES): m/z 286 [M+H]+.

Synthesis of I-46. To a stirred solution of 55.2 (114 mg, 0.4 mmol, 1 eq) and N-[2-(aminomethyl)pyridin-4-yl]cyclopropanesulfonamide (16.4, 90 mg, 0.4 mmol, 1 eq) in pyridine (5 mL) was added EDCI (151.9 mg, 0.79 mmol, 2 eq) at room temperature. The resulting mixture was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 5 um, 19*150 mm; Mobile Phase, water (0.1% NH4HCO3) and ACN (5% ACN up to 33% in 8 min); UV detection at 254/220 nm. The product-containing fractions were combined and evaporated partially in vacuum and lyophilized overnight to afford the title compound (25.3 mg, 13%) as a white solid, MS (ES): m/z 495 [M+H]+; 1H NMR (300 MHz, DMSO-d6) δ 9.21 (t, J=5.9 Hz, 1H), 8.54 (s, 1H), 8.35-8.15 (m, 3H), 8.06-7.96 (m, 2H), 7.91 (s, 1H), 7.13-6.95 (m, 2H), 4.51 (d, J=5.8 Hz, 2H), 4.43-4.26 (m, 3H), 4.00-3.88 (m, 2H), 3.29 (s, 3H), 2.75-2.60 (m, 1H), 1.01-0.83 (m, 4H).

Example 56: Synthesis of N-[4-[(2R)-1-[5-(6-ethoxypyrazin-2-yl)pyridine-2-carbonyl]pyrrolidin-2-yl]pyrimidin-2-yl]cyclopropanesulfonamide (I-47) and N-[4-[(2S)-1-[5-(6-ethoxypyrazin-2-yl)pyridine-2-carbonyl]pyrrolidin-2-yl]pyrimidin-2-yl]cyclopropanesulfonamide (I-34)

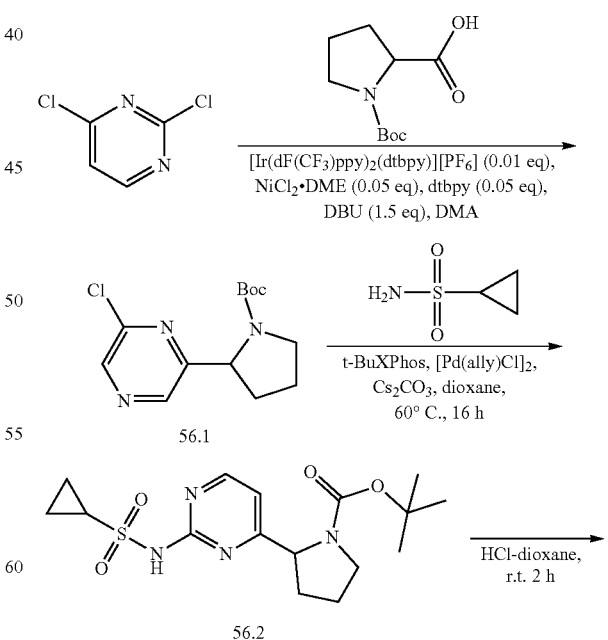

-continued

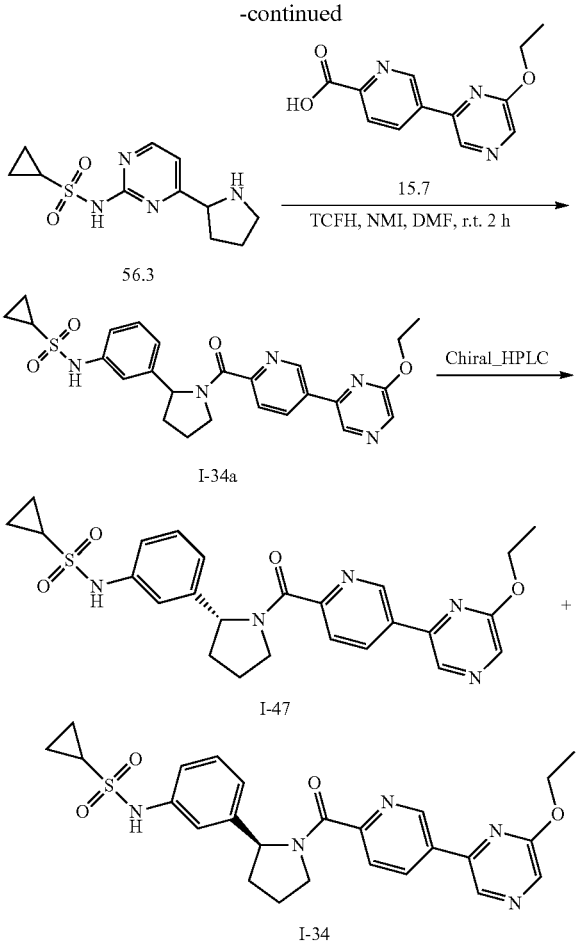

Synthesis of 56.1. To a stirred solution of photocatalyst Ir[dF(CF$_3$)ppy]$_2$(dtbbpy)PF$_6$ (33.6 mg, 0.03 mmol, 0.01 eq.) and 2,4-dichloropyrimidine (500 mg, 3.35 mmol, 1 eq.) in DMA (10 mL) was added (tert-butoxycarbonyl)proline (1.08 g, 5 mmol, 1.5 eq.), DBU (760 mg, 5.0 mmol, 1.5 eq.), NiCl$_2$·DME (33.5 mg, 0.16 mmol, 0.05 eq.) and 4,4'-di-tert-butyl-2,2'-bipyridine (43.6 mg, 0.16 mmol, 0.05 eq) at room temperature under nitrogen atmosphere. The reaction was stirred and irradiated with a 34 W blue LED lamp (7 cm away, with cooling fan to keep the reaction temperature at 25° C. for 6 h under nitrogen atmosphere. The mixture was diluted with water and extracted with ethyl acetate. The combined organic layer was washed with brine, dried over sodium sulfate and concentrated under reduced pressure. The resulting mixture was concentrated under reduced pressure. The residue was purified by silica gel column chromatography and eluted in 20% ethyl acetate in petroleum ether to afford tert-butyl 2-(2-chloropyrimidin-4-yl)pyrrolidine-1-carboxylate (56.1) as a yellow oil. (120 mg, 12%), MS (ES): m/z 284 [M+H]$^+$.

Synthesis of 56.2. To a stirred solution of 56.1 (120 mg, 0.42 mmol, 1 eq) and cyclopropanesulfonamide (152.5 mg, 1.26 mmol, 3 eq) in 1,4-dioxane (3 mL) were added cesium carbonate (547.7 mg, 1.68 mmol, 4 eq), Pd$_2$(allyl)$_2$C$_{1-2}$ (7.3 mg, 0.02 mmol, 0.05 eq) and t-Buxphos (17 mg, 0.04 mmol, 0.1 eq) at room temperature under nitrogen atmosphere. The resulting mixture was stirred for 16 h at 60° C. under nitrogen atmosphere. The mixture was cooled to room temperature, diluted with water. The pH value of the solution was adjusted to 4 with 1N hydrochloric acid and extracted with ethyl acetate. The combined organic layer was washed with brine, dried over sodium sulfate and concentrated under reduced pressure. The residue was purified by reverse flash with the following conditions: Column, C18 Column; Mobile Phase, water (10 mmol/mL NH$_4$HCO$_3$) and ACN (20% ACN up to 50% in 10 min); UV detection at 254/220 nm. The product-containing fractions were combined and concentrated under reduced pressure to afford tert-butyl 2-(2-cyclopropanesulfonamidopyrimidin-4-yl) pyrrolidine-1-carboxylate (56.2) as yellow oil. (100 mg, 84%), MS (ES): m/z 369 [M+H]$^+$.

Synthesis of 56.3. To a stirred solution of 56.2 (100 mg, 0.27 mmol, 1 eq) in dichloromethane (3 mL) was added hydrochloric acid in 1,4-dioxane (2M, 3 mL) at room temperature. The resulting mixture was stirred for overnight at room temperature. The resulting mixture was concentrated under vacuum to attain N-[4-(pyrrolidin-2-yl) pyrimidin-2-yl]cyclopropane sulfonamide (56.3) as an off-white solid. (70 mg, 96%), MS (ES): m/z 269 [M+H]$^+$.

Synthesis of I-34a. To a stirred solution of 56.3 (70 mg, 0.26 mmol, 1 eq) and 5-(6-ethoxypyrazin-2-yl)pyridine-2-carboxylic acid (15.7, 63.7 mg, 0.26 mmol, 1 eq) in acetonitrile (5 mL) was added NMI (213.2 mg, 2.60 mmol, 10 eq) and TCFH (145.6 mg, 0.52 mmol, 2 eq) at room temperature. The resulting mixture was stirred for 2 h at room temperature. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (0.1% FA) and ACN (30% ACN up to 55% in 7 min); UV detection at 254/220 nm. The product-containing fractions were combined and evaporated partially in vacuum and lyophilized overnight to afford V-(4-[1-[5-(6-ethoxypyrazin-2-yl)pyridine-2-carbonyl]pyrrolidin-2-yl] pyrimidin-2-yl)cyclopropanesulfonamide (I-34a) as a white solid. (6.2 mg, 4.7%), MS (ES): m/z 496 [M+H]$^+$; $^1$H NMR (300 MHz, CD$_3$OD) δ 9.32 (d, J=2.2 Hz, 0.565H), 9.07 (d, J=2.1 Hz, 0.417H), 8.78 (s, 0.591H), 8.65 (s, 0.435H), 8.63-8.55 (m, 0.598H), 8.49 (d, J=5.2 Hz, 0.592H), 8.42 (dd, J=8.3, 2.3 Hz, 0.403H), 8.40-8.26 (m, 0.412H), 8.29 (d, J=5.2 Hz, 0.574H), 8.21 (d, J=13.5 Hz, 0.384H), 7.89 (d, J=8.3 Hz, 0.543H), 7.76 (d, J=8.3 Hz, 0.385H), 7.14 (d, J=5.2 Hz, 0.556H), 6.83 (d, J=5.2 Hz, 0.399H), 5.78-5.69 (m, 0.399H), 5.25 (dd, J=8.1, 4.6 Hz, 0.580H), 4.59-4.43 (m, 2H), 4.19-4.10 (m, 0.527H), 4.08-3.95 (m, 0.443H), 3.93-3.92 (m, 1H), 3.39-3.32 (m, 0.474H), 3.28-3.18 (m, 0.484H), 2.60-2.40 (m, 1H), 2.18-1.91 (m, 3H), 1.51-1.37 (m, 3H), 1.36-1.12 (m, 2H), 1.11-0.81 (m, 2H).

Synthesis of I-47 and I-34. Compound I-34a (70 mg, 0.14 mmol) was separated by Chiral-Prep-HPLC with the following conditions: Column, CHIRALPAK IE-3, 4.6*50 mm 3 um; mobile Phase: MtBE (0.1% DEA): EtOH=50:50, UV detection at 254/220 nm. The product-containing fractions were combined and concentrated under reduced pressure to afford N-[4-[(2R)-1-[5-(6-ethoxypyrazin-2-yl)pyridine-2-carbonyl]pyrrolidin-2-yl]pyrimidin-2-yl]cyclopropane-sulfonamide (1$^{st}$ eluting peak, I-47, 27.5 mg, 21%) and N-[4-[(2S)-1-[5-(6-ethoxypyrazin-2-yl)pyridine-2-carbonyl]pyrrolidin-2-yl]pyrimidin-2-yl]cyclopropanesulfonamide as a white solid (2$^{nd}$ eluting peak, I-34, 29.8 mg, 32%). I-47: MS (ES): m/z 496 [M+H]$^+$; $^1$H NMR (300 MHz, CD$_3$OD) δ 9.34 (d, J=2.2 Hz, 0.599H), 9.09 (d, J=2.1 Hz, 0.451H), 8.78 (s, 0.622H), 8.67 (s, 0.465H), 8.65-8.57 (m, 0.608H), 8.51-8.44 (m, 1H), 8.42-8.28 (m, 1H), 8.23 (d, J=13.5 Hz, 0.575H), 7.91-7.78 (m, 0.414H), 7.16 (d, J=5.2 Hz, 0.575H), 6.85 (d, J=5.2 Hz, 0.418H), 5.80-5.71 (m, 0.432H), 5.27 (dd, J=8.1, 4.6 Hz, 0.61 OH), 4.61-4.45 (m, 2H), 4.21-4.12 (m, 0.571H), 4.10-3.97 (m, 0.446H), 3.96-3.94 (m, 1H), 3.41-3.34 (m, 0.629H), 3.30-3.20 (m, 0.454H), 2.62-2.42 (m, 1H), 2.28-2.16 (m, 0.586H), 2.14-1.93 (m, 2.338H), 1.51-1.37 (m, 3H), 1.36-1.12 (m, 2H), 1.11-0.81 (m, 2H). I-34: MS (ES): m/z 496 [M+H]$^+$; $^1$H NMR (300 MHz, CD$_3$OD) δ 9.34 (d, J=2.2 Hz, 0.576H), 9.09 (d, J=2.1 Hz, 0.432H), 8.78-8.67 (m, 1H), 8.65-8.57 (m, 0.662H), 8.50-8.42 (m, 1H), 8.32-8.23 (m, 1H), 7.97-7.89 (m, 0.562H), 7.78-7.71 (m, 0.403H), 7.16 (d, J=5.2 Hz, 0.553H), 6.85 (d, J=5.2 Hz, 0.404H), 5.80-5.71 (m, 0.420H), 5.27 (dd, J=8.1, 4.6 Hz, 0.609H), 4.61-4.45 (m, 2H), 4.21-4.12 (m, 0.557H), 4.10-3.97 (m, 0.465H), 3.96-3.94 (m, 1H), 3.41-3.34 (m, 0.529H), 3.30-3.20 (m, 0.584H), 2.62-2.42 (m, 1H), 2.28-2.16 (m, 0.612H), 2.14-1.93 (m, 2.529H), 1.51-1.37 (m, 3H), 1.36-1.25 (m, 1H), 1.27-1.18 (m, 1H), 1.11-0.81 (m, 2H).

Example 57: Synthesis of N-[(5-cyclopropanesulfonamidopyridin-3-yl)methyl]-4-(6-ethoxypyrazin-2-yl)benzamide (I-36)

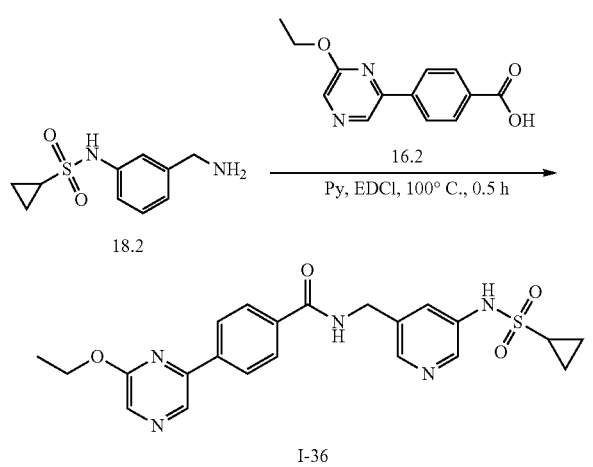

Synthesis of I-36. A mixture of 4-(6-ethoxypyrazin-2-yl) benzoic acid (16.2, 50 mg, 0.2 mmol, 1 eq), N-[5-(aminomethyl)pyridin-3-yl]cyclopropanesulfonamide (18.2, 46.5 mg, 0.2 mmol, 1 eq) and EDCI (78.4 mg, 0.4 mmol, 2 eq) in Pyridine (2 mL) was stirred for 30 min at 100° C. The residue was purified by reverse flash chromatography with the following conditions: column, C18 silica gel; mobile phase, ACN water, 10% to 70% gradient in 10 min; detector, UV 254 nm. The crude product (40 mg) was purified by Prep-HPLC with the following conditions: Column: SunFire Prep C18 OBD, 19×150 mm 5 um 10 nm; Mobile Phase, water (0.1% FA) and ACN (20% ACN up to 40% in 10 min); UV detection at 254/210 nm. The product-containing fractions were combined and evaporated partially in vacuum and lyophilized overnight to afford the title compound (27 mg, 29.1%) as a white solid. MS (ES): m/z 454 [M+H]$^+$; $^1$H NMR (400 MHz, DMSO-d$_6$) δ 10.05 (s, 1H), 9.25 (t, J=5.9 Hz, 1H), 8.89 (s, 1H), 8.36-8.21 (m, 5H), 8.05-7.99 (m, 2H), 7.62 (s, 1H), 4.55-4.45 (m, 4H), 2.69-2.60 (m, 1H), 1.41 (t, J=7.0 Hz, 3H), 0.93-0.91 (m, 4H).

Example 58: Synthesis of N-[(4-cyclopropanesulfonamidopyridin-2-yl)methyl]-5-(6-ethoxypyrazin-2-yl)-1,3,4-thiadiazole-2-carboxamide (I-51)

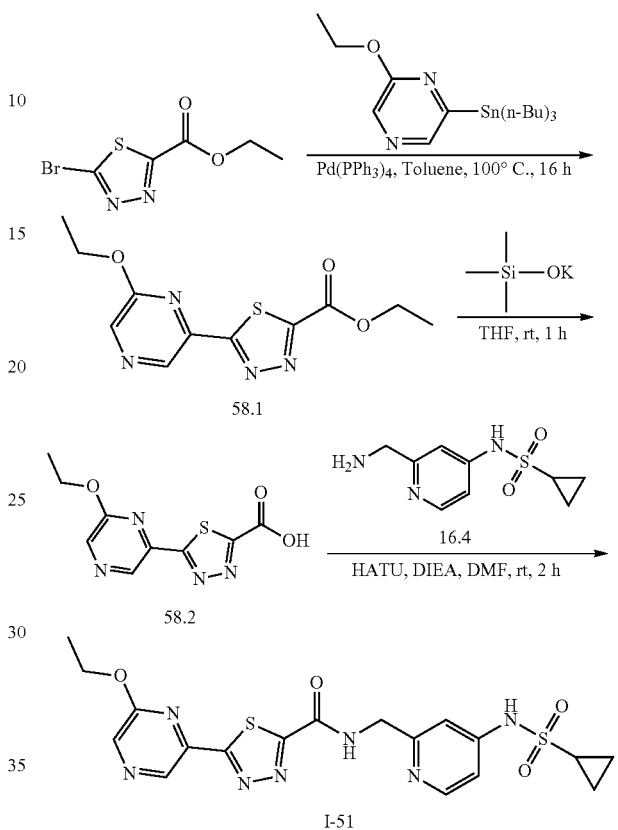

Synthesis of 58.1. To a stirred solution of ethyl 5-bromo-1,3,4-thiadiazole-2-carboxylate (600 mg, 2.53 mmol, 1 eq) and 2-ethoxy-6-(tributylstannyl) pyrazine (1 g, 2.53 mmol, 1 eq) in toluene (10 mL) was added Pd(PPh$_3$)$_4$ (292.4 mg, 0.25 mmol, 0.1 eq) at room temperature under nitrogen atmosphere. The resulting mixture was stirred for 16 h at 100° C. under nitrogen atmosphere. The mixture was cooled to r.t and concentrated under reduced pressure. The residue was purified by reverse phase flash with the following conditions: Column, C18 Column; Mobile Phase, water (0.1% NH$_4$HCO$_3$) and ACN (10% ACN up to 45% in 7 min); UV detection at 254/220 nm. The product-containing fractions were combined and concentrated under reduced pressure to obtain ethyl 5-(6-ethoxypyrazin-2-yl)-1,3,4-thiadiazole-2-carboxylate (58.1) as a white solid (300 mg, 42%). MS (ES): m/z 281 [M+H]$^+$.

Synthesis of 58.2. To a stirred solution of 58.1 (56 mg, 0.2 mmol, 1 eq) in tetrahydrofuran (5 mL) was added potassium trimethylsilanolate (51.2 mg, 0.4 mmol, 2 eq) at room temperature. The resulting mixture was stirred for 1 h at room temperature. The mixture was concentrated to afford 5-(6-ethoxypyrazin-2-yl)-1,3,4-thiadiazole-2-carboxylic acid (58.2) as a yellow solid (56 mg, 99%). MS (ES): m/z 253 [M+H]$^+$.

Synthesis of I-51. To a stirred solution of 58.2 (100 mg, 0.39 mmol, 1 eq) and N-[2-(aminomethyl)pyridin-4-yl]cyclopropanesulfonamide (16.4, 135.1 mg, 0.59 mmol, 1.5 eq) in dimethylformamide (5 mL) was added DIEA (153.7 mg, 1.18 mmol, 3 eq) and HATU (165.8 mg, 0.43 mmol, 1.1 eq) at room temperature. The resulting solution was stirred for 2 h at room temperature. The residue was purified by reverse phase flash with the following conditions: Column, C18 Column; Mobile Phase, water (0.1% FA) and ACN (15% ACN up to 50% in 8 min); UV detection at 254/220 nm. The product-containing fractions were combined and concentrated under reduced pressure. The residue was purified by Prep-HPLC with the following conditions: Column: SunFire Prep C18 OBD Column, 19×150 mm 5 um; Mobile Phase, water (0.1% FA) and ACN (17% ACN up to 47% in 7 min); UV detection at 254/220 nm. The product-containing fractions were combined and evaporated partially in vacuum and lyophilized overnight to afford the title compound as a white solid (28.4 mg, 15%). MS (ES): m/z 462 [M+H]$^+$; $^1$H NMR (400 MHz, de-DMSO) δ 9.93 (t, J=6.1 Hz, 1H), 9.07 (s, 1H), 8.54 (s, 1H), 8.20 (s, 1H), 7.15-7.05 (m, 2H), 4.57 (d, J=6.1 Hz, 2H), 4.47 (q, J=7.1 Hz, 2H), 2.78 (s, 1H), 1.42 (t, J=7.0 Hz, 3H), 1.03-0.94 (m, 4H).

Example 59: Synthesis of N-[(4-cyclopropanesulfo-namidopyridin-2-yl)methyl]-2-(6-methoxypyrazin-2-yl)-1,3-thiazole-5-carboxamide (I-54)

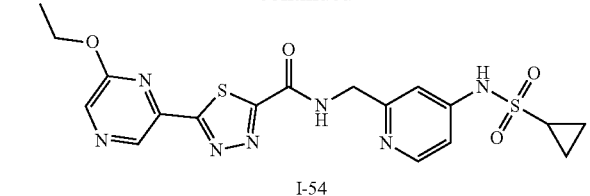

I-54

Synthesis of 59.1. To a stirred mixture of methanol (450 mg, 14 mmol, 1.05 eq) in tetrahydrofuran (60 mL) was added sodium hydride (390 mg, 60%, 16.2 mmol, 1.21 eq) in portions at 0° C. The reaction was carried out for 0.5 h and then 2-chloro-6-chloro-pyrazine (2 g, 13.4 mmol, 1. eq) was added at room temperature. The mixture was quenched with water and extracted with ethyl acetate. The combined organic layer was washed with brine, dried over sodium sulfate and concentrated under reduced pressure to afford 2-chloro-6-methoxy-pyrazine (59.1) as a yellow solid. (1.4 g, 72%), MS (ES): m/z 146 [M+H]$^+$.

Synthesis of 59.2. To a stirred mixture of 59.1 (1 g, 6.92 mmol, 1 eq) and bis(pinacolato)diboron (2.11 g, 8.31 mmol, 1.2 eq) in 1,4-dioxane (20 mL) were added potassium acetate (1.7 g, 17.3 mmol, 2.5 eq), Pd(dppf)Cl$_2$ (0.08 g, 0.36 mmol, 0.05 eq) and PCy$_3$ (190 mg, 0.68 mmol, 0.1 eq) at room temperature under nitrogen atmosphere. The resulting mixture was stirred for 2.5 h at 110° C. under nitrogen atmosphere. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 50% ethyl acetate in petroleum ether to obtain 6-methoxypyrazin-2-ylboronic acid (59.2, 620 mg, 58%) as a white solid. MS (ES): m/z 155 [M+H]$^+$.

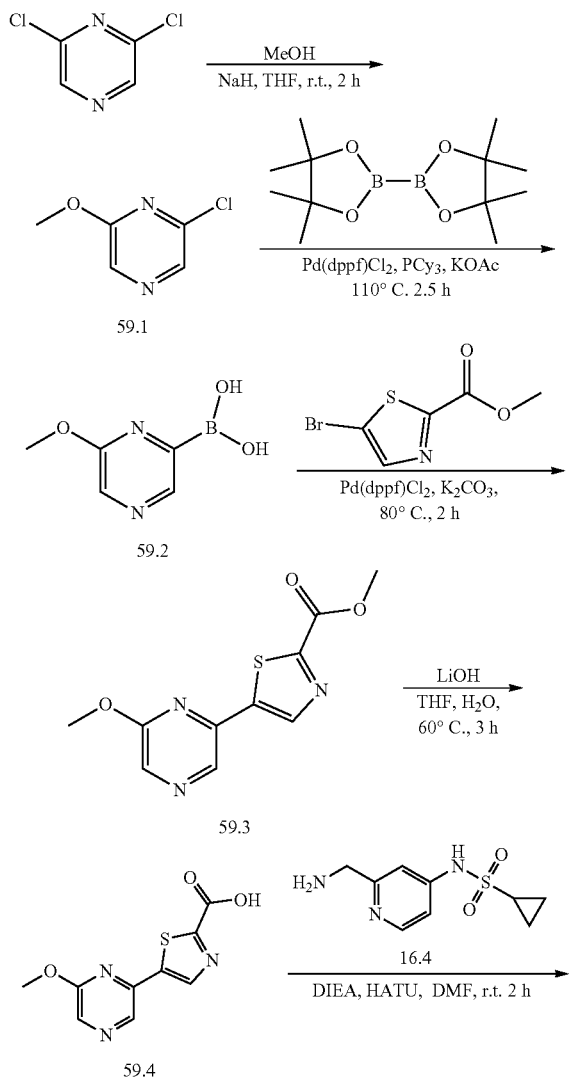

Synthesis of 59.3. To a stirred mixture of 59.2 (400 mg, 2.6 mmol, 1 eq) and methyl 2-bromo-1,3-thiazole-5-carboxylate (288.5 mg, 2.6 mmol, 1 eq) in 1,4-dioxane (16 mL) and water (4 mL) were added potassium carbonate (1.07 g, 7.8 mmol, 3 eq) and Pd(dppf)Cl$_2$ (190.1 mg, 0.26 mmol, 0.1 eq) at room temperature under nitrogen atmosphere. The resulting mixture was concentrated under reduced pressure. The resulting mixture was stirred for 2 h at 80° C. under nitrogen atmosphere. The mixture was cooled to r.t, diluted with water and extracted with ethyl acetate. The combined organic layer was washed with brine, dried over sodium sulfate and concentrated under reduced pressure. The residue was purified by reverse phase flash with the following conditions: Column, C18 Column; Mobile Phase, water (10 mmol/L NH$_4$HCO$_3$) and ACN (10% ACN up to 35% in 7 min); UV detection at 254/220 nm. The product-containing fractions were combined and concentrated under reduced pressure to obtain methyl 2-(6-methoxypyrazin-2-yl)-1,3-thiazole-5-carboxylate (59.3) as a yellow solid. (260 mg, 40%). MS (ES): m/z 252 [M+H]$^+$.

Synthesis of 59.4. To a stirred mixture of methyl 59.3 (30 mg, 0.12 mmol, 1 eq) in tetrahydrofuran (4 mL) and water (1 mL) was added lithium hydroxide (11.44 mg, 0.48 mmol, 4 eq). The resulting solution was stirred for 2 h at 60° C. The mixture was concentrated under vacuum. The residue was diluted with water. The pH value of the solution was adjusted to 3 with 1N hydrochloric acid. The solids were collected by filtration to obtain 2-(6-methoxypyrazin-2-yl)-1,3-thiazole-5-carboxylic acid (59.4) as a yellow solid. (25 mg, 88%), MS (ES): m/z 238 [M+H]$^+$.

Synthesis of I-54. To a stirred mixture of 59.4 (50 mg, 0.21 mmol, 1 eq) and N-[2-(aminomethyl)pyridin-4-yl]cyclopropanesulfonamide (16.4, 47.9 mg, 0.21 mmol, 1 eq) in dimethyl formamide (5 mL) was added DIEA (81.7 mg, 0.63 mmol, 3 eq) and HATH (80.1 mg, 0.21 mmol, 1 eq). The resulting solution was stirred for 2 h at room temperature. The residue was purified by reverse flash with the following conditions: Column, C18 Column; Mobile Phase, water (0.1% NH$_4$HCO$_3$) and ACN (11% ACN up to 20% in 10 min); UV detection at 254/220 nm. The product-containing fractions were combined and concentrated under reduced pressure. The residue was purified by Prep-HPLC with the following conditions: Column, XBridge Shield RP18 OBD Column, 5 um, 19*150 mm; Mobile Phase, water (0.1% NH$_4$HCO$_3$) and ACN (10% ACN up to 20% in 7 min); UV detection at 254/220 nm to afford the title compound as a white solid. (13 mg, 13%), MS (ES): m/z 447 [M+H]$^+$; $^1$H NMR (300 MHz, d$_6$-DMSO) δ 10.55 (s, 1H), 9.51 (t, J=6.1 Hz, 1H), 8.94 (s, 1H), 8.80 (s, 1H), 8.32-8.10 (m, 2H), 7.04 (s, 2H), 4.51 (d, J=6.1 Hz, 2H), 3.99 (s, 3H), 2.73 (s, 1H), 1.02-0.89 (m, 4H).

Example 60: Synthesis of 5-(6-ethoxypyrazin-2-yl)-N-[[3-(trifluoromethanesulfonamido) phenyl]methyl] pyridine-2-carboxamide (I-53)

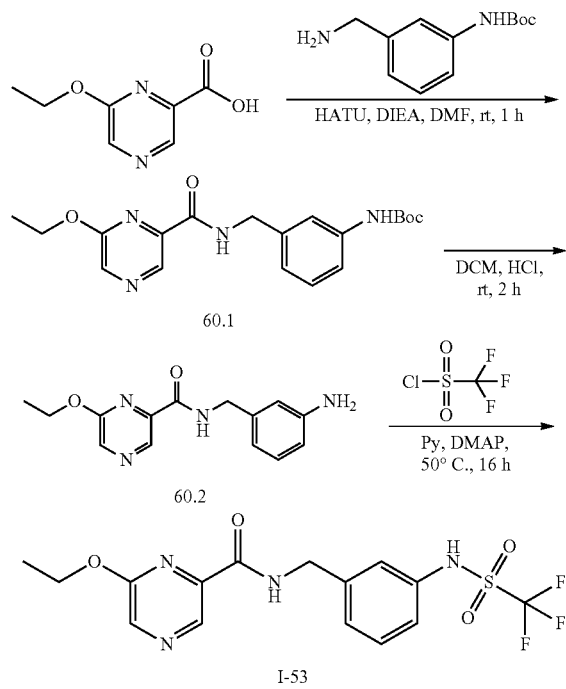

Synthesis of 60.1. To a stirred solution/mixture of tert-butyl N-[3-(aminomethyl) phenyl] carbamate (223 mg, 1 mmol, 1 eq) and 5-(6-ethoxypyrazin-2-yl) pyridine-2-carboxylic acid (246 mg, 1 mmol, 1 eq) in dimethyl formamide (3 mL) and N, N-diisopropylethylamine (0.5 mL, 2.87 mmol, 2.9 eq) were added 2-(-7-Azabenzotriazol-1-yl)-N, N, N', N'-tetramethyluronium hexafluoro phosphate (419.6 mg, 1.1 mmol, 1.1 eq) in portions at room temperature for 1 h. The residue was purified by reverse flash chromatography with the following conditions: column, C18 silica gel; mobile phase, methyl alcohol in water, 10% to 50% gradient in 10 min; UV detection at 254/220 nm. The resulting mixture was concentrated under reduced pressure. This resulted in tert-butyl N-[3-([[5-(6-ethoxypyrazin-2-yl)pyridin-2-yl]formamido]methyl)phenyl] carbamate (60.1, 176 mg, 87%) as a white solid, MS (ES): m/z 450 [M+H]$^+$.

Synthesis of 60.2. A solution of 60.1 (395 mg, 0.88 mmol, 1 eq) in methylene dichloride (9 mL) and 4 M HCL-dioxane (3 mL) was stirred for 2 h at room temperature. The resulting mixture was concentrated under reduced pressure. This resulted in N-[(3-aminophenyl) methyl]-5-(6-ethoxypyrazin-2-yl) pyridine-2-carboxamide (60.2, 307 mg, 99%) as a white solid, MS (ES): m/z 350 [M+H]$^+$.

Synthesis of I-53. To a stirred mixture of 60.2 (307 mg, 0.88 mmol, 1 eq) in Pyridine (10 mL) was added 4-dimethylaminopyridine (107.3 mg, 0.88 mmol, 1 eq) and trifluoromethanesulfonyl chloride (0.27 mL) dropwise at 50° C. for 16 h. The resulting mixture was cooled to room temperature and concentrated under reduced pressure. The residue was purified by reverse flash chromatography with the following conditions: Column, C18 silica gel; mobile phase, methyl alcohol in water, 10% to 50% gradient in 10 min; detector, UV 254 nm. The resulting mixture was concentrated under reduced pressure. The crude product (90 mg) was purified by Prep-HPLC with the following conditions (Column: SunFire Prep C18 OBD Column, 19×150 mm 5 um 10 nm; Mobile Phase A: Water (0.1% FA), Mobile Phase B: ACN; Flow rate:60 mL/min; Gradient: 40% B to 70% B in 8 min; 254/210 nm) to afford the title compound (25.6 mg, 6%) as a white solid, MS (ES): m/z 482 [M+H]$^+$; $^1$H NMR (300 MHz, DMSO-d6) δ 11.83 (s, 1H), 9.49 (t, J=6.5 Hz, 1H), 9.36 (d, J=2.2 Hz, 1H), 8.99 (s, 1H), 8.73-8.62 (m, 1H), 8.36 (s, 1H), 8.18 (d, J=8.2 Hz, 1H), 7.35 (t, J=7.9 Hz, 1H), 7.28-7.16 (m, 2H), 7.16-7.05 (m, 1H), 4.55-4.34 (m, 4H), 1.41 (t, J=7.0 Hz, 3H).

Example 61: Synthesis of 2-methyl-2-(2-(1-methylethylsulfonamido)thiazol-4-yl)-N-(5-(6-(trifluoromethyl)pyrazin-2-yl)pyridin-2-yl)propanamide (I-57)

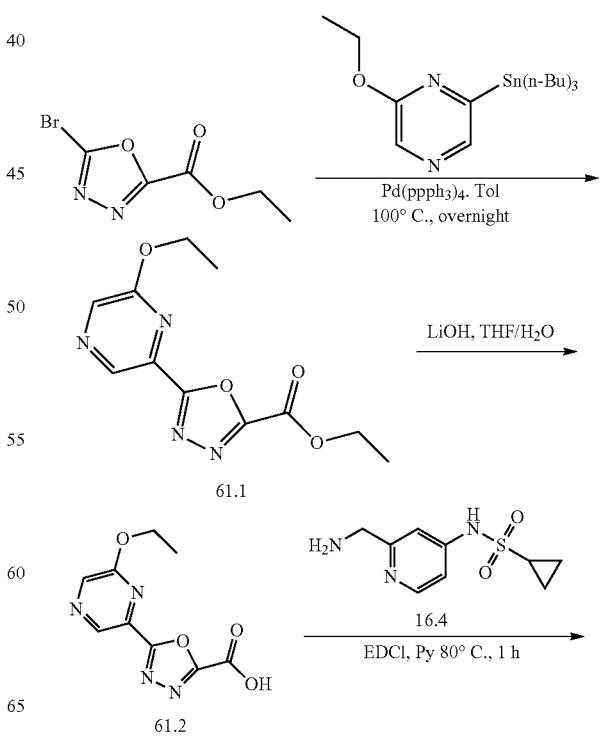

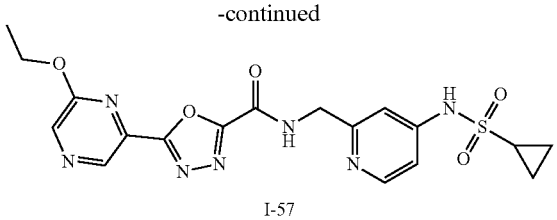

I-57

Synthesis of 61.1. To a stirred mixture of ethyl 5-bromo-1,3,4-oxadiazole-2-carboxylate (330 mg, 1.49 mmol, 1 eq) and 2-ethoxy-6-(tributylstannyl)pyrazine (740.3 mg, 1.79 mmol, 1.2 eq) in toluene (8 mL) was added Pd(PPh$_3$)$_4$ (172.5 mg, 0.15 mmol, 0.1 eq). The resulting mixture was stirred for 16 h at 100° C. under nitrogen atmosphere. The resulting mixture was concentrated under reduced pressure and purified by silica gel column chromatography and compound was eluted in 20% ethyl acetate in petroleum ether to obtain ethyl 5-(6-ethoxypyrazin-2-yl)-1,3,4-oxadiazole-2-carboxylate (61.1) as a yellow solid. (166 mg, 45.6%), MS (ES): m/z 241 [M+H]$^+$.

Synthesis of 61.2. To a solution of 61.1 (125 mg, 0.47 mmol, 1 eq) in tetrahydrofuran (5 mL) and water (1 mL) was added lithium hydroxide (99.3 mg, 2.36 mmol, 5 eq) at room temperature. The resulting solution was stirred for 4 h at room temperature. The mixture was concentrated under vacuum. The residue was diluted with water. The pH value of the solution was adjusted to 3 with 1N hydrochloric acid. The solids were collected by filtration to obtain 5-(6-ethoxypyrazin-2-yl)-1,3,4-oxadiazole-2-carboxylic acid (62.2) as a white solid. (25 mg, 22%), MS (ES): m/z 237 [M+H]$^+$.

Synthesis of I-57. To a stirred mixture of 62.2 (160 mg, 0.68 mmol, 1 eq) and N-[2-(aminomethyl)pyridin-4-yl]cyclopropanesulfonamide (16.4, 153.9 mg, 0.67 mmol, 1 eq) in N,N-dimethylformamide (8 mL) was added HATU (309.1 mg, 0.81 mmol, 1.2 eq) and DIEA (262.7 mg, 2.03 mmol, 3 eq) at room temperature. The resulting solution was stirred for 2 h at room temperature. The mixture was diluted with water and extracted with ethyl acetate. The combined organic layer was washed with brine, dried over sodium sulfate and concentrated under reduced pressure. The residue was purified by Prep-HPLC with the following conditions: Column: Xselect CSH OBD Column 30*150 mm 5 um; Mobile Phase: Water (0.05% FA), Mobile Phase CAN (9% to 33% in 7 min, UV detection at 210/254 nm), The product-containing fractions were combined and evaporated partially in vacuum and lyophilized overnight to afford the title compound as a white solid. (23 mg, 19%), $^1$H NMR (300 MHz, de-DMSO) δ 10.55 (s, 1H), 10.01 (t, J=6.0 Hz, 1H), 9.00 (s, 1H), 8.59 (s, 1H), 8.31 (s, 1H), 7.12-7.02 (m, 2H), 4.60-4.52 (m, 4H), 2.79-2.68 (m, 1H), 1.42 (t, J=7.0 Hz, 3H), 1.01-0.89 (m, 4H).

Example 62: Synthesis of N-[(5-cyclopropane sulfonamidopyridazin-3-yl) methyl]-4-(6-ethoxy-pyrazin-2-yl) benzamide (I-52)

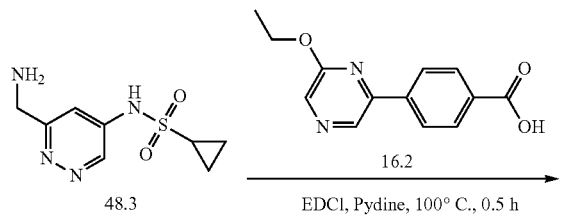

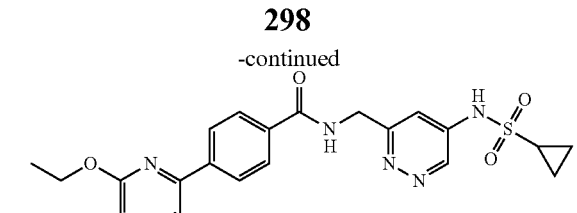

I-52

Synthesis of I-52. To a stirred mixture of N-[6-(aminomethyl) pyridazin-4-yl]cyclopropanesulfonamide (48.3, 30 mg, 0.13 mmol, 1 eq) and 4-(6-ethoxypyrazin-2-yl) benzoic acid (16.2, 32.1 mg, 0.13 mmol, 1 eq) in pyridine (2 ml) was added 1-ethyl-3-(3-dimethylaminopropyl)carbodiimide hydrochloride (37.7 mg, 0.19 mmol, 1.5 eq) under nitrogen. The resulting mixture was stirred for 0.5 h at 100° C. The resulting mixture was cooled to room temperature and concentrated under reduced pressure. The residue was purified by Prep-HPLC with the following conditions: Column: SunFire Prep C18 OBD Column, 19×150 mm 5 um 10 nm; Mobile Phase A: water (0.1% FA) and ACN (22% ACN to 42% ACN in 10 min); UV detection at 254/220 nm. This resulted in the title compound as a white solid (9.7 mg, 16.1%), MS (ES): m/z 455 [M+H]$^+$; $^1$H NMR (400 MHz, DMSO-d$_6$) δ 9.33 (t, J=5.6 Hz, 1H), 8.91 (s, 1H), 8.35-8.25 (m, 4H), 8.07-8.01 (m, 2H), 7.17 (d, J=2.6 Hz, 1H), 4.57 (d, J=5.7 Hz, 2H), 4.51 (q, J=7.0 Hz, 2H), 2.56-2.50 (m, 1H), 1.42 (t, J=7.0 Hz, 3H), 0.92-0.78 (m, 4H).

Example 63: Synthesis of N-[(4-cyclopropanesulfonamidopyridin-2-yl)methyl]-6-(6-ethoxypyrazin-2-yl)-2-oxo-1H-pyridine-3-carboxamide (I-49)

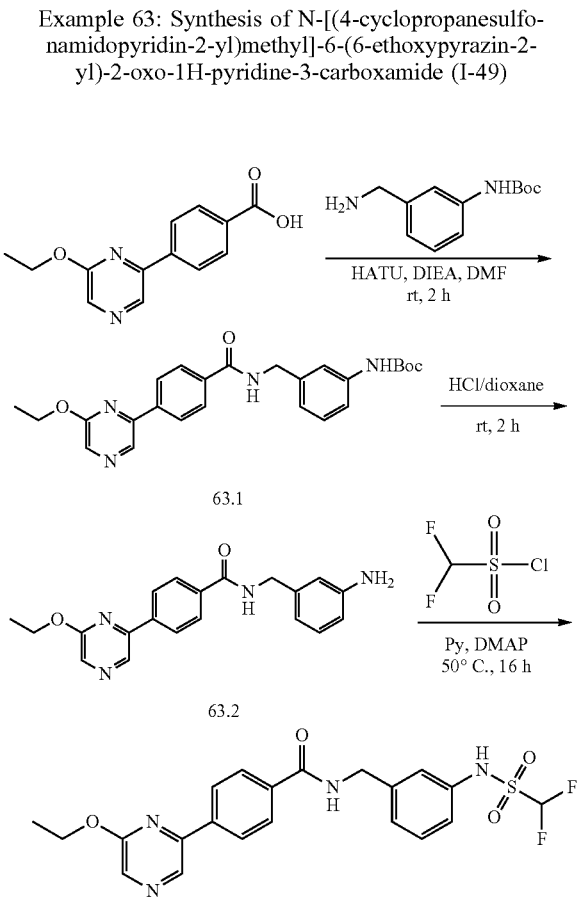

I-49

Synthesis of 63.1. To a stirred mixture of 4-(6-ethoxypyrazin-2-yl)benzoic acid (16.2, 244 mg, 1 mmol, 1 eq), tert-butyl N-[3-(aminomethyl)phenyl]carbamate (222.1 mg, 1 mmol, 1 eq) and 2-(-7-Azabenzotriazol-1-yl)-N,N,N',N"-tetramethyluronium hexafluorophosphate (417.8 mg, 1.1 mmol, 1.1 eqv) in N,N-dimethylformamide (3 mL) was added N, N-diisopropylethylamine (387.3 mg, 2.99 mmol, 3 eq) dropwise at room temperature under nitrogen atmosphere. After completion, the reaction mixture was diluted with EtOAc, washed with brine and concentrated in vacuo. The residue was purified by reverse phase flash with the following conditions: Column, C18 Column; Mobile Phase, water (0.1% NH$_4$HCO$_3$) and ACN (10% ACN up to 70% in 10 min); UV detection at 254/220 nm. The product-containing fractions were combined and concentrated under reduced pressure to obtain tert-butyl N-[3-([[4-(6-ethoxypyrazin-2-yl)phenyl]formamido]methyl)phenyl]carbamate (63.1) as a yellow solid. (313 mg, 69%), MS (ES): m/z 448[M+H]$^+$.

Synthesis of 63.2. A mixture of 63.1 (313 mg, 0.7 mmol, 1 eq) in HCl in 1,4-dioxane (4 M, 10 mL) was stirred for 2 h at room temperature. The resulting mixture was concentrated under vacuum and neutralized to pH 9 with saturated sodium bicarbonate. The mixture was diluted with water and extracted with ethyl acetate. The combined organic layer was washed with brine, dried over sodium sulfate and concentrated under reduced pressure to obtain N-[(3-aminophenyl)methyl]-4-(6-ethoxypyrazin-2-yl)benzamide (63.2) as a yellow solid. (200 mg, 82%), MS (ES): m/z 348 [M+H]$^+$.

Synthesis of I-49. To a stirred mixture of 63.2 (69.6 mg, 0.2 mmol, 1 eq) and 4-dimethylaminopyridine (2.4 mg, 0.02 mmol, 0.1 equiv) in pyridine (2 mL) was added difluoromethanesulfonyl chloride (89.9 mg, 0.59 mmol, 3 equiv). The resulting mixture was stirred for 16 h at 50° C. The mixture was cooled to room temperature, diluted with water and extracted with ethyl acetate. The combined organic layer was washed with brine, dried over sodium sulfate and concentrated under reduced pressure. The crude product was purified by Prep-HPLC with the following conditions: Column, SunFire Prep C18 OBD Column, 19×150 mm 5 um 10 nm; Mobile Phase: Water (0.1% FA) and ACN (38% to 58% in 10 min, UV detection at 254/210 nm; The product-containing fractions were combined and evaporated partially in vacuum and lyophilized overnight to afford the title compound as a white solid. (17 mg, 18.5%), MS (ES): m/z 463 [M+H]$^+$; $^1$H NMR (400 MHz, d$_6$-DMSO) δ 10.94 (brs, 1H), 9.20 (t, J=6.0 Hz, 1H), 8.90 (s, 1H), 8.30 (s, 1H), 8.25 (d, J=9.6 Hz, 2H), 8.04 (d, J=8.4 Hz, 2H), 7.36-7.29 (m, 1H), 7.26-7.08 (m, 4H), 4.53-4.46 (m, 4H), 1.42 (t, J=7.0 Hz, 3H).

Example 64: Synthesis of N-((4-(cyclopropanesulfonamido)pyridin-2-yl)methyl)-5-(6-ethoxypyrazin-2-yl)oxazole-2-carboxamide (I-56)

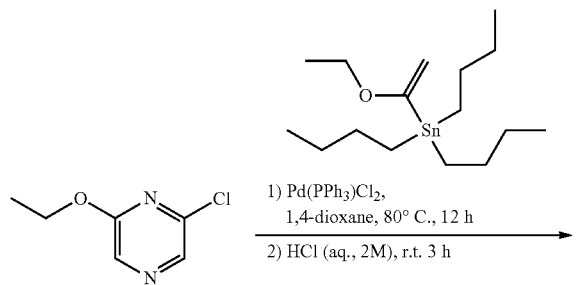

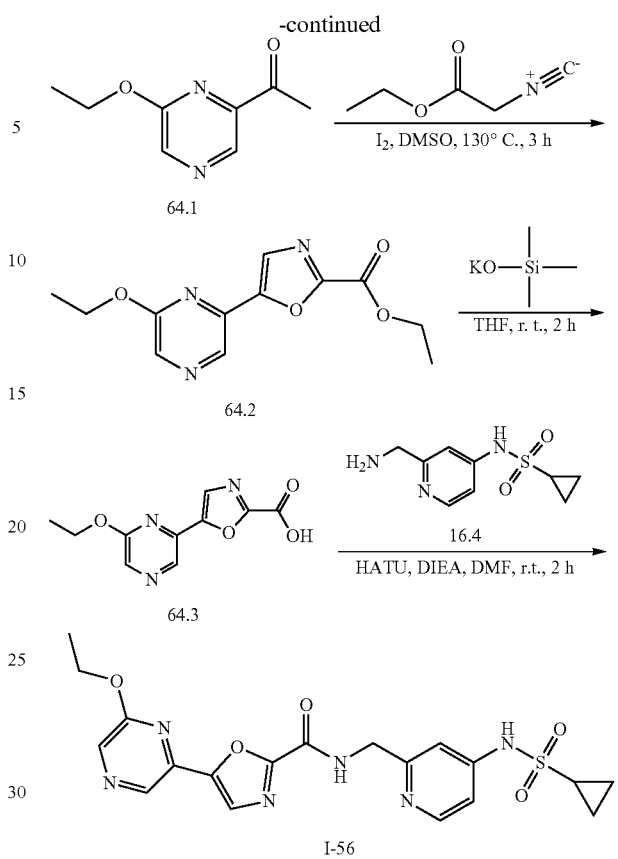

Synthesis of 64.1. To a solution of 2-chloro-6-ethoxypyrazine (1.8 g, 11.35 mmol, 1 eq) and tributyl(1-ethoxyethenyl)stannane (6.15 g, 17.03 mmol, 1.5 eq) in 1,4-dioxane (20 mL) was added Pd(PPh$_3$)$_2$C$_{1-2}$ (796.6 mg, 1.14 mmol, 0.1 eq) at room temperature under nitrogen atmosphere. After the reaction was stirred for 12 h at 80° C. under nitrogen atmosphere and cooled down to room temperature, to the above mixture was added 2N hydrochloric acid (10 mL) and the resulting mixture was stirred for another 3 h at room temperature. The mixture was diluted with water and extracted with ethyl acetate. The combined organic layer was washed with brine, dried over sodium sulfate and concentrated under reduced pressure. The residue was purified by silica gel column chromatography and compound was eluted in 20% ethyl acetate in petroleum ether to obtain 1-(6-ethoxypyrazin-2-yl)ethenone (64.1) as a brown solid. (1 g, 53%), MS (ES): m/z 167 [M+H]$^+$.

Synthesis of 64.2. To a stirred solution of 64.1 (835 mg, 5.02 mmol, 1 eq) and ethyl 2-isocyanoacetate (1.14 g, 10.04 mmol, 2 eq) in dimethyl sulfoxide (20 mL) was added iodine (2.04 g, 8.03 mmol, 1.6 eq) in portions at room temperature under nitrogen atmosphere. The resulting mixture was stirred for 3 h at 120° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by reverse flash chromatography with the following conditions: Column, C18 silica gel; Mobile phase, Water (0.1% TFA) and ACN (10% ACN up to 90% in 20 min); UV detection at 254/220 nm to afford ethyl 5-(6-ethoxypyrazin-2-yl)-1,3-oxazole-2-carboxylate (64.2) as a brown solid. (45 mg, 3%), MS (ES): m/z 264 [M+H]$^+$.

Synthesis of 64.3. To a stirred solution of 64.2 (45 mg, 0.17 mmol, 1 eq) in tetrahydrofuran (8 mL) was added potassium trimethylsilanolate (43.9 mg, 0.34 mmol, 2 eq) in portions at 0° C. The resulting mixture was stirred for 1 h at 0° C. The resulting mixture was concentrated under vacuum to afford 5-(6-ethoxypyrazin-2-yl)-1,3-oxazole-2-carboxylic acid (64.3) as a brown solid. (40 mg, 99%), MS (ES): m/z 236 [M+H]⁺.

Synthesis of I-56. To a stirred mixture of potassium 64.3 (40 mg, 0.17 mmol, 1 eq) and N-[2-(aminomethyl)pyridin-4-yl]cyclopropanesulfonamide (16.4, 44.9 mg, 0.2 mmol, 1.2 eq) in N,N-dimethylformamide (4 mL) were added N, N-diisopropylethylamine (63.8 mg, 0.49 mmol, 3 eq) and 2-(-7-azabenzotriazol-1-yl)-N,N,N',N''-tetramethyluronium hexafluorophosphate (93.9 mg, 0.25 mmol, 1.5 eq) in portions at 0° C. The resulting mixture was stirred for additional 2 h at room temperature. After completion, the reaction was quenched with water, extracted with EtOAc, the organic phase was concentrated in vacuo. The crude product was purified by reverse phase flash and Prep-HPLC with the following conditions: Column, SunFire Prep C18 OBD Column, 19×150 mm 5 um 10 nm; Mobile phase, water (0.1% FA) and ACN (5% ACN up to 25% in 10 min); UV detection at 254/220 nm to afford the title compound as a white solid. (17.4 mg, 23%), MS (ES): m/z 445 [M+H]⁺; ¹H NMR (300 MHz, CD₃OD) δ 8.69-8.61 (m, 1H), 8.30-8.16 (m, 2H), 7.94 (s, 1H), 7.26 (d, J=2.2 Hz, 1H), 7.17 (dd, J=6.0, 2.3 Hz, 1H), 4.68 (s, 2H), 4.56-4.45 (m, 2H), 2.81-2.66 (m, 1H), 1.45 (t, J=6.6, 7.2 Hz, 3H), 1.21-0.98 (m, 4H).

Example 65: Synthesis of N-((5-(cyclopropanesulfonamido)-1,2,4-thiadiazol-3-yl)methyl)-4-(6-ethoxypyrazin-2-yl)benzamide (I-48)

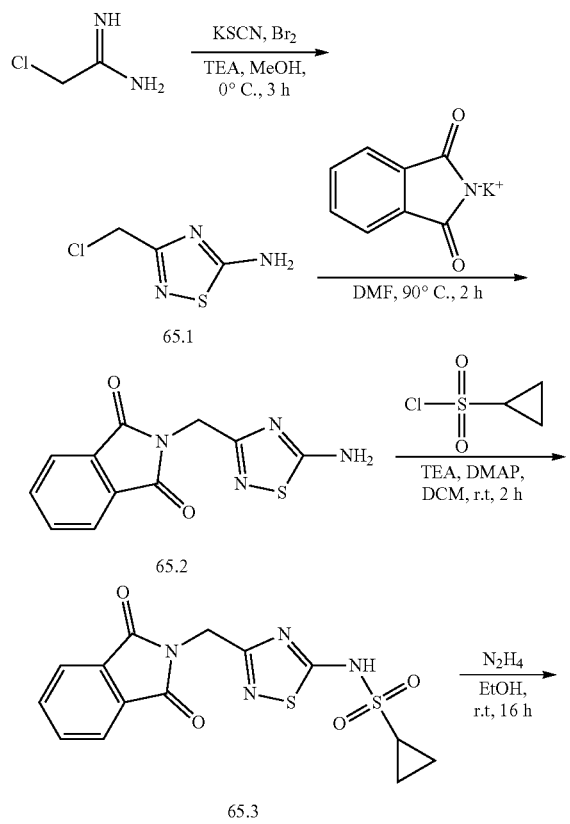

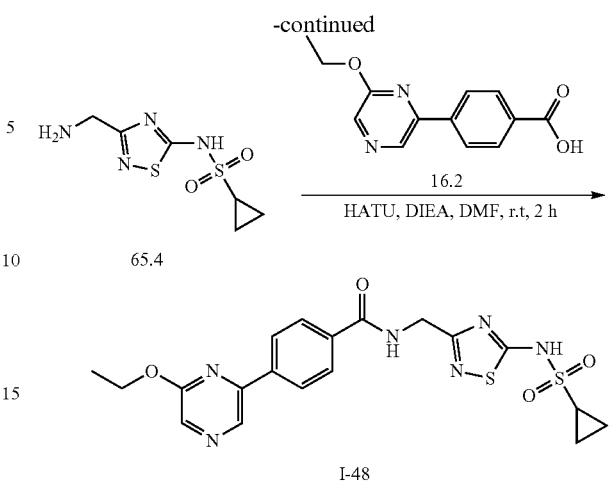

Synthesis of 65.1. To a solution of 2-chloroethanimidamide hydrochloride (1.29 g, 9.98 mmol, 1 eq) in anhydrous methanol (40 mL) were added bromine (1.44 g, 8.98 mmol, 0.9 eq) and trimethyl amine (2.53 g, 24.95 mmol, 2.5 eq) dropwise over 5 min at 0° C. After 1 h potassium rhodanide (1.02 g, 10.48 mmol, 1.1 eq) in methanol (15 mL) was added dropwise at 0° C. The resulting mixture was stirred at 0° C. for 3 h. The mixture was warmed to room temperature, diluted with water and extracted with ethyl acetate. The combined organic layer was washed with brine, dried over sodium sulfate and concentrated under reduced pressure. The residue was purified by silica gel column chromatography and compound was eluted in 25% ethyl acetate in petroleum ether to obtain 3-(chloromethyl)-1,2,4-thiadiazol-5-amine (65.1) as an off-white solid. (700 mg, 47%), MS (ES): m/z 150 [M+H]⁺.

Synthesis of 65.2. To a solution of 65.1 (700 mg, 4.68 mmol, 1 eq) and 1,3-dioxo-2-potassiylium-2H-2lambda4-isoindol-2-ide (1.73 g, 9.35 mmol, 2 eq) in A, N-dimethylformamide (30 mL) was stirred for 2 h at 90° C. The mixture was warmed to room temperature, diluted with water and extracted with ethyl acetate. The combined organic layer was washed with brine, dried over sodium sulfate and concentrated under reduced pressure. The residue was purified by reverse phase flash with the following conditions: Column, C18 Column; Mobile Phase, water (0.1% NH4HCO3) and ACN (25% ACN up to 50% in 10 min); UV detection at 254/220 nm. The product-containing fractions were combined and concentrated under reduced pressure to afford 2-[(5-amino-1,2,4-thiadiazol-3-yl) methyl]isoindole-1,3-dione (65.2) as a white solid. (500 mg, 41%), MS (ES): m/z 260 [M+H]⁺.

Synthesis of 65.3. To a solution of 65.2 (500 mg, 1.92 mmol, 1 eq) and cyclopropanesulfonyl chloride (807.7 mg, 5.76 mmol, 3 eq) in dichloromethane (15 mL) was added trimethylamine (971.9 mg, 9.6 mmol, 5 eq) and 4-dimethylaminopyridine (23.4 mg, 0.19 mmol, 0.1 eq). The resulting solution was stirred for 2 h at room temperature. The resulting mixture was concentrated under reduced pressure. The residue was purified by reverse phase flash with the following conditions: Column, C18 Column; Mobile Phase, water (0.1% NH₄HCO₃) and ACN (20% ACN up to 50% in 10 min); UV detection at 254/220 nm. The product-containing fractions were combined and concentrated under reduced pressure to afford N-[3-[(1,3-dioxoisoindol-2-yl) methyl]-1,2,4-thiadiazol-5-yl]cyclopropanesulfonamide (65.3) as a white solid. (200 mg, 28%), MS (ES): m/z 365 [M+H]⁺.

Synthesis of 65.4. To a solution of 65.3 (200 mg, 0.55 mmol, 1 eq) in ethanol (9 mL) was added hydrazine hydrate (274.4 mg, 5.49 mmol, 10 eq). The resulting solution was stirred for 16 h at room temperature. The residue was purified by reverse phase flash with the following conditions: Column, C18 Column; Mobile Phase, water (0.1% NH$_4$HCO$_3$) and ACN (35% ACN up to 50% in 10 min); UV detection at 254/220 nm. The product-containing fractions were combined and concentrated under reduced pressure to afford N-[3-(aminomethyl)-1,2,4-thiadiazol-5-yl]cyclopropanesulfonamide (65.4) as a white solid. (100 mg, 78%), MS (ES): m/z 234 [M+H]$^+$.

Synthesis of I-48. To a solution of 65.4 (60 mg, 0.25 mmol, 1.0 eq) and 4-(6-ethoxypyrazin-2-yl)benzoic acid (16.2, 62.5 mg, 0.26 mmol, 1.0 eq) in N,N-dimethylformamide (2 mL) were added 2-(-7-azabenzotriazol-1-yl)-N,N,N',N'-tetramethyluronium hexafluorophosphate (116.8 mg, 0.3 mmol, 1.2 eq) and N,N-diisopropylethylamine (99.2 mg, 0.76 mmol, 3 eq) under nitrogen. The resulting solution was stirred for 2 h at room temperature. After completion, the mixture was diluted with water, extracted with EtOAc. The organic phase was concentrated in vacuo. The residue was purified by Prep-HPLC with the following conditions: Column, YMC-Triart Diol Hilic, 20*150 mm 5 um; Mobile Phase: water (0.1% NH$_4$HCO$_3$) and ACN (10% to 40% in 7 min), UV detection at 254/210 nm. The product-containing fractions were combined and evaporated partially in vacuum and lyophilized overnight to afford the title compound as a white solid. (21.5 mg, 18%), MS (ES): m/z 461 [M+H]$^+$; $^1$H NMR (300 MHz, J6-DMSO) δ 8.69 (s, 1H), 8.15-8.13 (m, 3H), 7.93 (d, J=8.3 Hz, 2H), 4.45-4.39 (m, 4H), 2.58-2.50 (m, 1H), 1.34 (t, J=7.0 Hz, 3H), 0.83 (m, 4H).

Example 66: Synthesis of N-[(4-cyclopropanesulfonamidopyridin-2-yl) methyl]-6-methyl-5-[(3R)-3-(trifluoromethyl) piperidin-1-yl] pyrazine-2-carboxamide (I-55)

Synthesis of 66.1. To a stirred mixture of 5-chloro-6-methylpyrazine-2-carboxylic acid (200 mg, 1.15 mmol, 1 eq) and 16.4 (263.4 mg, 1.15 mmol, 1 eq) in N,N-dimethylformamide (5 mL) were added N,N-diisopropylethylamine (449.4 mg, 3.47 mmol, 3 eq) and 2-(-7-azabenzotriazol-1-yl)-N,N,N',N'-tetramethyluronium hexafluorophosphate (528.8 mg, 1.39 mmol, 1.2 eq) at 0° C. under nitrogen. The resulting mixture was stirred for 2 h at room temperature. The residue was purified by reverse flash chromatography with the following conditions: column, C18 silica gel; mobile phase, ACN in water, 10% to 50% gradient in 10 min; UV detection at 254 nm. This resulted in 5-chloro-N-[(4-cyclopropanesulfonamidopyridin-2-yl) methyl]-6-methyl pyrazine-2-carboxamide (66.1) as a light yellow solid. (141 mg, 32%), MS (ES): m/z 382 [M+H]$^+$.

Synthesis of I-55. To a stirred mixture of 66.1 (28 mg, 0.07 mmol, 1 eq) and 3-(trifluoromethyl)piperidine hydrochloride (41.6 mg, 0.22 mmol, 3 eq) in dimethyl sulfoxide (1 mL) was added N, N-diisopropylethylamine (47.4 mg, 0.37 mmol, 5 eq) at room temperature. The resulting mixture was stirred for 12 h at 100° C. under nitrogen atmosphere. The resulting mixture was purified by Prep-HPLC with the following conditions (Column: SunFire Prep C18 OBD Column, 19×150 mm 5 um 10 nm; Mobile Phase A: water (0.1% FA), Mobile Phase B: ACN; Flow rate:60 mL/min; Gradient: 20% B to 50% B in 7 min, 50% B to 100% B in 20 min, 100% B to 100% B in 5 min; UV detection at 254/210 nm. The product-containing fractions were collected and evaporated in vacuo and lyophilized overnight to afford the title compound (31.6 mg, 78.3%) as a white solid. MS (ES): m/z 499 [M+H]$^+$; $^1$H NMR (300 MHz, d$_6$-DMSO) δ 9.05 (t, J=6.0 Hz, 1H), 8.63 (s, 1H), 8.20 (s, 1H), 7.08-6.91 (m, 2H), 4.50 (d, J=6.0 Hz, 2H), 3.93 (d, J=12 Hz, 1H), 3.75 (d, J=12.6 Hz, 1H), 2.99-2.91 (m, 2H), 2.81-2.60 (m, 2H), 2.55 (s, 3H), 2.08-1.97 (m, 1H), 1.90-1.82 (m, 1H), 1.60-1.40 (m, 2H), 2.01-0.95 (m, 4H).

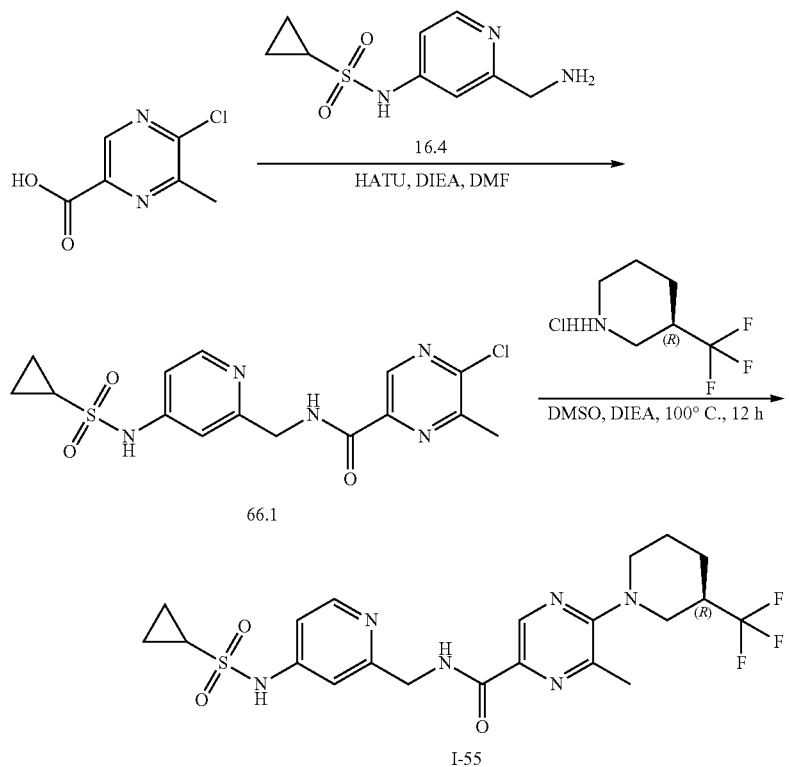

Example 67: Synthesis of N-[(4-cyclopropanesulfo-namidopyridin-2-yl)methyl]-5-(6-ethoxypyrazin-2-yl)-1,3-thiazole-2-carboxamide (I-50)

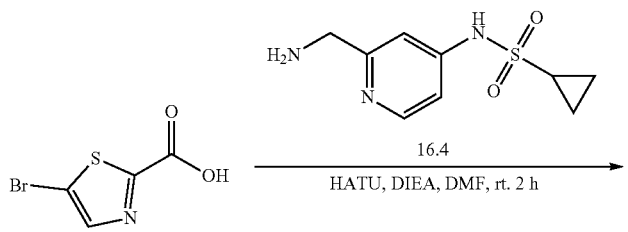

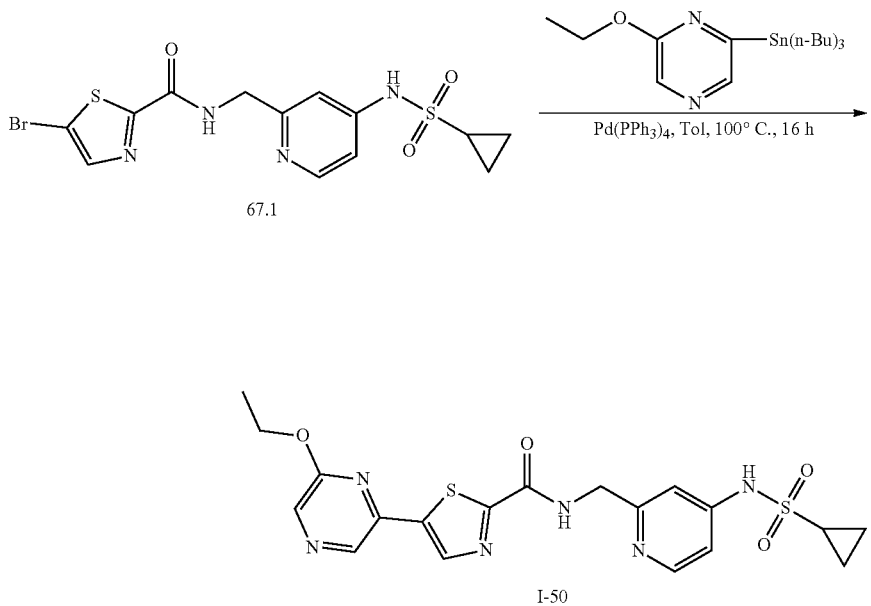

Synthesis of 67.1. To a stirred solution of 5-bromo-1,3-thiazole-2-carboxylic acid (100 mg, 0.48 mmol, 1 eq) and 16.4 (131.1 mg, 0.58 mmol, 1.2 eq) in V, V-dimethylformamide (5 mL) were added N,N-diisopropylethylamine (186.3 mg, 1.44 mmol, 3 eq) and 2-(-7-Azabenzotriazol-1-yl)-N,N,N',N'-tetramethyluronium hexafluorophosphate (201 mg, 0.52 mmol, 1.1 eq). The resulting solution was stirred for 2 h at room temperature. After the starting acid was consumed completely, the residue was purified by reverse phase flash with the following conditions: Column, C18 Column; Mobile Phase, water (0.1% $NH_4HCO_3$) and ACN (10% ACN up to 30% in 8 min); UV detection at 254/220 nm. The product-containing fractions were combined and concentrated under reduced pressure to obtain 5-bromo-N-[(4-cyclopropanesulfonamidopyridin-2-yl)methyl]-1,3-thiazole-2-carboxamide (67.1) as a yellow solid. (115 mg, 54%), MS (ES): m/z 417/419 [M+H]$^+$.

Synthesis of I-50. To a stirred solution of 67.1 (100 mg, 0.24 mmol, 1 eq) and 2-ethoxy-6-(tributylstannyl)pyrazine (148.5 mg, 0.36 mmol, 1.5 eq) in toluene (10 mL) was added Pd(PPh$_3$)$_4$ (27.6 mg, 0.02 mmol, 0.1 eq) at room temperature. The resulting mixture was degassed three times with nitrogen and stirred for 16 h at 100° C. The residue was purified by reverse phase flash with the following conditions: Column, C18 Column; Mobile Phase: water (0.1% FA) and ACN (18% ACN up to 48% in 8 min); UV detection at 254/220 nm. The product-containing fractions were combined and concentrated under reduced pressure. The crude product was purified by Prep-HPLC with the following conditions: Column, XBridge Prep OBD C18 Column, 19*150 mm, 5 um; Mobile Phase: water (0.1% FA) and ACN (20% ACN up to 50% in 7 min); UV detection at 254/220 nm. The product-containing fractions were combined and evaporated partially in vacuum and lyophilized overnight to afford the title compound as a white solid. (12.2 mg, 11%), MS (ES): m/z 461 [M+H]$^+$; $^1$H NMR (300 MHz, t/g-DMSO) δ 11.03 (brs, 1H), 9.50 (t, J=6.1 Hz, 1H), 8.92 (s, 1H), 8.81 (s, 1H), 8.28-8.14 (m, 2H), 7.01 (d, J=5.2 Hz, 2H), 4.50 (d, J=6.2 Hz, 2H), 4.41 (t, J=7.0 Hz, 2H), 2.72-2.71 (m, 1H), 1.38 (t, J=7.0 Hz, 3H), 0.96-0.91 (m, 4H).

Example 68: Synthesis of N-[(4-cyclopropanesulfo-namidopyridin-2-yl)methyl]-6-(6-ethoxypyrazin-2-yl)-2-oxo-1H-pyridine-3-carboxamide (I-59)

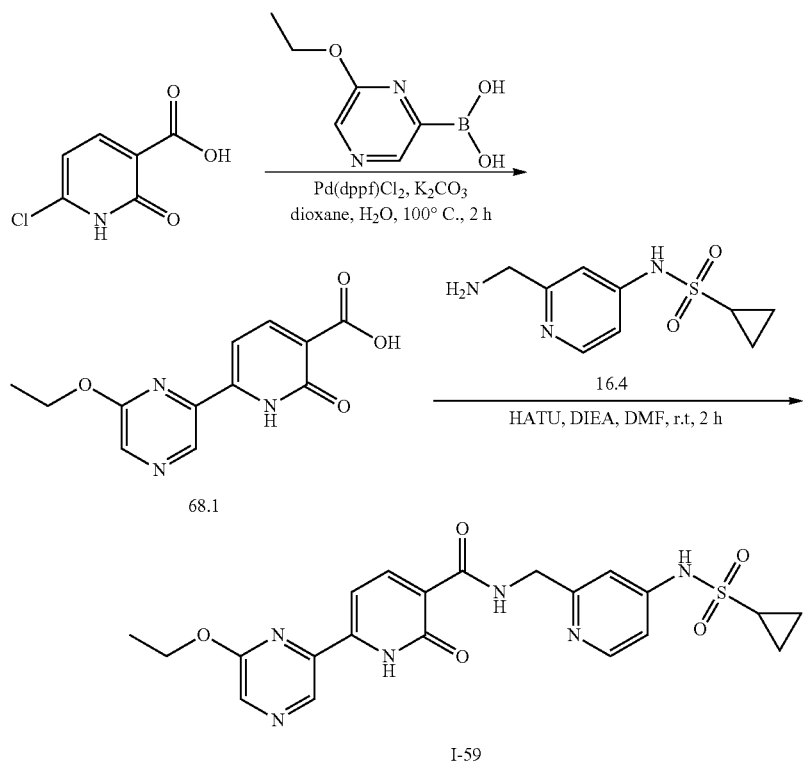

Synthesis of 68.1. To a stirred mixture of 6-chloro-2-oxo-1H-pyridine-3-carboxylic acid (200 mg, 1.15 mmol, 1 eq) and 6-ethoxypyrazin-2-ylboronic acid (251.6 mg, 1.5 mmol, 1.3 eq) in 1,4-dioxane (5 mL) and water (1 mL) were added cesium carbonate (1.13 g, 3.46 mmol, 3 eq) and Pd(dppf)Cl$_2$ (84.3 mg, 0.12 mmol, 0.1 eq). The resulting mixture was stirred for 2 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (0.1% FA) and ACN (20% ACN up to 60% in 20 min); UV detection at 254/220 nm. The product-containing fractions were combined and concentrated under reduced pressure to afford 6-(6-ethoxypyrazin-2-yl)-2-oxo-1H-pyridine-3-carboxylic acid (68.1) as a yellow solid. (91 mg, 27%), MS (ES): m/z 262 [M+H]$^+$.

Synthesis of I-59. To a stirred mixture of 68.1 (82 mg, 0.31 mmol, 1 eq) and 16.4 (71.3 mg, 0.31 mmol, 1 eq) in pyridine (3 mL) was added 1-ethyl-3-(3-dimethylaminopropyl) carbodiie hydrochlolide (238.7 mg, 0.63 mmol, 2 eq) at room temperature. The resulting solution was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column, SunFire Prep C18 OBD, 19×150 mm 5 um 10 nm; Mobile Phase: Water (0.1% FA) and ACN (10% to 40% in 7 min), UV detection at 254/210 nm. The product-containing fractions were combined and evaporated partially in vacuum and lyophilized overnight to afford the title compound as a yellow solid. (40 mg, 27%), MS (ES): m/z 471[M+H]$^+$; $^1$H NMR (400 MHz, d$_6$-DMSO) δ 10.28 (t, J=6.0 Hz, 1H), 8.96 (s, 1H), 8.47-8.45 (m, 1H), 8.42 (s, 1H), 8.24 (s, 1H), 7.34 (d, J=7.5 Hz, 1H), 7.03 (d, J=4.9 Hz, 2H), 4.63-4.53 (m, 4H), 2.75-2.68 (m, 1H), 1.40 (t, J=7.1 Hz, 3H), 0.98-0.94 (m, 4H).

Example 69: Synthesis of (R)—N-((4-(cyclopropanesulfonamido)pyridin-2-yl)methyl)-6-methyl-5-(2-propylazetidin-1-yl)pyrazine-2-carboxamide (I-60) and (S)—N-((4-(cyclopropanesulfonamido)pyridin-2-yl)methyl)-6-methyl-5-(2-propylazetidin-1-yl)pyrazine-2-carboxamide (I-58)

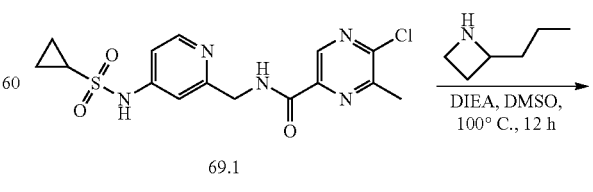

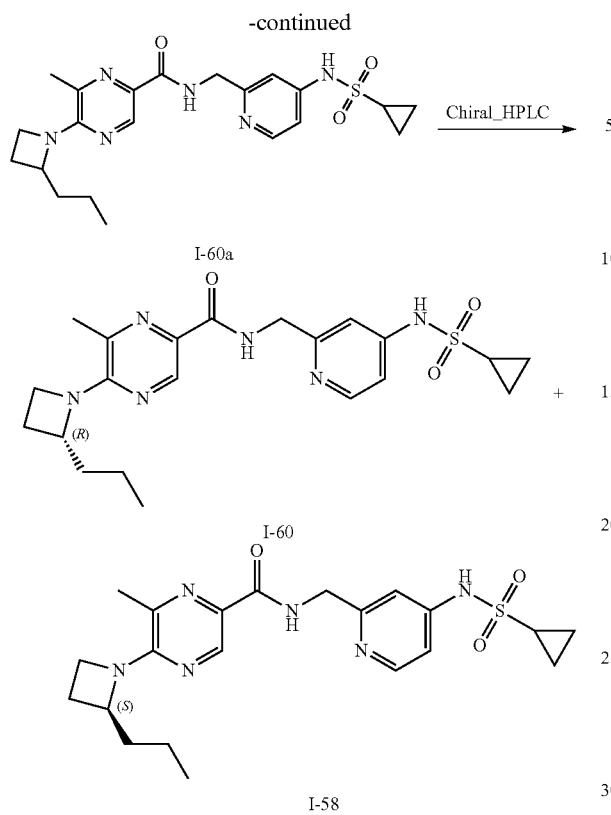

Synthesis of I-60a. To a solution of 5-chloro-N-[(4-cyclopropanesulfonamidopyridin-2-yl)methyl]-6-methylpyrazine-2-carboxamide (69.1, 54 mg, 0.14 mmol, 1 eq) in dimethylsulfoxide (2 mL) was added N,N-diisopropylethyl amine (54.8 mg, 0.42 mmol, 3 eq). The resulting solution was stirred for 12 h at 100° C. The mixture was cooled to room temperature, diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (10 mmol/L NH$_4$HCO$_3$) and ACN (10% ACN up to 46% in 20 min); UV detection at 254/220 nm. The product-containing fractions were combined and concentrated under reduced pressure to afford N-((4-(cyclopropanesulfonamido)pyridin-2-yl)methyl)-6-methyl-5-(2-propylazetidin-1-yl)pyrazine-2-carboxamide (I-60a) as a white solid. (40 mg, 63%), MS (ES): m/z 445 [M+H]$^+$.

Synthesis of compound I-60 and I-58. The racemic I-60a (40 mg, 0.09 mmol, 1 eq) was separated by Chiral-Prep-HPLC with the following conditions: Column, CHIRAL-PAK IA, 2*25 mm, 5 um; mobile phase, Hex (0.1% FA):IPA=70:30; UV detection at 254/220 nm. The product-containing fractions were combined and concentrated under reduced pressure to afford (R)—N-((4-(cyclopropanesulfonamido)pyridine-2-yl)methyl)-6-methyl-5-(2-propylazetidin-1-yl)pyrazine-2-carboxamide (1$^{st}$ eluting peak, I-60) (15.1 mg, 37%) and (S)—N-((4-(cyclopropanesulfonamido)pyridin-2-yl)methyl)-6-methyl-5-(2-propylazetidin-1-yl)pyrazine-2-carboxamide as a white solid (2$^{nd}$ eluting peak, I-58, 11.3 mg, 28%) respectively.
I-60: MS (ES): m/z 445 [M+H]$^+$; $^1$H NMR (400 MHz, CD$_3$OD) δ 8.43 (s, 1H), 8.08 (s, 1H), 7.06 (s, 1H), 7.01 (d, J=6.2 Hz, 1H), 4.66-4.54 (m, 3H), 4.40-4.34 (m, 1H), 4.10-4.05 (m, 1H), 2.69-2.65 (m, 1H), 2.48 (s, 3H), 2.49- 2.38 (m, 1H), 2.10-1.98 (m, 1H), 1.93-1.88 (m, 1H), 1.68-1.55 (m, 1H), 1.38-1.25 (m, 2H), 1.07-0.98 (m, 2H), 0.92-0.78 (m, 5H).
I-58: MS (ES): m/z 445 [M+H]$^+$; $^1$H NMR (400 MHz, CD$_3$OD) δ 8.55 (s, 1H), 8.20 (d, J=6.0 Hz, 1H), 7.18 (d, J=2.3 Hz, 1H), 7.13-7.11 (m, 1H), 4.63 (s, 2H), 4.68-4.56 (m, 1H), 4.43-4.38 (m, 1H), 4.18-4.12 (m, 1H), 2.70-2.64 (m, 1H), 2.50 (s, 3H), 2.51-2.40 (m, 1H), 2.18-2.08 (m, 1H), 2.02-1.95 (m, 1H), 1.68-1.62 (m, 1H), 1.50-1.32 (m, 2H), 1.15-1.08 (m, 2H), 1.02-0.94 (m, 5H).

Example 70: Synthesis of N-[(4-cyclopropanesulfonamidopyridin-2-yl) methyl]-3-(6-ethoxypyrazin-2-yl) bicycle [1.1.1] pentane-1-carboxamide (I-68)

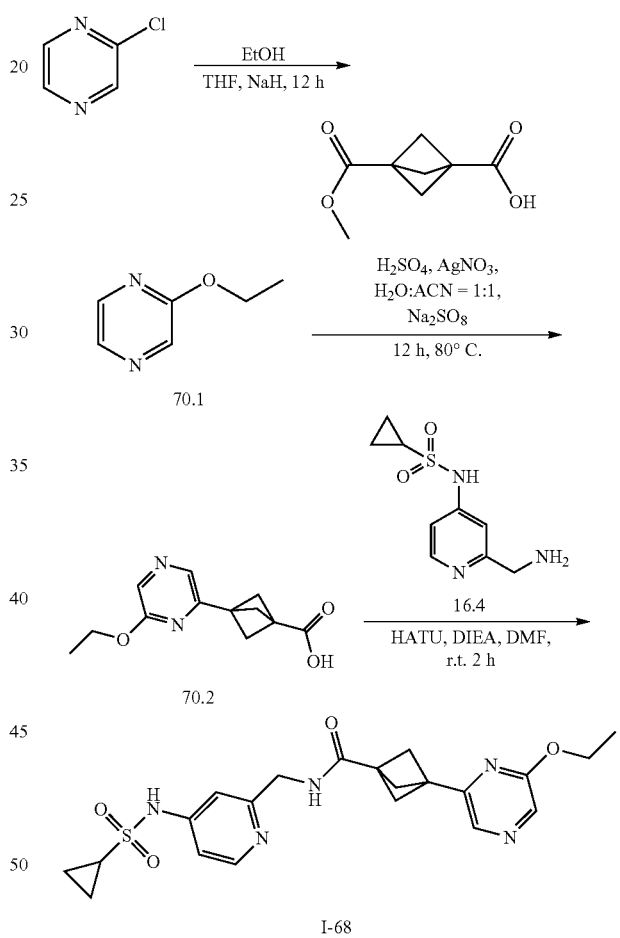

Synthesis of 70.1. To a solution of ethanol (1.81 g, 39.3 mmol, 1.5 eq) in tetrahydrofuran (60 mL) was added sodium hydride (60%, 1.57 g, 39.3 mmol, 1.5 eq) at 0° C. The mixture was stirred for 30 min at 0° C. Then 2-chloropyrazine (3 g, 26.2 mmol, 1 equiv) was added at 0° C. The mixture was stirred for 12 h at room temperature. The reaction was quenched with water and extracted with dichloromethane. The combined organic layers were washed with brine, dried over anhydrous sodium sulfate and concentrated under reduced pressure to obtain 2-ethoxypyrazine (70.1) as a light yellow oil. (2.1 g, 64%) MS (ES): m/z 125 [M+H]$^+$.

Synthesis of 70.2. To a stirred mixture of 70.1 (408.5 mg, 3.29 mmol, 1 eq) and 4-(methoxycarbonyl)bicyclo[1.1.1]

pentane-2-carboxylic acid (839.9 mg, 4.93 mmol, 1.5 eq) in acetonitrile (15 mL) were added sulfuric acid (32.3 mg, 0.33 mmol, 0.1 eq), silver nitrate (111.8 mg, 0.66 mmol, 0.2 eq) and potassium peroxydisulfate (889.5 mg, 3.29 mmol, 1 eq) at room temperature under nitrogen atmosphere. The resulting mixture was stirred for 12 h at 80° C. under nitrogen atmosphere. The mixture was cooled to room temperature, diluted with water and extracted with ethyl acetate. The combined organic layer was washed with brine, dried over sodium sulfate and concentrated under reduced pressure to obtain 3-(6-ethoxypyrazin-2-yl)bicyclo[1.1.1]pentane-1-carboxylic acid (70.2) as a brown yellow solid. (366 mg, 47%), MS (ES): m/z 235 [M+H]⁺.

Synthesis of I-68. To a stirred solution of 70.2 (51.6 mg, 0.22 mmol, 1. eq) and 16.4 (60.1 mg, 0.26 mmol, 1.2 eq) in dimethylformamide (3 mL) were added 2-(-7-azabenzotriazol-1-yl)-N,N,N',N'-tetramethyluronium hexafluorophosphate (100.5 mg, 0.26 mmol, 1.2 eq) and N,N-diisopropylethylamine (142.3 mg, 1.1 mmol, 5 eq) at room temperature. The resulting mixture was stirred for 2 h at room temperature under nitrogen. After completion, the reaction mixture was purified by reverse flash chromatography with the following conditions: column, C18 silica gel; mobile phase, water (0.1% NH₄HCO₃) and ACN (10% ACN up to 50% in 10 min); UV detection at 254 nm. The product-containing fractions were combined and concentrated under reduced pressure. The crude product was purified by Prep-HPLC with the following conditions (Column: YMC-Triart Diol Hilic, 20*150 mm 5 um; Mobile Phase A: water (0.1% NH₄HCO₃), Mobile Phase B: ACN; UV detection at 254/210 nm; the title compound was obtained as an off-white solid. (41.6 mg, 42%), MS (ES): m/z 444 [M+H]⁺; ¹H NMR (300 MHz, CD₃OD) δ 8.48 (d, J=6.8 Hz, 1H), 8.10-7.97 (m, 2H), 7.58 (d, J=2.4 Hz, 1H), 7.50 (dd, J=6.8, 2.5 Hz, 1H), 4.63 (s, 2H), 4.43 (q, J=7.1 Hz, 2H), 2.98-2.93 (m, 1H), 2.50 (s, 6H), 1.45 (t, J=7.1 Hz, 3H), 1.34-1.17 (m, 4H).

Example 71: synthesis of N-[(4-cyclopropanesulfonamido pyridin-2-yl)methyl]-2-[(2A)-2-methylpyrrolidin-1-yl]pyrazolo[1,5-a]pyridine-6-carboxamide (I-67)

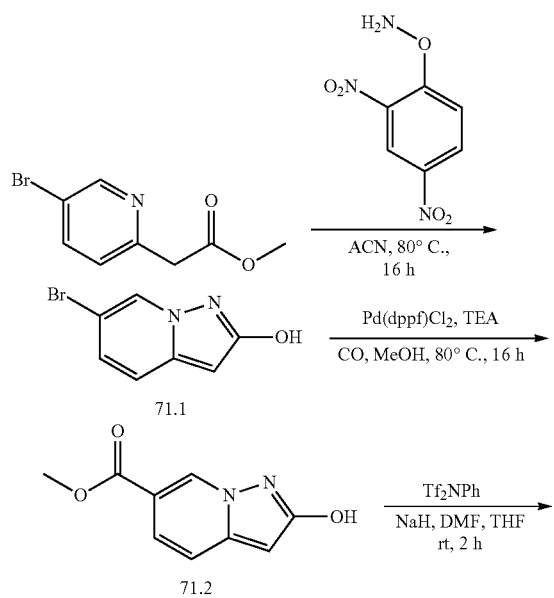

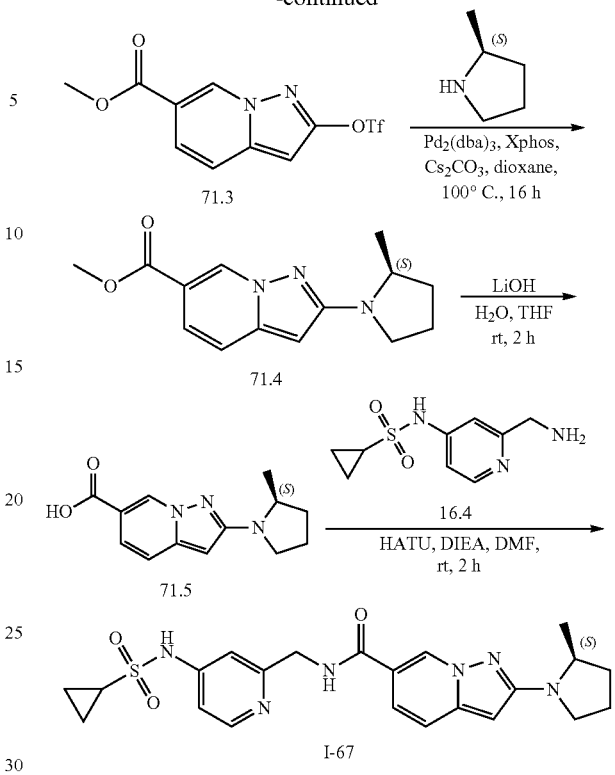

Synthesis of 71.1. A mixture of methyl 2-(5-bromopyridin-2-yl)acetate (5 g, 21.7 mmol, 1 eq) and O-(2,4-dinitrophenyl)hydroxyl amine (4.37 g, 21.9 mmol, 1 eq) in acetonitrile (30 mL) was stirred for 16 h at 80° C. The mixture was cooled to room temperature, diluted with water and extracted with ethyl acetate. The combined organic layer was washed with brine, dried over sodium sulfate and concentrated under reduced pressure. The residue was purified by silica gel column chromatography and compound was eluted in 5% methanol in dichloromethane to obtain 6-bromo-1H-pyrazolo[1,5-a]pyridin-2-one (71.1) as a purple solid. (500 mg, 10%), MS (ES): m/z 213 [M+H]⁺.

Synthesis of 71.2. To a stirred mixture of 71.1 (160 mg, 0.75 mmol, 1 eq) in methanol (60 mL) was added trimethylamine (228 mg, 2.25 mmol, 3 eq) and Pd(dppf)Cl₂ (54.9 mg, 0.08 mmol, 0.1 eq). The resulting mixture was stirred for overnight at 60° C. under CO atmosphere. The mixture was cooled to room temperature, diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (0.1% FA) and ACN (20% ACN up to 60% in 20 min); UV detection at 254/220 nm. The product-containing fractions were combined and concentrated under reduced pressure to obtain methyl 2-oxo-1H-pyrazolo[1,5-a]pyridine-6-carboxylate (71.2) as a white solid. (80 mg, 55%), MS (ES): m/z 193 [M+H]⁺.

Synthesis of 71.3. To a stirred mixture of 71.2 (38.4 mg, 0.2 mmol, 1 eq) in tetrahydrofuran (10 mL) and N,N-dimethylformamide (10 mL) was added sodium hydride (41.2 mg, 1.72 mmol, 1.5 eq) dropwise at 0° C. under nitrogen atmosphere. To the above mixture was added 1,1,1-trifluoro-N-phenyl-N-trifluoromethanesulfonylmethanesulfonamide (490.8 mg, 1.37 mmol, 1.2 eq) dropwise over 2 h at 0° C. The resulting mixture was stirred for additional 0.5 h at room temperature under nitrogen atmosphere. The mixture was diluted with ice water and extracted with ethyl acetate. The combined organic layer was washed with brine, dried over sodium sulfate and concentrated under reduced pressure. The residue was purified by Prep-TLC with 16% ethyl acetate in petroleum ether to afford methyl 2-(trifluoromethanesulfonyloxy)pyrazolo[1,5-a]pyridine-6-carboxylate (71.3, 200 mg, 54%) as a purple oil. MS (ES): m/z 325 [M+H]$^+$.

Synthesis of 71.4. To a stirred mixture of 71.3 (150 mg, 0.46 mmol, 1 eq), (2S)-2-methylpyrrolidine (157.6 mg, 1.85 mmol, 4 eq) and cesium carbonate (452.2 mg, 1.39 mmol, 3 eq) in 1,4-dioxane (5 mL) were added Pd$_2$(dba)$_3$ (42.4 mg, 0.05 mmol, 0.1 eq) and Xphos (44.1 mg, 0.09 mmol, 0.2 eq) at room temperature under nitrogen atmosphere. The resulting mixture was stirred for 16 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (0.1% FA) and ACN (20% ACN up to 60% in 20 min); UV detection at 254/220 nm. The product-containing fractions were combined and concentrated under reduced pressure methyl 2-[(2A)-2-methylpyrrolidin-1-yl]pyrazolo[1,5-a]pyridine-6-carboxylate (71.4) as a white solid (30 mg, 25%), MS (ES): m/z 260 [M+H]$^+$.

Synthesis of 71.5. A mixture of 71.4 (30 mg, 0.12 mmol, 1 eq) and lithium hydroxide (14.5 mg, 0.35 mmol, 3 eq) in tetrahydrofuran (3 mL) and water (0.6 mL) was stirred for 2 h at room temperature under air atmosphere. The mixture was concentrated under vacuum. The residue was diluted with water. The pH value of the solution was adjusted to 3 with 1N hydrochloric acid. The solids were collected by filtration to obtain 2-[(2A)-2-methylpyrrolidin-1-yl]pyrazolo[1,5-a]pyridine-6-carboxylic acid (71.5) as a white solid (28 mg, 98%), MS (ES): m/z 246 [M+H]$^+$.

Synthesis of I-67. To a mixture of 71.5 (33 mg, 0.13 mmol, 1 eq), 16.4 (91.7 mg, 0.4 mmol, 3 eq), 2-(-7-azabenzotriazol-1-yl)-N,N,N',N'-tetramethyluronium hexafluorophosphate (61.4 mg, 0.16 mmol, 1.2 eq) and N,N-diisopropylethylamine (104.3 mg, 0.81 mmol, 6 eq) in N,N-dimethylformamide (1 mL) was stirred for 2 h at room temperature under nitrogen. The mixture was diluted with water and extracted with ethyl acetate. The combined organic layer was washed with brine, dried over sodium sulfate and concentrated under reduced pressure. The residue was purified by Prep-HPLC with the following conditions: Column: SunFire Prep C18 OBD Column, 19×150 mm 5 um 10 nm; Mobile Phase, water 0.1% FA) and ACN (15% ACN up to 35% in 7 min); UV detection at 254/220 nm. The product-containing fractions were combined and evaporated partially in vacuum and lyophilized overnight to afford the title compound as a white solid. (5.5 mg, 8.9%), MS (ES): m/z 455 [M+H]$^+$; $^1$H NMR (400 MHz, CD$_3$OD) δ 8.87 (s, 1H), 8.21 (s, 1H), 7.54 (dd, J=9.3, 1.7 Hz, 1H), 7.33 (d, J=9.3 Hz, 1H), 7.23 (d, J=2.3 Hz, 1H), 7.12 (dd, J=6.1, 2.3 Hz, 1H), 5.85 (s, 1H), 4.64 (s, 2H), 3.95-3.93 (m, 1H), 3.62-3.51 (m, 1H), 3.42-3.35 (m, 1H), 2.70-2.68 (m, 1H), 2.23-2.07 (m, 2H), 2.07-1.93 (m, 1H), 1.76-1.74 (m, 1H), 1.28 (d, J=6.2 Hz, 3H), 1.13-1.11 (m, 2H), 1.09-0.95 (m, 2H).

Example 72: Synthesis of N-[[3-(difluoromethanesulfonamido)phenyl]methyl]-5-(6-ethoxypyrazin-2-yl)pyridine-2-carboxamide (I-63)

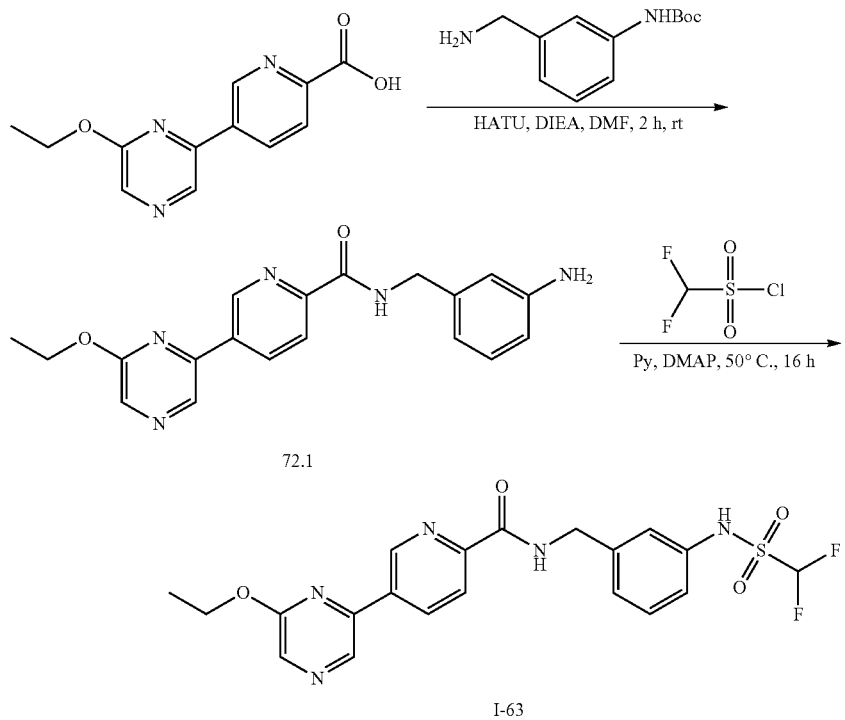

Synthesis of 72.1. To a stirred solution of 5-(6-ethoxypyrazin-2-yl)pyridine-2-carboxylic acid (130 mg, 0.53 mmol, 1 eq) and 3-(aminomethyl) aniline (64.7 mg, 0.53 mmol, 1 eq) in N,N-dimethyl formamide (5 mL) were added 2-(-7-azabenzotriazol-1-yl)-N,N,N',N'-tetramethyluronium hexafluorophosphate (302.3 mg, 0.79 mmol, 1.5 eq) and N,N-diisopropylethylamine (205.5 mg, 1.59 mmol, 3 eq) dropwise at room temperature. The resulting mixture was stirred for 2 h at room temperature under nitrogen. The residue was purified by reverse flash chromatography with the following conditions: column, C18 silica gel; Mobile Phase, water (0.1% NH$_4$HCO$_3$) and ACN (20% ACN up to 70% in 20 min); UV detection at 254/220 nm. The resulting mixture was concentrated under reduced pressure to afford N-[3-(aminomethyl)phenyl]-5-(6-ethoxypyrazin-2-yl)pyridine-2-carboxamide (72.1) as a white solid. (73 mg, 28%), MS (ES): m/z 350 [M+H]$^+$.

Synthesis of I-63. To a stirred mixture of 72.1 (73 mg, 0.20 mmol, 1 eq) and difluoromethanesulfonyl chloride (94.3 mg, 0.62 mmol, 3 eq) in pyridine (2 mL) was added 4-dimethylaminopyridine (2.5 mg, 0.02 mmol, 0.1 eq) in portions at room temperature. The resulting mixture was stirred for 16 h at 50° C. The mixture was cooled to room temperature and concentrated under reduced pressure. The residue was purified by reverse flash chromatography with the following conditions: column, C18 silica gel; Mobile Phase, water (0.1% NH$_4$HCO$_3$) and ACN (30% ACN up to 80% in 20 min); UV detection at 254/220 nm. The resulting mixture was concentrated under reduced pressure. The crude product was purified by Prep-HPLC with the following conditions: Column, SunFire Prep C18 OBD Column, 19×150 mm 5 um 10 nm; Mobile Phase, water (0.1% FA) and ACN (40% ACN up to 60% ACN in 10 min); UV detection at 254/220 nm. The product-containing fractions were combined and evaporated partially in vacuum and lyophilized overnight to afford the title compound as a white solid. (8.5 mg, 27.9%), MS (ES): m/z 461 [M+H]$^+$; $^1$H NMR (400 MHz, CD$_3$OD) δ 9.34 (d, J=1.6 Hz, 1H), 8.79 (s, 1H), 8.65 (dd, J=8.2, 2.2 Hz, 1H), 8.28-8.22 (m, 2H), 7.37-7.29 (m, 2H), 7.24-7.20 (m, 2H), 6.64 (t, J=12.8 Hz, 1H), 4.66 (s, 2H), 4.57 (q, J=7.0 Hz, 2H), 1.49 (t, J=7.1 Hz, 3H).

Example 73. Intermediates

Synthesis of intermediate 73.4.

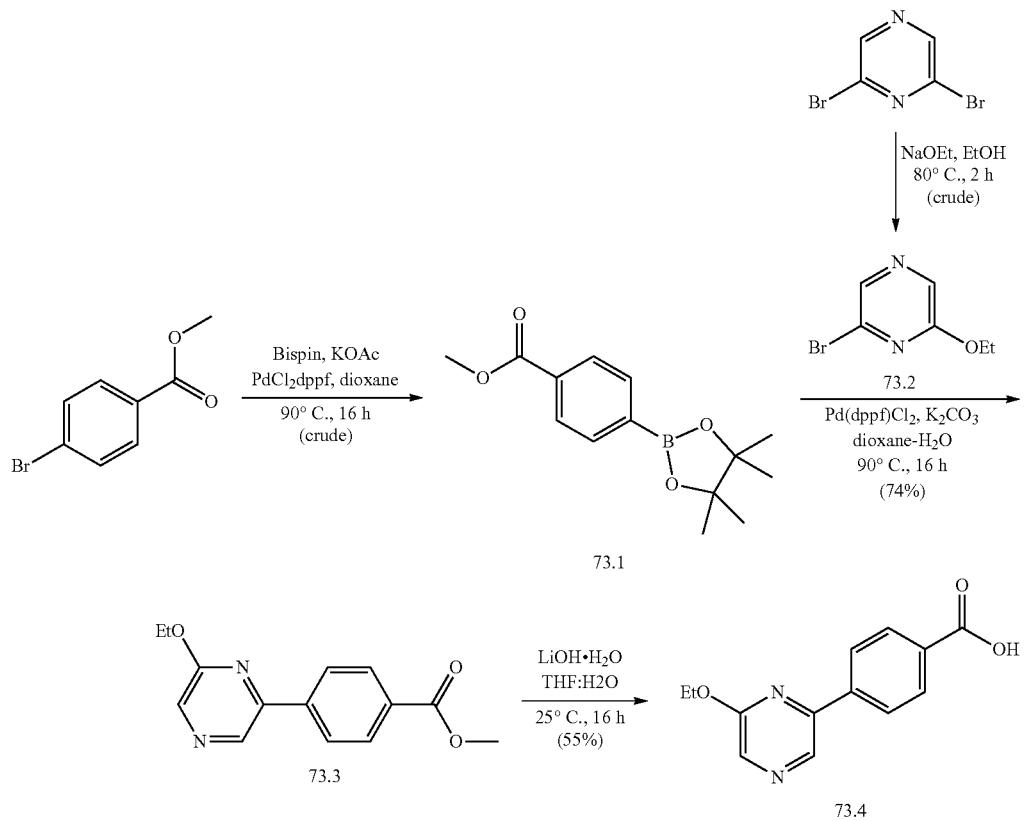

Synthesis of 73.1. (General Procedure E): To a stirred solution of methyl 4-bromobenzoate (500 mg, 2.32 mmol, 1.0 eq) and Bis(pinacolato)diboron (1.47 g, 5.81 mmol, 2.5 eq) in dioxane (8 mL) and H2O (2 mL) (4:1) was added potassium acetate (1.3 g, 13.9 mmol, 6.0 eq). The reaction mixture was degassed for 10 min under argon atmosphere. Then PdCl$_2$dppf (340 mg, 0.46 mmol, 0.2 eq) was added to the reaction mixture and degassed for another 10 min. The reaction mixture was heated at 90° C. for 16 h. After completion of the reaction, the reaction mixture was filtered through celite bed and the filtrate was diluted with ethyl acetate. Combined organic layer was washed with water, dried over Na$_2$SO$_4$ and concentrated under reduced pressure to provide 73.1 (600 mg, crude) as a brown sticky solid. MS(ES): m/z 263.1 [M+H]$^+$, LCMS purity 80%.

Synthesis of compound 73.2. To a stirred solution of 2,6-dibromopyrazine (1.0 g, 4.20 mmol, 1 eq) in MeOH (10 mL) was added NaOEt (572 mg, 8.41 mmol, 2 eq) and the reaction mixture was heated at 80° C. for 1 h. After completion of the reaction, the reaction mixture was evaporated under reduced pressure to remove the volatiles and extracted with ethylacetate. Combined organic layer was washed with aqueous NaHCO$_3$ solution, brine, dried over Na$_2$SO$_4$ and concentrated to provide 73.2 (740 mg, crude) as an orange liquid. 1H NMR (DMSO-d6, 400 MHz): 8.35 (d, J=25.0 Hz, 2H), 4.31 (q, J=7.0 Hz, 2H), 1.34 (t, J=7.0 Hz, 3H).

Synthesis of compound 73.3. (General Procedure F): To a stirred solution of 73.1 (700 mg, 2.67 mmol, 1 eq) and 73.2 (539 mg, 2.67 mmol, 1 eq) in dioxane (8 mL) and H2O (2 mL) (4:1) was added potassium carbonate (738 mg, 5.34 mmol, 2 eq). The reaction mixture was degassed for 10 min under argon atmosphere. Then PdCl$_2$dppf (195 mg, 0.26 mmol, 0.1 eq) was added to the reaction mixture and degassed for another 10 min. The reaction mixture was heated at 90° C. for 16 h. After completion of the reaction, the reaction mixture was filtered through a celite bed and concentrated under reduced pressure to obtain crude product. This was purified by combi-flash column chromatography (RediSepRf 12 g flash column) and eluted in 40% ethylacetate in hexane to provide pure 73.3 (380 mg, 55%) as white solid. MS(ES): m/z 258.8 [M+H]$^+$, LCMS purity 99.82%.

Synthesis of compound 73.4. (General Procedure G): To a stirred solution of 73.3 (100 mg, 0.38 mmol, 1 eq) in THF and H$_2$O (4:2) was added LiOH·H$_2$O (29.2 mg, 0.67 mmol, 1.8 eq), and the resultant reaction mixture was stirred at 25° C. for 3 h. After completion, the reaction mixture was concentrated in vacuo to obtain crude product. The crude was diluted with water and neutralized with 1N aqueous HCl. Resulting solid was filtered, triturated with ether and dried under reduced pressure to afford pure 73.4 (70 mg, 74%) as white solid. MS(ES): m/z 245.0 [M+H]$^+$, LCMS purity 89.06%.

Synthesis of 73.5.

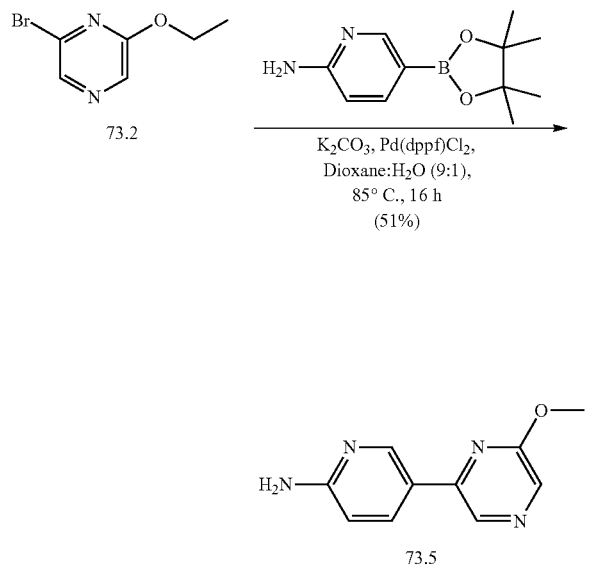

Synthesis of 73.5. Compound 73.5 was synthesized from 2-bromo-6-ethoxypyrazine (500 mg, 2.27 mmol, 1 eq) and 5-(6-methoxypyrazin-2-yl)pyridin-2-amine (507 mg, 1.10 mmol, 1.1 eq) using general procedure F to obtain 250 mg product (Yield: 51%). MS(ES): m/z 217.1 [M+H]$^+$, LCMS purity 97.57%.

Synthesis of Intermediate 15.7.

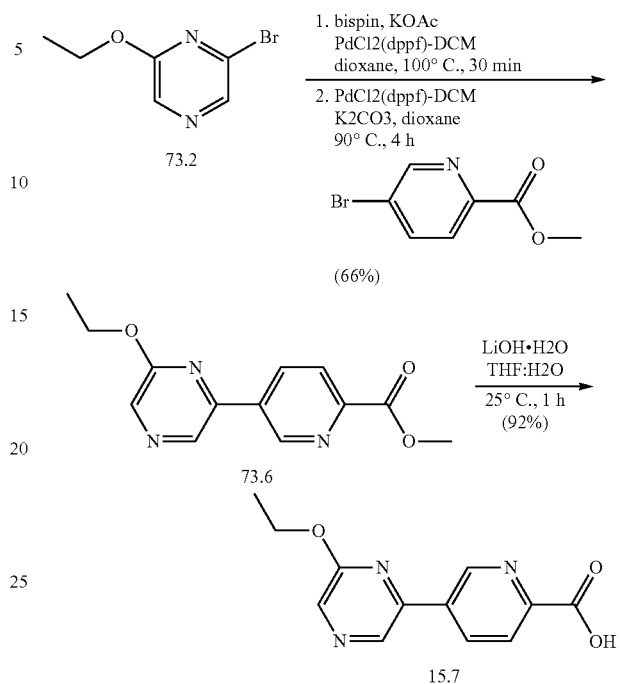

Synthesis of compound 73.6. To a stirred solution of 73.2 (1 g, 4.93 mmol, 1 eq) in dioxane (30 mL) was added bis(pinacolato)diboron (1.38 g, 5.42 mmol, 1.1 eq) and KOAc (1.93 g, 19.7 mmol, 4 eq); the solution was degassed with argon for 5 min, followed by the addition of PdCl$_2$(dppf)-CH2Cl2 (201 mg, 0.25 mmol, 0.05 eq) while degassing continued for another 2 minutes. The reaction mixture was then heated at 100° C. for 30 minutes. The crude LCMS showed desired product mass. This reaction mass was used for the next step as a one pot reaction. (Formation of intermediate was confirmed by LCMS, MS(ES): m/z 169.3 [M+H]$^+$, LCMS purity 62%). To the above reaction mixture was added anhydrous K$_2$CO$_3$ (1.32 g, 9.53 mmol, 2 eq) and methyl 5-bromopicolinate (1.03 g, 4.76 mmol, 1 eq), which was degassed with argon, followed by addition of PdCl$_2$(dppf)-DCM (194 mg, 0.24 mmol, 0.05 eq), and the reaction mixture was heated at 90° C. for 4 h. The reaction mass was filtered through celite bed and concentrated in vacuum to get crude mass. This was purified by combi-flash column chromatography (RediSepRf 40 g flash column) and compound was eluted in 30% ethyl acetate in hexane to obtain compound 73.6 (810 mg, 66%) as an off white solid. MS(ES): m/z 260.2 [M+H]$^+$, LCMS purity 66%, 1H NMR (DMSO-d6, 400 MHz): 9.41 (d, J=1.7 Hz, 1H), 8.99 (s, 1H), 8.66 (dd, J=6.1 Hz, 1H), 8.37 (s, 1H), 8.18 (d, J=8.2 Hz, 1H), 4.51 (q, J=7.1 Hz, 2H), 3.92 (s, 3H), 1.41 (t, J=7 Hz, 3H).

Synthesis of compound 15.7. Compound 15.7 was synthesized from 73.6 (700 mg, 2.7 mmol, 1 eq) using general procedure G to obtain 610 mg product (Yield: 92%). MS(ES): m/z 244.1 [M−H]$^+$, LCMS purity 95%, 1HNMR (DMSO-d6, 400 MHz): 13.34 (s, 1H), 9.41 (s, 1H), 8.98 (s, 1H), 8.64 (d, J=8.2 Hz, 1H), 8.37 (s, 1H), 8.17 (d, J=8.1 Hz, 1H), 4.51 (q, J=7.1 Hz, 2H), 1.41 (t, J=7 Hz, 3H).

Example 74: Synthesis of N-((2-(cyclopropane-sulfonamido)pyridin-4-yl)methyl)-4-(6-ethoxy-pyrazin-2-yl)benzamide, I-17

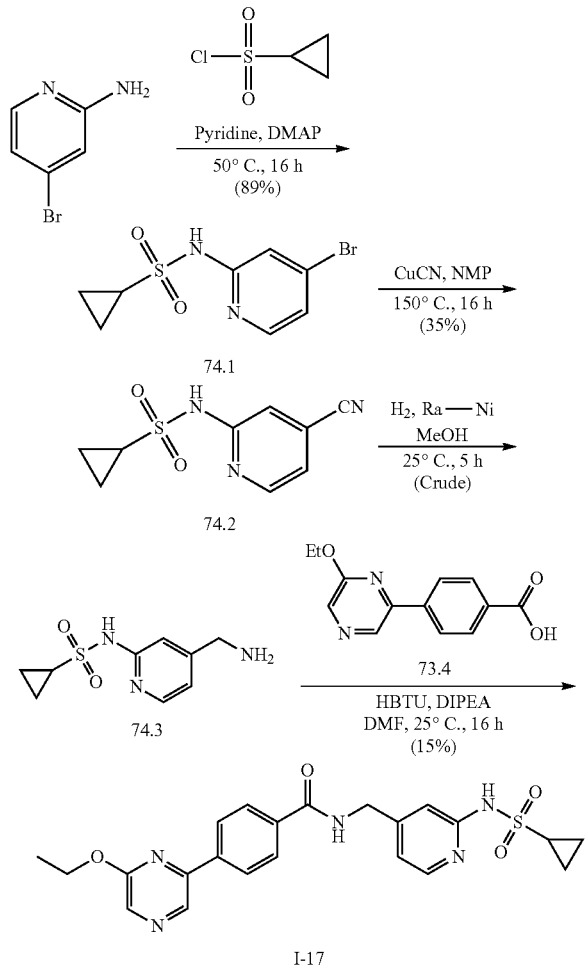

I-17

Synthesis of compound 74.1. (General Procedure A): To a stirred solution of 4-bromopyridin-2-amine (500 mg, 2.98 mmol, 1 eq) in Pyridine (5 mL) were added cyclopropane-sulfonyl chloride (1.22 g, 8.72 mmol, 3 eq) and DMAP (3.55 mg, 0.03 mmol, 0.01 eq) and the resultant reaction mixture was stirred at 50° C. for 16 h. After completion of the reaction, the reaction mixture was evaporated under reduced pressure to remove the volatiles and extracted with ethyl-acetate. Combined organic layer was dried over anhydrous Na$_2$SO$_4$ and concentrated under reduced pressure to provide the crude product. This was purified by combi-flash column chromatography (RediSepRf 12 g flash column) and the compound was eluted in 25% ethylacetate in hexane to provide pure 74.1 (720 g, 89%) as off-white solid. MS(ES): m/z 277.1 [M+H]$^+$, LCMS purity 97.15%.

Synthesis of compound 74.2. (General Procedure B): To a stirred solution of 74.1 (700 mg, 2.52 mmol, 1 eq) in NMP (2 mL) was added CuCN (452 mg, 5.05 mmol, 2 eq) and the resulting mixture was heated at 150° C. for 16 h. After completion of the reaction, the reaction mixture was filtered through celite bed and the filtrate was concentrated under reduced pressure to provide crude product. This was purified by combi-flash column chromatography (RediSepRf 12 g flash column) and the compound was eluted in 25% ethyl-acetate in hexane to provide pure 74.2 (200 mg, 35%) as an off-white solid. MS(ES): m/z 224.2 [M+H]$^+$, LCMS purity 98%.

Synthesis of compound 74.3. (General Procedure C): To a stirred solution of 74.2 (200 mg, 0.89 mmol, 1.0 eq) was added Raney Ni (100 mg) and 2 drops of methanolic ammonia at 25° C. The reaction mixture was stirred at 25° C. for 16 h under hydrogen balloon pressure. After completion of the reaction, the reaction mixture was filtered through celite bed. The filtrate was concentrated under reduced pressure to provide 74.3 (170 mg, crude) as a colorless sticky liquid. MS(ES): m/z 228.2 [M+H]$^+$, LCMS purity 52%.

Synthesis of compound I-17. (General Procedure D): To a stirred solution of 74.3 (90 mg, 0.36 mmol, 1 eq) in DMF (5 mL), were added DIPEA (0.25 ml, 1.47 mmol, 4 eq), HBTU (209 mg, 0.55 mmol, 1.5 eq) followed by the addition of 73.4 (167 mg, 0.73 mmol, 2 eq) at 25° C. and the resultant reaction mixture was stirred at 25° C. for 16 h. After completion of the reaction, the reaction mixture was diluted with water and extracted with ethyl acetate. Combined organic layer was washed with aqueous NaHCO$_3$ solution, brine, dried over anhydrous Na$_2$SO$_4$ and concentrated under reduced pressure to provide the crude product. This was purified by prep-HPLC to provide pure I-17 (26.3 mg, 15%) as off-white sticky solid. MS(ES): m/z 454.1 [M+H]$^+$, LCMS purity 97.64%, HPLC purity 98.99%, 1H NMR (DMSO-d6, 400 MHz): 11.15-11.04 (m, 1H), 9.24 (t, J=5.6 Hz, 1H), 8.90 (s, 1H), 8.29 (s, 1H), 8.25 (d, J=8.3 Hz, 2H), 8.03 (d, J=8.3 Hz, 3H), 7.00 (s, 1H), 6.88 (bs, 1H), 4.51 (t, J=7.0 Hz, 2H), 4.48-4.46 (m, 2H), 2.91 (bs, 1H), 1.41 (t, J=7.0 Hz, 3H), 0.97 (s, 2H), 0.91 (d, J=7.4 Hz, 2H).

Example 75: Synthesis of 2-(3-(cyclopropanesulfo-namido)-1H-pyrazol-1-yl)-N-(5-(6-ethoxypyrazin-2-yl)pyridin-2-yl)-2-methylpropanamide, I-19

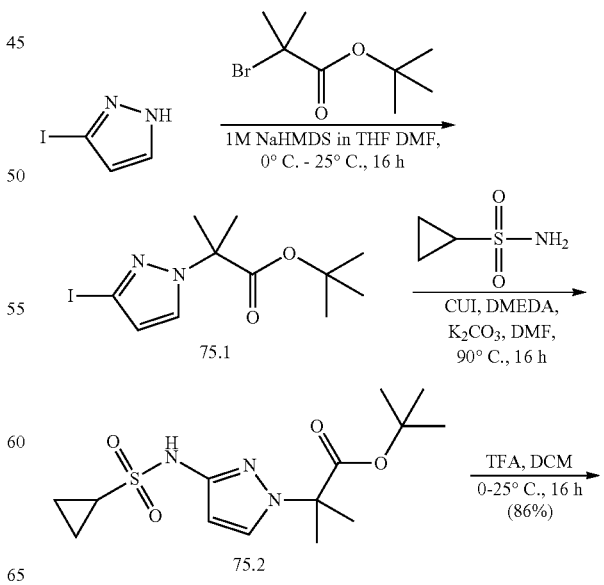

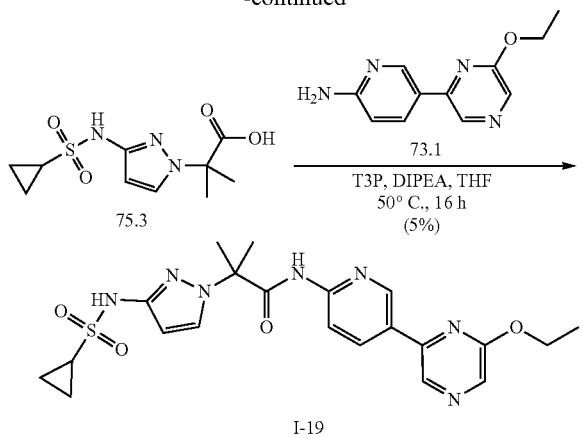

and extracted with ethyl acetate. Combined organic layer was washed with aqueous NaHCO$_3$ solution and brine, dried over Na$_2$SO$_4$ and concentrated under reduced pressure to provide the crude product. This crude was purified by prep-HPLC to afford the pure compound I-19 (4.23 mg, 5%) as a brown solid. MS(ES): m/z 472.2 [M+H]$^+$, LCMS purity 95.52%, HPLC purity 98.98%, 1H NMR (DMSO-d6, 400 MHz): 10.07 (bs, 1H), 9.60 (s, 1H), 9.00 (s, 1H), 8.83 (s, 1H), 8.51 (d, J=8.8 Hz, 1H), 8.24 (s, 1H), 8.17 (d, J=8.8 Hz, 1H), 8.89 (s, 1H), 8.13 (d, J=2.3 Hz, 1H), 7.88 (d, J=2.12 Hz, 1H), 6.14 (d, J=2.32 Hz, 1H), 4.44 (q, J=7.0 Hz, 2H), 3.48 (t, J=5.3 Hz, 1H), 3.41 (d, J=5.0 Hz, 1H), 2.67-2.61 (m, 1H), 1.83 (s, 6H), 1.39 (t, J=7.0 Hz, 3H), 0.91-0.86 (m, 2H).

Example 76: N-(1-(1-(cyclopropylsulfonyl)-1H-indol-4-yl)cyclopropyl)-5-(6-ethoxypyrazin-2-yl)picolinamide, I-20

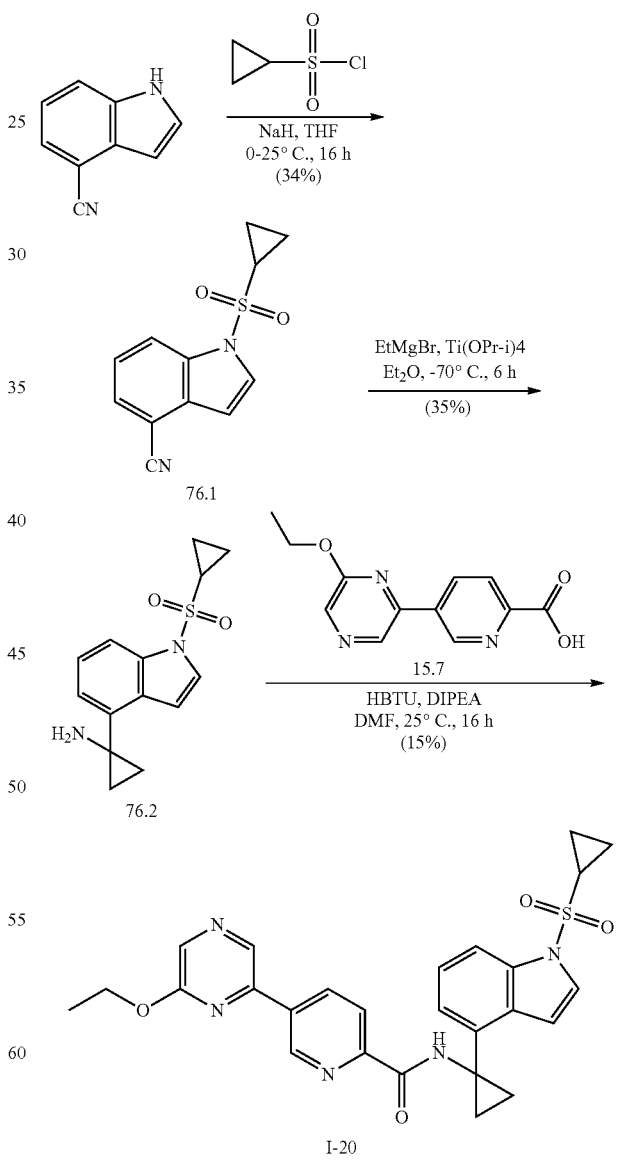

Synthesis of compound 75.1. To a stirred solution of 3-Iodo-1H-pyrazole (500 mg, 2.50 mmol, 1 eq) in DMF (5 mL), was added NaHMDS (1M in THF) (1.3 ml, 3.8 mmol, 1.5 eq) drop wise at 0° C. After 5 min, a solution of tert-Butyl α-bromoisobutyrate (572 mg, 2.5 mmol, 1 eq) in DMF (5 mL) was added to the above mixture dropwise at 0° C. The resultant reaction mixture stirred at 25° C. for 3 h. After completion of the reaction, the reaction mixture was quenched with saturated NH$_4$Cl and extracted with ethyl acetate. Combined organic layer was washed with brine, dried over Na$_2$SO$_4$ and concentrated under reduced pressure to get the crude product. This was purified by combi-flash column chromatography (RediSepRf 12 g flash column), and the compound was eluted in 5% ethyl acetate in hexane to afford pure 75.1 (367 mg, 42%) as a brown solid. MS(ES): m/z 336.8 [M+H]$^+$, LCMS purity 99.3%.

Synthesis of compound 75.2. To a stirred solution of 75.1 (200 mg, 0.59 mmol, 1 eq) in DMF (3 mL), was added cyclopropyl sulfonamide (108 mg, 0.89 mmol, 1.5 eq) and K$_2$CO$_3$ (176 mg, 1.2 mmol, 2 eq). The reaction mixture was degassed for 10 min under argon atmosphere. After that CUI (11.3 mg, 0.06 mmol, 0.1 eq), DMEDA (10.4 mg, 0.12 mmol, 0.2 eq) were added to the reaction mixture and degassed for another 10 min. The reaction mixture was heated at 90° C. for 16 h. After completion of the reaction, the reaction mixture was filtered through celite bed and the filtrate was concentrated in vacuo to obtain crude product. This was purified by combi-flash column chromatography (RediSepRf 12 g flash column), compound was eluted in 4% methanol in DCM to afford pure 75.2 (120 mg, 61%) as a brown solid. MS(ES): m/z 329.8 [M+H]$^+$, LCMS purity 99.23%.

Synthesis of compound 75.3. To a stirred solution of 75.2 (100 mg, 0.30 mmol, 1 eq) in DCM (1 mL), was added trifluoro acetic acid (0.46 mL, 6.07 mmol, 20 eq) at 0° C. and the reaction mixture was stirred at 25° C. for 16 h. After completion, the reaction mixture was evaporated under reduced pressure to give the crude product. This crude product was triturated with diethyl ether to afford pure 75.3 (98.1 mg, 86%) as a white solid. MS(ES): m/z 273.9 [M+H]$^+$, LCMS purity 99.51%.

Synthesis of I-19. To a stirred solution of 75.3 (50 mg, 0.18 mmol, 1 eq) in THF (1 mL), were added DIPEA (0.09 ml, 0.54 mmol, 3 eq) and T$_3$P (50% in Ethyl acetate) (116 mg, 0.36 mmol, 1.5 eq) followed by the addition of 73.1 (59.3 mg, 0.27 mmol, 1.5 eq) at 25° C. and the resultant reaction mixture was stirred at 50° C. for 16 h. After completion, the reaction mixture was quenched with water Synthesis of compound 76.1. To a stirred solution of 1H-indole-4-carbonitrile (1 g, 7.03 mmol, 1 eq) and THF (10 mL) at 0° C. was added NaH (203 mg, 8.44 mmol, 2 eq) portion wise. The reaction mixture then stirred at 25° C. for 30 min followed by the dropwise addition of cyclopropanesulfonyl chloride (1.18 g, 8.44 mmol, 1.2 eq). The reaction mixture was stirred at 25° C. for 16 h. After completion, the reaction was quenched with saturated NH₄Cl and extracted with ethyl acetate. Combined organic layer was washed with brine, dried over Na₂SO₄ and concentrated under reduced pressure to provide the crude product. This was purified by combi-flash column chromatography (RediSepRf 12 g flash column), in 60% ethyl acetate in hexane to afford pure 76.1 (600 mg, 34%) as a brown solid. MS(ES): m/z 247.5 [M+H]⁺, LCMS purity 93%.

Synthesis of compound 76.2. To a stirred solution of 76.1 (250 mg, 1.05 mmol, 1 eq) in diethyl ether (5 ml) at −78° C. was added titanium isopropoxide (0.42 ml, 1.52 mmol, 1.5 eq). The reaction mixture was stirred for 10 min at −78° C., ethyl magnesium bromide (3M in Ether) (0.8 ml, 3.04 mmol, 3 eq) was added at −78° C., and the reaction mixture stirred at −78° C. for 1 h. After 1 h, the reaction mixture stirred at 25° C. for another 1 h. Boron trifluoroetharate (0.56 ml, 4.56 mmol, 4.5 eq) was added in the reaction mixture drop wise and stirred at 25° C. for 2 h. After completion, the reaction mixture was quenched with saturated sodium bicarbonate solution and extracted with ethyl acetate. Combined organic layer was washed with brine, dried over Na₂SO₄ and concentrated under reduced pressure to provide the crude product. This was purified by combi-flash column chromatography (RediSepRf 12 g flash column) and eluted in 40% ethyl acetate in hexane to afford pure 76.2 (100 mg, 35%) as a white solid. MS(ES): m/z 277.1 [M+H]⁺, LCMS purity 83%.

Synthesis of compound I-20. Compound I-20 was synthesized from 15.7 (35 mg, 0.14 mmol, 1 eq) and 76.2 (42 mg, 0.14 mmol, 1 eq) using general procedure D to obtain 10 mg product (Yield: 15%) as light yellow sticky solid. MS(ES): m/z 504.1 [M+H]⁺, LCMS purity 98%, HPLC purity 97.49%, 1H NMR (DMSO-d6, 400 MHz): 9.75 (s, 1H), 9.31 (s, 1H), 8.96 (s, 1H), 8.61 (dd, J=8.1 Hz, 2.0 Hz, 1H), 8.34 (s, 1H), 8.06 (d, J=8.2 Hz, 1H), 7.76 (d, J=8.3 Hz, 1H), 7.61 (d, J=3.6 Hz, 1H), 7.50-7.46 (m, 2H), 7.29 (t, J=8.2 Hz, 1H), 4.46 (q, J=6.9 Hz, 2H), 3.05-3.01 (m, 1H), 1.41-1.37 (m, 4H), 1.22 (s, 4H), 1.04 (d, J=5.5 Hz, 2H).

Example 77: Synthesis of N-((6-(cyclopropanesulfonamido)pyrimidin-4-yl)methyl)-4-(6-ethoxypyrazin-2-yl)benzamide, I-29

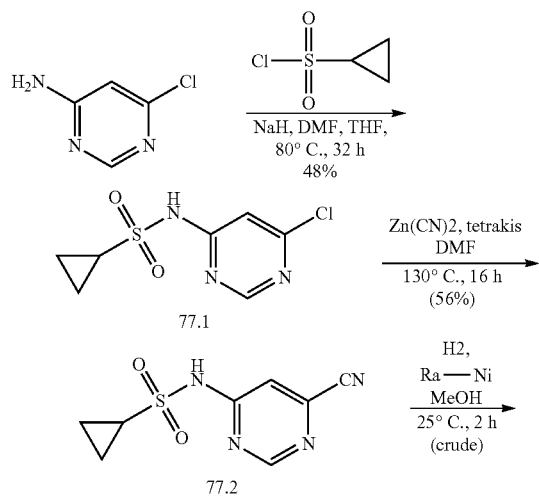

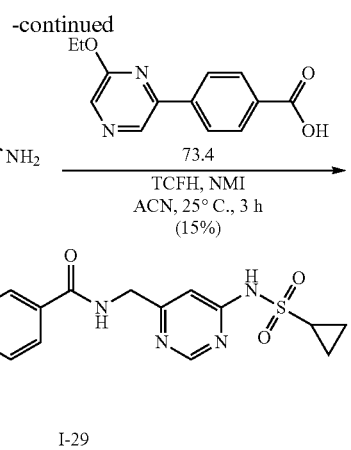

Synthesis of 77.1. To a stirred solution of 4-Amino-6-chloropyrimidine (300 mg, 2.32 mmol, 1 eq) in DMF and THF (1:1) (6 mL) was added NaH (102 mg, 4.65 mmol, 2 eq) portion wise at 0° C. The reaction mixture was stirred at 25° C. for 30 min, followed by the dropwise addition of Cyclopropanesulfonyl chloride (0.97 mL, 6.97 mmol, 3 eq). The reaction mixture was stirred at 25° C. for 16 h. After completion, the reaction was quenched with saturated NH₄Cl and extracted with ethyl acetate. Combined organic layer was washed with brine, dried over Na₂SO₄ and concentrated under reduced pressure to provide the crude product. This was purified by combi-flash column chromatography (RediSepRf 12 g flash column), and was eluted in 60% ethyl acetate in hexane to afford pure 77.1 (210 mg, 48%) as a brown solid. MS(ES): m/z 234.01 [M+H]⁺, LCMS purity 99.3%.

Synthesis of 77.2. To a stirred solution of compound 77.1 (200 mg, 0.85 mmol, 1 eq) in DMF (8 mL), was added Zn(CN)₂ (470 mg, 3.4 mmol, 1.5 eq). The reaction mixture was degassed with argon for 10 min. Pd(PPh₃)₄ (99 mg, 0.08 mmol, 0.1 eq) was added to the reaction mixture and was degassed for another 10 min. The reaction mixture was heated at 130° C. for 16 h. After completion, the reaction mixture was filtered through a celite bed and the filtrate was concentrated in vacuo to obtain crude product. This crude product was purified by combi-flash column chromatography (RediSepRf 12 g flash column) and eluted in 40% acetone in hexane to afford pure 77.2 (105 mg, 56%) as a brownish yellow solid. MS(ES): m/z 224.04 [M+H]⁺, LCMS purity 98.3%.

Synthesis of compound 77.3. Compound 77.3 was synthesized from compound 77.2 (100 mg, 0.58 mmol, 1 eq) using general procedure C to obtain 92.1 mg product (Yield: 91%). MS(ES): m/z 229.1 [M+H]⁺, LCMS purity 94.8%.

Synthesis of compound I-29. (General Procedure H): To a stirred solution of compound 73.4 (85 mg, 0.23 mmol, 1 eq) and compound 77.3 (78.7 mg, 0.32 mmol, 1 eq) in acetonitrile (3 mL), were added TCFH (900 mg, 3.21 mmol, 10 eq) and N-methyl imidazole (0.26 mL, 3.21 mmol, 10 eq) at 25° C. and the resultant reaction mixture was stirred at 25° C. for 3 h. After completion, the reaction mixture was diluted with water and extracted with ethyl acetate. Combined organic layer was washed with aqueous NaHCO₃ solution, brine, dried over anhydrous Na₂SO₄ and concentrated under reduced pressure to get the crude product. This was purified by prep-HPLC to provide pure I-29 (24.1 mg, 15%) as white solid. MS(ES): m/z 455.1 [M+H]⁺, LCMS purity 100%, HPLC purity 99.48%. 1H NMR (DMSO-d6, 400 MHz): 11.3 (bs, 1H), 9.29 (t, J=5.9 Hz, 1H), 8.90 (s, 1H), 8.71 (bs, 1H), 8.28 (t, J=8.4 Hz, 3H), 8.05 (d, J=8.4 Hz, 2H), 6.98 (s, 1H), 4.53-4.47 (m, 4H), 3.03 (bs, 1H), 1.41 (t, J=7.0 Hz, 3H), 1.05-1.00 (m, 4H).

Example 78: Synthesis of N-(3-(cyclopropanesulfonamido)benzyl)-5-(6-ethoxypyrazin-2-yl)picolinamide, I-18

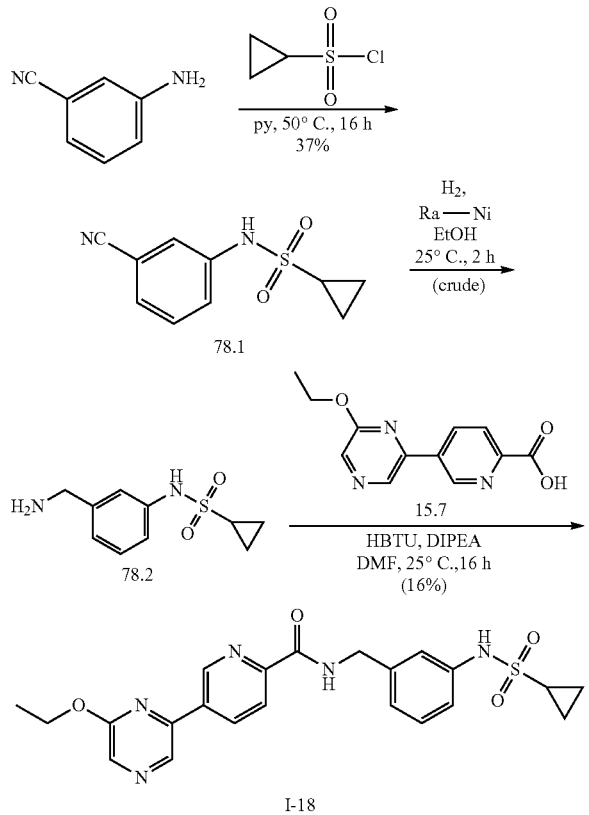

I-18

Synthesis of compound 78.1. Compound 78.1 was synthesized from 4-bromopyridin-2-amine (500 mg, 2.98 mmol, 1 eq) using general procedure A to obtain 350 mg product (Yield: 37%) as off-white solid. MS(ES): m/z 119.14 [M+H]$^+$, LCMS purity 96%.

Synthesis of compound 78.2. Compound 78.2 was synthesized from (350 mg, 0.89 mmol, 1.0 eq) using general procedure C to obtain 260 mg product (crude) as colorless sticky liquid. MS(ES): m/z 227.1 [M+H]$^+$, LCMS purity 98%.

Synthesis of compound I-18. Compound I-18 was synthesized from 15.7 (100 mg, 0.41 mmol, 1 eq) and 78.2 (184 mg, 0.82 mmol, 2 eq) using general procedure D to obtain 30.5 mg product (Yield: 16%). MS(ES): m/z 454.1 [M+H]$^+$, LCMS purity 99.35%, HPLC purity 99.48%. 1H NMR (DMSO-d6, 400 MHz): 9.34 (s, 1H), 9.02-8.98 (m, J=9.8 Hz, 2H), 8.66 (dd, J=8.0 Hz, 1.9 Hz, 1H), 8.35 (s, 1H), 8.16 (d, J=8.2 Hz, 1H), 7.38 (s, 1H), 4.51 (q, J=7.0 Hz, 2H), 3.41-3.33 (m, 1H), 3.17 (d, J=12.0 Hz, 1H), 2.90 (t, J=7.0 Hz, 1H), 2.20-2.06 (m, 3H), 1.80 (d, J=11.2 Hz, 1H), 1.48-1.45 (m, 1H), 1.43 (t, J=7.04, 3H).

Example 79: Synthesis of N-((6-(cyclopropanesulfonamido)pyridin-2-yl)methyl)-4-(6-ethoxypyrazin-2-yl)benzamide, Z-1

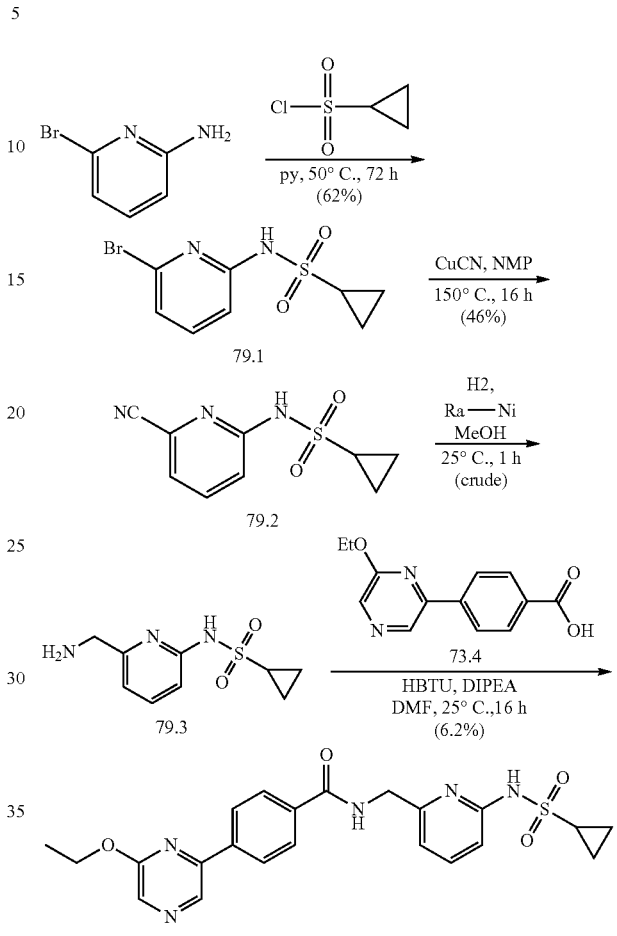

Z-1

Synthesis of compound 79.1. Compound 79.1 was synthesized from 6-bromopyridin-2-amine (500 mg, 2.91 mmol, 1 eq) and cyclopropanesulfonyl chloride (817 mg, 5.81 mmol, 2 eq) using general procedure A to obtain 500 mg product (Yield: 62%). MS(ES): m/z 278.8 [M+H]$^+$, LCMS purity 100%.

Synthesis of compound 79.2. Compound 79.2 was synthesized from compound 79.1 (400 mg, 1.44 mmol, 1 eq) using general procedure B to obtain 150 mg product (Yield: 46%). MS(ES): m/z 224.2 [M+H]$^+$, LCMS purity 97.39%.

Synthesis of compound 79.3. Compound 79.3 was synthesized from compound 79.2 (100 mg, 0.44 mmol, 1 eq) using general procedure C to obtain 95.1 mg product (crude). MS(ES): m/z 224.2 [M+H]$^+$, LCMS purity 97.39%.

Synthesis of compound Z-1. Compound Z-1 was synthesized from 73.4 (50 mg, 0.20 mmol, 1 eq) and 79.3 (93.1 mg, 0.41 mmol, 2 eq) using general procedure D to obtain 5.79 mg product (Yield: 6.2%). MS(ES): m/z 454.3 [M+H]$^+$, LCMS purity 100%, HPLC purity 99.47%, 1HNMR (DMSO-d6, 400 MHz): 10.51 (bs, 1H), 9.18 (t, J=5.8 Hz, 1H), 8.90 (s, 1H), 8.29 (s, 1H), 8.24 (d, J=8.3 Hz, 2H), 8.05 (d, J=8.3 Hz, 2H), 7.69 (t, J=7.9 Hz, 1H), 7.00-6.88 (m, 2H), 4.53-4.48 (m, 4H), 3.13 (bs, 1H), 1.41 (t, J=7.0 Hz, 3H), 1.06-1.00 (m, 2H), 0.90-0.88 (m, 2H).

Example 80: Synthesis of 2-(2-(cyclopropanesulfonamido)thiazol-4-yl)-N-(5-(6-ethoxypyrazin-2-yl)pyridin-2-yl)-2-methylpropanamide, Z-2

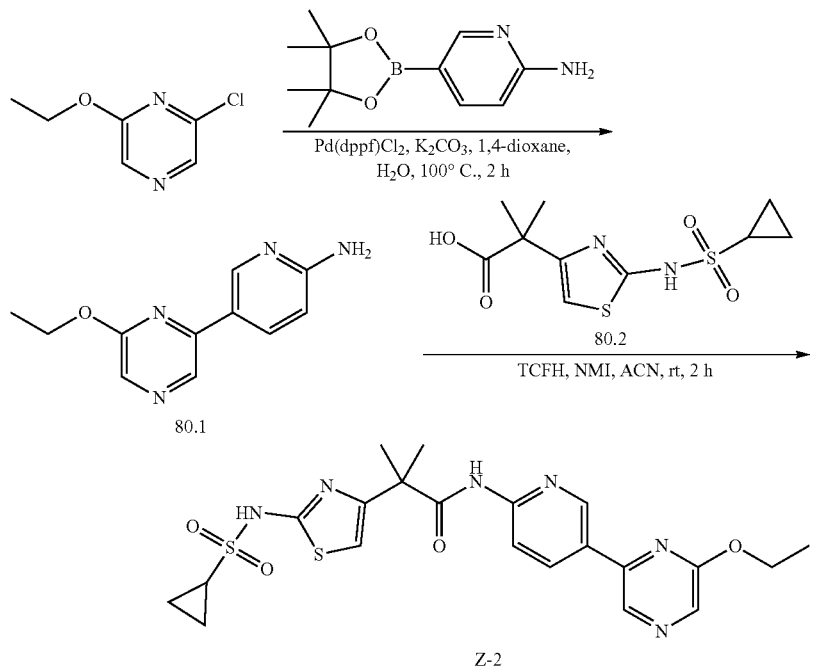

Synthesis of 80.1. To a solution of 2-chloro-6-ethoxypyrazine (3.16 g, 20.00 mmol, 1.0 eq) and 5-(4,4,5,5-tetramethyl-1,3,2-dioxaborolan-2-yl)pyridin-2-amine (5.28 g, 24.00 mmol, 1.2 eq) in 1,4-dioxane (120 mL) and water (40 mL) was added potassium carbonate (8.28 g, 60.00 mmol, 3.0 eq) and Pd(dppf)Cl$_2$ (1.63 g, 2.00 mmol, 0.1 eq). The resulting mixture was stirred for 2 h at 100° C. under nitrogren atmosphere. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 50% ethyl acetate in petroleum ether to obtain 5-(6-ethoxypyrazin-2-yl)pyridin-2-amine (80.1) as an off-white solid. (3.50 g, 81%), MS (ES): m/z 217 [M+H]$^+$.

Synthesis of Z-2. To a solution of 2-(2-(cyclopropanesulfonamido)thiazol-4-yl)-2-methylpropanoic acid (80.2, 80.0 mg, 0.28 mmol, 1.0 eq) and 80.1 (60.5 mg, 0.28 mmol, 1.0 eq) in acetonitrile (5 mL) was added TCFH (156.8 mg, 0.56 mmol, 2.0 equiv) and NMI (229.6 mg, 2.80 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (31% ACN up to 56% in 8 min); UV detection at 254/220 nm. The product-containing fractions were combined and evaporated partially in vacuo and lyophilized overnight to afford 2-(2-(cyclopropanesulfonamido)thiazol-4-yl)-N-(5-(6-ethoxypyrazin-2-yl)pyridin-2-yl)-2-methylpropanamide (Z-2) as a white solid. (31.5 mg, 23%), MS (ES): m/z 489 [M+H]$^+$; $^1$H NMR (400 MHz, $6?_6$-DMSO) δ 12.59 (br s, 1H), 10.12 (s, 1H), 9.09 (s, 1H), 8.87 (s, 1H), 8.53 (dd, J=8.8 Hz, 1H), 8.26 (s, 1H), 8.19 (d, J=8.4 Hz, 1H), 6.60 (s, 1H), 4.48 (q, J=7.2 Hz, 2H), 2.68-2.56 (m, 1H), 1.62 (s, 6H), 1.41 (t, J=6.8 Hz, 3H), 0.98-0.88 (m, 4H).

Example 81: Synthesis of 2-methyl-2-(2-(1-methylethylsulfonamido)thiazol-4-yl)-N-(5-(6-(trifluoromethyl)pyrazin-2-yl)pyridin-2-yl)propenamide, Z-3

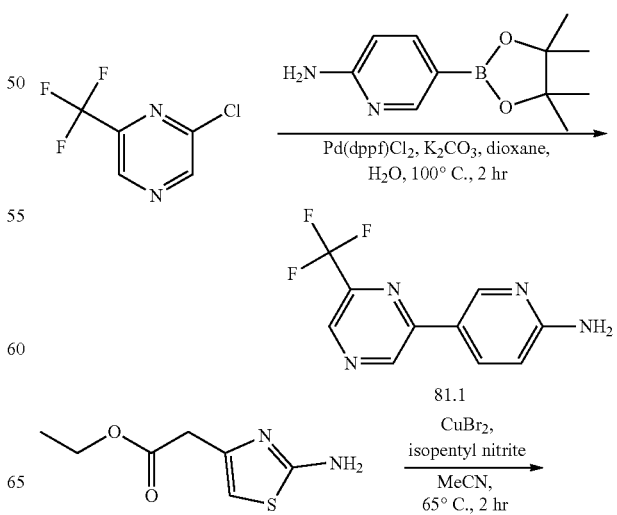

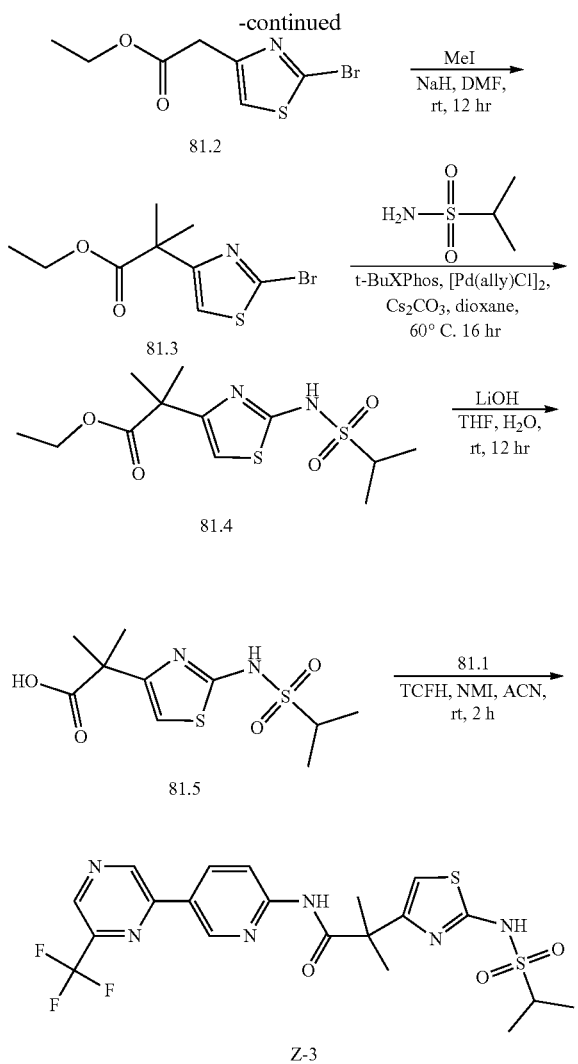

Synthesis of 81.1. To a solution of 2-chloro-6-(trifluoromethyl)pyrazine (1.82 g, 10.00 mmol, 1.0 eq) and 5-(4,4,5,5-tetramethyl-1,3,2-dioxaborolan-2-yl)pyridin-2-amine (2.64 g, 12.00 mmol, 1.2 eq) in 1,4-dioxane (50 mL) and water (10 mL) was added potassium carbonate (4.14 g, 30.00 mmol, 3.0 eq) and Pd(dppf)Cl$_2$ (816.0 mg, 1.00 mmol, 0.1 eq). The resulting solution was stirred for 2 h at 100° C. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 5% methanol in dichloromethane to obtain 5-(6-(trifluoromethyl)pyrazin-2-yl)pyridin-2-amine (81.1) as a yellow solid. (1.82 g, 76%), MS (ES): m/z 241 [M+H]$^+$.

Synthesis of 81.2. To a solution of ethyl 2-(2-aminothiazol-4-yl)acetate (4.65 g, 25.00 mmol, 1.0 eq) and copper(II) bromide (6.63 g, 30.00 mmol, 1.2 eq) in acetonitrile (200 mL) was added dropwise isopentyl nitrite (1.46 g, 12.50 mmol, 0.5 eq) at 0° C. The resulting solution was stirred for 2 h at 65° C. The mixture was cooled to r.t and concentrated under reduced pressure. The residue was purified by silica gel column chromatography and compound was eluted in 25% ethyl acetate in petroleum ether to obtain ethyl 2-(2-bromothiazol-4-yl)acetate (81.2) as a yellow oil. (2.40 g, 38%), MS (ES): m/z 250/252 [M+H]$^+$.

Synthesis of 81.3. To a solution of 81.2 (1.20 g, 4.80 mmol, 1.0 eq) in N,N-dimethylformamide (30 mL) was added sodium hydride (60%, 422.4 mg, 10.56 mmol, 2.2 eq) and iodomethane (1.50 g, 10.56 mmol, 2.2 eq) at 0° C. The resulting solution was stirred for 12 h at r.t. The mixture was diluted with water and extracted with ethyl acetate. The combined organic layer was washed with brine, dried over sodium sulfate and concentrated under reduced pressure. The residue was purified by silica gel column chromatography and compound was eluted in 25% ethyl acetate in petroleum ether to obtain ethyl 2-(2-bromothiazol-4-yl)-2-methylpropanoate (81.3) as a yellow oil. (0.80 g, 60%), MS (ES): m/z 278/280 [M+H]$^+$.

Synthesis of 81.4. To a solution of 81.3 (800.0 mg, 2.89 mmol, 1.0 eq) and propane-2-sulfonamide (710.9 mg, 5.78 mmol, 2.0 equiv) in 1,4-dioxane (20 mL) was added Cs$_2$CO$_3$ (2.83 g, 8.66 mmol, 3.0 equiv), t-BuXPhos (124.1 mg, 0.29 mmol, 0.1 equiv) and [Pd(ally)Cl]$_2$ (54.9 mg, 0.15 mmol, 0.05 equiv) at room temperature under nitrogen atmosphere. The reaction mixture was stirred for 16 h at 60° C. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 50% ethyl acetate in petroleum ether to obtain ethyl 2-methyl-2-(2-(1-methylethylsulfonamido)thiazol-4-yl)propanoate (81.4) as a yellow solid. (0.45 g, 49%), MS (ES): m/z 321 [M+H]$^+$.

Synthesis of 81.5. To a solution of 81.4 (450.0 mg, 1.41 mmol, 1.0 eq) in tetrahydrofuran (16 mL) and water (4 mL) was added lithiumol (101.3 mg, 4.22 mmol, 3.0 equiv). The resulting solution was stirred for 12 h at r.t. The mixture was concentrated under vacuum. The residue was diluted with water. The pH value of the solution was adjusted to 3 with 1N hydrochloric acid. The solids were collected by filtration and dried in an oven at 45° C. to obtain 2-methyl-2-(2-(1-methylethylsulfonamido)thiazol-4-yl)propanoic acid (81.5) as an off-white solid. (0.25 g, 61%), MS (ES): m/z 293 [M+H]$^+$.

Synthesis of Z-3. To a solution of 81.5 (50.0 mg, 0.17 mmol, 1.0 eq) and 5-(6-(trifluoromethyl)pyrazin-2-yl)pyridin-2-amine (81.1, 40.8 mg, 0.17 mmol, 1.0 eq) in acetonitrile (5 mL) was added TCFH (95.2 mg, 0.34 mmol, 2.0 equiv) and NMI (140.2 mg, 1.71 mmol, 10.0 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (35% ACN up to 65% in 7 min); UV detection at 254/220 nm. The product-containing fractions were combined and evaporated partially in vacuo and lyophilized overnight to afford 2-methyl-2-(2-(1-methylethylsulfonamido)thiazol-4-yl)-N-(5-(6-(trifluoromethyl)pyrazin-2-yl)pyridin-2-yl)propanamide (Z-3) as a white solid. (12.6 mg, 14%), MS (ES): m/z 515 [M+H]$^+$; $^1$H NMR (400 MHz, DMSO) δ 11.08 (s, 1H), 9.64 (s, 1H), 9.15-9.12 (m, 2H), 8.55 (dd, J=8.8 Hz, 1H), 8.26 (d, J=8.8 Hz, 1H), 6.66 (br s, 1H), 6.30 (s, 1H), 3.09-3.01 (m, 1H), 1.50 (s, 6H), 1.17 (d, J=6.8 Hz, 6H).

Examples 82: Synthesis of (S)—N-(1-(2-(cyclopropanesulfonamido)pyrimidin-4-yl)propyl)-4-(6-ethoxypyrazin-2-yl)-2-fluorobenzamide, Z-4 and (R)—N-(1-(2-(cyclopropanesulfonamido)pyrimidin-4-yl)propyl)-4-(6-ethoxypyrazin-2-yl)-2-fluorobenzamide, Z-5

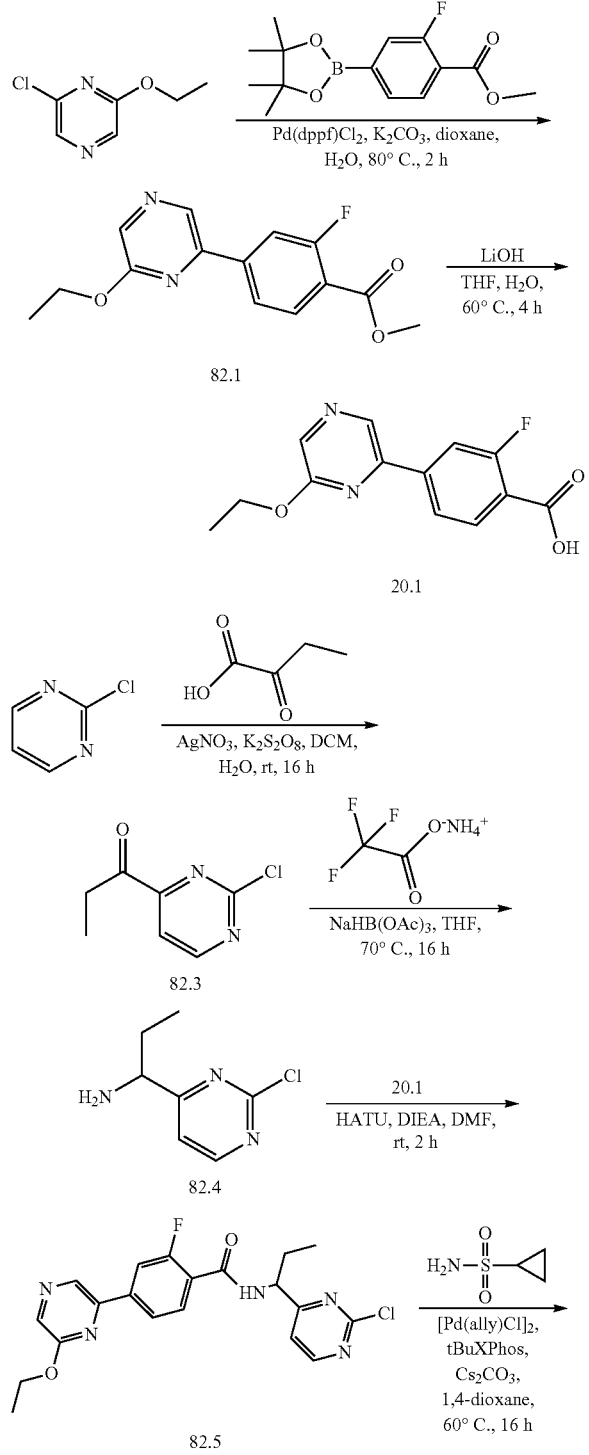

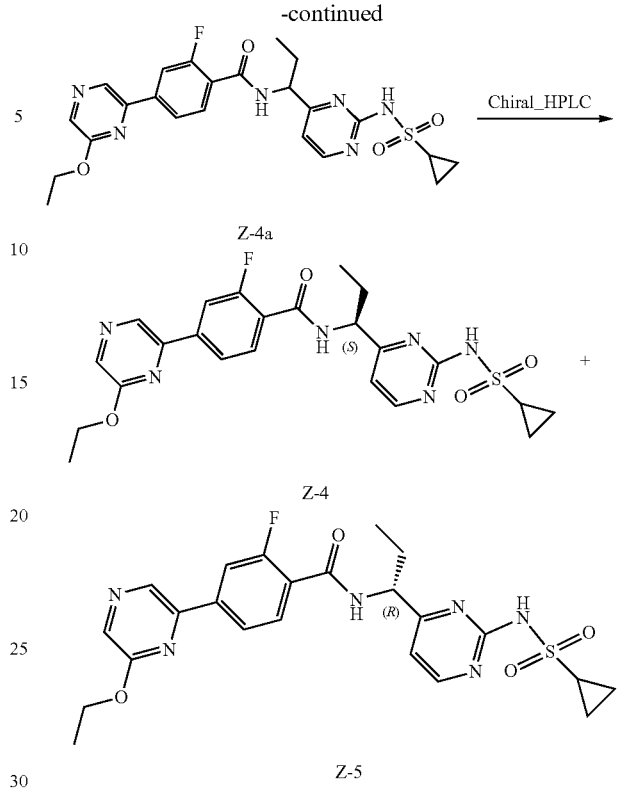

Synthesis of 82.1. To a solution of 2-chloro-6-ethoxypyrazine (4.74 g, 30.00 mmol, 1.0 eq) and methyl 4-(4,4,5,5-tetramethyl-1,3,2-dioxaborolan-2-yl)benzoate (10.08 g, 36.00 mmol, 1.2 eq) in 1,4-dioxane (120 mL) and water (40 mL) was added potassium carbonate (12.42 g, 90.00 mmol, 3.0 eq) and Pd(dppf)Cl$_2$ (1.22 g, 1.50 mmol, 0.05 eq). The resulting solution was stirred for 2 h at 80° C. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain methyl 4-(6-ethoxypyrazin-2-yl)-2-fluorobenzoate (82.1) as an off-white solid. (6.79 g, 82%), MS (ES): m/z 277 [M+H]$^+$.

Synthesis of 20.1. To a solution of 82.1 (6.79 g, 24.60 mmol, 1.0 eq) in tetrahydrofuran (100 mL) and water (20 mL) was added lithium hydroxide (1.77 g, 73.80 mmol, 3.0 equiv). The resulting solution was stirred for 4 h at 60° C. The mixture was cooled to r.t and concentrated under vacuum. The residue was diluted with water. The pH value of the solution was adjusted to 3 with 1N hydrochloric acid. The solids were collected by filtration and dried in an oven at 45° C. to obtain 4-(6-ethoxypyrazin-2-yl)-2-fluorobenzoic acid (20.1) as a white solid. (4.83 g, 75%), MS (ES): m/z 263 [M+H]$^+$.

Synthesis of 82.3. To a solution of 2-oxobutanoic acid (7.39 g, 72.47 mmol, 1.0 eq), 2-chloropyrimidine (10.00 g, 86.96 mmol, 1.2 eq) and potassium persulfate (19.57 g, 72.47 mmol, 1.0 eq) in dichloromethane (100 mL) and water (100 mL) was added silver nitrate (2.46 g, 14.50 mmol, 0.2 equiv) at 0° C. The resulting solution was stirred for 16 h at r.t. The mixture was diluted with water and extracted with dichloromethane. The combined organic layer was washed with brine, dried over sodium sulfate and concentrated under reduced pressure. The residue was purified by silica gel column chromatography and compound was eluted in 20% ethyl acetate in petroleum ether to obtain 1-(2-chloropyrimidin-4-yl)propan-1-one (82.3) as a yellow oil. (4.40 g, 36%), MS (ES): m/z 171 [M+H]+.

Synthesis of 82.4. To a solution of 82.3 (4.40 g, 25.88 mmol, 1.0 eq) and ammonium 2,2,2-trifluoroacetate (33.90 g, 258.80 mmol, 10.0 eq) in tetrahydrofuran (150 mL) was added sodium triacetoxyborohydride (8.23 g, 38.82 mmol, 1.5 equiv) at r.t. The resulting solution was stirred for 16 h at 70° C. The mixture was cooled to r.t, diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (10% NH$_4$HCO$_3$) and ACN (11% ACN up to 20% in 10 min); UV detection at 254/220 nm. The product-containing fractions were combined and concentrated under reduced pressure to afford 1-(2-chloropyrimidin-4-yl)propan-1-amine (82.4) as a yellow oil. (2.51 g, 57%), MS (ES): m/z 172 [M+H]+.

Synthesis of 82.5. To a solution of 82.4 (364.0 mg, 2.13 mmol, 1.0 eq) and 20.1 (558.0 mg, 2.13 mmol, 1.0 eq) in N,N-dimethylformamide (10 mL) was added DIEA (824.3 mg, 6.39 mmol, 3.0 equiv) and HATU (971.3 mg, 2.56 mmol, 1.2 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (10% NH$_4$HCO$_3$) and ACN (31% ACN up to 46% in 10 min); UV detection at 254/220 nm. The product-containing fractions were combined and concentrated under reduced pressure to afford N-(1-(2-chloropyrimidin-4-yl)propyl)-4-(6-ethoxypyrazin-2-yl)-2-fluorobenzamide (82.5) as a yellow solid. (0.48 g, 54%), MS (ES): m/z 416 [M+H]+.

Synthesis of Z-4a. To a solution of 82.5 (280 mg, 0.68 mmol, 1.00 equiv) and cyclopropanesulfonamide (164.5 mg, 1.36 mmol, 2.0 equiv) in 1,4-dioxane (10 mL) was added cesium carbonate (665.0 mg, 2.04 mmol, 3.0 equiv), t-BuXPhos (30.0 mg, 0.07 mmol, 0.1 equiv) and [Pd(ally)Cl]$_2$ (14.7 mg, 0.04 mmol, 0.05 equiv) at room temperature under nitrogen atmosphere. The reaction mixture was stirred for 16 h at 60° C. The mixture was cooled to r.t, diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 5 um, 19*150 mm; Mobile Phase, water (10% NH$_4$HCO$_3$) and ACN (29% ACN up to 41% in 7 min); UV detection at 254/220 nm. The product-containing fractions were combined and evaporated partially in vacuo and lyophilized overnight to afford N-(1-(2-(cyclopropanesulfonamido)pyrimidin-4-yl)propyl)-4-(6-ethoxypyrazin-2-yl)-2-fluorobenzamide (Z-4a) as a white solid. (90.0 mg, 27%), MS (ES): m/z 501 [M+H]+;

Synthesis of Z-4 and Z-5. The N-(1-(2-(cyclopropanesulfonamido)pyrimidin-4-yl)propyl)-4-(6-ethoxypyrazin-2-yl)-2-fluorobenzamide (60.0 mg, 0.12 mmol, 1.00 equiv) was separated by Chiral-Prep-HPLC with the following conditions: Column, CHIRALPAK AS-H, 2*25 mm, 5 um; mobile phase, Hex (0.1% FA): ethanol=70:30; UV detection at 254/220 nm. The product-containing fractions were combined and concentrated under reduced pressure to afford (S)—N-(1-(2-(cyclopropanesulfonamido)pyrimidin-4-yl) propyl)-4-(6-ethoxypyrazin-2-yl)-2-fluorobenzamide (Z-4, 23.9 mg, 40%, second peak) and (R)—N-(1-(2-(cyclopropanesulfonamido)pyrimidin-4-yl)propyl)-4-(6-ethoxypyrazin-2-yl)-2-fluorobenzamide as a white solid. (Z-5, 25.3 mg, 42%, first peak).

Z-4: MS (ES): m/z 501 [M+H]+; $^1$H NMR (400 MHz, CD$_3$OD) δ 8.75 (s, 1H), 8.52 (d, J=5.2 Hz, 1H), 8.21 (s, 1H), 8.06-8.00 (m, 2H), 7.87 (t, J=7.6 Hz, 1H), 7.13 (d, J=5.2 Hz, 1H), 5.06 (dd, J=8.8 Hz, 1H), 4.57 (q, J=7.2 Hz, 2H), 3.29-3.26 (m, 1H), 2.18-2.05 (m, 1H), 1.97-1.89 (m, 1H), 1.49 (t, J=7 Hz, 3H), 1.31-1.23 (m, 2H), 1.08 (t, J=7.4 Hz, 3H), 1.05-0.99 (m, 2H). Z-5: MS (ES): m/z 501 [M+H]+; $^1$H NMR (400 MHz, CD$_3$OD) δ 8.75 (s, 1H), 8.52 (d, J=5.2 Hz, 1H), 8.21 (s, 1H), 8.06-8.00 (m, 2H), 7.87 (t, J=7.6 Hz, 1H), 7.14 (d, J=5.2 Hz, 1H), 5.06 (dd, J=8.8 Hz, 1H), 4.57 (q, J=7.2 Hz, 2H), 3.29-3.26 (m, 1H), 2.18-2.05 (m, 1H), 1.97-1.89 (m, 1H), 1.49 (t, J=7 Hz, 3H), 1.31-1.23 (m, 2H), 1.08 (t, J=7.4 Hz, 3H), 1.05-0.99 (m, 2H).

Example 83: Synthesis of N-((2-(cyclopropanesulfonamido)thiazol-4-yl)methyl)-N-methyl-4-(6-(trifluoromethyl)pyrazin-2-yl)benzamide, Z-6

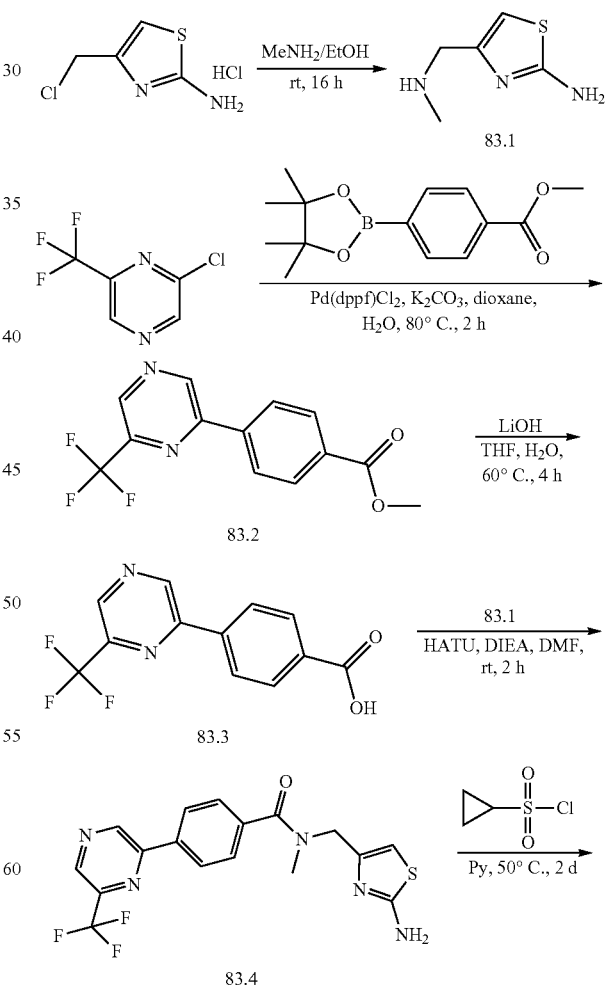

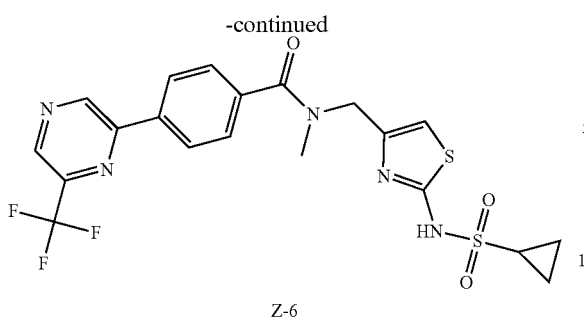

Z-6

Synthesis of 83.1. A solution of 4-(chloromethyl)thiazol-2-amine hydrochloride (740.0 mg, 4.00 mmol, 1.0 eq) in methylamineethanolsolution (30%, 20 mL) was stirred for 16 h at r.t. The mixture was concentrated under reduced pressure. The residue was purified by reverse flash with the following conditions: Column, C18 Column; Mobile Phase, water (10% NH$_4$HCO$_3$) and ACN (15% ACN up to 30% in 10 min); UV detection at 254/220 nm. The product-containing fractions were combined and concentrated under reduced pressure to afford 4-((methylamino)methyl)thiazol-2-amine (83.1) as a yellow solid. (0.30 g, 52%), MS (ES): m/z 144 [M+H]$^+$.

Synthesis of 83.2. To a solution of 2-chloro-6-(trifluoromethyl)pyrazine (546.0 mg, 3.00 mmol, 1.0 eq) and methyl 4-(4,4,5,5-tetramethyl-1,3,2-dioxaborolan-2-yl)benzoate (943.2 mg, 3.60 mmol, 1.2 eq) in 1,4-dioxane (20 mL) and water (4 mL) was added potassium carbonate (1.24 g, 9.00 mmol, 3.0 eq) and Pd(dppf)Cl$_2$ (244.8 mg, 0.30 mmol, 0.1 eq). The resulting solution was stirred for 2 h at 80° C. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 30% ethyl acetate in petroleum ether to obtain methyl 4-(6-(trifluoromethyl)pyrazin-2-yl)benzoate (83.2) as an off-white solid. (0.72 g, 85%), MS (ES): m/z 283 [M+H]$^+$.

Synthesis of 83.3. To a solution of 83.2 (720.0 mg, 2.55 mmol, 1.0 eq) in tetrahydrofuran (16 mL) and water (4 mL) was added lithium hydroxide (183.6 mg, 7.65 mmol, 3.0 equiv). The resulting solution was stirred for 4 h at 60° C. The mixture was cooled to r.t and concentrated under vacuum. The residue was diluted with water. The pH value of the solution was adjusted to 3 with 1N hydrochloric acid. The solids were collected by filtration and washed with water, dried at 45° C. to obtain 4-(6-(trifluoromethyl)pyrazin-2-yl)benzoic acid (83.3) as a white solid. (0.50 g, 73%), MS (ES): m/z 269 [M+H]$^+$.

Synthesis of 83.4. To a solution of 83.3 (300.0 mg, 1.12 mmol, 1.0 eq) and 83.1 (160.2 mg, 1.12 mmol, 1.0 eq) in N,N-dimethylformamide (10 mL) was added DIEA (433.4 mg, 3.36 mmol, 3.0 equiv) and HATU (509.2 mg, 1.34 mmol, 1.2 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (10% NH$_4$HCO$_3$) and ACN (21% ACN up to 36% in 10 min); UV detection at 254/220 nm. The product-containing fractions were combined and concentrated under reduced pressure to afford N-((2-aminothiazol-4-yl)methyl)-N-methyl-4-(6-(trifluoromethyl)pyrazin-2-yl)benzamide (83.4) as a yellow solid. (0.31 g, 71%), MS (ES): m/z 394 [M+H]$^+$.

Synthesis of Z-6. To a solution of 83.4 (310.0 mg, 0.79 mmol, 1.0 eq) in pyridine (5 mL) was added cyclopropanesulfonyl chloride (553.0 mg, 3.95 mmol, 5.0 equiv) at r.t. The resulting solution was stirred for 2 days at 50° C. The mixture was cooled to r.t, diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 5 um, 19*150 mm; Mobile Phase, water (10% NH$_4$HCO$_3$) and ACN (26% ACN up to 41% in 7 min); UV detection at 254/220 nm. The product-containing fractions were combined and evaporated partially in vacuo and lyophilized overnight to afford the title compound as a white solid. (17.7 mg, 4.5%), MS (ES): m/z 498 [M+H]$^+$; $^1$H NMR (400 MHz, d$_6$-DMSO) δ 12.62 (br s, 1H), 9.68 (s, 1H), 9.20 (s, 1H), 8.29 (d, J=7.2 Hz, 2H), 7.72 (d, J=7.2 Hz, 2H), 6.70 (s, 1H), 4.63-4.25 (m, 2H), 2.96 (s, 3H), 2.66-2.58 (m, 1H), 0.98-0.86 (m, 4H).

Example 84: Synthesis of tert-butyl 2-(3-(1-(2-(cyclopropanesulfonamido)thiazol-4-yl)-2-(4-(6-ethoxypyrazin-2-yl)phenylamino)-2-oxoethylamino)-3-oxopropoxy)ethylcarbamate, Z-7

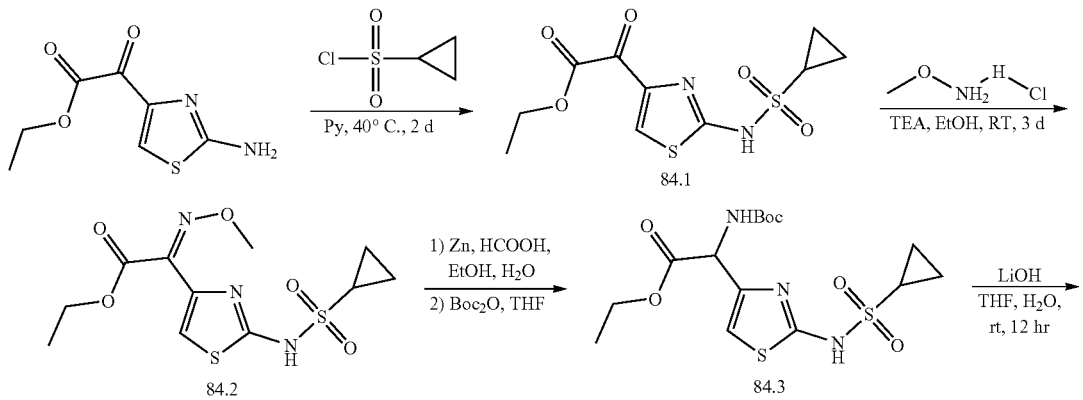

-continued

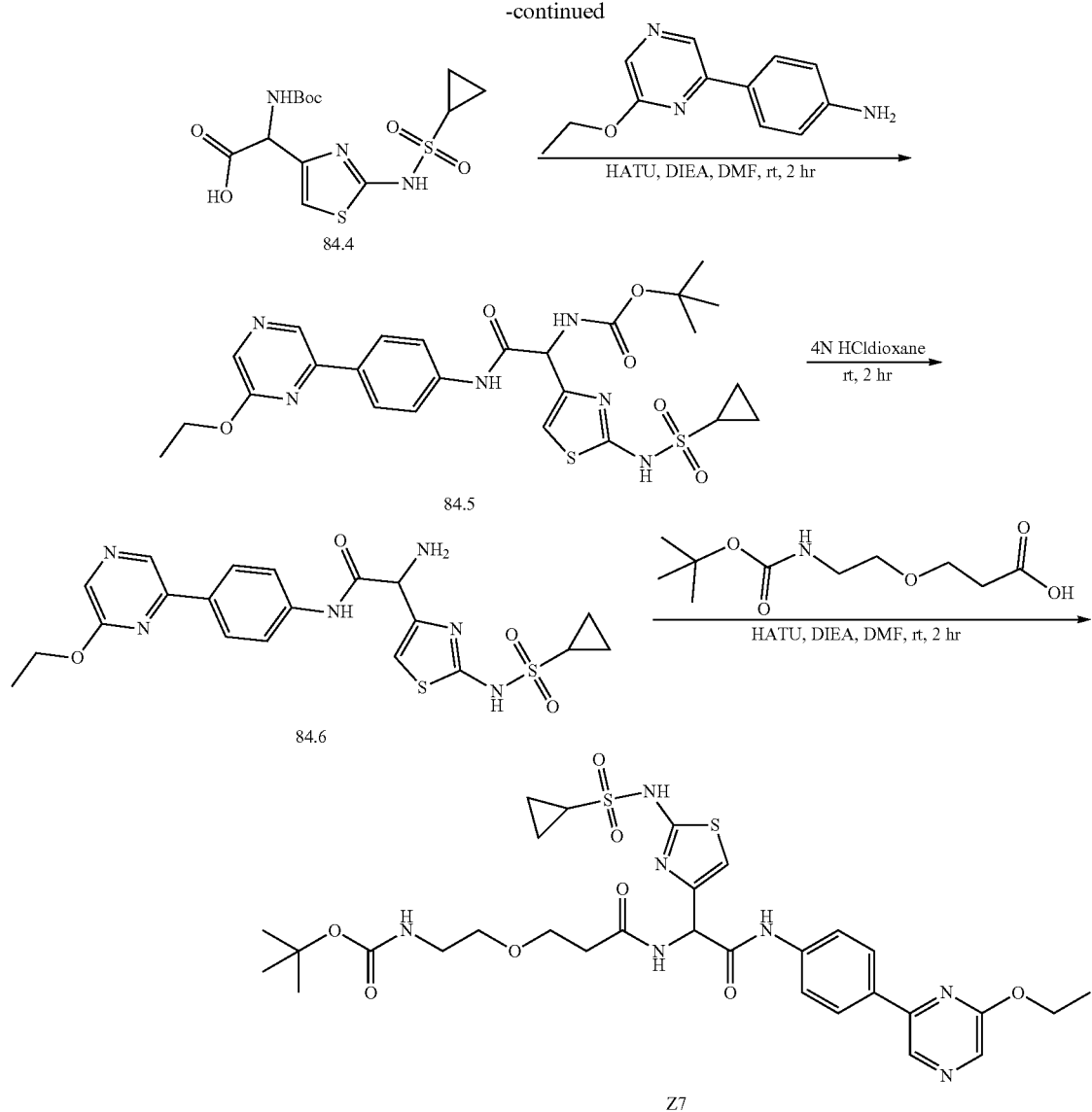

Synthesis of 84.1. To a solution of ethyl 2-(2-aminothiazol-4-yl)-2-oxoacetate (5.00 g, 25.00 mmol, 1.0 eq) in pyridine (100 mL) was added cyclopropanesulfonyl chloride (7.00 g, 50.00 mmol, 2.0 eq). The resulting solution was stirred for 2 d at 40° C. The mixture was cooled to r.t, diluted with water and extracted with ethyl acetate. The combined organic layer was washed with brine, dried over sodium sulfate and concentrated under reduced pressure. The residue was purified by silica gel column chromatography and compound was eluted in 50% ethyl acetate in petroleum ether to obtain ethyl 2-(2-(cyclopropanesulfonamido)thiazol-4-yl)-2-oxoacetate (84.1) as a brown oil. (2.46 g, 32%), MS (ES): m/z 305 [M+H]⁺.

Synthesis of 84.2. To a solution of 84.1 (2.46 g, 8.10 mmol, 1.0 eq) and O-methylhydroxylamine hydrochloride (1.02 g, 12.15 mmol, 1.5 eq) in ethanol (40 mL) was added triethylamine (1.64 g, 16.20 mmol, 2.0 eq) at r.t. The resulting solution was stirred for 3 d at r.t. The mixture was diluted with water and extracted with ethyl acetate. The combined organic layer was washed with brine, dried over sodium sulfate and concentrated under reduced pressure to obtain (E)-ethyl 2-(2-(cyclopropanesulfonamido)thiazol-4-yl)-2-(methoxyimino)acetate (84.2) as a yellow oil. (2.00 g, 74%), MS (ES): m/z 334 [M+H]⁺.

Synthesis of 84.3. To a solution of 84.2 (2.00 g, 5.99 mmol, 1.0 eq) in ethanol (25 mL) and water (8 mL) was added formic acid (8 mL) and zinc (1.17 g, 17.96 mmol, 3.0 eq) at 0° C. The resulting solution was stirred for 2 h at r.t. The solids were filtered out. The filtrate was concentrated under reduced pressure. To the residue was added tetrahydrofuran (30 mL), sat. sodium bicarbonate solution (30 mL) and di-tert-butyl dicarbonate (2.61 g, 11.98 mmol, 2.0 eq). The resulting solution was stirred for 2 h at r.t. The mixture was diluted with water and extracted with ethyl acetate. The combined organic layer was washed with brine, dried over sodium sulfate and concentrated under reduced pressure. The residue was purified by silica gel column chromatography and compound was eluted in 50% ethyl acetate in petroleum ether to obtain ethyl 2-(tert-butoxycarbonylamino)-2-(2-(cyclopropanesulfonamido)thiazol-4-yl)acetate (84.3) as a colorless gum. (0.80 g, 33%), MS (ES): m/z 406 [M+H]⁺.

Synthesis of 84.4. To a solution of 84.3 (0.80 g, 1.98 mmol, 1.0 eq) in tetrahydrofuran (16 mL) and water (4 mL) was added lithium hydroxide (142.6 mg, 5.94 mmol, 3.0 equiv). The resulting solution was stirred for 12 h at r.t. The mixture was concentrated under vacuum. The residue was diluted with water. The pH value of the solution was adjusted to 3 with 1N hydrochloric acid. The solids were collected by filtration and dried in an oven at 45° C. to obtain 2-(tert-butoxycarbonylamino)-2-(2-(cyclopropanesulfonamido)thiazol-4-yl)acetic acid (84.4) as an off-white solid. (0.61 g, 82%), MS (ES): m/z 322 [M−56+H]$^+$.

Synthesis of 84.5. To a solution of 84.4 (610.0 mg, 1.62 mmol, 1.0 eq) and 4-(6-ethoxypyrazin-2-yl)benzenamine (347.9 mg, 1.62 mmol, 1.0 eq) in N,N-dimethylformamide (10 mL) was added DIEA (626.2 mg, 4.86 mmol, 3.0 equiv) and HATU (737.8 mg, 1.94 mmol, 1.2 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by reverse flash with the following conditions: Column, C18 Column; Mobile Phase, water (10% NH$_4$HCO$_3$) and ACN (45% ACN up to 60% in 10 min); UV detection at 254/220 nm. The product-containing fractions were combined and concentrated under reduced pressure to afford tert-butyl 1-(2-(cyclopropanesulfonamido)thiazol-4-yl)-2-(4-(6-ethoxypyrazin-2-yl)phenylamino)-2-oxoethylcarbamate (84.5) as a yellow solid. (0.60 g, 65%), MS (ES): m/z 573 [M−H]$^+$.

Synthesis of 84.6. A solution of 84.5 (600.0 mg, 1.04 mmol, 1.0 eq) in hydrochloric acid in 1,4-dioxane (4.0 M, 8 mL) was stirred for 2 h at r.t. The mixture was concentrated under reduced pressure to afford 2-amino-2-(2-(cyclopropanesulfonamido)thiazol-4-yl)-N-(4-(6-ethoxypyrazin-2-yl)phenyl)acetamide hydrochloride (84.6) as an off-white solid. (0.54 g, 100%), MS (ES): m/z 475 [M+H]$^+$.

Synthesis of Z-7. To a solution of 84.6 (100.0 mg, 0.20 mmol, 1.0 eq) and 3-(2-(tert-butoxycarbonylamino)ethoxy)propanoic acid (45.7 mg, 0.20 mmol, 1.0 eq) in N, N-dimethylformamide (5 mL) was added DIEA (129.0 mg, 1.00 mmol, 5.0 equiv) and HATU (91.2 mg, 0.24 mmol, 1.2 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (30% ACN up to 45% in 7 min); UV detection at 254/220 nm. The product-containing fractions were combined and evaporated partially in vacuo and lyophilized overnight to afford the title compound as a white solid. (33.3 mg, 25%), MS (ES): m/z 690 [M+H]$^+$; $^1$H NMR (400 MHz, d$_6$-DMSO) δ 10.55 (s, 1H), 8.78 (s, 1H), 9.68 (d, J=7.6 Hz, 1H), 8.19 (s, 1H), 8.13 (d, J=8.8 Hz, 2H), 7.78 (d, J=8.8 Hz, 2H), 6.75 (t, J=5.2 Hz, 1H), 6.58 (s, 1H), 5.54 (d, J=7.6 Hz, 1H), 4.48 (q, J=7.2 Hz, 2H), 3.63 (t, J=4.8 Hz, 2H), 3.37 (t, J=6 Hz, 2H), 3.09-3.05 (m, 2H), 2.64-2.55 (m, 1H), 2.49-2.43 (m, 2H), 1.40 (t, J=7.2 Hz, 3H), 1.38 (s, 9H), 0.94-0.85 (m, 4H).

Example 85: Synthesis of tert-butyl 2-(2-(3-(1-(2-(cyclopropanesulfonamido)thiazol-4-yl)-2-(4-(6-ethoxypyrazin-2-yl)phenylamino)-2-oxoethylamino)-3-oxopropoxy)ethoxy)ethylcarbamate, Z-8

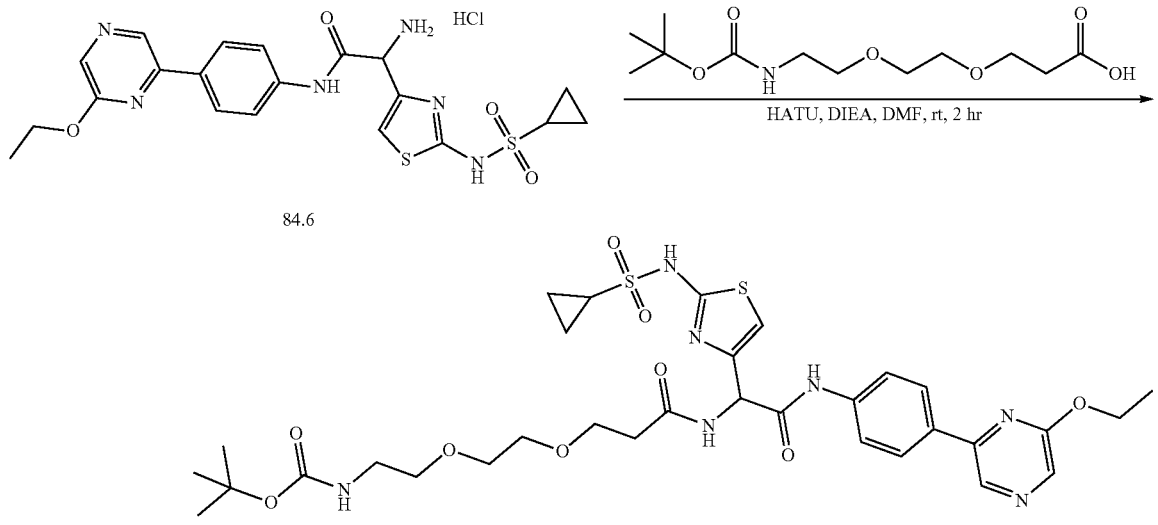

Synthesis of Z-8. To a solution of 84.6 (100.0 mg, 0.20 mmol, 1.0 eq) and 2,2-dimethyl-4-oxo-3,8,11-trioxa-5-azatetradecan-14-oic acid (55.4 mg, 0.20 mmol, 1.0 eq) in N/N-dimethylformamide (5 mL) was added DIEA (129.0 mg, 1.00 mmol, 5.0 equiv) and HATU (91.2 mg, 0.24 mmol, 1.2 equiv) at r.t. The resulting solution was stirred for 2 h at r.t. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Prep OBD C18 Column, 30*150 mm, 5 um; Mobile Phase, water (10% NH$_4$HCO$_3$) and ACN (26% ACN up to 41% in 7 min); UV detection at 254/220 nm. The product-containing fractions were combined and evaporated partially in vacuo and lyophilized overnight to afford the title compound as a white solid. (38.5 mg, 26%), MS (ES): m/z 734 [M+H]$^+$; $^1$H NMR (400 MHz, d₆-DMSO) δ 12.41 (br s, 1H), 10.55 (s, 1H), 8.78 (s, 1H), 8.67 (br s, 1H), 8.19 (s, 1H), 8.13 (d, J=8.4 Hz, 2H), 7.78 (d, J=8.8 Hz, 2H), 6.75 (s, 1H), 6.58 (s, 1H), 5.54 (d, J=7.2 Hz, 1H), 4.48 (q, J=7.2 Hz, 2H), 3.65 (t, J=6.4 Hz, 2H), 3.56-3.47 (m, 4H), 3.37 (t, J=5.6 Hz, 2H), 3.13-3.02 (m, 2H), 2.64-2.52 (m, 1H), 2.51 (t, J=5.6 Hz, 2H), 1.40 (t, J=7.2 Hz, 3H), 1.35 (s, 9H), 0.96-0.81 (m, 4H).

General Method 1

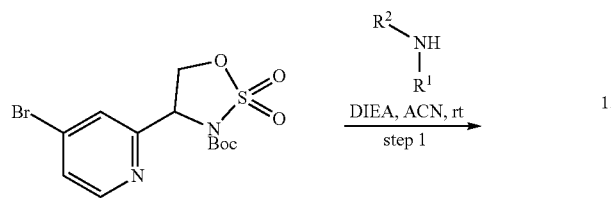

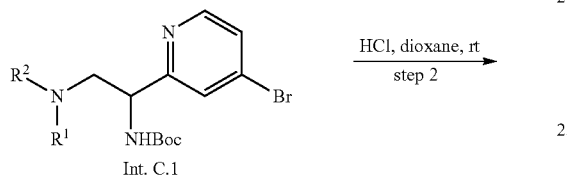

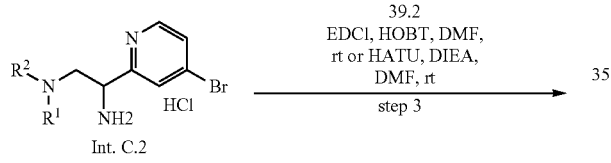

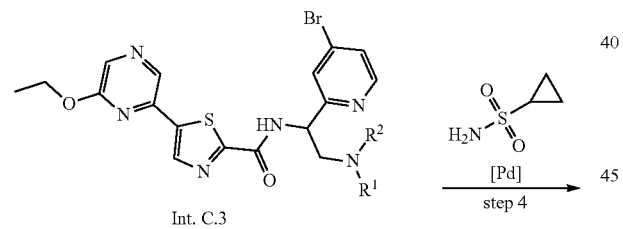

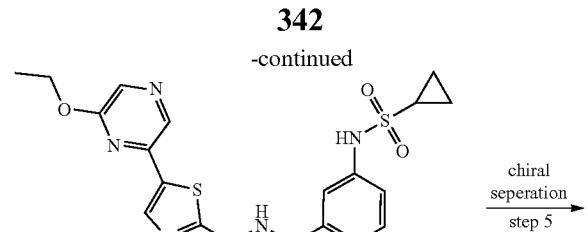

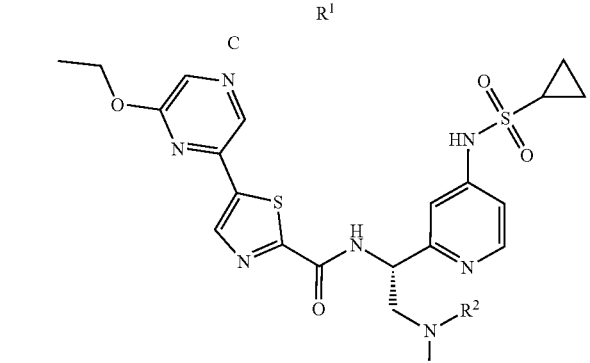

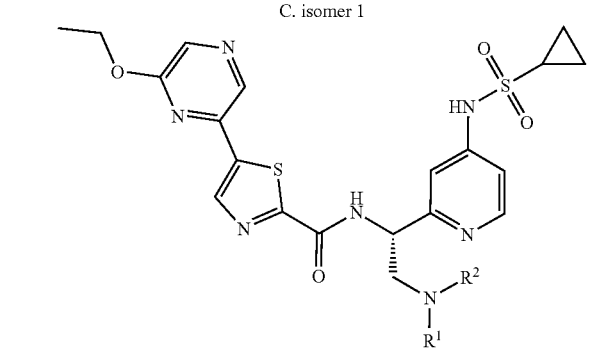

Example 87: Synthesis of N—((R)-2-((1R,4R)-2-oxa-5-azabicyclo[2.2.1]heptan-5-yl)-1-(4-(cyclopropanesulfonamido)pyridin-2-yl)ethyl)-5-(6-ethoxypyrazin-2-yl)thiazole-2-carboxamide, isomer 1 (I-112) and N—((S)-2-((1R,4R)-2-oxa-5-azabicyclo[2.2.1]heptan-5-yl)-1-(4-(cyclopropanesulfonamido)pyridin-2-yl)ethyl)-5-(6-ethoxypyrazin-2-yl)thiazole-2-carboxamide, isomer 2 (I-113). Stereochemistry Alpha to the Central Amide Arbitrarily Assigned

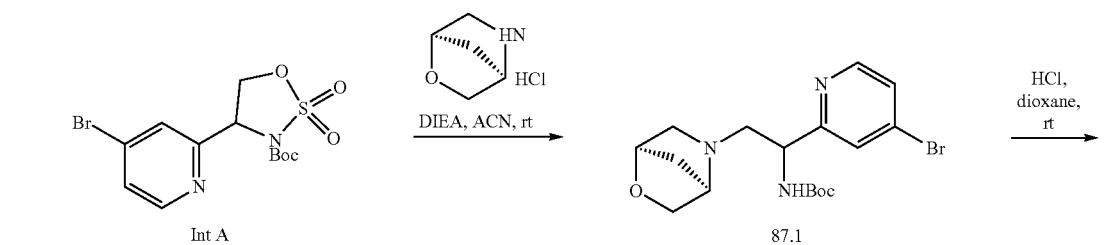

-continued

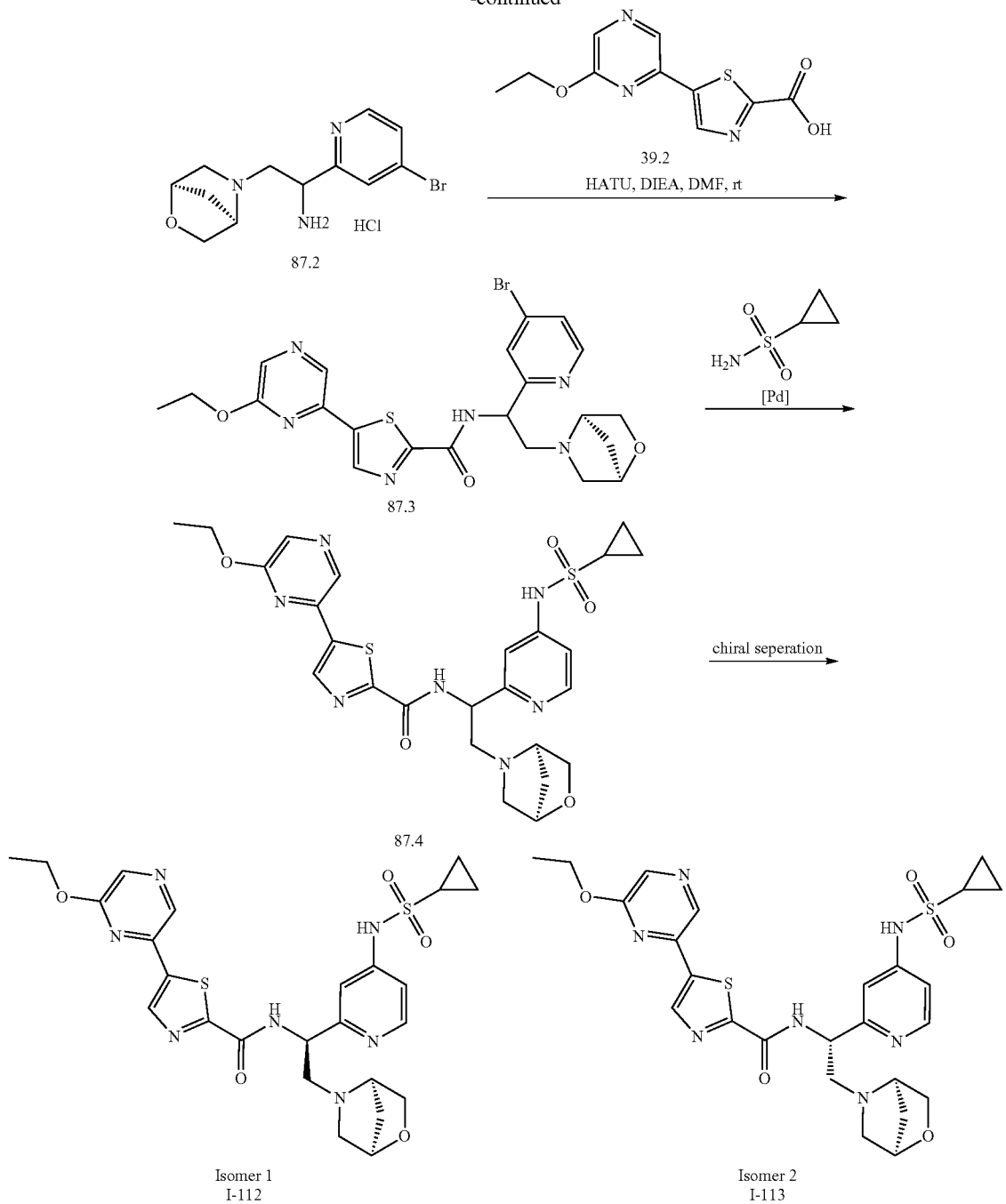

Isomer 1
I-112

Isomer 2
I-113

General Method 1, Step 1, synthesis of 87.1. A solution of (1R,4R)-2-oxa-5-azabicyclo[2.2.1] heptane hydrochloride (6.4 g, 47.1 mmol, 1.2 eq) and ethyldiisopropylamine (10.2 g, 79.1 mmol, 2 eq) in acetonitrile (120 mL) was stirred at room temperature for 30 min. Int. A (15 g, 39.6 mmol, 1 eq) was added in portions. The resulting mixture was stirred for 1 h at room temperature. The reaction was concentrated under reduced pressure. The residue was purified by flash column chromatography on C18 silica (compound eluted with 90% acetonitrile in water) to afford ter-butyl N-[1-(4-bromopyridin-2-yl)-2-[(1R,4R)-2-oxa-5-azabicyclo[2.2.1]heptan-5-yl]ethyl]carbamate (87.1, 13.6 g, 86%) as a light yellow solid. MS (ES): m/z 398/400 [M+H]$^+$.

General Method 1, Step 2, synthesis of 87.2. To a stirred solution of 87.1 (380 mg, 0.95 mmol, 1 equiv) in 1,4-dioxane (2 mL) was added HCl in 1,4-dioxane (4M, 2 mL, 8 mmol, 8.4 equiv) dropwise at room temperature. The resulting mixture was stirred at room temperature for 30 min. The reaction mixture was filtered. The solid was collected and dried under vacuum to afford 2-((1R,4R)-2-oxa-5-azabicyclo[2.2.1]heptan-5-yl)-1-(4-bromopyridin-2-yl)ethan-1-amine hydrochloride (87.2, 290 mg, HCl salt, 91%) as a white solid. MS (ES): m/z 298 [M+H]$^+$.

General Method 1, Step 3, synthesis of 87.3. To a stirred mixture of 87.2 (290 mg, 0.87 mmol, 1 equiv) and 39.2 (250 mg, 0.87 mmol, 1 equiv) in DMF (4 mL) were added HATU (397 mg, 1.04 mmol, 1.2 equiv) and DIEA (337 mg, 2.61 mmol, 3 equiv) in portions at room temperature. The resulting mixture was stirred at room temperature for 2 h. The reaction mixture was concentrated under vacuum. The residue was purified by flash column chromatography on silica gel (eluted with dichloromethane/methanol, 20/1) to afford N-[1-(4-bromopyridin-2-yl)-2-[(1S,4S)-2-oxa-5-azabicyclo[2.2.1]heptan-5-yl]ethyl]-5-(6-ethoxypyrazin-2-yl)-1,3-thiazole-2-carboxamide (87.3, 300 mg, 65%) as a yellow solid. MS (ES): m/z 531 [M+H]⁺.

General Method 1, Step 4, Synthesis of 87.4. To a stirred solution of 87.3 (300 mg, 0.57 mmol, 1 equiv) in 1,4-dioxane (3 mL) were added cyclopropanesulfonamide (274 mg, 2.28 mmol, 4 equiv), EPhos (30 mg, 0.06 mmol, 0.1 equiv), EPhos Pd G4 (104 mg, 0.11 mmol, 0.2 equiv), cesium carbonate (552 mg, 1.71 mmol, 3 equiv). The resulting solution was stirred for 2 h at 90° C. under nitrogen atmosphere. The mixture was concentrated under reduced pressure. The residue was purified by flash column chromatography on silica gel (eluted with dichloromethane/methanol, 10/1) to afford N-[1-(4-cyclopropanesulfonamidopyridin-2-yl)-2-[(1R,4R)-2-oxa-5-azabicyclo[2.2.1]heptan-5-yl]ethyl]-5-(6-ethoxypyrazin-2-yl)-1,3-thiazole-2-carboxamide (87.4, 200 mg, 61%) as a yellow solid. MS (ES): m/z 572 [M+H]⁺.

General Method 1, Step 5, synthesis of I-112 and I-113. 87.4 (200 g) was purified by chiral HPLC (Column: CHIRALPAK IG, 2*25 cm, 5 μm; Mobile Phase A: Hex:DCM=3:1(0.5% 2M NH₃-MeOH)-HPLC, Mobile Phase B: EtOH-HPLC; Flow rate: 20 mL/min; Gradient: 40% B to 40% B in 22 min; Wave Length: 220/254 nm) to give N—((R)-2-((1R,4R)-2-oxa-5-azabicyclo[2.2.1]heptan-5-yl)-1-(4-(cyclopropanesulfonamido)pyridin-2-yl)ethyl)-5-(6-ethoxypyrazin-2-yl)thiazole-2-carboxamide, isomer 1 (I-112, 24 mg, first eluting peak) and N—((S)-2-((1R,4R)-2-oxa-5-azabicyclo[2.2.1]heptan-5-yl)-1-(4-(cyclopropanesulfonamido)pyridin-2-yl)ethyl)-5-(6-ethoxypyrazin-2-yl)thiazole-2-carboxamide, isomer 2 I-113, 43 mg, second eluting peak). I-112: MS (ES): m/z 572 [M+H]⁺; ¹H NMR (300 MHz, Methana-d₄) δ 8.70 (s, 1H), 8.59 (s, 1H), 8.25 (d, J=6.0 Hz, 1H), 8.14 (s, 1H), 7.25 (d, J=2.4 Hz, 1H), 7.09 (dd, J=6.0, 2.0 Hz, 1H), 5.09-5.05 (m, 1H), 4.47 (q, J=7.2 Hz, 2H), 4.37 (s, 1H), 4.00 (d, J=7.8 Hz, 1H), 3.62 (dd, J=7.8, 1.8 Hz, 1H), 3.52 (s, 1H), 3.25-3.19 (m, 1H), 3.24-3.08 (m, 1H), 2.90-2.86 (m, 1H), 2.72-2.63 (m, 1H), 2.53 (d, J=10.2 Hz, 1H), 1.88-1.84 (m, 1H), 1.73-1.68 (m, 1H), 1.44 (t, J=7.2 Hz, 3H), 1.14-1.07 (m, 2H), 0.99-0.94 (m, 2H). I-112: MS (ES): m/z 572 [M+H]⁺; ¹H NMR (400 MHz, Methanal-d₄) δ 8.69 (s, 1H), 8.58 (s, 1H), 8.29 (d, J=6.0 Hz, 1H), 8.14 (s, 1H), 7.30 (d, J=2.0 Hz, 1H), 7.13 (dd, J=6.0, 2.0 Hz, 1H), 5.09-5.06 (m, 1H), 4.47 (q, J=7.2 Hz, 2H), 4.39 (s, 1H), 3.96 (d, J=7.6 Hz, 1H), 3.61 (dd, J=7.6, 1.6 Hz, 1H), 3.56 (s, 1H), 3.19-3.07 (m, 2H), 2.87-2.84 (m, 1H), 2.74-2.68 (m, 1H), 2.63 (d, J=10.0 Hz, 1H), 1.89-1.86 (m, 1H), 1.73-1.70 (m, 1H), 1.44 (t, J=7.2 Hz, 3H), 1.15-1.10 (m, 2H), 1.01-0.96 (m, 2H).

Table 3 shows compounds prepared according to General Method 1:

TABLE 3

| Compound Number | Name/Structure Stereochemistry alpha to central amide arbitrarily assigned | Amine reagent used in Step 1 | Chiral chromatography method | MS (ES): m/z [M + H]⁺ | ¹H NMR |
|---|---|---|---|---|---|
| I-241 | N-(1-(4-(cyclopropanesulfonamido)pyridin-2-yl)-2-(dimethylamino)ethyl)-5-(6-ethoxypyrazin-2-yl)thiazole-2-carboxamide 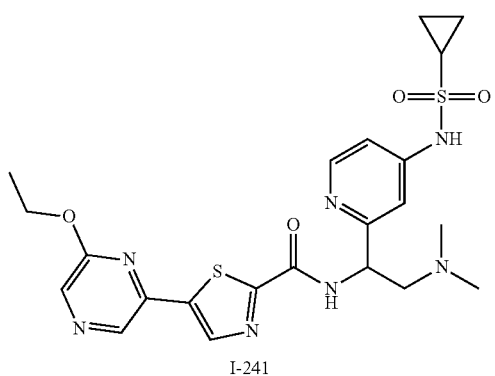 I-241 | Dimethylamine hydrochloride | | 518 | (400 MHz, Methanol-d₄) δ 8.72 (s, 1H), 8.62 (s, 1H), 8.37 (d, J = 6.0 Hz, 1H), 8.18 (s, 1H), 7.34 (d, J = 2.4 Hz, 1H), 7.18 (dd, J = 6.0, 2.4 Hz, 1H), 5.42 (dd, J = 8.8, 5.6 Hz, 1H), 4.50 (q, J = 7.2 Hz, 2H), 3.26-3.14 (m, 2H), 2.78-2.72 (m, 1H), 2.63 (s, 6H), 1.47 (t, J = 7.2 Hz, 3H), 1.19-1.14 (m, 2H), 1.03-0.99 (m, 2H). |

TABLE 3-continued

| Compound Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-233 | (R)-N-(1-(4-(cyclopropanesulfonamido)pyridin-2-yl)-2-(dimethylamino)ethyl)-5-(6-ethoxypyrazin-2-yl)thiazole-2-carboxamide<br><br>isomer 1<br>I-233 | dimethylamine | chiral HPLC (Column: CHIRALPAK IF, 2 * 25 cm, 5 μm; Mobile Phase A: MtBE (0.5% 2M NH$_3$—MeOH)--HPLC, Mobile Phase B: MeOH--HPLC; Flow rate: 16 mL/min; Gradient: 10% B to 10% B in 24 min; Wave Length: 220/254 nm) First eluting peak | 518 | (400 MHz, Methanol-d$_4$) δ 8.72 (s, 1H), 8.61 (s, 1H), 8.33 (d, J = 6.0 Hz, 1H), 8.17 (s, 1H), 7.32 (d, J = 2.4 Hz, 1H), 7.17 (dd, J = 6.0, 2.4 Hz, 1H), 5.30 (dd, J = 9.2, 5.6 Hz, 1H), 4.50 (q, J = 7.2 Hz, 2H), 3.04 (dd, J = 12.8, 9.2 Hz, 1H), 2.89 (dd, J = 12.8, 5.6 Hz, 1H), 2.77-2.71 (m, 1H), 2.45 (s, 6H), 1.47 (t, J = 7.2 Hz, 3H), 1.18-1.14 (m, 2H), 1.03-0.99 (m, 2H). |
| I-234 | (S)-N-(1-(4-(cyclopropanesulfonamido)pyridin-2-yl)-2-(dimethylamino)ethyl)-5-(6-ethoxypyrazin-2-yl)thiazole-2-carboxamide<br><br>isomer 2<br>I-234 | dimethylamine | Same as I-233 Second eluting peak | 518 | (400 MHz, Methanol-d$_4$) δ 8.71 (s, 1H), 8.61 (s, 1H), 8.32 (d, J = 6.0 Hz, 1H), 8.17 (s, 1H), 7.31 (d, J = 2.4 Hz, 1H), 7.16 (dd, J = 6.0, 2.4 Hz, 1H), 5.28 (dd, J = 9.2, 5.6 Hz, 1H), 4.50 (q, J = 7.2 Hz, 2H), 3.00 (dd, J = 12.8, 9.2 Hz, 1H), 2.84 (dd, J = 12.8, 5.6 Hz, 1H), 2.77-2.70 (m, 1H), 2.42 (s, 6H), 1.47 (t, J = 7.2 Hz, 3H), 1.18-1.13 (m, 2H), 1.03-0.98 (m, 2H). |
| I-245 | N-(1-(4-(cyclopropanesulfonamido)pyridin-2-yl)-2-morpholinoethyl)-5-(6-ethoxypyrazin-2-yl)thiazole-2-carboxamide<br><br>I-245 | morpholine | | 560 | (400 MHz, Methanol-d$_4$) δ 8.72 (s, 1H), 8.62 (s, 1H), 8.29 (d, J = 6.0 Hz, 1H), 8.17 (s, 1H), 7.31 (s, 1H), 7.12 (d, J = 6.0 Hz, 1H), 5.23 (dd, J = 8.8, 5.6 Hz, 1H), 4.50 (q, J = 7.2 Hz, 2H), 3.74-3.66 (m, 4H), 2.97-2.92 (m, 1H), 2.84-2.79 (m, 1H), 2.75-2.69 (m, 1H), 2.65-2.54 (m, 4H), 1.47 (t, J = 7.2 Hz, 3H), 1.17-1.10 (m, 2H), 1.02-0.97 (m, 2H) |

TABLE 3-continued

| Compound Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-235 | (S)-N-(1-(4-(cyclopropanesulfonamido)pyridin-2-yl)-2-morpholinoethyl)-5-(6-ethoxypyrazin-2-yl)thiazole-2-carboxamide<br>isomer 1<br>I-235 | morpholine | chiral HPLC (Column: CHIRALPAK ID, 2 * 25 cm, 5 μm; Mobile Phase A: MtBE (0.1% FA)--HPLC, Mobile Phase B: EtOH--HPLC; Flow rate: 18 mL/min; Gradient: 20% B to 20% B in 13 min; Wave Length: 254/220 nm) First eluting peak | 560 | (300 MHz, Methanol-$d_4$) δ 8.72 (s, 1H), 8.62 (s, 1H), 8.33 (d, J = 6.0 Hz, 1H), 8.17 (s, 1H), 7.34 (d, J = 2.4 Hz, 1H), 7.16 (dd, J = 6.0, 2.4 Hz, 1H), 5.25 (dd, J = 8.7, 5.7 Hz, 1H), 4.50 (q, J = 7.2 Hz, 2H), 3.75-3.65 (m, 4H), 2.99-2.92 (m, 1H), 2.87-2.81 (m, 1H), 2.79-2.72 (m, 1H), 2.68-2.53 (m, 4H), 1.47 (t, J = 7.2 Hz, 3H), 1.19-1.13 (m, 2H), 1.05-0.98 (m, 2H) |
| I-236 | (R)-N-(1-(4-(cyclopropanesulfonamido)pyridin-2-yl)-2-morpholinoethyl)-5-(6-ethoxypyrazin-2-yl)thiazole-2-carboxamide<br>isomer 2<br>I-236 | morpholine | Same as I-235 Second eluting peak | 560 | (300 MHz, Methanol-$d_4$) δ 8.72 (s, 1H), 8.61 (s, 1H), 8.33 (d, J = 6.0 Hz, 1H), 8.17 (s, 1H), 7.35 (d, J = 2.4 Hz, 1H), 7.16 (dd, J = 6.0, 2.1 Hz, 1H), 5.25 (dd, J = 8.7, 5.7 Hz, 1H), 4.50 (q, J = 7.2 Hz, 2H), 3.76-3.65 (m, 4H), 2.99-2.92 (m, 1H), 2.86-2.80 (m, 1H), 2.77-2.72 (m, 1H), 2.66-2.54 (m, 4H), 1.47 (t, J = 7.2 Hz, 3H), 1.20-1.13 (m, 2H), 1.06-0.98 (m, 2H) |
| I-228 | N-(2-(azetidin-1-yl)-1-(4-(cyclopropanesulfonamido)pyridin-2-yl)ethyl)-5-(6-ethoxypyrazin-2-yl)thiazole-2-carboxamide<br>I-228 | azetidine | | 530 | (400 MHz, Methanol-$d_4$) δ 8.72 (s, 1H), 8.61 (s, 1H), 8.33 (d, J = 6.0 Hz, 1H), 8.17 (s, 1H), 7.27 (d, J = 2.4 Hz, 1H), 7.17 (dd, J = 6.0, 2.4 Hz, 1H), 5.13 (t, J = 6.0 Hz, 1H), 4.50 (q, J = 7.2 Hz, 2H), 3.42 (t, J = 7.6 Hz, 4H), 3.14-3.08 (m, 2H), 2.77-2.70 (m, 1H), 2.19-2.12 (m, 2H), 1.47 (t, J = 7.2 Hz, 3H), 1.18-1.13 (m, 2H), 1.03-0.98 (m, 2H) |

TABLE 3-continued

| Compound Number | Name/Structure  Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-221 | (S)-N-(2-(azetidin-1-yl)-1-(4-(cyclopropanesulfonamido)pyridin-2-yl)ethyl)-5-(6-ethoxypyrazin-2-yl)thiazole-2-carboxamide<br><br>isomer 1<br>I-221 | azetidine | chiral HPLC (Column: CHIRALPAK IA, 5 * 25 cm, 5 μm; Mobile Phase A: Hex: DCM = 3:1 (0.5% 2M NH₃—MeOH)--HPLC, Mobile Phase B: EtOH--HPLC; Flow rate: 20 mL/min; Gradient: 15% B to 15% B in 11 min; Wave Length: 220/254 nm) First eluting peak | 530 | (400 MHz, Methanol-d₄) δ 8.72 (s, 1H), 8.62 (s, 1H), 8.35 (d, J = 6.0 Hz, 1H), 8.18 (s, 1H), 7.29 (s, d, J = 2.4 Hz, 1H), 7.17 (dd, J = 6.0, 2.4 Hz, 1H), 5.18 (t, J = 6.4 Hz, 1H), 4.50 (q, J = 7.2 Hz, 2H), 3.54 (t, J = 7.2 Hz, 4H), 3.21 (d, J = 7.2 Hz, 2H), 2.78-2.72 (m, 1H), 2.24-2.17 (m, 2H), 1.47 (t, J = 7.2 Hz, 3H), 1.18-1.14 (m, 2H), 1.02-0.97 (m, 2H) |
| I-222 | (R)-N-(2-(azetidin-1-yl)-1-(4-(cyclopropanesulfonamido)pyridin-2-yl)ethyl)-5-(6-ethoxypyrazin-2-yl)thiazole-2-carboxamide<br><br>isomer 2<br>I-222 | azetidine | Same as I-221 Second eluting peak | 530 | (400 MHz, Methanol-d₄) δ 8.72 (s, 1H), 8.61 (s, 1H), 8.36 (d, J = 6.0 Hz, 1H), 8.18 (s, 1H), 7.29 (d, J = 2.4 Hz, 1H), 7.17 (dd, J = 6.0, 2.4 Hz, 1H), 5.19 (t, J = 6.4 Hz, 1H), 4.50 (q, J = 7.2 Hz, 2H), 3.57 (t, J = 7.6 Hz, 4H), 3.24 (d, J = 7.6 Hz, 2H), 2.78-2.71 (m, 1H), 2.26-2.18 (m, 2H), 1.47 (t, J = 7.2 Hz, 3H), 1.18-1.14 (m, 2H), 1.04-0.99 (m, 2H) |
| I-207 | N-(1-(4-(cyclopropanesulfonamido)pyridin-2-yl)-2-(4-methylpiperazin-1-yl)ethyl)-5-(6-ethoxypyrazin-2-yl)thiazole-2-carboxamide<br><br>I-207 | 1-methylpiperazine | | 573 | (400 MHz, Methanol-d₄) δ 8.73 (s, 1H), 8.63 (s, 1H), 8.35 (d, J = 6.0 Hz, 1H), 8.18 (s, 1H), 7.38 (d, J = 2.4 Hz, 1H), 7.14 (d, J = 6.0, 2.4 Hz, 1H), 5.27 (dd, J = 8.8, 5.6 Hz, 1H), 4.50 (q, J = 7.2 Hz, 2H), 3.05-2.99 (m, 5H), 2.91-2.73 (m, 6H), 2.66 (s, 3H), 1.47 (t, J = 7.2 Hz, 3H), 1.17-1.14 (m, 2H), 1.06-1.00 (m, 2H) |

TABLE 3-continued

| Compound Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-191 | (S)-N-(1-(4-(cyclopropanesulfonamido)pyridin-2-yl)-2-(4-methylpiperazin-1-yl)ethyl)-5-(6-ethoxypyrazin-2-yl)thiazole-2-carboxamide<br><br>isomer 1<br>I-191 | 1-methylpiperazine | chiral HPLC (Column: CHIRALPAK ID-3, 2 * 25 cm, 5 μm; Mobile Phase A: Hex:DCM = 3:1 (0.5% 2M NH3—MeOH)--HPLC): PA-70:30 Mobile Phase B: IPA--HPLC; Flow rate: 20 mL/min; Gradient: 30% B to 30% B; Wave Length: 220/254 nm) First eluting peak | 573 | (400 MHz, Methanol-d4) δ 8.73 (s, 1H), 8.63 (s, 1H), 8.30 (d, J = 6.0 Hz, 1H), 8.18 (s, 1H), 7.31 (d, J = 2.4 Hz, 1H), 7.13 (d, J = 6.0, 2.4 Hz, 1H), 5.22 (dd, J = 8.8, 6.0 Hz, 1H), 4.50 (q, J = 7.2 Hz, 2H), 2.99-2.94 (m, 1H), 2.86-2.80 (m, 1H), 2.76-2.70 (m, 3H), 2.68-2.49 (m, 6H), 2.31 (s, 3H), 1.47 (t, J = 7.2 Hz, 3H), 1.17-1.13 (m, 2H), 1.03-0.97 (m, 2H) |
| I-192 | (R)-N-(1-(4-(cyclopropanesulfonamido)pyridin-2-yl)-2-(4-methylpiperazin-1-yl)ethyl)-5-(6-ethoxypyrazin-2-yl)thiazole-2-carboxamide<br><br>isomer 2<br>I-192 | 1-methylpiperazine | Same as I-191 Second eluting peak | 573 | (400 MHz, Methanol-d4) δ 8.73 (s, 1H), 8.63 (s, 1H), 8.30 (d, J = 6.0 Hz, 1H), 8.17 (s, 1H), 7.31 (d, J = 2.4 Hz, 1H), 7.13 (d, J = 6.0, 2.4 Hz, 1H), 5.22 (dd, J = 8.8, 5.6 Hz, 1H), 4.50 (q, J = 7.2 Hz, 2H), 3.00-2.94 (m, 1H), 2.86-2.81 (m, 1H), 2.76-2.70 (m, 3H), 2.68-2.51 (m, 6H), 2.33 (s, 3H), 1.47 (t, J = 7.2 Hz, 3H), 1.17-1.13 (m, 2H), 1.03-0.98 (m, 2H) |
| I-101 | N-((R)-2-((1S,4S)-2-oxa-5-azabicyclo[2.2.1]heptan-5-yl)-1-(4-(cyclopropanesulfonamido)pyridin-2-yl)ethyl)-5-(6-ethoxypyrazin-2-yl)thiazole-2-carboxamide<br><br>isomer 1<br>I-101 | (1S,4S)-2-oxa-5-azabicyclo[2.2.1]heptane hydrochloride | chiral HPLC (Column: CHIRALPAK IG, 2 * 25 cm, 5 μm; Mobile Phase A: Hex:DCM = 3:1 (0.5% 2M NH3—MeOH)--HPLC, Mobile Phase B: EtOH--HPLC; Flow rate: 20 mL/min; Gradient: 30% B to 30% B in 30 min; Wave Length: 220/254 nm) First eluting peak | 572 | (400 MHz, Methanol-d4) δ 8.69 (s,1H), 8.58 (s, 1H), 8.30 (d, J = 5.6 Hz, 1H), 8.14 (s, 1H), 7.30 (d, J = 2.0 Hz, 1H), 7.14 (dd, J = 5.6, 2.0 Hz, 1H), 5.10-5.06 (m, 1H), 4.47 (q, J = 7.2 Hz, 2H), 4.39 (s, 1H), 3.96 (d, J = 7.6 Hz, 1H), 3.61 (dd, J = 7.6, 1.6 Hz, 1H), 3.57 (s,1H), 3.19-3.08 (m, 2H), 2.87-2.84 (m, 1H), 2.74-2.68 (m, 1H), 2.63 (d, J = 10.0 Hz, 1H), 1.89-1.86 (m, 1H), 1.74-1.71 (m, 1H), 1.44 (t, J = 7.2 Hz, 3H), 1.16-1.11 (m, 2H), 1.02-0.97 (m, 2H) |

| Compound Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-102 | N-((S)-2-((1S,4S)-2-oxa-5-azabicyclo[2.2.1]heptan-5-yl)-1-(4-(cyclopropanesulfonamido)pyridin-2-yl)ethyl)-5-(6-ethoxypyrazin-2-yl)thiazole-2-carboxamide<br><br>isomer 2<br>I-102 | (1S,4S)-2-oxa-5-azabicyclo[2.2.1]heptane hydrochloride | Same as I-101 Second eluting peak | 572 | (400 MHz, Methanol-d4) δ 8.69 (s,1H), 8.59 (s, 1H), 8.34 (d, J = 5.6 Hz, 1H), 8.15 (s, 1H), 7.32 (d, J = 2.0 Hz, 1H), 7.15 (dd, J = 5.6, 2.0 Hz, 1H), 5.23-5.20 (m, 1H), 4.47 (q, J = 7.2 Hz, 2H), 4.45 (s, 1H), 4.06 (d, J = 8.4 Hz, 1H), 3.79 (s, 1H), 3.68 (dd, J = 8.4, 2.0 Hz, 1H), 3.41-3.33 (m, 2H), 3.06-3.03 (m, 1H), 2.80-2.69 (m, 2H), 1.98-1.95 (m, 1H), 1.85-1.82 (m, 1H), 1.45 (t, J = 7.2 Hz, 3H), 1.16-1.09 (m, 2H), 1.02-0.97 (m, 2H) |
| I-114 | N-((S)-2-((1R,5S)-3-oxa-6-azabicyclo[3.1.1]heptan-6-yl)-1-(4-(cyclopropanesulfonamido)pyridin-2-yl)ethyl)-5-(6-ethoxypyrazin-2-yl)thiazole-2-carboxamide<br><br>isomer 1<br>I-114 | (1R,5S)-3-oxa-6-azabicyclo[3.1.1]heptane hydrochloride | chiral HPLC (Column: CHIRAL ART Amylose-SA, 2 * 25 cm, 5 μm; Mobile Phase A: Hex: DCM = 3: 1 (0.5% 2M NH3-MeOH)--HPLC, Mobile Phase B: EtOH--HPLC; Flow rate: 20 mL/min; Gradient: 20% B to 20% B in 11 min; Wave Length: 220/254 nm) First eluting peak | 572 | (400 MHz, DMSO-d6) δ 9.04 (s, 1H), 8.93 (s, 1H), 8.83 (s, 1H), 8.34 (s, 1H), 8.29 (s,1H), 7.21 (s, 1H), 7.07-7.04 (m, 1H), 5.02-4.98 (m, 1H), 4.43 (q, J = 7.2 Hz, 2H), 4.09-4.04 (m, 2H), 3.59-3.52 (m, 2H), 3.27-3.18 (m, 2H), 3.07-3.03 (m, 1H), 2.83-2.76 (m, 1H), 2.47-2.42 (m, 2H), 1.65-1.63 (m, 1H), 1.40 (t, J = 7.2 Hz, 3H), 1.03-0.95 (m, 4H) |
| I-115 | N-((R)-2-((1R,5S)-3-oxa-6-azabicyclo[3.1.1]heptan-6-yl)-1-(4-(cyclopropanesulfonamido)pyridin-2-yl)ethyl)-5-(6-ethoxypyrazin-2-yl)thiazole-2-carboxamide<br><br>isomer 2<br>I-115 | (1R,5S)-3-oxa-6-azabicyclo[3.1.1]heptane hydrochloride | Same as I-114 Second eluting peak | 572 | (400 MHz, DMSO-d6) δ 9.04 (s, 1H), 8.93 (s, 1H), 8.82 (s, 1H), 8.34 (s, 1H), 8.29 (s, 1H), 7.21 (s, 1H), 7.06-7.04 (m, 1H), 5.03-4.97 (m, 1H), 4.41 (q, J = 7.2 Hz, 2H), 4.09-4.04 (m, 2H), 3.59-3.53 (m, 2H), 3.25-3.18 (m, 2H), 3.09-3.03 (m, 1H), 2.81-2.76 (m, 1H), 2.47-2.40 (m, 2H), 1.65-1.63 (m, 1H), 1.39 (t, J = 7.2 Hz, 3H), 1.03-0.95 (m, 4H) |

TABLE 3-continued

| Compound Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-122 | N-(1-(4-(cyclopropanesulfonamido)pyridin-2-yl)-2-(3,3-dimethylmorpholino)ethyl)-5-(6-ethoxypyrazin-2-yl)thiazole-2-carboxamide<br><br>I-122 | 3,3-dimethyl-morpholine | | 588 | (400 MHz, DMSO-$d_6$) δ 8.92 (s, 1H), 8.86-8.82 (m, 1H), 8.81 (s, 1H), 8.29 (s, 1H), 8.28-8.26 (m, 1H), 7.16 (s, 1H), 7.02-7.00 (m, 1H), 4.99-4.94 (m, 1H), 4.43 (q, J = 7.2 Hz, 2H), 3.56-3.52 (m, 2H), 3.13 (s, 2H), 2.78-2.70 (m, 3H), 2.59-2.53 (m, 2H), 1.39 (t, J = 7.2 Hz, 3H), 1.00-0.95 (m, 4H), 0.93 (s, 3H), 0.73 (s, 3H) |
| I-116 | (S)-N-(1-(4-(cyclopropanesulfonamido)pyridin-2-yl)-2-(3,3-dimethylmorpholino)ethyl)-5-(6-ethoxypyrazin-2-yl)thiazole-2-carboxamide<br><br>isomer 1<br>I-116 | 3,3-dimethyl-morpholine | chiral HPLC (Column: CHIRALPAK IA-3, 4.6 * 50 mm, 3 μm; Mobile Phase A: (Hex: DCM = 3: 1) (0.1% DEA): EtOH = 80: 20; Flow rate: 1 mL/min; Gradient: 0% B to 0% B) First eluting peak | 588 | (300 MHz, DMSO-$d_6$) δ 8.92 (s, 1H), 8.86 (s, 1H), 8.81 (s, 1H), 8.33 (s, 1H), 8.29 (s, 1H), 7.21 (s, 1H), 7.07-7.04 (m, 1H), 5.02-4.95 (m, 1H), 4.43 (q, J = 7.2 Hz, 2H), 3.58-3.51 (m, 2H), 3.13 (s, 2H), 2.76-2.69 (m, 4H), 2.57-2.53 (m, 1H), 1.39 (t, J = 7.2 Hz, 3H), 1.04-0.95 (m, 4H), 0.94 (s, 3H), 0.73 (s, 3H) |
| I-117 | (R)-N-(1-(4-(cyclopropanesulfonamido)pyridin-2-yl)-2-(3,3-dimethylmorpholino)ethyl)-5-(6-ethoxypyrazin-2-yl)thiazole-2-carboxamide<br><br>isomer 2<br>I-117 | 3,3-dimethyl-morpholine | Same as I-116 Second eluting peak | 588 | (300 MHz, DMSO-$d_6$) δ 10.53 (s, 1H), 8.92 (s, 1H), 8.84 (s, 1H), 8.81 (s, 1H), 8.40 (s, 1H), 8.29 (s, 1H), 7.26 (s, 1H), 7.12-7.05 (m, 1H), 5.03-4.96 (m, 1H), 4.43 (q, J = 7.2 Hz, 2H), 3.57-3.52 (m, 2H), 3.14 (s, 2H), 2.87-2.72 (m, 4H), 2.57-2.53 (m, 1H), 1.39 (t, J = 7.2 Hz, 3H), 1.07-0.98 (m, 4H), 0.95 (s, 3H), 0.72 (s, 3H) |

TABLE 3-continued

| Compound Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-111 | N-(1-(4-(cyclopropanesulfonamido)pyridin-2-yl)-2-(cis-3,5-dimethylmorpholino)ethyl)-5-(6-ethoxypyrazin-2-yl)thiazole-2-carboxamide<br />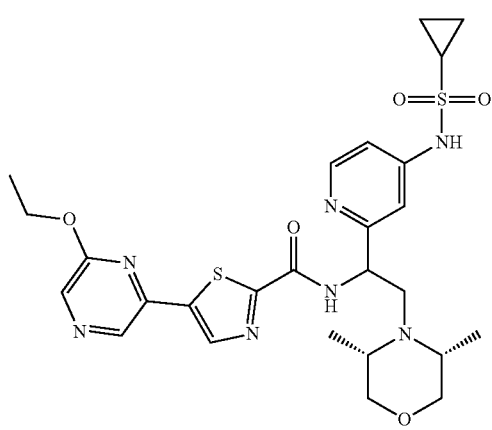<br />I-111 | cis-3,5-dimethyl-morpholine | | 588 | (400 MHz, Methanol-d4) δ 8.69 (s,1H), 8.58 (s, 1H), 8.36 (d, J = 6.0 Hz, 1H), 8.15 (s,1H), 7.30 (d, J = 2.0 Hz, 1H), 7.15 (dd, J = 6.0, 2.0 Hz, 1H), 5.18 (t, J = 7.2 Hz, 1H), 4.48 (q, J = 7.2 Hz, 2H), 3.68-3.64 (m, 1H), 3.60-3.57 (m, 1H), 3.21-3.05 (m, 4H), 2.78-2.73 (m, 1H), 2.65-2.61 (m, 2H), 1.45 (t, J = 7.2 Hz, 3H), 1.18-1.14 (m, 5H), 1.03-0.99 (m, 2H), 0.73 (d, J = 6.0 Hz, 3H) |
| I-109 | N-((S)-1-(4-(cyclopropanesulfonamido)pyridin-2-yl)-2-(cis-3,5-dimethylmorpholino)ethyl)-5-(6-ethoxypyrazin-2-yl)thiazole-2-carboxamide<br />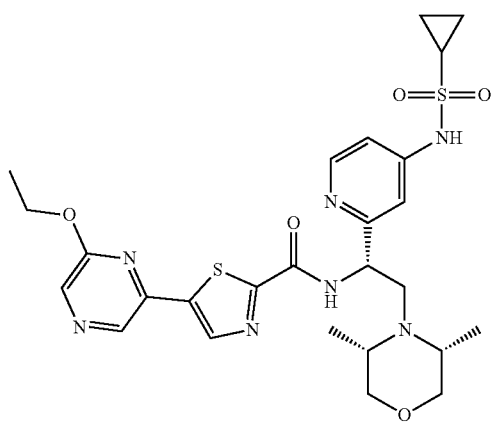<br />isomer 1<br />I-109 | cis-3,5-dimethyl-morpholine | chiral HPLC (Column: CHIRAL ART Amylose-SA, 2 * 25 cm, 5 μm; Mobile Phase A: Hex:DCM = 3:1 (0.5% 2M NH3—MeOH)--HPLC, Mobile Phase B: EtOH--HPLC; Flow rate: 20 mL/min; Gradient: 20% B to 20% B in 10 min; Wave Length: 220/254 nm) First eluting peak | 588 | (400 MHz, Methanol-d4) δ 8.69 (s,1H), 8.57 (s, 1H), 8.35 (d, J = 5.6 Hz, 1H), 8.14 (s,1H), 7.29 (d, J = 2.0 Hz, 1H), 7.15 (dd, J = 5.6, 2.0 Hz, 1H), 5.18 (t, J = 7.2 Hz, 1H), 4.48 (q, J = 7.2 Hz, 2H), 3.67-3.64 (m, 1H), 3.60-3.57 (m, 1H), 3.21-3.05 (m, 4H), 2.77-2.72 (m, 1H), 2.66-2.60 (m, 2H), 1.45 (t, J = 7.2 Hz, 3H), 1.17-1.14 (m, 5H), 1.03-0.99 (m, 2H), 0.73 (d, J = 6.4 Hz, 3H) |

TABLE 3-continued

| Compound Number | Name/Structure Stereochemistry alpha to central amide arbitrarily assigned | Amine reagent used in Step 1 | Chiral chromatography method | MS (ES): m/z [M + H]+ | $^1$H NMR |
|---|---|---|---|---|---|
| I-110 | N-((R)-1-(4-(cyclopropanesulfonamido)pyridin-2-yl)-2-(cis-3,5-dimethylmorpholino)ethyl)-5-(6-ethoxypyrazin-2-yl)thiazole-2-carboxamide<br><br>isomer 2<br>I-110 | cis-3,5-dimethyl-morpholine | Same as I-109 Second eluting peak | 588 | (400 MHz, DMSO-d$_6$) δ 9.05 (s, 1H), 8.92 (s,1H), 8.91 (s, 1H), 8.38-8.35 (m, 1H), 8.29 (s,1H), 7.24 (s, 1H), 7.08-7.05 (m, 1H), 5.15-5.09 (m, 1H), 4.43 (q, J = 7.2 Hz, 2H), 3.62-3.56 (m, 1H), 3.54-3.48 (m, 1H), 3.11-3.00 (m, 3H), 2.94-2.88 (m, 1H), 2.82-2.78 (m, 1H), 1.39 (t, J = 7.2 Hz, 3H), 1.07 (d, J = 6.4 Hz, 3H).1.04-0.97 (m, 4H), 0.67 (d, J = 6.4 Hz, 3H) |
| I-118 | (S)-N-(1-(4-(cyclopropanesulfonamido)pyridin-2-yl)-2-(4-isopropylpiperazin-1-yl)ethyl)-5-(6-ethoxypyrazin-2-yl)thiazole-2-carboxamide<br><br>isomer 1<br>I-118 | 1-isopropyl-piperazine | chiral HPLC (Column: CHIRAL ART Amylose-SA, 2 * 25 cm, 5 μm; Mobile Phase A: Hex: DCM = 3: 1 (0.5% 2M NH$_3$—MeOH)--HPLC, Mobile Phase B: EtOH--HPLC; Flow rate: 20 mL/min; Gradient: 20% B to 20% B in 7 min; Wave Length: 220/254 nm) First eluting peak | 601 | (300 MHz, Methanol-d$_4$) δ 8.70 (s, 1H), 8.60 (s, 1H), 8.27 (d, J = 5.7 Hz, 1H), 8.15 (s, 1H), 7.31 (d, J = 2.1 Hz, 1H), 7.09 (dd, J = 5.7, 2.1 Hz, 1H), 5.24-5.19 (m, 1H), 4.48 (q, J = 7.2 Hz, 2H), 2.99-2.92 (m, 2H), 2.88-2.66 (m, 10H), 1.45 (t, J = 7.2 Hz, 3H), 1.15-1.08 (m, 8H), 1.00-0.95 (m, 2H) |
| I-121 | (R)-N-(1-(4-(cyclopropanesulfonamido)pyridin-2-yl)-2-(4-isopropylpiperazin-1-yl)ethyl)-5-(6-ethoxypyrazin-2-yl)thiazole-2-carboxamide<br><br>isomer 2<br>I-121 | 1-isopropyl-piperazine | Same as I-118 Second eluting peak | 601 | (300 MHz, Methanol-d$_4$) δ 8.70 (s, 1H), 8.60 (s, 1H), 8.26 (d, J = 5.7 Hz, 1H), 8.15 (s, 1H), 7.29 (d, J = 2.1 Hz, 1H), 7.09 (dd, J = 5.7, 2.1 Hz, 1H), 5.23-5.18 (m, 1H), 4.48 (q, J = 7.2 Hz, 2H), 2.99-2.92 (m, 2H), 2.84-2.65 (m, 10H), 1.45 (t, J = 7.2 Hz, 3H), 1.15-1.08 (m, 8H), 0.99-0.95 (m, 2H) |

TABLE 3-continued

| Compound Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-119 | (S)-N-(1-(4-(cyclopropanesulfonamido)pyridin-2-yl)-2-(4-cyclopropylpiperazin-1-yl)ethyl)-5-(6-ethoxypyrazin-2-yl)thiazole-2-carboxamide<br><br>isomer 1<br>I-119 | 1-cyclopropyl-piperazine | chiral HPLC (Column: CHIRAL ART Amylose-SA, 2 * 25 cm, 5 μm; Mobile Phase A: Hex:DCM = 3:1 (0.5% 2M NH$_3$—MeOH)-- HPLC, Mobile Phase B: EtOH--HPLC; Flow rate: 20 mL/min; Gradient: 20% B to 20% B in 8 min; Wave Length: 220/254 nm) First eluting peak | 599 | (300 MHz, Methanol-d$_4$) δ 8.70 (s, 1H), 8.60 (s, 1H), 8.28 (d, J = 5.7 Hz, 1H), 8.15 (s, 1H), 7.30 (d, J = 2.1 Hz, 1H), 7.12 (dd, J = 5.7, 2.1 Hz, 1H), 5.22-5.18 (m, 1H), 4.48 (q, J = 7.2 Hz, 2H), 2.97-2.90 (m, 1H), 2.83-2.56 (m, 10H), 1.69-1.62 (m, 1H), 1.45 (t, J = 7.2 Hz, 3H), 1.16-1.10 (m, 2H), 1.02-0.95 (m, 2H), 0.51-0.38 (m, 4H) |
| I-120 | (R)-N-(1-(4-(cyclopropanesulfonamido)pyridin-2-yl)-2-(4-cyclopropylpiperazin-1-yl)ethyl)-5-(6-ethoxypyrazin-2-yl)thiazole-2-carboxamide<br><br>isomer 2<br>I-120 | 1-cyclopropyl-piperazine | Same as I-119 Second eluting peak | 599 | (300 MHz, Methanol-d$_4$) δ 8.70 (s, 1H), 8.60 (s, 1H), 8.27 (d, J = 6.0 Hz, 1H), 8.15 (s, 1H), 7.29 (d, J = 2.1 Hz, 1H), 7.12 (dd, J = 6.0, 2.1 Hz, 1H), 5.22-5.17 (m, 1H), 4.48 (q, J = 7.2 Hz, 2H), 2.97-2.90 (m, 1H), 2.83-2.56 (m, 10H), 1.69-1.62 (m, 1H), 1.45 (t, J = 7.2 Hz, 3H), 1.16-1.10 (m, 2H), 1.03-0.94 (m, 2H), 0.51-0.37 (m, 4H) |
| I-103 | (R)-N-(1-(4-(cyclopropanesulfonamido)pyridin-2-yl)-2-(4-(dimethylamino)piperidin-1-yl)ethyl)-5-(6-ethoxypyrazin-2-yl)thiazole-2-carboxamide<br><br>isomer 1<br>I-103 | N,N-dimethyl-piperidin-4-amine | chiral HPLC (Column: CHIRALPAK IG, 2 * 25 cm, 5 μm; Mobile Phase A: Hex: DCM = 3:1 (0.5% 2M NH$_3$—MeOH)-- HPLC, Mobile Phase B: EtOH--HPLC; Flow rate: 20 mL/min; Gradient: 20% B to 20% B in 25 min; Wave Length: 220/254 nm) First eluting peak | 601 | (300 MHz, DMSO-d$_6$) δ 9.01 (d, J = 7.8 Hz, 1H), 8.92 (s, 1H), 8.81 (s, 1H), 8.29 (s, 1H), 8.25 (d, J = 5.7 Hz, 1H), 7.15 (d, J = 2.1 Hz, 1H), 6.99 (d, J = 5.7, 2.1 Hz, 1H), 5.13-5.05 (m, 1H), 4.43 (q, J = 6.9 Hz, 2H), 2.97-2.85 (m, 3H), 2.74-2.64 (m, 2H), 2.19 (s, 6H), 2.10-1.97 (m, 3H), 1.73-1.69 (m, 2H), 1.39 (t, J = 6.9 Hz, 3H), 1.34-1.23 (m, 2H), 0.98-0.90 (m, 4H) |

TABLE 3-continued

| Compound Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-104 | (S)-N-(1-(4-(cyclopropanesulfonamido)pyridin-2-yl)-2-(4-(dimethylamino)piperidin-1-yl)ethyl)-5-(6-ethoxypyrazin-2-yl)thiazole-2-carboxamide<br />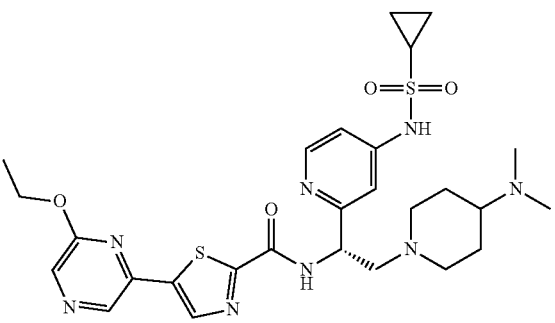<br />isomer 2<br />I-104 | N,N-dimethyl-piperidin-4-amine | Same as I-103 Second eluting peak | 601 | (300 MHz, DMSO-d$_6$) δ 9.01 (d, J = 7.8 Hz, 1H), 8.92 (s, 1H), 8.81 (s, 1H), 8.29 (s, 1H), 8.25 (d, J = 5.7 Hz, 1H), 7.14 (d, J = 2.1 Hz, 1H), 6.99 (dd, J = 5.7, 2.1 Hz, 1H), 5.13-5.05 (m, 1H), 4.43 (q, J = 6.9 Hz, 2H), 2.97-2.85 (m, 3H), 2.75-2.64 (m, 2H), 2.19 (s, 6H), 2.11-1.97 (m, 3H), 1.73-1.69 (m, 2H), 1.39 (t, J = 6.9 Hz, 3H), 1.35-1.23 (m, 2H), 0.98-0.90 (m, 4H) |

General Method 2

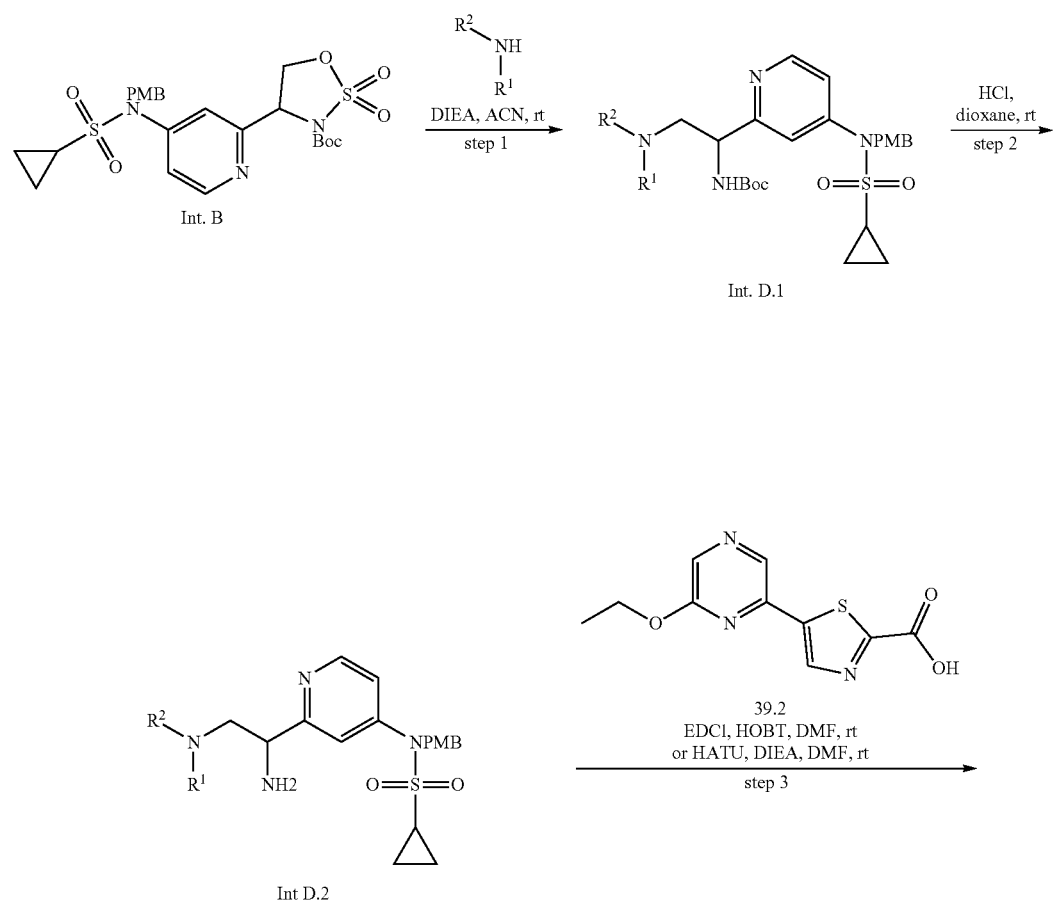

-continued
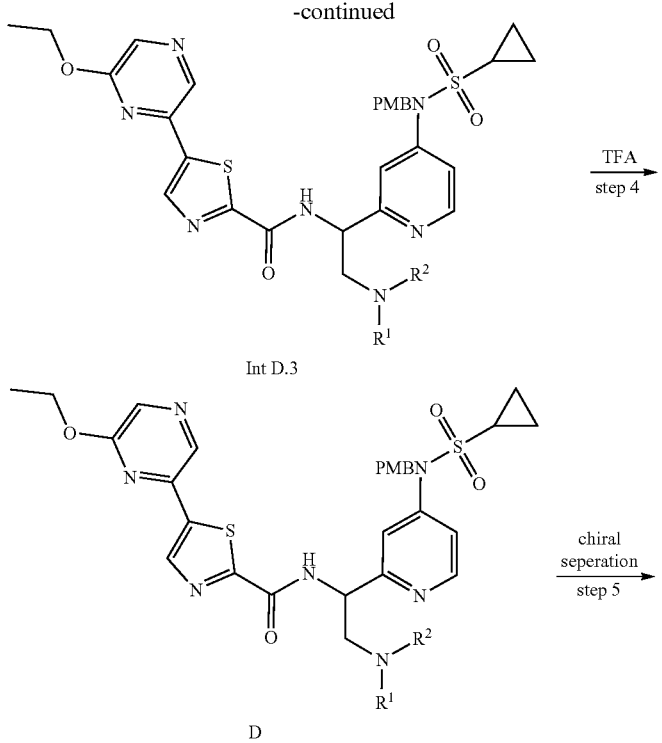
Int D.3
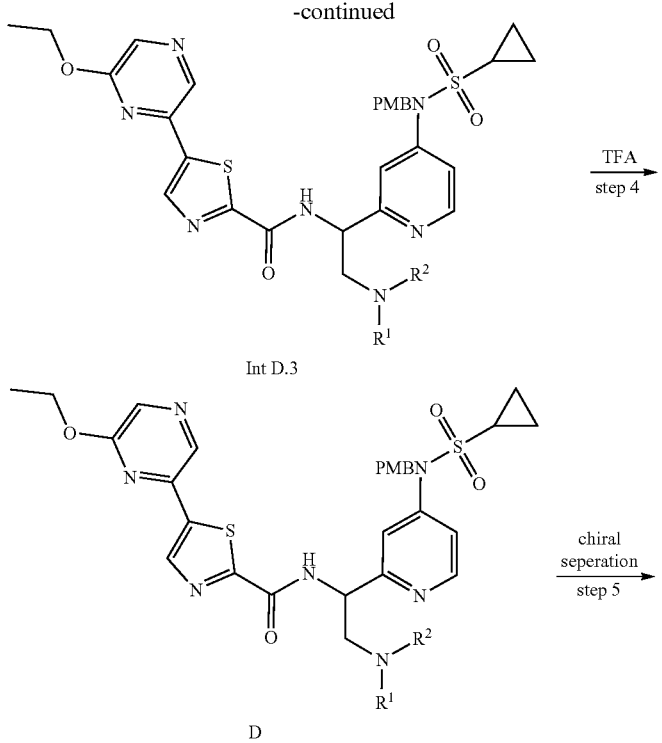
D
D. isomer 1     D. isomer 2
Example 88: Synthesis of N-(1-(4-(cyclopropane-sulfonamido)pyridin-2-yl)-2-(piperazin-1-yl)ethyl)-5-(6-ethoxypyrazin-2-yl)thiazole-2-carboxamide (I-217)
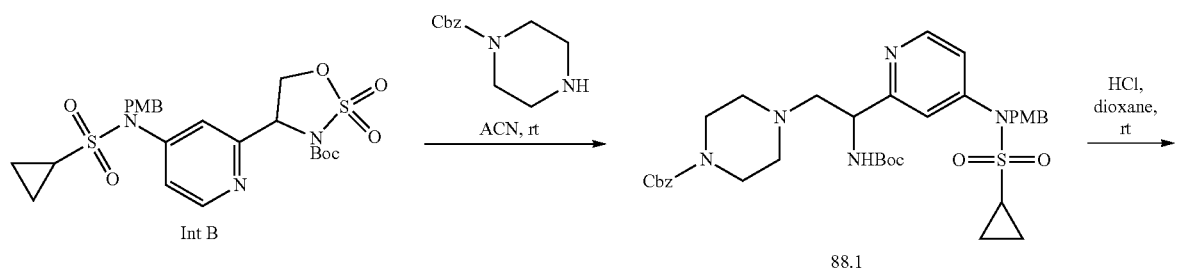

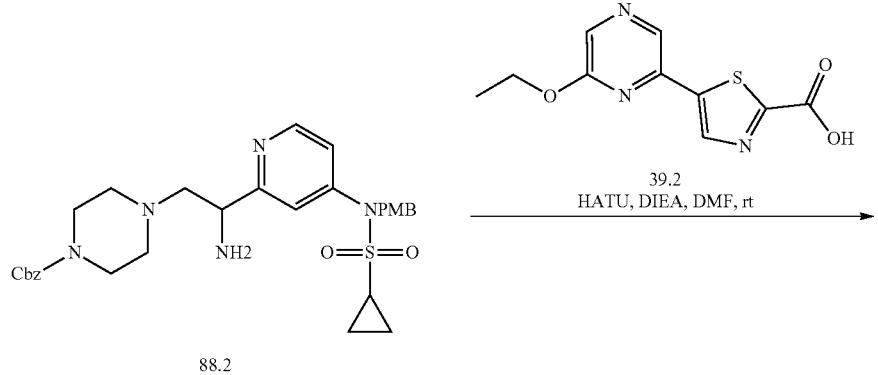

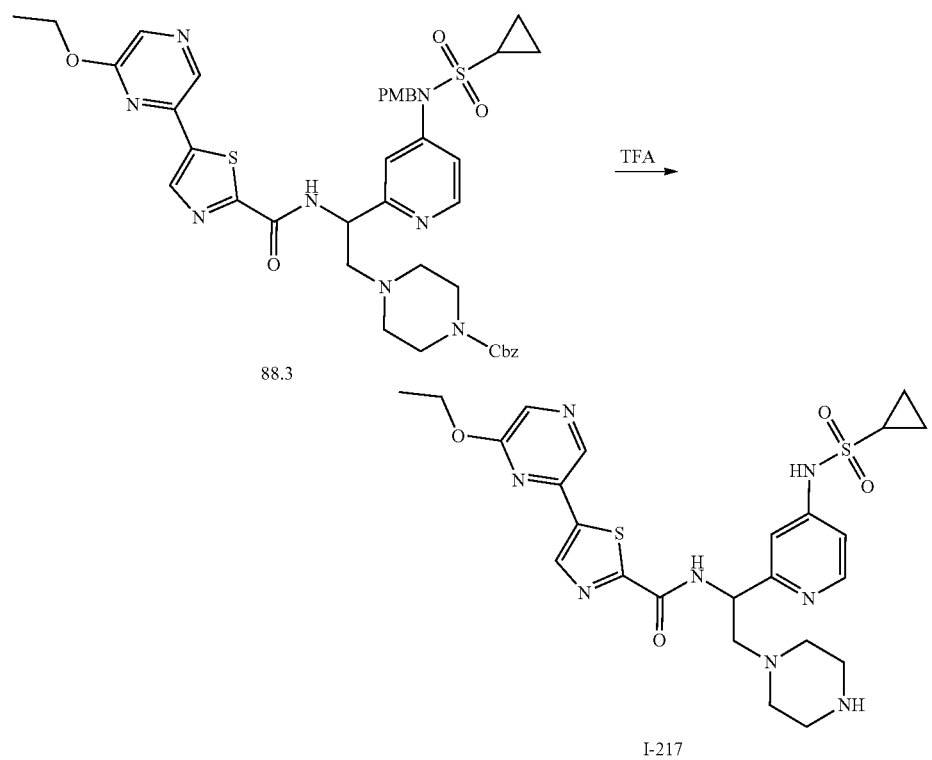

General Method 2, Step 1, synthesis of 88.1. To a stirred solution of Int B (260 mg, 0.48 mmol, 1 eq) in acetonitrile (5 mL) was added benzyl piperazine-1-carboxylate (318 mg, 1.45 mmol, 3 eq) at room temperature. The resulting mixture was stirred for 12 h at room temperature. The resulting mixture was diluted with water and extracted with ethyl acetate. The combined organic layers were washed with brine, dried over anhydrous sodium sulfate and concentrated under reduced pressure. The residue was purified by flash column chromatography on C18 silica (eluted with 90% acetonitrile in water) to afford benzyl 4-{2-[(tert-butoxycarbonyl)amino]-2-(4-{N-[(4-methoxyphenyl)methyl] cyclopropanesulfonamido}pyridin-2-yl)ethyl}piperazine-1-carboxylate as a brown oil. (88.1, 240 mg, 73%), MS (ES): m/z 680 [M+H]+.

General Method 2, Step 2, synthesis of 88.2. To a stirred solution of 88.1 (240 mg, 0.35 mmol, 1.0 eq) in dichloromethane (5 mL) were added hydrochloric acid (4M in 1,4-dioxane, 1 mL, 4.0 mmol, 11 equiv) dropwise at room temperature. The resulting mixture was stirred for 2 h at room temperature. The reaction mixture was concentrated under reduced pressure to afford benzyl 4-[2-amino-2-(4-{N-[(4-methoxyphenyl) methyl] cyclopropanesulfonamido}pyridin-2-yl) ethyl] piperazine- 1-carboxylate hydrochloride (88.2, 160 mg) as a yellow oil, used without further purification. MS (ES): m/z 580 [M+H]$^+$.

General Method 2, Step 3, synthesis of 88.3. To a stirred solution of 88.2 (160 mg) and 39.2 (87 mg) in N,N-dimethyl formamide (2 mL) were added HATU (205 mg, 0.54 mmol) and DIEA (178 mg, 1.38 mmol) at room temperature. The resulting mixture was stirred for 12 h at room temperature. The reaction mixture was concentrated under reduced pressure. The residue was purified by flash column chromatography on silica gel (eluted with dichloromethane/methanol, 95/5) to afford benzyl 4-(2-{[5-(6-ethoxypyrazin-2-yl)-1,3-thiazol-2-yl]formamido}-2-(4-{N-[(4-methoxyphenyl)methyl]cyclopropanesulfonamido}pyridin-2-yl)ethyl)piperazine-1-carboxylate (88.3, 30 mg) as a yellow solid. MS (ES): m/z 813 [M+H]$^+$.

General Method 2, Step 4, synthesis of I-217. A solution 88.3 (30 mg, 0.04 mmol, 1 equiv) in trifluoroacetic acid (3 mL) was stirred for 12 h at 50° C. The mixture was concentrated under reduced pressure. The residue was purified by Prep-HPLC (Column: XBridge Shield RP18 OBD Column, 30*150 mm, 5 µm; Mobile Phase: water (0.1% FA) and ACN (26% up to 56% in 8 min); Wavelength: 254/220 nm) to afford N-[1-(4-cyclopropanesulfonamidopyridin-2-yl)-2-(piperazin-1-yl)ethyl]-5-(6-ethoxypyrazin-2-yl)-1,3-thiazole-2-carboxamide (I-217, 5.3 mg, 25%) as a white solid. MS (ES): m/z 559 [M+H]$^+$; $^1$H NMR (300 MHz, DMSO-d$_6$) δ 8.81 (s, 1H), 8.71 (s, 1H), 8.22 (s, 1H), 8.05 (d, J=6.0 Hz, 1H), 6.96 (d, J=2.1 Hz, 1H), 6.83 (d, J=6.0, 2.1 Hz, 1H), 5.07-5.02 (m, 1H), 4.39 (q, J=12 Hz, 2H), 2.91-2.84 (m, 5H), 2.72-2.55 (m, 5H), 2.49-2.46 (m, 1H), 1.36 (t, J=12 Hz, 3H), 0.89-0.78 (m, 4H).

Example 89: Synthesis of (R)—N-(1-(4-(cyclopropanesulfonamido)pyridin-2-yl)-2-(piperazin-1-yl)ethyl)-5-(6-ethoxypyrazin-2-yl)thiazole-2-carboxamide, isomer 1 (I-205) and (S)—N-(1-(4-(cyclopropanesulfonamido)pyridin-2-yl)-2-(piperazin-1-yl)ethyl)-5-(6-ethoxypyrazin-2-yl)thiazole-2-carboxamide, isomer 2 (I-206).
Stereochemistry Arbitrarily Assigned

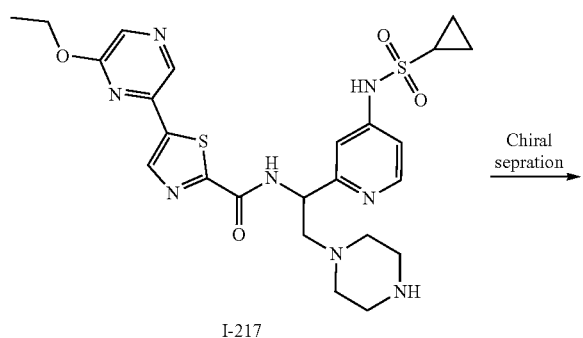

I-217

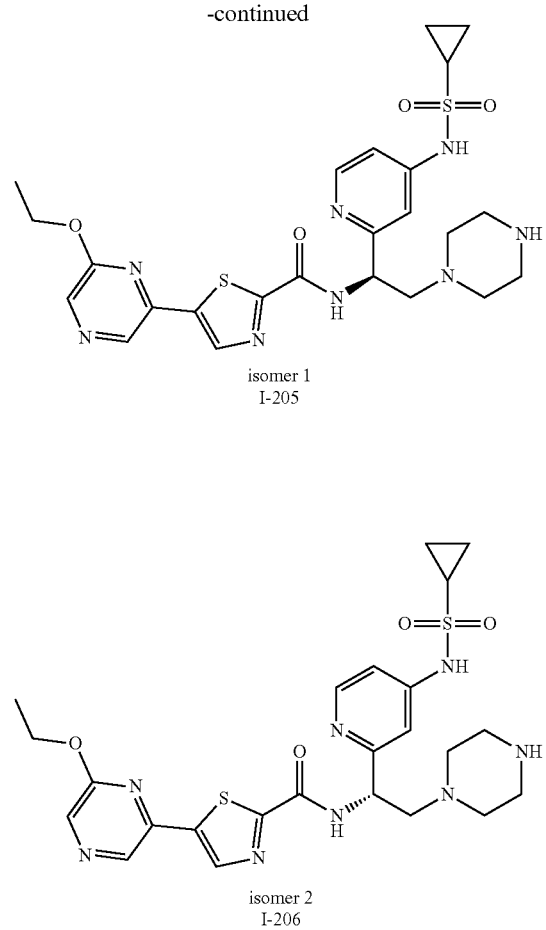

isomer 1
I-205 isomer 2
I-206

General Method 2, Step 5, synthesis of I-205 and I-206. I-217 (20 mg) was purified by chiral HPLC (Column: CHIRALPAK IG, 2*25 cm, 5 µm; Mobile Phase A: Hex:DCM=3:1(0.5% 2M NH$_3$-MeOH)-HPLC, Mobile Phase B: EtOH-HPLC; Flow rate: 20 mL/min; Gradient: 50% B to 50% B in 22 min; Wave Length: 220/254 nm) to afford (R)—N-(1-(4-(cyclopropanesulfonamido)pyridin-2-yl)-2-(piperazin-1-yl)ethyl)-5-(6-ethoxypyrazin-2-yl)thiazole-2-carboxamide, isomer 1 (I-205, first eluting peak, 5.1 mg) and (S)—N-(1-(4-(cyclopropanesulfonamido)pyridin-2-yl)-2-(piperazin-1-yl)ethyl)-5-(6-ethoxypyrazin-2-yl)thiazole-2-carboxamide, isomer 2 (I-206, second eluting peak, 5.3 mg) both as white solids. I-205: MS (ES): m/z 559 [M+H]$^+$; $^1$H NMR (400 MHz, DMSO-d$_6$) δ 8.82 (s, 1H), 8.71 (s, 1H), 8.22 (s, 1H), 8.02 (d, J=6.0 Hz, 1H), 6.93 (s, 1H), 6.81 (d, J=6.0 Hz, 1H), 5.06-5.02 (m, 1H), 4.39 (q, J=6.8 Hz, 2H), 2.90-2.83 (m, 4H), 2.69-2.55 (m, 4H), 2.49-2.42 (m, 3H), 1.36 (t, J=7.2 Hz, 3H), 0.85-0.75 (m, 4H). I-206: MS (ES): m/z 559 [M+H]$^+$; $^1$H NMR (400 MHz, DMSO-d$_6$) δ 8.81 (s, 1H), 8.70 (s, 1H), 8.22 (s, 1H), 8.00 (d, J=5.6 Hz, 1H), 6.91 (s, 1H), 6.79 (d, J=5.6 Hz, 1H), 5.05-5.01 (m, 1H), 4.39 (q, J=7.2 Hz, 2H), 2.90-2.83 (m, 4H), 2.69-2.55 (m, 4H), 2.49-2.40 (m, 3H), 1.36 (t, J=7.2 Hz, 3H), 0.84-0.75 (m, 4H).

Table 4 shows compounds prepared according to General Method 2:

| Example Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-216 | N-(1-(4-(cyclopropanesulfonamido)pyridin-2-yl)-2-(3-fluoroazetidin-1-yl)ethyl)-5-(6-ethoxypyrazin-2-yl)thiazole-2-carboxamide<br>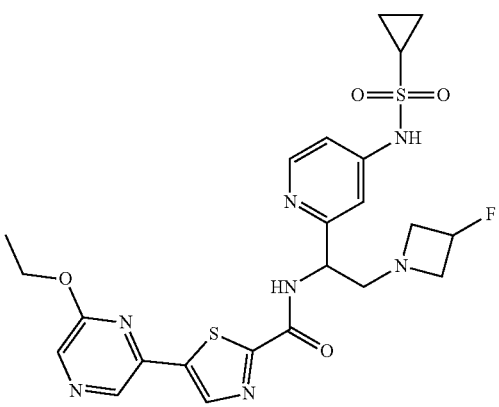<br>I-216 | 3-fluoroazetidine hydrochloride | | 548 | (400 MHz, Methanol-$d_4$) δ 8.71 (s, 1H), 8.60 (s, 1H), 8.34 (d, J = 6.0 Hz, 1H), 8.17 (s, 1H), 7.29 (d, J = 2.4 Hz, 1H), 7.16 (dd, J = 6.0, 2.4 Hz, 1H), 5.20-5.00 (m, 2H), 4.50 (q, J = 7.2 Hz, 2H), 3.72-3.60 (m, 2H), 3.30-3.21 (m, 2H), 3.16-3.05 (m, 2H), 2.78-2.71 (m, 1H), 1.47 (t, J = 7.2 Hz, 3H), 1.18-1.13 (m, 2H), 1.04-0.99 (m, 2H) |
| I-203 | (S)-N-(1-(4-(cyclopropanesulfonamido)pyridin-2-yl)-2-(3-fluoroazetidin-1-yl)ethyl)-5-(6-ethoxypyrazin-2-yl)thiazole-2-carboxamide<br>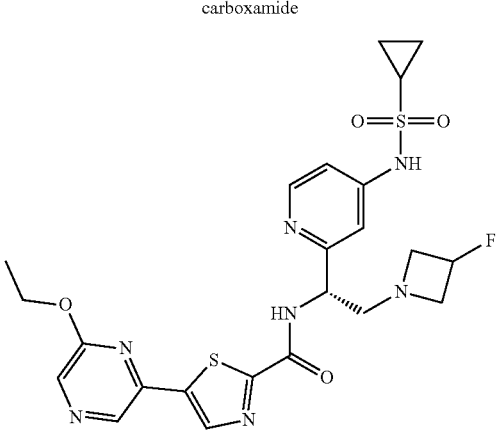<br>isomer 1<br>I-203 | 3-fluoroazetidine | chiral HPLC (Column: CHIRALPAK IF, 2 * 25 cm, 5 μm; Mobile Phase A: MtBE (0.5% 2M NH$_3$-MeOH)--HPLC, Mobile Phase B: EtOH--HPLC; Flow rate: 12 mL/min; Gradient: 50% B to 50% B in 18 min; Wave Length: 220/254 nm) First eluting peak | 548 | (400 MHz, Methanol-$d_4$) δ 8.72 (s, 1H), 8.61 (s, 1H), 8.35 (d, J = 6.0 Hz, 1H), 8.17 (s, 1H), 7.29 (d, J = 2.4 Hz, 1H), 7.17 (dd, J = 6.0, 2.4 Hz, 1H), 5.20-5.00 (m, 2H), 4.50 (q, J = 7.2 Hz, 2H), 3.72-3.60 (m, 2H), 3.30-3.21 (m, 2H), 3.16-3.05 (m, 2H), 2.78-2.72 (m, 1H), 1.47 (t, J = 7.2 Hz, 3H), 1.18-1.13 (m, 2H), 1.04-0.99 (m, 2H) |

| Example Number | Name/Structure Stereochemistry alpha to central amide arbitrarily assigned | Amine reagent used in Step 1 | Chiral chromatography method | MS (ES): m/z [M + H]⁺ | ¹H NMR |
|---|---|---|---|---|---|
| I-204 | (R)-N-(1-(4-(cyclopropanesulfonamido)pyridin-2-yl)-2-(3-fluoroazetidin-1-yl)ethyl)-5-(6-ethoxypyrazin-2-yl)thiazole-2-carboxamide<br><br>isomer 2<br>I-204 | 3-fluoroazetidine | Same as I-203 Second eluting peak | 548 | (400 MHz, Methanol-$d_4$) δ 8.72 (s, 1H), 8.61 (s, 1H), 8.35 (d, J = 6.0 Hz, 1H), 8.17 (s, 1H), 7.29 (d, J = 2.4 Hz, 1H), 7.17 (dd, J = 6.0, 2.4 Hz, 1H), 5.19-5.02 (m, 2H), 4.50 (q, J = 7.2 Hz, 2H), 3.72-3.61 (m, 2H), 3.30-3.22 (m, 2H), 3.16-3.05 (m, 2H), 2.78-2.72 (m, 1H), 1.47 (t, J = 7.2 Hz, 3H), 1.18-1.14 (m, 2H), 1.04-0.99 (m, 2H). |
| I-224 | N-(1-(4-(cyclopropanesulfonamido)pyridin-2-yl)ethyl)-2-(piperidin-1-yl)ethyl)-5-(6-ethoxypyrazin-2-yl)thiazole-2-carboxamide<br><br>I-224 | piperidine |  | 558 | (400 MHz, Methanol-$d_4$) δ 8.73 (s, 1H), 8.63 (s, 1H), 8.31 (d, J = 6.0 Hz, 1H), 8.17 (s, 1H), 7.31 (s, d, J = 2.0 Hz, 1H), 7.16 (dd, J = 6.0, 2.0 Hz, 1H), 5.27 (dd, J = 8.8, 5.6 Hz, 1H), 4.50 (q, J = 7.2 Hz, 2H), 3.03-2.97 (m, 1H), 2.94-2.89 (m, 1H), 2.77-2.67 (m, 3H), 2.64-2.60 (m, 2H), 1.70-1.62 (m, 4H), 1.54-1.48 (m, 2H), 1.47 (t, J = 7.2 Hz, 3H), 1.17-1.13 (m, 2H), 1.04-0.99 (m, 2H) |
| I-213 | (R)-N-(1-(4-(cyclopropanesulfonamido)pyridin-2-yl)-2-(piperidin-1-yl)ethyl)-5-(6-ethoxypyrazin-2-yl)thiazole-2-carboxamide<br><br>isomer 1<br>I-213 | piperidine | chiral HPLC (Column: CHIRAL ART Amylose-SA, 2 * 25 cm, 5 μm; Mobile Phase A: Hex (0.5% 2M NH₃—MeOH)-HPLC, Mobile Phase B: EtOH--HPLC; Flow rate: 20 mL/min; Gradient: 30% B to 30% B in 20 min; Wave Length: 220/254 nm): 17.44) First eluting peak | 558 | (400 MHz, Methanol-$d_4$) δ 8.72 (s, 1H), 8.62 (s, 1H), 8.28 (d, J = 6.0 Hz, 1H), 8.17 (s, 1H), 7.29 (d, J = 2.4 Hz, 1H), 7.14 (dd, J = 6.0, 2.4 Hz, 1H), 2.4 Hz, 1H), 5.23 (dd, J = 8.8, 5.6 Hz, 1H), 4.50 (q, J = 7.2 Hz, 2H), 2.97-2.91 (m, 1H), 2.86-2.81 (m, 1H), 2.75-2.69 (m, 1H), 2.66-2.60 (m, 2H), 2.57-2.52 (m, 2H), 1.64-1.58 (m, 4H), 1.53-1.48 (m, 2H), 1.47 (t, J = 7.2 Hz, 3H), 1.17-1.12 (m, 2H), 1.02-0.97 (m, 2H) |

| Example Number | Name/Structure Stereochemistry alpha to central amide arbitrarily assigned | Amine reagent used in Step 1 | Chiral chromatography method | MS (ES): m/z [M + H]+ | 1H NMR |
|---|---|---|---|---|---|
| I-214 | (S)-N-(1-(4-(cyclopropanesulfonamido)pyridin-2-yl)-2-(piperidin-1-yl)ethyl)-5-(6-ethoxypyrazin-2-yl)thiazole-2-carboxamide<br>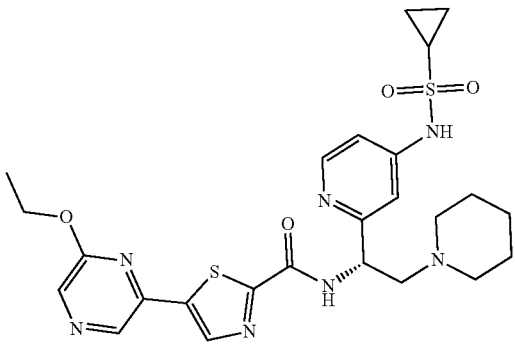<br>isomer 2<br>I-214 | piperidine | Same as I-213 Second eluting peak | 558 | (400 MHz, Methanol-d4) δ 8.72 (s, 1H), 8.61 (s, 1H), 8.28 (d, J = 5.6 Hz, 1H), 8.17 (s, 1H), 7.29 (d, J = 2.4 Hz, 1H), 7.14 (dd, J = 5.6, 2.4 Hz, 1H), 5.23 (dd, J = 8.8, 5.6 Hz, 1H), 4.50 (q, J = 7.2 Hz, 2H), 2.97-2.92 (m, 1H), 2.86-2.81 (m, 1H), 2.75-2.69 (m, 1H), 2.66-2.60 (m, 2H), 2.57-2.52 (m, 2H), 1.67-1.60 (m, 4H), 1.53-1.48 (m, 2H), 1.47 (t, J = 7.2 Hz, 3H), 1.17-1.12 (m, 2H), 1.02-0.97 (m, 2H) |
| I-208 | N-(1-(4-(cyclopropanesulfonamido)pyridin-2-yl)-2-(pyrrolidin-1-yl)ethyl)-5-(6-ethoxypyrazin-2-yl)thiazole-2-carboxamide<br>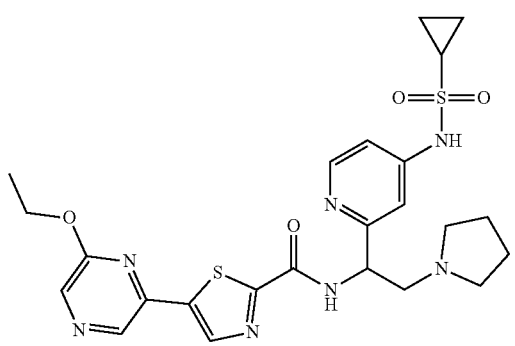<br>I-208 | pyrrolidine | | 544 | (400 MHz, Methanol-d4) δ 8.71 (s, 1H), 8.60 (s, 1H), 8.31 (d, J = 6.0 Hz, 1H), 8.17 (s, 1H), 7.31 (d, J = 2.4 Hz, 1H), 7.15 (dd, J = 6.0, 2.4 Hz, 1H), 5.29 (dd, J = 8.8, 5.6 Hz, 1H), 4.50 (q, J = 7.2 Hz, 2H), 3.25-3.19 (m, 1H), 3.09-3.04 (m, 1H), 2.81-2.70 (m, 5H), 1.89-1.85 (m, 4H), 1.47 (t, J = 7.2 Hz, 3H), 1.17-1.13 (m, 2H), 1.02-0.97 (m, 2H) |

Example 90: Synthesis of (S)—N-(1-(4-(cyclopropanesulfonamido)pyridin-2-yl)-2-(pyrrolidin-1-yl)ethyl)-5-(6-ethoxypyrazin-2-yl)thiazole-2-carboxamide, isomer 1 (I-198) and (R)—N-(1-(4-(cyclopropanesulfonamido)pyridin-2-yl)-2-(pyrrolidin-1-yl)ethyl)-5-(6-ethoxypyrazin-2-yl)thiazole-2-carboxamide, isomer 2 (I-199). Stereochemistry Arbitrarily Assigned

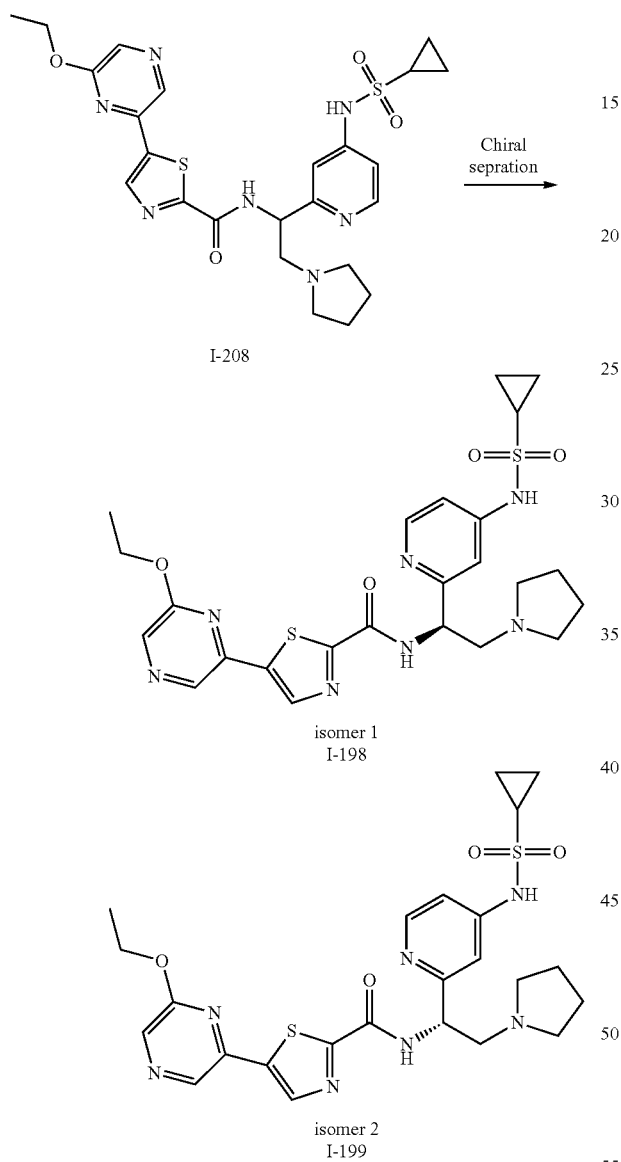

Synthesis of I-198 and I-199. I-208 was purified by chiral HPLC (Column: CHIRAL ART Amylose-SA, 2*25 cm, 5 μm; Mobile Phase A: Hex:DCM=3:1(0.5% 2M ML-MeOH)-HPLC, Mobile Phase B: EtOH-HPLC; Flow rate: 20 mL/min; Gradient: 10% B to 10% B in 13 min; Wave Length: 254/220 nm) to afford I-198 (first eluting peak) and I-199 (second eluting peak) both as white solid. I-198: MS (ES): m/z 544 [M+H]$^+$; $^1$H NMR (400 MHz, Methanal-d$_4$) δ 8.72 (s, 1H), 8.61 (s, 1H), 8.31 (d, J=6.0 Hz, 1H), 8.17 (s, 1H), 7.31 (d, J=2.4 Hz, 1H), 7.15 (dd, J=6.0, 2.4 Hz, 1H), 5.29 (dd, J=8.8, 5.6 Hz, 1H), 4.50 (q, J=7.2 Hz, 2H), 3.25-3.20 (m, 1H), 3.10-3.05 (m, 1H), 2.82-2.69 (m, 5H), 1.89-1.85 (m, 4H), 1.47 (t, J=7.2 Hz, 3H), 1.17-1.13 (m, 2H), 1.02-0.97 (m, 2H). I-199: MS (ES): m/z 544 [M+H]$^+$; $^1$H NMR (400 MHz, Methanal-7*) δ 8.72 (s, 1H), 8.61 (s, 1H), 8.31 (d, J=6.0 Hz, 1H), 8.17 (s, 1H), 7.31 (d, J=2.4 Hz, 1H), 7.15 (dd, 7=6.0, 2.4 Hz, 1H), 5.28 (dd, J=8.8, 5.6 Hz, 1H), 4.50 (q, J=7.2 Hz, 2H), 3.24-3.19 (m, 1H), 3.08-3.04 (m, 1H), 2.81-2.69 (m, 5H), 1.89-1.85 (m, 4H), 1.47 (t, J=7.2 Hz, 3H), 1.17-1.13 (m, 2H), 1.02-0.97 (m, 2H).

Example 91: Synthesis of N-(2-(1-(5-(6-ethoxypyrazin-2-yl)thiazole-2-carbonyl)piperazin-2-yl)pyridin-4-yl)cyclopropanesulfonamide (I-223)

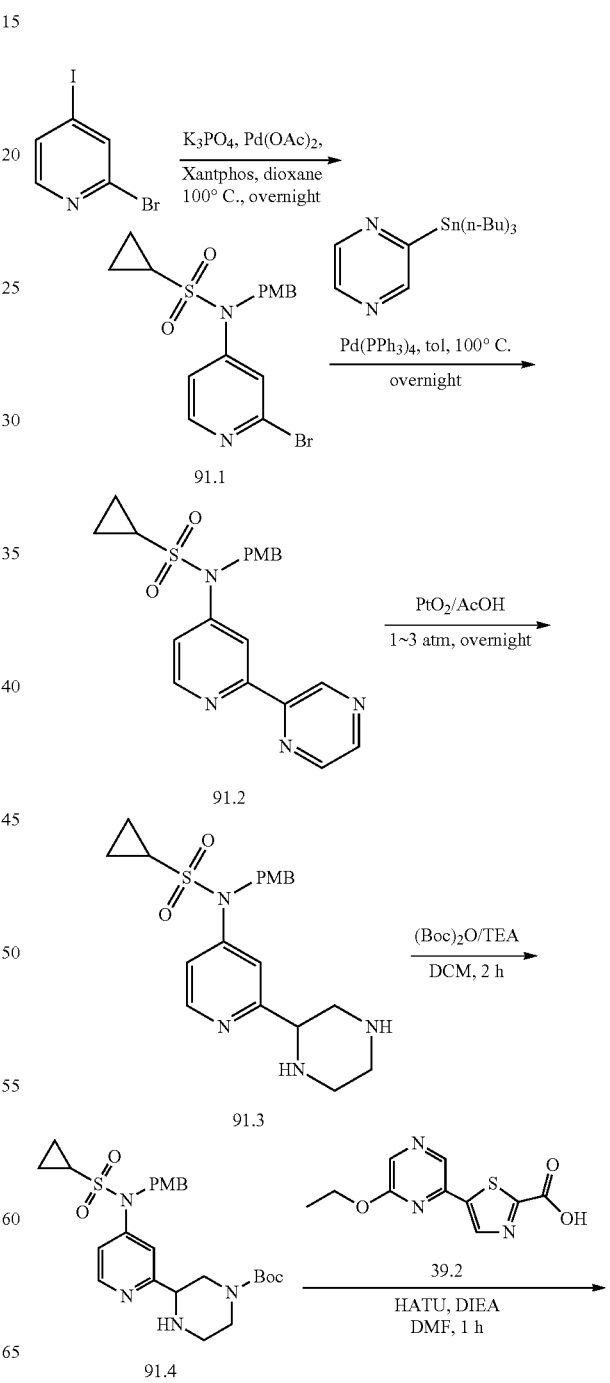

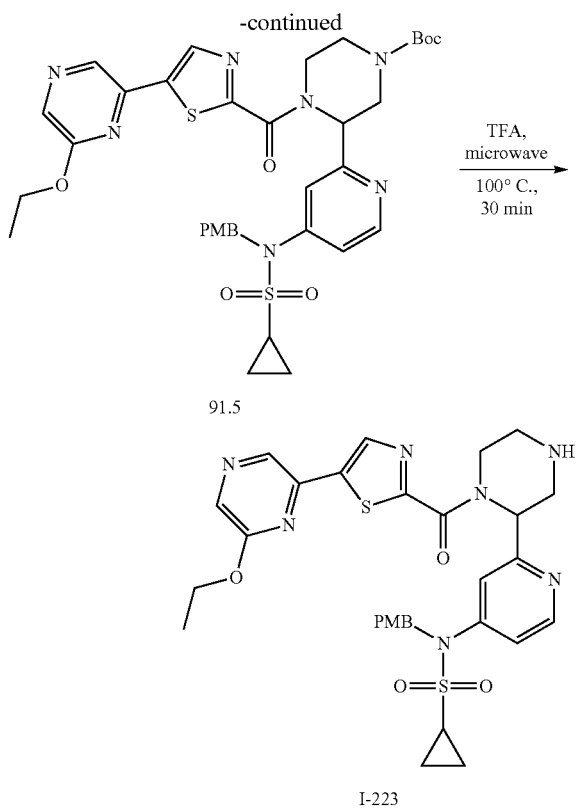

Synthesis of 91.1. To a solution of 2-bromo-4-iodopyridine (6 g, 21.13 mmol, 1 eq) and N-[(4-methoxyphenyl)methyl]cyclopropanesulfonamide (5.1 g, 21.13 mmol, 1 eq) in 1,4-dioxane (100 mL) was added potassium phosphate (13.46 g, 63.41 mmol, 3 eq), Xantphos (1.63 g, 2.82 mmol, 0.2 eq) and Pd(OAc)$_2$ (0.32 g, 1.41 mmol, 0.1 eq). The resulting solution was degassed three times with nitrogen and stirred overnight at 100° C. The mixture was cooled to room temperature, diluted with water and extracted with ethyl acetate. The combined organic layer was washed with brine, dried over sodium sulfate and concentrated under reduced pressure. The residue was purified by silica gel column chromatography (compound was eluted in 50% ethyl acetate in petroleum ether) to obtain N-(2-bromopyridin-4-yl)-N-[(4-methoxyphenyl)methyl]cyclopropanesulfonamide (91.1, 2.7 g, 32%) as a yellow solid. MS (ES): m/z 397/399 [M+H]$^+$.

Synthesis of 91.2. To a solution of 91.1 (2.7 g, 6.8 mmol, 1 eq) in toluene (80 mL) was added 2-(tributylstannyl)pyrazine (3.01 g, 8.15 mmol, 1.2 eq) and Pd(PPh$_3$)$_4$ (0.79 g, 0.68 mmol, 0.1 eq). The resulting solution was degassed three times with nitrogen and stirred overnight at 100° C. The mixture was cooled to room temperature and concentrated under vacuum. The residue was purified by reverse flash chromatography with the following conditions: Column, C18 Column; Mobile Phase, water (10 mmol/L NH$_4$HCO$_3$) and ACN (30% ACN up to 80% in 20 min); UV detection at 254/220 nm. The product-containing fractions were combined and concentrated under reduced pressure to obtain N-[(4-methoxyphenyl)methyl]-N-[2-(pyrazin-2-yl)pyridin-4-yl]cyclopropanesulfonamide (91.2, 0.7 g, 25%) as a white solid. MS (ES): m/z 397 [M+H]$^+$.

Synthesis of 91.3. A solution of 91.2 (700 mg, 1.76 mmol, 1 eq) in acetic acid (20 mL) was evacuated and flushed three times with nitrogen. To the solution was added PtO$_2$ (38 mg, 0.17 mmol, 0.1 eq). The resulting solution was flushed three times with nitrogen and hydrogen. The resulting solution was stirred for 12 h at 50° C. under hydrogen atmosphere using a hydrogen balloon. The mixture was cooled to room temperature, filtered through a Celite pad and concentrated under reduced pressure. The residue was purified by reverse flash chromatography with the following conditions: Column, C18 Column; Mobile Phase, water (0.1% FA) and ACN (10% ACN up to 50% in 20 min); UV detection at 254/220 nm. The product-containing fractions were combined and concentrated under reduced pressure to obtain N-[(4-methoxyphenyl)methyl]-N-[2-(piperazin-2-yl)pyridin-4-yl]cyclopropanesulfonamide (91.3, 300 mg, 42%) as off-white oil. MS (ES): m/z 403 [M+H]$^+$.

Synthesis of 91.4. To a solution of 91.3 (700 mg, 1.74 mmol, 1 eq) in dichloromethane (15 mL) was added triethylamine (528 mg, 5.22 mmol, 3 eq) and di-tert-butyl dicarbonate (190 mg, 0.87 mmol, 0.5 eq). The mixture was stirred 1 h at room temperature. The mixture was diluted with water and extracted with dichloromethane. The combined organic layer was washed with brine, dried over sodium sulfate and concentrated under reduced pressure. The residue was purified by reverse flash chromatography with the following conditions: Column, C18 Column; Mobile Phase, water (10 mmol/L NH$_4$HCO$_3$) and ACN (10% ACN up to 70% in 20 min); UV detection at 254/220 nm. The product-containing fractions were combined and concentrated under reduced pressure to obtain tert-butyl 3-(4-[N-[(4-methoxyphenyl)methyl]cyclopropanesulfonamido]pyridin-2-yl) piperazine-1-carboxylate (91.4, 200 mg, 22%) as a yellow solid. MS (ES): m/z 503 [M+H]$^+$.

Synthesis of 91.5. To a solution of 39.2 (150 mg), 91.4 (300 mg, 0.59 mmol, 1 eq) and 2-(-7-azabenzotriazol-1-yl)-N,N,N',N''-tetramethyluronium hexafluorophosphate (453 mg, 1.19 mmol, 2 eq) in N,N-dimethylformamide (4 mL) was added N,N-diisopropylethylamine (231 mg, 1.79 mmol, 3 eq) dropwise at room temperature under nitrogen atmosphere. The mixture was stirred 1 h at room temperature. After completion, the reaction mixture was purified by reverse phase flash chromatography with the following conditions: Column, C18 Column; Mobile Phase, water (10 mmol/L NH$_4$HCO$_3$) and ACN (10% ACN up to 70% in 10 min); UV detection at 254/220 nm. The product-containing fractions were combined and concentrated under reduced pressure to obtain tert-butyl 4-[5-(6-ethoxypyrazin-2-yl)-1,3-thiazole-2-carbonyl]-3-(4-[N-[(4-methoxyphenyl)methyl]cyclopropanesulfonamido]pyridin-2-yl)piperazine-1-carboxylate (91.5, 260 mg, 59%) as a yellow solid. MS (ES): m/z 736[M+H]$^+$.

Synthesis of I-223. A solution of 91.5 (60 mg, 0.08 mmol, 1 eq) in trifluoroacetic acid (3 mL) was heated in a microwave apparatus for 30 mins at 100° C. The mixture was concentrated under reduced pressure. The residue was purified by Prep-HPLC with the following conditions: Column: Sunfire prep C18 column; Mobile Phase, water (10 mmol/L NH$_4$HCO$_3$) and ACN (40% ACN up to 50% in 7 min); UV detection at 254/210 nm. The product-containing fractions were combined and evaporated partially in vacuum and lyophilized overnight to afford N-(2-[1-[5-(6-ethoxypyrazin-2-yl)-1,3-thiazole-2-carbonyl]piperazin-2-yl]pyridin-4-yl)cyclopropanesulfonamide (I-223, 5.2 mg, 12%) as a white solid. MS (ES): m/z 516 [M+H]$^+$; $^1$H NMR (300 MHz, CD$_3$OD) δ 8.69 (s, 1H), 8.63-8.45 (m, 1H), 8.37 (d, J=5.8 Hz, 1H), 8.17 (s, 1H), 7.38-7.23 (m, 1H), 7.14 (s, 1H), 6.85 (s, 0.5H), 5.75 (s, 0.5H), 5.52-5.33 (m, 0.5H), 4.84-4.47

(m, 2.5H), 3.94 (d, J=13.4 Hz, 1H), 3.32-2.83 (m, 4H), 2.80-2.55 (m, 1H), 1.47 (t, 7=7.1 Hz, 3H), 1.06 (d, J=41.0 Hz, 4H).

Example 92: Synthesis of (S)—N-(2-(1-(5-(6-ethoxypyrazin-2-yl)thiazole-2-carbonyl)piperazin-2-yl)pyridin-4-yl)cyclopropanesulfonamide, isomer (I-211) and (R)—N-(2-(1-(5-(6-ethoxypyrazin-2-yl)thiazole-2-carbonyl)piperazin-2-yl)pyridin-4-yl)cyclopropanesulfonamide, isomer 2 (I-212). Stereochemistry Arbitrarily Assigned mide, isomer 1 (I-211, 1$^{st}$ eluting peak, 12 mg, 41%) and (R)—N-(2-(1-(5-(6-ethoxypyrazin-2-yl)thiazole-2-carbonyl)piperazin-2-yl)pyridin-4-yl)cyclopropanesulfonamide, isomer 1 (I-212, 2$^{nd}$ eluting peak, 9.5 mg, 31%).

I-211: MS (ES): m/z 516 [M+H]$^+$; $^1$H NMR (300 MHz, Methanol-d$_4$) δ 8.69 (s, 1H), 8.68-8.48 (m, 1H), 8.37 (d, J=5.8 Hz, 1H), 8.17 (s, 1H), 7.30 (s, 1H), 7.14 (s, 1H), 6.94-6.75 (m, 0.5H), 5.74 (s, 0.5H), 5.42 (s, 0.5H), 4.51 (q, J=7.1 Hz, 2.5H), 3.93 (d, J=13.4 Hz, 1H), 3.66-3.40 (m, 1H), 3.30-3.21 (m, 1H), 3.20-3.05 (m, 1H), 3.05-2.92 (m, 1H), 2.78-2.60 (m, 1H), 1.47 (t, J=7.0 Hz, 3H), 1.22-0.92 (m, 4H). I-212: MS (ES): m/z 516 [M+H]$^+$; $^1$H NMR (300 MHz, CD$_3$OD) δ 8.69 (s, 1H), 8.77-8.54 (m, 1H), 8.35 (d, J=5.9 Hz, 1H), 8.17 (s, 1H), 7.29 (s, 1H), 7.12 (s, 1H), 6.91-6.75 (m, 0.5H), 5.74 (s, 0.5H), 5.42 (s, 0.5H), 4.51 (q, J=7.0 Hz, 2.5H), 3.92 (d, J=13.4 Hz, 1H), 3.27-2.86 (m, 4H), 2.77-2.50 (m, 1H), 1.47 (t, J=7.1 Hz, 3H), 1.20-0.85 (m, 4H).

Example 93: Synthesis of N-(2-(1-(5-(6-ethoxy-pyrazin-2-yl) thiazole-2-carbonyl)-4-methylpiper-azin-2-yl)pyridin-4-yl)cyclopropanesulfonamide (I-218)

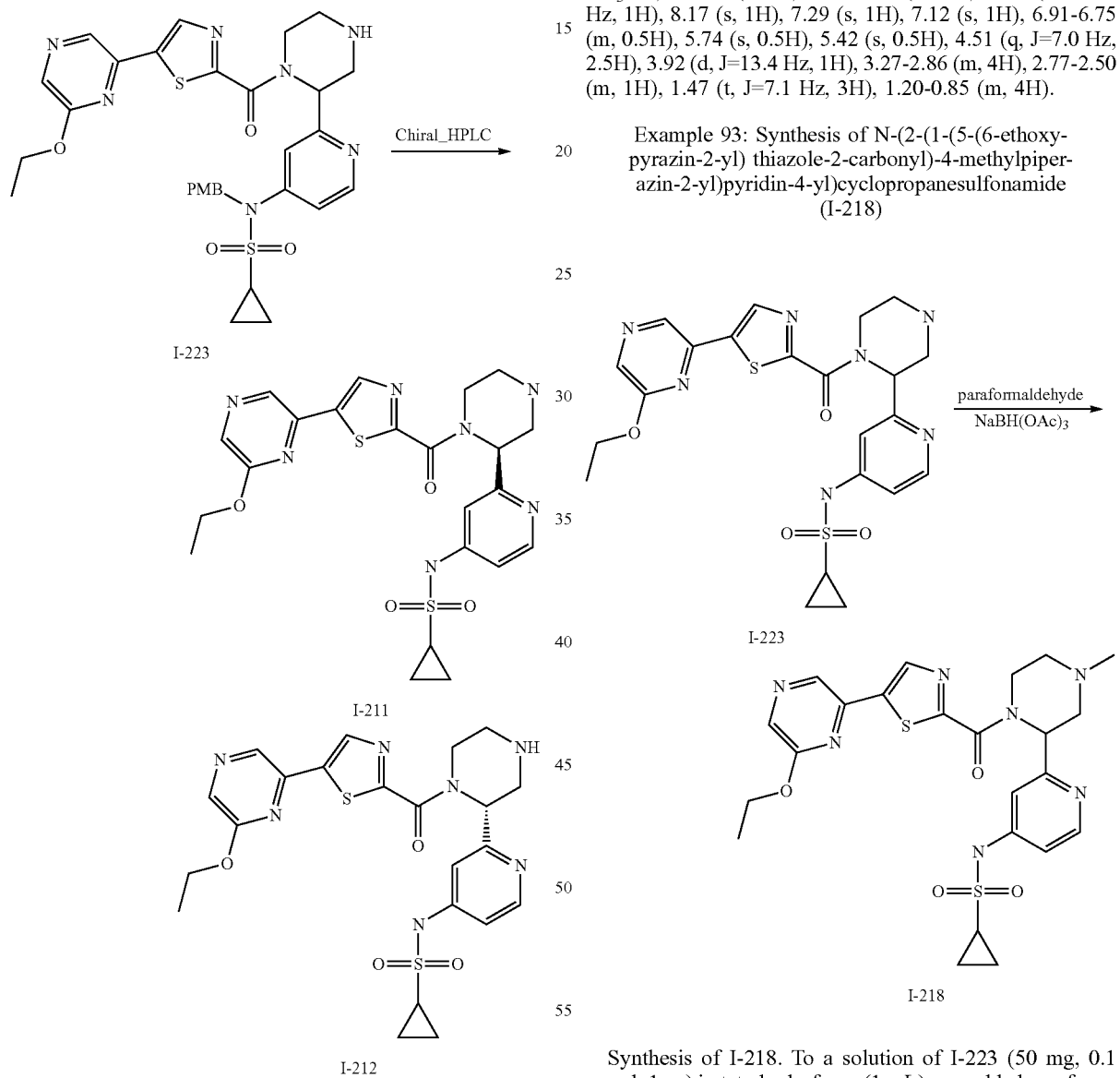

Synthesis of I-211 and I-212. I-223 (60 mg, 0.09 mmol, 1 eq) was separated by Chiral-Prep-HPLC with the following conditions: Column, CHIRALPAK IE-3, 4.6*50 mm, 3 um; mobile phase, MtBE(0.1% DEA):MeOH=50:50; UV detection at 254/220 nm. The product-containing fractions were combined and concentrated under reduced pressure to afford (S)—N-(2-(1-(5-(6-ethoxypyrazin-2-yl)thiazole-2-carbonyl)piperazin-2-yl)pyridin-4-yl)cyclopropanesulfona- Synthesis of I-218. To a solution of I-223 (50 mg, 0.1 mmol, 1 eq) in tetrahydrofuran (1 mL) was added paraformaldehyde (26 mg, 0.29 mmol, 3 eq) and NaBH(OAc)$_3$ (62 mg, 0.29 mmol, 3 eq). The mixture was stirred 1 h at room temperature. The residue was concentrated under reduced pressure and purified by Prep-HPLC with the following conditions: Column: Sunfire prep C18 column; Mobile Phase, water (10 mmol/L NH$_4$HCO$_3$) and ACN (40% ACN up to 50% in 10 min); UV detection at 254/210 nm. The product-containing fractions were combined and evaporated partially in vacuum and lyophilized overnight to afford N-(2-{1-[5-(6-ethoxypyrazin-2-yl)-1,3-thiazole-2-carbonyl]-4-methylpiperazin-2-yl}pyridin-4-yl)cyclopropanesulfonamide (I-218, 5.1 mg, 9.9%) as a white solid. MS (ES): m/z 530 [M+H]+. 1H NMR (300 MHz, Methanol-d4) δ 8.77-8.42 (m, 2H), 8.31 (d, J=5.9 Hz, 1H), 8.16 (s, 1H), 7.29 (d, J=2.2 Hz, 1H), 7.12 (s, 1H), 6.88 (s, 0.458H), 5.79 (s, 0.373H), 5.55 (s, 0.371H), 4.69-4.39 (m, 2.634H), 3.79 (d, J=12.1 Hz, 1H), 3.27-3.10 (m, 1H), 2.99-2.85 (m, 1H), 2.78-2.52 (m, 2H), 2.45-2.20 (m, 4H), 1.47 (t, J=7.1 Hz, 3H), 1.20-0.89 (m, 4H).

Example 94: Synthesis of N-(4-{1-[5-(6-ethoxypyrazin-2-yl)-1,3-thiazole-2-carbonyl]piperazin-2-yl}pyrimidin-2-yl)cyclopropanesulfonamide, Formic Acid Salt (I-181)

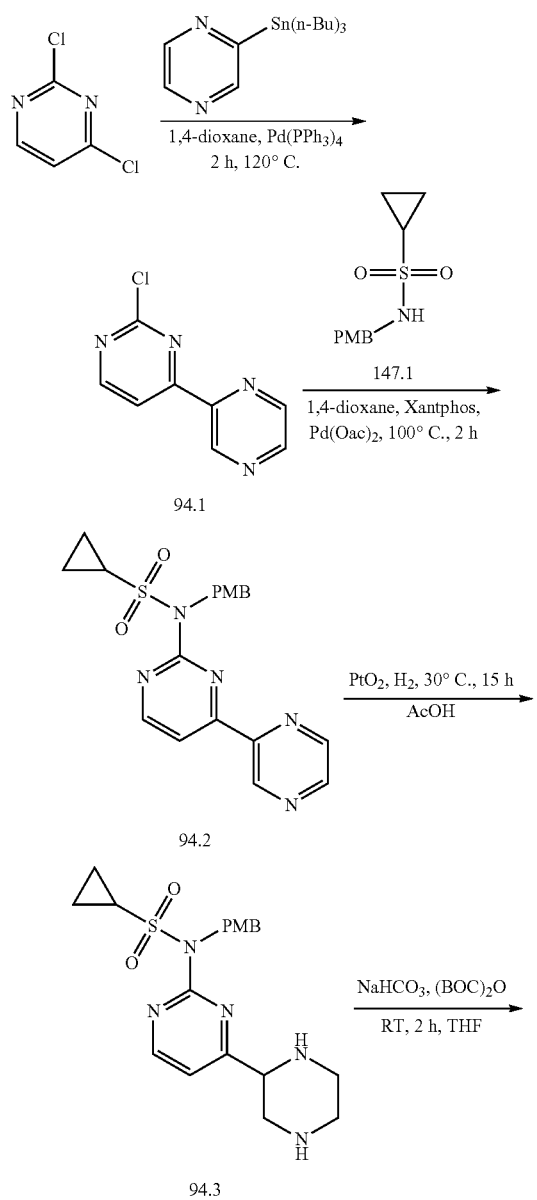

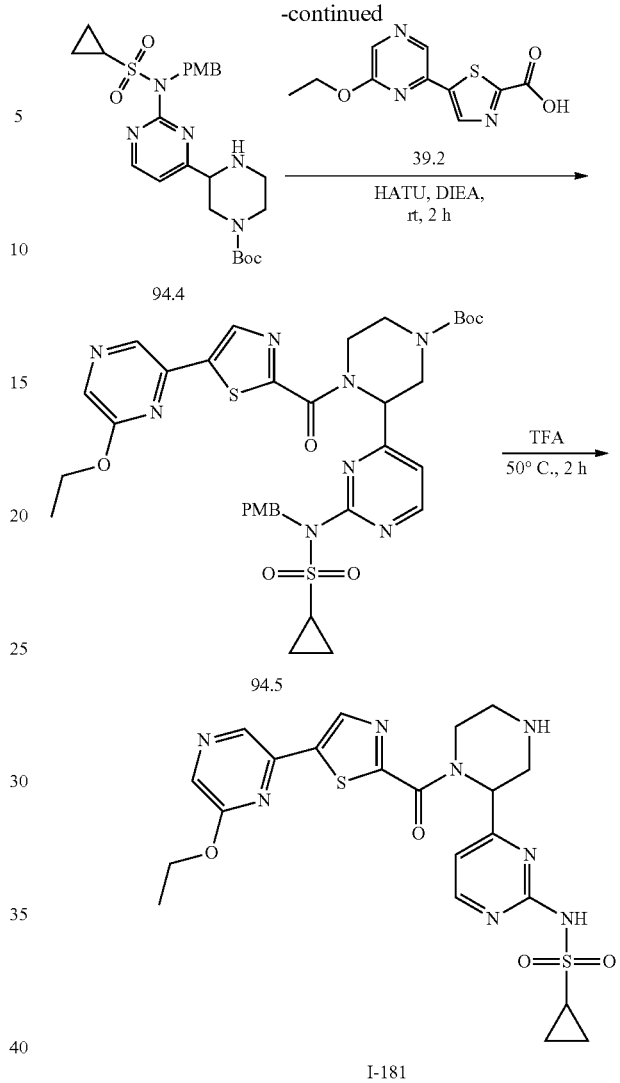

Synthesis of 94.1. To a stirred mixture of 2,4-dichloropyrimidine (3 g, 19.8 mmol, 1 eq) and 2-(tributylstannyl)pyrazine (8.8 g, 23.8 mmol, 1.2 eq) in 1,4-dioxane (50 mL) were added Pd(PPh3)4 (2.28 g, 1.96 mmol, 0.1 eq) at room temperature under nitrogen atmosphere. The resulting mixture was degassed three times with nitrogen and stirred for 2 h at 120° C. under nitrogen atmosphere. The resulting mixture was concentrated under vacuum. The residue was purified by reverse phase flash chromatography (compound was eluted in 40% acetonitrile in water) to obtain 4-chloro-2-(pyrazin-2-yl)pyrimidine (94.1, 2.42 g, 62%) as a yellow solid. MS (ES): m/z 193 [M+H]+.

Synthesis of 94.2. To a stirred mixture of 94.1 (2.42 g, 15.59 mmol, 1.0 eq) and 147.1 (4.71 g, 18.85 mmol, 1.5 eq) in 1,4-dioxane (40 mL) were added potassium phosphate (5.38 g, 25.1 mmol, 2 eq) and XantPhos (1.51 g, 2.5 mmol, 0.2 eq) and Pd(OAc)2 (283 mg, 1.25 mmol, 0.1 eq) in portions at room temperature under nitrogen atmosphere. The resulting mixture was degassed three times with nitrogen and stirred for 2 h at 100° C. under nitrogen atmosphere. The resulting mixture was concentrated under vacuum. The residue was purified by reverse phase flash chromatography (eluted in 40% acetonitrile in water) to obtain N-[(4-methoxyphenyl)methyl]-N-[2-(pyrazin-2-yl)pyrimidin-4- yl]cyclopropanesulfonamide (94.2, 1.05 g, 21%) as a yellow oil. MS (ES): m/z 398 [M+H]+.

Synthesis of 94.3. A stirred mixture of 94.2 (1.05 g, 2.64 mmol, 1 eq) in acetic acid (15 mL) was purged three times with nitrogen. To the solution was added $PtO_2$ (59 mg, 0.27 mmol, 0.1 eq) in portions. The resulting solution was flushed three times with nitrogen and hydrogen. The resulting solution was stirred for 15 h at 30° C. under hydrogen atmosphere. The resulting mixture filtered, the filter cake was washed with ethyl acetate. The filtrate was concentrated under reduced pressure. The residue was purified by reverse phase flash chromatography (compound was eluted in 30% acetonitrile in water) to obtain N-[(4-methoxyphenyl)methyl]-N-[2-(piperazin-2-yl)pyrimidin-4-yl]cyclopropanesulfonamide (94.3, 370 mg, 35%) as a yellow solid. MS (ES): m/z 404 [M+H]+.

Synthesis of 94.4. To a stirred mixture of 94.3 (370 mg, 0.92 mmol, 1 eq) and sodium bicarbonate (231 mg, 2.76 mmol, 3 eq) in tetrahydrofuran (5 mL) and water (1 mL) was added di-tert-butyl dicarbonate (80 mg, 0.37 mmol, 0.4 eq) in portions at room temperature. The resulting mixture was stirred for 2 h at room temperature. The mixture was diluted with water and extracted with ethyl acetate. The combined organic layer was washed with brine, dried over sodium sulfate and concentrated under reduced pressure. The residue was purified by reverse phase flash chromatography (compound was eluted in 60% acetonitrile in water) to obtain tert-butyl 3-(2-{N-[(4-methoxyphenyl)methyl]cyclopropanesulfonamido}pyrimidin-4-yl)piperazine-1-carboxylate (94.4, 210 mg, 45%) as a yellow solid. MS (ES): m/z 504 [M+H]+.

Synthesis of 94.5. To a stirred mixture of 94.4 (210 mg, 0.42 mmol, 1 eq) and 39.2 (125 mg) in dichlormethane (5 mL) were added 2-(-7-azabenzotriazol-1-yl)-N, N, N', N'-tetramethyluronium hexafluorophosphate (190 mg, 0.5 mmol, 1.2 eq) and N, N-diisopropylethylamine (162 mg, 1.26 mmol, 3 eq) in portions at room temperature. The resulting mixture was stirred for 2 h at room temperature. The resulting mixture was concentrated under vacuum. The residue was purified by reverse phase flash chromatography (compound was eluted in 80% acetonitrile in water) to obtain tert-butyl 4-[5-(6-ethoxypyrazin-2-yl)-1,3-thiazole-2-carbonyl]-3-(2-{N-[(4-methoxyphenyl)methyl]cyclopropanesulfonamido}pyrimidin-4-yl)piperazine-1-carboxylate (94.5, 150 mg, 48%) as a yellow solid. MS (ES): m/z 737 [M+H]+.

Synthesis of I-181. A solution of 94.5 (150 mg) in trifluoroacetic acid (4 mL) was stirred for 2 h at 50° C. The resulting mixture was concentrated under vacuum. The residue was purified by reverse phase flash chromatography (compound was eluted in 35% acetonitrile in water). The crude product (100 mg) was purified by Prep-HPLC with the following conditions: Column: Sunfire prep C18 column, 30*150 mm, 5 µm; Mobile Phase, water (0.1% FA) and ACN (5% ACN up to 35% in 7 min); UV detection at 254/210 nm. The product-containing fractions were combined, evaporated partially in vacuum and lyophilized overnight to afford N-(4-{1-[5-(6-ethoxypyrazin-2-yl)-1,3-thiazole-2-carbonyl]piperazin-2-yl}pyrimidin-2-yl)cyclopropanesulfonamide-formic acid salt as a white solid. (I-181, 65 mg, 62%) MS (ES): m/z 517 [M+H]+. $^1$H NMR (300 MHz, DMSO-$d_6$) δ 8.93-8.84 (m, 1H), 8.78-8.64 (m, 1H), 8.62-8.52 (m, 1H), 8.29 (d, J=7.1 Hz, 1H), 8.19 (s, 1H), 7.14 (t, J=4.4 Hz, 1H), 6.68 (s, 0.5H), 5.61-5.23 (m, 1H), 4.49-4.32 (m, 2.5H), 3.79 (d, J=13.7 Hz, 1H), 3.56-3.48 (m, 0.5H), 3.17-3.05 (m, 2.5H), 3.01-2.92 (m, 1H), 2.85-2.62 (m, 1H), 1.40 (t, J=6.9 Hz, 3H), 1.08-0.90 (m, 4H).

Example 95: Synthesis of (R)—N-(4-(1-(5-(6-ethoxypyrazin-2-yl)thiazole-2-carbonyl)piperazin-2-yl)pyrimidin-2-yl)cyclopropanesulfonamide, isomer 1 (I-167) and (S)—N-(4-(1-(5-(6-ethoxypyrazin-2-yl)thiazole-2-carbonyl)piperazin-2-yl)pyrimidin-2-yl)cyclopropanesulfonamide, isomer 2 (I-168). Stereochemistry Arbitrarily Assigned

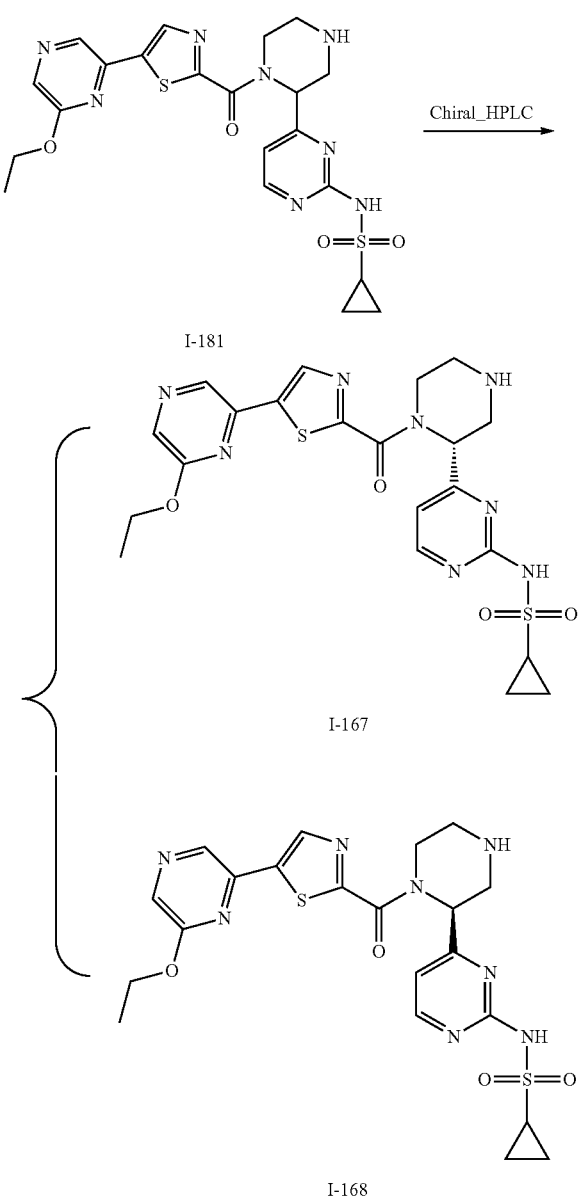

Synthesis of I-167 and I-168. I-181 (50 mg, 0.09 mmol, 1 eq) was separated by Chiral-Prep-HPLC with the following conditions: Column, CHIRALPAK IF, 2*25 mm, 5 um; mobile phase, (Hex:DCM=3:1)(0.3% TFA):EtOH=60:40; UV detection at 254/220 nm. The product-containing fractions were combined and concentrated under reduced pressure to afford (R)—N-(4-(1-(5-(6-ethoxypyrazin-2-yl)thiazole-2-carbonyl)piperazin-2-yl)pyrimidin-2-yl)cyclopropanesulfonamide, isomer 1 (I-167, 1$^{st}$ eluting peak, 3.7 mg, 14%) and (S)—N-(4-(1-(5-(6-ethoxypyrazin-2-yl)

thiazole-2-carbonyl)piperazin-2-yl)pyrimidin-2-yl)cyclopropanesulfonamide, isomer 2 (I-168, $2^{nd}$ eluting peak, 2.1 mg, 8.4%). I-167: MS (ES): m/z 517 [M+H]$^+$; $^1$H NMR (300 MHz, DMSO-d$_6$) δ 8.94-8.86 (m, 1H), 8.80-8.66 (m, 1H), 8.62-8.52 (m, 1H), 8.29 (d, J=7.1 Hz, 1H), 7.21 (t, J=4.4 Hz, 1H), 6.78 (s, 0.5H), 5.75-5.60 (m, 0.5H), 5.48-5.29 (m, 0.5H), 4.49-4.32 (m, 2.5H), 3.92-3.79 (m, 1H), 3.56-3.51 (m, 0.5H), 3.30-3.15 (m, 2.5H), 3.15-3.05 (m, 1H), 3.02-2.82 (m, 1H), 1.40 (t, J=6.9 Hz, 3H), 1.15-0.95 (m, 4H). I-168: MS (ES): m/z 517 [M+H]$^+$; $^1$H NMR (300 MHz, DMSO-d$_6$) δ 8.96-8.87 (m, 1H), 8.82-8.68 (m, 1H), 8.62-8.52 (m, 1H), 8.32 (d, J=7.1 Hz, 1H), 7.26 (t, J=4.4 Hz, 1H), 7.00 (s, 0.5H), 5.92-5.88 (m, 0.5H), 5.65-5.51 (m, 0.5H), 4.65-4.50 (m, 0.5H), 4.49-4.36 (m, 2H), 4.02 (d, J=13.7 Hz, 1H), 3.67-3.50 (m, 1.5H), 3.30-3.09 (m, 3.5H), 1.40 (t, J=6.9 Hz, 3H), 1.18-0.90 (m, 4H).

Example 96: Synthesis of N-(2-{4-[5-(6-ethoxypyrazin-2-yl)-1,3-thiazole-2-carbonyl]morpholin-3-yl}pyridin-4-yl)cyclopropanesulfonamide (I-209)

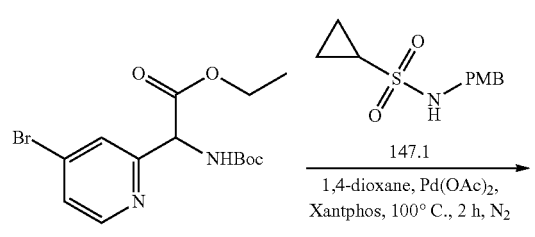

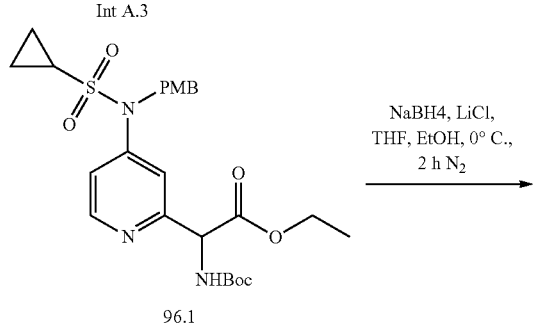

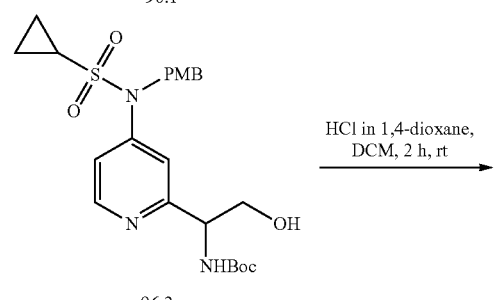

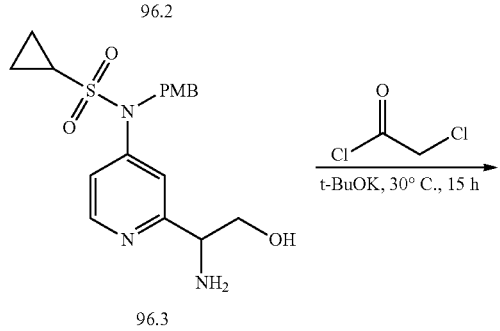

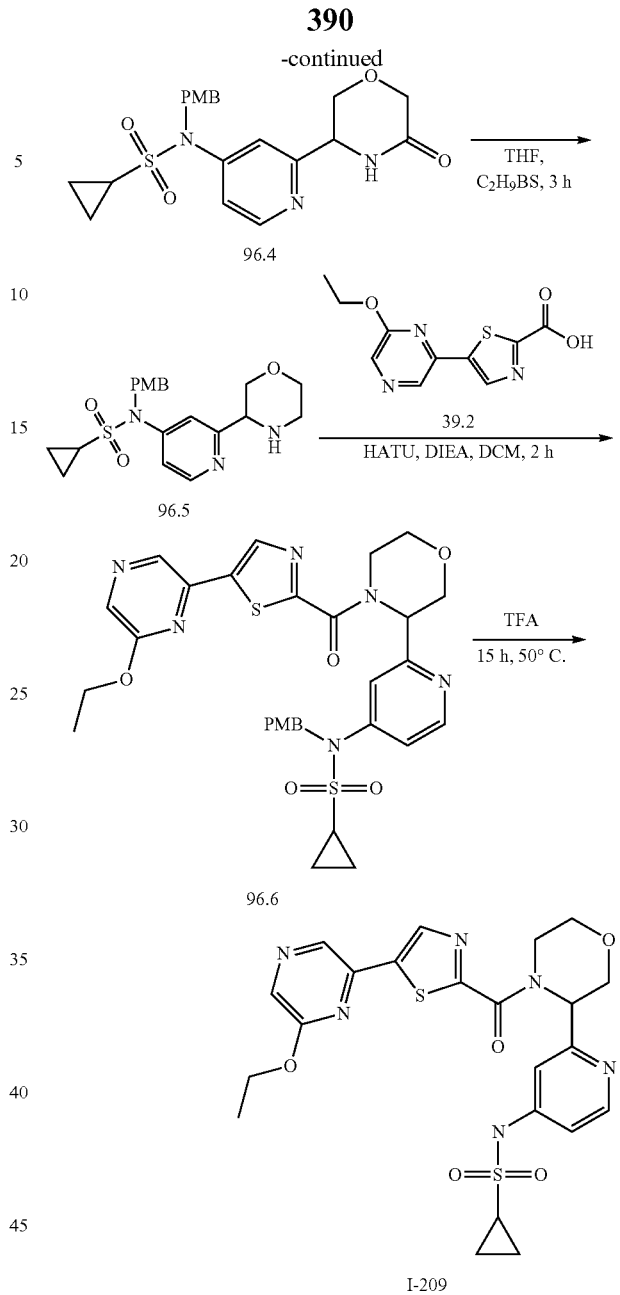

Synthesis of 96.1. To a stirred mixture of Int A.3 (2.7 g, 7.38 mmol, 1 eq) and 147.1 (2.7 g, 11.07 mmol, 1.5 eq) in 1,4-dioxane (30 mL) was added XantPhos (0.9 g, 1.48 mmol, 0.2 eq) and Pd(OAc)$_2$ (0.2 g, 0.74 mmol, 0.1 eq) at room temperature under nitrogen atmosphere. The resulting mixture was degassed three times with nitrogen a 34nd stirred for 2 h at 100° C. under nitrogen atmosphere. The resulting mixture filtration, the filter cake was washed with ethyl acetate. The filtrate was concentrated under reduced pressure. The residue was purified by reverse phase flash chromatography (compound was eluted in 60% acetonitrile in water) to obtain ethyl 2-[(tert-butoxycarbonyl)amino]-2-(4-{N-[(4-methoxyphenyl)methyl]cyclopropanesulfonamido}pyridin-2-yl)acetate (96.1, 2 g, 52%) as a yellow oil. MS (ES): m/z 520 [M+H]$^+$.

Synthesis of 96.2. To a stirred mixture of 96.1 (2 g, 3.85 mmol, 1 eq) in tetrahydrofuran (30 mL) and ethyl alcohol (3 mL) was added lithium chloride (0.3 g, 7.69 mmol, 2 eq) and sodium borohydride (0.6 g, 15.39 mmol, 4 eq) at 0° C. under nitrogen atmosphere. The resulting mixture was stirred for 2 h at 0° C. under nitrogen atmosphere. The resulting mixture was concentrated under vacuum. The residue was purified by reverse phase flash chromatography (compound was eluted in 60% acetonitrile in water) to obtain tert-butyl N-[2-hydroxy-1-(4-{N-[(4-methoxyphenyl)methyl] cyclopropanesulfonamido}pyridin-2-yl)ethyl]carbamate (96.2, 700 mg, 38%) as a yellow solid. MS (ES): m/z 478 [M+H]+.

Synthesis of 96.3. To a stirred mixture of 96.2 (650 mg, 1.36 mmol, 1 eq) in dichloromethane (13 mL) was added 4N HCl in 1,4-dioxane (13 mL) at room temperature. The resulting mixture was stirred for 2 h at room temperature. The resulting mixture was concentrated under vacuum. The crude product (96.3, 500 mg) was used in the next step directly without further purification. MS (ES): m/z 378 [M+H]+.

Synthesis of 96.4. A solution of 96.3 (514 mg) and N,N-diisopropylethylamine (528 mg, 4.09 mmol, 3 eq) in tetrahydrofuran (5 mL) was degassed three times with nitrogen and cooled to −78° C. To the resulting mixture was added chloroacetyl chloride (123 mg, 1.09 mmol, 0.8 eq) under nitrogen atmosphere. The resulting mixture was stirred for 2 h at room temperature. Potassium tert-butoxide (458 mg, 4.09 mmol, 3 eq) was added at room temperature. The resulting mixture was stirred for 15 h at 30° C. under nitrogen atmosphere. The reaction was quenched by the addition of NH4Cl (aq) at 0° C. The mixture was cooled to room temperature, diluted with water and extracted with ethyl acetate. The combined organic layer was washed with brine, dried over sodium sulfate and concentrated to obtain N-[(4-methoxyphenyl)methyl]-N-[2-(5-oxomorpholin-3-yl) pyridin-4-yl]cyclopropanesulfonamide (96.4, 200 mg, 32%) as a yellow solid. MS (ES): m/z 418 [M+H]+.

Synthesis of 96.5. To a stirred solution of 96.4 (160 mg, 0.38 mmol, 1 eq) in tetrahydrofuran was added borane dimethyl sulfide complex, 2M in tetrahydrofuran (0.28 mL, 0.57 mmol, 1.5 eq) at room temperature. The resulting mixture was stirred for 1 h at room temperature. To the above mixture was added hydrochloric acid in 1,4-dioxane (2 mL). The resulting mixture was stirred for additional 1 h at room temperature. The resulting mixture was concentrated under vacuum. The residue was purified by reverse phase flash chromatography (compound was eluted in 30% acetonitrile in water) to obtain N-[(4-methoxyphenyl) methyl]-N-[2-(morpholin-3-yl)pyridin-4-yl]cyclopropanesulfonamide (96.5, 60 mg, 38%) as a yellow oil. MS (ES): m/z 404 [M+H]+.

Synthesis of 96.6. To a stirred mixture of 96.5 (100 mg, 0.25 mmol, 1 eq) and 39.2 (62 mg) in dichlormethane was added 2-(-7-azabenzotriazol-1-yl)-N, N, N', N'-tetramethyluronium hexafluorophosphate (113 mg, 0.3 mmol, 1.2 eq) and N, N-diisopropylethylamine (96 mg, 0.74 mmol, 3 eq). The resulting mixture was stirred for 2 h at room temperature. The resulting mixture was concentrated under reduced pressure and purified by silica gel column chromatography (compound was eluted in 30% ethyl acetate in petroleum ether) to obtain N-(2-{4-[5-(6-ethoxypyrazin-2-yl)-1,3-thiazole-2-carbonyl]morpholin-3-yl}pyridin-4-yl)-N-[(4-methoxyphenyl)methyl]cyclopropanesulfonamide (96.6, 50 mg, 31%) as a yellow solid. MS (ES): m/z 637 [M+H]+.

Synthesis of I-209. A stirred mixture of 96.6 (25 mg, 0.04 mmol, 1 eq) in trifluoroacetic acid was stirred for 15 h at 50° C. under nitrogen atmosphere. The residue was concentrated under reduced pressure and purified by Prep-HPLC with the following conditions Column: Sunfire prep C18 column, 30*150 mm, 5 μm; Mobile Phase, water (0.1% FA) and ACN (10% ACN up to 35% in 8 min); UV detection at 254/210 nm. The product-containing fractions were combined and evaporated partially in vacuum and lyophilized overnight to afford N-(2-{4-[5-(6-ethoxypyrazin-2-yl)-1,3-thiazole-2-carbonyl]morpholin-3-yl}pyridin-4-yl)cyclopropanesulfonamide (I-209, 9.7 mg, 48%) as a white solid. MS (ES): m/z 517 [M+H]+; 1H NMR (400 MHz, Methanol-d4) δ 8.78-8.32 (m, 3H), 8.16 (s, 1H), 7.31 (s, 1H), 7.15 (s, 1H), 6.75 (s, 0.5H), 5.71-5.40 (m, 1H), 4.77 (d, J=11.8 Hz, 1H), 4.62-4.40 (m, 2.5H), 4.08-3.90 (m, 2H), 3.82-3.65 (m, 1.5H), 3.29-3.20 (m, 0.5H), 2.79-2.60 (m, 1H), 1.47 (t, J=7.1 Hz, 3H), 1.19-1.10 (m, 2H), 1.05-0.95 (m, 2H).

Example 97: Synthesis of (S)-5-cyclobutyl-N-((4-(cyclopropanesulfonamido)pyridin-2-yl)methyl)-7-methyl-5,6,7,8-tetrahydropyrido[2,3-b]pyrazine-2-carboxamide, isomer 1 (I-263) and (R)-5-cyclobutyl-N-((4-(cyclopropanesulfonamido) pyridin-2-yl)methyl)-7-methyl-5,6,7,8-tetrahydropyrido[2,3-b]pyrazine-2-carboxamide, isomer 2 (I-264). Stereochemistry Arbitrarily Assigned

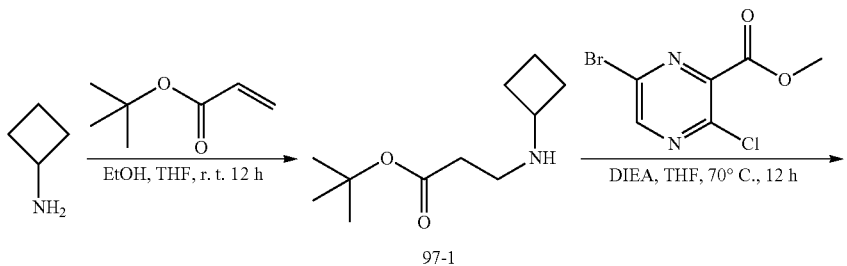

97-1

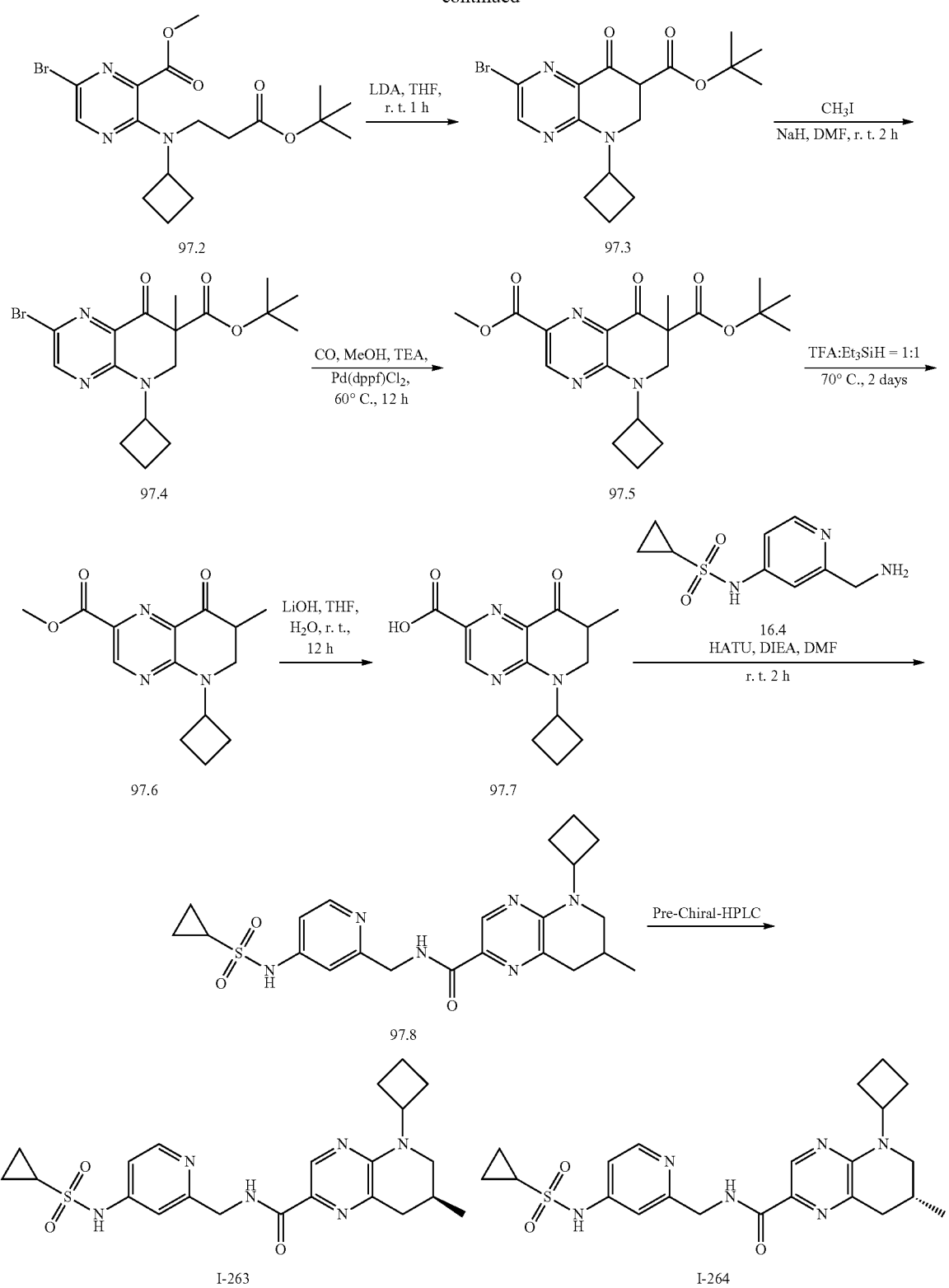

Synthesis of 97.1. A solution of tert-butyl prop-2-enoate (7.2 g, 56.24 mmol, 1 eq) and cyclobutylamine (4 g, 56.24 mmol, 1 eq) in ethanol (40 mL) and tetrahydrofuran (40 mL) was stirred for 12 h at room temperature under nitrogen atmosphere. The resulting mixture was concentrated under reduced pressure to obtain tert-butyl 3-(cyclobutylamino) propanoate (97.1, 8 g, 71%) as a colorless oil. MS (ES): m/z 200 [M+H]$^+$.

Synthesis of 97.2. To a stirred solution of 97.1 (8 g, 40 mmol, 4 eq) and methyl 6-bromo-3-chloropyrazine-2-carboxylate (2.51 g, 10 mmol, 1 eq) in tetrahydrofuran (80 mL) was added N, N-diisopropylethylamine (3.87 g, 30 mmol, 3 eq) dropwise at room temperature. The resulting mixture was stirred for 12 h at 70° C. The mixture was quenched with ammonium chloride and extracted with ethyl acetate. The combined organic layer was washed with brine, dried over sodium sulfate and concentrated under reduced pressure. The residue was purified by silica gel column chromatography (compound was eluted in 5% ethyl acetate in petroleum ether) to afford methyl 6-bromo-3-[[3-(tert-butoxy)-3-oxopropyl](cyclobutyl)amino]pyrazine-2-carboxylate (97.2, 4 g, 97%) as a yellow oil. MS (ES): m/z 414 [M+H]$^+$.

Synthesis of 97.3. A stirred solution of methyl 97.2 (4 g, 9.7 mmol, 1 eq) in tetrahydrofuran (50 mL) was degassed three times with nitrogen and cooled to −78° C. To the solution was added lithium diisopropylamide (2M in tetrahydrofuran, 24.2 mL, 48.31 mmol, 5 eq) dropwise at −78° C. under nitrogen atmosphere. The resulting mixture stirred for 1 h at −78° C. under nitrogen atmosphere. The mixture was quenched with ammonium chloride and extracted with ethyl acetate. The combined organic layer was washed with brine, dried over sodium sulfate and concentrated under reduced pressure. The residue was purified by silica gel column chromatography (compound was eluted in 10% ethyl acetate in petroleum ether) to afford tert-butyl 2-bromo-5-cyclobutyl-8-oxo-6H, 7H-pyrido[2,3-b]pyrazine-7-carboxylate (97.3, 3 g, 81%) as a white solid. MS (ES): m/z 382 [M+H]$^+$.

Synthesis of 97.4. To a stirred solution of 97.3 (3 g, 7.85 mmol, 1 eq) in N,N-dimethyl formamide (20 mL) was added sodium hydride (628 mg, 15.7 mmol, 2 eq, 60% w/w in mineral oil) dropwise at 0° C. under nitrogen atmosphere. After 1 h, to the above mixture was added methyl iodide (5.57 g, 39.24 mmol, 5 eq) dropwise over 10 min at 0° C. The resulting mixture was stirred for 2 h at room temperature under nitrogen atmosphere. The mixture was quenched with ammonium chloride and extracted with ethyl acetate. The combined organic layer was washed with brine, dried over sodium sulfate and concentrated under reduced pressure. The residue was purified by silica gel column chromatography (compound was eluted in 5% ethyl acetate in petroleum ether) to afford tert-butyl 2-bromo-5-cyclobutyl-7-methyl-8-oxo-6H-pyrido[2,3-b]pyrazine-7-carboxylate (97.4, 2 g, 64%) as a yellow solid. MS (ES): m/z 396 [M+H]$^+$.

Synthesis of 97.5. To a solution of 97.4 (1 g, 2.52 mmol, 1 eq) in methanol (20 mL) was added triethylamine (766 mg, 7.57 mmol, 3 eq) and Pd(dppf)Cl$_2$ (184 mg, 0.25 mmol, 0.1 eq) in a pressure tank. The mixture was purged with nitrogen for 5 min and then was pressurized to 30 atm with carbon monoxide at 60° C. for 12 h. The reaction mixture was cooled to room temperature and filtered to remove insoluble solids. The resulting mixture was diluted with water and extracted with ethyl acetate. The combined organic layer was washed with brine, dried over sodium sulfate and concentrated under reduced pressure. The residue was purified by silica gel column chromatography (compound was eluted in 10% ethyl acetate in petroleum ether) to afford 7-tert-butyl 2-methyl 5-cyclobutyl-7-methyl-8-oxo-6H-pyrido[2,3-b]pyrazine-2,7-dicarboxylate (97.5, 800 mg, 84%) as a yellow solid. MS (ES): m/z 376 [M+H]$^+$.

Synthesis of 97.6. Into a 50 mL sealed tube was added 97.5 (600 mg, 1.6 mmol, 1 eq), trifluoroacetic acid (10 mL) and triethyl silane (10 mL) at room temperature. The resulting mixture was stirred for 2 days at 70° C. The reaction mixture was cooled to room temperature and diluted with water and extracted with ethyl acetate. The combined organic layer was washed with brine, dried over sodium sulfate and concentrated under reduced pressure. The residue was purified by silica gel column chromatography (compound was eluted in 100% ethyl acetate in petroleum ether) to afford methyl 5-cyclobutyl-7-methyl-6H, 7H, 8H-pyrido[2,3-b]pyrazine-2-carboxylate (97.6, 90 mg, 21%) as a yellow oil. MS (ES): m/z 262 [M+H]$^+$.

Synthesis of 97.7. To a stirred solution of 97.6 (90 mg, 0.34 mmol, 1 eq) in tetrahydrofuran (5 mL) and water (1 mL) was added lithium hydroxide (25 mg, 1.03 mmol, 3 eq) at room temperature. The resulting mixture was stirred for 12 h at room temperature. The resulting mixture was diluted with water and adjusted pH to 3 with 1M hydrochloric acid (aq.). The precipitated solids were collected by filtration to afford 5-cyclobutyl-7-methyl-6H, 7H, 8H-pyrido[2,3-b]pyrazine-2-carboxylic acid (97.7, 80 mg, 94%) as a yellow solid. MS (ES): m/z 248 [M+H]$^+$.

Synthesis of 97.8. To a stirred solution of 97.7 (80 mg, 0.32 mmol, 1 eq) and 16.4 (184 mg, 0.81 mmol, 2.5 eq) in N,N-dimethyl formamide (5 mL) was added N, N-diisopropylethylamine (209 mg, 1.62 mmol, 5 eq) and 2-(-7-azabenzotriazol-1-yl)-N, N, N', N'-tetramethyluronium hexafluorophosphate (184 mg, 0.48 mmol, 1.5 eq) at room temperature. The resulting mixture was stirred for 2 h at room temperature. The resulting mixture was diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 30*150 mm, 5 um; Mobile Phase, water (0.1% FA) and ACN (15% ACN up to 45% in 7 min); UV detection at 254/220 nm. The product-containing fractions were combined and evaporated partially in vacuum and lyophilized overnight to afford 7-5-cyclobutyl-N-[(4-cyclopropanesulfonamidopyridin-2-yl) methyl]-7-methyl-6H, 7H, 8H-pyrido[2,3-b]pyrazine-2-carboxamide (97.8, 60 mg, 41%) as a white solid. MS (ES): m/z 457 [M+H]$^+$.

Synthesis of I-263 and I-264. 97.8 (60 mg, 0.13 mmol, 1.0 eq) was separated by Chiral-Prep-HPLC with the following conditions: Column, CHIRALPAK IH-3, 3.0*50 mm, 3 μm; mobile Phase: MtBE (0.1% DEA): MeOH=50:50 Detector, UV 254/220 nm. The product-containing fractions were combined and concentrated under reduced pressure to afford (S)-5-cyclobutyl-N-((4-(cyclopropanesulfonamido)pyridin-2-yl)methyl)-7-methyl-5,6,7,8-tetrahydropyrido[2,3-b]pyrazine-2-carboxamide, isomer 1 (I-263, 1$^{st}$ eluting peak, 15 mg, 10%) and (R)-5-cyclobutyl-N-((4-(cyclopropanesulfonamido)pyridin-2-yl)methyl)-7-methyl-5,6,7,8-tetrahydropyrido[2,3-b]pyrazine-2-carboxamide, isomer 2 (I-264, 2$^{nd}$ eluting peak, 13 mg, 8.9%). I-263: MS (ES): m/z 457 [M+H]$^+$; $^1$H NMR (400 MHz, CD$_3$OD) δ 8.52 (s, 1H), 8.19 (d, J=6.1 Hz, 1H), 7.20-7.05 (m, 2H), 5.23-5.09 (m, 1H), 4.62 (s, 2H), 3.70-3.63 (m, 1H), 3.17 (dd, J=12.3, 9.1 Hz, 1H), 3.06-2.98 (m, 1H), 2.74-2.55 (m, 2H), 2.40-2.09 (m, 5H), 1.85-1.70 (m, 2H), 1.21-1.08 (m, 5H), 1.02-0.95 (m, 2H). I-264: MS (ES): m/z 457 [M+H]⁺; ¹H NMR (400 MHz, CD₃OD) δ 8.52 (s, 1H), 8.20 (d, J=6.1 Hz, 1H), 7.21-7.11 (m, 2H), 5.24-5.11 (m, 1H), 4.63 (s, 2H), 3.70-3.63 (m, 1H), 3.17 (dd, J=12.3, 9.1 Hz, 1H), 3.07-2.97 (m, 1H), 2.75-2.56 (m, 2H), 2.37-2.08 (m, 5H), 1.85-1.70 (m, 2H), 1.21-1.09 (m, 5H), 1.03-0.93 (m, 2H).
Example 98: Synthesis of 98: N-[4-(1-{5-[7-(2,2-difluoroethyl)-5H-pyrrolo[2,3-b] pyrazin-2-yl]-1,3-thiazole-2-carbonyl}pyrrolidin-2-yl) pyrimidin-2-yl] cyclopropanesulfonamide (I-132)
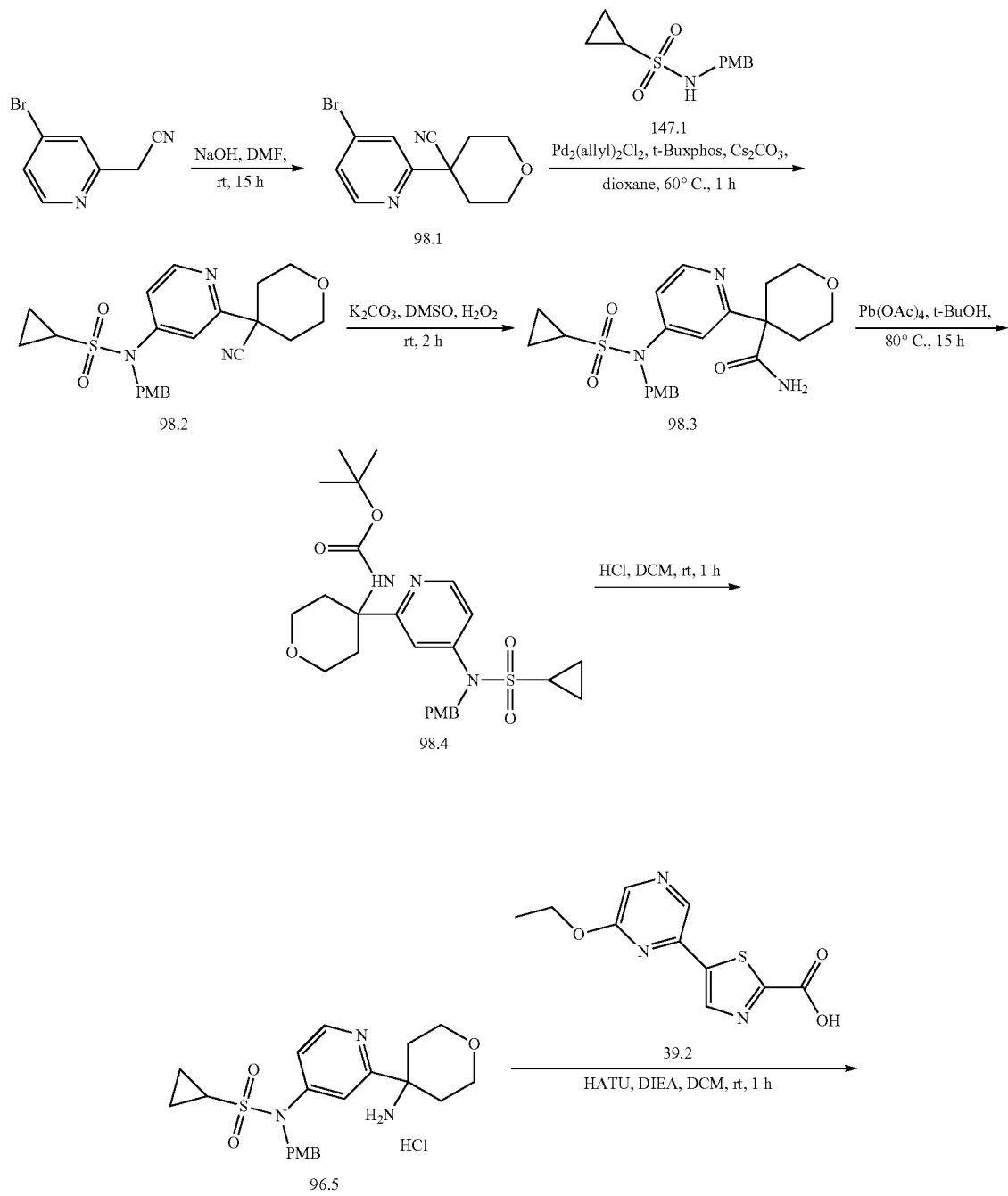

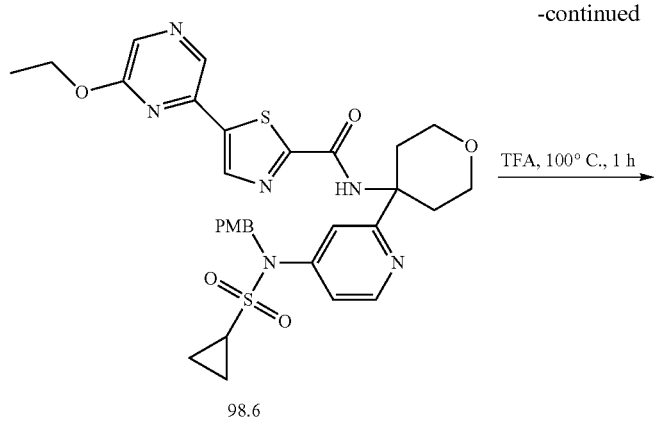

98.6

TFA, 100° C., 1 h →

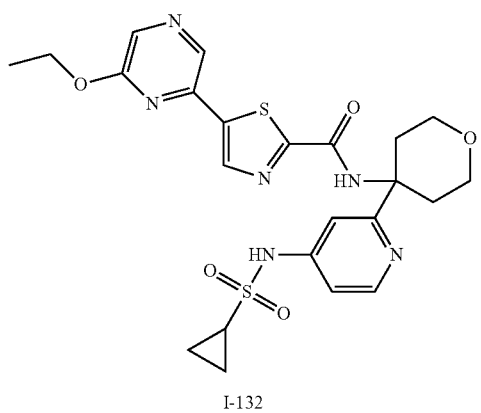

I-132

Synthesis of 98.1. To a stirred mixture of 2-(4-bromopyridin-2-yl) acetonitrile (500 mg, 2.54 mmol, 1 eq) and 1-bromo-2-(2-bromoethoxy) ethane (706 mg, 3.05 mmol, 1.2 eq) in N,N-dimethylformamide (25 mL) was added sodium hydroxide (254 mg, 6.34 mmol, 2.5 eq) in portions at room temperature under nitrogen atmosphere. The mixture was stirred for 15 h at room temperature. The resulting mixture was extracted with ethyl acetate. The combined organic layers were washed with water and dried over anhydrous sodium sulfate. After filtration, the filtrate was concentrated under reduced pressure to obtain 4-(4-bromopyridin-2-yl) oxane-4-carbonitrile (98.1, 500 mg, 73%) as light yellow oil. MS (ES): m/z 267/269 (M+H$^+$).

Synthesis of 98.2. To a stirred mixture of 98.1 (500 mg, 1.88 mmol, 1 eq) and 147.1 (455 mg, 3.76 mmol, 2 eq) in 1,4-dioxane (10 mL) was added cesium carbonate (1.8 g, 5.64 mmol, 3 eq), Pd$_2$(allyl)$_2$Cl$_2$ (69 mg, 0.18 mmol, 0.1 eq) and t-Buxphos (159 mg, 0.37 mmol, 0.2 eq) in portions at room temperature under nitrogen atmosphere. The resulting mixture was degassed three times with nitrogen and stirred for 1 h at 60° C. under nitrogen atmosphere. The resulting mixture was extracted with ethyl acetate. The combined organic layers were washed with water, dried over anhydrous sodium sulfate. After filtration, the filtrate was concentrated under reduced pressure. The residue was purified by Prep-TLC (ethyl acetate/petroleum ether=1/3) to afford N-[2-(4-cyanooxan-4-yl) pyridin-4-yl]-N-[(4-methoxyphenyl) methyl] cyclopropanesulfonamide (98.2, 400 mg, 50%) as a light yellow oil. MS (ES): m/z 428 (M+H$^+$).

Synthesis of 98.3. To a stirred mixture of 98.2 (330 mg, 0.77 mmol, 1 eq) in dimethyl sulfoxide (10 mL) and hydrogen peroxide (5 mL) was added potassium carbonate (320 mg, 2.32 mmol, 3 eq) at room temperature under nitrogen atmosphere. The resulting mixture was stirred for 2 h at room temperature under nitrogen atmosphere. The resulting mixture was extracted with ethyl acetate. The combined organic layers were washed with water, dried over anhydrous sodium sulfate. After filtration, the filtrate was concentrated under reduced pressure. The residue was purified by reverse flash chromatography with the following conditions: Column, C18; mobile phase, Water (10 mmol/L NH$_4$HCO$_3$) and ACN (0% ACN up to 30% in 15 min); Detector, UV 254/220 nm. The reaction was concentrated under reduced pressure to afford 4-(4-{N-[(4-methoxyphenyl) methyl] cyclopropanesulfonamido} pyridin-2-yl) oxane-4-carboxamide (98.3, 230 mg, 66%) as a light yellow oil. MS (ES): m/z 446 (M+H$^+$).

Synthesis of 98.4. To a stirred mixture of 98.3 (230 mg, 0.52 mmol, 1 eq) in t-BuOH (5 mL) was added Pb(OAc)$_4$ (229 mg, 0.52 mmol, 1 eq) at room temperature under nitrogen atmosphere. The mixture was stirred for 15 h at 80° C. The mixture was allowed to cool down to room temperature. The resulting mixture was diluted with water and extracted with ethyl acetate. The combined organic layers were washed with brine, dried over anhydrous sodium sulfate. After filtration, the filtrate was concentrated under reduced pressure. The residue was purified by silica gel column chromatography (dichlormethane/methanol=15/1) to afford tert-butyl N-[4-(4-{N-[(4-methoxyphenyl) methyl] cyclopropanesulfonamido} pyridin-2-yl) oxan-4-yl] carbamate (98.4, 150 mg, 64%) as a brown yellow solid. MS (ES): m/z 518 (M+H$^+$).

Synthesis of 98.5. To a stirred mixture of 98.4 (150 mg, 0.29 mmol, 1 eq) in dichloromethane (2 mL) was added hydrochloric acid in 1,4-dioxane (4N, 2 mL). The mixture was stirred for 1 h at room temperature. The resulting mixture was concentrated under reduced pressure to afford crude N-[2-(4-aminooxan-4-yl) pyridin-4-yl]-N-[(4-methoxyphenyl) methyl]cyclopropanesulfonamide hydrochloride (98.5, 130 mg, 99%) as a brown yellow solid. MS (ES): m/z 418 (M+H$^+$).

Synthesis of 98.6. To a stirred mixture of 98.5 (130 mg, 0.28 mmol, 1 eq) and 39.2 (78 mg) in dichloromethane (5 mL) was added 2-(-7-azabenzotriazol-1-yl)-N, N, N', N'-tetramethyluronium hexafluorophosphate (178 mg, 0.46 mmol, 1.5 eq) and N, N-diisopropylethylamine (161 mg, 1.24 mmol, 4 eq) at room temperature. The mixture was stirred for 15 h at room temperature. The resulting mixture was diluted with water and extracted with ethyl acetate. The combined organic layers were washed with brine, dried over anhydrous sodium sulfate. After filtration, the filtrate was concentrated under reduced pressure. The residue was purified by silica gel column chromatography (dichlormethane/methanol=20/1) to afford 5-(6-ethoxypyrazin-2-yl)-N-[4-(4-{N-[(4-methoxyphenyl) methyl] cyclopropanesulfonamido}pyridin-2-yl) oxan-4-yl]-1,3-thiazole-2-carboxamide (98.6, 80 mg, 59%) as a brown yellow oil. MS (ES): m/z 651 (M+H$^+$).

Synthesis of I-132. A stirred mixture of 98.6 (80 mg, 0.12 mmol, 1 eq) in trifluoroacetic acid (2 mL) was stirred for 1 h at 100° C. under nitrogen atmosphere. The mixture was allowed to cool down to room temperature. The resulting mixture was concentrated under reduced pressure and purified by Prep-HPLC with the following conditions Column, C18; mobile phase, Water (10 mmol/L NH$_4$HCO$_3$) and ACN (30% ACN up to 40% in 8 min); UV detection at 254/220 nm. The product-containing fractions were combined and evaporated partially in vacuum and lyophilized overnight to afford N-[4-(4-cyclopropanesulfonamidopyridin-2-yl) oxan-4-yl]-5-(6-ethoxypyrazin-2-yl)-1,3-thiazole-2-carboxamide (I-132, 26 mg, 39%) as an off-white solid. MS (ES): m/z 531 (M+H$^+$); $^1$H NMR (400 MHz, Methanol-d$_4$) δ 8.72 (s, 1H), 8.63 (s, 1H), 8.30 (d, J=5.7 Hz, 1H), 8.17 (s, 1H), 7.43 (d, J=2.1 Hz, 1H), 7.08 (dd, J=5.9, 2.2 Hz, 1H), 4.49 (q, J=7.1 Hz, 2H), 3.99-3.80 (m, 4H), 2.75-2.63 (m, 1H), 2.50-2.34 (m, 4H), 1.46 (t, J=7.1 Hz, 3H), 1.15-1.08 (m, 2H), 1.02-0.93 (m, 2H).

Example 99; Synthesis of (R)-2-(4-(cyclopropanesulfonamido)pyridin-2-yl)-N-(5-(6-ethoxypyrazin-2-yl)pyridin-2-yl)-2-fluorobutanamide, isomer 1 (I-258) and (S)-2-(4-(cyclopropanesulfonamido)pyridin-2-yl)-N-(5-(6-ethoxypyrazin-2-yl)pyridin-2-yl)-2-fluorobutanamide, isomer 2 (I-259). Stereochemistry Arbitrarily Assigned

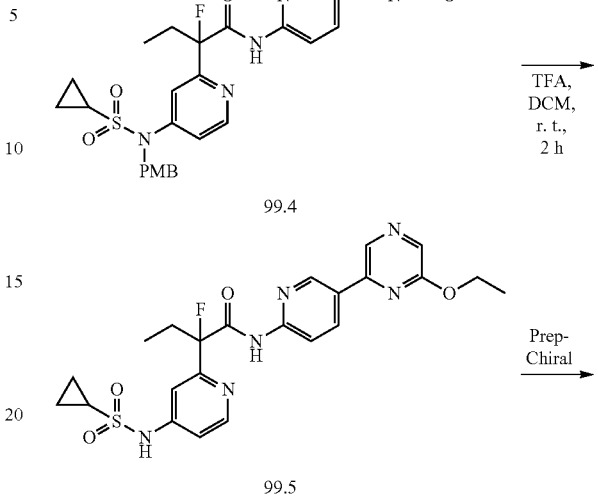
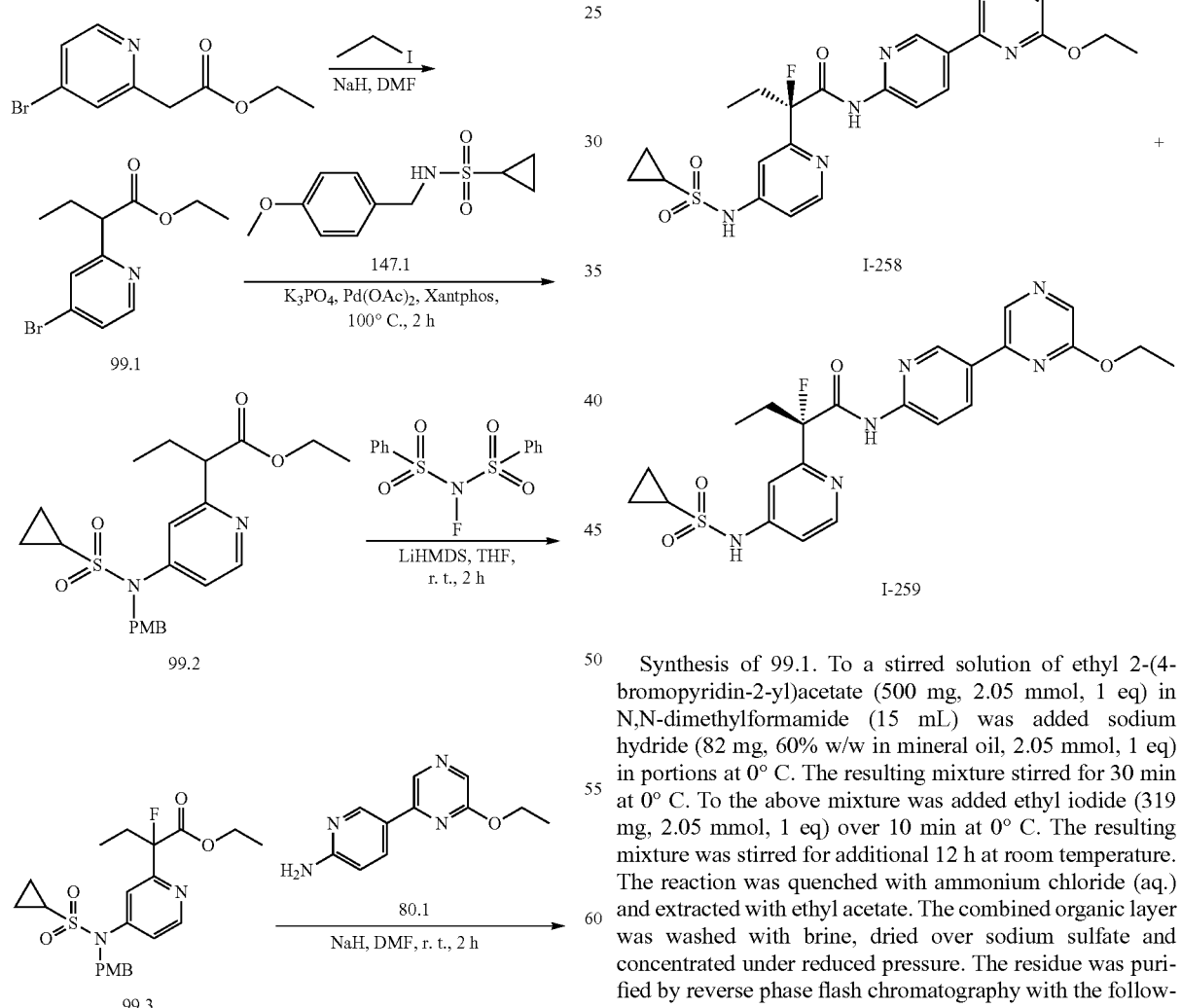

Synthesis of 99.1. To a stirred solution of ethyl 2-(4-bromopyridin-2-yl)acetate (500 mg, 2.05 mmol, 1 eq) in N,N-dimethylformamide (15 mL) was added sodium hydride (82 mg, 60% w/w in mineral oil, 2.05 mmol, 1 eq) in portions at 0° C. The resulting mixture stirred for 30 min at 0° C. To the above mixture was added ethyl iodide (319 mg, 2.05 mmol, 1 eq) over 10 min at 0° C. The resulting mixture was stirred for additional 12 h at room temperature. The reaction was quenched with ammonium chloride (aq.) and extracted with ethyl acetate. The combined organic layer was washed with brine, dried over sodium sulfate and concentrated under reduced pressure. The residue was purified by reverse phase flash chromatography with the following conditions: Column, C18 Column; Mobile Phase, water (10 mmol/L NH$_4$HCO$_3$) and ACN (10% ACN up to 60% in 10 min); UV detection at 254/220 nm. The product-containing fractions were combined and concentrated under reduced pressure to obtain ethyl 2-(4-bromopyridin-2-yl)butanoate (99.1, 480 mg, 86%) as yellow oil. MS (ES): m/z 272/274 [M+H]⁺.

Synthesis of 99.2. To a stirred solution of 99.1 (950 mg, 4.15 mmol, 1 eq) and 147.1 (2 g, 8.31 mmol, 2 eq) in 1,4-dioxane (40 mL) were added potassium phosphate (1.76 g, 8.31 mmol, 2 eq), Pd(OAc)$_2$ (93 mg, 0.42 mmol, 0.1 eq) and Xantphos (481 mg, 0.83 mmol, 0.2 eq) at room temperature under nitrogen atmosphere. The resulting mixture was degassed three times with nitrogen and stirred for 2 h at 100° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by silica gel column chromatography (compound was eluted in 50% ethyl acetate in petroleum ether) to obtain ethyl 2-(2-[N-[(4-methoxyphenyl)methyl]cyclopropanesulfonamido]pyrimidin-4-yl)butanoate (99.2, 1.12 g, 62%) as a yellow oil. MS (ES): m/z 433 [M+H]⁺.

Synthesis of 99.3. A stirred solution of 99.2 (1.12 g, 2.58 mmol, 1 eq) in tetrahydrofuran (50 mL) was degassed three times with nitrogen and cooled to −78° C. To the solution was added lithium hexamethyldisilazide (1N in tetrahydrofuran, 10 mL) dropwise at −78° C. under nitrogen atmosphere. After 1 h, to the above mixture was added N-(benzenesulfonyl)-N-fluorobenzenesulfonamide (1.1 g, 3.36 mmol, 1.3 eq) in tetrahydrofuran (10 mL) dropwise over 10 min at −78° C. The resulting mixture was stirred for 2 h at room temperature under nitrogen atmosphere. The reaction was quenched with sat. ammonium chloride (aq.) and extracted with ethyl acetate. The residue was purified by silica gel column chromatography (compound was eluted in 20% ethyl acetate in petroleum ether) to obtain ethyl 2-2-fluoro-2-(2-[N-[(4-methoxyphenyl)methyl]cyclopropanesulfonamido]pyrimidin-4-yl)butanoate (99.3, 1.14 g, 98%) as a yellow oil. MS (ES): m/z 449 [M+H]⁺.

Synthesis of 99.4. To a stirred solution of 80.1 (437 mg, 2.02 mmol, 0.8 eq) in N,N-dimethylformamide (9 mL) was added sodium hydride (151 mg, 60% w/w in mineral oil, 3.79 mmol, 1.5 eq) in portions at 0° C. under nitrogen atmosphere. After 1 h, to the above mixture was added 99.3 (1.14 g, 2.53 mmol, 1 eq) in N,N-dimethylformamide (3 mL) dropwise at 0° C. The resulting mixture was stirred for additional 2 h at room temperature. The reaction was quenched with sat. ammonium chloride (aq.) and extracted with ethyl acetate. The residue was purified by silica gel column chromatography (compound was eluted in 90% ethyl acetate in petroleum ether) to obtain N-(5-(6-ethoxypyrazin-2-yl)pyridin-2-yl)-2-fluoro-2-(4-(N-(4-methoxybenzyl)cyclopropanesulfonamido)pyridin-2-yl)butanamide (99.4, 950 mg, 61%) as a yellow oil. MS (ES): m/z 621 [M+H]⁺.

Synthesis of 99.5. To a stirred solution of 99.4 (200 mg, 0.32 mmol, 1 eq) in dichloromethane (4 mL) was added trifluoroacetic acid (4 mL) dropwise at 0° C. The resulting mixture was stirred for additional 2 h at room temperature. The resulting mixture was concentrated under vacuum and basified to pH 9 with saturated sodium bicarbonate. The mixture was diluted with water and extracted with ethyl acetate. The combined organic layer washed with brine, dried over sodium sulfate and concentrated under reduced pressure. The residue was purified by Prep-HPLC with the following conditions: Column, XBridge Shield RP18 OBD Column, 30*150 mm, 5 um; Mobile Phase, water (0.1% FA) and ACN (23% ACN up to 42% in 8 min); UV detection at 254/220 nm. The product-containing fractions were combined and evaporated partially in vacuum and lyophilized overnight to afford 2-(4-(cyclopropanesulfonamido)pyridin-2-yl)-N-(5-(6-ethoxypyrazin-2-yl)pyridin-2-yl)-2-fluorobutanamide (99.5, 100 mg, 62%) as a white solid. MS (ES): m/z 501 [M+H]⁺.

Synthesis of I-258 and I-259. 99.5 (100 mg, 0.20 mmol, 1.0 eq) was separated by Chiral-Prep-HPLC with the following conditions: Column, CHIRALPAK IH-3, 3.0*50 mm, 3 μm; mobile Phase: MtBE (0.1% DEA): MeOH=50:50 Detector, UV 254/220 nm. The product-containing fractions were combined and concentrated under reduced pressure to afford (R)-2-(4-(cyclopropanesulfonamido)pyridin-2-yl)-N-(5-(6-ethoxypyrazin-2-yl)pyridin-2-yl)-2-fluorobutanamide, isomer 1 (I-258, 1$^{st}$ eluting peak, 44 mg, 44%) and (S)-2-(4-(cyclopropanesulfonamido)pyridin-2-yl)-N-(5-(6-ethoxypyrazin-2-yl)pyridin-2-yl)-2-fluorobutanamide, isomer 2 (I-259, 2$^{ed}$ eluting peak, 39 mg, 39%). I-258: MS (ES): m/z 502 [M+H]⁺; ¹H NMR (400 MHz, Methanol-d₄) δ 9.08 (d, J=6.4 Hz, 1H), 8.69 (s, 1H), 8.57-8.49 (m, 2H), 8.27-8.26 (m, 1H), 8.17 (s, 1H), 7.72 (d, J=2.3 Hz, 1H), 7.50 (d, J=6.4 Hz, 1H), 4.55 (q, J=7.1 Hz, 2H), 2.89-2.86 (m, 1H), 2.70-2.33 (m, 2H), 1.48 (t, J=7.1 Hz, 3H), 1.27-1.24 (m, 2H), 1.19-1.03 (m, 5H). I-259: MS (ES): m/z 502 [M+H]⁺; ¹H NMR (400 MHz, Methanol-d₄) δ 9.07 (d, J=6.0 Hz, 1H), 8.70 (s, 1H), 8.57-8.49 (m, 2H), 8.27 (m, 1H), 8.17 (s, 1H), 7.72 (d, J=2.3 Hz, 1H), 7.49 (d, J=6.0 Hz, 1H), 4.55 (q, J=7.0 Hz, 2H), 2.88 (m, 1H), 2.69-2.33 (m, 2H), 1.48 (t, J=7.0 Hz, 3H), 1.33-1.22 (m, 2H), 1.14-1.01 (m, 5H).

Example 100: Synthesis of N-[(1R)-1-[3-(difluoromethanesulfonamido)phenyl]ethyl]-5-(6-ethoxypyrazin-2-yl)-1,3-thiazole-2-carboxamide (I-272)

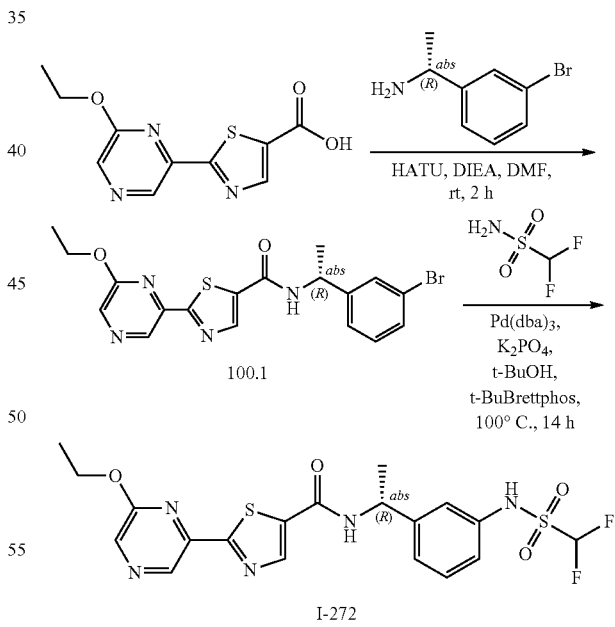

Synthesis of 100.1. To a stirred solution of 39.2 (125 mg) and (1R)-1-(3-bromophenyl)ethanamine (100 mg, 0.5 mmol, 1 eq) in dimethyl formamide (4 mL) was added 2-(-7-azabenzotriazol-1-yl)-N, N, N', N'-tetramethyluronium hexafluorophosphate (228 mg, 0.6 mmol, 1.2 eq) and N, N-diisopropylethylamine (194 mg, 1.5 mmol, 3 eq) in portions at room temperature. The resulting mixture was stirred for 2 h at room temperature under nitrogen atmosphere. The residue was purified by reverse flash chromatography with the following conditions: Column, C18 Column; Mobile Phase, water (0.1% FA) and ACN (5% up to 90% in 20 min); UV detection at 254/220 nm. The resulting mixture was concentrated under reduced pressure to obtain N-[(1R)-1-(3-bromophenyl)ethyl]-5-(6-ethoxypyrazin-2-yl)-1,3-thiazole-2-carboxamide (100.1, 77 mg, 35%) as a white solid. MS (ES): m/z 433 [M+H]$^+$.

Synthesis of I-272. To a stirred mixture of 100.1 (77 mg, 0.18 mmol, 1 eq) and difluoromethanesulfonamide (70 mg, 0.53 mmol, 3 eq) in tert-butanol (4 mL) was added potassium phosphate (113 mg, 0.53 mmol, 3 eq), t-BuBrettPhos (17 mg, 0.03 mmol, 0.2 eq) and Pd$_2$(dba)$_3$ (16 mg, 0.02 mmol, 0.1 eq). The resulting solution was degassed three times with nitrogen and stirred for overnight at 100° C. The mixture was cooled to room temperature, concentrated under reduced pressure and purified by reverse phase flash chromatography with the following conditions: Column, C18 Column; Mobile Phase, water (0.1% FA) and ACN (5% up to 90% in 20 min); UV detection at 254/220 nm. The product-containing fractions were combined and concentrated under reduced pressure. The crude product was purified by Prep-HPLC with the following conditions (Column: YMC-Actus Triart C18 ExRS, 30*250, 5 um; Mobile Phase A: Water (10 mmol/L NH$_4$HCO$_3$+0.1% NH$_3$·H$_2$O) and ACN (18% ACN up to 45% in 9 min); UV detection at 254/210 nm. The product-containing fractions were combined and evaporated partially in vacuum and lyophilized overnight to afford N-[(1R)-1-[3-(difluoromethanesulfonamido)phenyl]ethyl]-5-(6-ethoxypyrazin-2-yl)-1,3-thiazole-2-carboxamide (I-272, 9.7 mg, 11%) as a white solid. MS (ES): m/z 484 [M+H]$^+$; $^1$H NMR (400 MHz, Methanol-d$_4$) δ 8.67 (s, 1H), 8.55 (d, J=0.8 Hz, 1H), 8.13 (s, 1H), 7.31-7.27 (m, 2H), 7.27-7.15 (m, 2H), 6.56 (t, J=53.3 Hz, 1H), 5.21 (q, J=7.0 Hz, 1H), 4.50 (q, J=7.1 Hz, 2H), 1.60 (d, J=7.0 Hz, 3H), 1.46 (t, J=7.1 Hz, 3H).

Example 101: Synthesis of N-[(1S)-1-[3-(difluoromethanesulfonamido)phenyl]ethyl]-5-(6-ethoxypyrazin-2-yl)-1,3-thiazole-2-carboxamide (I-273)

Synthesis of I-273. I-273 was synthesized from 39.2 following similar methods to that described for I-272 but using (1S)-1-(3-bromophenyl)ethanamine. MS (ES): m/z 484 [M+H]$^+$. $^1$H NMR (400 MHz, Methanol-d$_4$) δ 8.69 (s, 1H), 8.57 (s, 1H), 8.16 (s, 1H), 7.35-7.25 (m, 2H), 7.25-7.15 (m, 2H), 6.56 (t, J=53.4 Hz, 1H), 5.21 (q, J=7.0 Hz, 1H), 4.50 (q, J=7.1 Hz, 2H), 1.62 (d, J=7.1 Hz, 3H), 1.47 (t, J=7.1 Hz, 3H).

Example 102: Synthesis of N-{2-[3-(difluoromethanesulfonamido)phenyl]propan-2-yl}-5-(6-ethoxypyrazin-2-yl)-1,3-thiazole-2-carboxamide (I-262)

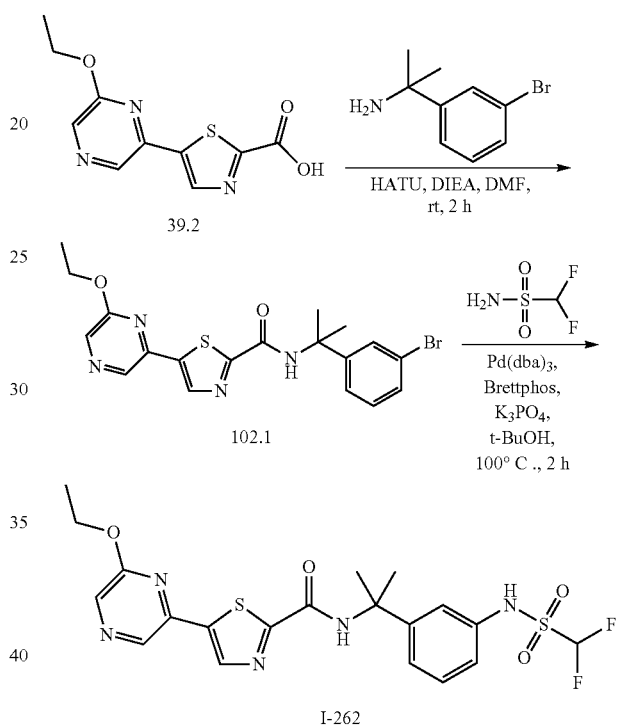

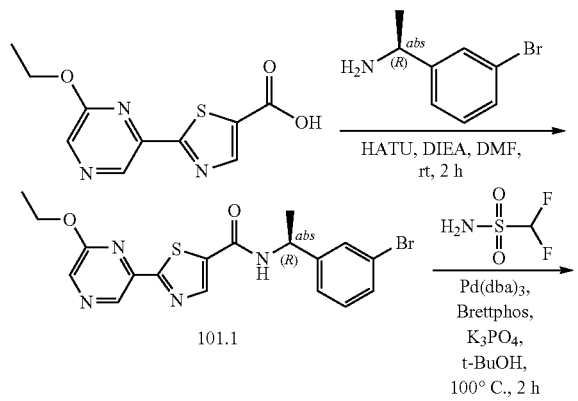

Synthesis of I-262. I-262 was synthesized from 39.2 following similar methods to that described for I-272 but using 2-(3-bromophenyl)propan-2-amine. MS (ES): m/z 498 [M+H]$^+$. $^1$H NMR (400 MHz, Methanol-d$_4$) δ 8.70 (s, 1H), 8.58 (s, 1H), 8.16 (s, 1H), 7.41-7.39 (m, 1H), 7.37-7.28 (m, 2H), 7.18-7.16 (m 1H), 6.61 (t, J=53.1 Hz, 1H), 4.49 (q, J=7.0 Hz, 2H), 1.81 (s, 6H), 1.46 (t, J=7.1 Hz, 3H).

Example 103: Synthesis of N-[(3-cyclopropanesulfonamido-2,6-difluorophenyl)methyl]-5-(6-ethoxypyrazin-2-yl)-1,3-thiazole-2-carboxamide (I-248)

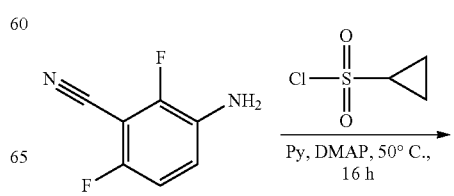

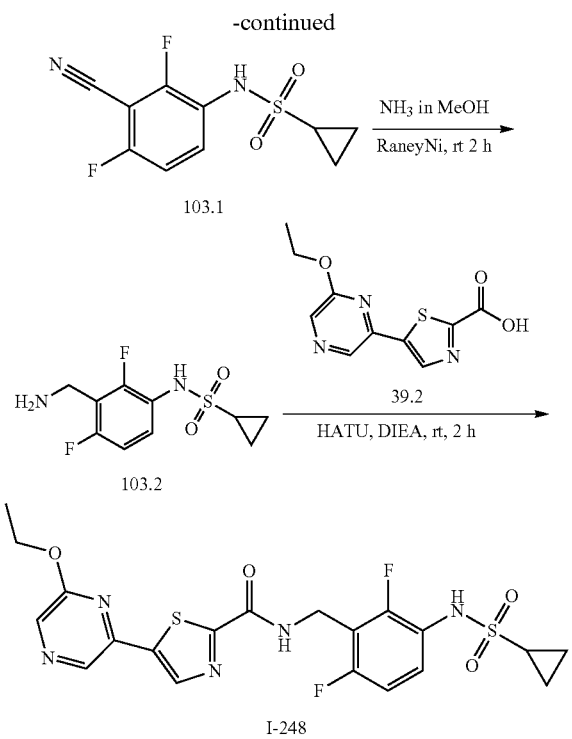

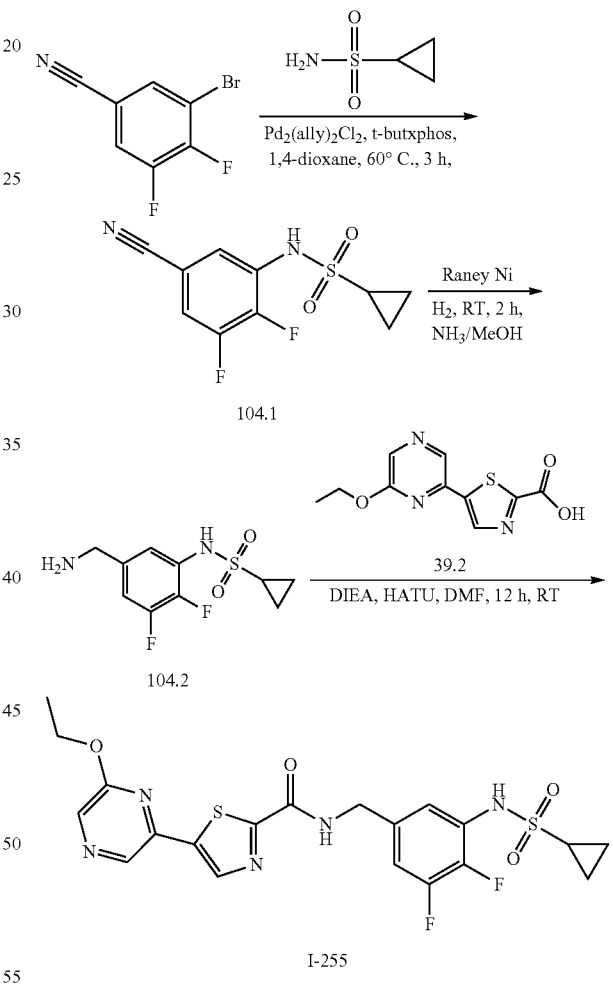

Synthesis of 103.1. To a stirred solution of 3-amino-2,6-difluorobenzonitrile (200 mg, 1.29 mmol, 1 eq) and cyclopropanesulfonyl chloride (547 mg, 3.89 mmol, 3 eq) in pyridine (7 mL) was added 4-dimethylaminopyridine (16 mg, 0.13 mmol, 0.1 eq). The resulting mixture was stirred for 16 h at 50° C. The resulting mixture was cooled to room temperature, concentrated under vacuum and purified by Prep-TLC (petroleum ether/ethyl acetate=1:1) to afford N-(3-cyano-2,4-difluorophenyl)cyclopropanesulfonamide (103.1, 150 mg, 53%), as a light yellow solid. MS (ES): m/z 259 [M+H]$^+$.

Synthesis of 103.2. A stirred solution of 103.1 (150 mg, 0.58 mmol, 1 eq) in ammonia methanol solution (7N, 6 mL) was flushed three times with nitrogen. To the solution was added Raney nickel (75 mg, 1.27 mmol, 2.2 eq), followed by flushing with nitrogen and then hydrogen. The mixture was stirred 2 h at room temperature under an atmosphere of hydrogen. The solid was filtered and the filtrate was concentrated under reduced pressure to obtain crude N-[3-(aminomethyl)-2,4-difluorophenyl]cyclopropanesulfonamide (103.2, 100 mg, 98%) as a grey solid. MS (ES): m/z 263 [M+H]$^+$.

Synthesis of I-248. To a stirred solution of 103.2 (100 mg, 0.38 mmol, 1 eq) and 39.2 (96 mg) in N, N-dimethyl formamide (3 mL) was added N, N-diisopropylethylamine (0.2 mL, 1.14 mmol, 3 eq) and 2-(-7-azabenzotriazol-1-yl)-N, N, N', N'-tetramethyluronium hexafluorophosphate (217 mg, 0.57 mmol, 1.5 eq). The resulting mixture was stirred for 2 h at room temperature. The residue was purified by reverse flash chromatography with the following conditions: Column, C18 Column; Mobile Phase, water (10 mmol/L NH$_4$HCO$_3$) and ACN (28% ACN up to 41% in 10 min); UV detection at 254/220 nm. The crude product was purified by Prep-HPLC with the following conditions: Column: Sunfire prep C18 column, 30*150, 5 um; Mobile Phase Water (0.1% FA) and ACN (40% B to 70% B in 7 min); UV detection at 254/220 nm. The product-containing fractions were combined and evaporated partially in vacuum and lyophilized overnight to afford N-[(3-cyclopropanesulfonamido-2,6-difluorophenyl)methyl]-5-(6-ethoxypyrazin-2-yl)-1,3-thiazole-2-carboxamide (I-248, 6.4 mg, 3.4%) as a white solid. MS (ES): m/z 496 [M+H]$^+$; $^1$H NMR (300 MHz, DMSO-d$_6$) δ 9.57 (s, 1H), 9.41 (t, J=5.4 Hz, 1H), 8.90 (s, 1H), 8.75 (s, 1H), 8.28 (s, 1H), 7.44-7.30 (m, 1H), 7.09 (t, J=9.1 Hz, 1H), 4.57 (d, J=5.6 Hz, 2H), 4.43 (q, J=7.1 Hz, 2H), 2.68-2.57 (m, 1H), 1.39 (t, J=7.0 Hz, 3H), 1.01-0.90 (m, 2H), 0.90-0.79 (m, 2H).

Example 104: Synthesis of N-[(3-cyclopropane-sulfonamido-4,5-difluorophenyl)methyl]-5-(6-ethoxypyrazin-2-yl)-1,3-thiazole-2-carboxamide (I-255)

Synthesis of 104.1. To a stirred solution of 3-bromo-4,5-difluorobenzonitrile (1 g, 4.59 mmol, 1 eq) and cyclopropanesulfonamide (1.1 g, 9.17 mmol, 2 eq) in 1,4-dioxane (10 mL) was added cesium carbonate (4.5 g, 13.76 mmol, 3 eq), t-Buxphos (195 mg, 0.46 mmol, 0.1 eq) and Pd$_2$(allyl)$_2$Cl$_2$ (55 mg, 0.15 mmol, 0.05 eq). The resulting solution was degassed three times with nitrogen and stirred for 3 h at 60° C. The mixture was cooled to room temperature, diluted with water and extracted with ethyl acetate. The combined organic layer was washed with brine, dried over sodium sulfate and concentrated under reduced pressure. The residue was purified by silica gel column chromatography (compound eluted in 33% ethyl acetate in petroleum ether) to obtain N-(5-cyano-2,3-difluorophenyl)cyclopropanesulfonamide (104.1, 1.1 g, 92%) as a yellow solid. MS (ES): m/z 257 [M−H]⁻.

Synthesis of 104.2. A stirred solution of 104.1 (258 mg, 1 mmol, 1 eq) in ammonia methanol solution (7N, 6 mL) was flushed three times with nitrogen. To the solution was added Raney nickel (20 mg, 0.33 mmol, 2.2 eq), followed by flushing with nitrogen and then hydrogen. The mixture was stirred 2 h at room temperature under an atmosphere of hydrogen. The solid was filtered and the filtrate was concentrated under reduced pressure to obtain N-[5-(aminomethyl)-2,3-difluorophenyl]cyclopropanesulfonamide (104.2, 120 mg, 45%) as a light yellow solid. MS (ES): m/z 263 [M+H]⁺.

Synthesis of I-255. To a stirred mixture of 104.2 (120 mg, 0.46 mmol, 1 eq) and 39.2 (115 mg) in dimethyl formamide (3 mL) was added N, N-diisopropylethylamine (177 mg, 1.37 mmol, 3 eq) and 2-(-7-azabenzotriazol-1-yl)-N, N, N', N'-tetramethyluronium hexafluorophosphate (174 mg, 0.458 mmol, 1 eq). The resulting mixture was stirred for 12 h at room temperature under nitrogen atmosphere. The resulting mixture was extracted with ethyl acetate. The combined organic layer was washed with brine, dried over sodium sulfate and concentrated under reduced pressure. The residue was purified by silica gel column chromatography (compound eluted in 90% ethyl acetate in petroleum ether) to obtain the crude product. The crude product was purified by Prep-HPLC with the following conditions: Column: Sunfire prep C18 column, 30*150 mm, 5 μm; Mobile Phase: Water (0.1% FA) and ACN (40% ACN up to 70% in 7 min); UV detection at 254/210 nm. The product-containing fractions were combined and evaporated partially in vacuum and lyophilized overnight to afford N-[(3-cyclopropanesulfonamido-4,5-difluorophenyl)methyl]-5-(6-ethoxypyrazin-2-yl)-1,3-thiazole-2-carboxamide (I-255, 12 mg, 5%) as a white solid. MS (ES): m/z 496 [M+H]⁺; ¹H NMR (400 MHz, DMSO-d₆) δ 10.11 (s, 1H), 9.58 (t, J=6.4 Hz, 1H), 8.91 (s, 1H), 8.79 (s, 1H), 8.28 (s, 1H), 7.32-7.11 (m, 2H), 4.44-4.35 (m, 4H), 2.68-2.63 (m, 1H), 1.39 (t, J=7.0 Hz, 3H), 0.97-0.91 (m, 4H).

Example 105: Synthesis of N-[(5-cyclopropanesulfonamido-2,3-difluorophenyl)methyl]-2-(5-ethoxypyrazin-2-yl)-1,3-thiazole-5-carboxamide (I-249)

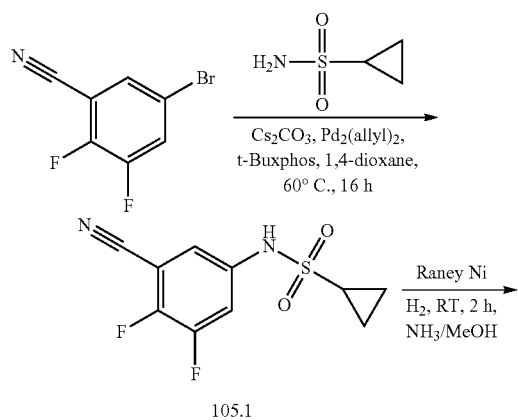

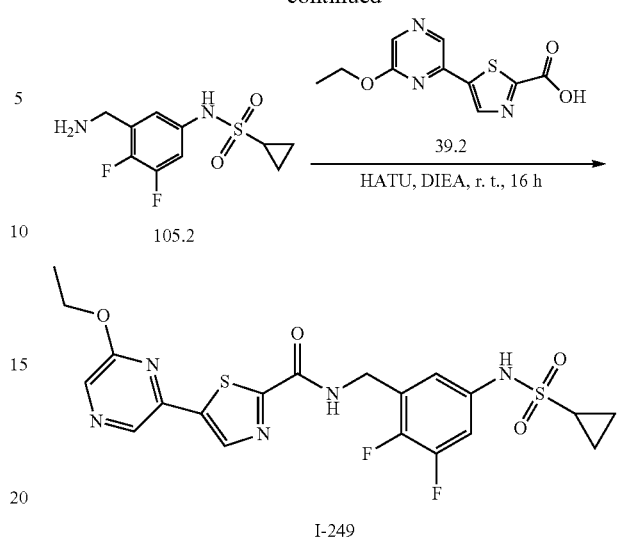

I-249

Synthesis of I-249. I-249 was synthesized from 3-bromo-2,5-difluorobenzonitrile following similar methods to that described for I-255. MS (ES): m/z 496 [M+H]⁺; ¹H NMR (400 MHz, DMSO-d₆) δ 9.93-9.92 (m, 1H), 9.56-9.53 (m, 1H), 8.92 (s, 1H), 8.80 (s, 1H), 8.29 (s, 1H), 7.30-7.15 (m, 2H), 4.54-4.40 (m, 4H), 2.72-2.63 (m, 1H), 1.39 (t, J=7.0 Hz, 3H), 1.00-0.89 (m, 4H).

Example 106: Synthesis of N-[(3-cyclopropanesulfonamido-2,5-difluorophenyl)methyl]-5-(6-ethoxypyrazin-2-yl)-1,3-thiazole-2-carboxamide (I-250)

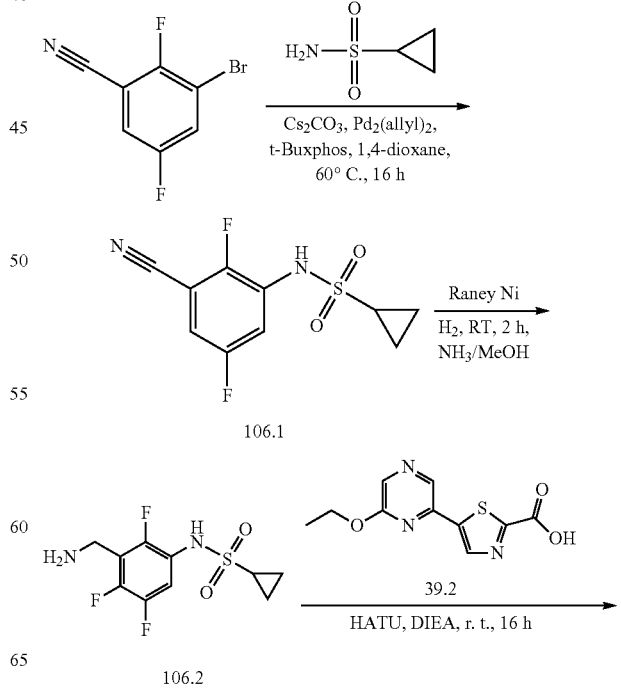

-continued

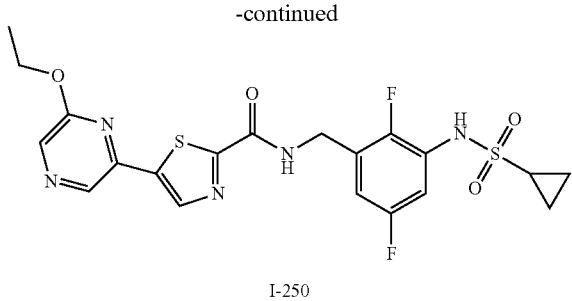

I-250

Synthesis of I-250. I-250 was synthesized from 3-bromo-2,5-difluorobenzonitrile following similar methods to that described for I-255. MS (ES): m/z 496 [M+H]+; 1H NMR (400 MHz, DMSO-d6) δ 9.99-9.89 (m, 1H), 9.58-9.53 (m, 1H), 8.92 (s, 1H), 8.80 (s, 1H), 8.29 (s, 1H), 7.23-7.11 (m, 1H), 7.05-6.95 (m, 1H), 4.59-4.52 (m, 2H), 4.46-4.40 (m, 2H), 2.77-2.73 (m, 1H), 1.39 (t, J=7.0 Hz, 3H), 1.03-0.90 (m, 4H).

Example 107: Synthesis of N-[(4-cyclopropane-sulfonamidopyridin-2-yl)methyl]-6-(dimethyl-amino)-5-(2-methylpropoxy)pyrazine-2-carboxamide (I-256)

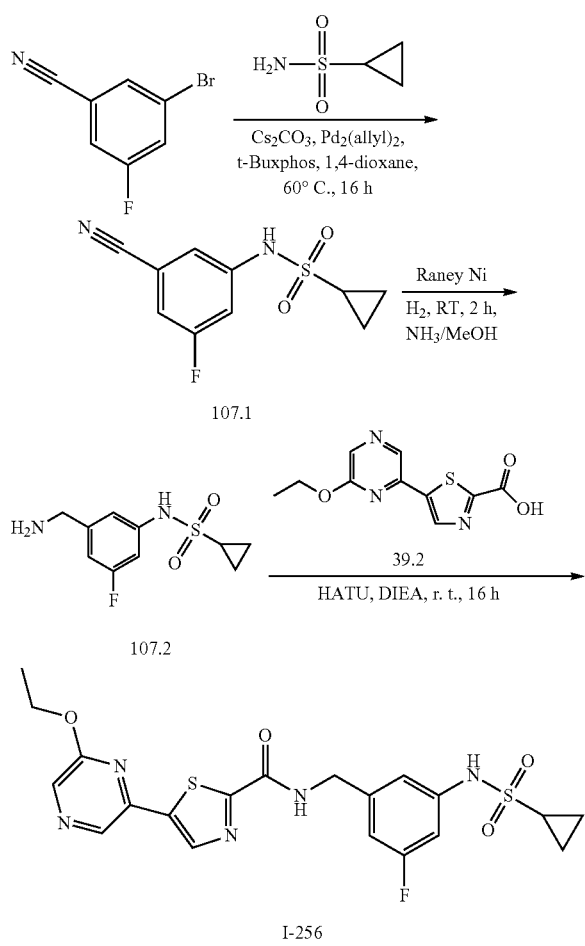

Synthesis of I-256. I-256 was synthesized from 3-bromo-2,5-difluorobenzonitrile following similar methods to that described for I-255. MS (ES): m/z 478 [M+H]+; 1H NMR (400 MHz, DMSO-d6) δ 9.61-9.53 (m, 1H), 8.92 (s, 1H), 8.80 (s, 1H), 8.29 (s, 1H), 7.02 (s, 1H), 6.96-6.82 (m, 2H), 4.59-4.40 (m, 4H), 2.75-2.63 (m, 1H), 1.39 (t, J=7.0 Hz, 3H), 1.00-0.90 (m, 4H).

Example 108: Synthesis of N-[(1R)-1-(4-cyclopropanesulfonamidopyridin-2-yl)propyl]-5-(6-ethoxy-pyrazin-2-yl)-1,3-thiazole-2-carboxamide (I-277)

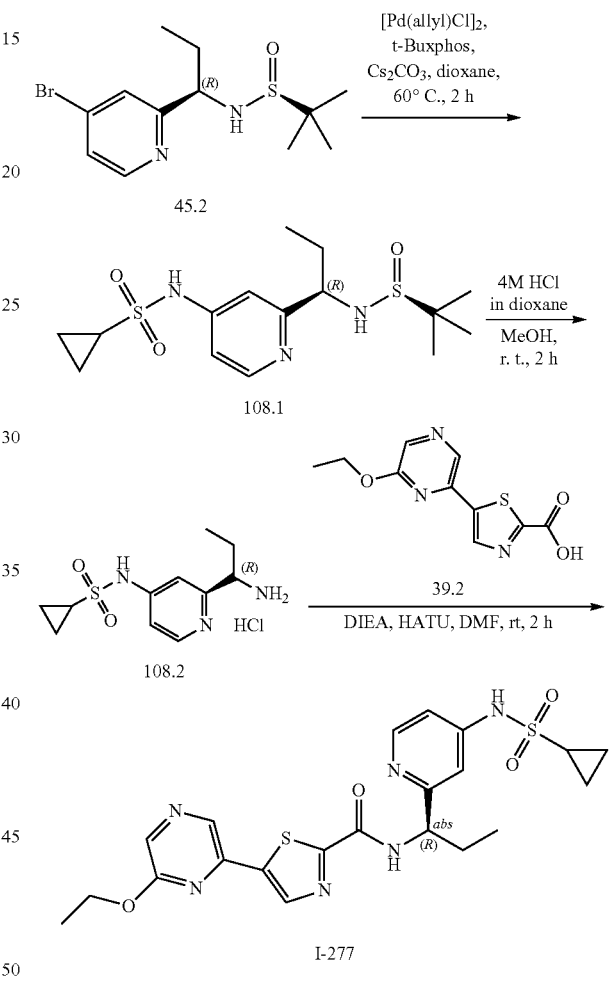

Synthesis of 108.1. To a stirred solution of 45.2 (200 mg, 0.63 mmol, 1 eq) and cyclopropanesulfonamide (152 mg, 1.25 mmol, 2 eq) in dioxane (5 mL) were added cesium carbonate (612 mg, 1.88 mmol, 3 eq), Pd2(allyl)2Cl2 (23 mg, 0.06 mmol, 0.1 eq) and t-Buxphos (53 mg, 0.12 mmol, 0.2 eq). The resulting solution was degassed three times with nitrogen and stirred for 2 h at 60° C. The mixture was cooled to room temperature, diluted with water and extracted with ethyl acetate. The combined organic layer was washed with brine, dried over sodium sulfate and concentrated under reduced pressure. The residue was purified by silica gel column chromatography (compound was eluted in 10% methanol in dichloromethane) to obtain N-[2-[(1R)-1-[[CY)-2-methylpropane-2-sulfinyl]amino]propyl]pyridin-4-yl]cyclopropanesulfonamide (108.1, 220 mg, 97%) as a yellow solid. MS (ES): m/z 360 [M+H]+.

Synthesis of 108.2 To a stirred solution of 108.1 (280 mg, 0.78 mmol, 1 eq) in methanol (5 mL) was added hydrochloric acid in 1,4-dioxane (4M, 2 mL) at room temperature. The resulting mixture was stirred for 2 h at room temperature. The resulting mixture was concentrated under reduced pressure. The crude product 108.2 (180 mg, yellow solid) was used in the next step. MS (ES): m/z 256 [M+H]+.

Synthesis of I-277. To a stirred solution of 108.2 (40 mg) and 39.2 (39 mg) in N,N-dimethylformamide (4 mL) was added N, N-diisopropylethylamine (61 mg, 0.47 mmol, 3.0 eq) and 2-(-7-azabenzotriazol-1-yl)-N, N, N', N'-tetramethyluronium hexafluorophosphate (89 mg, 0.23 mmol, 1.5 eq) at room temperature. The resulting mixture was stirred for 2 h at room temperature. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 30*150 mm, 5 um; Mobile Phase, water (0.1% FA) and ACN (20% ACN up to 50% in 9 min); UV detection at 254/220 nm. The product-containing fractions were combined and evaporated partially in vacuum and lyophilized overnight to afford N-[(1R)-1-(4-cyclopropanesulfonamidopyridin-2-yl)propyl]-5-(6-ethoxypyrazin-2-yl)-1,3-thiazole-2-carboxamide as a white solid. (I-277, 10 mg, 14%), MS (ES): m/z 489 [M+H]+; 1H NMR (400 MHz, CD3OD) δ 8.71 (s, 1H), 8.61 (s, 1H), 8.31 (s, 1H), 8.17 (s, 1H), 7.27 (d, J=2.2 Hz, 1H), 7.16 (dd, J=5.9, 2.3 Hz, 1H), 5.00 (dd, J=8.3, 6.3 Hz, 1H), 4.50 (q, J=7.1 Hz, 2H), 2.78-2.68 (m, 1H), 2.10-1.92 (m, 2H), 1.47 (t, J=7.1 Hz, 3H), 1.19-1.10 (m, 2H), 1.08-0.93 (m, 5H).

Example 109: Synthesis of N-[(1S)-1-(4-cyclopropane sulfonamidopyridin-2-yl)propyl]-5-(6-ethoxypyrazin-2-yl)-1,3-thiazole-2-carboxamide (I-278)

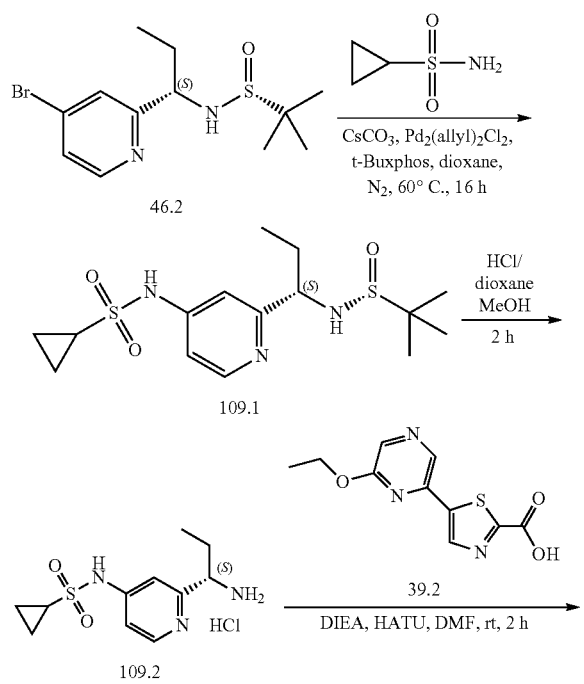

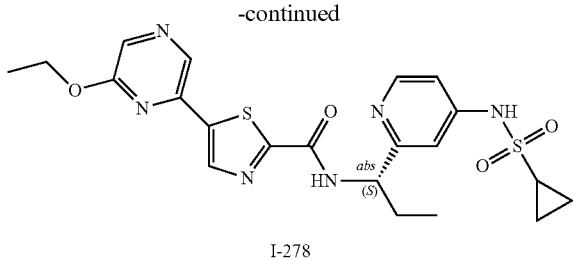

I-278

Synthesis of 109.1. To a stirred solution of 46.2 (3.9 g, 12.22 mmol, 1 eq) and cyclopropanesulfonamide (2.96 g, 24.45 mmol, 2 eq) in 1,4-dioxane (40 mL) was added cesium carbonate (11.95 g, 36.67 mmol, 3 eq), Pd2(allyl)2Cl2 (223 mg, 0.61 mmol, 0.05 eq) and t-Buxphos (517 mg, 1.22 mmol, 0.1 eq) in portions at room temperature. The resulting mixture was degassed three times with nitrogen and stirred for 16 h at 60° C. under nitrogen atmosphere. The resulting mixture was filtered, the filter cake was washed with ethyl acetate. The filtrate was concentrated under reduced pressure. The residue was purified by silica gel column chromatography (compound was eluted in 100% ethyl acetate in petroleum ether) to obtain N-[2-(1-[[(R)-2-methylpropane-2-sulfinyl]amino]propyl)pyridin-4-yl]cyclopropanesulfonamide (109.1, 3.12 g, 71%) as a yellow oil. MS (ES): m/z 360 [M+H]+.

Synthesis of 109.2. To a stirred solution of 109.1 (3.12 g, 8.66 mmol, 1 eq) in methanol (10 mL) was added hydrochloric acid in 1,4-dioxane (4N, 10 mL). The reaction mixture stirred at room temperature for 2 h. The resulting mixture was concentrated under reduced pressure to obtain the crude product. The crude product 109.2 was used in the next step directly without further purification. MS (ES): m/z 256 [M+H]+.

Synthesis of I-278. To a stirred solution of 109.2 (2 g) and 39.2 (1.96 g) in N,N-dimethylformamide (20 mL) was added 2-(-7-azabenzotriazol-1-yl)-N, N, N', N'-tetramethyluronium hexafluorophosphate (4.45 g, 11.71 mmol) and N, N-diisopropylethylamine (4.03 g, 31.24 mmol). The resulting mixture stirred for 2 h at room temperature under nitrogen atmosphere. The resulting mixture was concentrated under reduced pressure. The residue was purified by silica gel column chromatography (compound was eluted in 80% ethyl acetate in petroleum ether) to obtain the crude product. The crude product was purified by Prep-HPLC with the following conditions (SunFire Prep C18 OBD Column, 19×150 mm 5 um 10 nm; Mobile Phase: Water (0.1% FA) and CAN (20% to 50% in 9 min, UV detection at 254/210 nm). The product-containing fractions were combined and evaporated partially in vacuum and lyophilized overnight to afford N-[(1S)-1-(4-cyclopropanesulfonamidopyridin-2-yl)propyl]-5-(6-ethoxypyrazin-2-yl)-1,3-thiazole-2-carboxamide (I-278, 329 mg) as a white solid. MS (ES): m/z 489 [M+H]+; 1H NMR (400 MHz, Methanol-d4) δ 8.71 (d, J=2.5 Hz, 1H), 8.61 (d, J=2D Hz, 1H), 8.31 (d, J=6.0 Hz, 1H), 8.17 (d, J=1.9 Hz, 1H), 7.28 (d, J=2.3 Hz, 1H), 7.17 (dd, J=6.0, 2.3 Hz, 1H), 5.01 (dd, J=8.3, 6.2 Hz, 1H), 4.55-4.45 (m, 2H), 2.80-2.69 (m, 1H), 2.15-1.94 (m, 2H), 1.56 (t, J=7.2 Hz, 3H), 1.23-1.10 (m, 2H), 1.09-0.95 (m, 5H).

Example 110: Synthesis of N-[(1S)-1-(4-cyclopropanesulfonamidopyridin-2-yl)propyl]-5-(6-ethoxypyrazin-2-yl)-1,3,4-thiadiazole-2-carboxamide (I-239)

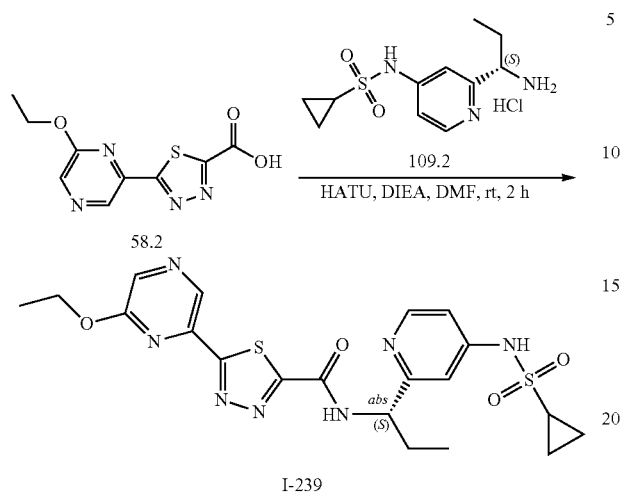

Synthesis of I-239. To a stirred mixture of 58.2 (80 mg, 0.317 mmol, 1 eq) and 109.2 (81 mg) in N,N-dimethylformamide (5 mL) was added 2-(-7-azabenzotriazol-1-yl)-N,N,N',N'-tetramethyluronium hexafluorophosphate (145 mg, 0.38 mmol, 1.2 eq) and N, N-diisopropylethylamine (123 mg, 0.95 mmol, 3 eq) in portions at room temperature. The resulting mixture was stirred for 2 h at room temperature. The residue was purified by reverse phase flash chromatography (compound was eluted in 40% acetonitrile in water) to obtain crude product. The crude product was purified by Prep-HPLC with the following conditions: Column: XBridge Prep C18 OBD Column, 30*100 mm, 5 μm; Mobile Phase Water (10 mmol/L $NH_4HCO_3$) and ACN (20% to 50% in 9 min, UV detection at 254/210 nm). The product-containing fractions were combined and evaporated partially in vacuum and lyophilized overnight to afford N-[(1S)-1-(4-cyclopropanesulfonamidopyridin-2-yl)propyl]-5-(6-ethoxypyrazin-2-yl)-1,3,4-thiadiazole-2-carboxamide (I-239, 23 mg, 14%) as a white solid. MS (ES): m/z 490, $^1$H NMR (400 MHz, DMSO-$d_6$) δ 10.68 (s, 1H), 9.66 (s, 1H), 9.05 (s, 1H), 8.53 (d, J=4.0 Hz, 1H), 8.30 (s, 1H), 7.18 (s, 1H), 7.04 (d, J=4.8 Hz, 1H), 4.99-4.89 (m, 1H), 4.46 (q, J=7.1 Hz, 2H), 2.82-2.72 (m, 1H), 2.05-1.88 (m, 2H), 1.41 (t, J=7.0 Hz, 3H), 1.04-0.89 (m, 7H).

Example 111: Synthesis of (R)—N-(1-(5-(cyclopropanesulfonamido)pyridin-2-yl)propyl)-5-(6-ethoxypyrazin-2-yl)-1,3,4-thiadiazole-2-carboxamide (I-240)

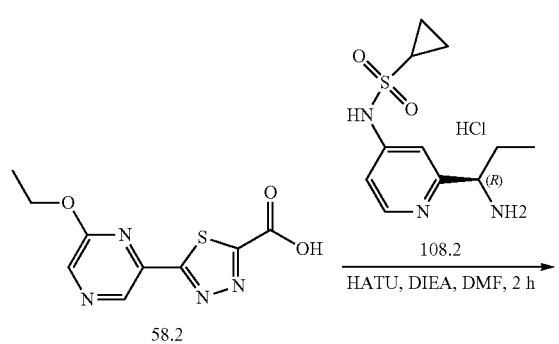

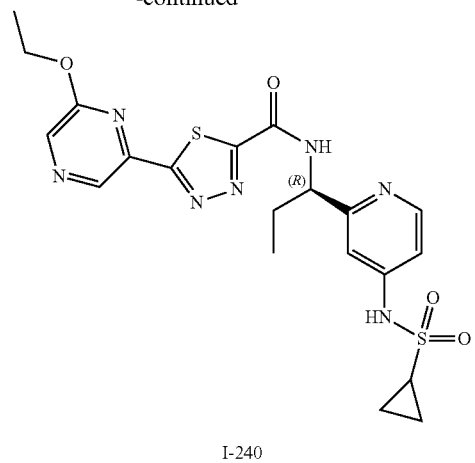

Synthesis of I-240. I-240 was synthesized following similar methods to that described for I-239 but using 108.2 as the amine. MS (ES): m/z 490, NMR (400 MHz, DMSO-$d_6$) 9.64 (d, J=8.3 Hz, 1H), 9.05 (s, 1H), 8.53 (s, 1H), 8.30 (s, 1H), 7.17 (s, 1H), 7.03 (d, J=5.7 Hz, 1H), 4.99-4.88 (m, 1H), 4.46 (q, J=7.0 Hz, 2H), 2.82-2.75 (m, 1H), 2.02-1.95 (m, 2H), 1.41 (t, J=7.0 Hz, 3H), 1.06-0.87 (m, 7H).

Example 112: Synthesis of 5-{5-chloropyrazolo[1,5-a]pyridin-3-yl}-N-[1-(4-cyclopropanesulfonamidopyridin-2-yl)propyl]-1,3-thiazole-2-carboxamide (I-174)

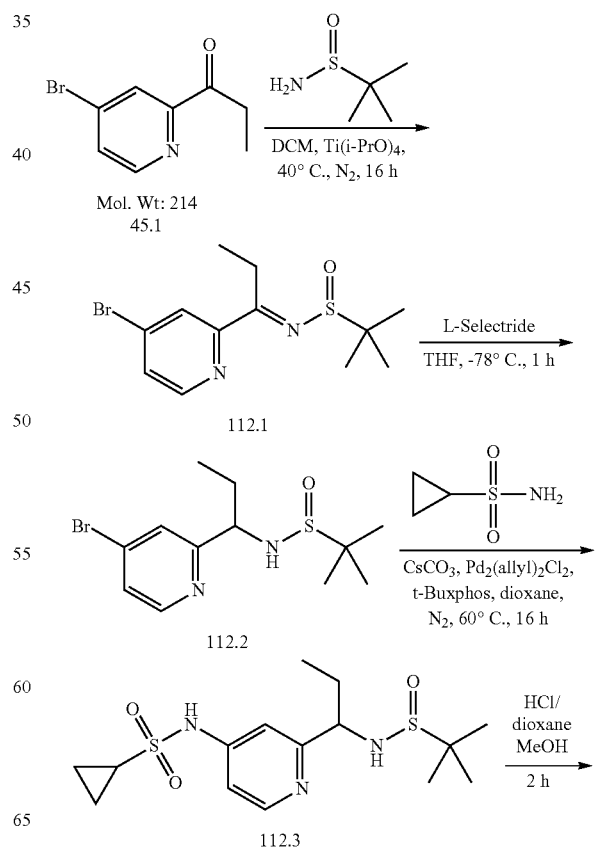

-continued

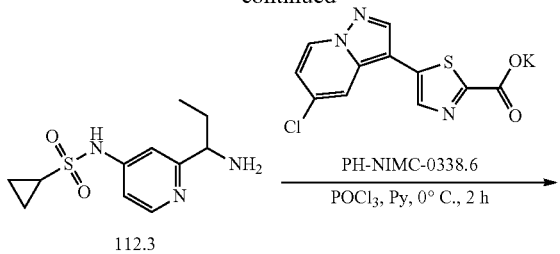

Synthesis of 112.1. To a stirred solution of 45.1 (8.5 g, 39.7 mmol, 1 eq) and 2-methylpropane-2-sulfmamide (5.77 g, 47.66 mmol, 1.2 eq) in dichlormethane (100 mL) was added titanium tetraisopropanolate (22.55 g, 79.4 mmol, 2 eq) in portions at 0° C. The resulting mixture stirred for 16 h at 40° C. under nitrogen atmosphere. The resulting mixture filtered, diluted with water and extracted with ethyl acetate. The combined organic layers were washed with brine, dried over anhydrous sodium sulfate. After filtration, the filtrate was concentrated under reduced pressure. The residue was purified by silica gel column chromatography (compound was eluted in 20% ethyl acetate in petroleum ether) to obtain (E)-N-(1-(4-bromopyridin-2-yl)propylidene)-2-methylpropane-2-sulfinamide (112.1, 5.06 g, 39%) as a yellow oil MS(ES): m/z 317/319 [M+H]+.

Synthesis of 112.2. A stirred solution of 112.1 (5.06 g, 15.96 mmol, 1 eq) in anhydrous tetrahydrofuran (50 mL) was degassed three times with nitrogen and cooled to −78° C. To the solution was added L-Selectride (32 mL, 31.92 mmol, 2 eq) at −78° C. under nitrogen atmosphere. The reaction mixture was stirred at −78° C. for 1 h. The reaction quenched with ammonium chloride. The resulting mixture was extracted with dichloromethane. The combined organic layers were washed with brine, dried over anhydrous sodium sulfate. After filtration, the filtrate was concentrated under reduced pressure to obtain N-(1-(4-bromopyridin-2-yl)propyl)-2-methylpropane-2-sulfmamide (112.2, 3.9 g, 76%) as a yellow oil. MS (ES): m/z 319/321 [M+H]+.

Synthesis of 112.3. To a stirred solution of 112.2 (3.9 g, 12.22 mmol, 1 eq) and cyclopropanesulfonamide (2.96 g, 24.45 mmol, 2 eq) in 1,4-dioxane (40 mL) was added cesium carbonate (11.95 g, 36.67 mmol, 3 eq), Pd$_2$(allyl)$_2$Cl$_2$ (223 mg, 0.61 mmol, 0.05 eq) and t-Buxphos (517 mg, 1.22 mmol, 0.1 eq) in portions at room temperature. The resulting mixture was degassed three times with nitrogen and stirred for 16 h at 60° C. under nitrogen atmosphere. The resulting mixture filtered, the filter cake was washed with ethyl acetate. The filtrate was concentrated under reduced pressure. The residue was purified by silica gel column chromatography (compound was eluted in 100% ethyl acetate in petroleum ether) to obtain N-(2-(1-((tert-butylsulfinyl) amino)propyl)pyridin-4-yl)cyclopropanesulfonamide (112.3, 3.12 g, 71%) as a yellow oil. MS (ES): m/z 360 [M+H]+.

Synthesis of 112.4. To a stirred solution of 112.3 (3.12 g, 8.66 mmol, 1 eq) in methanol (10 mL) was added hydrochloric acid in 1,4-dioxane (4N, 10 mL). The reaction mixture stirred at room temperature for 2 h. The resulting mixture was concentrated under reduced pressure to obtain the crude product. The crude product N-(2-(1-aminopropyl) pyridin-4-yl)cyclopropanesulfonamide hydrogen chloride (112.4, 2.4 g) was used without further purification. MS (ES): m/z 256 [M+H]+.

Synthesis of I-174. To a stirred solution 169.6 (90 mg) and 112.4 (82 mg) in pyridine (1.5 mL) was added phosphorous oxychloride (247 mg, 1.61 mmol) at 0° C. under nitrogen atmosphere. The resulting mixture was stirred for 1 h at 0° C. under nitrogen atmosphere. The resulting mixture was concentrated under reduced pressure and purified by reverse flash chromatography with the following conditions: Column, C18 Column; Mobile Phase, water (10 mmol/L NH$_4$HCO$_3$) and ACN (10% ACN up to 60% in 20 min); LTV detection at 254/220 nm. The crude product was purified by Prep-HPLC with the following conditions Column: Sunfire prep C18 column; Mobile Phase, water (0.1% FA) and ACN (15% ACN up to 50% in 5 min); LTV detection at 254/210 nm. The product-containing fractions were combined and evaporated partially in vacuum and lyophilized overnight to afford 5-{5-chloropyrazolo[1,5-a]pyridin-3-yl}-N-[1-(4-cyclopropanesulfonamidopyridin-2-yl)propyl]-1,3-thiazole-2-carboxamide (I-174, 4.1 mg) as a white solid. MS (ES): m/z 517 [M+H], NMR (400 MHz, Methanol-d$_4$) δ 8.64 (dd, J=7.4, 0.8 Hz, 1H), 8.41 (s, 1H), 8.31 (s, 1H), 8.24 (s, 1H), 7.99 (dd, J=2.2, 0.8 Hz, 1H), 7.27 (d, J=2.2 Hz, 1H), 7.16 (dd, J=6.0, 2.3 Hz, 1H), 7.05 (dd, J=7.4, 2.3 Hz, 1H), 5.01 (dd, J=8.3, 6.2 Hz, 1H), 2.78-2.68 (m, 1H), 2.12-1.94 (m, 2H), 1.21-1.10 (m, 2H), 1.08-0.97 (m, 5H).

Example 113: Synthesis of (S)-5-(5-chloropyrazolo[1,5-a]pyridin-3-yl)-N-(1-(4-(cyclopropanesulfonamido)pyridin-2-yl)propyl)thiazole-2-carboxamide, isomer 1 (I-150) and (R)-5-(5-chloropyrazolo[1,5-a]pyridin-3-yl)-N-(1-(4-(cyclopropanesulfonamido) pyridin-2-yl)propyl)thiazole-2-carboxamide, isomer 2 (I-151). Stereochemistry Arbitrarily Assigned

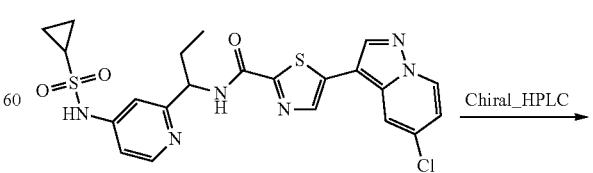

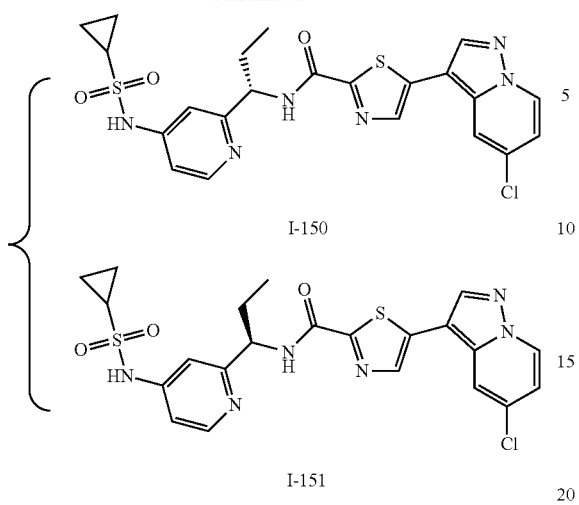

I-150

I-151

Synthesis of I-150 and I-151. I-174 (80 mg 0.15 mmol, 1 eq) was separated by Chiral-Prep-HPLC with the following conditions: Column, CHIRALPAK IF-3, 4.6*50 mm, 3 um; mobile phase, (Hex:DCM=3:1)(0.1% DEA):EtOH=50:50; UV detection at 254/220 nm. The product-containing fractions were combined and concentrated under reduced pressure to afford (S)-5-(5-chloropyrazolo[1,5-a]pyridin-3-yl)-N-(1-(4-(cyclopropanesulfonamido)pyridin-2-yl)propyl) thiazole-2-carboxamide, isomer 1 (I-150, 1$^{st}$ eluting peak, 14.9 mg, 37%) and (R)-5-(5-chloropyrazolo[1,5-a]pyridin-3-yl)-N-(1-(4-(cyclopropanesulfonamido)pyridin-2-yl)propyl)thiazole-2-carboxamide (I-151, 2$^{nd}$ eluting peak, 16.8 mg, 42%) as white solids. I-150: MS (ES): m/z 517 [M+H]$^+$; $^1$H NMR (300 MHz, Methanol-d$_4$) δ 8.64 (dd, J=7.4, 0.8 Hz, 1H), 8.40 (s, 1H), 8.31 (d, J=6.1 Hz, 1H), 8.24 (s, 1H), 7.99 (d, J=2.2 Hz, 1H), 7.27 (d, J=2.2 Hz, 1H), 7.16 (dd, J=6.0, 2.3 Hz, 1H), 7.05 (dd, J=7.4, 2.3 Hz, 1H), 5.01 (t, J=7.2 Hz, 1H), 2.81-2.66 (m, 1H), 2.14-1.91 (m, J=6.9 Hz, 2H), 1.22-1.09 (m, 2H), 1.09-0.95 (m, 5H). I-151: MS (ES): m/z 517 [M+H]$^+$; $^1$H NMR (300 MHz, Methanol-d$_4$) δ 8.64 (d, J=8.7 Hz, 1H), 8.40 (s, 1H), 8.31 (d, J=6.1 Hz, 1H), 8.24 (s, 1H), 7.99 (d, J=2.2 Hz, 1H), 7.27 (d, J=2.2 Hz, 1H), 7.16 (dd, J=6.0, 2.3 Hz, 1H), 7.05 (dd, J=7.4, 2.3 Hz, 1H), 5.01 (t, J=7.2 Hz, 1H), 2.81-2.66 (m, 1H), 2.14-1.91 (m, J=6.9 Hz, 2H), 1.20-1.09 (m, 2H), 1.09-0.95 (m, 5H).

Example 114: Synthesis of N-[1-(4-cyclopropanesulfonamidopyridin-2-yl)propyl]-5-(6-ethoxypyrazin-2-yl)-4-methyl-1,3-thiazole-2-carboxamide (I-227)

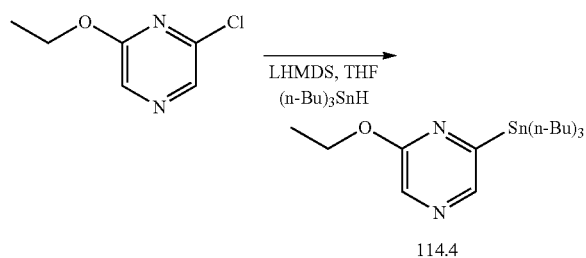

114.4

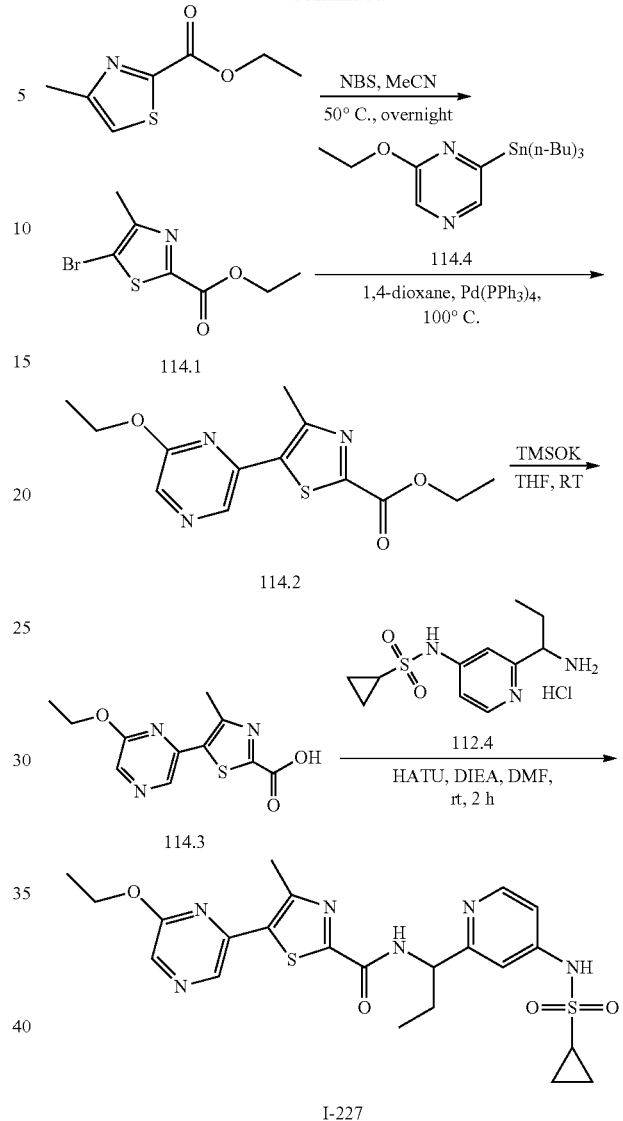

I-227

Synthesis of 114.1. To a stirred solution of ethyl 4-methyl-1,3-thiazole-2-carboxylate (590 mg, 3.44 mmol, 1 eq) in MeCN (12 mL) was added 1-bromopyrrolidine-2,5-dione (1.22 g, 6.89 mmol, 2 eq) at room temperature. The resulting solution was degassed three times with nitrogen and stirred for overnight at 50° C. The mixture was cooled to room temperature, concentrated under reduced pressure and purified by reverse flash chromatography with the following conditions: Column, C18 Column; Mobile Phase, water (10 mmol/L NH$_4$HCO$_3$) and ACN (10% ACN up to 70% in 20 min); UV detection at 254/220 nm. The product-containing fractions were combined and concentrated under reduced pressure to obtain ethyl 5-bromo-4-methyl-1,3-thiazole-2-carboxylate (114.1, 500 mg, 58%) as white solid. MS (ES): m/z 250/252 [M+H]$^+$.

Synthesis of 114.4. To a solution of 2-chloro-6-ethoxypyrazine (1.58 g, 10.0 mmol, 1.0 eq) in tetrahydrofuran (40 mL) was added dropwise LiHMDS in tetrahydrofuran (1 M, 12 mL, 12.0 mmol, 1.2 eq) at −78° C. After 30 min, tributyltin hydride (4.35 g, 15.0 mmol, 1.5 eq) was added still maintaining the temperature at −78° C. The resulting mixture was stirred for 16 h at room temperature under nitrogren atmosphere. The mixture was quenched with water and extracted with ethyl acetate. The combined organic layer was washed with brine, dried over sodium sulfate and concentrated under reduced pressure. The residue was purified by silica gel column chromatography (compound was eluted in 10% ethyl acetate in petroleum ether) to obtain 2-ethoxy-6-(tributylstannyl)pyrazine (114.4, 2.25 g, 54%) as a red oil. MS (ES): m/z 415 [M+H]+.

Synthesis of 114.2. To a stirred solution of 114.1 (500 mg, 2 mmol, 1 eq) and 114.4 (991 mg, 2.4 mmol, 1.2 eq) in 1,4-dioxane (10 mL) was added Pd(PPh$_3$)$_4$ (231 mg, 0.2 mmol, 0.1 eq). The resulting solution was degassed three times with nitrogen and stirred for overnight at 100° C. The mixture was allowed to cool down to room temperature, concentrated under reduced pressure and purified by Prep-TLC (petroleum ether/ethyl acetate=5/1) to afford ethyl 5-(6-ethoxypyrazin-2-yl)-4-methyl-1,3-thiazole-2-carboxylate (114.2, 420 mg, 71%) as a yellow oil. MS (ES): m/z 294 [M+H]$^+$.

Synthesis of 114.3. To a stirred solution of 114.2 (420 mg, 1.43 mmol, 1 eq) in tetrahydrofuran (7 mL) was added potassium trimethylsilanolate (367 mg, 2.86 mmol, 2 eq). The resulting mixture was stirred for 1 h at room temperature. The resulting mixture was concentrated under reduced pressure and the crude product 114.3 was used in the next step directly without further purification. MS (ES): m/z 266 [M+H]+.

Synthesis of I-227. To a stirred solution of crude 114.3 (350 mg) and N-[2-(1-aminopropyl)pyridin-4-yl]cyclopropanesulfonamide 112.4 (336 mg, 1.32 mmol, 1 eq) in N,N-dimethyl formamide (6 mL) was added 2-(-7-azabenzotriazol-1-yl)-N, N, N', N'-tetramethyluronium hexafluorophosphate (752 mg, 1.98 mmol, 1.5 eq) and N, N-diisopropylethylamine (852 mg, 6.59 mmol, 5 eq). The resulting mixture was stirred for 2 h at room temperature. The residue purified by reverse flash chromatography with the following conditions: Column, C18 Column; Mobile Phase, water (10 mmol/L NH$_4$HCO$_3$) and ACN (10% ACN up to 50% in 20 min); UV detection at 254/220 nm. The crude product was purified by Prep-HPLC with the following conditions (Column: XBridge Prep OBD C18 Column, 30*150 mm, 5 μm; Mobile Phase: Water (10 mmol/L NH$_4$HCO$_3$), and ACN (33% ACN up to 50% in 9 min); UV detection at 254/210 nm. The product-containing fractions were combined and evaporated partially in vacuum and lyophilized overnight to afford N-[1-(4-cyclopropanesulfonamidopyridin-2-yl)propyl]-5-(6-ethoxypyrazin-2-yl)-4-methyl-1,3-thiazole-2-carboxamide (I-227, 106 mg, 16%) as a white solid. MS (ES): m/z 503 [M+H]$^+$. NMR (400 MHz, Methanol-A) δ 8.51 (s, 1H), 8.28 (d, J=5.9 Hz, 1H), 8.16 (s, 1H), 7.24 (d, J=2.3 Hz, 1H), 7.14 (dd, J=5.9, 2.3 Hz, 1H), 4.99 (t, J=8.2, 6.3 Hz, 1H), 4.49 (q, J=7.1 Hz, 2H), 2.82 (s, 3H), 2.72-2.60 (m, 1H), 2.12-1.91 (m, 2H), 1.46 (t, J=7.1 Hz, 3H), 1.21-1.09 (m, 2H), 1.06-0.93 (m, 5H).

Example 115: Synthesis of (S)—N-(1-(4-(cyclopropanesulfonamido)pyridin-2-yl)propyl)-5-(6-ethoxypyrazin-2-yl)-4-methylthiazole-2-carboxamide, isomer 1 (I-219) and (R)—N-(1-(4-(cyclopropanesulfonamido)pyridin-2-yl)propyl)-5-(6-ethoxypyrazin-2-yl)-4-methylthiazole-2-carboxamide, isomer 2 (I-220). Stereochemistry Arbitrarily Assigned

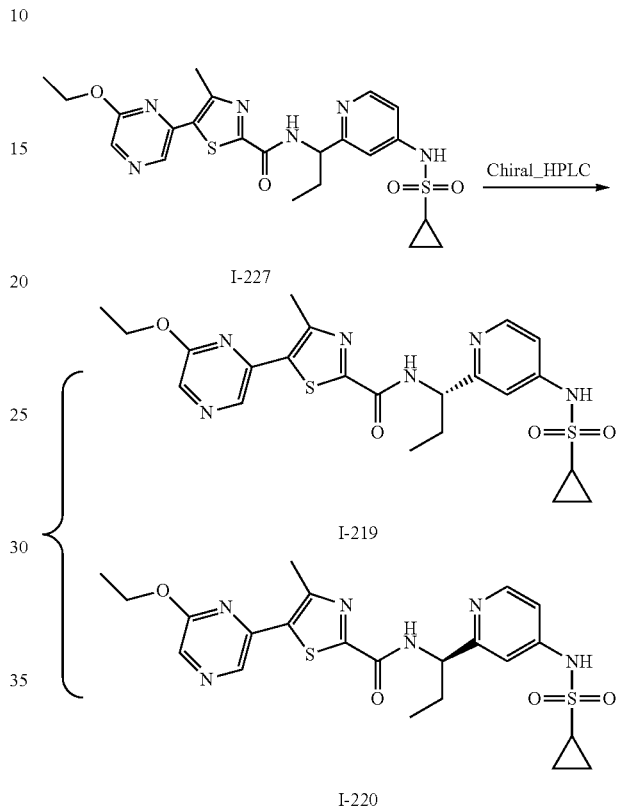

Synthesis of I-219 and I-220. I-227 (100 mg 0.2 mmol, 1 eq) was separated by Chiral-Prep-HPLC with the following conditions: Column: CHIRALPAK ID, 2*25 cm, 5 μm; Mobile Phase, MtBE(0.1% DEA): EtOH=80:20; UV detection at 254/220 nm. The product-containing fractions were combined evaporated partially in vacuum and lyophilized overnight to afford (S)—N-(1-(4-(cyclopropanesulfonamido)pyridin-2-yl)propyl)-5-(6-ethoxypyrazin-2-yl)-4-methylthiazole-2-carboxamide (I-219, 1$^{st}$ eluting peak, 21 mg, 42%) and (R)—N-(1-(4-(cyclopropanesulfonamido)pyridin-2-yl)propyl)-5-(6-ethoxypyrazin-2-yl)-4-methylthiazole-2-carboxamide (I-220, 2$^{nd}$ eluting peak, 26 mg, 52%) a white solids.

I-219: MS (ES): m/z 503; [M+H]$^+$. $^1$H NMR (400 MHz, Methanol-d$_4$) δ 8.51 (s, 1H), 8.32 (s, 1H), 8.16 (s, 1H), 7.27 (d, J=2.3 Hz, 1H), 7.14 (dd, J=5.9, 2.3 Hz, 1H), 4.99 (t, J=8.2, 6.3 Hz, 1H), 4.49 (q, J=7.1 Hz, 2H), 2.82 (s, 3H), 2.79-2.68 (m, 1H), 2.12-1.91 (m, 2H), 1.46 (t, J=7.1 Hz, 3H), 1.21-1.09 (m, 2H), 1.06-0.93 (m, 5H). I-220: MS (ES): m/z 503; $^1$H NMR (400 MHz, Methanol-d$_4$) δ 8.51 (s, 1H), 8.32 (s, 1H), 8.16 (s, 1H), 7.27 (d, J=2.3 Hz, 1H), 7.14 (dd, 7=5.9, 2.3 Hz, 1H), 4.99 (t, J=8.2, 6.3 Hz, 1H), 4.50 (q, J=7.1 Hz, 2H), 2.82 (s, 3H), 2.79-2.68 (m, 1H), 2.12-1.91 (m, 2H), 1.46 (t, J=7.1 Hz, 3H), 1.21-1.09 (m, 2H), 1.06-0.93 (m, 5H).

Example 116: Synthesis of N-[4-[(2R)-1-[4-(6-ethoxypyrazin-2-yl)-2-fluorobenzoyl]pyrrolidin-2-yl]pyrimidin-2-yl]cyclopropanesulfonamide, isomer 1 (I-285) and N-[4-[(2S)-1-[4-(6-ethoxypyrazin-2-yl)-2-fluorobenzoyl]pyrrolidin-2-yl]pyrimidin-2-yl]cyclopropanesulfonamide, isomer 2 (I-286). Stereochemistry Arbitrarily Assigned

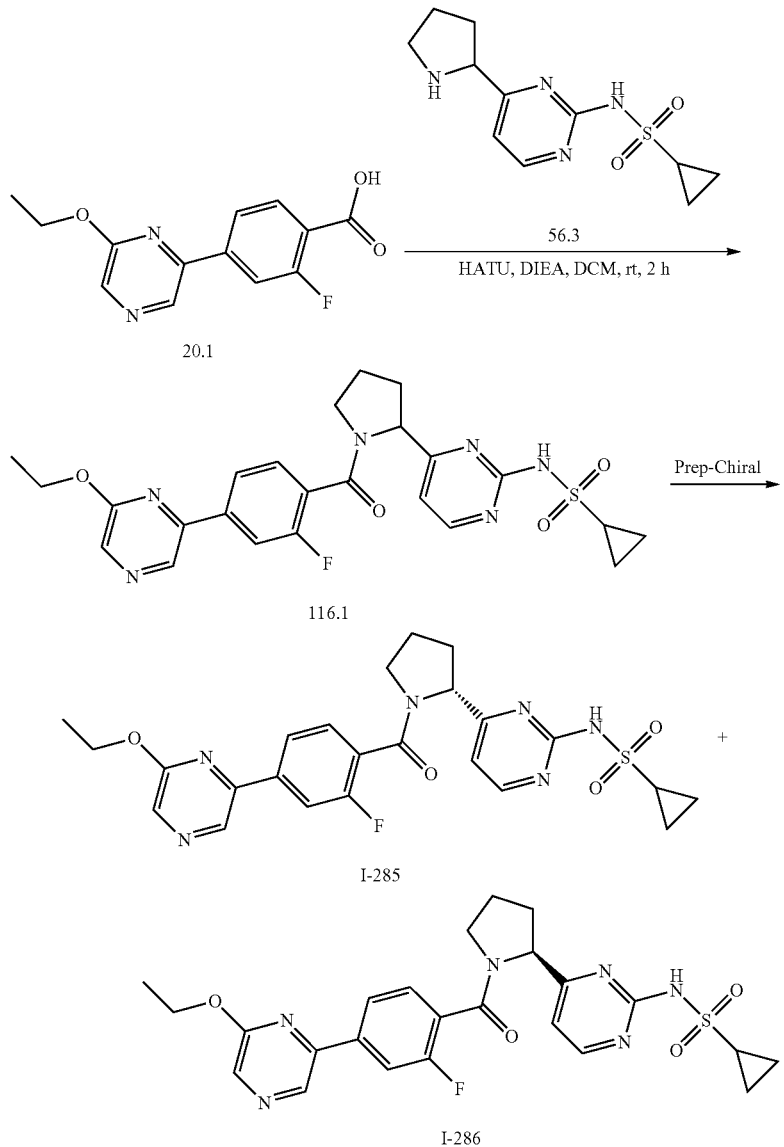

Synthesis of 116.1. To a stirred mixture of 20.1 (27 mg, 0.1 mmol, 1 eq) and 56.3 (27 mg, 0.1 mmol, 1 eq) in dichloromethane (0.5 mL) were added 2-(-7-azabenzotriazol-1-yl)-N, N, N', N'-tetramethyluronium hexafluorophosphate (46 mg, 0.12 mmol, 1.2 eq) and diisopropylethylamine (39 mg, 0.3 mmol, 3 eq). The resulting mixture was stirred for 2 h at room temperature. The resulting mixture was concentrated under reduced pressure and purified by reverse phase flash chromatography with the following conditions: Column, C18 Column; Mobile Phase, water (0.1% $NH_4HCO_3$) and ACN (10% ACN up to 60% in 10 min); UV detection at 254/220 nm. The crude product was purified by Prep-HPLC with the following conditions: Column: YMC-Actus Triart C18 30*250.5 um; Mobile Phase, water (10 mmol/L $NH_4HCO_3$+0.1% $NH_3 \cdot H_2O$) and ACN (8% ACN up to 38% in 7 min); UV detection at 254/210 nm. The product-containing fractions were combined and evaporated partially in vacuum and lyophilized overnight to afford N-[4-[2-1-[4-(6-ethoxypyrazin-2-yl)-2-fluorobenzoyl]pyrrolidin-2-yl]pyrimidin-2-yl]cyclopropanesulfonamide (116.1.17 mg, 30%) as a white solid. MS (ES): m/z 513 $[M+H]^+$.

Synthesis of I-285 and I-286. 116.1 (17 mg, 0.03 mmol, 1 eq) was separated by Chiral-Prep-HPLC with the following conditions: Column, CHIRALPAK IH-3, 3.0*50 mm, 3 µm; mobile Phase: MtBE (0.1% DEA): MeOH=50:50 Detector, UV 254/220 nm. The product-containing fractions were combined and concentrated under reduced pressure to afford N-[4-[(2R)-1-[4-(6-ethoxypyrazin-2-yl)-2-fluorobenzoyl]pyrrolidin-2-yl]pyrimidin-2-yl]cyclopropanesulfonamide, isomer 1 (I-285, 1$^{st}$ eluting peak, 1.7 mg, 18%) and N-[4-[(2S)-1-[4-(6-ethoxypyrazin-2-yl)-2-fluorobenzoyl]pyrrolidin-2-yl]pyrimidin-2-yl]cyclopropanesulfonamide, isomer 2 (I-286, 2$^{nd}$ eluting peak, 2.1 mg, 23%) as white solids. I-285: MS (ES): m/z 513 [M+H]$^+$; $^1$H NMR (400 MHz, DMSO-d$_6$) δ 11.29 (s, 1H), 8.93 (s, 0.8H), 8.82 (s, 0.2H), 8.59 (d, J=5.1 Hz, 0.7H), 8.39-8.26 (m, 1.3H), 8.13-8.05 (m, 1.5H), 7.92-7.81 (m, 0.5H), 7.69-7.62 (m, 0.7H), 7.39-6.63 (m, 1.3H), 5.08 (t, J=4 Hz, 0.8H), 4.80 (t, J=4 Hz, 0.2H), 4.49 (q, J=7.2 Hz, 2H), 3.87-3.40 (m, 2H), 3.28-3.06 (m, 1H), 2.48-2.38 (m, 1H), 1.99-1.89 (m, 3H), 1.40 (t, J=7.2 Hz, 3H), 1.18-0.95 (m, 4H). NMR showed the presence of rotamers. I-286: MS (ES): m/z 513 [M+H]$^+$; $^1$H NMR (400 MHz, DMSO-d$_6$) δ 11.25 (s, 1H), 8.92 (s, 0.8H), 8.74 (s, 0.2H), 8.59 (d, J=5.1 Hz, 0.7H), 8.38 (d, J=5.1 Hz, 0.3H), 8.39-8.26 (m, 1H), 8.13-8.05 (m, 1.5H), 7.92-7.81 (m, 0.5H), 7.69-7.62 (m, 0.7H), 7.39-7.28 (m, 0.3H), 7.12 (s, 0.7H), 6.88 (s, 0.3H), 5.08 (t, J=4 Hz, 0.8H), 4.80 (t, J=4 Hz, 0.2H), 4.49 (q, J=7.2 Hz, 2H), 3.87-3.40 (m, 2H), 3.28-3.06 (m, 1H), 2.48-2.38 (m, 1H), 1.99-1.89 (m, 3H), 1.40 (t, J=7.2 Hz, 3H), 1.18-0.95 (m, 4H). NMR showed the presence of rotamers.

Example 117: Synthesis of N-[4-[(2R)-1-[1-(6-ethoxypyrazin-2-yl)imidazole-4-carbonyl]pyrrolidin-2-yl]pyrimidin-2-yl]cyclopropanesulfonamide, isomer 1 (I-275 and N-[4-[(2S)-1-[1-(6-ethoxypyrazin-2-yl)imidazole-4-carbonyl]pyrrolidin-2-yl]pyrimidin-2-yl]cyclopropanesulfonamide, isomer 2 (I-276). Stereochemistry Arbitrarily Assigned

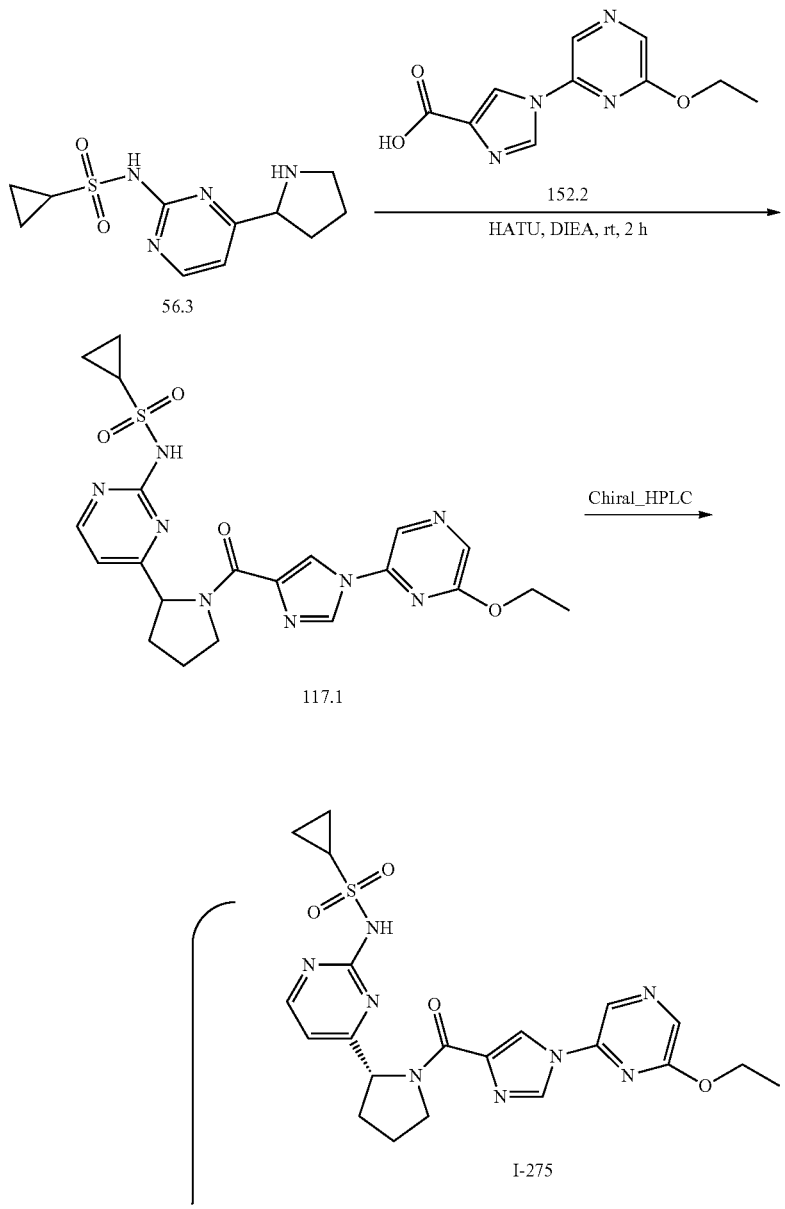

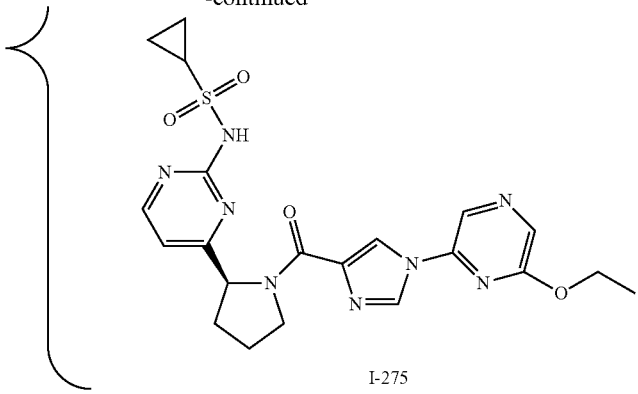

I-275

Synthesis of I-275 and I-276. I-275 and I-276 were prepared following similar methods to that described for I-285 and I-286 but using 152.2 as the acid. I-275, 1st eluting peak, MS (ES): m/z 485 [M+H]+; 1H NMR (400 MHz, CD3OD) δ 8.62-8.18 (m, 5H), 7.09 (d, J=5.2 Hz, 0.6H), 6.99 (d, J=5.2 Hz, 0.4H), 6.24-6.18 (dd, J=8.1, 4.4 Hz, 0.4H), 5.25 (dd, J=8.1, 4.4 Hz, 0.6H), 4.43-3.78 (m, 4H), 3.30-3.22 (m, 1H), 2.58-1.92 (m, 4H), 1.46 (t, J=7.2 Hz, 3H), 1.34-0.91 (m, 4H). NMR showed the presence of rotamers. I-276, 2nd eluting peak, MS (ES): m/z 485 [M+H]+; 1H NMR (400 MHz, CD3OD) δ 8.62-8.18 (m, 5H), 7.09 (d, J=5.2 Hz, 0.6H), 6.99 (d, J=5.2 Hz, 0.4H), 6.24-6.18 (dd, J=8.1, 4.4 Hz, 0.4H), 5.25 (dd, J=8.1, 4.4 Hz, 0.6H), 4.43-3.78 (m, 4H), 3.30-3.22 (m, 1H), 2.58-1.92 (m, 4H), 1.46 (t, J=7.2 Hz, 3H), 1.34-0.91 (m, 4H). NMR showed the presence of rotamers.

Example 118: Synthesis of N-[4-[(2R)-1-[5-(6-ethoxypyrazin-2-yl)-1,3-thiazole-2-carbonyl]pyrrolidin-2-yl]pyrimidin-2-yl]cyclopropanesulfonamide, isomer 1 (I-270) and (N-[4-[(2S)-1-[5-(6-ethoxypyrazin-2-yl)-1,3-thiazole-2-carbonyl]pyrrolidin-2-yl]pyrimidin-2-yl]cyclopropanesulfonamide, isomer 2 (I-271). Stereochemistry Arbitrarily Assigned

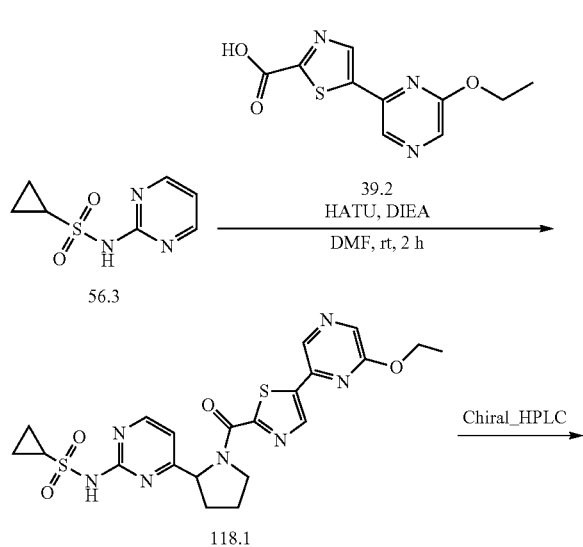

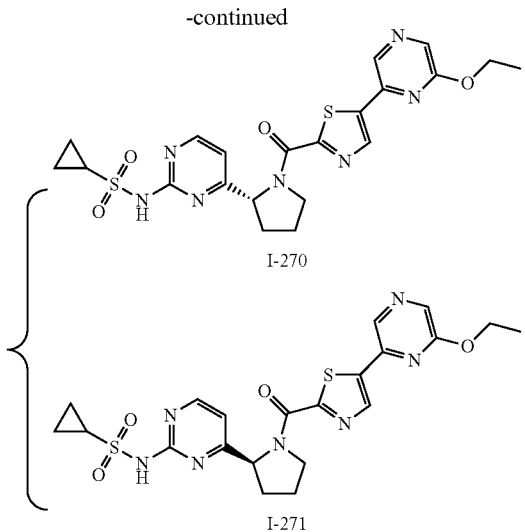

I-270

I-271

Synthesis of compound I-270 and I-271. I-270 and I-271 were prepared following similar methods to that described for I-285 and I-286 but using 39.2 as the acid. I-270: 1st eluting peak, MS (ES): m/z 502 [M+H]+; 1H NMR (400 MHz, CD3OD) δ 8.71 (s, 0.5H), 8.61 (d, J=14.5 Hz, 1H), 8.49 (d, J=5.3 Hz, 0.5H), 8.42 (d, J=5.3 Hz, 0.5H), 8.34 (s, 0.5H), 8.15 (d, J=16.0 Hz, 1H), 7.10 (d, J=5.2 Hz, 0.5H), 7.05 (d, J=5.2 Hz, 0.5H), 6.27-6.20 (m, 0.5H), 5.32-5.25 (m, 0.5H), 4.56-4.42 (m, 3H), 4.11-4.00 (m, 0.5H), 3.92-3.81 (m, 0.5H), 3.28-3.17 (m, 1H), 2.65-1.93 (m, 4H), 1.47-1.43 (m, 3H), 1.35-1.03 (m, 2H), 1.00-0.77 (m, 2H). NMR showed the presence of rotamers. I-271: 2nd eluting peak, MS (ES): m/z 502 [M+H]+; 1H NMR (400 MHz, CD3OD) δ 8.71 (s, 0.5H), 8.61 (d, J=14.5 Hz, 1H), 8.49 (d, J=5.3 Hz, 0.5H), 8.42 (d, J=5.3 Hz, 0.5H), 8.34 (s, 0.5H), 8.15 (d, J=16.0 Hz, 1H), 7.10 (d, J=5.2 Hz, 0.5H), 7.05 (d, J=5.2 Hz, 0.5H), 6.27-6.20 (m, 0.5H), 5.32-5.25 (m, 0.5H), 4.56-4.42 (m, 3H), 4.11-4.00 (m, 0.5H), 3.92-3.81 (m, 0.5H), 3.28-3.17 (m, 1H), 2.65-1.93 (m, 4H), 1.47-1.43 (m, 3H), 1.35-1.03 (m, 3H), 1.00-0.77 (m, 1H). NMR showed the presence of rotamers.

Example 119: Synthesis of N-[4-(1-{5-[7-(2,2-difluoroethyl)-5H-pyrrolo[2,3-b] pyrazin-2-yl]-1,3-thiazole-2-carbonyl}pyrrolidin-2-yl) pyrimidin-2-yl] cyclopropanesulfonamide (I-137)
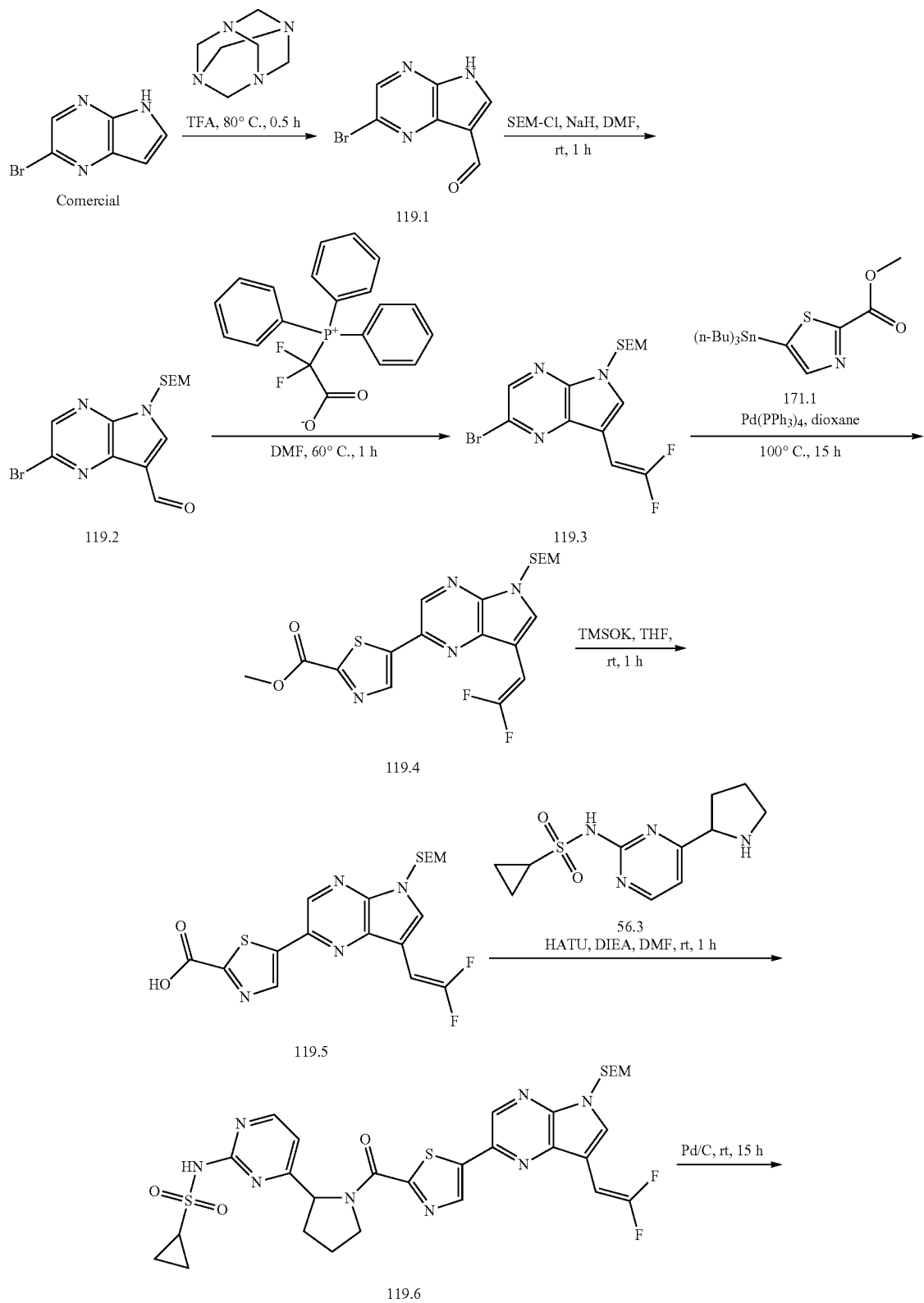

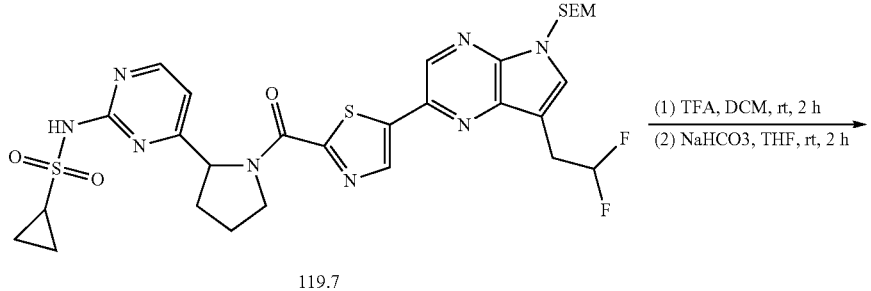

119.7

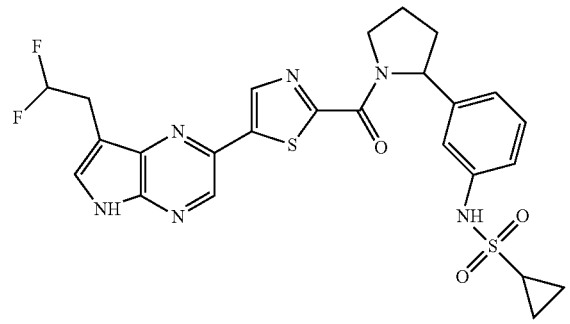

I-137

Synthesis of 119.1. To a stirred mixture of 2-bromo-5H-pyrrolo[2,3-b] pyrazine (3 g, 15.15 mmol, 1 eq) and 1,3,5,7-tetraazaadamantane (3.2 g, 22.73 mmol, 1.5 eq) in trifluoroacetic acid (30 mL) at room temperature under nitrogen atmosphere. The reaction mixture was heated in a microwave apparatus for 15 min at 80° C. The mixture was allowed to cool down to room temperature. The pH of the mixture was adjusted PH to 7 with aqueous saturated sodium carbonate. The precipitated solids were collected by filtration and washed with water. The crude product 119.1 (3.5 g) was used in the next step directly without further purification. MS (ES): m/z 226/228 [M+H]$^+$.

Synthesis of 119.2. A stirred mixture of crude 119.1 (4 g) in N, N-dimethyl formamide (50 mL) was degassed three times with nitrogen and cooled to 0° C. To the solution was added sodium hydride (1.06 g, 26.54 mmol, 60% w/w in mineral oil) in portion at 0° C. under nitrogen atmosphere. The mixture was stirred for 0.5 h at room temperature. To the above mixture was added dropwise [2-(chloromethoxy) ethyl] trimethyl silane (3.54 g, 21.23 mmol) at 0° C. under nitrogen atmosphere. The mixture was stirred for additional 0.5 h at room temperature. The mixture was quenched with water and extracted with ethyl acetate. The combined organic layers were washed with brine, dried over anhydrous sodium sulfate. After filtration, the filtrate was concentrated under reduced pressure. The residue was purified column chromatography on silica gel (petroleum ether/ethyl acetate (3/1)) to afford 2-bromo-5-{[2-(trimethylsilyl) ethoxy]methyl} pyrrolo[2,3-b] pyrazine-7-carbaldehyde (119.2, 800 mg) as a brown yellow oil. MS (ES): m/z 356/358 [M+H]$^+$.

Synthesis of 119.3. A solution of 119.2 (860 mg, 2.41 mmol, 1 eq) and difluoro(triphenylphosphaniumyl)acetate (1.7 g, 4.83 mmol, 2 eq) in N, N-dimethyl formamide (12 mL) was stirred for 1 h at 60° C. The mixture was allowed to cool down to room temperature. The mixture was diluted water and extracted with ethyl acetate. The combined organic layers were washed with brine, dried over anhydrous sodium sulfate. After filtration, the filtrate was concentrated under reduced pressure. The residue was purified by Prep-TLC (petroleum ether/ethyl acetate=10/1) to afford 2-bromo-7-(2,2-difluoroethenyl)-5-{[2-(trimethylsilyl) ethoxy]methyl} pyrrolo[2,3-b] pyrazine (119.3, 520 mg, 54%) as a yellow solid. MS (ES): m/z 390/392 [M+H]$^+$.

Synthesis of 119.4. To a stirred mixture of 119.3 (200 mg, 0.51 mmol, 1 eq) and 171.1 (221 mg, 0.51 mmol, 1 eq) in dioxane (3 mL) was added Pd(PPh$_3$)$_4$ (59 mg, 0.05 mmol, 0.1 eq) at room temperature. The mixture was degassed three times with nitrogen and stirred for 15 h at 100° C. under nitrogen atmosphere. The mixture was allowed to cool down to room temperature. The resulting mixture was diluted water and extracted with ethyl acetate. The combined organic layers were washed with brine, dried over anhydrous sodium sulfate. After filtration, the filtrate was concentrated under reduced pressure. The residue was purified by Prep-TLC (petroleum ether/ethyl acetate=2/1) to afford methyl 5-[7-(2,2-difluoroethenyl)-5-{[2-(trimethylsilyl) ethoxy]methyl} pyrrolo[2,3-b] pyrazin-2-yl]-1,3-thiazole-2-carboxylate (119.4, 150 mg, 58%) as a brown yellow solid. MS (ES): m/z 453 [M+H]$^+$.

Synthesis of 119.5. To a stirred mixture of 119.4 (130 mg, 0.28 mmol, 1 eq) in THF (3 mL) was added potassium trimethylsilanolate (44 mg, 0.34 mmol, 1.2 eq) at room temperature. The mixture was stirred for 1 h at room temperature. The resulting mixture was concentrated under reduced pressure to afford the crude product 119.5 (130 mg) which was used without further purification. MS (ES): m/z 439 [M+H]$^+$.

Synthesis of 119.6. To a stirred mixture of 119.5 (130 mg) and 56.3 (119 mg, 0.44 mmol) in N, N-dimethyl formamide (2 mL) was added 2-(-7-azabenzotriazol-1-yl)-N, N, N', N'-tetramethyluronium hexafluorophosphate (169 mg, 0.44 mmol) and N, N-diisopropylethylamine (153 mg, 1.18 mmol) in portions at room temperature. The mixture was stirred for 1 h at room temperature. The resulting mixture was diluted water and extracted with ethyl acetate. The combined organic layers were washed with brine, dried over anhydrous sodium sulfate. After filtration, the filtrate was concentrated under reduced pressure. The residue was purified by Prep-TLC (dichloromethane/methanol=15/1) to afford N-[4-(1-{5-[7-(2,2-difluoroethenyl)-5-{[2-(trimethylsilyl) ethoxy] methyl} pyrrolo[2,3-b] pyrazin-2-yl]-1,3-thiazole-2-carbonyl}pyrrolidin-2-yl) pyrimidin-2-yl] cyclopropanesulfonamide (119.6, 50 mg) as a brown yellow solid. MS (ES): m/z 689 [M+H]$^+$.

Synthesis of 119.7. A stirred solution of 119.6 (40 mg, 0.06 mmol, 1 eq) in methanol (2 mL) was evacuated and flushed three times with nitrogen. To the solution was added 10% w/w Pd/C (6 mg, 0.006 mmol, 0.1 eq). The result mixture was flushed with nitrogen and hydrogen three times. The mixture was stirred for 15 h at 30° C. under hydrogen atmosphere at 10 atm. The resulting mixture was filtered; the solids were washed with methanol. The filtrate was concentrated under reduced pressure to afford the crude product 119.7 (50 mg) which was used without further purification. MS (ES): m/z 691 [M+H]$^+$.

Synthesis of I-137. A solution of 119.7 (40 mg) in trifluoroacetaldehyde (1 mL) and dichloromethane (1 mL) was stirred for 2 h at room temperature. The resulting mixture was concentrated under reduced pressure. To the above mixture was added saturated aqueous sodium bicarbonate solution (1 mL) and tetrahydrofuran (1 mL) at room temperature. The mixture was stirred for 2 h at room temperature. The resulting mixture was diluted water and extracted with ethyl acetate. The combined organic layers were washed with brine, dried over anhydrous sodium sulfate. After filtration, the filtrate was concentrated under reduced pressure. The residue was purified by Prep-HPLC with the following conditions Column, C18; mobile phase, Water (10 mmol/L NH$_4$HCO$_3$) and ACN (30% ACN up to 37% in 8 min); UV detection at 254/220 nm. The product-containing fractions were combined and evaporated partially in vacuum and lyophilized overnight to afford N-[4-(1-{5-[7-(2,2-difluoroethyl)-5H-pyrrolo[2,3-b] pyrazin-2-yl]-1,3-thiazole-2-carbonyl}343yrrolidine-2-yl) pyrimidin-2-yl] cyclopropanesulfonamide (I-137, 2.3 mg) as a white solid. MS (ES): m/z 561 [M+H]$^+$; $^1$H NMR (400 MHz, DMSO) δ 8.97 (s, 0.5H), δ 8.91 (s, 0.5H), 8.74 (s, 0.5H), 8.49 (s, 0.5H), 8.27-8.22 (m, 1H), 7.88 (d, J=9.4 Hz, 1H), 6.72-6.38 (m, 1H), 6.07 (dd, J=8.2, 3.4 Hz, 0.5H), 5.06 (dd, J=8.2, 3.4 Hz, 0.5H), 4.46-4.18 (m, 1H), 3.92-3.68 (m, 1H), 3.40 (d, J=4.1 Hz, 2H), 3.09-3.01 (m, 1H), 2.48-1.69 (m, 4H), 0.97-0.48 (m, 4H)

Example 120: Synthesis of N-[6-[(2R)-1-[5-(6-ethoxypyrazin-2-yl)-1,3-thiazole-2-carbonyl]pyrrolidin-2-yl]pyridin-2-yl]cyclopropanesulfonamide (I-230)

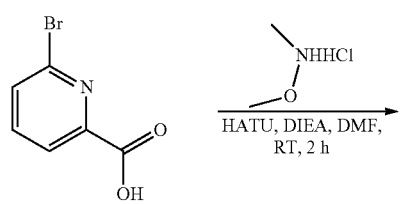

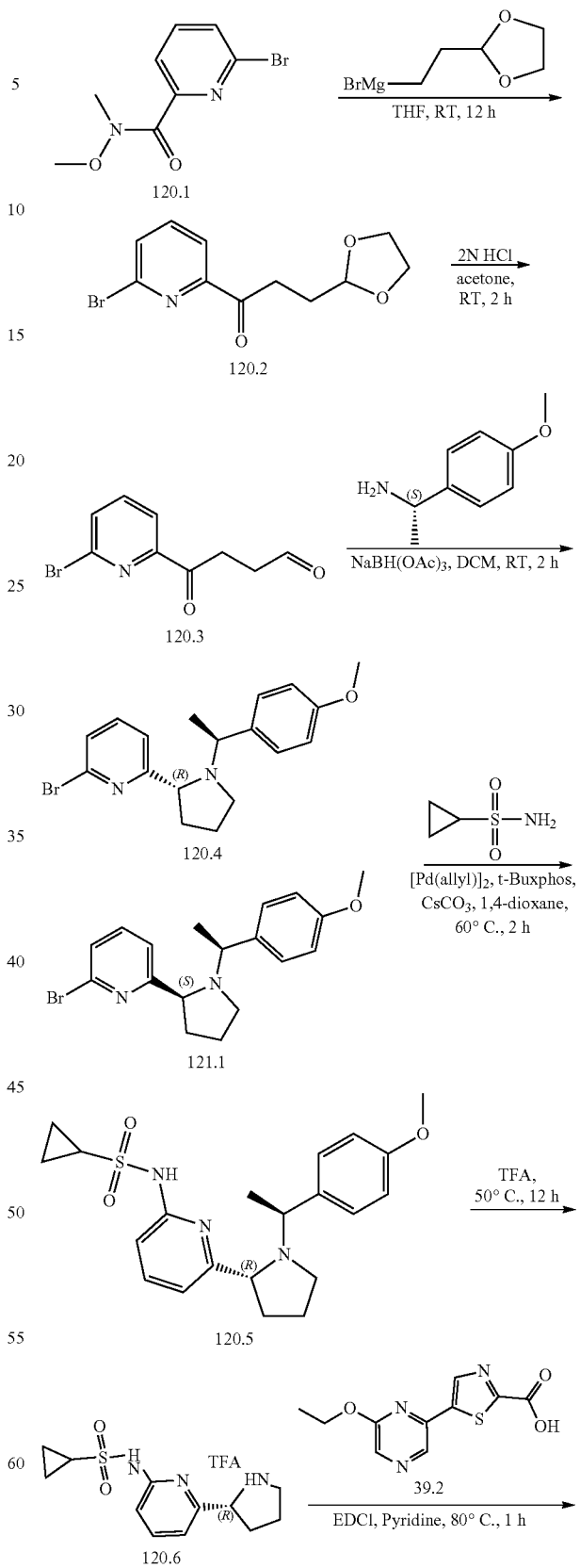

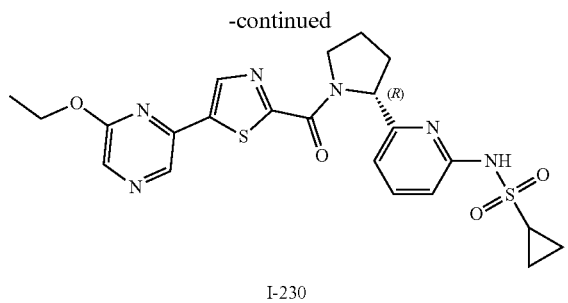

I-230

Synthesis of 120.1. To a stirred solution of 6-bromopicolinic acid (5 g, 24.75 mmol, 1 eq) and N,O-dimethylhydroxylamine hydrochloride (2.4 g, 24.75 mmol, 1 eq) in A/N-dimethyl formamide (150 mL) was added N, N-diisopropylethylamine (16 g, 123.75 mmol, 5 eq) and 2-(-7-azabenzotriazol-1-yl)-N, N, N', N'-tetramethyluronium hexafluorophosphate (14.1 g, 47.18 mmol, 1.5 eq) at room temperature. The resulting mixture was stirred for 2 h at room temperature. The mixture was diluted with water and extracted with ethyl acetate. The combined organic layer was washed with brine, dried over sodium sulfate and concentrated under reduced pressure. The residue was purified by reverse phase flash with the following conditions: Column, C18 Column; Mobile Phase, water (10 mmol/L $NH_4HCO_3$) and ACN (10% ACN up to 60% in 10 min); UV detection at 254/220 nm. The product-containing fractions were combined and concentrated under reduced pressure to obtain 6-bromo-N-methoxy-N-methylpicolinamide (120.1, 5.30 g, 88%) as white oil. MS (ES): m/z 245/247 $[M+H]^+$.

Synthesis of 120.2. To a stirred solution of 120.1 (3.5 g, 14.28 mmol, 1 eq.) in tetrahydrofuran (70 mL) was added (2-(1,3-dioxolan-2-yl)ethyl)magnesium bromide (8.65 g, 42.84 mmol, 3 eq) at 0° C. under nitrogen atmosphere. The resulting mixture was stirred for 12 h at room temperature. The mixture was quenched with ammonium chloride and extracted with ethyl acetate. The combined organic layer was washed with brine, dried over sodium sulfate and concentrated under reduced pressure. The residue was purified by reverse phase flash with the following conditions: Column, C18 Column; Mobile Phase, water (10 mmol/L $NH_4HCO_3$) and ACN (10% ACN up to 60% in 10 min); UV detection at 254/220 nm. The product-containing fractions were combined and concentrated under reduced pressure to obtain 1-(6-bromopyridin-2-yl)-3-(1,3-dioxolan-2-yl)propan-1-one (120.2, 2.1 g, 51%), MS (ES): m/z 286/288 $[M+H]^+$.

Synthesis of 120.3. To a stirred solution of 120.2 (2.1 g, 7.34 mmol, 1 eq) in acetone (20 mL) was added hydrochloric acid (2N, 10 mL) at 0° C. The resulting mixture was stirred for 12 h at room temperature. The resulting mixture was concentrated under vacuum and basified pH to 9 with saturated aqueous sodium bicarbonate. The mixture was diluted with water and extracted with ethyl acetate. The combined organic layer was washed with brine, dried over sodium sulfate and concentrated under reduced pressure to obtain 4-(6-bromopyridin-2-yl)-4-oxobutanal (120.3, 1.4 g, 79%), MS (ES): m/z 242/244 $[M+H]^+$.

Synthesis of 120.4. To a stirred solution of 120.3 (1.4 g, 5.78 mmol, 1 eq) and (1S)-1-(4-methoxyphenyl)ethanamine (873 mg, 5.78 mmol, 1 eq) in dichloromethane (30 mL) was added sodium triacetoxyborohydride (3.68 g, 17.34 mmol, 3 eq) at 0° C. under nitrogen atmosphere. The resulting mixture was stirred for 2 h at room temperature. The mixture was diluted with water and extracted with dichloromethane. The combined organic layer was washed with brine, dried over sodium sulfate and concentrated under reduced pressure. The residue was purified by reverse phase flash chromatography with the following conditions: Column, C18 Column; Mobile Phase, water (10 mmol/L $NH_4HCO_3$) and ACN (10% ACN up to 60% in 10 min); UV detection at 254/220 nm. The product-containing fractions were combined and concentrated under reduced pressure to obtain 2-bromo-6-((R)-1-((S)-1-(4-methoxyphenyl)ethyl)pyrrolidin-2-yl)pyridine (120.4, 800 mg, 38%) and 2-bromo-6-((S)-1-((S)-1-(4-methoxyphenyl)ethyl)pyrrolidin-2-yl)pyridine (121.1, 260 mg, 12%) as brown solids. 120.4. MS (ES): m/z 361/363 $[M+H]^+$. 121.1. MS (ES): m/z 361/363 $[M+H]^+$.

Synthesis of 120.5. To a stirred solution of 120.4 (800 mg, 2.22 mmol, 1 eq) and cyclopropanesulfonamide (537 mg, 4.44 mmol, 2 eq) in 1,4-dioxane (15 mL) was added cesium carbonate (2.17 g, 6.66 mmol, 3 eq), $Pd_2(allyl)_2Cl_2$ (40 mg, 0.11 mmol, 0.05 eq) and t-Buxphos (95 mg, 0.22 mmol, 0.1 eq). The resulting mixture was degassed three times with nitrogen and stirred for 2 h at 60° C. under nitrogen atmosphere. The mixture was cooled to room temperature, diluted with water and extracted with ethyl acetate. The combined organic layer was washed with brine, dried over sodium sulfate and concentrated under reduced pressure. The residue was purified by reverse phase flash with the following conditions: Column, C18 Column; Mobile Phase, water (0.1% FA) and ACN (10% ACN up to 60% in 7 min); UV detection at 254/220 nm. The product-containing fractions were combined and concentrated under reduced pressure to obtain N-(6-((R)-1-((S)-1-(4-methoxyphenyl)ethyl)pyrrolidin-2-yl)pyridin-2-yl)cyclopropanesulfonamide, isomer 1 (120.5, 800 mg, 90%) as a yellow solid. MS (ES): m/z 402 $[M+H]^+$.

Synthesis of 120.6. Into a 5 mL sealed tube was added 120.5 (800 mg, 1.99 mmol, 1 eq) and trifluoroacetic acid (10 mL) at room temperature. The resulting mixture was stirred 12 h at 50° C. The mixture was cooled to room temperature and concentrated under vacuum to obtain crude product 120.6 (400 mg) as a yellow solid, used without further purification. MS (ES): m/z 268 $[M+H]^+$.

Synthesis of I-230. To a stirred solution of 120.6 (130 mg) and 39.2 (121 mg) in pyridine (5 mL) were added 1-ethyl-3-(3-dimethylaminopropyl)carbodiimide hydrochlolide (184 mg, 0.96 mmol) at room temperature. The resulting mixture was stirred for 1 h at 80° C. The mixture was cooled to room temperature. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 30*150 mm, 5 um; Mobile Phase, water (0.1% FA) and ACN (42% ACN up to 58% in 10 min); UV detection at 254/220 nm. The product-containing fractions were combined and evaporated partially in vacuum and lyophilized overnight to afford (R)—N-(6-(1-(5-(6-ethoxypyrazin-2-yl)picolinoyl)pyrrolidin-2-yl)pyridin-2-yl)cyclopropanesulfonamide (I-230, 26 mg) as a white solid. MS (ES): m/z 495 $[M+H]^+$; $^1$H NMR (400 MHz, $d_6$-DMSO) δ 10.49 (s, 1H), 8.90 (s, 0.6H), 8.79 (d, J=3.3 Hz, 1H), 8.56 (s, 0.4H), 8.28 (s, 0.6H), 8.24 (s, 0.4H), 7.72-7.56 (m, 1H), 7.04-6.66 (m, 2H), 6.17 (d, J=8.0 Hz, 0.4H), 5.24 (d, J=8.0 Hz, 0.6H), 4.48-4.12 (m, 3.3H), 3.97-3.63 (m, 0.7H), 3.12-3.09 (m, 1H), 2.47-2.24 (m, 1H), 2.15-1.75 (m, 3H), 1.39 (t, J=4.8 Hz, 3H), 1.15-0.65 (m, 4H).

Example 121: Synthesis of N-[6-[(2S)-1-[5-(6-ethoxypyrazin-2-yl)-1,3-thiazole-2-carbonyl]pyrrolidin-2-yl]pyridin-2-yl]cyclopropanesulfonamide (I-231)

Example 122: Synthesis of Example 122: N-(5-(1-(5-(6-ethoxypyrazin-2-yl)thiazole-2-carbonyl)pyrrolidin-2-yl)pyridin-3-yl)cyclopropanesulfonamide (I-232)

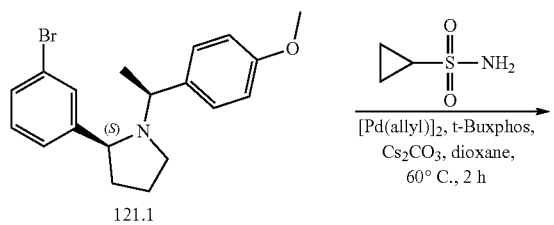

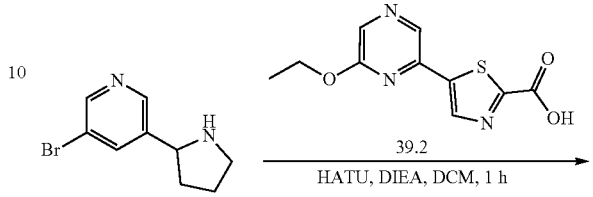

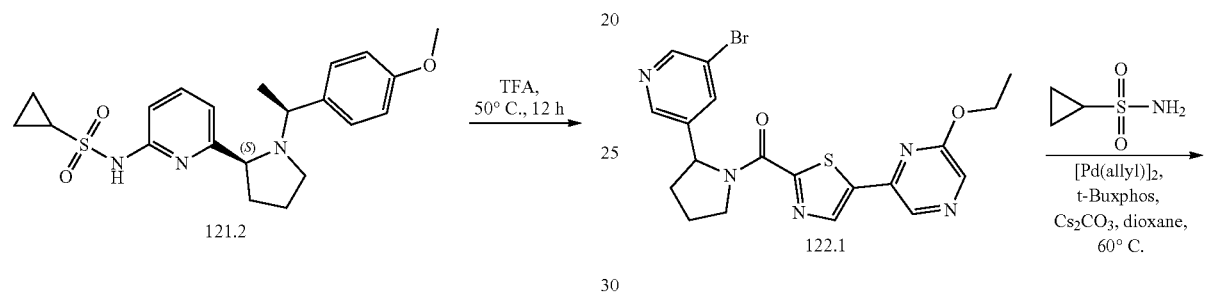

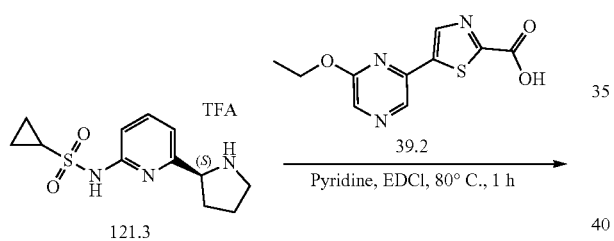

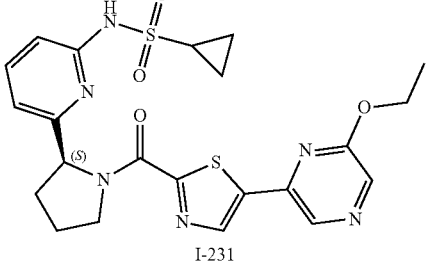

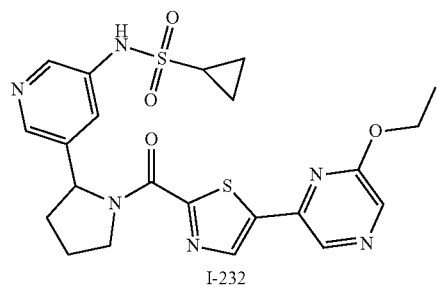

Synthesis of I-231. I-231 was prepared following similar methods to that described for I-230 (step 5, 6 and 7), using 121.1 as the aryl bromide. MS (ES): m/z 495 [M+H]+; 1H NMR (400 MHz, 6?6-DMSO) δ 10.49 (s, 1H), 8.90 (s, 0.6H), 8.79 (d, J=3.3 Hz, 1H), 8.56 (s, 0.4H), 8.28 (s, 0.6H), 8.24 (s, 0.4H), 7.72-7.56 (m, 1H), 7.04-6.66 (m, 2H), 6.17 (d, J=8.0 Hz, 0.4H), 5.24 (d, J=8.0 Hz, 0.6H), 4.48-4.12 (m, 3.2H), 3.97-3.63 (m, 0.8H), 3.12-3.09 (m, 1H), 2.47-2.24 (m, 1H), 2.15-1.75 (m, 3H), 1.39 (t, J=4.8 Hz, 3H), 1.15-0.65 (m, 4H).

Synthesis of 122.1. To a stirred solution of 3-bromo-5-(pyrrolidin-2-yl)pyridine (100 mg, 0.44 mmol, 1 eq) and 39.2 (111 mg) in dichloromethane (10 mL) was added N,N-diisopropylethylamine (284 mg, 2.2 mmol, 5 eq) and 2-(7-azabenzotriazol-1-yl)-N,N,N,N-tetramethyluronium hexafluorophosphate (106 mg, 0.44 mmol, 1 eq). The resulting mixture was stirred for 1 h at room temperature. The resulting mixture was concentrated under reduced pressure and purified by reverse flash chromatography with the following conditions: column, C18 silica gel; mobile phase, methanol in water, 10% to 50% gradient in 10 min; detector, UV 254 nm. The product-containing fractions were combined and evaporated partially in vacuum to afford 2-{2-[2-(5-bromopyridin-3-yl)pyrrolidine-1-carbonyl]-1,3-thiazol-5-yl}-6-ethoxypyrazine (122.1, 80 mg, 39%) as a yellow solid. MS (ES): m/z 461 [M+H]+.

Synthesis of I-232. To a stirred solution of 122.1 (80 mg, 0.17 mmol, 1 eq) and cyclopropanesulfonamide (42 mg, 0.34 mmol, 2 eq) in dioxane (4 mg, 0.04 mmol, 0.26 eq) was added cesium carbonate (171 mg, 0.52 mmol, 3 eq), Pd$_2$(allyl)$_2$Cl$_2$ (4 mg, 0.01 mmol, 0.05 eq) and t-Buxphos (7 mg, 0.02 mmol, 0.1 eq). The resulting mixture was degassed three times with nitrogen and stirred for 2 h at 60° C. under nitrogen atmosphere. The mixture was cooled to room temperature, diluted with water and extracted with ethyl acetate. The combined organic layer was washed with brine, dried over sodium sulfate and concentrated under reduced pressure. The crude product was purified by Prep-HPLC with the following conditions (Column: XBridge Prep OBD C18 Column, 30*150 mm, 5 μm; water (0.1% FA) and ACN (48% ACN up to 58% in 10 min); UV detection at 254/220 nm. The product-containing fractions were combined and evaporated partially in vacuum and lyophilized overnight to afford N-(5-{1-[5-(6-ethoxypyrazin-2-yl)-1,3-thiazole-2-carbonyl]pyrrolidin-2-yl}pyridin-3-yl)cyclopropanesulfonamide (I-232, 15 mg, 17%) as a white solid. MS (ES): m/z 501 [M+H]$^+$, NMR (400 MHz, Methanol-d$_4$) δ 8.70 (s, 0.5H), 8.63 (s, 0.5H), 8.58 (s, 0.5H), 8.38-8.28 (m, 1.5H), 8.25 (t, J=1.9 Hz, 1H), 8.14 (d, J=14.8 Hz, 1H), 7.69 (t, J=2.2 Hz, 0.6H), 7.59 (t, J=2.3 Hz, 0.4H), 6.34 (d, J=7.4 Hz, 0.4H), 5.37 (d, J=7.4 Hz, 0.6H), 4.47 (q, J=7.1 Hz, 3H), 4.07-3.87 (m, 1H), 2.67-2.42 (m, 2H), 2.21-2.05 (m, 2H), 2.09-1.88 (m, 1H), 1.45 (td, J=7.1 Hz, 3H), 1.08-0.81 (m, 4H).

Example 123: Synthesis of (R)—N-(5-(1-(5-(6-ethoxypyrazin-2-yl)thiazole-2-carbonyl)pyrrolidin-2-yl)pyridin-3-yl)cyclopropanesulfonamide, isomer 1 (I-225) and (S)—N-(5-(1-(5-(6-ethoxypyrazin-2-yl)thiazole-2-carbonyl)pyrrolidin-2-yl)pyridin-3-yl)cyclopropanesulfonamide, isomer 2 (I-226). Stereochemistry Arbitrarily Assigned

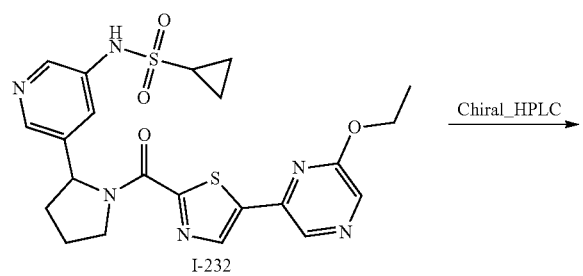

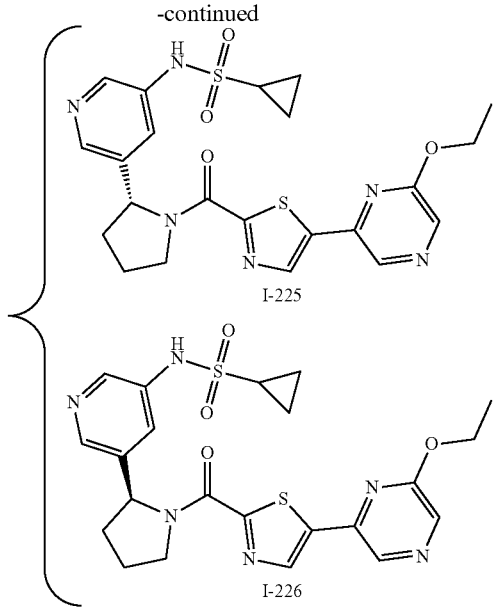

Synthesis of I-225 and I-226. I-232 (50 mg) was separated by Chiral-Prep-HPLC with the following conditions: Column: CHIRAL ART Cellulose-SB, 4.6*100 mm, 3 μm; Mobile Phase: MtBE(0.1% TFA): EtOH=80:20; Detector, LTV 254/220 nm. The product-containing fractions were combined and concentrated under reduced pressure to afford (R)—N-(5-(1-(5-(6-ethoxypyrazin-2-yl)thiazole-2-carbonyl)pyrrolidin-2-yl)pyridin-3-yl)cyclopropanesulfonamide, isomer 1 (I-225, 1$^{st}$ eluting peak, 24 mg) and (S)—N-(5-(1-(5-(6-ethoxypyrazin-2-yl)thiazole-2-carbonyl)pyrrolidin-2-yl)pyridin-3-yl)cyclopropanesulfonamide (I-226, 2$^{nd}$ eluting peak, 23 mg). I-225: MS (ES): m/z 501 [M+H]$^+$; $^1$H NMR (400 MHz, Methanol-d$_4$) δ 8.70 (s, 0.5H), 8.63 (s, 0.5H), 8.58 (s, 0.5H), 8.38-8.28 (m, 1.5H), 8.25 (t, J=1.9 Hz, 1H), 8.14 (d, J=14.8 Hz, 1H), 7.69 (t, J=2.2 Hz, 0.6H), 7.59 (t, J=2.3 Hz, 0.4H), 6.34 (d, J=7.4 Hz, 0.4H), 5.37 (d, J=7.4 Hz, 0.6H), 4.47 (q, J=7.1 Hz, 3H), 4.07-3.87 (m, 1H), 2.67-2.42 (m, 2H), 2.21-2.05 (m, 2H), 2.09-1.88 (m, 1H), 1.45 (td, J=7.1, 3H), 1.08-0.81 (m, 4H). I-226: MS (ES): m/z 501 [M+H]$^+$; NMR (400 MHz, Methanol-d$_4$) δ 8.70 (s, 0.5H), 8.63 (s, 0.5H), 8.58 (s, 0.5H), 8.38-8.28 (m, 1.5H), 8.25 (t, J=1.9 Hz, 1H), 8.14 (d, J=14.8 Hz, 1H), 7.69 (t, J=2.2 Hz, 0.6H), 7.59 (t, J=2.3 Hz, 0.4H), 6.34 (d, J=7.4 Hz, 0.4H), 5.37 (d, J=7.4 Hz, 0.6H), 4.47 (q, J=7.1 Hz, 3H), 4.07-3.87 (m, 1H), 2.67-2.42 (m, 2H), 2.21-1.88 (m, 3H), 1.45 (td, J=7.1, 3H), 1.08-0.81 (m, 4H).
General Method 3

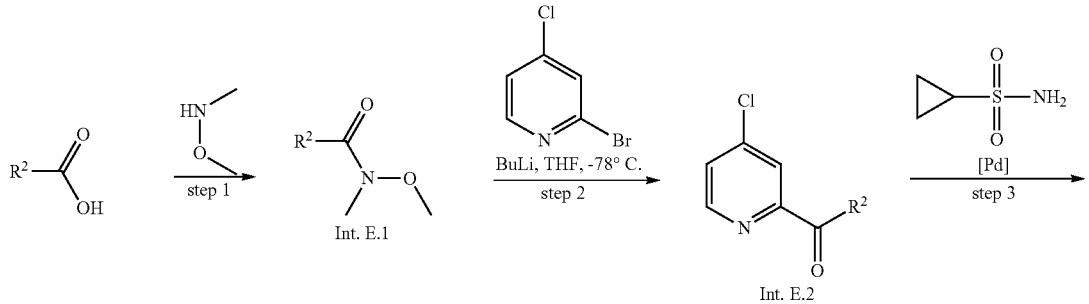

-continued
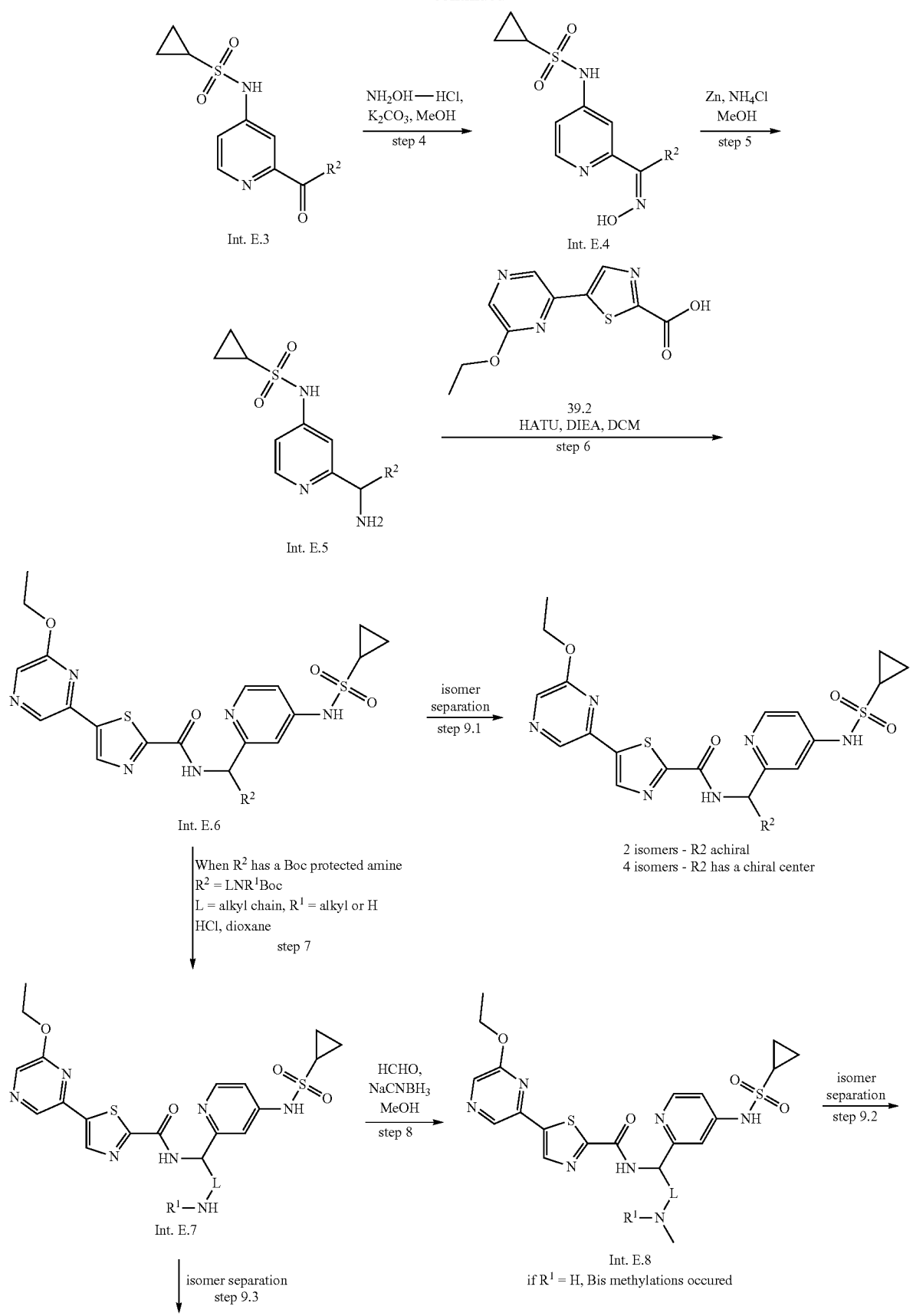

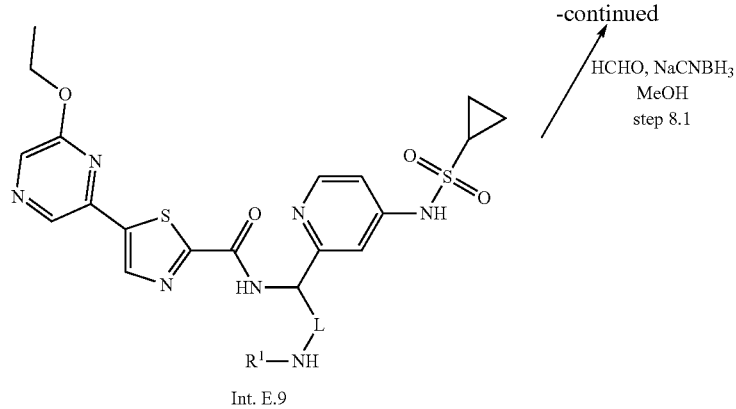

Int. E.9

Example 124: Synthesis of N-((4-(cyclopropane-sulfonamido)pyridin-2-yl)(piperidin-4-yl)methyl)-5-(6-ethoxypyrazin-2-yl)thiazole-2-carboxamide (I-153)

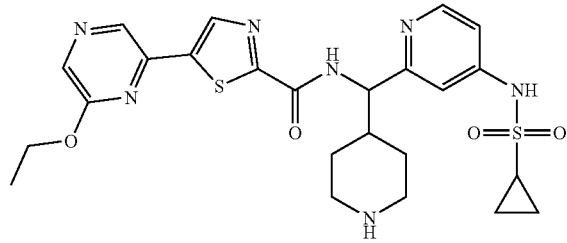

I-153

General Method 3, Step 1: Synthesis of 124.1.

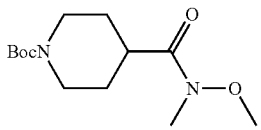

124.1

To a stirred solution of 1-(tert-butoxycarbonyl)piperidine-4-carboxylic acid (2.3 g, 10 mmol, 1 equiv) and N,O-dimethylhydroxylamine (735 mg, 12 mmol, 1.2 equiv) in dichloromethane (20 mL) were added HATU (7.6 g, 20 mmol, 2 equiv) and DIEA (2.6 g, 20 mmol, 2 equiv) in portions at room temperature. The resulting mixture was stirred for 4 h at room temperature. The reaction was diluted with dichloromethane (30 mL) and washed with water (20 mL). The organic layer was concentrated under vacuum. The residue was purified by flash column chromatography on C18 silica (eluted with 25% acetonitrile in water) to afford tert-butyl 4-(methoxy(methyl)carbamoyl)piperidine-1-carboxylate (124.1, 2 g, 73%) as a light yellow oil. MS (ES): m/z 273 [M+H]⁺.

General Method 3, Step 2: Synthesis of 124.2.

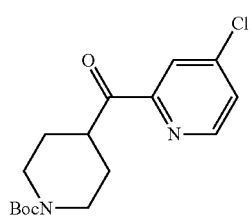

124.2

To a stirred solution of 2-bromo-4-chloropyridine (2.1 g, 11.0 mmol, 1.5 equiv) in THF (10 mL) was added n-butyl-lithium (2.5 M in THF, 4.4 mL, 11.0 mmol, 1.5 equiv) dropwise at −78° C. under nitrogen atmosphere. The resulting mixture was stirred at −78° C. for 30 min. Then a solution of 124.1 (2 g, 7.34 mmol, 1 equiv) in THF (2 mL) was added dropwise at −78° C. under nitrogen atmosphere. The resulting mixture was allowed to warm to room temperature and stirred for 2 h. The reaction was quenched with aqueous saturated ammonium chloride (20 mL) and extracted with ethyl acetate (3×15 mL). The combined organic layers were concentrated under vacuum. The residue was purified by flash column chromatography on C18 silica (eluted with 45% acetonitrile in water) to afford tert-butyl 4-(4-chloropyridine-2-carbonyl) piperidine-1-carboxylate (124.2, 1 g, 41%) as a brown solid. MS (ES): m/z 325 [M+H]⁺.

General Method 3, Step 3: Synthesis of 124.3.

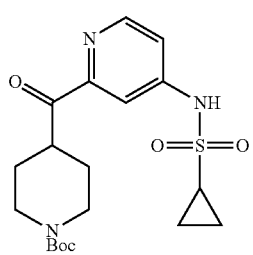

124.3

To a stirred solution of 124.2 (800 mg, 2.46 mmol, 1 equiv) and cyclopropanesulfonamide (1.5 g, 12.3 mmol, 5 equiv) in 1,4-dioxane (4 mL) were added EPhos (132 mg, 0.25 mmol, 0.1 equiv), EPhos Pd G4 (226 mg, 0.25 mmol, 0.1 equiv) and cesium carbonate (2.4 g, 7.39 mmol, 3 equiv). The resulting mixture was stirred for 2 h at 90° C. under nitrogen atmosphere. The reaction was concentrated under reduced pressure. The residue was purified by flash column chromatography on C18 silica (eluted with 32% acetonitrile in water) to afford tert-butyl 4-(4-cyclopropanesulfonamidopyridine-2-carbonyl) piperidine-1-carboxylate (124.3, 500 mg, 49%) as brown solid. MS (ES): m/z 410 [M+H]⁺.

General Method 3, Step 4: Synthesis of 124.4.

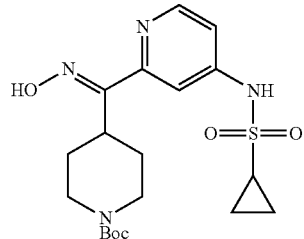

124.4

To a stirred solution of 124.3 (500 mg, 1.22 mmol, 1 equiv) and NH₂OH—HCl (424 mg, 6.11 mmol, 5 equiv) in methanol (3 mL) was added potassium carbonate (337 mg, 2.44 mmol, 2 equiv). The resulting mixture was stirred overnight at room temperature. The reaction mixture was filtered and the solid was rinsed with methanol (10 mL). The filtrate was concentrated under reduced pressure to afford tert-butyl 4-[(1 E)-(4-cyclopropanesulfonamidopyridin-2-yl)(hydroxyimino)methyl] piperidine-1-carboxylate (124.4, 500 mg, 96%) as a yellow oil, which was used for next step without further purification. MS (ES): m/z 425 [M+H]⁺.

General Method 3, Step 5: Synthesis of 124.5.

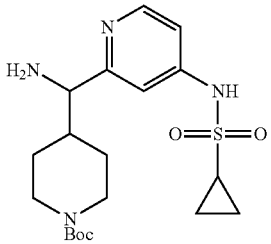

124.5

To a stirred solution of 124.4 (500 mg, 1.18 mmol, 1 equiv) and ammonium chloride (315 mg, 5.89 mmol, 5 equiv) in methanol (6 mL) was added zinc powder (385 mg, 5.89 mmol, 5 equiv) in portions. The resulting mixture was stirred overnight at 60° C. The reaction mixture was filtered and the solid was rinsed with methanol (20 mL). The filtrate was concentrated under reduced pressure. The residue was purified by flash column chromatography on C18 silica (eluted with 10% acetonitrile in water) to afford tert-butyl 4-[amino(4-cyclopropanesulfonamidopyridin-2-yl) methyl] piperidine-1-carboxylate (124.5, 450 mg, 93%) as a yellow oil. MS (ES): m/z 411

General Method 3, Step 6: Synthesis of 124.6.

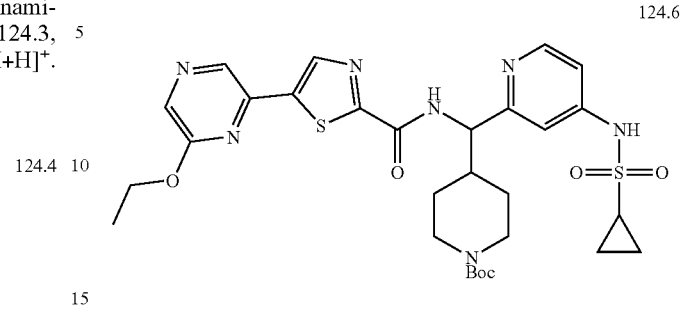

124.6

To a stirred solution of 124.5 (400 mg, 0.97 mmol, 1 equiv) and 39.2 (245 mg) in N,N-dimethylformamide (5 mL) were added HOBT (263 mg, 1.95 mmol, 2 equiv) and EDCI (374 mg, 1.95 mmol, 2 equiv) in portions. The resulting mixture was stirred for 2 h at room temperature. The mixture was diluted with water (20 mL) and extracted with ethyl acetate (3×15 mL). The combined organic layers were concentrated under reduced pressure. The residue was purified by flash column chromatography on C18 silica (eluted with 45% acetonitrile in water) to afford tert-butyl 4-[(4-cyclopropanesulfonamidopyridin-2-yl({[5-(6-ethoxy-pyrazin-2-yl)-1,3-thiazol-2-yl]formamido}) methyl] piperidine-1-carboxylate (124.6, 300 mg, 48%) as a white solid. MS (ES): m/z 644 [M+H]⁺.

General Method 3, Step 7: Synthesis of I-153.

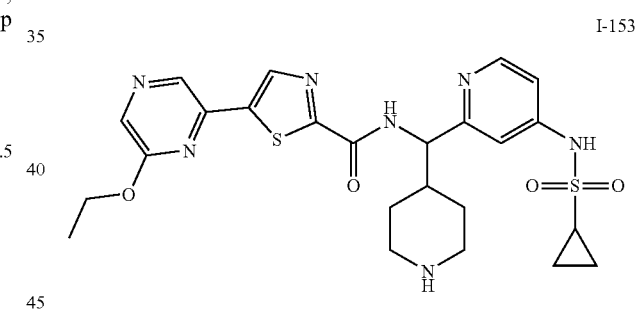

I-153

To a stirred solution of 124.6 (50 mg, 0.08 mmol, 1 equiv) in dichloromethane (2 mL) was added HCl in 1,4-dioxane (4M, 0.1 mL 0.4 mmol, 5 equiv) dropwise at room temperature. The resulting mixture was stirred at room temperature for 30 min. Then reaction was concentrated under reduced pressure. The residue was purified by prep-HPLC (Column: XBridge Prep OBD C 18 Column, 30*150 mm, 5 μm; Mobile Phase A: water (10 mMNH₄HCO₃), Mobile Phase B: AC N; Flow rate: 60 mL/min; Gradient: 10% B to 50% B in 8 min; Wave Length: 254/220 nm) to afford N-[(4-cyclopropanesulfonamidopyridin-2-yl) (piperidin-4-yl) methyl]-5-(6-ethoxypyrazin-2-yl)-1,3-thiazole-2-carboxamide (I-153, 10.5 mg, 25%) as a white solid. MS (ES): m/z 544 [M+H]⁺; ¹H NMR (400 MHz, Methanol-7*) δ 8.71 (s, 1H), 8.60 (s, 1H), 8.22 (d, J=6.0 Hz, 1H), 8.17 (s, 1H), 7.16 (d, J=2.0 Hz, 1H), 7.04 (dd, J=6.0, 2.0 Hz, 1H), 4.93-4.91 (m, 1H), 4.50 (q, J=7.2 Hz, 2H), 3.41-3.35 (m, 2H), 2.97-2.82 (m, 2H), 2.69-2.63 (m, 1H), 2.31-2.23 (m, 1H), 2.12-2.06 (m, 1H), 1.64-1.51 (m, 3H), 1.47 (t, J=7.2 Hz, 3H), 1.14-1.10 (m, 2H), 0.97-0.92 (m, 2H).

Example 125: Synthesis of N-((4-(cyclopropane-sulfonamido)pyridin-2-yl)(1-methylpiperidin-4-yl)methyl)-5-(6-ethoxypyrazin-2-yl)thiazole-2-carboxamide (I-146)

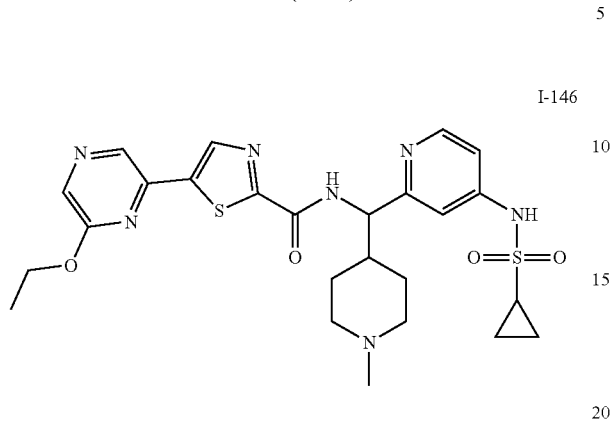

I-146

General Method 3, Step 8: Synthesis of I-146.

To a stirred solution of I-153 (40 mg, 0.07 mmol, 1 equiv) and formaldehyde solution (1M, 0.1 mL 0.1 mmol, 1.3 equiv) in methanol (2 mL) was added sodium cyanoborohydride (5 mg, 0.22 mmol, 3 equiv). The resulting mixture was stirred for 2 h at room temperature. The reaction was concentrated under reduced pressure The residue was purified by prep-HPLC (Column: XBridge Prep OBD C18 Column, 30*150 mm, 5 μm; Mobile Phase A: water (10 mM NH$_4$HCO$_3$), Mobile Phase B: ACN; Flow rate: 60 mL/min; Gradient: 10% B to 50% B in 8 min; Wave Length: 254/220 nm) to afford N-[(4-cyclopropanesulfonamidopyridin-2-yl (1-methylpiperidin-4-ylmethyl]-5-(6-ethoxypyrazin-2-yl)-1,3-thiazole-2-carboxamide (I-146, 8.9 mg, 21%) as an off-white solid. MS (ES): m/z 558 [M+H]$^+$; $^1$H NMR (400 MHz, Methanol-7*) δ 8.71 (s, 1H), 8.59 (s, 1H), 8.32 (d, J=6.0 Hz, 1H), 8.17 (s, 1H), 7.23 (d, J=2.0 Hz, 1H), 7.14 (dd, J=6.0, 2.0 Hz, 1H), 4.94-4.91 (m, 1H), 4.50 (q, J=7.2 Hz, 2H), 3.13-3.02 (m, 2H), 2.76-2.70 (m, 1H), 2.43 (s, 3H), 2.35-2.22 (m, 2H), 2.15-1.99 (m, 2H), 1.60-1.50 (m, 3H), 1.47 (t, J=7.2 Hz, 3H), 1.17-1.15 (m, 2H), 1.02-0.97 (m, 2H).

Example 126: Synthesis of (R)—N-((4-(cyclopropanesulfonamido)pyridin-2-yl)(1-methylpiperidin-4-yl)methyl)-5-(6-ethoxypyrazin-2-yl)thiazole-2-carboxamide, isomer 1 (I-147) and (S)—N-((4-(cyclopropanesulfonamido)pyridin-2-yl)(1-methylpiperidin-4-yl)methyl)-5-(6-ethoxypyrazin-2-yl)thiazole-2-carboxamide, isomer 2 (I-148), Stereochemistry Arbitrarily Assigned

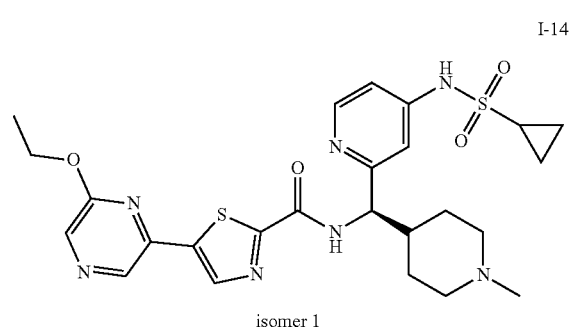

isomer 1

I-147

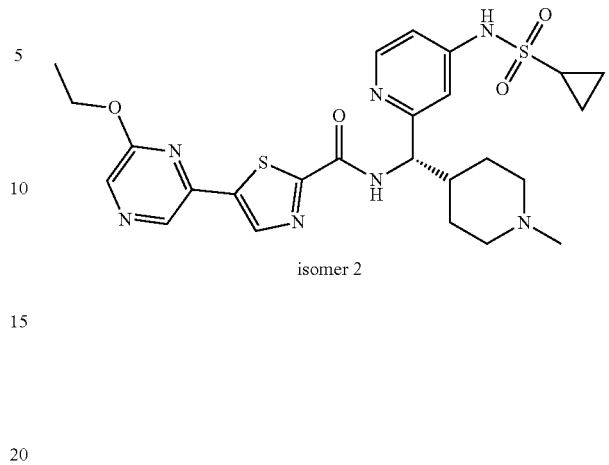

isomer 2

I-148

General Method 3, Step 9.2: synthesis of I-147 and I-148.

I-146 (180 mg, 0.32 mmol) was purified by chiral HPLC (Column: CHIRALPAK IG, 2*25 cm, 5 μm; Mobile Phase A: Hex:DCM=3:1(0.5% 2M NH$_3$-MeOH)-HPLC, Mobile Phase B: EtOH-HPLC; Flow rate: 20 mL/min; Gradient: 30% B to 30% B in 21 min; Wave Length: 220/254 nm) to afford (R)—N-((4-(cyclopropanesulfonamido)pyridin-2-yl)(1-methylpiperidin-4-yl)methyl)-5-(6-ethoxypyrazin-2-yl)thiazole-2-carboxamide, isomer 1 (I-147, first eluting peak, 45 mg) and (S)—N-((4-(cyclopropanesulfonamido)pyridin-2-yl)(I-methylpiperidin-4-yl)methyl)-5-(6-ethoxypyrazin-2-yl)thiazole-2-carboxamide, isomer 2 (I-148, second eluting peak, 39 mg) both as white solid. I-147: MS (ES): m/z 558 [M+H]$^+$; $^1$H NMR (400 MHz, Methanol-7*) δ 8.70 (s, 1H), 8.59 (s, 1H), 8.38 (d, J=6.0 Hz, 1H), 8.16 (s, 1H), 7.28 (d, J=2.0 Hz, 1H), 7.15 (dd, J=6.0, 2.0 Hz, 1H), 4.97 (d, J=8.8 Hz, 1H), 4.49 (q, J=7.2 Hz, 2H), 3.26-3.22 (m, 1H), 2.79-2.73 (m, 1H), 2.68-2.65 (m, 1H), 2.63 (s, 3H), 2.60-2.55 (m, 1H), 2.27-2.18 (m, 1H), 2.12-2.07 (m, 1H), 1.68-1.50 (m, 4H), 1.47 (t, J=7.2 Hz, 3H), 1.20-1.15 (m, 2H), 1.05-0.99 (m, 2H). I-148: LCMS (ES): m/z 558 [M+H]$^+$; $^1$H NMR (400 MHz, Methanol-7*) δ 8.69 (s, 1H), 8.57 (s, 1H), 8.30 (d, J=6.0 Hz, 1H), 8.15 (s, 1H), 7.21 (d, J=2.4 Hz, 1H), 7.13 (dd, J=6.0, 2.4 Hz, 1H), 4.93-4.91 (m, 1H), 4.48 (q, J=12 Hz, 2H), 3.11-2.99 (m, 2H), 2.75-2.69 (m, 1H), 2.40 (s, 3H), 2.32-2.17 (m, 2H), 2.12-1.98 (m, 2H), 1.60-1.48 (m, 3H), 1.46 (t, J=7.2 Hz, 3H), 1.16-1.14 (m, 2H), 1.01-0.98 (m, 2H).

Example 127: Synthesis of N—((S)-(4-(cyclopropanesulfonamido)pyridin-2-yl)((1s, 3R)-3-(dimethylamino)cyclobutyl)methyl)-5-(6-ethoxypyrazin-2-yl)thiazole-2-carboxamide, isomer 1 (I-105), N—((S)-(4-(cyclopropanesulfonamido)pyridin-2-yl)((1R,3S)-3-(dimethylamino)cyclobutyl)methyl)-5-(6-ethoxypyrazin-2-yl)thiazole-2-carboxamide, isomer 2 (I-106), N-((4-(cyclopropanesulfonamido)pyridin-2-yl)((1r, 3r)-3-(dimethylamino)cyclobutyl)methyl)-5-(6-ethoxypyrazin-2-yl)thiazole-2-carboxamide, isomer 3 (I-107) and N—((S)-(4-(cyclopropanesulfonamido)pyridin-2-yl)((1s, 3R)-3-(dimethylamino)cyclobutyl)methyl)-5-(6-ethoxypyrazin-2-yl)thiazole-2-carboxamide, isomer 4 (I-108). Stereochemistry Arbitrarily Assigned

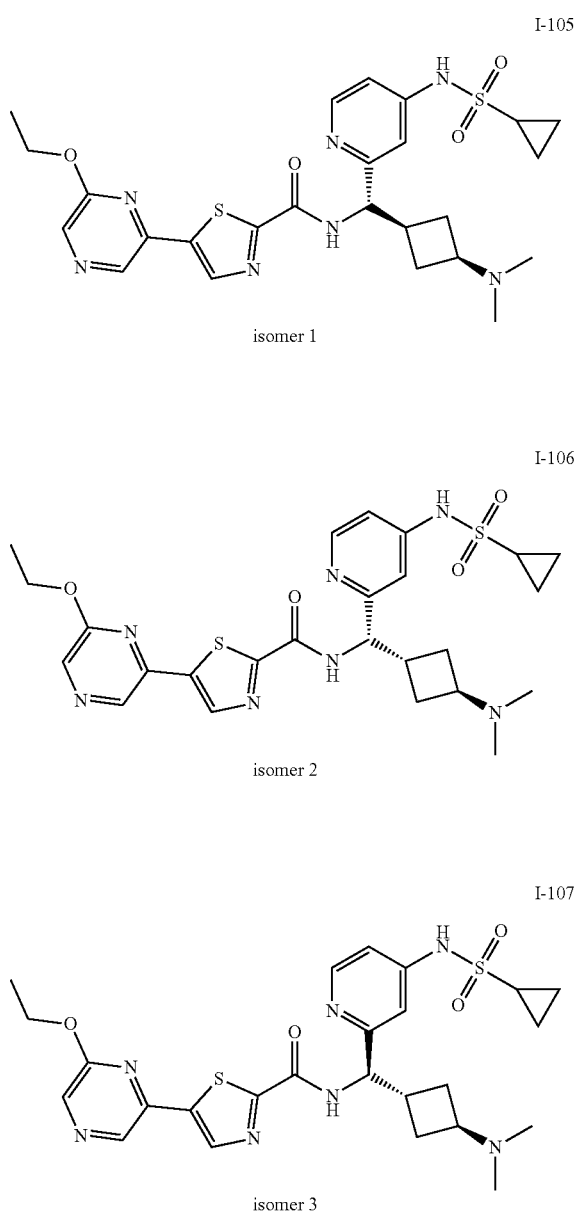

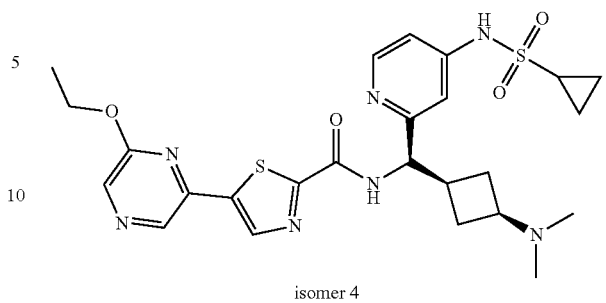

Synthesis of I-105, I-106, I-107 and I-108, I-105, I-106, I-107 and I-108 were prepared following General Method 3, starting from commercially available 3-(dimethylamino)cyclobutane-1-carboxylic acid. After step 6, N-((4-(cyclopropanesulfonamido)pyridin-2-yl)(3-(dimethylamino)cyclobutyl) methyl)-5-(6-ethoxypyrazin-2-yl)thiazole-2-carboxamide was purified by achiral SFC (Column: YMC-Actus Triart Diol-HILIC, 2*25 cm, 5 μm; Mobile Phase A: C02, Mobile Phase B: ACN:MeOH=4:1 (0.1% 2M NH3-MEOH); Flow rate: 50 mL/min; Gradient: isocratic 45% B; Column Temperature (° C.): 35; Back Pressure (bar): 100; Wave Length: 254 nm) to afford two mixtures of isomers. The first isomer was purified by chiral HPLC (Column: CHIRALPAK IG, 2*25 cm, 5 μm; Mobile Phase A: Hex:DCM=3:1(0.5% 2M NH$_3$-MeOH)-HPLC, Mobile Phase B: EtOH-HPLC; Flow rate: 20 mL/min; Gradient: 40% B to 40% B in 15 min; Wave Length: 220/254 nm) to afford I-105 (first eluting peak) and I-108 (second eluting peak) both as white solids. The second isomer was resolved by chiral HPLC (Column: CHIRALPAK IF, 2*25 cm, 5 μm; Mobile Phase A: Hex:DCM=3:1(0.5% 2M NH$_3$-MeOH)-HPLC, Mobile Phase B: EtOH-HPLC; Flow rate: 20 mL/min; Gradient: 20% B to 20% B in 12 min; Wave Length: 220/254 nm) to afford I-106 (first eluting peak) and I-107 (second eluting peak) both as white solids. I-105: MS (ES): m/z 558 [M+H]$^+$; $^1$H NMR (400 MHz, DMSO-d$_6$) δ 9.30 (d, J=8.4 Hz, 1H), 8.91 (s, 1H), 8.79 (s, 1H), 8.28 (s, 1H), 8.24 (d, J=6.0 Hz, 1H), 7.09 (d, J=2.0 Hz, 1H), 6.99 (dd, J=6.0, 2.0 Hz, 1H), 4.91 (t, J=8.4 Hz, 1H), 4.43 (q, J=7.2 Hz, 2H), 2.76-2.69 (m, 1H), 2.51-2.46 (m, 2H), 2.15-2.08 (m, 1H), 2.04 (s, 6H), 2.00-1.94 (m, 1H), 1.69-1.62 (m, 2H), 1.39 (t, J=7.2 Hz, 3H), 1.00-0.89 (m, 4H). I-106. MS (ES): m/z 558 [M+H]$^+$; $^1$H NMR (400 MHz, DMSO-d$_6$) δ 9.09-9.07 (m, 1H), 8.92 (s, 1H), 8.78 (s, 1H), 8.28 (s, 1H), 8.26-8.23 (m, 1H), 7.15 (s, 1H), 7.01-6.99 (m, 1H), 5.07-5.02 (m, 1H), 4.42 (q, J=7.2 Hz, 2H), 2.78-2.69 (m, 3H), 2.04 (s, 6H), 1.98-1.95 (m, 2H), 1.89-1.79 (m, 2H), 1.39 (t, J=7.2 Hz, 3H), 0.99-0.92 (m, 4H). I-107. MS (ES): m/z 558 [M+H]$^+$; $^1$H NMR (400 MHz, DMSO-d6) δ 9.09-9.07 (m, 1H), 8.92 (s, 1H), 8.78 (s, 1H), 8.28 (s, 1H), 8.26-8.23 (m, 1H), 7.15 (s, 1H), 7.00-6.98 (m, 1H), 5.07-5.02 (m, 1H), 4.42 (q, J=7.2 Hz, 2H), 2.78-2.71 (m, 3H), 2.03 (s, 6H), 1.98-1.94 (m, 2H), 1.90-1.81 (m, 2H), 1.39 (t, J=7.2 Hz, 3H), 0.99-0.92 (m, 4H). I-108. MS (ES): m/z 558 [M+H]$^+$; $^1$H NMR (400 MHz, DMSO-d$_6$) δ 9.30 (d, J=8.0 Hz, 1H), 8.91 (s, 1H), 8.80 (s, 1H), 8.28 (s, 1H), 8.24 (d, J=5.6 Hz, 1H), 7.10 (s, 1H), 6.99 (d, J=5.6 Hz, 1H), 4.92 (t, J=8.4 Hz, 1H), 4.43 (q, J=7.2 Hz, 2H), 2.77-2.72 (m, 1H), 2.52-2.46 (m, 2H), 2.14-2.10 (m, 1H), 2.05 (s, 6H), 2.01-1.95 (m, 1H), 1.69-1.62 (m, 2H), 1.39 (t, J=7.2 Hz, 3H), 0.99-0.92 (m, 4H).

Example 128: Synthesis of N-(4-amino-1-(4-(cyclopropanesulfonamido)pyridin-2-yl)butyl)-5-(6-ethoxypyrazin-2-yl)thiazole-2-carboxamide (I-166)

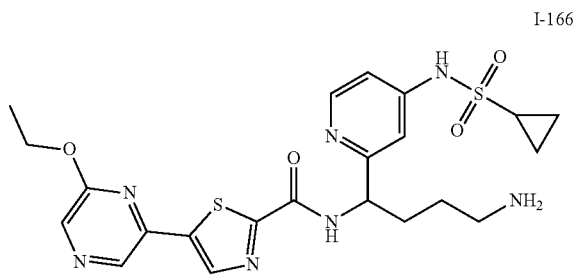 [SMILES: CCOc1cncc(-c2cnc(C(=O)NC(CCCN)c3cc(NS(=O)(=O)C4CC4)ccn3)s2)n1]

I-166

Synthesis of I-166. I-166 was prepared following General Method 3 (ending after step 7), starting from commercially available 3-((7c/7-butoxycarbonyl)amino)propanoic acid. MS (ES): m/z 518 [M+H]$^+$; $^1$H NMR (400 MHz, DMSO-d$_6$) δ 8.92 (s, 1H), 8.79 (s, 1H), 8.29 (s, 1H), 7.98 (d, J=6.4 Hz, 1H), 6.76-6.74 (m, 2H), 4.87 (t, J=6.4 Hz, 1H), 4.43 (q, J=7.2 Hz, 2H), 2.76 (t, J=7.2 Hz, 2H), 2.41-2.34 (m, 1H), 1.96-1.82 (m, 2H), 1.58-1.50 (m, 2H), 1.39 (t, J=7.2 Hz, 3H), 0.82-0.78 (m, 2H), 0.72-0.67 (m, 2H).

Example 129: Synthesis of N-(1-(4-(cyclopropanesulfonamido)pyridin-2-yl)-4-(dimethylamino)butyl)-5-(6-ethoxypyrazin-2-yl)thiazole-2-carboxamide, formic acid salt (I-173)

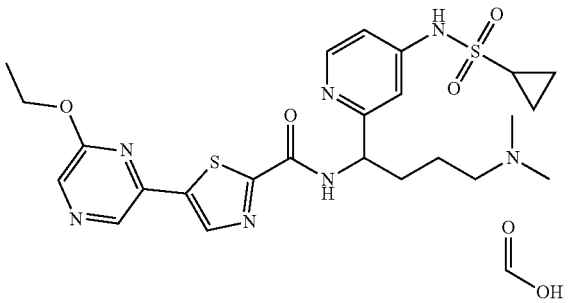

I-173

Synthesis of I-173. I-173 was prepared following step 8 of the General Method 3, using I-166. I-173. MS (ES): m/z 546 [M+H]$^+$; $^1$H NMR (400 MHz, DMSO-d$_6$) δ 9.46 (d, J=8.0 Hz, 1H), 8.93 (s, 1H), 8.82 (s, 1H), 8.29 (s, 1H), 8.28-8.26 (m, 1H), 8.23-8.21 (m, 1H), 7.14 (s, 1H), 7.03 (d, J=6.0 Hz, 1H), 5.03-4.98 (m, 1H), 4.43 (q, J=7.2 Hz, 2H), 2.78-2.72 (m, 1H), 2.48-2.44 (m, 2H), 2.32-2.29 (m, 6H), 1.97-1.91 (m, 2H), 1.60-1.45 (m, 2H), 1.39 (t, J=7.2 Hz, 3H), 1.02-0.91 (m, 4H).

Example 130: Synthesis of (S)—N-(1-(4-(cyclopropanesulfonamido)pyridin-2-yl)-4-(dimethylamino)butyl)-5-(6-ethoxypyrazin-2-yl)thiazole-2-carboxamide, isomer 1 (I-155) and (R)—N-(1-(4-(cyclopropanesulfonamido)pyridin-2-yl)-4-(dimethylamino)butyl)-5-(6-ethoxypyrazin-2-yl)thiazole-2-carboxamide, isomer 2 (I-156). Stereochemistry arbitrarily assigned

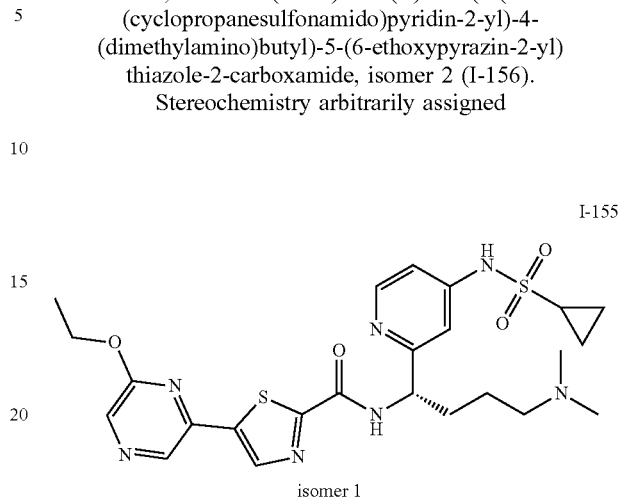

isomer 1 isomer 2

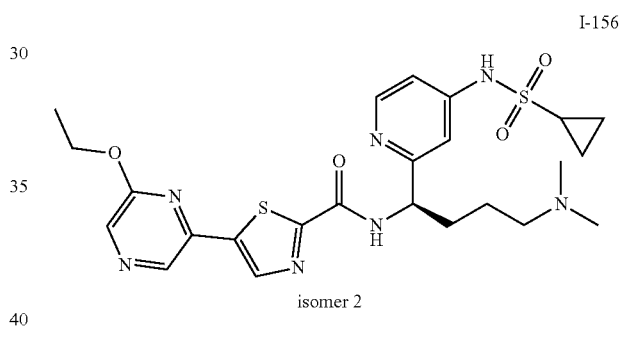

Synthesis of I-155 and I-156. I-155 and I-156 were prepared following chiral separation of I-173 (step 9.2, General Method 3; chiral HPLC conditions: Column: CHIRALPAK IG, 2*25 cm, 5 μm; Mobile Phase A: Hex:DCM=3:1(0.5% 2M NH$_3$-MeOH)-HPLC, Mobile Phase B: EtOH-HPLC; Flow rate: 20 mL/min; Gradient: 20% B to 20% B in 35 min; Wave Length: 220/254 nm). I-155 (first eluting peak): MS (ES): m/z 546 [M+H]$^+$; $^1$H NMR (400 MHz, DMSO-d$_6$) δ 9.45 (d, J=8.0 Hz, 1H), 8.93 (s, 1H), 8.82 (s, 1H), 8.29 (s, 1H), 8.25 (d, J=6.0 Hz, 1H), 7.09 (d, J=2.4 Hz, 1H), 6.99 (dd, J=6.0, 2.4 Hz, 1H), 5.00-4.95 (m, 1H), 4.43 (q, J=7.2 Hz, 2H), 2.75-2.70 (m, 1H), 2.30-2.27 (m, 2H), 2.16 (s, 6H), 1.96-1.90 (m, 2H), 1.53-1.43 (m, 2H), 1.39 (t, J=7.2 Hz, 3H), 0.98-0.89 (m, 4H). I-156 (second eluting peak): MS (ES): m/z 546 [M+H]$^+$; $^1$H NMR (400 MHz, DMSO-d$_6$) δ 9.45 (d, J=8.0 Hz, 1H), 8.93 (s, 1H), 8.82 (s, 1H), 8.29 (s, 1H), 8.25 (d, J=5.6 Hz, 1H), 7.08 (d, J=2.0 Hz, 1H), 6.99 (dd, J=5.6, 2.0 Hz, 1H), 5.00-4.95 (m, 1H), 4.43 (q, J=7.2 Hz, 2H), 2.74-2.70 (m, 1H), 2.30-2.26 (m, 2H), 2.15 (s, 6H), 1.96-1.90 (m, 2H), 1.53-1.43 (m, 2H), 1.39 (t, J=7.2 Hz, 3H), 0.99-0.88 (m, 4H).

Example 131: Synthesis of N—((S)-1-(4-(cyclopropanesulfonamido)pyridin-2-yl)-2-((R)-piperidin-2-yl)ethyl)-5-(6-ethoxypyrazin-2-yl)thiazole-2-carboxamide, isomer 1 (I-169) (mixture of 2 isomers) and N—((R)-1-(4-(cyclopropanesulfonamido)pyridin-2-yl)-2-((R)-piperidin-2-yl)ethyl)-5-(6-ethoxypyrazin-2-yl)thiazole-2-carboxamide, isomer 2 (I-172) (mixture of 2 isomers). Isomer 1 and Isomer 2 are Mixtures of Cis or Trans Isomers. Stereochemistry Arbitrarily Assigned

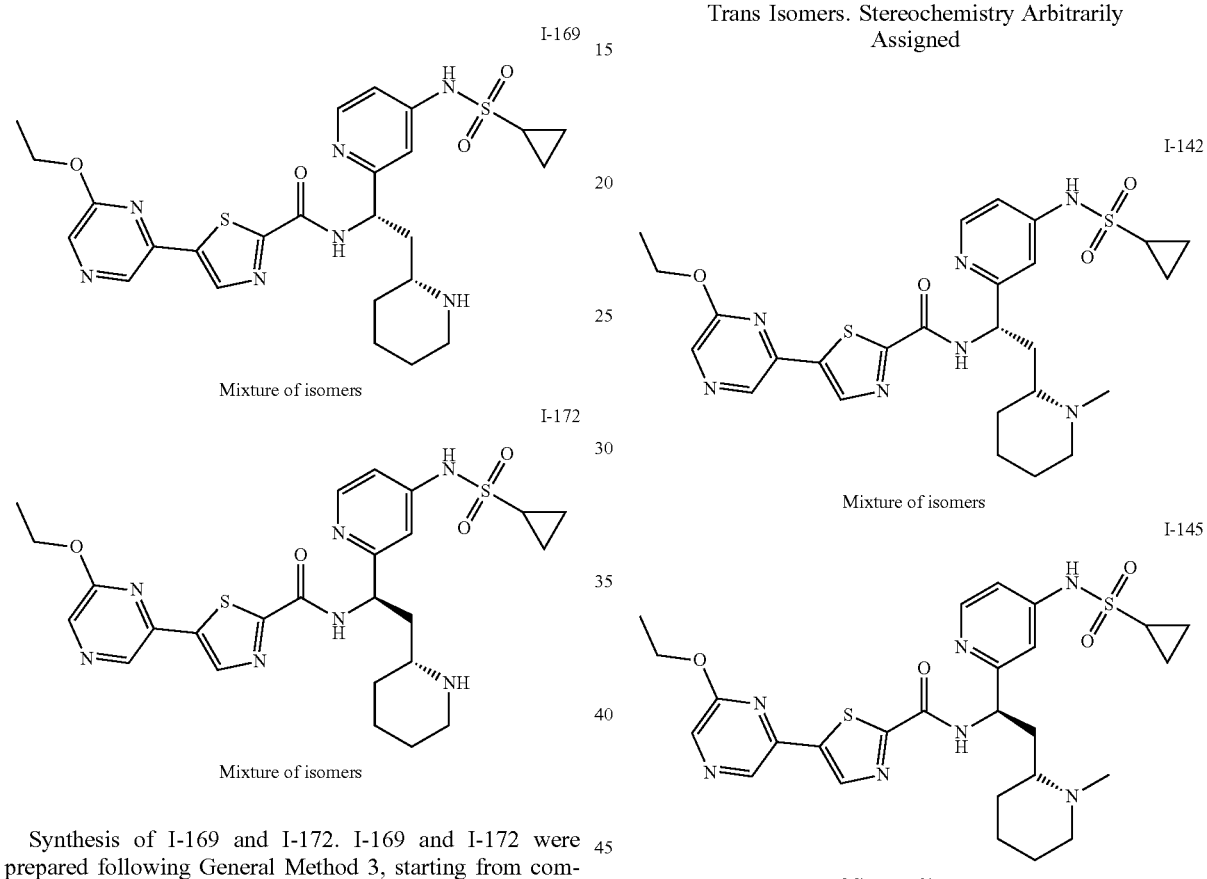

Mixture of isomers (I-169)

Mixture of isomers (I-172)

Synthesis of I-169 and I-172. I-169 and I-172 were prepared following General Method 3, starting from commercially available 2-(1-(tert-butoxycarbonyl)piperidin-2-yl)acetic acid. After step 6, tert-butyl 2-(2-(4-(cyclopropanesulfonamido)pyridin-2-yl)-2-(5-(6-ethoxypyrazin-2-yl)thiazole-2-carboxamido)ethyl)piperidine-1-carboxylate was purified by flash column chromatography on silica gel (eluted with 17% dichloromethane in ethyl acetate) to give two mixtures of cis and trans isomers. Removal of the Boc groups (General Method 3, step 7) afforded I-169 and I-172 as white solids. I-169. MS (ES): m/z 558 [M+H]$^+$; $^1$H NMR (400 MHz, Methanol-d$_4$) δ 8.72 (s, 1H), 8.62 (s, 1H), 8.45 (d, J=6.0 Hz, 1H), 8.18 (s, 1H), 7.37 (d, J=2.0 Hz, 1H), 7.18 (dd, J=6.0, 2.0 Hz, 1H), 5.37-5.33 (m, 1H), 4.50 (q, J=7.2 Hz, 2H), 3.52-3.46 (m, 1H), 3.26-3.21 (m, 1H), 3.06-2.99 (m, 1H), 2.81-2.74 (m, 1H), 2.36-2.30 (m, 1H), 2.24-2.17 (m, 1H), 2.07-2.02 (m, 1H), 1.94-1.89 (m, 2H), 1.74-1.56 (m, 3H), 1.47 (t, J=7.2 Hz, 3H), 1.20-1.15 (m, 2H), 1.06-0.99 (m, 2H). I-172. MS (ES): m/z 558 [M+H]$^+$; $^1$H NMR (400 MHz, Methanol-7*) δ 8.72 (s, 1H), 8.62 (s, 1H), 8.40 (d, J=6.0 Hz, 1H), 8.17 (s, 1H), 7.36 (d, J=2.0 Hz, 1H), 7.17 (dd, J=6.0, 2.0 Hz, 1H), 5.37-5.33 (m, 1H), 4.50 (q, J=7.2 Hz, 2H), 3.45-3.30 (m, 1H), 3.29-3.23 (m, 1H), 3.07-3.00 (m, 1H), 2.79-2.72 (m, 1H), 2.38-2.23 (m, 3H), 1.96-1.89 (m, 2H), 1.72-1.55 (m, 3H), 1.47 (t, J=7.2 Hz, 3H), 1.18-1.13 (m, 2H), 1.03-1.00 (m, 2H).

Example 132: Synthesis of N—((S)-1-(4-(cyclopropanesulfonamido)pyridin-2-yl)-2-((R)-1-methylpiperidin-2-yl)ethyl)-5-(6-ethoxypyrazin-2-yl)thiazole-2-carboxamide, isomer 1 (I-142) (mixture of 2 isomers) and N—((R)-1-(4-(cyclopropanesulfonamido)pyridin-2-yl)-2-((R)-1-methylpiperidin-2-yl)ethyl)-5-(6-ethoxypyrazin-2-yl)thiazole-2-carboxamide, isomer 2 (I-145) (mixture of 2 isomers). Isomer 1 and Isomer 2 are Mixtures of Cis or Trans Isomers. Stereochemistry Arbitrarily Assigned

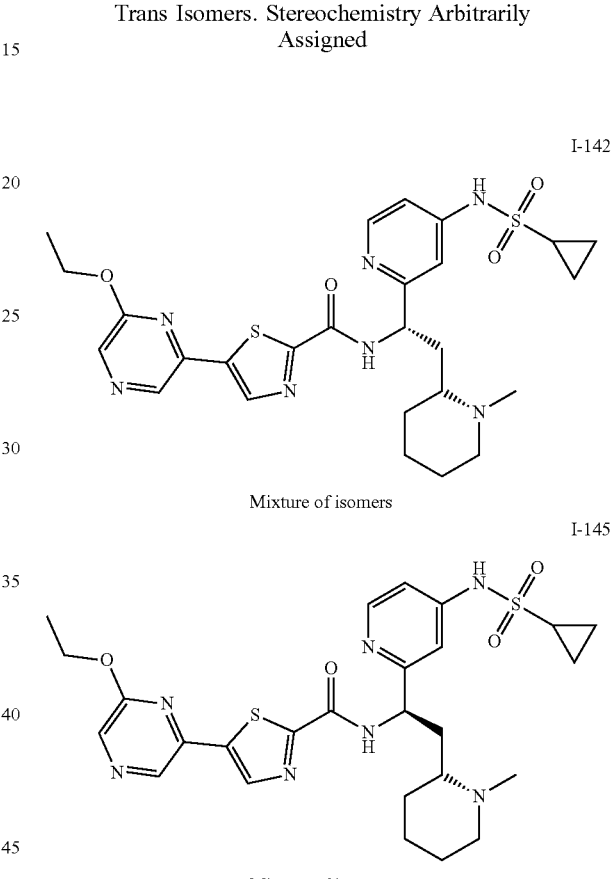

Mixture of isomers (I-142)

Mixture of isomers (I-145)

Synthesis of I-142 and I-145. I-142 and I-145 were prepared following General Method 3 step 8.1 (methylation condition methods similar to step 8, described for I-146). I-142: MS (ES): m/z 572 [M+H]$^+$; $^1$H NMR (400 MHz, Methanol-7*) δ 8.70 (s, 1H), 8.59 (s, 1H), 8.39 (d, J=5.6 Hz, 1H), 8.16 (s, 1H), 7.34 (d, J=2.4 Hz, 1H), 7.17 (dd, J=5.6, 2.4 Hz, 1H), 5.28 (t, J=7.2 Hz, 1H), 4.49 (q, J=12 Hz, 2H), 3.30-3.27 (m, 1H), 2.95-2.86 (m, 2H), 2.77 (s, 3H), 2.76-2.73 (m, 1H), 2.69-2.63 (m, 1H), 2.16-2.03 (m, 2H), 1.85-1.61 (m, 4H), 1.56-1.49 (m, 1H), 1.47 (t, J=12 Hz, 3H), 1.18-1.14 (m, 2H), 1.04-1.00 (m, 2H). I-145: MS (ES): m/z 572 [M+H]$^+$; $^1$H NMR (400 MHz, Methanol-7*) δ 8.72-8.68 (m, 1H), 8.62-8.55 (m, 1H), 8.40-8.37 (m, 1H), 8.18-8.15 (m, 1H), 7.35 (d, J=2.0 Hz, 1H), 7.17 (dd, J=5.6, 2.4 Hz, 1H), 5.32 (dd, J=10.4, 4.0 Hz, 1H), 4.50-4.44 (m, 2H), 3.40-3.26 (m, 1H), 3.20-3.14 (m, 1H), 3.05-2.98 (m, 1H), 2.85 (s, 3H), 2.79-2.72 (m, 1H), 2.65-2.59 (m, 1H), 2.25-2.17 (m, 2H), 1.92-1.79 (m, 3H), 1.74-1.52 (m, 2H), 1.49-1.44 (m, 3H), 1.18-1.13 (m, 2H), 1.04-0.97 (m, 2H).

Example 133: Synthesis of N—((S)-1-(4-(cyclopropanesulfonamido)pyridin-2-yl)-2-((R)-piperidin-2-yl)ethyl)-5-(6-ethoxypyrazin-2-yl)thiazole-2-carboxamide, isomer 1 (I-138), N—((S)-1-(4-(cyclopropanesulfonamido)pyridin-2-yl)-2-((S)-piperidin-2-yl)ethyl)-5-(6-ethoxypyrazin-2-yl)thiazole-2-carboxamide, isomer 2 (I-139), N—((R)-1-(4-(cyclopropanesulfonamido)pyridin-2-yl)-2-((R)-piperidin-2-yl)ethyl)-5-(6-ethoxypyrazin-2-yl)thiazole-2-carboxamide, isomer 3 (I-140) and N—((R)-1-(4-(cyclopropanesulfonamido)pyridin-2-yl)-2-((S)-piperidin-2-yl)ethyl)-5-(6-ethoxypyrazin-2-yl)thiazole-2-carboxamide, isomer 4 (I-141). Stereochemistry Arbitrarily Assigned

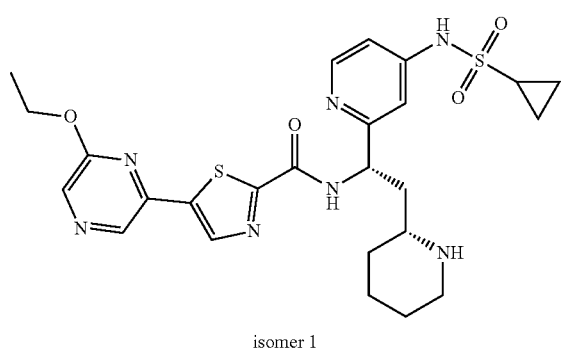

isomer 1 (I-138)

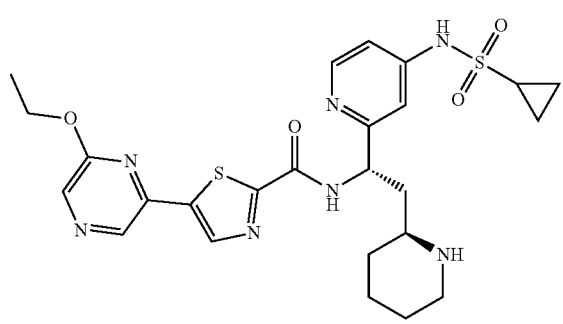

isomer 2 (I-139)

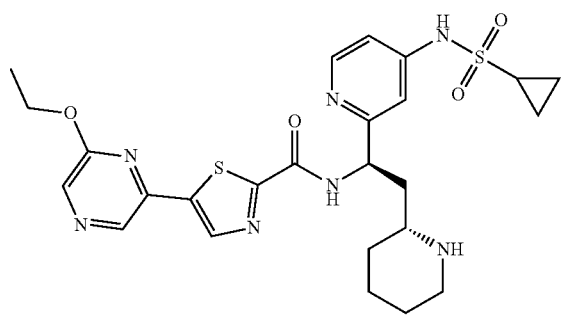

isomer 3 (I-140)

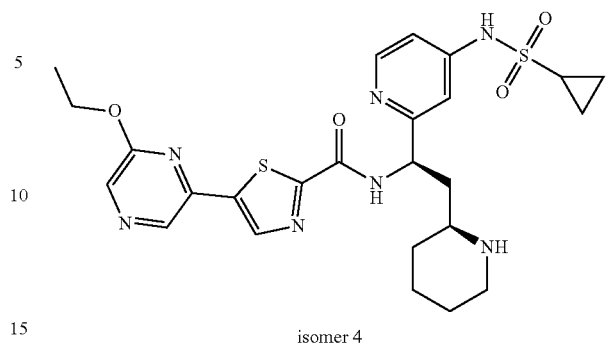

isomer 4 (I-141)

Synthesis of I-138, I-140. I-169 was purified by chiral HPLC (Column: CHIRALPAK IG, 2*25 cm, 5 μm; Mobile Phase A: Hex:DCM=3:1(0.5% 2M NH₃-MeOH)-HPLC, Mobile Phase B: IPA-HPLC; Flow rate: 20 mL/min; Gradient: 50% B to 50% B in 27 min; Wave Length: 220/254 nm) to afford I-138 (first eluting peak) and I-140 (second eluting peak) both as white solids. I-138. MS (ES): m/z 558 [M+H]$^+$; $^1$H NMR (400 MHz, DMSO-d$_6$) δ 8.90 (s, 1H), 8.79 (s, 1H), 8.28 (s, 1H), 8.09 (d, J=5.6 Hz, 1H), 6.91 (s, 1H), 6.83 (d, J=5.6 Hz, 1H), 5.11-5.08 (m, 1H), 4.42 (q, J=7.2 Hz, 2H), 3.17-3.14 (m, 1H), 2.88-2.81 (m, 1H), 2.74-2.67 (m, 1H), 2.48-2.44 (m, 1H), 2.08-1.98 (m, 2H), 1.78-1.62 (m, 3H), 1.48-1.42 (m, 1H), 1.39 (t, J=7.2 Hz, 3H), 1.34-1.22 (m, 2H), 0.88-0.76 (m, 4H). I-140. MS (ES): m/z 558 [M+H]$^+$; $^1$H NMR (400 MHz, DMSO-d$_6$) δ 8.92 (s, 1H), 8.81 (s, 1H), 8.29 (s, 1H), 8.17-8.14 (m, 1H), 6.99 (s, 1H), 6.90-6.87 (m, 1H), 5.15-5.12 (m, 1H), 4.43 (q, J=7.2 Hz, 2H), 3.21-3.16 (m, 1H), 2.96-2.89 (m, 1H), 2.79-2.73 (m, 1H), 2.59-2.55 (m, 1H), 2.09-2.05 (m, 2H), 1.81-1.64 (m, 3H), 1.47-1.30 (m, 6H), 0.90-0.81 (m, 4H).

Synthesis of I-139, I-141. I-172 was purified by chiral HPLC (Column: CHIRAL ART Amylose-SA, 2*25 cm, 5 (mi; Mobile Phase A: Hex:DCM=3:1(0.5% 2M NH₃-MeOH)-HPLC, Mobile Phase B: EtOH-HPLC; Flow rate: 20 mL/min; Gradient: 10% B to 10% B in 13 min; Wave Length: 220/254 nm) to afford I-139 (first eluting peak) and I-141 (second eluting peak) both as white solids. I-139: MS (ES): m/z 558 [M+H]$^+$; $^1$H NMR (300 MHz, DMSO-d$_6$) δ 8.87 (s, 1H), 8.76 (s, 1H), 8.26 (s, 1H), 8.10 (d, J=5.7 Hz, 1H), 6.96 (d, J=2.1 Hz, 1H), 6.86 (d, J=5.7, 2.1 Hz, 1H), 5.10-5.05 (m, 1H), 4.42 (q, J=7.2 Hz, 2H), 3.25-3.17 (m, 1H), 2.99-2.93 (m, 1H), 2.84-2.75 (m, 1H), 2.62-2.55 (m, 1H), 2.21-1.96 (m, 3H), 1.77-1.67 (m, 2H), 1.53-1.43 (m, 1H), 1.40-1.33 (m, 5H), 0.89-0.76 (m, 4H). I-141: MS (ES): m/z 558 [M+H]$^+$; $^1$H NMR (300 MHz, DMSO-de) δ 8.90 (s, 1H), 8.79 (s, 1H), 8.28 (s, 1H), 8.16 (d, J=5.7 Hz, 1H), 7.01 (d, J=2.1 Hz, 1H), 6.91 (d, J=5.7, 2.1 Hz, 1H), 5.13-5.08 (m, 1H), 4.42 (q, J=7.2 Hz, 2H), 3.25-3.17 (m, 1H), 3.00-2.94 (m, 1H), 2.84-2.74 (m, 1H), 2.62-2.55 (m, 1H), 2.23-1.96 (m, 3H), 1.77-1.67 (m, 2H), 1.55-1.43 (m, 1H), 1.40-1.34 (m, 5H), 0.92-0.82 (m, 4H).

Example 134: Synthesis of Example 134: N—((S)-1-(4-(cyclopropanesulfonamido)pyridin-2-yl)-2-((R)-1-methylpiperidin-2-yl)ethyl)-5-(6-ethoxypyrazin-2-yl)thiazole-2-carboxamide, isomer 1 (I-133), N—((S)-1-(4-(cyclopropanesulfonamido) pyridin-2-yl)-2-((S)-1-methylpiperidin-2-yl)ethyl)-5-(6-ethoxypyrazin-2-yl)thiazole-2-carboxamide, isomer 2 (I-134), N—((R)-1-(4-(cyclopropanesulfonamido)pyridin-2-yl)-2-((R)-1-methylpiperidin-2-yl)ethyl)-5-(6-ethoxypyrazin-2-yl)thiazole-2-carboxamide, isomer 3 (I-135) and N—((R)-1-(4-(cyclopropanesulfonamido)pyridin-2-yl)-2-((S)-1-methylpiperidin-2-yl)ethyl)-5-(6-ethoxypyrazin-2-yl)thiazole-2-carboxamide, isomer 4 (I-136). Stereochemistry arbitrarily assigned

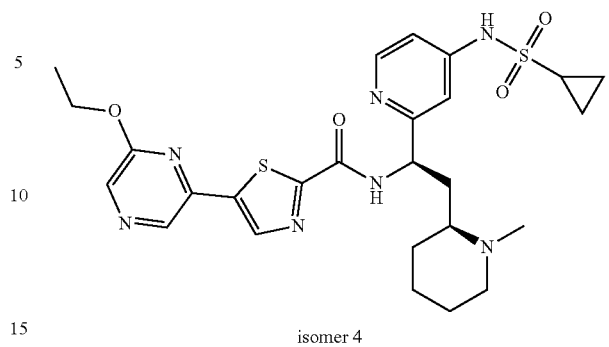

isomer 4

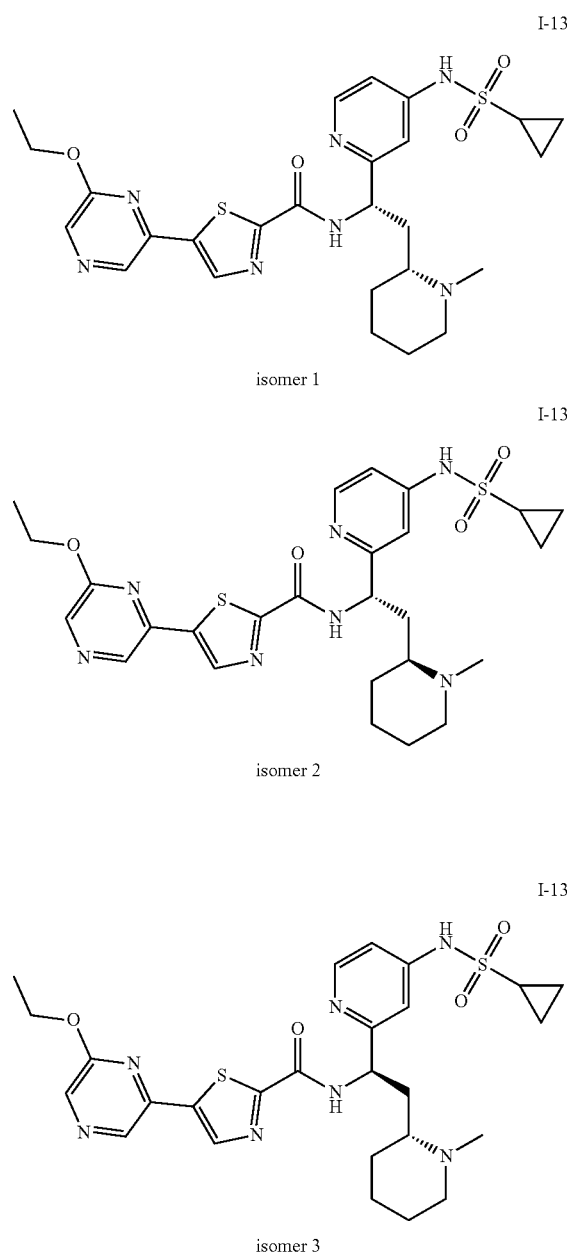

Synthesis of I-133, I-135. I-142 was purified by chiral HPLC (Column: CHIRAL ART Amylose-SA, 2*25 cm, 5 µm; Mobile Phase A: Hex:DCM=3:1(0.5% 2M NH$_3$-MeOH)-HPLC, Mobile Phase B: EtOH-HPLC; Flow rate: 20 mL/min; Gradient: 10% B to 10% B in 10 min; Wave Length: 220/254 nm) to afford I-133 (first eluting peak) and I-135 (second eluting peak) both as white solids. I-133: MS (ES): m/z 572 [M+H]$^+$; $^1$H NMR (400 MHz, Methanol-d$_4$) δ 8.69 (s, 1H), 8.58 (s, 1H), 8.29 (d, J=5.6 Hz, 1H), 8.16 (s, 1H), 7.26 (d, J=2.4 Hz, 1H), 7.11 (d, J=5.6, 2.4 Hz, 1H), 5.19 (t, J=7.2 Hz, 1H), 4.49 (q, J=7.2 Hz, 2H), 3.06-3.01 (m, 1H), 2.74-2.68 (m, 1H), 2.57-2.50 (m, 1H), 2.48 (s, 3H), 2.45-2.41 (m, 1H), 2.36-2.33 (m, 1H), 2.04-1.94 (m, 2H), 1.80-1.75 (m, 1H), 1.70-1.62 (m, 2H), 1.56-1.49 (m, 1H), 1.47 (t, J=7.2 Hz, 3H), 1.41-1.34 (m, 1H), 1.15-1.13 (m, 2H), 1.00-0.97 (m, 2H). I-135: MS (ES): m/z 572 [M+H]$^+$; $^1$H NMR (400 MHz, Methanol-d$_4$) δ 8.70 (s, 1H), 8.59 (s, 1H), 8.29 (d, J=6.0 Hz, 1H), 8.16 (s, 1H), 7.26 (d, J=2.4 Hz, 1H), 7.11 (d, J=6.0, 2.4 Hz, 1H), 5.19 (t, J=7.2 Hz, 1H), 4.49 (q, J=7.2 Hz, 2H), 3.06-3.01 (m, 1H), 2.74-2.68 (m, 1H), 2.56-2.50 (m, 1H), 2.48 (s, 3H), 2.47-2.41 (m, 1H), 2.39-2.33 (m, 1H), 2.04-1.94 (m, 2H), 1.80-1.75 (m, 1H), 1.70-1.62 (m, 2H), 1.56-1.49 (m, 1H), 1.47 (t, J=12 Hz, 3H), 1.41-1.34 (m, 1H), 1.16-1.12 (m, 2H), 1.01-0.96 (m, 2H).

Synthesis of I-134, I-136. I-145 was purified by chiral HPLC (Column: CHIRAL ART Amylose-SA, 2*25 cm, 5 µm; Mobile Phase A: Hex:DCM=3:1(0.5% 2M NH$_3$-MeOH)-HPLC, Mobile Phase B: EtOH-HPLC; Flow rate: 20 mL/min; Gradient: 10% B to 10% B in 10 min; Wave Length: 220/254 nm) to afford I-134 (first eluting peak) and I-136 (second eluting peak) both as white solids. I-134: MS (ES): m/z 572 [M+H]$^+$; $^1$H NMR (400 MHz, Methanol-d$_4$) δ 8.71 (s, 1H), 8.61 (s, 1H), 8.33 (d, J=5.6 Hz, 1H), 8.17 (s, 1H), 7.30 (d, J=2.4 Hz, 1H), 7.14 (d, J=5.6, 2.4 Hz, 1H), 5.30-5.26 (m, 1H), 4.49 (q, J=7.2 Hz, 2H), 3.23-3.17 (m, 1H), 2.84-2.70 (m, 3H), 2.68 (s, 3H), 2.60-2.53 (m, 1H), 2.14-2.03 (m, 2H), 2.04-1.94 (m, 2H), 1.87-1.70 (m, 3H), 1.63-1.51 (m, 2H), 1.47 (t, J=7.2 Hz, 3H), 1.16-1.12 (m, 2H), 1.02-0.96 (m, 2H). I-136: MS (ES): m/z 572 [M+H]$^+$; $^1$H NMR (400 MHz, Methanol-d$_4$) δ 8.71 (s, 1H), 8.60 (s, 1H), 8.32 (d, J=5.6 Hz, 1H), 8.17 (s, 1H), 7.29 (d, J=2.4 Hz, 1H), 7.13 (d, J=5.6, 2.4 Hz, 1H), 5.29-5.25 (m, 1H), 4.48 (q, J=7.2 Hz, 2H), 3.20-3.15 (m, 1H), 2.79-2.70 (m, 3H), 2.68 (s, 3H), 2.59-2.51 (m, 1H), 2.13-2.01 (m, 2H), 2.04-1.94 (m, 2H), 1.87-1.70 (m, 3H), 1.61-1.51 (m, 2H), 1.47 (t, J=12 Hz, 3H), 1.16-1.12 (m, 2H), 1.02-0.97 (m, 2H).

Example 135: Synthesis of Example 135: N—((R)-(4-(cyclopropanesulfonamido)pyridin-2-yl)((R)-tetrahydrofuran-3-yl)methyl)-5-(6-ethoxypyrazin-2-yl)thiazole-2-carboxamide, isomer 1 (I-92), N—((R)-(4-(cyclopropanesulfonamido)pyridin-2-yl)((S)-tetrahydrofuran-3-yl)methyl)-5-(6-ethoxypyrazin-2-yl)thiazole-2-carboxamide, isomer 2 (I-93), N—((S)-(4-(cyclopropanesulfonamido)pyridin-2-yl)((S)-tetrahydrofuran-3-yl)methyl)-5-(6-ethoxypyrazin-2-yl)thiazole-2-carboxamide, isomer 3 (I-94) and N—((S)-(4-(cyclopropanesulfonamido)pyridin-2-yl)((R)-tetrahydrofuran-3-yl)methyl)-5-(6-ethoxypyrazin-2-yl)thiazole-2-carboxamide, isomer 4 (I-95). Stereochemistry arbitrarily assigned

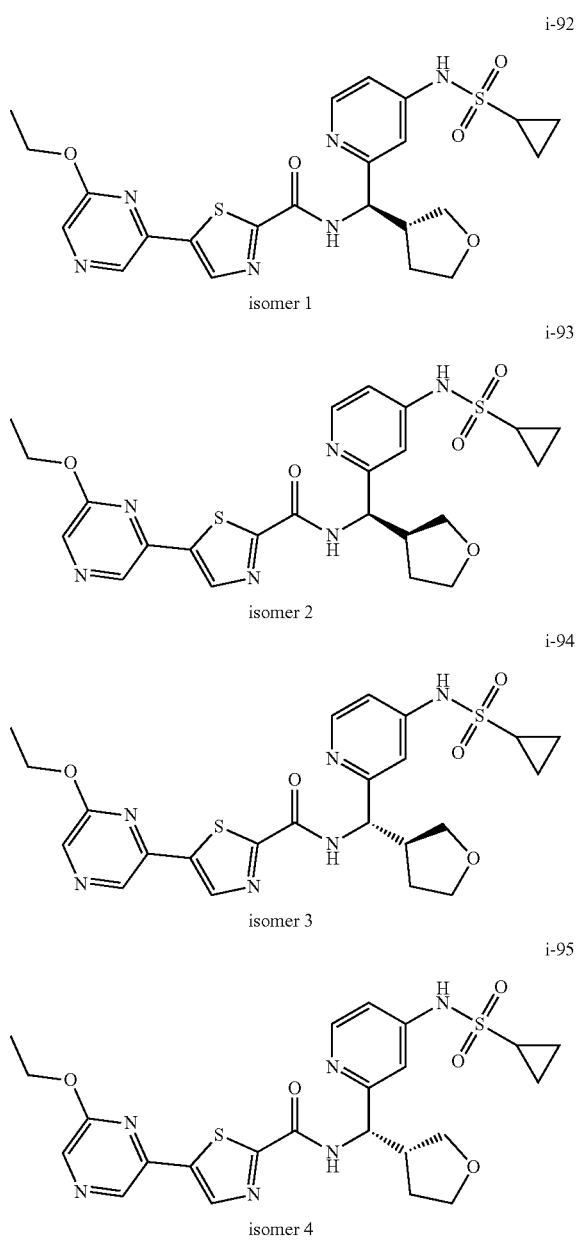

Synthesis of I-92, I-93, I-94 and I-95. I-92, I-93, I-94 and I-95 were prepared following General Method 3 starting from commercially available tetrahydrofuran-3-carboxylic acid. After step 6, N-((4-(cyclopropanesulfonamido)pyridin-2-yl)(tetrahydrofuran-3-yl)methyl)-5-(6-ethoxypyrazin-2-yl)thiazole-2-carboxamide was purified by chiral HPLC (Column: CHIRAL ART Amylose-SA, 2*25 cm, 5 μm; Mobile Phase A: Hex:DCM=3:1(0.5% 2M ML-MeOH)-HPLC, Mobile Phase B: EtOH-HPLC; Flow rate: 20 mL/min; Gradient: 20% B to 20% B in 12 min; Wave Length: 220/254 nm to afford a mixture of I-92 and I-93 (isomers eluting together), I-94 (pure, third eluting isomer), and I-95 (pure, fourth eluting isomer), all as white solids. The mixture of I-92 and I-93 was further purified by chiral HPLC (Column: CHIRALPAK IF, 2*25 cm, 5 μm; Mobile Phase A: Hex:DCM=3:1(0.5% 2M $NH_3$-MeOH)-HPLC, Mobile Phase B: EtOH-HPLC; Flow rate: 20 mL/min; Gradient: 20% B to 20% B in 14.5 min; Wave Length: 220/254 nm) to afford I-92 (first eluting peak), I-93 (second eluting peak), as white solids. I-92: MS (ES): m/z 531 $[M+H]^+$; $^1H$ NMR (400 MHz, DMSO-$d_6$) δ 10.56 (s, 1H), 9.32 (s, 1H), 8.92 (s, 1H), 8.80 (s, 1H), 8.37 (s, 1H), 8.29 (s, 1H), 7.27 (s, 1H), 7.08-7.05 (m, 1H), 4.97 (t, J=9.2 Hz, 1H), 4.42 (q, J=7.2 Hz, 2H), 3.80-3.74 (m, 1H), 3.65-3.60 (m, 1H), 3.55-3.51 (m, 1H), 3.45-3.42 (m, 1H), 3.00-2.90 (m, 1H), 2.87-2.82 (m, 1H), 2.06-1.99 (m, 1H), 1.79-1.70 (m, 1H), 1.39 (t, J=7.2 Hz, 3H), 1.06-0.98 (m, 4H). I-93: MS (ES): m/z 531 $[M+H]^+$; $^1H$ NMR (400 MHz, DMSO-$d_6$) δ 10.56 (s, 1H), 9.26 (d, J=8.4 Hz, 1H), 8.92 (s, 1H), 8.79 (s, 1H), 8.38 (d, J=5.6 Hz, 1H), 8.28 (s, 1H), 7.30 (s, 1H), 7.06 (d, J=5.6 Hz, 1H), 4.95 (t, J=9.2 Hz, 1H), 4.42 (q, J=7.2 Hz, 2H), 3.80-3.76 (m, 2H), 3.63-3.57 (m, 2H), 2.98-2.92 (m, 1H), 2.87-2.83 (m, 1H), 1.75-1.67 (m, 1H), 1.63-1.57 (m, 1H), 1.39 (t, J=7.2 Hz, 3H), 1.06-0.98 (m, 4H). I-94: MS (ES): m/z 531 $[M+H]^+$; $^1H$ NMR (400 MHz, DMSO-A) δ 10.69 (s, 1H), 9.30 (d, J=8.4 Hz, 1H), 8.92 (s, 1H), 8.80 (s, 1H), 8.34-8.31 (m, 1H), 8.28 (s, 1H), 7.22 (s, 1H), 7.03 (d, J=5.6 Hz, 1H), 4.96 (t, J=9.2 Hz, 1H), 4.42 (q, J=7.2 Hz, 2H), 3.80-3.74 (m, 1H), 3.65-3.60 (m, 1H), 3.55-3.51 (m, 1H), 3.45-3.42 (m, 1H), 3.00-2.91 (m, 1H), 2.82-2.77 (m, 1H), 2.06-1.98 (m, 1H), 1.79-1.70 (m, 1H), 1.39 (t, J=7.2 Hz, 3H), 1.03-0.94 (m, 4H). I-95: MS (ES): m/z 531 $[M+H]^+$; $^1H$ NMR (400 MHz, DMSO-A) δ 10.76 (s, 1H), 9.27 (d, J=8.4 Hz, 1H), 8.91 (s, 1H), 8.79 (s, 1H), 8.32-8.29 (m, 1H), 8.28 (s, 1H), 7.23 (s, 1H), 7.03 (d, J=6.0 Hz, 1H), 4.93 (t, J=9.2 Hz, 1H), 4.42 (q, J=7.2 Hz, 2H), 3.80-3.75 (m, 2H), 3.63-3.57 (m, 2H), 2.98-2.90 (m, 1H), 2.80-2.75 (m, 1H), 1.76-1.68 (m, 1H), 1.65-1.56 (m, 1H), 1.39 (t, J=7.2 Hz, 3H), 1.02-0.94 (m, 4H).

Example 136: Synthesis of N-[1-(4-cyclopropanesulfonamidopyridin-2-yl)-3-methoxypropyl]-5-(6-ethoxypyrazin-2-yl)-1,3-thiazole-2-carboxamide (I-186)

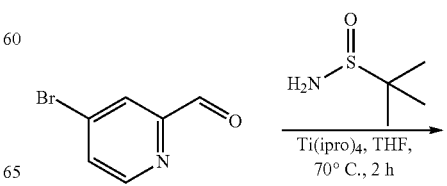

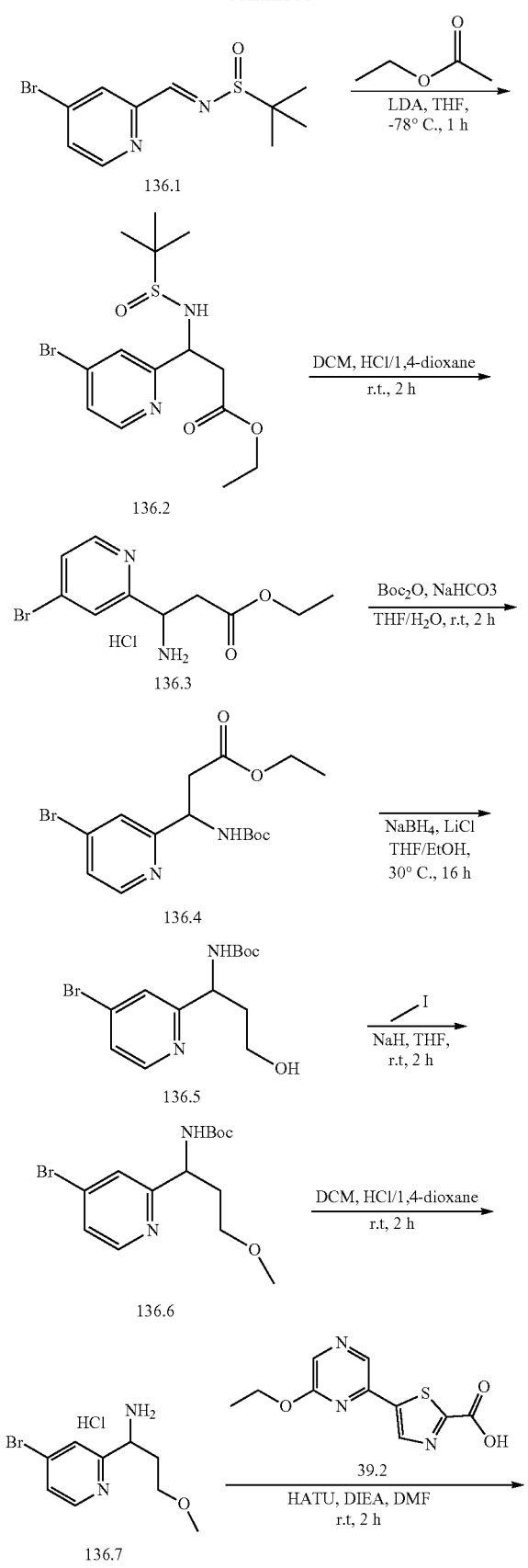

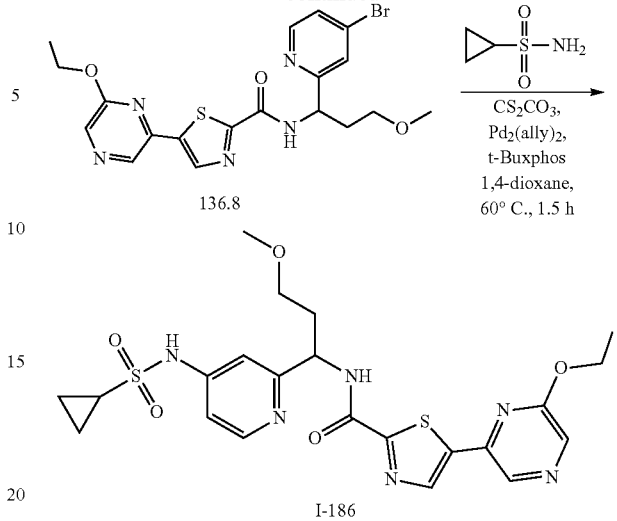

Synthesis of 136.1. To a stirred mixture of 4-bromopyridine-2-carbaldehyde (3 g, 15 mmol, 1 eq) in tetrahydrofuran (76 mL) were added tert-butanesulfinamide (2.35 g, 19.35 mmol, 1.2 eq) and titanium(IV) isopropoxide (9.17 g, 32.26 mmol, 2 eq). The resulting mixture was stirred for 2 h at 70° C. under nitrogen atmosphere. The mixture was allowed to cool down to room temperature, diluted with water. The resulting mixture filtered, the filter cake was washed with ethyl acetate. The filtrate was extracted with ethyl acetate, the combined organic layer was washed with brine, dried over sodium sulfate and concentrated under reduced pressure. The residue was purified by silica gel column chromatography and compound was eluted in 10% ethyl acetate in petroleum ether to obtain N-[(1E)-(4-bromopyridin-2-yl)methylidene]-2-methylpropane-2-sulfinamide (136.1, 2.58 g, 44%) as a yellow solid. MS (ES): m/z 289/291 [M+H]$^+$.

Synthesis 136.2. A stirred mixture of ethyl acetate (1.55 g, 17.57 mmol, 2 eq) in tetrahydrofuran (41 mL) was degassed three times with nitrogen and cooled to −78° C., to the above mixture were added lithium diisopropylamide (1N, 17.57 mL, 17.57 mmol, 2 eq). The resulting mixture was stirred for 0.5 h at −78° C. under nitrogen atmosphere. To the above mixture was added 136.1 (2.54 g, 8.78 mmol, 1 eq) in tetrahydrofuran (9 mL) at −78° C. under nitrogen atmosphere. The resulting mixture was additional for 1 h at −78° C. under nitrogen atmosphere. The reaction was quenched with ammonium chloride solution at 0° C. The resulting mixture was extracted with ethyl acetate, the combined organic layer was washed with brine, dried over sodium sulfate and concentrated under reduced pressure to afford ethyl 3-(4-bromopyridin-2-yl)-3-[(2-methylpropane-2-sulfinyl)amino]propanoate (136.2, 2 g, 60%) as a white solid. MS (ES): m/z 377 [M+H]$^+$.

Synthesis of 136.3. To a stirred mixture of 136.2 (3.8 g, 10.07 mmol, 1 eq) in dichloromethane (30 mL) was added dropwise hydrochloric acid in 1,4-dioxane (4N, 30 mL) at room temperature. The resulting mixture was stirred for 2 h at room temperature. The resulting mixture was concentrated under reduced pressure. The crude product ethyl 3-amino-3-(4-bromopyridin-2-yl)propanoate hydrochloride (136.3, 1.82 g) was used in the next step directly without further purification, MS (ES): m/z 273/275 [M+H]$^+$.

Synthesis of 136.4. To a stirred mixture of 136.3 (1.82 g) in tetrahydrofuran (18 mL) and water (18 mL) was added di-tert-butyl pyrocarbonate (1 g) and sodium bicarbonate (500 mg) at room temperature. The resulting mixture was stirred for 4 h at room temperature. The resulting mixture was extracted with ethyl acetate. The combined organic layer was washed with brine, dried over sodium sulfate and concentrated under reduced pressure. The residue was purified by silica gel column chromatography (compound was eluted in 90% ethyl acetate in petroleum ether) to obtain ethyl 3-(4-bromopyridin-2-yl)-3-((tert-butoxycarbonyl)amino)propanoate (136.4, 1.88 g) as white solid. MS (ES): m/z 373/375 [M+H]$^+$.

Synthesis of 136.5. To a stirred mixture of 136.4 (1.78 g, 4.77 mmol, 1 eq) in tetrahydrofuran (50 mL) and ethyl alcohol (5 mL) were added sodium borohydride (0.72 g, 19.08 mmol, 4 eq) and lithium chloride (0.81 g, 19.08 mmol, 4 eq) in portions at 0° C. The resulting mixture was stirred for 16 h at 30° C. under nitrogen atmosphere. The reaction was quenched by ammonium chloride solution at 0° C. The resulting mixture was extracted with ethyl acetate. The combined organic layer was washed with brine, dried over sodium sulfate and concentrated under reduced pressure. The residue was purified by silica gel column chromatography (compound was eluted in 100% ethyl acetate) to obtain tert-butyl (1-(4-bromopyridin-2-yl)-3-hydroxypropyl)carbamate (136.5, 1.06 g, 67%) as a yellow oil. MS (ES): m/z 331/333 [M+H]$^+$.

Synthesis of 136.6. To a stirred mixture of 136.5 (725 mg, 2.19 mmol, 1 eq) in tetrahydrofuran (26 mL) was degassed three times with nitrogen and cooled to −15° C. To the solution was added sodium hydride (60% w/w in mineral oil, 219 mg, 5.47 mmol, 2.5 eq), stirred for 0.5 h at −15° C. under nitrogen atmosphere. To the above mixture was added iodomethane (0.13 mL, 2.19 mmol, 1 eq) at −15° C. The resulting mixture was stirred for additional 3 h at room temperature under nitrogen atmosphere. The reaction was quenched with ammonium chloride, extracted with ethyl acetate. The combined organic layers were washed with water, dried over anhydrous sodium sulfate. After filtration, the filtrate was concentrated under reduced pressure and purified by Prep-TLC (petroleum ether/ethyl acetate=3:1) to obtain tert-butyl N-[1-(4-bromopyridin-2-yl)-3-methoxypropyl]carbamate (136.6, 280 mg, 37%) as a brown yellow solid. MS (ES): m/z 345/347 [M+H]$^+$.

Synthesis of 136.7. To a stirred mixture of 136.6 (450 mg, 1.3 mmol, 1 eq) in dichloromethane (7 mL) was added hydrochloric acid in 1,4-dioxane (4N, 7 mL) at room temperature. The resulting mixture was stirred for 1.5 h at room temperature. The resulting mixture was concentrated under reduced pressure. The crude product 1-(4-bromopyridin-2-yl)-3-methoxypropan-1-amine hydrochloride (136.7, 320 mg) was used in the next step directly without further purification, MS (ES): m/z 245/247 [M+H]$^+$.

Synthesis of 136.8. To a stirred mixture of 136.7 (320 mg) and 39.2 (328 mg) in N,N-dimethylformamide (7 mL) was added 2-(-7-azabenzotriazol-1-yl)-N, N, N', N'-tetramethyluronium hexafluorophosphate (595 mg, 1.57 mmol) and N,N-diisopropylethylamine (506 mg, 3.92 mmol). The resulting mixture was stirred for 2 h at room temperature. The residue was purified by reverse flash chromatography with the following conditions: Column, C18 Column; Mobile Phase, water (0.1% FA) and ACN (5% ACN up to 100% in 20 min); UV detection at 254/220 nm. The resulting mixture was concentrated under reduced pressure to obtain N-[1-(4-bromopyridin-2-yl)-3-methoxypropyl]-5-(6-ethoxypyrazin-2-yl)-1,3-thiazole-2-carboxamide (136.8, 600 mg) as a yellow solid. MS (ES): m/z 478/480 [M+H]$^+$.

Synthesis of I-186. To a stirred mixture of 136.8 (340 mg, 0.69 mmol, 1 eq) and cyclopropanesulfonamide (171 mg, 1.38 mmol, 2 eq) in 1,4-dioxane (5 mL) were added cesium carbonate (693 mg, 2.07 mmol, 3 eq), t-BuXPhos (90 mg, 0.21 mmol, 0.3 eq) and Pd$_2$(ally)$_2$Cl$_2$ (39 mg, 0.1 mmol, 0.15 eq). The resulting solution was degassed three times with nitrogen and stirred for 1.5 h at 60° C. The mixture was allowed to cool down to room temperature. The resulting mixture was concentrated under reduced pressure and purified by reverse flash chromatography with the following conditions: Column, C18 Column; Mobile Phase, water (0.1% NH$_4$HCO$_3$) and ACN (5% ACN up to 100% in 20 min); UV detection at 254/220 nm. The resulting mixture was concentrated under reduced pressure. The crude product was purified by Prep-HPLC with the following conditions: Column, C$_{1-8}$ Column; Mobile Phase, water (0.1% FA) and ACN (21% ACN up to 39% in 10 min); UV detection at 254/220 nm. The product-containing fractions were combined and evaporated partially in vacuum and lyophilized overnight to afford N-[1-(4-cyclopropanesulfonamidopyridin-2-yl)-3-methoxypropyl]-5-(6-ethoxypyrazin-2-yl)-1,3-thiazole-2-carboxamide (I-186, 168 mg, 45%) as a white solid. MS (ES): m/z 519 [M+H]$^+$; $^1$H NMR (400 MHz, DMSO-d$_6$) δ 8.87 (s, 1H), 8.77 (s, 1H), 8.37-8.25 (m, 2H), 7.11 (s, 1H), 7.02 (s, 1H), 5.08 (t, J=7.0 Hz, 1H), 4.40 (q, J=7.0 Hz, 2H), 3.41-3.34 (m, 2H), 3.22 (s, 3H), 2.78-2.69 (m, 1H), 2.13 (q, J=6.5 Hz, 2H), 1.37 (t, J=7.0 Hz, 3H), 1.02-0.88 (m, 4H).

Example 137: Synthesis of Example 137: (S)—N-(1-(4-(cyclopropanesulfonamido)pyridin-2-yl)-3-methoxypropyl)-5-(6-ethoxypyrazin-2-yl)thiazole-2-carboxamide, isomer 1 (I-183) and (R)—N-(1-(4-(cyclopropanesulfonamido)pyridin-2-yl)-3-methoxypropyl)-5-(6-ethoxypyrazin-2-yl)thiazole-2-carboxamide, isomer 2 (I-184). Stereochemistry Arbitrarily Assigned

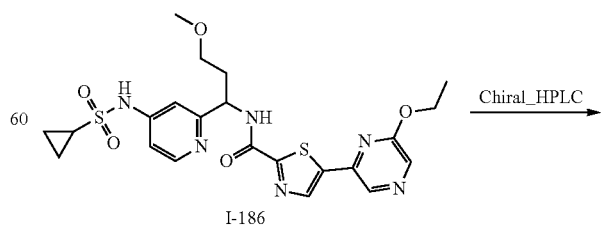

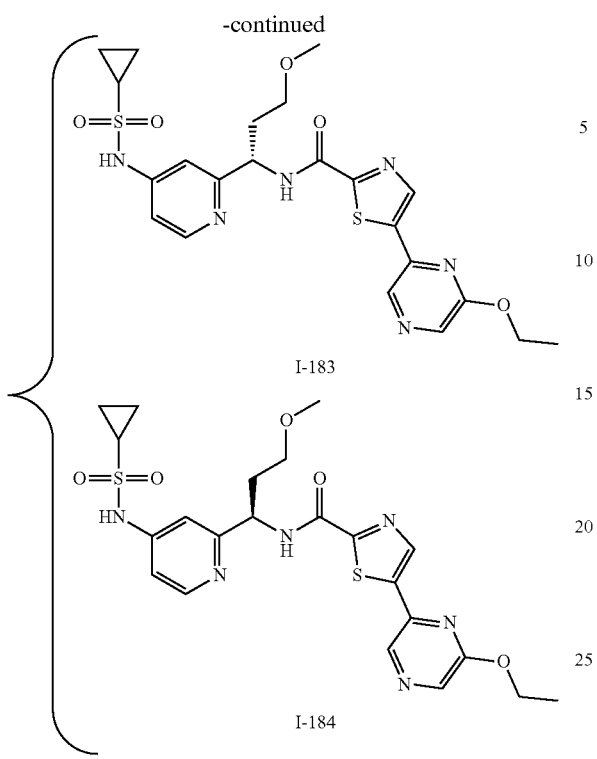

Example 138: Synthesis of N-[2-(4-cyclopropane-sulfonamidopyridin-2-yl)-4-methoxybutan-2-yl]-5-(6-ethoxypyrazin-2-yl)-1,3-thiazole-2-carboxamide (I-178)

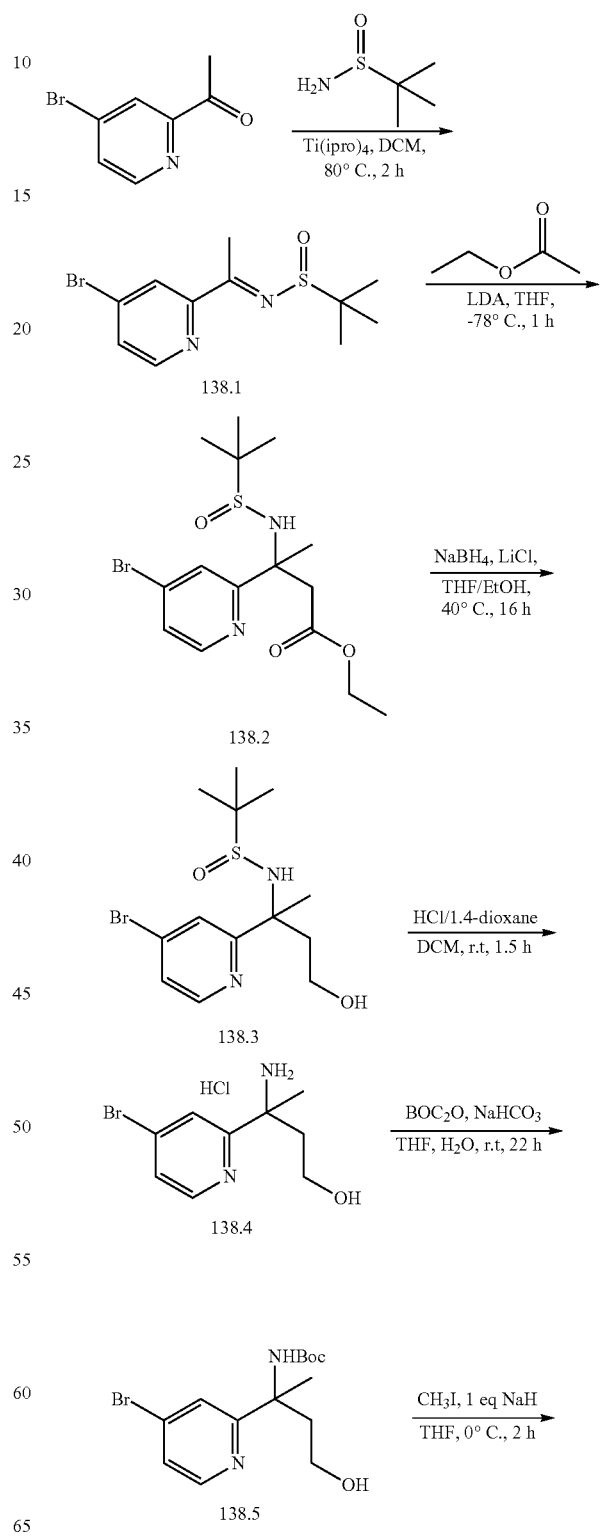

Synthesis of I-183 and I-184. I-186 (150 mg, 0.289 mmol) was separated by Chiral-Prep-HPLC with the following conditions: Column: CHIRALPAK ID, 2*25 cm, 5 μm; Mobile Phase A: Hex: DCM=3:1 (0.5% 2M NH3-MeOH)-HPLC, Mobile Phase B: IPA-HPLC; Wave Length: 220/254 nm. The product-containing fractions were combined and evaporated partially in vacuum and lyophilized overnight to afford (S)—N-(1-(4-(cyclopropanesulfonamido)pyridin-2-yl)-3-methoxypropyl)-5-(6-ethoxypyrazin-2-yl)thiazole-2-carboxamide, isomer 1 (1$^{st}$ eluting peak, I-183, 27 mg, 36%) as a white solid and (R)—N-(1-(4-(cyclopropanesulfona-mido)pyridin-2-yl)-3-methoxypropyl)-5-(6-ethoxypyrazin-2-yl)thiazole-2-carboxamide, isomer 2 (2$^{nd}$ eluting peak, I-184.23 mg, 31%) as a white solid. I-183: MS (ES): m/z 519 [M+H]$^+$; $^1$H NMR (400 MHz, DMSO-d$_6$) δ10.55 (s, 1H), 9.26 (s, 1H), 8.94 (s, 1H), 8.82 (s, 1H), 8.38 (s, 1H), 8.30 (s, 1H), 7.25-7.00 (m, 2H), 5.20-5.08 (m, 1H), 4.46-4.38 (m, 2H), 3.43-3.33 (m, 2H), 3.24 (s, 3H), 2.90-2.80 (m, 1H), 2.23-2.10 (m, 2H), 1.40 (t, J=7.0 Hz, 3H), 1.10-0.90 (m, 4H). I-184: MS (ES): m/z 519 [M+H]$^+$. $^1$H NMR (400 MHz, DMSO-d$_6$) δ 10.54 (s, 1H), 9.26-9.24 (m, 1H), 8.94 (s, 1H), 8.82 (s, 1H), 8.43-8.37 (m, 1H), 8.30 (s, 1H), 7.20 (s, 1H), 7.07 (s, 1H), 5.17-5.15 (m, 1H), 4.47-4.40 (m, 2H), 3.43-3.32 (m, 2H), 3.25 (s, 3H), 2.87-2.76 (s, 1H), 2.23-2.10 (m, 2H), 1.40 (t, J=7.0 Hz, 3H), 1.08-0.88 (m, 4H).

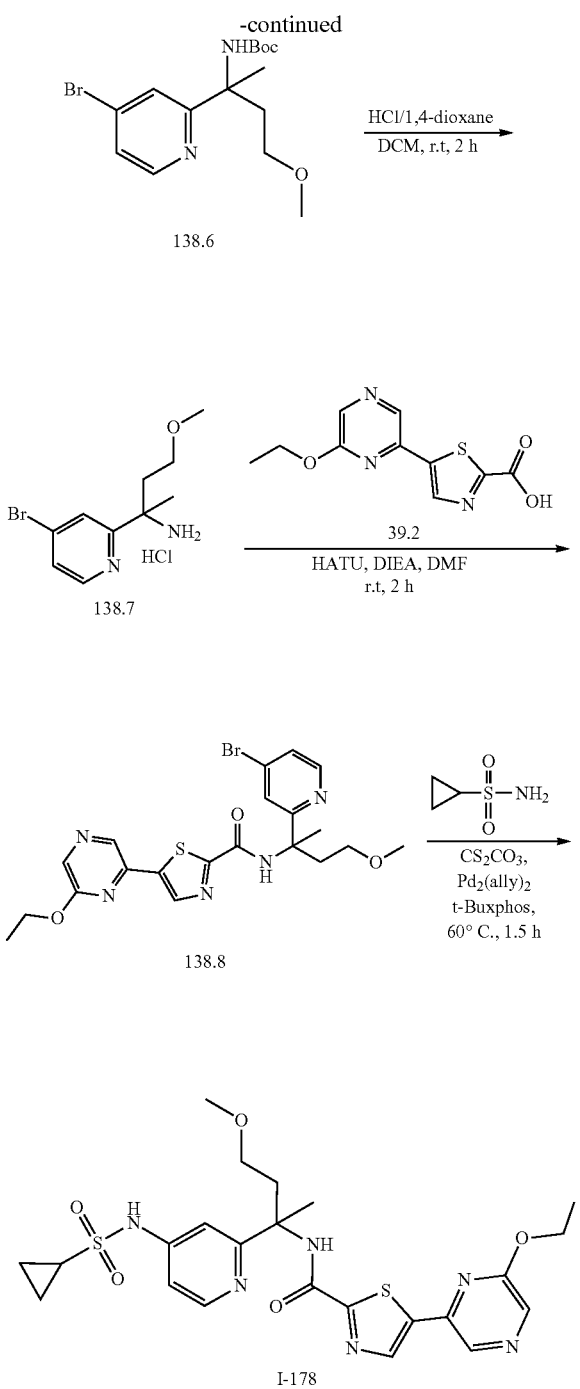
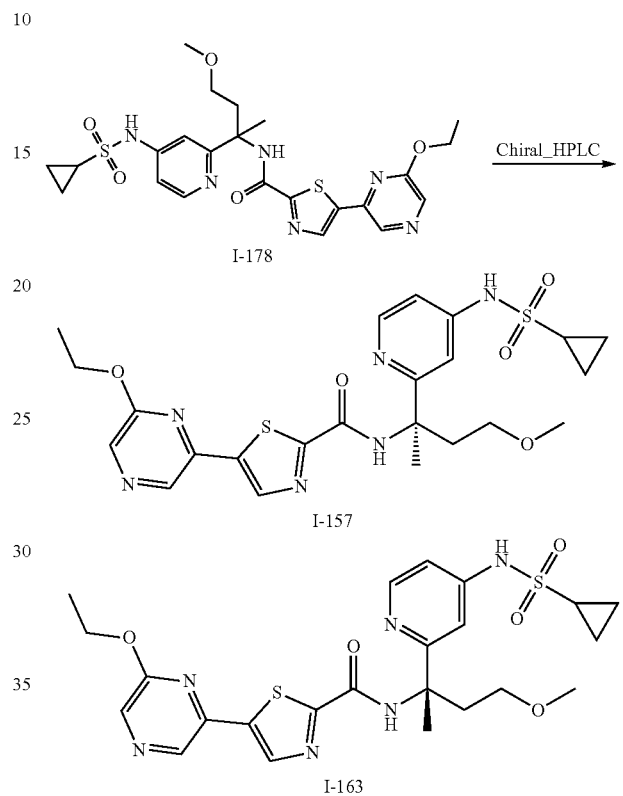

Synthesis of I-178. I-178 was synthesized in a manner similar to that described in the synthesis of I-186, using 1-(4-bromopyridin-2-yl)ethan-1-one as starting material. MS (ES): m/z 533 [M+H]+; 1H NMR (400 MHz, Chloroform-d) δ 9.63 (s, 1H), 8.54 (s, 1H), 8.45 (d, J=5.7 Hz, 1H), 8.37 (s, 1H), 8.17 (s, 1H), 7.26-7.25 (m, 1H), 7.09-7.06 (m, 1H), 4.47 (q, J=7.0 Hz, 2H), 3.47-3.36 (m, 2H), 3.31 (s, 3H), 2.67-2.56 (m, 2H), 2.31-2.24 (m, 1H), 1.99 (s, 3H), 1.47 (t, J=7.1 Hz, 3H), 1.32-1.24 (m, 2H), 1.11-1.04 (m, 2H).

Example 139: Synthesis of (R)—N-(2-(4-(cyclopropanesulfonamido)pyridin-2-yl)-4-methoxybutan-2-yl)-5-(6-ethoxypyrazin-2-yl)thiazole-2-carboxamide, isomer 1 (I-157) and (S)—N-(2-(4-(cyclopropanesulfonamido)pyridin-2-yl)-4-methoxybutan-2-yl)-5-(6-ethoxypyrazin-2-yl)thiazole-2-carboxamide, isomer 2 (I-163). Stereochemistry arbitrarily assigned Synthesis of I-157 and I-163. I-178 (100 mg, 0.19 mmol) was separated by Chiral-Prep-HPLC with the following conditions: Column: CHIRALPAK IG, 2*25 cm, 5 μm; Mobile Phase A: Hex: DCM=3:1 (0.5% 2M NH3-MeOH)-HPLC, Mobile Phase B: EtOH-HPLC; Flow rate: 20 mL/min; Gradient: 10% B to 10% B in 20 min; Wave Length: 220/254 nm; The product-containing fractions were combined and evaporated partially in vacuum and lyophilized overnight to afford (S)—N-(2-(4-(cyclopropanesulfonamido)pyridin-2-yl)-4-methoxybutan-2-yl)-5-(6-ethoxypyrazin-2-yl)thiazole-2-carboxamide, isomer 2 I-163, 1st eluting peak, 30 mg, 59%) as a white solid and (R)—N-(2-(4-(cyclopropanesulfonamido)pyridin-2-yl)-4-methoxybutan-2-yl)-5-(6-ethoxypyrazin-2-yl)thiazole-2-carboxamide, isomer 1 (I-157, 2nd eluting peak, 24 mg, 48%) as a white solid. I-157: MS (ES): m/z 533 [M+H]+; 1H NMR (400 MHz, Chloroform-d) δ 9.62 (s, 1H), 8.54 (s, 1H), 8.46 (d, J=5.8 Hz, 1H), 8.37 (s, 1H), 8.17 (s, 1H), 7.30-7.28 (m, 1H), 7.18-7.09 (m, 1H), 4.48 (q, J=7.0 Hz, 2H), 3.49-3.35 (m, 2H), 3.32 (s, 3H), 2.69-2.57 (m, 2H), 2.35-2.20 (m, 1H), 2.00 (s, 3H), 1.47 (t, J=7.1 Hz, 3H), 1.36-1.25 (m, 2H), 1.11-1.05 (m, 2H). I-163: MS (ES): m/z 533 [M+H]+; 1H NMR (400 MHz, Chloroform-d) δ 9.62 (s, 1H), 8.54 (s, 1H), 8.46 (d, J=5.8 Hz, 1H), 8.37 (s, 1H), 8.17 (s, 1H), 7.30-7.28 (m, 1H), 7.15-7.06 (m, 1H), 4.51-4.40 (m, 2H), 3.49-3.35

(m, 2H), 3.32 (s, 3H), 2.69-2.57 (m, 2H), 2.35-2.22 (m, 1H), 2.00 (s, 3H), 1.47 (t, J=7.1 Hz, 3H), 1.36-1.24 (m, 2H), 1.11-1.05 (m, 2H).

Example 140: Synthesis of N-[1-(4-cyclopropanesulfonamidopyridin-2-yl)-2-methoxyethyl]-5-(6-ethoxypyrazin-2-yl)-1,3-thiazole-2-carboxamide (I-194)

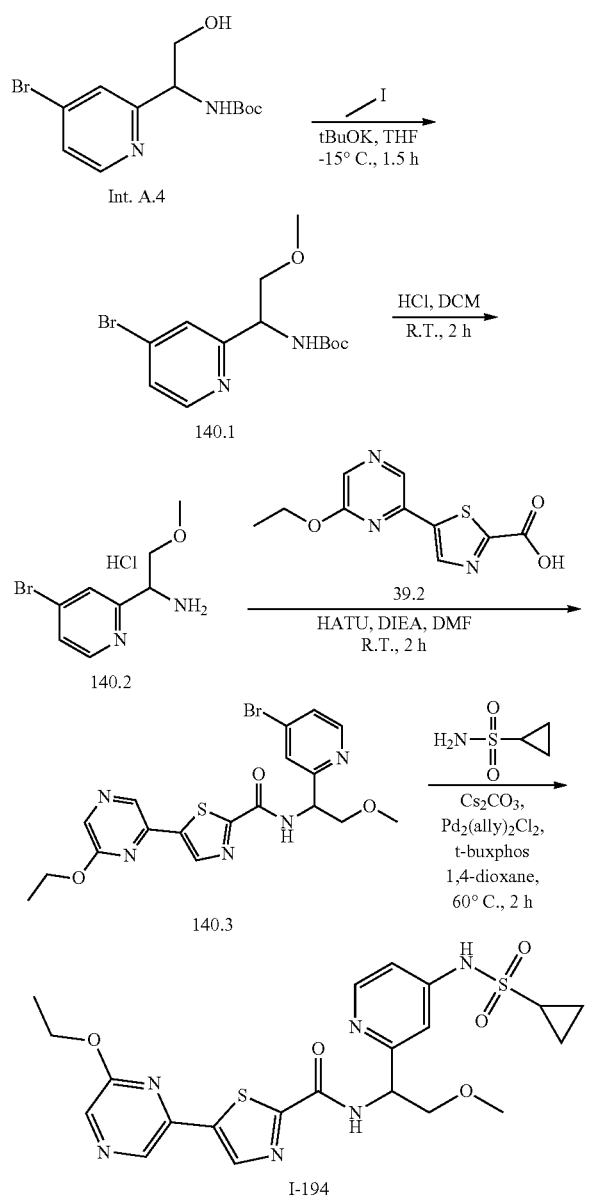

Synthesis of 140.1. A stirred solution of Int. A. 4 (620 mg, 1.95 mmol, 1 eq) in tetrahydrofuran (10 mL) was degassed three times with nitrogen and cooled to −15° C. To the solution was added potassium tert-butoxide (0.5 mL, 3.9 mmol, 2 eq) and the mixture was stirred for 0.5 h at −15° C. under nitrogen atmosphere. To the above mixture was added iodomethane (0.12 mL, 1.95 mmol, 1 eq) at −15° C. The resulting mixture was stirred for additional 1.5 h at −15° C. The reaction was quenched with ammonium chloride, extracted with ethyl acetate. The combined organic layers were washed with water, dried over anhydrous sodium sulfate. After filtration, the filtrate was concentrated under reduced pressure and purified by Prep-TLC (petroleum ether/ethyl acetate=2/1) to afford tert-butyl N-[1-(4-bromopyridin-2-yl)-2-methoxyethyl]carbamate (140.1, 300 mg, 46%) as a light yellow oil. MS (ES): m/z 331/333 [M+H]⁺.

Synthesis of 140.2. To a stirred mixture of 140.1 (260 mg, 0.78 mmol, 1 eq) in dichloromethane (3 mL) was added 4N HCl in 1,4-dioxane (3 mL) at room temperature. The resulting mixture was stirred for 2 h at room temperature. The resulting mixture was concentrated under reduced pressure to obtain the crude product 1-(4-bromopyridin-2-yl)-2-methoxyethanamine; hydrochloride (140.2, 200 mg) used in the next step directly without further purification, MS (ES): m/z 231/233 [M+H]⁺.

Synthesis of 140.3. To a stirred mixture of 39.2 (130 mg) and N, N-diisopropylethylamine (268 mg, 2 mmol) in N,N-dimethylformamide (12 mL) were added 140.2 (120 mg) and 2-(-7-azabenzotriazol-1-yl)-N, N, N', N'-tetramethyluronium hexafluorophosphate (237 mg, 0.6 mmol). The resulting mixture was stirred for 2 h at room temperature. The residue was purified by reverse phase flash chromatography (compound was eluted in 30% acetonitrile in water) to obtain N-[1-(4-bromopyridin-2-yl)-2-methoxyethyl]-5-(6-ethoxypyrazin-2-yl)-1,3-thiazole-2-carboxamide (140.3, 180 mg) as a white solid. MS (ES): m/z 464/466 [M+H]⁺.

Synthesis of I-194. To a stirred mixture of 140.3 (180 mg, 0.39 mmol, 1 eq) and cyclopropanesulfonamide (93.6 mg, 0.78 mmol, 2 eq) in 1,4-dioxane (5 mL) were added cesium carbonate (378 mg, 1.17 mmol, 3 eq), Pd₂(allyl)₂Cl₂ (21.6 mg, 0.04 mmol, 0.1 eq) and t-Buxphos (48.6 mg, 0.11 mmol, 0.3 eq). The resulting mixture was degassed three times with nitrogen and stirred for 2 h at 60° C. under nitrogen atmosphere. The mixture was allowed to cool down to room temperature, concentrated under reduced pressure and purified by reverse flash chromatography (compound was eluted in 80% acetonitrile in water) to obtain N-[1-(4-cyclopropanesulfonamidopyridin-2-yl)-2-methoxyethyl]-5-(6-ethoxypyrazin-2-yl)-1,3-thiazole-2-carboxamide (I-194, 98 mg, 51%) as a white solid. MS (ES): m/z 504 [M+H]⁺; ¹H NMR (300 MHz, CD₃OD-d₄) δ 8.72 (s, 1H), 8.61 (s, 1H), 8.31 (d, J=8.1 Hz, 1H), 8.17 (s, 1H), 7.50-7.30 (m, 1H), 7.30-7.00 (m, 1H), 5.57-5.27 (m, 1H), 4.47 (q, J=7.0 Hz, 2H), 3.95-3.78 (m, 2H), 3.43 (s, 3H), 2.81-2.60 (m, 1H), 1.49 (t, J=7.0 Hz, 3H), 1.23-1.06 (m, 2H), 1.06-0.93 (m, 2H).

Example 141: Synthesis of R)—N-(1-(4-(cyclopropanesulfonamido)pyridin-2-yl)-2-methoxyethyl)-5-(6-ethoxypyrazin-2-yl)thiazole-2-carboxamide, isomer 1 (I-187) and (S)—N-(1-(4-(cyclopropanesulfonamido)pyridin-2-yl)-2-methoxyethyl)-5-(6-ethoxypyrazin-2-yl)thiazole-2-carboxamide, isomer 2 (I-188). Stereochemistry Arbitrarily Assigned

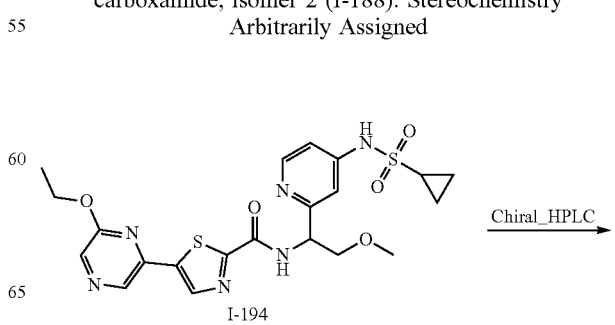

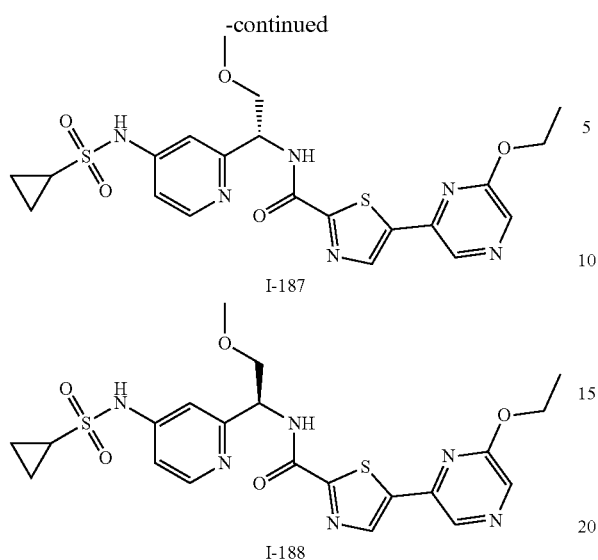

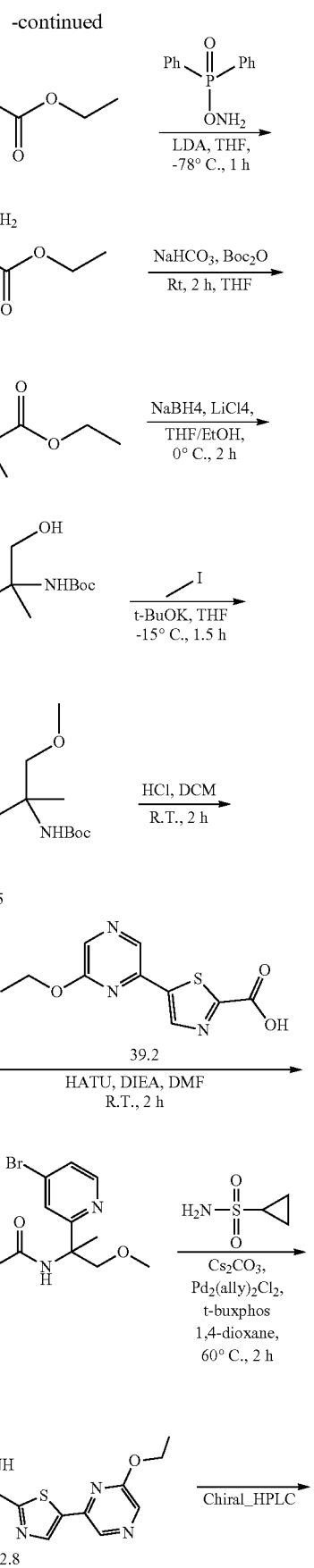

Synthesis of I-187 and I-188. I-194 (80 mg, 0.16 mmol) was purified by Chiral-Prep-HPLC with the following conditions: Column: CHIRALPAK IG, 2*25 cm, 5 μm; Mobile Phase A: Hex: DCM=3:1 (0.5% 2M NH3-MeOH)-HPLC, Mobile Phase B: IPA-HPLC; Flow rate: 20 mL/min; Gradient: 50% B to 50% B in 27 min; Wave Length: 220/254 nm. The product-containing fractions were combined and concentrated under reduced pressure to afford N-[(1S)-1-(4-cyclopropanesulfonamidopyridin-2-yl)-2-methoxyethyl]-5-(6-ethoxypyrazin-2-yl)-1,3-thiazole-2-carboxamide, isomer 2 (I-188, 1$^{st}$ eluting peak, 16 mg, 39%) and N-[(1R)-1-(4-cyclopropanesulfonamidopyridin-2-yl)-2-methoxyethyl]-5-(6-ethoxypyrazin-2-yl)-1,3-thiazole-2-carboxamide, isomer 1 (I-187, 2$^{ed}$ eluting peak, 32 mg, 79%) as white solids. I-188: MS (ES): m/z 504 [M+H]$^+$; $^1$H NMR (400 MHz, DMSO-d$_6$) δ 9.16 (d, J=8.1 Hz, 1H), 8.93 (s, 1H), 8.82 (s, 1H), 8.37-8.31 (m, 2H), 7.21 (s, 1H), 7.13-7.06 (m, 1H), 5.27-5.17 (m, 1H), 4.43 (q, J=7.0 Hz, 2H), 3.90-3.81 (m, 1H), 3.80-3.72 (m, 1H), 3.30 (s, 3H), 2.84-2.76 (m, 1H), 1.39 (t, J=7.0 Hz, 3H), 1.07-0.92 (m, 4H). I-187: MS (ES): m/z 504 [M+H]$^+$; $^1$H NMR (400 MHz, DMSO-d$_6$) δ 9.16 (d, J=8.2 Hz, 1H), 8.93 (s, 1H), 8.82 (s, 1H), 8.40-8.25 (m, 2H), 7.21 (s, 1H), 7.08 (s, 1H), 5.27-5.16 (m, 1H), 4.49-4.37 (m, 2H), 3.85 (dd, J=9.9, 7.4 Hz, 1H), 3.76 (dd, J=10.0, 5.1 Hz, 1H), 3.29 (s, 3H), 2.85-2.76 (m, 1H), 1.40 (t, J=7.0 Hz, 3H), 1.07-0.92 (m, 4H).

Example 142: Synthesis of (S)—N-(2-(4-(cyclopropanesulfonamido)pyridin-2-yl)-1-methoxypropan-2-yl)-5-(6-ethoxypyrazin-2-yl)thiazole-2-carboxamide, isomer 1 (I-90) and (R)—N-(2-(4-(cyclopropanesulfonamido)pyridin-2-yl)-1-methoxypropan-2-yl)-5-(6-ethoxypyrazin-2-yl)thiazole-2-carboxamide, isomer 2 (I-91). Stereochemistry arbitrarily assigned

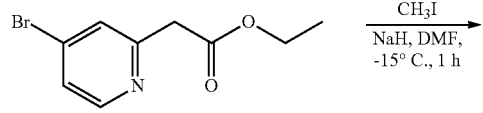

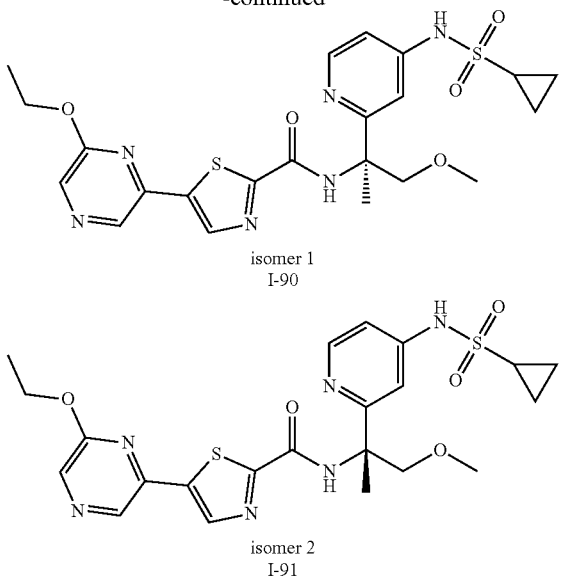

isomer 1
I-90 isomer 2
I-91

Synthesis of 142.1. A stirred solution of ethyl 2-(4-bromopyridin-2-yl)acetate (6 g, 24.58 mmol, 1 eq) in N,N-dimethyformamide (120 mL) was degassed three times with nitrogen and cooled to 0° C. To the solution was added sodium hydride (786 mg, 60% w/w in mineral oil, 19.66 mmol, 0.8 eq) and stirred for 0.5 h at 0° C. under nitrogen atmosphere. To the above mixture was added iodomethane (3.49 g, 24.58 mmol, 1 eq) over 10 min at 0° C. The resulting mixture was stirred for additional 1 h at room temperature. The reaction was quenched with saturated aqueous ammonium chloride, and extracted with ethyl acetate. The combined organic layers were washed with water, dried over anhydrous sodium sulfate. After filtration, the filtrate was concentrated under reduced pressure and purified by silica gel column chromatography (compound was eluted in 10% ethyl acetate in petroleum ether) to obtain ethyl 2-(4-bromopyridin-2-yl)propanoate (142.1, 3.6 g, 56%) as yellow oil. MS (ES): m/z 258 [M+H]$^+$.

Synthesis of 142.2. A stirred mixture of 142.1 (3 g, 11.62 mmol, 1 eq) in tetrahydrofuran (50 mL) was degassed three times with nitrogen and cooled to −78° C. To the above mixture were added lithium diisopropylamide (1N in THF, 23.24 mL, 23.24 mmol, 2 eq). The resulting mixture was stirred for 0.5 h at −78° C. under nitrogen atmosphere. To the above mixture was added (aminooxy)diphenylphosphine oxide (4.07 g, 17.43 mmol, 1.5 eq) in tetrahydrofuran (9 mL) at −78° C. under nitrogen atmosphere. The resulting mixture was additional for 1 h at −78° C. under nitrogen atmosphere. The reaction was quenched with saturated aqueous ammonium chloride solution at 0° C. The resulting mixture was extracted with ethyl acetate, the combined organic layer was washed with brine, dried over sodium sulfate and concentrated under reduced pressure to afford crude product ethyl 2-amino-2-(4-bromopyridin-2-yl)propanoate (142.2, 3.5 g), used without further purification. MS (ES): m/z 273 [M+H]$^+$.

Synthesis of 142.3. 142.3 was synthesized from 142.2 in a manner similar to that described in the synthesis of 136.4. MS (ES): m/z 373/375 [M+H]$^+$.

Synthesis of 142.4. 142.4 was synthesized from 142.3 in a manner similar to that described in the synthesis of 136.5. MS (ES): m/z 331/333 [M+H]$^+$.

Synthesis of 142.8. 142.8 was synthesized from 142.4 following similar protocols to that described in the synthesis of I-194. MS (ES): m/z 519 [M+H]$^+$.

Synthesis of I-90 and I-91. 142.8 (80 mg, 0.15 mmol) was separated by Chiral-Prep-HPLC with the following conditions: Column: CHIRALPAK IG, 2*25 cm, 5 μm; Mobile Phase A: Hex: DCM=3:1 (0.5% 2M NH$_3$-MeOH)-HPLC, Mobile Phase B: EtOH-HPLC, Detector, UV 254/220 nm. The product-containing fractions were combined and concentrated under reduced pressure to afford (S)—N-(2-(4-(cyclopropanesulfonamido)pyridin-2-yl)-1-methoxypropan-2-yl)-5-(6-ethoxypyrazin-2-yl)thiazole-2-carboxamide, isomer 1 (I-90, 1$^{st}$ eluting peak, 24 mg, 59%) and (R)—N-(2-(4-(cyclopropanesulfonamido)pyridin-2-yl)-1-methoxypropan-2-yl)-5-(6-ethoxypyrazin-2-yl)thiazole-2-carboxamide, isomer 2 (I-91, 2$^{ed}$ eluting peak, 26 mg, 66%). I-90: MS (ES): m/z 519 [M+H]$^+$; $^1$H NMR (400 MHz, DMSO-de) δ 10.61 (s, 1H), 9.18 (s, 1H), 8.92 (s, 1H), 8.80 (s, 1H), 8.47-8.26 (m, 2H), 7.27 (s, 1H), 7.15-7.04 (m, 1H), 4.54-4.34 (m, 2H), 3.97 (d, J=9.4 Hz, 1H), 3.80 (d, J=9.4 Hz, 1H), 3.21 (s, 3H), 2.88-2.74 (m, 1H), 1.72 (s, 3H), 1.39 (t, J=7.0 Hz, 3H), 1.10-0.91 (m, 4H). I-91: MS (ES): m/z 519 [M+H]$^+$; $^1$H NMR (400 MHz, DMSO-d$_6$) δ 10.58 (s, 1H), 9.17 (s, 1H), 8.93 (s, 1H), 8.80 (s, 1H), 8.45-8.24 (m, 2H), 7.27 (s, 1H), 7.17-7.03 (m, 1H), 4.52-4.35 (m, 2H), 3.97 (d, J=9.4 Hz, 1H), 3.80 (d, J=9.5 Hz, 1H), 3.22 (s, 3H), 2.85-2.75 (m, 1H), 1.72 (s, 3H), 1.39 (t, J=7.0 Hz, 3H), 1.10-0.95 (m, 4H).

Example 143: Synthesis of (R)—N-(1-(4-(cyclopropanesulfonamido)pyridin-2-yl)-2-ethoxyethyl)-5-(6-ethoxypyrazin-2-yl)thiazole-2-carboxamide, isomer (I-96) and (S)—N-(1-(4-(cyclopropanesulfonamido)pyridin-2-yl)-2-ethoxyethyl)-5-(6-ethoxypyrazin-2-yl)thiazole-2-carboxamide, isomer 2 (I-97). Stereochemistry Arbitrarily Assigned

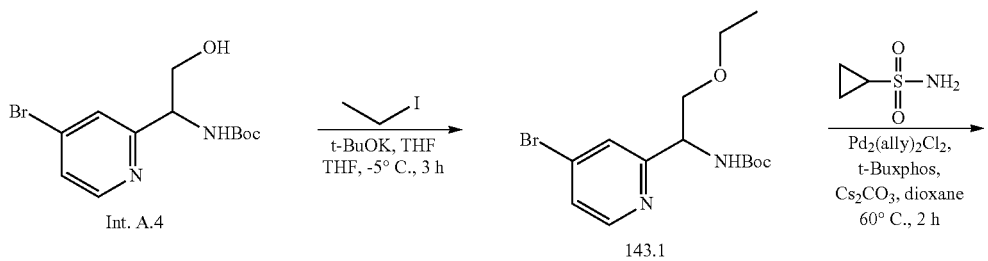

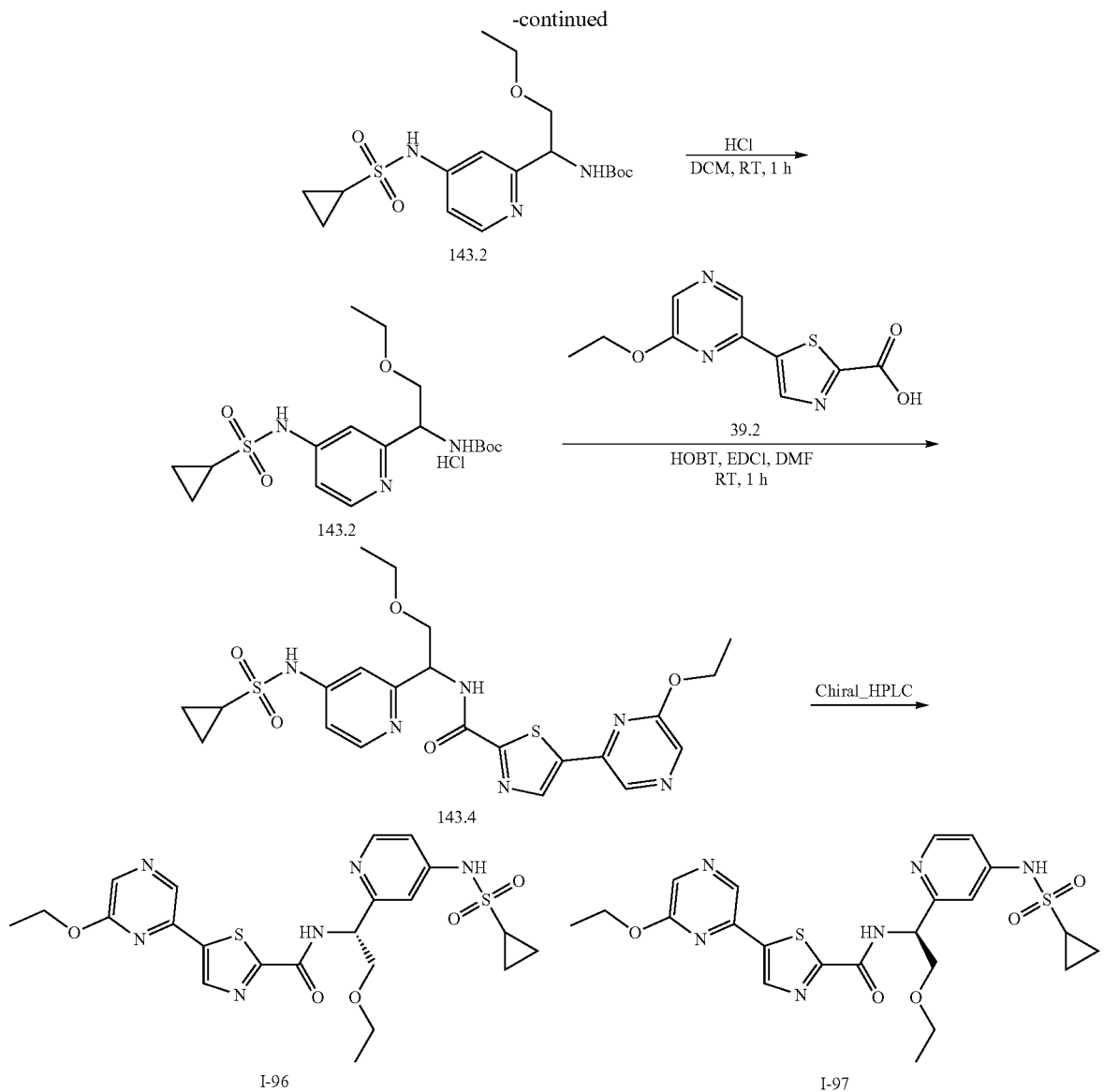

Synthesis of 143.1. A stirred solution of Int. A. 4 (1 g, 3.16 mmol, 1 eq) in tetrahydrofuran (15 mL) was degassed three times with nitrogen and cooled to −5° C. To the solution was added potassium tert-butoxide (1N in THF, 6.32 mL, 6.32 mmol, 2 eq) and the mixture was stirred for 0.5 h at −5° C. under nitrogen atmosphere. To the above mixture was added iodoethane (987 mg, 6.32 mmol, 2 eq) at −5° C. The resulting mixture was stirred for additional 1.5 h at −5° C. The reaction was quenched with saturated aqueous ammonium chloride and extracted with ethyl acetate. The combined organic layers were washed with water, dried over anhydrous sodium sulfate. After filtration, the filtrate was concentrated under reduced pressure and purified by Prep-TLC (petroleum ether/ethyl acetate=1/1) to afford tert-butyl (1-(4-bromopyridin-2-yl)-2-ethoxyethyl)carbamate (143.1, 305 mg, 28%) as a light yellow oil. MS (ES): m/z 345 [M+H]$^+$.

Synthesis of 143.2. To a stirred mixture of 143.1 (305 mg, 0.88 mmol, 1 eq) and cyclopropanesulfonamide (212 mg, 1.77 mmol, 2 eq) in 1,4-dioxane (5 mL) were added cesium carbonate (858 mg, 2.65 mmol, 3 eq), Pd$_2$(allyl)$_2$Cl$_2$ (49 mg, 0.09 mmol, 0.1 eq) and t-Buxphos (117 mg, 0.26 mmol, 0.3 eq). The resulting mixture was degassed three times with nitrogen and stirred for 2 h at 60° C. under nitrogen atmosphere. The mixture was allowed to cool down to room temperature, concentrated under reduced pressure and purified by reverse flash chromatography (compound was eluted in 40% acetonitrile in water) to obtain tert-butyl (1-(4-(cyclopropanesulfonamido)pyridin-2-yl)-2-ethoxyethyl)carbamate (143.2, 240 mg, 70%) as a yellow oil. MS (ES): m/z 386 [M+H]$^+$.

Synthesis of 143.3. To a stirred mixture of 143.2 (240 mg, 0.62 mmol, 1 eq) in dichlormethane (3 mL) was added 4N HCl in 1,4-dioxane (3 mL) at room temperature. The resulting mixture was stirred for 2 h at room temperature. The resulting mixture was concentrated under reduced pressure to obtain the crude product N-(2-(1-amino-2-ethoxyethyl)pyridine-4-yl)cyclopropanesulfonamide; hydrogen chloride (143.3, 200 mg) used in the next step directly without further purification. MS (ES): m/z 286 [M+H]$^+$.

Synthesis of 143.4 To a stirred mixture of 143.3 (200 mg) and 39.2 (200 mg) in N,N-dimethylformamide (5 mL) was added 1-hydroxybenzotriazole (192 mg, 1.42 mmol) and 1-ethyl-3-(3-dimethylaminopropyl)carbodiimide hydrochloride (408 mg, 2.12 mmol). The resulting mixture was stirred for 1 h at room temperature. The mixture was diluted with water and extracted with ethyl acetate. The combined organic layer was washed with brine, dried over sodium sulfate and concentrated under reduced pressure. The residue was purified by silica gel column chromatography (compound was eluted in 7% methanol in dichloromethane) to obtain N-[1-(4-cyclopropanesulfonamidopyridin-2-yl)-2-ethoxyethyl]-5-(6-ethoxypyrazin-2-yl)-1,3-thiazole-2-carboxamide (143.4, 130 mg) as a yellow oil. MS (ES): m/z 519 [M+H]$^+$.

Synthesis of I-96 and I-97. 143.4 (130 mg, 0.25 mmol) was separated by Chiral-Prep-HPLC with the following conditions: Column: CHIRAL ART Amylose-SA, 2*25 cm, 5 μm; Mobile Phase A: Hex: DCM=3:1 (0.5% 2M NH3-MeOH)-HPLC, Mobile Phase B: EtOH-HPLC; Flow rate: 20 mL/min; Gradient: 20% B to 20% B in 9 min; Wave Length: 220/254 nm. The product-containing fractions were combined and concentrated under reduced pressure to afford (S)—N-(1-(4-(cyclopropanesulfonamido)pyridin-2-yl)-2-ethoxyethyl)-5-(6-ethoxypyrazin-2-yl)thiazole-2-carboxamide, isomer 2 (I-97, 1$^{st}$ eluting peak, 33 mg, 50%) and (R)—N-(1-(4-(cyclopropanesulfonamido)pyridin-2-yl)-2-ethoxyethyl)-5-(6-ethoxypyrazin-2-yl)thiazole-2-carboxamide, isomer 1 (I-96, 2$^{nd}$ eluting peak, 30 mg, 46%). I-96: MS (ES): m/z 519 [M+H]$^+$; $^1$H NMR (400 MHz, DMSO-d$_6$) δ 10.71 (s, 1H), 9.09 (d, J=8.2 Hz, 1H), 8.93 (s, 1H), 8.82 (s, 1H), 8.29 (s, 2H), 7.14 (s, 1H), 7.03-7.02 (m, 1H), 5.19-5.12 (m, 1H), 4.43 (q, J=7.1 Hz, 2H), 3.88-3.74 (m, 2H), 3.52-3.41 (m, 2H), 2.80-2.70 (m, 1H), 1.39 (t, J=7.0 Hz, 3H), 1.10 (t, J=7.0 Hz, 3H), 1.03-0.87 (m, 4H). I-97: MS (ES): m/z 519 [M+H]$^+$; $^1$H NMR (400 MHz, DMSO-d$_6$) δ 10.54 (s, 1H), 9.12 (s, 1H), 8.93 (s, 1H), 8.82 (s, 1H), 8.38 (s, 1H), 8.29 (s, 1H), 7.22 (s, 1H), 7.08 (s, 1H), 5.21-5.16 (m, 1H), 4.43 (q, J=7.0 Hz, 2H), 3.89-3.76 (m, 2H), 3.52-3.40 (m, 2H), 2.85-2.70 (m, 1H), 1.39 (t, J=7.0 Hz, 3H), 1.08 (t, J=7.0 Hz, 3H), 1.08-0.90 (m, 4H).

Example 144: Synthesis of N-[(5-cyclopropanesulfonamido-1,2-thiazol-3-yl)methyl]-5-(6-ethoxypyrazin-2-yl)pyridine-2-carboxamide (I-284)

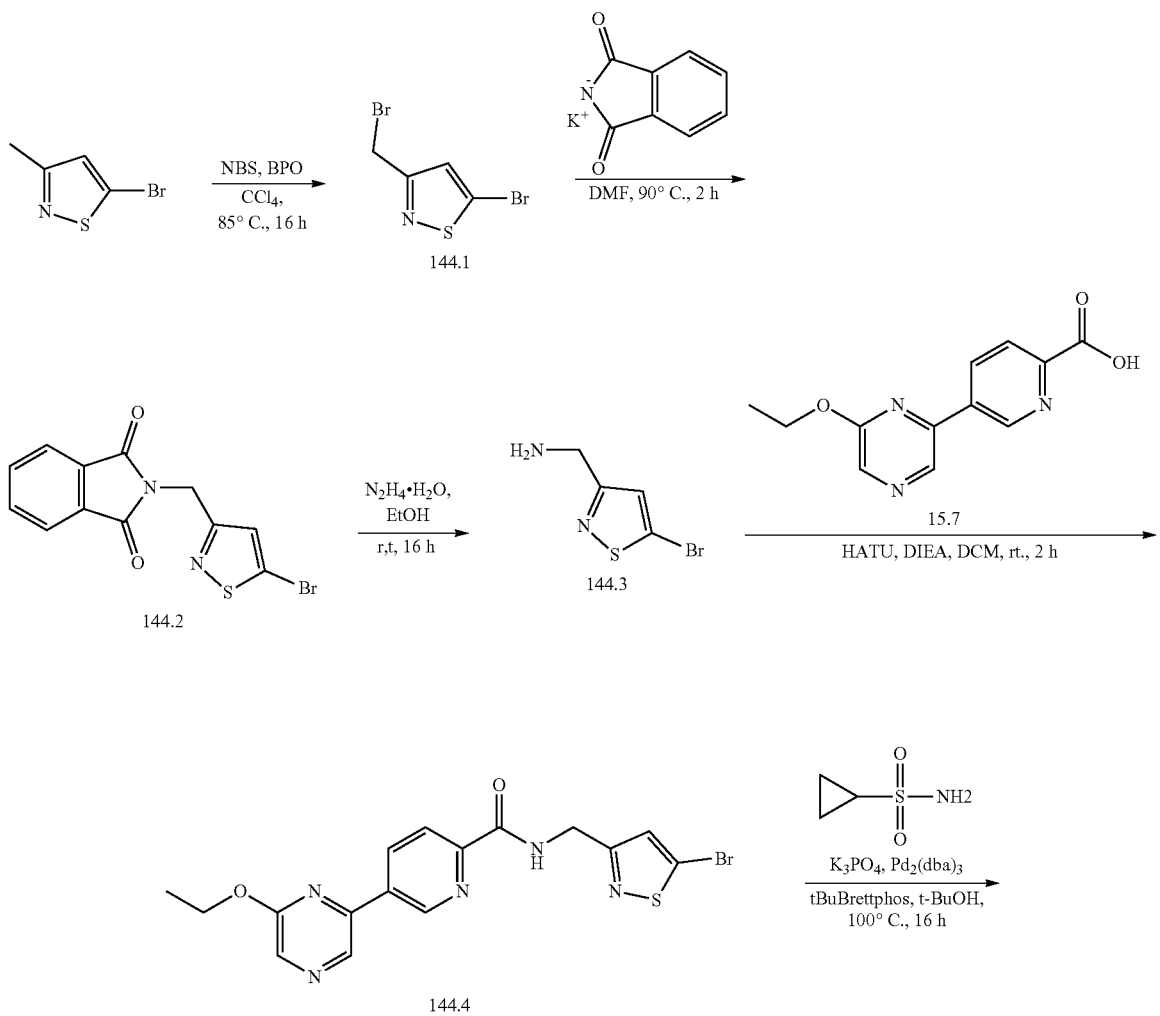

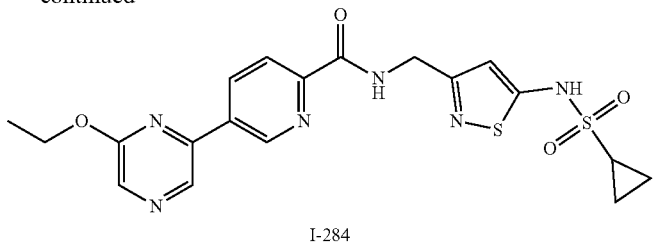

I-284

Synthesis of 144.1. To a stirred solution of 5-bromo-3-methyl-1,2-thiazole (1.20 g, 6.74 mmol, 1 eq) in carbon tetrachloride (20 mL) was added N-bromosuccinimide (1.2 g, 6.74 mmol, 1 eq) and benzoyl peroxide (172.7 mg, 0.67 mmol, 0.1 eq). The resulting solution was degassed three times with nitrogen and stirred for overnight at 85° C. The mixture was cooled to room temperature, diluted with water and extracted with ethyl acetate. The combined organic layer was washed with brine, dried over sodium sulfate and concentrated under reduced pressure. The residue was purified by silica gel column chromatography (compound was eluted in 50% ethyl acetate in petroleum ether) to obtain 5-bromo-3-(bromomethyl)-1,2-thiazole (144.1, 800 mg, 46%) as a light yellow solid. MS (ES): m/z 256/258/260 [M+H]$^+$.

Synthesis of 144.2. A stirred solution of 144.1 (800 mg, 3.11 mmol, 1 eq) and potassium phthalimide (1.15 g, 6.22 mmol, 2 eq) in N,N-dimethylformamide (5 mL) was stirred for 2 h at 90° C. The resulting mixture was cooled down to room temperature and purified by reverse flash chromatography with the following conditions: Column, C18 Column; Mobile Phase, water (10 mmol/L NH$_4$HCO$_3$) and ACN (30% ACN up to 80% in 20 min); UV detection at 254/220 nm. The product-containing fractions were combined and concentrated under reduced pressure to obtain 2-[(5-bromo-1,2-thiazol-3-yl)methyl]isoindole-1,3-dione (144.2, 360 mg, 35%) as a brown solid. MS (ES): m/z 323/325 [M+H]$^+$.

Synthesis of 144.3. To a stirred solution of 144.2 (360 mg, 1.11 mmol, 1 eq) in ethanol (5 mL) were added hydrazine hydrate (278.8 mg, 5.57 mmol, 5 eq). The resulting solution was stirred at room temperature for 16 h. The residue was purified by reverse flash chromatography with the following conditions Column, C18 Column; Mobile Phase, water (0.1% FA) and ACN (10% ACN up to 40% in 20 min); UV detection at 254/220 nm. The product-containing fractions were combined and concentrated under reduced pressure to obtain 1-(5-bromo-1,2-thiazol-3-yl)methanamine (144.3, 120 mg, 55%) as a brown oil. MS (ES): m/z 193/195 [M+H]$^+$.

Synthesis of 144.4. To a solution of 144.3 (110 mg, 0.57 mmol, 1 eq) and 15.7 (140 mg) in dichloromethane (4 mL) was added N, N-diisopropylethylamine (221 mg, 1.7 mmol, 3 eq) and 2-(-7-azabenzotriazol-1-yl)-N, N, N', N'-tetramethyluronium hexafluorophosphate (260 mg, 0.68 mmol, 1.2 eq) at room temperature. The resulting solution was stirred for 2 h at room temperature. The resulting mixture was diluted with water and extracted with dichloromethane. The combined organic layers were washed with brine, and dried over anhydrous sodium sulfate. After filtration, the filtrate was concentrated under reduced pressure and purified by Prep-TLC to obtain N-[(5-bromo-1,2-thiazol-3-yl)methyl]-5-(6-ethoxypyrazin-2-yl)pyridine-2-carboxamide (144.4, 130 mg, 54%) as a white solid. MS (ES): m/z 420 [M−H]$^−$.

Synthesis of I-284. To a solution of 144.4 (100 mg, 0.23 mmol, 1 eq), potassium phosphate (151 mg, 0.71 mmol, 3 eq) and cyclopropanesulfonamide (86 mg, 0.71 mmol, 3 eq) in tert-butyl alcohol (5 mL) was added t-BuBrettphos (23 mg, 0.05 mmol, 0.2 eq) and Pd$_2$(dba)$_3$ (22 mg, 0.02 mmol, 0.1 eq). The resulting solution was degassed three times with nitrogen and stirred for overnight at 100° C. After completion, the reaction mixture was concentrated under reduced pressure and purified by Prep-HPLC with the following conditions: Column: Sunfire Prep C18 OBD Column, 19*250 mm, 10 μm; mobile phase, water (0.1% FA) and ACN (35% ACN up to 60% in 7 min); UV detection at 254/220 nm. The desired fractions were combined and evaporated to afford N-[(5-cyclopropanesulfonamido-1,2-thiazol-3-yl)methyl]-5-(6-ethoxypyrazin-2-yl)pyridine-2-carboxamide (I-284, 20 mg, 18%) as a white solid. MS (ES): m/z 461 [M+H]$^+$; $^1$H NMR (300 MHz, DMSO-d$_6$) δ 11.46 (s, 1H), 9.45 (t, J=6.2 Hz, 1H), 9.38 (d, J=1.5 Hz, 1H), 9.01 (s, 1H), 8.71-8.68 (m, 1H), 8.37 (s, 1H), 8.20 (d, J=8.2 Hz, 1H), 6.75 (s, 1H), 4.59-4.40 (m, 4H), 2.85-2.73 (m, 1H), 1.42 (t, J=7.0 Hz, 3H), 1.09-0.95 (m, 4H).

Example 147: Synthesis of N-[(6-cyclopropanesulfonamidopyridazin-4-yl)methyl]-5-(6-ethoxypyrazin-2-yl)pyridine-2-carboxamide (I-246)

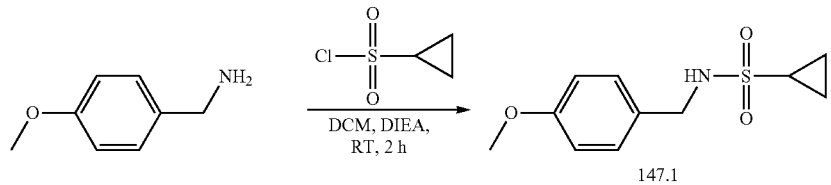

147.1

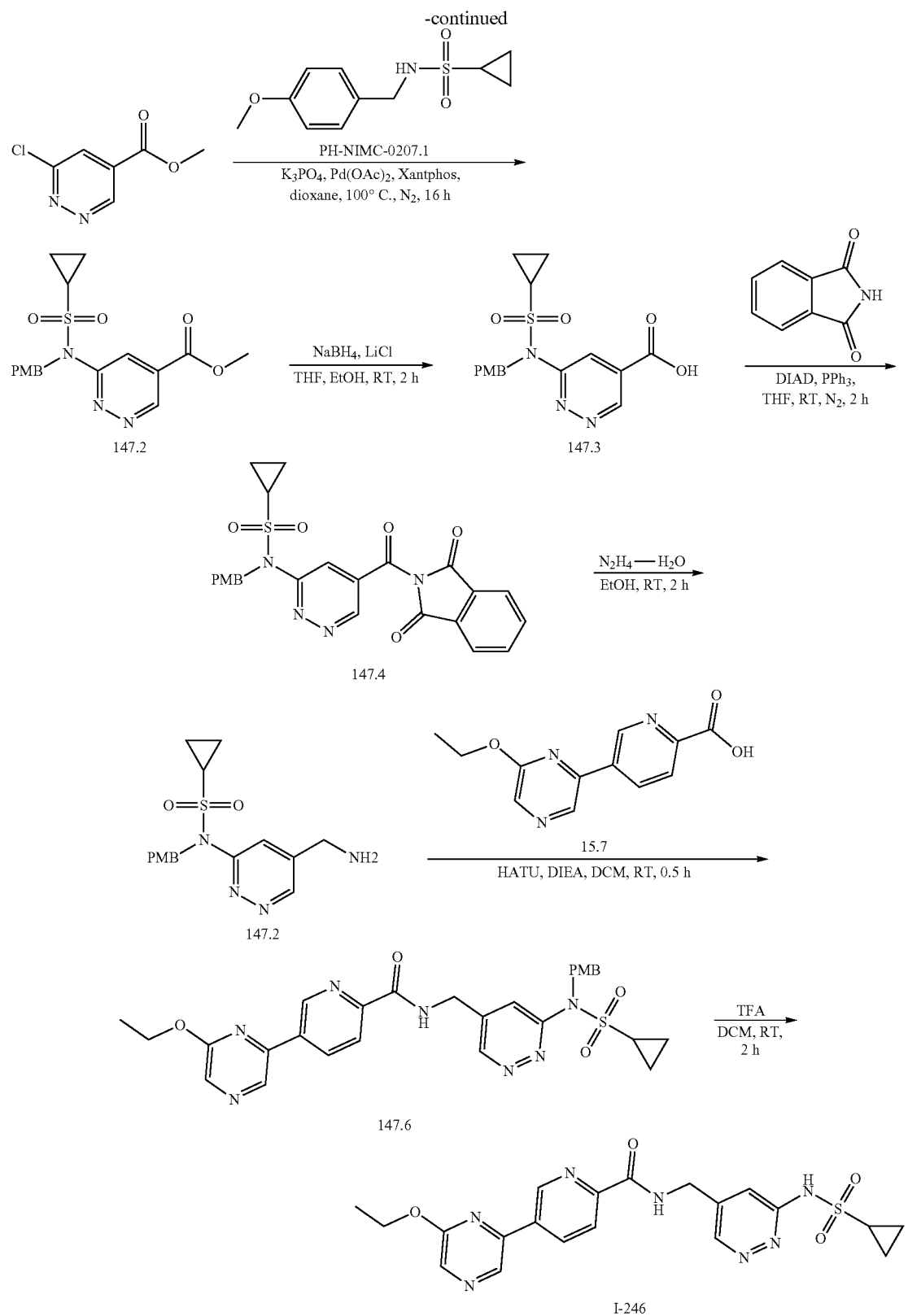
Synthesis of 147.1. To a stirred solution of (4-methoxyphenyl)methanamine (13.7 g, 100 mmol, 1 eq) in dichloromethane (100 mL) was added N,N-diisopropylethylamine (38.7 g, 300 mmol, 3 eq). The resulting solution was cooled to 0° C., to the above mixture was added cyclopropanesulfonyl chloride (21 g, 150 mmol, 1.5 eq). The resulting solution was degassed three times with nitrogen and stirred for 2 h at room temperature. The mixture was diluted with water and extracted with dichloromethane. The combined organic layer was washed with brine, dried over sodium sulfate and concentrated under reduced pressure. The residue was purified by silica gel column chromatography (compound was eluted in 20% ethyl acetate in petroleum ether) to obtain N-(4-methoxybenzyl)cyclopropanesulfonamide (147.1, 18 g, 75%) as a white solid. MS (ES): m/z 240 [M−H]⁻.

Synthesis of compound 147.2. To a stirred solution of methyl 6-chloropyridazine-4-carboxylate (600 mg, 3.48 mmol, 1 eq) and 147.1 (1.26 g, 5.23 mmol, 1.5 eq) in 1,4-dioxane (18 mL) was added potassium phosphate (1.48 g, 6.95 mmol, 2 eq), palladium acetate (78 mg, 0.35 mmol, 0.1 eq) and XantPhos (402 mg, 0.70 mmol, 0.2 eq). The resulting solution was degassed three times with nitrogen and stirred for overnight at 100° C. The mixture was cooled to room temperature, diluted with water and extracted with ethyl acetate. The combined organic layer was washed with brine, dried over sodium sulfate and concentrated under reduced pressure. The residue was purified by Prep-TLC (petroleum ether/ethyl acetate=2/1) to afford methyl 6-[N-[(4-methoxyphenyl)methyl]cyclopropanesulfonamido]pyridazine-4-carboxylate (147.2, 750 mg, 57%) as a yellow oil. MS (ES): m/z 378 [M+H]⁺.

Synthesis of 147.3. To a stirred solution of 147.2 (750 mg, 2 mmol, 1 eq) in tetrahydrofuran (15 mL) and methanol (1.5 mL) was added lithium chloride (168 mg, 4 mmol, 2 eq) and sodium borohydride (301 mg, 8 mmol, 4 eq). The resulting mixture was stirred for 2 h at room temperature. The reaction was quenched by ammonium chloride solution at 0° C. The resulting mixture was extracted with ethyl acetate, the combined organic layer was washed with brine, dried over sodium sulfate and concentrated under reduced pressure. The residue was purified by Prep-TLC (petroleum ether/ethyl acetate=1/1) to afford N-[5-(hydroxymethyl)pyridazin-3-yl]-N-[(4-methoxyphenyl)methyl] cyclopropanesulfonamide (147.3, 261 mg, 37%) as a yellow oil. MS (ES): m/z 350 [M+H]⁺.

Synthesis of compound 147.4. To a stirred solution of diisopropyl azodicarboxylate (181 mg, 0.9 mmol, 1.2 eq) in tetrahydrofuran (4 mL) was added triphenylphosphine (235 mg, 0.9 mmol, 1.2 eq). The resulting solution was degassed three times with nitrogen and stirred for 0.5 h at room temperature. To the above mixture was added 147.3 (261 mg, 0.75 mmol, 1 eq) and phthalimide (110 mg, 0.75 mmol, 1 eq). The resulting mixture was stirred for additional 16 h at room temperature. The mixture was 74444 diluted with water and extracted with ethyl acetate. The combined organic layer was washed with brine, dried over sodium sulfate and concentrated under reduced pressure. The residue was purified by Prep-TLC (dichlormethane/methanol=15/1) to afford N-[5-[(1,3-dioxoisoindol-2-yl)methyl]pyridazin-3-yl]-N-[(4-methoxyphenyl)methyl]cyclopropanesulfonamide (147.4, 380 mg, crude) as a yellow oil. MS (ES): m/z 479 [M+H]⁺.

Synthesis of 147.5. 147.5 was synthesized from 147.4 in a manner similar to that described in the synthesis of 144.3. MS (ES): m/z 349 [M+H]⁺.

Synthesis of 147.6. 147.6 was synthesized from 147.5 in a manner similar to that described in the synthesis of 144.4. MS (ES): m/z 576 [M+H]⁺.

Synthesis of I-246. To a stirred solution of 147.6 (48 mg, 0.09 mmol, 1 eq) in dichloromethane (1.5 mL) was added trifluoroacetic acid (1.5 mL). The resulting mixture was stirred for 2 h at room temperature. The residue was concentrated under reduced pressure and purified by Prep-HPLC with the following conditions: Column: SunFire Prep C18 OBD Column, 19×150 mm 5 um 10 nm; Mobile Phase: Water (0.1% FA) and ACN (20% ACN to 50% in 7 min), UV detection at 254/210 nm. The product-containing fractions were combined and evaporated partially in vacuum and lyophilized overnight to afford N-[(6-cyclopropanesulfonamidopyridazin-4-yl)methyl]-5-(6-ethoxypyrazin-2-yl)pyridine-2-carboxamide (I-246, 8 mg, 20%) as a white solid. MS (ES): m/z 456 [M+H]⁺; ¹H NMR (400 MHz, DMSO-d₆) δ 9.63 (t, J=6.2 Hz, 1H), 9.38 (s, 1H), 9.01 (s, 1H), 8.70 (dd, J=8.3, 2.3 Hz, 1H), 8.37 (s, 2H), 8.18 (d, J=8.2 Hz, 1H), 7.65 (s, 1H), 4.54-4.48 (m, 4H), 2.70-2.62 (m, 1H), 1.42 (t, J=7.0 Hz, 3H), 0.98-0.78 (m, 4H).

Example 148: Synthesis of Synthesis of N-[(4-cyclopropanesulfonamido-1,3-thiazol-2-yl)methyl]-5-(6-ethoxypyrazin-2-yl)pyridine-2-carboxamide (I-195)

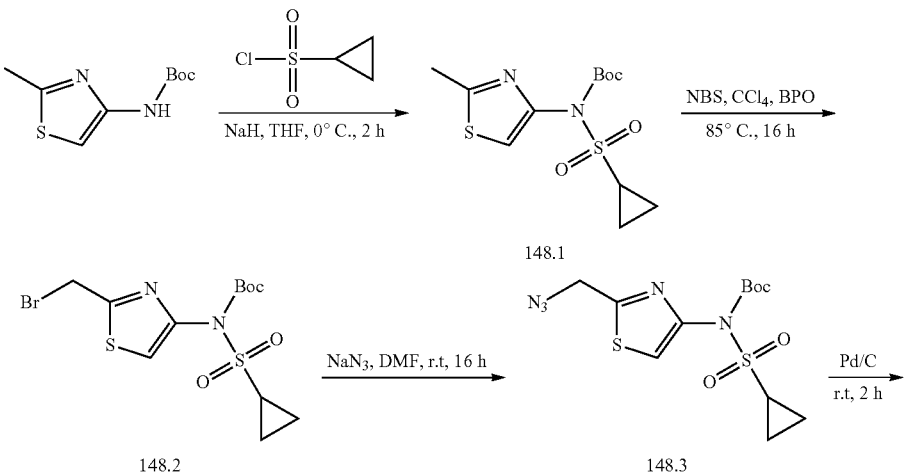

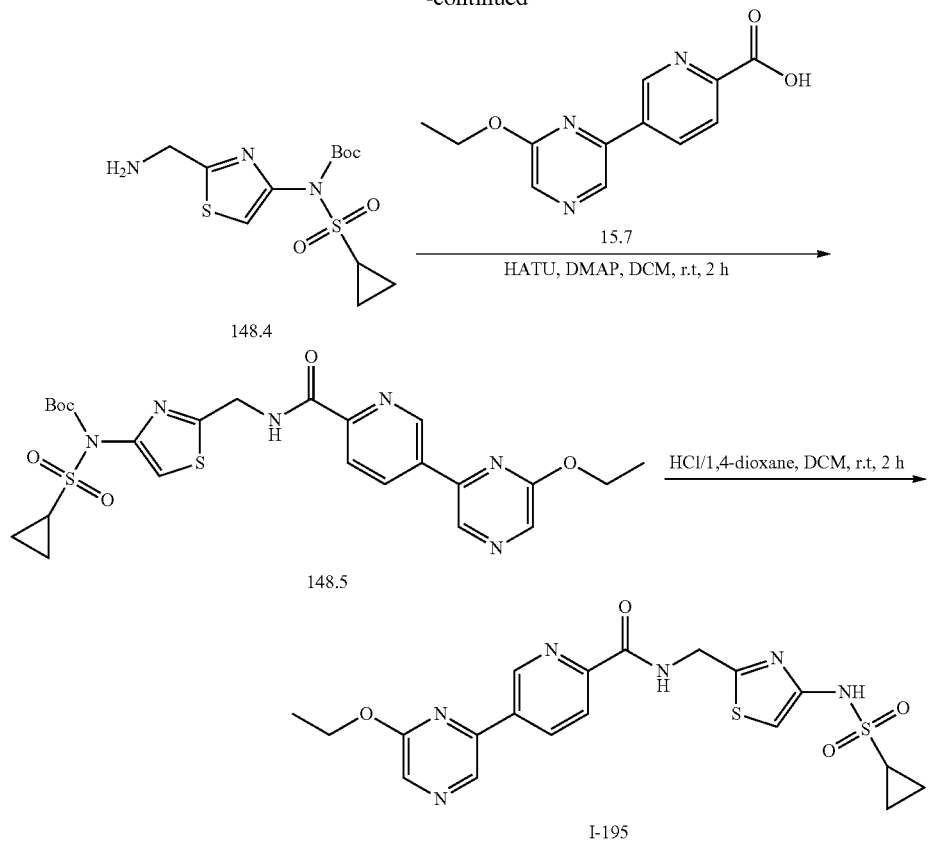

Synthesis of 148.1. A stirred mixture of tert-butyl N-(2-methyl-1,3-thiazol-4-yl)carbamate (1 g, 4.67 mmol, 1 eq) in tetrahydrofuran (20 mL) was degassed three times with nitrogen and cooled to 0° C. To the solution was added sodium hydride (467 mg, 60% w/w in mineral oil, 11.67 mmol, 2.5 eq), stirred for 30 min at 0° C. under nitrogen atmosphere. To the above mixture was added cyclopropanesulfonyl chloride (0.98 g, 7.00 mmol, 1.5 eq) at 0° C. The resulting mixture was stirred for additional 1 h at room temperature under nitrogen atmosphere. The reaction was quenched with ammonium chloride, extracted with ethyl acetate. The combined organic layers were washed with water, dried over anhydrous sodium sulfate. After filtration, the filtrate was concentrated under reduced pressure and purified by Prep-TLC (petroleum ether/ethyl acetate=1:1) to obtain tert-butyl N-(cyclopropanesulfonyl)-N-(2-methyl-1,3-thiazol-4-yl)carbamate (148.1, 826 mg, 55%) as a yellow solid. MS (ES): m/z 319 [M+H]$^+$.

Synthesis of 148.2. 148.2 was synthesized from 148.1 in a manner similar to that described in the synthesis of 144.1. MS (ES): m/z 398 [M+H]$^+$.

Synthesis of 148.3. To a stirred mixture of 148.2 (440 mg, 1.11 mmol, 1 eq) in N, N-dimethyl formamide (6 mL) was added sodium azide (86 mg, 1.33 mmol, 1.2 eq). The resulting mixture was degassed three times with nitrogen and stirred for 2 h at room temperature under nitrogen atmosphere. The mixture was diluted with water and extracted with ethyl acetate. The combined organic layer was washed with brine, and dried over sodium sulfate. After filtration, the filtrate was concentrated under reduced pressure to 8 afford tert-butyl N-[2-(azidomethyl)-1,3-thiazol-4-yl]-N-(cyclopropanesulfonyl)carbamate (148.3, 410 mg, crude) as a yellow oil. MS (ES): m/z 360 [M+H]$^+$.

Synthesis of 148.4. A stirred mixture of 148.3 (410 mg) in methanol (10 mL) was flushed three times with nitrogen. To the solution was added palladium 10% on carbon (100 mg) and the reaction mixture was flushed with nitrogen and hydrogen. The mixture was stirred for 2 h at room temperature under an atmosphere of hydrogen. The solids were filtered out and the filtrate was concentrated under reduced pressure to afford tert-butyl N-[2-(aminomethyl)-1,3-thiazol-4-yl]-N-(cyclopropanesulfonyl)carbamate (148.4, 380 mg, crude) as a yellow solid. MS (ES): m/z 334 [M+H]$^+$.

Synthesis of 148.5. 148.5 was synthesized from 148.4 in a manner similar to that described in the synthesis of 144.4. MS (ES): m/z 561 [M+H]$^+$.

Synthesis of I-195. To a stirred mixture of 148.5 (70 mg, 0.12 mmol, 1 eq) in dichloromethane (2 mL) was added hydrochloric acid in 1,4-dioxane (4 M, 2 mL). The resulting mixture was stirred for 2 h at room temperature. The resulting mixture was concentrated under reduced pressure and purified by Prep-HPLC with the following conditions: Column, C18 Column; Mobile Phase, water (10 mmol/L NH$_4$HCO$_3$) and ACN (30% ACN up to 44% in 10 min); UV detection at 254/220 nm. The product-containing fractions were combined and evaporated partially in vacuum and lyophilized overnight to afford N-[(4-cyclopropanesulfonamido-1,3-thiazol-2-yl)methyl]-5-(6-ethoxypyrazin-2-yl)pyridine-2-carboxamide (I-195, 9.3 mg, 16%) as a white solid. MS (ES): m/z 461 [M+H]$^+$; $^1$H NMR (300 MHz, DMSO-d$_6$) δ 10.10-9.69 (m, 2H), 9.39 (s, 1H), 9.01 (s, 1H), 8.76-8.63 (m, 1H), 8.37 (s, 1H), 8.26-8.19 (m, 1H), 6.85 (s, 1H), 4.82-4.71 (m, 2H), 4.59-4.45 (m, 2H), 2.74 (s, 1H), 1.42 (t, J=7.0 Hz, 3H), 1.09-0.84 (m, 4H).

Example 149: Synthesis of N-[1-[3-(difluoromethanesulfonamido)phenyl]cyclopropyl]-1-(6-ethoxypyrazin-2-yl)pyrazole-4-carboxamide (I-274)

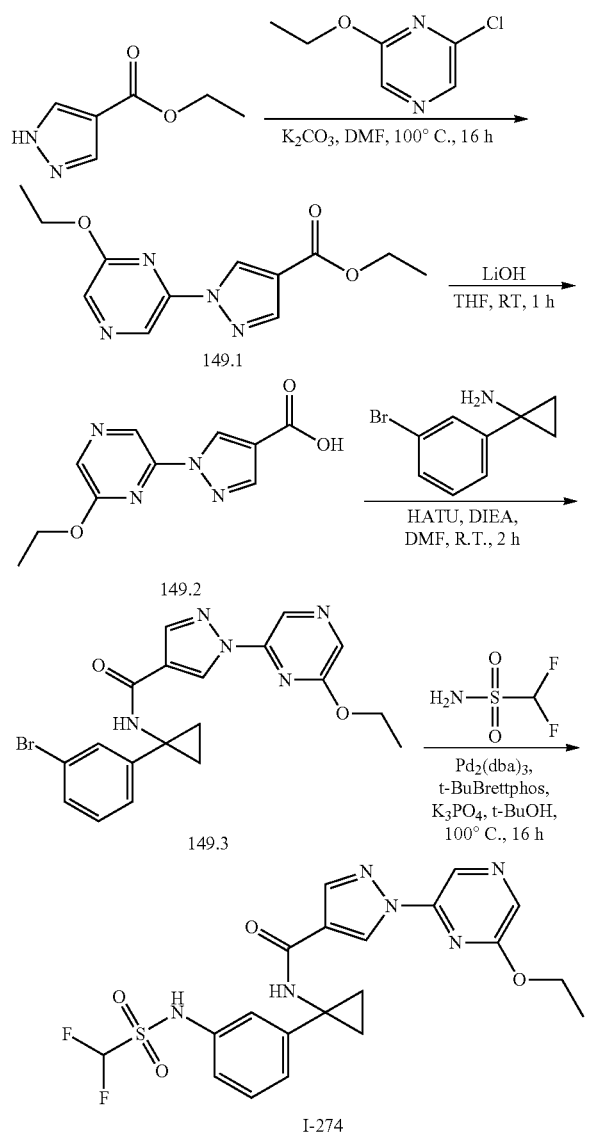

Synthesis of 149.1 To a stirred solution of ethyl 1H-pyrazole-4-carboxylate (1 g, 7.14 mmol, 1 eq) in N,N-dimethylformamide (40 mL) was added potassium carbonate (2.9 g, 21.4 mmol, 3 eq) and 2-chloro-6-ethoxy-pyrazine (1.4 g, 8.55 mmol, 1.2 eq) at room temperature. The resulting mixture was stirred for 16 h at 100° C. The mixture was cooled to room temperature, purified by reverse flash chromatography (compound was eluted in 80% acetonitrile in water) to obtain ethyl 1-(6-ethoxypyrazin-2-yl)-1H-pyrazole-4-carboxylate (149.1, 1.15 g, 61%) as white solid. MS (ES): m/z 263 [M+H]+.

Synthesis of 149.2. To a stirred mixture of 149.1 (262 mg, 1.0 mmol, 1 eq) in tetrahydrofuran (5 mL) was added lithium hydroxide (48 mg, 2.0 mmol, 2 eq) in water (1 mL). The mixture was stirred for 1 h at room temperature. The residue was diluted with water. The pH value of the solution was adjusted to 3 with 1M aqueous hydrochloric acid. The solids were collected by filtration to obtain the crude product 1-(6-ethoxypyrazin-2-yl)pyrazole-4-carboxylic acid (149.2, 270 mg) which was used in the next step directly without further purification.

Synthesis of 149.3. To a stirred mixture of 149.2 (270 mg) and 1-(3-bromophenyl)cyclopropan-1-amine (244 mg, 1.15 mmol, 1 eq) in N,N-dimethylformamide (5 mL) were added N, N-diisopropylethylamine (179 mg, 1.38 mmol, 1.2 eq) and 2-(-7-azabenzotriazol-1-yl)-N, N, N', N'-tetramethyluronium hexafluorophosphate (1.75 g, 4.62 mmol, 4 eq). The resulting mixture was stirred for 2 h at room temperature. The mixture was purified by reverse flash chromatography with the following conditions: Column, C18 silica gel; mobile phase, ACN in water, 10% to 50% gradient in 25 min; detector, UV 254 nm. The mixture was concentrated under vacuum to obtain N-[1-(3-bromophenyl)cyclopropyl]-1-(6-ethoxypyrazin-2-yl)pyrazole-4-carboxamide (149.3, 130 mg, 26%) as a light yellow solid. MS (ES): m/z 428/430 [M+H]+.

Synthesis of I-274. To a stirred mixture of 149.3 (100 mg, 0.23 mmol, 1 eq) and difluoromethanesulfonamide (61 mg, 0.47 mmol, 2 eq) in tert-butyl alcohol (3 mL) was added potassium carbonate (149 mg, 0.75 mmol, 3 eq), Pd$_2$(dba)$_3$ (21.4 mg, 0.02 mmol, 0.1 eq) and t-BuBrettphos (25.1 mg, 0.05 mmol, 0.2 eq). The resulting solution was degassed three times with nitrogen and stirred for overnight at 100° C. The mixture was cooled to room temperature, concentrated under reduced pressure and purified by reverse phase flash with the following conditions: Column, C18 Column; Mobile Phase, water (0.1% FA) and ACN (10% up to 50% in 20 min); UV detection at 254/220 nm. The product-containing fractions were combined and concentrated under reduced pressure. The crude product was purified by Prep-HPLC with the following conditions: Column, Sunfire prep C18 column, 30*150 mm, 5 μm; Mobile Phase: Water (0.1% FA) and: ACN (40% ACN up to 70% in 7 min) UV detection at 254/220 nm. The product-containing fractions were combined and evaporated partially in vacuum and lyophilized overnight to afford N-[1-[3-(difluoromethanesulfonamido)phenyl]cyclopropyl]-1-(6-ethoxypyrazin-2-yl)pyrazole-4-carboxamide (I-274, 8.1 mg, 7.25%) as a white solid. MS (ES): m/z 479 [M+H]+. 1H NMR (400 MHz, CD$_3$OD) δ 9.13 (s, 1H), 8.77 (s, 1H), 8.22 (d, J=3.6 Hz, 2H), 7.32-7.22 (m, 2H), 7.15-7.05 (m, 2H), 6.76-6.46 (t, J=53.2, 53.2 Hz, 1H), 4.55 (q, J=7.1 Hz, 2H), 1.49 (t, J=7.1 Hz, 3H), 1.45-1.31 (m, 4H).

Example 150: Synthesis of N-(1-(3-(((difluoromethyl)sulfonamido)phenyl)cyclopropyl)-5-(6-ethoxypyrazin-2-yl)thiophene-2-carboxamide (I-269)

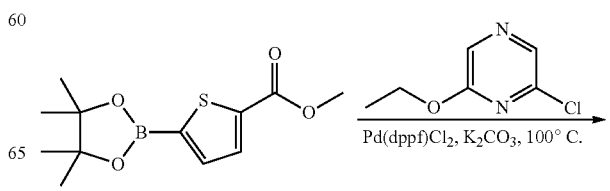

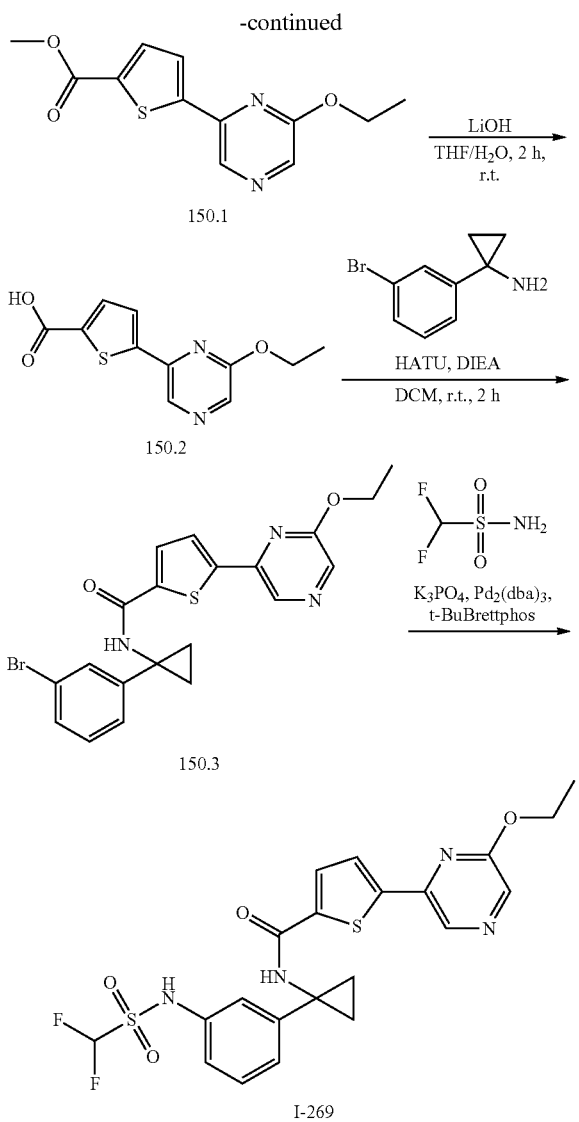

MS (ES): m/z 495 [M+H]+; ¹H NMR (400 MHz, Methanol-d₄) δ 8.63 (s, 1H), 8.10 (s, 1H), 7.83-7.76 (m, 2H), 7.32-7.21 (m, 2H), 7.16-7.07 (m, 2H), 6.62 (t, J=52.8, 53.2 Hz, 1H), 4.50 (q, J=7.1 Hz, 2H), 1.46 (t, J=7.1 Hz, 3H), 1.43-1.32 (m, 4H).

Example 151: Synthesis of N-[1-[3-(difluoromethanesulfonamido)phenyl]cyclopropyl]-1-(6-ethoxypyrazin-2-yl)pyrazole-3-carboxamide (I-282)

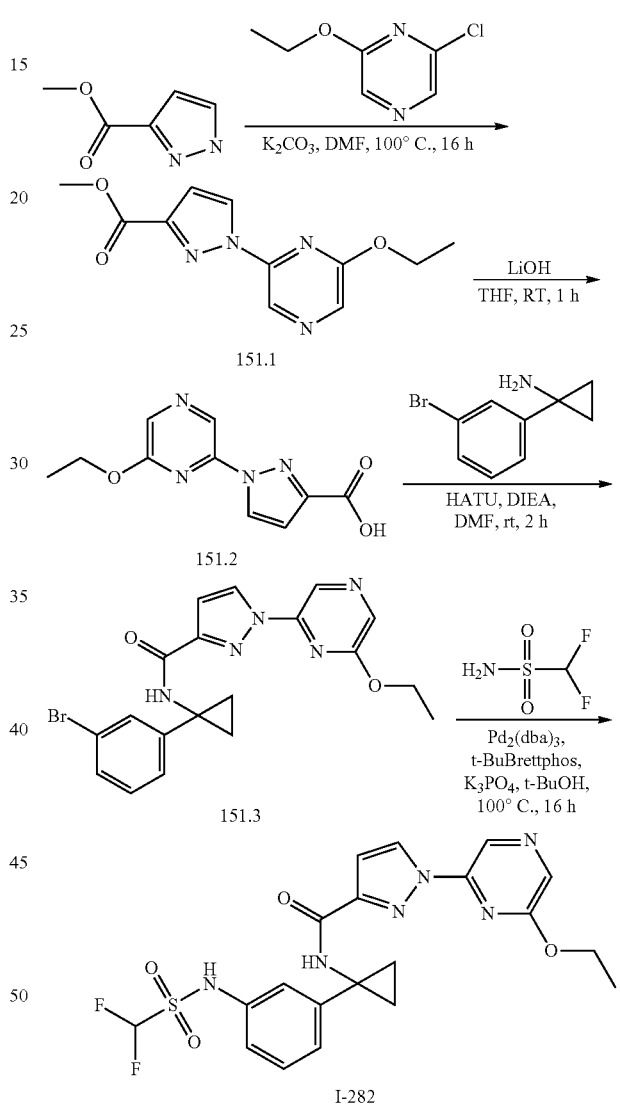

Synthesis of 150.1. To a solution of methyl 5-(4,4,5,5-tetramethyl-1,3,2-dioxaborolan-2-yl)thiophene-2-carboxylate (268 mg, 1 mmol, 1 eq) and 2-chloro-6-ethoxypyrazine (158 mg, 1 mmol, 1 eq) in 1,4-dioxane (8 mL) and water (2 mL) was added potassium carbonate (414 mg, 3 mmol, 3 eq) and Pd(dppf)Cl₂ (76 mg, 0.1 mmol, 0.1 eq). The resulting solution was degassed three times with nitrogen and stirred for 2 h at 100° C. The mixture was cooled to room temperature, and diluted with water. The resulting mixture was extracted with ethyl acetate. The combined organic layers were washed with brine, dried over anhydrous sodium sulfate and concentrated under reduced pressure. The resulting mixture was purified by Prep-TLC, eluted with petroleum ether/ethyl acetate=1/1 to afford methyl 5-(6-ethoxypyrazin-2-yl) thiophene-2-carboxylate (150.1, 123 mg, 46%) as a white solid. MS (ES): m/z 265 [M+H]⁺.

Synthesis of 150.2. 150.2 was synthesized from 150.1 in a manner similar to that described in the synthesis of 149.2. MS (ES): m/z 251 [M+H]⁺.

Synthesis of 150.3. 150.3 was synthesized from 150.2 in a manner similar to that described in the synthesis of 150.3. MS (ES): m/z 444 [M+H]⁺.

Synthesis of I-269. I-269 was synthesized from 150.3 in a manner similar to that described in the synthesis of I-274.

Synthesis of I-282. I-282 was synthesized from methyl 1H-pyrazole-3-carboxylate in a manner similar to that described in the synthesis of I-274. MS (ES): m/z 479, ¹H NMR (400 MHz, CD₃OD) δ 8.89 (s, 1H), 8.62 (d, J=2.7 Hz, 1H), 8.18 (s, 1H), 7.31-7.21 (m, 2H), 7.13-7.09 (m, 2H), 6.98 (d, J=2.7 Hz, 1H), 6.59 (t, J=70.8, 70.8 Hz, 1H), 4.54 (q, J=7.1 Hz, 2H), 1.53-1.29 (m, 7H).

Example 152: Synthesis of N-[1-[3-(difluoromethanesulfonamido)phenyl]cyclopropyl]-1-(6-ethoxypyrazin-2-yl)imidazole-4-carboxamide (I-283)

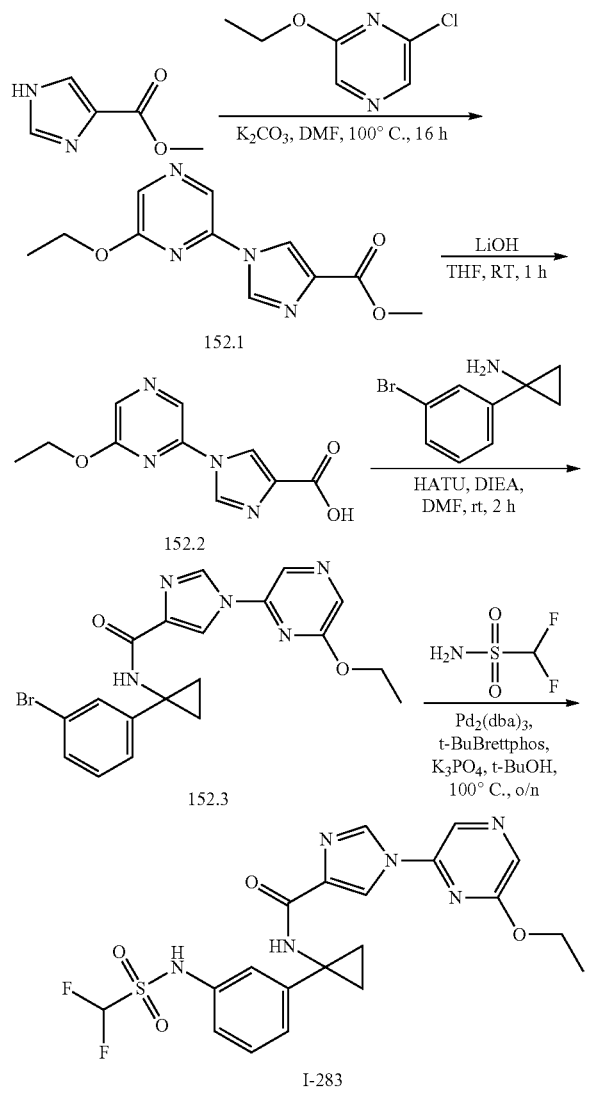

Synthesis of 152.1. To a stirred solution of methyl 1H-imidazole-4-carboxylate (900 mg, 7.14 mmol, 1 eq) in N,N-dimethylformamide (40 mL) was added potassium carbonate (2.9 g, 21.4 mmol, 3 eq) and 2-chloro-6-ethoxy-pyrazine (1.4 g, 8.55 mmol, 1.2 eq) at room temperature. The resulting mixture was stirred 16 h at 100° C. The mixture was cooled to room temperature, purified by reverse flash chromatography (compound was eluted in 84% acetonitrile in water) to obtain methyl 1-(6-ethoxypyrazin-2-yl)-1H-imidazole-4-carboxylate (152.1, 1.05 g, 59%) as white solid. MS (ES): m/z 249 [M+H]$^+$.

Synthesis of 152.2. To a stirred mixture of 152.1 (248 mg, 1.0 mmol, 1 eq) in tetrahydrofuran (5 mL) was added lithium hydroxide (48 mg, 2.0 mmol, 2 eq) in water (1 mL). The mixture was stirred for 1 h at room temperature. The residue was diluted with water. The pH value of the solution was adjusted to 3 with 1N aqueous hydrochloric acid. The solids were collected by filtration to obtain the crude product 1-(6-ethoxypyrazin-2-yl)-1H-imidazole-4-carboxylic acid (152.2, 200 mg), which was used in the next step directly without further purification. MS (ES): m/z 235 [M+H]$^+$.

Synthesis of 152.3. To a stirred mixture of 152.2 (100 mg) and 1-(3-bromophenyl)cyclopropan-1-amine (91 mg, 0.42 mmol, 1 eq) in N,N-dimethylformamide (5 mL) were added N,N-diisopropylethylamine (65 mg, 0.50 mmol, 1.2 eq) and 2-(-7-azabenzotriazol-1-yl)-N, N, N', N'-tetramethyluronium hexafluorophosphate (636 mg, 1.68 mmol, 4 eq). The resulting mixture was stirred for 2 h at room temperature. The mixture was purified by reverse flash chromatography with the following conditions: column, C18 silica gel; mobile phase, ACN in water, 10% to 50% gradient in 25 min; detector, UV 254 nm. The mixture was concentrated under vacuum to obtain N-(1-(3-bromophenyl)cyclopropyl)-1-(6-ethoxypyrazin-2-yl)-1H-imidazole-4-carboxamide (152.3, 122 mg, 67%) as a light yellow solid. MS (ES): m/z 428/430[M+H]$^+$.

Synthesis of I-283. To a stirred mixture of 152.3 (100 mg, 0.23 mmol, 1 eq) and difluoromethanesulfonamide (61 mg, 0.47 mmol, 2 eq) in tert-butyl alcohol (3 mL) was added potassium carbonate (149 mg, 0.75 mmol, 3 eq), Pd$_2$(dba)$_3$ (21.4 mg, 0.02 mmol, 0.1 eq) and t-BuBrettphos (25.1 mg, 0.05 mmol, 0.2 eq). The resulting solution was degassed three times with nitrogen and stirred for overnight at 100° C. The mixture was cooled to room temperature, concentrated under reduced pressure and purified by reverse phase flash chromatography with the following conditions: Column, C18 Column; Mobile Phase, water (0.1% FA) and ACN (10% up to 50% in 20 min); UV detection at 254/220 nm. The product-containing fractions were combined and concentrated under reduced pressure. The crude product was purified by Prep-HPLC with the following conditions: Column: Sunfire prep C18 column, 30*150 mm, 5 µm; Mobile Phase: Water (0.1% FA) and: ACN (30% ACN up to 60% in 7 min) UV detection at 254/220 nm. The product-containing fractions were combined and evaporated partially in vacuum and lyophilized overnight to afford N-[1-[3-(difluoromethanesulfonamido)phenyl]cyclopropyl]-1-(6-ethoxypyrazin-2-yl)imidazole-4-carboxamide (I-283, 7 mg, 6%) as a white solid. MS (ES): m/z 479 [M+H]+; $^1$H NMR (400 MHz, CD$_3$OD) δ 8.63-8.55 (m, 2H), 8.45 (s, 1H), 8.24 (s, 1H), 7.31-7.20 (m, 2H), 7.16-7.05 (m, 2H), 6.61 (t, J=52.8, 53.2 Hz, 1H), 4.54 (q, J=7.0 Hz, 2H), 1.48 (t, J=7.1 Hz, 3H), 1.47-1.29 (m, 4H).

Example 153: Synthesis of N-[1-[3-(difluoromethanesulfonamido)phenyl]cyclopropyl]-5-(6-ethoxypyrazin-2-yl)pyridine-2-carboxamide (I-265)

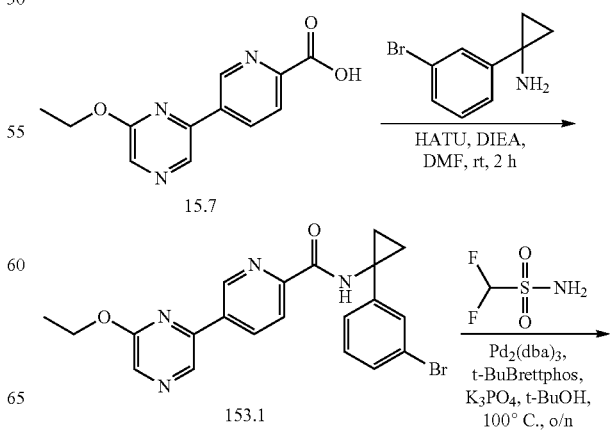

-continued

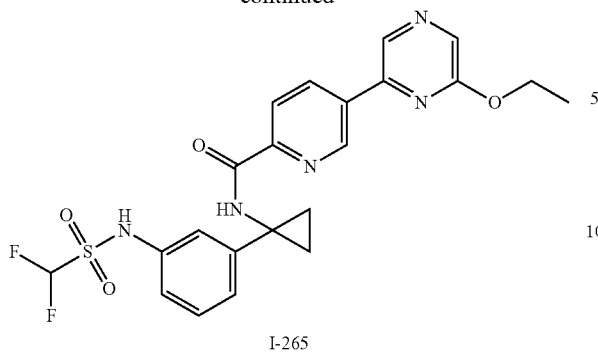

I-265

Synthesis of I-265. I-265 was synthesized from 15.7 in a manner similar to that described in the synthesis of I-274 (step 3 and 4). MS (ES): m/z 490 [M+H]+; ¹H NMR (400 MHz, CD₃OD) δ 9.36 (d, J=1.6 Hz, 1H), 8.80 (s, 1H), 8.65 (dd, J=8.2, 2.2 Hz, 1H), 8.27-8.19 (m, 2H), 7.29-7.21 (m, 2H), 7.12-7.05 (m, 2H), 6.58 (t, J=52.8, 53.2 Hz, 1H), 4.58 (q, J=7.1 Hz, 2H), 1.55-1.33 (m, 7H).

Example 154: Synthesis of N-(1-(3-((difluoromethyl)sulfonamido)phenyl)cyclopropyl)-4-(6-ethoxypyrazin-2-yl)benzamide (I-266)

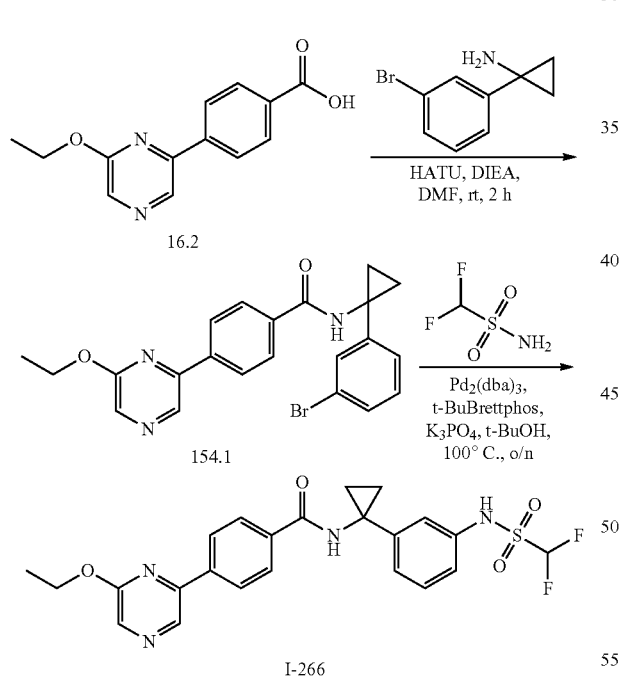

Synthesis of I-266. I-266 was synthesized from 16.2 in a manner similar to that described in the synthesis of I-274 (step 3 and 4). MS (ES): m/z 489 [M+H]+; ¹H NMR (400 MHz, DMSO-d₆) δ 8.73 (s, 1H), 8.23 (d, J=8.8 Hz, 2H), 8.18 (s, 1H), 8.01 (d, J=8.4 Hz, 2H), 7.33-7.27 (m, 2H), 7.15-7.09 (m, 2H), 6.62 (t, J=53.2, 53.2 Hz, 1H), 4.63-4.55 (m, 2H), 1.49 (t, J=7.1 Hz, 3H), 1.43-1.39 (m, 4H).

Example 155: Synthesis of N-[1-[3-(difluoromethanesulfonamido)phenyl]cyclopropyl]-4-(6-ethoxypyrazin-2-yl)-2-fluorobenzamide (I-267)

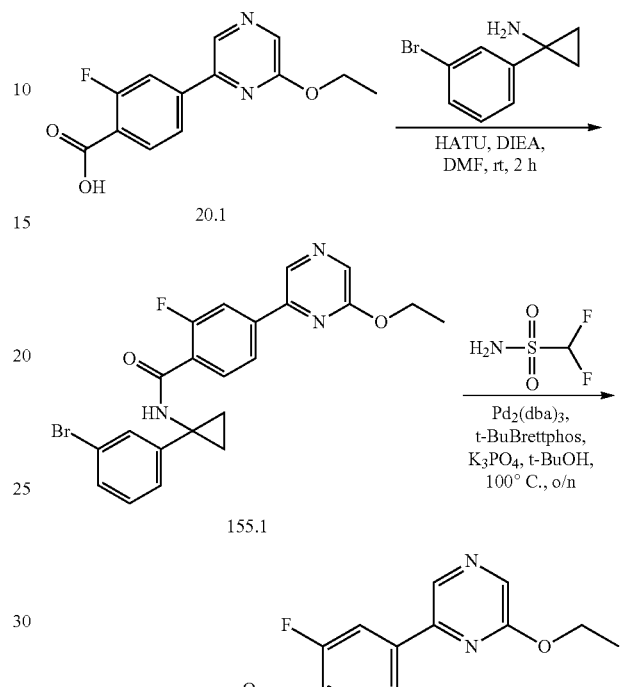

Synthesis of I-267. I-267 was synthesized from 20.1 in a manner similar to that described in the synthesis of I-274 (step 3 and 4). MS (ES): m/z 507 [M+H]+; ¹H NMR (400 MHz, CD₃OD) δ 8.75 (s, 1H), 8.22 (s, 1H), 8.06-7.97 (m, 2H), 7.85 (t, J=7.7 Hz, 1H), 7.32-7.24 (m, 2H), 7.15-7.06 (m, 2H), 6.58 (t, J=53.2, 53.2 Hz, 1H), 4.57 (q, J=7.1 Hz, 2H), 1.49 (t, J=7.1 Hz, 3H), 1.43-1.33 (m, 4H).

Example 156: Synthesis of 5-[1-azaspiro[3.5]nonan-1-yl]-N-[(4-cyclopropanesulfonamidopyridin-2-yl)methyl]-6-methylpyrazine-2-carboxamide (I-279)

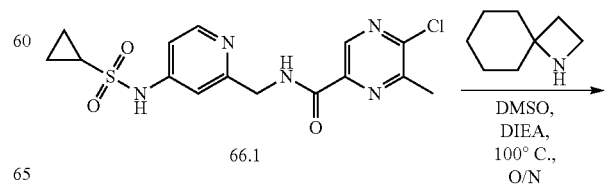

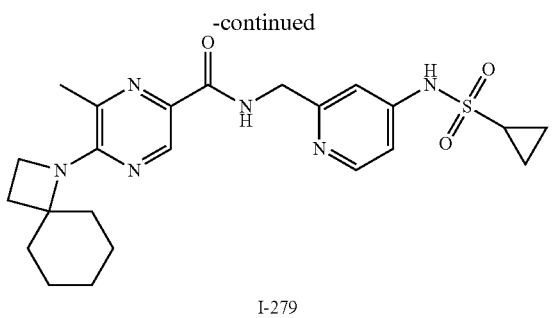

I-279

Synthesis of I-279. To a stirred mixture of 66.1 (50 mg, 0.13 mmol, 1 eq) and 1-azaspiro[3.5]nonane (16 mg, 0.13 mmol, 1 eq) in dimethysulfoxide (1 mL) was added N,N-diisopropylethylamine (85 mg, 0.65 mmol, 5 eq). The resulting mixture was stirred for overnight at 100° C. The mixture was purified by Prep-HPLC with the following conditions: Column: YMC-Actus Triart C18 ExRS, 30*250, 5 um; Mobile Phase, water (10 mmol/L NH$_4$HCO$_3$) and ACN (28% ACN up to 53% in 8 min); UV detection at 254/220 nm. The product-containing fractions were combined and evaporated partially in vacuum and lyophilized overnight to afford 5-[1-azaspiro[3.5]nonan-1-yl]-N-[(4-cyclopropanesulfonamidopyridin-2-yl)methyl]-6-methylpyrazine-2-carboxamide (I-279, 4.4 mg, 7.1%) as a white solid. MS (ES): m/z 471 [M+H]$^+$; $^1$H NMR (400 MHz, CD$_3$OD) δ 8.44 (s, 1H), 8.18 (d, J=6.0 Hz, 1H), 7.16 (d, J=2.3 Hz, 1H), 7.11 (dd, J=6.1, 2.3 Hz, 1H), 4.61 (s, 2H), 4.58-4.50 (m, 2H), 2.73-2.60 (m, 3H), 2.56 (s, 3H), 2.25-2.16 (m, 2H), 1.83 (d, J=12.6 Hz, 2H), 1.74 (d, J=13.4 Hz, 2H), 1.63 (d, J=12.8 Hz, 1H), 1.39-1.36 (m, 2H), 1.44-1.20 (m, 1H), 1.16-1.04 (m, 2H), 1.01-0.93 (m, 2H).

Example 157: Synthesis of N-[(4-cyclopropane-sulfonamidopyridin-2-yl)methyl]-1-(6-ethoxy-pyrazin-2-yl)pyrazole-4-carboxamide (I-244)

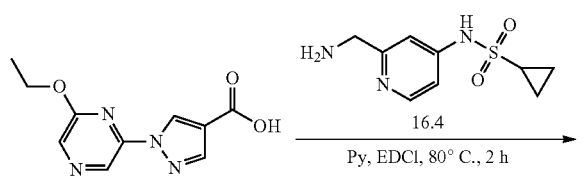

Synthesis of I-244. To a stirred solution of 149.2 (80 mg, 0.34 mmol, 1 eq) in pyridine (4 mL) was added 1-ethyl-3-(3-dimethylamino propyl) carbodiimide hydrochloride (131 mg, 0.68 mmol, 2 eq) and 16.4 (80 mg, 0.34 mmol, 1 eq). The resulting mixture was stirred for 2 h at 80° C. The resulting mixture was concentrated under reduced pressure. The residue was purified by reverse flash chromatography with the following conditions: Column, C18 Column; Mobile Phase, water (10 mmol/L NH$_4$HCO$_3$) and ACN (10% ACN up to 70% in 20 min); UV detection at 254/220 nm. The product-containing fractions were combined and concentrated under reduced pressure to afford the crude product. The crude product was purified by Prep-HPLC with the following conditions Column, XBridge Prep C18 OBD Column, 30*100 mm, 5 Im; Mobile Phase: Water (10 mmol/L NH$_4$HCO$_3$) and: ACN (10% ACN up to 40% in 7 min) UV detection at 254/220 nm. The product-containing fractions were combined and evaporated partially in vacuum and lyophilized overnight to afford N-[(4-cyclopropane-sulfonamidopyridin-2-yl)methyl]-1-(6-ethoxypyrazin-2-yl)pyrazole-4-carboxamide (I-244, 20 mg, 13%) as a purple solid. MS (ES): m/z 444 [M+H]$^+$. $^1$H NMR (400 MHz, Methanol-d$_4$) δ 9.13 (s, 1H), 8.78 (s, 1H), 8.22 (d, J=9.5 Hz, 3H), 7.25 (d, J=2.3 Hz, 1H), 7.13 (dd, J=6.1, 2.3 Hz, 1H), 4.62 (s, 2H), 4.55 (q, J=7.1 Hz, 2H), 2.75-2.65 (m, 1H), 1.49 (t, J=7.1 Hz, 3H), 1.18-1.10 (m, 2H), 1.04-0.95 (m, 2H).

Example 158: Synthesis of N-[(4-cyclopropane-sulfonamidopyridin-2-yl)methyl]-1-(6-ethoxy-pyrazin-2-yl)imidazole-4-carboxamide (I-238)

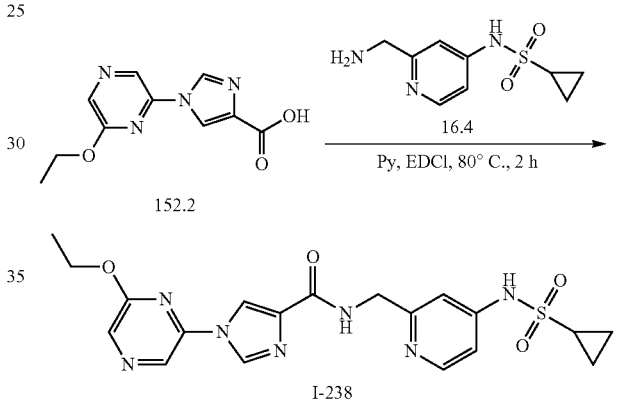

I-238

Synthesis of I-238. I-238 was synthesized from 152.2 in a manner similar to that described in the synthesis of I-244. MS (ES): m/z 444 [M+H]$^+$; $^1$H NMR (400 MHz, CD$_3$OD) δ 8.64-8.56 (m, 2H), 8.48 (d, J=1.3 Hz, 1H), 8.39-8.29 (m, 2H), 7.24 (d, J=2.3 Hz, 1H), 7.14 (dd, J=6.0, 2.3 Hz, 1H), 4.65 (s, 2H), 4.54 (q, J=7.1 Hz, 2H), 2.77-2.65 (m, 1H), 1.49 (t, J=7.1 Hz, 3H), 1.18-1.09 (m, 2H), 1.05-0.95 (m, 2H).

Example 159: Synthesis of N-[(4-cyclopropane-sulfonamidopyridin-2-yl)methyl]-5-[6-(trifluoromethyl)pyrazine-2-yl]-1,3-thiazole-2-carboxamide (I-253)

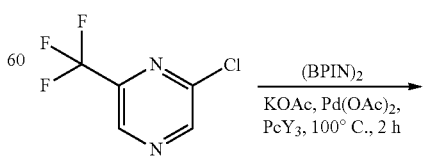

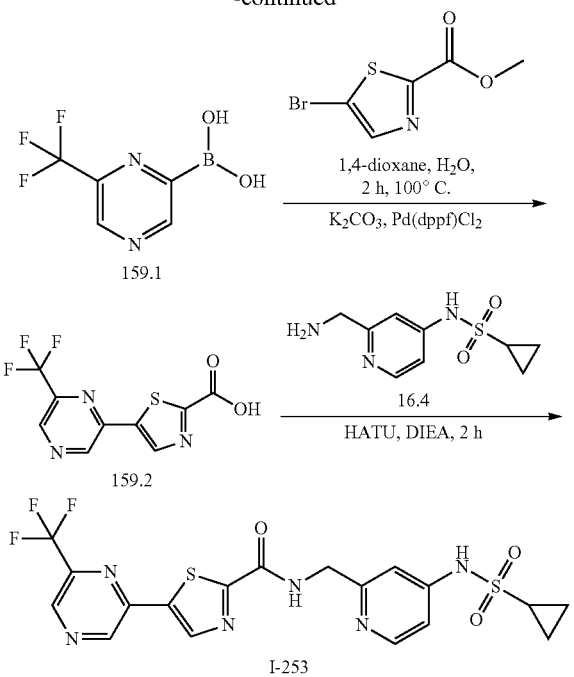

Synthesis of I-253. To a solution of 159.2 (80 mg, 0.29 mmol, 1 eq) and 16.4 (67 mg, 0.29 mmol, 1 eq) in N,N-dimethylformamide (2 mL) was added N, N-diisopropylethylamine (113 mg, 0.87 mmol, 3 eq) and 2-(-7-azabenzotriazol-1-yl)-N, N, N', N'-tetramethyluronium hexafluorophosphate (133 mg, 0.34 mmol, 1.2 eq). The resulting solution was stirred for 2 h at room temperature. The mixture was diluted with water and extracted with ethyl acetate. The combined organic layer was washed with brine, dried over sodium sulfate and concentrated under reduced pressure. The residue was purified by reverse flash and Prep-HPLC with the following conditions: Column: Sunfire prep C18 column, 30*150 mm, 5 μm; Mobile Phase: Water (0.1% FA), and ACN (25% ACN up to 45% in 10 min); UV detection at 254/210 nm. The product-containing fractions were combined and evaporated partially in vacuum and lyophilized overnight to afford N-[(4-cyclopropanesulfonamidopyridin-2-yl)methyl]-5-[6-(trifluoromethyl)pyrazin-2-yl]-1,3-thiazole-2-carboxamide (I-253, 9.2 mg, 6.5%) as a white solid. MS (ES): m/z 485 [M+H]$^+$; $^1$H NMR (400 MHz, Methanol-d$_4$) δ 9.51 (s, 1H), 9.01 (s, 1H), 8.80 (s, 1H), 8.26 (d, J=6.0 Hz, 1H), 7.25 (d, J=2.3 Hz, 1H), 7.20-7.14 (m, 1H), 4.68 (s, 2H), 2.77-2.66 (m, 1H), 1.19-1.10 (m, 2H), 1.08-0.96 (m, 2H).

Example 160: Synthesis of N-[(4-cyclopropanesulfonamidopyridin-2-yl)methyl]-2-fluoro-4-[6-(trifluoromethyl)pyrazin-2-yl]benzamide (I-254)

Synthesis of 159.1. To a solution of 2-chloro-6-(trifluoromethyl)pyrazine (500 mg, 2.73 mmol, 1 eq) and bis(pinacolato)diboron (835 mg, 3.28 mmol, 1.2 eq) in 1,4-dioxane (14 mL) was added potassium acetate (672 mg, 6.84 mmol, 2.5 eq), Pd(OAc)$_2$ (61 mg, 0.27 mmol, 0.1 eq) and PCy$_3$ (38 mg, 0.13 mmol, 0.05 eq). The resulting solution was degassed three times with nitrogen and stirred for 2 h at 100° C. The mixture was cooled to room temperature, diluted with water and extracted with ethyl acetate. The combined organic layer was washed with brine, dried over sodium sulfate and concentrated under reduced pressure. The residue was purified by reverse flash chromatography with the following conditions: Column, C18 Column; Mobile Phase, water (0.1% FA) and ACN (10% ACN up to 50% in 20 min); UV detection at 254/220 nm. The product-containing fractions were combined and concentrated under reduced pressure to obtain 6-(trifluoromethyl)pyrazin-2-yl-boronic acid (159.1, 340 mg, 64%) as a white solid. MS (ES): m/z 193 [M+H]$^+$.

Synthesis of 159.2. To a solution of 159.1 (340 mg, 1.77 mmol, 1 eq) and methyl 5-bromothiazole-2-carboxylate (472 mg, 2.16 mmol, 1.2 eq) in 1,4-dioxane (8 mL) and water (2 mL) was added potassium carbonate (735 mg, 5.31 mmol, 3 eq) and Pd(dppf)Cl$_2$ (130 mg, 0.17 mmol, 0.1 eq). The resulting solution was degassed three times with nitrogen and stirred for 2 h at 100° C. The mixture was cooled to room temperature, and diluted with water. The pH value of the solution was adjusted to 3 with 1N aqueous hydrochloric acid. The resulting mixture was extracted with ethyl acetate. The combined organic layers were washed with brine, dried over anhydrous sodium sulfate and concentrated under reduced pressure. The residue was purified by reverse flash chromatography with the following conditions: Column, C18 Column; Mobile Phase, water (0.1% FA) and ACN (5% ACN up to 40% in 20 min); UV detection at 254/220 nm. The product-containing fractions were combined and concentrated under reduced pressure to obtain methyl 5-[6-(trifluoromethyl) pyrazin-2-yl]-1,3-thiazole-2-carboxylate (159.2, 190 mg, 39%) as a white solid. MS (ES): m/z 276 [M+H]$^+$.

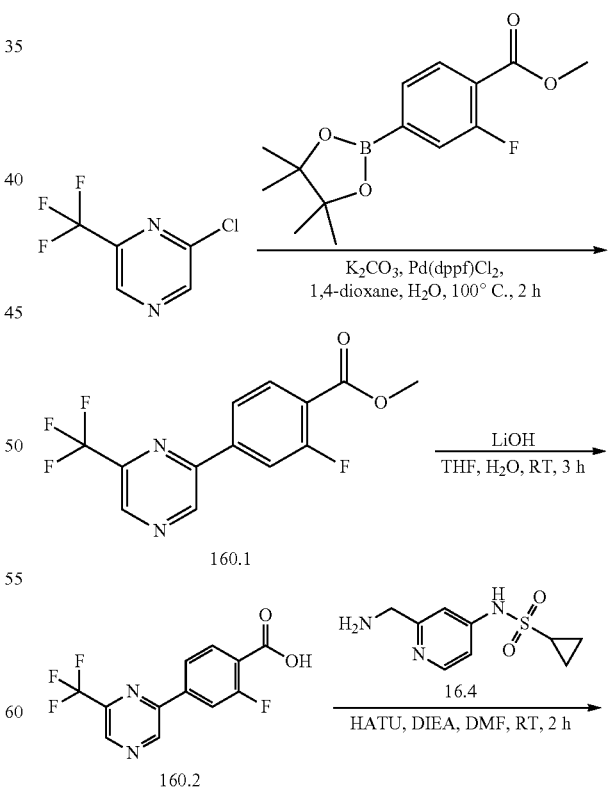

-continued

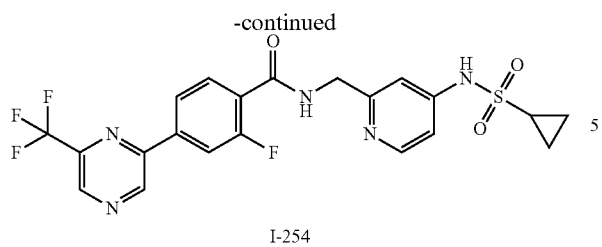

I-254

Synthesis of 160.1. To a solution of 2-chloro-6-(trifluoromethyl)pyrazine (100 mg, 0.55 mmol, 1 eq) and methyl 2-fluoro-4-(4,4,5,5-tetramethyl-1,3,2-dioxaborolan-2-yl)benzoate (460 mg, 1.65 mmol, 1 eq) in 1,4-dioxane (4 mL) and water (1 mL) was added potassium carbonate (227 mg, 1.64 mmol, 3 eq) and Pd(dppf)Cl$_2$ (40 mg, 0.06 mmol, 0.1 eq). The resulting solution was degassed three times with nitrogen and stirred for 2 h at 100° C. The mixture was cooled to room temperature, diluted with water and extracted with ethyl acetate. The combined organic layer was washed with brine, dried over sodium sulfate and concentrated under reduced pressure. The resulting mixture was purified by Prep-TLC, eluted with petroleum ether/ethyl acetate=5/1 to afford methyl 2-fluoro-4-[6-(trifluoromethyl)pyrazin-2-yl]benzoate (160.1, 100 mg, 60%) as a yellow oil. MS (ES): m/z 300 [M+H]$^+$.

Synthesis of 160.2. To a stirred solution of methyl 160.1 (100 mg, 0.33 mmol, 1 eq) in tetrahydrofuran (2.5 mL) was added lithium hydroxide (33 mg, 1.37 mmol, 4.1 eq) in water (0.5 mL). The resulting solution was stirred for 3 h at room temperature. The residue was diluted with water. The pH value of the solution was adjusted to 3 with 1N aqueous hydrochloric acid. The resulting mixture was extracted with ethyl acetate. The combined organic layers were washed with brine, dried over anhydrous sodium sulfate and concentrated under reduced pressure. The crude product 2-fluoro-4-[6-(trifluoromethyl)pyrazin-2-yl]benzoic acid (160.2, 100 mg) was used in the next step directly without further purification. MS (ES): m/z 287 [M+H]$^+$.

Synthesis of I-254. To a solution of 160.2 (100 mg) and 16.4 (79 mg, 0.29 mmol, 1 eq) in N,N-dimethylformamide (2 mL) was added N, N-diisopropylethylamine (136 mg, 1.05 mmol, 3 eq) and 2-(-7-azabenzotriazol-1-yl)-N, N, N', N'-tetramethyluronium hexafluorophosphate (159 mg, 0.42 mmol, 1.2 eq). The resulting solution was stirred for 2 h at room temperature. The mixture was diluted with water and extracted with ethyl acetate. The combined organic layer was washed with brine, dried over sodium sulfate and concentrated under reduced pressure. The crude product purified by Prep-HPLC with the following conditions (Column: Sunfire prep C18 column, 30*150, 5 um; Mobile Phase, water (0.1% FA) and ACN (20% ACN up to 50% in 7 min); UV detection at 254/220 nm. The product-containing fractions were combined and evaporated partially in vacuum and lyophilized overnight to afford N-[(4-cyclopropanesulfonamidopyridin-2-yl)methyl]-2-fluoro-4-[6-(trifluoromethyl)pyrazin-2-yl]benzamide (I-254, 15 mg, 8%) as a white solid. MS (ES): m/z 496 [M+H]$^+$; $^1$H NMR (400 MHz, DMSO-d$_6$) δ 9.72 (s, 1H), 9.23 (s, 1H), 8.30-8.13 (m, 4H), 7.92 (t, J=7.7 Hz, 1H), 7.12 (s, 1H), 7.02 (dd, J=6.1, 2.3 Hz, 1H), 4.52 (s, 2H), 2.75-2.70 (m, 1H), 1.05-0.91 (m, 4H).

Example 161: Synthesis of N-((4-(cyclopropanesulfonamido)pyridin-2-yl)methyl)-5-(5-(trifluoromethyl)pyridin-3-yl)thiazole-2-carboxamide (I-251)

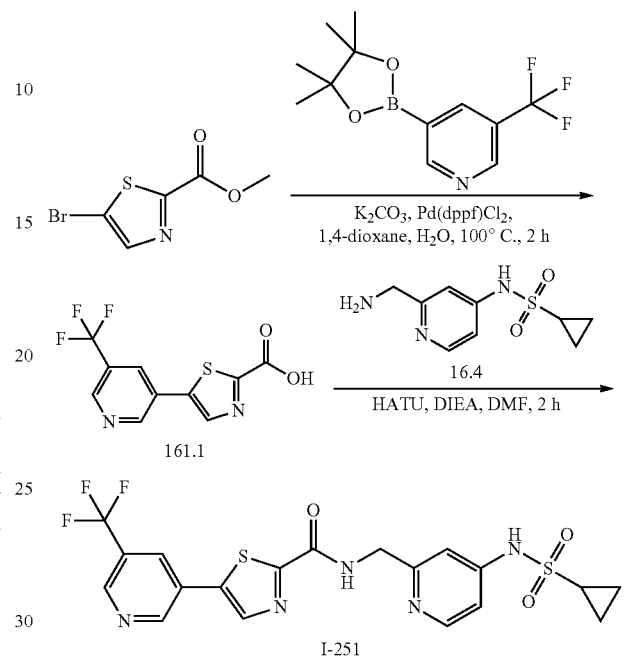

I-251

Synthesis of I-251. I-251 was synthesized in a manner similar to that described in the synthesis of I-253 using 3-(4,4,5,5-tetramethyl-1,3,2-dioxaborolan-2-yl)-5-(trifluoromethyl)pyridine as the boron reagent. Final product purification: Prep-HPLC with the following conditions (Column: Sunfire prep C18 column, 30*150, 5 um; Mobile Phase, water (0.1% FA) and ACN (20% ACN up to 50% in 7 min); UV detection at 254/220 nm). MS (ES): m/z 484 [M+H]$^+$; $^1$H NMR (400 MHz, Methanol-d$_4$) δ 9.20 (d, J=2.2 Hz, 1H), 8.93 (dd, J=2.2, 0.9 Hz, 1H), 8.50 (d, J=4.6 Hz, 2H), 8.26 (s, 1H), 7.25 (d, J=2.2 Hz, 1H), 7.16 (dd, J=6.0, 2.3 Hz, 1H), 4.68 (s, 2H), 2.79-2.65 (m, 1H), 1.19-1.13 (m, 2H), 1.11-0.96 (m, 2H).

Example 162: Synthesis of N-((4-(cyclopropanesulfonamido)pyridin-2-yl)methyl)-5-(5-ethoxypyridin-3-yl)thiazole-2-carboxamide (I-242)

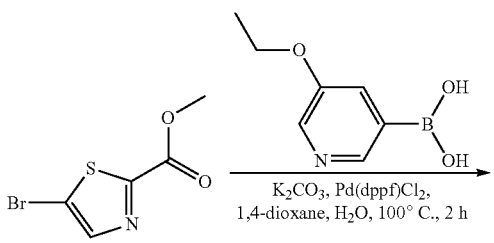

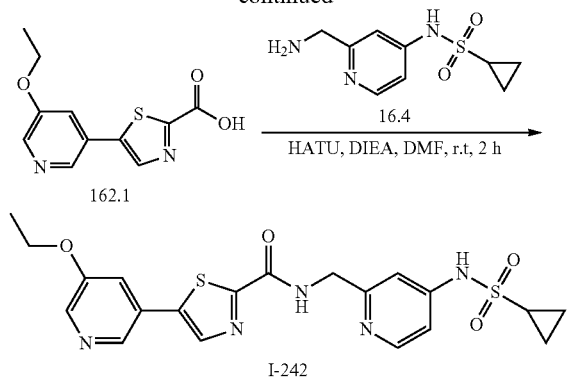

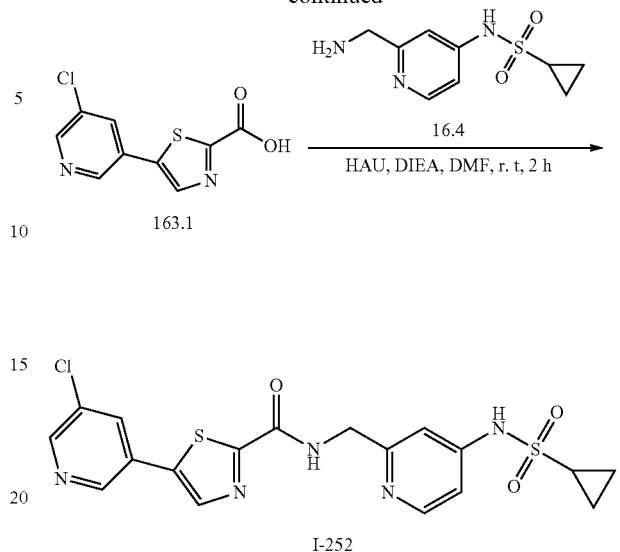

Synthesis of I-242. I-242 was synthesized in a manner similar to that described in the synthesis of I-253 using methyl 5-bromothiazole-2-carboxylate and (5-ethoxypyridin-3-yl)boronic acid as the boron reagent. Final product purification: Prep-HPLC with the following conditions: Column: Sunfire prep C18 column, 30*150, 5 um; Mobile Phase Water (0.1% FA) and ACN (20% ACN up to 50% in 7 min); UV detection at 254/220 nm. MS (ES): m/z 460 [M+H]$^+$; $^1$H NMR (300 MHz, CD$_3$OD) δ 8.49 (d, J=1.9 Hz, 1H), 8.37 (s, 1H), 8.31-8.21 (m, 2H), 7.70 (dd, J=2.7, 1.9 Hz, 1H), 7.25 (d, J=2.3 Hz, 1H), 7.16 (dd, J=6.0, 2.3 Hz, 1H), 4.67 (s, 2H), 4.23 (q, J=7.0 Hz, 2H), 2.77-2.67 (m, 1H), 1.47 (t, J=7.0 Hz, 3H), 1.21-1.12 (m, 2H), 1.12-0.94 (m, 2H).

Example 163: Synthesis of 5-(5-chloropyridin-3-yl)-N-[(4-cyclopropanesulfonamidopyridin-2-yl)methyl]-1,3-thiazole-2-carboxamide (I-252)

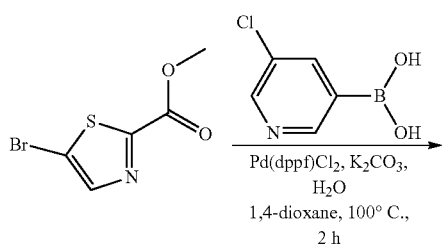

Synthesis of I-252. I-252 was synthesized in a manner similar to that described in the synthesis of I-253 using (5-chloropyridin-3-yl)boronic acid as the boron reagent. Final product purification: Prep-HPLC with the following conditions (Column: Sunfire prep C18 column, 30*150 mm, 5 μm; Mobile Phase: Water (0.1% FA) and ACN (17% ACN up to 37% in 10 min); UV detection at 254/220 nm). MS (ES): m/z 450 [M+H]$^+$; $^1$H NMR (400 MHz, Methanol-d$_4$) δ 8.87 (d, 2.0 Hz, 1H), 8.61 (d, J=2.2 Hz, 1H), 8.42 (s, 1H), 8.33-8.18 (m, 2H), 7.25 (s, 1H), 7.16-7.14 (m, 1H), 4.67 (s, 2H), 2.77-2.69 (m, 1H), 1.16-1.12 (m, 2H), 1.11-0.98 (m, 2H).

Example 164: Synthesis of N-[(4-cyclopropanesulfonamidopyridin-2-yl)methyl]-5-[6-(2,2,2-trifluoroethoxy)pyrazin-2-yl]-1,3-thiazole-2-carboxamide (I-243)

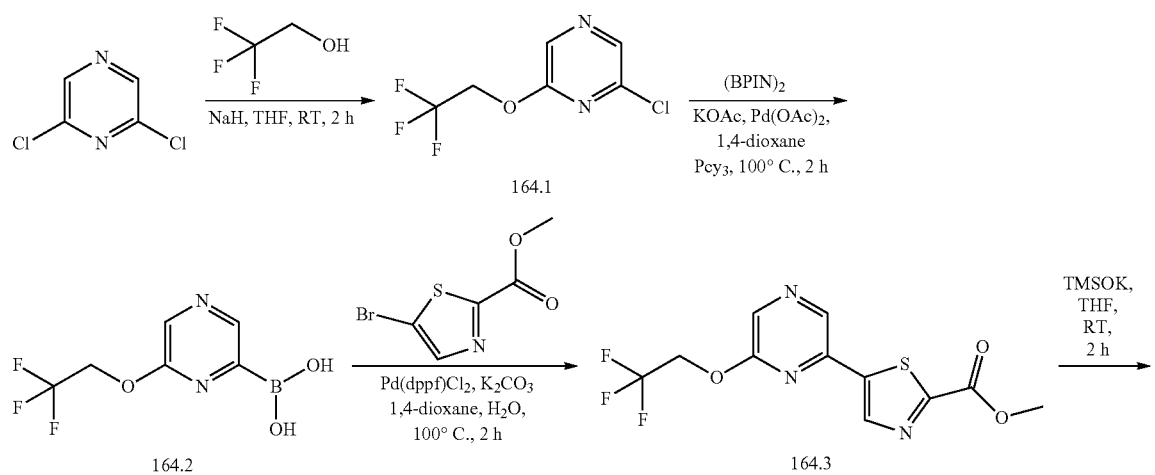

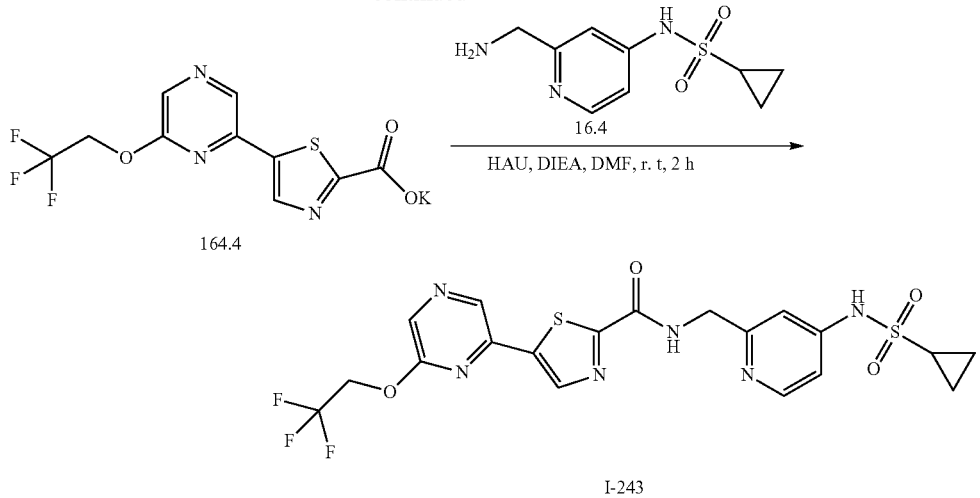

I-243

Synthesis of 164.1. A stirred mixture of trifluoroethanol (0.71 g, 7.1 mmol, 1 eq) in tetrahydrofuran (20 mL) was degassed three times with nitrogen and cooled to 0° C. To the solution was added sodium hydride (60% w/w, 0.316 g, 7.9 mmol, 1.1 eq), stirred for 0.5 h at 0° C. under nitrogen atmosphere. To the above mixture was added 2,6-dichloropyrazine (1 g, 6.7 mmol, 1 eq) at 0° C. The resulting mixture was stirred for additional 1 h at room temperature under nitrogen atmosphere. The reaction was quenched with saturated aqueous ammonium chloride, and extracted with ethyl acetate. The combined organic layers were washed with water, and dried over anhydrous sodium sulfate. After filtration, the filtrate was concentrated under reduced pressure and purified by Prep-TLC (petroleum ether/ethyl acetate=6:1) to obtain 2-chloro-6-(2, 2, 2-trifluoroethoxy) pyrazine (164.1, 0.7 g, 49%) as a yellow liquid. MS (ES): m/z 213 [M+H]$^+$.

Synthesis of 164.2. 164.2 was synthesized from 164.1 in a manner similar to that described in the synthesis of 159.1. MS (ES): m/z 223 [M+H]$^+$.

Synthesis of 164.3. 164.3 was synthesized from 164.2 in a manner similar to that described in the synthesis of 159.1. MS (ES): m/z 320 [M+H]$^+$.

Synthesis of 164.4. To a stirred solution of 164.3 (228 mg, 0.71 mmol, 1 eq) in tetrahydrofuran (10 mL) was added potassium trimethylsilanolate (182 mg, 1.42 mmol, 2 eq). The resulting mixture was stirred for 1 h at room temperature. The resulting mixture was concentrated under reduced pressure to obtain the crude product potassium 5-(6-(2,2,2-trifluoroethoxy)pyrazin-2-yl)thiazole-2-carboxylate (164.4, 200 mg) was used in the next step directly without further purification. MS (ES): m/z 306 [M+H]$^+$.

Synthesis of I-243. To a solution of 164.4 (200 mg) and 16.4 (130 mg, 0.57 mmol) in N,N-dimethylformamide (5 mL) was added N, N-diisopropylethylamine (250 mg, 1.93 mmol) and 2-(-7-azabenzotriazol-1-yl)-N,N, N', N'-tetramethyluronium hexafluorophosphate (330 mg, 0.867 mmol). The resulting solution was stirred for 2 h at room temperature. The mixture was diluted with water and extracted with ethyl acetate. The combined organic layer was washed with brine, dried over sodium sulfate and concentrated under reduced pressure. The crude product was purified by Prep-HPLC with the following conditions (Column: XBridge Prep C18 OBD Column, 30*100 mm, 5 um; Mobile Phase: Water (10 mmol/L NH$_4$HCO$_3$) and ACN (25% ACN up to 55% in 7 min); UV detection at 254/220 nm. The product-containing fractions were combined and evaporated partially in vacuum and lyophilized overnight to afford N-[(4-cyclopropanesulfonamidopyridin-2-yl)methyl]-5-[6-(2,2,2-trifluoroethoxy)pyrazin-2-yl]-1,3-thiazole-2-carboxamide (I-243, 34 mg, 19%) as a pink solid. MS (ES): m/z 515 [M+H]$^+$; $^1$H NMR (400 MHz, Methanol-d$_4$) δ 8.88 (s, 1H), 8.66 (s, 1H), 8.36 (s, 1H), 8.25 (d, J=6.0 Hz, 1H), 7.24 (d, J=2.2 Hz, 1H), 7.15 (dd, J=6.0, 2.3 Hz, 1H), 5.02 (q, J=8.6 Hz, 2H), 4.67 (s, 2H), 2.75-2.67 (m, 1H), 1.17-1.12 (m, 2H), 1.07-0.96 (m, 2H).

Example 165: Synthesis of N-[(4-cyclopropanesulfonamidopyridin-2-yl)methyl]-3-[(dimethylamino)methyl]-5-(6-ethoxypyrazin-2-yl)pyridine-2-carboxamide (I-229)

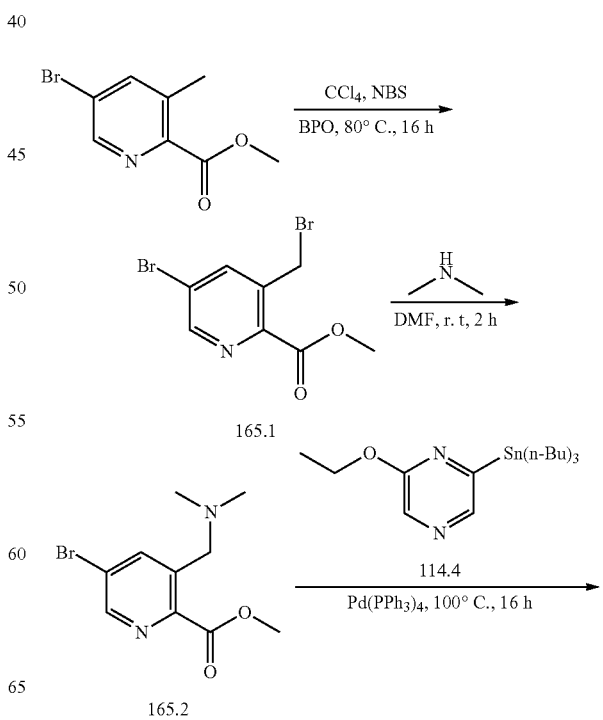

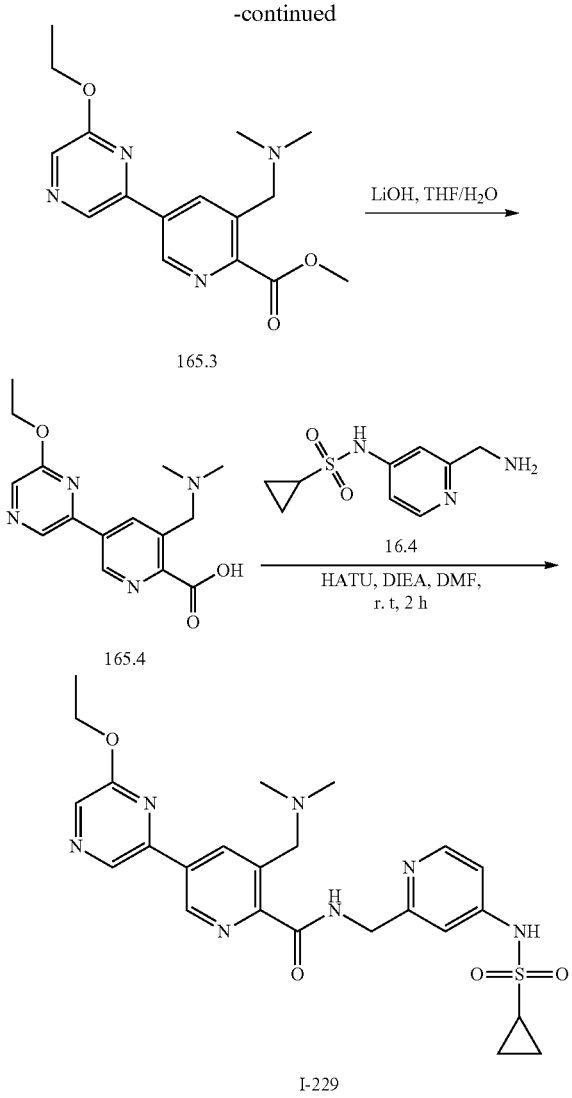

Synthesis of 165.1. To a stirred solution of methyl 5-bromo-3-methylpicolinate (460 mg, 2 mmol, 1 eq) in carbon tetrachloride (10 mL) was added N-bromosuccinimide (356 mg, 2 mmol, 1 eq) and benzoyl peroxide (51 mg, 0.2 mmol, 0.1 eq). The resulting solution was degassed three times with nitrogen and stirred for overnight at 85° C. The mixture was cooled to room temperature, diluted with water and extracted with dichloromethane. The combined organic layer was washed with brine, dried over sodium sulfate and concentrated under reduced pressure. The residue was purified by silica gel column chromatography (compound was eluted in 50% ethyl acetate in petroleum ether) to obtain 5-bromo-3-(bromomethyl)pyridine-2-carboxylate (165.1, 253 mg, 40%) as a light yellow solid. MS (ES): m/z 310 [M+H]+.

Synthesis of 165.2. To a stirred mixture of 165.1 (447 mg, 1.4 mmol, 1 eq) in N, N-dimethyl formamide (6.5 mL) was added dimethylamine (2 M in THF, 1.5 mL) at 0° C. The resulting mixture was stirred for 2 h at room temperature. The mixture diluted with water and extracted with ethyl acetate. The combined organic layer was washed with brine, dried over sodium sulfate and concentrated under reduced pressure to afford the crude product methyl 5-bromo-3-[(dimethylamino)methyl]pyridine-2-carboxylate (165.2, 333 mg, 87%) as a yellow solid. MS (ES): m/z 273/275 [M−H]+.

Synthesis of 165.3. To a stirred mixture of 165.2 (333 mg, 1.22 mmol, 1 eq) and 114.4 (504 mg, 1.22 mmol, 1 eq) in 1,4-dioxane (10 mL) was added Pd(PPh3)4 (141 mg, 0.12 mmol, 0.1 eq). The resulting solution was degassed three times with nitrogen and stirred for overnight at 100° C. The mixture was allowed to cool down to room temperature. The resulting mixture was concentrated under reduced pressure and purified by reverse flash chromatography (compound was eluted in 80% acetonitrile in water) to obtain methyl 3-((dimethylamino)methyl)-5-(6-ethoxypyrazin-2-yl)picolinate (165.3, 100 mg, 26%) as a yellow solid. MS (ES): m/z 317 [M+H]+.

Synthesis of 165.4. 165.4 was synthesized from 165.3 in a manner similar to that described in the synthesis of 160.2. MS (ES): m/z 303 [M+H]+.

Synthesis of I-229. I-229 was synthesized from 165.4 and 16.4 in a manner similar to that described in the synthesis of I-253 (final amide coupling step). Final product purification: Prep-HPLC with the following conditions (Column: XBridge Prep C18 OBD Column, 30*100 mm, 5 um; Mobile Phase: Water (0.1% FA) and ACN (2% ACN up to 20% in 7 min); UV detection at 254/220 nm)—formic acid salt obtained from evaporation. MS (ES): m/z 512 [M+H]+; 1H NMR (400 MHz, CD3OD) δ9.51 (d, J=2.0 Hz, 1H), 8.87 (s, 1H), 8.72 (d, J=2.0 Hz, 1H), 8.44 (s, 1H), 8.31 (s, 1H), 8.26 (d, J=2.0 Hz, 1H), 7.35 (d, J=2.0 Hz, 1H), 7.11-7.08 (m, 1H), 4.75 (s, 2H), 4.67 (s, 2H), 4.61 (q, J=8.6 Hz, 2H), 2.95 (s, 6H), 2.80-2.70 (m, 1H), 1.52 (t, J=7.0 Hz, 3H), 1.17-1.13 (m, 2H), 1.05-0.97 (m, 2H).

Example 166: Synthesis of N-[(4-cyclopropanesulfonamido-3-methoxypyridin-2-yl)methyl]-4-(6-ethoxypyrazin-2-yl)-2-fluorobenzamide (I-257)

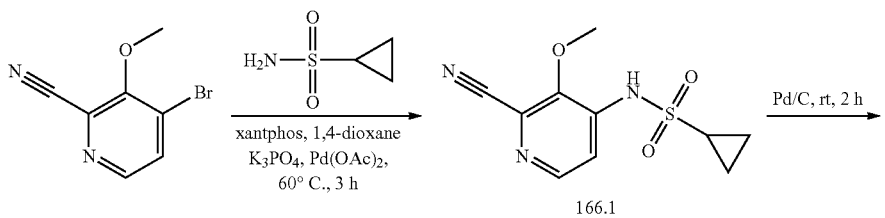

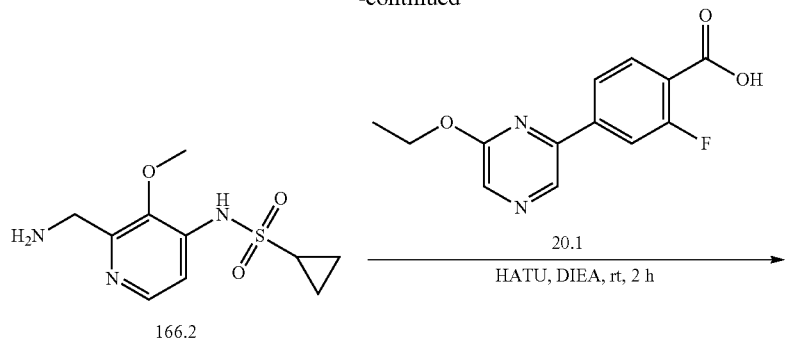

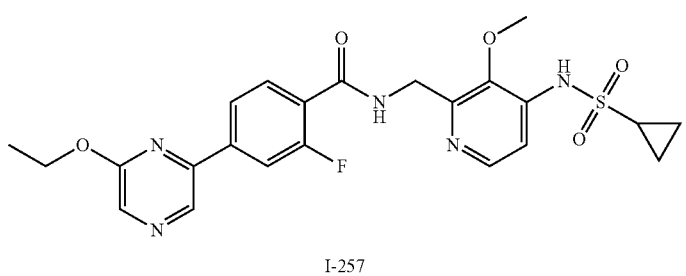

Synthesis of 166.1. To a stirred solution of 4-bromo-3-methoxypyridine-2-carbonitrile (200 mg, 0.93 mmol, 1 eq) and cyclopropanesulfonamide (227 mg, 1.87 mmol, 2 eq) in 1,4-dioxane (5 mL) was added cesium carbonate (0.92 g, 2.81 mmol, 3 eq), Pd$_2$(allyl)$_2$Cl$_2$ (17 mg, 0.04 mmol, 0.1 eq) and t-Buxphos (40 mg, 0.09 mmol, 0.1 eq). The resulting solution was degassed three times with nitrogen and stirred for 3 h at 60° C. The mixture was allowed to cool down to room temperature. The resulting mixture was extracted with ethyl acetate. The combined organic layers were washed with brine, and dried over anhydrous sodium sulfate. After filtration, the filtrate was concentrated under reduced pressure. The residue was purified by Prep-TLC (petroleum ether/ethyl acetate=2:1) to afford N-(2-cyano-3-methoxy-pyridin-4-yl)cyclopropanesulfonamide (166.1, 210 mg, 88%) as a yellow oil. MS (ES): m/z 254 [M+H]$^+$.

Synthesis of 166.2. A stirred solution of 166.1 (210 mg, 0.83 mmol, 1 eq) in ammonia methanol solution (7N, 10 mL) was flushed three times with nitrogen. To the solution was added palladium 10% on carbon (21 mg) and the reaction mixture was degassed with nitrogen and hydrogen. The mixture was stirred for 2 h at room temperature under an atmosphere of hydrogen. The solids were filtered out and the filtrate was concentrated under reduced pressure to afford N-[2-(aminomethyl)-3-methoxypyridin-4-yl]cyclopropanesulfonamide (166.2, 180 mg, 84%) as a grey solid. MS (ES): m/z 258 [M+H]$^+$.

Synthesis of I-257. I-257 was synthesized from 166.2 and 20.1 in a manner similar to that described in the synthesis of I-253 (final amide coupling step). Final product purification: Prep-HPLC with the following conditions (Column: Sunfire prep C18 column, 30*150, 5 um; Mobile Phase: Water (0.1% FA) and ACN (35% ACN up to 40% in 10 min); UV detection at 254/220 nm. MS (ES): m/z 502 [M+H]$^+$. $^1$H NMR (400 MHz, 373 K, DMSO-d$_6$) δ 8.79 (s, 1H), 8.24 (s, 1H), 8.12-7.83 (m, 4H), 7.41 (s, 1H), 4.62 (s, 2H), 4.50 (q, J=7.0 Hz, 2H), 3.85 (s, 3H), 2.75-2.72 (m, 1H), 1.41 (t, J=7.0 Hz, 3H), 1.08-0.90 (m, 4H).

Example 167: Synthesis of N-((4-(cyclopropane-sulfonamido)pyridin-2-yl)methyl)-5-(pyrazolo[1,5-a]pyridin-3-yl)thiazole-2-carboxamide (I-237)

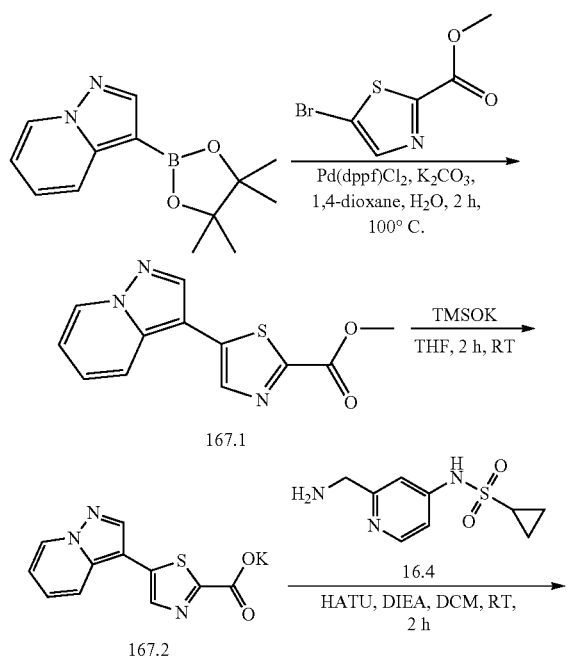

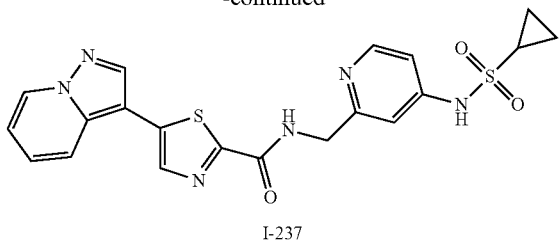

I-237

Synthesis of I-237. I-237 was synthesized in a manner similar to that described in the synthesis of I-243 (step 3, 4 and 5) using 3-(4,4,5,5-tetramethyl-1,3,2-dioxaborolan-2-yl)pyrazolo[1,5-a]pyridine as the boron reagent. Final product purification: Prep-HPLC with the following conditions: Column: XBridge Prep OBD C18 Column, 30*150 mm, 5 um; Mobile Phase Water (10 mmol/L NH$_4$HCO$_3$) and ACN (15% ACN up to 25% in 10 min); UV detection at 254/220 nm. MS (ES): m/z 455 [M+H]$^+$; $^1$H NMR (400 MHz, DMSO-d$_6$) δ 10.85 (s, 1H), 9.39 (t, J=6.1 Hz, 1H), 8.82 (d, J=7.0 Hz, 1H), 8.58 (s, 1H), 8.39 (s, 1H), 8.25 (d, J=5.7 Hz, 1H), 8.05 (d, J=9.0 Hz, 1H), 7.49 (t, J=7.8 Hz, 1H), 7.15-6.95 (m, 3H), 4.52 (d, J=6.2 Hz, 2H), 2.78-2.68 (m, 1H), 1.03-0.89 (m, 4H).

Example 168: Synthesis of 5-{6-chloropyrazolo[1,5-a]pyridin-3-yl}-N-[(4-cyclopropanesulfonamidopyridin-2-yl)methyl]-1,3-thiazole-2-carboxamide (I-202)

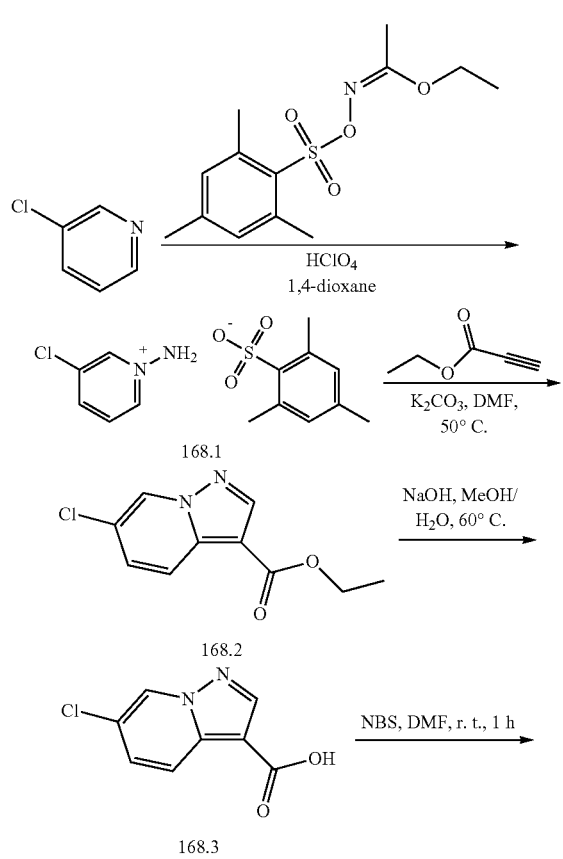

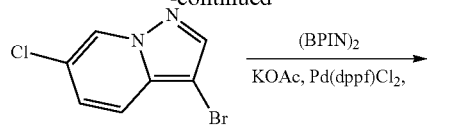

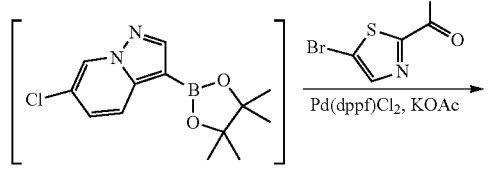

168.5
Not isolated

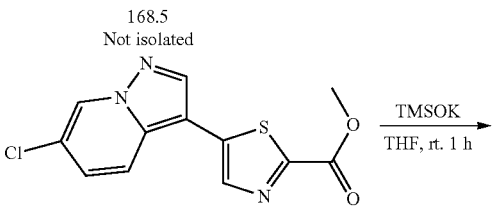

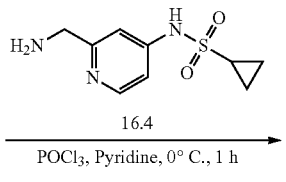

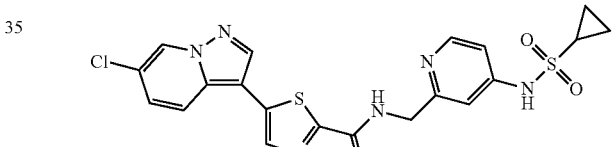

I-202

Synthesis of 168.1. To a stirred mixture of (E)-(ethyl N-[(2,4,6-trimethylbenzenesulfonyl)oxy]ethanimidate) (1.01 g, 3.53 mmol, 1.2 eq) in 1,4-dioxane (3 mL) was added dropwise HClO$_4$ (4 mL) at 0° C. The resulting mixture was stirred for 50 min at 0° C. Ice-water was added and the precipitate was collected by filtration (caution: it could explode, if this solid is completely dried). After washing with water, the solid was dissolved in wet condition into dichloromethane (5 mL), the organic layer was separated and dried over magnesium sulfate. The above-mentioned dichloromethane solution (which was dried over magnesium sulfate) was added to 3-chloropyridine (334 mg, 2.94 mmol, 1 eq) stirring in dichloromethane (6 mL) at 0° C. The mixture was stirred at room temperature for 30 minutes. Diethyl ether (30 mL) was then added, the solids were collected by filtration and washed with ethyl ether to afford 1-amino-3-chloropyridin-1-ium 2,4,6-trimethylbenzenesulfonate (168.1, 804 mg, 83%) as a white solid. MS (ES): m/z 129 [M+H]$^+$.

Synthesis of 168.2. To a stirred mixture of 168.1 (3.35 g, 10.19 mmol, 1 eq) in N,N-dimethylformamide (35 mL) was added ethyl propiolate (1 g, 10.19 mmol, 1 eq) and potassium carbonate (4.22 g, 30.56 mmol, 3 eq). The resulting mixture was stirred for 2 h at 50° C. The mixture was allowed to cool down to room temperature. The mixture was diluted with water and extracted with ethyl acetate. The combined organic layer was washed with brine, dried over sodium sulfate and concentrated under reduced pressure. The residue was purified by silica gel column chromatography (eluted with petroleum ether/ethyl acetate (5:1)) to afford ethyl 6-chloropyrazolo[1,5-a]pyridine-3-carboxylate (168.2, 643 mg, 28%) as a brown yellow solid. MS (ES): m/z 226 [M+H]$^+$.

Synthesis of 168.3. To a stirred mixture of 168.2 (400 mg, 1.78 mmol, 1 eq) in methyl alcohol (4 mL) and water (1 mL) were added sodium hydroxide (142 mg, 3.56 mmol, 2 eq). The resulting mixture was stirred for 1 h at 60° C. The mixture was allowed to cool down to room temperature and diluted with water. The pH value of the solution was adjusted to 3 with 1N aqueous hydrochloric acid. The solids were collected by filtration to obtain the crude product 6-chloropyrazolo [1,5-a]pyridine-3-carboxylic acid (168.3, 346 mg, 98%) as a white solid. MS (ES): m/z 197 [M+H]$^+$.

Synthesis of 168.4. To a stirred mixture of 168.3 (829 mg, 4.22 mmol, 1.0 eq) in N,N-dimethylformamide (15 mL) was added NBS (901 mg, 5.06 mmol, 1.2 eq). The resulting mixture was stirred for 1 h at room temperature. The mixture was diluted with water and extracted with ethyl acetate. The combined organic layer was washed with brine, dried over sodium sulfate and concentrated under reduced pressure. The residue was purified by Prep-TLC (petroleum ether/ethyl acetate=3/1) to afford 3-bromo-6-chloropyrazolo[1,5-a]pyridine (168.4, 480 mg, 50%) as a yellow solid. MS (ES): m/z 231/233 [M+H]$^+$.

Synthesis of 168.6. To a solution of 168.4 (100 mg, 0.43 mmol, 1 eq) and bis(pinacolato)diboron (220 mg, 0.86 mmol, 2 eq) in 1,4-dioxane (8 mL) was added potassium acetate (85 mg, 0.86 mmol, 2 eq) and Pd(dppf)Cl$_2$ (36 mg, 0.08 mmol, 0.2 eq). The resulting solution was degassed three times with nitrogen and stirred for 1 h at 100° C. The mixture was allowed to cool down to room temperature, methyl 5-bromothiazole-2-carboxylate (97 mg, 0.43 mmol, 1 eq) and water (1 mL) added. The resulting solution was degassed three times with nitrogen and stirred for another 1 h at 100° C. The mixture was allowed to cool down to room temperature, diluted with water and extracted with ethyl acetate. The combined organic layer was washed with brine, dried over sodium sulfate and concentrated under reduced pressure. The residue was purified by Prep-TLC (petroleum ether/ethyl acetate=1/1) to afford methyl 5-(6-chloropyrazolo[1,5-a]pyridin-3-yl)thiazole-2-carboxylate (168.6, 20 mg, 15%) as a yellow solid. MS (ES): m/z 294 [M+H]$^+$.

Synthesis of 168.7. 168.7 was synthesized in a manner similar to that described in the synthesis of 164.4, using 168.6. MS (ES): m/z 280 [M+H]$^+$.

Synthesis of I-202. To a stirred solution of 168.7 (40 mg) and 16.4 (39 mg, 0.17 mmol, 1.2 eq) in pyridine (3 mL) was added phosphorus oxychloride (110 mg, 0.71 mmol, 5 eq) at 0° C. The resulting mixture was stirred for 1 h at 0° C. The reaction was concentrated under reduced pressure. The residue was purified by reverse phase flash chromatography with the following conditions: Column, C18 Column; Mobile Phase, water (10 mmol/L NH$_4$HCO$_3$) and ACN (10% ACN up to 60% in 10 min); LTV detection at 254/220 nm. The product-containing fractions were combined and concentrated under reduced pressure. The residue was further purified by Prep-HPLC with the following conditions: Column, XBridge Shield RP18 OBD Column, 30*150 mm, 5 um; Mobile Phase, water (0.1% FA) and ACN (26% ACN up to 56% in 8 min); LTV detection at 254/220 nm. The product-containing fractions were combined and evaporated partially in vacuum and lyophilized overnight to afford 5-{6-chloropyrazolo[1,5-a]pyridin-3-yl}-N-[(4-cyclopropanesulfonamidopyridin-2-yl)methyl]-1,3-thiazole-2-carboxamide (I-202, 7.3 mg, 10%) as a red solid. MS (ES): m/z 489 [M+H]$^+$; $^1$H NMR (400 MHz, d$_6$-DMSO) δ 10.72 (s, 1H), 9.39 (t, J=6.2 Hz, 1H), 9.21 (s, 1H), 8.62 (s, 1H), 8.42 (s, 1H), 8.28-8.17 (m, 1H), 8.10 (d, J=9.5 Hz, 1H), 7.57-7.47 (m, 1H), 7.02 (d, J=4.7 Hz, 2H), 4.51 (d, J=5.9 Hz, 2H), 2.76-2.66 (m, 1H), 1.02-0.87 (m, 4H).

Example 169: Synthesis of 5-{5-chloropyrazolo[1,5-a] pyridin-3-yl}-N-[(4-cyclopropanesulfonamidopyridin-2-yl)methyl]-1,3-thiazole-2-carboxamide (I-197)

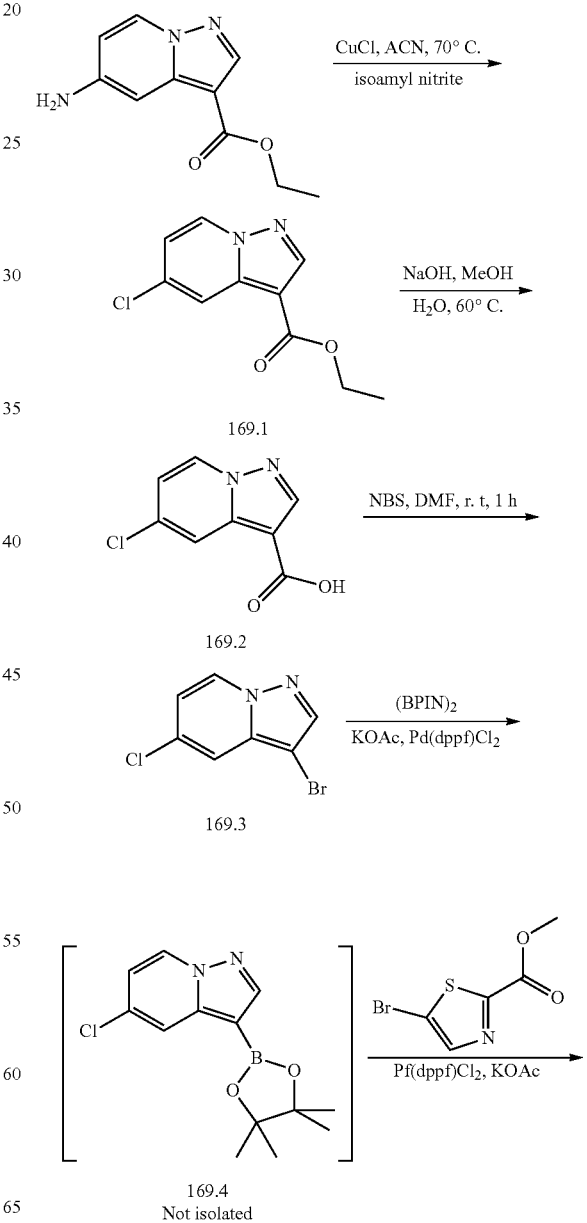

-continued

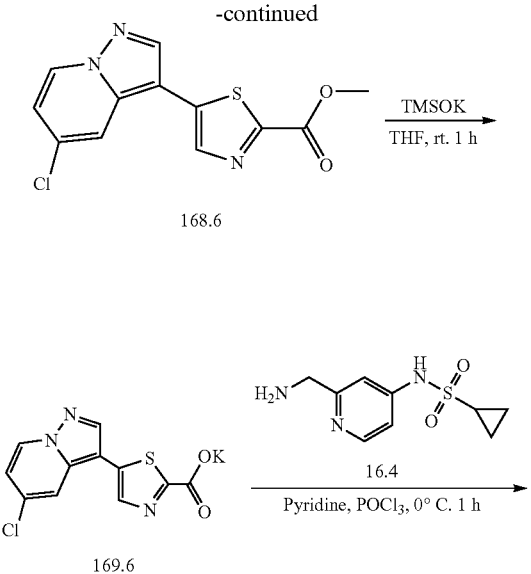

Synthesis of 169.1. A mixture of ethyl 5-aminopyrazolo[1,5-a]pyridine-3-carboxylate (1.03 g, 5.01 mmol, 1 eq) and cuprous chloride (745 mg, 7.53 mmol, 1.5 eq) in acetonitrile (10 mL) was stirred for 15 min at room temperature. To the above mixture was added isoamyl nitrite (965 mg, 10.03 mmol, 2 eq). The resulting mixture was stirred for additional 1 h at 70° C. The mixture was allowed to cool down to room temperature. The resulting mixture was filtered, the filter cake was washed with ethyl acetate and water. The filtrate was extracted with ethyl acetate. The combined organic layer was washed with brine, dried over sodium sulfate and concentrated under reduced pressure. The residue was purified by reverse flash chromatography with the following conditions: Column, $C_{1-8}$ Column; Mobile Phase, water (0.1% FA) and ACN (10% ACN up to 40% in 20 min); UV detection at 254/220 nm. The product-containing fractions were combined and concentrated under reduced pressure to obtain ethyl 5-chloropyrazolo[1,5-a]pyridine-3-carboxylate (169.1, 530 mg, 47%) as a brown yellow solid. MS (ES): m/z 225 [M+H]⁺.

Synthesis of 169.2. To a stirred mixture of 169.1 (400 mg, 1.78 mmol, 1 eq) in methyl alcohol (4 mL) and water (1 mL) were added sodium hydroxide (142 mg, 3.56 mmol, 2 eq). The resulting mixture was stirred for 1 h at 60° C. The mixture was allowed to cool down to room temperature and diluted with water. The pH value of the solution was adjusted to 3 with 1N aqueous hydrochloric acid. The solids were collected by filtration to obtain the crude product 5-chloropyrazolo[1,5-a]pyridine-3-carboxylic acid (169.2, 300 mg, 85%) as a white solid. MS (ES): m/z 197 [M+H]⁺.

Synthesis of 169.3. To a stirred mixture of 169.2 (829 mg, 4.22 mmol, 1.0 eq) in N,N-dimethylformamide (15 mL) was added NBS (901 mg, 5.06 mmol, 1.2 eq). The resulting mixture was stirred for 1 h at room temperature. The mixture was diluted with water and extracted with ethyl acetate. The combined organic layer was washed with brine, dried over sodium sulfate and concentrated under reduced pressure. The residue was purified by Prep-TLC (petroleum ether/ethyl acetate=3/1) to afford 3-bromo-5-chloropyrazolo[1,5-a]pyridine (169.3, 440 mg, 47%) as a yellow solid. MS (ES): m/z 231/233 [M+H]⁺.

Synthesis of 169.5. To a solution of 169.3 (100 mg, 0.43 mmol, 1 eq) and bis(pinacolato)diboron (220 mg, 0.86 mmol, 2 eq) in 1,4-dioxane (8 mL) was added potassium acetate (85 mg, 0.86 mmol, 2 eq) and Pd(dppf)Cl₂ (36 mg, 0.08 mmol, 0.2 eq). The resulting solution was degassed three times with nitrogen and stirred for 1 h at 100° C. The mixture was allowed to cool down to room temperature, then methyl 5-bromothiazole-2-carboxylate (97 mg, 0.43 mmol, 1 eq) and water (1 mL) were added. The resulting solution was degassed three times with nitrogen and stirred for another 1 h at 100° C. The mixture was allowed to cool down to room temperature, diluted with water and extracted with ethyl acetate. The combined organic layer was washed with brine, dried over sodium sulfate and concentrated under reduced pressure. The residue was purified by Prep-TLC (petroleum ether/ethyl acetate=1/1) to afford methyl 5-(5-chloropyrazolo[1,5-a]pyridin-3-yl) thiazole-2-carboxylate (169.5, 15 mg, 12%) as a yellow solid. MS (ES): m/z 294 [M+H]⁺.

Synthesis of 169.6. To a stirred solution of 169.5 (64 mg, 0.21 mmol, 1 eq) in tetrahydrofuran (2 mL) was added potassium trimethylsilanolate (54 mg, 0.42 mmol, 2 eq). The resulting mixture was stirred for 1 h at room temperature. The resulting mixture was concentrated under reduced pressure to obtain the crude product potassium 5-(5-chloropyrazolo[1,5-a]pyridin-3-yl)thiazole-2-carboxylate (169.6, 70 mg). MS (ES): m/z 280 [M+H]⁺.

Synthesis of I-197. To a stirred solution of 169.6 (70 mg) and 16.4 (60 mg) in pyridine (3 mL) was added phosphorus oxychloride (200 mg) at 0° C. The resulting mixture was stirred for 1 h at 0° C. The reaction was concentrated under reduced pressure. The residue was purified by reverse phase flash chromatography with the following conditions: Column, C18 Column; Mobile Phase, water (10 mmol/L NH₄HCO₃) and ACN (10% ACN up to 60% in 10 min); UV detection at 254/220 nm. The product-containing fractions were combined and concentrated under reduced pressure. The crude product was purified by Prep-HPLC with the following conditions: Column: XBridge Prep OBD C18 Column, 30*150 mm, 5 lm; Mobile Phase Water (0.1% FA) and ACN (28% ACN up to 59% in 8 min); UV detection at 254/220 nm. The product-containing fractions were combined and evaporated partially in vacuum and lyophilized overnight to afford 5-{5-chloropyrazolo[1,5-a]pyridin-3-yl}-N-[(4-cyclopropanesulfonamidopyridin-2-yl)methyl]-1,3-thiazole-2-carboxamide (I-197, 6.1 mg, 6%) as a red solid. MS (ES): m/z 489 [M+H]⁺; ¹H NMR (400 MHz, d₆-DMSO) δ 9.38 (d, J=7.0 Hz, 1H), 8.87 (d, J=7.4 Hz, 1H), 8.61 (s, 1H), 8.44 (s, 1H), 8.19-8.09 (m, 2H), 7.14 (d, J=7.5 Hz, 1H), 7.02 (s, 2H), 4.51 (d, J=6.1 Hz, 2H), 2.75-2.65 (m, 1H), 1.01-0.88 (m, 4H).

Example 170: Synthesis of N-[(4-cyclopropane-sulfonamidopyridin-2-yl)methyl]-5-[5-(trifluoromethyl)pyrazolo[1,5-a]pyridin-3-yl]-1,3-thiazole-2-carboxamide (I-177)

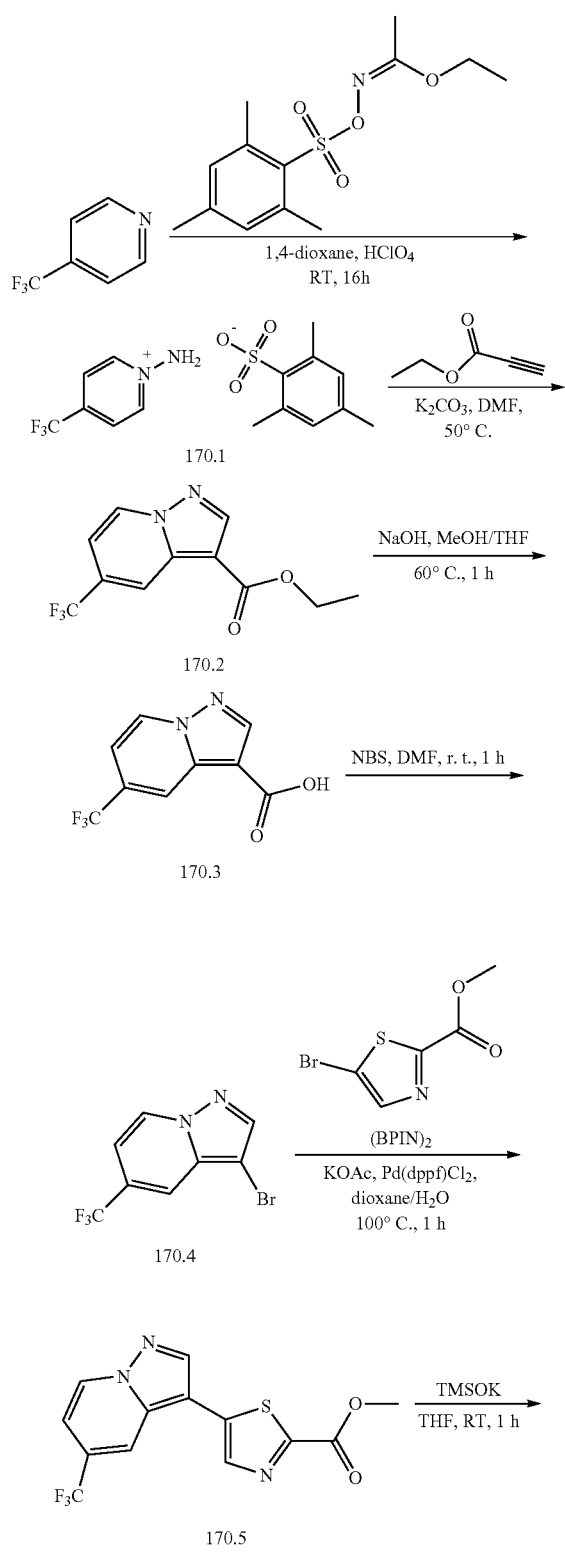

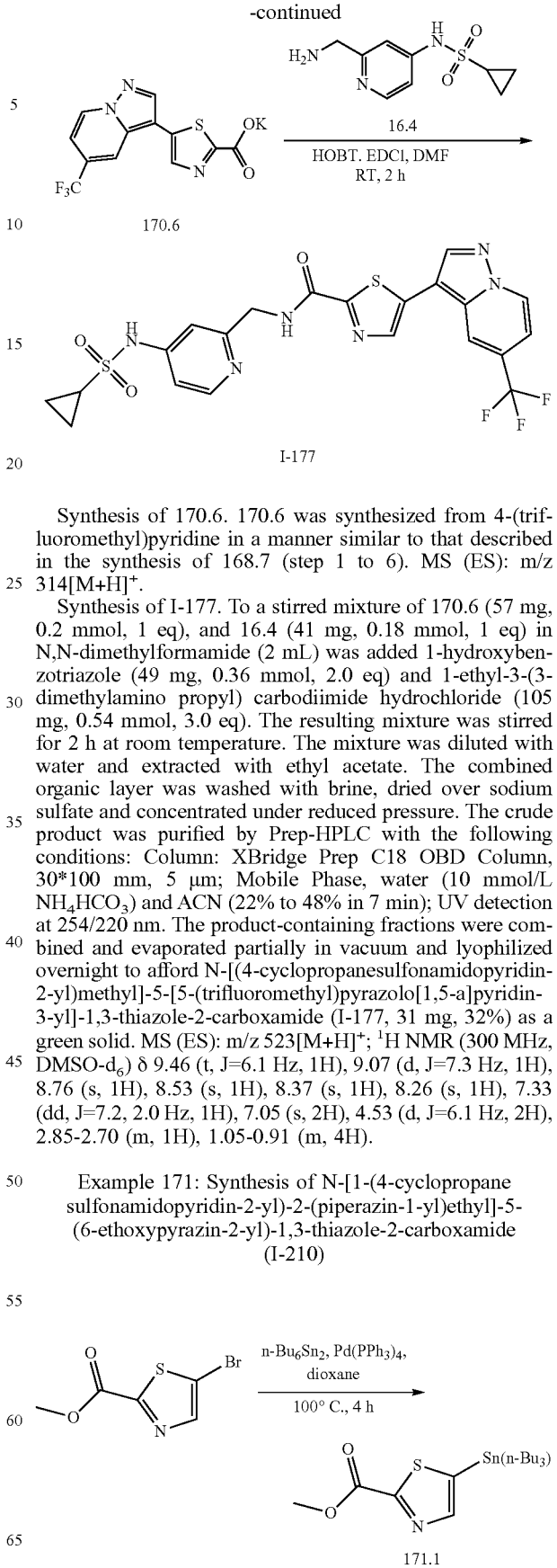

Synthesis of 170.6. 170.6 was synthesized from 4-(trifluoromethyl)pyridine in a manner similar to that described in the synthesis of 168.7 (step 1 to 6). MS (ES): m/z 314[M+H]$^+$.

Synthesis of I-177. To a stirred mixture of 170.6 (57 mg, 0.2 mmol, 1 eq), and 16.4 (41 mg, 0.18 mmol, 1 eq) in N,N-dimethylformamide (2 mL) was added 1-hydroxybenzotriazole (49 mg, 0.36 mmol, 2.0 eq) and 1-ethyl-3-(3-dimethylamino propyl) carbodiimide hydrochloride (105 mg, 0.54 mmol, 3.0 eq). The resulting mixture was stirred for 2 h at room temperature. The mixture was diluted with water and extracted with ethyl acetate. The combined organic layer was washed with brine, dried over sodium sulfate and concentrated under reduced pressure. The crude product was purified by Prep-HPLC with the following conditions: Column: XBridge Prep C18 OBD Column, 30*100 mm, 5 μm; Mobile Phase, water (10 mmol/L NH$_4$HCO$_3$) and ACN (22% to 48% in 7 min); UV detection at 254/220 nm. The product-containing fractions were combined and evaporated partially in vacuum and lyophilized overnight to afford N-[(4-cyclopropanesulfonamidopyridin-2-yl)methyl]-5-[5-(trifluoromethyl)pyrazolo[1,5-a]pyridin-3-yl]-1,3-thiazole-2-carboxamide (I-177, 31 mg, 32%) as a green solid. MS (ES): m/z 523[M+H]$^+$; $^1$H NMR (300 MHz, DMSO-d$_6$) δ 9.46 (t, J=6.1 Hz, 1H), 9.07 (d, J=7.3 Hz, 1H), 8.76 (s, 1H), 8.53 (s, 1H), 8.37 (s, 1H), 8.26 (s, 1H), 7.33 (dd, J=7.2, 2.0 Hz, 1H), 7.05 (s, 2H), 4.53 (d, J=6.1 Hz, 2H), 2.85-2.70 (m, 1H), 1.05-0.91 (m, 4H).

Example 171: Synthesis of N-[1-(4-cyclopropane sulfonamidopyridin-2-yl)-2-(piperazin-1-yl)ethyl]-5-(6-ethoxypyrazin-2-yl)-1,3-thiazole-2-carboxamide (I-210)

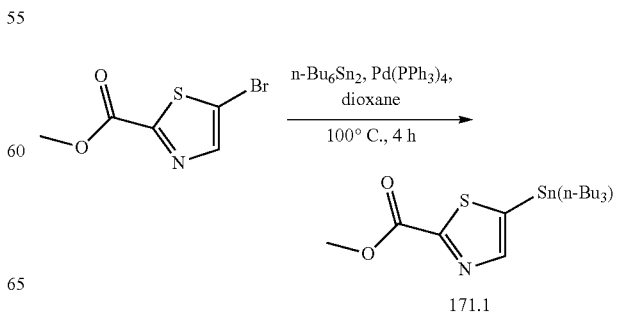

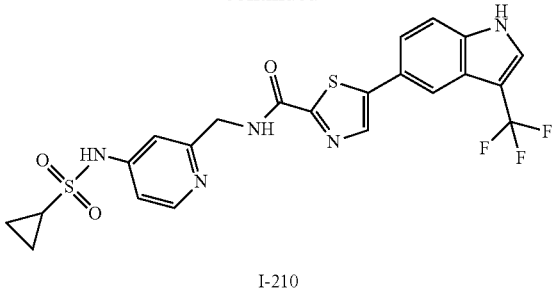

I-210

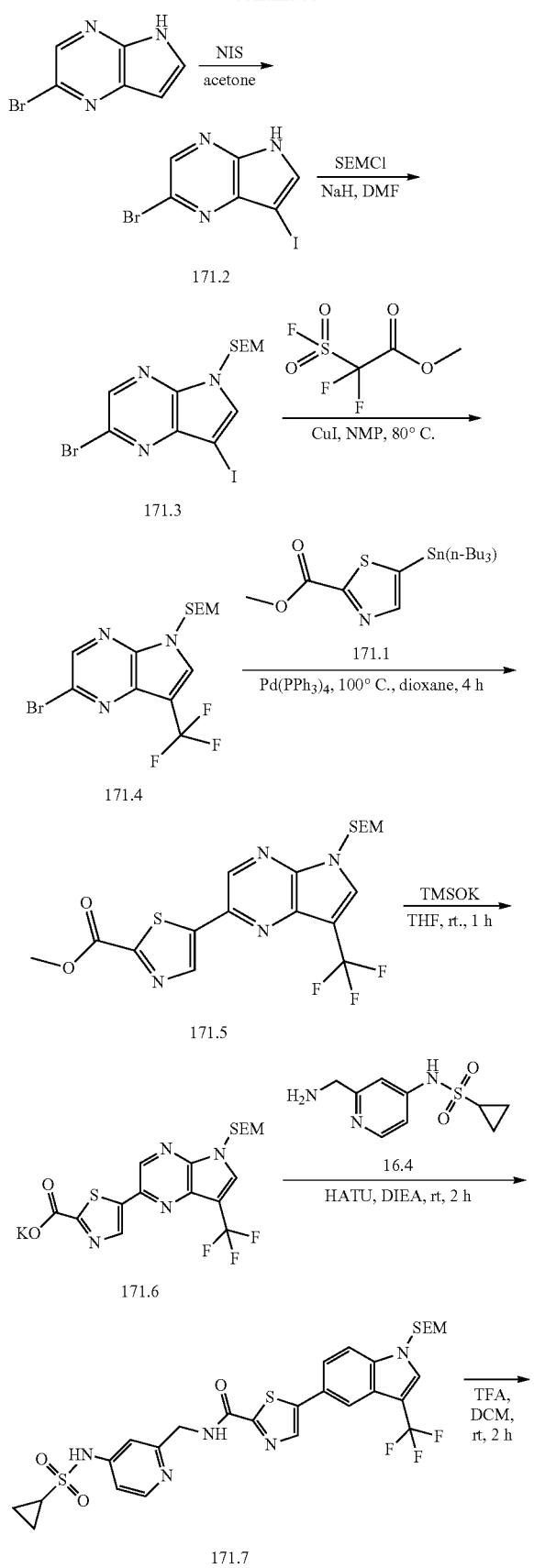

Synthesis of 171.1. To a stirred solution of methyl 5-bromothiazole-2-carboxylate (222 mg, 1 mmol, 1 eq) and hexa-n-butylditin (1.16 g, 2 mmol, 2 eq) in 1,4-dioxane (4 mL) was added Pd(PPh$_3$)$_4$ (115 mg, 0.1 mmol, 0.1 eq). The resulting solution was degassed three times with nitrogen and stirred for 4 h at 100° C. The mixture was allowed to cool down to room temperature. The resulting mixture was diluted with water and extracted with ethyl acetate. The combined organic layers were washed with brine, dried over anhydrous sodium sulfate and concentrated under reduced pressure. The residue was purified by Prep-TLC (compound was eluted in 30% ethyl acetate in petroleum ether) to afford methyl 5-(tributylstannyl)-1,3-thiazole-2-carboxylate (171.1, 67 mg, 15%) as a yellow solid. MS (ES): m/z 434 [M+H]$^+$.

Synthesis of 171.2. To a stirred mixture of 2-bromo-5H-pyrrolo[2,3-b]pyrazine (1 g, 5.05 mmol, 1 eq) in acetone (15 mL) was added N-iodosuccinimide (1 g, 6.06 mmol, 1.2 eq). The resulting mixture was stirred for 1 h at room temperature. The mixture was diluted with water and extracted with ethyl acetate. The combined organic layer was washed with brine, dried over sodium sulfate and concentrated under reduced pressure. The residue was purified by silica gel column chromatography (compound was eluted in 30% ethyl acetate in petroleum ether) to afford 2-bromo-7-iodo-5H-pyrrolo[2,3-b]pyrazine (171.2, 1.39 g, 85%) as a yellow solid. MS (ES): m/z 324/326 [M+H]$^+$.

Synthesis of 171.3. A solution of 171.2 (500 mg, 1.55 mmol, 1 eq) in N,N-dimethylformamide (5 mL) was degassed three times with nitrogen and cooled to 0° C. To the solution was added sodium hydride (60% w/w in mineral oil, 93 mg, 2.32 mmol, 1.5 eq) stirred for 0.5 h at 0° C. under nitrogen atmosphere. To the above mixture was added [2-(chloromethoxy) ethyl] trimethylsilane (283 mg, 1.7 mmol, 1.1 eq). The resulting mixture was stirred for an additional 1 h at room temperature under nitrogen atmosphere. The reaction was quenched with saturated aqueous ammonium chloride and extracted with ethyl acetate. The combined organic layers were washed with water, dried over anhydrous sodium sulfate. After filtration, the filtrate was concentrated under reduced pressure and purified by Prep-TLC (petroleum ether/ethyl acetate=6:1) to afford 2-bromo-7-iodo-5-((2-(trimethylsilyl)ethoxy)methyl)-5H-pyrrolo[2,3-b]pyrazine (171.3, 480 mg, 68%) as a light yellow solid. MS (ES): m/z 454/456 [M+H]$^+$.

Synthesis of 171.4 To a stirred mixture of 171.3 (480 mg, 1.06 mmol, 1 eq) in N-methyl pyrrolidone (5 mL) was added cuprous iodide (242 mg, 1.27 mmol, 1.2 eq) and methyl 2,2-difluoro-2-(fluorosulfonyl)acetate (203 mg, 1.06 mmol, 1 eq). The resulting mixture was stirred for overnight at 80° C. The mixture was diluted with water and extracted with ethyl acetate. The combined organic layer was washed with brine, dried over sodium sulfate and concentrated under reduced pressure. The residue was purified by silica gel column chromatography and compound was eluted in 20% ethyl acetate in petroleum ether to afford 2-bromo-7-(trifluoromethyl)-5-((2-(trimethylsilyl)ethoxy)methyl)-5H-pyrrolo[2,3-b]pyrazine (171.4, 110 mg, 26%) as a yellow solid. MS (ES): m/z 396/398 [M+H]$^+$.

Synthesis of 171.5. To a stirred solution of 171.1 (200 mg, 0.51 mmol, 1 eq) and 171.4 (220 mg, 0.51 mmol, 1 eq) in 1,4-dioxane (4 mL) was added Pd(PPh$_3$)$_4$ (58 mg, 0.05 mmol, 0.1 eq). The resulting solution was degassed three times with nitrogen and stirred for 4 h at 100° C. The mixture was allowed to cool down to room temperature. The resulting mixture was diluted with water and extracted with ethyl acetate. The combined organic layers were washed with brine, dried over anhydrous sodium sulfate and concentrated under reduced pressure. The residue was purified by Prep-TLC (compound was eluted in 30% ethyl acetate in petroleum ether) to afford methyl 5-[7-(trifluoromethyl)-5-{[2-(trimethylsilyl) ethoxy] methyl} pyrrolo[2,3-b] pyrazin-2-yl]-1,3-thiazole-2-carboxylate (171.5, 123 mg, 53%) as a yellow solid. MS (ES): m/z 459 [M+H]$^+$.

Synthesis of 171.6. 171.6 was synthesized from 171.5 in a manner similar to that described in the synthesis of 164.4. MS (ES): m/z 445 [M+H]$^+$.

Synthesis of 171.7. 171.7 was synthesized from 171.6 and 16.4 in a manner similar to that described in the synthesis of I-253 (amide coupling step). MS (ES): m/z 654 [M+H]$^+$.

Synthesis of I-210. To a stirred solution of 171.7 (50 mg, 0.06 mmol, 1 eq) in dichloromethane (5 mL) was added trifluoroacetic acid (2 mL). The resulting mixture was stirred for 2 h at room temperature. The resulting mixture was concentrated under reduced pressure. To the above mixture was added tetrahydrofuran (1.5 mL) and saturated aqueous sodium bicarbonate solution (0.75 mL). The resulting mixture was stirred for additional 1.5 h at room temperature. The residue was extracted with ethyl acetate. The combined organic layers were washed with brine, dried over anhydrous sodium sulfate. After filtration, the filtrate was concentrated under reduced pressure. The crude product was purified by Prep-HPLC with the following conditions: Column, XBridge Shield RP18 OBD Column, 30*150 mm, 5 um; Mobile Phase, water (0.1% FA) and ACN (5% ACN up to 70% in 5.5 min); UV detection at 254/220 nm. The product-containing fractions were combined and evaporated partially in vacuum and lyophilized overnight to afford N-[1-(4-cyclopropanesulfonamidopyridin-2-yl)-2-(piperazin-1-yl)ethyl]-5-(6-ethoxypyrazin-2-yl)-1,3-thiazole-2-carboxamide (I-210, 14 mg, 43%) as a white solid. MS (ES): m/z 524 [M+H]$^+$; $^1$H NMR (300 MHz, d$_6$-DMSO) δ 9.48 (t, J=6.2 Hz, 1H), 9.22 (s, 1H), 8.84 (s, 1H), 8.61 (s, 1H), 8.31-8.17 (m, 1H), 7.05 (d, J=7.3 Hz, 2H), 4.53 (d, J=6.1 Hz, 2H), 2.80-2.64 (m, 1H), 1.03-0.91 (m, 4H).

Example 172: N-[(4-cyclopropanesulfonamidopyridin-2-yl)methyl]-5-[7-(2,2-difluoroethyl)-5H-pyrrolo[2,3-b] pyrazin-2-yl]-1,3-thiazole-2-carboxamide (I-215)

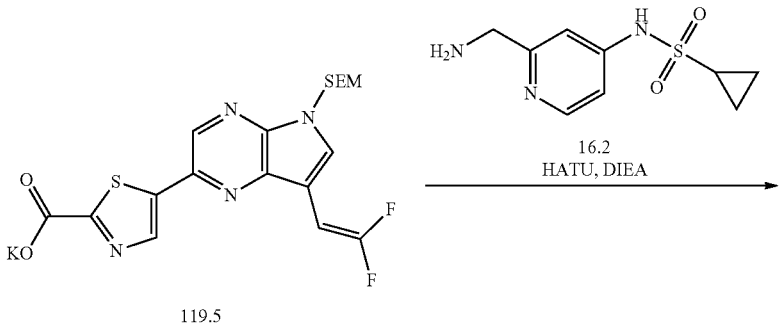

119.5

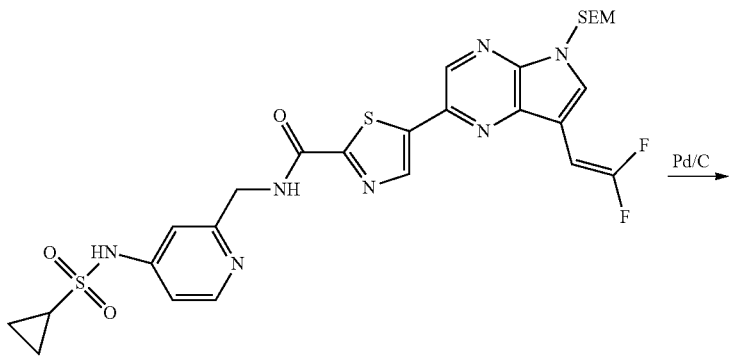

172.1

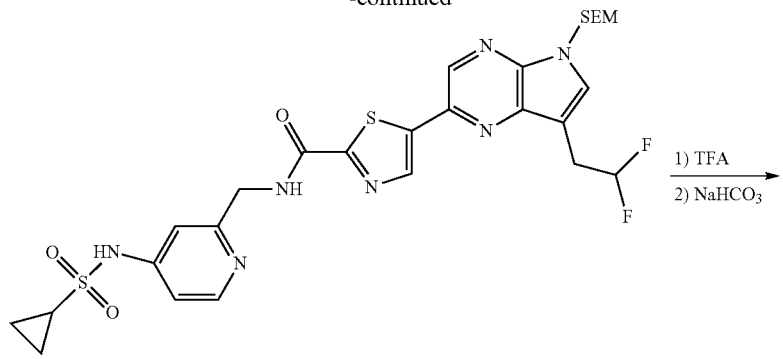

172.2

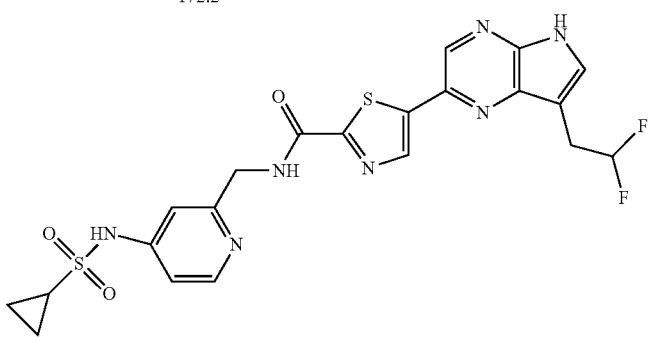

I-215

Synthesis of 172.1 172.1 was synthesized in a manner similar to that described in the synthesis of I-253 (amide coupling step) using 119.5 and 16.4. MS (ES): m/z 648 [M+H]+.

Synthesis of 172.2. A stirred mixture of 172.1 (50 mg, 0.07 mmol, 1.0 eq) in methyl alcohol (3 mL) was evacuated and flushed three times with nitrogen. To the solution was added palladium 10% on carbon (10 mg). The mixture was flushed with nitrogen, then hydrogen, repeating the operation three times. The mixture was stirred for 15 h at 30° C. under hydrogen atmosphere at 10 atm. The resulting mixture was filtered and the filter cake was washed with methanol. The filtrate was concentrated under reduced pressure to afford crude N-((4-(cyclopropanesulfonamido)pyridin-2-yl)methyl)-5-(7-(2,2-difluoroethyl)-5-((2-(trimethylsilyl)ethoxy)methyl)-5H-pyrrolo[2,3-b]pyrazin-2-yl)thiazole-2-carboxamide (172.2, 40 mg, 87%). MS (ES): m/z 650 [M+H]+.

Synthesis of I-215. I-215 was synthesized in a manner similar to that described in the synthesis of I-210 (final step) but using 172.2. Final product purification: Prep-HPLC with the following conditions (Column: Column: XBridge Prep C18 OBD Column, 19*150 mm, 5 µm; Mobile Phase, water (10 mmol/L NH$_4$HCO$_3$) and ACN (15% ACN up to 35% in 7 min); UV detection at 254/220 nm). MS (ES): m/z 520 [M+H]+; $^1$H NMR (400 MHz, DMSO-d$_6$) δ 12.28 (s, 1H), 9.41 (s, 1H), 9.08 (s, 1H), 8.79 (s, 1H), 8.20 (s, 1H), 7.91 (s, 1H), 6.99 (s, 2H), 6.41 (t, J=56.8, 56.4 Hz, 1H), 4.50 (d, J=5.8 Hz, 2H), 3.45-3.35 (m, 2H), 2.70-2.61 (m, 1H), 0.97-0.80 (m, 4H).

Example 173: Synthesis of N-((4-(cyclopropanesulfonamido)pyridin-2-yl)methyl)-5-(5-ethylpyrrolo[1,2-b]pyridazin-3-yl)thiazole-2-carboxamide (I-196)

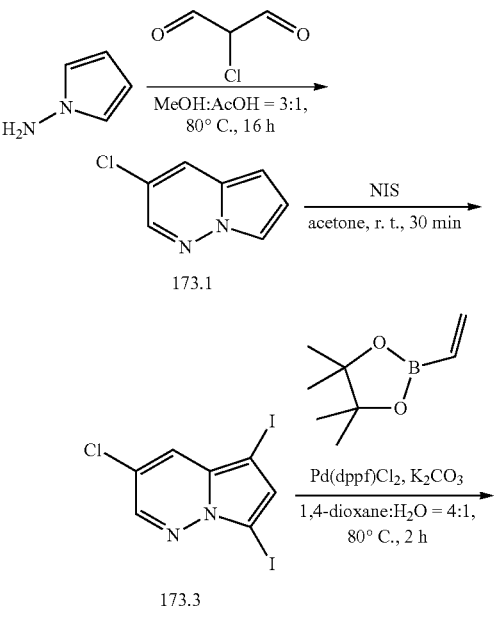

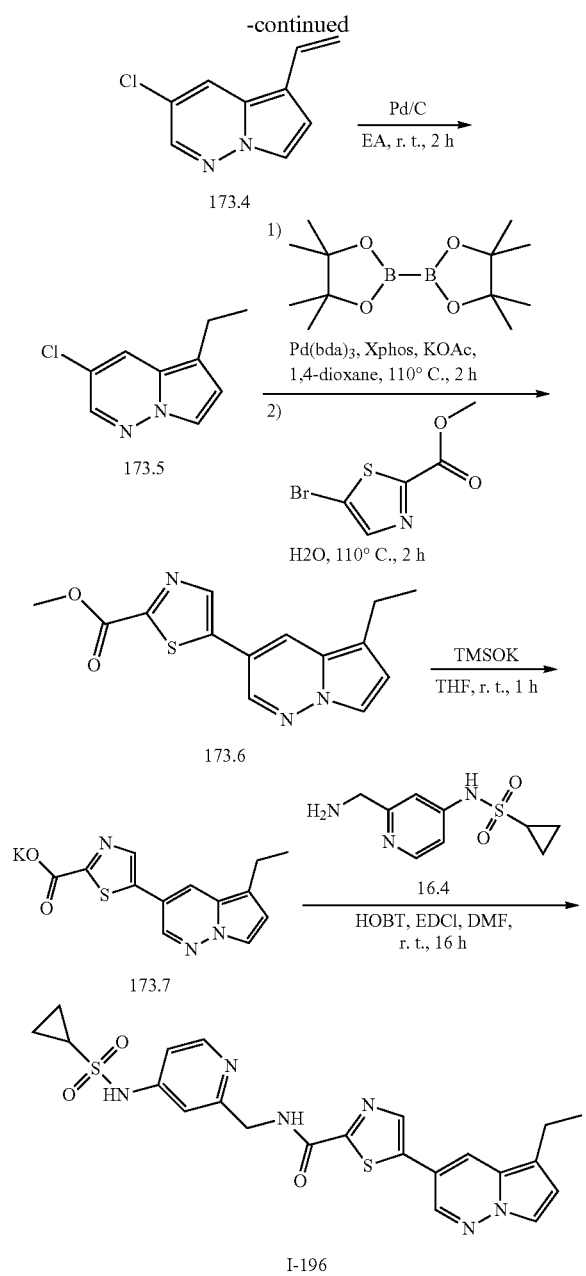

Synthesis of 173.2. To a stirred solution of 173.1 (600 mg, 3.93 mmol, 1 eq) in acetone (20 mL) was added N-iodosuccinimide (2.65 g, 11.79 mmol, 3 eq). The resulting mixture was stirred for 2 h at room temperature, then was concentrated under reduced pressure. The resulting mixture was diluted with water and extracted with ethyl acetate. The combined organic layers were washed with water and dried over anhydrous sodium sulfate. After filtration, the filtrate was concentrated under reduced pressure and purified by Prep-TLC (Petroleum ether/Ethyl acetate=20/1) to afford 3-chloro-5,7-diiodopyrrolo[1,2-b]pyridazine (173.2, 1.2 g, 75%) as a yellow solid. $^1$H NMR (400 MHz, Chloroform-J) δ 8.08 (d, J=2.4 Hz, 1H), 7.62 (d, J=2.4 Hz, 1H), 7.16 (s, 1H).

Synthesis of 173.3. A stirred solution of 173.2 (940 mg, 2.32 mmol, 1 eq) in tetrahydrofuran (30 mL) was degassed three times with nitrogen and cooled to −78° C. To the solution was added n-BuLi (1.12 mL, 2.79 mmol, 2.5 M in n-hexane) at −78° C. The resulting mixture was stirred for 0.5 h at −78° C. under nitrogen atmosphere. The reaction was quenched with saturated aqueous ammonium chloride, and extracted with ethyl acetate. The combined organic layers were washed with water, dried over anhydrous sodium sulfate. After filtration, the filtrate was concentrated under reduced pressure to afford the crude product 3-chloro-5-iodopyrrolo[1,2-b]pyridazine (173.3, 500 mg, 77%) as dark green solid. $^1$H NMR (400 MHz, Chloroform-d) δ 7.92 (d, J=2.4 Hz, 1H), 7.73 (dd, J=2D, 0.7 Hz, 1H), 7.65 (dd, J=2.4, 0.7 Hz, 1H), 6.99 (d, J=2D Hz, 1H).

Synthesis of 173.4. To a stirred solution of 173.3 (290 mg, 1.04 mmol, 1 eq) and 2-ethenyl-4,4,5,5-tetramethyl-1,3,2-dioxaborolane (241 mg, 1.56 mmol, 1.5 eq) in 1,4-dioxane (12 mL) and water (3 mL) were added potassium carbonate (431 mg, 3.12 mmol, 3 eq) and Pd(dppf)Cl$_2$·CHCl$_3$ (85 mg, 0.1 mmol, 0.1 eq) at room temperature. The resulting solution was degassed three times with nitrogen and stirred for 2 h at 60° C. The mixture was allowed to cool down to room temperature. The resulting mixture was diluted with water and extracted with dichloromethane. The combined organic layers were washed with brine and dried over anhydrous sodium sulfate. After filtration, the filtrate was concentrated under reduced pressure and purified by Prep-TLC (Petroleum ether) to afford 3-chloro-5-ethenylpyrrolo[1,2-b]pyridazine (173.4, 110 mg, 59%) as yellow oil. NMR (400 MHz, Chloroform-J) δ 7.92 (d, J=2.5 Hz, 1H), 7.81 (d, J=2.5 Hz, 1H), 7.67 (d, J=3.0 Hz, 1H), 7.03 (d, J=2.9 Hz, 1H), 6.81 (dd, J=17.5, 11.0 Hz, 1H), 5.60 (dd, J=17.4, 1.3 Hz, 1H), 5.19 (dd, J=11.0, 1.3 Hz, 1H).

Synthesis of 173.5. A stirred mixture of 173.4 (110 mg, 0.62 mmol, 1 eq) in ethyl acetate (10 mL) was evacuated and flushed three times with nitrogen. To the solution was added 10% on carbon palladium (20 mg). The mixture was flushed with nitrogen, then hydrogen, repeating the operation three times. The mixture was stirred for 2 h at 30° C. under hydrogen atmosphere at 2 atm. The resulting mixture was filtered and the filter cake was washed with ethyl acetate. The filtrate was concentrated under reduced pressure to afford the crude product 3-chloro-5-ethylpyrrolo[1,2-b]pyridazine (173.5, 110 mg) as a yellow oil, used without purification in subsequent steps.

Synthesis of 173.6. To a stirred solution of 173.5 (100 mg, 0.55 mmol, 1 eq) and bis(pinacolato)diboron (421 mg, 1.66 mmol, 3 eq) in 1,4-dioxane (2 mL) were added Pd$_2$(dba)$_3$ (51 mg, 0.05 mmol, 0.1 eq) and XPhos (53 mg, 0.11 mmol, 0.2 eq) at room temperature under nitrogen atmosphere. The resulting solution was degassed three times with nitrogen and stirred for 2 h at 100° C. The mixture was allowed to Synthesis of 173.1. To a stirred solution of pyrrol-1-amine (2 g, 24.36 mmol, 1 eq) in methyl alcohol (30 mL) and acetic acid (10 mL) was added 2-chloropropanedial (3.1 g, 29.23 mmol, 1.2 eq) at room temperature. The resulting mixture was stirred for overnight at 80° C. under nitrogen atmosphere. The mixture was allowed to cool down to room temperature. The resulting mixture was filtered, and the filter cake washed with dichloromethane. The filtrate was concentrated under reduced pressure. The resulting mixture was diluted with water, extracted with dichloromethane. The combined organic layers were washed with water, dried over anhydrous sodium sulfate. After filtration, the filtrate was concentrated under reduced pressure and purified by TLC (Ethyl acetate/Petroleum ether=1:20) to afford 3-chloropyrrolo[1,2-b]pyridazine (173.1, 1 g, 27%) as a green solid. $^1$H NMR (400 MHz, Chloroform-J) δ 7.96 (d, J=2.5 Hz, 1H), 7.77-7.70 (m, 2H), 6.89 (dd, J=4.3, 2.7 Hz, 1H), 6.48 (dd, J=4.3, 1.5 Hz, 1H).

cool down to room temperature, then methyl 5-bromothiazole-2-carboxylate (246 mg, 1.1 mmol, 2 eq) and water (1 mL) were added. The resulting solution was degassed three times with nitrogen and stirred for another 2 h at 100° C. The mixture was allowed to cool down to room temperature, diluted with water and extracted with ethyl acetate. The combined organic layer was washed with brine, dried over sodium sulfate and concentrated under reduced pressure. The residue was purified by Prep-TLC (petroleum ether/ ethyl acetate=5/1) to afford methyl 5-{5-ethylpyrrolo[1,2-b]pyridazin-3-yl}-1,3-thiazole-2-carboxylate (173.6, 150 mg, 94%) as a dark yellow solid. MS (ES): m/z 288 [M+H]$^+$.

Synthesis of 173.7. To a stirred solution of 173.6 (120 mg, 0.41 mmol, 1 eq) in tetrahydrofuran (10 mL) was added potassium trimethylsilanolate (107 mg, 0.83 mmol, 2 eq). The resulting mixture was stirred for 1 h at room temperature. The resulting mixture was concentrated under reduced pressure to obtain the crude product potassium 5-(5-ethylpyrrolo[1,2-b] pyridazin-3-yl)thiazole-2-carboxylate (173.7, 140 mg), which was used in the next step directly without further purification. MS (ES): m/z 274 [M+H]$^+$.

Synthesis of I-196. I-196 was synthesized in a manner similar to that described in the synthesis of I-177 (amide coupling step) using 173.7 and 16.4. Final product purification: Prep-HPLC with the following conditions (Column: XBridge Prep OBD C18 Column, 30*150 mm, 5 µm; Mobile Phase: Water (10 mmol/L NH$_4$HCO$_3$) and ACN (38% ACN up to 62% in 8 min); UV detection at 254/220 nm). MS (ES): m/z 483 [M+H]$^+$; $^1$H NMR (400 MHz, Chloroform-d) δ 8.40 (d, J=5.7 Hz, 1H), 8.30-8.18 (m, 2H), 8.02 (s, 1H), 7.86 (d, J=2.4 Hz, 1H), 7.75 (d, J=2.7 Hz, 1H), 7.15 (d, J=6.0 Hz, 2H), 6.81 (d, J=2.7 Hz, 1H), 4.76 (d, J=5.6 Hz, 2H), 2.83 (q, 7=7.6 Hz, 2H), 2.71-2.60 (m, 1H), 1.42-1.26 (m, 5H), 1.14-1.04 (m, 2H).

Example 174: Synthesis of N-((4-(cyclopropanesulfonamido)pyridin-2-yl)methyl)-5-(pyrrolo[1,2-b]pyridazin-3-yl)thiazole-2-carboxamide (I-200)

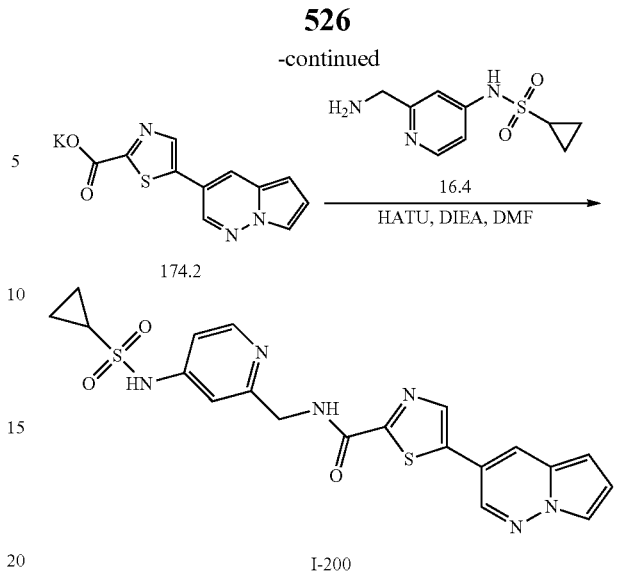

Synthesis of I-200. I-200 was synthesized in a manner similar to that described in the synthesis of I-196 (step 6, 7 and 8) using 173.1 as the chloride reagent. Final product purification: Prep-HPLC with the following conditions (Column: XBridge Prep OBD C18 Column, 30*150 mm, 5 µm; Mobile Phase: Water (10 mmol/L NH$_4$HCO$_3$) and ACN (27% ACN up to 46% in 8 min); UV detection at 254/220 nm). MS (ES): m/z 455 [M+H]$^+$; $^1$H NMR (400 MHz, DMSO-7) δ 9.45 (t, J=5.6, 5.6 Hz, 1H), 8.72 (d, J=2.4 Hz, 1H), 8.58 (s, 1H), 8.42 (d, J=2.4 Hz, 1H), 8.26 (s, 1H), 8.02-7.99 (s, 1H), 7.11-6.94 (m, 3H), 6.71 (d, J=4.4 Hz, 1H), 4.52 (d, J=6.2 Hz, 2H), 2.84-2.70 (m, 1H), 1.10-0.86 (m, 4H).

Example 175: Synthesis of N-[(4-cyclopropanesulfonamidopyridin-2-yl)methyl]-5-{2-methylpyrazolo[1,5-c] pyrimidin-4-yl}-1,3-thiazole-2-carboxamide (I-185)

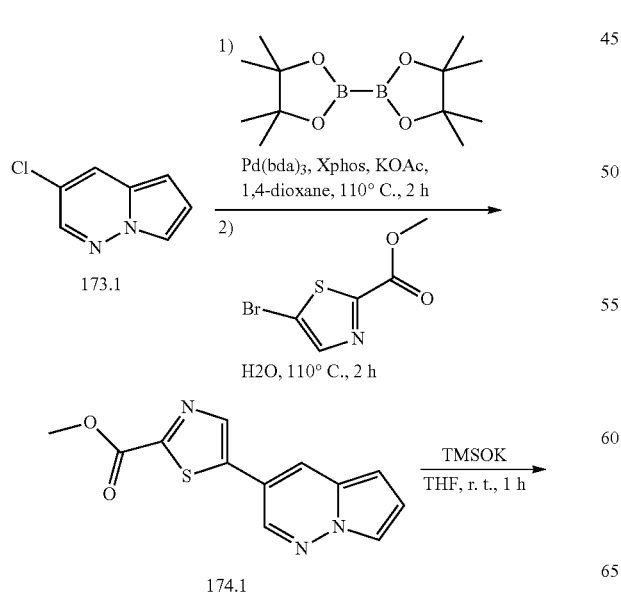

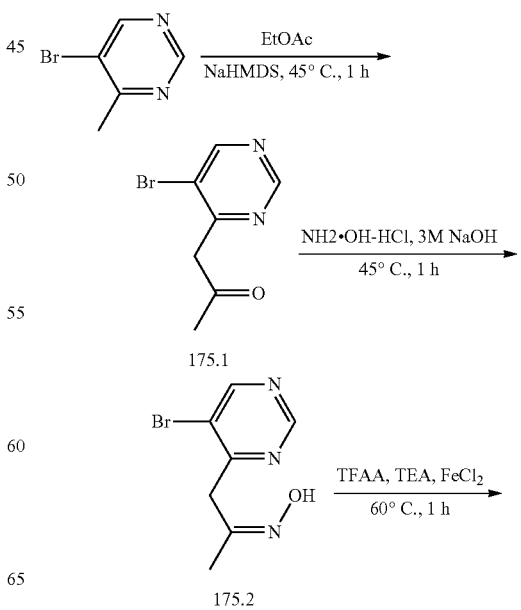

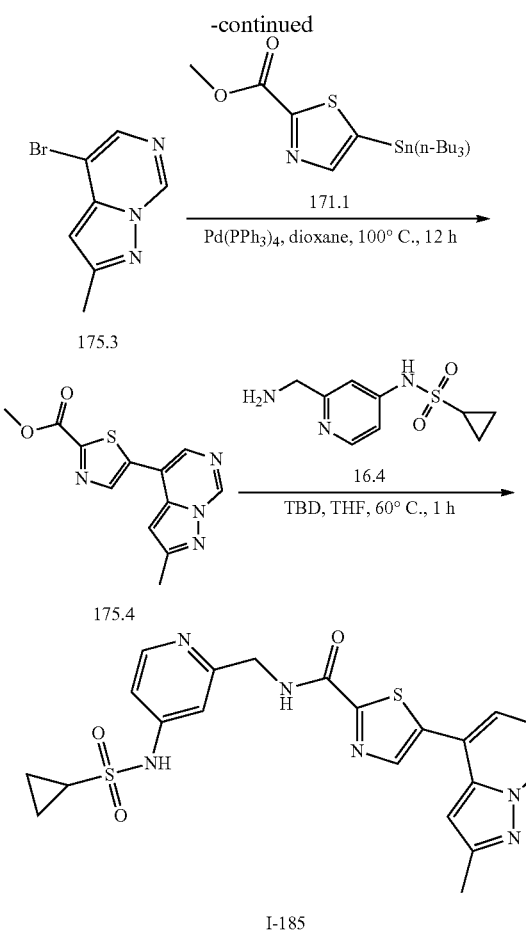

Synthesis of 175.1. A stirred solution of 5-bromo-4-methylpyrimidine (1.5 g, 8.67 mmol, 1.0 eq) in tetrahydrofuran (40 mL) was degassed three times with nitrogen and cooled to 0° C. To the solution was added NaHMDS (2M in tetrahydrofuran, 8.7 mL, 2.0 eq) and the reaction mixture was stirred for 0.5 h at 0° C. under nitrogen atmosphere. To the above mixture was added ethyl acetate (7.64 g, 86.7 mmol, 10 eq) dropwise over 10 min at 0° C. under nitrogen atmosphere. The resulting mixture was stirred for additional 1 h at 45° C. under nitrogen atmosphere. The mixture was allowed to cool down to room temperature. The mixture was quenched with saturated aqueous ammonium chloride and extracted with ethyl acetate. The combined organic layer was washed with brine, dried over sodium sulfate and concentrated under reduced pressure. The residue was purified by Prep-TLC (compound was eluted in 50% ethyl acetate in petroleum ether) to afford 1-(5-bromopyrimidin-4-yl) propan-2-one (175.1, 1.5 g, 80%) as yellow oil. MS (ES): m/z 215/217 [M+H]$^+$.

Synthesis of 175.2. Into a 50 mL vial was added 175.1 (600 mg, 2.79 mmol, 1 eq) and sodium hydroxide (3M in water, 9.3 mL, 10 eq). Hydroxylamine hydrochloride (969 mg, 13.95 mmol, 5 eq) was then added at room temperature. The resulting mixture was stirred for 1 h at 45° C. The mixture was allowed to cool down to room temperature. The mixture was diluted with water and extracted with ethyl acetate. The combined organic layer was washed with brine, dried over sodium sulfate and concentrated under reduced pressure. The residue was purified by Prep-TLC (compound was eluted in 100% ethyl acetate in petroleum) to afford (Z)-1-(5-bromopyrimidin-4-yl)propan-2-one oxime (175.2, 450 mg, 70%) as a yellow solid. MS (ES): m/z 230/232 [M+H]$^+$.

Synthesis of 175.3. To a stirred solution of 175.2 (450 mg, 1.96 mmol, 1 eq) in ethylene glycol dimethyl ether (10 mL) was added trifluoroacetic anhydride (412 mg, 1.96 mmol, 1 eq) and triethylamine (594 mg, 5.88 mmol, 3 eq) at 0° C. under nitrogen atmosphere. The resulting mixture was stirred for 45 min at room temperature under nitrogen atmosphere. To the above mixture was added ferrous chloride (75 mg, 0.59 mmol, 0.3 eq) at room temperature. The resulting mixture was stirred for additional 1 h at 60° C. The mixture was allowed to cool down to room temperature. The resulting mixture was concentrated under reduced pressure. The residue was purified by Prep-TLC and compound was eluted in 100% ethyl acetate in petroleum to afford 4-bromo-2-methylpyrazolo[1,5-c] pyrimidine (175.3, 208 mg, 50%) as a white solid. MS (ES): m/z 212/214 [M+H]$^+$.

Synthesis of 175.4. 175.4 was synthesized in a manner similar to that described in the synthesis of 171.5 (but reaction time 12 h), using 175.3 and 171.1. MS (ES): m/z 275 [M+H]$^+$.

Synthesis of I-185. To a stirred solution of 175.4 (40 mg, 0.15 mmol, 1 eq) and 16.4 (40 mg, 0.17 mmol, 1.2 eq) in tetrahydrofuran (4 mL) was added 1,3,4,6,7,8-hexahydro-2H-pyrimido[1,2-A] pyrimidine (30 mg, 0.22 mmol, 1.5 eq) at room temperature. The resulting mixture was stirred for 1 h at 60° C. The residue was purified by Prep-TLC and compound was eluted in 5% methanol in dichloromethane. The crude product was purified by Prep-HPLC with the following conditions: Column, XBridge Shield RP18 OBD Column, 30*150 mm, 5 um; Mobile Phase, water (0.1% FA) and ACN (5% ACN up to 35% in 7 min); UV detection at 254/220 nm. The product-containing fractions were combined and evaporated partially in vacuum and lyophilized overnight to afford N-[(4-cyclopropanesulfonamidopyridin-2-yl) methyl]-5-{2-methylpyrazolo[1,5-c] pyrimidin-4-yl}-1,3-thiazole-2-carboxamide (I-185, 7.1 mg, 10%) as a yellow solid. MS (ES): m/z 470 [M+H]$^+$; $^1$H NMR (400 MHz, d$_6$-DMSO) δ 9.58-9.45 (m, 2H), 8.69 (s, 1H), 8.35 (s, 1H), 8.25 (d, J=5.7 Hz, 1H), 7.09-6.97 (m, 3H), 4.53 (d, J=6.1 Hz, 2H), 2.79-2.65 (m, 1H), 2.50 (s, 3H), 1.02-0.88 (m, 4H).

Example 176: Synthesis of 5-{3-chloropyrazolo[1,5-a] pyrazine-7-yl}-N-[(4-cyclopropanesulfonamidopyridin-2-yl)methyl]-1,3-thiazole-2-carboxamide (I-154)

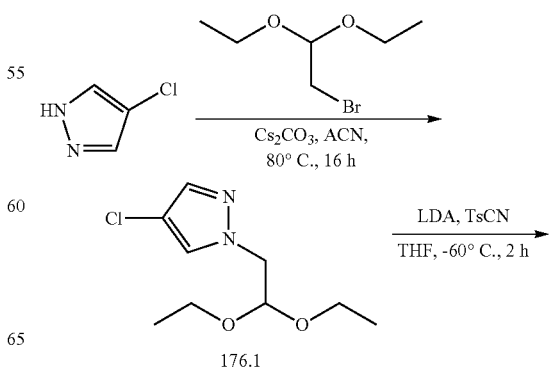

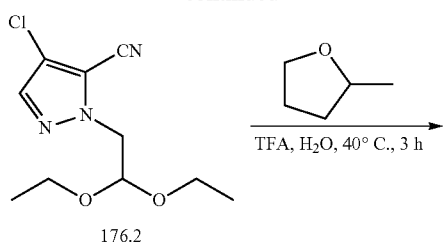

176.2

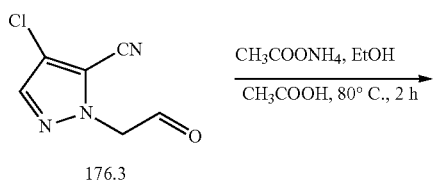

176.3

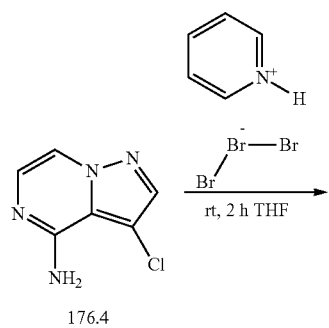

176.4

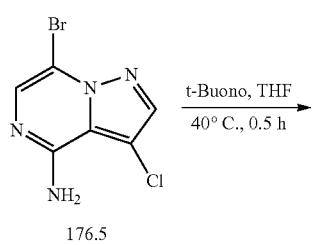

176.5

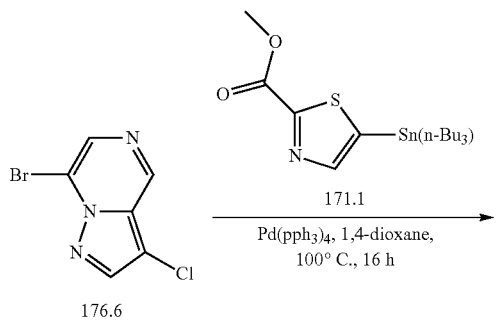

176.6

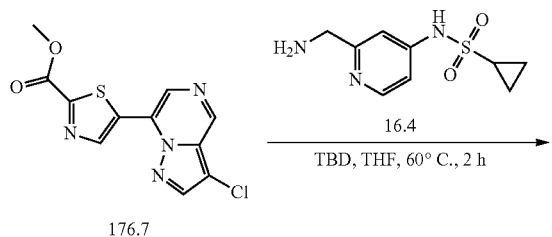

176.7

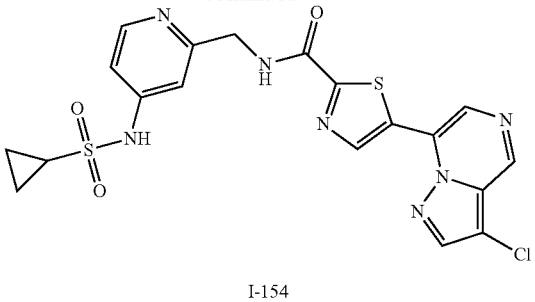

I-154

Synthesis 176.1. To a stirred solution of 4-chloro-1H-pyrazole (20.6 g, 200.93 mmol, 1 eq) in acetonitrile (200 mL) was added cesium carbonate (98.2 g, 301.4 mmol, 1.5 eq) and 2-bromo-1,1-diethoxyethane (41.5 g, 210.98 mmol, 1 eq). The resulting mixture was stirred for 16 h at 50° C. under nitrogen atmosphere. After filtration, the filtrate was concentrated under reduced pressure and purified by reverse phase flash chromatography with the following conditions: Column, C18 Column; Mobile Phase, water (0.1% FA) and ACN (0% ACN up to 100% in 20 min); UV detection at 254/220 nm. The product-containing fractions were combined and concentrated under reduced pressure to obtain 4-chloro-1-(2,2-diethoxyethyl)pyrazole (176.1, 10 g, 23%) as a white solid. MS (ES): m/z 219 [M+H]$^+$.

Synthesis of 176.2. A stirred solution of 176.1 (10 g, 45.73 mmol, 1 eq) in THF (300 mL) was degassed three times with nitrogen and then cooled to –60° C. To the solution was added LDA (59.44 mL, 59.44 mmol, 1 M in THF) at –60° C. The resulting mixture was stirred for 1 h at –78° C. under nitrogen atmosphere. To the resulting mixture was added 4-methylbenzene-1-sulfonyl cyanide (10.7 g, 59.44 mmol, 1.3 eq) in tetrahydrofuran (30 mL) at –78° C. under nitrogen atmosphere. The resulting mixture was stirred for further 1 h at –78° C. under nitrogen atmosphere. The reaction was quenched with saturated aqueous ammonium chloride and extracted with ethyl acetate. The combined organic layers were washed with water, dried over anhydrous sodium sulfate. After filtration, the filtrate was concentrated under reduced pressure and purified by reverse phase flash chromatography with the following conditions: Column, C18 Column; Mobile Phase, water (0.1% FA) and ACN (0% ACN up to 100% in 10 min); UV detection at 254/220 nm. The product-containing fractions were combined and concentrated under reduced pressure to obtain 4-chloro-2-(2,2-diethoxyethyl)pyrazole-3-carbonitrile (176.2, 3.3 g, 29%) as a white solid. MS (ES): m/z 244 [M+H]$^+$.

Synthesis 176.3. To a solution of 176.2 (1.07 g, 4.39 mmol, 1 eq) in water (2.5 mL) and 2-methyltetrahydrofuran (2.5 mL) was added trifluoroacetic acid (5 mL). The resulting mixture was stirred for 3 h at 40° C. The resulting mixture was concentrated under reduced pressure to obtain the crude product 4-chloro-2-(2-oxoethyl)pyrazole-3-carbonitrile (176.3, 1.44 g), which was used in the next step directly without further purification. MS (ES): m/z 170 [M+H]$^+$.

Synthesis of 176.4. To a solution of 176.3 (746 mg, 4.39 mmol, 1 eq) in ethyl alcohol (22 mL) and acetic acid (1 mL) was added ammonium acetate (2.03 g, 26.39 mmol, 6 eq). The resulting mixture was stirred for 2 h at 80° C. The residue was concentrated under reduced pressure and purified by reverse phase flash chromatography with the following conditions: Column, C18 Column; Mobile Phase, water (10 mmol/L NH$_4$HCO$_3$) and ACN (10% ACN up to 60% in 10 min); UV detection at 254/220 nm. The product-containing fractions were combined and concentrated under reduced pressure to obtain 3-chloropyrazolo[1,5-a]pyrazin-4-amine (176.4, 285 mg, 38%) as a white solid. MS (ES): m/z 169 [M+H]$^+$.

Synthesis of 176.5. A solution of 176.4 (884 mg, 5.24 mmol, 1 eq) in tetrahydrofuran (100 mL) was added pyridinium bromide perbromide (1.67 g, 5.24 mmol, 1 eq) at 0° C. The resulting mixture was stirred for 2 h. The precipitated solids were collected by filtration and washed with dichloromethane. The crude product 7-bromo-3-chloropyrazolo[1,5-a]pyrazin-4-amine (176.5, 666 mg) was used in the next step directly without further purification. MS (ES): m/z 247/249 [M+H]$^+$.

Synthesis of 176.6. To a solution of 176.5 (550 mg, 2.22 mmol, 1 eq) in tetrahydrofuran (7.3 mL) was added isoamyl nitrite (520.7 mg, 4.44 mmol, 2 eq). The resulting mixture was stirred for 0.5 h at room temperature. The resulting mixture was concentrated under reduced pressure. The residue was purified by reverse phase flash chromatography with the following conditions: Column, C18 Column; Mobile Phase, water (0.1% FA) and ACN (0% ACN up to 100% in 20 min); UV detection at 254/220 nm. The product-containing fractions were combined and concentrated under reduced pressure to obtain 7-bromo-3-chloropyrazolo[1,5-a]pyrazine (176.6, 150 mg, 29%) as a white solid. MS (ES): m/z 232/234 [M+H]$^+$.

Synthesis of 176.7. 176.7 was synthesized in a manner similar to that described in the synthesis of 171.5 (reaction time 16 h) using 176.6 as the bromide reagent. MS (ES): m/z 295 [M+H]$^+$.

Synthesis of I-154. I-154 was synthesized in a manner similar to that described in the synthesis of I-185 (amide coupling reaction) using 176.7 and 16.4. Final product purification: Prep-HPLC with the following conditions: Column: XBridge Prep OBD C18 Column, 30*150 mm, 5 μm; Mobile Phase A: Water (10 mmol/L NH$_4$HCO$_3$) and ACN (20% ACN up to 46% in 8 min); UV detection at 254/220 nm. MS (ES): m/z 490 [M+H]$^+$; $^1$H NMR (400 MHz, DMSO-d$_6$) δ 9.57 (t, J=5.6, 6.1 Hz, 1H), 9.29 (s, 1H), 9.21 (s, 1H), 9.00 (s, 1H), 8.60 (s, 1H), 8.21 (d, J=5.8 Hz, 1H), 7.05-6.95 (m, 2H), 4.52 (d, J=6.1 Hz, 2H), 2.74-2.63 (m, 1H), 0.98-0.68 (m, 4H).

Example 177: Synthesis of 5-(6-chloro-1H-benzo[d]imidazol-1-yl)-N-((4-(cyclopropanesulfonamido)pyridin-2-yl)methyl)thiazole-2-carboxamide (I-193)

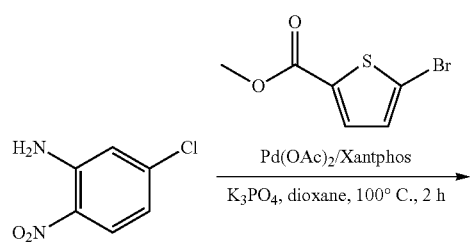

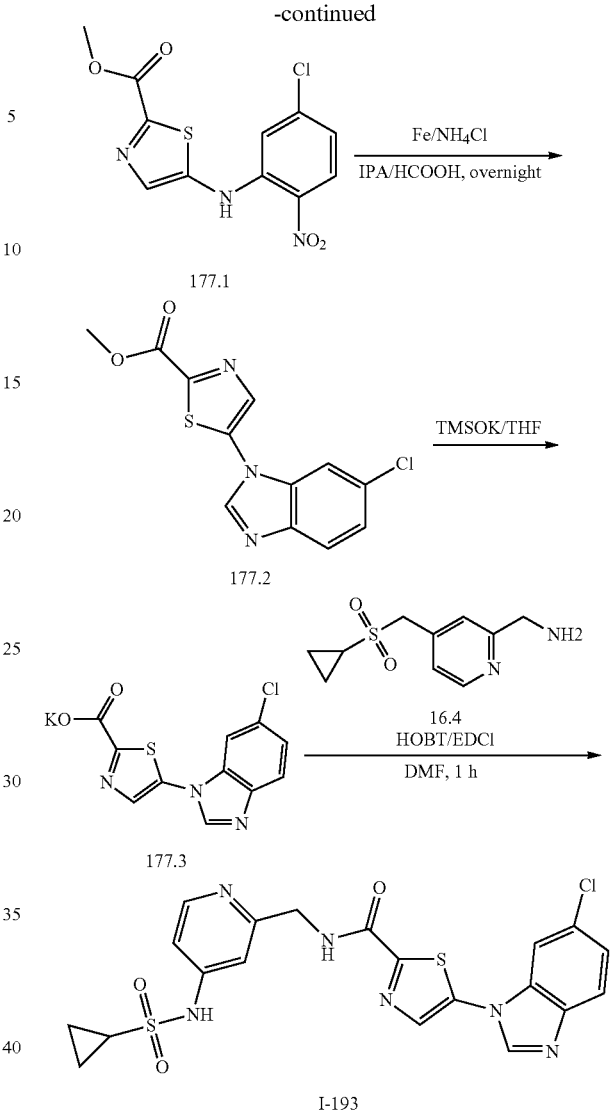

Synthesis of 177.1. To a solution of methyl 5-bromo-1,3-thiazole-2-carboxylate (650 mg, 2.75 mmol, 1 eq) and 5-chloro-2-nitroaniline (475 mg, 2.75 mmol, 1 eq) in 1,4-dioxane (12 mL) was added Xantphos (319 mg, 0.55 mmol, 0.2 eq) and Pd(OAc)$_2$ (62 mg, 0.27 mmol, 0.1 eq). The resulting solution was degassed three times with nitrogen and stirred for 2 h at 100° C. The mixture was cooled to room temperature, diluted with water and extracted with ethyl acetate. The combined organic layer was washed with brine, dried over sodium sulfate and concentrated under reduced pressure. The residue was purified by Prep-TLC (PE/EA=2/1) to afford methyl 5-[(5-chloro-2-nitrophenyl)amino]-1,3-thiazole-2-carboxylate (177.1, 200 mg, 23%) as a yellow solid. MS (ES): m/z 314 [M+H]$^+$.

Synthesis of 177.2. To a stirred solution of 177.1 (200 mg, 0.638 mmol, 1 eq) in isopropyl alcohol (16 mL) and formic acid (16 mL) was added iron powder (356 mg, 6.38 mmol, 10 eq) and ammonium chloride (341 mg, 6.38 mmol, 10 eq). The resulting solution was degassed three times with nitrogen and stirred for overnight at 80° C. The residue was cooled to room temperature and diluted with water. The pH value of the solution was adjusted to 8 with saturated sodium bicarbonate solution. The resulting mixture was extracted with ethyl acetate. The combined organic layers were washed with brine, dried over anhydrous sodium sulfate and concentrated under reduced pressure to afford the crude product methyl 5-(6-chloro-1,3-benzodiazol-1-yl)-1,3-thiazole-2-carboxylate (177.2, 159 mg), which was used in the next step directly without further purification. MS (ES): m/z 294 [M+H]+.

Synthesis of 177.3. 177.3 was synthesized in a manner similar to that described in the synthesis of 164.4 using 177.2. MS (ES): m/z 280 [M+H]+.

Synthesis of I-193. I-193 was synthesized in a manner similar to that described in the synthesis of I-177 (amide coupling reaction) using 177.3 and 16.4. Final product purification: Prep-HPLC with the following conditions: Column: XBridge Prep OBD C18 Column, 30*150 mm, 5p m; Mobile Phase: Water (10 mmol/L NH$_4$HCO$_3$) and ACN (13% ACN up to 70% in 8 min); UV detection at 254/220 nm. MS (ES): m/z 489 [M+H]+; $^1$H NMR (300 MHz, Methanol-d$_4$) δ 8.56 (s, 1H), 8.33-8.22 (m, 2H), 7.78 (d, J=8.6 Hz, 1H), 7.71 (d, J=1.9 Hz, 1H), 7.44 (dd, J=8.6, 1.9 Hz, 1H), 7.27 (d, J=1.8 Hz, 1H), 7.22-7.11 (m, 1H), 4.69 (s, 2H), 2.85-2.64 (m, 1H), 1.20-1.12 (m, 2H), 1.09-0.98 (m, 2H).

Example 178: Synthesis of 5-{6-chloroimidazo[1,2-a] pyridin-3-yl}-N-[(4-cyclopropanesulfonamidopyridin-2-yl)methyl]-1,3-thiazole-2-carboxamide (I-170)

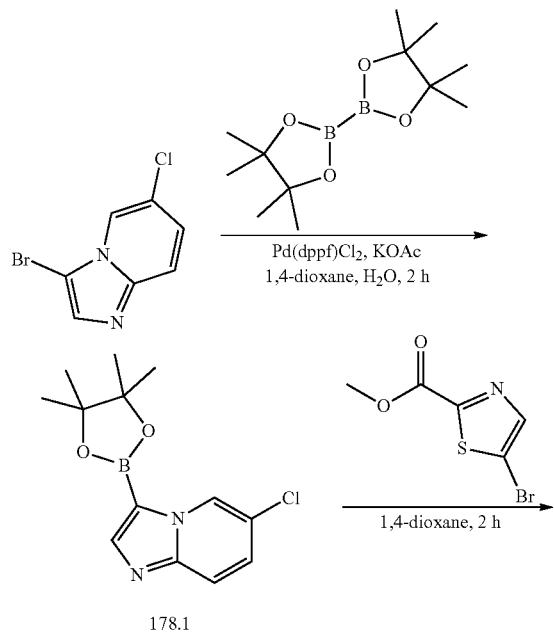

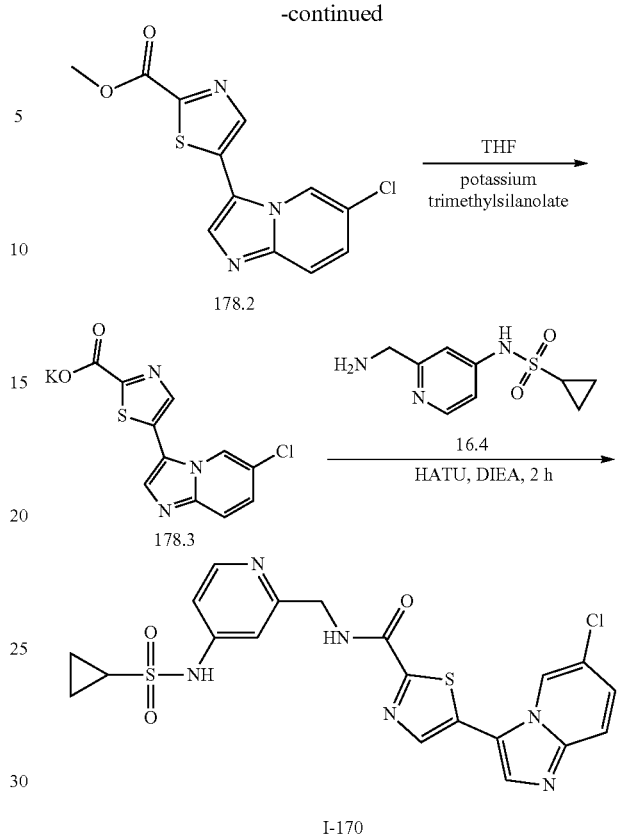

Synthesis of I-170. I-170 was synthesized in a manner similar to that described in the synthesis of I-243 (step 2 to 5) using 3-bromo-6-chloroimidazo[1,2-a]pyridine as the bromide reagent. The boronic ester intermediate was obtained after step 1 compared to the boronic acid in I-243. Final product purification: Prep-HPLC with the following conditions (Column: Sunfire prep C18 column, 30*150 mm, 5 μm; Mobile Phase: Water (0.1% FA) and ACN (7% ACN up to 19% in 10 min); UV detection at 254/220 nm. MS (ES): m/z 489 [M+H]+; $^1$H NMR (300 MHz, DMSO-d$_6$) δ 10.93 (s, 1H), 9.52 (t, J=6.1, 5.7 Hz, 1H), 8.80 (d, J=1.9 Hz, 1H), 8.55 (s, 1H), 8.25 (d, J=5.9 Hz, 1H), 8.11 (s, 1H), 7.80 (d, J=9.5 Hz, 1H), 7.49 (dd, J=9.6, 2.0 Hz, 1H), 7.04 (d, J=4.0 Hz, 2H), 4.53 (d, J=6.1 Hz, 2H), 2.79-2.65 (m, 1H), 1.05-0.87 (m, 4H).

Example 179: Synthesis of N-((4-(cyclopropanesulfonamido) pyridin-2-yl)methyl)-5-(1-ethyl-1H-pyrazolo[3,4-b]pyrazin-6-yl)thiazole-2-carboxamide (I-149)

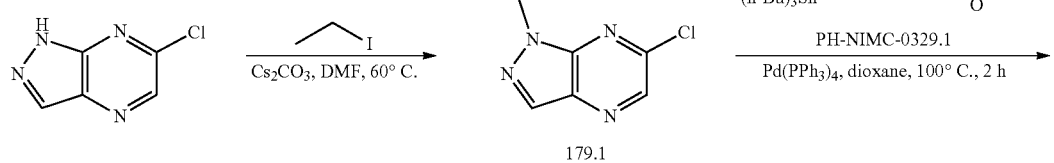

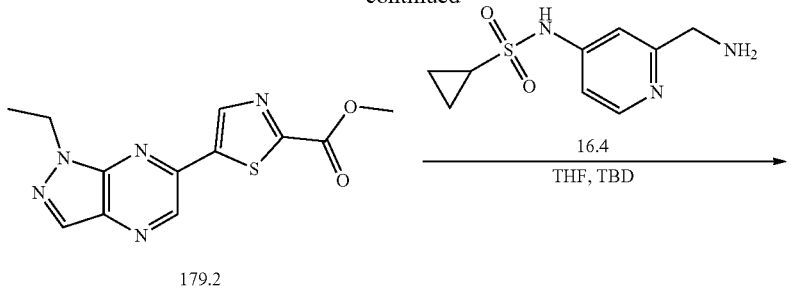

179.2

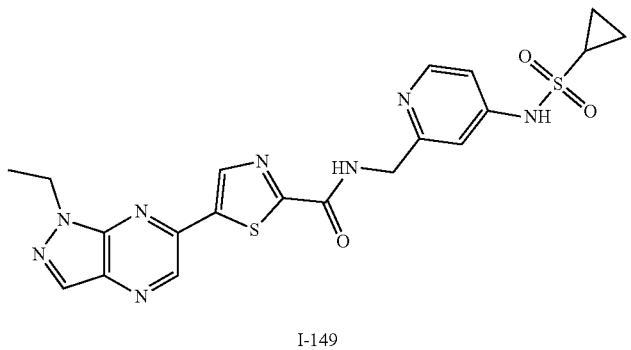

I-149

Synthesis of 179.1. To a stirred solution of 6-chloro-1H-pyrazolo[3,4-b]pyrazine (2.5 g, 16.17 mmol, 1 eq) in N,N-dimethyl formamide (10 mL) was added cesium carbonate (7.9 g, 24.26 mmol, 1.5 eq) and ethyl iodide (3.78 g, 24.26 mmol, 1.5 eq). The reaction mixture was stirred for 2 h at 60° C. The mixture was cooled to room temperature, diluted with water and extracted with ethyl acetate. The combined organic layer was washed with brine, dried over sodium sulfate and concentrated under reduced pressure. The residue was purified by reverse flash chromatography with the following conditions: Column, C18 Column; Mobile Phase, water (0.1% FA) and ACN (10% ACN up to 50% in 20 min); UV detection at 254/220 nm. The product-containing fractions were combined and concentrated under reduced pressure to afford 6-chloro-1-ethylpyrazolo[3,4-b]pyrazine (179.1, 700 mg, 23%) as a yellow solid. MS (ES): m/z 183 [M+H]⁺.

Synthesis of I-149. I-149 was synthesized in a manner similar to that described in the synthesis of I-185 (step 4 and 5) using 179.1 as the halide coupling reagent. Final product purification: Prep-HPLC with the following conditions (Column: XBridge Prep OBD C18 Column, 30*150 mm, 5 μm; Mobile Phase: Water (10 mmol/L NH₄HCO₃) and ACN (20% ACN up to 30% in 8 min); UV detection at 254/220 nm. MS (ES): m/z 485 [M+H]⁺; ¹H NMR (400 MHz, DMSO-d₆) 9.50-9.32 (m, 2H), 9.02 (s, 1H), 8.91 (s, 1H), 8.09 (s, 1H), 7.95-7.80 (m, 2H), 4.55 (q, J=7.6, 7.2 Hz, 2H), 4.45 (d, J=5.2 Hz, 2H), 3.30-3.11 (m, 1H), 1.57 (t, J=7.2, 7.6 Hz, 3H), 0.95-0.78 (m, 4H).

Example 180: N-[(4-cyclopropanesulfonamidopyridin-2-yl)methyl]-2-methyl-4-oxo-5H-pyrrolo[1,2-a]quinoxaline-8-carboxamide (I-162)

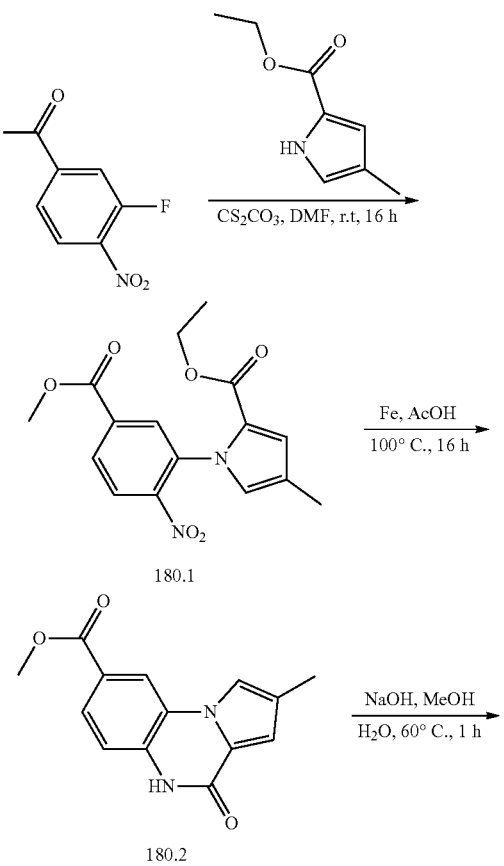

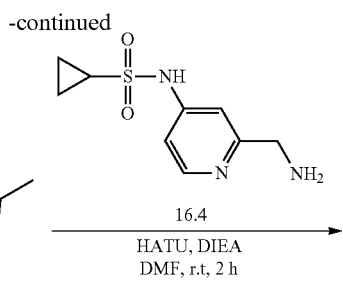

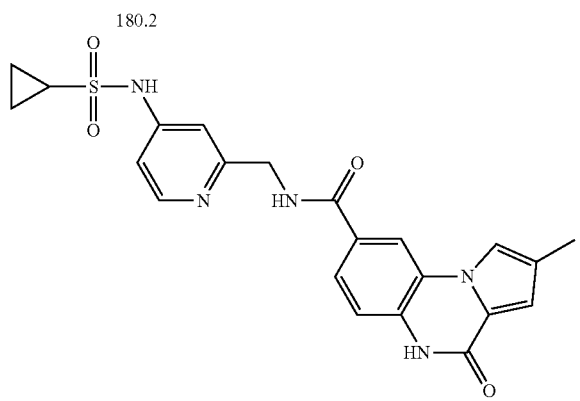

I-162

Synthesis of 180.1. To a stirred mixture of methyl 3-fluoro-4-nitrobenzoate (1 g, 5.02 mmol, 1 eq) and ethyl 4-methyl-1H-pyrrole-2-carboxylate (0.77 g, 5.02 mmol, 1 eq) in N,N-dimethylformamide (26 mL) was added cesium carbonate (4.91 g, 15.07 mmol, 3.0 eq). The resulting mixture was stirred for 16 h at room temperature. The mixture was diluted with water and extracted with ethyl acetate. The combined organic layer was washed with brine, dried over sodium sulfate and concentrated under reduced pressure. The residue was purified by reverse flash chromatography with the following conditions: Column, C18 Column; Mobile Phase, water (10 mmol/L NH$_4$HCO$_3$) and ACN (10% to 100% in 20 min); UV detection at 254/220 nm. The product-containing fractions were combined and concentrated under reduced pressure to obtain ethyl 1-[2-amino-5-(methoxycarbonyl)phenyl]-4-methylpyrrole-2-carboxylate (180.1, 1.06 g, 63%) as a yellow oil. MS (ES): m/z 333 [M+H]$^+$.

Synthesis of 180.2. To a stirred mixture of 180.1 (1 g, 1.51 mmol, 1.0 eq) in acetic acid (8 mL) was added iron powder (420 mg, 7.53 mmol, 5.0 eq). The resulting solution was degassed three times with nitrogen and stirred for 16 h at 100° C. The mixture was allowed to cool down to room temperature. The resulting mixture filtered, the filter cake was washed with acetonitrile. The filtrate was concentrated under reduced pressure and purified by reverse flash chromatography with the following conditions: Column, C18 Column; Mobile Phase, water (0.1% FA) and ACN (10% to 100% in 20 min); UV detection at 254/220 nm. The product-containing fractions were combined and concentrated under reduced pressure to obtain methyl 2-methyl-4-oxo-5H-pyrrolo[1,2-a]quinoxaline-8-carboxylate (180.2, 100 mg, 25%) as a yellow oil. MS (ES): m/z 257 [M+H]$^+$.

Synthesis of 180.3. To a stirred mixture of 180.2 (74 mg, 0.29 mmol, 1.0 eq) in methanol (3 mL) and water (1 mL) were added sodium hydroxide (23 mg, 0.58 mmol, 2.0 eq). The resulting mixture was stirred for 1 h at 60° C. The residue was diluted with water. The pH value of the solution was adjusted to 3 with 1N hydrochloric acid. The resulting mixture was extracted with ethyl acetate. The combined organic layers were washed with brine, dried over anhydrous sodium sulfate and concentrated under reduced pressure. The crude product 2-methyl-4-oxo-5H-pyrrolo[1,2-a]quinoxaline-8-carboxylic acid (180.3, 60 mg) was used in the next step directly without further purification. MS (ES): m/z 243 [M+H]$^+$.

Synthesis of I-162. I-162 was synthesized in a manner similar to that described in the synthesis of I-254 (amide coupling step) using 180.3 and 16.4. Final product purification: Prep-HPLC with the following conditions: Column, C18 Column; Mobile Phase, water (10 mmol/L NH$_4$HCO$_3$) and ACN (18% ACN up to 28% in 8 min); UV detection at 254/220 nm. MS (ES): m/z 452 [M+H]$^+$; $^1$H NMR (400 MHz, CD$_3$OD-d$_4$) 8.43 (d, J=2.1 Hz, 1H), 8.19 (d, J=6.1 Hz, 1H), 7.90 (s, 1H), 7.84 (dd, J=5.6, 6.0 Hz, 1H), 7.38 (d, J=6.6 Hz, 1H), 7.28 (d, J=2.1 Hz, 1H), 7.11-7.01 (m, 2H), 4.68 (s, 2H), 2.70-2.61 (m, 1H), 2.34 (s, 3H), 1.15-1.09 (m, 2H), 1.00-0.90 (m, 2H).

Example 181: Synthesis of N-((4-(cyclopropanesulfonamido)pyridin-2-yl)methyl)-3-ethyl-2-oxo-1,2-dihydroquinoxaline-6-carboxamide (I-171)

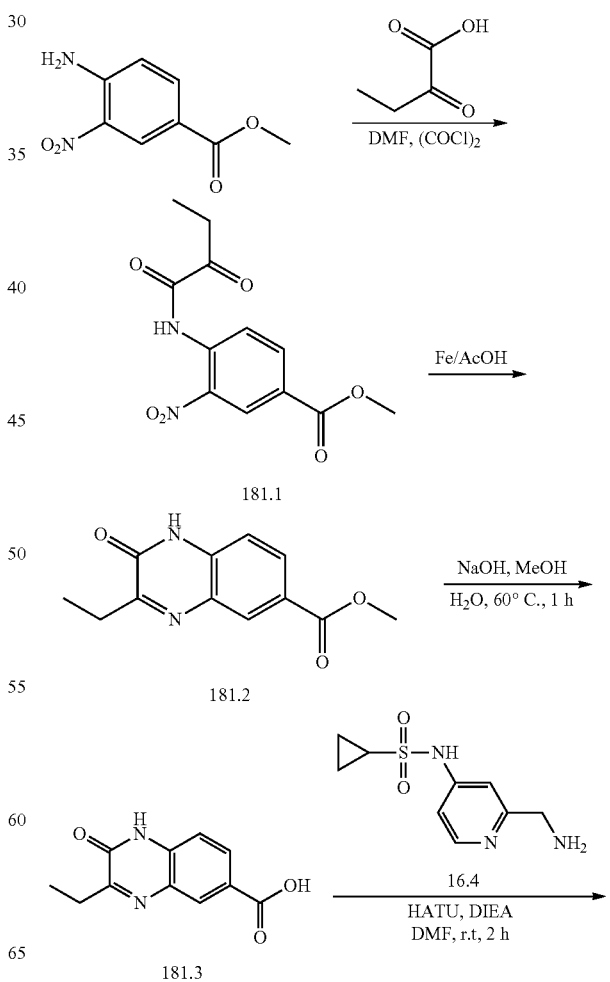

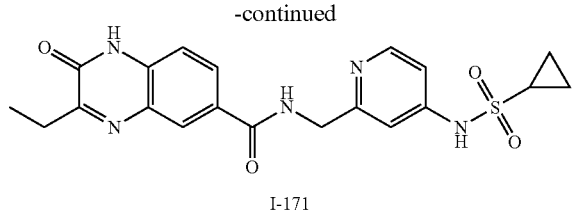

I-171

Synthesis of 181.1. To a stirred solution of 2-oxobutanoic acid (1 g, 9.9 mmol, 1.5 eq) in tetrahydrofuran (20 mL) were added N, N-dimethyl formamide (60 mg, 0.86 mmol, 0.13 eq) and (COCl)$_2$ (1.3 g, 9.9 mmol, 1.5 eq) at 0° C. The resulting mixture was stirred for 1 h at room temperature. The resulting mixture was concentrated under reduced pressure. The residue was dissolved in tetrahydrofuran (5 mL) and added to methyl 4-amino-3-nitrobenzoate (1.3 g, 6.6 mmol, 1 eq) and triethylamine (2 g, 19.8 mmol, 3 eq) in tetrahydrofuran (20 mL). The resulting mixture was stirred for additional 4 h at room temperature. The resulting mixture was concentrated under reduced pressure and purified by reverse flash chromatography with the following conditions: Column, C18 Column; Mobile Phase, water (0.1% FA) and ACN (10% to 100% in 20 min); UV detection at 254/220 nm. The product-containing fractions were combined and concentrated under reduced pressure to obtain methyl 3-nitro-4-(2-oxobutanamido)benzoate (181.1, 540 mg, 29%) as a brown solid. MS (ES): m/z 281 [M+H]$^+$.

Synthesis of I-171. I-171 was synthesized in a manner similar to that described in the synthesis of I-162 (step 2, 3 and 4) using 181.1. Final product purification: prep-HPLC using the following conditions—Column: Sunfire prep C18 column, 30*150 mm, 5 μm; Mobile Phase: Water (0.05% TFA) and ACN (2% ACN up to 30% in 8 min); UV detection at 254/220 nm. MS (ES): m/z 428 [M−H]$^+$; $^1$H NMR (400 MHz, DMSO-d$_6$) δ 12.53 (s, 1H), 10.65 (s, 1H), 9.25 (t, J=5.6, 5.9 Hz, 1H), 8.37 (d, J=1.9 Hz, 1H), 8.22 (s, 1H), 8.01 (dd, J=8.5, 2.0 Hz, 1H), 7.35 (d, J=8.5 Hz, 1H), 7.03 (s, 2H), 4.50 (d, J=5.8 Hz, 2H), 2.84 (q, J=7.4, 7.6 Hz, 2H), 2.75-2.60 (m, 1H), 1.25 (t, J=7.4, 7.6 Hz, 3H), 1.05-0.84 (m, 4H).

Example 182: Synthesis of N-((4-(cyclopropanesulfonamido)pyridin-2-yl)methyl)-2-ethyl-3-oxo-3,4-dihydroquinoxaline-6-carboxamide (I-180)

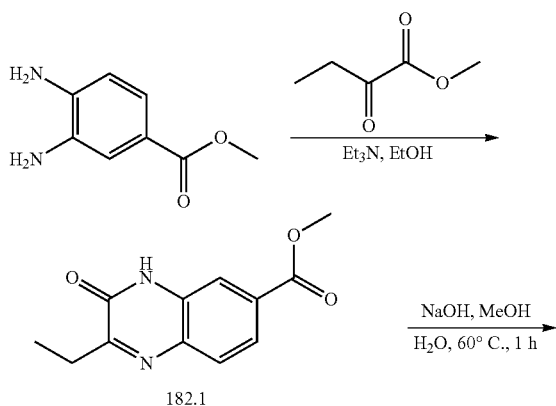

182.1

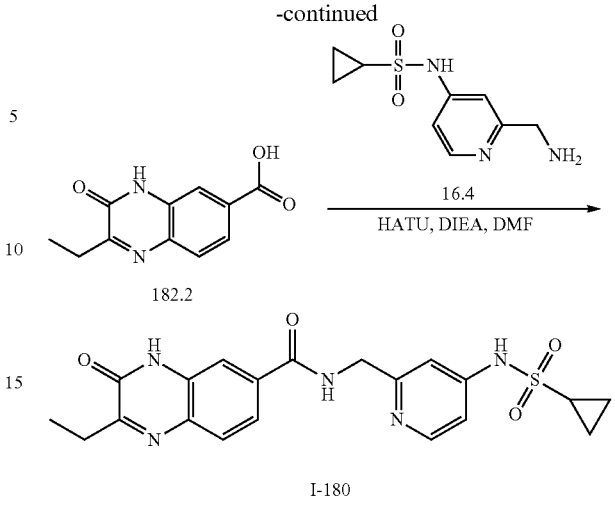

182.2

I-180

Synthesis of 182.1. To a stirred mixture of methyl 3,4-diaminobenzoate (1 g, 6 mmol, 1 eq) and methyl 2-oxobutanoate (1.05 g, 9 mmol, 1.5 eq) in ethyl alcohol (10 mL) was added triethylamine (1.22 g, 12 mmol, 2 eq). The resulting mixture was stirred for overnight at 60° C. The precipitated solids were collected by filtration, washed with ethyl alcohol and dried to afford methyl 2-ethyl-3-oxo-4H-quinoxaline-6-carboxylate (182.1, 600 mg, 42%) as a white solid. MS (ES): m/z 233 [M+H]$^+$.

Synthesis of I-180. I-180 was synthesized in a manner similar to that described in the synthesis of I-162 (step 3 and 4) using 181.1. Final product purification: prep-HPLC using the following conditions—Column: RP C18 Column, 30*150 mm, 5 μm; Mobile Phase: water (10 mmol/L NH$_4$HCO$_3$) and ACN (10% ACN up to 400% in 10 min); UV detection at 254/220 nm. MS (ES): m/z 428 [M+H]$^+$; $^1$H NMR (400 MHz, DMSO-d$_6$) δ 12.48 (s, 1H), 10.65 (s, 1H), 9.30 (t, J=5.6, 5.9 Hz, 1H), 8.24 (s, 1H), 7.87-7.76 (m, 3H), 7.04 (s, 2H), 4.50 (d, J=5.8 Hz, 2H), 2.84 (q, J=7.3, 7.6 Hz, 2H), 2.77-2.65 (m, 1H), 1.24 (t, J=7.4, 7.6 Hz, 3H), 1.05-0.82 (m, 4H).

Example 183: Synthesis of N-[[3-(difluoromethanesulfonamido)phenyl]methyl]-3-(6-ethoxypyrazin-2-yl)benzamide (I-280)

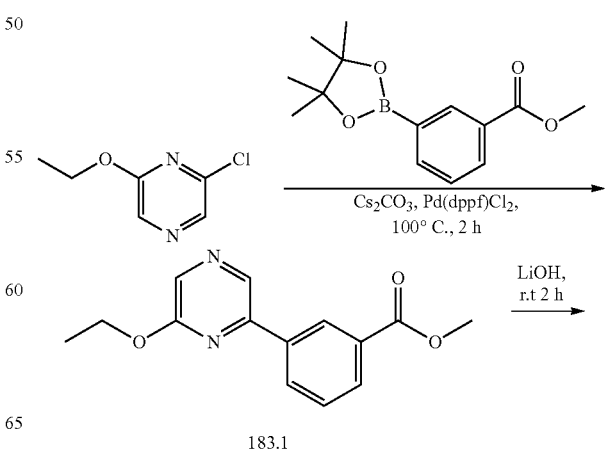

183.1

-continued

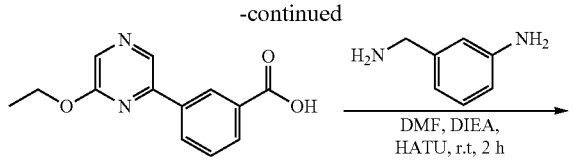

183.2

DMF, DIEA,
HATU, r.t, 2 h

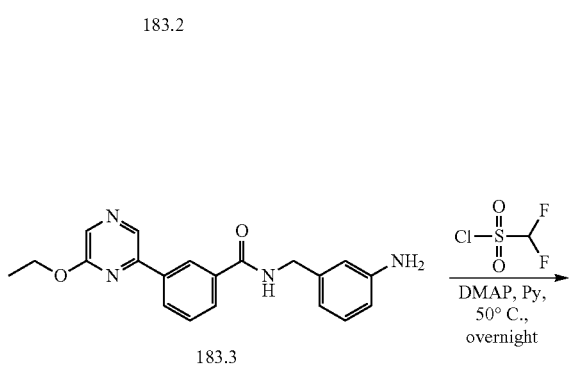

183.3

DMAP, Py,
50° C.,
overnight

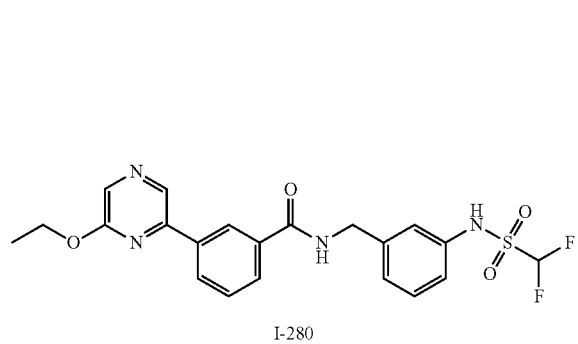

I-280

Synthesis of 183.3. 183.3 was synthesized in a manner similar to that described in the synthesis of I-254 (step 1, 2 and 3) using 2-chloro-6-ethoxy-pyrazine. MS (ES): m/z 349 [M+H]$^+$.

Synthesis of I-280. To a stirred mixture of 183.3 (134 mg, 0.39 mmol, 1 eq) and difluoromethanesulfonyl chloride (174 mg, 1.16 mmol, 3 eq) in pyridine (2 mL) were added 4-dimethylaminopyridine (4.7 mg, 0.04 mmol, 0.1 eq). The resulting mixture was stirred for 16 h at 50° C. The mixture was allowed to cool down to room temperature. The resulting mixture was concentrated under reduced pressure. The residue was purified by reverse phase flash with the following conditions: Column, C18 Column; Mobile Phase, water (0.1% FA) and ACN (5% ACN up to 100% in 20 min); UV detection at 254/220 nm. The resulting mixture was concentrated under reduced pressure. The crude product was purified by Prep-HPLC with the following conditions (Column: Sunfire prep C18 column, 30*150, 5 um; Mobile Phase: Water (0.1% FA) and ACN (40% ACN up to 60% in 10 min); UV detection at 254/220 nm. The product-containing fractions were combined and evaporated partially in vacuum and lyophilized overnight to afford N-[[3-(difluoromethanesulfonamido)phenyl]methyl]-3-(6-ethoxy-pyrazin-2-yl)benzamide as a white solid (I-280, 17 mg, 10%), MS (ES): m/z 463 [M+H]$^+$; $^1$H NMR (400 MHz, CD$_3$OD) δ 8.72 (s, 1H), 8.60 (t, J=1.9 Hz, 1H), 8.30 (dd, J=7.8, 1.5 Hz, 1H), 8.16 (s, 1H), 7.97 (dd, J=7.8, 1.4 Hz, 1H), 7.66-7.62 (m, 1H), 7.39-7.30 (m, 2H), 7.27-7.17 (m, 2H), 6.64 (t, J=53.2, 53.2 Hz, 1H), 4.87-4.55 (m, 4H), 1.48 (t, J=7.1, 6.8 Hz, 3H).

Example 184: Synthesis of N-[1-(2-cyclopropane-sulfonamido-1,3-thiazol-4-yl)cyclopropyl]-4-[5H, 6H, 7H, 8H-imidazo[1,2-a]pyridin-3-yl]benzamide, formic acid (I-260)

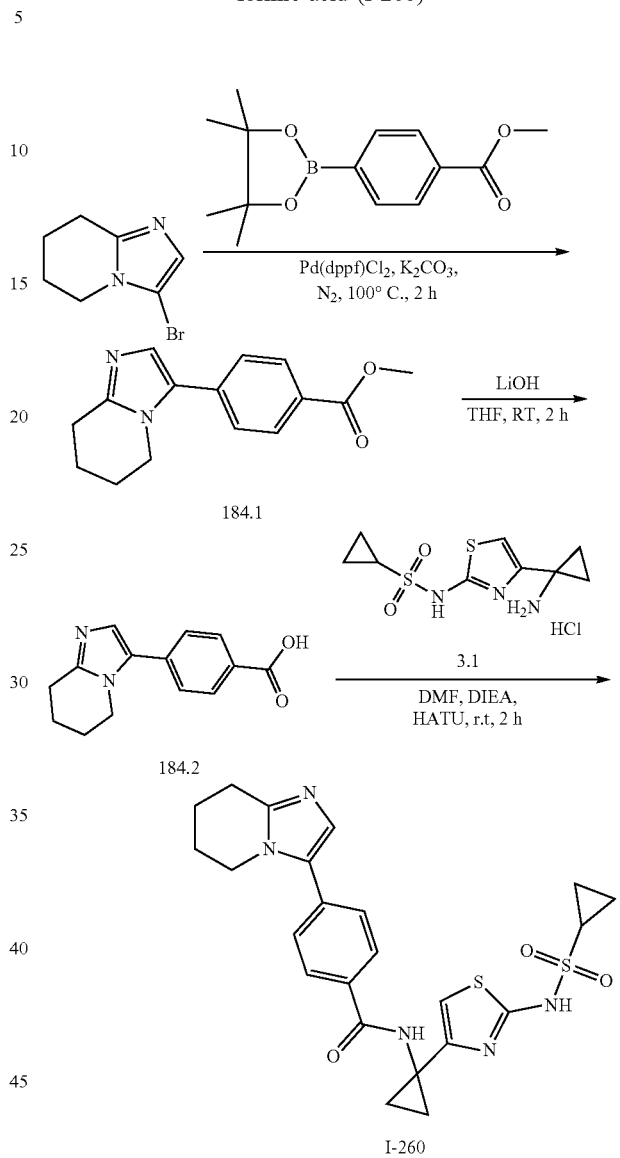

Synthesis of I-260. I-260 was synthesized in a manner similar to that described in the synthesis of I-254 using 3-bromo-5,6,7,8-tetrahydroimidazo[1,2-a]pyridine as the halide reagent and methyl 4-(4,4,5,5-tetramethyl-1,3,2-dioxaborolan-2-yl)benzoate in step 1. Final product purification: Prep-HPLC with the following conditions—Column: Sunfire prep C18 column, 30*150 mm, 5 μm; Mobile Phase: Water (0.1% FA) ACN (40% ACN up to 60% in 10 min); UV detection at 254/220 nm. MS (ES): m/z 484 [M+H]$^+$; $^1$H NMR (400 MHz, Methanol-d$_4$) δ 8.34 (s, 1H), 7.98 (d, J=8.4 Hz, 2H), 7.63 (d, J=8.8 Hz, 2H), 7.30 (s, 1H), 6.48 (s, 1H), 4.15-4.06 (m, 2H), 3.05-2.95 (m, 2H), 2.69-2.59 (m, 1H), 2.11-1.99 (m, 4H), 1.47-1.40 (m, 2H), 1.36-1.29 (m, 2H), 1.14-1.01 (m, 2H), 1.00-0.92 (m, 2H).

Example 185: Synthesis of N-[1-(2-cyclopropane-sulfonamido-1,3-thiazol-4-yl)cyclopropyl]-4-(1,5-dimethylpyrazol-4-yl)benzamide (I-261)

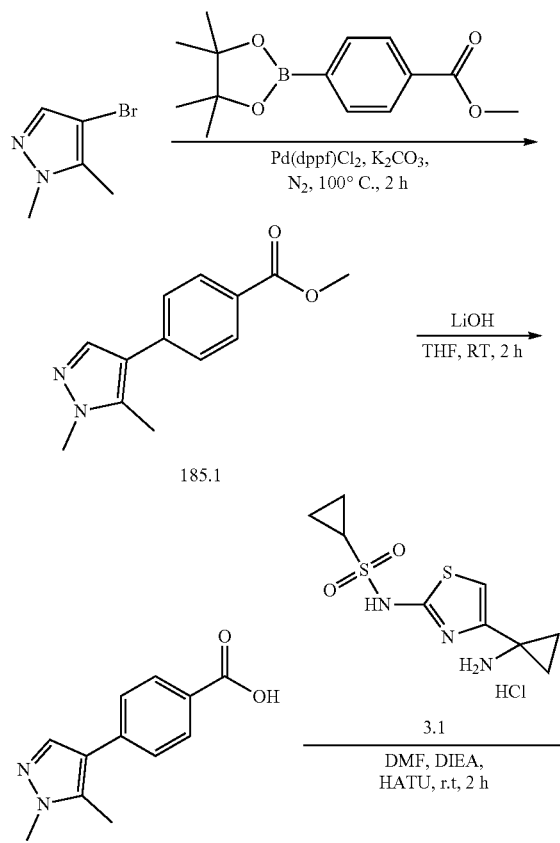

General Method 4

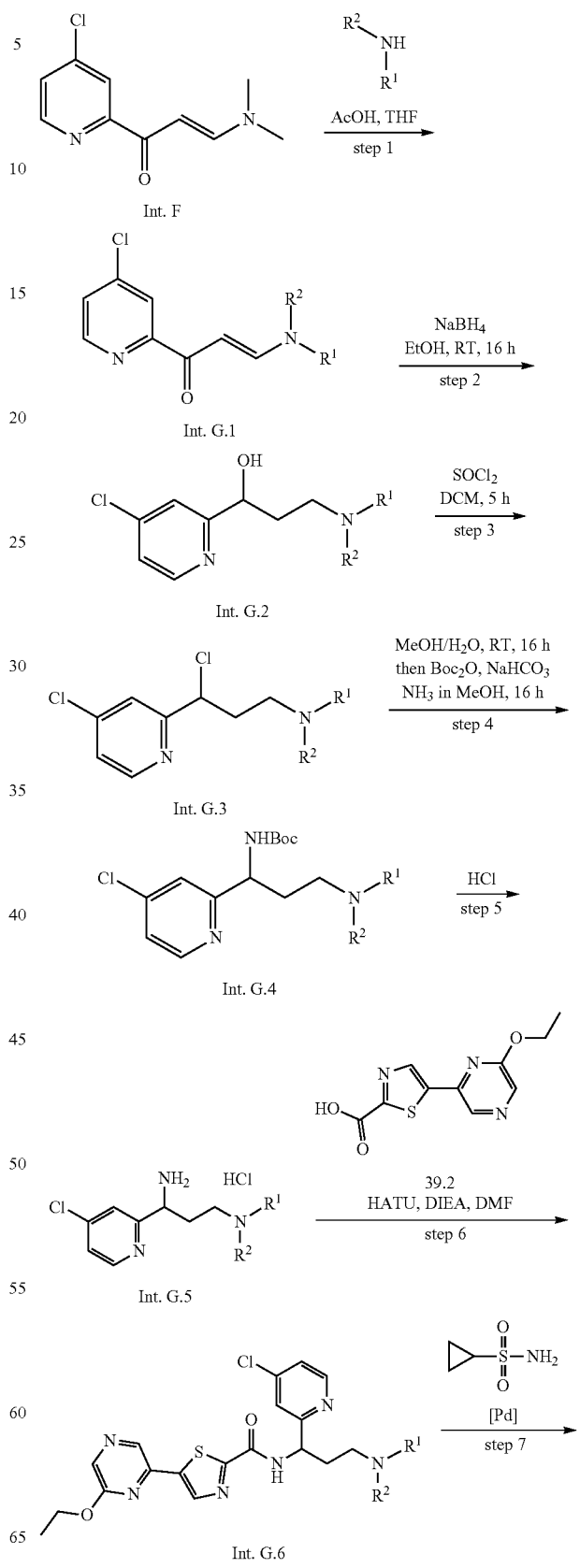

Synthesis of I-261. I-261 was synthesized in a manner similar to that described in the synthesis of I-254 using 4-bromo-1,5-dimethyl-1H-pyrazole and methyl 4-(4,4,5,5-tetramethyl-1,3,2-dioxaborolan-2-yl)benzoate. Final product purification: Prep-HPLC with the following conditions—Column: Sunfire prep C18 column, 30*150, 5 um; Mobile Phase: Water (0.1% FA) and CAN (18% to 38% in 10 min); UV detection at 254/220 nm. MS (ES): m/z 458 [M+H]$^+$; $^1$H NMR (400 MHz, CD$_3$OD) δ 7.92-7.90 (m, 2H), 7.64 (s, 1H), 7.54-7.52 (m, 2H), 6.47 (s, 1H), 3.87 (s, 3H), 2.67-2.55 (m, 1H), 2.46 (s, 3H), 1.45-1.39 (m, 2H), 1.38-1.30 (m, 2H), 1.13-1.07 (m, 2H), 0.99-0.94 (m, 2H).

-continued

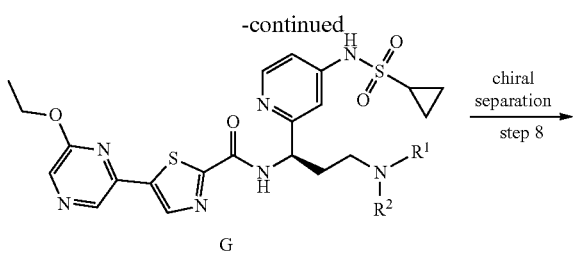
G

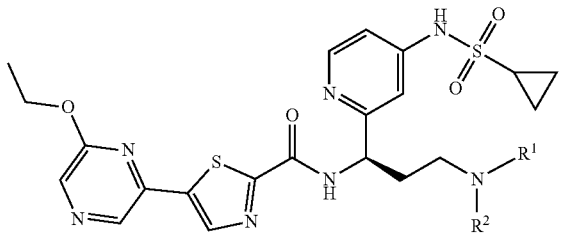
G-isomer 1

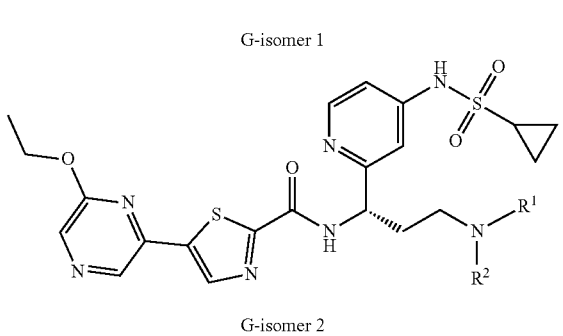
G-isomer 2 chiral separation
step 8

Example 186: Synthesis of N-(1-(4-(cyclopropane-sulfonamido)pyridin-2-yl)-3-((R)-3-fluoropyrrolidin-1-yl)propyl)-5-(6-ethoxypyrazin-2-yl)thiazole-2-carboxamide (I-131)

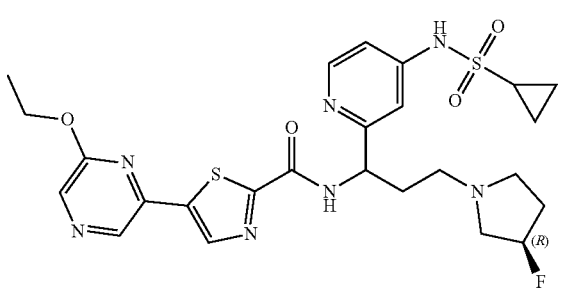
I-131

General Method 4, Step 1: Synthesis of 186.1

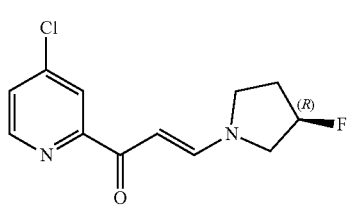
186.1

To a stirred mixture of Int. F (1 g, 4.75 mmol, 1 equiv) and (3R)-3-fluoropyrrolidine (1.27 g, 14.2 mmol, 3 equiv) in THF (30 mL) was added acetic acid (10 mL) dropwise at room temperature. The resulting mixture was stirred for 2 h at 60° C. The reaction mixture was concentrated under reduced pressure. The residue was neutralized to pH 10 with saturated aqueous sodium bicarbonate and extracted with ethyl acetate (3×30 mL). The combined organic layers were concentrated under reduced pressure. The residue was purified by flash column chromatography on C18 silica (eluted with 45% acetonitrile in water) to afford (2E)-1-(4-chloropyridin-2-yl)-3-[(3S)-3-fluoropyrrolidin-1-yl]prop-2-en-1-one (186.1, 1.07 g, 88%) as a light brown solid. MS (ES): m/z 255 [M+H]+.

General Method 4, Step 2: Synthesis of 186.2

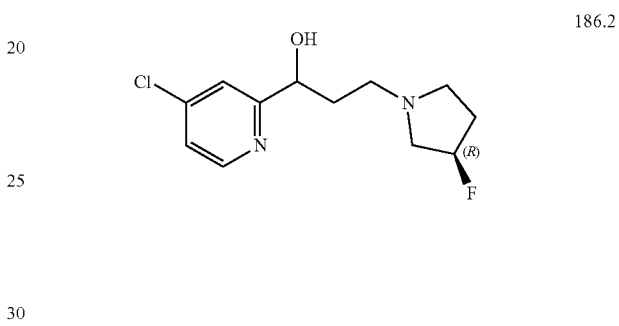
186.2

To a stirred solution of 186.1 (2.37 g, 9.3 mmol, 1 equiv) in ethanol (20 mL) was added sodium borohydride (3.52 g, 93.1 mmol, 10 equiv) in portions at 0° C. The resulting mixture was stirred for 16 h at room temperature. The reaction was quenched with methanol (5 mL) at 0° C., diluted with water (30 mL) and extracted with dichloromethane (4×30 mL). The combined organic layers were concentrated under reduced pressure. The residue was purified by flash column chromatography on C18 silica (eluted with 40% acetonitrile in water) to afford 1-(4-chloropyridin-2-yl)-3-[(3R)-3-fluoropyrrolidin-1-yl]propan-1-ol (186.2, 2.04 g, 84%) as an light yellow oil. MS (ES): m/z 259 [M+H]+.

General Method 4, Step 3: Synthesis of 186.3

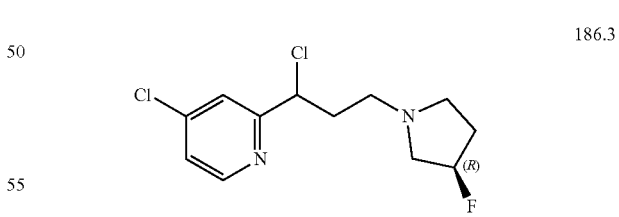
186.3

To a stirred solution of 186.2 (1.0 g, 3.86 mmol, 1 equiv) in dichloromethane (10 mL) was added thionyl chloride (1 mL, 8.33 mmol, 2.2 equiv) dropwise at 0° C. The resulting mixture was stirred for 1 h at room temperature. The reaction was concentrated under reduced pressure to afford 4-chloro-2-{1-chloro-3-[(3R)-3-fluoropyrrolidin-1-yl]propyl}pyridine (186.3, 876 mg, 99%) as a colorless oil, which was used in the next step directly without further purification. MS (ES): m/z 277 [M+H]+.

General Method 4, Step 4: Synthesis of 186.4

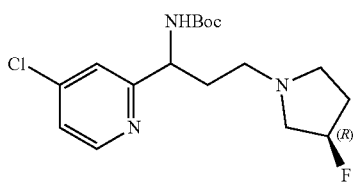
186.4

A mixture of 186.3 (1.07 g, 3.86 mmol, 1 equiv) and sodium iodide (1.16 g, 7.72 mmol, 2 equiv) in ammonium methanol solution (2M, 15 mL) was stirred for 16 h at 40° C. The solid was removed by filtration and washed with methanol (3 mL). The filtrate was concentrated and re-dissolved with methanol (10 mL), followed by the addition of di-tert-butyl pyrocarbonate (4.22 g, 19.34 mmol, 5 equiv) and saturated sodium bicarbonate aqueous solution (10 mL). The resulting mixture was stirred for 4 h at room temperature. The reaction was extracted with dichloromethane (4×10 mL). The combined organic layers were concentrated under reduced pressure. The residue was purified by flash column chromatography on C18 silica (eluted with 65% acetonitrile in water) to afford tert-butyl N-[1-(4-chloropyridin-2-yl)-3-[(3R)-3-fluoropyrrolidin-1-yl]propyl]carbamate (186.4, 600 mg, 43%) as a yellow solid. MS (ES): m/z 358 [M+H]$^+$.

General Method 4, Step 5: Synthesis of 186.5.

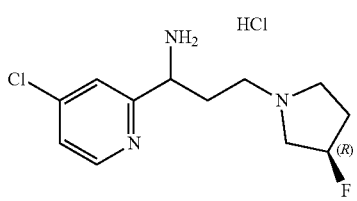
186.5

To a mixture of 186.4 (501 mg, 1.40 mmol, 1 equiv) in 1,4-dioxane (4 mL) was added HCl in 1,4-dioxane (4M, 1.4 mL 5.60 mmol, 4 equiv) dropwise at room temperature. The resulting mixture was stirred at room temperature for 30 min. The reaction was concentrated under reduced pressure to afford 1-(4-chloropyridin-2-yl)-3-[(3R)-3-fluoropyrrolidin-1-yl] propan-1-amine (186.5, 360 mg) as a light yellow solid, which was used in the next step directly without further purification. MS (ES): m/z 258 [M+H]$^+$.

General Method 4, Step 6: Synthesis of 186.6

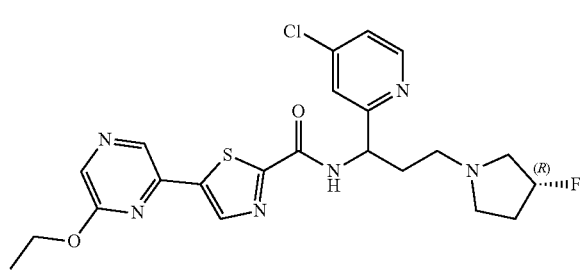
186.6

To a stirred mixture of 186.5 (217 mg) and 39.2 (212 mg) in N,N-dimethylformamide (5 mL) were added HATU (384 mg, 1.01 mmol) and DIEA (326 mg, 2.52 mmol) in portions at room temperature. The resulting mixture was stirred for 2 h at room temperature. The mixture was diluted with water (20 mL) and extracted with ethyl acetate (3×15 mL). The combined organic layers were concentrated under reduced pressure. The residue was purified by flash column chromatography on silica gel (eluted with 7% methanol in dichloromethane) to afford N-[1-(4-chloropyridin-2-yl)-3-[(3R)-3-fluoropyrrolidin-1-yl]propyl]-5-(6-ethoxypyrazin-2-yl)-1,3-thiazole-2-carboxamide (186.6, 270 mg) as a white solid. MS (ES): m/z 491[M+H]$^+$.

General Method 4, Step 7: Synthesis of I-131

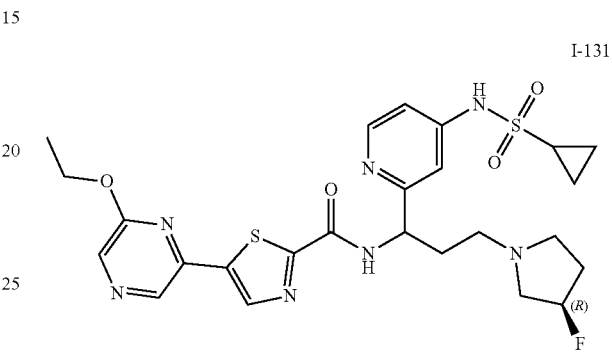
I-131

To a stirred mixture of 186.6 (200 mg, 0.40 mmol, 1 equiv), cyclopropanesulfonamide (99 mg, 0.81 mmol, 2 equiv) and cesium carbonate (398 mg, 1.22 mmol, 3 equiv) in 1,4-dioxane (5 mL) were added EPhos Pd G4 (22 mg, 0.04 mmol, 0.1 equiv) and EPhos (18 mg, 0.04 mmol, 0.1 equiv) in portions at room temperature. The resulting mixture was stirred for 1 h at 100° C. under nitrogen atmosphere. The solid was removed by filtering through Celite and washed with methanol (20 mL). The combined organic layers were concentrated under reduced pressure. The residue was purified by Prep-HPLC (Column: Sunfire prep C18 column, 30*150 mm, 5 μm; Mobile Phase: water (0.1% FA) and ACN (7% to 23% in 7 min); Wave Length: 254/220 nm) to afford N-(2-{[5-(6-ethoxypyrazin-2-yl)pyrazolo[3,4-c]pyridin-1-yl]methyl}pyridin-4-yl)cyclopropanesulfonamide (I-131, 9.4 mg, 4%) as a white solid. MS (ES): m/z 576 [M+H]$^+$; $^1$H NMR (400 MHz, DMSO-d$_6$) δ 10.56 (s, 1H), 9.70-9.61 (m, 1H), 8.93 (s, 1H), 8.80 (s, 1H), 8.32-8.31 (m, 1H), 8.29 (s, 1H), 7.15 (s, 1H), 7.06-7.02 (m, 1H), 5.31-5.28 (m, 1H), 5.15-5.10 (m, 1H), 4.43 (q, J=7.2 Hz, 2H), 2.79-2.72 (m, 4H), 2.46-2.34 (m, 3H), 2.24-2.07 (m, 3H), 2.00-1.85 (m, 1H), 1.39 (t, J=7.2 Hz, 3H), 1.01-0.93 (m, 4H).

Example 187: Synthesis of N—((R)-1-(4-(cyclopropanesulfonamido)pyridin-2-yl)-3-((R)-3-fluoropyrrolidin-1-yl)propyl)-5-(6-ethoxypyrazin-2-yl)thiazole-2-carboxamide, isomer 1 (I-127) and N—((S)-1-(4-(cyclopropanesulfonamido)pyridin-2-yl)-3-((R)-3-fluoropyrrolidin-1-yl)propyl)-5-(6-ethoxypyrazin-2-yl)thiazole-2-carboxamide, isomer 2-(I-128) Stereochemistry Alpha to the Central Amide Arbitrarily Assigned

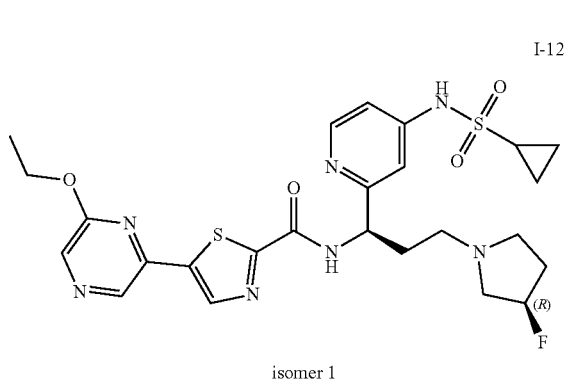

isomer 1

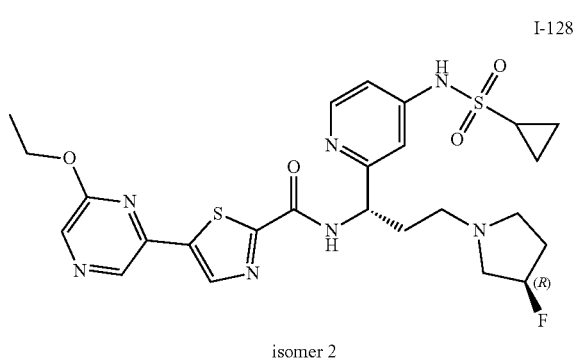

isomer 2

General Method 4, Step 8: synthesis of I-127 and I-128. I-131 (135 mg) was purified by chiral HPLC (Column: CHIRALPAK IF, 2*25 cm, 5 μm; Mobile Phase A: Hex: DCM=3:1(0.5% 2M NH$_3$-MeOH)-HPLC, Mobile Phase B: EtOH-HPLC; Flow rate: 20 mL/min; Gradient: 20% B to 20% B in 12 min; Wave Length: 220/254 nm) to afford I-127 (first eluting peak, 26 mg, 20%) and I-128 (second eluting peak, 23 mg, 17%) both as white solid. I-127: MS (ES): m/z 576 [M+H]$^+$; $^1$H NMR (400 MHz, DMSO-d$_6$) δ 10.53 (s, 1H), 9.71-9.69 (m, 1H), 8.93 (s, 1H), 8.80 (s, 1H), 8.32-8.31 (m, 1H), 8.28 (s, 1H), 7.15 (s, 1H), 7.06-7.04 (m, 1H), 5.31-5.28 (m, 1H), 5.16-5.09 (m, 1H), 4.43 (q, J=7.2 Hz, 2H), 2.82-2.71 (m, 4H), 2.45-2.34 (m, 3H), 2.22-2.07 (m, 3H), 2.01-1.87 (m, 1H), 1.39 (t, J=7.2 Hz, 3H), 1.00-0.93 (m, 4H). I-128: MS (ES): m/z 576 [M+H]$^+$; $^1$H NMR (400 MHz, DMSO-d$_6$) δ 10.59 (s, 1H), 9.64-9.62 (m, 1H), 8.93 (s, 1H), 8.81 (s, 1H), 8.35-8.32 (m, 1H), 8.29 (s, 1H), 7.14 (s, 1H), 7.06-7.02 (m, 1H), 5.30-5.26 (m, 1H), 5.15-5.07 (m, 1H), 4.43 (q, J=7.2 Hz, 2H), 2.79-2.70 (m, 4H), 2.48-2.41 (m, 3H), 2.22-2.07 (m, 3H), 1.97-1.85 (m, 1H), 1.39 (t, J=7.2 Hz, 3H), 0.99-0.93 (m, 4H).

Example 188: Synthesis of N-(1-(4-(cyclopropanesulfonamido)pyridin-2-yl)-3-((S)-3-fluoropyrrolidin-1-yl)propyl)-5-(6-ethoxypyrazin-2-yl)thiazole-2-carboxamide, Formic Acid (I-130)

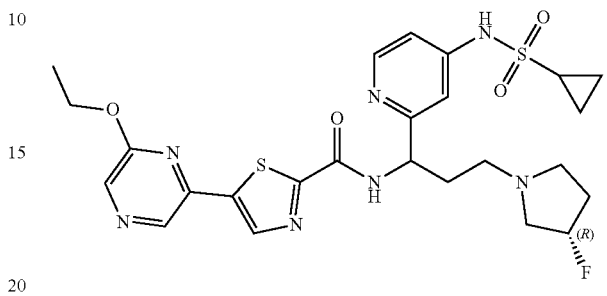

NDI-207384

Synthesis of I-130. Starting from commercially available (S)-3-fluoropyrrolidine, I-130 was prepared following General Method 4 (until step 7). MS (ES): m/z 576 [M+H]$^+$; $^1$H NMR (400 MHz, DMSO-d$_6$) δ 9.71-9.62 (m, 1H), 8.93 (s, 1H), 8.81 (s, 1H), 8.32-8.31 (m, 1H), 8.29 (s, 1H), 8.16 (s, 1H), 7.15 (s, 1H), 7.06-7.04 (m, 1H), 5.31-5.28 (m, 1H), 5.16-5.10 (m, 1H), 4.43 (q, J=7.2 Hz, 2H), 2.80-2.72 (m, 4H), 2.46-2.31 (m, 3H), 2.22-2.09 (m, 3H), 2.01-1.96 (m, 1H), 1.39 (t, J=7.2 Hz, 3H), 1.00-0.94 (m, 4H).

Example 189: Synthesis of N—((R)-1-(4-(cyclopropanesulfonamido)pyridin-2-yl)-3-((S)-3-fluoropyrrolidin-1-yl)propyl)-5-(6-ethoxypyrazin-2-yl)thiazole-2-carboxamide, isomer 1 (I-126) and N—((S)-1-(4-(cyclopropanesulfonamido)pyridin-2-yl)-3-((S)-3-fluoropyrrolidin-1-yl)propyl)-5-(6-ethoxypyrazin-2-yl)thiazole-2-carboxamide, isomer 2 (I-129) Stereochemistry Alpha to the Central Amide Arbitrarily Assigned

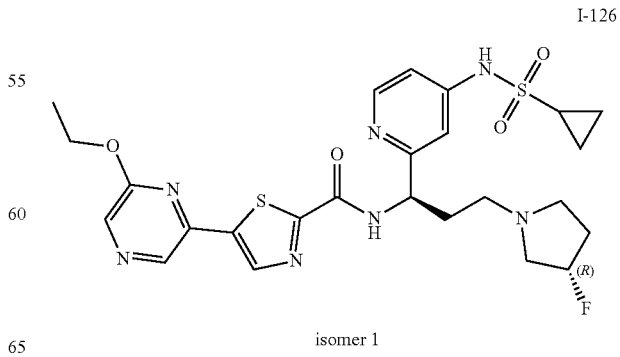

isomer 1

551
-continued

I-129

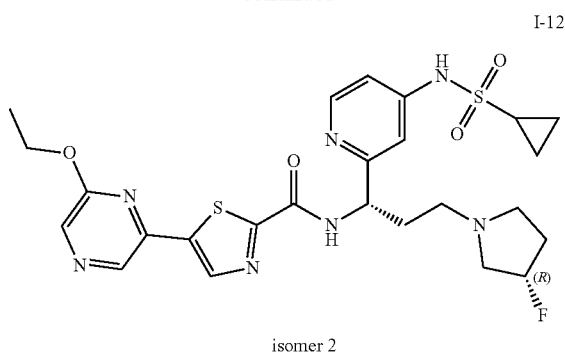

isomer 2

Synthesis of I-126 and I-129. I-126 and I-129 were prepared following General Method 4, Step 8 using I-130 with the following method: chiral HPLC, Column: CHIRALPAK IF, 2*25 cm, 5 μm; Mobile Phase A: Hex:DCM=3:1(0.5% 2M NH₃-MeOH)-HPLC, MobilePhase B: EtOH-HPLC; Flow rate: 20 mL/min; Gradient: 20% B to 20% B in 12 min; Wave Length: 220/254 nm). I-126. First eluting peak, MS (ES): m/z 576 [M+H]⁺; ¹H NMR (400 MHz, DMSO-d₆) δ 9.62 (s, 1H), 8.93 (s, 1H), 8.81 (s, 1H), 8.32-8.31 (m, 1H), 8.29 (s, 1H), 7.14 (s, 1H), 7.06-7.02 (m, 1H), 5.31-5.28 (m, 1H), 5.16-5.10 (m, 1H), 4.43 (q, J=7.2 Hz, 2H), 2.79-2.68 (m, 4H), 2.48-2.41 (m, 3H), 2.23-2.07 (m, 3H), 1.96-1.85 (m, 1H), 1.39 (t, J=7.2 Hz, 3H), 1.01-0.93 (m, 4H). I-129. Second eluting peak, MS (ES): m/z 576 [M+H]⁺; ¹H NMR (400 MHz, DMSO-d₆) δ 9.71-9.69 (m, 1H), 8.93 (s, 1H), 8.81 (s, 1H), 8.32-8.31 (m, 1H), 8.29 (s, 1H), 7.13 (s, 1H), 7.05-7.03 (m, 1H), 5.31-5.28 (m, 1H), 5.16-5.08 (m, 1H), 4.43 (q, J=7.2 Hz, 2H), 2.80-2.71 (m, 4H), 2.46-2.33 (m, 3H), 2.25-2.07 (m, 3H), 2.01-1.87 (m, 1H), 1.39 (t, J=7.2 Hz, 3H), 0.99-0.93 (m, 4H).

General Method 5

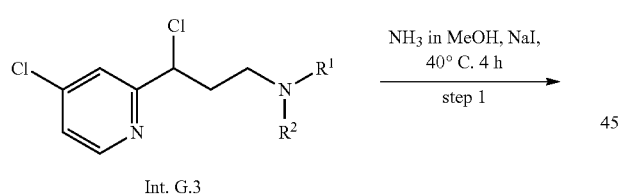

Int. G.3

552
-continued

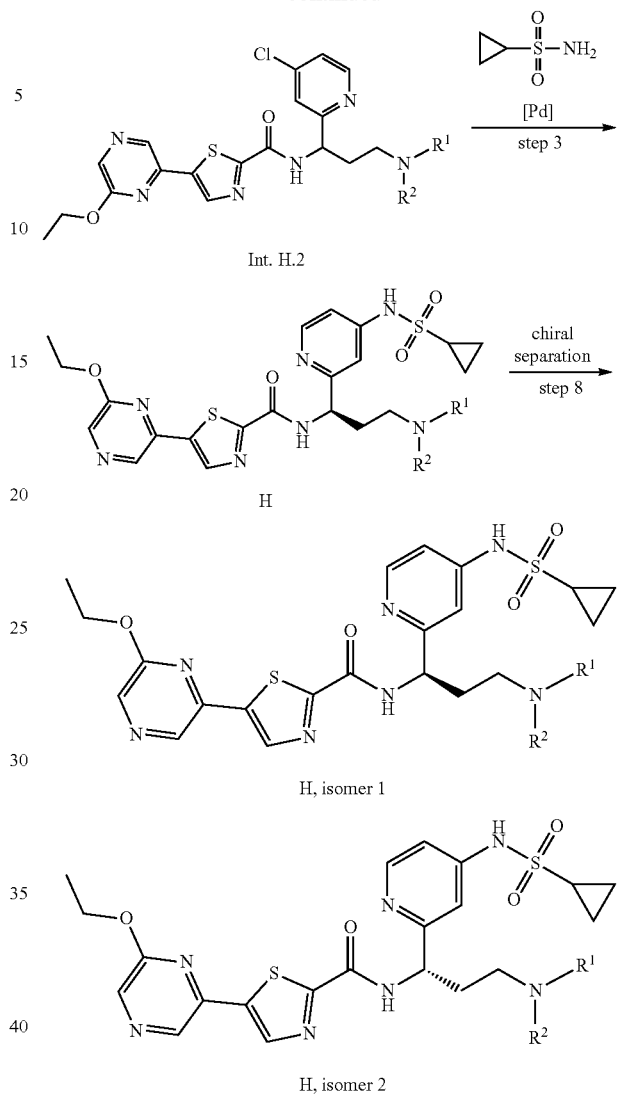

Example 190: Synthesis of N-(1-(4-(cyclopropanesulfonamido)pyridin-2-yl)-3-(pyrrolidin-1-yl)propyl)-5-(6-ethoxypyrazin-2-yl)thiazole-2-carboxamide (I-175)

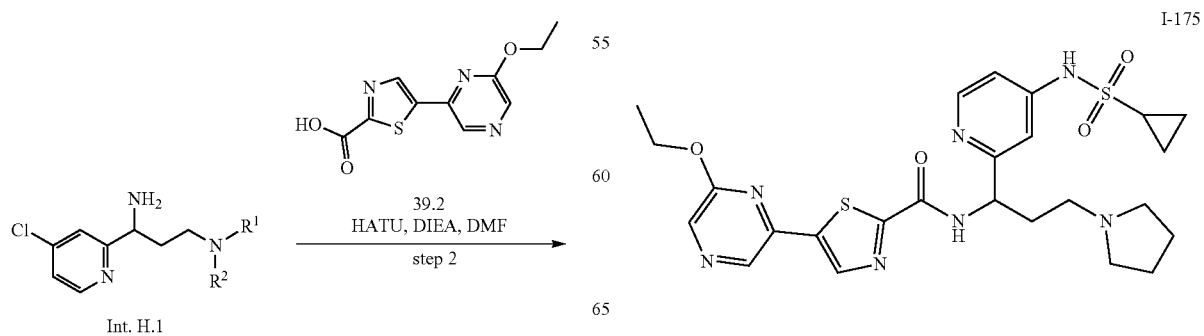

Synthesis of 190.1

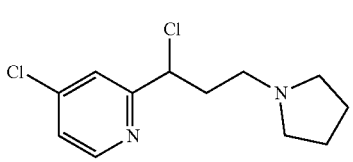

190.1

190.1 was prepared following General Method 4, Step 1 to 3 using pyrolidine as the amine reagent. MS (ES): m/z 259/261 [M+H]+.

General Method 5, Step 1: Synthesis 190.2

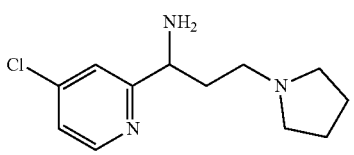

190.2

To a solution of ammonia in methanol (7M, 9 mL) were added 190.1 (750 mg, 2.90 mmol, 1 eq) and sodium iodide (867 mg, 5.80 mmol, 2 eq) in portions at room temperature. The resulting mixture was stirred for 4 h at 40° C. under nitrogen atmosphere. The reaction mixture was filtered. The filtrate concentrated under reduced pressure to afford 1-(4-chloropyridin-2-yl)-3-(pyrrolidin-1-yl)propan-1-amine (190.2, 720 mg, crude) as a yellow oil, which was used in the next step directly without further purification. MS (ES): m/z 240 [M+H], General Method 5, Step 2: Synthesis of 190.3

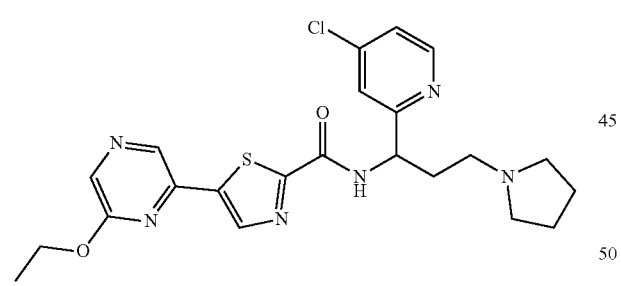

190.3

To a stirred solution of 190.2 (720 mg, 3.00 mmol, 1 eq) and 39.2 (755 mg, 3.00 mmol, 1 eq) in N,N-dimethylformamide (10 mL) were added HATU (1.26 g, 3.30 mmol, 1.1 eq), DIEA (1.55 g, 12.01 mmol, 4 eq) and DMAP (367 mg, 3.00 mmol, 1 eq) in portions at room temperature. The resulting mixture was stirred for 2 h at room temperature. The mixture was diluted with water (40 mL) and extracted with ethyl acetate (3×15 mL). The combined organic layers were concentrated under reduced pressure. The residue was purified by flash column chromatography on C18 silica (eluted with 50% acetonitrile in water) to afford N-[1-(4-chloropyridin-2-yl)-3-(pyrrolidin-1-yl)propyl]-5-(6-ethoxy-pyrazin-2-yl)-1,3-thiazole-2-carboxamide (190.3, 350 mg, 25%) as a white solid. MS (ES): m/z 473 [M+H].

General Method 5, Step 3: Synthesis of I-175

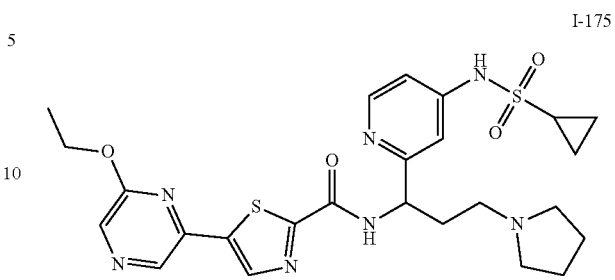

I-175

To a stirred solution of 190.3 (350 mg, 0.74 mmol, 1 eq) and cyclopropanesulfonamide (179 mg, 1.48 mmol, 2 eq) in 1,4-dioxane (3 mL) was added cesium carbonate (723 mg, 2.22 mmol, 3 eq), EPhos (79 mg, 0.15 mmol, 0.2 eq) and EPhos Pd G4 (67 mg, 0.07 mmol, 0.1 eq) in portions at room temperature. The resulting mixture was stirred for 1 h at 100° C. under nitrogen atmosphere. The solid was removed by filtering through Celite and washed with methanol (20 mL). The filtrate was concentrated under reduced pressure. The residue was purified by Prep-HPLC (Column: XBridge BEH130 Prep C18 OBD Column, 19*150 mm, 5 μm; Mobile Phase A: water (10 mM NH$_4$HCO$_3$), Mobile Phase B: ACN; Flow rate: 25 mL/min; Gradient: 25% B to 45% B in 5 min; Wave Length: 254 nm) to afford N-[1-(4-cyclopropanesulfonamidopyridin-2-yl)-3-(pyrrolidin-1-yl)propyl]-5-(6-ethoxypyrazin-2-yl)-1,3-thiazole-2-carboxamide (I-175, 13 mg, 3.12%) as a white solid. MS (ES): m/z 558 [M+H]+; $^1$H NMR (400 MHz, Methanol-d$_4$) δ 8.72 (s, 1H), 8.61 (s, 1H), 8.27 (d, J=6.0 Hz, 1H), 8.17 (s, 1H), 7.26 (d, J=2.4 Hz, 1H), 7.10 (dd, J=6.0, 2.4 Hz, 1H), 5.22-5.19 (m, 1H), 4.50 (q, J=7.2 Hz, 2H), 2.88-2.80 (m, 6H), 2.71-2.65 (m, 1H), 2.36-2.28 (m, 1H), 2.26-2.17 (m, 1H), 1.98-1.92 (m, 4H), 1.47 (t, J=7.2 Hz, 3H), 1.13-1.11 (m, 2H), 0.99-0.94 (m, 2H).

Example 191: Synthesis of (R)—N-(1-(4-(cyclopropanesulfonamido)pyridin-2-yl)-3-(pyrrolidin-1-yl)propyl)-5-(6-ethoxypyrazin-2-yl)thiazole-2-carboxamide, isomer 1 (I-158) and (S)—N-(1-(4-(cyclopropanesulfonamido)pyridin-2-yl)-3-(pyrrolidin-1-yl)propyl)-5-(6-ethoxypyrazin-2-yl)thiazole-2-carboxamide, isomer 1 (I-159).
Stereochemistry Alpha to the Central Amide Arbitrarily Assigned

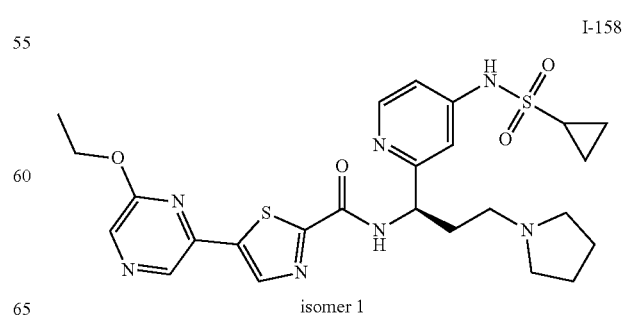

I-158 isomer 1

-continued

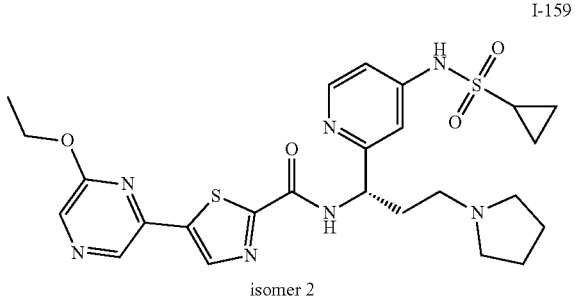

isomer 2
I-159

General Method 5, Step 4: synthesis of I-158 and I-159. I-175 (180 mg) was purified by chiral HPLC (Column: CHIRAL ART Amylose-SA, 2*25 cm, 5 μm; Mobile Phase A: Hex (0.5% 2M NH₃-MeOH)-HPLC, Mobile Phase B: EtOH-HPLC; Flow rate: 20 mL/min; Gradient: 30% B to 30% B in 30 min; Wave Length: 220/254 nm) to afford I-158 (first eluting peak, 23 mg, 13%) and I-159 (second eluting peak, 19 mg, 11%) both as white solids. I-158: MS (ES): m/z 558 [M+H]⁺; ¹H NMR (400 MHz, Methanol-d₄) δ 8.72 (s, 1H), 8.61 (s, 1H), 8.27 (d, J=6.0 Hz, 1H), 8.17 (s, 1H), 7.26 (d, J=2.4 Hz, 1H), 7.10 (dd, J=6.0, 2.4 Hz, 1H), 5.22-5.19 (m, 1H), 4.50 (q, J=7.2 Hz, 2H), 2.87-2.81 (m, 6H), 2.72-2.65 (m, 1H), 2.36-2.28 (m, 1H), 2.26-2.17 (m, 1H), 1.98-1.95 (m, 4H), 1.47 (t, J=7.2 Hz, 3H), 1.13-1.11 (m, 2H), 0.99-0.94 (m, 2H). I-159: MS (ES): m/z 558 [M+H]⁺; ¹H NMR (400 MHz, Methanol-d₄) δ 8.71 (s, 1H), 8.60 (s, 1H), 8.26 (d, J=6.0 Hz, 1H), 8.17 (s, 1H), 7.25 (d, J=2.4 Hz, 1H), 7.10 (dd, J=6.0, 2.4 Hz, 1H), 5.22-5.18 (m, 1H), 4.50 (q, J=7.2 Hz, 2H), 2.85-2.78 (m, 6H), 2.71-2.65 (m, 1H), 2.36-2.27 (m, 1H), 2.25-2.16 (m, 1H), 1.97-1.94 (m, 4H), 1.47 (t, J=7.2 Hz, 3H), 1.13-1.10 (m, 2H), 0.98-0.94 (m, 2H).

Example 192: Synthesis of N-(1-(4-(cyclopropanesulfonamido)pyridin-2-yl)-3-(piperidin-1-yl)propyl)-5-(6-ethoxypyrazin-2-yl)thiazole-2-carboxamide (I-176)

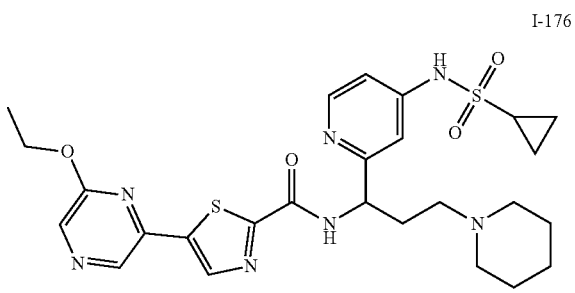 [SMILES: CCOc1cncc(-c2cnc(C(=O)NC(CCN3CCCCC3)c3cc(NS(=O)(=O)C4CC4)ccn3)s2)n1]

I-176

Synthesis of 192.1

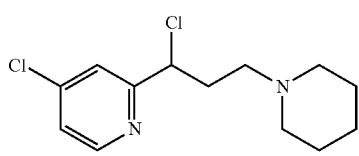

192.1

192.1 was prepared following General Method 4, Step 1 to 3 using piperidine as the amine reagent. MS (ES): m/z 273/275 [M+H]⁺.

Synthesis of I-176. I-176 was prepared following General Method 5, using 192.1 as the chloride reagent. MS (ES): m/z 572 [M+H]⁺; ¹H NMR (300 MHz, DMSO-d₆) δ 10.05 (d, J=7.5 Hz, 1H), 8.96 (s, 1H), 8.83 (s, 1H), 8.31 (d, J=5.7 Hz, 1H), 8.30 (s, 1H), 8.19 (s, 1H), 7.11 (s, 1H), 7.04 (d, J=5.7 Hz, 1H), 5.13-5.09 (m, 1H), 4.43 (q, J=7.2 Hz, 2H), 2.78-2.69 (m, 1H), 2.45-2.31 (m, 6H), 2.71-2.65 (m, 1H), 2.23-2.14 (m, 1H), 2.08-1.98 (m, 1H), 1.67-1.62 (m, 3H), 1.47-1.41 (m, 2H), 1.40 (t, J=7.2 Hz, 3H), 0.99-0.93 (m, 4H).

Example 193: Synthesis of (R)—N-(1-(4-(cyclopropanesulfonamido)pyridin-2-yl)-3-(piperidin-1-yl)propyl)-5-(6-ethoxypyrazin-2-yl)thiazole-2-carboxamide, isomer 1 (I-160) and (S)—N-(1-(4-(cyclopropanesulfonamido)pyridin-2-yl)-3-(piperidin-1-yl)propyl)-5-(6-ethoxypyrazin-2-yl)thiazole-2-carboxamide, isomer 1 (I-161).
Stereochemistry Alpha to the Central Amide Arbitrarily Assigned

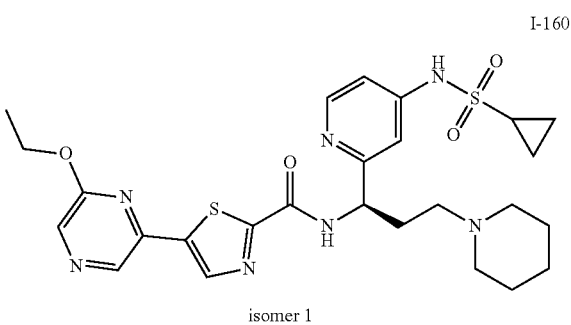

isomer 1
I-160

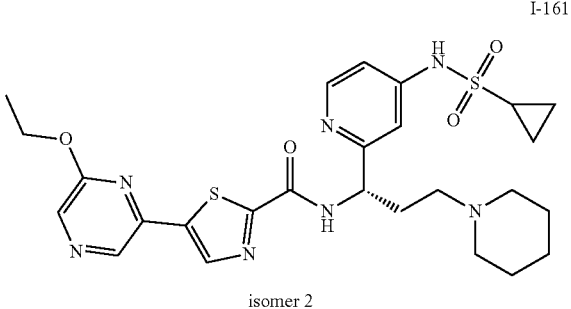

isomer 2
I-161

Synthesis of I-160 and I-161. I-160 and I-161 were prepared following General Method 5, Step 4 using I-176 with the following method: chiral HPLC, Column: CHIRAL ART Amylose-SA, 2*25 cm, 5 μm; Mobile Phase A: Hex (0.5% 2M NH₃-MeOH)-HPLC, Mobile Phase B: EtOH-HPLC; Flow rate: 20 mL/min; Gradient: 30% B to 30% B in 15 min; Wave Length: 220/254 nm). I-160: First eluting peak, MS (ES): m/z 572 [M+H]⁺; ¹H NMR (300 MHz, Methanol-d₄) δ 8.73 (s, 1H), 8.63 (s, 1H), 8.28 (d, J=5.7 Hz, 1H), 8.17 (s, 1H), 7.27 (d, J=2.1 Hz, 1H), 7.10 (dd, J=5.7, 2.1 Hz, 1H), 5.22-5.18 (m, 1H), 4.50 (q, J=7.2 Hz, 2H), 2.70-2.57 (m, 6H), 2.39-2.30 (m, 1H), 2.19-2.12 (m, 2H), 1.81-1.74 (m, 4H), 1.61-1.55 (m, 2H), 1.47 (t, J=7.2 Hz, 3H), 1.13-1.10 (m, 2H), 0.97-0.94 (m, 2H). I-161: Second eluting peak, MS (ES): m/z 572 [M+H]⁺; ¹H NMR (300 MHz, Methanol-7*) δ 8.73 (s, 1H), 8.62 (s, 1H), 8.28 (d, J=5.7 Hz, 1H), 8.17 (s, 1H), 7.27 (d, J=2.1 Hz, 1H), 7.10 (dd, J=5.7, 2.1 Hz, 1H), 5.22-5.18 (m, 1H), 4.50 (q, 7=7.2 Hz, 2H), 2.72-2.58 (m, 6H), 2.39-2.27 (m, 1H), 2.21-2.12 (m, 2H), 1.81-1.74 (m, 4H), 1.61-1.55 (m, 2H), 1.47 (t, J=7.2 Hz, 3H), 1.13-1.11 (m, 2H), 0.99-0.94 (m, 2H).

Example 194: Synthesis of N-(1-(4-(cyclopropanesulfonamido)pyridin-2-yl)-3-morpholinopropyl)-5-(6-ethoxypyrazin-2-yl)thiazole-2-carboxamide (I-179)

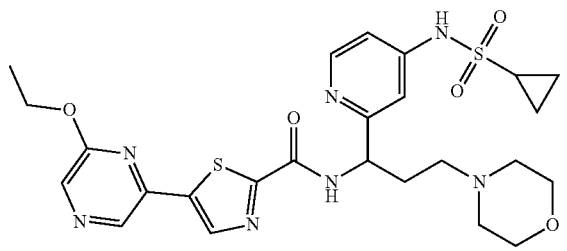

I-179

Synthesis of 194.1

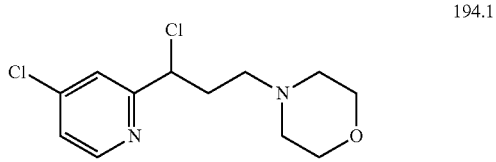 [SMILES: Clc1ccnc(C(Cl)CCN2CCOCC2)c1]

194.1

194.1 was prepared following General Method 4, Step 1 to 3 using morpholine as the amine reagent. MS (ES): m/z 275/277 [M+H]⁺.

Synthesis of I-179. I-179 was prepared following General Method 5, using 194.1 as the chloride reagent. MS (ES): m/z 574 [M+H]⁺; ¹H NMR (400 MHz, DMSO-d₆) δ 9.86-9.84 (m, 1H), 8.95 (s, 1H), 8.85 (s, 1H), 8.29 (s, 1H), 8.24-8.22 (m, 1H), 7.05 (s, 1H), 6.98-6.96 (m, 1H), 5.11-5.05 (m, 1H), 4.43 (q, J=7.2 Hz, 2H), 3.71-3.65 (m, 4H), 2.70-2.64 (m, 1H), 2.46-2.40 (m, 2H), 2.39-2.30 (m, 4H), 2.18-2.10 (m, 1H), 2.05-1.96 (m, 1H), 1.39 (t, J=7.2 Hz, 3H), 0.94-0.86 (m, 4H).

Example 195: Synthesis of (R)—N-(1-(4-(cyclopropanesulfonamido)pyridin-2-yl)-3-morpholinopropyl)-5-(6-ethoxypyrazin-2-yl)thiazole-2-carboxamide, isomer 1 (I-164) and (S)—N-(1-(4-(cyclopropanesulfonamido)pyridin-2-yl)-3-morpholinopropyl)-5-(6-ethoxypyrazin-2-yl)thiazole-2-carboxamide, isomer 2 (I-165). Stereochemistry Alpha to the Central Amide Arbitrarily Assigned

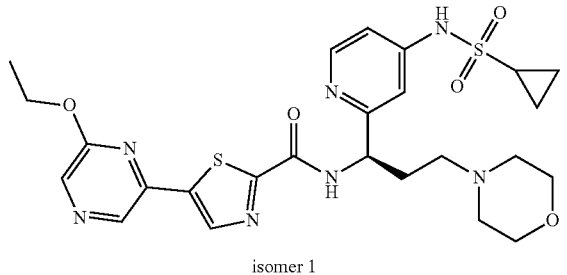

isomer 1

I-164

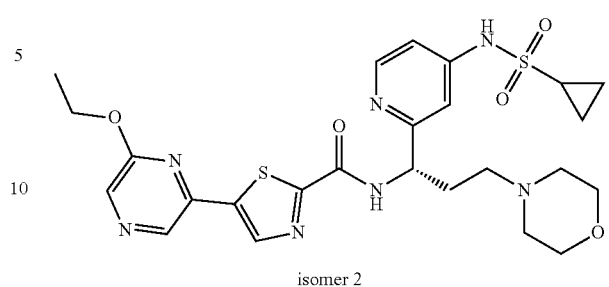

I-165 isomer 2

Synthesis of I-164 and I-165. I-164 and I-165 were prepared following General Method 5, Step 4 using with the following method: chiral HPLC (Column: CHIRALPAK IF, 2*25 cm, 5 μm; Mobile Phase A: Hex:DCM=3:1(0.5% 2M NH₃-MeOH)-HPLC, Mobile Phase B: EtOH-HPLC; Flow rate: 20 mL/min; Gradient: 20% B to 20% B in 15 min; Wave Length: 220/254 nm). I-164: First eluting peak, MS (ES): m/z 574 [M+H]⁺; ¹H NMR (400 MHz, DMSO-d₆) δ 10.53 (s, 1H), 9.91 (s, 1H), 8.95 (s, 1H), 8.86 (s, 1H), 8.39-8.35 (m, 1H), 8.29 (s, 1H), 7.17 (s, 1H), 7.05 (s, 1H), 5.15-5.08 (m, 1H), 4.43 (q, J=7.2 Hz, 2H), 3.72-3.65 (m, 4H), 2.83-2.74 (m, 1H), 2.47-2.42 (m, 2H), 2.37-2.31 (m, 4H), 2.20-2.12 (m, 1H), 2.06-1.99 (m, 1H), 1.39 (t, J=7.2 Hz, 3H), 1.01-0.94 (m, 4H). I-165: Second eluting peak, MS (ES): m/z 574 [M+H]⁺; ¹H NMR (400 MHz, DMSO-d₆) δ 10.53 (s, 1H), 9.91 (s, 1H), 8.95 (s, 1H), 8.86 (s, 1H), 8.39-8.35 (m, 1H), 8.29 (s, 1H), 7.17 (s, 1H), 7.05 (s, 1H), 5.15-5.08 (m, 1H), 4.43 (q, J=7.2 Hz, 2H), 3.71-3.67 (m, 4H), 2.82-2.75 (m, 1H), 2.47-2.42 (m, 2H), 2.37-2.31 (m, 4H), 2.20-2.12 (m, 1H), 2.06-1.99 (m, 1H), 1.39 (t, J=7.2 Hz, 3H), 1.00-0.94 (m, 4H).

General Method 6

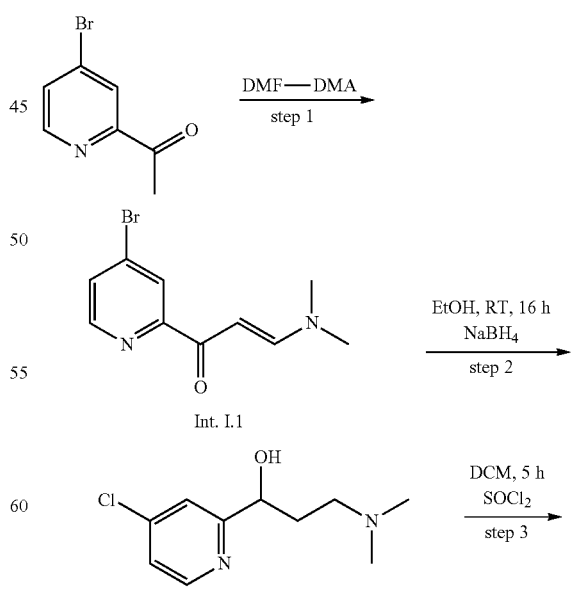

-continued

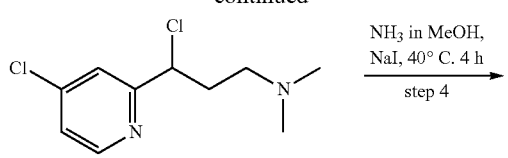

Int. I.3

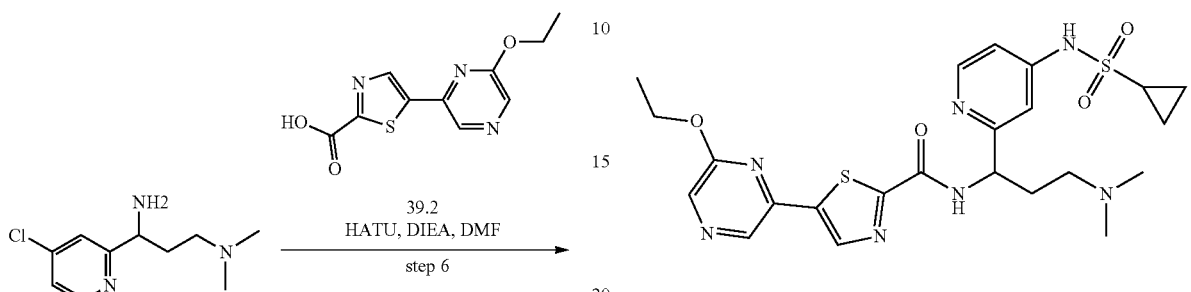

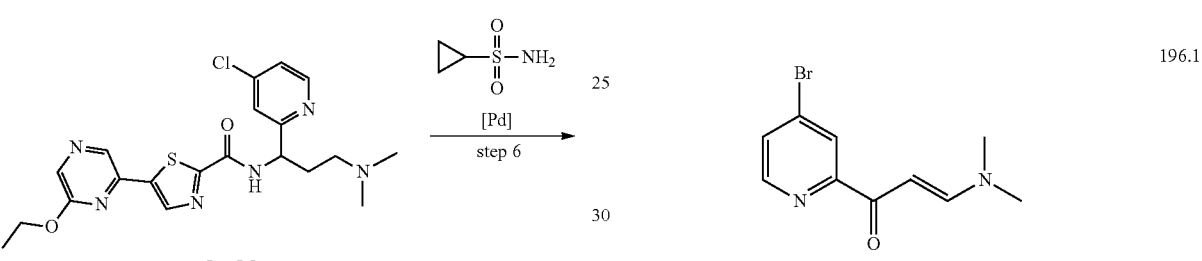

Int. I.5

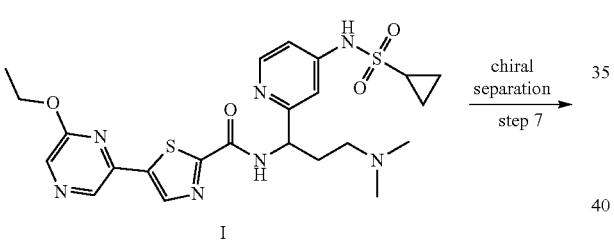

I

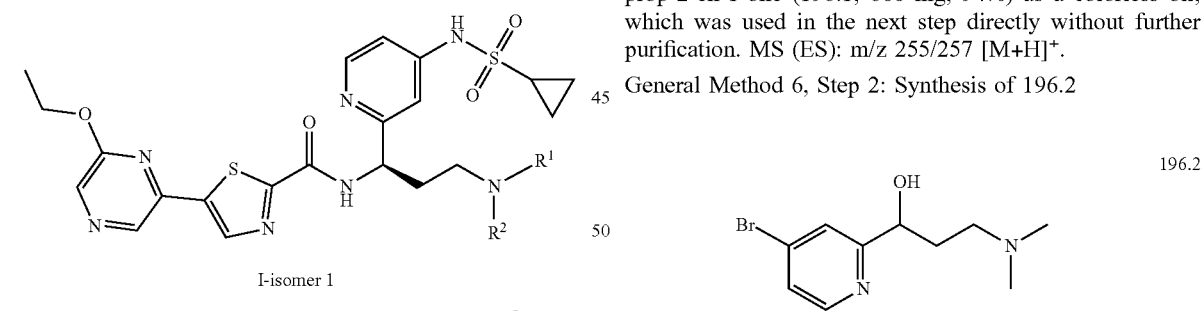

I-isomer 1

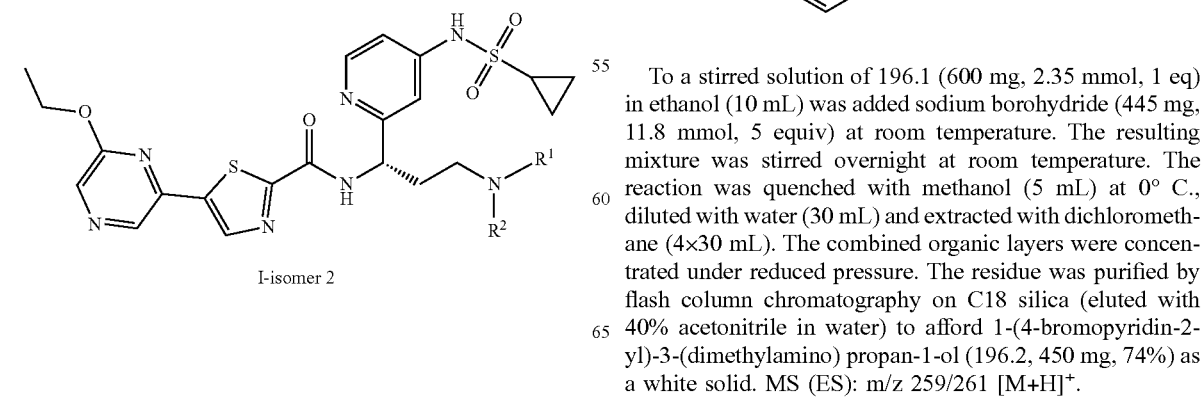

I-isomer 2

Example 196: Synthesis of N-(1-(4-(cyclopropane-sulfonamido)pyridin-2-yl)-3-(dimethylamino)propyl)-5-(6-ethoxypyrazin-2-yl)thiazole-2-carboxamide (I-201)

I-201

General Method 6, Step 1: Synthesis of 196.1

196.1

A solution of 1-(4-bromopyridin-2-yl)ethanone (500 mg, 2.50 mmol, 1 equiv) and DMA-DMF (387 mg, 3.25 mmol, 1.3 equiv) in N,N-dimethylformamide (10 mL) was stirred for 3 h at 80° C. The reaction was diluted with water (30 mL) and extracted with ethyl acetate (3×25 mL). The combined organic layers were concentrated under reduced pressure to afford (E)-1-(4-bromopyridin-2-yl)-3-(dimethylamino) prop-2-en-1-one (196.1, 600 mg, 94%) as a colorless oil, which was used in the next step directly without further purification. MS (ES): m/z 255/257 [M+H]+.

General Method 6, Step 2: Synthesis of 196.2

196.2

To a stirred solution of 196.1 (600 mg, 2.35 mmol, 1 eq) in ethanol (10 mL) was added sodium borohydride (445 mg, 11.8 mmol, 5 equiv) at room temperature. The resulting mixture was stirred overnight at room temperature. The reaction was quenched with methanol (5 mL) at 0° C., diluted with water (30 mL) and extracted with dichloromethane (4×30 mL). The combined organic layers were concentrated under reduced pressure. The residue was purified by flash column chromatography on C18 silica (eluted with 40% acetonitrile in water) to afford 1-(4-bromopyridin-2-yl)-3-(dimethylamino) propan-1-ol (196.2, 450 mg, 74%) as a white solid. MS (ES): m/z 259/261 [M+H]+.

General Method 6, Step 3: Synthesis of 196.3

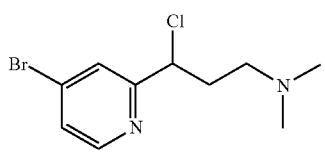

196.3

To a stirred solution of 196.2 (450 mg, 1.74 mmol, 1 equiv) in anhydrous dichloromethane (10 mL) was added thionyl chloride (1.03 g, 8.68 mmol, 5 equiv) dropwise at 0° C. under nitrogen atmosphere. The resulting mixture was stirred for 1 h at room temperature under nitrogen atmosphere The reaction was concentrated under reduced pressure. The residue was purified by flash column chromatography on silica gel (eluted with dichloromethane/methanol, 8/1) afford [3-(4-bromopyridin-2-yl)-3-chloropropyl] dimethylamine (196.3, 420 mg, 87%) as a yellow solid. MS (ES): m/z 277/279 $[M+H]^+$.

General Method 6, Step 4: Synthesis of 196.4.

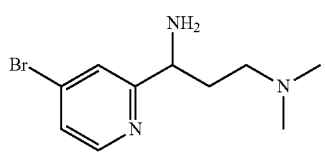

196.4

To a solution of ammonia in methanol (7M, 9 mL) were added 196.3 (410 mg, 1.48 mmol, 1 equiv) and sodium iodide (332 mg, 2.22 mmol, 1.5 equiv) in portions at room temperature. The resulting mixture was stirred for 4 h at 40° C. under nitrogen atmosphere. The reaction mixture was filtered. The filtrate concentrated under reduced pressure to afford 1-(4-bromopyridin-2-yl)-N,N-dimethylpropane-1,3-diamine (196.4, 370 mg, crude) as a yellow oil, which was used in the next step directly without further purification. MS (ES): m/z 258/260 $[M+H]^+$.

General Method 6, Step 5: Synthesis of 196.5

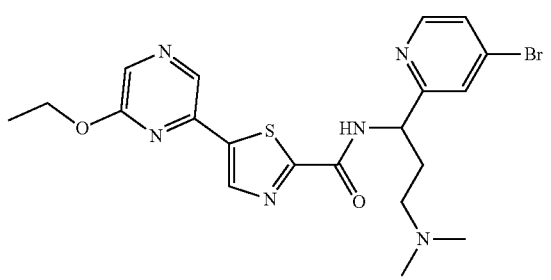

196.5

A solution of 196.4 (400 mg, 1.55 mmol, 1 equiv), 39.2 (389 mg, 1.55 mmol, 1 equiv), DIEA (600 mg, 4.65 mmol, 3 equiv) and HATU (707 mg, 1.86 mmol, 1.2 equiv) in N,N-dimethylformamide (5 mL) was stirred for 2 h at room temperature. The mixture was diluted with water (40 mL) and extracted with ethyl acetate (3×15 mL). The combined organic layers were concentrated under reduced pressure. The residue was purified by flash column chromatography on silica gel (eluted with dichloromethane/methanol, 15/1) to afford N-[1-(4-bromopyridin-2-yl)-3-(dimethylamino) propyl]-5-(6-ethoxypyrazin-2-yl)-1,3-thiazole-2-carboxamide (196.5, 240 mg, 32%) as a yellow solid. MS (ES): m/z 491/493 $[M+H]^+$.

General Method 6, Step 6: synthesis of I-201

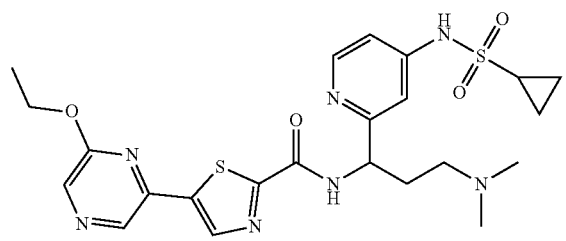

I-201

To a solution of 196.5 (230 mg, 0.47 mmol, 1 equiv) and cyclopropanesulfonamide (85 mg, 0.71 mmol, 1.5 equiv) in 1,4-dioxane (8 mL) were added cesium carbonate (458 mg, 1.40 mmol, 3 equiv), t-BuXPhos (40 mg, 0.094 mmol, 0.2 equiv) and $[PdCl(allyl)]_2$ (17 mg, 0.047 mmol, 0.1 equiv) in portions. The resulting mixture was stirred for 1 h at 60° C. under nitrogen atmosphere. The solid was removed by filtering through Celite and washed with methanol (20 mL). The filtrate was concentrated under reduced pressure. The residue was purified by Prep-HPLC (Column: XBridge Prep OBD C18 Column, 30*150 mm, 5 μm; Mobile Phase A: water (10 mM $NH_4HCO_3$), Mobile Phase B: ACN; Flow rate: 60 mL/min; Gradient: 24% B to 34% B in 9 min; Wave Length: 254/220 nm) to afford N-[1-(4-cyclopropanesulfonamidopyridin-2-yl)-3-(dimethylamino)propyl]-5-(6-ethoxypyrazin-2-yl)-1,3-thiazole-2-carboxamide (I-201, 89 mg, 36%) as a white solid. MS (ES): m/z 532 $[M+H]^+$; $^1H$ NMR (400 MHz, DMSO-$d_6$) δ 9.62 (d, J=8.0 Hz, 1H), 8.93 (s, 1H), 8.81 (s, 1H), 8.29 (s, 1H), 8.28-8.25 (m, 1H), 7.09 (s, 1H), 7.01-6.99 (m, 1H), 5.11-5.05 (m, 1H), 4.43 (q, J=7.2 Hz, 2H), 2.74-2.65 (m, 1H), 2.37-2.25 (m, 2H), 2.20 (s, 6H), 2.09-2.01 (m, 2H), 1.39 (t, J=7.2 Hz, 3H), 0.99-0.89 (m, 4H).

Example 197: Synthesis of (R)—N-(1-(4-(cyclopropanesulfonamido)pyridin-2-yl)-3-(dimethylamino) propyl)-5-(6-ethoxypyrazin-2-yl)thiazole-2-carboxamide, isomer 1 (I-189) and (S)—N-(1-(4-(cyclopropanesulfonamido)pyridin-2-yl)-3-(dimethylamino)propyl)-5-(6-ethoxypyrazin-2-yl) thiazole-2-carboxamide, isomer 2 (I-190).

Stereochemistry Alpha to the Central Amide Arbitrarily Assigned

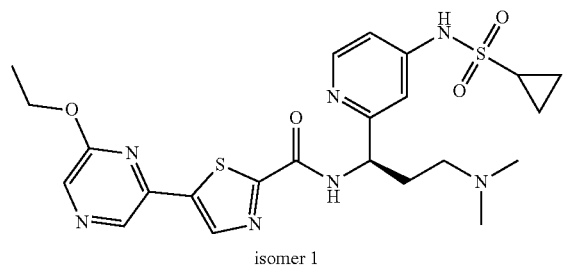

I-189 isomer 1

-continued

I-190

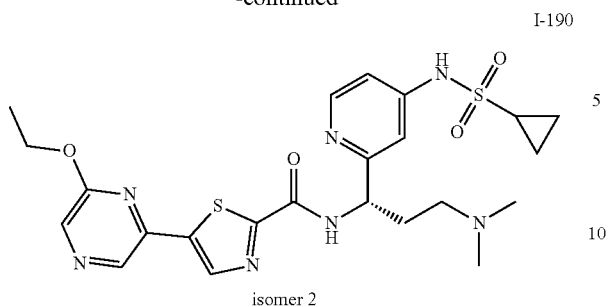

isomer 2

General Method 6, Step 6: synthesis of I-189 and I-190. I-201 (80 mg) was purified by chiral HPLC (Column: CHIRALPAK ID, 2*25 cm, 5 μm; Mobile Phase A: Hex:DCM=3:1(0.5% 2M NH3-MeOH)-HPLC, Mobile Phase B: IPA-HPLC; Flow rate: 20 mL/min; Gradient: 30% B to 30% B in 19 min; Wave Length: 220/254 nm) to afford I-189 (first eluting peak, 32 mg, 40%) and I-190 (second eluting peak, 35 mg, 44%) both as white solid. I-189: MS (ES): m/z 532 [M+H]$^+$; $^1$H NMR (400 MHz, DMSO-d$_6$) δ 9.63 (d, J=10.4 Hz, 1H), 8.93 (s, 1H), 8.82 (s, 1H), 8.29 (s, 1H), 8.28-8.25 (m, 1H), 7.12 (s, 1H), 7.04-7.01 (m, 1H), 5.12-5.05 (m, 1H), 4.43 (q, J=7.2 Hz, 2H), 2.78-2.69 (m, 1H), 2.37-2.27 (m, 2H), 2.21 (s, 6H), 2.10-2.03 (m, 2H), 1.39 (t, J=7.2 Hz, 3H), 0.99-0.92 (m, 4H). I-190: MS (ES): m/z 532 [M+H]$^+$; $^1$H NMR (400 MHz, DMSO-d$_6$) δ 9.64 (d, J=8.0 Hz, 1H), 8.93 (s, 1H), 8.82 (s, 1H), 8.29 (s, 1H), 8.28-8.25 (m, 1H), 7.12 (s, 1H), 7.03-7.01 (m, 1H), 5.11-5.06 (m, 1H), 4.43 (q, J=7.2 Hz, 2H), 2.75-2.70 (m, 1H), 2.37-2.26 (m, 2H), 2.21 (s, 6H), 2.10-2.03 (m, 2H), 1.39 (t, J=7.2 Hz, 3H), 0.99-0.92 (m, 4H).

Example 198: Synthesis of N-(3-(azetidin-1-yl)-1-(4-(cyclopropanesulfonamido)pyridin-2-yl)propyl)-5-(6-ethoxypyrazin-2-yl)thiazole-2-carboxamide (I-182)

I-182

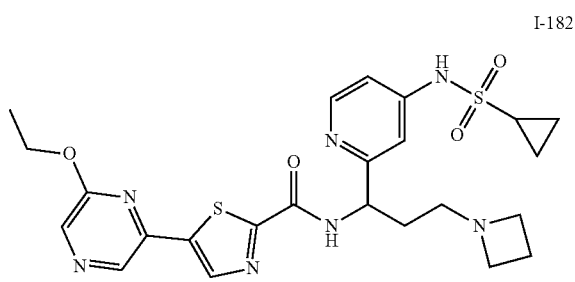 [SMILES: CCOc1cncc(-c2cnc(C(=O)NC(CCN3CCC3)c3cc(NS(=O)(=O)C4CC4)ccn3)s2)n1]

Synthesis of 198.2

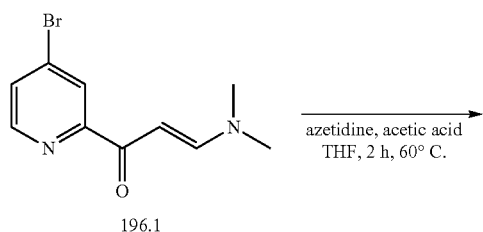

198.2

Synthesis of 198.2. 196.1. (200 mg, 0.78 mmol, 1 equiv) was treated with azetidine (448 mg, 7.84 mmol, 10 equiv) and acetic acid (5 mg, 0.078 mmol, 0.1 equiv) in tetrahydrofuran (5 mL) for 2 h at 60° C. The reaction mixture was concentrated under reduced pressure. The residue was purified by flash column chromatography on silica gel (eluted with dichloromethane/methanol, 9/1) to afford (2)-3-(azetidin-1-yl)-1-(4-bromopyridin-2-yl)prop-2-en-1-one (198.2, 143 mg, 65%) as a yellow solid. MS (ES): m/z 267/269 [M+H]$^+$.

Synthesis of I-182. I-182 was prepared following General Method 6, steps 2 to 6, using 198.2 as the bromide reagent. MS (ES): m/z 544 [M+H]$^+$; $^1$H NMR (300 MHz, Methanol-d$_4$) δ 8.69 (s, 1H), 8.55 (s, 1H), 8.16 (s, 1H), 8.15-8.09 (m, 1H), 6.96 (d, J=2.4 Hz, 1H), 6.89-6.86 (m, 1H), 5.92-5.75 (m, 1H), 4.85-4.77 (m, 1H), 4.50 (q, J=7.2 Hz, 2H), 4.09-4.02 (m, 2H), 4.09-4.02 (m, 2H), 3.85-3.64 (m, 1H), 3.49-3.38 (m, 1H), 3.28-2.98 (m, 2H), 2.77-2.41 (m, 2H), 1.47 (t, J=7.2 Hz, 3H), 1.09-1.03 (m, 2H), 0.94-0.86 (m, 2H).

Example 199: Synthesis of (S)—N-(1-(4-(cyclopropanesulfonamido)pyridin-2-yl)-2-(1-methylpiperidin-4-yl)ethyl)-5-(6-ethoxypyrazin-2-yl)thiazole-2-carboxamide, isomer 1 (I-99) and (R)—N-(1-(4-(cyclopropanesulfonamido)pyridin-2-yl)-2-(1-methylpiperidin-4-yl)ethyl)-5-(6-ethoxypyrazin-2-yl)thiazole-2-carboxamide, isomer 2 (I-100). Stereochemistry Arbitrarily Assigned

I-99

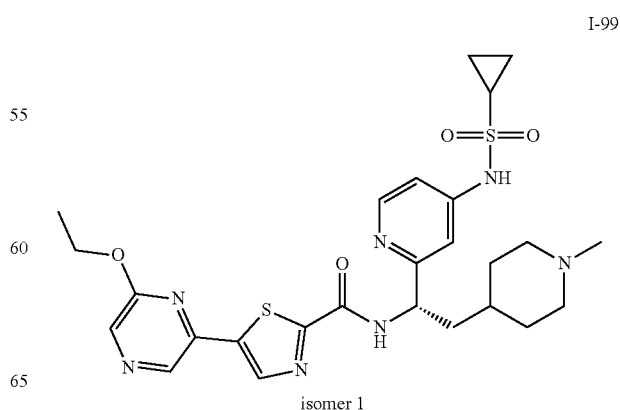

isomer 1

-continued

I-100

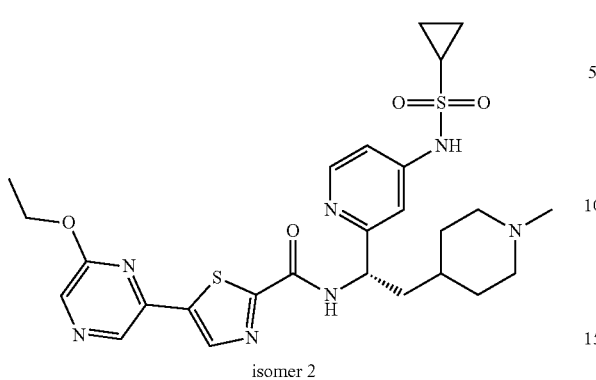

isomer 2

Synthesis of I-99 and I-100. I-99 and I-100 were prepared following General Method 3 (ending after step 9.2), starting from commercially available 2-(1-(tert-butoxycarbonyl)piperidin-4-yl)acetic acid. Final product purification method: chiral HPLC (Column: CHIRALPAK IG, 2*25 cm, 5 μm; Mobile Phase A: Hex:DCM=3:1(0.5% 2M NH$_3$-MeOH)-HPLC, Mobile Phase B: EtOH-HPLC; Flow rate: 20 mL/min; Gradient: 30% B to 30% B in 20 min; Wave Length: 220/254 nm). I-99 (first eluting peak). MS (ES): m/z 572 [M+H]$^+$; $^1$H NMR (400 MHz, Methanol-7*) δ 8.69 (s, 1H), 8.58 (s, 1H), 8.22 (d, J=5.6 Hz, 1H), 8.15 (s, 1H), 7.21 (d, J=2.4 Hz, 1H), 7.06 (dd, J=5.6, 2.4 Hz, 1H), 5.20-5.16 (m, 1H), 4.48 (t, J=7.2 Hz, 2H), 3.04-3.01 (m, 2H), 2.70-2.63 (m, 1H), 2.40 (s, 3H), 2.30-2.21 (m, 2H), 2.00-1.82 (m, 4H), 1.47-1.37 (m, 6H), 1.12-1.10 (m, 2H), 0.98-0.93 (m, 2H). I-100 (second eluting peak). MS (ES): m/z 572 [M+H]$^+$; $^1$H NMR (400 MHz, Methanol-7*) δ 8.69 (s, 1H), 8.58 (s, 1H), 8.22 (d, J=5.6 Hz, 1H), 8.15 (s, 1H), 7.21 (d, J=2.4 Hz, 1H), 7.06 (dd, J=5.6, 2.4 Hz, 1H), 5.20-5.16 (m, 1H), 4.48 (t, J=12 Hz, 2H), 3.04-3.01 (m, 2H), 2.70-2.64 (m, 1H), 2.40 (s, 3H), 2.30-2.21 (m, 2H), 2.00-1.82 (m, 4H), 1.46-1.35 (m, 6H), 1.12-1.10 (m, 2H), 0.98-0.92 (m, 2H).

Example 200: Synthesis of (R)—N-(1-(3-((difluoromethyl)sulfonamido)phenyl)-2-morpholinoethyl)-5-(6-ethoxypyrazin-2-yl)thiazole-2-carboxamide (I-247)

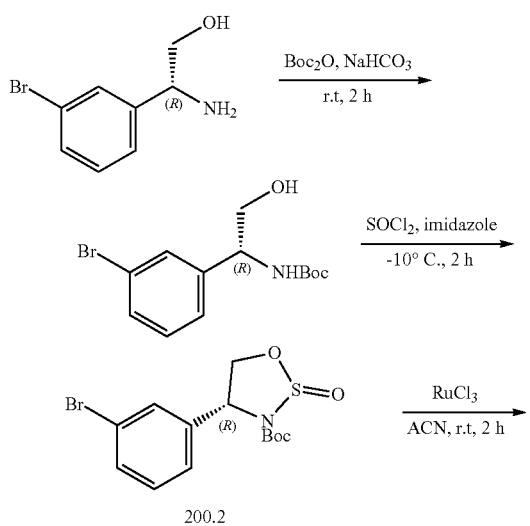

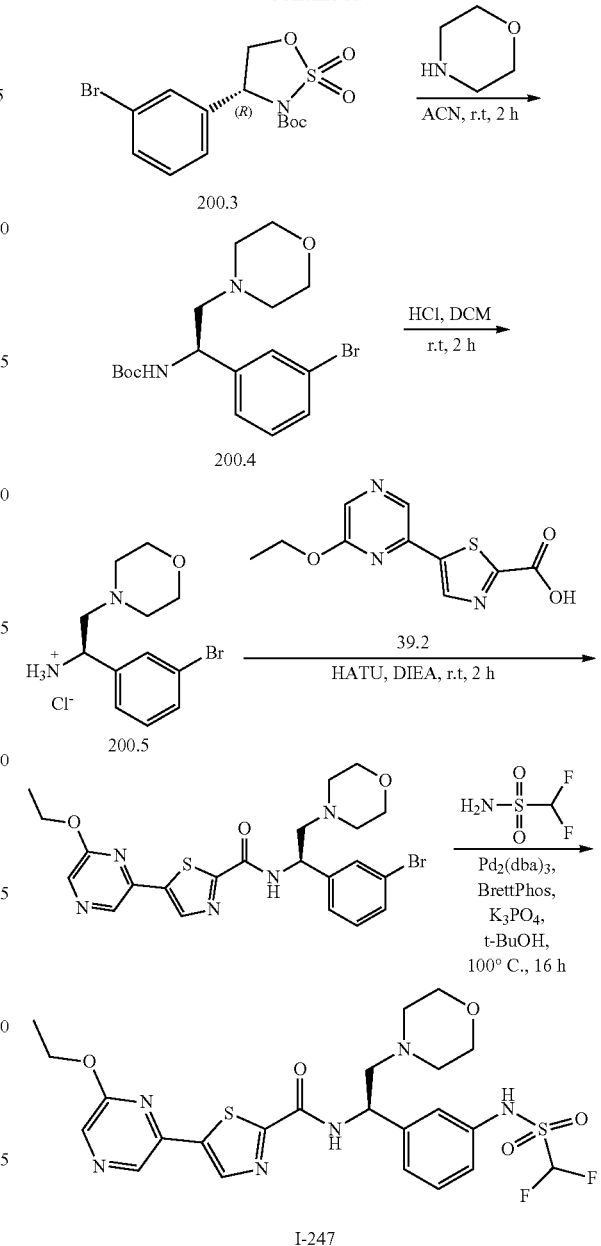

Synthesis of 200.1. To a solution of (2R)-2-amino-2-(3-bromophenyl)ethanol (1 g, 4.63 mmol, 1 eq) and sodium bicarbonate (1.2 g, 13.9 mmol, 3 eq) in tetrahydrofuran (14 mL) and water (14 mL) was added di-tert-butyl dicarbonate (1.2 g, 5.55 mmol, 1.2 eq) in portions at room temperature. The resulting mixture was stirred for 2 h at room temperature and was extracted with ethyl acetate (3×10 mL). The combined organic layers were washed with brine (10 mL), dried over anhydrous sodium sulfate and concentrated under reduced pressure to afford tert-butyl (R)-(1-(3-bromophenyl)-2-hydroxyethyl)carbamate (200.1, 948 mg, 65%) as a light yellow oil, which was used directly in the next step without further purification. MS (ES): m/z 316/318 [M+H]$^+$.

Synthesis of 200.2. A solution of imidazole (1.2 g, 18 mmol, 6 eq) and thionyl chloride (642 mg, 5.4 mmol, 1.8 eq) in dichloromethane (8 mL) was stirred for 1 h at −10° C. under nitrogen atmosphere. 200.1 (948 mg, 3 mmol, 1 eq)

was then added in portions at −10° C. The resulting mixture was stirred for 1 h at −10° C., then was diluted with water (30 mL) and extracted with dichioromethane (3×10 mL). The combined organic layers were washed with brine (10 mL), dried over anhydrous sodium sulfate and concentrated under reduced pressure to afford tert-butyl (4R)-4-(3-bromophenyl)-1,2,3-oxathiazolidine-3-carboxylate 2-oxide (200.2, 800 mg, 74%) as a light yellow solid, which was used directly in the next step without further purification. MS (ES): m/z 362/364 [M+H]+.

Synthesis of 200.3. To a solution of 200.2 (800 mg, 2.2 mmol, 1 eq) and RuCl$_3$·H$_2$O (25 mg, 0.11 mmol, 0.05 eq) in acetonitrile (11 mL) was added dropwise NaIO$_4$ (472 mg, 2.2 mmol, 1 eq) in water (11 mL) at 0° C. The resulting mixture was stirred for 2 h at room temperature under nitrogen atmosphere. The reaction mixture was diluted with water (30 mL) and extracted with ethyl acetate (3×20 mL). The combined organic layers were washed with brine (10 mL), dried over anhydrous sodium sulfate and concentrated under reduced pressure. The residue was purified by flash column chromatography on silica gel (eluted with petroleum ether/ethyl acetate, 3:1) to afford tert-butyl (R)-4-(3-bromophenyl)-1,2,3-oxathiazolidine-3-carboxylate 2,2-dioxide (200.3, 360 mg, 43%) as a light yellow solid. MS (ES): m/z 378/380 [M+H]+.

Synthesis of 200.4. A mixture of 200.3 (320 mg, 0.85 mmol, 1 eq) and morpholine (74 mg, 0.85 mmol, 1 eq) in acetonitrile (5 mL) was stirred for 2 h at room temperature. The reaction mixture was diluted with water (20 mL) and extracted with ethyl acetate (3×10 mL). The combined organic layers were washed with brine (10 mL), dried over anhydrous sodium sulfate and concentrated under reduced pressure. The residue was purified by flash column chromatography on silica gel (eluted with petroleum ether/ethyl acetate, 1:1) to afford tert-butyl (R)-(1-(3-bromophenyl)-2-morpholinoethyl)carbamate (200.4, 300 mg, 92%) as a light yellow solid. MS (ES): m/z 385/387 [M+H]+.

Synthesis of 200.5. A mixture of 200.4 (300 mg, 0.78 mmol, 1 eq) and hydrochloric acid in 1,4-dioxane (4.0 M, 2.5 mL, 10 mmol, 12.8 eq) in dichloromethane (2.5 mL) was stirred for 2 h at room temperature. The resulting mixture was concentrated under reduced pressure to afford (R)-1-(3-bromophenyl)-2-morpholinoethan-1-amine hydrochloride (200.5, 240 mg, 96%) as a yellow solid, which was used in the next step directly without further purification. MS (ES): m/z 285/287 [M+H]+.

Synthesis of 200.6. To a stirred mixture of 200.5 (116 mg, 0.36 mmol, 1 eq) and DIEA (182 mg, 1.4 mmol, 4 eq) in dichloromethane (5 mL) were added 39.2 (88 mg, 0.35 mmol, 1 eq) and HATU (160 mg, 0.42 mmol, 1.2 eq) in portions at room temperature. The resulting mixture was stirred for 16 h at room temperature. The reaction mixture was diluted with water (20 mL) and extracted with dichloromethane (3×10 mL). The combined organic layers were washed with brine (10 mL), dried over anhydrous sodium sulfate and concentrated under reduced pressure. The residue was purified by flash column chromatography on silica gel (eluted with dichloromethane/methanol, 12:1) to afford N-[(1R)-1-(3-bromophenyl)-2-(morpholin-4-yl)ethyl]-5-(6-ethoxypyrazin-2-yl)-1,3-thiazole-2-carboxamide (200.6, 90 mg, 48%) as a white solid. MS (ES): m/z 518/520 [M+H]+.

Synthesis of I-247. To a stirred mixture of 200.6 (136 mg, 0.27 mmol, 1 eq) and difluoromethanesulfonamide (70 mg, 0.54 mmol, 2 eq) in tert-butyl alcohol (5 mL) were added potassium phosphate (170 mg, 0.81 mmol, 3 eq) and Pd$_2$(dba)$_3$ (24 mg, 0.03 mmol, 0.1 eq) and BrettPhos (29 mg, 0.05 mmol, 0.2 eq) in portions. The resulting mixture was stirred for 16 h at 100° C. under nitrogen atmosphere. The mixture was concentrated under reduced pressure. The residue was purified by flash column chromatography on C18 silica (eluted with acetonitrile/water, 7/3) to give 80 mg of crude product, which was further purified by prep-HPLC (Column: XBridge Prep C18 OBD Column, 30*100 mm, 5 μm; Mobile Phase A: water (10 mM NH$_4$HCO$_3$), Mobile Phase B: ACN; Flow rate: 60 mL/min; Gradient:2% B to 9% B in 2 min, 19% B to 39% B in 10 min, UV detection at 254/220 nm) to afford N-[(1R)-1-[3-(difluoromethanesulfonamido)phenyl]-2-(morpholin-4-yl)ethyl]-5-(6-ethoxypyrazin-2-yl)-1,3-thiazole-2-carboxamide, I-247, 26 mg, 17%), as a white solid. MS (ES): m/z 569 [M+H]+; $^1$H NMR (300 MHz, Methanol-d$_4$) δ 8.71 (s, 1H), 8.61 (s, 1H), 8.17 (s, 1H), 7.38-7.20 (m, 4H), 6.64 (t, J=52.8 Hz, 1H), 5.27-5.22 (m, 1H), 4.50 (q, J=7.2 Hz, 2H), 3.72-3.67 (m, 4H), 2.97-2.90 (m, 1H), 2.75-2.62 (m, 3H), 2.55-2.45 (m, 2H), 1.47 (t, J=7.2 Hz, 3H).

Example 201: Synthesis of (N-(1-(3-(cyclopropanesulfonamido)-2,6-difluorophenyl)-3-(dimethylamino)propyl)-5-(6-ethoxypyrazin-2-yl)thiazole-2-carboxamide (I-123)

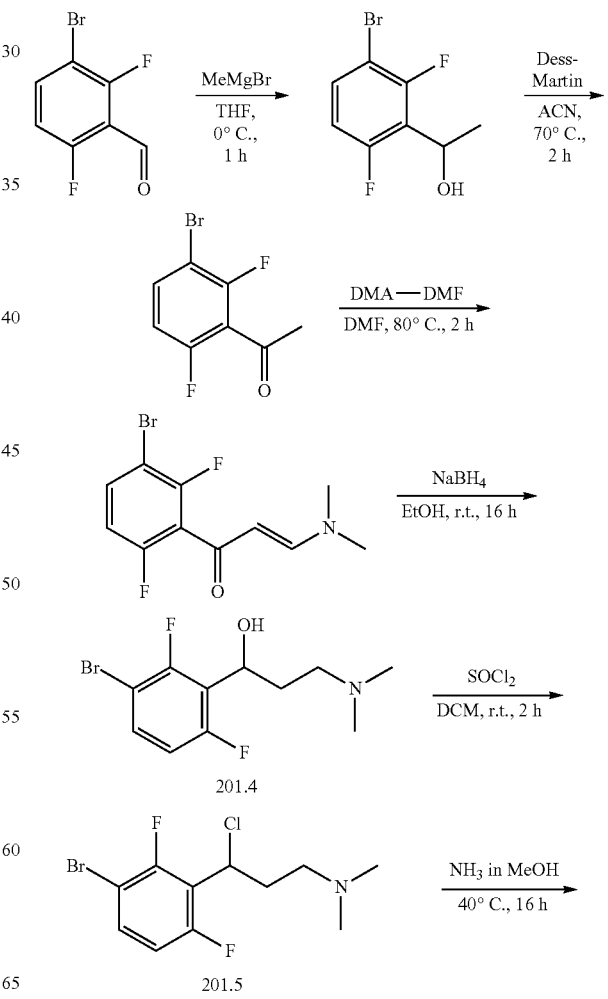

-continued

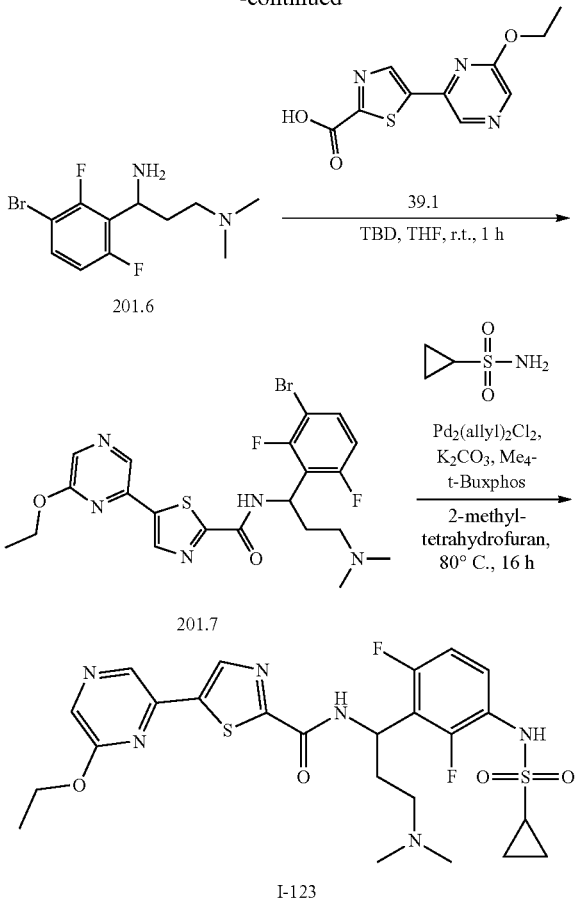

Synthesis of 201.1. To a stirred solution of 3-bromo-2,6-difluorobenzaldehyde (2.9 g, 13.1 mmol, 1 equiv) in tetrahydrofuran (40 mL) was added dropwise bromo(methyl)magnesium (1 M in THF, 26.2 mL, 26.2 mmol, 2 equiv) at −15° C. under nitrogen atmosphere. The resulting mixture was stirred for 1 h at 0° C. under nitrogen atmosphere. The reaction was quenched by the addition of ice water (60 mL) at 0° C. The resulting mixture was extracted with ethyl acetate (3×50 mL). The combined organic layers were washed with brine (60 mL), dried over anhydrous sodium sulfate and concentrated under reduced pressure. The residue was purified by flash column chromatography on silica gel (eluted with petroleum ether/ethyl acetate, 5/1) to afford 1-(3-bromo-2,6-difluorophenyl)ethanol (201.1, 2.9 g, 93%) as colorless semi-oil. $^1$H NMR (300 MHz, DMSO-d$_6$) δ 7.75-7.57 (m, 1H), 7.15-7.00 (m, 1H), 5.50 (d, J=4.5 Hz, 1H), 5.16-5.02 (m, 1H), 1.47 (d, J=6.6 Hz, 3H).

Synthesis of 201.2. To a stirred solution of 201.1 (2.9 g, 12.2 mmol, 1 equiv) in acetonitrile (40 mL) was added Dess-Martin periodinane (10.4 g, 24.4 mmol, 2 equiv) in portions at room temperature. The resulting mixture was stirred for 2 h at 70° C. under nitrogen atmosphere. The reaction was quenched by water (60 mL) at room temperature. The resulting mixture was extracted with ethyl acetate (3×50 mL). The combined organic layers were washed with brine (50 mL), dried over anhydrous sodium sulfate and concentrated under reduced pressure. The residue was purified by flash column chromatography on silica gel (eluted with petroleum ether/ethyl acetate, 5/1) to afford 1-(3-bromo-2,6-difluorophenyl)ethanone (201.2, 2.0 g, 70%) as colorless semi-oil. $^1$H NMR (300 MHz, DMSO-de) δ 8.00-7.86 (m, 1H), 7.33-7.20 (m, 1H), 2.59 (s, 3H).

Synthesis of 201.3. To a stirred solution of 201.2 (2.9 g, 12.3 mmol, 1 equiv) in DMF (40 mL) was added DMF-DMA (2.21 g, 18.5 mmol, 1.5 equiv) at room temperature. The resulting mixture was stirred for 2 h at 80° C. under nitrogen atmosphere. The resulting mixture was diluted with water (100 mL) and extracted with ethyl acetate (3×90 mL). The combined organic layers were washed with brine (60 mL), dried over anhydrous sodium sulfate and concentrated under reduced pressure to afford (2)-1-(3-bromo-2,6-difluorophenyl)-3-(dimethylamino)prop-2-en-1-one (201.3, 3.0 g, 84%) as light yellow oil, which was used directly in the next step without further purification. MS (ES): m/z 290/292 [M+H]$^+$.

Synthesis of 201.4. To a stirred solution of 201.3 (3.0 g, 7.23 mmol, 1 equiv) in ethanol (40 mL) was added sodium borohydride (2.7 g, 72.4 mmol, 10 equiv) in portions at 0° C. The resulting mixture was stirred for 16 h at room temperature under nitrogen atmosphere. The reaction was quenched with ice water (80 mL) at 0° C. The resulting mixture was extracted with ethyl acetate (3×50 mL). The combined organic layers were washed with brine (60 mL), dried over anhydrous sodium sulfate and concentrated under reduced pressure. The residue was purified by flash column chromatography on C18 silica (eluted with acetonitrile/water, 1/1) to afford 1-(3-bromo-2,6-difluorophenyl)-3-(dimethylamino)propan-1-ol (201.4, 1.58 g, 74%) as light yellow semi-solid. MS (ES): m/z 294/296 [M+H]$^+$.

Synthesis of 201.5. To a stirred solution of 201.4 (1.58 g, 5.37 mmol, 1.00 equiv) in dichloromethane (10 mL) was added thionyl chloride (10 mL, 84.0 mmol, 15.6 equiv) dropwise at 0° C. The resulting mixture was stirred for 2 h at room temperature under nitrogen atmosphere. The resulting mixture was concentrated under reduced pressure to afford 3-(3-bromo-2,6-difluorophenyl)-3-chloro-/N,N-dimethylpropan-1-amine (201.5, 1.68 g) as a light yellow oil, which was used in the next step directly without further purification. MS (ES): m/z 312/314 [M+H]$^+$.

Synthesis of 201.6. To a solution of NH$_3$ in MeOH (7M, 10 mL) was added 201.5 (1.68 g, 5.38 mmol) in portions. The resulting mixture was stirred for 16 h at 40° C. The reaction mixture was concentrated under reduced pressure. The residue was purified by flash column chromatography on C18 silica (eluted with acetonitrile/water, ⅓) to afford [3-amino-3-(3-bromo-2,6-difluorophenyl)propyl]dimethylamine (201.6, 480 mg), as a colorless semi-solid. MS (ES): m/z 293/295 [M+H]$^+$.

Synthesis of 201.7. To a stirred solution of 201.6 (480 mg, 1.64 mmol, 1 equiv) and 39.1 (434 mg, 1.64 mmol, 1 equiv) in tetrahydrofuran (10 mL) was added 1,5,7-triazabicyclo[4.4.0]dec-5-ene (456 mg, 3.27 mmol, 2 equiv) at room temperature. The resulting mixture was stirred for 1 h at room temperature. The resulting mixture was diluted with water (60 mL) and extracted with ethyl acetate (3×30 mL). The combined organic layers were washed with brine (30 mL), dried over anhydrous sodium sulfate and concentrated under reduced pressure. The residue was purified by flash column chromatography on silica gel (eluted with dichloromethane/ethyl acetate, 3/1) to afford N-[1-(3-bromo-2,6-difluorophenyl)-3-(dimethylamino)propyl]-5-(6-ethoxypyrazin-2-yl)-1,3-thiazole-2-carboxamide (201.7, 250 mg, 29%) as a light grey solid. MS (ES): m/z 526/528 [M+H]$^+$.

Synthesis of compound I-123. To a stirred solution of 201.7 (250 mg, 0.48 mmol, 1 equiv), cyclopropanesulfonamide (115 mg, 0.96 mmol, 2 equiv) and potassium carbonate (197 mg, 1.44 mmol, 3 equiv) in 2-methyltetrahydrofuran (10 mL) were added Pd₂(allyl)₂Cl₂ (17 mg, 0.048 mmol, 0.1 equiv) and Me₄-tBuXPhos (44 mg, 0.095 mmol, 0.2 equiv) at room temperature. The resulting mixture was stirred for 1 h at room temperature. The resulting mixture was diluted with water (50 mL) and extracted with ethyl acetate (3×30 mL). The combined organic layers were washed with brine (20 mL), dried over anhydrous sodium sulfate and concentrated under reduced pressure. The residue was purified by Prep-HPLC (Column: XBridge Prep OBD C18 Column, 30*150 mm, 5 μm; Mobile Phase A: water (10 mM FA), Mobile Phase B: ACN; Flow rate: 60 mL/min; Gradient: 45% B to 52% B in 9 min; Wave Length: 254/220 nm) to afford N-[1-(3-cyclopropanesulfonamido-2,6-difluorophenyl)-3-(dimethylamino)propyl]-5-(6-ethoxypyrazin-2-yl)-1,3-thiazole-2-carboxamide (I-123, 2.0 mg, 0.7%) as a white solid. MS (ES): m/z 567 [M+H]⁺; ¹H NMR (400 MHz, Methanol-d₄) δ 8.67 (s, 1H), 8.52 (s, 1H), 8.14 (s, 1H), 7.49-7.43 (m, 1H), 7.02-6.97 (m, 1H), 4.48 (q, J=7.2 Hz, 2H), 4.26-4.22 (m, 1H), 3.52-3.39 (m, 2H), 2.63-2.56 (m, 1H), 2.45-2.39 (m, 1H), 2.37-2.30 (m, 1H), 2.28 (s, 6H), 1.45 (t, J=7.2 Hz, 3H), 0.99-0.95 (m, 4H).

Example 202: Synthesis of (R)—N-(1-(3-(cyclopropanesulfonamido)-2,6-difluorophenyl)-3-(dimethylamino)propyl)-5-(6-ethoxypyrazin-2-yl)thiazole-2-carboxamide, isomer 1 (I-124) and (S)—N-(1-(3-(cyclopropanesulfonamido)-2,6-difluorophenyl)-3-(dimethylamino)propyl)-5-(6-ethoxypyrazin-2-yl)thiazole-2-carboxamide, isomer 2 (I-125). Stereochemistry Arbitrarily Assigned

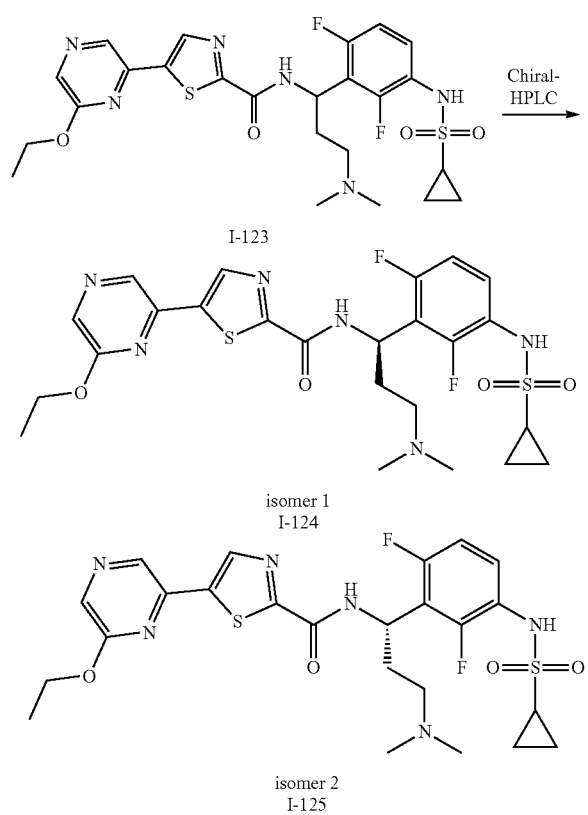

Synthesis of I-124 and I-125. I-123 (80 mg) was purified by chiral HPLC (Column: CHIRAL ART Amylose-SA, 2*25 cm, 5 μm; Mobile Phase A: Hex:DCM=3:1(0.5% 2M NH₃-MeOH)-HPLC, Mobile Phase B: EtOH-HPLC; Flow rate: 20 mL/min; Gradient: 30% B to 30% B in 15 min; Wave Length: 220/254 nm) to afford I-124 (first eluting peak, 28 mg, 35%) and I-125 (second eluting peak, 23 mg, 29%) both as white solid. I-124: MS (ES): m/z 567 [M+H]⁺; ¹H NMR (400 MHz, Methanol-d₄) δ 8.67 (s, 1H), 8.51 (s, 1H), 8.14 (s, 1H), 7.49-7.43 (m, 1H), 7.02-6.97 (m, 1H), 4.48 (q, J=7.2 Hz, 2H), 4.26-4.22 (m, 1H), 3.52-3.39 (m, 2H), 2.63-2.56 (m, 1H), 2.46-2.39 (m, 1H), 2.37-2.30 (m, 1H), 2.28 (s, 6H), 1.45 (t, J=7.2 Hz, 3H), 1.00-0.96 (m, 4H). I-125: MS (ES): m/z 567 [M+H]⁺; ¹H NMR (400 MHz, Methanol-d₄) δ 8.67 (s, 1H), 8.51 (s, 1H), 8.14 (s, 1H), 7.49-7.43 (m, 1H), 7.01-6.97 (m, 1H), 4.48 (q, J=7.2 Hz, 2H), 4.25-4.21 (m, 1H), 3.50-3.41 (m, 2H), 2.62-2.56 (m, 1H), 2.46-2.39 (m, 1H), 2.37-2.30 (m, 1H), 2.27 (s, 6H), 1.45 (t, J=7.2 Hz, 3H), 0.99-0.96 (m, 4H).

Example 203: Synthesis of N-(1-(3-(cyclopropanesulfonamido)phenyl)-3-(dimethylamino)propyl)-5-(6-ethoxypyrazin-2-yl)thiazole-2-carboxamide (I-152)

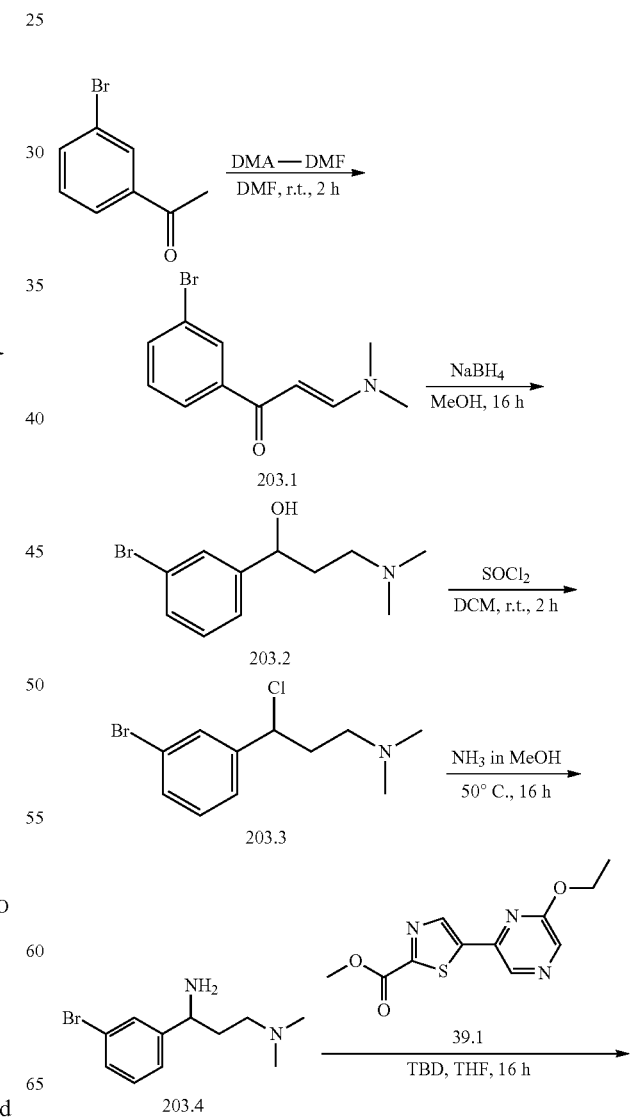

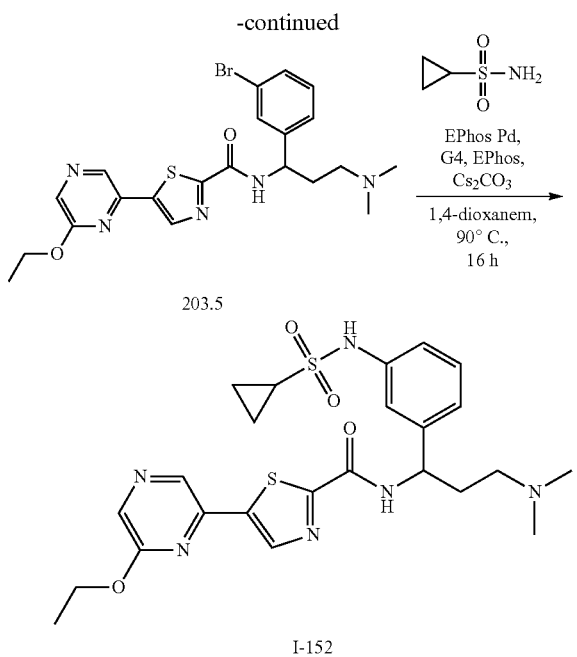

Synthesis of 203.1. To a stirred solution of meta-bromoacetophenone (5 g, 25.1 mmol, 1 equiv) in DMF (40 mL) was added DMF-DMA (4.5 g, 37.7 mmol, 1.5 equiv) at room temperature. The resulting mixture was stirred for 2 h at 80° C. under nitrogen atmosphere. The resulting mixture was diluted with water (100 mL) and extracted with ethyl acetate (3×90 mL). The combined organic layers were washed with brine (60 mL), dried over anhydrous sodium sulfate and concentrated under reduced pressure to afford (2)-1-(3-bromophenyl)-3-(dimethylamino)prop-2-en-1-one (203.1, 5.5 g, 86%) as a yellow oil, which was used directly in the next step without further purification. MS (ES): m/z 254/256 [M+H]$^+$.

Synthesis of 203.2. To a stirred solution of 203.1 (5 g, 19.6 mmol, 1 equiv) in methanol (40 mL) was added sodium borohydride (2.2 g, 58.8 mmol, 3 equiv) in portions. The resulting mixture was stirred at room temperature overnight. The reaction was quenched with ice water (80 mL) at 0° C. The resulting mixture was extracted with ethyl acetate (3×50 mL). The combined organic layers were washed with brine (60 mL), dried over anhydrous sodium sulfate and concentrated under reduced pressure. The residue was purified by flash column chromatography on C18 silica (eluted with acetonitrile/water, 1/1) to afford 1-(3-bromophenyl)-3-(dimethylamino)propan-1-ol (203.2, 5 g, 99%) as an orange oil. MS (ES): m/z 258/260 [M+H]$^+$.

Synthesis of 203.3. To a stirred solution of 1 203.2 (5 g, 19.3 mmol, 1 equiv) in dichloromethane (40 mL) was added thionyl chloride (2.1 mL, 29.1 mmol, 1.5 equiv) dropwise at 0° C. The resulting mixture was stirred for 2 h at room temperature under nitrogen atmosphere. The resulting mixture was concentrated under reduced pressure to afford [3-(3-bromophenyl)-3-chloropropyl]dimethylamine (203.3, 5 g, 94%) as an orange solid, which was used in the next step directly without further purification. MS (ES): m/z 276/278 [M+H]$^+$.

Synthesis of 203.4. To a solution of NH$_3$ in MeOH (7M, 30 mL) was added 203.3 (5 g, 18.1 mmol, 1 equiv) in portions. The resulting mixture was stirred for 16 h at 50° C. The reaction mixture was concentrated under reduced pressure. The residue was purified by flash column chromatography on C18 silica (eluted with acetonitrile/water, ¼) to afford [3-amino-3-(3-bromophenyl)propyl]dimethylamine (203.4, 1.2 g, 26%) as a yellow oil. MS (ES): m/z 257/259 [M+H]$^+$.

Synthesis of 203.5. To a stirred mixture of 203.4 (600 mg, 2.33 mmol, 1 equiv), 39.1 (1.24 g, 4.66 mmol, 2 equiv) in tetrahydrofuran (5 mL) was added 1,5,7-triazabicyclo[4.4.0]dec-5-ene (649 mg, 4.66 mmol, 2 equiv) in portions. The resulting mixture was stirred overnight at room temperature. The resulting mixture was diluted with water (30 mL) and extracted with ethyl acetate (3×15 mL). The combined organic layers were washed with brine (15 mL), dried over anhydrous sodium sulfate and concentrated under reduced pressure. The residue was purified by flash column chromatography on silica gel (eluted with dichloromethane/ethyl acetate, 3/1) to afford N-[1-(3-bromophenyl)-3-(dimethylamino)propyl]-5-(6-ethoxypyrazin-2-yl)-1,3-thiazole-2-carboxamide (203.5, 380 mg, 33%) as a yellow oil. MS (ES): m/z 490/492 [M+H]$^+$.

Synthesis of I-152. A mixture of 203.5 (80 mg, 0.16 mmol, 1 equiv), cyclopropanesulfonamide (39 mg, 0.32 mmol, 2 equiv), EPhos (17 mg, 0.03 mmol, 0.2 equiv), EPhos Pd G4 (14.98 mg, 0.016 mmol, 0.1 equiv) and cesium carbonate (159 mg, 0.48 mmol, 3 equiv) in 1,4-dioxane (2 mL) was stirred overnight at 90° C. under nitrogen atmosphere. The resulting mixture was diluted with water (20 mL) and extracted with ethyl acetate (3×10 mL). The combined organic layers were washed with brine (10 mL), dried over anhydrous sodium sulfate and concentrated under reduced pressure. The residue was purified by Prep-HPLC (Column: XBridge Prep OBD C18 Column, 30*150 mm, 5 μm; Mobile Phase A: water (10 mMNH$_4$HCO$_3$), Mobile Phase B: ACN; Flow rate: 60 mL/min; Gradient: 40% B to 50% B in 8 min; Wave Length: 254/220 nm) to afford N-[1-(3-cyclopropanesulfonamidophenyl)-3-(dimethylamino)propyl]-5-(6-ethoxypyrazin-2-yl)-1,3-thiazole-2-carboxamide (I-152, 1.5 mg, 1.7%) as a white solid. MS (ES): m/z 531 [M+H]$^+$; $^1$H NMR (400 MHz, DMSO-d$_6$) δ 9.80 (d, J=8.4 Hz, 1H), 9.71 (s, 1H), 8.92 (s, 1H), 8.79 (s, 1H), 8.28 (s, 1H), 7.31-7.27 (m, 2H), 7.17 (d, J=8.0 Hz, 1H), 7.10 (d, J=8.0 Hz, 1H), 5.10-5.04 (m, 1H), 4.42 (q, J=7.2 Hz, 2H), 2.62-2.56 (m, 1H), 2.30-2.20 (m, 2H), 2.17 (s, 6H), 2.06-1.95 (m, 2H), 1.39 (t, J=7.2 Hz, 3H), 0.92-0.87 (m, 4H).

Example 204: Synthesis of (R)—N-(1-(3-(cyclopropanesulfonamido)phenyl)-3-(dimethylamino)propyl)-5-(6-ethoxypyrazin-2-yl)thiazole-2-carboxamide, isomer 1 (I-143) and (S)—N-(1-(3-(cyclopropanesulfonamido)phenyl)-3-(dimethylamino)propyl)-5-(6-ethoxypyrazin-2-yl)thiazole-2-carboxamide, isomer 2 (I-144).
Stereochemistry Arbitrarily Assigned

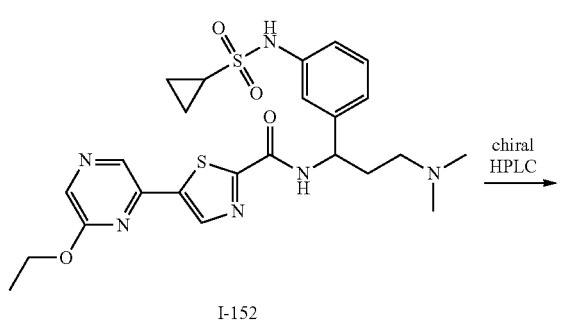

I-152

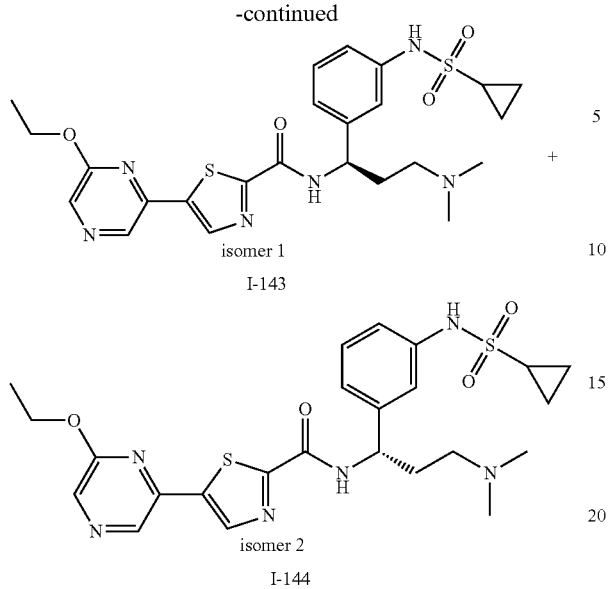

isomer 1
I-143 isomer 2
I-144

Synthesis of I-143 and I-144. I-152 (130 mg) was purified by chiral HPLC (Column: CHIRAL ART Amylose-SA, 2*25 cm, 5 μm; Mobile Phase A: Hex:DCM=3:1(0.5% 2M NH$_3$-MeOH)-HPLC, Mobile Phase B: EtOH-HPLC; Flow rate: 20 mL/min; Gradient: 50% B to 50% B in 10 min; Wave Length: 220/254 nm) to afford I-143 (first eluting peak, 21 mg, 16%) and I-144 (second eluting peak, 23 mg, 17%) both as white solids. I-143: MS (ES): m/z 531 [M+H]$^+$; $^1$H NMR (400 MHZ, DMSO-d$_6$) δ 9.80 (d, J=8.4 HZ, 1H), 9.71 (s, 1H), 8.91 (s, 1H), 8.79 (s, 1H), 8.28 (s, 1H), 7.31-7.27 (m, 2H), 7.18 (d, J=8.0 Hz, 1H), 7.11 (d, J=8.0 Hz, 1H), 5.10-5.04 (m, 1H), 4.42 (q, J=7.2 Hz, 2H), 2.62-2.56 (m, 1H), 2.29-2.19 (m, 2H), 2.16 (s, 6H), 2.06-1.95 (m, 2H), 1.39 (t, J=7.2 Hz, 3H), 0.92-0.88 (m, 4H). I-144: MS (ES): m/z 531 [M+H]$^+$; $^1$H NMR (400 MHz, DMSO-d$_6$) δ 9.81 (d, J=8.4 Hz, 1H), 9.66 (s, 1H), 8.92 (s, 1H), 8.80 (s, 1H), 8.28 (s, 1H), 7.31-7.27 (m, 2H), 7.18 (d, J=8.0 Hz, 1H), 7.11 (d, J=8.0 Hz, 1H), 5.10-5.04 (m, 1H), 4.42 (q, J=7.2 Hz, 2H), 2.62-2.56 (m, 1H), 2.29-2.19 (m, 2H), 2.16 (s, 6H), 2.06-1.95 (m, 2H), 1.39 (t, J=7.2 Hz, 3H), 0.92-0.88 (m, 4H).

Example 205: Synthesis of 5-(6-ethoxypyrazin-2-yl)-N-[(4-methanesulfonamidopyridin-2-yl) methyl] pyridine-2-carboxamide (Z-9)

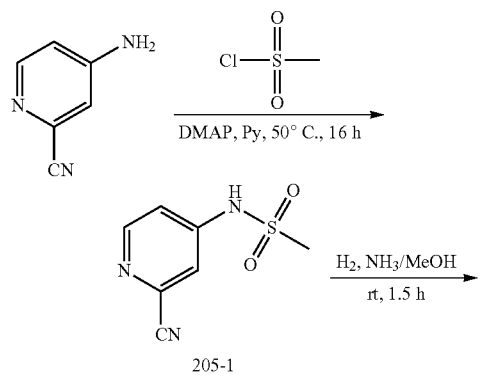

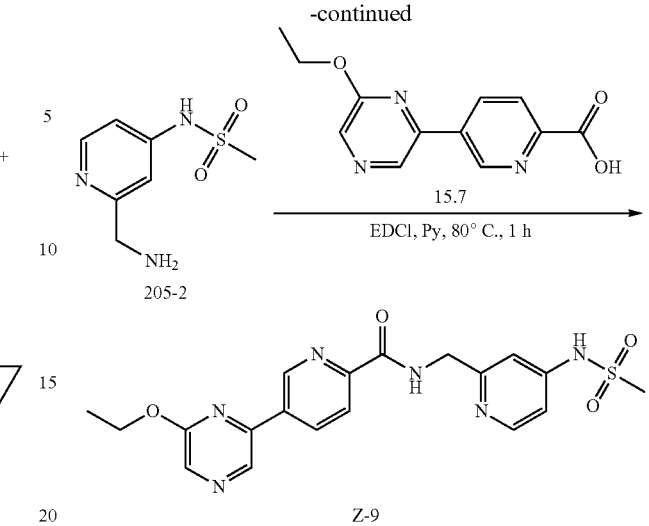

Z-9

Synthesis of 205.1. To a stirred mixture of 4-aminopyridine-2-carbonitrile (240 mg, 2 mmol, 1 eq) and 4-dimethylaminopyridine (25 mg, 0.2 mmol, 0.1 eq) in pyridine (5 mL) was added methanesulfonyl chloride (692 mg, 6 mmol, 3 eq). The resulting mixture was stirred for 16 h at 50° C. The mixture was cooled to room temperature and concentrated under reduced pressure. The residue was purified by reverse phase flash chromatography with the following conditions: Column, C18 Column; Mobile Phase, water (0.1% FA) and ACN (5% ACN up to 30% in 15 min); UV detection at 254/220 nm. The product-containing fractions were combined and concentrated under reduced pressure to obtain N-(2-cyanopyridin-4-yl) methanesulfonamide (205.1, 226 mg, 56%) as a yellow solid. MS (ES): m/z 198 [M+H]$^+$.

Synthesis of 205.2. A solution of 205.1 (226 mg, 1.15 mmol, 1 eq) in ammonia methanol solution (7N, 25 mL) was degassed three times with nitrogen. To the solution was added palladium on carbon (10% w/w, 30 mg) and the reaction mixture was degassed between nitrogen and hydrogen atmosphere. The mixture was stirred 1.5 h at room temperature under an atmosphere of hydrogen. The solid was filtered out and the solution was concentrated under reduced pressure to obtain crude product N-[2-(aminomethyl) pyridin-4-yl] methanesulfonamide (205.2, 210 mg, 91%) as a green solid. MS (ES): m/z 202 [M+H]$^+$.

Synthesis of (Z-9). To a mixture of 205.2 (50 mg, 0.25 mmol, 1 eq) and 15.7 (61 mg, 0.25 mmol, 1 eq) in pyridine (3 mL) was added 1-ethyl-3-(3-dimethylamino propyl) carbodiimide hydrochloride (96 mg, 0.5 mmol, 2 eq). The resulting solution was stirred for 1 h at 80° C. The mixture was cooled to room temperature, diluted with water and extracted with ethyl acetate. The combined organic layer was washed with brine, dried over sodium sulfate and concentrated under reduced pressure. The residue was purified by Prep-HPLC with the following conditions: Column XBridge Shield RP18 OBD Column, 30*150 mm, 5 um; Mobile Phase, water (10 mmol/L NH$_4$HCO$_3$+0.1% NH$_3$·H$_2$O) and ACN (34% ACN up to 50% in 7 min); UV detection at 254/210 nm. The product-containing fractions were combined, evaporated partially in vacuum and then lyophilized overnight to afford 5-(6-ethoxypyrazin-2-yl)-N-[(4-methanesulfonamidopyridin-2-yl) methyl]pyridine-2-carboxamide ((Z-9), 15 mg, 14%) as a white solid. MS (ES): m/z 429 [M+H]$^+$; NMR (400 MHz, d$_6$-DMSO) δ 9.47 (t, J=5.6 Hz, 1H), 9.41 (d, J=2.0 Hz, 1H), 9.01 (s, 1H), 8.71 (dd, J=8.0, 2.0 Hz, 1H), 8.38 (s, 1H), 8.27-8.16 (m, 2H), 6.97 (d, J=3.6 Hz, 2H), 4.60-4.49 (m, 4H), 3.03 (s, 3H), 1.41 (t, J=10.2 Hz, 3H).

Example 206: Synthesis of N-((2-(azetidine-1-sulfonamido)pyrimidin-4-yl)methyl)-5-(6-ethoxypyrazin-2-yl)picolinamide (I-82)

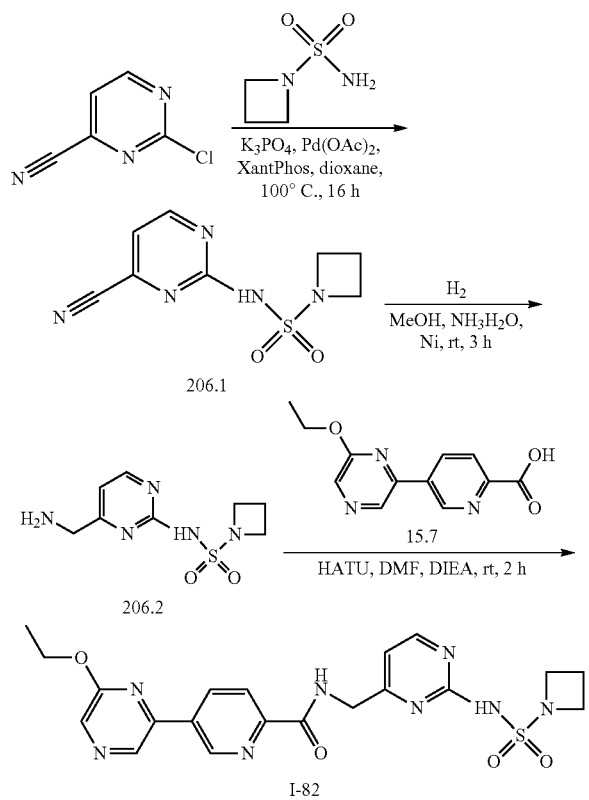

Synthesis of 206.1. To a stirred solution of 2-chloropyrimidine-4-carbonitrile (100 mg, 0.71 mmol, 1 eq) and azetidine-1-sulfonamide (117 mg, 0.86 mmol, 1.2 eq) in 1,4-dioxane (4 mL) was added potassium phosphate (456 mg, 2.15 mmol, 3 eq), Pd(AcO)$_2$ (16 mg, 0.07 mmol, 0.1 eq) and XantPhos (83 mg, 0.14 mmol, 0.2 eq). The resulting solution was degassed three times with nitrogen and stirred for 16 h at 100° C. The mixture was cooled to room temperature, concentrated under reduced pressure and purified by reverse phase flash chromatography with the following conditions: C18 Column; Mobile Phase, water (0.1% FA) and ACN (10% up to 50% in 20 min); UV detection at 254/220 nm. The product-containing fractions were combined and concentrated under reduced pressure to obtain N-(4-cyanopyrimidin-2-yl)azetidine-1-sulfonamide (206.1, 100 mg, 58%) as a white solid. MS (ES): m/z 240 [M+H]$^+$.

Synthesis of 206.2. A solution of 206.1 (100 mg, 0.41 mmol, 1.0 eq) in ammonia methanol solution (7N, 10 mL) was degassed three times with nitrogen. To the solution was added Raney Nickel (7 mg), followed by degassing with nitrogen and then hydrogen. The mixture was stirred for 3 h at room temperature under an atmosphere of hydrogen. The solids were filtered out and the filtrate was concentrated under reduced pressure to obtain N-[4-(aminomethyl)pyrimidin-2-yl]azetidine-1-sulfonamide 206.2, 70 mg, 68%) as a white solid. MS (ES): m/z 244 [M+H]$^+$.

Synthesis of I-82. To a stirred solution of 206.2 (60 mg, 0.24 mmol, 1 eq) and 15.7 (90.7 mg, 0.37 mmol, 1.5 eq) in N,N-dimethylformamide (3.0 mL) was added N, N-diisopropylethylamine (159 mg, 1.23 mmol, 5 eq) and 2-(-7-azabenzotriazol-1-yl)-N, N, N', N'-tetramethyluronium hexafluorophosphate (103 mg, 0.27 mmol, 1.1 eq). The resulting solution was stirred for 2 h at room temperature. The residue was purified by reverse phase flash chromatography with the following conditions: Column, C18 Column; Mobile Phase, water (0.1% FA) and ACN (10% up to 70% in 20 min); UV detection at 254/220 nm. The product-containing fractions were combined and concentrated under reduced pressure. The residue was purified by Prep-HPLC with the following conditions: Column, Sunfire prep C18 column, 30*150 mm, 5 um; Mobile Phase, water (0.1% FA) and ACN (36% ACN up to 43% in 7 min); UV detection at 254/220 nm. The product-containing fractions were combined and evaporated partially in vacuum and then lyophilized overnight to afford N-([2-[(azetidine-1-sulfonyl)amino]pyrimidin-4-yl]methyl)-5-(6-ethoxypyrazin-2-yl)pyridine-2-carboxamide (I-82, 4.5 mg, 3.9%) as a white solid. MS (ES): m/z 471 [M+H]$^+$; $^1$H NMR (400 MHz, d$_6$-DMSO) δ 9.52 (s, 1H), 9.40 (d, J=2.2 Hz, 1H), 9.01 (s, 1H), 8.71-8.65 (m, 1H), 8.51 (d, J=5.4 Hz, 1H), 8.38 (s, 1H), 8.20 (d, J=8.2 Hz, 1H), 6.99 (s, 1H), 4.59-4.45 (m, 4H), 4.09-4.00 (m, 4H), 2.13-1.99 (m, 2H), 1.43 (t, J=7.2 Hz, 3H).

Example 207: Synthesis of N-[(4-cyclopropanesulfonamidopyridin-2-yl)methyl]-5-[(3S)-3-ethylpyrrolidin-1-yl]-6-methylpyrazine-2-carboxamide (I-81)

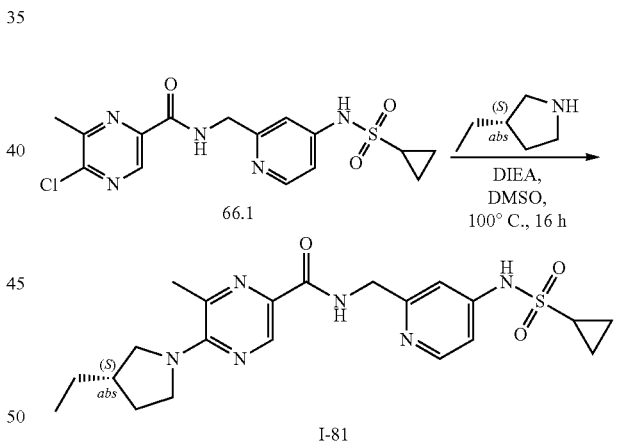

Synthesis of I-81. To a stirred mixture of 66.1 (57 mg, 0.15 mmol, 1 eq) and (3S)-3-ethylpyrrolidin-1-amine (20 mg, 0.18 mmol, 1.2 eq) in dimethylsulfoxide (1 mL) was added diisopropylethylamine (58 mg, 0.45 mmol, 3 eq). The resulting mixture was stirred for 16 mh at 100° C. The resulting mixture was concentrated under reduced pressure. The residue was purified by Prep-HPLC with the following conditions: Column: YMC-Actus Triart C18 30*250.5 um; Mobile Phase, water (0.1% FA) and ACN (18% ACN up to 38% in 7 min); UV detection at 254/210 nm. The product-containing fractions were combined and evaporated partially in vacuum and then lyophilized overnight to afford N-[(4-cyclopropanesulfonamidopyridin-2-yl)methyl]-5-[(3S)-3-ethylpyrrolidin-1-yl]-6-methylpyrazine-2-carboxamide (I-81.17 mg, 23%) as off-white solid. MS (ES): m/z 445

[M+H]⁺; ¹H NMR (300 MHz, Methanol-d₄) δ 8.52 (s, 1H), 8.20 (d, J=6.1 Hz, 1H), 7.19 (d, J=2.3 Hz, 1H), 7.15-7.10 (m, 1H), 4.63 (s, 2H), 3.95-3.68 (m, 3H), 3.42-3.33 (m, 1H), 2.71 (s, 3H), 2.70-2.63 (m, 1H), 2.30-2.08 (m, 2H), 1.72-1.45 (m, 3H), 1.19-0.90 (m, 7H).

Example 208: Synthesis of N-[(4-cyclopropanesulfonamidopyridin-2-yl)methyl]-6-(dimethylamino)-5-(2-methylpropoxy)pyrazine-2-carboxamide (Z-10)

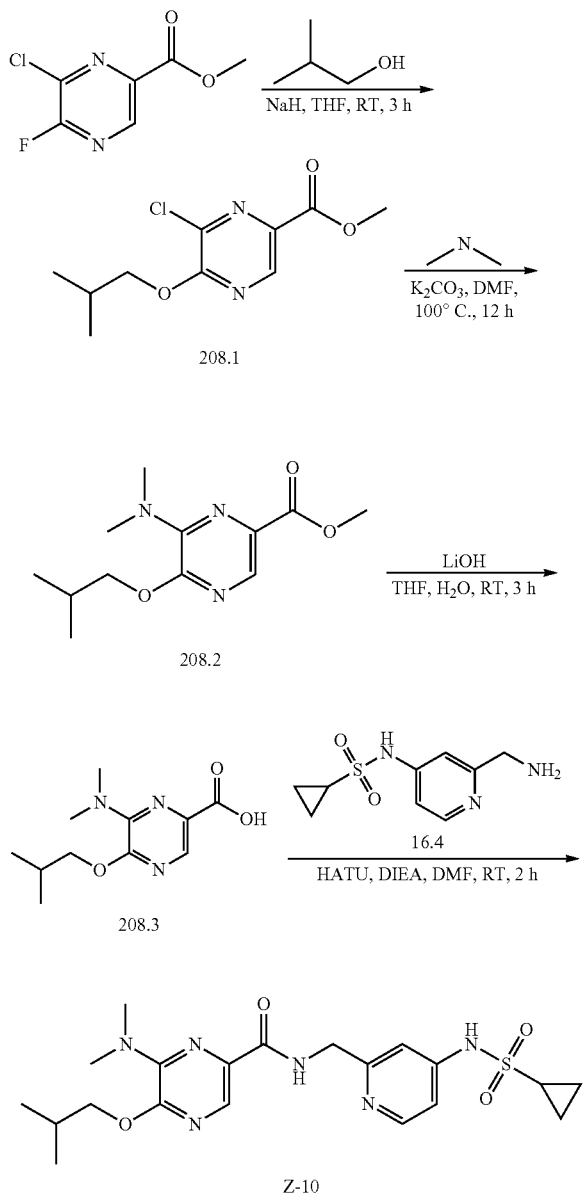

Synthesis of 208.1. A solution of isobutanol (155 mg, 2 mmol, 1 eq) in tetrahydrofuran (10 mL) was degassed three times with nitrogen and cooled to 0° C. To the solution was added sodium hydride (60% w/w in mineral oil, 96 mg, 2.4 mmol, 1.2 eq) at 0° C. and the reaction mixture was stirred for 0.5 h at 0° C. under nitrogen atmosphere. To the above mixture was added methyl 6-chloro-5-fluoropyrazine-2-carboxylate (380 mg, 2 mmol, 1 eq) at 0° C. The resulting mixture was stirred for additional 3 h at room temperature under nitrogen atmosphere. The reaction was quenched with saturated aqueous ammonium chloride, then extracted with ethyl acetate. The combined organic layers were washed with water, dried over anhydrous sodium sulfate. After filtration, the filtrate was concentrated under reduced pressure and purified by Prep-TLC (petroleum ether/ethyl acetate=7:1) to obtain methyl 6-chloro-5-(2-methylpropoxy) pyrazine-2-carboxylate (208.1, 80 mg, 16%) as a yellow liquid. MS (ES): m/z 245 [M+H]⁺.

Synthesis of 208.2. To a solution of 208.1 (70 mg, 0.3 mmol, 1 eq) in N,N-dimethylformamide (5 mL) was added potassium carbonate (118 mg, 0.9 mmol, 3 eq) and dimethylamine (26 mg, 0.6 mmol, 2 eq) at 0° C. The resulting solution was stirred for 12 h at 100° C. The mixture was diluted with water and extracted with ethyl acetate. The combined organic layer was washed with brine, dried over sodium sulfate and concentrated under reduced pressure. The residue was purified by Prep-TLC (petroleum ether/ethyl acetate=5:1) to afford methyl 6-(dimethylamino)-5-(2-methylpropoxy)pyrazine-2-carboxylate (208.2, 25 mg, 35%) as a yellow liquid. MS (ES): m/z 254 [M+H]⁺.

Synthesis of 208.3 To a solution of 208.2 (70 mg, 0.3 mmol, 1 eq) in tetrahydrofuran (4 mL) and water (1 mL) was added lithium hydroxide (11 mg, 0.45 mmol, 1.5 eq). The resulting solution was stirred for 3 h at room temperature. The mixture was diluted with water. The pH value of the solution was adjusted to 3 with 1N aqueous hydrochloric acid. The mixture was extracted with ethyl acetate. The combined organic layer was washed with brine, dried over sodium sulfate and concentrated under reduced pressure. The residue was purified by Prep-TLC (petroleum ether/ethyl acetate=1:1) to afford 6-(dimethylamino)-5-(2-methylpropoxy) pyrazine-2-carboxylic acid (208.3, 40 mg, 61%) as a yellow solid. MS (ES): m/z 240 [M+H]⁺.

Synthesis of Z-10. To a solution of 208.3 (30 mg, 0.1 mmol, 1 eq) and 16.4 (57 mg, 0.3 mmol, 2 eq) in N,N-dimethylformamide (2 mL) was added N,N-diisopropylethylamine (49 mg, 0.4 mmol, 3 eq) and 2-(-7-azabenzotriazol-1-yl)-N,N,N',N'-tetramethyluronium hexafluorophosphate (48 mg, 0.1 mmol, 1 eq) at room temperature. The reaction mixture was stirred for 2 h at room temperature. The mixture was diluted with water and extracted with ethyl acetate. The combined organic layer was washed with brine, dried over sodium sulfate and concentrated under reduced pressure. The residue was purified by Prep-HPLC with the following conditions: Column: Xselect CSH OBD Column 30*150 mm 5 um, 10 nm; Mobile Phase water (0.1% FA) and ACN (20% ACN up to 40% in 10 min); UV detection at 254/210 nm. The product-containing fractions were combined, evaporated partially in vacuum and then lyophilized overnight to afford N-[(4-cyclopropanesulfonamidopyridin-2-yl) methyl]-6-(dimethylamino)-5-(2-methylpropoxy)pyrazine-2-carboxamide (Z-10, 4.2 mg, 7%) as a white solid. MS (ES): m/z 449 [M+H]⁺; ¹H NMR (400 MHz, CD₃OD) δ 8.21 (d, J=6.1 Hz, 1H), 8.10 (s, 1H), 7.20 (d, J=1.6 Hz, 1H), 7.17-7.11 (m, 1H), 4.65 (s, 2H), 4.22 (d, J=6.5 Hz, 2H), 3.24 (s, 6H), 2.75-2.66 (m, 1H), 2.23-2.12 (m, 1H), 1.16-1.04 (m, 8H), 1.02-0.96 (m, 2H).

Example 209: Synthesis of N-[3-[(2R)-1-[1-(6-ethoxypyrazin-2-yl)pyrazole-3-carbonyl]pyrrolidin-2-yl]phenyl]-1,1-difluoromethanesulfonamide (I-79)

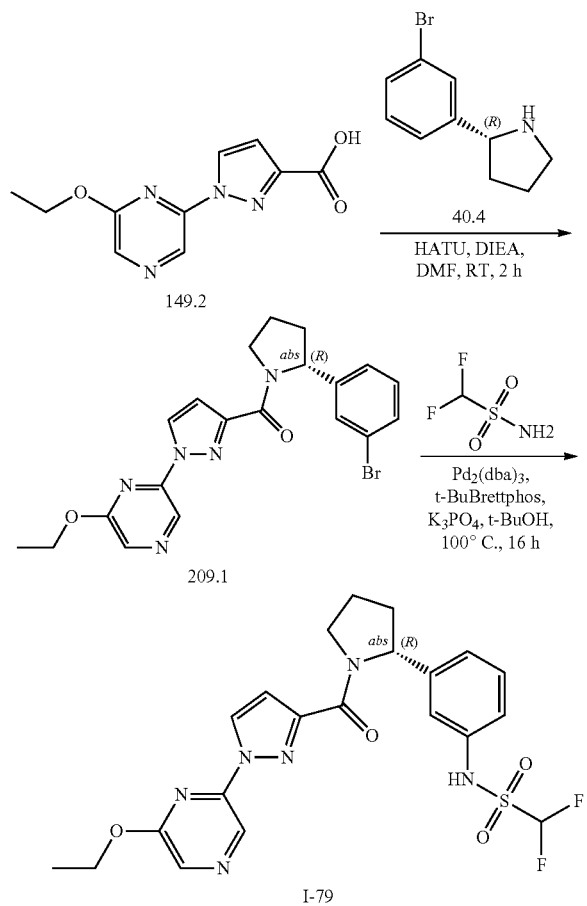

Synthesis of 209.1. To a stirred mixture of 149.2 (80 mg, 0.34 mmol, 1 eq) and 40.4 (62 mg, 0.27 mmol, 0.8 eq) in N,N-dimethylformamide (3 mL) were added N,N-diisopropylethylamine (132 mg, 1.02 mmol, 3 eq) and 2-(-7-azabenzotriazol-1-yl)-N,N,N',N'-tetramethyluronium hexafluorophosphate (143 mg, 0.37 mmol, 1.1 eq). The resulting mixture was stirred for 2 h at room temperature. The mixture was purified by reverse flash chromatography with the following conditions: column C18 silica gel; mobile phase, ACN in water, 10% to 50% gradient in 25 min; detector, UV 254 nm. The mixture was concentrated under vacuum to obtain 2-[3-[(2R)-2-(3-bromophenyl)pyrrolidine-1-carbonyl]pyrazol-1-yl]-6-ethoxypyrazine (209.1, 83 mg, 55%) as a white solid. MS (ES): m/z 442/444 [M+H]+.

Synthesis of I-79. To a stirred mixture of 209.1 (50 mg, 0.11 mmol, 1 eq), difluoromethanesulfonamide (44 mg, 0.33 mmol, 3 eq) and potassium phosphate (72 mg, 0.33 mmol, 3 eq) in tert-butyl alcohol (3 mL) was added Pd$_2$(dba)$_3$ (10 mg, 0.01 mmol, 0.1 eq) and t-BuBrettphos (12 mg, 0.02 mmol, 0.2 eq). The resulting solution was degassed three times with nitrogen and stirred for 16 h at 100° C. The mixture was cooled to room temperature, concentrated under reduced pressure and purified by Prep-HPLC with the following conditions: Sunfire prep C18 column, 30*150, 5 um; Mobile Phase: water (0.1% FA) and ACN (40% ACN up to 70% in 7 min); UV detection at 254/220 nm. The product-containing fractions were combined, evaporated partially in vacuum and then lyophilized overnight to afford N-[3-[(2R)-1-[1-(6-ethoxypyrazin-2-yl)pyrazole-3-carbonyl]pyrrolidin-2-yl]phenyl]-1,1-difluoromethanesulfonamide (I-79, 13 mg, 23%) as a white solid. MS (ES): m/z 493 [M+H]+; $^1$H NMR (400 MHz, CD$_3$OD) δ 8.70 (s, 0.5H), 8.50 (d, J=2.7 Hz, 0.5H), 8.30 (d, J=2.7 Hz, 0.5H), 8.08 (d, J=3.4 Hz, 1H), 7.98 (s, 0.5H), 7.24-7.12 (m, 1H), 7.11-7.06 (m, 0.5H), 7.05-6.96 (m, 2.5H), 6.86 (d, J=2.7 Hz, 0.5H), 6.71 (d, J=2.7 Hz, 0.5H), 6.65-6.30 (m, 1H), 5.87 (dd, J=7.8, 2.1 Hz, 0.5H), 5.24 (dd, J=7.9, 4.1 Hz, 0.5H), 4.47-4.10 (m, 3H), 3.89-3.71 (m, 1H), 2.45-2.26 (m, 1H), 2.06-1.73 (m, 3H), 1.35 (t, J=7.2 Hz, 3H). NMR showed the presence of rotamers.

Example 210: Synthesis of (R)—N-(3-(1-(1-(6-ethoxypyrazin-2-yl)-1H-imidazole-4-carbonyl)pyrrolidin-2-yl)phenyl)-1,1-difluoromethanesulfonamide (I-83)

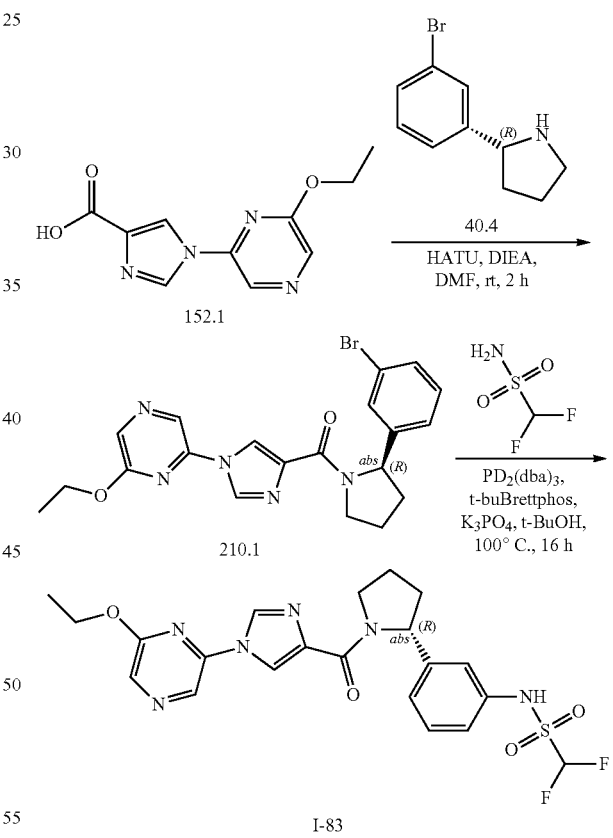

Synthesis of I-83 was synthesized in a manner similar to that described in the synthesis of I-79 using 152.1. Final product purification: Prep-HPLC with the following conditions: Column, SunFire Prep C18 OBD Column, 19*150 mm, 5 um; Mobile Phase, water (0.1% FA) and ACN (35% ACN up to 60% in 7 min); UV detection at 254/220 nm. MS (ES): m/z 493 [M+H]+; $^1$H NMR (400 MHz, CD$_3$OD) δ 8.49 (d, J=8 Hz, 1H), 8.31-8.25 (m, 1.5H), 8.11 (s, 0.5H), 8.04 (s, 0.5H), 7.86 (s, 0.5H), 7.21-6.90 (m, 4H), 6.65-6.38 (m, 1H), 5.88 (d, J=6.4 Hz, 0.5H), 5.21 (d, J=6.4 Hz, 0.5H), 4.43-4.10

(m, 3H), 3.82-3.77 (m, 1H), 2.34-2.31 (m, 1H), 1.94-1.76 (m, 3H), 1.34 (t, J=6.8 Hz, 3H). NMR showed the presence of rotamers.

Example 211: Synthesis of N-(4-[1-[2-(6-ethoxypyrazin-2-yl)-1,3-thiazole-5-carbonyl]pyrrolidin-2-yl]pyrimidin-2-yl)cyclopropanesulfonamide (I-84)

Example 212: Synthesis of N-[4-(1-[5-[6-(trifluoromethyl)pyrazin-2-yl]pyridine-2-carbonyl]pyrrolidin-2-yl)pyrimidin-2-yl]cyclopropanesulfonamide (I-85)

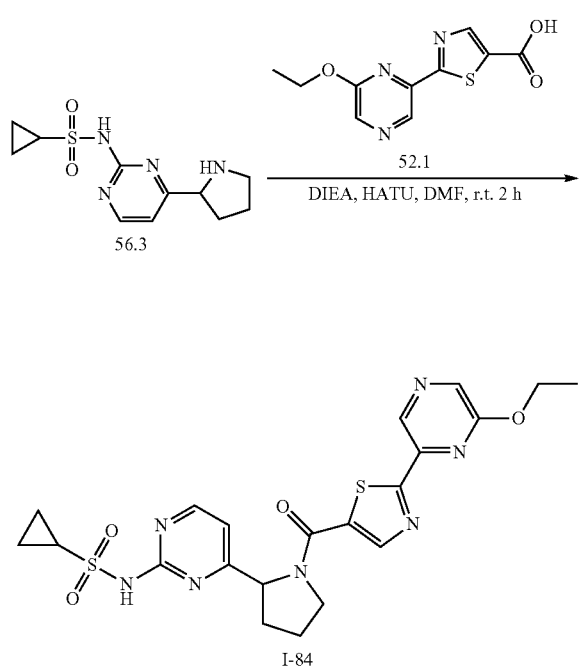

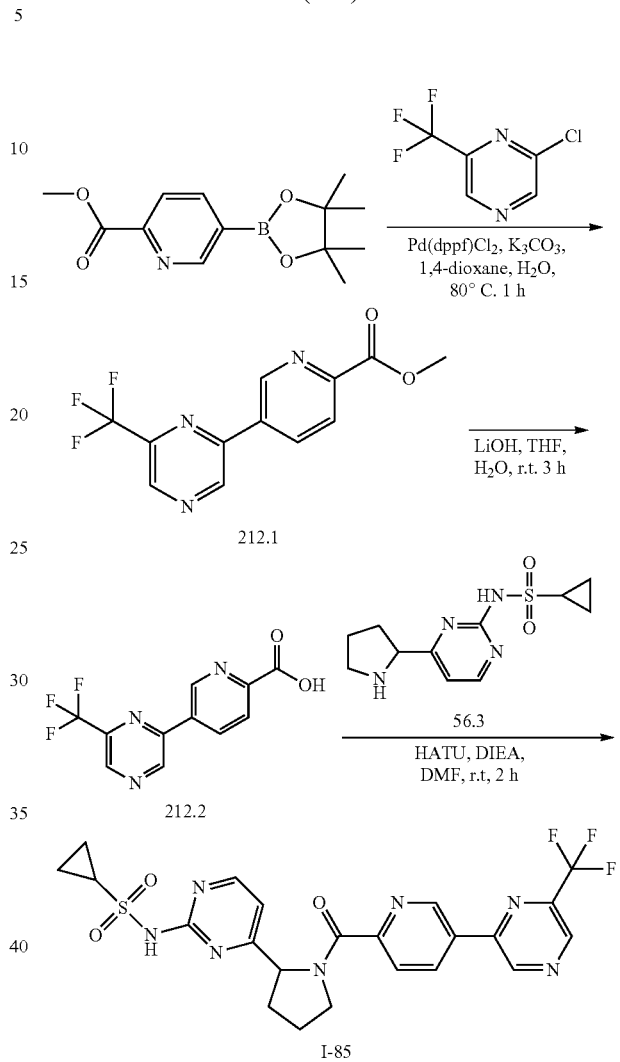

Synthesis of I-84. To a stirred solution of 56.3 (40 mg, 0.15 mmol, 1.0 eq) and 52.1 (37 mg, 0.15 mmol, 1.0 eq) in N,N-dimethylformamide (3 mL) was added N,N-diisopropylethylamine (58 mg, 0.45 mmol, 3.0 eq) and 2-(-7-azabenzotriazol-1-yl)-N,N,N',N'-tetramethyluronium hexafluorophosphate (85 mg, 0.22 mmol, 1.5 eq) at room temperature. The resulting mixture was stirred for 2 h at room temperature. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 30*150 mm, 5 um; Mobile Phase, water (10 mmol/L $NH_4HCO_3$) and ACN (10% ACN up to 30% in 10 min); UV detection at 254/220 nm. The product-containing fractions were combined, evaporated partially in vacuum and then lyophilized overnight to afford N-(4-[1-[2-(6-ethoxypyrazin-2-yl)-1,3-thiazole-5-carbonyl]pyrrolidin-2-yl]pyrimidin-2-yl)cyclopropanesulfonamide (I-84, 8.9 mg, 12%) as a white solid. MS (ES): m/z 502 $[M+H]^+$; $^1H$ NMR (400 MHz, $CD_3OD$) δ 8.80-8.65 (m, 1H), 8.45-8.32 (m, 2H), 8.20-8.15 (m, 1H), 6.99-6.80 (m, 1H), 5.39-5.07 (m, 1H), 4.52-4.29 (m, 2H), 4.19-3.79 (m, 2H), 3.14-2.99 (m, 1H), 2.45-2.30 (m, 1H), 2.23-1.85 (m, 3H), 1.36 (t, J=7.1 Hz, 3H), 1.21-0.99 (m, 2H), 0.99-0.66 (m, 2H).

Synthesis of 212.1. To a stirred solution of methyl 5-(4,4,5,5-tetramethyl-1,3,2-dioxaborolan-2-yl) pyridine-2-carboxylate (500 mg, 1.9 mmol, 1 eq) and 2-chloro-6-(trifluoromethyl) pyrazine (347 mg, 1.9 mmol, 1 eq) in 1,4-dioxane (12 mL) and water (3 mL) were added potassium carbonate (788 mg, 5.7 mmol, 3 eq) and $Pd(dppf)Cl_2$ (278 mg, 0.38 mmol, 0.2 eq) at room temperature. The resulting solution was degassed three times with nitrogen and stirred for 1 h at 80° C. The mixture was diluted with water and extracted with ethyl acetate. The combined organic layer was washed with brine, dried over sodium sulfate and concentrated under reduced pressure. The residue was purified by Prep-TLC (petroleum ether/ethyl acetate=1:1) to afford methyl 5-[6-(trifluoromethyl) pyrazin-2-yl] pyridine-2-carboxylate (212.1, 290 mg, 53%) as a white solid. MS (ES): m/z 284 $[M+H]^+$.

Synthesis of 212.2. A mixture of 212.1 (290 mg, 1.02 mmol, 1 eq) and lithium hydroxide (123 mg, 5.12 mmol, 5 eq) in tetrahydrofuran (8 mL) and water (2 mL) was stirred for 3 h at room temperature. The residue was diluted with water. The pH value of the solution was adjusted to 3 with 1N aqueous hydrochloric acid. The solids were collected by filtration to obtain 5-[6-(trifluoromethyl) pyrazin-2-yl] pyridine-2-carboxylic acid (212.2, 180 mg, 65%) as a white solid. MS (ES): m/z 270 [M+H]+.

Synthesis of I-85. To a stirred mixture of 212.2 (50 mg, 0.18 mmol, 1 eq) and 56.3 (50 mg, 0.18 mmol, 1 eq) in NA-dimethylformamide (3 mL) were added 2-(-7-azabenzotriazol-1-yl)-N,N,N',N'-tetramethyluronium hexafluorophosphate (85 mg, 0.22 mmol, 1.2 eq) and N,N-diisopropylethylamine (72 mg, 0.55 mmol, 3 eq). The resulting mixture was stirred for 2 h at room temperature. The mixture was diluted with water and extracted with ethyl acetate. The combined organic layer was washed with brine, dried over sodium sulfate and concentrated under reduced pressure. The residue was purified by Prep-HPLC with the following conditions: Column, XBridge Shield RP18 OBD Column, 30*150 mm, 5 um; Mobile Phase, water (0.1% FA) and ACN (32% ACN up to 60% in 7 min); UV detection at 254/220 nm. The product-containing fractions were combined, evaporated partially in vacuum and lyophilized overnight to afford N-[4-(1-[5-[6-(trifluoromethyl)pyrazin-2-yl]pyridine-2-carbonyl]pyrrolidin-2-yl)pyrimidin-2-yl]cyclopropanesulfonamide (I-85, 4.8 mg, 4%) as a white solid. MS (ES): m/z 520 [M+H]+; $^1$H NMR (400 MHz, Methanol-$d_4$) δ 9.48 (s, 0.5H), 9.37 (s, 0.5H), 9.30 (d, J=2.2 Hz, 0.5H), 9.06 (d, J=2.2 Hz, 0.5H), 8.99 (d, J=12.6 Hz, 1H), 8.62 (d, J=3.2 Hz, 0.5H), 8.47-8.35 (m, 1H), 8.21 (d, J=5.2 Hz, 0.5H), 7.87 (d, J=8.2 Hz, 0.5H), 7.74 (d, J=8.2 Hz, 0.5H), 7.06 (d, J=5.2 Hz, 0.5H), 6.76 (d, J=5.2 Hz, 0.5H), 5.66 (d, J=3.2 Hz, 0.5H), 5.17 (d, J=3.1 Hz, 0.5H), 4.08-3.92 (m, 1H), 3.89-3.78 (m, 1H), 3.33-3.25 (m, 0.5H), 3.17-3.10 (m, 0.5H), 2.52-2.30 (m, 1H), 2.15-2.02 (m, 0.5H), 2.02-1.25 (m, 2.5H), 1.26-1.15 (m, 1H), 1.15-1.05 (m, 1H), 1.05-0.80 (m, 2H). NMR showed the presence of rotamers.

Example 213: Synthesis of N-[4-[(2R)-1-[4-[6-(trifluoromethyl)pyrazin-2-yl]benzoyl]pyrrolidin-2-yl] pyrimidin-2-yl]cyclopropanesulfonamide, isomer 1 (I-86) and N-[4-[(2S)-1-[4-[6-(trifluoromethyl) pyrazin-2-yl]benzoyl]pyrrolidin-2-yl]pyrimidin-2-yl] cyclopropanesulfonamide, isomer 2 (I-87). Stereochemistry Arbitrarily Assigned

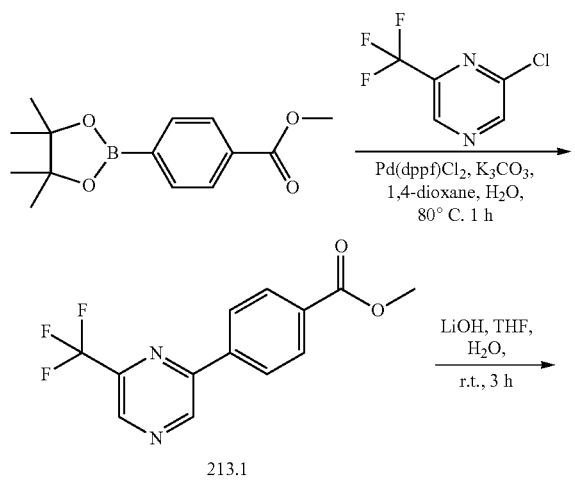

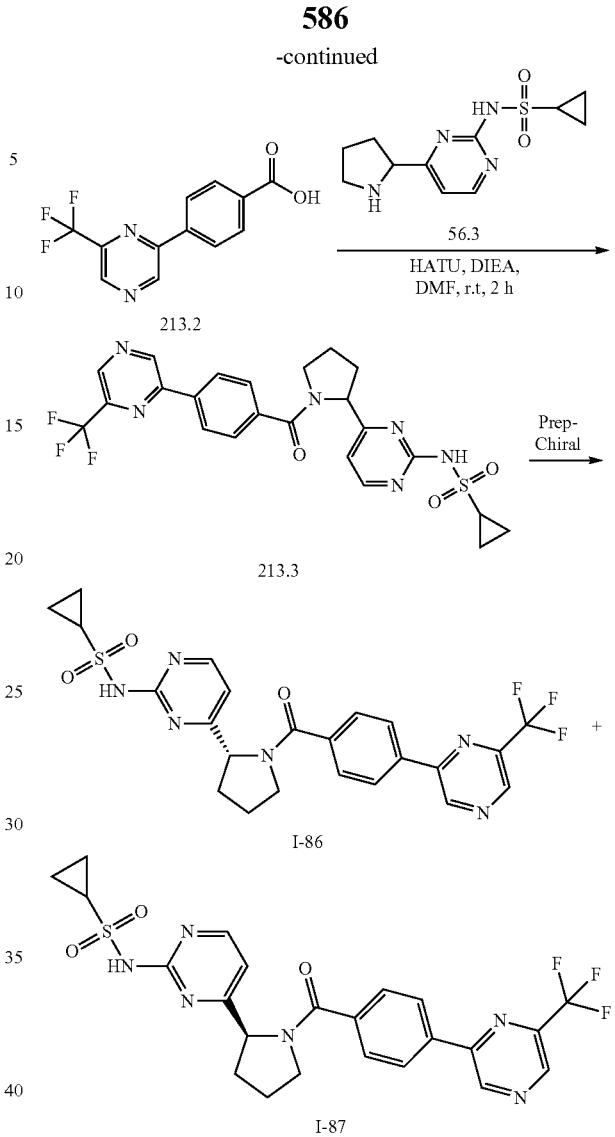

Synthesis of 213.3. 213.3 was synthesized in a manner similar to that described in the synthesis of I-85 using methyl 4-(4,4,5,5-tetramethyl-1,3,2-dioxaborolan-2-yl)benzoate. MS (ES): m/z 519 [M+H]+.

Synthesis of I-86 and I-87. Racemic 213.3 (16 mg) was purified by Chiral-Prep-HPLC with the following conditions: Column: CHIRALPAK ID, 2*25 cm, 5 μm; Mobile Phase A: MTBE (0.1% TFA)—HPLC, Mobile Phase B: IPA-HPLC; Flow rate: 16 mL/min; Gradient: 50% B to 50% B in 18 min; Wave Length: 220/254 nm. The product-containing fractions were combined and concentrated under reduced pressure to afford N-[4-[(2R)-1-[4-[6-(trifluoromethyl)pyrazin-2-yl]benzoyl]pyrrolidin-2-yl]pyrimidin-2-yl]cyclopropanesulfonamide ($1^{st}$ eluting peak, I-86, 3.1 mg, 38%) and N-[4-[(2S)-1-[4-[6-(trifluoromethyl)pyrazin-2-yl]benzoyl]pyrrolidin-2-yl]pyrimidin-2-yl]cyclopropanesulfonamide ($2^{nd}$ eluting peak, I-87, 2.8 mg, 35%) as white solid. I-86: MS (ES): m/z 519 [M+H]+; $^1$H NMR (400 MHz, CD$_3$OD) δ 9.51 (s, 0.5H), 9.41 (s, 0.5H), 9.01 (d, J=15.1 Hz, 1H), 8.49 (d, J=5.4 Hz, 0.5H), 8.33-8.31 (m, 1.5H), 8.22 (d, J=5.1 Hz, 0.5H), 8.13-8.07 (m, 0.5H), 7.89-7.81 (m, 1.5H), 7.44 (d, J=8.4 Hz, 0.5H), 7.11 (d, J=5.0 Hz, 0.5H), 6.58 (d, J=5.0 Hz, 0.5H), 5.23 (d, J=5.6 Hz, 0.5H), 5.05 (d, J=5.6 Hz, 0.5H), 4.02-3.96 (m, 0.5H), 3.96-3.85 (m, 1H), 3.74-3.64

(m, 0.5H), 3.30-3.20 (m, 1H), 2.60-2.45 (m, 1H), 2.25-1.92 (m, 3H), 1.33-1.20 (m, 2H), 1.15-0.86 (m, 2H). NMR showed the presence of rotamers. I-87: MS (ES): m/z 519 [M+H]$^+$; $^1$H NMR (400 MHz, CD$_3$OD) δ 9.41-9.30 (m, 1H), 8.91 (d, J=15.0 Hz, 1H), 8.38 (d, J=5.1 Hz, 0.5H), 8.26-8.19 (m, 1.5H), 8.13 (d, J=5.1 Hz, 0.5H), 7.97 (d, J=5.1 Hz, 0.5H), 7.79-7.71 (m, 1.5H), 7.21 (d, J=8.4 Hz, 0.5H), 7.03 (d, J=5.1 Hz, 0.5H), 6.51 (d, J=5.1 Hz, 0.5H), 5.13 (d, J=5.6 Hz, 0.5H), 4.95 (d, J=3.5 Hz, 0.5H), 3.90-3.70 (m, 1H), 3.68-3.50 (m, 1H), 3.20-3.10 (m, 1H), 2.50-2.35 (m, 1H), 2.15-1.82 (m, 3H), 1.23-1.10 (m, 2H), 1.02-0.80 (m, 2H). NMR showed the presence of rotamers.

Example 214: Synthesis of Example 214: N-[4-[(2R)-1-[4-(6-ethoxypyrazin-2-yl)benzoyl]pyrrolidin-2-yl]pyrimidin-2-yl]cyclopropanesulfonamide, isomer 1 (I-88) and N-[4-[(2S)-1-[4-(6-ethoxypyrazin-2-yl)benzoyl]pyrrolidin-2-yl]pyrimidin-2-yl]cyclopropanesulfonamide, isomer 2 (I-89). Stereochemistry Arbitrarily Assigned

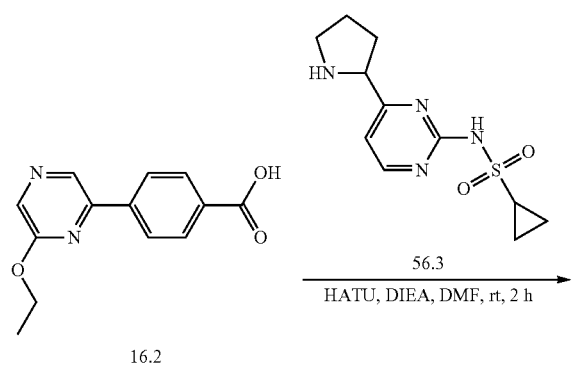

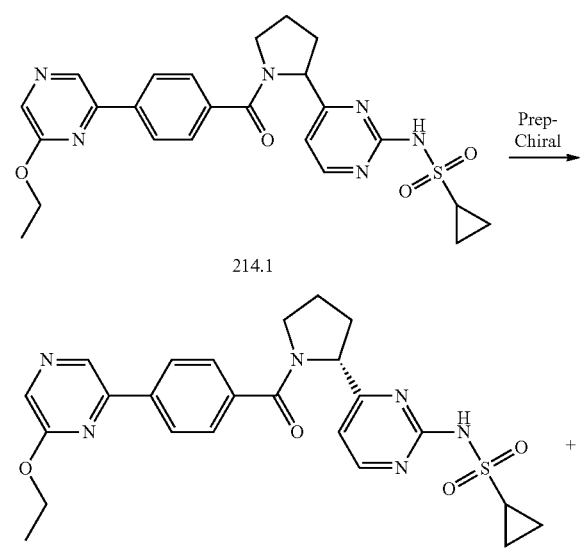

Synthesis of 214.1. To a stirred mixture of 16.2 (27 mg, 0.11 mmol, 1 eq) and 56.3 (29 mg, 0.11 mmol, 1 eq) in N,N-dimethylformamide (2 mL) was added diisopropylethylamine (42 mg, 0.33 mmol, 3 eq) and 2-(-7-azabenzotriazol-1-yl)-N,N,N',N'-tetramethyluronium hexafluorophosphate (50 mg, 0.13 mmol, 1.2 eq). The resulting mixture was stirred for 2 h at room temperature. The mixture was diluted with water and extracted with ethyl acetate. The combined organic layer was washed with brine, dried over sodium sulfate and concentrated under reduced pressure. The residue was purified by Prep-HPLC with the following conditions: Column: YMC-Actus Triart C18 30*250.5 um; Mobile Phase, water (0.1% FA) and ACN (10% ACN up to 30% in 10 min); UV detection at 254/210 nm to afford N-[2-[(2R)-1-[5-(6-ethoxypyrazin-2-yl)pyridine-2-carbonyl]pyrrolidin-2-yl]pyridin-4-yl]cyclopropanesulfonamide (214.1.19 mg, 39%) as a white solid. MS (ES): m/z 495 [M+H]$^+$.

Synthesis of I-88 and I-89. 214.1 (17 mg) was separated by Chiral-Prep-HPLC with the following conditions: Column: CHIRALPAK IH, 2*25 cm, 5 n m: Mobile Phase A: MTBE(0.1% TFA)~HPLC, Mobile Phase B: EtOH-HPLC; Flow rate: 20 mL/min; Gradient: 15% B to 15% B in 13 min; Wave Length: 220/254 nm. The product-containing fractions were combined and concentrated under reduced pressure to afford N-[4-[(2R)-1-[4-(6-ethoxypyrazin-2-yl)benzoyl]pyrrolidin-2-yl]pyrimidin-2-yl]cyclopropanesulfonamide(1$^{st}$ eluting peak, I-88, 1.1 mg, 12%) and N-[4-[(2S)-1-[4-(6-ethoxypyrazin-2-yl)benzoyl]pyrrolidin-2-yl]pyrimidin-2-yl]cyclopropanesulfonamide (2$^{nd}$ eluting peak, I-89, 1.3 mg, 13%) as a white solid. I-88: MS (ES): m/z 495 [M+H]$^+$; $^1$H NMR (400 MHz, Methanol-d$_4$) δ 8.67 (d, J=39.6 Hz, 1H), 8.48 (d, J=5.2 Hz, 0.5H), 8.27-8.20 (m, 1.5H), 8.15 (d, J=15.3 Hz, 1H), 8.04-7.98 (m, 0.5H), 7.78 (d, J=8.4 Hz, 1.5H), 7.38 (d, J=8.4 Hz, 0.5H), 7.10 (d, J=5.2 Hz, 0.5H), 6.58 (d, J=5.1 Hz, 0.5H), 5.25-5.20 (m, 0.5H), 5.07-5.00 (m, 0.5H), 4.67-4.51 (m, 2H), 4.05-3.95 (m, 0.5H), 3.95-3.83 (m, 1H), 3.78-3.68 (m, 0.5H), 3.31-3.20 (m, 1H), 2.60-2.45 (m, 1H), 2.25-2.14 (m, 1H), 2.11-1.95 (m, 2H), 1.55-1.44 (m, 3H), 1.36-1.23 (m, 2H), 1.11-0.87 (m, 2H). NMR showed the presence of rotamers. I-89: MS (ES): m/z 495 [M+H]$^+$; $^1$H NMR (400 MHz, Methanol-d$_4$) δ 8.73 (s, 0.5H), 8.61 (s, 0.5H), 8.49 (d, J=5.2 Hz, 0.5H), 8.27-8.10 (m, 2.5H), 8.04-7.98 (m, 0.5H), 7.79 (d, J=8.4 Hz, 1.5H), 7.38 (d, J=8.4 Hz, 0.5H), 7.10 (d, J=5.2 Hz, 0.5H), 6.58 (d, J=5.1 Hz, 0.5H), 5.25-5.20 (m, 0.5H), 5.07-5.00 (m, 0.5H), 4.63-4.51 (m, 2H), 4.04-3.83 (m, 1.5H), 3.78-3.68 (m, 0.5H), 3.31-3.20 (m, 1H), 2.60-2.45 (m, 1H), 2.25-2.10 (m, 1H), 2.10-1.90 (m, 2H), 1.55-1.40 (m, 3H), 1.29-1.20 (m, 2H), 1.10-0.88 (m, 2H). NMR showed the presence of rotamers.

Example 215: hCTPS1 Biochemical Assay

The enzyme inhibitory activities of the compounds of the invention against the target of interest were determined using the ADP-Glo™ assay (Promega). Assays for human CTPS1 and CTPS2 were performed in 1× assay buffer containing 50 mM HEPES (Life Technologies), 10 mM $Mg^{2+}$, 5 mM KCl, 2 mM DTT, 0.01% F-127, pH to 7.4 accordingly. All reagents are from Sigma-Aldrich, unless specified otherwise. Purified human full length active N-terminal FLAG-8×HIS-TEV tagged CTPS1 (UniprotKB-P17812, MDYKDDDDKGTHHHHHHHHENLYFQGS-CTPS1 [1-591]) was generated using a mammalian expression system at Viva Biotech (Shanghai) Ltd.

Purified human CTPS1 protein was prepared in 1× assay buffer to the final working protein concentration required for the reaction. A 2.5 uL volume per well of human CTPS1 protein was mixed with 0.1 uL per well of test compound dissolved in DMSO and pre-incubated at 25 degrees C. for 10 minutes. 2.5 uL per well of the reaction precursors ATP (UltraPure ATP from ADP-Glo™ kit) and UTP were then added and pre-incubated for an additional 10 minutes at 25 degrees C. Finally, the reaction was initiated by the addition of 5 uL of the reaction precursors L-glutamine and GTP. The final concentration of all reaction components in the assay: ATP (120 uM), UTP (160 uM), GTP (60 uM), L-Glutamine (100 uM), DMSO (1%), hCTPS1 (25 nM). This mixture was incubated for an appropriate amount of time within the determined linear phase of the reaction at 25 degrees C. under sealed plate conditions with constant agitation at 500 revolutions per minute (rpm). ADP-Glo™ reagent was added for 60 minutes (10 uL per well) and subsequently ADP-Glo™ development reagent was added for 60 minutes (20 uL per well) prior to signal detection in a microplate reader (Envision Multilabel Reader, Perkin Elmer). Following each reagent addition over the course of the assay, assay plates were pulse centrifuged for 1 minute at 1000 rpm.

The enzyme converts ATP to ADP and the ADP-Glo™ reagent subsequently depletes any remaining ATP in the reaction system. The ADP-Glo™ detection reagents converts the ADP that has been produced by the enzyme back into ATP, which is then utilized as a substrate together with luciferin for the enzyme luciferase. Light generated by this chemiluminescent reaction is quantified and is directly proportional to the amount of ADP produced by the CTPS1 enzyme reaction. A reduction in this signal by compound treatment demonstrates enzyme inhibition, and the percentage inhibition produced by each concentration of compound was calculated as: % inhibition=$1-((Mean_{min}-Mean_{inh})/(Mean_{min}-Mean_{max}))\times100$. The data for all compounds tested are presented below in Table 5. A is <100 nM, 100 nm<B<1 µM, C=1 µM or higher.

TABLE 5

| Compound | CTPS1 IC50 | Compound | CTPS1 IC50 | Compound | CTPS1 IC50 | Compound | CTPS1 IC50 |
|---|---|---|---|---|---|---|---|
| I-1 | B | I-22 | A | I-43 | B | I-64 | A |
| I-2 | C | I-23 | A | I-44 | C | I-65 | A |
| I-3 | C | I-24 | A | I-45 | C | I-66 | A |
| I-4 | C | I-25 | A | I-46 | C | I-67 | C |
| I-5 | C | I-26 | A | I-47 | C | I-68 | C |
| I-6 | A | I-27 | B | I-48 | A | I-69 | A |
| I-7 | C | I-28 | C | I-49 | A | I-70 | A |
| I-8 | C | I-29 | A | I-50 | A | I-71 | A |
| I-9 | C | I-30 | A | I-51 | A | I-72 | A |
| I-10 | C | I-31 | C | I-52 | A | I-73 | A |
| I-11 | C | I-32 | A | I-53 | A | I-74 | A |
| I-12 | A | I-33 | A | I-54 | A | I-75 | B |
| I-13 | B | I-34 | A | I-55 | B | I-76 | B |
| I-12a | B | I-35 | A | I-56 | C | I-77 | B |
| I-14 | C | I-36 | A | I-57 | C | I-78 | B |
| I-15 | A | I-37 | A | I-58 | B | I-79 | C |
| I-16 | A | I-38 | A | I-59 | B | I-80 | C |
| I-17 | B | I-39 | A | I-60 | C | I-81 | C |
| I-18 | B | I-40 | A | I-61 | A | I-82 | C |
| I-19 | B | I-41 | B | I-62 | A | Z-7 | A |
| I-20 | C | I-42 | B | I-63 | A | Z-8 | A |
| I-210 | A | I-170 | B | I-114 | A | I-265 | A |
| I-211 | B | I-171 | C | I-115 | A | I-266 | A |
| I-212 | A | I-172 | A | I-116 | A | I-267 | A |
| I-213 | A | I-154 | A | I-117 | A | I-258 | A |
| I-214 | A | I-155 | A | I-118 | A | I-259 | A |
| I-215 | A | I-156 | A | I-119 | A | I-260 | C |
| I-216 | A | I-157 | B | I-120 | A | I-261 | C |
| I-217 | A | I-158 | A | I-121 | A | I-262 | A |
| I-218 | B | I-159 | A | I-122 | A | I-253 | A |
| I-202 | B | I-160 | B | I-105 | A | I-254 | B |
| I-203 | A | I-161 | A | I-106 | A | I-255 | C |
| I-204 | A | I-162 | B | I-107 | A | I-256 | A |
| I-205 | A | I-163 | A | I-108 | A | I-257 | A |
| I-206 | A | I-164 | A | I-109 | A | I-246 | A |
| I-207 | A | I-165 | A | I-110 | A | I-247 | A |
| I-208 | A | I-166 | A | I-111 | A | I-248 | A |
| I-209 | A | I-146 | A | I-99 | A | I-249 | C |
| I-195 | B | I-147 | A | I-100 | A | I-250 | A |
| I-196 | A | I-148 | A | I-101 | A | I-251 | B |
| I-197 | A | I-149 | C | I-102 | A | I-252 | A |
| I-198 | A | I-150 | A | I-103 | A | I-242 | A |
| I-199 | A | I-151 | A | I-104 | A | I-243 | A |
| I-200 | B | I-152 | A | I-90 | A | I-244 | B |
| I-201 | A | I-153 | A | I-91 | B | I-245 | A |
| I-189 | A | I-138 | A | I-92 | A | I-238 | B |

TABLE 5-continued

| Compound | CTPS1 IC50 | Compound | CTPS1 IC50 | Compound | CTPS1 IC50 | Compound | CTPS1 IC50 |
|---|---|---|---|---|---|---|---|
| I-190 | A | I-139 | A | I-93 | A | I-239 | A |
| I-191 | A | I-140 | A | I-94 | A | I-240 | A |
| I-192 | A | I-141 | A | I-95 | A | I-241 | A |
| I-193 | B | I-142 | A | I-96 | A | I-233 | A |
| I-194 | A | I-143 | C | I-97 | A | I-234 | A |
| I-187 | A | I-144 | A | I-282 | A | I-235 | A |
| I-188 | A | I-145 | A | I-285 | B | I-236 | A |
| I-185 | B | I-132 | A | I-286 | A | I-237 | B |
| I-186 | A | I-133 | A | I-277 | A | I-229 | B |
| I-183 | A | I-134 | B | I-278 | A | I-230 | A |
| I-184 | A | I-135 | A | I-279 | A | I-231 | B |
| I-181 | B | I-136 | A | I-280 | C | I-232 | A |
| I-182 | C | I-137 | A | I-282 | C | I-225 | A |
| I-173 | A | I-123 | C | I-283 | A | I-226 | B |
| I-174 | A | I-124 | C | I-272 | A | I-227 | A |
| I-175 | A | I-125 | C | I-273 | A | I-228 | A |
| I-176 | A | I-126 | A | I-274 | A | I-219 | A |
| I-177 | A | I-127 | A | I-275 | C | I-220 | A |
| I-178 | B | I-128 | A | I-276 | A | I-221 | B |
| I-179 | A | I-129 | A | I-269 | A | I-222 | A |
| I-180 | C | I-130 | A | I-270 | B | I-223 | B |
| I-167 | C | I-131 | A | I-271 | A | I-224 | A |
| I-168 | B | I-112 | A | I-263 | C | | |
| I-169 | A | I-113 | A | I-264 | C | | |

We claim:

1. A compound of formula I:

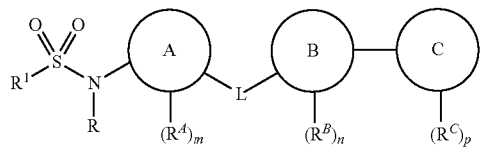

or a pharmaceutically acceptable salt thereof, wherein:

$R^1$ is selected from —$CF_3$, —$CHF_2$,

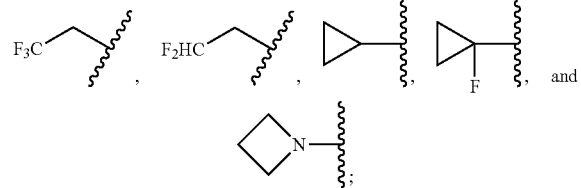

and

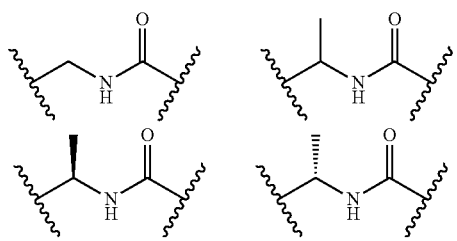

Ring A is a 6-membered monocyclic heteroaryl ring having 1 or 2 nitrogen atoms;

L is

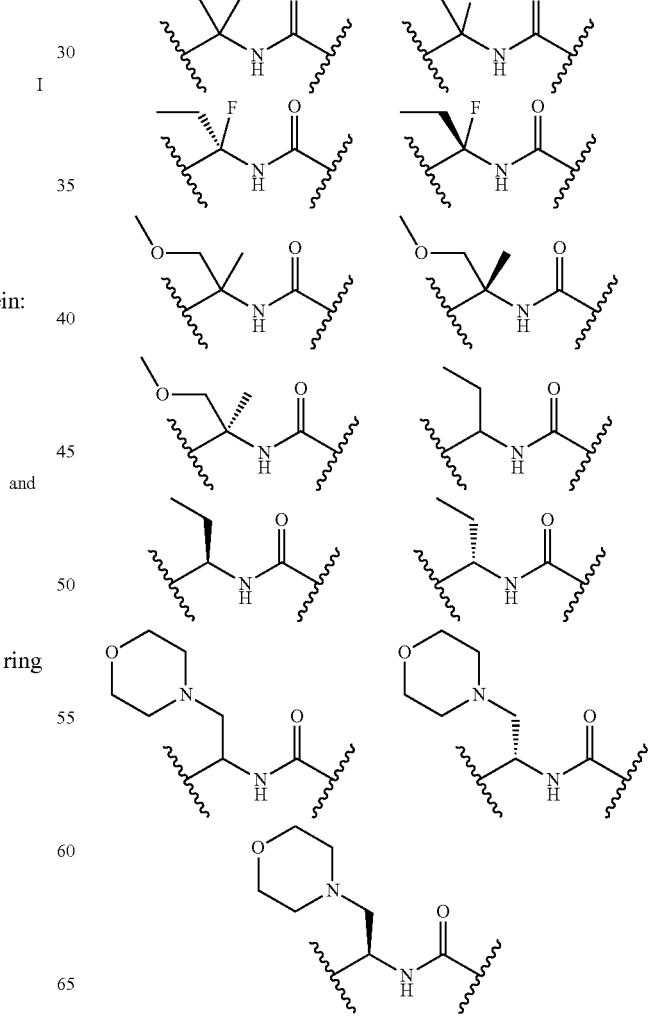

593
-continued
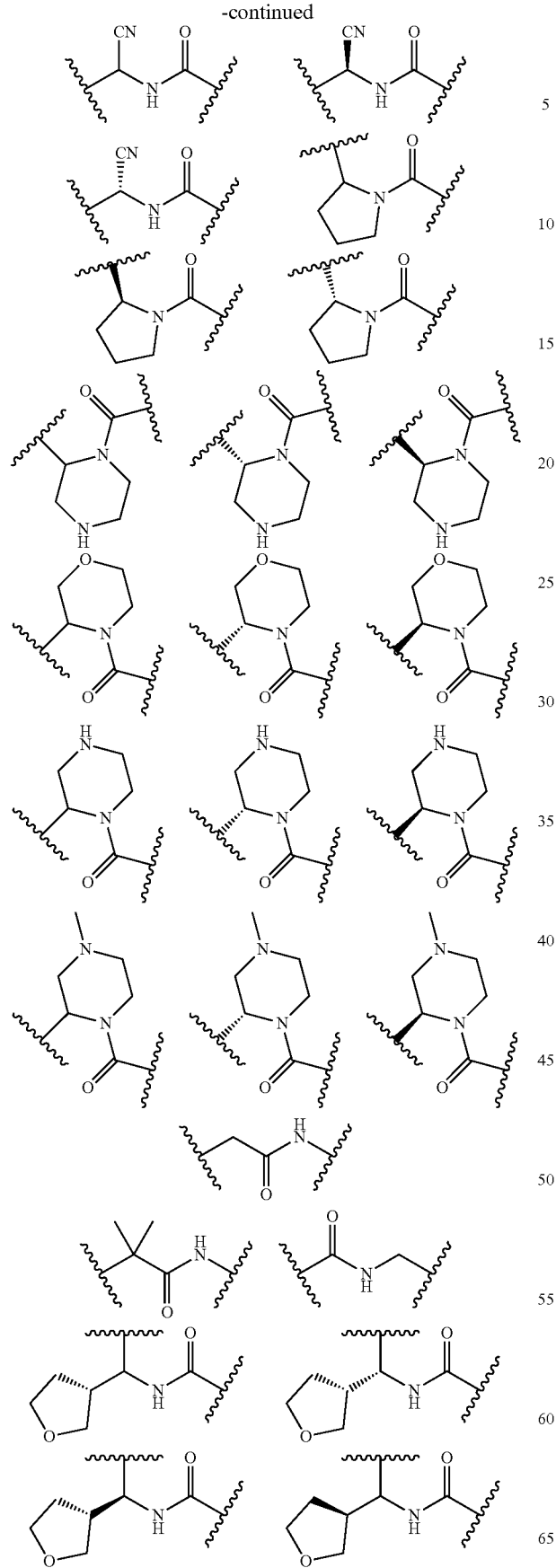
594
-continued
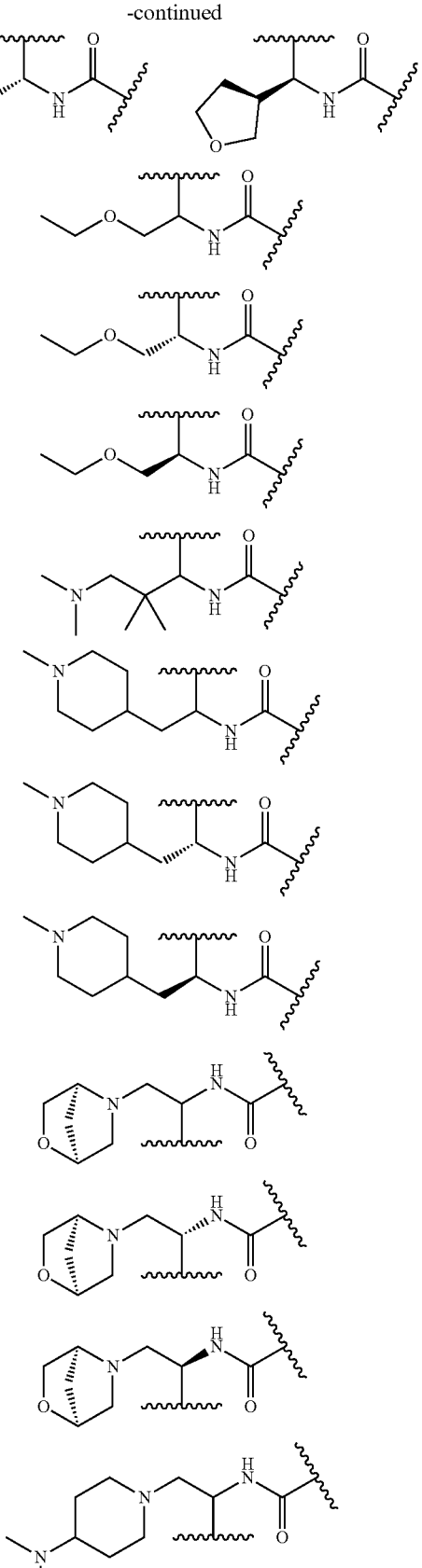

595
-continued
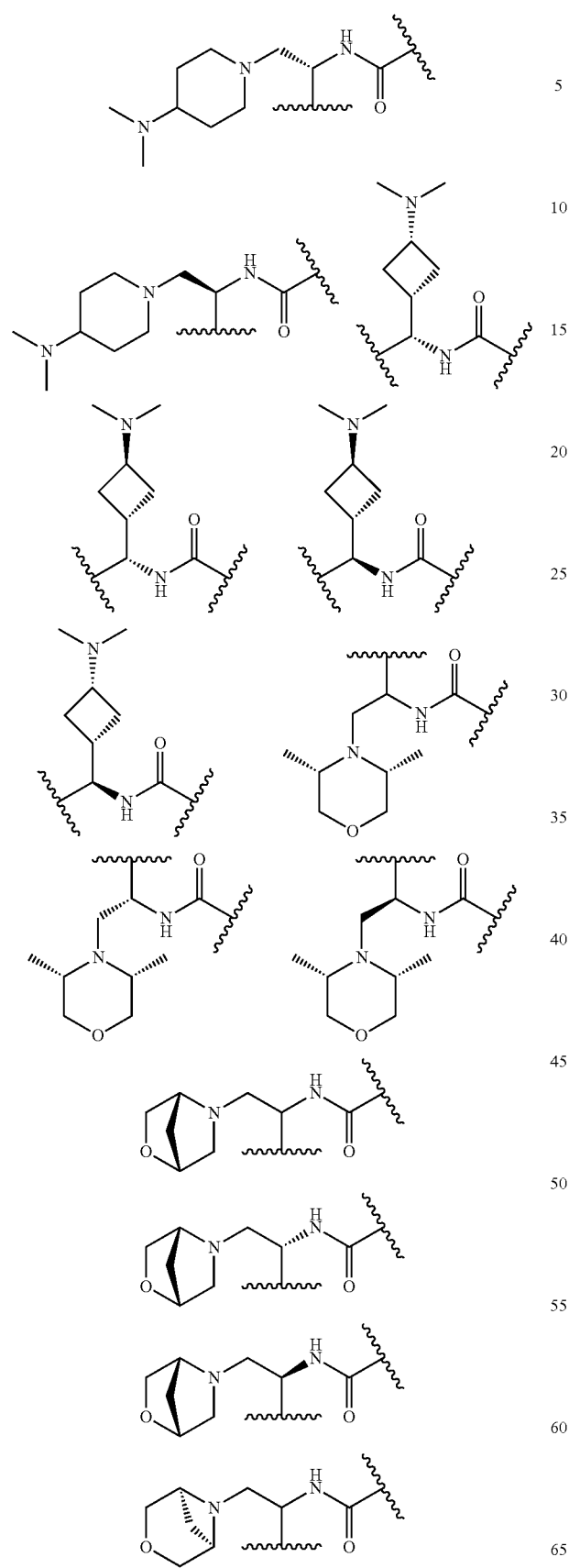
596
-continued
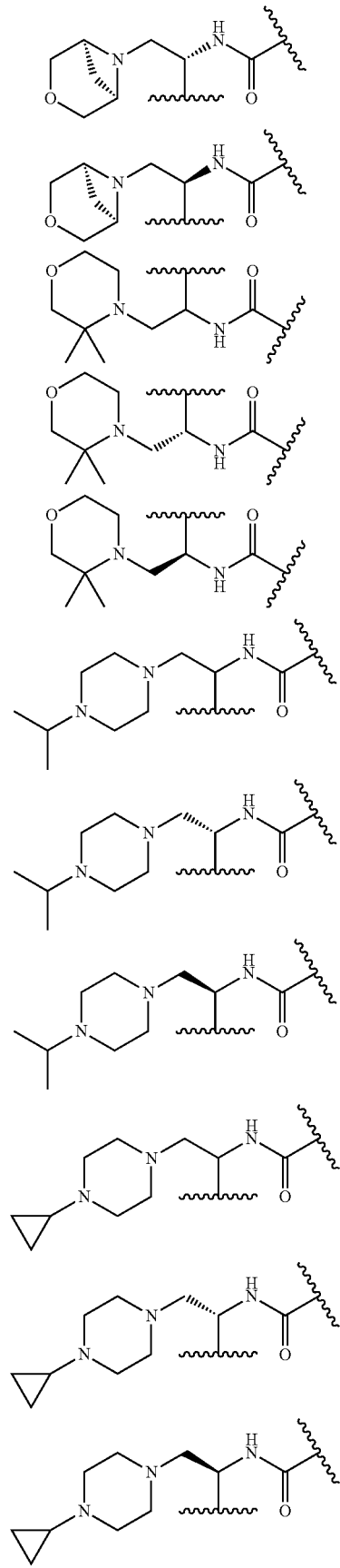

597
-continued
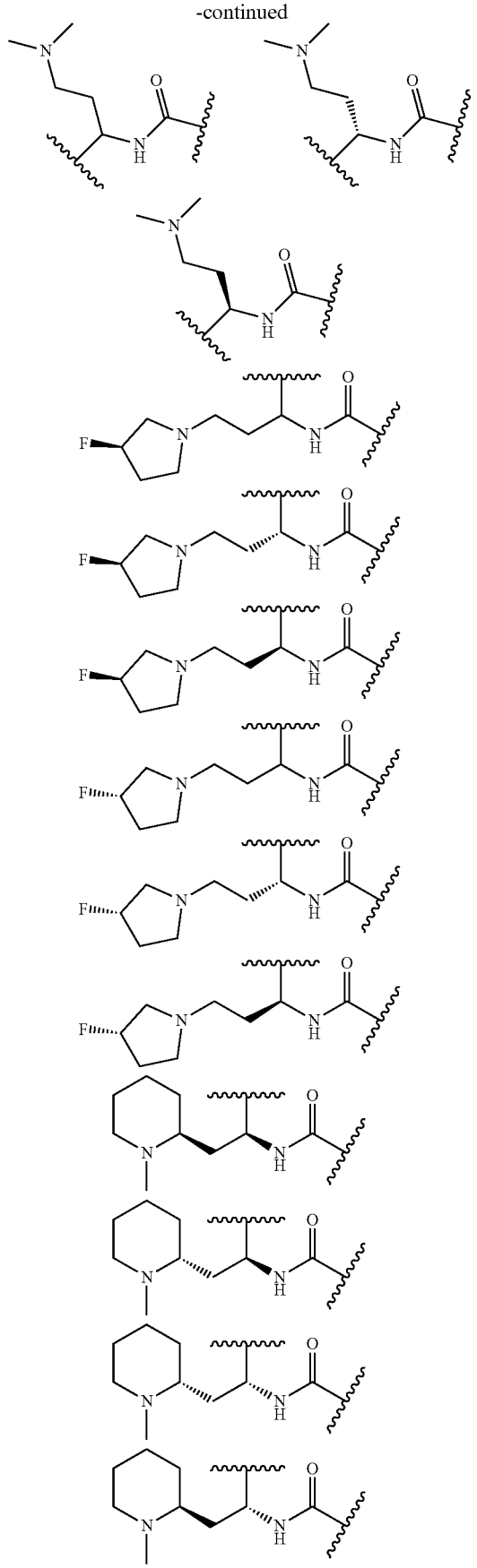
598
-continued
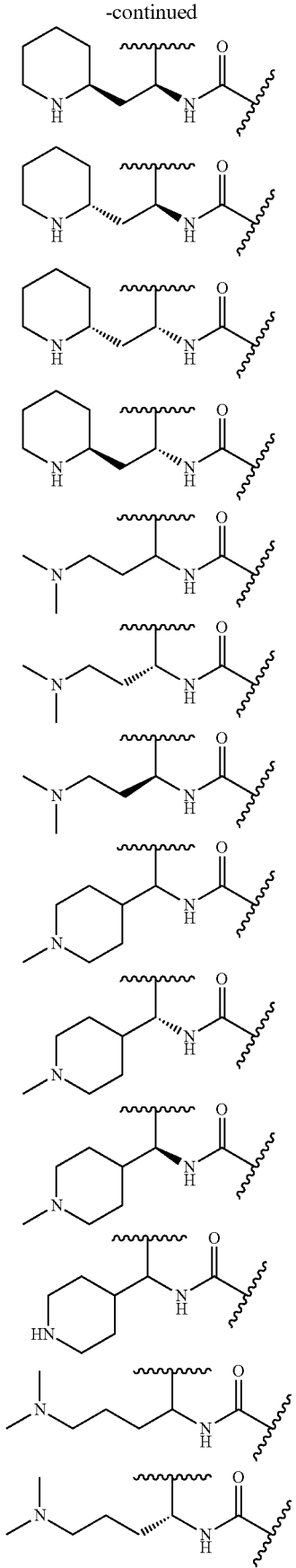

599
-continued
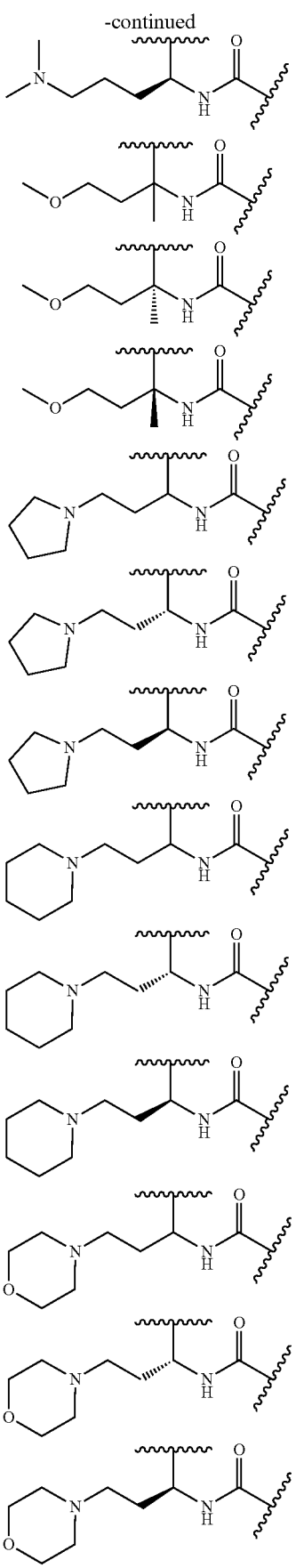
600
-continued
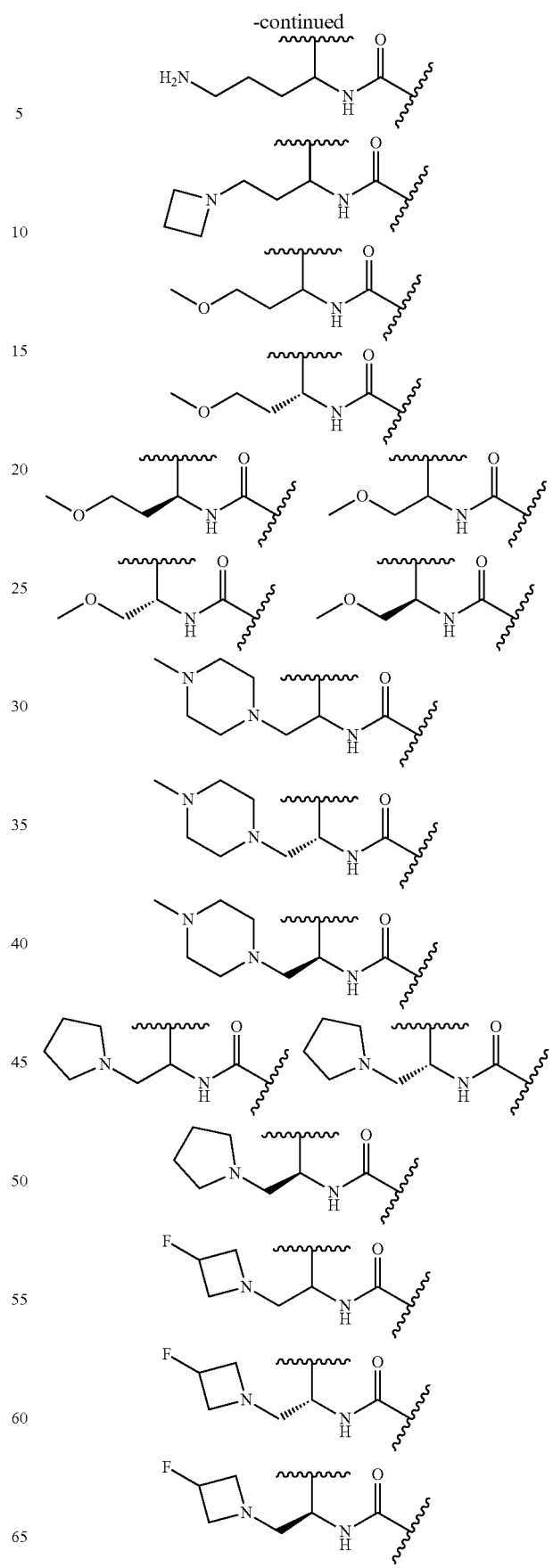

-continued

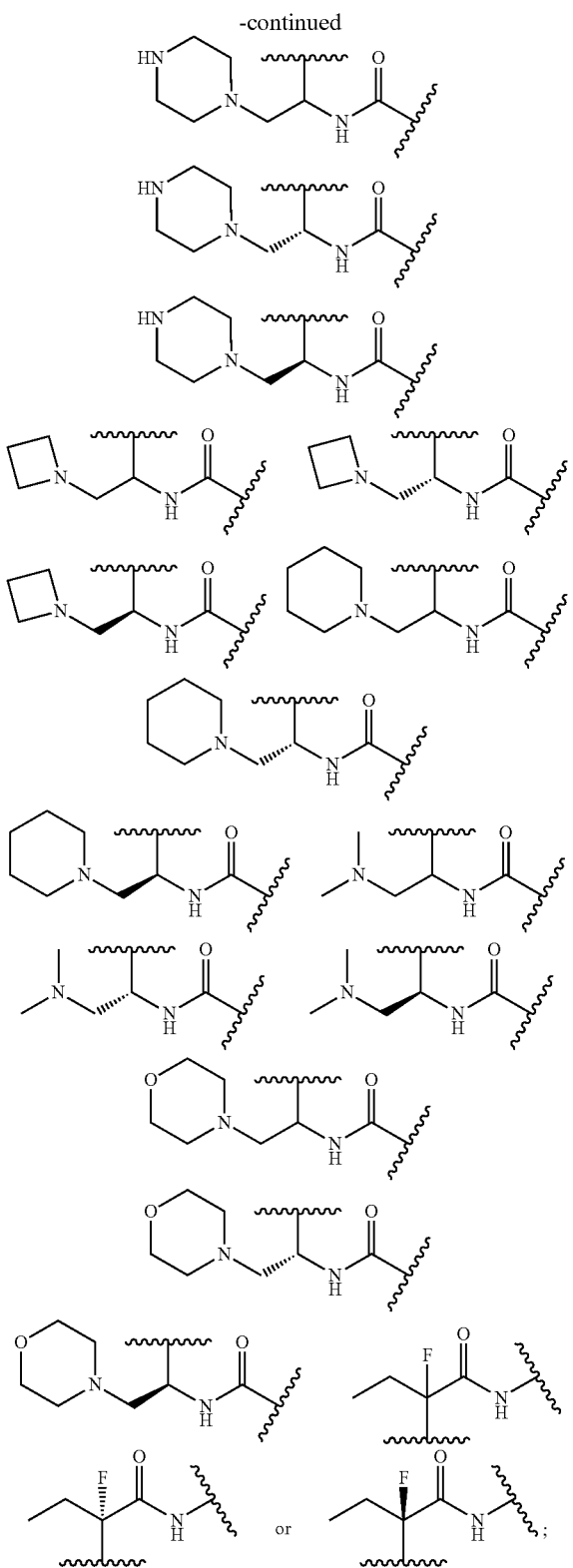

Ring B is selected from phenyl; a 5-6 membered monocyclic heteroaryl ring having 1-4 heteroatoms independently selected from nitrogen, oxygen, and sulfur; a 5-11 membered saturated or partially unsaturated fused, bridged, or spiro, bicyclic carbocyclic ring; a 7-11 membered fused bicyclic aryl ring; a 7-11 membered saturated or partially unsaturated fused, bridged, or spiro, bicyclic heterocyclic ring having 1-4 heteroatoms independently selected from nitrogen, oxygen, and sulfur; and a 7-11 membered fused bicyclic heteroaryl ring having 1-4 heteroatoms independently selected from nitrogen, oxygen, and sulfur;

Ring C is selected from a 6-membered monocyclic heteroaryl ring having 1-4 nitrogen atoms; and a 7-11 membered fused bicyclic heteroaryl ring having 1-4 heteroatoms independently selected from nitrogen, oxygen, and sulfur;

each instance of $R^A$, $R^B$, and $R^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of $R^C$ is independently an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of $R^D$; or two $R^C$ groups are optionally taken together with the atoms to which each $R^C$ is attached, to form an optionally substituted 3-7 membered saturated or partially unsaturated monocyclic carbocyclic ring; a 5-7 membered heteroaryl ring having 1-2 heteroatoms independently selected from nitrogen, oxygen, and sulfur; or a 3-7 membered saturated or partially unsaturated monocyclic heterocyclic ring having 1-2 heteroatoms independently selected from nitrogen, oxygen, and sulfur;

each instance of $R^D$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR, or —P(O)R$_2$;

each R is independently hydrogen, —CN, halogen, or an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or two R groups are taken together with the atoms to which each R is attached, to form an optionally substituted 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur;

m is 0, 1, or 2;
n is 0, 1, or 2;
p is 0, 1, or 2;
each r is independently 0, 1, 2, 3, or 4; and
each s is independently 0, 1, 2, 3, or 4;
provided that when:
$R^1$ is

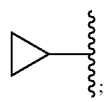 [SMILES: *C1CC1]

the R group of the sulfonamide moiety

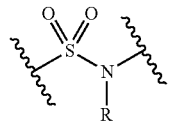

is hydrogen or para-methoxybenzyl;
L is not

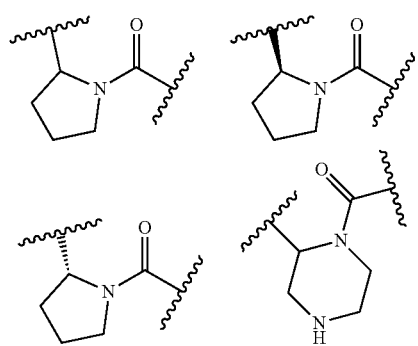

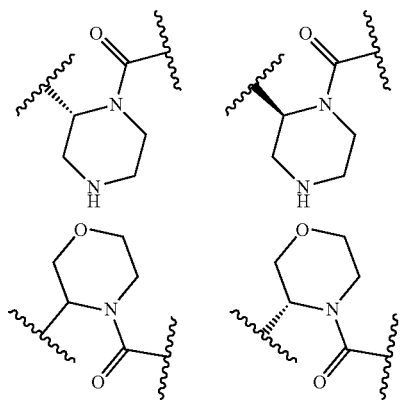

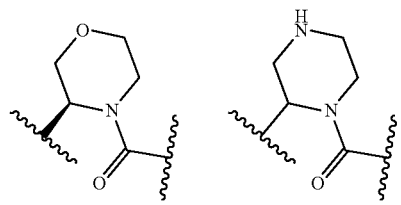

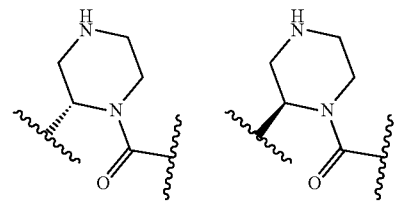

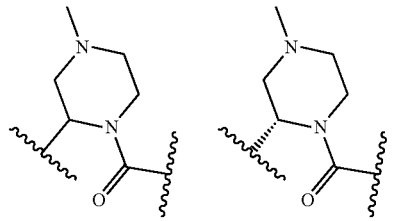

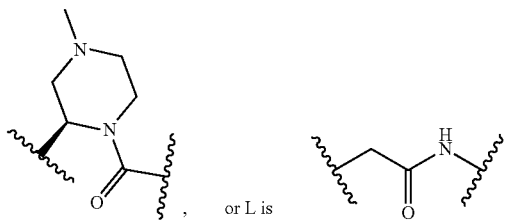, or L is

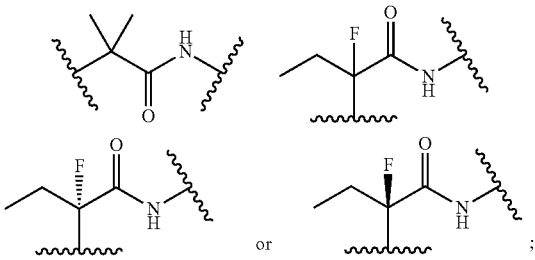

Ring B is phenyl or a 6-membered monocyclic heteroaryl ring having 1-4 heteroatoms independently selected from nitrogen, oxygen, and sulfur; and Ring C is a 6-membered monocyclic heteroaryl ring having 1-4 nitrogen atoms and is attached to Ring B in the para position relative to the L group;

then Ring A and its $R^A$ substituents are other than

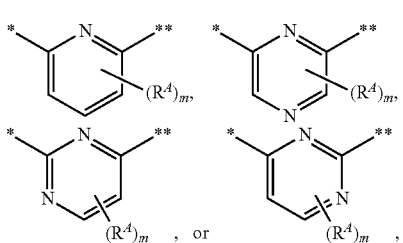

where * denotes attachment to the

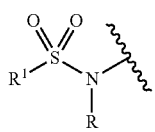

moiety and ** denotes attachment to the

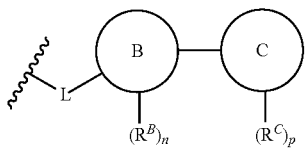

moiety.

2. The compound of claim 1, wherein $R^1$ is —$CHF_2$ or

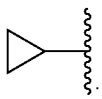

3. The compound of claim 1, wherein Ring A is

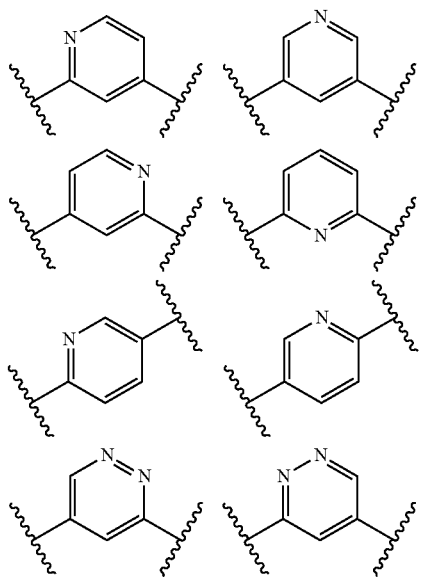

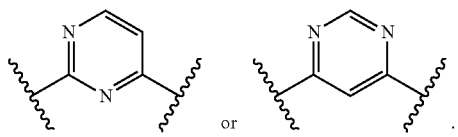

4. The compound of claim 1, wherein Ring B is selected from phenyl; a 5-6 membered monocyclic heteroaryl ring having 1-4 heteroatoms independently selected from nitrogen, oxygen, and sulfur; and a 7-11 membered fused bicyclic heteroaryl ring having 1-4 heteroatoms independently selected from nitrogen, oxygen, and sulfur.

5. The compound of claim 1, wherein Ring B is

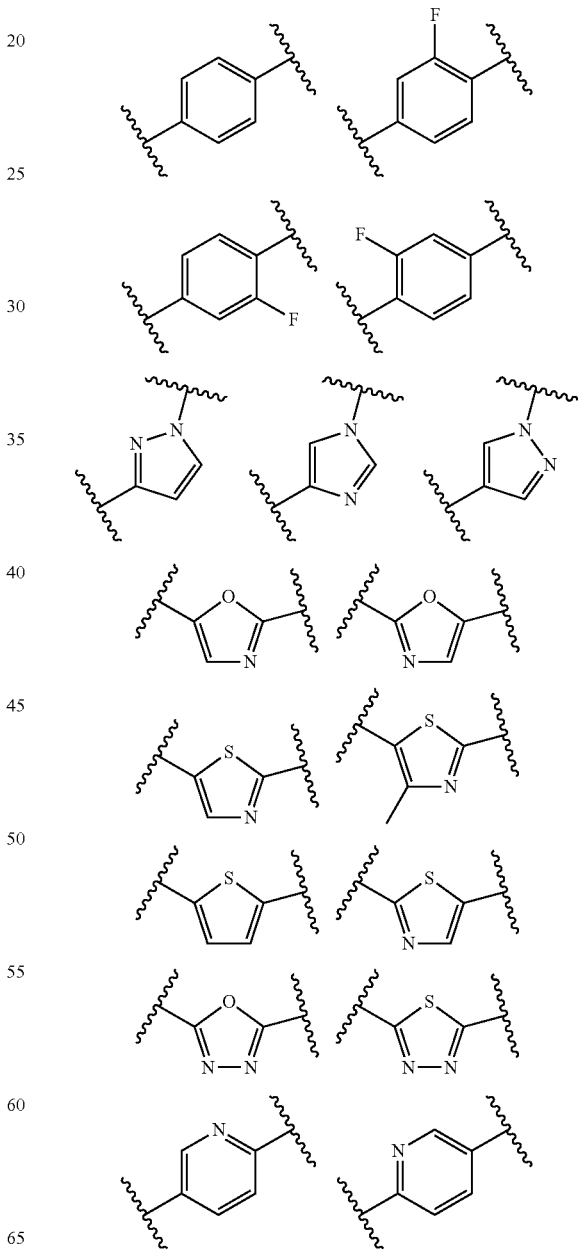

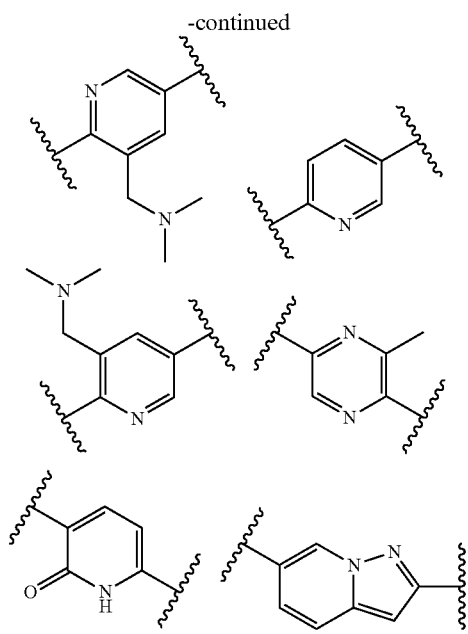
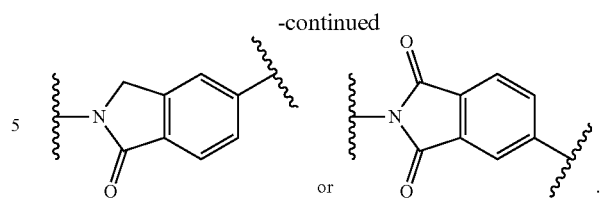
6. The compound of claim 1, wherein Ring C is 6-membered monocyclic heteroaryl ring having 1-4 nitrogen atoms.
7. The compound of claim 1, wherein Ring C is
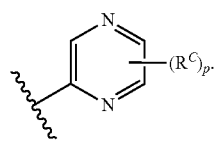
8. A compound selected from those depicted below, or a pharmaceutically acceptable salt thereof:
| Compound | Structure |
| --- | --- |
| I-1 | 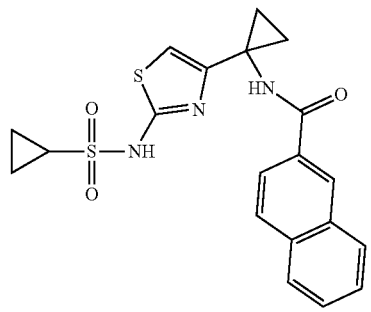 [SMILES: O=C(NC1(c2csc(NS(=O)(=O)C3CC3)n2)CC1)c1ccc2ccccc2c1] |
| I-2 | 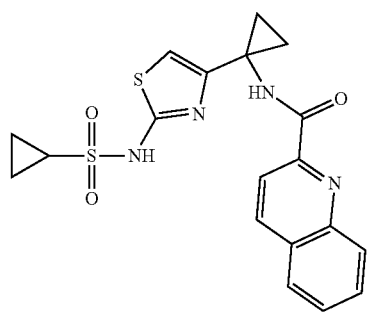 [SMILES: O=C(NC1(c2csc(NS(=O)(=O)C3CC3)n2)CC1)c1ccc2ccccc2n1] |
| I-3 | 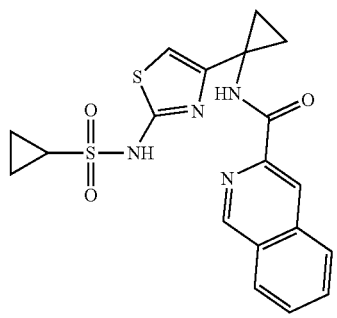 [SMILES: O=C(NC1(c2csc(NS(=O)(=O)C3CC3)n2)CC1)c1cc2ccccc2cn1] |

-continued
| Compound | Structure |
|---|---|
| I-4 | 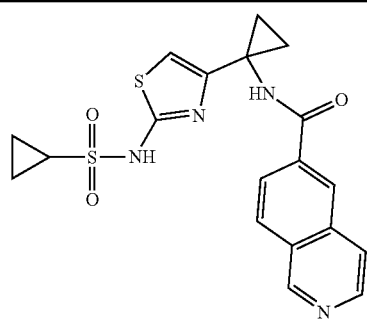 |
| I-5 | 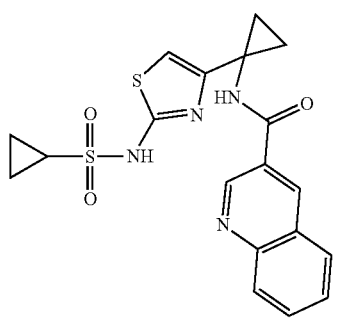 [SMILES: O=C(NC1(c2csc(NS(=O)(=O)C3CC3)n2)CC1)c1cnc2ccccc2c1] |
| I-6 | 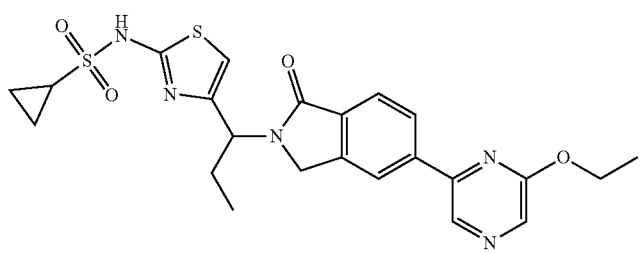 |
| I-7 | 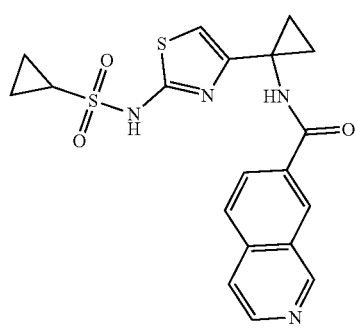 [SMILES: O=C(NC1(c2csc(NS(=O)(=O)C3CC3)n2)CC1)c1ccc2ccncc2c1] |
| I-8 | 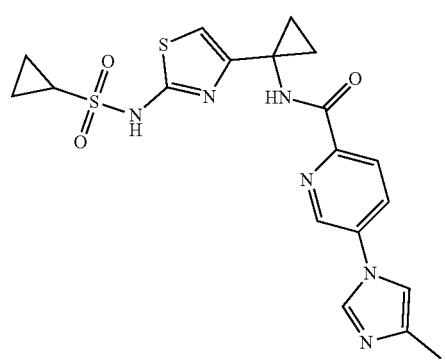 [SMILES: Cc1cn(-c2ccc(C(=O)NC3(c4csc(NS(=O)(=O)C5CC5)n4)CC3)nc2)cn1] |

-continued
| Compound | Structure |
|---|---|
| I-9 | 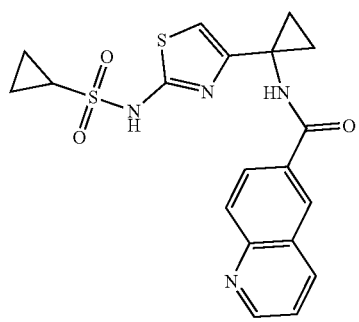 [SMILES: O=C(NC1(c2csc(NS(=O)(=O)C3CC3)n2)CC1)c1ccc2ncccc2c1] |
| I-10 | 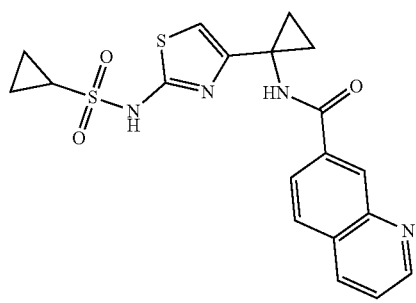 [SMILES: O=C(NC1(c2csc(NS(=O)(=O)C3CC3)n2)CC1)c1ccc2cccnc2c1] |
| I-11 | 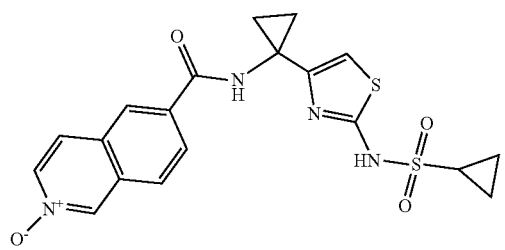 [SMILES: O=C(NC1(c2csc(NS(=O)(=O)C3CC3)n2)CC1)c1ccc2c[n+]([O-])ccc2c1] |
| I-12 | 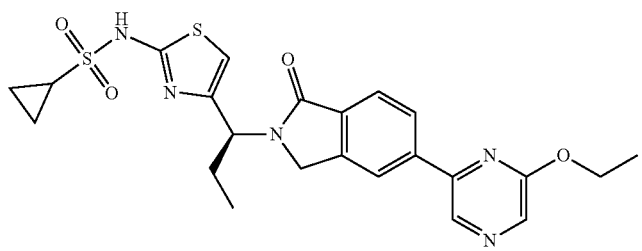 [SMILES: CCOc1cncc(-c2ccc3c(c2)CN([C@@H](CC)c2csc(NS(=O)(=O)C4CC4)n2)C3=O)n1] |
| I-13 | 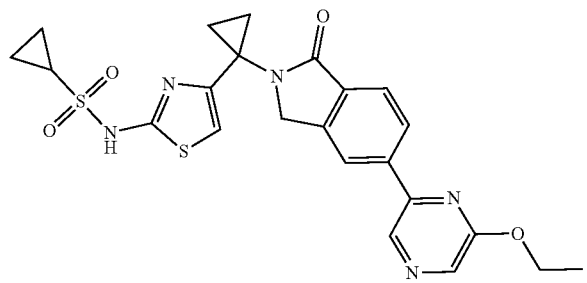 [SMILES: CCOc1cncc(-c2ccc3c(c2)CN(C2(c4csc(NS(=O)(=O)C5CC5)n4)CC2)C3=O)n1] |

-continued
| Compound | Structure |
|---|---|
| I-12a | 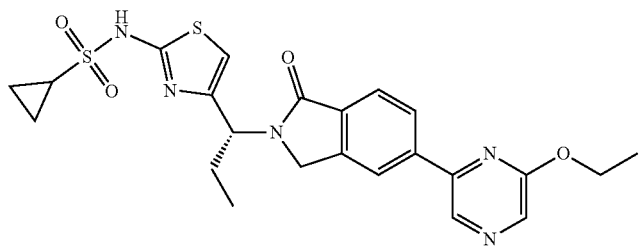 |
| I-14 | 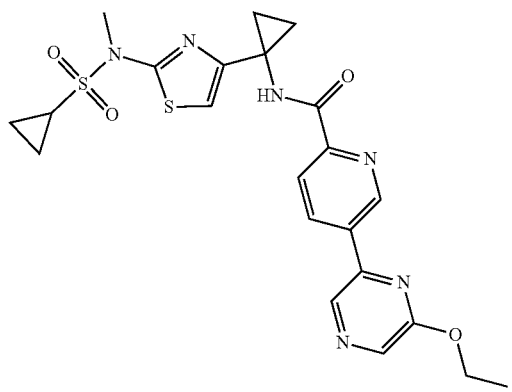 [SMILES: CCOc1cncc(-c2ccc(C(=O)NC3(c4csc(N(C)S(=O)(=O)C5CC5)n4)CC3)nc2)n1] |
| I-15 | 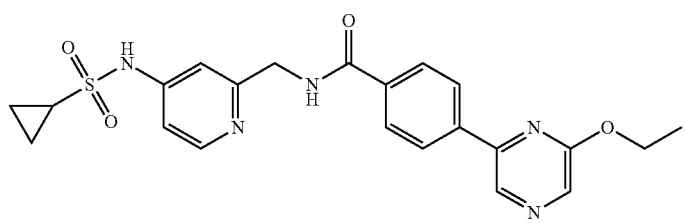 [SMILES: CCOc1cncc(-c2ccc(C(=O)NCc3cc(NS(=O)(=O)C4CC4)ccn3)cc2)n1] |
| I-16 | 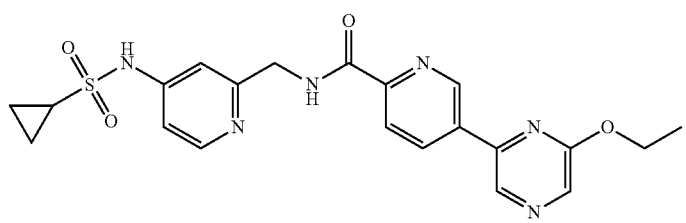 [SMILES: CCOc1cncc(-c2ccc(C(=O)NCc3cc(NS(=O)(=O)C4CC4)ccn3)nc2)n1] |
| I-17 | 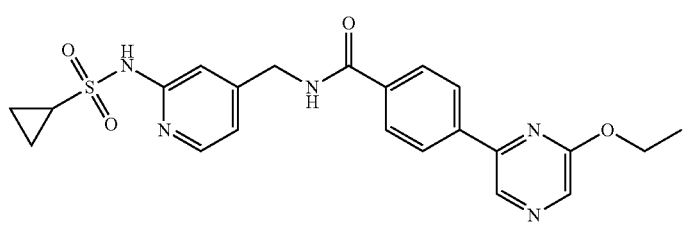 [SMILES: CCOc1cncc(-c2ccc(C(=O)NCc3ccnc(NS(=O)(=O)C4CC4)c3)cc2)n1] |
| I-19 | 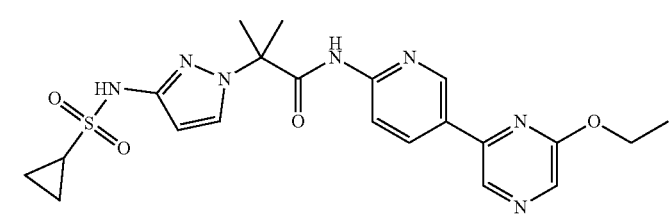 [SMILES: CCOc1cncc(-c2ccc(NC(=O)C(C)(C)n3ccc(NS(=O)(=O)C4CC4)n3)nc2)n1] |

| Compound | Structure |
|---|---|
| I-20 | 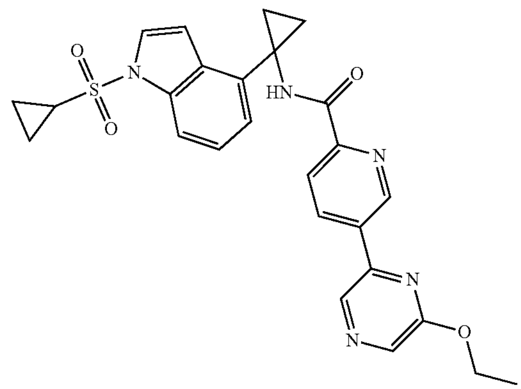 [SMILES: CCOc1cncc(-c2ccc(C(=O)NC3(c4cccc5c4ccn5S(=O)(=O)C4CC4)CC3)nc2)n1] |
| I-22 | 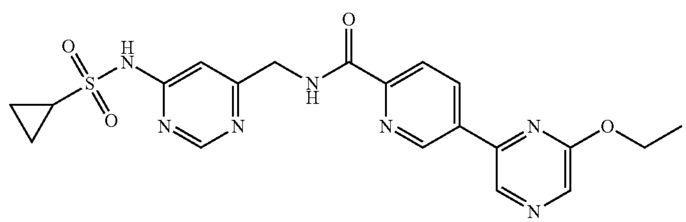 [SMILES: CCOc1cncc(-c2ccc(C(=O)NCc3cc(NS(=O)(=O)C4CC4)ncn3)nc2)n1] |
| I-23 | 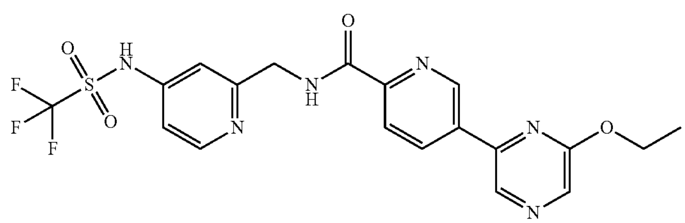 [SMILES: CCOc1cncc(-c2ccc(C(=O)NCc3cc(NS(=O)(=O)C(F)(F)F)ccn3)nc2)n1] |
| I-24 | 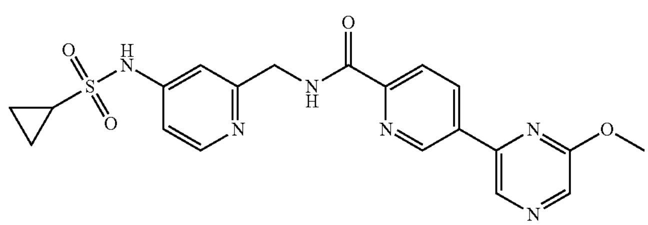 [SMILES: COc1cncc(-c2ccc(C(=O)NCc3cc(NS(=O)(=O)C4CC4)ccn3)nc2)n1] |
| I-25 | 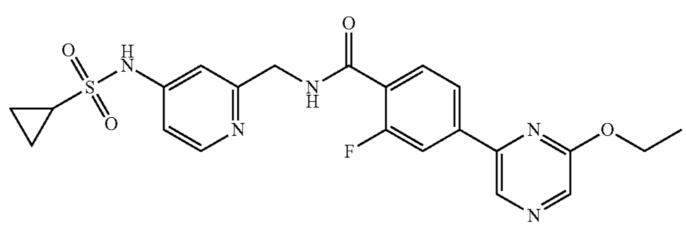 [SMILES: CCOc1cncc(-c2ccc(C(=O)NCc3cc(NS(=O)(=O)C4CC4)ccn3)c(F)c2)n1] |
| I-26 | 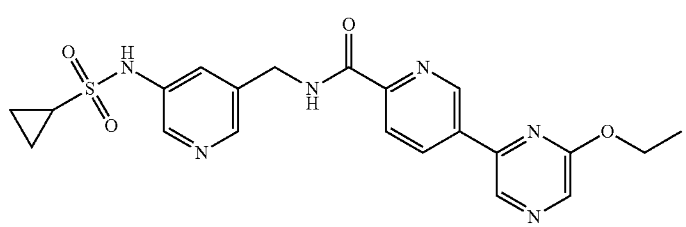 [SMILES: CCOc1cncc(-c2ccc(C(=O)NCc3cncc(NS(=O)(=O)C4CC4)c3)nc2)n1] |

-continued
| Compound | Structure |
|---|---|
| I-29 | 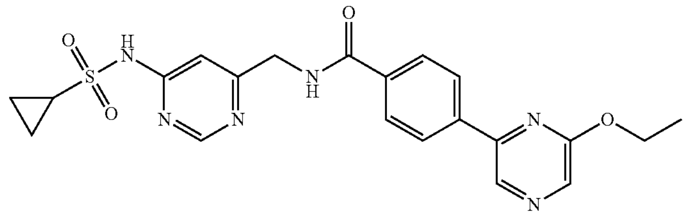 [SMILES: CCOc1cncc(-c2ccc(C(=O)NCc3cc(NS(=O)(=O)C4CC4)ncn3)cc2)n1] |
| I-30 | 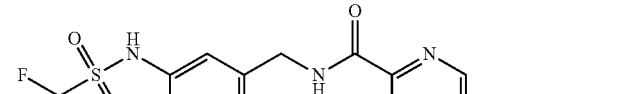 |
| I-31 | 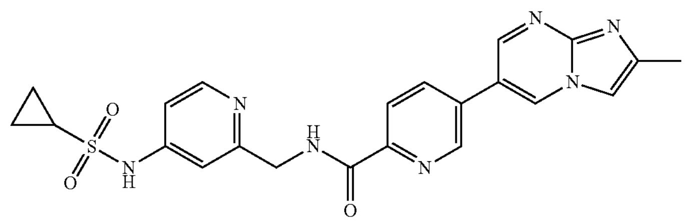 [SMILES: Cc1cn2cc(-c3ccc(C(=O)NCc4cc(NS(=O)(=O)C5CC5)ccn4)nc3)cnc2n1] |
| I-32 | 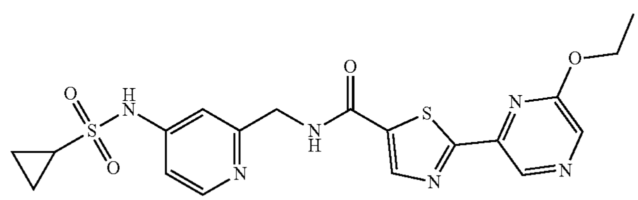 [SMILES: CCOc1cncc(-c2ncc(C(=O)NCc3cc(NS(=O)(=O)C4CC4)ccn3)s2)n1] |
| I-33 | 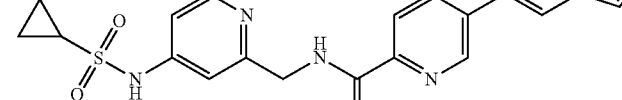 |
| I-34 | 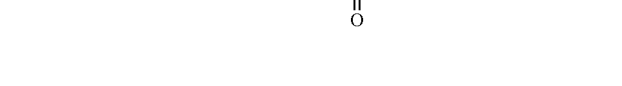 |
| I-35 | 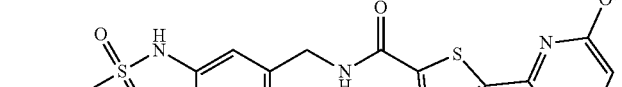 |

-continued
| Compound | Structure |
|---|---|
| I-36 | 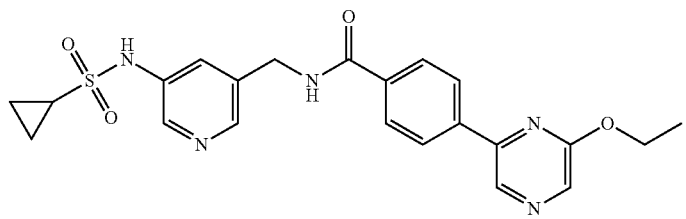 [SMILES: CCOc1cncc(-c2ccc(C(=O)NCc3cncc(NS(=O)(=O)C4CC4)c3)cc2)n1] |
| I-37 | 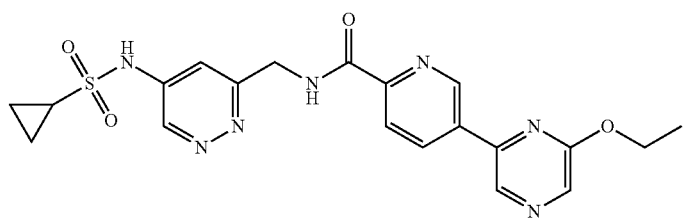 [SMILES: CCOc1cncc(-c2ccc(C(=O)NCc3cc(NS(=O)(=O)C4CC4)cnn3)nc2)n1] |
| I-38 | 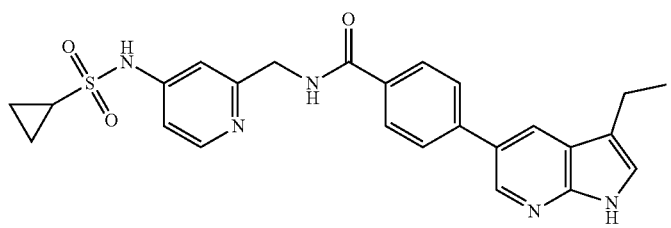 [SMILES: CCc1c[nH]c2ncc(-c3ccc(C(=O)NCc4cc(NS(=O)(=O)C5CC5)ccn4)cc3)cc12] |
| I-39 | 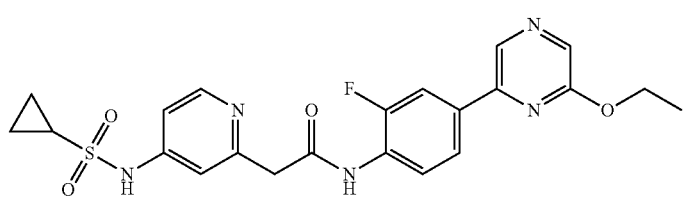 [SMILES: CCOc1cncc(-c2ccc(NC(=O)Cc3cc(NS(=O)(=O)C4CC4)ccn3)c(F)c2)n1] |
| I-40 | 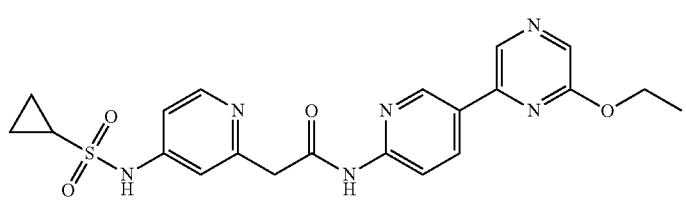 [SMILES: CCOc1cncc(-c2ccc(NC(=O)Cc3cc(NS(=O)(=O)C4CC4)ccn3)nc2)n1] |
| I-41 | 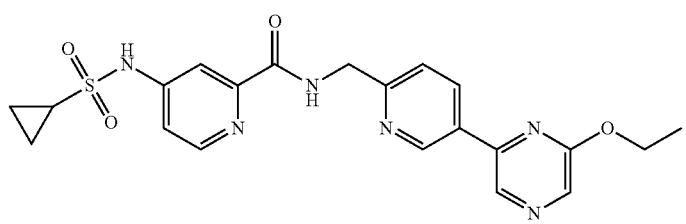 [SMILES: CCOc1cncc(-c2ccc(CNC(=O)c3cc(NS(=O)(=O)C4CC4)ccn3)nc2)n1] |
| I-42 | 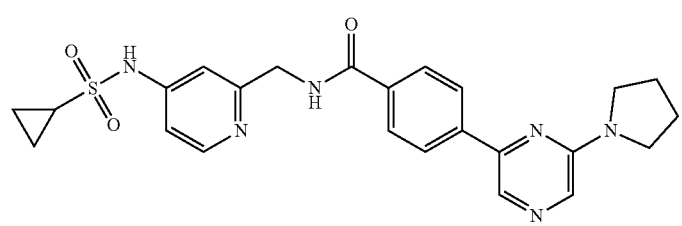 [SMILES: O=C(NCc1cc(NS(=O)(=O)C2CC2)ccn1)c1ccc(-c2cncc(N3CCCC3)n2)cc1] |

-continued

| Compound | Structure |
|---|---|
| I-43 | 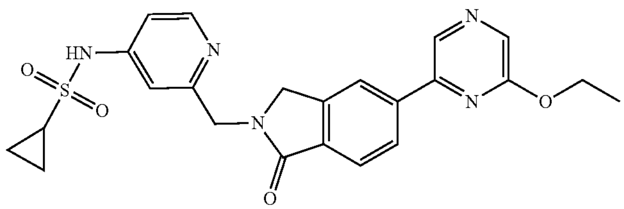 [SMILES: CCOc1cncc(-c2ccc3c(c2)CN(Cc2cc(NS(=O)(=O)C4CC4)ccn2)C3=O)n1] |
| I-44 | 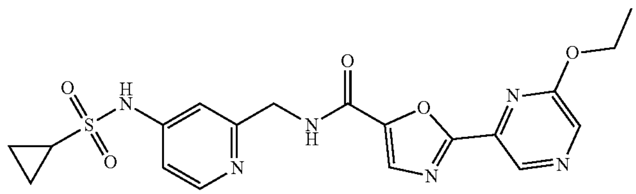 |
| I-45 | 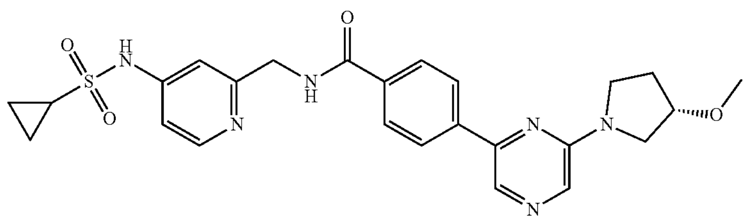 [SMILES: CO[C@H]1CCN(c2cncc(-c3ccc(C(=O)NCc4cc(NS(=O)(=O)C5CC5)ccn4)cc3)n2)C1] |
| I-46 | 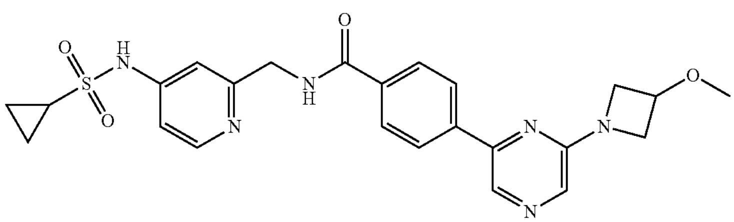 [SMILES: COC1CN(c2cncc(-c3ccc(C(=O)NCc4cc(NS(=O)(=O)C5CC5)ccn4)cc3)n2)C1] |
| I-47 | 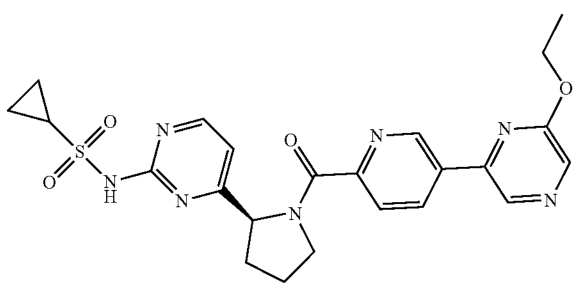 [SMILES: CCOc1cncc(-c2ccc(C(=O)N3CCC[C@H]3c3ccnc(NS(=O)(=O)C4CC4)n3)nc2)n1] |
| I-48 | 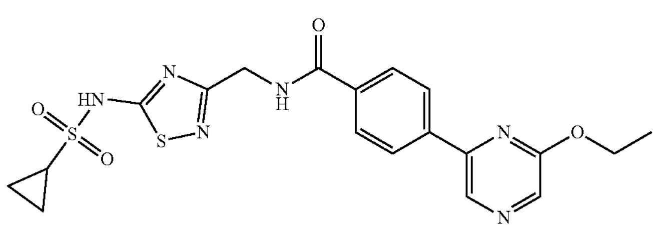 [SMILES: CCOc1cncc(-c2ccc(C(=O)NCc3nsc(NS(=O)(=O)C4CC4)n3)cc2)n1] |
| I-50 | 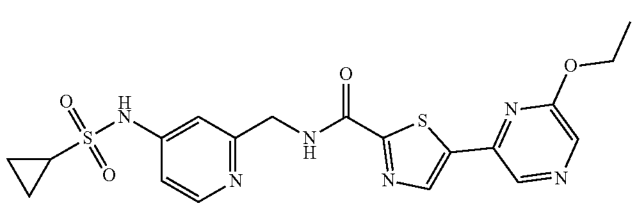 |

-continued

| Compound | Structure |
|---|---|
| I-51 | 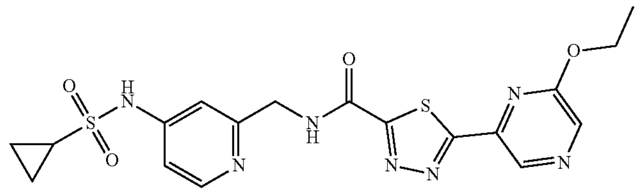 |
| I-52 | 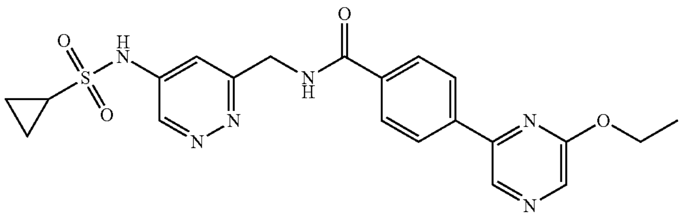 |
| I-54 | 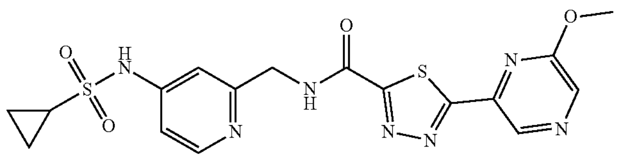 [SMILES: COc1cncc(-c2nnc(C(=O)NCc3cc(NS(=O)(=O)C4CC4)ccn3)s2)n1] |
| I-55 | 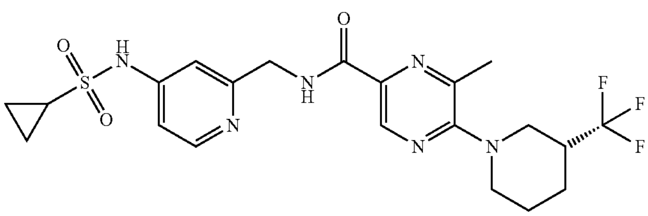 |
| I-56 | 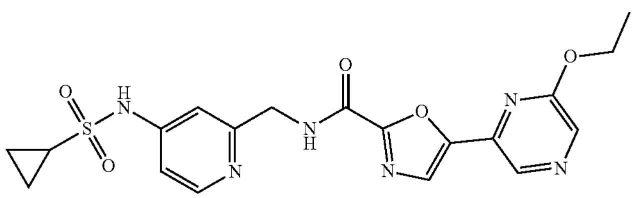 |
| I-57 | 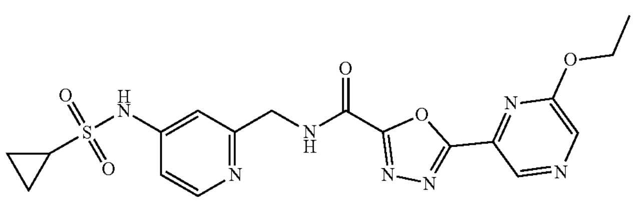 |
| I-58 | 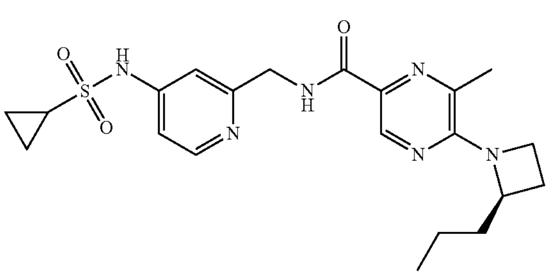 [SMILES: CCC[C@@H]1CCN1c1ncc(C(=O)NCc2cc(NS(=O)(=O)C3CC3)ccn2)nc1C] |

| Compound | Structure |
|---|---|
| I-59 | 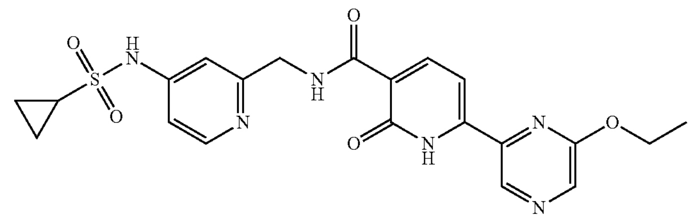 [SMILES: CCOc1cncc(-c2ccc(C(=O)NCc3cc(NS(=O)(=O)C4CC4)ccn3)c(=O)[nH]2)n1] |
| I-60 | 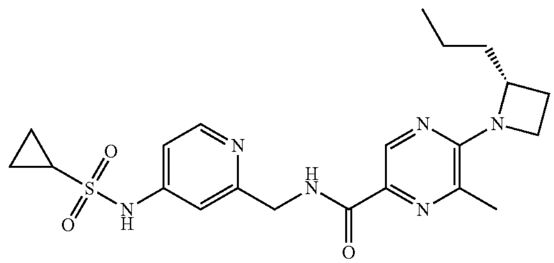 [SMILES: CCC[C@@H]1CCN1c1ncc(C(=O)NCc2cc(NS(=O)(=O)C3CC3)ccn2)nc1C] |
| I-64 | 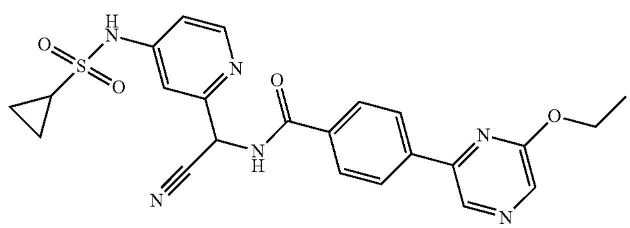 [SMILES: CCOc1cncc(-c2ccc(C(=O)NC(C#N)c3cc(NS(=O)(=O)C4CC4)ccn3)cc2)n1] |
| I-65 | 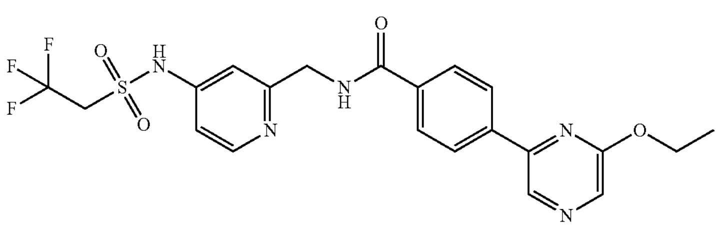 [SMILES: CCOc1cncc(-c2ccc(C(=O)NCc3cc(NS(=O)(=O)CC(F)(F)F)ccn3)cc2)n1] |
| I-66 | 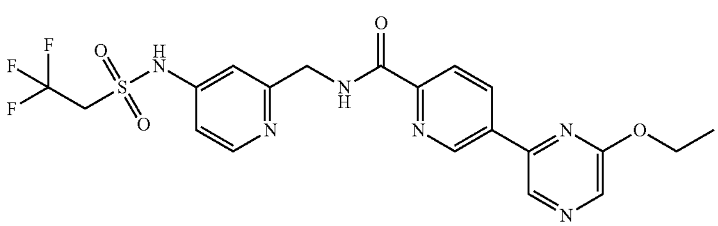 |
| I-67 | 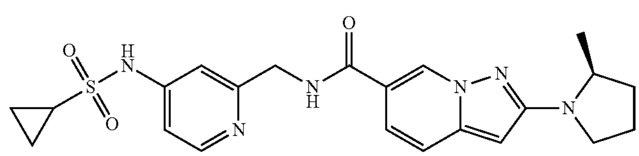 [SMILES: C[C@H]1CCCN1c1cc2ccc(C(=O)NCc3cc(NS(=O)(=O)C4CC4)ccn3)cn2n1] |
| I-71 | 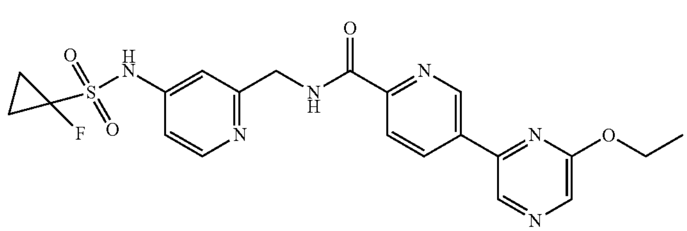 [SMILES: CCOc1cncc(-c2ccc(C(=O)NCc3cc(NS(=O)(=O)C4(F)CC4)ccn3)nc2)n1] |

-continued
| Compound | Structure |
|---|---|
| I-72 | 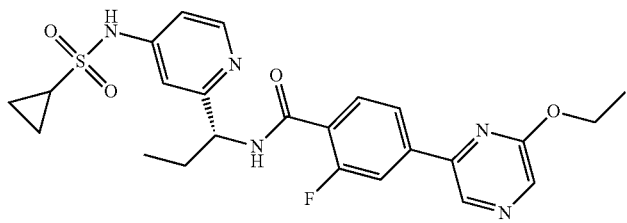 [SMILES: CCOc1cncc(-c2ccc(C(=O)N[C@H](CC)c3cc(NS(=O)(=O)C4CC4)ccn3)c(F)c2)n1] |
| I-73 | 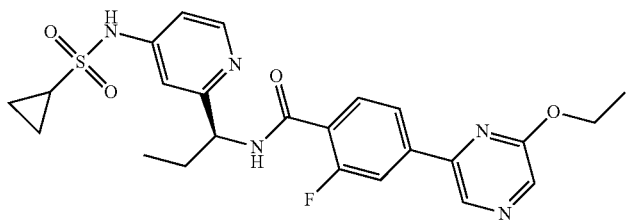 [SMILES: CCOc1cncc(-c2ccc(C(=O)N[C@@H](CC)c3cc(NS(=O)(=O)C4CC4)ccn3)c(F)c2)n1] |
| I-75 | 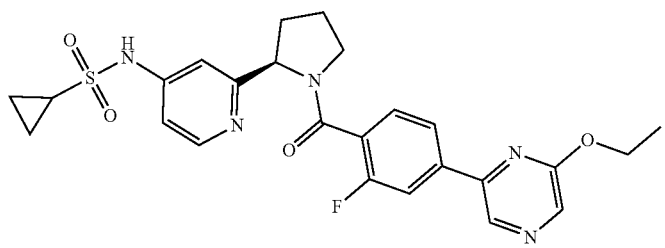 [SMILES: CCOc1cncc(-c2ccc(C(=O)N3CCC[C@@H]3c3cc(NS(=O)(=O)C4CC4)ccn3)c(F)c2)n1] |
| I-76 | 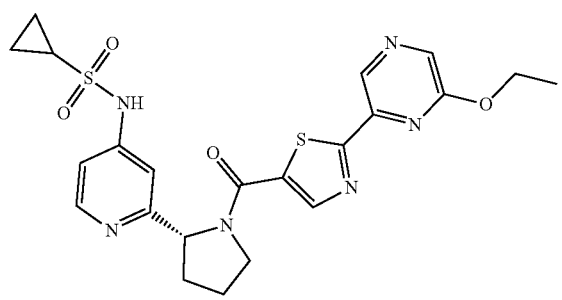 [SMILES: CCOc1cncc(-c2ncc(C(=O)N3CCC[C@@H]3c3cc(NS(=O)(=O)C4CC4)ccn3)s2)n1] |
| I-77 | 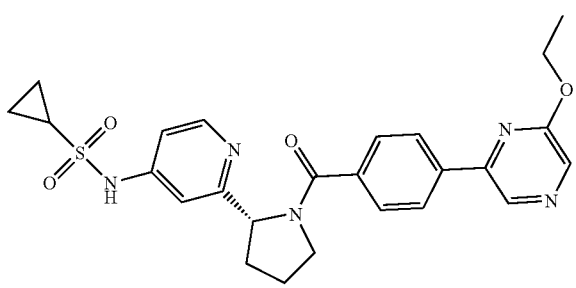 [SMILES: CCOc1cncc(-c2ccc(C(=O)N3CCC[C@@H]3c3cc(NS(=O)(=O)C4CC4)ccn3)cc2)n1] |
| I-78 | 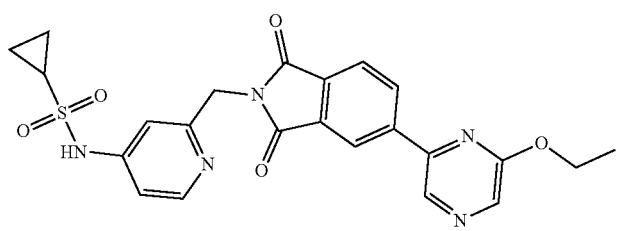 [SMILES: CCOc1cncc(-c2ccc3c(c2)C(=O)N(Cc2cc(NS(=O)(=O)C4CC4)ccn2)C3=O)n1] |

| Compound | Structure |
|---|---|
| I-80 | 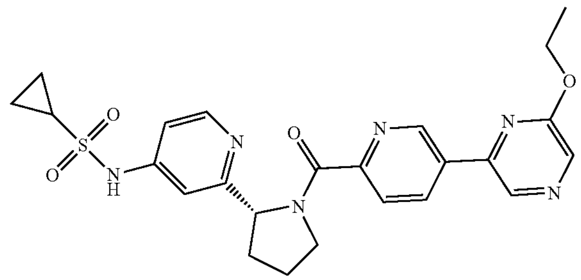 [SMILES: CCOc1cncc(-c2ccc(C(=O)N3CCC[C@@H]3c3cc(NS(=O)(=O)C4CC4)ccn3)nc2)n1] |
| I-81 | 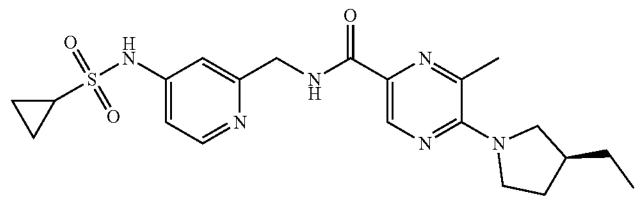 [SMILES: CC[C@H]1CCN(c2ncc(C(=O)NCc3cc(NS(=O)(=O)C4CC4)ccn3)nc2C)C1] |
| I-82 | 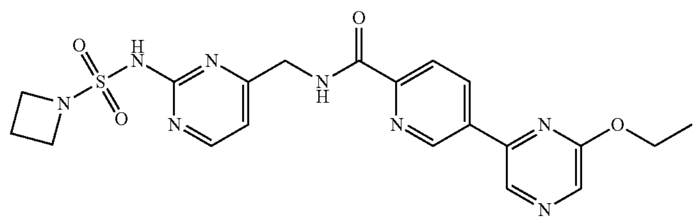 [SMILES: CCOc1cncc(-c2ccc(C(=O)NCc3ccnc(NS(=O)(=O)N4CCC4)n3)nc2)n1] |
| I-84 | 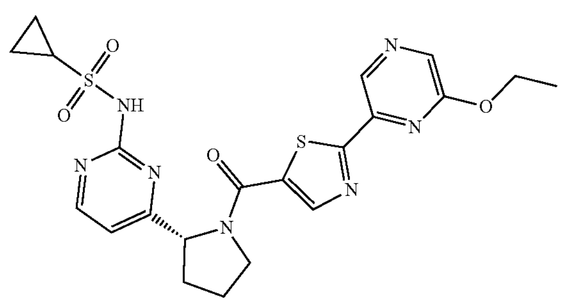 [SMILES: CCOc1cncc(-c2ncc(C(=O)N3CCC[C@@H]3c3ccnc(NS(=O)(=O)C4CC4)n3)s2)n1] |
| I-85 | 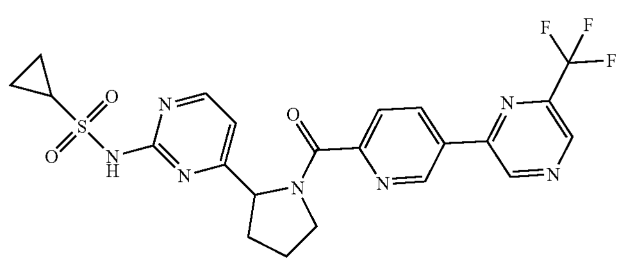 [SMILES: O=C(c1ccc(-c2cncc(C(F)(F)F)n2)cn1)N1CCCC1c1ccnc(NS(=O)(=O)C2CC2)n1] |
| I-86 | 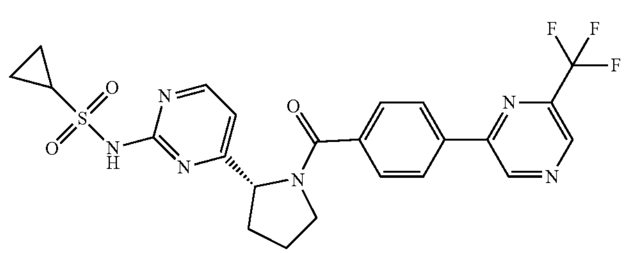 [SMILES: O=C(c1ccc(-c2cncc(C(F)(F)F)n2)cc1)N1CCC[C@@H]1c1ccnc(NS(=O)(=O)C2CC2)n1] |

| Compound | Structure |
|---|---|
| I-87 | 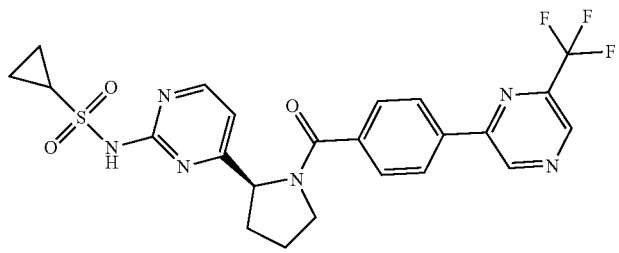 [SMILES: O=C(c1ccc(-c2cncc(C(F)(F)F)n2)cc1)N1CCC[C@H]1c1ccnc(NS(=O)(=O)C2CC2)n1] |
| I-88 | 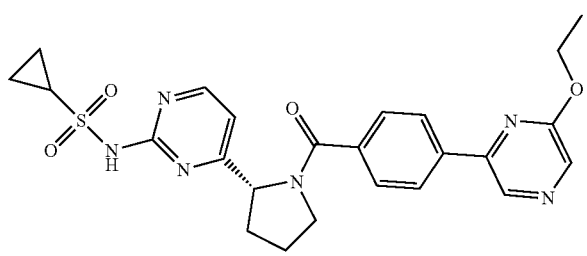 [SMILES: CCOc1cncc(-c2ccc(C(=O)N3CCC[C@@H]3c3ccnc(NS(=O)(=O)C4CC4)n3)cc2)n1] |
| I-89 | 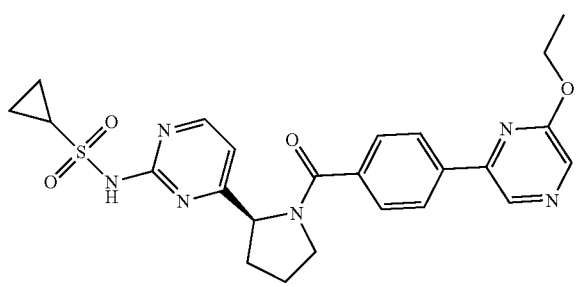 [SMILES: CCOc1cncc(-c2ccc(C(=O)N3CCC[C@H]3c3ccnc(NS(=O)(=O)C4CC4)n3)cc2)n1] |
| I-90 | 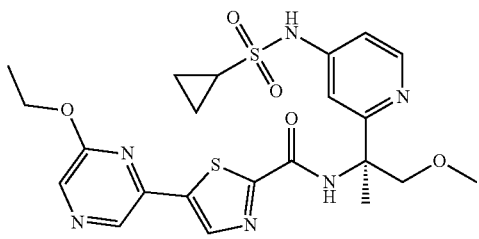 [SMILES: CCOc1cncc(-c2cnc(C(=O)N[C@](C)(COC)c3cc(NS(=O)(=O)C4CC4)ccn3)s2)n1] |
| I-91 | 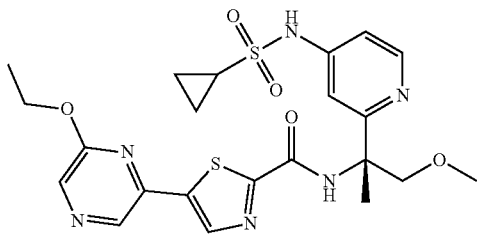 [SMILES: CCOc1cncc(-c2cnc(C(=O)N[C@@](C)(COC)c3cc(NS(=O)(=O)C4CC4)ccn3)s2)n1] |
| I-92 | 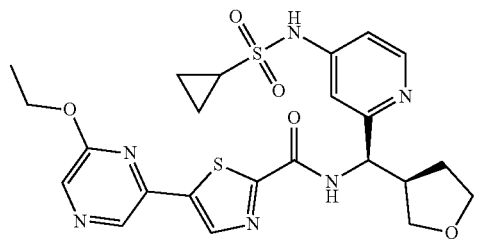 [SMILES: CCOc1cncc(-c2cnc(C(=O)N[C@@H](c3cc(NS(=O)(=O)C4CC4)ccn3)[C@H]3CCOC3)s2)n1] |

-continued
| Compound | Structure |
|---|---|
| I-93 | 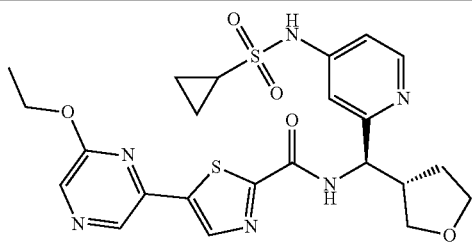 [SMILES: CCOc1cncc(-c2cnc(C(=O)N[C@@H](c3cc(NS(=O)(=O)C4CC4)ccn3)[C@@H]3CCOC3)s2)n1] |
| I-94 | 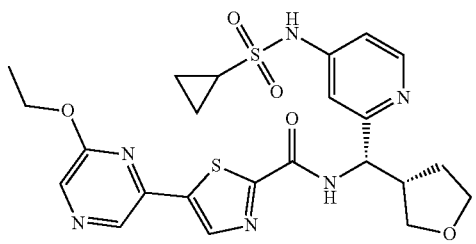 [SMILES: CCOc1cncc(-c2cnc(C(=O)N[C@H](c3cc(NS(=O)(=O)C4CC4)ccn3)[C@@H]3CCOC3)s2)n1] |
| I-95 | 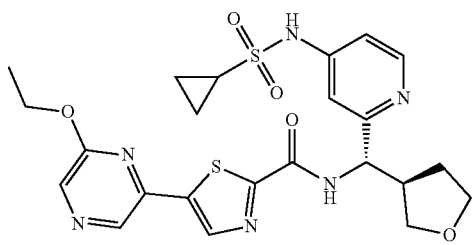 [SMILES: CCOc1cncc(-c2cnc(C(=O)N[C@H](c3cc(NS(=O)(=O)C4CC4)ccn3)[C@H]3CCOC3)s2)n1] |
| I-96 | 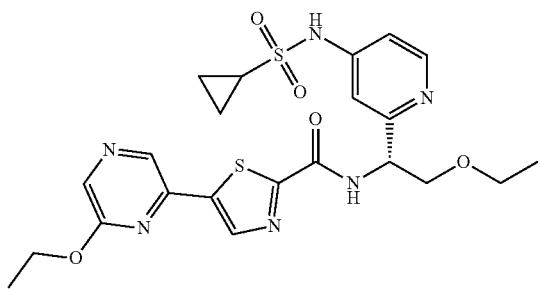 [SMILES: CCOC[C@H](NC(=O)c1ncc(-c2cncc(OCC)n2)s1)c1cc(NS(=O)(=O)C2CC2)ccn1] |
| I-97 | 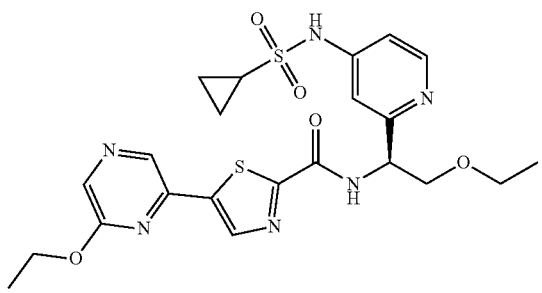 [SMILES: CCOC[C@@H](NC(=O)c1ncc(-c2cncc(OCC)n2)s1)c1cc(NS(=O)(=O)C2CC2)ccn1] |
| I-99 | 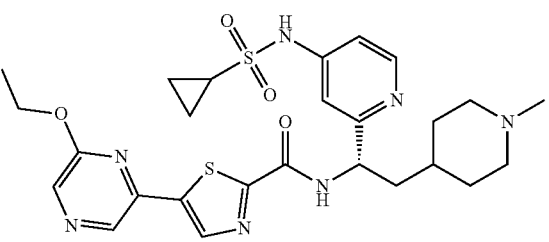 [SMILES: CCOc1cncc(-c2cnc(C(=O)N[C@@H](CC3CCN(C)CC3)c3cc(NS(=O)(=O)C4CC4)ccn3)s2)n1] |

-continued
| Compound | Structure |
|---|---|
| I-100 | 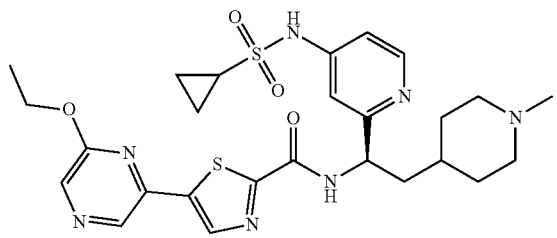 [SMILES: CCOc1cncc(-c2cnc(C(=O)N[C@H](CC3CCN(C)CC3)c3cc(NS(=O)(=O)C4CC4)ccn3)s2)n1] |
| I-101 | 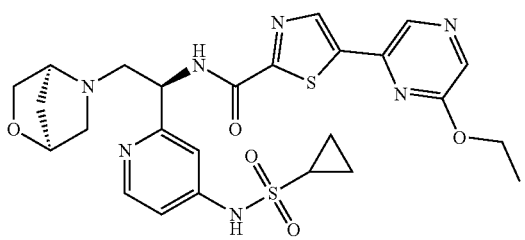 [SMILES: CCOc1cncc(-c2cnc(C(=O)N[C@H](CN3C[C@@H]4C[C@H]3CO4)c3cc(NS(=O)(=O)C4CC4)ccn3)s2)n1] |
| I-102 | 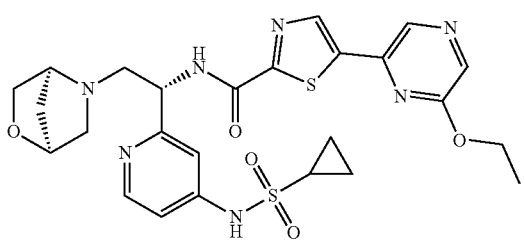 [SMILES: CCOc1cncc(-c2cnc(C(=O)N[C@@H](CN3C[C@@H]4C[C@H]3CO4)c3cc(NS(=O)(=O)C4CC4)ccn3)s2)n1] |
| I-103 | 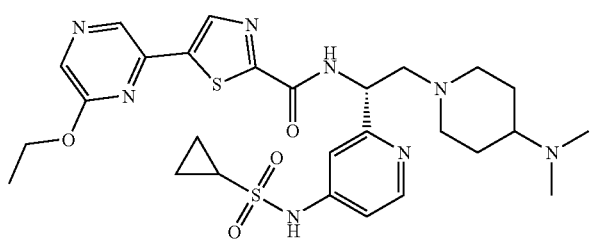 [SMILES: CCOc1cncc(-c2cnc(C(=O)N[C@H](CN3CCC(N(C)C)CC3)c3cc(NS(=O)(=O)C4CC4)ccn3)s2)n1] |
| I-104 | 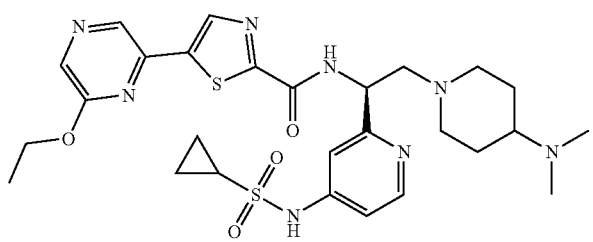 [SMILES: CCOc1cncc(-c2cnc(C(=O)N[C@@H](CN3CCC(N(C)C)CC3)c3cc(NS(=O)(=O)C4CC4)ccn3)s2)n1] |
| I-105 | 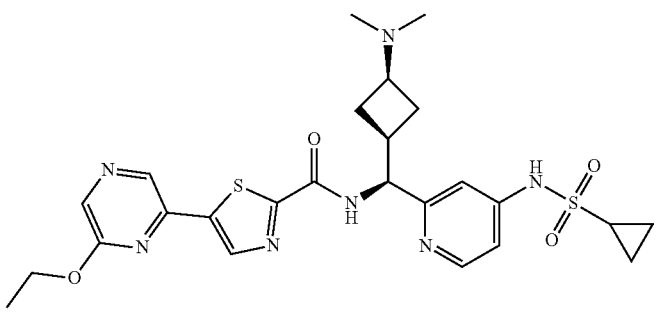 [SMILES: CCOc1cncc(-c2cnc(C(=O)N[C@H](c3cc(NS(=O)(=O)C4CC4)ccn3)[C@H]3C[C@@H](N(C)C)C3)s2)n1] |

-continued
| Compound | Structure |
|---|---|
| I-106 | 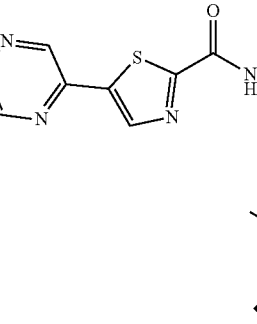 |
| I-107 | 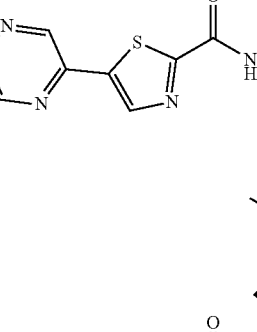 |
| I-108 | 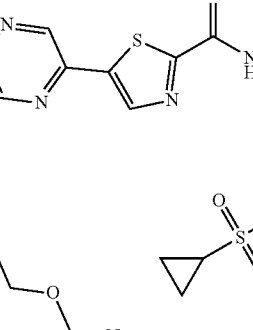 |
| I-109 | 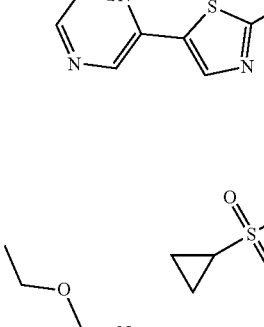 |
| I-110 | 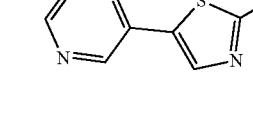 |

| Compound | Structure |
|---|---|
| I-111 | 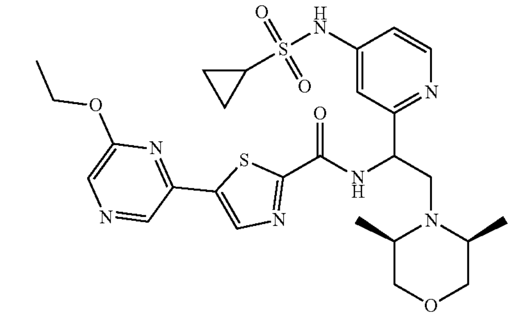 [SMILES: CCOc1cncc(-c2cnc(C(=O)NC(CN3[C@H](C)COC[C@@H]3C)c3cc(NS(=O)(=O)C4CC4)ccn3)s2)n1] |
| I-112 | 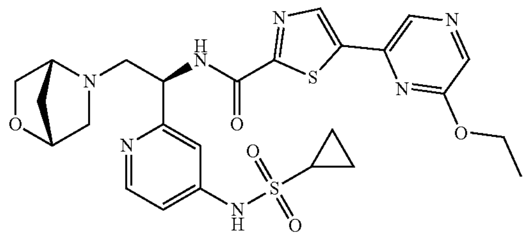 [SMILES: CCOc1cncc(-c2cnc(C(=O)N[C@H](CN3C[C@H]4C[C@@H]3CO4)c3cc(NS(=O)(=O)C4CC4)ccn3)s2)n1] |
| I-113 | 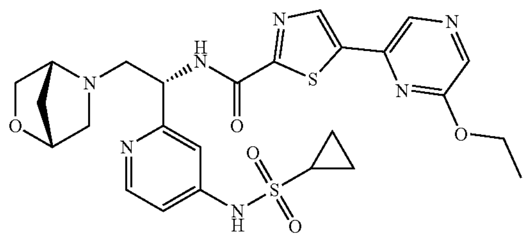 [SMILES: CCOc1cncc(-c2cnc(C(=O)N[C@@H](CN3C[C@H]4C[C@@H]3CO4)c3cc(NS(=O)(=O)C4CC4)ccn3)s2)n1] |
| I-114 | 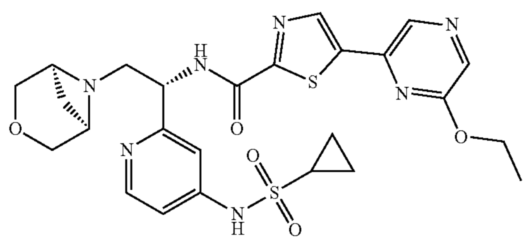 [SMILES: CCOc1cncc(-c2cnc(C(=O)N[C@@H](CN3[C@@H]4COC[C@H]3C4)c3cc(NS(=O)(=O)C4CC4)ccn3)s2)n1] |
| I-115 | 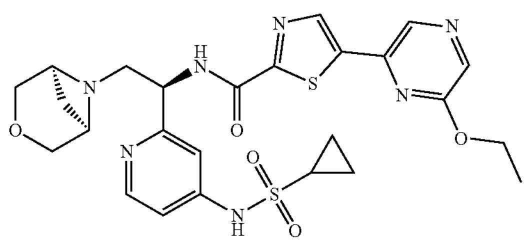 [SMILES: CCOc1cncc(-c2cnc(C(=O)N[C@H](CN3[C@@H]4COC[C@H]3C4)c3cc(NS(=O)(=O)C4CC4)ccn3)s2)n1] |
| I-116 | 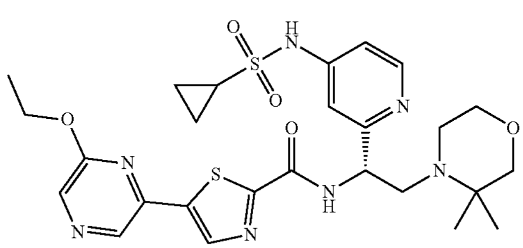 [SMILES: CCOc1cncc(-c2cnc(C(=O)N[C@@H](CN3CCOCC3(C)C)c3cc(NS(=O)(=O)C4CC4)ccn3)s2)n1] |

-continued
| Compound | Structure |
|---|---|
| I-117 | 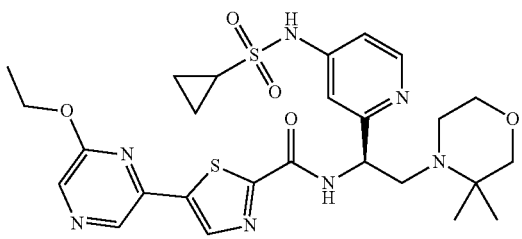 [SMILES: CCOc1cncc(-c2cnc(C(=O)N[C@H](CN3CCOCC3(C)C)c3cc(NS(=O)(=O)C4CC4)ccn3)s2)n1] |
| I-118 | 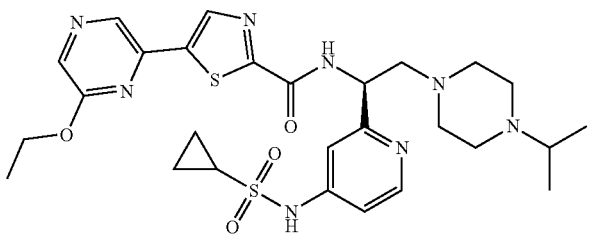 [SMILES: CCOc1cncc(-c2cnc(C(=O)N[C@@H](CN3CCN(C(C)C)CC3)c3cc(NS(=O)(=O)C4CC4)ccn3)s2)n1] |
| I-119 | 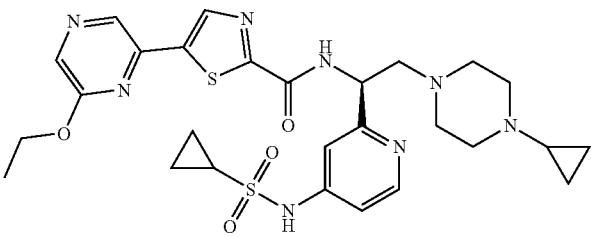 [SMILES: CCOc1cncc(-c2cnc(C(=O)N[C@@H](CN3CCN(C4CC4)CC3)c3cc(NS(=O)(=O)C4CC4)ccn3)s2)n1] |
| I-120 | 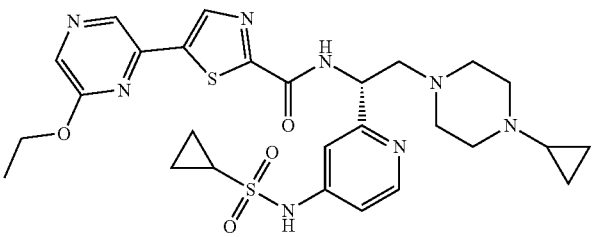 [SMILES: CCOc1cncc(-c2cnc(C(=O)N[C@H](CN3CCN(C4CC4)CC3)c3cc(NS(=O)(=O)C4CC4)ccn3)s2)n1] |
| I-121 | 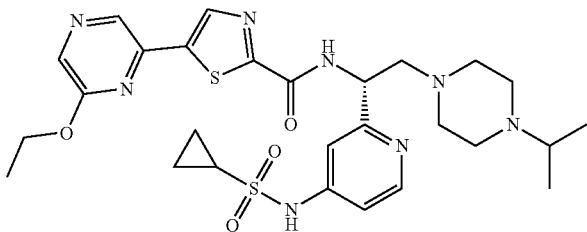 [SMILES: CCOc1cncc(-c2cnc(C(=O)N[C@H](CN3CCN(C(C)C)CC3)c3cc(NS(=O)(=O)C4CC4)ccn3)s2)n1] |
| I-122 | 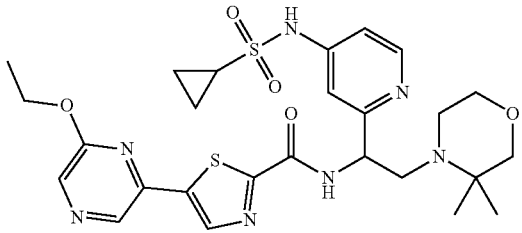 [SMILES: CCOc1cncc(-c2cnc(C(=O)NC(CN3CCOCC3(C)C)c3cc(NS(=O)(=O)C4CC4)ccn3)s2)n1] |

| Compound | Structure |
|---|---|
| I-126 | 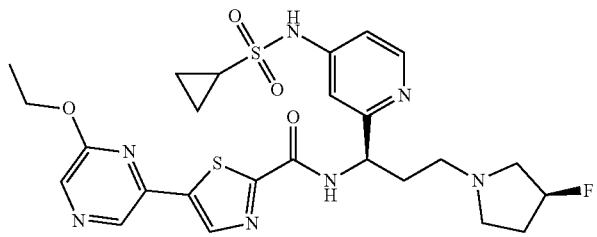 [SMILES: CCOc1cncc(-c2cnc(C(=O)N[C@H](CCN3CC[C@H](F)C3)c3cc(NS(=O)(=O)C4CC4)ccn3)s2)n1] |
| I-127 | 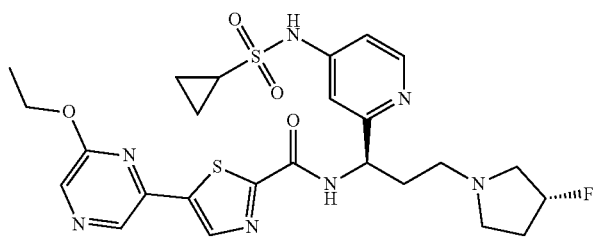 [SMILES: CCOc1cncc(-c2cnc(C(=O)N[C@H](CCN3CC[C@@H](F)C3)c3cc(NS(=O)(=O)C4CC4)ccn3)s2)n1] |
| I-128 | 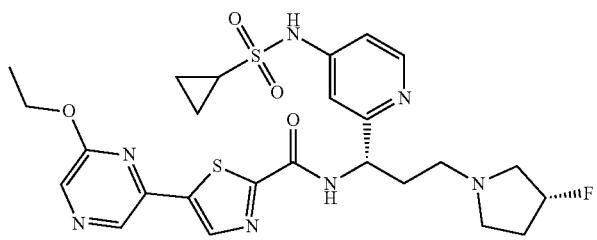 |
| I-129 | 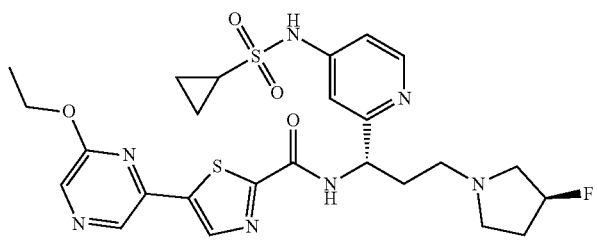 |
| I-130 | 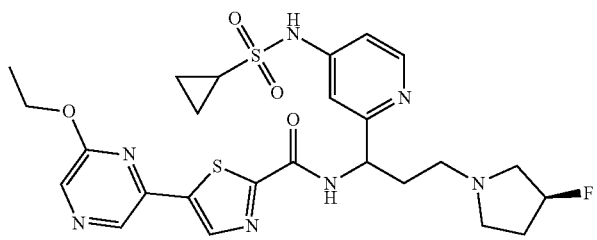 |
| I-131 | 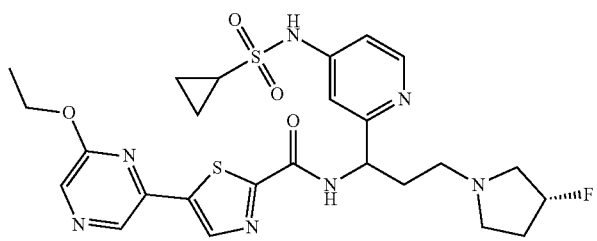 |

| Compound | Structure |
|---|---|
| I-132 | 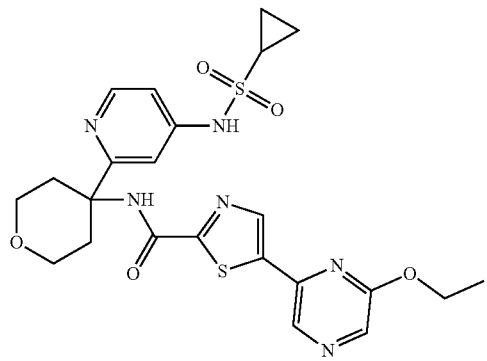 [SMILES: CCOc1cncc(-c2cnc(C(=O)NC3(c4cc(NS(=O)(=O)C5CC5)ccn4)CCOCC3)s2)n1] |
| I-133 | 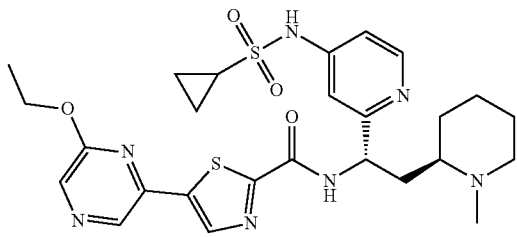 [SMILES: CCOc1cncc(-c2cnc(C(=O)N[C@@H](C[C@H]3CCCCN3C)c3cc(NS(=O)(=O)C4CC4)ccn3)s2)n1] |
| I-134 | 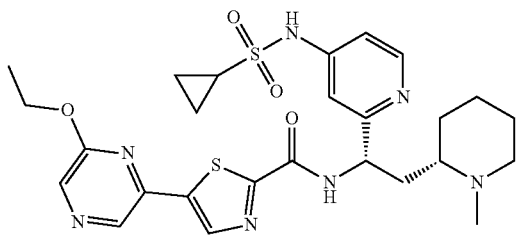 [SMILES: CCOc1cncc(-c2cnc(C(=O)N[C@@H](C[C@@H]3CCCCN3C)c3cc(NS(=O)(=O)C4CC4)ccn3)s2)n1] |
| I-135 | 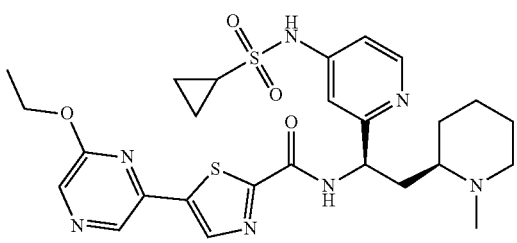 [SMILES: CCOc1cncc(-c2cnc(C(=O)N[C@H](C[C@H]3CCCCN3C)c3cc(NS(=O)(=O)C4CC4)ccn3)s2)n1] |
| I-136 | 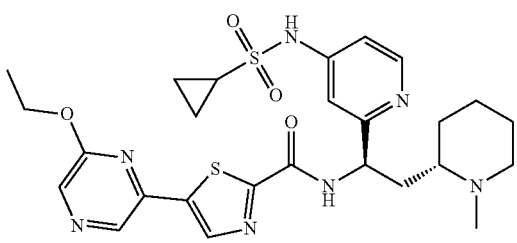 [SMILES: CCOc1cncc(-c2cnc(C(=O)N[C@H](C[C@@H]3CCCCN3C)c3cc(NS(=O)(=O)C4CC4)ccn3)s2)n1] |

| Compound | Structure |
|---|---|
| I-137 | 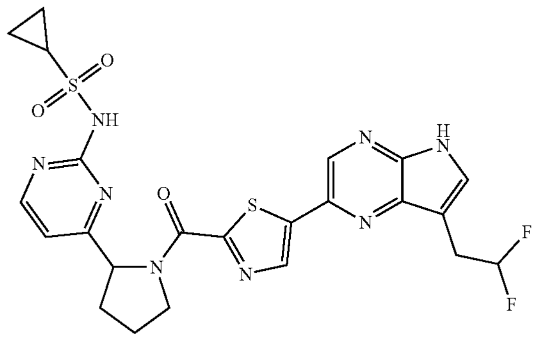 [SMILES: O=C(c1ncc(-c2cnc3[nH]cc(CC(F)F)c3n2)s1)N1CCCC1c1ccnc(NS(=O)(=O)C2CC2)n1] |
| I-138 | 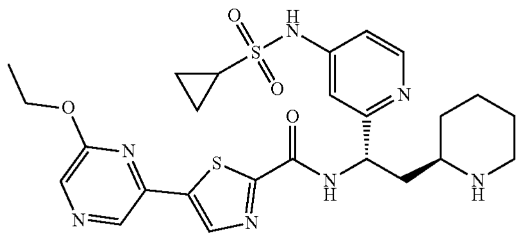 |
| I-139 | 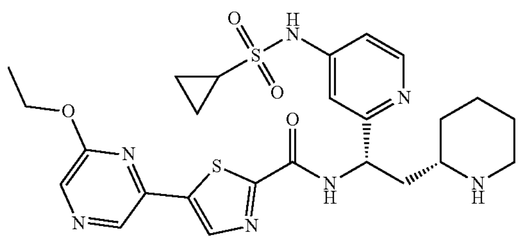 [SMILES: CCOc1cncc(-c2cnc(C(=O)N[C@@H](C[C@@H]3CCCCN3)c3cc(NS(=O)(=O)C4CC4)ccn3)s2)n1] |
| I-140 | 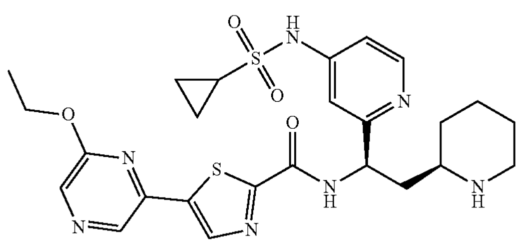 [SMILES: CCOc1cncc(-c2cnc(C(=O)N[C@H](C[C@H]3CCCCN3)c3cc(NS(=O)(=O)C4CC4)ccn3)s2)n1] |
| I-141 | 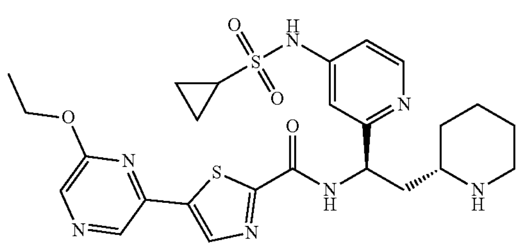 [SMILES: CCOc1cncc(-c2cnc(C(=O)N[C@H](C[C@@H]3CCCCN3)c3cc(NS(=O)(=O)C4CC4)ccn3)s2)n1] |
| I-142 | 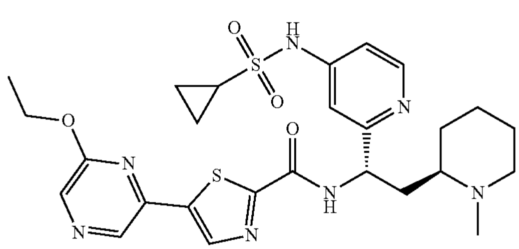 [SMILES: CCOc1cncc(-c2cnc(C(=O)N[C@@H](C[C@H]3CCCCN3C)c3cc(NS(=O)(=O)C4CC4)ccn3)s2)n1] |

| Compound | Structure |
|---|---|
| I-145 | 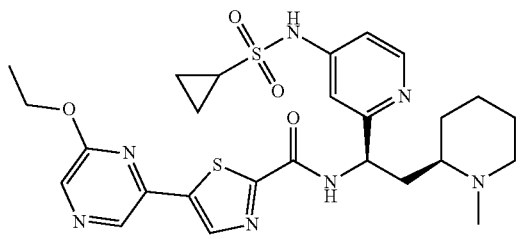 [SMILES: CCOc1cncc(-c2cnc(C(=O)N[C@H](C[C@H]3CCCCN3C)c3cc(NS(=O)(=O)C4CC4)ccn3)s2)n1] |
| I-146 | 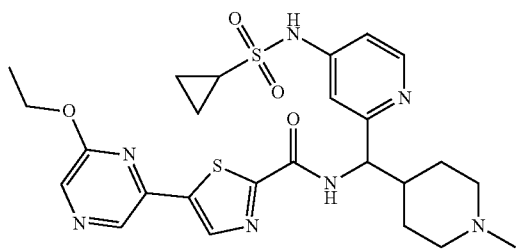 [SMILES: CCOc1cncc(-c2cnc(C(=O)NC(c3cc(NS(=O)(=O)C4CC4)ccn3)C3CCN(C)CC3)s2)n1] |
| I-147 | 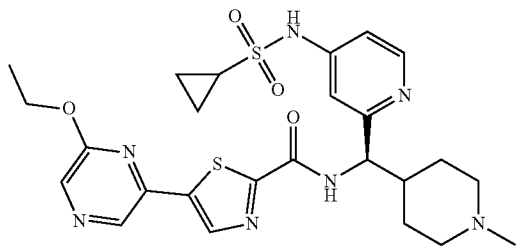 [SMILES: CCOc1cncc(-c2cnc(C(=O)N[C@@H](c3cc(NS(=O)(=O)C4CC4)ccn3)C3CCN(C)CC3)s2)n1] |
| I-148 | 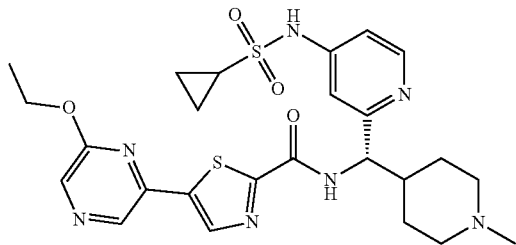 [SMILES: CCOc1cncc(-c2cnc(C(=O)N[C@H](c3cc(NS(=O)(=O)C4CC4)ccn3)C3CCN(C)CC3)s2)n1] |
| I-149 | 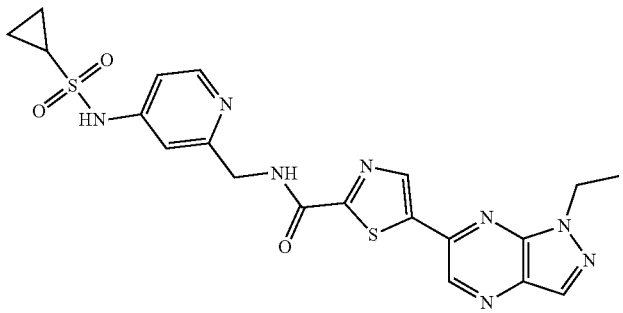 [SMILES: CCn1ncc2ncc(-c3cnc(C(=O)NCc4cc(NS(=O)(=O)C5CC5)ccn4)s3)nc21] |
| I-150 | 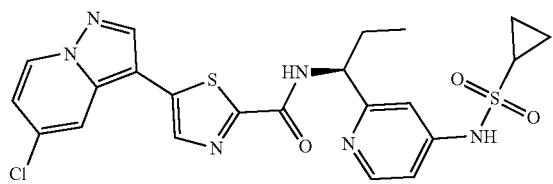 [SMILES: CC[C@H](NC(=O)c1ncc(-c2cnn3ccc(Cl)cc23)s1)c1cc(NS(=O)(=O)C2CC2)ccn1] |

| Compound | Structure |
|---|---|
| I-151 | 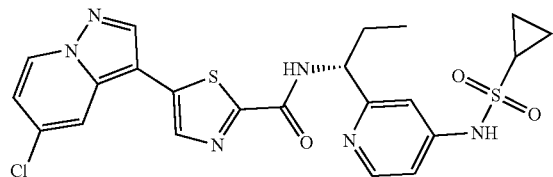 [SMILES: CC[C@@H](NC(=O)c1ncc(-c2cnn3ccc(Cl)cc23)s1)c1cc(NS(=O)(=O)C2CC2)ccn1] |
| I-153 | 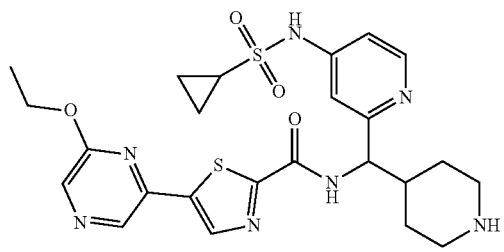 [SMILES: CCOc1cncc(-c2cnc(C(=O)NC(c3cc(NS(=O)(=O)C4CC4)ccn3)C3CCNCC3)s2)n1] |
| I-154 | 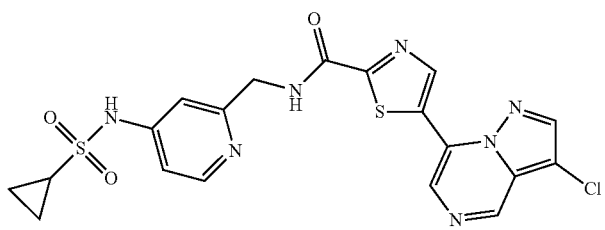 [SMILES: O=C(NCc1cc(NS(=O)(=O)C2CC2)ccn1)c1ncc(-c2cncc3c(Cl)cnn23)s1] |
| I-155 | 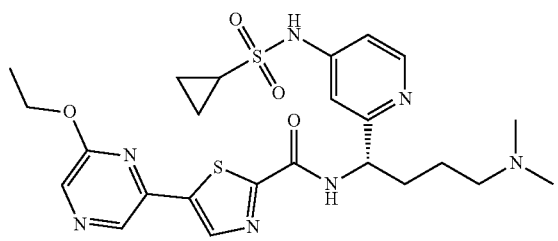 [SMILES: CCOc1cncc(-c2cnc(C(=O)N[C@@H](CCCN(C)C)c3cc(NS(=O)(=O)C4CC4)ccn3)s2)n1] |
| I-156 | 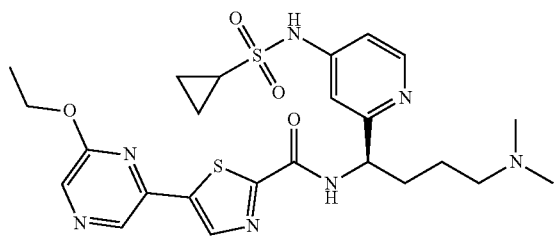 [SMILES: CCOc1cncc(-c2cnc(C(=O)N[C@H](CCCN(C)C)c3cc(NS(=O)(=O)C4CC4)ccn3)s2)n1] |
| I-157 | 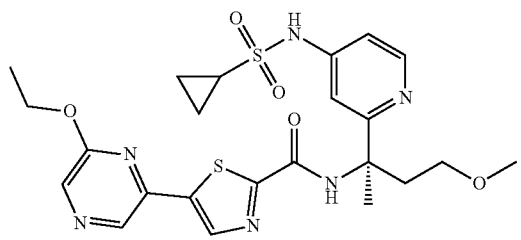 [SMILES: CCOc1cncc(-c2cnc(C(=O)N[C@](C)(CCOC)c3cc(NS(=O)(=O)C4CC4)ccn3)s2)n1] |

-continued
| Compound | Structure |
|---|---|
| I-158 | 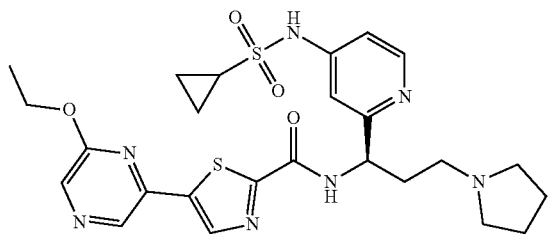 |
| I-159 | 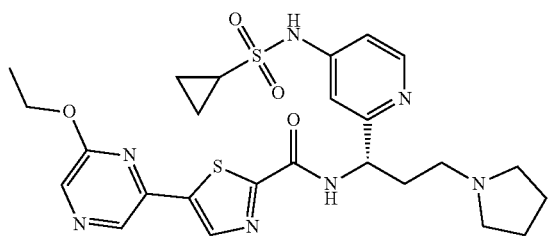 |
| I-160 | 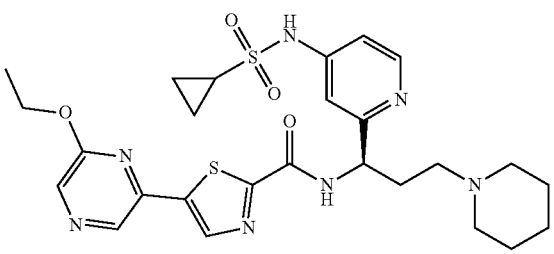 [SMILES: CCOc1cncc(-c2cnc(C(=O)N[C@H](CCN3CCCCC3)c3cc(NS(=O)(=O)C4CC4)ccn3)s2)n1] |
| I-161 | 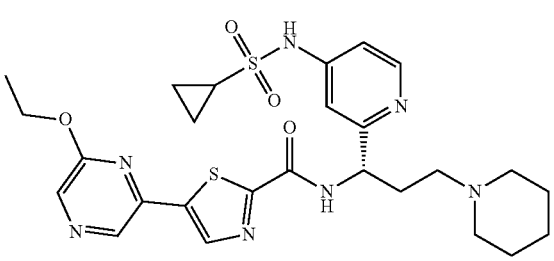 [SMILES: CCOc1cncc(-c2cnc(C(=O)N[C@@H](CCN3CCCCC3)c3cc(NS(=O)(=O)C4CC4)ccn3)s2)n1] |
| I-162 | 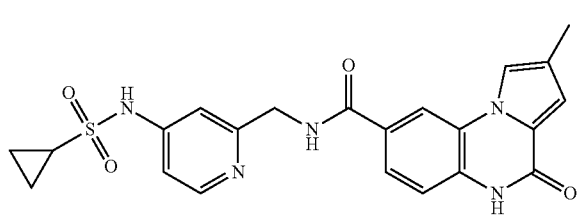 [SMILES: Cc1cc2c(=O)[nH]c3ccc(C(=O)NCc4cc(NS(=O)(=O)C5CC5)ccn4)cc3n2c1] |
| I-163 | 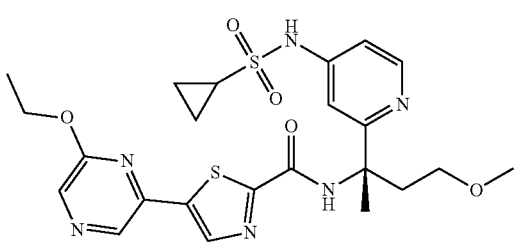 [SMILES: CCOc1cncc(-c2cnc(C(=O)N[C@@](C)(CCOC)c3cc(NS(=O)(=O)C4CC4)ccn3)s2)n1] |

| Compound | Structure |
|---|---|
| I-164 | 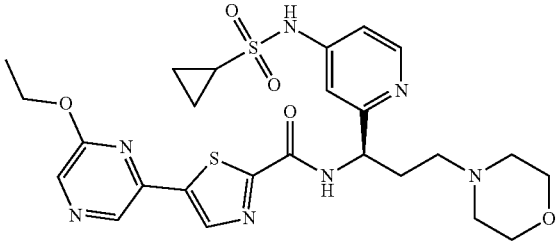 [SMILES: CCOc1cncc(-c2cnc(C(=O)N[C@H](CCN3CCOCC3)c3cc(NS(=O)(=O)C4CC4)ccn3)s2)n1] |
| I-165 | 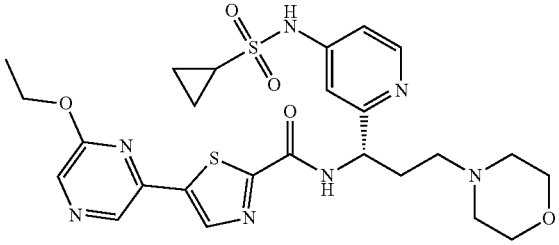 [SMILES: CCOc1cncc(-c2cnc(C(=O)N[C@@H](CCN3CCOCC3)c3cc(NS(=O)(=O)C4CC4)ccn3)s2)n1] |
| I-166 | 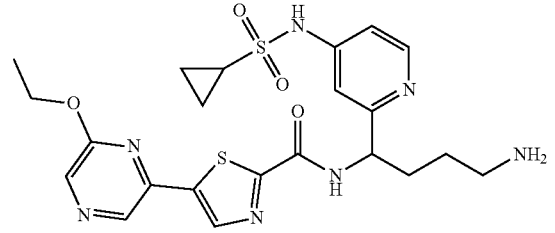 [SMILES: CCOc1cncc(-c2cnc(C(=O)NC(CCCN)c3cc(NS(=O)(=O)C4CC4)ccn3)s2)n1] |
| I-167 | 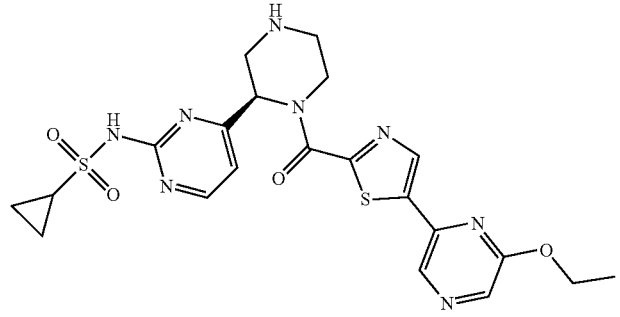 [SMILES: CCOc1cncc(-c2cnc(C(=O)N3CCNC[C@@H]3c3ccnc(NS(=O)(=O)C4CC4)n3)s2)n1] |
| I-168 | 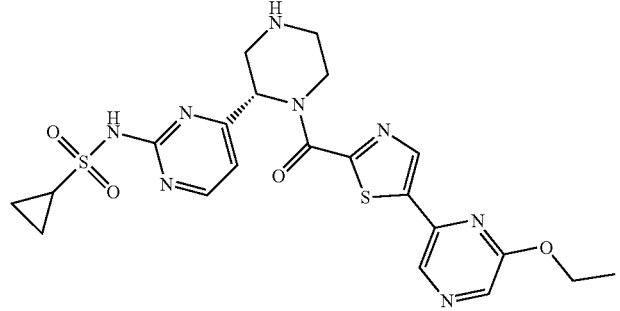 [SMILES: CCOc1cncc(-c2cnc(C(=O)N3CCNC[C@H]3c3ccnc(NS(=O)(=O)C4CC4)n3)s2)n1] |

-continued
| Compound | Structure |
|---|---|
| I-169 | 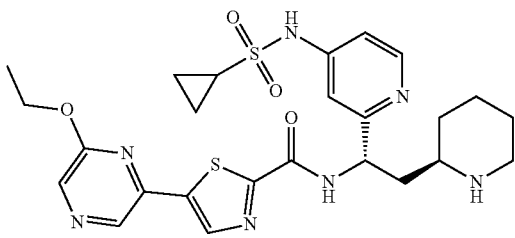 [SMILES: CCOc1cncc(-c2cnc(C(=O)N[C@@H](C[C@H]3CCCCN3)c3cc(NS(=O)(=O)C4CC4)ccn3)s2)n1] |
| I-170 | 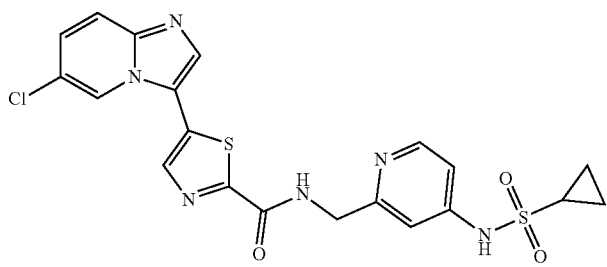 [SMILES: O=C(NCc1cc(NS(=O)(=O)C2CC2)ccn1)c1ncc(-c2cnc3ccc(Cl)cn23)s1] |
| I-171 | 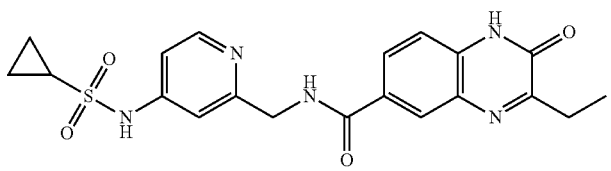 [SMILES: CCc1nc2cc(C(=O)NCc3cc(NS(=O)(=O)C4CC4)ccn3)ccc2[nH]c1=O] |
| I-172 | 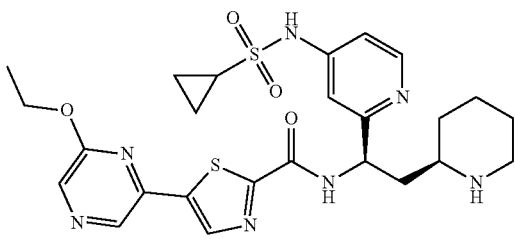 [SMILES: CCOc1cncc(-c2cnc(C(=O)N[C@H](C[C@H]3CCCCN3)c3cc(NS(=O)(=O)C4CC4)ccn3)s2)n1] |
| I-173 | 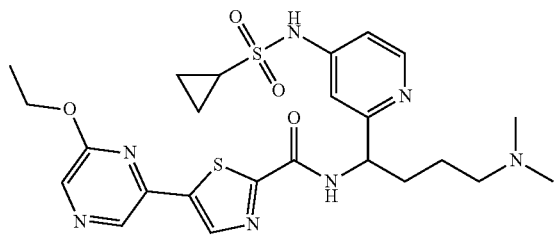 [SMILES: CCOc1cncc(-c2cnc(C(=O)NC(CCCN(C)C)c3cc(NS(=O)(=O)C4CC4)ccn3)s2)n1] |
| I-174 | 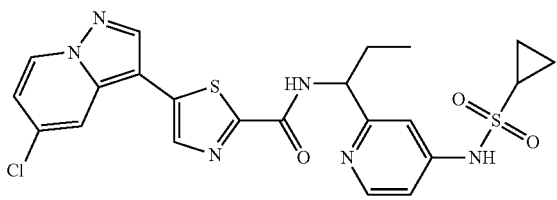 [SMILES: CCC(NC(=O)c1ncc(-c2cnn3ccc(Cl)cc23)s1)c1cc(NS(=O)(=O)C2CC2)ccn1] |

-continued
| Compound | Structure |
|---|---|
| I-175 | 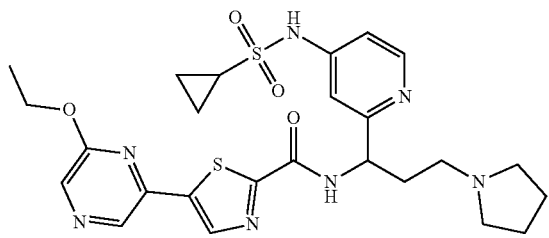 |
| I-176 | 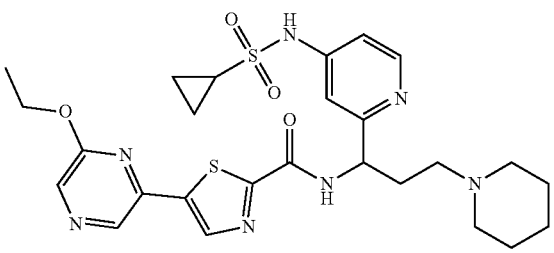 |
| I-177 | 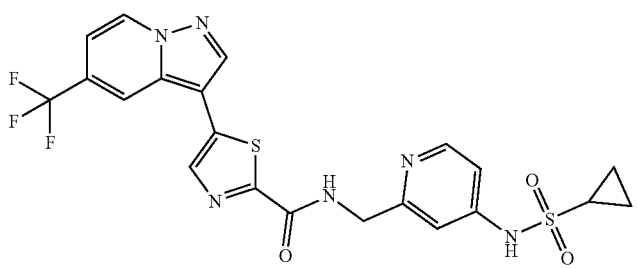 [SMILES: O=C(NCc1cc(NS(=O)(=O)C2CC2)ccn1)c1ncc(-c2cnn3ccc(C(F)(F)F)cc23)s1] |
| I-178 | 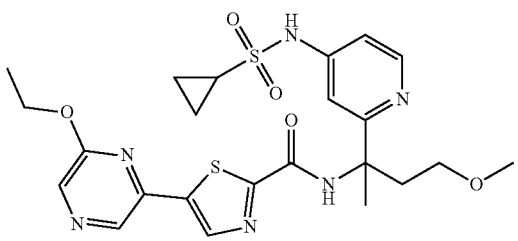 [SMILES: CCOc1cncc(-c2cnc(C(=O)NC(C)(CCOC)c3cc(NS(=O)(=O)C4CC4)ccn3)s2)n1] |
| I-179 | 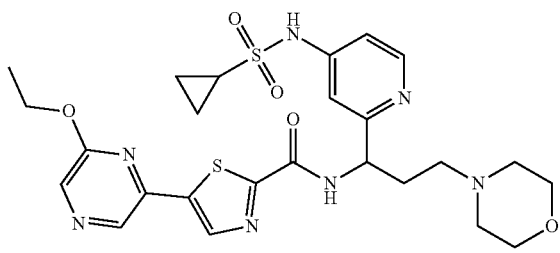 |
| I-180 | 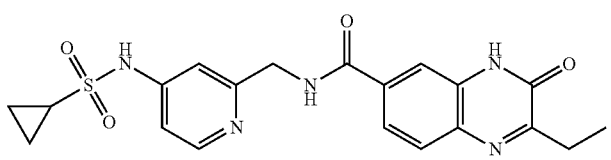 [SMILES: CCc1nc2ccc(C(=O)NCc3cc(NS(=O)(=O)C4CC4)ccn3)cc2[nH]c1=O] |

-continued
| Compound | Structure |
|---|---|
| I-181 | 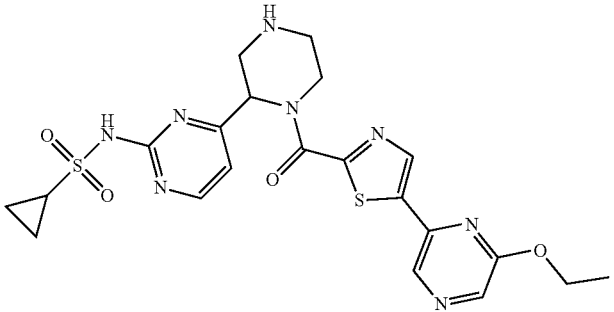 [SMILES: CCOc1cncc(-c2cnc(C(=O)N3CCNCC3c3ccnc(NS(=O)(=O)C4CC4)n3)s2)n1] |
| I-182 | 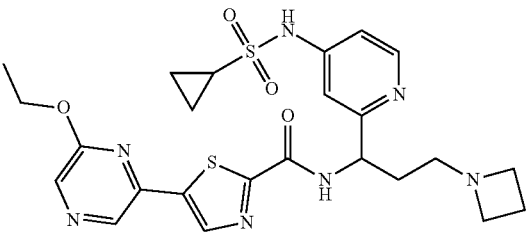 [SMILES: CCOc1cncc(-c2cnc(C(=O)NC(CCN3CCC3)c3cc(NS(=O)(=O)C4CC4)ccn3)s2)n1] |
| I-183 | 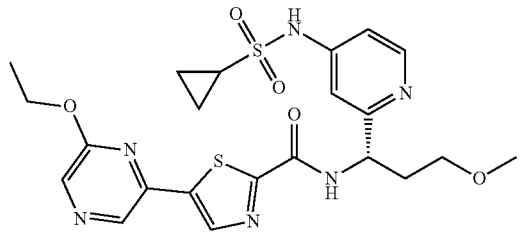 [SMILES: CCOc1cncc(-c2cnc(C(=O)N[C@@H](CCOC)c3cc(NS(=O)(=O)C4CC4)ccn3)s2)n1] |
| I-184 | 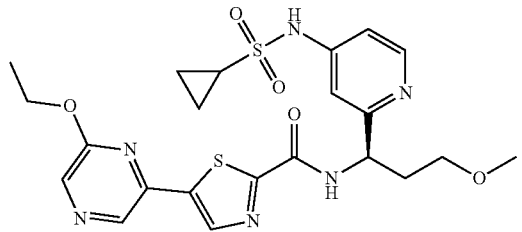 [SMILES: CCOc1cncc(-c2cnc(C(=O)N[C@H](CCOC)c3cc(NS(=O)(=O)C4CC4)ccn3)s2)n1] |
| I-185 | 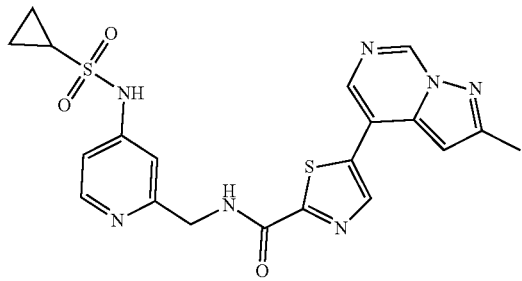 [SMILES: Cc1cc2c(-c3cnc(C(=O)NCc4cc(NS(=O)(=O)C5CC5)ccn4)s3)cncn2n1] |
| I-186 | 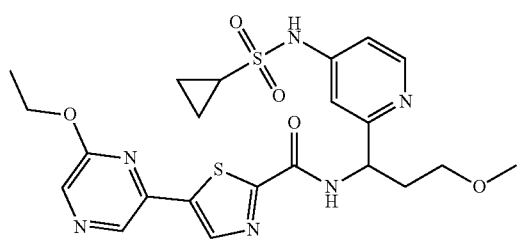 |

| Compound | Structure |
|---|---|
| I-187 | 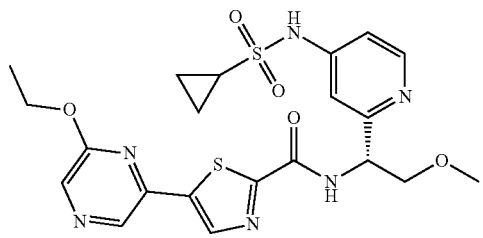 [SMILES: CCOc1cncc(-c2cnc(C(=O)N[C@@H](COC)c3cc(NS(=O)(=O)C4CC4)ccn3)s2)n1] |
| I-188 | 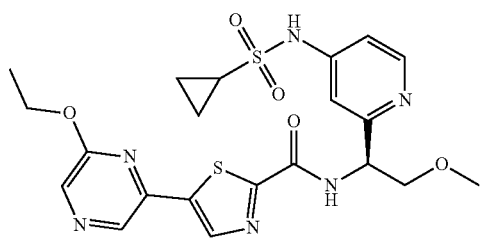 [SMILES: CCOc1cncc(-c2cnc(C(=O)N[C@H](COC)c3cc(NS(=O)(=O)C4CC4)ccn3)s2)n1] |
| I-189 | 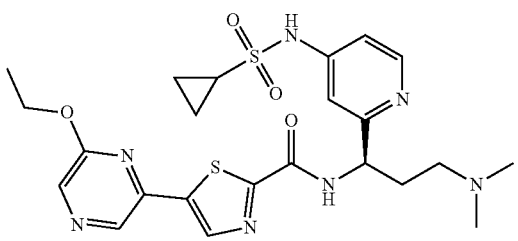 [SMILES: CCOc1cncc(-c2cnc(C(=O)N[C@H](CCN(C)C)c3cc(NS(=O)(=O)C4CC4)ccn3)s2)n1] |
| I-190 | 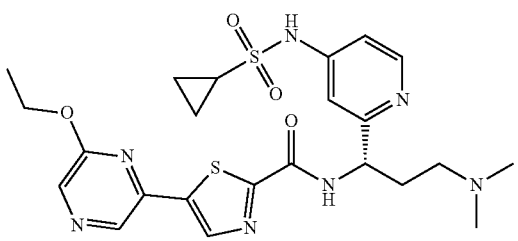 [SMILES: CCOc1cncc(-c2cnc(C(=O)N[C@@H](CCN(C)C)c3cc(NS(=O)(=O)C4CC4)ccn3)s2)n1] |
| I-191 | 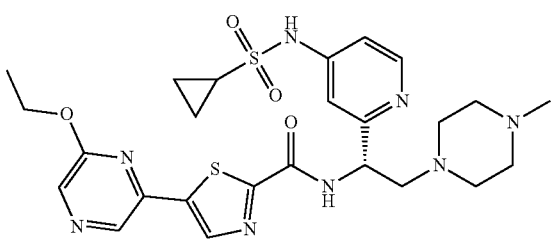 [SMILES: CCOc1cncc(-c2cnc(C(=O)N[C@@H](CN3CCN(C)CC3)c3cc(NS(=O)(=O)C4CC4)ccn3)s2)n1] |
| I-192 | 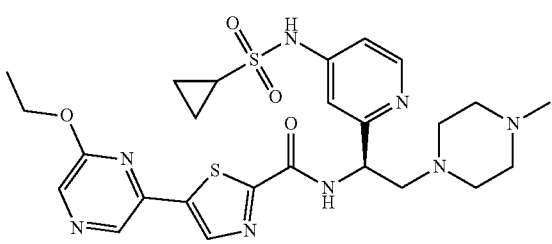 [SMILES: CCOc1cncc(-c2cnc(C(=O)N[C@H](CN3CCN(C)CC3)c3cc(NS(=O)(=O)C4CC4)ccn3)s2)n1] |

-continued

| Compound | Structure |
|---|---|
| I-193 | 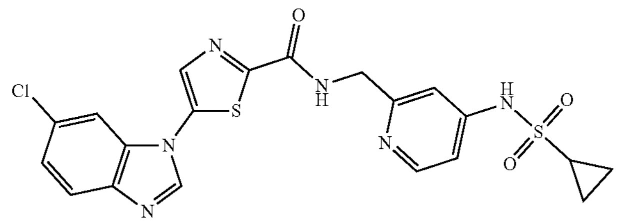 [SMILES: O=C(NCc1cc(NS(=O)(=O)C2CC2)ccn1)c1ncc(-n2cnc3ccc(Cl)cc32)s1] |
| I-194 | 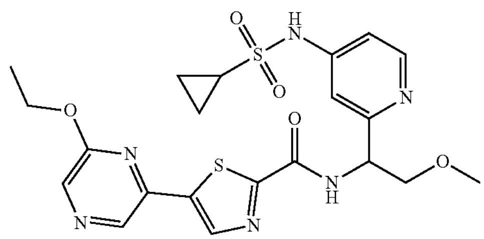 [SMILES: CCOc1cncc(-c2cnc(C(=O)NC(COC)c3cc(NS(=O)(=O)C4CC4)ccn3)s2)n1] |
| I-195 | 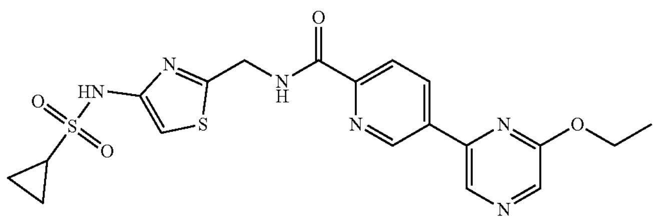 [SMILES: CCOc1cncc(-c2ccc(C(=O)NCc3nc(NS(=O)(=O)C4CC4)cs3)nc2)n1] |
| I-196 | 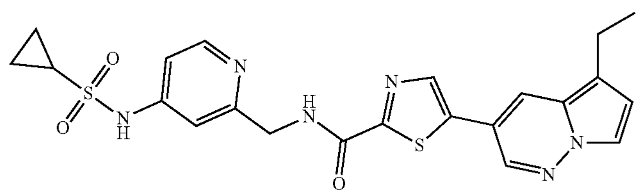 [SMILES: CCc1ccn2ncc(-c3cnc(C(=O)NCc4cc(NS(=O)(=O)C5CC5)ccn4)s3)cc12] |
| I-197 | 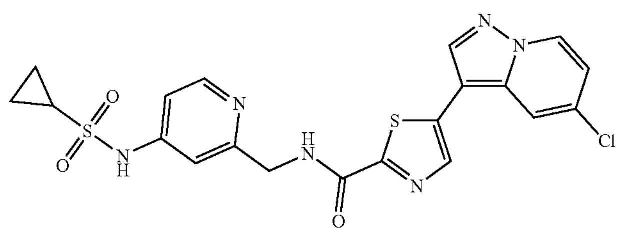 [SMILES: O=C(NCc1cc(NS(=O)(=O)C2CC2)ccn1)c1ncc(-c2cnn3ccc(Cl)cc23)s1] |
| I-198 | 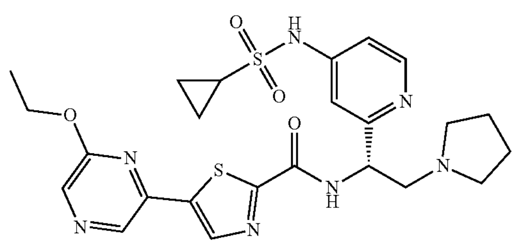 [SMILES: CCOc1cncc(-c2cnc(C(=O)N[C@@H](CN3CCCC3)c3cc(NS(=O)(=O)C4CC4)ccn3)s2)n1] |
| I-199 | 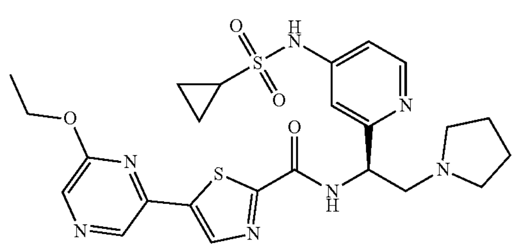 [SMILES: CCOc1cncc(-c2cnc(C(=O)N[C@H](CN3CCCC3)c3cc(NS(=O)(=O)C4CC4)ccn3)s2)n1] |

-continued
| Compound | Structure |
|---|---|
| I-200 | 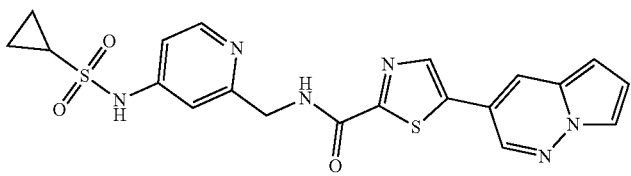 [SMILES: O=C(NCc1cc(NS(=O)(=O)C2CC2)ccn1)c1ncc(-c2cnn3cccc3c2)s1] |
| I-201 | 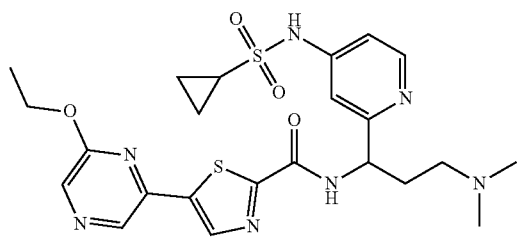 [SMILES: CCOc1cncc(-c2cnc(C(=O)NC(CCN(C)C)c3cc(NS(=O)(=O)C4CC4)ccn3)s2)n1] |
| I-202 | 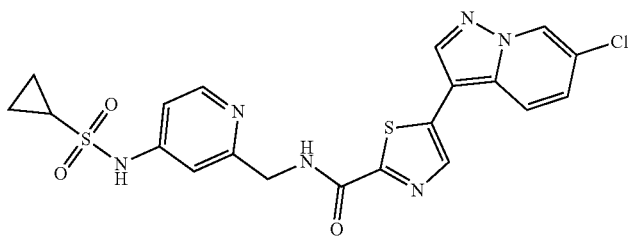 [SMILES: O=C(NCc1cc(NS(=O)(=O)C2CC2)ccn1)c1ncc(-c2cnn3cc(Cl)ccc23)s1] |
| I-203 | 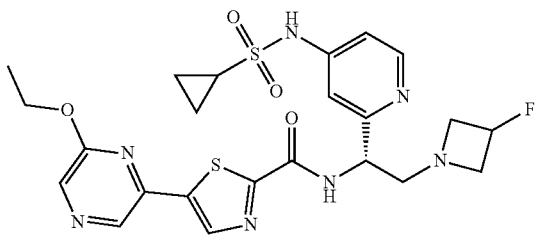 [SMILES: CCOc1cncc(-c2cnc(C(=O)N[C@@H](CN3CC(F)C3)c3cc(NS(=O)(=O)C4CC4)ccn3)s2)n1] |
| I-204 | 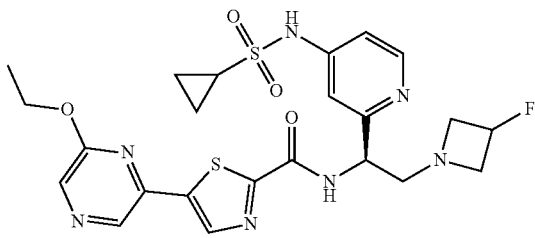 [SMILES: CCOc1cncc(-c2cnc(C(=O)N[C@H](CN3CC(F)C3)c3cc(NS(=O)(=O)C4CC4)ccn3)s2)n1] |
| I-205 | 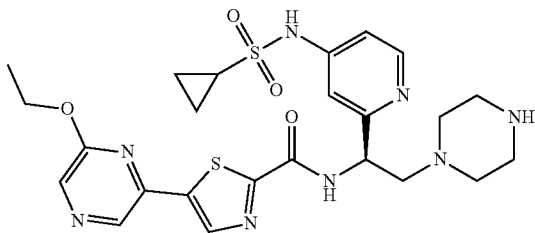 [SMILES: CCOc1cncc(-c2cnc(C(=O)N[C@H](CN3CCNCC3)c3cc(NS(=O)(=O)C4CC4)ccn3)s2)n1] |

| Compound | Structure |
|---|---|
| I-206 | 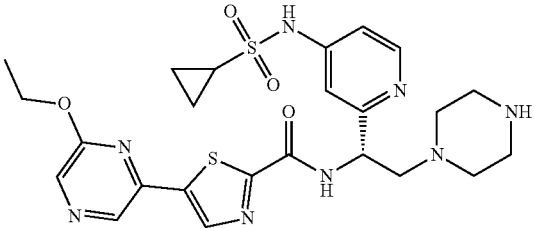 |
| I-207 | 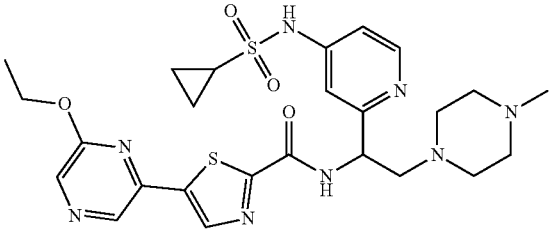 |
| I-208 | 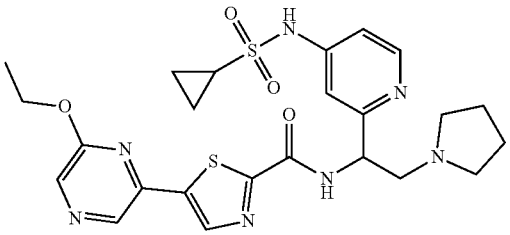 [SMILES: CCOc1cncc(-c2cnc(C(=O)NC(CN3CCCC3)c3cc(NS(=O)(=O)C4CC4)ccn3)s2)n1] |
| I-209 | 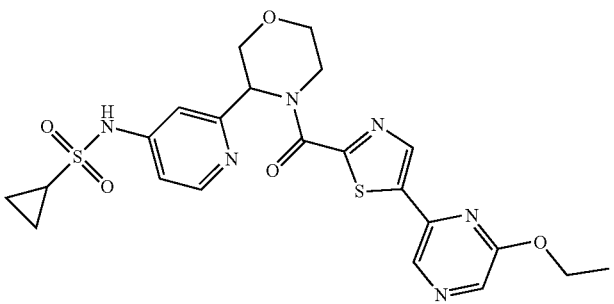 [SMILES: CCOc1cncc(-c2cnc(C(=O)N3CCOCC3c3cc(NS(=O)(=O)C4CC4)ccn3)s2)n1] |
| I-210 | 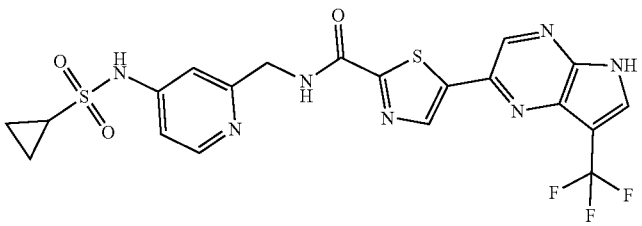 [SMILES: O=C(NCc1cc(NS(=O)(=O)C2CC2)ccn1)c1ncc(-c2cnc3[nH]cc(C(F)(F)F)c3n2)s1] |
| I-211 | 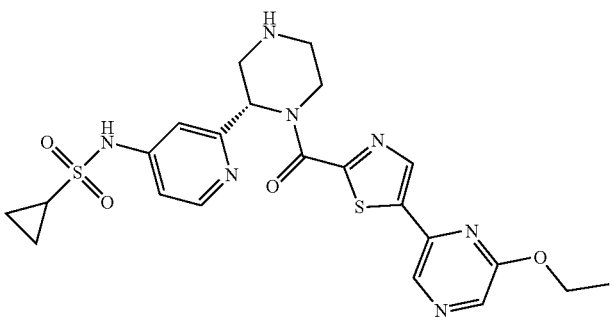 [SMILES: CCOc1cncc(-c2cnc(C(=O)N3CCNC[C@H]3c3cc(NS(=O)(=O)C4CC4)ccn3)s2)n1] |

-continued

| Compound | Structure |
|---|---|
| I-212 | 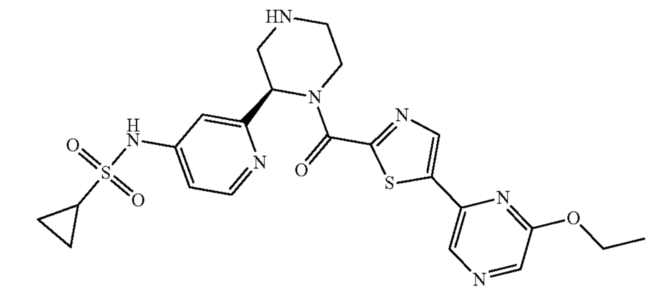 [SMILES: CCOc1cncc(-c2cnc(C(=O)N3CCNC[C@@H]3c3cc(NS(=O)(=O)C4CC4)ccn3)s2)n1] |
| I-213 | 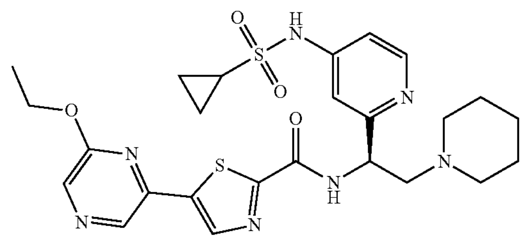 [SMILES: CCOc1cncc(-c2cnc(C(=O)N[C@H](CN3CCCCC3)c3cc(NS(=O)(=O)C4CC4)ccn3)s2)n1] |
| I-214 | 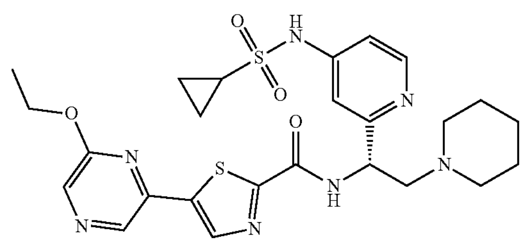 [SMILES: CCOc1cncc(-c2cnc(C(=O)N[C@@H](CN3CCCCC3)c3cc(NS(=O)(=O)C4CC4)ccn3)s2)n1] |
| I-215 | 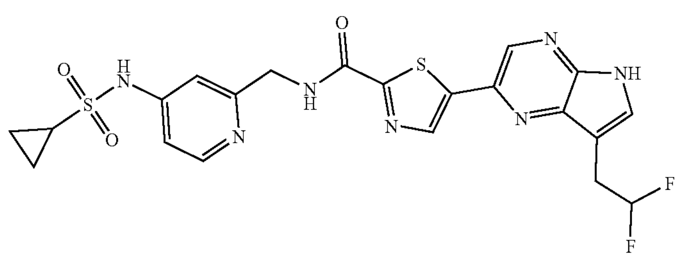 [SMILES: O=C(NCc1cc(NS(=O)(=O)C2CC2)ccn1)c1ncc(-c2cnc3[nH]cc(CC(F)F)c3n2)s1] |
| I-216 | 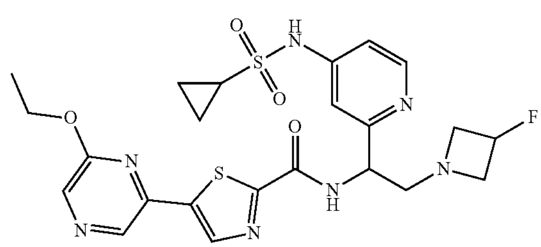 [SMILES: CCOc1cncc(-c2cnc(C(=O)NC(CN3CC(F)C3)c3cc(NS(=O)(=O)C4CC4)ccn3)s2)n1] |
| I-217 | 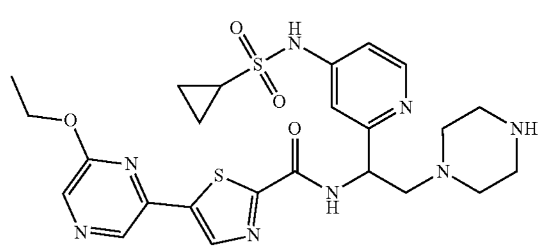 [SMILES: CCOc1cncc(-c2cnc(C(=O)NC(CN3CCNCC3)c3cc(NS(=O)(=O)C4CC4)ccn3)s2)n1] |

-continued
| Compound | Structure |
|---|---|
| I-218 | 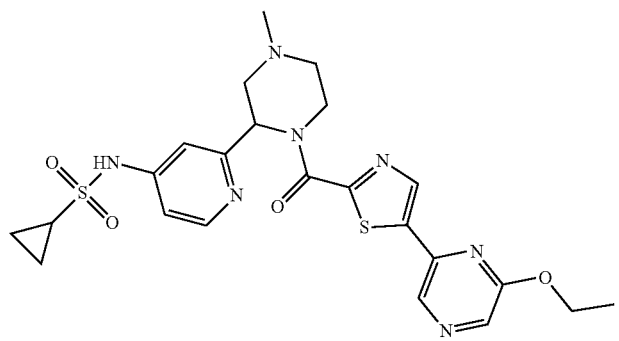 [SMILES: CCOc1cncc(-c2cnc(C(=O)N3CCN(C)CC3c3cc(NS(=O)(=O)C4CC4)ccn3)s2)n1] |
| I-219 | 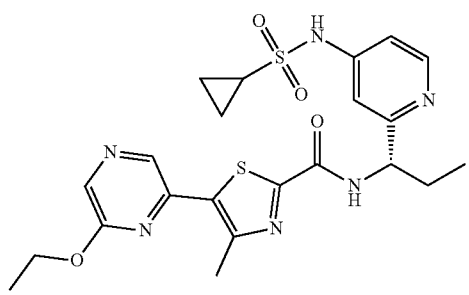 [SMILES: CCOc1cncc(-c2sc(C(=O)N[C@@H](CC)c3cc(NS(=O)(=O)C4CC4)ccn3)nc2C)n1] |
| I-220 | 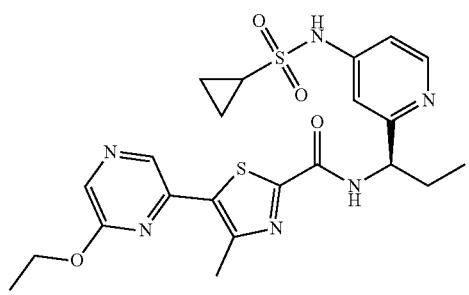 [SMILES: CCOc1cncc(-c2sc(C(=O)N[C@H](CC)c3cc(NS(=O)(=O)C4CC4)ccn3)nc2C)n1] |
| I-221 | 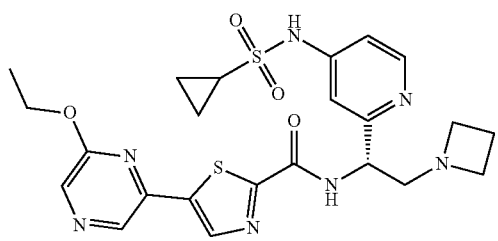 [SMILES: CCOc1cncc(-c2cnc(C(=O)N[C@@H](CN3CCC3)c3cc(NS(=O)(=O)C4CC4)ccn3)s2)n1] |
| I-222 | 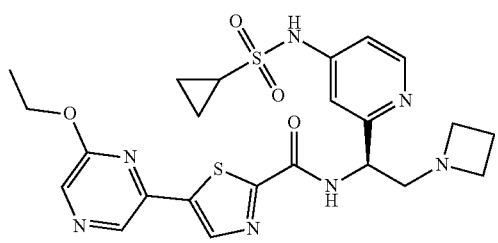 |

-continued
| Compound | Structure |
|---|---|
| I-223 | 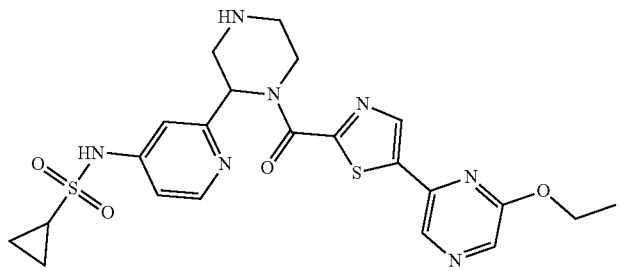 [SMILES: CCOc1cncc(-c2cnc(C(=O)N3CCNCC3c3cc(NS(=O)(=O)C4CC4)ccn3)s2)n1] |
| I-224 | 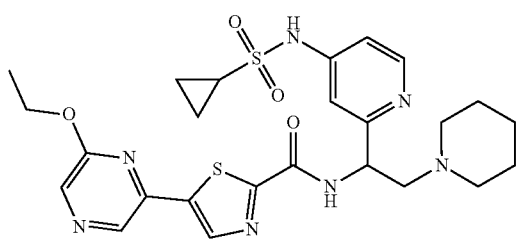 [SMILES: CCOc1cncc(-c2cnc(C(=O)NC(CN3CCCCC3)c3cc(NS(=O)(=O)C4CC4)ccn3)s2)n1] |
| I-225 | 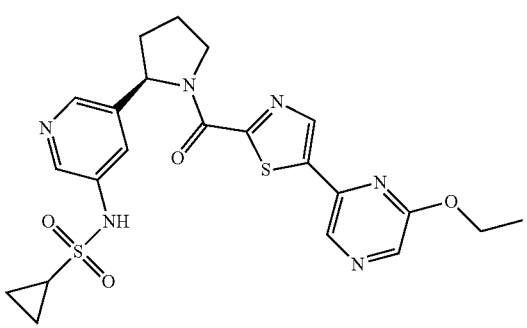 [SMILES: CCOc1cncc(-c2cnc(C(=O)N3CCC[C@@H]3c3cncc(NS(=O)(=O)C4CC4)c3)s2)n1] |
| I-226 | 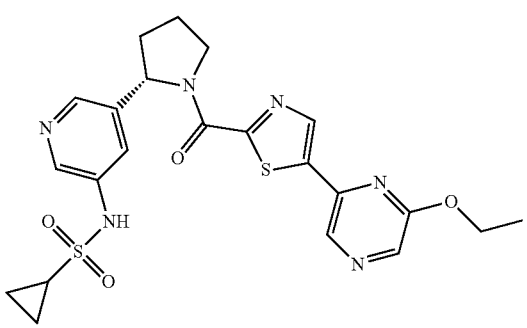 [SMILES: CCOc1cncc(-c2cnc(C(=O)N3CCC[C@H]3c3cncc(NS(=O)(=O)C4CC4)c3)s2)n1] |
| I-227 | 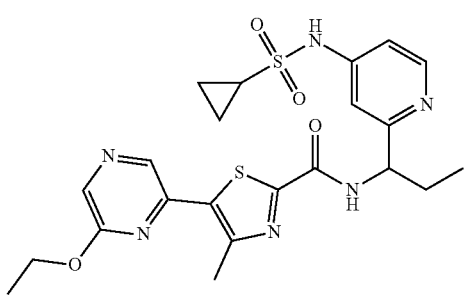 [SMILES: CCOc1cncc(-c2sc(C(=O)NC(CC)c3cc(NS(=O)(=O)C4CC4)ccn3)nc2C)n1] |

-continued
| Compound | Structure |
|---|---|
| I-228 | 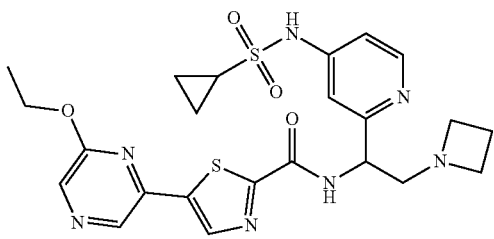 |
| I-229 | 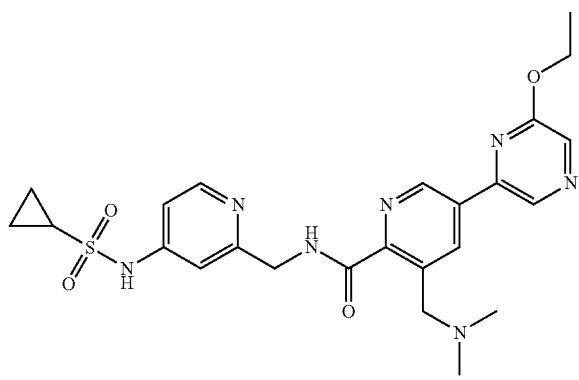 [SMILES: CCOc1cncc(-c2cnc(C(=O)NCc3cc(NS(=O)(=O)C4CC4)ccn3)c(CN(C)C)c2)n1] |
| I-230 | 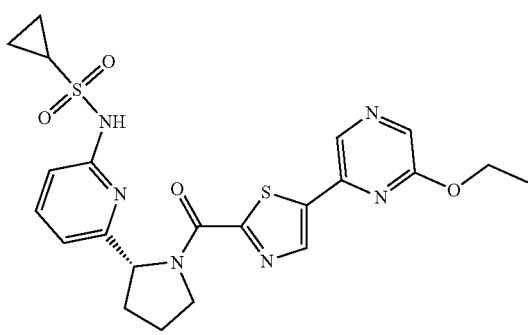 [SMILES: CCOc1cncc(-c2cnc(C(=O)N3CCC[C@@H]3c3cccc(NS(=O)(=O)C4CC4)n3)s2)n1] |
| I-231 | 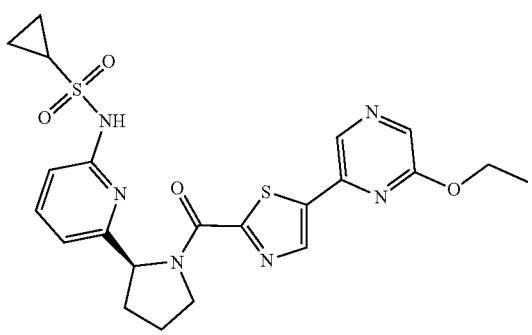 [SMILES: CCOc1cncc(-c2cnc(C(=O)N3CCC[C@H]3c3cccc(NS(=O)(=O)C4CC4)n3)s2)n1] |
| I-232 | 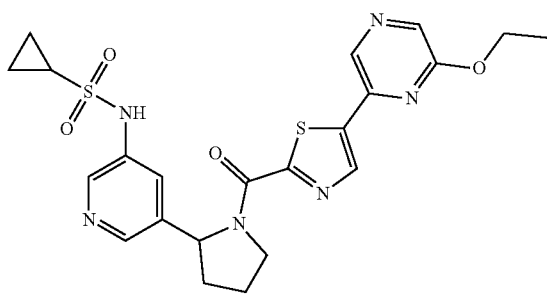 [SMILES: CCOc1cncc(-c2cnc(C(=O)N3CCCC3c3cncc(NS(=O)(=O)C4CC4)c3)s2)n1] |

-continued
| Compound | Structure |
|---|---|
| I-233 | 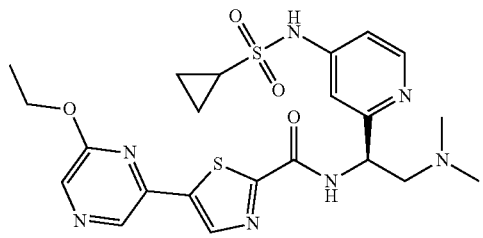 [SMILES: CCOc1cncc(-c2cnc(C(=O)N[C@H](CN(C)C)c3cc(NS(=O)(=O)C4CC4)ccn3)s2)n1] |
| I-234 | 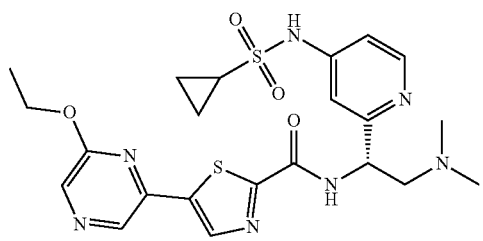 |
| I-235 | 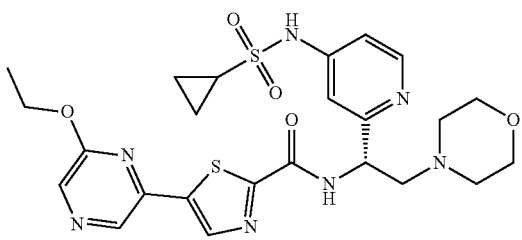 [SMILES: CCOc1cncc(-c2cnc(C(=O)N[C@@H](CN3CCOCC3)c3cc(NS(=O)(=O)C4CC4)ccn3)s2)n1] |
| I-236 | 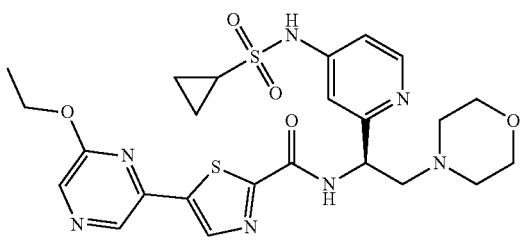 |
| I-237 | 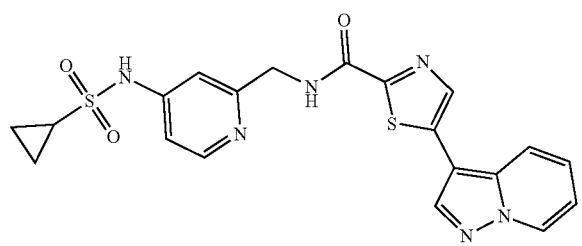 [SMILES: O=C(NCc1cc(NS(=O)(=O)C2CC2)ccn1)c1ncc(-c2cnn3ccccc23)s1] |
| I-238 | 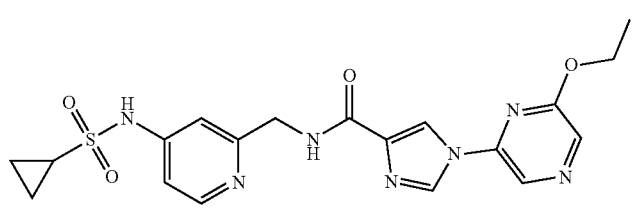 [SMILES: CCOc1cncc(-n2cnc(C(=O)NCc3cc(NS(=O)(=O)C4CC4)ccn3)c2)n1] |

-continued

| Compound | Structure |
|---|---|
| I-239 | 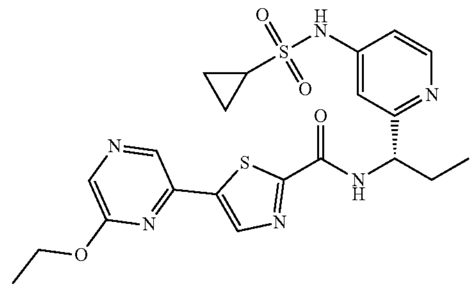 [SMILES: CCOc1cncc(-c2cnc(C(=O)N[C@@H](CC)c3cc(NS(=O)(=O)C4CC4)ccn3)s2)n1] |
| I-240 | 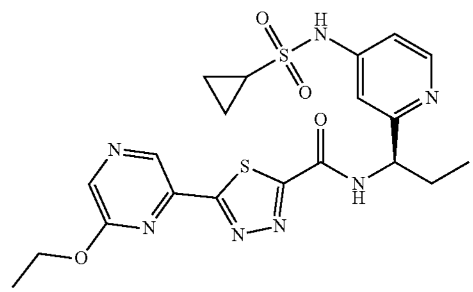 [SMILES: CCOc1cncc(-c2nnc(C(=O)N[C@H](CC)c3cc(NS(=O)(=O)C4CC4)ccn3)s2)n1] |
| I-241 | 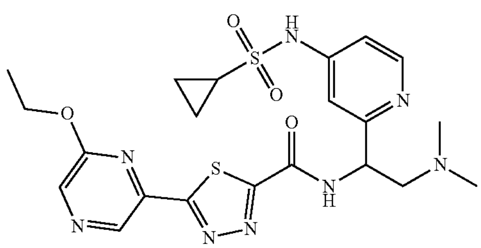 [SMILES: CCOc1cncc(-c2nnc(C(=O)NC(CN(C)C)c3cc(NS(=O)(=O)C4CC4)ccn3)s2)n1] |
| I-242 | 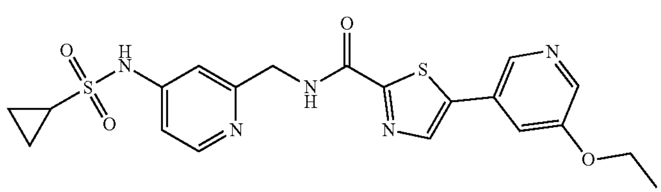 [SMILES: CCOc1cncc(-c2cnc(C(=O)NCc3cc(NS(=O)(=O)C4CC4)ccn3)s2)c1] |
| I-243 | 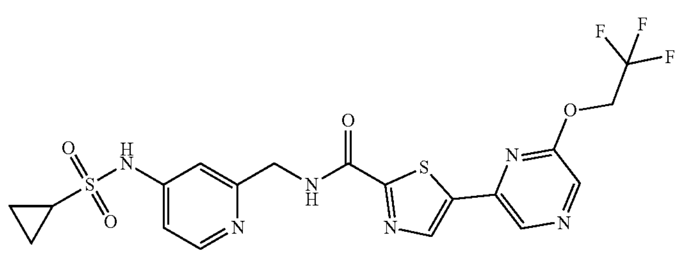 [SMILES: O=C(NCc1cc(NS(=O)(=O)C2CC2)ccn1)c1ncc(-c2cncc(OCC(F)(F)F)n2)s1] |
| I-244 | 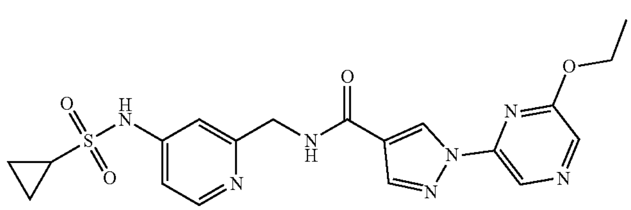 [SMILES: CCOc1cncc(-n2cc(C(=O)NCc3cc(NS(=O)(=O)C4CC4)ccn3)cn2)n1] |

-continued

| Compound | Structure |
|---|---|
| I-245 | 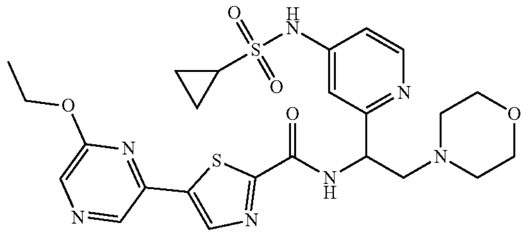 |
| I-246 | 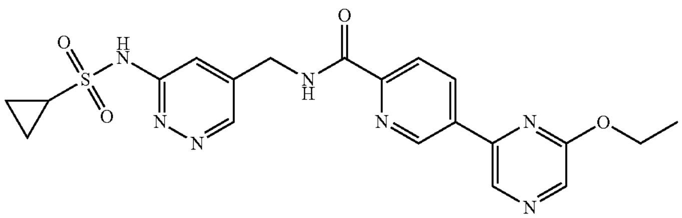 [SMILES: CCOc1cncc(-c2ccc(C(=O)NCc3cnnc(NS(=O)(=O)C4CC4)c3)nc2)n1] |
| I-251 | 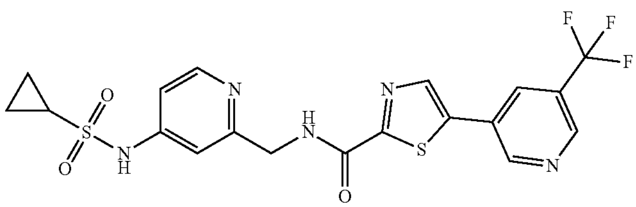 [SMILES: O=C(NCc1cc(NS(=O)(=O)C2CC2)ccn1)c1ncc(-c2cncc(C(F)(F)F)c2)s1] |
| I-252 | 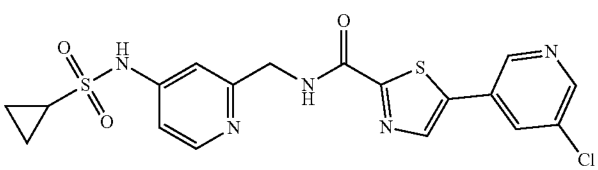 [SMILES: O=C(NCc1cc(NS(=O)(=O)C2CC2)ccn1)c1ncc(-c2cncc(Cl)c2)s1] |
| I-253 | 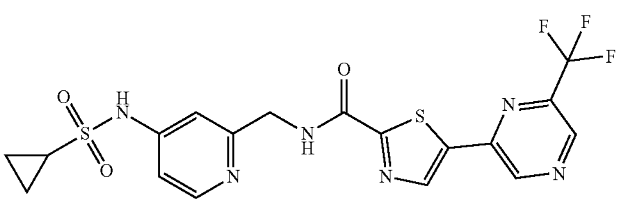 [SMILES: O=C(NCc1cc(NS(=O)(=O)C2CC2)ccn1)c1ncc(-c2cncc(C(F)(F)F)n2)s1] |
| I-254 | 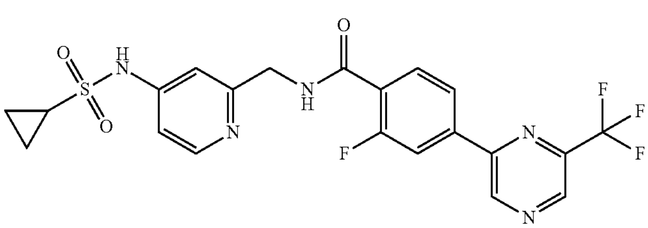 [SMILES: O=C(NCc1cc(NS(=O)(=O)C2CC2)ccn1)c1ccc(-c2cncc(C(F)(F)F)n2)cc1F] |
| I-257 | 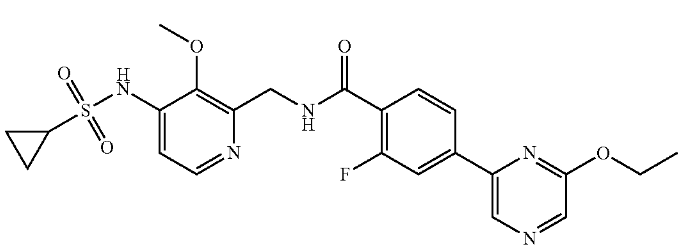 [SMILES: CCOc1cncc(-c2ccc(C(=O)NCc3nccc(NS(=O)(=O)C4CC4)c3OC)c(F)c2)n1] |

-continued
| Compound | Structure |
|---|---|
| I-258 | 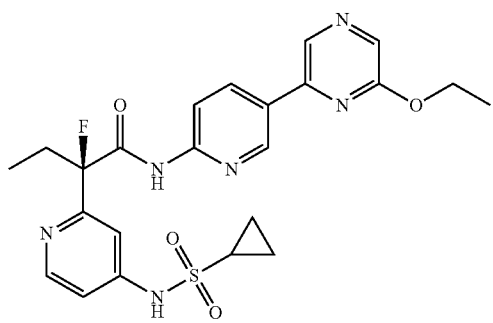 [SMILES: CCOc1cncc(-c2ccc(NC(=O)[C@@](F)(CC)c3cc(NS(=O)(=O)C4CC4)ccn3)nc2)n1] |
| I-259 | 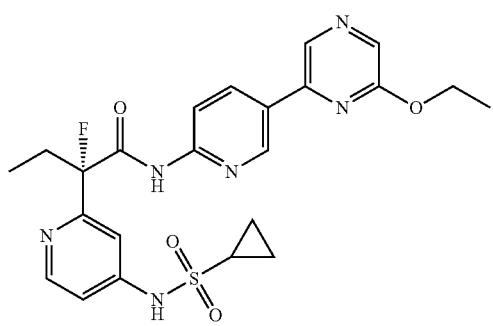 [SMILES: CCOc1cncc(-c2ccc(NC(=O)[C@](F)(CC)c3cc(NS(=O)(=O)C4CC4)ccn3)nc2)n1] |
| I-260 | 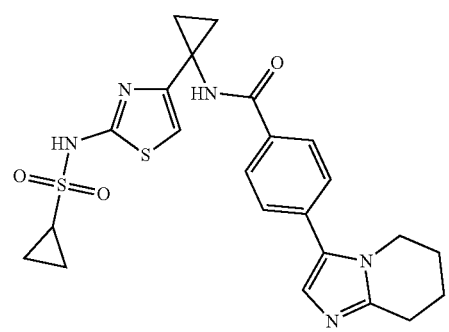 [SMILES: O=C(NC1(c2csc(NS(=O)(=O)C3CC3)n2)CC1)c1ccc(-c2cnc3n2CCCC3)cc1] |
| I-261 | 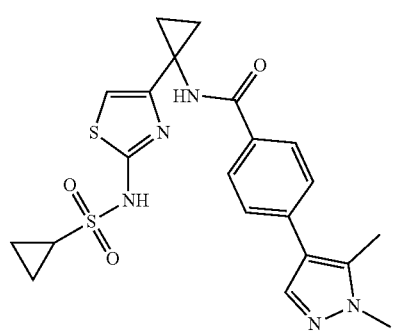 [SMILES: Cc1c(-c2ccc(C(=O)NC3(c4csc(NS(=O)(=O)C5CC5)n4)CC3)cc2)cnn1C] |
| I-263 | 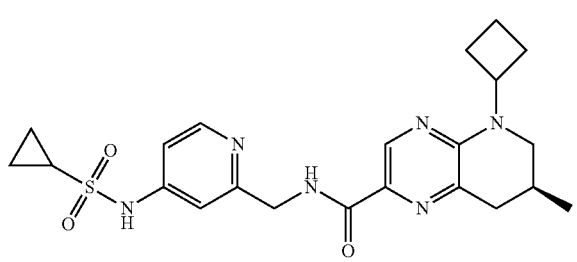 [SMILES: C[C@H]1Cc2nc(C(=O)NCc3cc(NS(=O)(=O)C4CC4)ccn3)cnc2N(C2CCC2)C1] |

| Compound | Structure |
|---|---|
| I-264 | 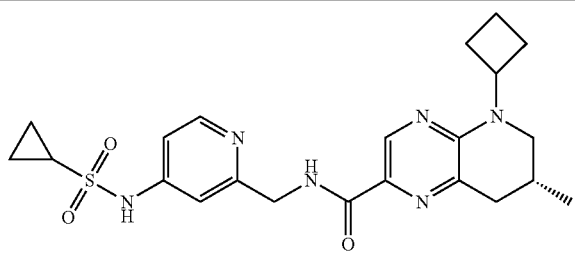 [SMILES: C[C@@H]1Cc2nc(C(=O)NCc3cc(NS(=O)(=O)C4CC4)ccn3)cnc2N(C2CCC2)C1] |
| I-270 | 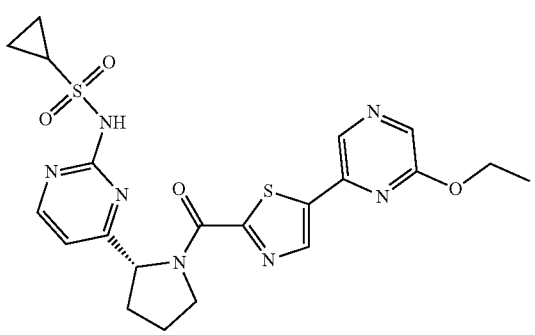 [SMILES: CCOc1cncc(-c2cnc(C(=O)N3CCC[C@@H]3c3ccnc(NS(=O)(=O)C4CC4)n3)s2)n1] |
| I-271 | 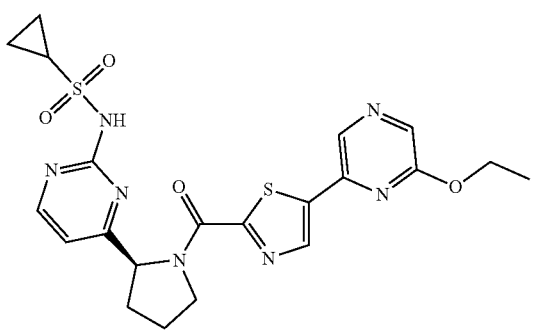 [SMILES: CCOc1cncc(-c2cnc(C(=O)N3CCC[C@H]3c3ccnc(NS(=O)(=O)C4CC4)n3)s2)n1] |
| I-275 | 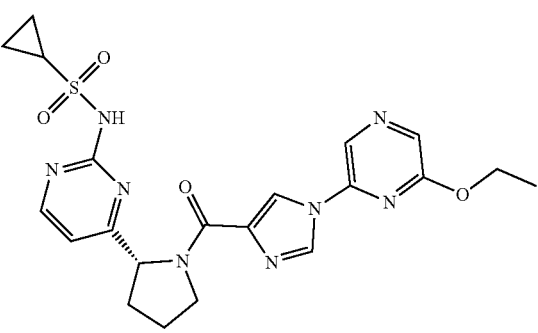 [SMILES: CCOc1cncc(-n2cnc(C(=O)N3CCC[C@@H]3c3ccnc(NS(=O)(=O)C4CC4)n3)c2)n1] |
| I-276 | 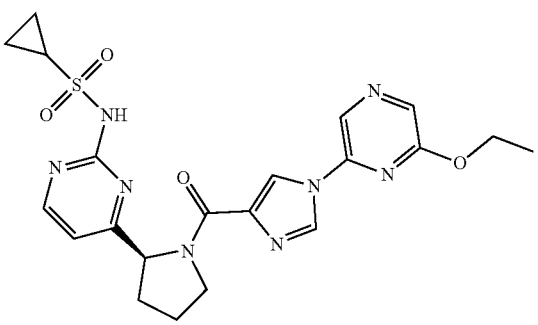 [SMILES: CCOc1cncc(-n2cnc(C(=O)N3CCC[C@H]3c3ccnc(NS(=O)(=O)C4CC4)n3)c2)n1] |

| Compound | Structure |
|---|---|
| I-277 | 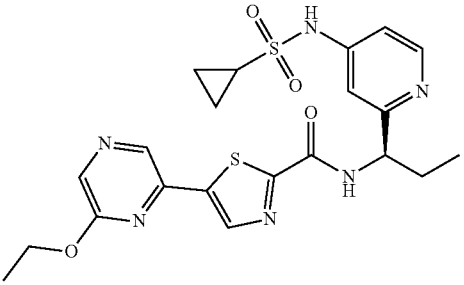 [SMILES: CCOc1cncc(-c2cnc(C(=O)N[C@H](CC)c3cc(NS(=O)(=O)C4CC4)ccn3)s2)n1] |
| I-278 | 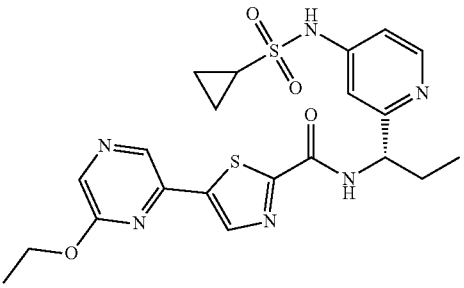 [SMILES: CCOc1cncc(-c2cnc(C(=O)N[C@@H](CC)c3cc(NS(=O)(=O)C4CC4)ccn3)s2)n1] |
| I-279 | 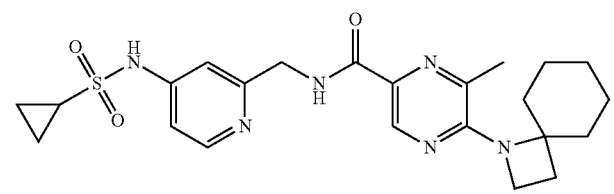 [SMILES: Cc1nc(C(=O)NCc2cc(NS(=O)(=O)C3CC3)ccn2)cnc1N1CCC12CCCCC2] |
| I-284 | 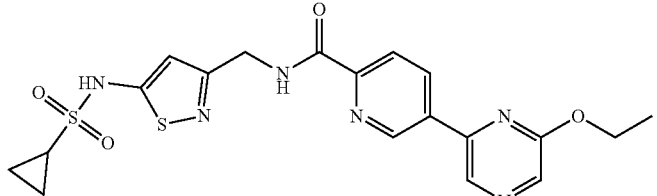 |
| I-285 | 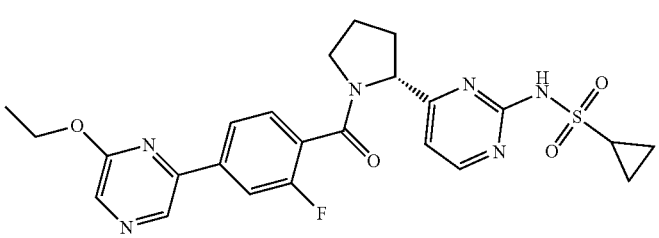 [SMILES: CCOc1cncc(-c2ccc(C(=O)N3CCC[C@@H]3c3ccnc(NS(=O)(=O)C4CC4)n3)c(F)c2)n1] |
| I-286 | 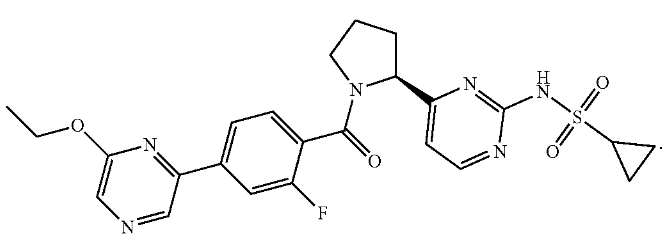 [SMILES: CCOc1cncc(-c2ccc(C(=O)N3CCC[C@H]3c3ccnc(NS(=O)(=O)C4CC4)n3)c(F)c2)n1] |

9. A compound selected from those depicted below, or a pharmaceutically acceptable salt thereof:
| Compound | Structure |
|---|---|
| Z-1 | 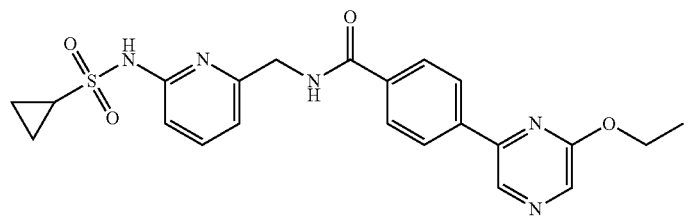 [SMILES: CCOc1cncc(-c2ccc(C(=O)NCc3cccc(NS(=O)(=O)C4CC4)n3)cc2)n1] |
| Z-2 | 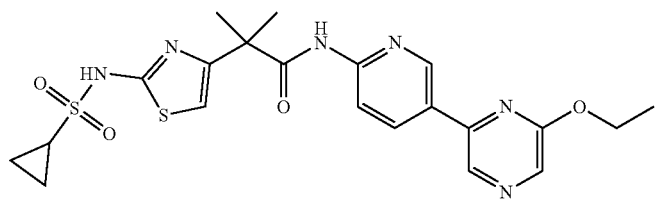 [SMILES: CCOc1cncc(-c2ccc(NC(=O)C(C)(C)c3csc(NS(=O)(=O)C4CC4)n3)nc2)n1] |
| Z-3 | 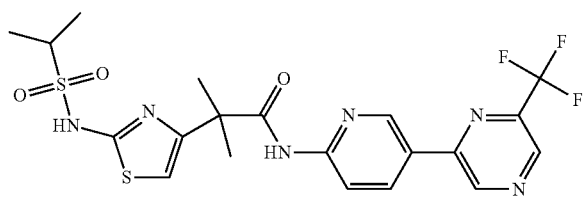 [SMILES: CC(C)S(=O)(=O)Nc1nc(C(C)(C)C(=O)Nc2ccc(-c3cncc(C(F)(F)F)n3)cn2)cs1] |
| Z-4 | 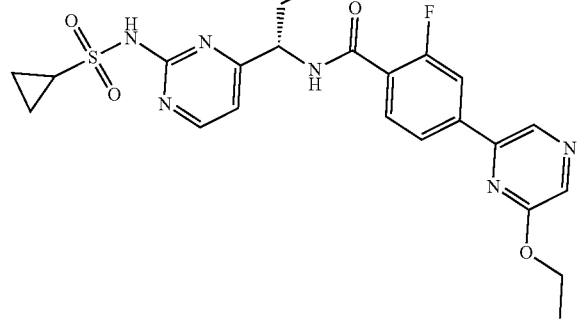 |
| Z-5 | 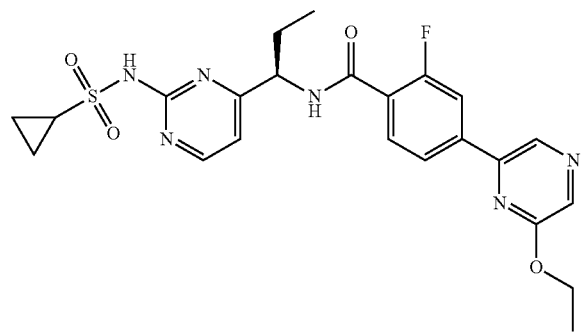 [SMILES: CCOc1cncc(-c2ccc(C(=O)N[C@H](CC)c3ccnc(NS(=O)(=O)C4CC4)n3)c(F)c2)n1] |

| Compound | Structure |
|---|---|
| Z-6 | 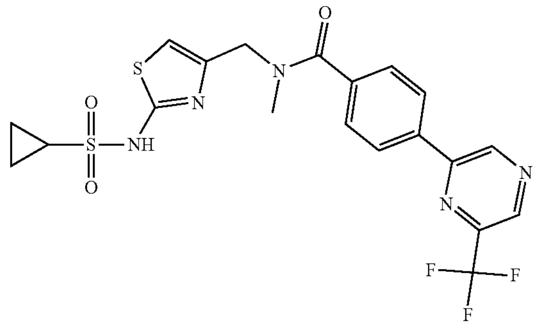 [SMILES: CN(Cc1csc(NS(=O)(=O)C2CC2)n1)C(=O)c1ccc(-c2cncc(C(F)(F)F)n2)cc1] |
| Z-7 | 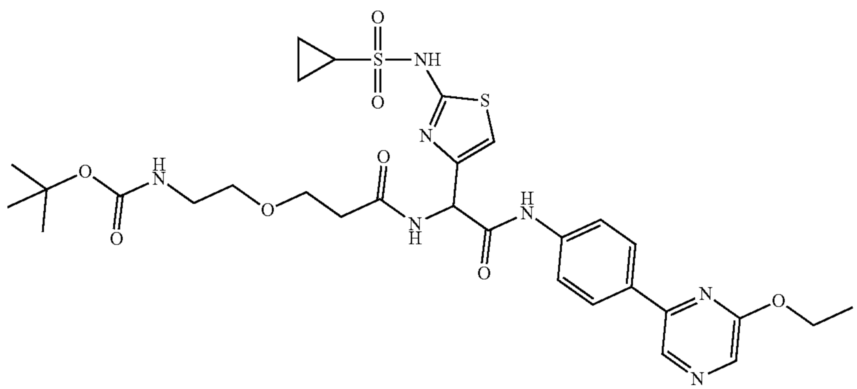 [SMILES: CCOc1cncc(-c2ccc(NC(=O)C(NC(=O)CCOCCNC(=O)OC(C)(C)C)c3csc(NS(=O)(=O)C4CC4)n3)cc2)n1] |
| Z-8 | 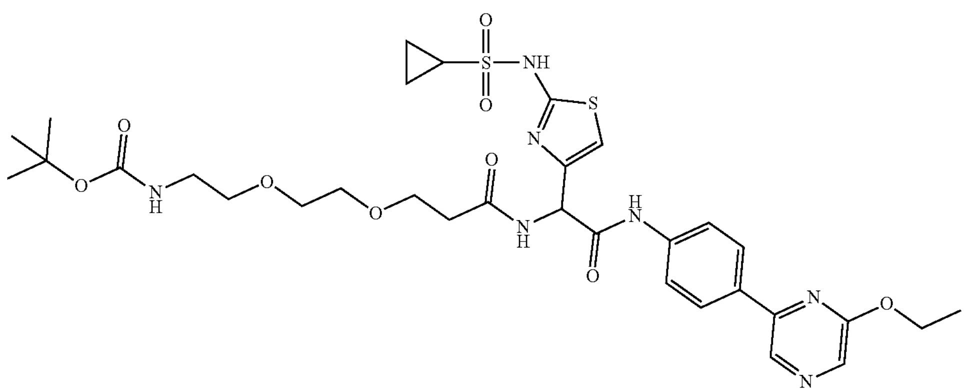 [SMILES: CCOc1cncc(-c2ccc(NC(=O)C(NC(=O)CCOCCOCCNC(=O)OC(C)(C)C)c3csc(NS(=O)(=O)C4CC4)n3)cc2)n1] |
| Z-9 | 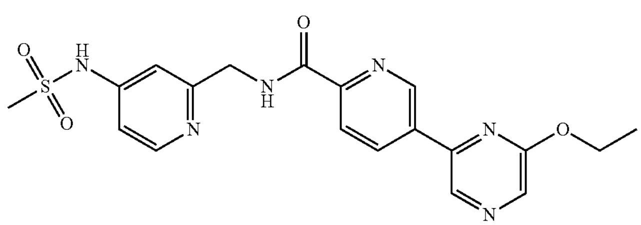 [SMILES: CCOc1cncc(-c2ccc(C(=O)NCc3cc(NS(C)(=O)=O)ccn3)nc2)n1] |
| Z-10 | 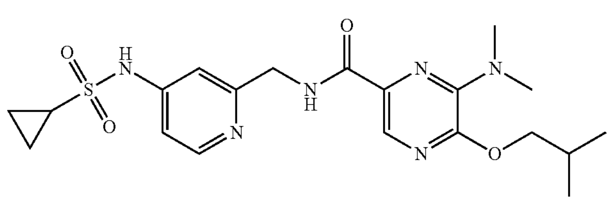 [SMILES: CC(C)COc1ncc(C(=O)NCc2cc(NS(=O)(=O)C3CC3)ccn2)nc1N(C)C] |

10. A pharmaceutical composition comprising a compound according to claim 1, or a pharmaceutically acceptable salt thereof, and a pharmaceutically acceptable carrier, adjuvant, or vehicle.

* * * * *